United States Patent
Schmolz et al.

(10) Patent No.: US 8,361,730 B2
(45) Date of Patent: Jan. 29, 2013

(54) ILCS BASED PATTERN RECOGNITION OF SEPSIS

(75) Inventors: Manfred Schmolz, Reutlingen (DE); Marion E. Schneider, Ulm (DE)

(73) Assignees: EDI GmbH, Reutlingen (DE); Unversitat Ulm, Ulm (DE)

( * ) Notice: Subject to any disclaimer, the term of this patent is extended or adjusted under 35 U.S.C. 154(b) by 0 days.

(21) Appl. No.: 11/960,413

(22) Filed: Dec. 19, 2007

(65) Prior Publication Data
US 2008/0213751 A1 Sep. 4, 2008

(30) Foreign Application Priority Data
Dec. 20, 2006 (DE) .......................... 10 2006 062 398

(51) Int. Cl.
*G01N 33/53* (2006.01)
(52) U.S. Cl. ...................................................... 435/7.1
(58) Field of Classification Search ........................ None
See application file for complete search history.

(56) References Cited

U.S. PATENT DOCUMENTS

| | | | |
|---|---|---|---|
| 2002/0039734 A1* | 4/2002 | Hanrahan et al. | 435/6 |
| 2004/0224306 A1* | 11/2004 | Kuhne et al. | 435/5 |
| 2005/0148029 A1* | 7/2005 | Buechler et al. | 435/7.1 |
| 2005/0272055 A1 | 12/2005 | Das et al. | |
| 2006/0246495 A1* | 11/2006 | Garrett et al. | 435/6 |

OTHER PUBLICATIONS

Weighardt et al, Infect. Immun. 74(6), 3618 (2006).*
Lucas et al, J. Immunol. 171: 2610 (2003).*
Ausubel et al, "Short Protocols in Molecular Biology" 3$^{rd}$ Ed. John Wiley and Sons. pp. iii-xxii (1995).
Ausebel, F.M. et al "Current Protocols in Molecular Biology" (1993), John Wiley & Sons, pp. 2.10.1-2.10.16 & 6.3.1-6.3.6 (2000).
Teng et al, Proc. Natl. Acad.Sci, USA, "Construction and testing of mouse-human heteromyelomas for human monoclonal antibody production" 80; 7308-7312 (1983).
Kozbor, et al., "The production of monoclonal antibodies from human lymphocytes", Immunology Today, 4:72 (1983).
Olsson et all, "Human-Human Monoclonal Antibody-Producing hybridomas: Technical Aspects", Meth.Enzymol., 92:3-16, (1982).
Muller, C. & Zielinksi, C.C., Impaired lipopolysaccharide-inducible tumor necrosis factor production in vitro by peripheral blood monocytes of patients with viral hepatitis. Hepatology (1990) 12 (5) 1118-24.
Mookherjee, N.: Modulation of the TLR-mediated inflammatory response by the endogenous human host defense peptide LL-37. J. Immunol. (Feb. 15, 2006) 176(4) 2455-64.
Ishii Ken J. et al., "Toll-like receptors and sepsis" Current Infectious Disease Reports, Current Science, Philadelphia, PA, US, vol. 6, No. 5, 361, 2004.

* cited by examiner

*Primary Examiner* — James Martinell
(74) *Attorney, Agent, or Firm* — Matthew S. Gordon; Myriad Genetics IP Department

(57) ABSTRACT

The present invention refers to a method for recognizing and/or characterizing cellular activity patterns, in particular for diagnostic purposes and/or for tracking the therapy of diseases. Blood cells are stimulated in a culture medium at least with toll-like receptor ligands (TLR ligands) and the stimulated blood cells and/or the culture medium are examined.

24 Claims, 740 Drawing Sheets
(714 of 740 Drawing Sheet(s) Filed in Color)

NHD    Sepsis patients

FIG. 8
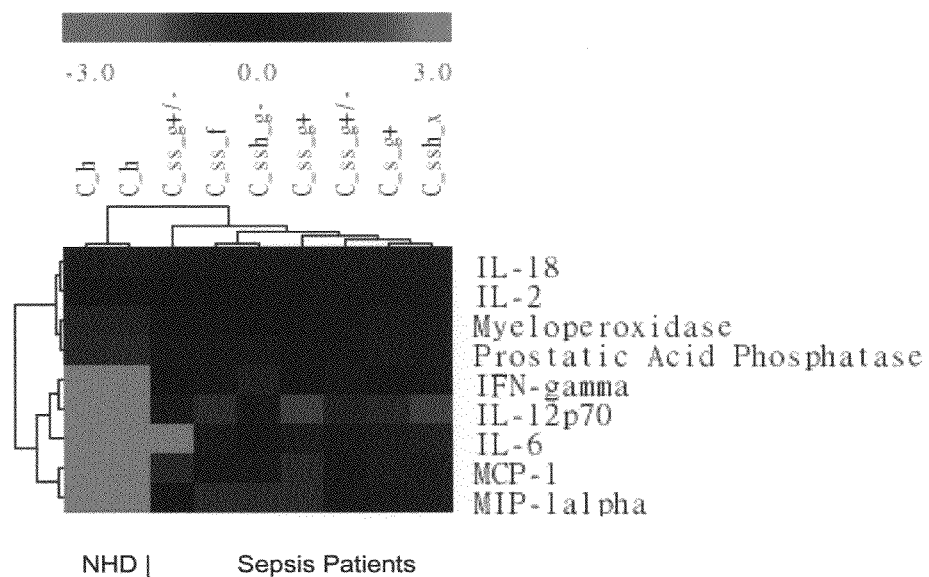
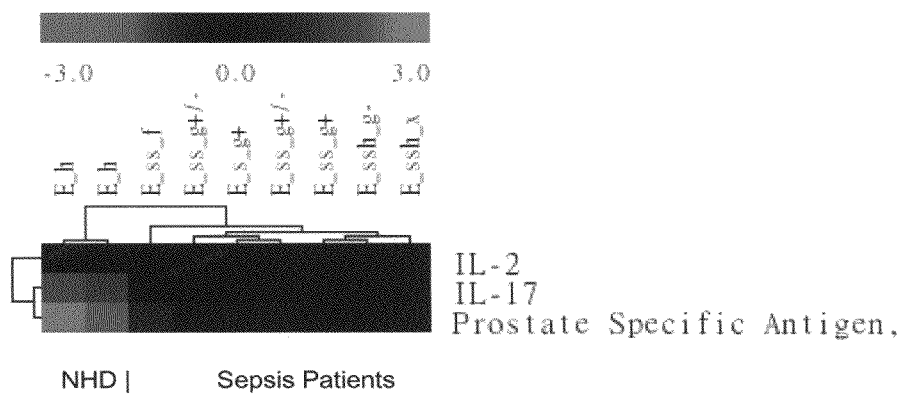

FIG. 12A.1

| | Alpha-1 Antitrypsin mg/mL | Adiponectin ug/mL | Alpha-2 Macroglobulin mg/mL | Alpha-Fetoprotein ng/mL | Amphiregulin pg/mL |
|---|---|---|---|---|---|
| Least Detectable Dose | 0.011 | 0.20 | 0.061 | 0.43 | 36 |
| RBM Low Plasma Range | 1.2 | 1.6 | 0.13 | | Pending |
| RBM High Plasma Range | 3.1 | 14 | 1.0 | 6.7 | Pending |
| Donor_1 3. Aliquot A | 2.6 | 2.0 | 0.29 | 2.8 | 469 |
| Donor_1 3. Aliquot B | 2.8 | 2.1 | 0.30 | 2.6 | 455 |
| Donor_1 3. Aliquot C | 2.9 | 2.1 | 0.30 | 2.3 | 104 |
| Donor_1 3. Aliquot D | 3.1 | 2.1 | 0.31 | 2.8 | 431 |
| Donor_1 3. Aliquot E | 2.8 | 2.1 | 0.27 | 2.5 | 443 |
| Donor_1 3. Aliquot F | 2.6 | 2.0 | 0.66 | 2.3 | 414 |
| Donor_1 3. Aliquot G | 2.9 | 2.1 | 0.30 | 2.5 | 401 |
| Donor_1 3. Aliquot H | 2.7 | 2.0 | 0.42 | 2.7 | <LOW> |
| Donor_1 3. Aliquot I | 2.7 | 2.0 | 0.26 | 2.5 | 419 |
| Donor_2 3. Aliquot A | 2.2 | 4.4 | 0.28 | 2.1 | 133 |
| Donor_2 3. Aliquot B | 2.3 | 4.5 | 0.30 | 2.3 | 50 |
| Donor_2 3. Aliquot C | 2.3 | 4.5 | 0.29 | 1.4 | <LOW> |
| Donor_2 3. Aliquot D | 2.2 | 4.3 | 0.29 | 3.4 | 104 |
| Donor_2 3. Aliquot E | 2.3 | 4.5 | 0.28 | 2.5 | 39 |
| Donor_2 3. Aliquot F | 2.3 | 4.2 | 0.64 | 2.0 | <LOW> |
| Donor_2 3. Aliquot G | 2.3 | 4.3 | 0.32 | 1.8 | 597 |
| Donor_2 3. Aliquot H | 2.2 | 4.4 | 0.33 | 1.8 | <LOW> |
| Donor_2 3. Aliquot I | 2.1 | 4.0 | 0.29 | 1.9 | 24 |
| Donor_3 3. Aliquot A | 2.9 | 3.0 | 0.35 | 2.7 | <LOW> |
| Donor_3 3. Aliquot B | 3.0 | 2.7 | 0.35 | 2.6 | <LOW> |
| Donor_3 3. Aliquot C | 3.0 | 2.8 | 0.34 | 1.9 | <LOW> |
| Donor_3 3. Aliquot D | 2.8 | 2.7 | 0.34 | 3.3 | 97 |
| Donor_3 3. Aliquot E | 3.1 | 2.8 | 0.36 | 3.5 | 116 |
| Donor_3 3. Aliquot F | 2.7 | 2.6 | 0.65 | 2.5 | 60 |
| Donor_3 3. Aliquot G | 3.1 | 2.8 | 0.35 | 1.4 | 97 |
| Donor_3 3. Aliquot H | 2.8 | 2.7 | 0.41 | 1.7 | <LOW> |
| Donor_3 3. Aliquot I | 2.8 | 2.6 | 0.33 | 1.3 | 39 |
| Donor_4 3. Aliquot A | 1.7 | 5.3 | 0.40 | 2.4 | <LOW> |

FIG. 12A.2

| | Alpha-1 Antitrypsin mg/mL | Adiponectin ug/mL | Alpha-2 Macroglobulin mg/mL | Alpha-Fetoprotein ng/mL | Amphiregulin pg/mL |
|---|---|---|---|---|---|
| Least Detectable Dose | 0.011 | 0.20 | 0.061 | 0.43 | 36 |
| RBM Low Plasma Range | 1.2 | 1.6 | 0.13 | | Pending |
| RBM High Plasma Range | 3.1 | 14 | 1.0 | 6.7 | Pending |
| Donor_4 3. Aliquot B | 1.5 | 5.4 | 0.40 | 2.1 | <LOW> |
| Donor_4 3. Aliquot C | 1.6 | 5.2 | 0.41 | 2.0 | 39 |
| Donor_4 3. Aliquot D | 1.6 | 5.3 | 0.42 | 3.6 | <LOW> |
| Donor_4 3. Aliquot E | 1.5 | 5.3 | 0.38 | 2.8 | <LOW> |
| Donor_4 3. Aliquot F | 1.6 | 5.3 | 0.98 | 1.8 | <LOW> |
| Donor_4 3. Aliquot G | 1.6 | 5.5 | 0.48 | 2.1 | 76 |
| Donor_4 3. Aliquot H | 1.5 | 5.3 | 0.65 | 2.1 | 76 |
| Donor_4 3. Aliquot I | 1.5 | 5.4 | 0.41 | 1.9 | <LOW> |
| Donor_5 3. Aliquot A | 2.9 | 2.8 | 0.27 | 3.2 | 127 |
| Donor_5 3. Aliquot B | 2.9 | 2.6 | 0.29 | 3.2 | 178 |
| Donor_5 3. Aliquot C | 3.2 | 2.7 | 0.29 | 2.5 | 50 |
| Donor_5 3. Aliquot D | 3.2 | 2.6 | 0.28 | 4.1 | 159 |
| Donor_5 3. Aliquot E | 3.1 | 2.8 | 0.28 | 4.0 | 187 |
| Donor_5 3. Aliquot F | 2.9 | 2.6 | 0.46 | 2.3 | <LOW> |
| Donor_5 3. Aliquot G | 3.0 | 2.5 | 0.29 | 3.0 | 208 |
| Donor_5 3. Aliquot H | 3.0 | 2.5 | 0.33 | 3.0 | 138 |
| Donor_5 3. Aliquot I | 3.0 | 2.4 | 0.28 | 3.3 | 39 |
| Donor_6 3. Aliquot A | 2.8 | 1.2 | 0.26 | 1.5 | <LOW> |
| Donor_6 3. Aliquot B | 2.7 | 1.2 | 0.24 | 1.9 | <LOW> |
| Donor_6 3. Aliquot C | 2.8 | 1.2 | 0.24 | 1.8 | <LOW> |
| Donor_6 3. Aliquot D | 2.7 | 1.2 | 0.24 | 1.9 | <LOW> |
| Donor_6 3. Aliquot E | 2.6 | 1.3 | 0.25 | 2.4 | 39 |
| Donor_6 3. Aliquot F | 2.7 | 1.2 | 0.25 | 1.6 | <LOW> |
| Donor_6 3. Aliquot G | 2.9 | 1.2 | 0.27 | 1.8 | <LOW> |
| Donor_6 3. Aliquot H | 2.5 | 1.3 | 0.29 | 1.6 | 599 |
| Donor_6 3. Aliquot I | 2.5 | 1.1 | 0.26 | 1.5 | 24 |

FIG. 12A.3

| | Alpha-1 Antitrypsin mg/mL | Adiponectin ug/mL | Alpha-2 Macroglobulin mg/mL | Alpha-Fetoprotein ng/mL | Amphiregulin pg/mL |
|---|---|---|---|---|---|
| Least Detectable Dose | 0.011 | 0.20 | 0.061 | 0.43 | 36 |
| RBM Low Plasma Range | 1.2 | 1.6 | 0.13 | | Pending |
| RBM High Plasma Range | 3.1 | 14 | 1.0 | 6.7 | Pending |
| Donor_7_3_Aliquot A | 1.8 | 0.90 | 0.39 | 1.9 | 104 |
| Donor_7_3_Aliquot B | 1.7 | 0.92 | 0.37 | 2.5 | <LOW> |
| Donor_7_3_Aliquot C | 1.9 | 0.83 | 0.38 | 1.3 | <LOW> |
| Donor_7_3_Aliquot D | 1.7 | 0.81 | 0.36 | 2.6 | 104 |
| Donor_7_3_Aliquot E | 1.2 | 0.90 | 0.40 | 2.5 | <LOW> |
| Donor_7_3_Aliquot F | 1.8 | 0.90 | 0.45 | 1.5 | <LOW> |
| Donor_7_3_Aliquot G | 1.6 | 0.87 | 0.43 | 2.2 | 370 |
| Donor_7_3_Aliquot H | 1.7 | 0.79 | 0.51 | 1.5 | <LOW> |
| Donor_7_3_Aliquot I | 1.8 | 0.82 | 0.38 | 1.9 | <LOW> |
| Donor_8_3_Aliquot A | 0.96 | 4.3 | 0.39 | 1.7 | <LOW> |
| Donor_8_3_Aliquot B | 0.97 | 4.3 | 0.39 | 1.3 | <LOW> |
| Donor_8_3_Aliquot C | 0.96 | 4.1 | 0.40 | 0.53 | <LOW> |
| Donor_8_3_Aliquot D | 0.88 | 4.0 | 0.39 | 4.4 | <LOW> |
| Donor_8_3_Aliquot E | 0.88 | 4.0 | 0.39 | 3.5 | 127 |
| Donor_8_3_Aliquot F | 0.99 | 4.5 | 0.46 | 1.6 | 50 |
| Donor_8_3_Aliquot G | 0.92 | 4.2 | 0.48 | 1.2 | 90 |
| Donor_8_3_Aliquot H | 1.0 | 4.4 | 0.58 | 1.6 | <LOW> |
| Donor_8_3_Aliquot I | 0.94 | 4.2 | 0.40 | 1.2 | <LOW> |
| Donor_9_3_Aliquot A | 1.2 | 3.5 | 0.34 | 1.1 | 51 |
| Donor_9_3_Aliquot B | 1.3 | 3.5 | 0.38 | 1.8 | 51 |
| Donor_9_3_Aliquot C | 1.3 | 3.6 | 0.41 | 2.0 | 51 |
| Donor_9_3_Aliquot D | 1.2 | 3.3 | 0.38 | 4.2 | 101 |
| Donor_9_3_Aliquot E | 1.3 | 3.7 | 0.45 | 3.2 | 42 |
| Donor_9_3_Aliquot F | 1.2 | 3.8 | 0.40 | 2.1 | <LOW> |
| Donor_9_3_Aliquot G | 1.4 | 3.5 | 0.49 | 2.1 | 169 |
| Donor_9_3_Aliquot H | 1.2 | 3.5 | 0.54 | 2.3 | 78 |
| Donor_9_3_Aliquot I | 1.3 | 3.6 | 0.36 | 1.3 | <LOW> |
| EDTA Plasma | | | | | |

FIG. 12A.4

| | Alpha-1 Antitrypsin mg/mL | Adiponectin ug/mL | Alpha-2 Macroglobulin mg/mL | Alpha-Fetoprotein ng/mL | Amphiregulin pg/mL |
|---|---|---|---|---|---|
| Least Detectable Dose | 0.011 | 0.20 | 0.061 | 0.43 | 36 |
| RBM Low Plasma Range | | | | | Pending |
| RBM High Plasma Range | | | | | Pending |
| donor #1 plasma | 1.2 | 1.6 | 0.13 | | 441 |
| donor #2 plasma | 3.1 | 14 | 1.0 | 6.7 | <LOW> |
| donor #3 plasma | 2.9 | 2.1 | 0.25 | 2.3 | <LOW> |
| donor #4 plasma | 3.0 | 6.1 | 0.29 | 1.7 | 33 |
| donor #5 plasma | 4.7 | 4.2 | 0.36 | 2.9 | <LOW> |
| donor #6 plasma | 2.2 | 7.5 | 0.34 | 2.4 | <LOW> |
| donor #7 plasma | 4.4 | 3.6 | 0.25 | 3.6 | 78 |
| donor #8 plasma | 3.7 | 1.7 | 0.24 | 2.1 | 72 |
| donor #9 plasma | 2.3 | 1.3 | 0.35 | 2.8 | <LOW> |
| | 1.0 | 5.1 | 0.34 | 1.9 | |
| | 1.9 | 4.8 | 0.37 | 2.1 | |

FIG. 12B.1

|  | Apolipoprotein A1 mg/mL | Apolipoprotein CIII ug/mL | Apolipoprotein H ug/mL | Beta-2 Microglobulin ug/mL |
|---|---|---|---|---|
| Least Detectable Dose | 0.0066 | 2.7 | 8.8 | 0.013 |
| RBM Low Plasma Range | 0.19 | 28 | 131 | 1.2 |
| RBM High Plasma Range | 0.89 | 224 | 430 | 6.2 |
| Donor_1 3. Aliquot A | 0.10 | 52 | 138 | 17 |
| Donor_1 3. Aliquot B | 0.10 | 64 | 148 | 15 |
| Donor_1 3. Aliquot C | 0.11 | 60 | 143 | 16 |
| Donor_1 3. Aliquot D | 0.11 | 60 | 150 | 16 |
| Donor_1 3. Aliquot E | 0.11 | 53 | 141 | 16 |
| Donor_1 3. Aliquot F | 0.097 | 57 | 142 | 14 |
| Donor_1 3. Aliquot G | 0.098 | 61 | 151 | 16 |
| Donor_1 3. Aliquot H | 0.089 | 48 | 141 | 15 |
| Donor_1 3. Aliquot I | 0.11 | 60 | 150 | 16 |
| Donor_2 3. Aliquot A | 0.11 | 58 | 152 | 20 |
| Donor_2 3. Aliquot B | 0.12 | 64 | 143 | >24 |
| Donor_2 3. Aliquot C | 0.12 | 64 | 154 | 23 |
| Donor_2 3. Aliquot D | 0.098 | 48 | 142 | 19 |
| Donor_2 3. Aliquot E | 0.097 | 52 | 154 | 20 |
| Donor_2 3. Aliquot F | 0.090 | 66 | 152 | 19 |
| Donor_2 3. Aliquot G | 0.094 | 67 | 153 | 21 |
| Donor_2 3. Aliquot H | 0.095 | 61 | 148 | 21 |
| Donor_2 3. Aliquot I | 0.11 | 54 | 141 | 19 |
| Donor_3 3. Aliquot A | 0.13 | 38 | 150 | 2.6 |
| Donor_3 3. Aliquot B | 0.14 | 38 | 144 | 2.3 |
| Donor_3 3. Aliquot C | 0.13 | 41 | 153 | 2.4 |
| Donor_3 3. Aliquot D | 0.13 | 38 | 149 | 2.4 |
| Donor_3 3. Aliquot E | 0.14 | 36 | 157 | 2.5 |
| Donor_3 3. Aliquot F | 0.12 | 42 | 148 | 2.2 |
| Donor_3 3. Aliquot G | 0.15 | 44 | 149 | 2.3 |
| Donor_3 3. Aliquot H | 0.13 | 41 | 144 | 2.3 |
| Donor_3 3. Aliquot I | 0.14 | 42 | 150 | 2.2 |
| Donor_4 3. Aliquot A | 0.056 | 13 | 105 | 7.6 |

FIG. 12B.2

| | Apolipoprotein A1 mg/mL | Apolipoprotein CIII ug/mL | Apolipoprotein H ug/mL | Beta-2 Microglobulin ug/mL |
|---|---|---|---|---|
| Least Detectable Dose | 0.0066 | 2.7 | 8.8 | 0.013 |
| RBM Low Plasma Range | 0.19 | 28 | 131 | 1.2 |
| RBM High Plasma Range | 0.89 | 224 | 430 | 6.2 |
| Donor_4_3. Aliquot B | 0.050 | 12 | 96 | 7.2 |
| Donor_4_3. Aliquot C | 0.049 | 11 | 102 | 8.0 |
| Donor_4_3. Aliquot D | 0.044 | 13 | 102 | 7.7 |
| Donor_4_3. Aliquot E | 0.048 | 9.1 | 93 | 8.3 |
| Donor_4_3. Aliquot F | 0.054 | 15 | 93 | 8.5 |
| Donor_4_3. Aliquot G | 0.047 | 11 | 100 | 8.1 |
| Donor_4_3. Aliquot H | 0.051 | 11 | 91 | 8.2 |
| Donor_4_3. Aliquot I | 0.052 | 12 | 99 | 8.0 |
| Donor_5_3. Aliquot A | 0.12 | 70 | 253 | 12 |
| Donor_5_3. Aliquot B | 0.13 | 77 | 266 | 13 |
| Donor_5_3. Aliquot C | 0.14 | 77 | 265 | 13 |
| Donor_5_3. Aliquot D | 0.14 | 78 | 263 | 13 |
| Donor_5_3. Aliquot E | 0.14 | 71 | 257 | 15 |
| Donor_5_3. Aliquot F | 0.12 | 83 | 238 | 11 |
| Donor_5_3. Aliquot G | 0.14 | 78 | 246 | 12 |
| Donor_5_3. Aliquot H | 0.14 | 81 | 245 | 13 |
| Donor_5_3. Aliquot I | 0.13 | 75 | 250 | 11 |
| Donor_6_3. Aliquot A | 0.100 | 43 | 141 | 1.2 |
| Donor_6_3. Aliquot B | 0.10 | 42 | 148 | 1.1 |
| Donor_6_3. Aliquot C | 0.12 | 36 | 141 | 1.2 |
| Donor_6_3. Aliquot D | 0.11 | 43 | 143 | 1.2 |
| Donor_6_3. Aliquot E | 0.12 | 42 | 131 | 1.2 |
| Donor_6_3. Aliquot F | 0.094 | 45 | 143 | 1.2 |
| Donor_6_3. Aliquot G | 0.12 | 52 | 152 | 1.2 |
| Donor_6_3. Aliquot H | 0.11 | 40 | 131 | 1.1 |
| Donor_6_3. Aliquot I | 0.12 | 40 | 134 | 1.1 |

FIG. 12B.3

| | Apolipoprotein A1 mg/mL | Apolipoprotein CIII ug/mL | Apolipoprotein H ug/mL | Beta-2 Microglobulin ug/mL |
|---|---|---|---|---|
| Least Detectable Dose | 0.0066 | 2.7 | 8.8 | 0.013 |
| | | | | |
| RBM Low Plasma Range | 0.19 | 28 | 131 | 1.2 |
| RBM High Plasma Range | 0.89 | 224 | 430 | 6.2 |
| Donor_7 3. Aliquot A | 0.14 | 50 | 180 | 2.0 |
| Donor_7 3. Aliquot B | 0.14 | 36 | 183 | 2.0 |
| Donor_7 3. Aliquot C | 0.16 | 44 | 183 | 2.1 |
| Donor_7 3. Aliquot D | 0.15 | 41 | 169 | 2.0 |
| Donor_7 3. Aliquot E | 0.12 | 33 | 138 | 2.1 |
| Donor_7 3. Aliquot F | 0.16 | 54 | 190 | 1.9 |
| Donor_7 3. Aliquot G | 0.14 | 43 | 161 | 1.9 |
| Donor_7 3. Aliquot H | 0.15 | 41 | 173 | 1.9 |
| Donor_7 3. Aliquot I | 0.13 | 42 | 173 | 1.9 |
| | | | | |
| Donor_8 3. Aliquot A | 0.24 | 57 | 117 | 1.2 |
| Donor_8 3. Aliquot B | 0.28 | 72 | 117 | 1.2 |
| Donor_8 3. Aliquot C | 0.28 | 75 | 119 | 1.2 |
| Donor_8 3. Aliquot D | 0.26 | 55 | 111 | 1.2 |
| Donor_8 3. Aliquot E | 0.24 | 61 | 113 | 1.2 |
| Donor_8 3. Aliquot F | 0.29 | 69 | 121 | 1.3 |
| Donor_8 3. Aliquot G | 0.29 | 58 | 111 | 1.2 |
| Donor_8 3. Aliquot H | 0.25 | 59 | 127 | 1.2 |
| Donor_8 3. Aliquot I | 0.25 | 53 | 122 | 1.2 |
| | | | | |
| Donor_9 3. Aliquot A | 0.21 | 39 | 101 | 0.83 |
| Donor_9 3. Aliquot B | 0.22 | 43 | 104 | 0.79 |
| Donor_9 3. Aliquot C | 0.21 | 33 | 96 | 0.93 |
| Donor_9 3. Aliquot D | 0.18 | 34 | 99 | 0.87 |
| Donor_9 3. Aliquot E | 0.20 | 36 | 105 | 0.88 |
| Donor_9 3. Aliquot F | 0.23 | 39 | 103 | 0.90 |
| Donor_9 3. Aliquot G | 0.22 | 42 | 113 | 0.86 |
| Donor_9 3. Aliquot H | 0.19 | 37 | 97 | 0.83 |
| Donor_9 3. Aliquot I | 0.21 | 33 | 97 | 0.82 |
| EDTA Plasma | | | | |

FIG. 12B.4

| | Apolipoprotein A1 mg/mL | Apolipoprotein CIII ug/mL | Apolipoprotein H ug/mL | Beta-2 Microglobulin ug/mL |
|---|---|---|---|---|
| Least Detectable Dose | 0.0066 | 2.7 | 8.8 | 0.013 |
| RBM Low Plasma Range | | | | |
| RBM High Plasma Range | | | | |
| donor #1 plasma | 0.19 | 28 | 131 | 1.2 |
| donor #2 plasma | 0.89 | 224 | 430 | 6.2 |
| donor #3 plasma | 0.069 | 34 | 127 | 11 |
| donor #4 plasma | 0.11 | 65 | 166 | 19 |
| donor #5 plasma | 0.14 | 47 | 193 | 2.5 |
| donor #6 plasma | 0.047 | 14 | 106 | 9.1 |
| donor #7 plasma | 0.12 | 91 | 316 | 14 |
| donor #8 plasma | 0.100 | 34 | 163 | 1.1 |
| donor #9 plasma | 0.17 | 52 | 214 | 2.3 |
| donor #8 plasma | 0.25 | 46 | 113 | 1.1 |
| donor #9 plasma | 0.30 | 39 | 147 | 0.88 |

FIG. 12C.1

| | Brain-Derived Neurotrophic Factor | Complement 3 | Cancer Antigen 125 | Cancer Antigen 19-9 | Calcitonin |
|---|---|---|---|---|---|
| | ng/mL | mg/mL | U/mL | U/mL | pg/mL |
| Least Detectable Dose | 0.32 | 0.0053 | 4.2 | 0.25 | 6.0 |
| | | | | | |
| RBM Low Plasma Range | | 0.76 | | | |
| RBM High Plasma Range | 16 | 2.1 | 12 | 9.2 | 12 |
| Donor_1_3. Aliquot A | 2.4 | 0.73 | 132 | 28 | 36 |
| Donor_1_3. Aliquot B | 3.3 | 0.71 | 123 | 28 | 32 |
| Donor_1_3. Aliquot C | 1.6 | 0.71 | 141 | 13 | 34 |
| Donor_1_3. Aliquot D | 2.6 | 0.71 | 157 | 28 | 37 |
| Donor_1_3. Aliquot E | 2.3 | 0.69 | 135 | 28 | 36 |
| Donor_1_3. Aliquot F | 1.3 | 1.5 | 128 | 24 | 31 |
| Donor_1_3. Aliquot G | 0.048 | 0.77 | 140 | 32 | 32 |
| Donor_1_3. Aliquot H | 3.4 | 1.2 | 143 | 12 | 31 |
| Donor_1_3. Aliquot I | 2.8 | 0.71 | 125 | 28 | 33 |
| | | | | | |
| Donor_2_3. Aliquot A | 3.4 | 0.92 | 121 | 476 | 29 |
| Donor_2_3. Aliquot B | 4.6 | 0.93 | 125 | 510 | 31 |
| Donor_2_3. Aliquot C | 1.3 | 0.89 | 119 | 408 | 24 |
| Donor_2_3. Aliquot D | 2.5 | 0.92 | 197 | 468 | 33 |
| Donor_2_3. Aliquot E | 2.3 | 0.94 | 158 | 488 | 31 |
| Donor_2_3. Aliquot F | 1.6 | 2.3 | 123 | 413 | 30 |
| Donor_2_3. Aliquot G | 0.49 | 0.98 | 138 | 495 | 20 |
| Donor_2_3. Aliquot H | 2.3 | 1.3 | 106 | 459 | 29 |
| Donor_2_3. Aliquot I | 1.8 | 0.90 | 102 | 447 | 26 |
| | | | | | |
| Donor_3_3. Aliquot A | 3.0 | 0.68 | 35 | 3.3 | <LOW> |
| Donor_3_3. Aliquot B | 4.5 | 0.70 | 33 | 3.6 | 5.1 |
| Donor_3_3. Aliquot C | 2.9 | 0.73 | 35 | 3.6 | <LOW> |
| Donor_3_3. Aliquot D | 3.4 | 0.73 | 87 | 3.3 | <LOW> |
| Donor_3_3. Aliquot E | 3.8 | 0.77 | 74 | 3.6 | 7.3 |
| Donor_3_3. Aliquot F | 1.6 | 1.2 | 39 | 4.1 | <LOW> |
| Donor_3_3. Aliquot G | 0.047 | 0.72 | 29 | 4.6 | <LOW> |
| Donor_3_3. Aliquot H | 2.3 | 1.1 | 27 | 3.2 | <LOW> |
| Donor_3_3. Aliquot I | 2.2 | 0.74 | 31 | 2.8 | <LOW> |
| | | | | | |
| Donor_4_3. Aliquot A | 2.0 | 0.45 | 512 | 15 | 18 |

FIG. 12C.2

| | Brain-Derived Neurotrophic Factor | Complement 3 | Cancer Antigen 125 | Cancer Antigen 19-9 | Calcitonin |
|---|---|---|---|---|---|
| | ng/mL | mg/mL | U/mL | U/mL | pg/mL |
| Least Detectable Dose | 0.029 | 0.0053 | 4.2 | 0.25 | 6.0 |
| RBM Low Plasma Range | | | | | |
| RBM High Plasma Range | | | | | |
| Donor_4 3. Aliquot B | 16 | 2.1 | 12 | 9.2 | 12 |
| Donor_4 3. Aliquot C | 2.8 | 0.41 | 495 | 16 | 20 |
| Donor_4 3. Aliquot D | 0.49 | 0.45 | 462 | 15 | 15 |
| Donor_4 3. Aliquot E | 1.6 | 0.43 | 542 | 16 | 19 |
| Donor_4 3. Aliquot F | 1.0 | 0.44 | 520 | 20 | 16 |
| Donor_4 3. Aliquot G | 0.88 | 0.80 | 465 | 16 | 15 |
| Donor_4 3. Aliquot H | 0.049 | 0.43 | 462 | 17 | 10 |
| Donor_4 3. Aliquot I | 0.53 | 0.69 | 509 | 15 | 17 |
| Donor_4 3. Aliquot J | 1.2 | 0.43 | 494 | 15 | 17 |
| Donor_5 3. Aliquot A | 5.8 | 0.72 | 21 | 8.8 | 105 |
| Donor_5 3. Aliquot B | 4.5 | 0.76 | 21 | 9.2 | 97 |
| Donor_5 3. Aliquot C | 2.3 | 0.77 | 21 | 9.9 | 74 |
| Donor_5 3. Aliquot D | 2.9 | 0.78 | 87 | 10 | 92 |
| Donor_5 3. Aliquot E | 4.5 | 0.73 | 74 | 10 | 90 |
| Donor_5 3. Aliquot F | 2.3 | 1.2 | 12 | 7.1 | 86 |
| Donor_5 3. Aliquot G | 0.16 | 0.80 | 20 | 8.6 | 67 |
| Donor_5 3. Aliquot H | 4.8 | 1.1 | 16 | 8.9 | 101 |
| Donor_5 3. Aliquot I | 3.1 | 0.72 | 17 | 8.0 | 94 |
| Donor_6 3. Aliquot A | 4.4 | 0.73 | 29 | 3.7 | <LOW> |
| Donor_6 3. Aliquot B | 3.4 | 0.77 | 42 | 2.6 | <LOW> |
| Donor_6 3. Aliquot C | 1.1 | 0.72 | 24 | 4.4 | <LOW> |
| Donor_6 3. Aliquot D | 3.9 | 0.75 | 82 | 3.9 | <LOW> |
| Donor_6 3. Aliquot E | 2.1 | 0.67 | 85 | 3.5 | <LOW> |
| Donor_6 3. Aliquot F | 1.9 | 0.71 | 27 | 2.9 | <LOW> |
| Donor_6 3. Aliquot G | 0.064 | 0.78 | 28 | 5.2 | <LOW> |
| Donor_6 3. Aliquot H | 3.1 | 1.1 | 23 | 3.7 | <LOW> |
| Donor_6 3. Aliquot I | 1.7 | 0.68 | 29 | 3.0 | <LOW> |

FIG. 12C.3

| | Brain-Derived Neurotrophic Factor | Complement 3 | Cancer Antigen 125 | Cancer Antigen 19-9 | Calcitonin |
|---|---|---|---|---|---|
| | ng/mL | mg/mL | U/mL | U/mL | pg/mL |
| Least Detectable Dose | 0.029 | 0.0053 | 4.2 | 0.25 | 6.0 |
| RBM Low Plasma Range | 0.32 | 0.76 | | | |
| RBM High Plasma Range | 16 | 2.1 | 12 | 9.2 | 12 |
| Donor_7 3. Aliquot A | 2.8 | 0.67 | 53 | 5.3 | 1.5 |
| Donor_7 3. Aliquot B | 3.1 | 0.68 | 48 | 5.1 | <LOW> |
| Donor_7 3. Aliquot C | 2.2 | 0.73 | 39 | 5.1 | <LOW> |
| Donor_7 3. Aliquot D | 2.9 | 0.66 | 91 | 4.8 | <LOW> |
| Donor_7 3. Aliquot E | 2.3 | 0.51 | 53 | 5.2 | <LOW> |
| Donor_7 3. Aliquot F | 1.2 | 0.72 | 40 | 4.7 | <LOW> |
| Donor_7 3. Aliquot G | 0.043 | 0.74 | 38 | 7.8 | <LOW> |
| Donor_7 3. Aliquot H | 1.6 | 1.1 | 34 | 5.2 | <LOW> |
| Donor_7 3. Aliquot I | 1.6 | 0.67 | 39 | 3.7 | 3.3 |
| Donor_8 3. Aliquot A | 3.3 | 0.45 | 5.6 | 4.9 | <LOW> |
| Donor_8 3. Aliquot B | 5.3 | 0.49 | 9.0 | 3.9 | <LOW> |
| Donor_8 3. Aliquot C | 3.2 | 0.43 | 4.4 | 3.9 | <LOW> |
| Donor_8 3. Aliquot D | 4.5 | 0.44 | 164 | 5.5 | 4.6 |
| Donor_8 3. Aliquot E | 6.0 | 0.43 | 136 | 5.1 | 6.5 |
| Donor_8 3. Aliquot F | 2.3 | 0.51 | 16 | 4.5 | <LOW> |
| Donor_8 3. Aliquot G | 0.060 | 0.44 | 9.0 | 5.2 | <LOW> |
| Donor_8 3. Aliquot H | 6.3 | 0.72 | 13 | 4.0 | <LOW> |
| Donor_8 3. Aliquot I | 6.1 | 0.46 | 15 | 3.6 | <LOW> |
| Donor_9 3. Aliquot A | 2.5 | 0.39 | 14 | 3.0 | <LOW> |
| Donor_9 3. Aliquot B | 3.5 | 0.39 | 11 | 3.3 | <LOW> |
| Donor_9 3. Aliquot C | 1.2 | 0.39 | 21 | 3.3 | <LOW> |
| Donor_9 3. Aliquot D | 3.7 | 0.37 | 140 | 6.0 | 3.9 |
| Donor_9 3. Aliquot E | 2.6 | 0.40 | 104 | 3.7 | 3.2 |
| Donor_9 3. Aliquot F | 1.9 | 0.39 | 12 | 2.6 | <LOW> |
| Donor_9 3. Aliquot G | 0.21 | 0.41 | 14 | 3.1 | 0.91 |
| Donor_9 3. Aliquot H | 4.3 | 0.64 | 4.9 | 3.1 | <LOW> |
| Donor_9 3. Aliquot I | 3.5 | 0.39 | 8.3 | 2.6 | <LOW> |
| EDTA Plasma | | | | | |

FIG. 12C.4

| | Brain-Derived Neurotrophic Factor | Complement 3 | Cancer Antigen 125 | Cancer Antigen 19-9 | Calcitonin |
|---|---|---|---|---|---|
| | ng/mL | mg/mL | U/mL | U/mL | pg/mL |
| Least Detectable Dose | 0.029 | 0.0053 | 4.2 | 0.25 | 6.0 |
| RBM Low Plasma Range | 0.32 | 0.76 | | | |
| RBM High Plasma Range | 16 | 2.1 | 12 | 9.2 | 12 |
| donor #1 plasma | 1.2 | 0.59 | 60 | 7.6 | 40 |
| donor #2 plasma | 0.40 | 0.98 | 63 | 241 | 51 |
| donor #3 plasma | 0.89 | 0.90 | 28 | 2.1 | 8.9 |
| donor #4 plasma | 0.35 | 0.47 | 431 | 10 | 36 |
| donor #5 plasma | 3.6 | 0.88 | 18 | 4.2 | 164 |
| donor #6 plasma | 1.5 | 0.87 | 18 | 1.6 | 3.7 |
| donor #7 plasma | 1.4 | 0.80 | 30 | 6.0 | 5.0 |
| donor #8 plasma | 3.1 | 0.42 | 16 | 7.5 | <LOW> |
| donor #9 plasma | 0.21 | 0.55 | <LOW> | 6.3 | <LOW> |

FIG. 12D.1

| | CD40 | CD40 Ligand | Carcinoembryonic Antigen | Creatine Kinase-MB | C Reactive Protein | EGF | ENA-78 |
|---|---|---|---|---|---|---|---|
| | ng/mL | ng/mL | ng/mL | ng/mL | ug/mL | pg/mL | ng/mL |
| Least Detectable Dose | 0.021 | 0.020 | 0.84 | 0.42 | 0.0015 | 7.4 | 0.076 |
| RBM Low Plasma Range | 0.17 | | | | 0.25 | | 0.069 |
| RBM High Plasma Range | 1.5 | 1.1 | 4.8 | 1.1 | 50 | 505 | 5.3 |
| Donor_1 3. Aliquot A | 11 | 0.66 | 1.5 | 0.16 | >47 | 128 | 7.9 |
| Donor_1 3. Aliquot B | 9.2 | 0.82 | 1.4 | 0.11 | >47 | 131 | 8.2 |
| Donor_1 3. Aliquot C | 10 | 0.82 | 1.4 | 0.12 | >47 | 119 | 1.7 |
| Donor_1 3. Aliquot D | 9.0 | 0.60 | 1.7 | 0.18 | >47 | 109 | 10 |
| Donor_1 3. Aliquot E | 8.7 | 0.47 | 1.6 | 0.11 | >47 | 101 | 5.9 |
| Donor_1 3. Aliquot F | 9.3 | 0.39 | 1.2 | 0.15 | >47 | 101 | 1.2 |
| Donor_1 3. Aliquot G | 12 | 0.18 | 1.5 | 0.11 | >47 | 693 | 5.3 |
| Donor_1 3. Aliquot H | 11 | 0.55 | 1.9 | 0.11 | >47 | 197 | 1.6 |
| Donor_1 3. Aliquot I | 10 | 0.84 | 1.4 | 0.12 | >47 | 114 | 1.8 |
| Donor_2 3. Aliquot A | 16 | 0.70 | 4.6 | 0.40 | >47 | 92 | 45 |
| Donor_2 3. Aliquot B | 18 | 0.65 | 4.9 | 0.44 | >47 | 145 | 45 |
| Donor_2 3. Aliquot C | 16 | 0.61 | 4.7 | 0.32 | >47 | 83 | 0.66 |
| Donor_2 3. Aliquot D | 16 | 0.47 | 6.2 | 0.60 | >47 | 61 | 51 |
| Donor_2 3. Aliquot E | 19 | 0.50 | 5.0 | 0.43 | >47 | 62 | 55 |
| Donor_2 3. Aliquot F | 16 | 0.42 | 4.0 | 0.50 | >47 | 66 | 0.74 |
| Donor_2 3. Aliquot G | 21 | 0.28 | 5.4 | 0.49 | >47 | 792 | 214 |
| Donor_2 3. Aliquot H | 18 | 0.44 | 4.8 | 0.40 | >47 | 85 | 1.4 |
| Donor_2 3. Aliquot I | 17 | 0.47 | 4.5 | 0.21 | >47 | 59 | 1.2 |
| Donor_3 3. Aliquot A | 1.4 | 0.54 | 2.8 | 0.59 | 22 | 40 | 20 |
| Donor_3 3. Aliquot B | 1.7 | 0.43 | 3.3 | 0.67 | 24 | 64 | 13 |
| Donor_3 3. Aliquot C | 1.4 | 0.50 | 3.3 | 0.54 | 25 | 38 | 0.96 |
| Donor_3 3. Aliquot D | 1.5 | 0.52 | 3.6 | 0.53 | 25 | 47 | 35 |
| Donor_3 3. Aliquot E | 1.5 | 0.68 | 4.3 | 0.61 | 24 | 60 | 31 |
| Donor_3 3. Aliquot F | 1.4 | 0.36 | 3.2 | 0.24 | 26 | 39 | 0.65 |
| Donor_3 3. Aliquot G | 3.4 | 0.29 | 2.7 | 0.29 | 26 | 535 | 1.6 |
| Donor_3 3. Aliquot H | 1.4 | 0.50 | 2.4 | 0.37 | 23 | 39 | 0.47 |
| Donor_3 3. Aliquot I | 1.3 | 0.42 | 2.4 | 0.39 | 24 | 33 | 0.55 |
| Donor_4 3. Aliquot A | 4.3 | 0.20 | 3.4 | 0.078 | >47 | 25 | 0.77 |

FIG. 12D.2

| | CD40 | CD40 Ligand | Carcinoembryonic Antigen | Creatine Kinase-MB | C Reactive Protein | EGF | ENA-78 |
|---|---|---|---|---|---|---|---|
| | ng/mL | ng/mL | ng/mL | ng/mL | ug/mL | pg/mL | ng/mL |
| Least Detectable Dose | 0.021 | 0.020 | 0.84 | 0.42 | 0.0015 | 7.4 | 0.076 |
| RBM Low Plasma Range | 0.17 | | | | 0.25 | | 0.069 |
| RBM High Plasma Range | 1.5 | 1.1 | 4.8 | 1.1 | 50 | 505 | 5.3 |
| Donor_4_3, Aliquot B | 4.7 | 0.18 | 3.8 | 0.066 | >47 | 35 | 1.4 |
| Donor_4_3, Aliquot C | 4.3 | 0.088 | 3.6 | 0.064 | >47 | 12 | 0.18 |
| Donor_4_3, Aliquot D | 4.0 | 0.13 | 4.4 | 0.17 | >47 | 21 | 23 |
| Donor_4_3, Aliquot E | 4.3 | 0.13 | 3.7 | 0.066 | >47 | 15 | 21 |
| Donor_4_3, Aliquot F | 4.0 | 0.083 | 3.3 | 0.093 | >47 | 9.8 | 0.59 |
| Donor_4_3, Aliquot G | 4.9 | 0.063 | 3.3 | 0.057 | >47 | 256 | 1.2 |
| Donor_4_3, Aliquot H | 4.0 | 0.081 | 3.4 | 0.045 | >47 | 11 | 0.14 |
| Donor_4_3, Aliquot I | 3.9 | 0.092 | 3.2 | 0.076 | >47 | 19 | 0.20 |
| Donor_5_3, Aliquot A | 18 | 0.51 | 1.7 | 0.18 | >47 | 87 | 21 |
| Donor_5_3, Aliquot B | 18 | 0.34 | 2.4 | 0.18 | >47 | 90 | 23 |
| Donor_5_3, Aliquot C | 19 | 0.32 | 1.6 | 0.11 | >47 | 71 | 0.25 |
| Donor_5_3, Aliquot D | 20 | 0.40 | 3.1 | 0.24 | >47 | 60 | 31 |
| Donor_5_3, Aliquot E | 21 | 0.47 | 2.9 | 0.28 | >47 | 70 | 33 |
| Donor_5_3, Aliquot F | 18 | 0.29 | 1.4 | 0.086 | >47 | 59 | 0.71 |
| Donor_5_3, Aliquot G | 19 | 0.24 | 1.7 | 0.12 | >47 | 647 | 7.0 |
| Donor_5_3, Aliquot H | 18 | 0.32 | 4.2 | 0.17 | >47 | 83 | 0.41 |
| Donor_5_3, Aliquot I | 17 | 0.27 | 3.6 | 0.11 | >47 | 53 | 0.22 |
| Donor_6_3, Aliquot A | 0.98 | 0.88 | 0.82 | 0.25 | >47 | 195 | 4.4 |
| Donor_6_3, Aliquot B | 1.1 | 0.77 | 0.58 | 0.24 | >47 | 213 | 6.0 |
| Donor_6_3, Aliquot C | 1.0 | 0.61 | 1.1 | 0.26 | >47 | 160 | 0.54 |
| Donor_6_3, Aliquot D | 1.0 | 0.95 | 1.3 | 0.26 | >47 | 152 | 10 |
| Donor_6_3, Aliquot E | 0.96 | 0.60 | 1.6 | 0.30 | >47 | 110 | 12 |
| Donor_6_3, Aliquot F | 0.90 | 0.47 | 0.63 | 0.19 | >47 | 132 | 0.68 |
| Donor_6_3, Aliquot G | 3.8 | 0.30 | 0.44 | 0.30 | >47 | 2020 | 4.3 |
| Donor_6_3, Aliquot H | 0.81 | 0.45 | 0.91 | 0.21 | >47 | 139 | 0.43 |
| Donor_6_3, Aliquot I | 0.73 | 0.45 | 0.96 | 0.21 | >47 | 101 | 0.51 |

FIG. 12D.3

| | CD40 | CD40 Ligand | Carcinoembryonic Antigen | Creatine Kinase-MB | C Reactive Protein | EGF | ENA-78 |
|---|---|---|---|---|---|---|---|
| | ng/mL | ng/mL | ng/mL | ng/mL | ug/mL | pg/mL | ng/mL |
| Least Detectable Dose | 0.021 | 0.020 | 0.84 | 0.42 | 0.0015 | 7.4 | 0.076 |
| | | | | | | | |
| RBM Low Plasma Range | 0.17 | | | | 0.25 | | 0.069 |
| RBM High Plasma Range | 1.5 | 1.1 | 4.8 | 1.1 | 50 | 505 | 5.3 |
| Donor_7_3. Aliquot A | 0.93 | 0.25 | 3.6 | 1.2 | 29 | 30 | 33 |
| Donor_7_3. Aliquot B | 0.89 | 0.21 | 2.8 | 1.5 | 33 | 45 | 17 |
| Donor_7_3. Aliquot C | 0.77 | 0.40 | 3.0 | 0.99 | 30 | 37 | 0.56 |
| Donor_7_3. Aliquot D | 0.73 | 0.30 | 3.9 | 1.1 | 27 | 28 | 26 |
| Donor_7_3. Aliquot E | 0.62 | 0.20 | 3.2 | 1.1 | 24 | 22 | 20 |
| Donor_7_3. Aliquot F | 0.61 | 0.11 | 2.9 | 1.2 | 27 | 11 | 0.25 |
| Donor_7_3. Aliquot G | 1.8 | 0.071 | 3.0 | 1.1 | 27 | 403 | 3.6 |
| Donor_7_3. Aliquot H | 0.71 | 0.18 | 4.1 | 1.0 | 28 | 20 | 0.23 |
| Donor_7_3. Aliquot I | 0.50 | 0.15 | 2.7 | 0.93 | 29 | 15 | 0.19 |
| | | | | | | | |
| Donor_8_3. Aliquot A | 0.57 | 0.32 | 1.1 | 0.15 | 0.096 | 93 | 1.1 |
| Donor_8_3. Aliquot B | 0.60 | 0.42 | 0.82 | 0.19 | 0.14 | 110 | 1.3 |
| Donor_8_3. Aliquot C | 0.63 | 0.51 | 0.75 | 0.15 | 0.13 | 114 | 0.81 |
| Donor_8_3. Aliquot D | 0.72 | 0.33 | 3.5 | 0.36 | 0.14 | 105 | 1.4 |
| Donor_8_3. Aliquot E | 0.63 | 0.49 | 3.9 | 0.39 | 0.12 | 132 | 2.4 |
| Donor_8_3. Aliquot F | 0.49 | 0.15 | 1.4 | 0.24 | 0.16 | 63 | 0.37 |
| Donor_8_3. Aliquot G | 1.8 | 0.13 | 0.94 | 0.20 | 0.13 | 1050 | 4.5 |
| Donor_8_3. Aliquot H | 0.60 | 0.49 | 1.9 | 0.24 | 0.15 | 143 | 0.81 |
| Donor_8_3. Aliquot I | 0.65 | 0.45 | 1.6 | 0.14 | 0.13 | 125 | 0.87 |
| | | | | | | | |
| Donor_9_3. Aliquot A | 0.69 | 0.37 | 1.2 | 0.079 | Pending | 117 | 2.1 |
| Donor_9_3. Aliquot B | 0.69 | 0.43 | 1.5 | 0.19 | Pending | 156 | 2.2 |
| Donor_9_3. Aliquot C | 0.69 | 0.51 | 1.0 | 0.18 | Pending | 123 | 2.1 |
| Donor_9_3. Aliquot D | 0.81 | 0.46 | 5.3 | 0.40 | Pending | 131 | 2.4 |
| Donor_9_3. Aliquot E | 0.72 | 0.31 | 3.3 | 0.26 | Pending | 95 | 6.5 |
| Donor_9_3. Aliquot F | 0.61 | 0.19 | 1.7 | 0.16 | Pending | 78 | 0.65 |
| Donor_9_3. Aliquot G | 2.7 | 0.21 | 1.1 | 0.12 | Pending | 1300 | 16 |
| Donor_9_3. Aliquot H | 0.64 | 0.50 | 1.5 | 0.13 | Pending | 140 | 1.3 |
| Donor_9_3. Aliquot I | 0.66 | 0.45 | 0.89 | 0.083 | Pending | 134 | 1.5 |
| EDTA Plasma | | | | | | | |

FIG. 12D.4

| | CD40 | CD40 Ligand | Carcinoembryonic Antigen | Creatine Kinase-MB | C Reactive Protein | EGF | ENA-78 |
|---|---|---|---|---|---|---|---|
| | ng/mL | ng/mL | ng/mL | ng/mL | ug/mL | pg/mL | ng/mL |
| Least Detectable Dose | 0.021 | 0.020 | 0.84 | 0.42 | 0.0015 | 7.4 | 0.076 |
| | | | | | | | |
| RBM Low Plasma Range | 0.17 | | | | 0.25 | | 0.069 |
| RBM High Plasma Range | 1.5 | 1.1 | 4.8 | 1.1 | 50 | 505 | 5.3 |
| donor #1 plasma | 7.4 | 0.14 | 1.7 | 0.25 | Pending | 30 | 0.93 |
| donor #2 plasma | 18 | 0.21 | 3.9 | 0.99 | Pending | <LOW> | <LOW> |
| donor #3 plasma | 1.7 | 0.084 | 2.6 | 0.47 | Pending | <LOW> | <LOW> |
| donor #4 plasma | 5.2 | 0.10 | 4.9 | 0.24 | Pending | <LOW> | <LOW> |
| donor #5 plasma | 16 | 0.27 | 1.7 | 0.18 | Pending | 12 | 0.32 |
| donor #6 plasma | 0.46 | 0.021 | 1.1 | 0.39 | Pending | <LOW> | 0.26 |
| donor #7 plasma | 1.6 | 0.089 | 3.6 | 3.3 | Pending | <LOW> | 0.54 |
| donor #8 plasma | 0.58 | 0.16 | 1.4 | 0.56 | Pending | 22 | 0.48 |
| donor #9 plasma | 0.47 | 0.053 | 0.71 | 0.27 | Pending | <LOW> | 0.088 |

FIG. 12E.1

| | Endothelin-1 | EN-RAGE | Eotaxin | Epiregulin | Erythropoietin | Fatty Acid Binding Protein | Factor VII |
|---|---|---|---|---|---|---|---|
| | pg/mL | ng/mL | pg/mL | pg/mL | pg/mL | ng/mL | ng/mL |
| Least Detectable Dose | 7.2 | 0.25 | 41 | 36 | 166 | 3.0 | 1.0 |
| RBM Low Plasma Range | | 4.6 | | Pending | | | 106 |
| RBM High Plasma Range | 26 | 592 | 177 | Pending | 284 | 10 | 443 |
| Donor_1 3. Aliquot A | 8.1 | 82 | 179 | 161 | <LOW> | 32 | 157 |
| Donor_1 3. Aliquot B | <LOW> | 72 | 164 | 65 | <LOW> | 29 | 140 |
| Donor_1 3. Aliquot C | <LOW> | 74 | 130 | 33 | 37 | 34 | 89 |
| Donor_1 3. Aliquot D | <LOW> | 66 | 180 | 16 | <LOW> | 33 | 168 |
| Donor_1 3. Aliquot E | <LOW> | 75 | 170 | 40 | <LOW> | 33 | 171 |
| Donor_1 3. Aliquot F | <LOW> | 60 | 184 | 61 | <LOW> | 31 | 132 |
| Donor_1 3. Aliquot G | 22 | 54 | 10 | 149 | <LOW> | 41 | 174 |
| Donor_1 3. Aliquot H | 11 | 99 | 177 | <LOW> | 60 | 31 | 160 |
| Donor_1 3. Aliquot I | <LOW> | 76 | 172 | 31 | <LOW> | 29 | 139 |
| Donor_2 3. Aliquot A | 11 | 247 | 61 | 44 | <LOW> | 36 | 541 |
| Donor_2 3. Aliquot B | <LOW> | 230 | 48 | 26 | <LOW> | 40 | 577 |
| Donor_2 3. Aliquot C | <LOW> | 252 | 46 | 16 | <LOW> | 40 | 154 |
| Donor_2 3. Aliquot D | 15 | 212 | 48 | 52 | <LOW> | 45 | 694 |
| Donor_2 3. Aliquot E | 20 | 228 | 44 | 21 | <LOW> | 45 | 640 |
| Donor_2 3. Aliquot F | <LOW> | 258 | 27 | <LOW> | <LOW> | 40 | 580 |
| Donor_2 3. Aliquot G | 24 | 218 | 5.0 | 236 | <LOW> | 48 | 588 |
| Donor_2 3. Aliquot H | <LOW> | >269 | 36 | 26 | <LOW> | 39 | 567 |
| Donor_2 3. Aliquot I | <LOW> | 250 | 44 | <LOW> | <LOW> | 34 | 450 |
| Donor_3 3. Aliquot A | <LOW> | 142 | 66 | 40 | <LOW> | 14 | 147 |
| Donor_3 3. Aliquot B | <LOW> | 142 | 50 | 35 | <LOW> | 12 | 139 |
| Donor_3 3. Aliquot C | <LOW> | 135 | 44 | 24 | <LOW> | 12 | 31 |
| Donor_3 3. Aliquot D | <LOW> | 151 | 54 | 31 | <LOW> | 17 | 156 |
| Donor_3 3. Aliquot E | 11 | 159 | 52 | <LOW> | <LOW> | 16 | 160 |
| Donor_3 3. Aliquot F | <LOW> | 128 | 80 | <LOW> | <LOW> | 13 | 128 |
| Donor_3 3. Aliquot G | <LOW> | 122 | 5.0 | <LOW> | <LOW> | 15 | 116 |
| Donor_3 3. Aliquot H | <LOW> | 211 | 29 | 21 | <LOW> | 9.2 | 108 |
| Donor_3 3. Aliquot I | <LOW> | 169 | 36 | 13 | <LOW> | 11 | 123 |
| Donor_4 3. Aliquot A | <LOW> | >269 | 141 | 21 | <LOW> | 33 | 124 |

FIG. 12E.2

| | Endothelin-1 | EN-RAGE | Eotaxin | Epiregulin | Erythropoietin | Fatty Acid Binding Protein | Factor VII |
|---|---|---|---|---|---|---|---|
| | pg/mL | ng/mL | pg/mL | pg/mL | pg/mL | ng/mL | ng/mL |
| Least Detectable Dose | 7.2 | 0.25 | 41 | 36 | 166 | 3.0 | 1.0 |
| RBM Low Plasma Range | | 4.6 | 177 | Pending | | | 106 |
| RBM High Plasma Range | 26 | 592 | 177 | Pending | 284 | 10 | 443 |
| Donor_4_3. Aliquot B | <LOW> | 239 | 133 | 35 | <LOW> | 33 | 129 |
| Donor_4_3. Aliquot C | <LOW> | 175 | 122 | <LOW> | <LOW> | 30 | 9.2 |
| Donor_4_3. Aliquot D | 11 | 84 | 133 | <LOW> | <LOW> | 33 | 142 |
| Donor_4_3. Aliquot E | 22 | 66 | 120 | 29 | <LOW> | 33 | 115 |
| Donor_4_3. Aliquot F | <LOW> | 94 | 130 | <LOW> | <LOW> | 32 | 105 |
| Donor_4_3. Aliquot G | <LOW> | 127 | 10 | 69 | <LOW> | 34 | 75 |
| Donor_4_3. Aliquot H | <LOW> | >269 | 124 | <LOW> | <LOW> | 37 | 111 |
| Donor_4_3. Aliquot I | <LOW> | 185 | 139 | 31 | <LOW> | 34 | 125 |
| Donor_5_3. Aliquot A | 20 | 95 | 27 | 129 | <LOW> | 9.2 | >1113 |
| Donor_5_3. Aliquot B | 11 | 88 | 34 | 101 | 41 | 7.8 | 1020 |
| Donor_5_3. Aliquot C | <LOW> | 108 | 32 | 149 | <LOW> | 9.2 | 243 |
| Donor_5_3. Aliquot D | 11 | 52 | 32 | 105 | 100 | 13 | 940 |
| Donor_5_3. Aliquot E | 15 | 41 | 30 | 111 | 64 | 14 | 1100 |
| Donor_5_3. Aliquot F | <LOW> | 73 | 27 | 87 | <LOW> | 6.5 | 808 |
| Donor_5_3. Aliquot G | 15 | 91 | 7.6 | 161 | 50 | 10 | 936 |
| Donor_5_3. Aliquot H | <LOW> | 236 | 25 | 117 | 50 | 8.8 | 1000 |
| Donor_5_3. Aliquot I | <LOW> | 100 | 22 | 95 | <LOW> | 8.8 | 1050 |
| Donor_6_3. Aliquot A | <LOW> | 236 | 22 | 26 | <LOW> | 2.3 | 320 |
| Donor_6_3. Aliquot B | <LOW> | 229 | 25 | 31 | <LOW> | 2.6 | 329 |
| Donor_6_3. Aliquot C | <LOW> | 265 | 36 | <LOW> | <LOW> | 2.6 | 62 |
| Donor_6_3. Aliquot D | <LOW> | 109 | 25 | <LOW> | <LOW> | 5.4 | 345 |
| Donor_6_3. Aliquot E | 11 | 106 | 20 | 16 | <LOW> | 5.6 | 285 |
| Donor_6_3. Aliquot F | <LOW> | 153 | 34 | 177 | <LOW> | 2.2 | 311 |
| Donor_6_3. Aliquot G | <LOW> | 147 | 15 | <LOW> | <LOW> | 2.6 | 252 |
| Donor_6_3. Aliquot H | <LOW> | >269 | 18 | <LOW> | <LOW> | 2.0 | 336 |
| Donor_6_3. Aliquot I | <LOW> | 237 | 22 | <LOW> | <LOW> | 1.7 | 309 |

FIG. 12E.3

| | Endothelin-1 | EN-RAGE | Eotaxin | Epiregulin | Erythropoietin | Fatty Acid Binding Protein | Factor VII |
|---|---|---|---|---|---|---|---|
| | pg/mL | ng/mL | pg/mL | pg/mL | pg/mL | ng/mL | ng/mL |
| Least Detectable Dose | 7.2 | 0.25 | 41 | 36 | 166 | 3.0 | 1.0 |
| RBM Low Plasma Range | | 4.6 | | Pending | | | 106 |
| RBM High Plasma Range | 26 | 592 | 177 | Pending | 284 | 10 | 443 |
| Donor_7_3. Aliquot A | <LOW> | 150 | 138 | <LOW> | <LOW> | 463 | 144 |
| Donor_7_3. Aliquot B | <LOW> | 161 | 119 | <LOW> | <LOW> | 459 | 149 |
| Donor_7_3. Aliquot C | <LOW> | >269 | 105 | <LOW> | <LOW> | 466 | 34 |
| Donor_7_3. Aliquot D | <LOW> | 128 | 106 | <LOW> | <LOW> | 422 | 128 |
| Donor_7_3. Aliquot E | <LOW> | 122 | 117 | <LOW> | <LOW> | 434 | 143 |
| Donor_7_3. Aliquot F | <LOW> | 227 | 121 | <LOW> | <LOW> | 426 | 143 |
| Donor_7_3. Aliquot G | <LOW> | 182 | 18 | <LOW> | <LOW> | 511 | 139 |
| Donor_7_3. Aliquot H | <LOW> | >269 | 125 | <LOW> | <LOW> | 440 | 136 |
| Donor_7_3. Aliquot I | <LOW> | >269 | 111 | <LOW> | <LOW> | 451 | 141 |
| Donor_8_3. Aliquot A | 8.1 | 48 | 162 | <LOW> | <LOW> | <LOW> | 376 |
| Donor_8_3. Aliquot B | <LOW> | 46 | 153 | 35 | <LOW> | <LOW> | 411 |
| Donor_8_3. Aliquot C | <LOW> | 41 | 117 | 44 | <LOW> | <LOW> | 18 |
| Donor_8_3. Aliquot D | <LOW> | 64 | 165 | 42 | <LOW> | 8.3 | 410 |
| Donor_8_3. Aliquot E | <LOW> | 45 | 157 | 35 | <LOW> | 7.8 | 351 |
| Donor_8_3. Aliquot F | 15 | 47 | 208 | 58 | <LOW> | 0.81 | 426 |
| Donor_8_3. Aliquot G | <LOW> | 57 | 5.0 | 56 | <LOW> | <LOW> | 253 |
| Donor_8_3. Aliquot H | 11 | 143 | 142 | 16 | <LOW> | 0.56 | 382 |
| Donor_8_3. Aliquot I | <LOW> | 122 | 157 | <LOW> | <LOW> | 0.14 | 381 |
| Donor_9_3. Aliquot A | <LOW> | 47 | 254 | 86 | <LOW> | <LOW> | 196 |
| Donor_9_3. Aliquot B | 13 | 33 | 223 | 75 | <LOW> | 1.6 | 196 |
| Donor_9_3. Aliquot C | 9.8 | 48 | 184 | 106 | <LOW> | 0.42 | 44 |
| Donor_9_3. Aliquot D | 18 | 46 | 239 | 101 | <LOW> | 10 | 243 |
| Donor_9_3. Aliquot E | 19 | 67 | 209 | 79 | <LOW> | 6.6 | 201 |
| Donor_9_3. Aliquot F | 13 | 22 | 231 | 77 | <LOW> | 0.68 | 196 |
| Donor_9_3. Aliquot G | <LOW> | 96 | <LOW> | 123 | <LOW> | 0.81 | 147 |
| Donor_9_3. Aliquot H | 5.1 | 115 | 201 | 97 | <LOW> | <LOW> | 229 |
| Donor_9_3. Aliquot I | <LOW> | 50 | 232 | 83 | <LOW> | <LOW> | 184 |
| EDTA Plasma | | | | | | | |

FIG. 12E.4

|  | Endothelin-1 | EN-RAGE | Eotaxin | Epiregulin | Erythropoietin | Fatty Acid Binding Protein | Factor VII |
|---|---|---|---|---|---|---|---|
|  | pg/mL | ng/mL | pg/mL | pg/mL | pg/mL | ng/mL | ng/mL |
| Least Detectable Dose | 7.2 | 0.25 | 41 | 36 | 166 | 3.0 | 1.0 |
| RBM Low Plasma Range |  |  |  | Pending |  |  |  |
| RBM High Plasma Range | 26 | 4.6 | 177 | Pending | 284 |  | 106 |
| donor #1 plasma | 7.7 | 592 | 97 | 83 | 84 | 10 | 443 |
| donor #2 plasma | <LOW> | 65 | 42 | <LOW> | <LOW> | 32 | 141 |
| donor #3 plasma | 17 | >269 | 36 | 32 | <LOW> | 65 | 545 |
| donor #4 plasma | <LOW> | 49 | 87 | <LOW> | <LOW> | 25 | 135 |
| donor #5 plasma | 22 | 19 | 64 | 35 | 118 | 59 | 121 |
| donor #6 plasma | <LOW> | 145 | 14 | <LOW> | 37 | 13 | 891 |
| donor #7 plasma | <LOW> | 40 | 86 | <LOW> | <LOW> | 5.0 | 315 |
| donor #8 plasma | 9.8 | 71 | 294 | 35 | <LOW> | >617 | 187 |
| donor #9 plasma | <LOW> | 9.4 | 330 | 65 | <LOW> | <LOW> | 428 |
|  |  | 4.3 |  |  |  | 0.55 | 299 |

FIG. 12F.1

| | Ferritin | FGF basic | Fibrinogen | G-CSF | Growth Hormone | GM-CSF | Glutathione S-Transferase |
|---|---|---|---|---|---|---|---|
| | ng/mL | pg/mL | mg/mL | pg/mL | ng/mL | pg/mL | ng/mL |
| Least Detectable Dose | 1.4 | 98 | 0.0098 | 5.0 | 0.13 | 57 | 0.40 |
| RBM Low Plasma Range | | | | | | | |
| RBM High Plasma Range | 5.0 | 2000 | 2.2 | 37 | 4.4 | 152 | 3.1 |
| Donor_1 3. Aliquot A | 552 | 1850 | 8.0 | 417 | 1.8 | 8.4 | 0.64 |
| Donor_1 3. Aliquot B | 1290 | 1710 | 4.1 | 279 | 1.7 | 2.5 | 0.84 |
| Donor_1 3. Aliquot C | 1380 | 414 | 4.4 | 221 | 1.9 | 5.0 | 0.55 |
| Donor_1 3. Aliquot D | 1300 | 2050 | 4.2 | 355 | 2.1 | 4.5 | 0.69 |
| Donor_1 3. Aliquot E | 1400 | 1840 | 4.8 | 270 | 2.0 | 10 | 0.59 |
| Donor_1 3. Aliquot F | 1140 | 1400 | 4.1 | 197 | 1.5 | 2.5 | 0.50 |
| Donor_1 3. Aliquot G | 1280 | 1760 | 3.7 | 236 | 1.8 | <LOW> | 0.52 |
| Donor_1 3. Aliquot H | 1420 | 159 | 4.6 | 211 | 1.8 | 4.5 | 0.52 |
| Donor_1 3. Aliquot I | 1280 | 1470 | 4.0 | 219 | 1.8 | 4.0 | 0.55 |
| | 1160 | | 4.4 | | | | |
| Donor_2 3. Aliquot A | 1490 | 429 | 4.3 | 344 | 0.77 | 12 | <LOW> |
| Donor_2 3. Aliquot B | 1510 | 321 | 4.4 | 204 | 0.90 | 5.0 | 0.76 |
| Donor_2 3. Aliquot C | 1430 | 241 | 5.1 | 31 | 0.82 | <LOW> | 0.55 |
| Donor_2 3. Aliquot D | 1390 | 563 | 4.3 | 1470 | 1.2 | 24 | 1.7 |
| Donor_2 3. Aliquot E | 1390 | 563 | 4.0 | 1240 | 0.91 | 4.5 | 0.81 |
| Donor_2 3. Aliquot F | 1400 | 241 | 4.1 | 32 | 0.70 | 3.5 | 0.41 |
| Donor_2 3. Aliquot G | 1470 | 664 | 5.3 | 2160 | 0.87 | 180 | 0.69 |
| Donor_2 3. Aliquot H | 1330 | 176 | 3.9 | 36 | 0.78 | 3.5 | <LOW> |
| Donor_2 3. Aliquot I | 1320 | 225 | 5.2 | 32 | 0.71 | <LOW> | <LOW> |
| Donor_3 3. Aliquot A | 855 | <LOW> | 5.9 | 105 | 1.5 | 10 | 0.46 |
| Donor_3 3. Aliquot B | 757 | 29 | 5.5 | 41 | 1.4 | 7.8 | 1.4 |
| Donor_3 3. Aliquot C | 828 | 29 | 4.9 | <LOW> | 1.5 | 2.5 | 0.48 |
| Donor_3 3. Aliquot D | 799 | 209 | 5.2 | 1340 | 1.5 | 6.7 | 1.4 |
| Donor_3 3. Aliquot E | 797 | 159 | 6.0 | 1200 | 1.6 | 23 | 0.94 |
| Donor_3 3. Aliquot F | 824 | 29 | 5.2 | <LOW> | 1.3 | 18 | <LOW> |
| Donor_3 3. Aliquot G | 865 | 52 | 6.6 | 7.3 | 1.7 | <LOW> | <LOW> |
| Donor_3 3. Aliquot H | 758 | <LOW> | 5.3 | <LOW> | 1.3 | <LOW> | <LOW> |
| Donor_3 3. Aliquot I | 800 | 29 | 6.2 | <LOW> | 1.6 | <LOW> | <LOW> |
| Donor_4 3. Aliquot A | 328 | <LOW> | 2.0 | 5.6 | 4.1 | 3.5 | <LOW> |

FIG. 12F.2

| | Ferritin | FGF basic | Fibrinogen | G-CSF | Growth Hormone | GM-CSF | Glutathione S-Transferase |
|---|---|---|---|---|---|---|---|
| | ng/mL | pg/mL | mg/mL | pg/mL | ng/mL | pg/mL | ng/mL |
| Least Detectable Dose | 1.4 | 98 | 0.0098 | 5.0 | 0.13 | 57 | 0.40 |
| RBM Low Plasma Range | 5.0 | | | | | | |
| RBM High Plasma Range | 552 | 2000 | 2.2 | | | | |
| Donor_4_3. Aliquot B | 311 | 52 | 8.0 | 37 | 4.4 | 152 | 3.1 |
| Donor_4_3. Aliquot C | 286 | 29 | 2.0 | 9.6 | 4.2 | <LOW> | 0.99 |
| Donor_4_3. Aliquot D | 308 | 459 | 2.2 | <LOW> | 4.0 | <LOW> | <LOW> |
| Donor_4_3. Aliquot E | 319 | 474 | 2.0 | 976 | 4.2 | 18 | 1.2 |
| Donor_4_3. Aliquot F | 347 | 99 | 1.3 | 779 | 3.7 | 22 | 0.59 |
| Donor_4_3. Aliquot G | 338 | 90 | 1.8 | 18 | 3.3 | 5.0 | <LOW> |
| Donor_4_3. Aliquot H | 315 | <LOW> | 2.2 | 8.8 | 3.6 | <LOW> | 0.37 |
| Donor_4_3. Aliquot I | 352 | 52 | 1.7 | <LOW> | 4.1 | <LOW> | 0.39 |
| Donor_4_3. Aliquot I | 352 | 52 | 2.0 | <LOW> | 4.2 | 2.5 | <LOW> |
| Donor_5_3. Aliquot A | 1430 | 489 | 5.4 | 130 | 4.2 | 5.6 | 0.89 |
| Donor_5_3. Aliquot B | 1320 | 533 | 5.9 | 203 | 3.9 | <LOW> | 0.64 |
| Donor_5_3. Aliquot C | 1570 | 241 | 6.9 | 22 | 4.0 | <LOW> | 0.64 |
| Donor_5_3. Aliquot D | 1630 | 563 | 3.4 | 1480 | 3.7 | 23 | 1.3 |
| Donor_5_3. Aliquot E | 1510 | 533 | 5.2 | 3960 | 4.1 | 32 | 1.1 |
| Donor_5_3. Aliquot F | 1390 | 257 | 4.4 | 29 | 3.0 | <LOW> | <LOW> |
| Donor_5_3. Aliquot G | 1460 | 273 | 7.2 | 31 | 4.7 | 3.5 | <LOW> |
| Donor_5_3. Aliquot H | 1390 | 176 | 5.5 | 23 | 4.0 | 6.7 | <LOW> |
| Donor_5_3. Aliquot I | 1400 | 159 | 6.6 | 21 | 3.8 | <LOW> | 0.50 |
| Donor_6_3. Aliquot A | 382 | 72 | 4.1 | 12 | 3.0 | 7.8 | <LOW> |
| Donor_6_3. Aliquot B | 374 | <LOW> | 4.3 | 19 | 3.1 | 20 | 1.3 |
| Donor_6_3. Aliquot C | 370 | <LOW> | 4.9 | <LOW> | 2.8 | 3.0 | <LOW> |
| Donor_6_3. Aliquot D | 370 | 289 | 3.9 | 389 | 3.1 | 4.0 | 0.66 |
| Donor_6_3. Aliquot E | 364 | 289 | 3.2 | 975 | 2.9 | 7.8 | 1.4 |
| Donor_6_3. Aliquot F | 376 | <LOW> | 3.2 | <LOW> | 2.8 | 9.0 | <LOW> |
| Donor_6_3. Aliquot G | 391 | 192 | 5.5 | 20 | 3.2 | 6.7 | <LOW> |
| Donor_6_3. Aliquot H | 353 | <LOW> | 3.9 | <LOW> | 3.1 | 7.2 | <LOW> |
| Donor_6_3. Aliquot I | 375 | <LOW> | 3.4 | <LOW> | 3.0 | <LOW> | 0.37 |

FIG. 12F.3

| | Ferritin | FGF basic | Fibrinogen | G-CSF | Growth Hormone | GM-CSF | Glutathione S-Transferase |
|---|---|---|---|---|---|---|---|
| | ng/mL | pg/mL | mg/mL | pg/mL | ng/mL | pg/mL | ng/mL |
| Least Detectable Dose | 1.4 | 98 | 0.0098 | 5.0 | 0.13 | 57 | 0.40 |
| RBM Low Plasma Range | 5.0 | | 2.2 | | | | |
| RBM High Plasma Range | 5.0 | 2000 | 8.0 | 37 | 4.4 | 152 | 3.1 |
| Donor_7_3. Aliquot A | 552 | 2000 | 8.0 | 37 | 4.4 | 152 | 3.1 |
| Donor_7_3. Aliquot B | 468 | 391 | 3.0 | 334 | 0.32 | 20 | 0.39 |
| Donor_7_3. Aliquot C | 491 | 249 | 2.9 | 86 | 0.39 | 10 | 1.2 |
| Donor_7_3. Aliquot D | 535 | <LOW> | 3.2 | <LOW> | 0.22 | 5.6 | 0.48 |
| Donor_7_3. Aliquot E | 451 | 281 | 2.6 | 892 | 0.39 | 18 | 0.86 |
| Donor_7_3. Aliquot F | 490 | 265 | 2.1 | 270 | 0.31 | 18 | 0.50 |
| Donor_7_3. Aliquot G | 505 | <LOW> | 2.6 | <LOW> | 0.26 | 10 | <LOW> |
| Donor_7_3. Aliquot H | 471 | 233 | 2.9 | <LOW> | 0.23 | 3.0 | <LOW> |
| Donor_7_3. Aliquot I | 404 | 72 | 2.4 | <LOW> | 0.25 | 9.0 | <LOW> |
| Donor_7_3. Aliquot J | 409 | <LOW> | 3.0 | <LOW> | 0.29 | 9.0 | <LOW> |
| Donor_8_3. Aliquot A | 34 | <LOW> | 1.8 | 5.8 | 0.35 | 5.0 | 0.37 |
| Donor_8_3. Aliquot B | 32 | <LOW> | 1.7 | 4.7 | 0.35 | 6.7 | 1.8 |
| Donor_8_3. Aliquot C | 37 | 90 | 1.8 | <LOW> | 0.20 | 12 | <LOW> |
| Donor_8_3. Aliquot D | 48 | 414 | 1.7 | 1330 | 0.94 | 60 | 3.4 |
| Donor_8_3. Aliquot E | 39 | 336 | 1.7 | 1010 | 0.90 | 33 | 2.1 |
| Donor_8_3. Aliquot F | 32 | 273 | 1.7 | 4.7 | 0.36 | 18 | <LOW> |
| Donor_8_3. Aliquot G | 42 | <LOW> | 2.0 | <LOW> | 0.33 | 3.5 | <LOW> |
| Donor_8_3. Aliquot H | 38 | 142 | 1.7 | <LOW> | 0.30 | 17 | <LOW> |
| Donor_8_3. Aliquot I | 36 | <LOW> | 1.9 | <LOW> | 0.28 | 14 | 0.55 |
| Donor_9_3. Aliquot A | 4.8 | <LOW> | 1.5 | 17 | 7.2 | 11 | 0.73 |
| Donor_9_3. Aliquot B | 2.6 | 122 | 1.6 | 21 | 6.8 | 13 | 2.2 |
| Donor_9_3. Aliquot C | 5.7 | 94 | 1.4 | 19 | 6.6 | 21 | 0.40 |
| Donor_9_3. Aliquot D | 11 | 414 | 1.5 | 2320 | 6.8 | 29 | 2.6 |
| Donor_9_3. Aliquot E | 6.0 | 332 | 1.5 | 1490 | 6.8 | 13 | 2.4 |
| Donor_9_3. Aliquot F | 3.6 | 137 | 1.2 | 11 | 6.4 | 5.8 | 0.76 |
| Donor_9_3. Aliquot G | 12 | 179 | 1.9 | 39 | 6.2 | 17 | 0.56 |
| Donor_9_3. Aliquot H | 5.5 | 37 | 1.3 | 5.4 | 6.8 | 15 | 0.53 |
| Donor_9_3. Aliquot I | 3.3 | 37 | 1.6 | 5.4 | 6.4 | 8.7 | 0.37 |
| EDTA Plasma | | | | | | | |

FIG. 12F.4

| | Ferritin | FGF basic | Fibrinogen | G-CSF | Growth Hormone | GM-CSF | Glutathione S-Transferase |
|---|---|---|---|---|---|---|---|
| | ng/mL | pg/mL | mg/mL | pg/mL | ng/mL | pg/mL | ng/mL |
| Least Detectable Dose | 1.4 | 98 | 0.0098 | 5.0 | 0.13 | 57 | 0.40 |
| RBM Low Plasma Range | 5.0 | | 2.2 | | | | |
| RBM High Plasma Range | | | | | | | |
| donor #1 plasma | 552 | 2000 | 8.0 | 37 | 4.4 | 152 | 3.1 |
| donor #2 plasma | 1190 | 736 | 4.6 | 240 | 1.4 | 18 | 1.1 |
| donor #3 plasma | 1670 | 339 | 8.1 | 45 | 0.89 | 15 | <LOW> |
| donor #4 plasma | 934 | 94 | 8.7 | <LOW> | 1.5 | 27 | 1.0 |
| donor #5 plasma | 320 | 51 | 3.2 | 4.5 | 5.3 | 10.0 | <LOW> |
| donor #6 plasma | 1190 | 346 | 11 | 24 | 5.1 | 23 | 1.3 |
| donor #7 plasma | 382 | 21 | 6.7 | 6.2 | 4.1 | 20 | 0.69 |
| donor #8 plasma | 545 | <LOW> | 4.5 | 6.2 | 0.49 | 17 | <LOW> |
| donor #9 plasma | 22 | 87 | 2.0 | <LOW> | 0.38 | 15 | 0.46 |
| | 3.3 | 87 | 2.3 | 18 | 7.2 | 5.3 | 0.90 |

FIG. 12G.1

| | Haptoglobin | ICAM-1 | IFN-gamma | IgA | IgE | IGF-1 | IgM | IL-10 | IL-12p40 | IL-12p70 |
|---|---|---|---|---|---|---|---|---|---|---|
| | mg/mL | ng/mL | pg/mL | mg/mL | ng/mL | ng/mL | mg/mL | pg/mL | ng/mL | pg/mL |
| Least Detectable Dose | 0.025 | 3.2 | 4.6 | 0.0084 | 14 | 4.0 | 0.015 | 15 | 1.2 | 94 |
| RBM Low Plasma Range | 0.047 | 42 | Pending | 0.58 | | 177 | 0.24 | 1.8 | | |
| RBM High Plasma Range | 7.6 | 213 | Pending | 5.6 | 770 | 177 | 3.3 | 38 | 2.7 | 165 |
| Donor_1_3. Aliquot A | 1.0 | 467 | 3.8 | 2.0 | 13 | 49 | 0.63 | 180 | 0.30 | 45 |
| Donor_1_3. Aliquot B | 1.2 | 432 | 4.5 | 2.3 | 11 | 49 | 0.66 | 135 | 0.16 | 35 |
| Donor_1_3. Aliquot C | 1.1 | 452 | 2.7 | 2.2 | 1.8 | 67 | 0.68 | 15 | <LOW> | 28 |
| Donor_1_3. Aliquot D | 1.2 | 465 | <LOW> | 2.4 | 12 | 46 | 0.71 | 134 | 0.43 | 42 |
| Donor_1_3. Aliquot E | 1.1 | 438 | <LOW> | 2.1 | 13 | 45 | 0.63 | 58 | 0.13 | 37 |
| Donor_1_3. Aliquot F | 1.2 | 441 | <LOW> | 2.1 | 4.4 | 55 | 0.60 | 18 | <LOW> | 28 |
| Donor_1_3. Aliquot G | 1.2 | 471 | 4.5 | 2.3 | 11 | 100 | 0.70 | 15 | 0.19 | 39 |
| Donor_1_3. Aliquot H | 1.1 | 491 | <LOW> | 2.1 | 9.6 | 46 | 0.60 | 14 | <LOW> | 52 |
| Donor_1_3. Aliquot I | 1.1 | 438 | <LOW> | 2.3 | 6.2 | 46 | 0.65 | 16 | <LOW> | 32 |
| Donor_2_3. Aliquot A | 1.3 | 491 | 7.2 | 2.5 | 210 | 94 | 0.15 | 500 | 0.51 | 61 |
| Donor_2_3. Aliquot B | 1.8 | 495 | 6.7 | 2.5 | 217 | 90 | 0.15 | 483 | 0.26 | 35 |
| Donor_2_3. Aliquot C | 1.9 | 499 | <LOW> | 2.5 | 98 | 87 | 0.21 | 19 | <LOW> | 18 |
| Donor_2_3. Aliquot D | 1.5 | 489 | 31 | 2.4 | 258 | 81 | 0.14 | 977 | 2.8 | 40 |
| Donor_2_3. Aliquot E | 2.2 | 479 | 9.5 | 2.5 | 221 | 86 | 0.18 | 963 | 2.4 | 37 |
| Donor_2_3. Aliquot F | 2.1 | 504 | <LOW> | 2.5 | 177 | 73 | 0.17 | 28 | 0.26 | 45 |
| Donor_2_3. Aliquot G | 2.3 | 514 | 14 | 2.5 | 151 | 221 | 0.18 | 131 | 0.88 | 45 |
| Donor_2_3. Aliquot H | 1.9 | 490 | 2.7 | 2.6 | 175 | 75 | 0.18 | 22 | <LOW> | 35 |
| Donor_2_3. Aliquot I | 1.7 | 479 | 3.8 | 2.5 | 195 | 73 | 0.19 | 21 | <LOW> | 35 |
| Donor_3_3. Aliquot A | 0.014 | 283 | 8.5 | 1.5 | 26 | 380 | 0.66 | 480 | 0.43 | 50 |
| Donor_3_3. Aliquot B | 0.018 | 239 | <LOW> | 1.6 | 27 | 368 | 0.67 | 632 | 0.37 | 48 |
| Donor_3_3. Aliquot C | 0.019 | 278 | <LOW> | 1.6 | 7.6 | 408 | 0.66 | 26 | 0.13 | 55 |
| Donor_3_3. Aliquot D | 0.013 | 231 | 8.2 | 1.6 | 45 | 387 | 0.67 | 1640 | 3.3 | 45 |
| Donor_3_3. Aliquot E | 0.014 | 306 | 9.2 | 1.7 | 40 | 393 | 0.74 | 1660 | 2.7 | 55 |
| Donor_3_3. Aliquot F | 0.021 | 249 | <LOW> | 1.5 | 26 | 338 | 0.69 | 18 | <LOW> | 40 |
| Donor_3_3. Aliquot G | 0.087 | 259 | <LOW> | 1.6 | 14 | 546 | 0.72 | 11 | <LOW> | 35 |
| Donor_3_3. Aliquot H | 0.022 | 208 | <LOW> | 1.5 | 21 | 386 | 0.67 | 4.9 | <LOW> | 22 |
| Donor_3_3. Aliquot I | 0.051 | 221 | <LOW> | 1.5 | 29 | 403 | 0.69 | 11 | <LOW> | 42 |
| Donor_4_3. Aliquot A | 0.0075 | 456 | <LOW> | 2.5 | 12 | <LOW> | 0.39 | 46 | <LOW> | <LOW> |

FIG. 12G.2

| | Haptoglobin | ICAM-1 | IFN-gamma | IgA | IgE | IGF-1 | IgM | IL-10 | IL-12p40 | IL-12p70 |
|---|---|---|---|---|---|---|---|---|---|---|
| | mg/mL | ng/mL | pg/mL | mg/mL | ng/mL | ng/mL | mg/mL | pg/mL | ng/mL | pg/mL |
| Least Detectable Dose | 0.025 | 3.2 | 4.6 | 0.0084 | 14 | 4.0 | 0.015 | 15 | 1.2 | 94 |
| RBM Low Plasma Range | 0.047 | 42 | Pending | 0.58 | | | 0.24 | 1.8 | | |
| RBM High Plasma Range | 7.6 | 213 | Pending | 5.6 | 770 | 177 | 3.3 | 38 | 2.7 | 165 |
| Donor_4_3. Aliquot B | 0.014 | 466 | <LOW> | 2.3 | 14 | <LOW> | 0.29 | 251 | <LOW> | <LOW> |
| Donor_4_3. Aliquot C | 0.0086 | 453 | <LOW> | 2.4 | <LOW> | <LOW> | 0.36 | 11 | <LOW> | 39 |
| Donor_4_3. Aliquot D | 0.014 | 471 | 6.2 | 2.2 | 32 | <LOW> | 0.31 | 566 | 3.1 | 39 |
| Donor_4_3. Aliquot E | 0.0086 | 477 | 7.0 | 2.3 | 24 | <LOW> | 0.29 | 543 | 1.5 | 30 |
| Donor_4_3. Aliquot F | 0.019 | 467 | 3.8 | 2.3 | 13 | <LOW> | 0.31 | 232 | 0.37 | 24 |
| Donor_4_3. Aliquot G | 0.019 | 462 | <LOW> | 2.4 | 8.0 | 22 | 0.29 | 14 | <LOW> | 20 |
| Donor_4_3. Aliquot H | 0.013 | 474 | <LOW> | 2.3 | 8.0 | <LOW> | 0.28 | 10 | <LOW> | 15 |
| Donor_4_3. Aliquot I | 0.011 | 447 | <LOW> | 2.3 | 9.6 | <LOW> | 0.30 | 13 | <LOW> | <LOW> |
| Donor_5_3. Aliquot A | 3.7 | 241 | 7.5 | 1.1 | 321 | 323 | 0.24 | 117 | 0.34 | 20 |
| Donor_5_3. Aliquot B | 3.6 | 213 | 8.2 | 1.1 | 270 | 337 | 0.25 | 417 | 0.26 | 32 |
| Donor_5_3. Aliquot C | 3.8 | 246 | <LOW> | 1.1 | 84 | 330 | 0.24 | 7.0 | <LOW> | 26 |
| Donor_5_3. Aliquot D | 3.4 | 263 | 20 | 1.1 | 271 | 373 | 0.22 | 763 | 2.7 | 59 |
| Donor_5_3. Aliquot E | 3.2 | 261 | 21 | 1.2 | 274 | 382 | 0.23 | 1520 | 1.8 | <LOW> |
| Donor_5_3. Aliquot F | 3.1 | 164 | 7.2 | 1.0 | 204 | 350 | 0.23 | 37 | <LOW> | 20 |
| Donor_5_3. Aliquot G | 3.5 | 255 | 6.2 | 1.0 | 59 | 574 | 0.26 | 15 | 0.28 | 24 |
| Donor_5_3. Aliquot H | 3.2 | 223 | 3.8 | 1.0 | 296 | 355 | 0.26 | 10 | <LOW> | 28 |
| Donor_5_3. Aliquot I | 3.4 | 242 | 5.1 | 1.00 | 289 | 329 | 0.24 | 9.2 | <LOW> | 44 |
| Donor_6_3. Aliquot A | 4.2 | 130 | <LOW> | 0.79 | 317 | 47 | 0.38 | 85 | 0.13 | 32 |
| Donor_6_3. Aliquot B | 4.4 | 146 | <LOW> | 0.81 | 306 | 46 | 0.42 | 226 | <LOW> | 42 |
| Donor_6_3. Aliquot C | 4.2 | 157 | <LOW> | 0.78 | 139 | 54 | 0.37 | 7.0 | <LOW> | 50 |
| Donor_6_3. Aliquot D | 4.3 | 149 | 31 | 0.81 | 326 | 47 | 0.41 | 637 | 4.7 | <LOW> |
| Donor_6_3. Aliquot E | 3.9 | 120 | 74 | 0.94 | 269 | 50 | 0.34 | 1870 | 4.3 | 30 |
| Donor_6_3. Aliquot F | 4.3 | 120 | <LOW> | 0.82 | 222 | 45 | 0.33 | 45 | <LOW> | 47 |
| Donor_6_3. Aliquot G | 4.2 | 156 | <LOW> | 0.81 | 91 | 189 | 0.35 | 7.0 | <LOW> | 20 |
| Donor_6_3. Aliquot H | 4.1 | 146 | <LOW> | 0.71 | 340 | 42 | 0.35 | 6.0 | 0.16 | <LOW> |
| Donor_6_3. Aliquot I | 3.7 | 127 | <LOW> | 0.76 | 272 | 45 | 0.34 | 7.0 | <LOW> | <LOW> |

FIG. 12G.3

| | Haptoglobin | ICAM-1 | IFN-gamma | IgA | IgE | IGF-1 | IgM | IL-10 | IL-12p40 | IL-12p70 |
|---|---|---|---|---|---|---|---|---|---|---|
| | mg/mL | ng/mL | pg/mL | mg/mL | ng/mL | ng/mL | mg/mL | pg/mL | ng/mL | pg/mL |
| Least Detectable Dose | 0.025 | 3.2 | 4.6 | 0.0084 | 14 | 4.0 | 0.015 | 15 | | 94 |
| RBM Low Plasma Range | 0.047 | 42 | Pending | 0.58 | | | 0.24 | 1.8 | | |
| RBM High Plasma Range | 7.6 | 213 | Pending | 5.6 | 770 | 177 | 3.3 | 38 | 2.7 | 165 |
| Donor_7_3. Aliquot A | 2.6 | 85 | <LOW> | 1.5 | 56 | 14 | 0.63 | 379 | 0.64 | 39 |
| Donor_7_3. Aliquot B | 2.7 | 85 | <LOW> | 1.5 | 51 | 18 | 0.59 | 441 | 0.27 | 32 |
| Donor_7_3. Aliquot C | 2.7 | 89 | <LOW> | 1.6 | 14 | 26 | 0.63 | 13 | <LOW> | 39 |
| Donor_7_3. Aliquot D | 2.0 | 74 | <LOW> | 1.4 | 62 | 15 | 0.59 | 390 | 0.93 | 39 |
| Donor_7_3. Aliquot E | 1.9 | 84 | <LOW> | 1.1 | 56 | 17 | 0.48 | 297 | 0.93 | 42 |
| Donor_7_3. Aliquot F | 2.6 | 83 | <LOW> | 1.5 | 39 | 9.8 | 0.66 | 85 | <LOW> | 34 |
| Donor_7_3. Aliquot G | 2.3 | 93 | <LOW> | 1.4 | 25 | 98 | 0.60 | 13 | <LOW> | 22 |
| Donor_7_3. Aliquot H | 2.6 | 81 | <LOW> | 1.4 | 36 | 8.1 | 0.60 | 6.8 | <LOW> | <LOW> |
| Donor_7_3. Aliquot I | 2.7 | 79 | <LOW> | 1.5 | 46 | 12 | 0.60 | 11 | <LOW> | <LOW> |
| Donor_8_3. Aliquot A | 0.014 | 61 | 5.6 | 0.77 | 17 | 176 | 0.30 | 102 | 0.30 | 34 |
| Donor_8_3. Aliquot B | 0.016 | 66 | <LOW> | 0.85 | 8.0 | 168 | 0.34 | 218 | 0.19 | 22 |
| Donor_8_3. Aliquot C | 0.0065 | 50 | 550 | 0.83 | <LOW> | 163 | 0.31 | 4.9 | 0.57 | 3920 |
| Donor_8_3. Aliquot D | 0.013 | 63 | 1880 | 0.73 | 77 | 179 | 0.36 | 306 | 19 | 434 |
| Donor_8_3. Aliquot E | 0.037 | 59 | 283 | 0.73 | 65 | 162 | 0.32 | 1000 | 14 | 48 |
| Donor_8_3. Aliquot F | 0.018 | 63 | 118 | 0.85 | 15 | 166 | 0.32 | 219 | 0.71 | 42 |
| Donor_8_3. Aliquot G | 0.016 | 65 | <LOW> | 0.74 | 8.0 | 181 | 0.28 | 4.3 | <LOW> | 15 |
| Donor_8_3. Aliquot H | 0.016 | 64 | 41 | 0.84 | 10 | 177 | 0.37 | 4.1 | 0.23 | 30 |
| Donor_8_3. Aliquot I | 0.011 | 58 | 3.8 | 0.78 | 3.7 | 175 | 0.33 | 6.6 | <LOW> | 32 |
| Donor_9_3. Aliquot A | 0.018 | 79 | 17 | 1.0 | 9.3 | 745 | 1.0 | 220 | 0.26 | 52 |
| Donor_9_3. Aliquot B | 0.018 | 82 | 21 | 1.0 | 9.3 | 716 | 1.0 | 435 | 0.40 | 44 |
| Donor_9_3. Aliquot C | 0.012 | 69 | 519 | 1.0 | 4.1 | 784 | 0.97 | 43 | 0.80 | 1480 |
| Donor_9_3. Aliquot D | 0.0062 | 75 | 2360 | 1.0 | 63 | 681 | 1.0 | 1080 | 17 | 89 |
| Donor_9_3. Aliquot E | 0.013 | 71 | 490 | 1.00 | 39 | 651 | 1.0 | 1730 | 11 | 54 |
| Donor_9_3. Aliquot F | 0.0076 | 78 | 26 | 1.0 | 5.8 | 688 | 0.95 | 122 | 0.34 | 46 |
| Donor_9_3. Aliquot G | 0.016 | 68 | 7.6 | 1.1 | 5.2 | 636 | 1.1 | 13 | 0.25 | 41 |
| Donor_9_3. Aliquot H | 0.017 | 75 | 9.0 | 1.0 | 6.0 | 703 | 1.0 | 14 | 0.24 | 56 |
| Donor_9_3. Aliquot I | 0.012 | 76 | 14 | 1.0 | 6.2 | 732 | 1.1 | 4.2 | <LOW> | 31 |
| EDTA Plasma | | | | | | | | | | |

FIG. 12G.4

| | Haptoglobin | ICAM-1 | IFN-gamma | IgA | IgE | IGF-1 | IgM | IL-10 | IL-12p40 | IL-12p70 |
|---|---|---|---|---|---|---|---|---|---|---|
| | mg/mL | ng/mL | pg/mL | mg/mL | ng/mL | ng/mL | mg/mL | pg/mL | ng/mL | pg/mL |
| Least Detectable Dose | 0.025 | 3.2 | 4.6 | 0.0084 | 14 | 4.0 | 0.015 | 15 | 1.2 | 94 |
| RBM Low Plasma Range | 0.047 | 42 | Pending | 0.58 | | | 0.24 | 1.8 | | |
| RBM High Plasma Range | 7.6 | 213 | Pending | 5.6 | 770 | 177 | 3.3 | 38 | 2.7 | 165 |
| donor #1 plasma | 1.3 | 206 | 4.0 | 2.4 | 6.6 | <LOW> | 0.57 | 16 | 0.26 | 34 |
| donor #2 plasma | 3.6 | 371 | 10 | 4.0 | 172 | <LOW> | 0.22 | 21 | 0.19 | 23 |
| donor #3 plasma | 0.58 | 171 | 5.8 | 2.8 | 26 | 12 | 0.93 | 9.9 | <LOW> | 49 |
| donor #4 plasma | 0.0097 | 348 | <LOW> | 3.6 | 14 | <LOW> | 0.39 | 14 | <LOW> | 33 |
| donor #5 plasma | 5.9 | 136 | 13 | 1.8 | 318 | 18 | 0.32 | 12 | 0.15 | 56 |
| donor #6 plasma | 5.7 | 129 | <LOW> | 1.3 | 559 | <LOW> | 0.43 | 10 | <LOW> | 34 |
| donor #7 plasma | 4.6 | 109 | 5.8 | 2.4 | 81 | <LOW> | 0.79 | 16 | <LOW> | 23 |
| donor #8 plasma | 0.36 | 87 | <LOW> | 1.0 | 17 | 32 | 0.38 | 2.3 | <LOW> | 39 |
| donor #9 plasma | 0.32 | 100 | 4.0 | 1.4 | 3.5 | 325 | 1.5 | 5.1 | 0.14 | 35 |

FIG. 12H.1

| | IL-13 pg/mL | IL-15 ng/mL | IL-16 pg/mL | IL-17 pg/mL | IL-17E pg/mL | IL-18 pg/mL | IL-1alpha ng/mL | IL-1beta pg/mL | IL-1ra pg/mL | IL-2 pg/mL |
|---|---|---|---|---|---|---|---|---|---|---|
| Least Detectable Dose | 57 | 1.3 | 66 | 2.7 | 31 | 54 | 0.16 | 1.5 | 15 | 60 |
| RBM Low Plasma Range | | | 232 | PENDING | PENDING | 72 | | 8.7 | 17 | |
| RBM High Plasma Range | 133 | 4.6 | 3380 | PENDING | PENDING | 1020 | 0.35 | | 622 | 61 |
| Donor_1 3. Aliquot A | 36 | 0.41 | 575 | 6.7 | 643 | 1930 | 0.0025 | 75 | 3780 | <LOW> |
| Donor_1 3. Aliquot B | 37 | 0.40 | 535 | <LOW> | 559 | 1910 | <LOW> | 50 | 2300 | <LOW> |
| Donor_1 3. Aliquot C | 38 | 0.33 | 413 | <LOW> | 62 | 1980 | <LOW> | 4.4 | 987 | <LOW> |
| Donor_1 3. Aliquot D | 21 | 0.45 | 619 | <LOW> | 580 | 2080 | 0.0077 | 348 | 4230 | <LOW> |
| Donor_1 3. Aliquot E | 34 | 0.32 | 580 | <LOW> | 604 | 2140 | <LOW> | 69 | 2740 | <LOW> |
| Donor_1 3. Aliquot F | 36 | 0.30 | 502 | <LOW> | 486 | 1630 | <LOW> | 10 | 1040 | <LOW> |
| Donor_1 3. Aliquot G | 37 | 0.50 | 216 | 7.5 | 646 | 2130 | <LOW> | 6.8 | 2830 | <LOW> |
| Donor_1 3. Aliquot H | 35 | 0.28 | 299 | <LOW> | 56 | 1860 | <LOW> | 4.6 | 944 | <LOW> |
| Donor_1 3. Aliquot I | 33 | 0.26 | 588 | <LOW> | 502 | 1810 | <LOW> | 5.4 | 660 | <LOW> |
| Donor_2 3. Aliquot A | 37 | 0.41 | 654 | <LOW> | 29 | 631 | 0.012 | 132 | 16500 | <LOW> |
| Donor_2 3. Aliquot B | 37 | 0.43 | 712 | <LOW> | 40 | 709 | 0.0057 | 71 | 15500 | <LOW> |
| Donor_2 3. Aliquot C | 29 | 0.32 | 609 | <LOW> | 11 | 616 | <LOW> | 4.7 | 2000 | <LOW> |
| Donor_2 3. Aliquot D | 29 | 0.50 | 804 | <LOW> | 37 | 830 | 0.36 | 5020 | 54600 | <LOW> |
| Donor_2 3. Aliquot E | 36 | 0.37 | 782 | <LOW> | 29 | 754 | 0.11 | 1310 | 52400 | <LOW> |
| Donor_2 3. Aliquot F | 66 | 0.50 | 720 | <LOW> | 17 | 594 | 0.0034 | 32 | 3140 | <LOW> |
| Donor_2 3. Aliquot G | 40 | 0.66 | 432 | <LOW> | <LOW> | 681 | 0.045 | 387 | 6790 | <LOW> |
| Donor_2 3. Aliquot H | 27 | <LOW> | 393 | <LOW> | 23 | 595 | <LOW> | 9.7 | 4400 | <LOW> |
| Donor_2 3. Aliquot I | 36 | 0.21 | 642 | <LOW> | 34 | 538 | <LOW> | 6.6 | 2520 | <LOW> |
| Donor_3 3. Aliquot A | 49 | 0.53 | 1310 | <LOW> | 17 | 766 | 0.0054 | 62 | 12900 | <LOW> |
| Donor_3 3. Aliquot B | 43 | 0.56 | 1230 | <LOW> | 34 | 720 | 0.0056 | 32 | 11000 | <LOW> |
| Donor_3 3. Aliquot C | 57 | 0.41 | 1190 | <LOW> | 29 | 715 | 0.0036 | 5.3 | 2970 | <LOW> |
| Donor_3 3. Aliquot D | 40 | 0.47 | 1410 | <LOW> | 37 | 735 | 0.074 | 3890 | 41000 | <LOW> |
| Donor_3 3. Aliquot E | 39 | 0.47 | 1490 | <LOW> | 29 | 798 | 0.039 | 1610 | 32900 | <LOW> |
| Donor_3 3. Aliquot F | 51 | 0.28 | 1340 | <LOW> | 29 | 694 | 0.0050 | 18 | 3850 | <LOW> |
| Donor_3 3. Aliquot G | 43 | 0.32 | 556 | <LOW> | 29 | 766 | 0.0045 | 8.6 | 3260 | <LOW> |
| Donor_3 3. Aliquot H | 55 | 0.28 | 706 | <LOW> | <LOW> | 553 | 0.0029 | 2.2 | 1010 | <LOW> |
| Donor_3 3. Aliquot I | 81 | 0.47 | 1280 | <LOW> | 45 | 627 | 0.0043 | <LOW> | 79 | <LOW> |
| Donor_4 3. Aliquot A | 36 | 0.38 | 1240 | <LOW> | 42 | 690 | <LOW> | 7.3 | 2670 | <LOW> |

FIG. 12H.2

| | IL-13 | IL-15 | IL-16 | IL-17 | IL-17E | IL-18 | IL-1alpha | IL-1beta | IL-1ra | IL-2 |
|---|---|---|---|---|---|---|---|---|---|---|
| | pg/mL | ng/mL | pg/mL | pg/mL | pg/mL | pg/mL | ng/mL | pg/mL | pg/mL | pg/mL |
| Least Detectable Dose | 57 | 1.3 | 66 | 2.7 | 31 | 54 | 0.16 | 1.5 | 15 | 60 |
| RBM Low Plasma Range | | | 232 | PENDING | PENDING | 72 | | | | |
| RBM High Plasma Range | 133 | 4.6 | 3380 | PENDING | PENDING | 1020 | 0.35 | 8.7 | 17 | 61 |
| Donor_4_3. Aliquot B | 19 | 0.56 | 1130 | <LOW> | 40 | 700 | <LOW> | 46 | 622 | <LOW> |
| Donor_4_3. Aliquot C | 27 | 0.32 | 1050 | <LOW> | 56 | 608 | <LOW> | 3.8 | 3450 | <LOW> |
| Donor_4_3. Aliquot D | 38 | 0.43 | 986 | <LOW> | 29 | 724 | 0.29 | 2830 | 336 | <LOW> |
| Donor_4_3. Aliquot E | 23 | 0.56 | 812 | <LOW> | 51 | 633 | 0.075 | 957 | 13700 | <LOW> |
| Donor_4_3. Aliquot F | 28 | 0.47 | 1030 | <LOW> | 51 | 623 | 0.0036 | 47 | 13100 | <LOW> |
| Donor_4_3. Aliquot G | 29 | 0.24 | 431 | <LOW> | 56 | 612 | 0.0025 | 7.0 | 12900 | <LOW> |
| Donor_4_3. Aliquot H | 9.7 | 0.19 | 564 | <LOW> | 62 | 566 | <LOW> | 4.1 | 2530 | <LOW> |
| Donor_4_3. Aliquot I | 24 | 0.24 | 1150 | <LOW> | 62 | 597 | <LOW> | 0.63 | 1670 | <LOW> |
| | | | | | | | | | 228 | |
| Donor_5_3. Aliquot A | 33 | 0.71 | 536 | <LOW> | 74 | 340 | 0.0066 | 73 | 22900 | <LOW> |
| Donor_5_3. Aliquot B | 32 | 0.50 | 584 | <LOW> | 40 | 295 | 0.0094 | 75 | 22500 | <LOW> |
| Donor_5_3. Aliquot C | 48 | 0.50 | 455 | <LOW> | 20 | 271 | <LOW> | 3.0 | 2100 | <LOW> |
| Donor_5_3. Aliquot D | 32 | 0.73 | 592 | <LOW> | 17 | 428 | 0.35 | 3910 | 53300 | <LOW> |
| Donor_5_3. Aliquot E | 36 | 0.68 | 561 | <LOW> | 11 | 467 | 0.32 | 3280 | 51000 | <LOW> |
| Donor_5_3. Aliquot F | 38 | 0.28 | 430 | <LOW> | <LOW> | 216 | 0.0043 | 73 | 11100 | <LOW> |
| Donor_5_3. Aliquot G | 29 | 0.26 | 323 | <LOW> | 45 | 479 | 0.0048 | 36 | 16700 | <LOW> |
| Donor_5_3. Aliquot H | 27 | 0.19 | 390 | <LOW> | 31 | 367 | <LOW> | 15 | 9910 | <LOW> |
| Donor_5_3. Aliquot I | 47 | 0.13 | 492 | <LOW> | 34 | 255 | <LOW> | 2.8 | 3530 | <LOW> |
| Donor_6_3. Aliquot A | 70 | 0.32 | 1030 | <LOW> | 29 | 102 | 0.0052 | 35 | 7350 | <LOW> |
| Donor_6_3. Aliquot B | 57 | 0.24 | 828 | <LOW> | 51 | 95 | 0.012 | 46 | 9190 | <LOW> |
| Donor_6_3. Aliquot C | 59 | 0.24 | 1150 | <LOW> | 11 | 98 | 0.0050 | 1.5 | 1220 | <LOW> |
| Donor_6_3. Aliquot D | 68 | 0.56 | 682 | <LOW> | 17 | 138 | 0.21 | 1870 | 26100 | <LOW> |
| Donor_6_3. Aliquot E | 68 | 0.16 | 648 | <LOW> | 17 | 134 | 0.41 | 3760 | 31600 | <LOW> |
| Donor_6_3. Aliquot F | 86 | 0.43 | 969 | <LOW> | <LOW> | 113 | 0.0073 | 43 | 4970 | <LOW> |
| Donor_6_3. Aliquot G | 65 | <LOW> | 439 | <LOW> | 11 | 170 | 0.0043 | 27 | 9870 | <LOW> |
| Donor_6_3. Aliquot H | 65 | 0.19 | 815 | 5.0 | 54 | 107 | <LOW> | 2.8 | 1530 | <LOW> |
| Donor_6_3. Aliquot I | 59 | 0.28 | 1230 | <LOW> | 62 | 87 | <LOW> | 1.3 | 202 | <LOW> |

FIG. 12H.3

| | IL-13 pg/mL | IL-15 ng/mL | IL-16 pg/mL | IL-17 pg/mL | IL-17E pg/mL | IL-18 pg/mL | IL-1alpha ng/mL | IL-1beta pg/mL | IL-1ra pg/mL | IL-2 pg/mL |
|---|---|---|---|---|---|---|---|---|---|---|
| Least Detectable Dose | 57 | 1.3 | 66 | 2.7 | 31 | 54 | 0.16 | 1.5 | 15 | 60 |
| RBM Low Plasma Range | | | 232 | PENDING | PENDING | 72 | | | 17 | |
| RBM High Plasma Range | 133 | 4.6 | 3380 | PENDING | PENDING | 1020 | 0.35 | 8.7 | 622 | 61 |
| Donor_7 3. Aliquot A | 91 | 0.79 | 664 | <LOW> | 40 | 295 | 0.025 | 147 | 6320 | <LOW> |
| Donor_7 3. Aliquot B | 103 | 0.78 | 620 | <LOW> | 34 | 277 | 0.015 | 99 | 4590 | <LOW> |
| Donor_7 3. Aliquot C | 70 | 0.53 | 817 | <LOW> | 17 | 255 | 0.010 | 16 | 244 | <LOW> |
| Donor_7 3. Aliquot D | 82 | 0.49 | 662 | <LOW> | 23 | 275 | 0.31 | 2120 | 11000 | <LOW> |
| Donor_7 3. Aliquot E | 104 | 0.58 | 651 | <LOW> | 62 | 298 | 0.071 | 548 | 7580 | <LOW> |
| Donor_7 3. Aliquot F | 105 | 0.54 | 856 | <LOW> | 31 | 209 | 0.016 | 20 | 578 | <LOW> |
| Donor_7 3. Aliquot G | 56 | 0.19 | 428 | <LOW> | 85 | 300 | 0.0054 | 6.2 | 2730 | <LOW> |
| Donor_7 3. Aliquot H | 62 | 0.38 | 574 | <LOW> | 31 | 214 | 0.0057 | 3.4 | 361 | <LOW> |
| Donor_7 3. Aliquot I | 88 | 0.41 | 918 | <LOW> | 26 | 227 | 0.0066 | <LOW> | 61 | <LOW> |
| | | | | | | | | | | |
| Donor_8 3. Aliquot A | 81 | 0.32 | 340 | <LOW> | 17 | 150 | 0.0073 | 73 | 3870 | <LOW> |
| Donor_8 3. Aliquot B | 97 | 0.24 | 341 | <LOW> | <LOW> | 173 | 0.0089 | 59 | 3010 | <LOW> |
| Donor_8 3. Aliquot C | 80 | 0.32 | 309 | <LOW> | <LOW> | 157 | 0.0071 | 76 | 10200 | <LOW> |
| Donor_8 3. Aliquot D | 99 | 0.61 | 754 | 5.0 | 17 | 408 | 0.28 | 24700 | 11400 | <LOW> |
| Donor_8 3. Aliquot E | 99 | 0.64 | 533 | 9.7 | 45 | 359 | 0.27 | 17500 | 12800 | <LOW> |
| Donor_8 3. Aliquot F | 111 | 0.45 | 410 | 4.2 | 31 | 175 | 0.013 | 204 | 16400 | <LOW> |
| Donor_8 3. Aliquot G | 53 | 0.19 | 183 | 5.4 | 23 | 152 | <LOW> | 32 | 4000 | <LOW> |
| Donor_8 3. Aliquot H | 75 | 0.28 | 231 | <LOW> | 17 | 220 | 0.0041 | 75 | 7720 | <LOW> |
| Donor_8 3. Aliquot I | 80 | 0.32 | 522 | <LOW> | 29 | 195 | 0.0061 | 7.9 | 839 | <LOW> |
| | | | | | | | | | | |
| Donor_9 3. Aliquot A | 68 | 0.31 | 463 | 17 | 34 | 58 | 0.0080 | 29 | 3980 | <LOW> |
| Donor_9 3. Aliquot B | 77 | 0.44 | 398 | 7.2 | 66 | 48 | 0.013 | 42 | 4200 | <LOW> |
| Donor_9 3. Aliquot C | 74 | 0.35 | 407 | <LOW> | 83 | 52 | 0.018 | 67 | 9410 | <LOW> |
| Donor_9 3. Aliquot D | 71 | 0.51 | 780 | 8.1 | 44 | 340 | 2.6 | 26100 | 18300 | <LOW> |
| Donor_9 3. Aliquot E | 68 | 0.31 | 538 | 22 | 55 | 161 | 0.80 | 7830 | 15100 | <LOW> |
| Donor_9 3. Aliquot F | 83 | 0.30 | 369 | 13 | 28 | 38 | 0.011 | 60 | 12700 | <LOW> |
| Donor_9 3. Aliquot G | 36 | 0.31 | 411 | 22 | 44 | 92 | 0.0075 | 48 | 8240 | <LOW> |
| Donor_9 3. Aliquot H | 51 | 0.56 | 369 | 9.8 | 77 | 96 | 0.0086 | 39 | 4920 | <LOW> |
| Donor_9 3. Aliquot I | 56 | 0.22 | 455 | 8.1 | 83 | 69 | 0.0035 | 5.7 | 2110 | <LOW> |
| EDTA Plasma | | | | | | | | | | |

FIG. 12H.4

| | IL-13 pg/mL | IL-15 ng/mL | IL-16 pg/mL | IL-17 pg/mL | IL-17E pg/mL | IL-18 pg/mL | IL-1alpha ng/mL | IL-1beta pg/mL | IL-1ra pg/mL | IL-2 pg/mL |
|---|---|---|---|---|---|---|---|---|---|---|
| Least Detectable Dose | 57 | 1.3 | 66 | 2.7 | 31 | 54 | 0.16 | 1.5 | 15 | 60 |
| RBM Low Plasma Range | | | 232 | PENDING | PENDING | 72 | | | 17 | |
| RBM High Plasma Range | 133 | 4.6 | 3380 | PENDING | PENDING | 1020 | 0.35 | 8.7 | 622 | 61 |
| donor #1 plasma | 39 | 0.30 | 329 | 11 | 228 | 1670 | <LOW> | 2.8 | 1800 | <LOW> |
| donor #2 plasma | 24 | 0.13 | 620 | <LOW> | <LOW> | 628 | <LOW> | <LOW> | 555 | <LOW> |
| donor #3 plasma | 37 | 0.39 | 892 | <LOW> | 34 | 644 | 0.0027 | 1.1 | 137 | <LOW> |
| donor #4 plasma | 50 | 0.29 | 794 | <LOW> | <LOW> | 805 | <LOW> | <LOW> | 410 | <LOW> |
| donor #5 plasma | 37 | 0.64 | 314 | <LOW> | <LOW> | 188 | <LOW> | 1.5 | 354 | <LOW> |
| donor #6 plasma | 40 | 0.29 | 277 | 11 | 44 | 112 | <LOW> | <LOW> | 84 | <LOW> |
| donor #7 plasma | 39 | 0.29 | 514 | <LOW> | 28 | 404 | <LOW> | <LOW> | 559 | <LOW> |
| donor #8 plasma | 50 | 0.31 | 208 | <LOW> | <LOW> | 196 | 0.0035 | 1.4 | 68 | <LOW> |
| donor #9 plasma | 41 | 0.18 | 327 | <LOW> | 44 | 104 | 0.0032 | <LOW> | 80 | <LOW> |

FIG. 121.1

| | IL-23 | IL-3 | IL-4 | IL-5 | IL-6 | IL-7 | IL-8 | Insulin | Leptin | Lipoprotein (a) |
|---|---|---|---|---|---|---|---|---|---|---|
| | ng/mL | ng/mL | pg/mL | pg/mL | pg/mL | pg/mL | pg/mL | uIU/mL | ng/mL | ug/mL |
| Least Detectable Dose | <0.67 | 0.17 | 104 | 33 | 12 | 53 | 3.5 | 0.86 | 0.10 | 3.7 |
| RBM Low Plasma Range | PENDING | | | | | | | | | 3.0 |
| RBM High Plasma Range | PENDING | 1.2 | 103 | 62 | 25 | 125 | 59 | 34 | 0.41 | 858 |
| Donor_1 3. Aliquot A | 3.7 | 0.027 | 50 | <LOW> | 4690 | 169 | 23600 | 11 | 41 | 27 |
| Donor_1 3. Aliquot B | 1.2 | <LOW> | 53 | <LOW> | 1860 | 113 | 4450 | 9.8 | 132 | 34 |
| Donor_1 3. Aliquot C | <LOW> | <LOW> | 43 | <LOW> | 49 | 33 | 321 | 6.3 | 115 | 31 |
| Donor_1 3. Aliquot D | <LOW> | <LOW> | 49 | <LOW> | 7970 | 113 | 6730 | 11 | 124 | 32 |
| Donor_1 3. Aliquot E | 1.2 | <LOW> | 38 | <LOW> | 1700 | 131 | 6170 | 11 | 121 | 32 |
| Donor_1 3. Aliquot F | 1.2 | <LOW> | 42 | <LOW> | 77 | 57 | 1330 | 8.3 | 124 | 45 |
| Donor_1 3. Aliquot G | 2.1 | <LOW> | 38 | <LOW> | 57 | 100 | 5060 | 8.0 | 107 | 37 |
| Donor_1 3. Aliquot H | 1.9 | <LOW> | 51 | <LOW> | 54 | 33 | 672 | 9.4 | 112 | 32 |
| Donor_1 3. Aliquot I | <LOW> | <LOW> | 38 | <LOW> | 50 | 68 | 1480 | 9.9 | 119 | 30 |
| Donor_2 3. Aliquot A | 1.2 | 0.12 | 69 | 5.9 | 11100 | 215 | 100000 | 5.7 | 7.7 | 38 |
| Donor_2 3. Aliquot B | <LOW> | 0.095 | 78 | 8.2 | 6720 | 189 | 74900 | 6.1 | 8.4 | 46 |
| Donor_2 3. Aliquot C | <LOW> | <LOW> | 43 | <LOW> | 110 | 48 | 2290 | 2.3 | 9.0 | 47 |
| Donor_2 3. Aliquot D | 2.3 | 0.19 | 69 | 7.4 | 78400 | 201 | 146000 | 6.6 | 8.1 | 48 |
| Donor_2 3. Aliquot E | 2.5 | 0.21 | 77 | 8.2 | 63400 | 226 | 165000 | 6.4 | 8.3 | 58 |
| Donor_2 3. Aliquot F | <LOW> | <LOW> | 40 | 6.7 | 180 | 59 | 2230 | 4.7 | 7.7 | 128 |
| Donor_2 3. Aliquot G | 1.2 | 0.14 | 77 | 8.9 | 30900 | 223 | >344062 | 6.0 | 4.4 | 46 |
| Donor_2 3. Aliquot H | <LOW> | <LOW> | 45 | 5.1 | 187 | 74 | 3460 | 5.6 | 7.8 | 47 |
| Donor_2 3. Aliquot I | <LOW> | <LOW> | 56 | <LOW> | 153 | 48 | 3230 | 4.7 | 7.9 | 48 |
| Donor_3 3. Aliquot A | <LOW> | 0.12 | 9.4 | 4.3 | 6380 | 192 | 40600 | 19 | 8.1 | 61 |
| Donor_3 3. Aliquot B | 2.1 | 0.099 | 7.8 | <LOW> | 3880 | 201 | 32400 | 17 | 7.7 | 66 |
| Donor_3 3. Aliquot C | 2.1 | <LOW> | <LOW> | <LOW> | 90 | 66 | 1860 | 9.0 | 8.4 | 68 |
| Donor_3 3. Aliquot D | <LOW> | 0.15 | 20 | 7.4 | 105000 | 243 | 124000 | 15 | 7.8 | 58 |
| Donor_3 3. Aliquot E | 3.4 | 0.14 | 8.7 | 4.3 | 59800 | 234 | 146000 | 17 | 8.3 | 70 |
| Donor_3 3. Aliquot F | 1.2 | 0.050 | 7.8 | 5.9 | 169 | 82 | 2870 | 13 | 7.2 | 83 |
| Donor_3 3. Aliquot G | <LOW> | <LOW> | <LOW> | 2.5 | 63 | 78 | 24200 | 20 | 5.9 | 57 |
| Donor_3 3. Aliquot H | <LOW> | <LOW> | <LOW> | <LOW> | 26 | 38 | 924 | 15 | 6.9 | 61 |
| Donor_3 3. Aliquot I | 2.1 | 0.087 | <LOW> | 5.1 | 9.2 | 86 | 1080 | 15 | 7.8 | 66 |
| Donor_4 3. Aliquot A | <LOW> | <LOW> | 33 | <LOW> | 177 | 82 | 3240 | 12 | 11 | 23 |

FIG. 121.2

| | IL-23 | IL-3 | IL-4 | IL-5 | IL-6 | IL-7 | IL-8 | Insulin | Leptin | Lipoprotein (a) |
|---|---|---|---|---|---|---|---|---|---|---|
| | ng/mL | ng/mL | pg/mL | pg/mL | pg/mL | pg/mL | pg/mL | uIU/mL | ng/mL | ug/mL |
| Least Detectable Dose | <0.67 | 0.17 | 104 | 33 | 12 | 53 | 3.5 | 0.86 | 0.10 | 3.7 |
| RBM Low Plasma Range | PENDING | | | | | 3.7 | | | 0.41 | 3.0 |
| RBM High Plasma Range | PENDING | 1.2 | 103 | 62 | 25 | 125 | 59 | 34 | 41 | 858 |
| Donor_4 3. Aliquot B | 2.1 | <LOW> | 35 | <LOW> | 405 | 106 | 4210 | 12 | 12 | 21 |
| Donor_4 3. Aliquot C | 2.1 | <LOW> | 37 | <LOW> | 70 | 38 | 751 | 3.8 | 10 | 21 |
| Donor_4 3. Aliquot D | <LOW> | 0.039 | 50 | <LOW> | 46300 | 215 | 76000 | 13 | 9.7 | 24 |
| Donor_4 3. Aliquot E | <LOW> | 0.087 | 54 | <LOW> | 24300 | 214 | 70800 | 12 | 8.0 | 22 |
| Donor_4 3. Aliquot F | <LOW> | <LOW> | 32 | <LOW> | 5050 | 98 | 4030 | 12 | 8.4 | 24 |
| Donor_4 3. Aliquot G | 2.5 | <LOW> | 49 | <LOW> | 59 | 74 | 23400 | 14 | 7.3 | 22 |
| Donor_4 3. Aliquot H | 1.6 | <LOW> | 31 | <LOW> | 62 | 66 | 731 | 15 | 11 | 21 |
| Donor_4 3. Aliquot I | 2.1 | <LOW> | 29 | <LOW> | 52 | 38 | 550 | 11 | 10 | 25 |
| Donor_5 3. Aliquot A | <LOW> | 0.099 | 49 | 4.7 | 2370 | 203 | 146000 | 5.2 | 2.0 | 22 |
| Donor_5 3. Aliquot B | <LOW> | 0.11 | 51 | <LOW> | 4460 | 217 | 198000 | 5.4 | 1.7 | 20 |
| Donor_5 3. Aliquot C | 1.4 | 0.081 | 39 | <LOW> | 46 | 52 | 1740 | 2.0 | 2.0 | 21 |
| Donor_5 3. Aliquot D | <LOW> | 0.19 | 76 | 3.5 | 60400 | 247 | 211000 | 6.5 | 1.8 | 19 |
| Donor_5 3. Aliquot E | <LOW> | 0.15 | 57 | 2.5 | 71300 | 200 | >344062 | 8.0 | 1.9 | 21 |
| Donor_5 3. Aliquot F | <LOW> | <LOW> | 42 | <LOW> | 316 | 115 | 20400 | 3.6 | 1.3 | 39 |
| Donor_5 3. Aliquot G | 1.6 | <LOW> | 46 | <LOW> | 70 | 145 | 85000 | 3.8 | 2.0 | 18 |
| Donor_5 3. Aliquot H | 2.5 | <LOW> | 41 | <LOW> | 55 | 84 | 20000 | 4.9 | 1.9 | 17 |
| Donor_5 3. Aliquot I | 1.6 | <LOW> | 35 | <LOW> | 43 | 94 | 2590 | 4.3 | 1.7 | 18 |
| Donor_6 3. Aliquot A | <LOW> | 0.11 | 51 | 5.9 | 1500 | 182 | 17400 | 1.3 | 0.12 | 36 |
| Donor_6 3. Aliquot B | <LOW> | 0.11 | 55 | 11 | 3190 | 189 | 33200 | 1.4 | 0.10 | 40 |
| Donor_6 3. Aliquot C | <LOW> | 0.081 | 43 | 4.3 | 85 | 90 | 271 | 0.98 | 0.11 | 39 |
| Donor_6 3. Aliquot D | <LOW> | 0.13 | 54 | 6.3 | 50700 | 215 | 67300 | 1.8 | 0.25 | 43 |
| Donor_6 3. Aliquot E | 1.2 | 0.10 | 60 | 21 | 71700 | 229 | 116000 | 1.2 | 0.26 | 35 |
| Donor_6 3. Aliquot F | <LOW> | 0.12 | 44 | 8.9 | 517 | 124 | 3980 | 1.5 | <LOW> | 79 |
| Donor_6 3. Aliquot G | <LOW> | 0.032 | 46 | <LOW> | 74 | 128 | 26500 | 1.2 | 0.27 | 31 |
| Donor_6 3. Aliquot H | 3.7 | 0.025 | 39 | <LOW> | 84 | 94 | 692 | 1.3 | 0.13 | 32 |
| Donor_6 3. Aliquot I | <LOW> | <LOW> | 29 | 3.5 | 65 | 68 | 243 | 1.1 | 0.10 | 25 |

FIG. 12I.3

| | IL-23 | IL-3 | IL-4 | IL-5 | IL-6 | IL-7 | IL-8 | Insulin | Leptin | Lipoprotein (a) |
|---|---|---|---|---|---|---|---|---|---|---|
| | ng/mL | ng/mL | pg/mL | pg/mL | pg/mL | pg/mL | pg/mL | uIU/mL | ng/mL | ug/mL |
| Least Detectable Dose | <0.67 | 0.17 | 104 | 33 | 12 | 53 | 3.5 | 0.86 | 0.10 | 3.7 |
| RBM Low Plasma Range | PENDING | | | | | 3.7 | | | 0.41 | 3.0 |
| RBM High Plasma Range | PENDING | 1.2 | 103 | 62 | 25 | 125 | 59 | 34 | 41 | 858 |
| Donor_7_3. Aliquot A | <LOW> | 0.27 | 33 | 11 | 19900 | 273 | 89600 | 8.4 | 11 | 203 |
| Donor_7_3. Aliquot B | <LOW> | 0.21 | 27 | 20 | 5190 | 243 | 33900 | 7.8 | 11 | 222 |
| Donor_7_3. Aliquot C | <LOW> | 0.037 | 9.4 | 8.9 | 26 | 80 | 500 | 4.1 | 12 | 160 |
| Donor_7_3. Aliquot D | <LOW> | 0.15 | 29 | 5.9 | 54800 | 211 | 80600 | 6.5 | 11 | 192 |
| Donor_7_3. Aliquot E | <LOW> | 0.16 | 37 | 12 | 21600 | 247 | 41300 | 7.5 | 11 | 215 |
| Donor_7_3. Aliquot F | <LOW> | 0.12 | 23 | 13 | 242 | 138 | 812 | 6.2 | 11 | 548 |
| Donor_7_3. Aliquot G | <LOW> | <LOW> | 18 | <LOW> | 48 | 109 | 7810 | 6.6 | 6.9 | 148 |
| Donor_7_3. Aliquot H | <LOW> | <LOW> | <LOW> | <LOW> | 34 | 45 | 373 | 6.4 | 12 | 155 |
| Donor_7_3. Aliquot I | 1.2 | 0.044 | <LOW> | 4.3 | 16 | 80 | 225 | 6.1 | 12 | 190 |
| Donor_8_3. Aliquot A | 1.6 | 0.083 | 43 | 8.2 | 1400 | 166 | 4320 | 1.9 | 0.50 | 16 |
| Donor_8_3. Aliquot B | <LOW> | 0.12 | 49 | 12 | 1140 | 184 | 4770 | 2.4 | 0.49 | 16 |
| Donor_8_3. Aliquot C | <LOW> | 0.12 | 45 | 2.5 | 840 | 120 | 846 | 0.73 | 0.38 | 16 |
| Donor_8_3. Aliquot D | 3.0 | 0.18 | 60 | 5.9 | 99400 | 205 | 66900 | 2.2 | 0.62 | 13 |
| Donor_8_3. Aliquot E | 1.6 | 0.11 | 48 | 14 | 83900 | 217 | 58300 | 2.4 | 0.64 | 18 |
| Donor_8_3. Aliquot F | 3.0 | 0.25 | 48 | 14 | 6720 | 185 | 952 | 3.3 | 0.49 | 18 |
| Donor_8_3. Aliquot G | 1.6 | 0.025 | 43 | <LOW> | 42 | 86 | 2470 | 0.91 | 0.36 | 12 |
| Donor_8_3. Aliquot H | <LOW> | 0.081 | 40 | 5.1 | 129 | 169 | 5280 | 1.7 | 0.53 | 13 |
| Donor_8_3. Aliquot I | 1.2 | 0.12 | 44 | 2.5 | 12 | 117 | 895 | 1.7 | 0.37 | 14 |
| Donor_9_3. Aliquot A | 5.8 | 0.14 | 59 | 2.6 | 642 | 143 | 3910 | 6.2 | 2.0 | 18 |
| Donor_9_3. Aliquot B | 1.1 | 0.21 | 54 | 7.8 | 1100 | 156 | 4840 | 5.9 | 2.0 | 12 |
| Donor_9_3. Aliquot C | <LOW> | 0.20 | 59 | 5.3 | 1680 | 167 | 3560 | 3.1 | 1.6 | 13 |
| Donor_9_3. Aliquot D | 2.4 | 0.21 | 70 | 8.6 | 93100 | 209 | 48600 | 6.5 | 2.0 | 17 |
| Donor_9_3. Aliquot E | <LOW> | 0.17 | 67 | 5.3 | 61700 | 192 | 62300 | 6.3 | 1.8 | 16 |
| Donor_9_3. Aliquot F | <LOW> | 0.18 | 51 | 8.6 | 1900 | 159 | 1200 | 6.6 | 1.9 | 18 |
| Donor_9_3. Aliquot G | <LOW> | 0.11 | 75 | <LOW> | 131 | 126 | 21300 | 5.7 | 1.3 | 11 |
| Donor_9_3. Aliquot H | <LOW> | 0.098 | 55 | <LOW> | 57 | 141 | 1590 | 7.1 | 1.9 | 11 |
| Donor_9_3. Aliquot I | 1.7 | 0.10 | 43 | <LOW> | 19 | 62 | 797 | 5.3 | 1.9 | 14 |
| EDTA Plasma | | | | | | | | | | |

FIG. 121.4

| | IL-23 ng/mL | IL-3 ng/mL | IL-4 pg/mL | IL-5 pg/mL | IL-6 pg/mL | IL-7 pg/mL | IL-8 pg/mL | Insulin uIU/mL | Leptin ng/mL | Lipoprotein (a) ug/mL |
|---|---|---|---|---|---|---|---|---|---|---|
| Least Detectable Dose | <0.67 | 0.17 | 104 | 33 | 12 | 53 | 3.5 | 0.86 | 0.10 | 3.7 |
| RBM Low Plasma Range | PENDING | | | | | 3.7 | | | 0.41 | 3.0 |
| RBM High Plasma Range | PENDING | 1.2 | 103 | 62 | 25 | 125 | 59 | 34 | 41 | 858 |
| donor #1 plasma | 3.4 | <LOW> | <LOW> | <LOW> | 30 | 87 | 239 | 6.9 | 89 | 46 |
| donor #2 plasma | 1.1 | <LOW> | <LOW> | 8.2 | 102 | 42 | 319 | 5.8 | 9.7 | 109 |
| donor #3 plasma | 2.7 | <LOW> | <LOW> | 12 | 8.5 | 130 | 18 | 21 | 9.4 | 143 |
| donor #4 plasma | 2.4 | <LOW> | <LOW> | 4.0 | 49 | 52 | 102 | 16 | 15 | 31 |
| donor #5 plasma | 1.7 | <LOW> | <LOW> | 7.0 | 27 | 101 | 32 | 5.5 | 1.9 | 31 |
| donor #6 plasma | 1.9 | <LOW> | <LOW> | 7.0 | 54 | 103 | 24 | 0.57 | 0.046 | 91 |
| donor #7 plasma | <LOW> | <LOW> | <LOW> | 7.4 | 15 | 106 | 43 | 11 | 21 | 735 |
| donor #8 plasma | <LOW> | 0.14 | 44 | 6.1 | 1.8 | 83 | <LOW> | 1.0 | 0.64 | 17 |
| donor #9 plasma | 1.7 | 0.042 | 42 | 7.0 | <LOW> | 77 | <LOW> | 9.9 | 2.4 | 23 |

FIG. 12J.1

| | Lymphotactin ng/mL | MCP-1 pg/mL | MDC pg/mL | MIP-1alpha pg/mL | MIP-1beta pg/mL | MMP-2 ng/mL | MMP-3 ng/mL | MMP-9 ng/mL |
|---|---|---|---|---|---|---|---|---|
| Least Detectable Dose | 0.38 | 52 | 14 | 13 | 38 | 150 | 0.20 | 37 |
| RBM Low Plasma Range | | 35 | 162 | | 25 | 183 | | |
| RBM High Plasma Range | 0.57 | 401 | 774 | 89 | 595 | 3070 | 1.8 | 1050 |
| Donor_1 3. Aliquot A | 0.22 | 8710 | 197 | 3570 | 71300 | 474 | 12 | 74 |
| Donor_1 3. Aliquot B | <LOW> | 4230 | 187 | 1810 | 12800 | 440 | 11 | 53 |
| Donor_1 3. Aliquot C | <LOW> | 1210 | 180 | 94 | 610 | 71 | 12 | 30 |
| Donor_1 3. Aliquot D | 0.071 | 3940 | 203 | 3760 | 75700 | 443 | 13 | 56 |
| Donor_1 3. Aliquot E | 0.092 | 4040 | 185 | 1370 | 16800 | 456 | 12 | 57 |
| Donor_1 3. Aliquot F | <LOW> | 2120 | 146 | 197 | 2040 | 410 | 11 | 33 |
| Donor_1 3. Aliquot G | <LOW> | 8970 | <LOW> | 110 | 498 | 451 | 13 | 49 |
| Donor_1 3. Aliquot H | <LOW> | 1080 | 41 | 81 | 513 | 68 | 12 | 46 |
| Donor_1 3. Aliquot I | <LOW> | 1030 | 193 | 180 | 803 | 427 | 11 | 38 |
| Donor_2 3. Aliquot A | 0.26 | 9540 | 158 | 5430 | 94800 | 105 | 11 | 59 |
| Donor_2 3. Aliquot B | 0.22 | 3930 | 178 | 2250 | 52800 | 83 | 11 | 59 |
| Donor_2 3. Aliquot C | <LOW> | 499 | 160 | 91 | 1790 | 86 | 12 | 42 |
| Donor_2 3. Aliquot D | 0.28 | 3760 | 165 | 34700 | 460000 | 100 | 13 | 60 |
| Donor_2 3. Aliquot E | 0.25 | 4260 | 154 | 23000 | 331000 | 123 | 11 | 53 |
| Donor_2 3. Aliquot F | <LOW> | 810 | 141 | 191 | 4280 | 69 | 11 | 2.2 |
| Donor_2 3. Aliquot G | 0.28 | 42600 | <LOW> | 29600 | 95800 | 147 | 11 | 28 |
| Donor_2 3. Aliquot H | <LOW> | 917 | 33 | 360 | 7090 | 86 | 11 | 55 |
| Donor_2 3. Aliquot I | <LOW> | 555 | 156 | 179 | 5430 | 72 | 9.7 | 51 |
| Donor_3 3. Aliquot A | 0.33 | 11000 | 92 | 894 | 31700 | 30 | 5.4 | 72 |
| Donor_3 3. Aliquot B | 0.23 | 3820 | 86 | 387 | 17200 | 26 | 4.8 | 59 |
| Donor_3 3. Aliquot C | 0.15 | 228 | 87 | 46 | 1850 | 34 | 5.0 | 55 |
| Donor_3 3. Aliquot D | 0.32 | 2630 | 84 | 8550 | 254000 | 47 | 4.9 | 91 |
| Donor_3 3. Aliquot E | 0.39 | 2870 | 72 | 3710 | 126000 | 34 | 5.3 | 74 |
| Donor_3 3. Aliquot F | 0.39 | 246 | 70 | 66 | 2900 | 34 | 4.4 | 54 |
| Donor_3 3. Aliquot G | 0.21 | 521 | <LOW> | 60 | 1680 | 67 | 4.3 | 45 |
| Donor_3 3. Aliquot H | <LOW> | 126 | 12 | 42 | 633 | 23 | 3.9 | 49 |
| Donor_3 3. Aliquot I | 0.54 | 110 | 85 | 46 | 123 | <LOW> | 4.7 | 42 |
| Donor_4 3. Aliquot A | <LOW> | 2430 | 324 | 432 | 13100 | <LOW> | 7.5 | 26 |

FIG. 12J.2

| | Lymphotactin ng/mL | MCP-1 pg/mL | MDC pg/mL | MIP-1alpha pg/mL | MIP-1beta pg/mL | MMP-2 ng/mL | MMP-3 ng/mL | MMP-9 ng/mL |
|---|---|---|---|---|---|---|---|---|
| Least Detectable Dose | 0.38 | 52 | 14 | 13 | 38 | 150 | 0.20 | 37 |
| RBM Low Plasma Range | | 35 | 162 | | 25 | | | |
| RBM High Plasma Range | 0.57 | 401 | 774 | 89 | 595 | 183 | 1.8 | 1050 |
| Donor_4 3. Aliquot B | <LOW> | 2960 | 346 | 288 | 9460 | 3070 | 7.5 | 26 |
| Donor_4 3. Aliquot C | <LOW> | 578 | 280 | 137 | 994 | <LOW> | 6.8 | 4.9 |
| Donor_4 3. Aliquot D | 0.16 | 14900 | 335 | 31200 | 484000 | <LOW> | 7.4 | 27 |
| Donor_4 3. Aliquot E | 0.20 | 15800 | 259 | 17700 | 293000 | 43 | 6.6 | 49 |
| Donor_4 3. Aliquot F | 0.12 | 15400 | 251 | 1740 | 84100 | 50 | 6.6 | 14 |
| Donor_4 3. Aliquot G | <LOW> | 6110 | <LOW> | 547 | 3900 | <LOW> | 5.6 | 16 |
| Donor_4 3. Aliquot H | <LOW> | 641 | 66 | 106 | 3160 | 45 | 7.2 | 26 |
| Donor_4 3. Aliquot I | <LOW> | 269 | 298 | 63 | 287 | 15 | 6.8 | 9.3 |
| Donor_5 3. Aliquot A | 0.31 | 11900 | 298 | 6820 | 150000 | <LOW> | 21 | 46 |
| Donor_5 3. Aliquot B | 0.33 | 7660 | 424 | 9780 | 174000 | 106 | 19 | 43 |
| Donor_5 3. Aliquot C | 0.15 | 226 | 221 | 111 | 1790 | 112 | 21 | 52 |
| Donor_5 3. Aliquot D | 0.36 | 3740 | 190 | 36200 | 543000 | 115 | 19 | 78 |
| Donor_5 3. Aliquot E | 0.33 | 5360 | 205 | 46800 | 600000 | 132 | 20 | 57 |
| Donor_5 3. Aliquot F | 0.071 | 2920 | 171 | 1790 | 24300 | 138 | 16 | 55 |
| Donor_5 3. Aliquot G | 0.22 | 14900 | <LOW> | 527 | 3130 | 67 | 20 | 28 |
| Donor_5 3. Aliquot H | <LOW> | 523 | 55 | 328 | 5000 | 120 | 20 | 60 |
| Donor_5 3. Aliquot I | <LOW> | 231 | 218 | 119 | 3870 | 90 | 20 | 62 |
| Donor_6 3. Aliquot A | 0.72 | 3750 | 124 | 1810 | 27400 | 83 | 2.8 | 74 |
| Donor_6 3. Aliquot B | 0.72 | 2190 | 124 | 1690 | 22200 | 12 | 3.0 | 76 |
| Donor_6 3. Aliquot C | 0.62 | 218 | 110 | 55 | 376 | 15 | 2.5 | 33 |
| Donor_6 3. Aliquot D | 0.80 | 1360 | 136 | 29200 | 402000 | <LOW> | 2.9 | 80 |
| Donor_6 3. Aliquot E | 0.69 | 990 | 110 | 36100 | 441000 | 20 | 2.6 | 99 |
| Donor_6 3. Aliquot F | 0.79 | 2110 | 94 | 491 | 7470 | 28 | 2.6 | 18 |
| Donor_6 3. Aliquot G | 0.50 | 3670 | <LOW> | 800 | 3130 | <LOW> | 2.3 | 46 |
| Donor_6 3. Aliquot H | 0.50 | 240 | 29 | 143 | 3680 | 75 | 2.8 | 39 |
| Donor_6 3. Aliquot I | 0.52 | 146 | 113 | 49 | 317 | <LOW> | 2.7 | 32 |

FIG. 12J.3

| | Lymphotactin ng/mL | MCP-1 pg/mL | MDC pg/mL | MIP-1alpha pg/mL | MIP-1beta pg/mL | MMP-2 ng/mL | MMP-3 ng/mL | MMP-9 ng/mL |
|---|---|---|---|---|---|---|---|---|
| Least Detectable Dose | 0.38 | 52 | 14 | 13 | 38 | 150 | 0.20 | 37 |
| RBM Low Plasma Range | | 35 | 162 | 89 | 25 | 183 | 1.8 | 1050 |
| RBM High Plasma Range | 0.57 | 401 | 774 | 6080 | 595 | 3070 | 16 | 55 |
| Donor_7 3. Aliquot A | 0.96 | 14700 | 94 | 6080 | 188000 | 16 | 16 | 66 |
| Donor_7 3. Aliquot B | 0.78 | 5090 | 99 | 2700 | 68500 | <LOW> | 16 | <LOW> |
| Donor_7 3. Aliquot C | 0.53 | 314 | 83 | 46 | 680 | <LOW> | 16 | 79 |
| Donor_7 3. Aliquot D | 0.75 | 5040 | 92 | 7530 | 349000 | 23 | 14 | 60 |
| Donor_7 3. Aliquot E | 0.83 | 8810 | 96 | 4790 | 179000 | 23 | 15 | 2.2 |
| Donor_7 3. Aliquot F | 0.88 | 1260 | 72 | 152 | 5030 | <LOW> | 15 | 44 |
| Donor_7 3. Aliquot G | 0.24 | 3610 | <LOW> | 469 | 2280 | 47 | 15 | 30 |
| Donor_7 3. Aliquot H | 0.33 | 309 | 17 | 43 | 762 | <LOW> | 14 | 4.9 |
| Donor_7 3. Aliquot I | 0.53 | 265 | 84 | 38 | 156 | <LOW> | 15 | 8.2 |
| Donor_8 3. Aliquot A | 0.93 | 4750 | 223 | 1840 | 22700 | 37 | 3.4 | 26 |
| Donor_8 3. Aliquot B | 0.96 | 3720 | 221 | 1450 | 21000 | 37 | 3.5 | 23 |
| Donor_8 3. Aliquot C | 0.91 | 5420 | 154 | 2130 | 58500 | 23 | 2.8 | 94 |
| Donor_8 3. Aliquot D | 1.1 | 2170 | 337 | 67800 | 572000 | 89 | 3.9 | 81 |
| Donor_8 3. Aliquot E | 1.2 | 4380 | 245 | 46800 | 387000 | 75 | 3.4 | 31 |
| Donor_8 3. Aliquot F | 1.2 | 12700 | 138 | 6380 | 129000 | 53 | 3.6 | 9.3 |
| Donor_8 3. Aliquot G | 0.47 | 1940 | <LOW> | 931 | 7690 | 58 | 3.2 | 42 |
| Donor_8 3. Aliquot H | 0.80 | 7890 | 90 | 3290 | 29900 | 43 | 3.6 | 4.9 |
| Donor_8 3. Aliquot I | 0.80 | 385 | 256 | 266 | 4590 | 26 | 3.2 | 27 |
| Donor_9 3. Aliquot A | 0.68 | 5430 | 169 | 1250 | 24500 | 38 | 4.3 | 59 |
| Donor_9 3. Aliquot B | 0.73 | 3060 | 175 | 1690 | 23200 | 43 | 4.8 | 36 |
| Donor_9 3. Aliquot C | 0.69 | 16600 | 180 | 2140 | 46900 | 72 | 4.2 | 111 |
| Donor_9 3. Aliquot D | 0.62 | 6120 | 196 | 42300 | 431000 | 132 | 4.7 | 123 |
| Donor_9 3. Aliquot E | 0.71 | 9540 | 194 | 29700 | 355000 | 82 | 4.9 | 4.6 |
| Donor_9 3. Aliquot F | 0.86 | 12800 | 142 | 2410 | 78800 | 46 | 4.3 | 27 |
| Donor_9 3. Aliquot G | 0.20 | 15500 | <LOW> | 1820 | 12300 | 95 | 3.9 | 45 |
| Donor_9 3. Aliquot H | 0.38 | 2420 | 70 | 467 | 14400 | 48 | 4.3 | 13 |
| Donor_9 3. Aliquot I | 0.53 | 346 | 181 | 240 | 3670 | 42 | 3.6 | |

EDTA Plasma

FIG. 12J.4

| | Lymphotactin ng/mL | MCP-1 pg/mL | MDC pg/mL | MIP-1alpha pg/mL | MIP-1beta pg/mL | MMP-2 ng/mL | MMP-3 ng/mL | MMP-9 ng/mL |
|---|---|---|---|---|---|---|---|---|
| Least Detectable Dose | 0.38 | 52 | 14 | 13 | 38 | 150 | 0.20 | 37 |
| RBM Low Plasma Range | | 35 | 162 | | 25 | 183 | | |
| RBM High Plasma Range | 0.57 | 401 | 774 | 89 | 595 | 3070 | 1.8 | 1050 |
| donor #1 plasma | <LOW> | 230 | 187 | 69 | 209 | 1750 | 0.12 | 211 |
| donor #2 plasma | <LOW> | 66 | 236 | 60 | 239 | 3910 | 0.047 | 1340 |
| donor #3 plasma | 0.12 | 11 | 116 | 41 | 65 | 1540 | <LOW> | 653 |
| donor #4 plasma | <LOW> | 23 | 413 | 59 | 368 | 8190 | <LOW> | 194 |
| donor #5 plasma | 0.12 | 17 | 307 | 46 | 154 | 898 | 0.076 | 236 |
| donor #6 plasma | 0.28 | 32 | 155 | 34 | 68 | 972 | <LOW> | 367 |
| donor #7 plasma | 0.42 | 109 | 124 | 48 | 145 | 2270 | 0.090 | 115 |
| donor #8 plasma | 0.31 | 147 | 176 | 42 | 47 | 10 | 3.7 | 30 |
| donor #9 plasma | 0.33 | 89 | 159 | 44 | <LOW> | 46 | 4.2 | 3.2 |

FIG. 12K.1

| | Myeloperoxidase | Myoglobin | OSM (Oncostatin M) | PAI-1 | Prostatic Acid Phosphatase | PAPP-A |
|---|---|---|---|---|---|---|
| | ng/mL | ng/mL | pg/mL | ng/mL | ng/mL | mIU/mL |
| Least Detectable Dose | 68 | 1.1 | 28 | 0.90 | 0.034 | 0.037 |
| RBM Low Plasma Range | | 3.6 | PENDING | 10 | 0.058 | |
| RBM High Plasma Range | 1110 | 37 | PENDING | 87 | 0.54 | 0.48 |
| Donor_1 3. Aliquot A | 2010 | 85 | 312 | 159 | 0.12 | 0.079 |
| Donor_1 3. Aliquot B | 1590 | 94 | 188 | 171 | 0.11 | 0.082 |
| Donor_1 3. Aliquot C | 1390 | 101 | 21 | 172 | 0.045 | 0.059 |
| Donor_1 3. Aliquot D | 2050 | 102 | 143 | 156 | 0.11 | 0.054 |
| Donor_1 3. Aliquot E | 2330 | 90 | 312 | 152 | 0.12 | 0.062 |
| Donor_1 3. Aliquot F | 1970 | 95 | 120 | 135 | 0.041 | 0.073 |
| Donor_1 3. Aliquot G | 1750 | 104 | 422 | 187 | 0.086 | 0.11 |
| Donor_1 3. Aliquot H | 1740 | 95 | <LOW> | 184 | 0.078 | 0.087 |
| Donor_1 3. Aliquot I | 1380 | 89 | 76 | 160 | 0.035 | 0.049 |
| Donor_2 3. Aliquot A | 3520 | 60 | 603 | 178 | 0.24 | 0.023 |
| Donor_2 3. Aliquot B | 2910 | 62 | 334 | 190 | 0.24 | 0.032 |
| Donor_2 3. Aliquot C | 1540 | 61 | <LOW> | 155 | 0.16 | 0.0049 |
| Donor_2 3. Aliquot D | 4180 | 58 | 222 | 165 | 0.46 | 0.024 |
| Donor_2 3. Aliquot E | 3380 | 60 | 188 | 161 | 0.38 | 0.022 |
| Donor_2 3. Aliquot F | 1610 | 63 | 65 | 156 | 0.12 | 0.018 |
| Donor_2 3. Aliquot G | 3280 | 64 | 765 | 205 | 0.33 | 0.043 |
| Donor_2 3. Aliquot H | 4200 | 59 | 82 | 177 | 0.14 | 0.023 |
| Donor_2 3. Aliquot I | 1730 | 57 | 44 | 164 | 0.13 | 0.018 |
| Donor_3 3. Aliquot A | 2890 | 165 | 301 | 246 | 0.24 | 0.0063 |
| Donor_3 3. Aliquot B | 2640 | 150 | 329 | 221 | 0.22 | <LOW> |
| Donor_3 3. Aliquot C | 2210 | 164 | 98 | 199 | 0.16 | <LOW> |
| Donor_3 3. Aliquot D | 3310 | 159 | 395 | 225 | 0.41 | 0.0049 |
| Donor_3 3. Aliquot E | 3500 | 172 | 466 | 208 | 0.47 | 0.024 |
| Donor_3 3. Aliquot F | 2630 | 152 | 109 | 216 | 0.16 | 0.0063 |
| Donor_3 3. Aliquot G | 2240 | 162 | 705 | 246 | 0.17 | <LOW> |
| Donor_3 3. Aliquot H | 2830 | 143 | 165 | 207 | 0.14 | 0.0049 |
| Donor_3 3. Aliquot I | 2450 | 150 | 98 | 214 | 0.14 | <LOW> |
| Donor_4 3. Aliquot A | 2710 | 55 | <LOW> | 253 | 0.27 | 0.13 |

FIG. 12K.2

| | Myeloperoxidase | Myoglobin | OSM (Oncostatin M) | PAI-1 | Prostatic Acid Phosphatase | PAPP-A |
|---|---|---|---|---|---|---|
| | ng/mL | ng/mL | pg/mL | ng/mL | ng/mL | mIU/mL |
| Least Detectable Dose | 68 | 1.1 | 28 | 0.90 | 0.034 | 0.037 |
| RBM Low Plasma Range | | 3.6 | PENDING | 10 | 0.058 | |
| RBM High Plasma Range | 1110 | 37 | PENDING | 87 | 0.54 | 0.48 |
| Donor_4_3. Aliquot B | 1940 | 52 | 54 | 236 | 0.38 | 0.14 |
| Donor_4_3. Aliquot C | 3400 | 54 | <LOW> | 229 | 0.28 | 0.029 |
| Donor_4_3. Aliquot D | 3920 | 52 | 120 | 216 | 0.42 | 0.13 |
| Donor_4_3. Aliquot E | 4430 | 53 | 165 | 222 | 0.46 | 0.15 |
| Donor_4_3. Aliquot F | 4210 | 56 | <LOW> | 237 | 0.26 | 0.14 |
| Donor_4_3. Aliquot G | 1950 | 56 | 455 | 203 | 0.56 | 0.16 |
| Donor_4_3. Aliquot H | 4140 | 55 | 76 | 219 | 0.23 | 0.13 |
| Donor_4_3. Aliquot I | 3360 | 55 | 21 | 235 | 0.26 | 0.12 |
| Donor_5_3. Aliquot A | 6630 | 92 | 844 | 158 | 0.46 | 0.021 |
| Donor_5_3. Aliquot B | 6720 | 93 | 834 | 183 | 0.73 | 0.021 |
| Donor_5_3. Aliquot C | 4350 | 97 | 171 | 144 | 0.28 | 0.0078 |
| Donor_5_3. Aliquot D | 7840 | 92 | 1850 | 145 | 1.5 | 0.040 |
| Donor_5_3. Aliquot E | 7880 | 91 | 2320 | 155 | 2.9 | 0.032 |
| Donor_5_3. Aliquot F | 5110 | 87 | 188 | 167 | 0.27 | 0.018 |
| Donor_5_3. Aliquot G | 3130 | 96 | 1040 | 181 | 0.52 | 0.029 |
| Donor_5_3. Aliquot H | 6880 | 87 | 834 | 156 | 0.50 | 0.014 |
| Donor_5_3. Aliquot I | 4080 | 82 | 211 | 147 | 0.27 | 0.014 |
| Donor_6_3. Aliquot A | 2300 | 52 | 82 | 192 | 0.13 | 0.0056 |
| Donor_6_3. Aliquot B | 2240 | 50 | 109 | 174 | 0.24 | <LOW> |
| Donor_6_3. Aliquot C | 2640 | 52 | <LOW> | 152 | 0.22 | <LOW> |
| Donor_6_3. Aliquot D | 1490 | 52 | 65 | 181 | 0.26 | <LOW> |
| Donor_6_3. Aliquot E | 1800 | 50 | 87 | 153 | 0.38 | 0.0063 |
| Donor_6_3. Aliquot F | 2660 | 54 | <LOW> | 173 | 0.15 | <LOW> |
| Donor_6_3. Aliquot G | 1430 | 54 | 715 | 250 | 0.54 | <LOW> |
| Donor_6_3. Aliquot H | 2490 | 50 | 65 | 181 | 0.12 | <LOW> |
| Donor_6_3. Aliquot I | 2270 | 51 | <LOW> | 176 | 0.17 | <LOW> |

FIG. 12K.3

| | Myeloperoxidase | Myoglobin | OSM (Oncostatin M) | PAI-1 | Prostatic Acid Phosphatase | PAPP-A |
|---|---|---|---|---|---|---|
| | ng/mL | ng/mL | pg/mL | ng/mL | ng/mL | mIU/mL |
| Least Detectable Dose | 68 | 1.1 | 28 | 0.90 | 0.034 | 0.037 |
| RBM Low Plasma Range | 1110 | 3.6 | PENDING | 10 | 0.058 | 0.48 |
| RBM High Plasma Range | | 37 | PENDING | 87 | 0.54 | |
| Donor_7_3, Aliquot A | 2070 | 1790 | 194 | 210 | 0.10 | 0.012 |
| Donor_7_3, Aliquot B | 2710 | >1845 | 109 | 222 | 0.16 | 0.011 |
| Donor_7_3, Aliquot C | 1920 | >1845 | <LOW> | 215 | 0.068 | <LOW> |
| Donor_7_3, Aliquot D | 1780 | >1845 | 21 | 215 | 0.19 | 0.0085 |
| Donor_7_3, Aliquot E | 2160 | >1845 | 54 | 230 | 0.12 | 0.0049 |
| Donor_7_3, Aliquot F | 2150 | >1845 | <LOW> | 225 | 0.078 | <LOW> |
| Donor_7_3, Aliquot G | 1630 | >1845 | 143 | 229 | 0.063 | <LOW> |
| Donor_7_3, Aliquot H | 1880 | 1780 | 44 | 198 | 0.087 | 0.0092 |
| Donor_7_3, Aliquot I | 1800 | >1845 | <LOW> | 198 | 0.073 | <LOW> |
| Donor_8_3, Aliquot A | 1510 | 5.2 | <LOW> | 32 | 0.082 | 0.0070 |
| Donor_8_3, Aliquot B | 1450 | 3.7 | <LOW> | 35 | 0.13 | 0.0056 |
| Donor_8_3, Aliquot C | 3790 | 3.3 | <LOW> | 31 | 0.16 | <LOW> |
| Donor_8_3, Aliquot D | 8210 | 3.1 | 345 | 30 | 0.67 | 0.015 |
| Donor_8_3, Aliquot E | 6150 | 3.2 | 132 | 34 | 0.55 | 0.0092 |
| Donor_8_3, Aliquot F | 2590 | 3.2 | <LOW> | 30 | 0.15 | 0.0056 |
| Donor_8_3, Aliquot G | 1220 | 2.9 | 132 | 60 | 0.058 | 0.0092 |
| Donor_8_3, Aliquot H | 4710 | 3.3 | 54 | 41 | 0.14 | 0.014 |
| Donor_8_3, Aliquot I | 2000 | 3.5 | <LOW> | 40 | 0.079 | 0.0078 |
| Donor_9_3, Aliquot A | 1430 | 2.1 | <LOW> | 45 | 0.052 | 0.0053 |
| Donor_9_3, Aliquot B | 1150 | 1.9 | <LOW> | 63 | 0.088 | <LOW> |
| Donor_9_3, Aliquot C | 2030 | 1.7 | <LOW> | 71 | 0.074 | <LOW> |
| Donor_9_3, Aliquot D | 3500 | 1.3 | 96 | 72 | 0.50 | 0.013 |
| Donor_9_3, Aliquot E | 4800 | 1.9 | 42 | 65 | 0.34 | <LOW> |
| Donor_9_3, Aliquot F | 747 | 2.1 | <LOW> | 66 | 0.052 | 0.0077 |
| Donor_9_3, Aliquot G | 1560 | 1.7 | 247 | 97 | 0.040 | 0.010 |
| Donor_9_3, Aliquot H | 3250 | 2.1 | 42 | 71 | 0.037 | <LOW> |
| Donor_9_3, Aliquot I | 1070 | 2.1 | <LOW> | 70 | 0.034 | <LOW> |
| EDTA Plasma | | | | | | |

FIG. 12K.4

| | Myeloperoxidase | Myoglobin | OSM (Oncostatin M) | PAI-1 | Prostatic Acid Phosphatase | PAPP-A |
|---|---|---|---|---|---|---|
| | ng/mL | ng/mL | pg/mL | ng/mL | ng/mL | mIU/mL |
| Least Detectable Dose | 68 | 1.1 | 28 | 0.90 | 0.034 | 0.037 |
| RBM Low Plasma Range | | 3.6 | PENDING | 10 | 0.058 | |
| RBM High Plasma Range | 1110 | 37 | PENDING | 87 | 0.54 | 0.48 |
| donor #1 plasma | 111 | 77 | 1120 | 142 | 0.090 | 0.084 |
| donor #2 plasma | 158 | 64 | <LOW> | 151 | 0.13 | 0.052 |
| donor #3 plasma | 85 | 182 | <LOW> | 208 | 0.050 | 0.029 |
| donor #4 plasma | 322 | 61 | <LOW> | 218 | 0.65 | 0.26 |
| donor #5 plasma | 372 | 86 | <LOW> | 154 | 0.41 | 0.040 |
| donor #6 plasma | 9.9 | 57 | 151 | 149 | 0.15 | 0.017 |
| donor #7 plasma | 135 | >1845 | 133 | 242 | 0.078 | 0.066 |
| donor #8 plasma | 183 | 3.8 | <LOW> | 39 | 0.13 | 0.010 |
| donor #9 plasma | <LOW> | 1.4 | <LOW> | 61 | 0.071 | <LOW> |

FIG. 12L.1

| | Prostate Specific Antigen, Free | RANTES | Serum Amyloid P | Stem Cell Factor | SGOT | SHBG |
|---|---|---|---|---|---|---|
| | ng/mL | ng/mL | ug/mL | pg/mL | ug/mL | nmol/L |
| Least Detectable Dose | 0.023 | 0.048 | 0.058 | 56 | 3.7 | 1.3 |
| | | | | | | |
| RBM Low Plasma Range | | 2.6 | 15 | 281 | 3.9 | 12 |
| RBM High Plasma Range | 1.6 | 83 | 50 | 281 | 28 | 106 |
| Donor_1 3. Aliquot A | 0.44 | 16 | 26 | 757 | <LOW> | 18 |
| Donor_1 3. Aliquot B | 0.44 | 25 | 28 | 587 | <LOW> | 19 |
| Donor_1 3. Aliquot C | 0.47 | 22 | 28 | 599 | <LOW> | 19 |
| Donor_1 3. Aliquot D | 0.50 | 18 | 33 | 657 | <LOW> | 19 |
| Donor_1 3. Aliquot E | 0.47 | 14 | 29 | 666 | <LOW> | 19 |
| Donor_1 3. Aliquot F | 0.41 | 14 | 29 | 430 | <LOW> | 18 |
| Donor_1 3. Aliquot G | 0.50 | 24 | 26 | 645 | <LOW> | 19 |
| Donor_1 3. Aliquot H | 0.43 | 26 | 29 | 508 | <LOW> | 19 |
| Donor_1 3. Aliquot I | 0.45 | 19 | 29 | 508 | <LOW> | 18 |
| | | | | | | |
| Donor_2 3. Aliquot A | 0.11 | 20 | 22 | 1350 | <LOW> | 34 |
| Donor_2 3. Aliquot B | 0.11 | 24 | 26 | 1530 | <LOW> | 35 |
| Donor_2 3. Aliquot C | 0.072 | 15 | 23 | 607 | <LOW> | 36 |
| Donor_2 3. Aliquot D | 0.20 | 13 | 24 | 1640 | <LOW> | 35 |
| Donor_2 3. Aliquot E | 0.16 | 13 | 26 | 1670 | <LOW> | 34 |
| Donor_2 3. Aliquot F | 0.087 | 13 | 23 | 582 | <LOW> | 36 |
| Donor_2 3. Aliquot G | 0.13 | 21 | 22 | 1760 | <LOW> | 34 |
| Donor_2 3. Aliquot H | 0.083 | 13 | 27 | 595 | <LOW> | 36 |
| Donor_2 3. Aliquot I | 0.082 | 12 | 23 | 500 | <LOW> | 33 |
| | | | | | | |
| Donor_3 3. Aliquot A | 0.67 | 16 | 14 | 666 | <LOW> | 42 |
| Donor_3 3. Aliquot B | 0.65 | 21 | 14 | 434 | <LOW> | 40 |
| Donor_3 3. Aliquot C | 0.72 | 17 | 17 | 213 | <LOW> | 43 |
| Donor_3 3. Aliquot D | 0.71 | 16 | 15 | 882 | <LOW> | 39 |
| Donor_3 3. Aliquot E | 0.73 | 21 | 15 | 1020 | <LOW> | 42 |
| Donor_3 3. Aliquot F | 0.65 | 13 | 16 | 202 | <LOW> | 40 |
| Donor_3 3. Aliquot G | 0.74 | 26 | 15 | 183 | <LOW> | 41 |
| Donor_3 3. Aliquot H | 0.57 | 13 | 16 | 113 | <LOW> | 38 |
| Donor_3 3. Aliquot I | 0.61 | 14 | 16 | 138 | <LOW> | 36 |
| | | | | | | |
| Donor_4 3. Aliquot A | <LOW> | 4.4 | 8.7 | 426 | <LOW> | 54 |

FIG. 12L.2

| | Prostate Specific Antigen, Free | RANTES | Serum Amyloid P | Stem Cell Factor | SGOT | SHBG |
|---|---|---|---|---|---|---|
| | ng/mL | ng/mL | ug/mL | pg/mL | ug/mL | nmol/L |
| Least Detectable Dose | 0.023 | 0.048 | 0.058 | 56 | 3.7 | 1.3 |
| RBM Low Plasma Range | | 2.6 | 15 | | 3.9 | 12 |
| RBM High Plasma Range | 1.6 | 83 | 50 | 281 | 28 | 106 |
| Donor_4_3. Aliquot B | <LOW> | 4.6 | 9.6 | 475 | <LOW> | 53 |
| Donor_4_3. Aliquot C | <LOW> | 2.7 | 9.9 | 377 | <LOW> | 54 |
| Donor_4_3. Aliquot D | 0.045 | 3.4 | 10 | 957 | <LOW> | 55 |
| Donor_4_3. Aliquot E | <LOW> | 2.6 | 10 | 1010 | <LOW> | 50 |
| Donor_4_3. Aliquot F | <LOW> | 2.5 | 12 | 459 | <LOW> | 58 |
| Donor_4_3. Aliquot G | <LOW> | 5.9 | 8.8 | 459 | <LOW> | 57 |
| Donor_4_3. Aliquot H | <LOW> | 2.5 | 11 | 405 | <LOW> | 53 |
| Donor_4_3. Aliquot I | <LOW> | 3.2 | 10 | 352 | <LOW> | 51 |
| Donor_5_3. Aliquot A | 0.49 | 17 | 43 | 936 | <LOW> | 33 |
| Donor_5_3. Aliquot B | 0.48 | 13 | 41 | 815 | <LOW> | 31 |
| Donor_5_3. Aliquot C | 0.42 | 11 | 38 | 320 | <LOW> | 35 |
| Donor_5_3. Aliquot D | 0.61 | 14 | 46 | 965 | <LOW> | 31 |
| Donor_5_3. Aliquot E | 0.57 | 14 | 45 | 1290 | <LOW> | 31 |
| Donor_5_3. Aliquot F | 0.39 | 9.5 | 38 | 288 | 0.62 | 31 |
| Donor_5_3. Aliquot G | 0.45 | 16 | 40 | 541 | <LOW> | 32 |
| Donor_5_3. Aliquot H | 0.46 | 12 | 43 | 292 | <LOW> | 29 |
| Donor_5_3. Aliquot I | 0.49 | 9.0 | 41 | 348 | <LOW> | 29 |
| Donor_6_3. Aliquot A | 0.35 | 35 | 25 | 217 | <LOW> | 18 |
| Donor_6_3. Aliquot B | 0.40 | 34 | 27 | 187 | <LOW> | 19 |
| Donor_6_3. Aliquot C | 0.34 | 23 | 24 | 99 | <LOW> | 19 |
| Donor_6_3. Aliquot D | 0.44 | 35 | 31 | 272 | <LOW> | 19 |
| Donor_6_3. Aliquot E | 0.40 | 23 | 26 | 316 | <LOW> | 18 |
| Donor_6_3. Aliquot F | 0.31 | 20 | 26 | 99 | <LOW> | 17 |
| Donor_6_3. Aliquot G | 0.33 | 47 | 22 | 164 | <LOW> | 19 |
| Donor_6_3. Aliquot H | 0.33 | 22 | 23 | 69 | <LOW> | 18 |
| Donor_6_3. Aliquot I | 0.35 | 23 | 25 | 92 | <LOW> | 18 |

FIG. 12L.3

| | Prostate Specific Antigen, Free | RANTES | Serum Amyloid P | Stem Cell Factor | SGOT | SHBG |
|---|---|---|---|---|---|---|
| | ng/mL | ng/mL | ug/mL | pg/mL | ug/mL | nmol/L |
| Least Detectable Dose | 0.023 | 0.048 | 0.058 | 56 | 3.7 | 1.3 |
| RBM Low Plasma Range | | 2.6 | 15 | | 3.9 | 12 |
| RBM High Plasma Range | 1.6 | 83 | 50 | 281 | 28 | 106 |
| Donor_7_3. Aliquot A | 0.65 | 17 | 31 | 998 | 8.2 | 9.5 |
| Donor_7_3. Aliquot B | 0.63 | 17 | 35 | 607 | 12 | 11 |
| Donor_7_3. Aliquot C | 0.65 | 25 | 33 | 113 | 8.1 | 12 |
| Donor_7_3. Aliquot D | 0.61 | 19 | 30 | 790 | 11 | 10 |
| Donor_7_3. Aliquot E | 0.66 | 15 | 29 | 707 | 13 | 8.8 |
| Donor_7_3. Aliquot F | 0.57 | 9.7 | 35 | 127 | 11 | 10 |
| Donor_7_3. Aliquot G | 0.68 | 23 | 29 | 160 | 4.3 | 9.4 |
| Donor_7_3. Aliquot H | 0.64 | 12 | 31 | 72 | 16 | 9.7 |
| Donor_7_3. Aliquot I | 0.60 | 12 | 34 | 127 | 11 | 9.9 |
| Donor_8_3. Aliquot A | <LOW> | 12 | 5.7 | 92 | <LOW> | 65 |
| Donor_8_3. Aliquot B | <LOW> | 16 | 6.4 | 46 | <LOW> | 66 |
| Donor_8_3. Aliquot C | <LOW> | 17 | 5.4 | 69 | <LOW> | 61 |
| Donor_8_3. Aliquot D | 0.18 | 12 | 5.7 | 106 | <LOW> | 60 |
| Donor_8_3. Aliquot E | 0.13 | 14 | 5.9 | 72 | <LOW> | 62 |
| Donor_8_3. Aliquot F | <LOW> | 6.9 | 6.7 | 40 | <LOW> | 67 |
| Donor_8_3. Aliquot G | <LOW> | 19 | 5.2 | 99 | <LOW> | 57 |
| Donor_8_3. Aliquot H | <LOW> | 15 | 6.4 | 89 | <LOW> | 69 |
| Donor_8_3. Aliquot I | <LOW> | 17 | 6.5 | 56 | <LOW> | 64 |
| Donor_9_3. Aliquot A | <LOW> | 16 | Pending | 170 | <LOW> | Pending |
| Donor_9_3. Aliquot B | <LOW> | 21 | Pending | 229 | <LOW> | Pending |
| Donor_9_3. Aliquot C | <LOW> | 23 | Pending | 229 | <LOW> | Pending |
| Donor_9_3. Aliquot D | 0.18 | 21 | Pending | 307 | <LOW> | Pending |
| Donor_9_3. Aliquot E | 0.10 | 13 | Pending | 272 | <LOW> | Pending |
| Donor_9_3. Aliquot F | <LOW> | 9.1 | Pending | 137 | <LOW> | Pending |
| Donor_9_3. Aliquot G | <LOW> | 30 | Pending | 528 | <LOW> | Pending |
| Donor_9_3. Aliquot H | <LOW> | 21 | Pending | 97 | <LOW> | Pending |
| Donor_9_3. Aliquot I | <LOW> | 21 | Pending | 174 | <LOW> | Pending |
| EDTA Plasma | | | | | | |

FIG. 12L.4

| | Prostate Specific Antigen, Free | RANTES | Serum Amyloid P | Stem Cell Factor | SGOT | SHBG |
|---|---|---|---|---|---|---|
| | ng/mL | ng/mL | ug/mL | pg/mL | ug/mL | nmol/L |
| Least Detectable Dose | 0.023 | 0.048 | 0.058 | 56 | 3.7 | 1.3 |
| RBM Low Plasma Range | | 2.6 | 15 | | 3.9 | 12 |
| RBM High Plasma Range | 1.6 | 83 | 50 | 281 | 28 | 106 |
| donor #1 plasma | 0.28 | 9.4 | Pending | 351 | 40 | Pending |
| donor #2 plasma | 0.13 | 3.4 | Pending | 492 | 45 | Pending |
| donor #3 plasma | 0.74 | 6.4 | Pending | 161 | 54 | Pending |
| donor #4 plasma | <LOW> | 1.3 | Pending | 368 | 32 | Pending |
| donor #5 plasma | 0.47 | 8.7 | Pending | 550 | 70 | Pending |
| donor #6 plasma | 0.45 | 14 | Pending | 62 | 35 | Pending |
| donor #7 plasma | 0.82 | 12 | Pending | 212 | 46 | Pending |
| donor #8 plasma | 0.024 | 5.3 | Pending | 161 | <LOW> | Pending |
| donor #9 plasma | <LOW> | 1.2 | Pending | 203 | <LOW> | Pending |

FIG. 12M.1

| | Thyroxine Binding Globulin | Tissue Factor | TGF-alpha | TIMP-1 | TNF RII | TNF-alpha | TNF-beta |
|---|---|---|---|---|---|---|---|
| | ug/mL | ng/mL | pg/mL | ng/mL | ng/mL | pg/mL | pg/mL |
| Least Detectable Dose | 0.34 | 0.84 | 1.8 | 8.4 | 0.13 | 4.0 | 46 |
| RBM Low Plasma Range | 40 | | Pending | 59 | 3.1 | 27 | 120 |
| RBM High Plasma Range | 104 | 2.4 | Pending | 192 | 79 | 236 | 7.9 |
| Donor_1 3. Aliquot A | 27 | 3.7 | 22 | 521 | 29 | 75 | <LOW> |
| Donor_1 3. Aliquot B | 31 | 2.7 | 15 | 615 | 31 | 19 | <LOW> |
| Donor_1 3. Aliquot C | 29 | 0.91 | 1.8 | 611 | 28 | 300 | <LOW> |
| Donor_1 3. Aliquot D | 31 | 3.3 | 9.7 | 620 | 30 | 88 | <LOW> |
| Donor_1 3. Aliquot E | 29 | 3.0 | 13 | 549 | 29 | 35 | <LOW> |
| Donor_1 3. Aliquot F | 29 | 2.0 | 3.8 | 553 | 27 | 24 | <LOW> |
| Donor_1 3. Aliquot G | 29 | 2.0 | 24 | 645 | 30 | 19 | <LOW> |
| Donor_1 3. Aliquot H | 26 | 1.8 | 1.5 | 580 | 27 | 25 | <LOW> |
| Donor_1 3. Aliquot I | 28 | 1.6 | 1.6 | 495 | 24 | | |
| Donor_2 3. Aliquot A | 36 | 1.7 | 56 | 354 | 47 | 212 | 4.6 |
| Donor_2 3. Aliquot B | 37 | 1.9 | 44 | 391 | 49 | 94 | 6.0 |
| Donor_2 3. Aliquot C | 36 | <LOW> | 7.5 | 303 | 41 | 12 | <LOW> |
| Donor_2 3. Aliquot D | 38 | 7.1 | 46 | 359 | 45 | 2700 | 6.0 |
| Donor_2 3. Aliquot E | 37 | 3.5 | 43 | 376 | 48 | 1690 | 3.2 |
| Donor_2 3. Aliquot F | 39 | 0.47 | 5.6 | 305 | 40 | 24 | <LOW> |
| Donor_2 3. Aliquot G | 38 | 2.3 | 48 | 499 | 47 | 544 | 18 |
| Donor_2 3. Aliquot H | 34 | <LOW> | 20 | 304 | 40 | 21 | <LOW> |
| Donor_2 3. Aliquot I | 37 | 0.70 | 9.5 | 278 | 36 | 19 | <LOW> |
| Donor_3 3. Aliquot A | 56 | 1.9 | 20 | 183 | 14 | 157 | 7.3 |
| Donor_3 3. Aliquot B | 50 | 1.8 | 22 | 209 | 13 | 64 | <LOW> |
| Donor_3 3. Aliquot C | 57 | 0.15 | 5.6 | 156 | 8.1 | 13 | <LOW> |
| Donor_3 3. Aliquot D | 52 | 5.4 | 18 | 213 | 14 | 2600 | 14 |
| Donor_3 3. Aliquot E | 52 | 4.9 | 16 | 221 | 14 | 1150 | 11 |
| Donor_3 3. Aliquot F | 53 | 1.5 | 4.4 | 154 | 7.9 | 26 | <LOW> |
| Donor_3 3. Aliquot G | 54 | <LOW> | 15 | 205 | 10.0 | 21 | <LOW> |
| Donor_3 3. Aliquot H | 49 | 0.56 | 2.1 | 155 | 6.8 | 9.4 | <LOW> |
| Donor_3 3. Aliquot I | 51 | 0.99 | 0.63 | 153 | 6.5 | 4.2 | <LOW> |
| Donor_4 3. Aliquot A | 38 | 1.5 | 15 | 575 | 30 | 20 | <LOW> |

FIG. 12M.2

| | Thyroxine Binding Globulin | Tissue Factor | TGF-alpha | TIMP-1 | TNF RII | TNF-alpha | TNF-beta |
|---|---|---|---|---|---|---|---|
| | ug/mL | ng/mL | pg/mL | ng/mL | ng/mL | pg/mL | pg/mL |
| Least Detectable Dose | 0.34 | 0.84 | 1.8 | 8.4 | 0.13 | 4.0 | 46 |
| RBM Low Plasma Range | 40 | | Pending | 59 | 3.1 | 27 | |
| RBM High Plasma Range | 104 | 2.4 | Pending | 192 | 79 | 17 | 120 |
| Donor_4_3. Aliquot B | 35 | 0.87 | 22 | 590 | 30 | 17 | <LOW> |
| Donor_4_3. Aliquot C | 35 | <LOW> | 6.4 | 532 | 26 | 12 | <LOW> |
| Donor_4_3. Aliquot D | 34 | 5.4 | 19 | 622 | 33 | 1720 | 7.3 |
| Donor_4_3. Aliquot E | 35 | 3.4 | 16 | 632 | 36 | 618 | 15 |
| Donor_4_3. Aliquot F | 36 | 1.5 | 4.6 | 565 | 31 | 91 | 7.3 |
| Donor_4_3. Aliquot G | 36 | <LOW> | 16 | 499 | 30 | 12 | <LOW> |
| Donor_4_3. Aliquot H | 32 | 0.99 | 3.5 | 546 | 27 | 9.3 | <LOW> |
| Donor_4_3. Aliquot I | 35 | <LOW> | 3.8 | 557 | 28 | 4.8 | <LOW> |
| Donor_5_3. Aliquot A | 47 | 0.87 | 22 | 344 | 28 | 106 | 7.9 |
| Donor_5_3. Aliquot B | 47 | 0.87 | 20 | 368 | 31 | 146 | 7.3 |
| Donor_5_3. Aliquot C | 42 | <LOW> | 7.3 | 184 | 23 | 12 | <LOW> |
| Donor_5_3. Aliquot D | 45 | 6.3 | 17 | 327 | 34 | 1900 | 9.8 |
| Donor_5_3. Aliquot E | 46 | 4.4 | 23 | 360 | 35 | 1590 | 16 |
| Donor_5_3. Aliquot F | 43 | 0.15 | 7.1 | 233 | 23 | 105 | <LOW> |
| Donor_5_3. Aliquot G | 44 | <LOW> | 25 | 331 | 27 | 18 | 8.6 |
| Donor_5_3. Aliquot H | 40 | 0.56 | 7.0 | 228 | 23 | 12 | <LOW> |
| Donor_5_3. Aliquot I | 42 | <LOW> | 7.6 | 190 | 22 | 12 | <LOW> |
| Donor_6_3. Aliquot A | 29 | <LOW> | 13 | 139 | 5.5 | 41 | 6.6 |
| Donor_6_3. Aliquot B | 30 | <LOW> | 15 | 165 | 6.9 | 23 | 4.6 |
| Donor_6_3. Aliquot C | 27 | <LOW> | 1.2 | 111 | 2.5 | 3.2 | <LOW> |
| Donor_6_3. Aliquot D | 29 | 3.0 | 12 | 156 | 6.8 | 1910 | <LOW> |
| Donor_6_3. Aliquot E | 28 | 5.1 | 16 | 164 | 7.8 | 3210 | <LOW> |
| Donor_6_3. Aliquot F | 30 | <LOW> | 1.2 | 124 | 4.1 | 9.1 | <LOW> |
| Donor_6_3. Aliquot G | 30 | <LOW> | 11 | 260 | 5.1 | 12 | <LOW> |
| Donor_6_3. Aliquot H | 27 | <LOW> | 3.8 | 112 | 3.0 | 8.0 | 8.6 |
| Donor_6_3. Aliquot I | 28 | <LOW> | 1.5 | 100 | 2.4 | 1.7 | <LOW> |

FIG. 12M.3

| | Thyroxine Binding Globulin | Tissue Factor | TGF-alpha | TIMP-1 | TNF RII | TNF-alpha | TNF-beta |
|---|---|---|---|---|---|---|---|
| | ug/mL | ng/mL | pg/mL | ng/mL | ng/mL | pg/mL | pg/mL |
| Least Detectable Dose | 0.34 | 0.84 | 1.8 | 8.4 | 0.13 | 4.0 | 46 |
| RBM Low Plasma Range | 40 | | Pending | 59 | 3.1 | 27 | 120 |
| RBM High Plasma Range | 104 | 2.4 | Pending | 192 | 79 | 240 | 24 |
| Donor_7 3. Aliquot A | 25 | 2.4 | 9.2 | 210 | 14 | 67 | 14 |
| Donor_7 3. Aliquot B | 27 | 1.9 | 4.8 | 237 | 14 | 4.3 | 7.9 |
| Donor_7 3. Aliquot C | 25 | <LOW> | <LOW> | 198 | 7.8 | 1250 | 8.6 |
| Donor_7 3. Aliquot D | 25 | 4.1 | 4.6 | 241 | 13 | 338 | 19 |
| Donor_7 3. Aliquot E | 19 | 2.4 | 3.4 | 243 | 13 | 19 | 9.8 |
| Donor_7 3. Aliquot F | 26 | 0.15 | <LOW> | 187 | 8.4 | 17 | <LOW> |
| Donor_7 3. Aliquot G | 23 | <LOW> | 4.7 | 213 | 10.0 | 5.1 | <LOW> |
| Donor_7 3. Aliquot H | 22 | <LOW> | <LOW> | 158 | 6.4 | 2.7 | <LOW> |
| Donor_7 3. Aliquot I | 25 | 0.15 | <LOW> | 159 | 7.0 | | |
| Donor_8 3. Aliquot A | 31 | 1.2 | 2.7 | 84 | 3.8 | 129 | 7.9 |
| Donor_8 3. Aliquot B | 30 | <LOW> | 3.4 | 118 | 5.1 | 49 | 6.0 |
| Donor_8 3. Aliquot C | 29 | <LOW> | 2.7 | 50 | 1.7 | 184 | <LOW> |
| Donor_8 3. Aliquot D | 28 | 13 | 6.2 | 60 | 3.8 | 12200 | 11 |
| Donor_8 3. Aliquot E | 29 | 12 | 5.5 | 88 | 4.7 | 7570 | 11 |
| Donor_8 3. Aliquot F | 31 | 0.47 | 1.9 | 52 | 3.2 | 591 | 9.8 |
| Donor_8 3. Aliquot G | 27 | <LOW> | 4.2 | 118 | 2.8 | 22 | <LOW> |
| Donor_8 3. Aliquot H | 29 | 0.65 | 2.8 | 60 | 2.5 | 113 | 3.9 |
| Donor_8 3. Aliquot I | 31 | 0.65 | <LOW> | 61 | 1.9 | 14 | <LOW> |
| Donor_9 3. Aliquot A | Pending | 1.2 | 19 | 66 | 3.6 | 78 | 11 |
| Donor_9 3. Aliquot B | Pending | 2.0 | 16 | 92 | 4.4 | 51 | 8.8 |
| Donor_9 3. Aliquot C | Pending | 0.66 | 18 | 62 | 3.3 | 68 | 20 |
| Donor_9 3. Aliquot D | Pending | 15 | 18 | 69 | 5.2 | 6000 | 15 |
| Donor_9 3. Aliquot E | Pending | 8.6 | 20 | 93 | 5.6 | 4600 | 5.0 |
| Donor_9 3. Aliquot F | Pending | 2.1 | 12 | 48 | 2.7 | 81 | 18 |
| Donor_9 3. Aliquot G | Pending | 1.8 | 20 | 130 | 3.9 | 55 | 6.9 |
| Donor_9 3. Aliquot H | Pending | 1.5 | 12 | 56 | 2.5 | 22 | 10 |
| Donor_9 3. Aliquot I | Pending | 0.53 | 8.5 | 53 | 1.9 | 13 | <LOW> |
| EDTA Plasma | | | | | | | |

FIG. 12M.4

| | Thyroxine Binding Globulin | Tissue Factor | TGF-alpha | TIMP-1 | TNF RII | TNF-alpha | TNF-beta |
|---|---|---|---|---|---|---|---|
| | ug/mL | ng/mL | pg/mL | ng/mL | ng/mL | pg/mL | pg/mL |
| Least Detectable Dose | 0.34 | 0.84 | 1.8 | 8.4 | 0.13 | 4.0 | 46 |
| RBM Low Plasma Range | 40 | | Pending | 59 | 3.1 | 27 | 120 |
| RBM High Plasma Range | 104 | 2.4 | Pending | 192 | 79 | 14 | 10 |
| donor #1 plasma | Pending | 2.9 | <LOW> | 379 | 27 | 5.4 | <LOW> |
| donor #2 plasma | Pending | 1.1 | 1.2 | 248 | 51 | 5.4 | 8.8 |
| donor #3 plasma | Pending | 1.9 | <LOW> | 144 | 8.2 | 1.1 | <LOW> |
| donor #4 plasma | Pending | 2.0 | <LOW> | 478 | 34 | 2.3 | 11 |
| donor #5 plasma | Pending | 2.1 | <LOW> | 166 | 28 | <LOW> | 5.0 |
| donor #6 plasma | Pending | 0.95 | <LOW> | 82 | 2.6 | <LOW> | 13 |
| donor #7 plasma | Pending | 1.9 | <LOW> | 156 | 9.5 | 5.6 | <LOW> |
| donor #8 plasma | Pending | 1.0 | <LOW> | 40 | 1.2 | <LOW> | <LOW> |
| donor #9 plasma | Pending | 0.74 | 4.4 | 31 | 1.5 | <LOW> | <LOW> |

FIG. 12N.1

| | Thrombopoietin | Thyroid Stimulating Hormone | Thrombospondin-1 | VCAM-1 | VEGF |
|---|---|---|---|---|---|
| | ng/mL | uIU/mL | ng/mL | ng/mL | pg/mL |
| Least Detectable Dose | 3.2 | 0.028 | <25 | 2.6 | 7.5 |
| RBM Low Plasma Range | | | Pending | 284 | 91 |
| RBM High Plasma Range | | | Pending | 1310 | 1790 |
| Donor_1 3. Aliquot A | 6.2 | 3.7 | 15200 | 1350 | 2090 |
| Donor_1 3. Aliquot B | 1.9 | 17 | 21600 | 1440 | 2090 |
| Donor_1 3. Aliquot C | 1.5 | 16 | 17000 | 1350 | 2070 |
| Donor_1 3. Aliquot D | <LOW> | 18 | 15600 | 1420 | 2120 |
| Donor_1 3. Aliquot E | 1.9 | 17 | 13100 | 1320 | 2030 |
| Donor_1 3. Aliquot F | 1.9 | 17 | 12500 | 1310 | 1860 |
| Donor_1 3. Aliquot G | <LOW> | 17 | 11800 | 1450 | 2570 |
| Donor_1 3. Aliquot H | 1.3 | 17 | 24900 | 1320 | 2210 |
| Donor_1 3. Aliquot I | 0.86 | 17 | 16200 | 1350 | 1940 |
| | 0.69 | 17 | | | |
| Donor_2 3. Aliquot A | 2.7 | 10 | 19800 | 1090 | 4570 |
| Donor_2 3. Aliquot B | 3.2 | 10 | 21600 | 1190 | 4900 |
| Donor_2 3. Aliquot C | <LOW> | 9.9 | 12200 | 1160 | 5240 |
| Donor_2 3. Aliquot D | 2.4 | 12 | 13600 | 1070 | 4400 |
| Donor_2 3. Aliquot E | 2.7 | 11 | 12400 | 1150 | 4630 |
| Donor_2 3. Aliquot F | 1.5 | 10 | 12800 | 1100 | 4870 |
| Donor_2 3. Aliquot G | 3.0 | 9.9 | 12000 | 1180 | 5490 |
| Donor_2 3. Aliquot H | <LOW> | 9.5 | 13300 | 1090 | 4920 |
| Donor_2 3. Aliquot I | 0.49 | 9.1 | 12400 | 1080 | 4680 |
| Donor_3 3. Aliquot A | 2.5 | 0.99 | 14000 | 749 | 532 |
| Donor_3 3. Aliquot B | 2.5 | 0.98 | 18300 | 722 | 618 |
| Donor_3 3. Aliquot C | <LOW> | 0.99 | 12000 | 740 | 707 |
| Donor_3 3. Aliquot D | 2.2 | 1.1 | 13700 | 725 | 505 |
| Donor_3 3. Aliquot E | 3.9 | 1.2 | 16800 | 775 | 508 |
| Donor_3 3. Aliquot F | 2.1 | 0.94 | 10500 | 695 | 714 |
| Donor_3 3. Aliquot G | <LOW> | 1.0 | 12200 | 758 | 1590 |
| Donor_3 3. Aliquot H | <LOW> | 0.90 | 9670 | 694 | 678 |
| Donor_3 3. Aliquot I | 2.1 | 0.98 | 9250 | 690 | 734 |
| Donor_4 3. Aliquot A | 1.3 | 0.15 | 14100 | 2080 | 1190 |

FIG. 12N.2

| | Thrombopoietin | Thyroid Stimulating Hormone | Thrombospondin-1 | VCAM-1 | VEGF |
|---|---|---|---|---|---|
| | ng/mL | uIU/mL | ng/mL | ng/mL | pg/mL |
| Least Detectable Dose | 3.2 | 0.028 | <25 | 2.6 | 7.5 |
| RBM Low Plasma Range | | 0.18 | Pending | 284 | 91 |
| RBM High Plasma Range | 6.2 | 3.7 | Pending | 1310 | 1790 |
| Donor_4 3. Aliquot B | 1.4 | 0.15 | 16300 | 1940 | 1180 |
| Donor_4 3. Aliquot C | <LOW> | 0.16 | 4160 | 1990 | 1220 |
| Donor_4 3. Aliquot D | 2.0 | 0.26 | 11500 | 1950 | 1100 |
| Donor_4 3. Aliquot E | 2.3 | 0.19 | 10900 | 2070 | 1060 |
| Donor_4 3. Aliquot F | 1.2 | 0.14 | 5780 | 2200 | 1030 |
| Donor_4 3. Aliquot G | <LOW> | 0.13 | 4050 | 1970 | 2190 |
| Donor_4 3. Aliquot H | 1.2 | 0.14 | 4460 | 1980 | 1350 |
| Donor_4 3. Aliquot I | <LOW> | 0.13 | 6360 | 2020 | 1280 |
| Donor_5 3. Aliquot A | 2.9 | 0.28 | 22300 | 521 | 3600 |
| Donor_5 3. Aliquot B | 3.1 | 0.26 | 17800 | 510 | 3460 |
| Donor_5 3. Aliquot C | 0.69 | 0.32 | 13300 | 489 | 4460 |
| Donor_5 3. Aliquot D | 2.8 | 0.41 | 18600 | 525 | 3350 |
| Donor_5 3. Aliquot E | 2.7 | 0.38 | 17800 | 539 | 3650 |
| Donor_5 3. Aliquot F | 2.2 | 0.24 | 13200 | 495 | 3140 |
| Donor_5 3. Aliquot G | 1.0 | 0.28 | 14000 | 545 | 5580 |
| Donor_5 3. Aliquot H | 0.49 | 0.26 | 14800 | 510 | 3840 |
| Donor_5 3. Aliquot I | 0.49 | 0.26 | 10900 | 489 | 3520 |
| Donor_6 3. Aliquot A | 3.6 | 1.3 | 25000 | 258 | 874 |
| Donor_6 3. Aliquot B | 3.7 | 1.2 | 22900 | 252 | 648 |
| Donor_6 3. Aliquot C | 3.1 | 1.3 | 13800 | 261 | 840 |
| Donor_6 3. Aliquot D | 3.4 | 1.4 | 21100 | 274 | 530 |
| Donor_6 3. Aliquot E | 3.6 | 1.3 | 13800 | 253 | 471 |
| Donor_6 3. Aliquot F | 4.0 | 1.1 | 15700 | 254 | 581 |
| Donor_6 3. Aliquot G | 2.3 | 1.3 | 12400 | 284 | 2690 |
| Donor_6 3. Aliquot H | 1.7 | 1.2 | 14500 | 258 | 878 |
| Donor_6 3. Aliquot I | 1.7 | 1.2 | 12500 | 256 | 846 |

FIG. 12N.3

| | Thrombopoietin | Thyroid Stimulating Hormone | Thrombospondin-1 | VCAM-1 | VEGF |
|---|---|---|---|---|---|
| | ng/mL | uIU/mL | ng/mL | ng/mL | pg/mL |
| Least Detectable Dose | 3.2 | 0.028 | <25 | 2.6 | 7.5 |
| | | | | | |
| RBM Low Plasma Range | | 0.18 | Pending | 284 | 91 |
| RBM High Plasma Range | 6.2 | 3.7 | Pending | 1310 | 1790 |
| Donor_7_3. Aliquot A | 4.2 | 0.52 | 12100 | 789 | 295 |
| Donor_7_3. Aliquot B | 4.3 | 0.51 | 14600 | 802 | 237 |
| Donor_7_3. Aliquot C | 1.4 | 0.49 | 15800 | 861 | 345 |
| Donor_7_3. Aliquot D | 3.3 | 0.55 | 11600 | 740 | 210 |
| Donor_7_3. Aliquot E | 3.8 | 0.50 | 11200 | 816 | 235 |
| Donor_7_3. Aliquot F | 3.5 | 0.47 | 7230 | 781 | 203 |
| Donor_7_3. Aliquot G | 1.0 | 0.49 | 6360 | 803 | 1260 |
| Donor_7_3. Aliquot H | <LOW> | 0.49 | 7470 | 721 | 313 |
| Donor_7_3. Aliquot I | 2.2 | 0.47 | 7470 | 738 | 257 |
| | | | | | |
| Donor_8_3. Aliquot A | 3.6 | 2.2 | 10800 | 352 | 252 |
| Donor_8_3. Aliquot B | 4.7 | 2.1 | 14000 | 350 | 203 |
| Donor_8_3. Aliquot C | 4.4 | 1.8 | 10800 | 320 | 401 |
| Donor_8_3. Aliquot D | 4.4 | 2.4 | 8580 | 319 | 416 |
| Donor_8_3. Aliquot E | 4.2 | 2.2 | 11900 | 322 | 341 |
| Donor_8_3. Aliquot F | 5.6 | 2.0 | 4870 | 341 | 321 |
| Donor_8_3. Aliquot G | 1.4 | 1.9 | 5370 | 337 | 822 |
| Donor_8_3. Aliquot H | 3.7 | 2.2 | 12600 | 331 | 322 |
| Donor_8_3. Aliquot I | 3.8 | 2.0 | 13200 | 347 | 248 |
| | | | | | |
| Donor_9_3. Aliquot A | 3.2 | 0.34 | 13600 | 298 | 326 |
| Donor_9_3. Aliquot B | 3.4 | 0.28 | 16400 | 303 | 280 |
| Donor_9_3. Aliquot C | 3.6 | 0.33 | 15500 | 324 | 367 |
| Donor_9_3. Aliquot D | 2.9 | 0.65 | 13800 | 295 | 486 |
| Donor_9_3. Aliquot E | 3.1 | 0.53 | 11300 | 312 | 398 |
| Donor_9_3. Aliquot F | 4.3 | 0.29 | 6910 | 314 | 322 |
| Donor_9_3. Aliquot G | 1.2 | 0.22 | 9900 | 297 | 1170 |
| Donor_9_3. Aliquot H | 1.8 | 0.31 | 15900 | 297 | 380 |
| Donor_9_3. Aliquot I | 2.3 | 0.28 | 17000 | 290 | 243 |
| EDTA Plasma | | | | | |

FIG. 12N.4

| | Thrombopoietin | Thyroid Stimulating Hormone | Thrombospondin-1 | VCAM-1 | VEGF |
|---|---|---|---|---|---|
| | ng/mL | uIU/mL | ng/mL | ng/mL | pg/mL |
| Least Detectable Dose | 3.2 | 0.028 | <25 | 2.6 | 7.5 |
| RBM Low Plasma Range | | | | | |
| RBM High Plasma Range | 6.2 | | | | |
| donor #1 plasma | <LOW> | 0.18 | Pending | 284 | 91 |
| donor #2 plasma | <LOW> | 3.7 | Pending | 1310 | 1790 |
| donor #3 plasma | 0.81 | 12 | 14800 | 1230 | 1500 |
| donor #4 plasma | 1.4 | 9.7 | 4670 | 1280 | 4500 |
| donor #5 plasma | 1.8 | 1.0 | 7890 | 978 | 1290 |
| donor #6 plasma | 2.4 | 0.11 | 2310 | 2580 | 1400 |
| donor #7 plasma | 2.1 | 0.28 | 28600 | 577 | 3840 |
| donor #8 plasma | 1.4 | 1.7 | 16800 | 301 | 533 |
| donor #9 plasma | 0.44 | 0.59 | 13800 | 980 | 521 |
| | | 2.5 | 6520 | 340 | 281 |
| | | 0.30 | 818 | 385 | 295 |

FIG. 13A.1

| | Alpha-1 Antitrypsin | Adiponectin | Alpha-2 Macroglobulin | Alpha-Fetoprotein | Amphiregulin | Apolipoprotein A1 | Apolipoprotein CIII | Apolipoprotein H |
|---|---|---|---|---|---|---|---|---|
| Least Detectable Dose | mg/mL | ug/mL | mg/mL | ng/mL | pg/mL | mg/mL | ug/mL | ug/mL |
| | 0.011 | 0.20 | 0.061 | 0.43 | 36 | 0.0066 | 2.7 | 8.8 |
| RBM Low Plasma Range | 1.2 | 1.6 | 0.13 | | Pending | 0.19 | 28 | 131 |
| RBM High Plasma Range | 3.1 | 14 | 1.0 | 6.7 | Pending | 0.89 | 224 | 430 |
| Donor_1 3. Aliquot A | 2.6 | 2.0 | 0.29 | 2.8 | 469 | 0.10 | 52 | 138 |
| Donor_1 3. Aliquot B | 2.8 | 2.1 | 0.30 | 2.6 | 455 | 0.10 | 64 | 148 |
| Donor_1 3. Aliquot C | 2.9 | 2.1 | 0.30 | 2.3 | 104 | 0.11 | 60 | 143 |
| Donor_1 3. Aliquot D | 3.1 | 2.1 | 0.31 | 2.8 | 431 | 0.11 | 60 | 150 |
| Donor_1 3. Aliquot E | 2.8 | 2.1 | 0.27 | 2.5 | 443 | 0.11 | 53 | 141 |
| Donor_1 3. Aliquot F | 2.6 | 2.0 | 0.66 | 2.3 | 414 | 0.097 | 57 | 142 |
| Donor_1 3. Aliquot G | 2.9 | 2.1 | 0.30 | 2.5 | 401 | 0.098 | 61 | 151 |
| Donor_1 3. Aliquot H | 2.7 | 2.0 | 0.42 | 2.7 | 36 | 0.089 | 48 | 141 |
| Donor_1 3. Aliquot I | 2.7 | 2.0 | 0.26 | 2.5 | 419 | 0.11 | 60 | 150 |
| Donor_2 3. Aliquot A | 2.2 | 4.4 | 0.28 | 2.1 | 133 | 0.11 | 58 | 152 |
| Donor_2 3. Aliquot B | 2.3 | 4.5 | 0.30 | 2.3 | 50 | 0.12 | 64 | 143 |
| Donor_2 3. Aliquot C | 2.3 | 4.5 | 0.29 | 1.4 | 36 | 0.12 | 64 | 154 |
| Donor_2 3. Aliquot D | 2.2 | 4.3 | 0.29 | 3.4 | 104 | 0.098 | 48 | 142 |
| Donor_2 3. Aliquot E | 2.3 | 4.5 | 0.28 | 2.5 | 39 | 0.097 | 52 | 154 |
| Donor_2 3. Aliquot F | 2.3 | 4.2 | 0.64 | 2.0 | 36 | 0.090 | 66 | 152 |
| Donor_2 3. Aliquot G | 2.3 | 4.3 | 0.32 | 1.8 | 597 | 0.094 | 67 | 153 |
| Donor_2 3. Aliquot H | 2.2 | 4.4 | 0.33 | 1.8 | 36 | 0.095 | 61 | 148 |
| Donor_2 3. Aliquot I | 2.1 | 4.0 | 0.29 | 1.9 | 24 | 0.11 | 54 | 141 |
| Donor_3 3. Aliquot A | 2.9 | 3.0 | 0.35 | 2.7 | 36 | 0.13 | 38 | 150 |
| Donor_3 3. Aliquot B | 3.0 | 2.7 | 0.35 | 2.6 | 36 | 0.14 | 38 | 144 |
| Donor_3 3. Aliquot C | 3.0 | 2.8 | 0.34 | 1.9 | 36 | 0.13 | 41 | 153 |
| Donor_3 3. Aliquot D | 2.8 | 2.7 | 0.34 | 3.3 | 97 | 0.13 | 38 | 149 |
| Donor_3 3. Aliquot E | 3.1 | 2.8 | 0.36 | 3.5 | 116 | 0.14 | 36 | 157 |
| Donor_3 3. Aliquot F | 2.7 | 2.6 | 0.65 | 2.5 | 60 | 0.12 | 42 | 148 |
| Donor_3 3. Aliquot G | 3.1 | 2.8 | 0.35 | 1.4 | 97 | 0.15 | 44 | 149 |
| Donor_3 3. Aliquot H | 2.8 | 2.7 | 0.41 | 1.7 | 36 | 0.13 | 41 | 144 |
| Donor_3 3. Aliquot I | 2.8 | 2.6 | 0.33 | 1.3 | 39 | 0.14 | 42 | 150 |

FIG. 13A.2

| | Alpha-1 Antitrypsin | Adiponectin | Alpha-2 Macroglobulin | Alpha-Fetoprotein | Amphiregulin | Apolipoprotein A1 | Apolipoprotein CIII | Apolipoprotein H |
|---|---|---|---|---|---|---|---|---|
| Least Detectable Dose | mg/mL 0.011 | ug/mL 0.20 | mg/mL 0.061 | ng/mL 0.43 | pg/mL 36 | mg/mL 0.0066 | ug/mL 2.7 | ug/mL 8.8 |
| RBM Low Plasma Range | 1.2 | 1.6 | 0.13 | | Pending | 0.19 | 28 | 131 |
| RBM High Plasma Range | 3.1 | 14 | 1.0 | 6.7 | Pending | 0.89 | 224 | 430 |
| Donor_4_3. Aliquot A | 1.7 | 5.3 | 0.40 | 2.4 | 36 | 0.056 | 13 | 105 |
| Donor_4_3. Aliquot B | 1.5 | 5.4 | 0.40 | 2.1 | 36 | 0.050 | 12 | 96 |
| Donor_4_3. Aliquot C | 1.6 | 5.2 | 0.41 | 2.0 | 39 | 0.049 | 11 | 102 |
| Donor_4_3. Aliquot D | 1.6 | 5.3 | 0.42 | 3.6 | 36 | 0.044 | 13 | 102 |
| Donor_4_3. Aliquot E | 1.5 | 5.3 | 0.38 | 2.8 | 36 | 0.048 | 9.1 | 93 |
| Donor_4_3. Aliquot F | 1.6 | 5.3 | 0.98 | 1.8 | 36 | 0.054 | 15 | 93 |
| Donor_4_3. Aliquot G | 1.6 | 5.5 | 0.48 | 2.1 | 76 | 0.047 | 11 | 100 |
| Donor_4_3. Aliquot H | 1.5 | 5.3 | 0.65 | 2.1 | 76 | 0.051 | 11 | 91 |
| Donor_4_3. Aliquot I | 1.5 | 5.4 | 0.41 | 1.9 | 36 | 0.052 | 12 | 99 |
| Donor_5_3. Aliquot A | 2.9 | 2.8 | 0.27 | 3.2 | 127 | 0.12 | 70 | 253 |
| Donor_5_3. Aliquot B | 2.9 | 2.6 | 0.29 | 3.2 | 178 | 0.13 | 77 | 266 |
| Donor_5_3. Aliquot C | 3.2 | 2.7 | 0.29 | 2.5 | 50 | 0.14 | 77 | 265 |
| Donor_5_3. Aliquot D | 3.2 | 2.6 | 0.28 | 4.1 | 159 | 0.14 | 78 | 263 |
| Donor_5_3. Aliquot E | 3.1 | 2.8 | 0.28 | 4.0 | 187 | 0.14 | 71 | 257 |
| Donor_5_3. Aliquot F | 2.9 | 2.6 | 0.46 | 2.3 | 36 | 0.12 | 83 | 238 |
| Donor_5_3. Aliquot G | 3.0 | 2.5 | 0.29 | 3.0 | 208 | 0.14 | 78 | 246 |
| Donor_5_3. Aliquot H | 3.0 | 2.5 | 0.33 | 3.0 | 138 | 0.14 | 81 | 245 |
| Donor_5_3. Aliquot I | 3.0 | 2.4 | 0.28 | 3.3 | 39 | 0.13 | 75 | 250 |
| Donor_6_3. Aliquot A | 2.8 | 1.2 | 0.26 | 1.5 | 36 | 0.100 | 43 | 141 |
| Donor_6_3. Aliquot B | 2.7 | 1.2 | 0.24 | 1.9 | 36 | 0.10 | 42 | 148 |
| Donor_6_3. Aliquot C | 2.8 | 1.2 | 0.24 | 1.8 | 36 | 0.12 | 36 | 141 |
| Donor_6_3. Aliquot D | 2.7 | 1.2 | 0.24 | 1.9 | 36 | 0.11 | 43 | 143 |
| Donor_6_3. Aliquot E | 2.6 | 1.2 | 0.25 | 2.4 | 39 | 0.12 | 42 | 131 |
| Donor_6_3. Aliquot F | 2.7 | 1.2 | 0.25 | 1.6 | 36 | 0.094 | 45 | 143 |
| Donor_6_3. Aliquot G | 2.9 | 1.3 | 0.27 | 1.8 | 599 | 0.12 | 52 | 152 |
| Donor_6_3. Aliquot H | 2.5 | 1.3 | 0.29 | 1.6 | 36 | 0.11 | 40 | 131 |
| Donor_6_3. Aliquot I | 2.5 | 1.1 | 0.26 | 1.5 | 24 | 0.12 | 40 | 134 |

FIG. 13A.3

| | Alpha-1 Antitrypsin mg/mL 0.011 | Adiponectin ug/mL 0.20 | Alpha-2 Macroglobulin mg/mL 0.061 | Alpha-Fetoprotein ng/mL 0.43 | Amphiregulin pg/mL 36 | Apolipoprotein A1 mg/mL 0.0066 | Apolipoprotein CIII ug/mL 2.7 | Apolipoprotein H ug/mL 8.8 |
|---|---|---|---|---|---|---|---|---|
| Least Detectable Dose | | | | | | | | |
| RBM Low Plasma Range | 1.2 | 1.6 | 0.13 | | Pending | 0.19 | 28 | 131 |
| RBM High Plasma Range | 3.1 | 14 | 1.0 | 6.7 | Pending | 0.89 | 224 | 430 |
| Donor_7_3. Aliquot A | 1.8 | 0.90 | 0.39 | 1.9 | 104 | 0.14 | 50 | 180 |
| Donor_7_3. Aliquot B | 1.7 | 0.92 | 0.37 | 2.5 | 36 | 0.14 | 36 | 183 |
| Donor_7_3. Aliquot C | 1.9 | 0.83 | 0.38 | 1.3 | 36 | 0.16 | 44 | 183 |
| Donor_7_3. Aliquot D | 1.7 | 0.81 | 0.36 | 2.6 | 104 | 0.15 | 41 | 169 |
| Donor_7_3. Aliquot E | 1.2 | 0.90 | 0.40 | 2.5 | 36 | 0.12 | 33 | 138 |
| Donor_7_3. Aliquot F | 1.8 | 0.90 | 0.45 | 1.5 | 36 | 0.16 | 54 | 190 |
| Donor_7_3. Aliquot G | 1.6 | 0.87 | 0.43 | 2.2 | 370 | 0.14 | 43 | 161 |
| Donor_7_3. Aliquot H | 1.7 | 0.79 | 0.51 | 1.5 | 36 | 0.15 | 41 | 173 |
| Donor_7_3. Aliquot I | 1.8 | 0.82 | 0.38 | 1.9 | 36 | 0.13 | 42 | 173 |
| Donor_8_3. Aliquot A | 0.96 | 4.3 | 0.39 | 1.7 | 36 | 0.24 | 57 | 117 |
| Donor_8_3. Aliquot B | 0.97 | 4.3 | 0.39 | 1.3 | 36 | 0.28 | 72 | 117 |
| Donor_8_3. Aliquot C | 0.96 | 4.1 | 0.40 | 0.53 | 36 | 0.28 | 75 | 119 |
| Donor_8_3. Aliquot D | 0.88 | 4.0 | 0.39 | 4.4 | 36 | 0.26 | 55 | 111 |
| Donor_8_3. Aliquot E | 0.88 | 4.0 | 0.39 | 3.5 | 127 | 0.24 | 61 | 113 |
| Donor_8_3. Aliquot F | 0.99 | 4.5 | 0.46 | 1.6 | 50 | 0.29 | 69 | 121 |
| Donor_8_3. Aliquot G | 0.92 | 4.2 | 0.48 | 1.2 | 90 | 0.29 | 58 | 111 |
| Donor_8_3. Aliquot H | 1.0 | 4.4 | 0.58 | 1.6 | 36 | 0.25 | 59 | 127 |
| Donor_8_3. Aliquot I | 0.94 | 4.2 | 0.40 | 1.2 | 36 | 0.25 | 53 | 122 |
| Donor_9_3. Aliquot A | 1.2 | 3.5 | 0.34 | 1.1 | 51 | 0.21 | 39 | 101 |
| Donor_9_3. Aliquot B | 1.3 | 3.5 | 0.38 | 1.8 | 51 | 0.22 | 43 | 104 |
| Donor_9_3. Aliquot C | 1.3 | 3.6 | 0.41 | 2.0 | 51 | 0.21 | 33 | 96 |
| Donor_9_3. Aliquot D | 1.2 | 3.3 | 0.38 | 4.2 | 101 | 0.18 | 34 | 99 |
| Donor_9_3. Aliquot E | 1.3 | 3.7 | 0.45 | 3.2 | 42 | 0.20 | 36 | 105 |
| Donor_9_3. Aliquot F | 1.2 | 3.8 | 0.40 | 2.1 | 36 | 0.23 | 39 | 103 |
| Donor_9_3. Aliquot G | 1.4 | 3.5 | 0.49 | 2.1 | 169 | 0.22 | 42 | 113 |
| Donor_9_3. Aliquot H | 1.2 | 3.5 | 0.54 | 2.3 | 78 | 0.19 | 37 | 97 |
| Donor_9_3. Aliquot I | 1.3 | 3.6 | 0.36 | 1.3 | 36 | 0.21 | 33 | 97 |

FIG. 13A.4

| | Alpha-1 Antitrypsin mg/mL | Adiponectin ug/mL | Alpha-2 Macroglobulin mg/mL | Alpha-Fetoprotein ng/mL | Amphiregulin pg/mL | Apolipoprotein A1 mg/mL | Apolipoprotein CIII ug/mL | Apolipoprotein H ug/mL |
|---|---|---|---|---|---|---|---|---|
| Least Detectable Dose | 0.011 | 0.20 | 0.061 | 0.43 | 36 | 0.0066 | 2.7 | 8.8 |
| RBM Low Plasma Range | 1.2 | 1.6 | 0.13 | | Pending | 0.19 | 28 | 131 |
| RBM High Plasma Range | 3.1 | 14 | 1.0 | 6.7 | Pending | 0.89 | 224 | 430 |
| EDTA Plasma | | | | | | | | |
| donor #1 plasma | 2.9 | 2.1 | 0.25 | 2.3 | 441 | 0.069 | 34 | 127 |
| donor #2 plasma | 3.0 | 6.1 | 0.29 | 1.7 | 36 | 0.11 | 65 | 166 |
| donor #3 plasma | 4.7 | 4.2 | 0.36 | 2.9 | 36 | 0.14 | 47 | 193 |
| donor #4 plasma | 2.2 | 7.5 | 0.34 | 2.4 | 33 | 0.047 | 14 | 106 |
| donor #5 plasma | 4.4 | 3.6 | 0.25 | 3.6 | 36 | 0.12 | 91 | 316 |
| donor #6 plasma | 3.7 | 1.7 | 0.24 | 2.1 | 36 | 0.100 | 34 | 163 |
| donor #7 plasma | 2.3 | 1.3 | 0.35 | 2.8 | 78 | 0.17 | 52 | 214 |
| donor #8 plasma | 1.0 | 5.1 | 0.34 | 1.9 | 72 | 0.25 | 46 | 113 |
| donor #9 plasma | 1.9 | 4.8 | 0.37 | 2.1 | 36 | 0.30 | 39 | 147 |
| | | | | | | | | |
| Stimulations indices | | | | | | | | |
| Donor_1_3. Aliquot A | 1.0 | 1.0 | 1.1 | 1.1 | 1.1 | 0.9 | 0.9 | 0.9 |
| Donor_1_3. Aliquot B | 1.0 | 1.1 | 1.2 | 1.0 | 1.1 | 0.9 | 1.1 | 1.0 |
| Donor_1_3. Aliquot C | 1.0 | 1.0 | 1.1 | 0.9 | 0.2 | 1.0 | 1.0 | 1.0 |
| Donor_1_3. Aliquot D | 1.1 | 1.1 | 1.2 | 1.1 | 1.0 | 1.0 | 1.0 | 1.0 |
| Donor_1_3. Aliquot E | 1.0 | 1.0 | 1.0 | 1.0 | 1.1 | 1.0 | 0.9 | 0.9 |
| Donor_1_3. Aliquot F | 1.0 | 1.0 | 2.5 | 0.9 | 1.0 | 0.9 | 1.0 | 0.9 |
| Donor_1_3. Aliquot G | 1.1 | 1.0 | 1.2 | 1.0 | 1.0 | 0.9 | 1.0 | 1.0 |
| Donor_1_3. Aliquot H | 1.0 | 1.0 | 1.6 | 1.1 | 0.1 | 0.8 | 0.8 | 0.9 |
| Donor_1_3. Aliquot I | 1.0 | 1.0 | 1.0 | 1.0 | 1.0 | 1.0 | 1.0 | 1.0 |
| Donor_2_3. Aliquot A | 1.1 | 1.1 | 1.0 | 1.1 | 5.5 | 1.0 | 1.1 | 1.1 |
| Donor_2_3. Aliquot B | 1.1 | 1.1 | 1.0 | 1.2 | 2.1 | 1.2 | 1.2 | 1.1 |
| Donor_2_3. Aliquot C | 1.1 | 1.1 | 1.1 | 0.7 | 1.5 | 1.1 | 1.2 | 1.1 |
| Donor_2_3. Aliquot D | 1.1 | 1.1 | 1.0 | 1.8 | 4.3 | 0.9 | 0.9 | 1.0 |
| Donor_2_3. Aliquot E | 1.1 | 1.1 | 1.0 | 1.3 | 1.6 | 0.9 | 1.0 | 1.1 |
| Donor_2_3. Aliquot F | 1.0 | 1.0 | 2.2 | 1.1 | 1.5 | 0.8 | 1.2 | 1.1 |
| Donor_2_3. Aliquot G | 1.1 | 1.1 | 1.1 | 0.9 | 24.8 | 0.9 | 1.2 | 1.1 |

FIG. 13A.5

| | Alpha-1 Antitrypsin | Adiponectin | Alpha-2 Macroglobulin | Alpha-Fetoprotein | Amphiregulin | Apolipoprotein A1 | Apolipoprotein CIII | Apolipoprotein H |
|---|---|---|---|---|---|---|---|---|
| | mg/mL | ug/mL | mg/mL | ng/mL | pg/mL | mg/mL | ug/mL | ug/mL |
| Least Detectable Dose | 0.011 | 0.20 | 0.061 | 0.43 | 36 | 0.0066 | 2.7 | 8.8 |
| | | | | | | | | |
| RBM Low Plasma Range | 1.2 | 1.6 | 0.13 | | Pending | 0.19 | 28 | 131 |
| RBM High Plasma Range | 3.1 | 14 | 1.0 | 6.7 | Pending | 0.89 | 224 | 430 |
| Donor_2 3. Aliquot H | 1.1 | 1.1 | 1.1 | 1.0 | 1.5 | 0.9 | 1.1 | 1.0 |
| Donor_2 3. Aliquot I | 1.0 | 1.0 | 1.0 | 1.0 | 1.0 | 1.0 | 1.0 | 1.0 |
| | | | | | | | | |
| Donor_3 3. Aliquot A | 1.1 | 1.2 | 1.1 | 2.1 | 0.9 | 1.0 | 0.9 | 1.0 |
| Donor_3 3. Aliquot B | 1.1 | 1.0 | 1.0 | 2.0 | 0.9 | 1.0 | 0.9 | 1.0 |
| Donor_3 3. Aliquot C | 1.1 | 1.1 | 1.0 | 1.5 | 0.9 | 1.0 | 1.0 | 1.0 |
| Donor_3 3. Aliquot D | 1.0 | 1.1 | 1.0 | 2.5 | 2.5 | 1.0 | 0.9 | 1.0 |
| Donor_3 3. Aliquot E | 1.1 | 1.1 | 1.1 | 2.7 | 3.0 | 1.0 | 1.0 | 1.0 |
| Donor_3 3. Aliquot F | 1.1 | 1.0 | 2.0 | 1.9 | 1.5 | 0.9 | 1.0 | 1.0 |
| Donor_3 3. Aliquot G | 1.1 | 1.1 | 1.2 | 1.1 | 2.5 | 1.1 | 1.1 | 1.0 |
| Donor_3 3. Aliquot H | 1.0 | 1.0 | 1.2 | 1.3 | 0.9 | 0.9 | 1.0 | 1.0 |
| Donor_3 3. Aliquot I | 1.0 | 1.0 | 1.0 | 1.0 | 1.0 | 1.0 | 1.0 | 1.0 |
| | | | | | | | | |
| Donor_4 3. Aliquot A | 1.1 | 1.0 | 1.0 | 1.2 | 1.0 | 1.1 | 1.1 | 1.1 |
| Donor_4 3. Aliquot B | 1.0 | 1.0 | 1.0 | 1.1 | 1.0 | 1.0 | 1.0 | 1.0 |
| Donor_4 3. Aliquot C | 1.0 | 1.0 | 1.0 | 1.0 | 1.1 | 1.0 | 0.9 | 1.0 |
| Donor_4 3. Aliquot D | 1.1 | 1.0 | 1.0 | 1.9 | 1.0 | 0.8 | 1.0 | 1.0 |
| Donor_4 3. Aliquot E | 0.9 | 1.0 | 0.9 | 1.4 | 1.0 | 0.9 | 0.7 | 0.9 |
| Donor_4 3. Aliquot F | 1.0 | 1.0 | 2.4 | 0.9 | 2.1 | 0.9 | 1.2 | 0.9 |
| Donor_4 3. Aliquot G | 1.0 | 1.1 | 1.2 | 1.1 | 2.1 | 0.9 | 0.9 | 0.9 |
| Donor_4 3. Aliquot H | 1.0 | 1.0 | 1.6 | 1.1 | 1.0 | 1.0 | 1.0 | 0.9 |
| Donor_4 3. Aliquot I | 1.0 | 1.0 | 1.0 | 1.0 | 1.0 | 1.0 | 1.0 | 1.0 |
| | | | | | | | | |
| Donor_5 3. Aliquot A | 1.0 | 1.1 | 1.0 | 0.9 | 3.2 | 1.0 | 0.9 | 1.0 |
| Donor_5 3. Aliquot B | 1.0 | 1.1 | 1.0 | 1.0 | 4.5 | 1.0 | 1.0 | 1.1 |
| Donor_5 3. Aliquot C | 1.1 | 1.1 | 1.1 | 0.8 | 1.3 | 1.1 | 1.0 | 1.1 |
| Donor_5 3. Aliquot D | 1.1 | 1.1 | 1.0 | 1.2 | 4.0 | 1.1 | 1.0 | 1.1 |
| Donor_5 3. Aliquot E | 1.0 | 1.1 | 1.0 | 1.2 | 4.8 | 1.1 | 0.9 | 1.0 |
| Donor_5 3. Aliquot F | 1.0 | 1.1 | 1.7 | 0.7 | 0.9 | 1.0 | 1.1 | 1.0 |
| Donor_5 3. Aliquot G | 1.0 | 1.0 | 1.0 | 0.9 | 5.3 | 1.2 | 1.0 | 1.0 |

FIG. 13A.6

| | Alpha-1 Antitrypsin | Adiponectin | Alpha-2 Macroglobulin | Alpha-Fetoprotein | Amphiregulin | Apolipoprotein A1 | Apolipoprotein CIII | Apolipoprotein H |
|---|---|---|---|---|---|---|---|---|
| | mg/mL | ug/mL | mg/mL | ng/mL | pg/mL | mg/mL | ug/mL | ug/mL |
| Least Detectable Dose | 0.011 | 0.20 | 0.061 | 0.43 | 36 | 0.0066 | 2.7 | 8.8 |
| RBM Low Plasma Range | 1.2 | 1.6 | 0.13 | | Pending | 0.19 | 28 | 131 |
| RBM High Plasma Range | 3.1 | 14 | 1.0 | 6.7 | Pending | 0.89 | 224 | 430 |
| Donor_5 3. Aliquot H | 1.0 | 1.0 | 1.2 | 0.9 | 3.5 | 1.1 | 1.1 | 1.0 |
| Donor_5 3. Aliquot I | 1.0 | 1.0 | 1.0 | 1.0 | 1.0 | 1.0 | 1.0 | 1.0 |
| Donor_6 3. Aliquot A | 1.1 | 1.1 | 1.0 | 1.0 | 1.5 | 0.8 | 1.1 | 1.1 |
| Donor_6 3. Aliquot B | 1.1 | 1.1 | 0.9 | 1.3 | 1.5 | 0.9 | 1.0 | 1.1 |
| Donor_6 3. Aliquot C | 1.1 | 1.1 | 0.9 | 1.2 | 1.5 | 1.0 | 0.9 | 1.1 |
| Donor_6 3. Aliquot D | 1.1 | 1.1 | 1.0 | 1.3 | 1.5 | 1.0 | 1.1 | 1.1 |
| Donor_6 3. Aliquot E | 1.1 | 1.1 | 1.0 | 1.7 | 1.6 | 1.0 | 1.0 | 1.1 |
| Donor_6 3. Aliquot F | 1.1 | 1.1 | 1.1 | 1.1 | 1.5 | 0.8 | 1.0 | 1.1 |
| Donor_6 3. Aliquot G | 1.1 | 1.1 | 1.1 | 1.3 | 24.9 | 1.0 | 1.3 | 1.1 |
| Donor_6 3. Aliquot H | 1.0 | 1.0 | 1.3 | 1.1 | 1.5 | 0.9 | 1.0 | 1.0 |
| Donor_6 3. Aliquot I | 1.0 | 1.0 | 1.0 | 1.0 | 1.0 | 1.0 | 1.0 | 1.0 |
| Donor_7 3. Aliquot A | 1.0 | 1.1 | 1.0 | 1.0 | 2.9 | 1.0 | 1.2 | 1.0 |
| Donor_7 3. Aliquot B | 1.0 | 1.1 | 1.0 | 1.3 | 1.0 | 1.0 | 0.9 | 1.1 |
| Donor_7 3. Aliquot C | 1.0 | 1.0 | 1.0 | 0.7 | 1.0 | 1.2 | 1.0 | 1.1 |
| Donor_7 3. Aliquot D | 1.0 | 1.0 | 0.9 | 1.3 | 2.9 | 1.1 | 1.1 | 1.0 |
| Donor_7 3. Aliquot E | 0.7 | 1.1 | 1.0 | 1.3 | 1.0 | 0.9 | 0.8 | 0.8 |
| Donor_7 3. Aliquot F | 1.0 | 1.1 | 1.2 | 0.8 | 1.0 | 1.2 | 1.3 | 1.1 |
| Donor_7 3. Aliquot G | 0.9 | 1.1 | 1.1 | 1.2 | 10.3 | 1.2 | 1.0 | 0.9 |
| Donor_7 3. Aliquot H | 0.9 | 1.0 | 1.3 | 0.8 | 1.0 | 1.2 | 1.0 | 1.0 |
| Donor_7 3. Aliquot I | 1.0 | 1.0 | 1.0 | 1.0 | 1.0 | 1.0 | 1.0 | 1.0 |
| Donor_8 3. Aliquot A | 1.0 | 1.0 | 1.0 | 1.4 | 1.0 | 1.0 | 1.1 | 1.0 |
| Donor_8 3. Aliquot B | 1.0 | 1.0 | 1.0 | 1.1 | 1.0 | 1.1 | 1.4 | 1.0 |
| Donor_8 3. Aliquot C | 1.0 | 1.0 | 1.0 | 0.4 | 1.0 | 1.1 | 1.4 | 1.0 |
| Donor_8 3. Aliquot D | 0.9 | 0.9 | 1.0 | 3.6 | 1.0 | 1.0 | 1.0 | 0.9 |
| Donor_8 3. Aliquot E | 0.9 | 0.9 | 1.0 | 2.9 | 3.5 | 1.0 | 1.1 | 0.8 |
| Donor_8 3. Aliquot F | 1.1 | 1.1 | 1.1 | 1.3 | 1.4 | 1.2 | 1.3 | 1.0 |
| Donor_8 3. Aliquot G | 1.0 | 1.0 | 1.2 | 1.0 | 2.5 | 1.2 | 1.1 | 0.9 |

FIG. 13A.7

| | Alpha-1 Antitrypsin | Adiponectin | Alpha-2 Macroglobulin | Alpha-Fetoprotein | Amphiregulin | Apolipoprotein A1 | Apolipoprotein CIII | Apolipoprotein H |
|---|---|---|---|---|---|---|---|---|
| | mg/mL | ug/mL | mg/mL | ng/mL | pg/mL | mg/mL | ug/mL | ug/mL |
| Least Detectable Dose | 0.011 | 0.20 | 0.061 | 0.43 | 36 | 0.0066 | 2.7 | 8.8 |
| RBM Low Plasma Range | 1.2 | 1.6 | 0.13 | | Pending | 0.19 | 28 | 131 |
| RBM High Plasma Range | 3.1 | 14 | 1.0 | 6.7 | Pending | 0.89 | 224 | 430 |
| Donor_8 3. Aliquot H | 1.1 | 1.0 | 1.4 | 1.3 | 1.0 | 1.0 | 1.1 | 1.0 |
| Donor_8 3. Aliquot I | 1.0 | 1.0 | 1.0 | 1.0 | 1.0 | 1.0 | 1.0 | 1.0 |
| Donor_9 3. Aliquot A | 0.9 | 1.0 | 0.9 | 0.8 | 1.4 | 1.0 | 1.2 | 1.0 |
| Donor_9 3. Aliquot B | 1.0 | 1.0 | 1.1 | 1.4 | 1.4 | 1.0 | 1.3 | 1.1 |
| Donor_9 3. Aliquot C | 1.0 | 1.0 | 1.1 | 1.5 | 1.4 | 1.0 | 1.0 | 1.0 |
| Donor_9 3. Aliquot D | 0.9 | 0.9 | 1.1 | 3.2 | 2.8 | 0.9 | 1.0 | 1.0 |
| Donor_9 3. Aliquot E | 1.0 | 1.0 | 1.2 | 2.4 | 1.2 | 1.0 | 1.1 | 1.1 |
| Donor_9 3. Aliquot F | 0.9 | 1.1 | 1.1 | 1.6 | 1.0 | 1.1 | 1.2 | 1.1 |
| Donor_9 3. Aliquot G | 1.0 | 1.0 | 1.3 | 1.6 | 4.7 | 1.1 | 1.3 | 1.2 |
| Donor_9 3. Aliquot H | 0.9 | 1.0 | 1.5 | 1.7 | 2.2 | 0.9 | 1.1 | 1.0 |
| Donor_9 3. Aliquot I | 1.0 | 1.0 | 1.0 | 1.0 | 1.0 | 1.0 | 1.0 | 1.0 |

FIG. 13B.1

| | Beta-2 Microglobulin | Brain-Derived Neurotrophic Factor | Complement 3 | Cancer Antigen 125 | Cancer Antigen 19-9 | Calcitonin | CD40 | CD40 Ligand |
|---|---|---|---|---|---|---|---|---|
| | ug/mL | ng/mL | mg/mL | U/mL | U/mL | pg/mL | ng/mL | ng/mL |
| Least Detectable Dose | 0.013 | 0.029 | 0.0053 | 4.2 | 0.25 | 6.0 | 0.021 | 0.020 |
| RBM Low Plasma Range | 1.2 | 0.32 | 0.76 | | | | 0.17 | |
| RBM High Plasma Range | 6.2 | 16 | 2.1 | 12 | 9.2 | 12 | 1.5 | 1.1 |
| Donor_1 3. Aliquot A | 17 | 2.4 | 0.73 | 132 | 28 | 36 | 11 | 0.66 |
| Donor_1 3. Aliquot B | 15 | 3.3 | 0.71 | 123 | 28 | 32 | 9.2 | 0.82 |
| Donor_1 3. Aliquot C | 16 | 1.6 | 0.71 | 141 | 13 | 34 | 10 | 0.82 |
| Donor_1 3. Aliquot D | 16 | 2.6 | 0.71 | 157 | 28 | 37 | 9.0 | 0.60 |
| Donor_1 3. Aliquot E | 16 | 2.3 | 0.69 | 135 | 28 | 36 | 8.7 | 0.47 |
| Donor_1 3. Aliquot F | 14 | 1.3 | 1.5 | 128 | 24 | 31 | 9.3 | 0.39 |
| Donor_1 3. Aliquot G | 16 | 0.048 | 0.77 | 140 | 32 | 32 | 12 | 0.18 |
| Donor_1 3. Aliquot H | 15 | 3.4 | 1.2 | 143 | 12 | 31 | 11 | 0.55 |
| Donor_1 3. Aliquot I | 16 | 2.8 | 0.71 | 125 | 28 | 33 | 10 | 0.84 |
| Donor_2 3. Aliquot A | 20 | 3.4 | 0.92 | 121 | 476 | 29 | 16 | 0.70 |
| Donor_2 3. Aliquot B | >24 | 4.6 | 0.93 | 125 | 510 | 31 | 18 | 0.65 |
| Donor_2 3. Aliquot C | 23 | 1.3 | 0.89 | 119 | 408 | 24 | 16 | 0.61 |
| Donor_2 3. Aliquot D | 19 | 2.5 | 0.92 | 197 | 468 | 33 | 16 | 0.47 |
| Donor_2 3. Aliquot E | 20 | 2.3 | 0.94 | 158 | 488 | 31 | 19 | 0.50 |
| Donor_2 3. Aliquot F | 19 | 1.6 | 2.3 | 123 | 413 | 30 | 16 | 0.42 |
| Donor_2 3. Aliquot G | 21 | 0.49 | 0.98 | 138 | 495 | 20 | 21 | 0.28 |
| Donor_2 3. Aliquot H | 21 | 2.3 | 1.3 | 106 | 459 | 29 | 18 | 0.44 |
| Donor_2 3. Aliquot I | 19 | 1.8 | 0.90 | 102 | 447 | 26 | 17 | 0.47 |
| Donor_3 3. Aliquot A | 2.6 | 3.0 | 0.68 | 35 | 3.3 | 6 | 1.4 | 0.54 |
| Donor_3 3. Aliquot B | 2.3 | 4.5 | 0.70 | 33 | 3.6 | 5.1 | 1.7 | 0.43 |
| Donor_3 3. Aliquot C | 2.4 | 2.9 | 0.73 | 35 | 3.6 | 6 | 1.4 | 0.50 |
| Donor_3 3. Aliquot D | 2.4 | 3.4 | 0.73 | 87 | 3.3 | 6 | 1.5 | 0.52 |
| Donor_3 3. Aliquot E | 2.5 | 3.8 | 0.77 | 74 | 3.6 | 7.3 | 1.5 | 0.68 |
| Donor_3 3. Aliquot F | 2.2 | 1.6 | 1.2 | 39 | 4.1 | 6 | 1.4 | 0.36 |
| Donor_3 3. Aliquot G | 2.3 | 0.047 | 0.72 | 29 | 4.6 | 6 | 3.4 | 0.29 |
| Donor_3 3. Aliquot H | 2.3 | 2.3 | 1.1 | 27 | 3.2 | 6 | 1.4 | 0.50 |
| Donor_3 3. Aliquot I | 2.2 | 2.2 | 0.74 | 31 | 2.8 | 6 | 1.3 | 0.42 |

FIG. 13B.2

| | Beta-2 Microglobulin | Brain-Derived Neurotrophic Factor | Complement 3 | Cancer Antigen 125 | Cancer Antigen 19-9 | Calcitonin | CD40 | CD40 Ligand |
|---|---|---|---|---|---|---|---|---|
| | ug/mL | ng/mL | mg/mL | U/mL | U/mL | pg/mL | ng/mL | ng/mL |
| Least Detectable Dose | 0.013 | 0.029 | 0.0053 | 4.2 | 0.25 | 6.0 | 0.021 | 0.020 |
| RBM Low Plasma Range | 1.2 | 0.32 | 0.76 | | | | 0.17 | |
| RBM High Plasma Range | 6.2 | 16 | 2.1 | 12 | 9.2 | 12 | 1.5 | 1.1 |
| Donor_4_3. Aliquot A | 7.6 | 2.0 | 0.45 | 512 | 15 | 18 | 4.3 | 0.20 |
| Donor_4_3. Aliquot B | 7.2 | 2.8 | 0.41 | 495 | 16 | 20 | 4.7 | 0.18 |
| Donor_4_3. Aliquot C | 8.0 | 0.49 | 0.45 | 462 | 15 | 15 | 4.3 | 0.088 |
| Donor_4_3. Aliquot D | 7.7 | 1.6 | 0.43 | 542 | 16 | 19 | 4.0 | 0.13 |
| Donor_4_3. Aliquot E | 8.3 | 1.0 | 0.44 | 520 | 20 | 16 | 4.3 | 0.13 |
| Donor_4_3. Aliquot F | 8.5 | 0.88 | 0.80 | 465 | 16 | 15 | 4.0 | 0.083 |
| Donor_4_3. Aliquot G | 8.1 | 0.049 | 0.43 | 462 | 17 | 10 | 4.9 | 0.063 |
| Donor_4_3. Aliquot H | 8.2 | 0.53 | 0.69 | 509 | 15 | 17 | 4.0 | 0.081 |
| Donor_4_3. Aliquot I | 8.0 | 1.2 | 0.43 | 494 | 15 | 17 | 3.9 | 0.092 |
| Donor_5_3. Aliquot A | 12 | 5.8 | 0.72 | 21 | 8.8 | 105 | 18 | 0.51 |
| Donor_5_3. Aliquot B | 13 | 4.5 | 0.76 | 21 | 9.2 | 97 | 18 | 0.34 |
| Donor_5_3. Aliquot C | 13 | 2.3 | 0.77 | 21 | 9.9 | 74 | 19 | 0.32 |
| Donor_5_3. Aliquot D | 13 | 2.9 | 0.78 | 87 | 10 | 92 | 20 | 0.40 |
| Donor_5_3. Aliquot E | 15 | 4.5 | 0.73 | 74 | 10 | 90 | 21 | 0.47 |
| Donor_5_3. Aliquot F | 11 | 2.3 | 1.2 | 12 | 7.1 | 86 | 18 | 0.29 |
| Donor_5_3. Aliquot G | 12 | 0.16 | 0.80 | 20 | 8.6 | 67 | 19 | 0.24 |
| Donor_5_3. Aliquot H | 13 | 4.8 | 1.1 | 16 | 8.9 | 101 | 18 | 0.32 |
| Donor_5_3. Aliquot I | 11 | 3.1 | 0.72 | 17 | 8.0 | 94 | 17 | 0.27 |
| Donor_6_3. Aliquot A | 1.2 | 4.4 | 0.73 | 29 | 3.7 | 6 | 0.98 | 0.88 |
| Donor_6_3. Aliquot B | 1.1 | 3.4 | 0.77 | 42 | 2.6 | 6 | 1.1 | 0.77 |
| Donor_6_3. Aliquot C | 1.2 | 1.1 | 0.72 | 24 | 4.4 | 6 | 1.0 | 0.61 |
| Donor_6_3. Aliquot D | 1.2 | 3.9 | 0.75 | 82 | 3.9 | 6 | 1.0 | 0.95 |
| Donor_6_3. Aliquot E | 1.2 | 2.1 | 0.67 | 85 | 3.5 | 6 | 0.96 | 0.60 |
| Donor_6_3. Aliquot F | 1.2 | 1.9 | 0.71 | 27 | 2.9 | 6 | 0.90 | 0.47 |
| Donor_6_3. Aliquot G | 1.2 | 0.064 | 0.78 | 28 | 5.2 | 6 | 3.8 | 0.30 |
| Donor_6_3. Aliquot H | 1.1 | 3.1 | 1.1 | 23 | 3.7 | 6 | 0.81 | 0.45 |
| Donor_6_3. Aliquot I | 1.1 | 1.7 | 0.68 | 29 | 3.0 | 6 | 0.73 | 0.45 |

FIG. 13B.3

| | Beta-2 Microglobulin | Brain-Derived Neurotrophic Factor | Complement 3 | Cancer Antigen 125 | Cancer Antigen 19-9 | Calcitonin | CD40 | CD40 Ligand |
|---|---|---|---|---|---|---|---|---|
| | ug/mL | ng/mL | mg/mL | U/mL | U/mL | pg/mL | ng/mL | ng/mL |
| Least Detectable Dose | 0.013 | 0.029 | 0.0053 | 4.2 | 0.25 | 6.0 | 0.021 | 0.020 |
| RBM Low Plasma Range | 1.2 | 0.32 | 0.76 | | | | 0.17 | 1.1 |
| RBM High Plasma Range | 6.2 | 16 | 2.1 | 12 | 9.2 | 12 | 1.5 | |
| Donor_7_3. Aliquot A | 2.0 | 2.8 | 0.67 | 53 | 5.3 | 1.5 | 0.93 | 0.25 |
| Donor_7_3. Aliquot B | 2.0 | 3.1 | 0.68 | 48 | 5.1 | 6 | 0.89 | 0.21 |
| Donor_7_3. Aliquot C | 2.1 | 2.2 | 0.73 | 39 | 5.1 | 6 | 0.77 | 0.40 |
| Donor_7_3. Aliquot D | 2.0 | 2.9 | 0.66 | 91 | 4.8 | 6 | 0.73 | 0.30 |
| Donor_7_3. Aliquot E | 2.1 | 2.3 | 0.51 | 53 | 5.2 | 6 | 0.62 | 0.20 |
| Donor_7_3. Aliquot F | 1.9 | 1.2 | 0.72 | 40 | 4.7 | 6 | 0.61 | 0.11 |
| Donor_7_3. Aliquot G | 1.9 | 0.043 | 0.74 | 38 | 7.8 | 6 | 1.8 | 0.071 |
| Donor_7_3. Aliquot H | 1.9 | 1.6 | 1.1 | 34 | 5.2 | 6 | 0.71 | 0.18 |
| Donor_7_3. Aliquot I | 1.9 | 1.6 | 0.67 | 39 | 3.7 | 3.3 | 0.50 | 0.15 |
| Donor_8_3. Aliquot A | 1.2 | 3.3 | 0.45 | 5.6 | 4.9 | 6 | 0.57 | 0.32 |
| Donor_8_3. Aliquot B | 1.2 | 5.3 | 0.49 | 9.0 | 3.9 | 6 | 0.60 | 0.42 |
| Donor_8_3. Aliquot C | 1.2 | 3.2 | 0.43 | 4.4 | 3.9 | 6 | 0.63 | 0.51 |
| Donor_8_3. Aliquot D | 1.2 | 4.5 | 0.44 | 164 | 5.5 | 4.6 | 0.72 | 0.33 |
| Donor_8_3. Aliquot E | 1.2 | 6.0 | 0.43 | 136 | 5.1 | 6.5 | 0.63 | 0.49 |
| Donor_8_3. Aliquot F | 1.3 | 2.3 | 0.51 | 16 | 4.5 | 6 | 0.49 | 0.15 |
| Donor_8_3. Aliquot G | 1.2 | 0.060 | 0.44 | 9.0 | 5.2 | 6 | 1.8 | 0.13 |
| Donor_8_3. Aliquot H | 1.2 | 6.3 | 0.72 | 13 | 4.0 | 6 | 0.60 | 0.49 |
| Donor_8_3. Aliquot I | 1.2 | 6.1 | 0.46 | 15 | 3.6 | 6 | 0.65 | 0.45 |
| Donor_9_3. Aliquot A | 0.83 | 2.5 | 0.39 | 14 | 3.0 | 6 | 0.69 | 0.37 |
| Donor_9_3. Aliquot B | 0.79 | 3.5 | 0.39 | 11 | 3.3 | 6 | 0.69 | 0.43 |
| Donor_9_3. Aliquot C | 0.93 | 1.2 | 0.39 | 21 | 3.3 | 6 | 0.69 | 0.51 |
| Donor_9_3. Aliquot D | 0.87 | 3.7 | 0.37 | 140 | 6.0 | 3.9 | 0.81 | 0.46 |
| Donor_9_3. Aliquot E | 0.88 | 2.6 | 0.40 | 104 | 3.7 | 3.2 | 0.72 | 0.31 |
| Donor_9_3. Aliquot F | 0.90 | 1.9 | 0.39 | 12 | 2.6 | 6 | 0.61 | 0.19 |
| Donor_9_3. Aliquot G | 0.86 | 0.21 | 0.41 | 14 | 3.1 | 0.91 | 2.7 | 0.21 |
| Donor_9_3. Aliquot H | 0.83 | 4.3 | 0.64 | 4.9 | 3.1 | 6 | 0.64 | 0.50 |
| Donor_9_3. Aliquot I | 0.82 | 3.5 | 0.39 | 8.3 | 2.6 | 6 | 0.66 | 0.45 |

FIG. 13B.4

| | Beta-2 Microglobulin | Brain-Derived Neurotrophic Factor | Complement 3 | Cancer Antigen 125 | Cancer Antigen 19-9 | Calcitonin | CD40 | CD40 Ligand |
|---|---|---|---|---|---|---|---|---|
| | ug/mL | ng/mL | mg/mL | U/mL | U/mL | pg/mL | ng/mL | ng/mL |
| Least Detectable Dose | 0.013 | 0.029 | 0.0053 | 4.2 | 0.25 | 6.0 | 0.021 | 0.020 |
| RBM Low Plasma Range | 1.2 | 0.32 | 0.76 | | | | 0.17 | |
| RBM High Plasma Range | 6.2 | 16 | 2.1 | 12 | 9.2 | 12 | 1.5 | 1.1 |
| EDTA Plasma | | | | | | | | |
| donor #1 plasma | 11 | 1.2 | 0.59 | 60 | 7.6 | 40 | 7.4 | 0.14 |
| donor #2 plasma | 19 | 0.40 | 0.98 | 63 | 241 | 51 | 18 | 0.21 |
| donor #3 plasma | 2.5 | 0.89 | 0.90 | 28 | 2.1 | 8.9 | 1.7 | 0.084 |
| donor #4 plasma | 9.1 | 0.35 | 0.47 | 431 | 10 | 36 | 5.2 | 0.10 |
| donor #5 plasma | 14 | 3.6 | 0.88 | 18 | 4.2 | 164 | 16 | 0.27 |
| donor #6 plasma | 1.1 | 1.5 | 0.87 | 18 | 1.6 | 3.7 | 0.46 | 0.021 |
| donor #7 plasma | 2.3 | 1.4 | 0.80 | 30 | 6.0 | 5.0 | 1.6 | 0.089 |
| donor #8 plasma | 1.1 | 3.1 | 0.42 | 16 | 7.5 | 6 | 0.58 | 0.16 |
| donor #9 plasma | 0.88 | 0.21 | 0.55 | 4.2 | 6.3 | 6 | 0.47 | 0.053 |
| | | | | | | | | |
| *Stimulations indices* | | | | | | | | |
| Donor_1 3. Aliquot A | 1.1 | 0.9 | 1.0 | 1.1 | 1.0 | 1.1 | 1.1 | 0.8 |
| Donor_1 3. Aliquot B | 1.0 | 1.2 | 1.0 | 1.0 | 1.0 | 1.0 | 0.9 | 1.0 |
| Donor_1 3. Aliquot C | 1.0 | 0.6 | 1.0 | 1.1 | 0.5 | 1.0 | 1.0 | 0.7 |
| Donor_1 3. Aliquot D | 1.0 | 0.9 | 1.0 | 1.3 | 1.0 | 1.1 | 0.9 | 0.6 |
| Donor_1 3. Aliquot E | 1.0 | 0.8 | 1.0 | 1.1 | 1.0 | 1.1 | 0.9 | 0.5 |
| Donor_1 3. Aliquot F | 0.9 | 0.4 | 2.0 | 1.0 | 0.9 | 0.9 | 0.9 | 0.2 |
| Donor_1 3. Aliquot G | 1.0 | 0.0 | 1.1 | 1.1 | 1.2 | 1.0 | 1.2 | 0.7 |
| Donor_1 3. Aliquot H | 0.9 | 1.2 | 1.6 | 1.1 | 0.4 | 0.9 | 1.1 | 1.0 |
| Donor_1 3. Aliquot I | 1.0 | 1.0 | 1.0 | 1.0 | 1.0 | 1.0 | 1.0 | |
| | | | | | | | | |
| Donor_2 3. Aliquot A | 1.0 | 1.9 | 1.0 | 1.2 | 1.1 | 1.1 | 1.0 | 1.5 |
| Donor_2 3. Aliquot B | #VALUE! | 2.6 | 1.0 | 1.2 | 1.1 | 1.2 | 1.0 | 1.4 |
| Donor_2 3. Aliquot C | 1.2 | 0.7 | 1.0 | 1.2 | 0.9 | 0.9 | 1.0 | 1.3 |
| Donor_2 3. Aliquot D | 1.0 | 1.4 | 1.1 | 1.9 | 1.0 | 1.3 | 0.9 | 1.0 |
| Donor_2 3. Aliquot E | 1.1 | 1.3 | 1.1 | 1.5 | 1.1 | 1.2 | 1.1 | 1.1 |
| Donor_2 3. Aliquot F | 1.0 | 0.9 | 2.5 | 1.2 | 0.9 | 1.1 | 0.9 | 0.9 |
| Donor_2 3. Aliquot G | 1.1 | 0.3 | 1.1 | 1.4 | 1.1 | 0.8 | 1.3 | 0.6 |

FIG. 13B.5

| | Beta-2 Microglobulin | Brain-Derived Neurotrophic Factor | Complement 3 | Cancer Antigen 125 | Cancer Antigen 19-9 | Calcitonin | CD40 | CD40 Ligand |
|---|---|---|---|---|---|---|---|---|
| Least Detectable Dose | ug/mL 0.013 | ng/mL 0.029 | mg/mL 0.0053 | U/mL 4.2 | U/mL 0.25 | pg/mL 6.0 | ng/mL 0.021 | ng/mL 0.020 |
| RBM Low Plasma Range | 1.2 | 0.32 | 0.76 | | | | 0.17 | |
| RBM High Plasma Range | 6.2 | 16 | 2.1 | 12 | 9.2 | 12 | 1.5 | 1.1 |
| Donor_2 3. Aliquot H | 1.1 | 1.3 | 1.4 | 1.0 | 1.0 | 1.1 | 1.1 | 0.9 |
| Donor_2 3. Aliquot I | 1.0 | 1.0 | 1.0 | 1.0 | 1.0 | 1.0 | 1.0 | 1.0 |
| Donor_3 3. Aliquot A | 1.1 | 1.4 | 0.9 | 1.1 | 1.2 | 1.0 | 1.1 | 1.3 |
| Donor_3 3. Aliquot B | 1.0 | 2.1 | 0.9 | 1.1 | 1.3 | 0.9 | 1.3 | 1.0 |
| Donor_3 3. Aliquot C | 1.1 | 1.3 | 1.0 | 1.1 | 1.3 | 1.0 | 1.0 | 1.2 |
| Donor_3 3. Aliquot D | 1.1 | 1.6 | 1.0 | 2.8 | 1.2 | 1.0 | 1.1 | 1.2 |
| Donor_3 3. Aliquot E | 1.1 | 1.7 | 1.0 | 2.4 | 1.3 | 1.2 | 1.1 | 1.6 |
| Donor_3 3. Aliquot F | 1.0 | 0.7 | 1.6 | 1.3 | 1.5 | 1.0 | 1.0 | 0.9 |
| Donor_3 3. Aliquot G | 1.1 | 0.0 | 1.0 | 0.9 | 1.7 | 1.0 | 2.5 | 0.7 |
| Donor_3 3. Aliquot H | 1.0 | 1.1 | 1.5 | 0.9 | 1.1 | 1.0 | 1.0 | 1.2 |
| Donor_3 3. Aliquot I | 1.0 | 1.0 | 1.0 | 1.0 | 1.0 | 1.0 | 1.0 | 1.0 |
| Donor_4 3. Aliquot A | 0.9 | 1.6 | 1.0 | 1.0 | 1.0 | 1.1 | 1.1 | 2.2 |
| Donor_4 3. Aliquot B | 0.9 | 2.2 | 0.9 | 1.0 | 1.1 | 1.2 | 1.2 | 1.9 |
| Donor_4 3. Aliquot C | 1.0 | 0.4 | 1.0 | 0.9 | 1.0 | 0.9 | 1.1 | 1.0 |
| Donor_4 3. Aliquot D | 1.0 | 1.3 | 1.0 | 1.1 | 1.0 | 1.1 | 1.1 | 1.4 |
| Donor_4 3. Aliquot E | 1.0 | 0.8 | 1.0 | 1.1 | 1.3 | 0.9 | 1.1 | 1.4 |
| Donor_4 3. Aliquot F | 1.1 | 0.7 | 1.9 | 0.9 | 0.9 | 0.9 | 1.0 | 0.9 |
| Donor_4 3. Aliquot G | 1.0 | 0.0 | 1.0 | 0.9 | 1.1 | 0.6 | 1.2 | 0.7 |
| Donor_4 3. Aliquot H | 1.0 | 0.4 | 1.6 | 1.0 | 1.0 | 1.0 | 1.0 | 0.9 |
| Donor_4 3. Aliquot I | 1.0 | 1.0 | 1.0 | 1.0 | 1.0 | 1.0 | 1.0 | 1.0 |
| Donor_5 3. Aliquot A | 1.1 | 1.9 | 1.0 | 1.2 | 1.1 | 1.1 | 1.0 | 1.9 |
| Donor_5 3. Aliquot B | 1.1 | 1.5 | 1.1 | 1.3 | 1.2 | 1.0 | 1.1 | 1.3 |
| Donor_5 3. Aliquot C | 1.1 | 0.7 | 1.1 | 1.2 | 1.2 | 0.8 | 1.1 | 1.2 |
| Donor_5 3. Aliquot D | 1.2 | 0.9 | 1.1 | 5.1 | 1.3 | 1.1 | 1.1 | 1.5 |
| Donor_5 3. Aliquot E | 1.3 | 1.5 | 1.0 | 4.4 | 1.3 | 1.0 | 1.2 | 1.8 |
| Donor_5 3. Aliquot F | 1.0 | 0.8 | 1.7 | 0.7 | 0.9 | 0.9 | 1.0 | 1.1 |
| Donor_5 3. Aliquot G | 1.1 | 0.1 | 1.1 | 1.2 | 1.1 | 0.7 | 1.1 | 0.9 |

FIG. 13B.6

| | Beta-2 Microglobulin | Brain-Derived Neurotrophic Factor | Complement 3 | Cancer Antigen 125 | Cancer Antigen 19-9 | Calcitonin | CD40 | CD40 Ligand |
|---|---|---|---|---|---|---|---|---|
| | ug/mL | ng/mL | mg/mL | U/mL | U/mL | pg/mL | ng/mL | ng/mL |
| Least Detectable Dose | 0.013 | 0.029 | 0.0053 | 4.2 | 0.25 | 6.0 | 0.021 | 0.020 |
| RBM Low Plasma Range | 1.2 | 0.32 | 0.76 | | | | 0.17 | |
| RBM High Plasma Range | 6.2 | 16 | 2.1 | 12 | 9.2 | 12 | 1.5 | 1.1 |
| Donor_5 3. Aliquot H | 1.1 | 1.6 | 1.5 | 1.0 | 1.1 | 1.1 | 1.0 | 1.2 |
| Donor_5 3. Aliquot I | 1.0 | 1.0 | 1.0 | 1.0 | 1.0 | 1.0 | 1.0 | 1.0 |
| Donor_6 3. Aliquot A | 1.1 | 2.6 | 1.1 | 1.0 | 1.2 | 1.0 | 1.3 | 1.9 |
| Donor_6 3. Aliquot B | 1.0 | 2.0 | 1.1 | 1.4 | 0.9 | 1.0 | 1.5 | 1.7 |
| Donor_6 3. Aliquot C | 1.1 | 0.6 | 1.1 | 0.8 | 1.4 | 1.0 | 1.4 | 1.4 |
| Donor_6 3. Aliquot D | 1.1 | 2.3 | 1.1 | 2.8 | 1.3 | 1.0 | 1.4 | 2.1 |
| Donor_6 3. Aliquot E | 1.1 | 1.3 | 1.0 | 2.9 | 1.2 | 1.0 | 1.3 | 1.3 |
| Donor_6 3. Aliquot F | 1.1 | 1.1 | 1.1 | 0.9 | 1.0 | 1.0 | 1.2 | 1.2 |
| Donor_6 3. Aliquot G | 1.1 | 0.0 | 1.1 | 1.0 | 1.7 | 1.0 | 5.2 | 0.7 |
| Donor_6 3. Aliquot H | 1.0 | 1.8 | 1.6 | 0.8 | 1.2 | 1.0 | 1.1 | 1.0 |
| Donor_6 3. Aliquot I | 1.0 | 1.0 | 1.0 | 1.0 | 1.0 | 1.0 | 1.0 | 1.0 |
| Donor_7 3. Aliquot A | 1.1 | 1.7 | 1.0 | 1.4 | 1.4 | 0.4 | 1.9 | 1.8 |
| Donor_7 3. Aliquot B | 1.1 | 1.9 | 1.0 | 1.2 | 1.4 | 1.8 | 1.8 | 1.5 |
| Donor_7 3. Aliquot C | 1.1 | 1.3 | 0.9 | 1.0 | 1.1 | 1.8 | 1.6 | 2.8 |
| Donor_7 3. Aliquot D | 1.1 | 1.7 | 1.0 | 2.4 | 1.3 | 1.8 | 1.5 | 2.1 |
| Donor_7 3. Aliquot E | 1.1 | 1.4 | 0.8 | 1.4 | 1.3 | 1.8 | 1.2 | 1.4 |
| Donor_7 3. Aliquot F | 1.0 | 0.7 | 1.1 | 1.0 | 1.3 | 1.8 | 1.2 | 0.8 |
| Donor_7 3. Aliquot G | 1.0 | 0.0 | 1.7 | 1.0 | 2.1 | 1.8 | 3.6 | 0.5 |
| Donor_7 3. Aliquot H | 1.0 | 1.0 | 1.0 | 0.9 | 1.4 | 1.8 | 1.4 | 1.2 |
| Donor_7 3. Aliquot I | 1.0 | 1.0 | 1.0 | | | 1.0 | 1.0 | 1.0 |
| Donor_8 3. Aliquot A | 1.0 | 0.5 | 1.0 | 0.4 | 1.4 | 1.0 | 0.9 | 0.7 |
| Donor_8 3. Aliquot B | 1.0 | 0.9 | 1.1 | 0.6 | 1.1 | 1.0 | 0.9 | 0.9 |
| Donor_8 3. Aliquot C | 1.0 | 0.5 | 0.9 | 0.3 | 1.1 | 1.0 | 1.0 | 1.1 |
| Donor_8 3. Aliquot D | 1.0 | 0.7 | 1.0 | 11.2 | 1.5 | 0.8 | 1.1 | 0.7 |
| Donor_8 3. Aliquot E | 1.0 | 1.0 | 0.9 | 9.3 | 1.4 | 1.1 | 1.0 | 1.1 |
| Donor_8 3. Aliquot F | 1.1 | 0.4 | 1.1 | 1.1 | 1.2 | 1.0 | 0.8 | 0.3 |
| Donor_8 3. Aliquot G | 1.0 | 0.0 | 0.9 | 0.6 | 1.4 | 1.0 | 2.8 | 0.3 |

FIG. 13B.7

| | Beta-2 Microglobulin | Brain-Derived Neurotrophic Factor | Complement 3 | Cancer Antigen 125 | Cancer Antigen 19-9 | Calcitonin | CD40 | CD40 Ligand |
|---|---|---|---|---|---|---|---|---|
| | ug/mL | ng/mL | mg/mL | U/mL | U/mL | pg/mL | ng/mL | ng/mL |
| Least Detectable Dose | 0.013 | 0.029 | 0.0053 | 4.2 | 0.25 | 6.0 | 0.021 | 0.020 |
| RBM Low Plasma Range | 1.2 | 0.32 | 0.76 | | | | 0.17 | |
| RBM High Plasma Range | 6.2 | 16 | 2.1 | 12 | 9.2 | 12 | 1.5 | |
| Donor_8_3. Aliquot H | 1.0 | 1.0 | 1.6 | 0.9 | 1.1 | 1.0 | 0.9 | 1.1 |
| Donor_8_3. Aliquot I | 1.0 | 1.0 | 1.0 | 1.0 | 1.0 | 1.0 | 1.0 | 1.0 |
| Donor_9_3. Aliquot A | 1.0 | 0.7 | 1.0 | 1.7 | 1.1 | 1.0 | 1.1 | 0.8 |
| Donor_9_3. Aliquot B | 1.0 | 1.0 | 1.0 | 1.3 | 1.3 | 1.0 | 1.1 | 1.0 |
| Donor_9_3. Aliquot C | 1.1 | 0.3 | 1.0 | 2.5 | 1.3 | 1.0 | 1.1 | 1.1 |
| Donor_9_3. Aliquot D | 1.1 | 1.1 | 1.0 | 16.9 | 2.3 | 0.6 | 1.2 | 1.0 |
| Donor_9_3. Aliquot E | 1.1 | 0.7 | 1.0 | 12.5 | 1.4 | 0.5 | 1.1 | 0.7 |
| Donor_9_3. Aliquot F | 1.1 | 0.5 | 1.0 | 1.4 | 1.0 | 1.0 | 0.9 | 0.4 |
| Donor_9_3. Aliquot G | 1.0 | 0.1 | 1.0 | 1.7 | 1.2 | 0.2 | 4.1 | 0.5 |
| Donor_9_3. Aliquot H | 1.0 | 1.2 | 1.6 | 0.6 | 1.2 | 1.0 | 1.0 | 1.1 |
| Donor_9_3. Aliquot I | 1.0 | 1.0 | 1.0 | 1.0 | 1.0 | 1.0 | 1.0 | 1.0 |

FIG. 13C.1

| | Carcinoembryonic Antigen | Creatine Kinase-MB | C Reactive Protein | EGF | ENA-78 | Endothelin-1 | EN-RAGE | Eotaxin |
|---|---|---|---|---|---|---|---|---|
| | ng/mL | ng/mL | ug/mL | pg/mL | ng/mL | pg/mL | ng/mL | pg/mL |
| Least Detectable Dose | 0.84 | 0.42 | 0.0015 | 7.4 | 0.076 | 7.2 | 0.25 | 41 |
| RBM Low Plasma Range | | | 0.25 | | 0.069 | | 4.6 | |
| RBM High Plasma Range | 4.8 | 1.1 | 50 | 505 | 5.3 | 26 | 592 | 177 |
| Donor_1 3. Aliquot A | 1.5 | 0.16 | >47 | 128 | 7.9 | 8.1 | 82 | 179 |
| Donor_1 3. Aliquot B | 1.4 | 0.11 | >47 | 131 | 8.2 | 7.2 | 72 | 164 |
| Donor_1 3. Aliquot C | 1.4 | 0.12 | >47 | 119 | 1.7 | 7.2 | 74 | 130 |
| Donor_1 3. Aliquot D | 1.7 | 0.18 | >47 | 109 | 10 | 7.2 | 66 | 180 |
| Donor_1 3. Aliquot E | 1.6 | 0.11 | >47 | 101 | 5.9 | 7.2 | 75 | 170 |
| Donor_1 3. Aliquot F | 1.2 | 0.15 | >47 | 101 | 1.2 | 7.2 | 60 | 184 |
| Donor_1 3. Aliquot G | 1.5 | 0.11 | >47 | 693 | 5.3 | 22 | 54 | 10 |
| Donor_1 3. Aliquot H | 1.9 | 0.11 | >47 | 197 | 1.6 | 11 | 99 | 177 |
| Donor_1 3. Aliquot I | 1.4 | 0.12 | >47 | 114 | 1.8 | 7.2 | 76 | 172 |
| Donor_2 3. Aliquot A | 4.6 | 0.40 | >47 | 92 | 45 | 11 | 247 | 61 |
| Donor_2 3. Aliquot B | 4.9 | 0.44 | >47 | 145 | 45 | 7.2 | 230 | 48 |
| Donor_2 3. Aliquot C | 4.7 | 0.32 | >47 | 83 | 0.66 | 7.2 | 252 | 46 |
| Donor_2 3. Aliquot D | 6.2 | 0.60 | >47 | 61 | 51 | 15 | 212 | 48 |
| Donor_2 3. Aliquot E | 5.0 | 0.43 | >47 | 62 | 55 | 20 | 228 | 44 |
| Donor_2 3. Aliquot F | 4.0 | 0.50 | >47 | 66 | 0.74 | 7.2 | 258 | 27 |
| Donor_2 3. Aliquot G | 5.4 | 0.49 | >47 | 792 | 214 | 24 | 218 | 5.0 |
| Donor_2 3. Aliquot H | 4.8 | 0.40 | >47 | 85 | 1.4 | 7.2 | >269 | 36 |
| Donor_2 3. Aliquot I | 4.5 | 0.21 | >47 | 59 | 1.2 | 7.2 | 250 | 44 |
| Donor_3 3. Aliquot A | 2.8 | 0.59 | 22 | 40 | 20 | 7.2 | 142 | 66 |
| Donor_3 3. Aliquot B | 3.3 | 0.67 | 24 | 64 | 13 | 7.2 | 142 | 50 |
| Donor_3 3. Aliquot C | 3.3 | 0.54 | 25 | 38 | 0.96 | 7.2 | 135 | 44 |
| Donor_3 3. Aliquot D | 3.6 | 0.53 | 25 | 47 | 35 | 7.2 | 151 | 54 |
| Donor_3 3. Aliquot E | 4.3 | 0.61 | 24 | 60 | 31 | 11 | 159 | 52 |
| Donor_3 3. Aliquot F | 3.2 | 0.24 | 26 | 39 | 0.65 | 7.2 | 128 | 80 |
| Donor_3 3. Aliquot G | 2.7 | 0.29 | 26 | 535 | 1.6 | 7.2 | 122 | 5.0 |
| Donor_3 3. Aliquot H | 2.4 | 0.37 | 23 | 39 | 0.47 | 7.2 | 211 | 29 |
| Donor_3 3. Aliquot I | 2.4 | 0.39 | 24 | 33 | 0.55 | 7.2 | 169 | 36 |

FIG. 13C.2

| | Carcinoembryonic Antigen | Creatine Kinase-MB | C Reactive Protein | EGF | ENA-78 | Endothelin-1 | EN-RAGE | Eotaxin |
|---|---|---|---|---|---|---|---|---|
| | ng/mL | ng/mL | ug/mL | pg/mL | ng/mL | pg/mL | ng/mL | pg/mL |
| Least Detectable Dose | 0.84 | 0.42 | 0.0015 | 7.4 | 0.076 | 7.2 | 0.25 | 41 |
| RBM Low Plasma Range | | | 0.25 | | 0.069 | | 4.6 | |
| RBM High Plasma Range | 4.8 | 1.1 | 50 | 505 | 5.3 | 26 | 592 | 177 |
| Donor_4_3. Aliquot A | 3.4 | 0.078 | >47 | 25 | 0.77 | 7.2 | >269 | 141 |
| Donor_4_3. Aliquot B | 3.8 | 0.066 | >47 | 35 | 1.4 | 7.2 | 239 | 133 |
| Donor_4_3. Aliquot C | 3.6 | 0.064 | >47 | 12 | 0.18 | 7.2 | 175 | 122 |
| Donor_4_3. Aliquot D | 4.4 | 0.17 | >47 | 21 | 23 | 11 | 84 | 133 |
| Donor_4_3. Aliquot E | 3.7 | 0.066 | >47 | 15 | 21 | 22 | 66 | 120 |
| Donor_4_3. Aliquot F | 3.3 | 0.093 | >47 | 9.8 | 0.59 | 7.2 | 94 | 130 |
| Donor_4_3. Aliquot G | 3.3 | 0.057 | >47 | 256 | 1.2 | 7.2 | 127 | 10 |
| Donor_4_3. Aliquot H | 3.4 | 0.045 | >47 | 11 | 0.14 | 7.2 | >269 | 124 |
| Donor_4_3. Aliquot I | 3.2 | 0.076 | >47 | 19 | 0.20 | 7.2 | 185 | 139 |
| Donor_5_3. Aliquot A | 1.7 | 0.18 | >47 | 87 | 21 | 20 | 95 | 27 |
| Donor_5_3. Aliquot B | 2.4 | 0.18 | >47 | 90 | 23 | 11 | 88 | 34 |
| Donor_5_3. Aliquot C | 1.6 | 0.11 | >47 | 71 | 0.25 | 7.2 | 108 | 32 |
| Donor_5_3. Aliquot D | 3.1 | 0.24 | >47 | 60 | 31 | 11 | 52 | 32 |
| Donor_5_3. Aliquot E | 2.9 | 0.28 | >47 | 70 | 33 | 15 | 41 | 30 |
| Donor_5_3. Aliquot F | 1.4 | 0.086 | >47 | 59 | 0.71 | 7.2 | 73 | 27 |
| Donor_5_3. Aliquot G | 1.7 | 0.12 | >47 | 647 | 7.0 | 15 | 91 | 7.6 |
| Donor_5_3. Aliquot H | 4.2 | 0.17 | >47 | 83 | 0.41 | 7.2 | 236 | 25 |
| Donor_5_3. Aliquot I | 3.6 | 0.11 | >47 | 53 | 0.22 | 7.2 | 100 | 22 |
| Donor_6_3. Aliquot A | 0.82 | 0.25 | >47 | 195 | 4.4 | 7.2 | 236 | 22 |
| Donor_6_3. Aliquot B | 0.58 | 0.24 | >47 | 213 | 6.0 | 7.2 | 229 | 25 |
| Donor_6_3. Aliquot C | 1.1 | 0.26 | >47 | 160 | 0.54 | 7.2 | 265 | 36 |
| Donor_6_3. Aliquot D | 1.3 | 0.26 | >47 | 152 | 10 | 7.2 | 109 | 25 |
| Donor_6_3. Aliquot E | 1.6 | 0.30 | >47 | 110 | 12 | 11 | 106 | 20 |
| Donor_6_3. Aliquot F | 0.63 | 0.19 | >47 | 132 | 0.68 | 7.2 | 153 | 34 |
| Donor_6_3. Aliquot G | 0.44 | 0.30 | >47 | 2020 | 4.3 | 7.2 | 147 | 15 |
| Donor_6_3. Aliquot H | 0.91 | 0.21 | >47 | 139 | 0.43 | 7.2 | >269 | 18 |
| Donor_6_3. Aliquot I | 0.96 | 0.21 | >47 | 101 | 0.51 | 7.2 | 237 | 22 |

FIG. 13C.3

| | Carcinoembryonic Antigen | Creatine Kinase-MB | C Reactive Protein | EGF | ENA-78 | Endothelin-1 | EN-RAGE | Eotaxin |
|---|---|---|---|---|---|---|---|---|
| | ng/mL | ng/mL | ug/mL | pg/mL | ng/mL | pg/mL | ng/mL | pg/mL |
| Least Detectable Dose | 0.84 | 0.42 | 0.0015 | 7.4 | 0.076 | 7.2 | 0.25 | 41 |
| RBM Low Plasma Range | | | 0.25 | | 0.069 | | 4.6 | |
| RBM High Plasma Range | 4.8 | 1.1 | 50 | 505 | 5.3 | 26 | 592 | 177 |
| Donor_7 3. Aliquot A | 3.6 | 1.2 | 29 | 30 | 33 | 7.2 | 150 | 138 |
| Donor_7 3. Aliquot B | 2.8 | 1.5 | 33 | 45 | 17 | 7.2 | 161 | 119 |
| Donor_7 3. Aliquot C | 3.0 | 0.99 | 30 | 37 | 0.56 | 7.2 | >269 | 105 |
| Donor_7 3. Aliquot D | 3.9 | 1.1 | 27 | 28 | 26 | 7.2 | 128 | 106 |
| Donor_7 3. Aliquot E | 3.2 | 1.1 | 24 | 22 | 20 | 7.2 | 122 | 117 |
| Donor_7 3. Aliquot F | 2.9 | 1.2 | 27 | 11 | 0.25 | 7.2 | 227 | 121 |
| Donor_7 3. Aliquot G | 3.0 | 1.1 | 27 | 403 | 3.6 | 7.2 | 182 | 18 |
| Donor_7 3. Aliquot H | 4.1 | 1.0 | 28 | 20 | 0.23 | 7.2 | >269 | 125 |
| Donor_7 3. Aliquot I | 2.7 | 0.93 | 29 | 15 | 0.19 | 7.2 | >269 | 111 |
| Donor_8 3. Aliquot A | 1.1 | 0.15 | 0.096 | 93 | 1.1 | 8.1 | 48 | 162 |
| Donor_8 3. Aliquot B | 0.82 | 0.19 | 0.14 | 110 | 1.3 | 7.2 | 46 | 153 |
| Donor_8 3. Aliquot C | 0.75 | 0.15 | 0.13 | 114 | 0.81 | 7.2 | 41 | 117 |
| Donor_8 3. Aliquot D | 3.5 | 0.36 | 0.14 | 105 | 1.4 | 7.2 | 64 | 165 |
| Donor_8 3. Aliquot E | 3.9 | 0.39 | 0.12 | 132 | 2.4 | 7.2 | 45 | 157 |
| Donor_8 3. Aliquot F | 1.4 | 0.24 | 0.16 | 63 | 0.37 | 15 | 47 | 208 |
| Donor_8 3. Aliquot G | 0.94 | 0.20 | 0.13 | 1050 | 4.5 | 7.2 | 57 | 5.0 |
| Donor_8 3. Aliquot H | 1.9 | 0.24 | 0.15 | 143 | 0.81 | 11 | 143 | 142 |
| Donor_8 3. Aliquot I | 1.6 | 0.14 | 0.13 | 125 | 0.87 | 7.2 | 122 | 157 |
| Donor_9 3. Aliquot A | 1.2 | 0.079 | Pending | 117 | 2.1 | 7.2 | 47 | 254 |
| Donor_9 3. Aliquot B | 1.5 | 0.19 | Pending | 156 | 2.2 | 13 | 33 | 223 |
| Donor_9 3. Aliquot C | 1.0 | 0.18 | Pending | 123 | 2.1 | 9.8 | 48 | 184 |
| Donor_9 3. Aliquot D | 5.3 | 0.40 | Pending | 131 | 2.4 | 18 | 46 | 239 |
| Donor_9 3. Aliquot E | 3.3 | 0.26 | Pending | 95 | 6.5 | 19 | 67 | 209 |
| Donor_9 3. Aliquot F | 1.7 | 0.16 | Pending | 78 | 0.65 | 13 | 22 | 231 |
| Donor_9 3. Aliquot G | 1.1 | 0.12 | Pending | 1300 | 16 | 7.2 | 96 | 41 |
| Donor_9 3. Aliquot H | 1.5 | 0.13 | | 140 | 1.3 | 5.1 | 115 | 201 |
| Donor_9 3. Aliquot I | 0.89 | 0.083 | | 134 | 1.5 | 7.2 | 50 | 232 |

FIG. 13C.4

| | Carcinoembryonic Antigen | Creatine Kinase-MB | C Reactive Protein | EGF | ENA-78 | Endothelin-1 | EN-RAGE | Eotaxin |
|---|---|---|---|---|---|---|---|---|
| | ng/mL | ng/mL | ug/mL | pg/mL | ng/mL | pg/mL | ng/mL | pg/mL |
| Least Detectable Dose | 0.84 | 0.42 | 0.0015 | 7.4 | 0.076 | 7.2 | 0.25 | 41 |
| RBM Low Plasma Range | | | 0.25 | | 0.069 | | 4.6 | |
| RBM High Plasma Range | 4.8 | 1.1 | 50 | 505 | 5.3 | 26 | 592 | 177 |
| EDTA Plasma | | | | | | | | |
| donor #1 plasma | 1.7 | 0.25 | Pending | 30 | 0.93 | 7.7 | 65 | 97 |
| donor #2 plasma | 3.9 | 0.99 | Pending | 7.4 | 0.076 | 7.2 | >269 | 42 |
| donor #3 plasma | 2.6 | 0.47 | Pending | 7.4 | 0.076 | 17 | 49 | 36 |
| donor #4 plasma | 4.9 | 0.24 | Pending | 7.4 | 0.076 | 7.2 | 19 | 87 |
| donor #5 plasma | 1.7 | 0.18 | Pending | 12 | 0.32 | 22 | 145 | 64 |
| donor #6 plasma | 1.1 | 0.39 | Pending | 7.4 | 0.26 | 7.2 | 40 | 14 |
| donor #7 plasma | 3.6 | 3.3 | Pending | 7.4 | 0.54 | 7.2 | 71 | 86 |
| donor #8 plasma | 1.4 | 0.56 | Pending | 22 | 0.48 | 9.8 | 9.4 | 294 |
| donor #9 plasma | 0.71 | 0.27 | Pending | 7.4 | 0.088 | 7.2 | 4.3 | 330 |
| | | | | | | | | |
| Stimulations indices | | | | | | | | |
| Donor_1 3. Aliquot A | 1.1 | 1.3 | #VALUE! | 1.1 | 4.3 | 1.1 | 1.1 | 1.0 |
| Donor_1 3. Aliquot B | 1.0 | 0.9 | #VALUE! | 1.1 | 4.5 | 1.0 | 0.9 | 1.0 |
| Donor_1 3. Aliquot C | 1.0 | 1.0 | #VALUE! | 1.0 | 0.9 | 1.0 | 1.0 | 0.8 |
| Donor_1 3. Aliquot D | 1.3 | 1.5 | #VALUE! | 1.0 | 5.5 | 1.0 | 0.9 | 1.0 |
| Donor_1 3. Aliquot E | 1.2 | 0.9 | #VALUE! | 0.9 | 3.2 | 1.0 | 1.0 | 1.0 |
| Donor_1 3. Aliquot F | 0.9 | 1.3 | #VALUE! | 0.9 | 0.7 | 1.0 | 0.8 | 1.1 |
| Donor_1 3. Aliquot G | 1.1 | 0.9 | #VALUE! | 6.1 | 2.9 | 3.1 | 0.7 | 0.1 |
| Donor_1 3. Aliquot H | 1.4 | 0.9 | #VALUE! | 1.7 | 0.9 | 1.5 | 1.3 | 1.0 |
| Donor_1 3. Aliquot I | 1.0 | 1.0 | #VALUE! | 1.0 | 1.0 | 1.0 | 1.0 | 1.0 |
| | | | | | | | | |
| Donor_2 3. Aliquot A | 1.0 | 1.9 | #VALUE! | 1.5 | 38.3 | 1.5 | 1.0 | 1.4 |
| Donor_2 3. Aliquot B | 1.1 | 2.1 | #VALUE! | 2.4 | 38.5 | 1.0 | 0.9 | 1.1 |
| Donor_2 3. Aliquot C | 1.1 | 1.5 | #VALUE! | 1.4 | 0.6 | 1.0 | 1.0 | 1.0 |
| Donor_2 3. Aliquot D | 1.4 | 2.8 | #VALUE! | 1.0 | 43.4 | 2.0 | 0.8 | 1.1 |
| Donor_2 3. Aliquot E | 1.1 | 2.0 | #VALUE! | 1.0 | 46.3 | 2.8 | 0.9 | 1.0 |
| Donor_2 3. Aliquot F | 0.9 | 2.4 | #VALUE! | 1.1 | 0.6 | 1.0 | 1.0 | 0.6 |
| Donor_2 3. Aliquot G | 1.2 | 2.3 | #VALUE! | 13.3 | 181.4 | 3.4 | 0.9 | 0.1 |

FIG. 13C.5

| | Carcinoembryonic Antigen | Creatine Kinase-MB | C Reactive Protein | EGF | ENA-78 | Endothelin-1 | EN-RAGE | Eotaxin |
|---|---|---|---|---|---|---|---|---|
| | ng/mL | ng/mL | ug/mL | pg/mL | ng/mL | pg/mL | ng/mL | pg/mL |
| Least Detectable Dose | 0.84 | 0.42 | 0.0015 | 7.4 | 0.076 | 7.2 | 0.25 | 41 |
| RBM Low Plasma Range | | | | | | | | |
| RBM High Plasma Range | 4.8 | 1.1 | 0.25 | 505 | 0.069 | 26 | 4.6 | 177 |
| Donor_2 3. Aliquot H | 1.1 | 1.9 | 50 | 1.4 | 5.3 | 1.0 | 592 | 0.8 |
| Donor_2 3. Aliquot I | 1.0 | 1.0 | #VALUE! | 1.0 | 1.2 | 1.0 | #VALUE! | 1.0 |
| | | | #VALUE! | | 1.0 | | | |
| Donor_3 3. Aliquot A | 1.2 | 1.5 | 0.9 | 1.2 | 35.7 | 1.0 | 0.8 | 1.9 |
| Donor_3 3. Aliquot B | 1.4 | 1.7 | 1.0 | 2.0 | 22.6 | 1.0 | 0.8 | 1.4 |
| Donor_3 3. Aliquot C | 1.4 | 1.4 | 1.1 | 1.2 | 1.7 | 1.0 | 0.8 | 1.2 |
| Donor_3 3. Aliquot D | 1.5 | 1.4 | 1.1 | 1.4 | 63.9 | 1.0 | 0.9 | 1.5 |
| Donor_3 3. Aliquot E | 1.8 | 1.6 | 1.0 | 1.8 | 56.6 | 1.5 | 0.9 | 1.4 |
| Donor_3 3. Aliquot F | 1.4 | 0.6 | 1.1 | 1.2 | 1.2 | 1.0 | 0.8 | 2.2 |
| Donor_3 3. Aliquot G | 1.1 | 0.7 | 1.1 | 16.4 | 2.9 | 1.0 | 0.7 | 0.1 |
| Donor_3 3. Aliquot H | 1.0 | 1.0 | 1.0 | 1.2 | 0.9 | 1.0 | 1.2 | 0.8 |
| Donor_3 3. Aliquot I | 1.0 | 1.0 | 1.0 | 1.0 | 1.0 | 1.0 | 1.0 | 1.0 |
| Donor_4 3. Aliquot A | 1.1 | 1.0 | #VALUE! | 1.3 | 3.9 | 1.0 | #VALUE! | 1.0 |
| Donor_4 3. Aliquot B | 1.2 | 0.9 | #VALUE! | 1.9 | 7.2 | 1.0 | 1.3 | 1.0 |
| Donor_4 3. Aliquot C | 1.1 | 0.8 | #VALUE! | 0.7 | 0.9 | 1.0 | 0.9 | 0.9 |
| Donor_4 3. Aliquot D | 1.4 | 2.3 | #VALUE! | 1.1 | 117.9 | 1.5 | 0.5 | 1.0 |
| Donor_4 3. Aliquot E | 1.2 | 0.9 | #VALUE! | 0.8 | 105.6 | 3.1 | 0.4 | 0.9 |
| Donor_4 3. Aliquot F | 1.1 | 1.2 | #VALUE! | 0.5 | 3.0 | 1.0 | 0.5 | 0.9 |
| Donor_4 3. Aliquot G | 1.1 | 0.7 | #VALUE! | 13.5 | 6.0 | 1.0 | 0.7 | 0.1 |
| Donor_4 3. Aliquot H | 1.1 | 0.6 | #VALUE! | 0.6 | 0.7 | 1.0 | #VALUE! | 0.9 |
| Donor_4 3. Aliquot I | 1.0 | 1.0 | #VALUE! | 1.0 | 1.0 | 1.0 | 1.0 | 1.0 |
| Donor_5 3. Aliquot A | 0.5 | 1.6 | #VALUE! | 1.7 | 95.5 | 2.8 | 0.9 | 1.2 |
| Donor_5 3. Aliquot B | 0.7 | 1.6 | #VALUE! | 1.7 | 105.4 | 1.5 | 0.9 | 1.5 |
| Donor_5 3. Aliquot C | 0.5 | 1.0 | #VALUE! | 1.3 | 1.1 | 1.0 | 1.1 | 1.4 |
| Donor_5 3. Aliquot D | 0.9 | 2.1 | #VALUE! | 1.1 | 140.1 | 1.5 | 0.5 | 1.4 |
| Donor_5 3. Aliquot E | 0.8 | 2.5 | #VALUE! | 1.3 | 149.5 | 2.0 | 0.4 | 1.4 |
| Donor_5 3. Aliquot F | 0.4 | 0.8 | #VALUE! | 1.1 | 3.2 | 1.0 | 0.7 | 1.2 |
| Donor_5 3. Aliquot G | 0.5 | 1.0 | #VALUE! | 12.3 | 31.3 | 2.0 | 0.9 | 0.3 |

FIG. 13C.6

| | Carcinoembryonic Antigen | Creatine Kinase-MB | C Reactive Protein | EGF | ENA-78 | Endothelin-1 | EN-RAGE | Eotaxin |
|---|---|---|---|---|---|---|---|---|
| | ng/mL | ng/mL | ug/mL | pg/mL | ng/mL | pg/mL | ng/mL | pg/mL |
| Least Detectable Dose | 0.84 | 0.42 | 0.0015 | 7.4 | 0.076 | 7.2 | 0.25 | 41 |
| RBM Low Plasma Range | | | | | | | | |
| RBM High Plasma Range | 4.8 | 1.1 | 0.25 | 505 | 0.069 | 26 | 4.6 | 177 |
| Donor_5 3. Aliquot H | 1.2 | 1.5 | 50 | 1.6 | 5.3 | 1.0 | 592 | 1.1 |
| Donor_5 3. Aliquot I | 1.0 | 1.0 | #VALUE! | 1.0 | 1.8 | 1.0 | 2.4 | 1.0 |
| | | | #VALUE! | | 1.0 | | 1.0 | |
| Donor_6 3. Aliquot A | 0.9 | 1.2 | #VALUE! | 1.9 | 8.6 | 1.0 | 1.0 | 1.0 |
| Donor_6 3. Aliquot B | 0.6 | 1.1 | #VALUE! | 2.1 | 11.7 | 1.0 | 1.0 | 1.1 |
| Donor_6 3. Aliquot C | 1.2 | 1.2 | #VALUE! | 1.6 | 1.1 | 1.0 | 1.1 | 1.6 |
| Donor_6 3. Aliquot D | 1.3 | 1.2 | #VALUE! | 1.5 | 20.3 | 1.0 | 0.5 | 1.1 |
| Donor_6 3. Aliquot E | 1.7 | 1.4 | #VALUE! | 1.1 | 22.7 | 1.5 | 0.4 | 0.9 |
| Donor_6 3. Aliquot F | 0.7 | 0.9 | #VALUE! | 1.3 | 1.3 | 1.0 | 0.6 | 1.5 |
| Donor_6 3. Aliquot G | 0.5 | 1.4 | #VALUE! | 20.0 | 8.3 | 1.0 | 0.6 | 0.7 |
| Donor_6 3. Aliquot H | 1.0 | 1.0 | #VALUE! | 1.4 | 0.8 | 1.0 | #VALUE! | 0.8 |
| Donor_6 3. Aliquot I | 1.0 | 1.0 | | 1.0 | 1.0 | 1.0 | 1.0 | 1.0 |
| Donor_7 3. Aliquot A | 1.3 | 1.3 | 1.0 | 2.0 | 169.3 | 1.0 | #VALUE! | 1.2 |
| Donor_7 3. Aliquot B | 1.0 | 1.6 | 1.1 | 2.9 | 89.1 | 1.0 | #VALUE! | 1.1 |
| Donor_7 3. Aliquot C | 1.1 | 1.1 | 1.1 | 2.4 | 2.9 | 1.0 | #VALUE! | 0.9 |
| Donor_7 3. Aliquot D | 1.4 | 1.2 | 1.0 | 1.9 | 133.3 | 1.0 | #VALUE! | 1.0 |
| Donor_7 3. Aliquot E | 1.2 | 1.2 | 0.8 | 1.4 | 105.7 | 1.0 | #VALUE! | 1.1 |
| Donor_7 3. Aliquot F | 1.1 | 1.3 | 0.9 | 0.7 | 1.3 | 1.0 | #VALUE! | 1.1 |
| Donor_7 3. Aliquot G | 1.1 | 1.2 | 0.9 | 26.5 | 18.9 | 1.0 | #VALUE! | 0.2 |
| Donor_7 3. Aliquot H | 1.5 | 1.1 | 1.0 | 1.3 | 1.2 | 1.1 | #VALUE! | 1.1 |
| Donor_7 3. Aliquot I | 1.0 | 1.0 | 1.0 | 1.0 | 1.0 | 1.0 | 1.0 | 1.0 |
| Donor_8 3. Aliquot A | 0.7 | 1.0 | 0.7 | 0.7 | 1.2 | 1.0 | 0.4 | 1.0 |
| Donor_8 3. Aliquot B | 0.5 | 1.4 | 1.1 | 0.9 | 1.4 | 1.0 | 0.4 | 1.0 |
| Donor_8 3. Aliquot C | 0.5 | 1.0 | 1.1 | 0.9 | 0.9 | 1.0 | 0.3 | 0.7 |
| Donor_8 3. Aliquot D | 2.1 | 2.6 | 1.0 | 0.8 | 1.6 | 1.0 | 0.5 | 1.0 |
| Donor_8 3. Aliquot E | 2.4 | 2.8 | 1.0 | 1.1 | 2.7 | 1.0 | 0.4 | 1.0 |
| Donor_8 3. Aliquot F | 0.8 | 1.7 | 1.2 | 0.5 | 0.4 | 2.0 | 0.4 | 1.3 |
| Donor_8 3. Aliquot G | 0.6 | 1.4 | 1.0 | 8.4 | 5.1 | 1.0 | 0.5 | 0.0 |

FIG. 13C.7

| | Carcinoembryonic Antigen | Creatine Kinase-MB | C Reactive Protein | EGF | ENA-78 | Endothelin-1 | EN-RAGE | Eotaxin |
|---|---|---|---|---|---|---|---|---|
| | ng/mL | ng/mL | ug/mL | pg/mL | ng/mL | pg/mL | ng/mL | pg/mL |
| Least Detectable Dose | 0.84 | 0.42 | 0.0015 | 7.4 | 0.076 | 7.2 | 0.25 | 41 |
| RBM Low Plasma Range | | | 0.25 | | 0.069 | | 4.6 | |
| RBM High Plasma Range | 4.8 | 1.1 | 50 | 505 | 5.3 | 26 | 592 | 177 |
| Donor_8_3_Aliquot H | 1.2 | 1.7 | 1.1 | 1.1 | 0.9 | 1.5 | 1.2 | 0.9 |
| Donor_8_3_Aliquot I | 1.0 | 1.0 | 1.0 | 1.0 | 1.0 | 1.0 | 1.0 | 1.0 |
| Donor_9_3_Aliquot A | 1.3 | 1.0 | #VALUE! | 0.9 | 1.5 | 1.0 | 0.9 | 1.1 |
| Donor_9_3_Aliquot B | 1.7 | 2.3 | #VALUE! | 1.2 | 1.5 | 1.9 | 0.7 | 1.0 |
| Donor_9_3_Aliquot C | 1.2 | 2.1 | #VALUE! | 0.9 | 1.4 | 1.4 | 1.0 | 0.8 |
| Donor_9_3_Aliquot D | 6.0 | 4.9 | #VALUE! | 1.0 | 1.7 | 2.5 | 0.9 | 1.0 |
| Donor_9_3_Aliquot E | 3.6 | 3.1 | #VALUE! | 0.7 | 4.4 | 2.7 | 1.3 | 0.9 |
| Donor_9_3_Aliquot F | 2.0 | 1.9 | #VALUE! | 0.6 | 0.4 | 1.9 | 0.4 | 1.0 |
| Donor_9_3_Aliquot G | 1.3 | 1.4 | #VALUE! | 9.7 | 10.7 | 1.0 | 1.9 | 0.2 |
| Donor_9_3_Aliquot H | 1.6 | 1.6 | #VALUE! | 1.0 | 0.9 | 0.7 | 2.3 | 0.9 |
| Donor_9_3_Aliquot I | 1.0 | 1.0 | #VALUE! | 1.0 | 1.0 | 1.0 | 1.0 | 1.0 |

FIG. 13D.1

| | Epiregulin | Erythropoietin | Fatty Acid Binding Protein | Factor VII | Ferritin | FGF basic | Fibrinogen | G-CSF |
|---|---|---|---|---|---|---|---|---|
| | pg/mL | pg/mL | ng/mL | ng/mL | ng/mL | pg/mL | mg/mL | pg/mL |
| Least Detectable Dose | 36 | 166 | 3.0 | 1.0 | 1.4 | 98 | 0.0098 | 5.0 |
| RBM Low Plasma Range | Pending | | | | | | | |
| RBM High Plasma Range | Pending | 284 | 10 | 106 | 5.0 | 2000 | 2.2 | 37 |
| Donor_1 3. Aliquot A | 161 | 166 | 32 | 443 | 552 | 1850 | 8.0 | 417 |
| Donor_1 3. Aliquot B | 65 | 166 | 29 | 157 | 1290 | 1710 | 4.1 | 279 |
| Donor_1 3. Aliquot C | 33 | 37 | 34 | 140 | 1380 | 414 | 4.4 | 221 |
| Donor_1 3. Aliquot D | 16 | 166 | 33 | 89 | 1300 | 2050 | 4.2 | 355 |
| Donor_1 3. Aliquot E | 40 | 166 | 33 | 168 | 1400 | 1840 | 4.8 | 270 |
| Donor_1 3. Aliquot F | 61 | 166 | 31 | 171 | 1140 | 1400 | 4.1 | 197 |
| Donor_1 3. Aliquot G | 149 | 166 | 41 | 132 | 1280 | 1760 | 3.7 | 236 |
| Donor_1 3. Aliquot H | 36 | 60 | 31 | 174 | 1420 | 159 | 4.6 | 211 |
| Donor_1 3. Aliquot I | 31 | 166 | 29 | 160 | 1280 | 1470 | 4.0 | 219 |
| Donor_2 3. Aliquot A | 44 | 166 | 36 | 139 | 1490 | 429 | 4.3 | 344 |
| Donor_2 3. Aliquot B | 26 | 166 | 40 | 577 | 1510 | 321 | 4.4 | 204 |
| Donor_2 3. Aliquot C | 16 | 166 | 40 | 154 | 1430 | 241 | 5.1 | 31 |
| Donor_2 3. Aliquot D | 52 | 166 | 45 | 694 | 1390 | 563 | 4.3 | 1470 |
| Donor_2 3. Aliquot E | 21 | 166 | 45 | 640 | 1390 | 563 | 4.0 | 1240 |
| Donor_2 3. Aliquot F | 36 | 166 | 40 | 580 | 1400 | 241 | 4.1 | 32 |
| Donor_2 3. Aliquot G | 236 | 166 | 48 | 588 | 1470 | 664 | 5.3 | 2160 |
| Donor_2 3. Aliquot H | 26 | 166 | 39 | 567 | 1330 | 176 | 3.9 | 36 |
| Donor_2 3. Aliquot I | 36 | 166 | 34 | 450 | 1320 | 225 | 5.2 | 32 |
| Donor_3 3. Aliquot A | 40 | 166 | 14 | 147 | 855 | 98 | 5.9 | 105 |
| Donor_3 3. Aliquot B | 35 | 166 | 12 | 139 | 757 | 29 | 5.5 | 41 |
| Donor_3 3. Aliquot C | 24 | 166 | 12 | 31 | 828 | 29 | 4.9 | 5 |
| Donor_3 3. Aliquot D | 31 | 166 | 17 | 156 | 799 | 209 | 5.2 | 1340 |
| Donor_3 3. Aliquot E | 36 | 166 | 16 | 160 | 797 | 159 | 6.0 | 1200 |
| Donor_3 3. Aliquot F | 36 | 166 | 13 | 128 | 824 | 29 | 5.2 | 5 |
| Donor_3 3. Aliquot G | 36 | 166 | 15 | 116 | 865 | 52 | 6.6 | 7.3 |
| Donor_3 3. Aliquot H | 21 | 166 | 9.2 | 108 | 758 | 98 | 5.3 | 5 |
| Donor_3 3. Aliquot I | 13 | 166 | 11 | 123 | 800 | 29 | 6.2 | 5 |

FIG. 13D.2

| | Epiregulin | Erythropoietin | Fatty Acid Binding Protein | Factor VII | Ferritin | FGF basic | Fibrinogen | G-CSF |
|---|---|---|---|---|---|---|---|---|
| | pg/mL | pg/mL | ng/mL | ng/mL | ng/mL | pg/mL | mg/mL | pg/mL |
| Least Detectable Dose | 36 | 166 | 3.0 | 1.0 | 1.4 | 98 | 0.0098 | 5.0 |
| RBM Low Plasma Range | Pending | | | | | | 2.2 | |
| RBM High Plasma Range | Pending | 284 | 10 | 106 | 5.0 | 2000 | 8.0 | 37 |
| Donor_4_3. Aliquot A | 21 | 166 | 33 | 443 | 552 | 98 | 2.0 | 5.6 |
| Donor_4_3. Aliquot B | 35 | 166 | 33 | 124 | 328 | 52 | 2.0 | 9.6 |
| Donor_4_3. Aliquot C | 36 | 166 | 30 | 129 | 311 | 29 | 2.2 | 5 |
| Donor_4_3. Aliquot D | 36 | 166 | 33 | 9.2 | 286 | 459 | 2.0 | 976 |
| Donor_4_3. Aliquot E | 29 | 166 | 33 | 142 | 308 | 474 | 1.3 | 779 |
| Donor_4_3. Aliquot F | 36 | 166 | 32 | 115 | 319 | 99 | 1.8 | 18 |
| Donor_4_3. Aliquot G | 69 | 166 | 34 | 105 | 347 | 90 | 2.2 | 8.8 |
| Donor_4_3. Aliquot H | 36 | 166 | 37 | 75 | 338 | 98 | 1.7 | 5 |
| Donor_4_3. Aliquot I | 31 | 166 | 34 | 111 | 315 | 98 | 2.0 | 5 |
| | | | | 125 | 352 | 52 | | |
| Donor_5_3. Aliquot A | 129 | 166 | 9.2 | >1113 | 1430 | 489 | 5.4 | 130 |
| Donor_5_3. Aliquot B | 101 | 41 | 7.8 | 1020 | 1320 | 533 | 5.9 | 203 |
| Donor_5_3. Aliquot C | 149 | 166 | 9.2 | 243 | 1570 | 241 | 6.9 | 22 |
| Donor_5_3. Aliquot D | 105 | 100 | 13 | 940 | 1630 | 563 | 3.4 | 1480 |
| Donor_5_3. Aliquot E | 111 | 64 | 14 | 1100 | 1510 | 533 | 5.2 | 3960 |
| Donor_5_3. Aliquot F | 87 | 166 | 6.5 | 808 | 1390 | 257 | 4.4 | 29 |
| Donor_5_3. Aliquot G | 161 | 50 | 10 | 936 | 1460 | 273 | 7.2 | 31 |
| Donor_5_3. Aliquot H | 117 | 50 | 8.8 | 1000 | 1390 | 176 | 5.5 | 23 |
| Donor_5_3. Aliquot I | 95 | 166 | 8.8 | 1050 | 1400 | 159 | 6.6 | 21 |
| Donor_6_3. Aliquot A | 26 | 166 | 2.3 | 320 | 382 | 72 | 4.1 | 12 |
| Donor_6_3. Aliquot B | 31 | 166 | 2.6 | 329 | 374 | 98 | 4.3 | 19 |
| Donor_6_3. Aliquot C | 36 | 166 | 2.6 | 62 | 370 | 98 | 4.9 | 5 |
| Donor_6_3. Aliquot D | 36 | 166 | 5.4 | 345 | 370 | 289 | 3.9 | 389 |
| Donor_6_3. Aliquot E | 36 | 166 | 5.6 | 285 | 364 | 289 | 3.2 | 975 |
| Donor_6_3. Aliquot F | 16 | 166 | 2.2 | 311 | 376 | 98 | 3.2 | 5 |
| Donor_6_3. Aliquot G | 177 | 166 | 2.6 | 252 | 391 | 192 | 5.5 | 20 |
| Donor_6_3. Aliquot H | 36 | 166 | 2.0 | 336 | 353 | 98 | 3.9 | 5 |
| Donor_6_3. Aliquot I | 36 | 166 | 1.7 | 309 | 375 | 98 | 3.4 | 5 |

FIG. 13D.3

| | Epiregulin | Erythropoietin | Fatty Acid Binding Protein | Factor VII | Ferritin | FGF basic | Fibrinogen | G-CSF |
|---|---|---|---|---|---|---|---|---|
| | pg/mL | pg/mL | ng/mL | ng/mL | ng/mL | pg/mL | mg/mL | pg/mL |
| Least Detectable Dose | 36 | 166 | 3.0 | 1.0 | 1.4 | 98 | 0.0098 | 5.0 |
| RBM Low Plasma Range | Pending | | | | | | | |
| RBM High Plasma Range | Pending | 284 | 10 | 106 | 5.0 | 2000 | 2.2 | 37 |
| Donor_7_3. Aliquot A | 36 | 166 | 463 | 443 | 552 | 2000 | 8.0 | 334 |
| Donor_7_3. Aliquot B | 36 | 166 | 459 | 144 | 468 | 391 | 3.0 | 86 |
| Donor_7_3. Aliquot C | 36 | 166 | 466 | 149 | 491 | 249 | 2.9 | 5 |
| Donor_7_3. Aliquot D | 36 | 166 | 422 | 34 | 535 | 98 | 3.2 | 892 |
| Donor_7_3. Aliquot E | 36 | 166 | 434 | 128 | 451 | 281 | 2.6 | 270 |
| Donor_7_3. Aliquot F | 36 | 166 | 426 | 143 | 490 | 265 | 2.1 | 5 |
| Donor_7_3. Aliquot G | 36 | 166 | 511 | 143 | 505 | 98 | 2.6 | 5 |
| Donor_7_3. Aliquot H | 36 | 166 | 440 | 139 | 471 | 233 | 2.9 | 5 |
| Donor_7_3. Aliquot I | 36 | 166 | 451 | 136 | 404 | 72 | 2.4 | 5 |
| | | | | 141 | 409 | 98 | 3.0 | 5 |
| Donor_8_3. Aliquot A | 36 | 166 | 3 | 376 | 34 | 98 | 1.8 | 5.8 |
| Donor_8_3. Aliquot B | 35 | 166 | 3 | 411 | 32 | 98 | 1.7 | 4.7 |
| Donor_8_3. Aliquot C | 44 | 166 | 3 | 18 | 37 | 90 | 1.8 | 5 |
| Donor_8_3. Aliquot D | 42 | 166 | 8.3 | 410 | 48 | 414 | 1.7 | 1330 |
| Donor_8_3. Aliquot E | 35 | 166 | 7.8 | 351 | 39 | 336 | 1.7 | 1010 |
| Donor_8_3. Aliquot F | 58 | 166 | 0.81 | 426 | 32 | 273 | 1.7 | 4.7 |
| Donor_8_3. Aliquot G | 56 | 166 | 3 | 253 | 42 | 98 | 2.0 | 5 |
| Donor_8_3. Aliquot H | 16 | 166 | 0.56 | 382 | 38 | 142 | 1.7 | 5 |
| Donor_8_3. Aliquot I | 36 | 166 | 0.14 | 381 | 36 | 98 | 1.9 | 5 |
| Donor_9_3. Aliquot A | 86 | 166 | 3 | 196 | 4.8 | 98 | 1.5 | 17 |
| Donor_9_3. Aliquot B | 75 | 166 | 1.6 | 196 | 2.6 | 122 | 1.6 | 21 |
| Donor_9_3. Aliquot C | 106 | 166 | 0.42 | 44 | 5.7 | 94 | 1.4 | 19 |
| Donor_9_3. Aliquot D | 101 | 166 | 10 | 243 | 11 | 414 | 1.5 | 2320 |
| Donor_9_3. Aliquot E | 79 | 166 | 6.6 | 201 | 6.0 | 332 | 1.5 | 1490 |
| Donor_9_3. Aliquot F | 77 | 166 | 0.68 | 196 | 3.6 | 137 | 1.2 | 11 |
| Donor_9_3. Aliquot G | 123 | 166 | 0.81 | 147 | 12 | 179 | 1.9 | 39 |
| Donor_9_3. Aliquot H | 97 | 166 | 3 | 229 | 5.5 | 37 | 1.3 | 5.4 |
| Donor_9_3. Aliquot I | 83 | 166 | 3 | 184 | 3.3 | 37 | 1.6 | 5.4 |

FIG. 13D.4

| | Epiregulin | Erythropoietin | Fatty Acid Binding Protein | Factor VII | Ferritin | FGF basic | Fibrinogen | G-CSF |
|---|---|---|---|---|---|---|---|---|
| | pg/mL | pg/mL | ng/mL | ng/mL | ng/mL | pg/mL | mg/mL | pg/mL |
| Least Detectable Dose | 36 | 166 | 3.0 | 1.0 | 1.4 | 98 | 0.0098 | 5.0 |
| RBM Low Plasma Range | Pending | | | 106 | 5.0 | | 2.2 | |
| RBM High Plasma Range | Pending | 284 | 10 | 443 | 552 | 2000 | 8.0 | 37 |
| EDTA Plasma | | | | | | | | |
| donor #1 plasma | 83 | 84 | 32 | 141 | 1190 | 736 | 4.6 | 240 |
| donor #2 plasma | 36 | 166 | 65 | 545 | 1670 | 339 | 8.1 | 45 |
| donor #3 plasma | 32 | 166 | 25 | 135 | 934 | 94 | 8.7 | 5 |
| donor #4 plasma | 36 | 166 | 59 | 121 | 320 | 51 | 3.2 | 4.5 |
| donor #5 plasma | 35 | 118 | 13 | 891 | 1190 | 346 | 11 | 24 |
| donor #6 plasma | 36 | 37 | 5.0 | 315 | 382 | 21 | 6.7 | 6.2 |
| donor #7 plasma | 36 | 166 | >617 | 187 | 545 | 98 | 4.5 | 6.2 |
| donor #8 plasma | 35 | 166 | 3 | 428 | 22 | 87 | 2.0 | 5 |
| donor #9 plasma | 65 | 166 | 0.55 | 299 | 3.3 | 87 | 2.3 | 18 |
| | | | | | | | | |
| *Stimulations indices* | | | | | | | | |
| Donor_1 3. Aliquot A | 5.2 | 1.0 | 1.1 | 1.1 | 1.1 | 1.3 | 0.9 | 1.9 |
| Donor_1 3. Aliquot B | 2.1 | 1.0 | 1.0 | 1.0 | 1.2 | 1.2 | 1.0 | 1.3 |
| Donor_1 3. Aliquot C | 1.1 | 0.2 | 1.2 | 0.6 | 1.1 | 0.3 | 1.0 | 1.0 |
| Donor_1 3. Aliquot D | 0.5 | 1.0 | 1.1 | 1.2 | 1.2 | 1.4 | 1.1 | 1.6 |
| Donor_1 3. Aliquot E | 1.3 | 1.0 | 1.1 | 1.2 | 1.0 | 1.3 | 0.9 | 1.2 |
| Donor_1 3. Aliquot F | 2.0 | 1.0 | 1.1 | 0.9 | 1.1 | 1.0 | 0.8 | 0.9 |
| Donor_1 3. Aliquot G | 4.8 | 1.0 | 1.4 | 1.3 | 1.2 | 1.2 | 1.1 | 1.1 |
| Donor_1 3. Aliquot H | 1.2 | 0.4 | 1.1 | 1.2 | 1.1 | 0.1 | 0.9 | 1.0 |
| Donor_1 3. Aliquot I | 1.0 | 1.0 | 1.0 | 1.0 | 1.0 | 1.0 | 1.1 | 1.0 |
| | | | | | | | | |
| Donor_2 3. Aliquot A | 1.2 | 1.0 | 1.1 | 1.2 | 1.1 | 1.9 | 0.8 | 10.8 |
| Donor_2 3. Aliquot B | 0.7 | 1.0 | 1.2 | 1.3 | 1.1 | 1.4 | 0.8 | 6.4 |
| Donor_2 3. Aliquot C | 0.4 | 1.0 | 1.2 | 0.3 | 1.1 | 1.1 | 1.0 | 1.0 |
| Donor_2 3. Aliquot D | 1.5 | 1.0 | 1.3 | 1.5 | 1.1 | 2.5 | 0.8 | 45.9 |
| Donor_2 3. Aliquot E | 0.6 | 1.0 | 1.1 | 1.4 | 1.1 | 2.5 | 0.8 | 38.8 |
| Donor_2 3. Aliquot F | 1.0 | 1.0 | 1.2 | 1.3 | 1.1 | 1.1 | 1.0 | 1.0 |
| Donor_2 3. Aliquot G | 6.6 | 1.0 | 1.4 | 1.3 | 1.1 | 3.0 | 1.0 | 67.5 |

FIG. 13D.5

| | Epiregulin | Erythropoietin | Fatty Acid Binding Protein | Factor VII | Ferritin | FGF basic | Fibrinogen | G-CSF |
|---|---|---|---|---|---|---|---|---|
| | pg/mL | pg/mL | ng/mL | ng/mL | ng/mL | pg/mL | mg/mL | pg/mL |
| Least Detectable Dose | 36 | 166 | 3.0 | 1.0 | 1.4 | 98 | 0.0098 | 5.0 |
| RBM Low Plasma Range | Pending | | | 106 | 5.0 | | 2.2 | 37 |
| RBM High Plasma Range | Pending | 284 | 10 | 443 | 552 | 2000 | 8.0 | |
| Donor_2.3. Aliquot H | 0.7 | 1.0 | 1.1 | 1.3 | 1.0 | 0.8 | 0.8 | 1.1 |
| Donor_2.3. Aliquot I | 1.0 | 1.0 | 1.0 | 1.0 | 1.0 | 1.0 | 1.0 | 1.0 |
| Donor_3.3. Aliquot A | 3.1 | 1.0 | 1.3 | 1.2 | 1.1 | 3.3 | 1.0 | 21.0 |
| Donor_3.3. Aliquot B | 2.7 | 1.0 | 1.1 | 1.1 | 0.9 | 1.0 | 0.9 | 8.2 |
| Donor_3.3. Aliquot C | 1.8 | 1.0 | 1.0 | 0.3 | 1.0 | 1.0 | 0.8 | 1.0 |
| Donor_3.3. Aliquot D | 2.4 | 1.0 | 1.5 | 1.3 | 1.0 | 7.1 | 0.8 | 268.0 |
| Donor_3.3. Aliquot E | 2.8 | 1.0 | 1.4 | 1.3 | 1.0 | 5.4 | 1.0 | 240.0 |
| Donor_3.3. Aliquot F | 2.8 | 1.0 | 1.2 | 1.0 | 1.0 | 1.0 | 0.8 | 1.0 |
| Donor_3.3. Aliquot G | 2.8 | 1.0 | 1.3 | 0.9 | 1.1 | 1.8 | 1.1 | 1.5 |
| Donor_3.3. Aliquot H | 1.7 | 1.0 | 0.8 | 0.9 | 0.9 | 3.3 | 0.9 | 1.0 |
| Donor_3.3. Aliquot I | 1.0 | 1.0 | 1.0 | 1.0 | 1.0 | 1.0 | 1.0 | 1.0 |
| Donor_4.3. Aliquot A | 0.7 | 1.0 | 1.0 | 1.0 | 0.9 | 1.9 | 1.0 | 1.1 |
| Donor_4.3. Aliquot B | 1.1 | 1.0 | 0.9 | 0.1 | 0.9 | 1.0 | 1.0 | 1.9 |
| Donor_4.3. Aliquot C | 1.2 | 1.0 | 1.0 | 1.1 | 0.8 | 0.6 | 1.1 | 1.0 |
| Donor_4.3. Aliquot D | 1.2 | 1.0 | 1.0 | 0.9 | 0.9 | 8.8 | 1.0 | 195.2 |
| Donor_4.3. Aliquot E | 0.9 | 1.0 | 1.0 | 0.8 | 0.9 | 9.1 | 0.7 | 155.8 |
| Donor_4.3. Aliquot F | 1.2 | 1.0 | 1.0 | 0.6 | 1.0 | 1.9 | 0.9 | 3.6 |
| Donor_4.3. Aliquot G | 2.2 | 1.0 | 1.1 | 0.9 | 0.9 | 1.7 | 1.1 | 1.8 |
| Donor_4.3. Aliquot H | 1.2 | 1.0 | 1.1 | 1.0 | 1.0 | 1.9 | 0.8 | 1.0 |
| Donor_4.3. Aliquot I | 1.0 | 1.0 | 1.0 | #VALUE! | 1.0 | 1.0 | 1.0 | 1.0 |
| Donor_5.3. Aliquot A | 1.4 | 1.0 | 1.0 | 1.0 | 1.0 | 3.1 | 0.8 | 6.2 |
| Donor_5.3. Aliquot B | 1.1 | 0.2 | 0.9 | 1.0 | 0.9 | 3.4 | 0.9 | 9.7 |
| Donor_5.3. Aliquot C | 1.6 | 1.0 | 1.0 | 0.2 | 1.1 | 1.5 | 1.0 | 1.0 |
| Donor_5.3. Aliquot D | 1.1 | 0.6 | 1.5 | 0.9 | 1.2 | 3.5 | 0.5 | 70.8 |
| Donor_5.3. Aliquot E | 1.2 | 0.4 | 1.6 | 1.0 | 1.1 | 3.4 | 0.8 | 189.5 |
| Donor_5.3. Aliquot F | 0.9 | 1.0 | 0.7 | 0.8 | 1.0 | 1.6 | 0.7 | 1.4 |
| Donor_5.3. Aliquot G | 1.7 | 0.3 | 1.2 | 0.9 | 1.0 | 1.7 | 1.1 | 1.5 |

FIG. 13D.6

| | Epiregulin | Erythropoietin | Fatty Acid Binding Protein | Factor VII | Ferritin | FGF basic | Fibrinogen | G-CSF |
|---|---|---|---|---|---|---|---|---|
| | pg/mL | pg/mL | ng/mL | ng/mL | ng/mL | pg/mL | mg/mL | pg/mL |
| Least Detectable Dose | 36 | 166 | 3.0 | 1.0 | 1.4 | 98 | 0.0098 | 5.0 |
| RBM Low Plasma Range | Pending | | | 106 | 5.0 | | 2.2 | |
| RBM High Plasma Range | Pending | 284 | 10 | 443 | 552 | 2000 | 8.0 | 37 |
| Donor_5_3. Aliquot H | 1.2 | 0.3 | 1.0 | 1.0 | 1.0 | 1.1 | 0.8 | 1.1 |
| Donor_5_3. Aliquot I | 1.0 | 1.0 | 1.0 | 1.0 | 1.0 | 1.0 | 1.0 | 1.0 |
| | | | | | | | | |
| Donor_6_3. Aliquot A | 0.7 | 1.0 | 1.3 | 1.0 | 1.0 | 0.7 | 1.2 | 2.3 |
| Donor_6_3. Aliquot B | 0.9 | 1.0 | 1.5 | 1.1 | 1.0 | 1.0 | 1.3 | 3.8 |
| Donor_6_3. Aliquot C | 1.0 | 1.0 | 1.5 | 0.2 | 1.0 | 1.0 | 1.4 | 1.0 |
| Donor_6_3. Aliquot D | 1.0 | 1.0 | 3.1 | 1.1 | 1.0 | 2.9 | 1.1 | 77.8 |
| Donor_6_3. Aliquot E | 1.0 | 1.0 | 3.2 | 0.9 | 1.0 | 2.9 | 0.9 | 195.0 |
| Donor_6_3. Aliquot F | 0.4 | 1.0 | 1.2 | 1.0 | 1.0 | 1.0 | 0.9 | 1.0 |
| Donor_6_3. Aliquot G | 4.9 | 1.0 | 1.5 | 0.8 | 1.0 | 2.0 | 1.8 | 4.1 |
| Donor_6_3. Aliquot H | 1.0 | 1.0 | 1.1 | 1.1 | 0.9 | 1.0 | 1.1 | 1.0 |
| Donor_6_3. Aliquot I | 1.0 | 1.0 | 1.0 | 1.0 | 1.0 | 1.0 | 1.0 | 1.0 |
| | | | | | | | | |
| Donor_7_3. Aliquot A | 1.0 | 1.0 | 1.0 | 1.0 | 1.1 | 4.0 | 1.0 | 66.8 |
| Donor_7_3. Aliquot B | 1.0 | 1.0 | 1.0 | 1.1 | 1.2 | 2.5 | 0.9 | 17.1 |
| Donor_7_3. Aliquot C | 1.0 | 1.0 | 1.0 | 0.2 | 1.3 | 1.0 | 1.1 | 1.0 |
| Donor_7_3. Aliquot D | 1.0 | 1.0 | 0.9 | 0.9 | 1.1 | 2.9 | 0.9 | 178.4 |
| Donor_7_3. Aliquot E | 1.0 | 1.0 | 1.0 | 1.0 | 1.2 | 2.7 | 0.7 | 54.0 |
| Donor_7_3. Aliquot F | 1.0 | 1.0 | 0.9 | 1.0 | 1.2 | 1.0 | 0.9 | 1.0 |
| Donor_7_3. Aliquot G | 1.0 | 1.0 | 1.1 | 1.0 | 1.2 | 2.4 | 1.0 | 1.0 |
| Donor_7_3. Aliquot H | 1.0 | 1.0 | 1.0 | 1.0 | 1.0 | 0.7 | 0.8 | 1.0 |
| Donor_7_3. Aliquot I | 1.0 | 1.0 | 1.0 | 1.0 | 1.1 | 1.0 | 1.0 | 1.0 |
| | | | | | | | | |
| Donor_8_3. Aliquot A | 1.0 | 1.0 | 21.7 | 1.0 | 1.0 | 1.0 | 1.0 | 1.2 |
| Donor_8_3. Aliquot B | 1.0 | 1.0 | 21.7 | 1.1 | 0.9 | 1.0 | 0.9 | 0.9 |
| Donor_8_3. Aliquot C | 1.2 | 1.0 | 21.7 | 0.0 | 1.0 | 0.9 | 0.9 | 1.0 |
| Donor_8_3. Aliquot D | 1.2 | 1.0 | 60.3 | 1.1 | 1.3 | 4.2 | 0.9 | 266.0 |
| Donor_8_3. Aliquot E | 1.0 | 1.0 | 56.7 | 0.9 | 1.1 | 3.4 | 0.9 | 202.0 |
| Donor_8_3. Aliquot F | 1.6 | 1.0 | 5.8 | 1.1 | 0.9 | 2.8 | 0.9 | 0.9 |
| Donor_8_3. Aliquot G | 1.6 | 1.0 | 21.7 | 0.7 | 1.1 | 1.0 | 1.1 | 1.0 |

FIG. 13D.7

| | Epiregulin | Erythropoietin | Fatty Acid Binding Protein | Factor VII | Ferritin | FGF basic | Fibrinogen | G-CSF |
|---|---|---|---|---|---|---|---|---|
| Least Detectable Dose | pg/mL 36 | pg/mL 166 | ng/mL 3.0 | ng/mL 1.0 | ng/mL 1.4 | pg/mL 98 | mg/mL 0.0098 | pg/mL 5.0 |
| RBM Low Plasma Range | Pending | | | | 5.0 | | 2.2 | |
| RBM High Plasma Range | Pending | 284 | 10 | 106 | 552 | 2000 | 8.0 | 37 |
| Donor_8_3, Aliquot H | 0.4 | 1.0 | 4.1 | 443 | 1.1 | 1.4 | 0.9 | 1.0 |
| Donor_8_3, Aliquot I | 1.0 | 1.0 | 1.0 | 1.0 | 1.0 | 1.0 | 1.0 | 1.0 |
| Donor_9_3, Aliquot A | 1.0 | 1.0 | 1.0 | 1.1 | 1.4 | 2.7 | 0.9 | 3.1 |
| Donor_9_3, Aliquot B | 0.9 | 1.0 | 0.5 | 1.1 | 0.8 | 3.3 | 1.0 | 3.9 |
| Donor_9_3, Aliquot C | 1.3 | 1.0 | 0.1 | 0.2 | 1.7 | 2.6 | 0.9 | 3.6 |
| Donor_9_3, Aliquot D | 1.2 | 1.0 | 3.4 | 1.3 | 3.4 | 11.3 | 0.9 | 432.8 |
| Donor_9_3, Aliquot E | 1.0 | 1.0 | 2.2 | 1.1 | 1.8 | 9.0 | 0.9 | 278.0 |
| Donor_9_3, Aliquot F | 0.9 | 1.0 | 0.2 | 1.1 | 1.1 | 3.7 | 0.8 | 2.1 |
| Donor_9_3, Aliquot G | 1.5 | 1.0 | 0.3 | 0.8 | 3.6 | 4.9 | 1.2 | 7.4 |
| Donor_9_3, Aliquot H | 1.2 | 1.0 | 1.0 | 1.2 | 1.7 | 1.0 | 0.8 | 1.0 |
| Donor_9_3, Aliquot I | 1.0 | 1.0 | 1.0 | 1.0 | 1.0 | 1.0 | 1.0 | 1.0 |

FIG. 13E.1

| | Growth Hormone ng/mL | GM-CSF pg/mL | Glutathione S-Transferase ng/mL | Haptoglobin mg/mL | ICAM-1 ng/mL | IFN-gamma pg/mL | IgA mg/mL | IgE ng/mL |
|---|---|---|---|---|---|---|---|---|
| Least Detectable Dose | 0.13 | 57 | 0.40 | 0.025 | 3.2 | 4.6 | 0.0084 | 14 |
| RBM Low Plasma Range | | | | 0.047 | 42 | Pending | 0.58 | |
| RBM High Plasma Range | 4.4 | 152 | 3.1 | 7.6 | 213 | Pending | 5.6 | 770 |
| Samples | | | | | | | | |
| Donor_1 3. Aliquot A | 1.8 | 8.4 | 0.64 | 1.0 | 467 | 3.8 | 2.0 | 13 |
| Donor_1 3. Aliquot B | 1.7 | 2.5 | 0.84 | 1.2 | 432 | 4.5 | 2.3 | 11 |
| Donor_1 3. Aliquot C | 1.9 | 5.0 | 0.55 | 1.1 | 452 | 2.7 | 2.2 | 1.8 |
| Donor_1 3. Aliquot D | 2.1 | 4.5 | 0.69 | 1.2 | 465 | 4.6 | 2.4 | 12 |
| Donor_1 3. Aliquot E | 2.0 | 10 | 0.59 | 1.1 | 438 | 4.6 | 2.1 | 13 |
| Donor_1 3. Aliquot F | 1.5 | 2.5 | 0.50 | 1.2 | 441 | 4.5 | 2.1 | 4.4 |
| Donor_1 3. Aliquot G | 1.8 | 57 | 0.52 | 1.2 | 471 | 4.6 | 2.3 | 11 |
| Donor_1 3. Aliquot H | 1.8 | 4.5 | 0.52 | 1.1 | 491 | 4.6 | 2.1 | 9.6 |
| Donor_1 3. Aliquot I | 1.8 | 4.0 | 0.55 | 1.1 | 438 | 4.6 | 2.3 | 6.2 |
| Donor_2 3. Aliquot A | 0.77 | 12 | 0.4 | 1.3 | 491 | 7.2 | 2.5 | 210 |
| Donor_2 3. Aliquot B | 0.90 | 5.0 | 0.76 | 1.8 | 495 | 6.7 | 2.5 | 217 |
| Donor_2 3. Aliquot C | 0.82 | 57 | 0.55 | 1.9 | 499 | 4.6 | 2.5 | 98 |
| Donor_2 3. Aliquot D | 1.2 | 24 | 1.7 | 1.5 | 489 | 31 | 2.4 | 258 |
| Donor_2 3. Aliquot E | 0.91 | 4.5 | 0.81 | 2.2 | 479 | 9.5 | 2.5 | 221 |
| Donor_2 3. Aliquot F | 0.70 | 3.5 | 0.41 | 2.1 | 504 | 4.6 | 2.5 | 177 |
| Donor_2 3. Aliquot G | 0.87 | 180 | 0.69 | 2.3 | 514 | 14 | 2.5 | 151 |
| Donor_2 3. Aliquot H | 0.78 | 3.5 | 0.4 | 1.9 | 490 | 2.7 | 2.6 | 175 |
| Donor_2 3. Aliquot I | 0.71 | 57 | 0.4 | 1.7 | 479 | 3.8 | 2.5 | 195 |
| Donor_3 3. Aliquot A | 1.5 | 10 | 0.46 | 0.014 | 283 | 8.5 | 1.5 | 26 |
| Donor_3 3. Aliquot B | 1.4 | 7.8 | 1.4 | 0.018 | 239 | 4.6 | 1.6 | 27 |
| Donor_3 3. Aliquot C | 1.5 | 2.5 | 0.48 | 0.019 | 278 | 4.6 | 1.6 | 7.6 |
| Donor_3 3. Aliquot D | 1.5 | 6.7 | 1.4 | 0.013 | 231 | 8.2 | 1.6 | 45 |
| Donor_3 3. Aliquot E | 1.6 | 23 | 0.94 | 0.014 | 306 | 9.2 | 1.7 | 40 |
| Donor_3 3. Aliquot F | 1.3 | 18 | 0.4 | 0.021 | 249 | 4.6 | 1.5 | 26 |
| Donor_3 3. Aliquot G | 1.7 | 57 | 0.4 | 0.087 | 259 | 4.6 | 1.6 | 14 |
| Donor_3 3. Aliquot H | 1.3 | 57 | 0.4 | 0.022 | 208 | 4.6 | 1.5 | 21 |
| Donor_3 3. Aliquot I | 1.6 | 57 | 0.4 | 0.051 | 221 | 4.6 | 1.5 | 29 |

FIG. 13E.2

| | Growth Hormone ng/mL | GM-CSF pg/mL | Glutathione S-Transferase ng/mL | Haptoglobin mg/mL | ICAM-1 ng/mL | IFN-gamma pg/mL | IgA mg/mL | IgE ng/mL |
|---|---|---|---|---|---|---|---|---|
| Least Detectable Dose | 0.13 | 57 | 0.40 | 0.025 | 3.2 | 4.6 | 0.0084 | 14 |
| RBM Low Plasma Range | | | | 0.047 | 42 | Pending | 0.58 | |
| RBM High Plasma Range | | 152 | 3.1 | 7.6 | 213 | Pending | 5.6 | 770 |
| Donor_4_3. Aliquot A | 4.4 | 3.5 | 0.4 | 0.0075 | 456 | 4.6 | 2.5 | 12 |
| Donor_4_3. Aliquot B | 4.1 | 57 | 0.99 | 0.014 | 466 | 4.6 | 2.3 | 14 |
| Donor_4_3. Aliquot C | 4.2 | 57 | 0.4 | 0.0086 | 453 | 4.6 | 2.4 | 14 |
| Donor_4_3. Aliquot D | 4.0 | 18 | 1.2 | 0.014 | 471 | 6.2 | 2.2 | 32 |
| Donor_4_3. Aliquot E | 4.2 | 22 | 0.59 | 0.0086 | 477 | 7.0 | 2.3 | 24 |
| Donor_4_3. Aliquot F | 3.7 | 5.0 | 0.4 | 0.019 | 467 | 3.8 | 2.3 | 13 |
| Donor_4_3. Aliquot G | 3.3 | 57 | 0.37 | 0.019 | 462 | 4.6 | 2.4 | 8.0 |
| Donor_4_3. Aliquot H | 3.6 | 57 | 0.39 | 0.013 | 474 | 4.6 | 2.3 | 8.0 |
| Donor_4_3. Aliquot I | 4.1 | 2.5 | 0.4 | 0.011 | 447 | 4.6 | 2.3 | 9.6 |
| Donor_5_3. Aliquot A | 4.2 | 5.6 | 0.89 | 3.7 | 241 | 7.5 | 1.1 | 321 |
| Donor_5_3. Aliquot B | 3.9 | 57 | 0.64 | 3.6 | 213 | 8.2 | 1.1 | 270 |
| Donor_5_3. Aliquot C | 4.0 | 57 | 0.64 | 3.8 | 246 | 4.6 | 1.1 | 84 |
| Donor_5_3. Aliquot D | 3.7 | 23 | 1.3 | 3.4 | 263 | 20 | 1.1 | 271 |
| Donor_5_3. Aliquot E | 4.1 | 32 | 1.1 | 3.2 | 261 | 21 | 1.2 | 274 |
| Donor_5_3. Aliquot F | 3.0 | 57 | 0.4 | 3.1 | 164 | 7.2 | 1.0 | 204 |
| Donor_5_3. Aliquot G | 4.7 | 3.5 | 0.4 | 3.5 | 255 | 6.2 | 1.0 | 59 |
| Donor_5_3. Aliquot H | 4.0 | 6.7 | 0.4 | 3.2 | 223 | 3.8 | 1.0 | 296 |
| Donor_5_3. Aliquot I | 3.8 | 57 | 0.50 | 3.4 | 242 | 5.1 | 1.00 | 289 |
| Donor_6_3. Aliquot A | 3.0 | 7.8 | 0.4 | 4.2 | 130 | 4.6 | 0.79 | 317 |
| Donor_6_3. Aliquot B | 3.1 | 20 | 1.3 | 4.4 | 146 | 4.6 | 0.81 | 306 |
| Donor_6_3. Aliquot C | 2.8 | 3.0 | 0.4 | 4.2 | 157 | 4.6 | 0.78 | 139 |
| Donor_6_3. Aliquot D | 3.1 | 4.0 | 0.66 | 4.3 | 149 | 31 | 0.81 | 326 |
| Donor_6_3. Aliquot E | 2.9 | 7.8 | 1.4 | 3.9 | 120 | 74 | 0.94 | 269 |
| Donor_6_3. Aliquot F | 2.8 | 9.0 | 0.4 | 4.3 | 120 | 4.6 | 0.82 | 222 |
| Donor_6_3. Aliquot G | 3.2 | 6.7 | 0.4 | 4.2 | 156 | 4.6 | 0.81 | 91 |
| Donor_6_3. Aliquot H | 3.1 | 7.2 | 0.4 | 4.1 | 146 | 4.6 | 0.71 | 340 |
| Donor_6_3. Aliquot I | 3.0 | 57 | 0.37 | 3.7 | 127 | 4.6 | 0.76 | 272 |

FIG. 13E.3

| | Growth Hormone ng/mL | GM-CSF pg/mL | Glutathione S-Transferase ng/mL | Haptoglobin mg/mL | ICAM-1 ng/mL | IFN-gamma pg/mL | IgA mg/mL | IgE ng/mL |
|---|---|---|---|---|---|---|---|---|
| Least Detectable Dose | 0.13 | 57 | 0.40 | 0.025 | 3.2 | 4.6 | 0.0084 | 14 |
| RBM Low Plasma Range | | | | 0.047 | 42 | Pending | 0.58 | |
| RBM High Plasma Range | 4.4 | 152 | 3.1 | 7.6 | 213 | Pending | 5.6 | 770 |
| Donor_7_3. Aliquot A | 0.32 | 20 | 0.39 | 2.6 | 85 | 4.6 | 1.5 | 56 |
| Donor_7_3. Aliquot B | 0.39 | 10 | 1.2 | 2.7 | 85 | 4.6 | 1.5 | 51 |
| Donor_7_3. Aliquot C | 0.22 | 5.6 | 0.48 | 2.7 | 89 | 4.6 | 1.6 | 14 |
| Donor_7_3. Aliquot D | 0.39 | 18 | 0.86 | 2.0 | 74 | 4.6 | 1.4 | 62 |
| Donor_7_3. Aliquot E | 0.31 | 18 | 0.50 | 1.9 | 84 | 4.6 | 1.1 | 56 |
| Donor_7_3. Aliquot F | 0.26 | 10 | 0.4 | 2.6 | 83 | 4.6 | 1.5 | 39 |
| Donor_7_3. Aliquot G | 0.23 | 3.0 | 0.4 | 2.3 | 93 | 4.6 | 1.4 | 25 |
| Donor_7_3. Aliquot H | 0.25 | 9.0 | 0.4 | 2.6 | 81 | 4.6 | 1.4 | 36 |
| Donor_7_3. Aliquot I | 0.29 | 9.0 | 0.4 | 2.7 | 79 | 4.6 | 1.5 | 46 |
| Donor_8_3. Aliquot A | 0.35 | 5.0 | 0.37 | 0.014 | 61 | 5.6 | 0.77 | 17 |
| Donor_8_3. Aliquot B | 0.35 | 6.7 | 1.8 | 0.016 | 66 | 4.6 | 0.85 | 8.0 |
| Donor_8_3. Aliquot C | 0.20 | 12 | 0.4 | 0.0065 | 50 | 550 | 0.83 | 14 |
| Donor_8_3. Aliquot D | 0.94 | 60 | 3.4 | 0.013 | 63 | 1880 | 0.73 | 77 |
| Donor_8_3. Aliquot E | 0.90 | 33 | 2.1 | 0.037 | 59 | 283 | 0.73 | 65 |
| Donor_8_3. Aliquot F | 0.36 | 18 | 0.4 | 0.018 | 63 | 118 | 0.85 | 15 |
| Donor_8_3. Aliquot G | 0.33 | 3.5 | 0.4 | 0.016 | 65 | 4.6 | 0.74 | 8.0 |
| Donor_8_3. Aliquot H | 0.30 | 17 | 0.4 | 0.016 | 64 | 41 | 0.84 | 10 |
| Donor_8_3. Aliquot I | 0.28 | 14 | 0.55 | 0.011 | 58 | 3.8 | 0.78 | 3.7 |
| Donor_9_3. Aliquot A | 7.2 | 11 | 0.73 | 0.018 | 79 | 17 | 1.0 | 9.3 |
| Donor_9_3. Aliquot B | 6.8 | 13 | 2.2 | 0.018 | 82 | 21 | 1.0 | 9.3 |
| Donor_9_3. Aliquot C | 6.6 | 21 | 0.40 | 0.012 | 69 | 519 | 1.0 | 4.1 |
| Donor_9_3. Aliquot D | 6.8 | 29 | 2.6 | 0.0062 | 75 | 2360 | 1.0 | 63 |
| Donor_9_3. Aliquot E | 6.8 | 13 | 2.4 | 0.013 | 71 | 490 | 1.00 | 39 |
| Donor_9_3. Aliquot F | 6.4 | 5.8 | 0.76 | 0.0076 | 78 | 26 | 1.0 | 5.8 |
| Donor_9_3. Aliquot G | 6.2 | 17 | 0.56 | 0.016 | 68 | 7.6 | 1.1 | 5.2 |
| Donor_9_3. Aliquot H | 6.8 | 15 | 0.53 | 0.017 | 75 | 9.0 | 1.0 | 6.0 |
| Donor_9_3. Aliquot I | 6.4 | 8.7 | 0.37 | 0.012 | 76 | 14 | 1.0 | 6.2 |

FIG. 13E.4

| | Growth Hormone ng/mL | GM-CSF pg/mL | Glutathione S-Transferase ng/mL | Haptoglobin mg/mL | ICAM-1 ng/mL | IFN-gamma pg/mL | IgA mg/mL | IgE ng/mL |
|---|---|---|---|---|---|---|---|---|
| Least Detectable Dose | 0.13 | 57 | 0.40 | 0.025 | 3.2 | 4.6 | 0.0084 | 14 |
| | | | | | | | | |
| RBM Low Plasma Range | | | | 0.047 | 42 | Pending | 0.58 | |
| RBM High Plasma Range | 4.4 | 152 | 3.1 | 7.6 | 213 | Pending | 5.6 | 770 |
| EDTA Plasma | | | | | | | | |
| donor #1 plasma | 1.4 | 18 | 1.1 | 1.3 | 206 | 4.0 | 2.4 | 6.6 |
| donor #2 plasma | 0.89 | 15 | 0.4 | 3.6 | 371 | 10 | 4.0 | 172 |
| donor #3 plasma | 1.5 | 27 | 1.0 | 0.58 | 171 | 5.8 | 2.8 | 26 |
| donor #4 plasma | 5.3 | 10.0 | 0.4 | 0.0097 | 348 | 4.6 | 3.6 | 14 |
| donor #5 plasma | 5.1 | 23 | 1.3 | 5.9 | 136 | 13 | 1.8 | 318 |
| donor #6 plasma | 4.1 | 20 | 0.69 | 5.7 | 129 | 4.6 | 1.3 | 559 |
| donor #7 plasma | 0.49 | 17 | 0.4 | 4.6 | 109 | 5.8 | 2.4 | 81 |
| donor #8 plasma | 0.38 | 15 | 0.46 | 0.36 | 87 | 4.6 | 1.0 | 17 |
| donor #9 plasma | 7.2 | 5.3 | 0.90 | 0.32 | 100 | 4.0 | 1.4 | 3.5 |
| | | | | | | | | |
| *Stimulations indices* | | | | | | | | |
| Donor_1 3. Aliquot A | 1.0 | 2.1 | 1.2 | 1.0 | 1.1 | 0.8 | 0.9 | 2.0 |
| Donor_1 3. Aliquot B | 1.0 | 0.6 | 1.5 | 1.1 | 1.0 | 1.0 | 1.0 | 1.8 |
| Donor_1 3. Aliquot C | 1.1 | 1.3 | 1.0 | 1.0 | 1.0 | 0.6 | 1.0 | 0.3 |
| Donor_1 3. Aliquot D | 1.2 | 1.1 | 1.3 | 1.1 | 1.1 | 1.0 | 1.1 | 1.9 |
| Donor_1 3. Aliquot E | 1.1 | 2.6 | 1.1 | 1.1 | 1.0 | 1.0 | 0.9 | 2.1 |
| Donor_1 3. Aliquot F | 0.8 | 0.6 | 0.9 | 1.1 | 1.0 | 1.0 | 0.9 | 0.7 |
| Donor_1 3. Aliquot G | 1.0 | 14.4 | 1.0 | 1.1 | 1.1 | 1.0 | 1.0 | 1.8 |
| Donor_1 3. Aliquot H | 1.0 | 1.1 | 1.0 | 1.1 | 1.1 | 1.0 | 0.9 | 1.6 |
| Donor_1 3. Aliquot I | 1.0 | 1.0 | 1.7 | 1.0 | 1.1 | 1.0 | 1.0 | 1.0 |
| | | | | | | | | |
| Donor_2 3. Aliquot A | 1.1 | 0.2 | 1.0 | 0.8 | 1.0 | 1.9 | 1.0 | 1.1 |
| Donor_2 3. Aliquot B | 1.3 | 0.1 | 1.9 | 1.0 | 1.0 | 1.7 | 1.0 | 1.1 |
| Donor_2 3. Aliquot C | 1.2 | 1.0 | 1.4 | 1.1 | 1.0 | 1.2 | 1.0 | 0.5 |
| Donor_2 3. Aliquot D | 1.6 | 0.4 | 4.1 | 0.9 | 1.0 | 8.1 | 1.0 | 1.3 |
| Donor_2 3. Aliquot E | 1.3 | 0.1 | 2.0 | 1.3 | 1.0 | 2.5 | 1.0 | 1.1 |
| Donor_2 3. Aliquot F | 1.0 | 0.1 | 1.0 | 1.2 | 1.1 | 1.2 | 1.0 | 0.9 |
| Donor_2 3. Aliquot G | 1.2 | 3.2 | 1.7 | 1.3 | 1.1 | 3.7 | 1.0 | 0.8 |

FIG. 13E.5

| | Growth Hormone ng/mL | GM-CSF pg/mL | Glutathione S-Transferase ng/mL | Haptoglobin mg/mL | ICAM-1 ng/mL | IFN-gamma pg/mL | IgA mg/mL | IgE ng/mL |
|---|---|---|---|---|---|---|---|---|
| Least Detectable Dose | 0.13 | 57 | 0.40 | 0.025 | 3.2 | 4.6 | 0.0084 | 14 |
| RBM Low Plasma Range | 4.4 | 152 | 3.1 | 0.047 | 42 | Pending | 0.58 | 770 |
| RBM High Plasma Range | | | | 7.6 | 213 | Pending | 5.6 | |
| Donor_2_3. Aliquot H | 1.1 | 0.1 | 1.0 | 1.1 | 1.0 | 0.7 | 1.1 | 0.9 |
| Donor_2_3. Aliquot I | 1.0 | 1.0 | 1.0 | 1.0 | 1.0 | 1.0 | 1.0 | 1.0 |
| Donor_3_3. Aliquot A | 0.9 | 0.2 | 1.1 | 0.3 | 1.3 | 1.8 | 1.0 | 0.9 |
| Donor_3_3. Aliquot B | 0.9 | 0.1 | 3.4 | 0.4 | 1.1 | 1.0 | 1.0 | 0.9 |
| Donor_3_3. Aliquot C | 0.9 | 0.0 | 1.2 | 0.4 | 1.3 | 1.0 | 1.1 | 0.3 |
| Donor_3_3. Aliquot D | 0.9 | 0.1 | 3.5 | 0.2 | 1.0 | 1.8 | 1.0 | 1.5 |
| Donor_3_3. Aliquot E | 1.0 | 0.4 | 2.3 | 0.3 | 1.4 | 2.0 | 1.1 | 1.4 |
| Donor_3_3. Aliquot F | 0.8 | 0.3 | 1.0 | 0.4 | 1.1 | 1.0 | 1.0 | 0.9 |
| Donor_3_3. Aliquot G | 1.0 | 1.0 | 1.0 | 1.7 | 1.2 | 1.0 | 1.0 | 0.5 |
| Donor_3_3. Aliquot H | 0.8 | 1.0 | 1.0 | 0.4 | 0.9 | 1.0 | 1.0 | 0.7 |
| Donor_3_3. Aliquot I | 1.0 | 1.0 | 1.0 | 1.0 | 1.0 | 1.0 | 1.0 | 1.0 |
| Donor_4_3. Aliquot A | 1.0 | 1.4 | 1.0 | 0.7 | 1.0 | 1.0 | 1.1 | 1.2 |
| Donor_4_3. Aliquot B | 1.0 | 22.9 | 2.5 | 1.4 | 1.1 | 1.0 | 1.0 | 1.4 |
| Donor_4_3. Aliquot C | 1.0 | 22.9 | 1.0 | 0.8 | 1.0 | 1.0 | 1.0 | 1.5 |
| Donor_4_3. Aliquot D | 1.0 | 7.3 | 2.9 | 1.3 | 1.1 | 1.3 | 1.0 | 3.3 |
| Donor_4_3. Aliquot E | 0.9 | 8.8 | 1.5 | 0.8 | 1.1 | 1.5 | 1.0 | 2.4 |
| Donor_4_3. Aliquot F | 0.8 | 2.0 | 1.0 | 1.8 | 1.1 | 0.8 | 1.0 | 1.4 |
| Donor_4_3. Aliquot G | 0.9 | 22.9 | 0.9 | 1.8 | 1.2 | 1.0 | 1.1 | 0.8 |
| Donor_4_3. Aliquot H | 1.0 | 22.9 | 1.0 | 1.2 | 0.7 | 1.0 | 1.0 | 0.8 |
| Donor_4_3. Aliquot I | 1.0 | 1.0 | 1.0 | 1.0 | 1.1 | 1.0 | 1.0 | 1.0 |
| Donor_5_3. Aliquot A | 1.1 | 0.1 | 1.8 | 1.1 | 1.0 | 1.5 | 1.1 | 1.1 |
| Donor_5_3. Aliquot B | 1.0 | 1.0 | 1.3 | 1.1 | 0.9 | 1.6 | 1.1 | 0.9 |
| Donor_5_3. Aliquot C | 1.1 | 1.0 | 1.3 | 1.1 | 1.0 | 0.9 | 1.1 | 0.3 |
| Donor_5_3. Aliquot D | 1.0 | 0.4 | 2.6 | 1.0 | 1.1 | 4.0 | 1.0 | 0.9 |
| Donor_5_3. Aliquot E | 1.1 | 0.6 | 2.2 | 0.9 | 1.1 | 4.2 | 1.2 | 0.9 |
| Donor_5_3. Aliquot F | 0.8 | 1.0 | 0.8 | 0.9 | 0.7 | 1.4 | 1.0 | 0.7 |
| Donor_5_3. Aliquot G | 1.2 | 0.1 | 0.8 | 1.0 | 1.1 | 1.2 | 1.0 | 0.2 |

FIG. 13E.6

| | Growth Hormone ng/mL | GM-CSF pg/mL | Glutathione S-Transferase ng/mL | Haptoglobin mg/mL | ICAM-1 ng/mL | IFN-gamma pg/mL | IgA mg/mL | IgE ng/mL |
|---|---|---|---|---|---|---|---|---|
| Least Detectable Dose | 0.13 | 57 | 0.40 | 0.025 | 3.2 | 4.6 | 0.0084 | 14 |
| RBM Low Plasma Range | | | | 0.047 | 42 | Pending | 0.58 | |
| RBM High Plasma Range | 4.4 | 152 | 3.1 | 7.6 | 213 | Pending | 5.6 | 770 |
| Donor_5 3. Aliquot H | 1.1 | 0.1 | 0.8 | 0.9 | 0.9 | 0.8 | 1.0 | 1.0 |
| Donor_5 3. Aliquot I | 1.0 | 1.0 | 1.0 | 1.0 | 1.0 | 1.0 | 1.0 | 1.0 |
| Donor_6 3. Aliquot A | 1.0 | 0.1 | 1.1 | 1.1 | 1.0 | 1.0 | 1.0 | 1.2 |
| Donor_6 3. Aliquot B | 1.0 | 0.3 | 3.4 | 1.2 | 1.1 | 1.0 | 1.1 | 1.1 |
| Donor_6 3. Aliquot C | 1.0 | 0.1 | 1.1 | 1.1 | 1.2 | 1.0 | 1.0 | 0.5 |
| Donor_6 3. Aliquot D | 1.1 | 0.1 | 1.8 | 1.1 | 1.2 | 6.8 | 1.1 | 1.2 |
| Donor_6 3. Aliquot E | 1.0 | 0.1 | 3.7 | 1.1 | 0.9 | 16.1 | 1.2 | 1.0 |
| Donor_6 3. Aliquot F | 0.9 | 0.2 | 1.1 | 1.2 | 0.9 | 1.0 | 1.1 | 0.8 |
| Donor_6 3. Aliquot G | 1.1 | 0.1 | 1.1 | 1.1 | 1.2 | 1.0 | 1.1 | 0.3 |
| Donor_6 3. Aliquot H | 1.0 | 0.1 | 1.1 | 1.1 | 1.1 | 1.0 | 0.9 | 1.3 |
| Donor_6 3. Aliquot I | 1.0 | 1.0 | 1.0 | 1.0 | 1.0 | 1.0 | 1.0 | 1.0 |
| Donor_7 3. Aliquot A | 1.1 | 2.3 | 1.0 | 1.0 | 1.1 | 1.0 | 1.0 | 1.2 |
| Donor_7 3. Aliquot B | 1.3 | 1.1 | 3.0 | 1.0 | 1.1 | 1.0 | 1.0 | 1.1 |
| Donor_7 3. Aliquot C | 0.8 | 0.6 | 1.2 | 1.0 | 0.9 | 1.0 | 1.0 | 0.3 |
| Donor_7 3. Aliquot D | 1.3 | 2.0 | 2.2 | 0.7 | 0.9 | 1.0 | 0.9 | 1.3 |
| Donor_7 3. Aliquot E | 1.1 | 2.0 | 1.3 | 0.7 | 1.1 | 1.0 | 0.7 | 1.2 |
| Donor_7 3. Aliquot F | 0.9 | 1.1 | 1.0 | 1.0 | 1.0 | 1.0 | 1.0 | 0.8 |
| Donor_7 3. Aliquot G | 0.8 | 0.3 | 1.0 | 0.9 | 1.2 | 1.0 | 0.9 | 0.5 |
| Donor_7 3. Aliquot H | 0.9 | 1.0 | 1.0 | 1.1 | 1.1 | 1.0 | 0.9 | 0.8 |
| Donor_7 3. Aliquot I | 1.0 | 1.0 | 1.0 | 1.0 | 1.0 | 1.0 | 1.0 | 1.0 |
| Donor_8 3. Aliquot A | 1.3 | 0.4 | 0.7 | 1.4 | 1.0 | 1.5 | 1.0 | 4.6 |
| Donor_8 3. Aliquot B | 1.3 | 0.5 | 3.3 | 1.6 | 1.1 | 1.2 | 1.1 | 2.2 |
| Donor_8 3. Aliquot C | 0.7 | 0.8 | 0.7 | 0.6 | 0.9 | 143.6 | 1.1 | 3.8 |
| Donor_8 3. Aliquot D | 3.4 | 4.2 | 6.1 | 1.2 | 1.1 | 490.9 | 0.9 | 21.0 |
| Donor_8 3. Aliquot E | 3.3 | 2.3 | 3.8 | 3.5 | 1.0 | 73.9 | 0.9 | 17.8 |
| Donor_8 3. Aliquot F | 1.3 | 1.3 | 0.7 | 1.7 | 1.1 | 30.8 | 1.1 | 4.0 |
| Donor_8 3. Aliquot G | 1.2 | 0.2 | 0.7 | 1.6 | 1.1 | 1.2 | 1.0 | 2.2 |

FIG. 13E.7

| | Growth Hormone ng/mL | GM-CSF pg/mL | Glutathione S-Transferase ng/mL | Haptoglobin mg/mL | ICAM-1 ng/mL | IFN-gamma pg/mL | IgA mg/mL | IgE ng/mL |
|---|---|---|---|---|---|---|---|---|
| Least Detectable Dose | 0.13 | 57 | 0.40 | 0.025 | 3.2 | 4.6 | 0.0084 | 14 |
| RBM Low Plasma Range | | | | 0.047 | 42 | Pending | 0.58 | |
| RBM High Plasma Range | 4.4 | 152 | 3.1 | 7.6 | 213 | Pending | 5.6 | 770 |
| Donor_8 3. Aliquot H | 1.1 | 1.2 | 0.7 | 1.6 | 1.1 | 10.7 | 1.1 | 2.8 |
| Donor_8 3. Aliquot I | 1.0 | 1.0 | 1.0 | 1.0 | 1.0 | 1.0 | 1.0 | 1.0 |
| Donor_9 3. Aliquot A | 1.1 | 1.3 | 2.0 | 1.6 | 1.0 | 1.2 | 1.0 | 1.5 |
| Donor_9 3. Aliquot B | 1.1 | 1.5 | 5.9 | 1.6 | 1.1 | 1.5 | 1.0 | 1.5 |
| Donor_9 3. Aliquot C | 1.0 | 2.4 | 1.1 | 1.0 | 0.9 | 37.6 | 1.0 | 0.7 |
| Donor_9 3. Aliquot D | 1.1 | 3.3 | 7.0 | 0.5 | 1.0 | 171.0 | 1.0 | 10.2 |
| Donor_9 3. Aliquot E | 1.1 | 1.4 | 6.6 | 1.1 | 0.9 | 35.5 | 1.0 | 6.2 |
| Donor_9 3. Aliquot F | 1.0 | 0.7 | 2.1 | 0.6 | 1.0 | 1.9 | 1.0 | 0.9 |
| Donor_9 3. Aliquot G | 1.0 | 1.9 | 1.5 | 1.3 | 0.9 | 0.6 | 1.1 | 0.8 |
| Donor_9 3. Aliquot H | 1.1 | 1.7 | 1.4 | 1.5 | 1.0 | 0.7 | 1.0 | 1.0 |
| Donor_9 3. Aliquot I | 1.0 | 1.0 | 1.0 | 1.0 | 1.0 | 1.0 | 1.0 | 1.0 |

FIG. 13F.1

| | IGF-1<br>ng/mL | IgM<br>mg/mL | IL-10<br>pg/mL | IL-12p40<br>ng/mL | IL-12p70<br>pg/mL | IL-13<br>pg/mL | IL-15<br>ng/mL | IL-16<br>pg/mL |
|---|---|---|---|---|---|---|---|---|
| Least Detectable Dose | 4.0 | 0.015 | 15 | 1.2 | 94 | 57 | 1.3 | 66 |
| RBM Low Plasma Range | | 0.24 | 1.8 | | | | | 232 |
| RBM High Plasma Range | 177 | 3.3 | 38 | 2.7 | 165 | 133 | 4.6 | 3380 |
| Donor_1 3. Aliquot A | 49 | 0.63 | 180 | 0.30 | 45 | 36 | 0.41 | 575 |
| Donor_1 3. Aliquot B | 49 | 0.66 | 135 | 0.16 | 35 | 37 | 0.40 | 535 |
| Donor_1 3. Aliquot C | 67 | 0.68 | 15 | 1.2 | 28 | 38 | 0.33 | 413 |
| Donor_1 3. Aliquot D | 46 | 0.71 | 134 | 0.43 | 42 | 21 | 0.45 | 619 |
| Donor_1 3. Aliquot E | 45 | 0.63 | 58 | 0.13 | 37 | 34 | 0.32 | 580 |
| Donor_1 3. Aliquot F | 55 | 0.60 | 18 | 1.2 | 28 | 36 | 0.30 | 502 |
| Donor_1 3. Aliquot G | 100 | 0.70 | 15 | 0.19 | 39 | 37 | 0.50 | 216 |
| Donor_1 3. Aliquot H | 46 | 0.60 | 14 | 1.2 | 52 | 35 | 0.28 | 299 |
| Donor_1 3. Aliquot I | 46 | 0.65 | 16 | 1.2 | 32 | 33 | 0.26 | 588 |
| Donor_2 3. Aliquot A | 94 | 0.15 | 500 | 0.51 | 61 | 37 | 0.41 | 654 |
| Donor_2 3. Aliquot B | 90 | 0.15 | 483 | 0.26 | 35 | 37 | 0.43 | 712 |
| Donor_2 3. Aliquot C | 87 | 0.21 | 19 | 1.2 | 18 | 29 | 0.32 | 609 |
| Donor_2 3. Aliquot D | 81 | 0.14 | 977 | 2.8 | 40 | 29 | 0.50 | 804 |
| Donor_2 3. Aliquot E | 86 | 0.18 | 963 | 2.4 | 37 | 36 | 0.37 | 782 |
| Donor_2 3. Aliquot F | 73 | 0.17 | 28 | 0.26 | 45 | 66 | 0.50 | 720 |
| Donor_2 3. Aliquot G | 221 | 0.18 | 131 | 0.88 | 45 | 40 | 0.66 | 432 |
| Donor_2 3. Aliquot H | 75 | 0.18 | 22 | 1.2 | 35 | 27 | 1.3 | 393 |
| Donor_2 3. Aliquot I | 73 | 0.19 | 21 | 1.2 | 35 | 36 | 0.21 | 642 |
| Donor_3 3. Aliquot A | 380 | 0.66 | 480 | 0.43 | 50 | 49 | 0.53 | 1310 |
| Donor_3 3. Aliquot B | 368 | 0.67 | 632 | 0.37 | 48 | 43 | 0.56 | 1230 |
| Donor_3 3. Aliquot C | 408 | 0.66 | 26 | 0.13 | 55 | 57 | 0.41 | 1190 |
| Donor_3 3. Aliquot D | 387 | 0.67 | 1640 | 3.3 | 45 | 40 | 0.47 | 1410 |
| Donor_3 3. Aliquot E | 393 | 0.74 | 1660 | 2.7 | 55 | 39 | 0.47 | 1490 |
| Donor_3 3. Aliquot F | 338 | 0.69 | 18 | 1.2 | 40 | 51 | 0.28 | 1340 |
| Donor_3 3. Aliquot G | 546 | 0.72 | 11 | 1.2 | 35 | 43 | 0.32 | 556 |
| Donor_3 3. Aliquot H | 386 | 0.67 | 4.9 | 1.2 | 22 | 55 | 0.28 | 706 |
| Donor_3 3. Aliquot I | 403 | 0.69 | 11 | 1.2 | 42 | 81 | 0.47 | 1280 |

FIG. 13F.2

| | IGF-1 ng/mL | IgM mg/mL | IL-10 pg/mL | IL-12p40 ng/mL | IL-12p70 pg/mL | IL-13 pg/mL | IL-15 ng/mL | IL-16 pg/mL |
|---|---|---|---|---|---|---|---|---|
| Least Detectable Dose | 4.0 | 0.015 | 15 | 1.2 | 94 | 57 | 1.3 | 66 |
| RBM Low Plasma Range | 177 | 0.24 | 1.8 | | | | | 232 |
| RBM High Plasma Range | 4 | 3.3 | 38 | 2.7 | 165 | 133 | 4.6 | 3380 |
| Donor_4_3. Aliquot A | 4 | 0.39 | 46 | 1.2 | 94 | 36 | 0.38 | 1240 |
| Donor_4_3. Aliquot B | 4 | 0.29 | 251 | 1.2 | 94 | 19 | 0.56 | 1130 |
| Donor_4_3. Aliquot C | 4 | 0.36 | 11 | 1.2 | 39 | 27 | 0.32 | 1050 |
| Donor_4_3. Aliquot D | 4 | 0.31 | 566 | 3.1 | 39 | 38 | 0.43 | 986 |
| Donor_4_3. Aliquot E | 4 | 0.29 | 543 | 1.5 | 30 | 23 | 0.56 | 812 |
| Donor_4_3. Aliquot F | 4 | 0.31 | 232 | 0.37 | 24 | 28 | 0.47 | 1030 |
| Donor_4_3. Aliquot G | 22 | 0.29 | 14 | 1.2 | 20 | 29 | 0.24 | 431 |
| Donor_4_3. Aliquot H | 4 | 0.28 | 10 | 1.2 | 15 | 9.7 | 0.19 | 564 |
| Donor_4_3. Aliquot I | 4 | 0.30 | 13 | 1.2 | 94 | 24 | 0.24 | 1150 |
| Donor_5_3. Aliquot A | 323 | 0.24 | 117 | 0.34 | 20 | 33 | 0.71 | 536 |
| Donor_5_3. Aliquot B | 337 | 0.25 | 417 | 0.26 | 32 | 32 | 0.50 | 584 |
| Donor_5_3. Aliquot C | 330 | 0.24 | 7.0 | 1.2 | 26 | 48 | 0.50 | 455 |
| Donor_5_3. Aliquot D | 373 | 0.22 | 763 | 2.7 | 59 | 32 | 0.73 | 592 |
| Donor_5_3. Aliquot E | 382 | 0.23 | 1520 | 1.8 | 94 | 36 | 0.68 | 561 |
| Donor_5_3. Aliquot F | 350 | 0.23 | 37 | 1.2 | 20 | 38 | 0.28 | 430 |
| Donor_5_3. Aliquot G | 574 | 0.26 | 15 | 0.28 | 24 | 29 | 0.26 | 323 |
| Donor_5_3. Aliquot H | 355 | 0.26 | 10 | 1.2 | 28 | 27 | 0.19 | 390 |
| Donor_5_3. Aliquot I | 329 | 0.24 | 9.2 | 1.2 | 44 | 47 | 0.13 | 492 |
| Donor_6_3. Aliquot A | 47 | 0.38 | 85 | 0.13 | 32 | 70 | 0.32 | 1030 |
| Donor_6_3. Aliquot B | 46 | 0.42 | 226 | 1.2 | 42 | 57 | 0.24 | 828 |
| Donor_6_3. Aliquot C | 54 | 0.37 | 7.0 | 1.2 | 50 | 59 | 0.24 | 1150 |
| Donor_6_3. Aliquot D | 47 | 0.41 | 637 | 4.7 | 94 | 68 | 0.56 | 682 |
| Donor_6_3. Aliquot E | 50 | 0.34 | 1870 | 4.3 | 30 | 68 | 0.16 | 648 |
| Donor_6_3. Aliquot F | 45 | 0.33 | 45 | 1.2 | 47 | 86 | 0.43 | 969 |
| Donor_6_3. Aliquot G | 189 | 0.35 | 7.0 | 1.2 | 20 | 65 | 1.3 | 439 |
| Donor_6_3. Aliquot H | 42 | 0.35 | 6.0 | 0.16 | 94 | 65 | 0.19 | 815 |
| Donor_6_3. Aliquot I | 45 | 0.34 | 7.0 | 1.2 | 94 | 59 | 0.28 | 1230 |

FIG. 13F.3

| | IGF-1 ng/mL | IgM mg/mL | IL-10 pg/mL | IL-12p40 ng/mL | IL-12p70 pg/mL | IL-13 pg/mL | IL-15 ng/mL | IL-16 pg/mL |
|---|---|---|---|---|---|---|---|---|
| Least Detectable Dose | 4.0 | 0.015 | 15 | 1.2 | 94 | 57 | 1.3 | 66 |
| RBM Low Plasma Range | 177 | 0.24 | 1.8 | | | | | 232 |
| RBM High Plasma Range | | 3.3 | 38 | 2.7 | 165 | 133 | 4.6 | 3380 |
| Donor_7_3. Aliquot A | 14 | 0.63 | 379 | 0.64 | 39 | 91 | 0.79 | 664 |
| Donor_7_3. Aliquot B | 18 | 0.59 | 441 | 0.27 | 32 | 103 | 0.78 | 620 |
| Donor_7_3. Aliquot C | 26 | 0.63 | 13 | 1.2 | 39 | 70 | 0.53 | 817 |
| Donor_7_3. Aliquot D | 15 | 0.59 | 390 | 0.93 | 39 | 82 | 0.49 | 662 |
| Donor_7_3. Aliquot E | 17 | 0.48 | 297 | 0.93 | 42 | 104 | 0.58 | 651 |
| Donor_7_3. Aliquot F | 9.8 | 0.66 | 85 | 1.2 | 34 | 105 | 0.54 | 856 |
| Donor_7_3. Aliquot G | 98 | 0.60 | 13 | 1.2 | 22 | 56 | 0.19 | 428 |
| Donor_7_3. Aliquot H | 8.1 | 0.60 | 6.8 | 1.2 | 94 | 62 | 0.38 | 574 |
| Donor_7_3. Aliquot I | 12 | 0.60 | 11 | 1.2 | 94 | 88 | 0.41 | 918 |
| Donor_8_3. Aliquot A | 176 | 0.30 | 102 | 0.30 | 34 | 81 | 0.32 | 340 |
| Donor_8_3. Aliquot B | 168 | 0.34 | 218 | 0.19 | 22 | 97 | 0.24 | 341 |
| Donor_8_3. Aliquot C | 163 | 0.31 | 4.9 | 0.57 | 3920 | 80 | 0.32 | 309 |
| Donor_8_3. Aliquot D | 179 | 0.36 | 306 | 19 | 434 | 99 | 0.61 | 754 |
| Donor_8_3. Aliquot E | 162 | 0.32 | 1000 | 14 | 48 | 99 | 0.64 | 533 |
| Donor_8_3. Aliquot F | 166 | 0.32 | 219 | 0.71 | 42 | 111 | 0.45 | 410 |
| Donor_8_3. Aliquot G | 181 | 0.28 | 4.3 | 1.2 | 15 | 53 | 0.19 | 183 |
| Donor_8_3. Aliquot H | 177 | 0.37 | 4.1 | 0.23 | 30 | 75 | 0.28 | 231 |
| Donor_8_3. Aliquot I | 175 | 0.33 | 6.6 | 1.2 | 32 | 80 | 0.32 | 522 |
| Donor_9_3. Aliquot A | 745 | 1.0 | 220 | 0.26 | 52 | 68 | 0.31 | 463 |
| Donor_9_3. Aliquot B | 716 | 1.0 | 435 | 0.40 | 44 | 77 | 0.44 | 398 |
| Donor_9_3. Aliquot C | 784 | 0.97 | 43 | 0.80 | 1480 | 74 | 0.35 | 407 |
| Donor_9_3. Aliquot D | 681 | 1.0 | 1080 | 17 | 89 | 71 | 0.51 | 780 |
| Donor_9_3. Aliquot E | 651 | 1.0 | 1730 | 11 | 54 | 68 | 0.31 | 538 |
| Donor_9_3. Aliquot F | 688 | 0.95 | 122 | 0.34 | 46 | 83 | 0.30 | 369 |
| Donor_9_3. Aliquot G | 636 | 1.1 | 13 | 0.25 | 41 | 36 | 0.31 | 411 |
| Donor_9_3. Aliquot H | 703 | 1.0 | 14 | 0.24 | 56 | 51 | 0.56 | 369 |
| Donor_9_3. Aliquot I | 732 | 1.1 | 4.2 | 1.2 | 31 | 56 | 0.22 | 455 |

FIG. 13F.4

| | IGF-1 ng/mL | IgM mg/mL | IL-10 pg/mL | IL-12p40 ng/mL | IL-12p70 pg/mL | IL-13 pg/mL | IL-15 ng/mL | IL-16 pg/mL |
|---|---|---|---|---|---|---|---|---|
| Least Detectable Dose | 4.0 | 0.015 | 15 | 1.2 | 94 | 57 | 1.3 | 66 |
| RBM Low Plasma Range | | 0.24 | 1.8 | | | | | 232 |
| RBM High Plasma Range | 177 | 3.3 | 38 | 2.7 | 165 | 133 | 4.6 | 3380 |
| EDTA Plasma | | | | | | | | |
| donor #1 plasma | 4 | 0.57 | 16 | 0.26 | 34 | 39 | 0.30 | 329 |
| donor #2 plasma | 4 | 0.22 | 21 | 0.19 | 23 | 24 | 0.13 | 620 |
| donor #3 plasma | 12 | 0.93 | 9.9 | 1.2 | 49 | 37 | 0.39 | 892 |
| donor #4 plasma | 4 | 0.39 | 14 | 1.2 | 33 | 50 | 0.29 | 794 |
| donor #5 plasma | 18 | 0.32 | 12 | 0.15 | 56 | 37 | 0.64 | 314 |
| donor #6 plasma | 4 | 0.43 | 10 | 1.2 | 34 | 40 | 0.29 | 277 |
| donor #7 plasma | 4 | 0.79 | 16 | 1.2 | 23 | 39 | 0.29 | 514 |
| donor #8 plasma | 32 | 0.38 | 2.3 | 1.2 | 39 | 50 | 0.31 | 208 |
| donor #9 plasma | 325 | 1.5 | 5.1 | 0.14 | 35 | 41 | 0.18 | 327 |
| | | | | | | | | |
| *Stimulations indices* | | | | | | | | |
| Donor_1 3. Aliquot A | 1.1 | 1.0 | 11.0 | 0.2 | 1.4 | 1.1 | 1.6 | 1.0 |
| Donor_1 3. Aliquot B | 1.1 | 1.0 | 8.3 | 0.1 | 1.1 | 1.1 | 1.5 | 0.9 |
| Donor_1 3. Aliquot C | 1.4 | 1.1 | 0.9 | 1.0 | 0.9 | 1.2 | 1.3 | 0.7 |
| Donor_1 3. Aliquot D | 1.0 | 1.1 | 8.2 | 0.4 | 1.3 | 0.6 | 1.7 | 1.1 |
| Donor_1 3. Aliquot E | 1.0 | 1.0 | 3.5 | 0.1 | 1.2 | 1.0 | 1.2 | 1.0 |
| Donor_1 3. Aliquot F | 1.2 | 0.9 | 1.1 | 1.0 | 0.9 | 1.1 | 1.1 | 0.9 |
| Donor_1 3. Aliquot G | 2.2 | 1.1 | 0.9 | 0.2 | 1.2 | 1.1 | 1.9 | 0.4 |
| Donor_1 3. Aliquot H | 1.0 | 0.9 | 0.9 | 1.0 | 1.6 | 1.1 | 1.1 | 0.5 |
| Donor_1 3. Aliquot I | 1.0 | 1.0 | 1.0 | 1.0 | 1.0 | 1.0 | 1.0 | 1.0 |
| Donor_2 3. Aliquot A | 1.3 | 0.8 | 24.0 | 0.4 | 1.7 | 1.0 | 1.9 | 1.0 |
| Donor_2 3. Aliquot B | 1.2 | 0.8 | 23.2 | 0.2 | 1.0 | 1.0 | 2.0 | 1.1 |
| Donor_2 3. Aliquot C | 1.2 | 1.1 | 0.9 | 1.0 | 0.5 | 0.8 | 1.5 | 0.9 |
| Donor_2 3. Aliquot D | 1.1 | 0.7 | 47.0 | 2.3 | 1.1 | 0.8 | 2.4 | 1.3 |
| Donor_2 3. Aliquot E | 1.2 | 0.9 | 46.3 | 2.0 | 1.0 | 1.0 | 1.7 | 1.2 |
| Donor_2 3. Aliquot F | 1.0 | 0.9 | 1.3 | 0.2 | 1.3 | 1.8 | 2.4 | 1.1 |
| Donor_2 3. Aliquot G | 3.0 | 0.9 | 6.3 | 0.7 | 1.3 | 1.1 | 3.1 | 0.7 |

FIG. 13F.5

| | IGF-1 ng/mL | IgM mg/mL | IL-10 pg/mL | IL-12p40 ng/mL | IL-12p70 pg/mL | IL-13 pg/mL | IL-15 ng/mL | IL-16 pg/mL |
|---|---|---|---|---|---|---|---|---|
| Least Detectable Dose | 4.0 | 0.015 | 15 | 1.2 | 94 | 57 | 1.3 | 66 |
| RBM Low Plasma Range | | 0.24 | 1.8 | | | | | 232 |
| RBM High Plasma Range | 177 | 3.3 | 38 | 2.7 | 165 | 133 | 4.6 | 3380 |
| Donor_2 3. Aliquot H | 1.0 | 0.9 | 1.1 | 1.0 | 1.0 | 0.7 | 6.1 | 0.6 |
| Donor_2 3. Aliquot I | 1.0 | 1.0 | 1.0 | 1.0 | 1.0 | 1.0 | 1.0 | 1.0 |
| Donor_3 3. Aliquot A | 0.9 | 0.9 | 44.4 | 0.4 | 1.2 | 0.6 | 1.1 | 1.0 |
| Donor_3 3. Aliquot B | 0.9 | 1.0 | 58.5 | 0.3 | 1.2 | 0.5 | 1.2 | 1.0 |
| Donor_3 3. Aliquot C | 1.0 | 0.9 | 2.4 | 0.1 | 1.3 | 0.7 | 0.9 | 0.9 |
| Donor_3 3. Aliquot D | 1.0 | 1.0 | 151.9 | 2.8 | 1.1 | 0.5 | 1.0 | 1.1 |
| Donor_3 3. Aliquot E | 1.0 | 1.1 | 153.7 | 2.2 | 1.3 | 0.5 | 1.0 | 1.2 |
| Donor_3 3. Aliquot F | 0.8 | 1.0 | 1.6 | 1.0 | 0.8 | 0.6 | 0.6 | 1.0 |
| Donor_3 3. Aliquot G | 1.4 | 1.0 | 1.0 | 1.0 | 0.5 | 0.5 | 0.7 | 0.4 |
| Donor_3 3. Aliquot H | 1.0 | 1.0 | 0.5 | 1.0 | 0.5 | 0.7 | 0.6 | 0.6 |
| Donor_3 3. Aliquot I | 1.0 | 1.0 | 1.0 | 1.0 | 1.0 | 1.0 | 1.0 | 1.0 |
| Donor_4 3. Aliquot A | 1.0 | 1.3 | 3.5 | 1.0 | 1.0 | 1.5 | 1.6 | 1.1 |
| Donor_4 3. Aliquot B | 1.0 | 1.0 | 19.0 | 1.0 | 0.4 | 0.8 | 2.4 | 1.0 |
| Donor_4 3. Aliquot C | 1.0 | 1.2 | 0.8 | 1.0 | 0.4 | 1.1 | 1.3 | 0.9 |
| Donor_4 3. Aliquot D | 1.0 | 1.1 | 42.9 | 2.6 | 0.3 | 1.6 | 1.8 | 0.9 |
| Donor_4 3. Aliquot E | 1.0 | 1.0 | 41.1 | 1.3 | 0.3 | 1.0 | 2.4 | 0.7 |
| Donor_4 3. Aliquot F | 1.0 | 1.0 | 17.6 | 0.3 | 0.2 | 1.1 | 2.0 | 0.9 |
| Donor_4 3. Aliquot G | 5.5 | 1.0 | 1.0 | 1.0 | 0.2 | 1.2 | 1.0 | 0.4 |
| Donor_4 3. Aliquot H | 1.0 | 1.0 | 0.8 | 1.0 | 0.2 | 0.4 | 0.8 | 0.5 |
| Donor_4 3. Aliquot I | 1.0 | 1.0 | 1.0 | 1.0 | 1.0 | 1.0 | 1.0 | 1.0 |
| Donor_5 3. Aliquot A | 1.0 | 1.0 | 12.7 | 0.3 | 0.5 | 0.7 | 5.6 | 1.1 |
| Donor_5 3. Aliquot B | 1.0 | 1.1 | 45.2 | 0.2 | 0.7 | 0.7 | 4.0 | 1.2 |
| Donor_5 3. Aliquot C | 1.0 | 1.0 | 0.8 | 1.0 | 0.6 | 1.0 | 4.0 | 0.9 |
| Donor_5 3. Aliquot D | 1.1 | 0.9 | 82.8 | 2.3 | 1.4 | 0.7 | 5.8 | 1.2 |
| Donor_5 3. Aliquot E | 1.2 | 1.0 | 164.9 | 1.5 | 2.2 | 0.8 | 5.4 | 1.1 |
| Donor_5 3. Aliquot F | 1.1 | 1.0 | 4.0 | 1.0 | 0.5 | 0.8 | 2.2 | 0.9 |
| Donor_5 3. Aliquot G | 1.7 | 1.1 | 1.6 | 0.2 | 0.6 | 0.6 | 2.0 | 0.7 |

FIG. 13F.6

| | IGF-1 ng/mL | IgM mg/mL | IL-10 pg/mL | IL-12p40 ng/mL | IL-12p70 pg/mL | IL-13 pg/mL | IL-15 ng/mL | IL-16 pg/mL |
|---|---|---|---|---|---|---|---|---|
| Least Detectable Dose | 4.0 | 0.015 | 15 | 1.2 | 94 | 57 | 1.3 | 66 |
| RBM Low Plasma Range | | 0.24 | 1.8 | | | | | 232 |
| RBM High Plasma Range | 177 | 3.3 | 38 | 2.7 | 165 | 133 | 4.6 | 3380 |
| Donor_5 3. Aliquot H | 1.1 | 1.1 | 1.1 | 1.0 | 0.6 | 0.6 | 1.5 | 0.8 |
| Donor_5 3. Aliquot I | 1.0 | 1.0 | 1.0 | 1.0 | 1.0 | 1.0 | 1.0 | 1.0 |
| Donor_6 3. Aliquot A | 1.0 | 1.1 | 12.0 | 0.1 | 0.3 | 1.2 | 1.1 | 0.8 |
| Donor_6 3. Aliquot B | 1.0 | 1.2 | 32.1 | 1.0 | 0.4 | 1.0 | 0.9 | 0.7 |
| Donor_6 3. Aliquot C | 1.2 | 1.1 | 1.0 | 1.0 | 0.5 | 1.0 | 0.9 | 0.9 |
| Donor_6 3. Aliquot D | 1.0 | 1.2 | 90.5 | 3.9 | 1.0 | 1.2 | 2.0 | 0.6 |
| Donor_6 3. Aliquot E | 1.1 | 1.0 | 265.6 | 3.6 | 0.3 | 1.2 | 0.6 | 0.5 |
| Donor_6 3. Aliquot F | 1.0 | 1.0 | 6.4 | 1.0 | 0.5 | 1.5 | 1.6 | 0.8 |
| Donor_6 3. Aliquot G | 4.2 | 1.0 | 1.0 | 1.0 | 0.2 | 1.1 | 4.7 | 0.4 |
| Donor_6 3. Aliquot H | 0.9 | 1.0 | 0.8 | 0.1 | 1.0 | 1.1 | 0.7 | 0.7 |
| Donor_6 3. Aliquot I | 1.0 | 1.0 | 1.0 | 1.0 | 1.0 | 1.0 | 1.0 | 1.0 |
| Donor_7 3. Aliquot A | 1.1 | 1.0 | 33.2 | 0.5 | 0.4 | 1.0 | 1.9 | 0.7 |
| Donor_7 3. Aliquot B | 1.4 | 1.0 | 38.7 | 0.2 | 0.3 | 1.2 | 1.9 | 0.7 |
| Donor_7 3. Aliquot C | 2.1 | 1.1 | 1.2 | 1.0 | 0.4 | 0.8 | 1.3 | 0.9 |
| Donor_7 3. Aliquot D | 1.2 | 1.0 | 34.2 | 0.8 | 0.4 | 0.9 | 1.2 | 0.7 |
| Donor_7 3. Aliquot E | 1.4 | 0.8 | 26.1 | 0.8 | 0.4 | 1.2 | 1.4 | 0.7 |
| Donor_7 3. Aliquot F | 0.8 | 1.1 | 7.4 | 1.0 | 0.4 | 1.2 | 1.3 | 0.9 |
| Donor_7 3. Aliquot G | 7.9 | 1.0 | 1.1 | 1.0 | 0.2 | 0.6 | 0.5 | 0.5 |
| Donor_7 3. Aliquot H | 0.7 | 1.0 | 0.6 | 1.0 | 1.0 | 0.7 | 0.9 | 0.6 |
| Donor_7 3. Aliquot I | 1.0 | 1.0 | 1.0 | 1.0 | 1.0 | 1.0 | 1.0 | 1.0 |
| Donor_8 3. Aliquot A | 1.0 | 0.9 | 15.4 | 0.2 | 1.1 | 1.0 | 1.0 | 0.7 |
| Donor_8 3. Aliquot B | 1.0 | 1.0 | 33.0 | 0.2 | 0.7 | 1.2 | 0.8 | 0.7 |
| Donor_8 3. Aliquot C | 0.9 | 1.0 | 0.7 | 0.5 | 123.3 | 1.0 | 1.0 | 0.6 |
| Donor_8 3. Aliquot D | 1.0 | 1.1 | 46.3 | 16.2 | 13.6 | 1.2 | 1.9 | 1.4 |
| Donor_8 3. Aliquot E | 0.9 | 1.0 | 151.3 | 11.4 | 1.5 | 1.2 | 2.0 | 1.0 |
| Donor_8 3. Aliquot F | 0.9 | 1.0 | 33.1 | 0.6 | 1.3 | 1.4 | 1.4 | 0.8 |
| Donor_8 3. Aliquot G | 1.0 | 0.9 | 0.6 | 1.0 | 0.5 | 0.7 | 0.6 | 0.4 |

FIG. 13F.7

| | IGF-1 ng/mL | IgM mg/mL | IL-10 pg/mL | IL-12p40 ng/mL | IL-12p70 pg/mL | IL-13 pg/mL | IL-15 ng/mL | IL-16 pg/mL |
|---|---|---|---|---|---|---|---|---|
| Least Detectable Dose | 4.0 | 0.015 | 15 | 1.2 | 94 | 57 | 1.3 | 66 |
| RBM Low Plasma Range | 177 | 0.24 | 1.8 | | | | | 232 |
| RBM High Plasma Range | | 3.3 | 38 | 2.7 | 165 | 133 | 4.6 | 3380 |
| Donor_8 3. Aliquot H | 1.0 | 1.1 | 0.6 | 0.2 | 0.9 | 0.9 | 0.9 | 0.4 |
| Donor_8 3. Aliquot I | 1.0 | 1.0 | 1.0 | 1.0 | 1.0 | 1.0 | 1.0 | 1.0 |
| Donor_9 3. Aliquot A | 1.0 | 1.0 | 52.3 | 0.2 | 1.7 | 1.2 | 1.4 | 1.0 |
| Donor_9 3. Aliquot B | 1.0 | 0.9 | 103.3 | 0.3 | 1.4 | 1.4 | 2.0 | 0.9 |
| Donor_9 3. Aliquot C | 1.1 | 0.9 | 10.2 | 0.7 | 48.2 | 1.3 | 1.6 | 0.9 |
| Donor_9 3. Aliquot D | 0.9 | 1.0 | 256.5 | 14.0 | 2.9 | 1.3 | 2.3 | 1.7 |
| Donor_9 3. Aliquot E | 0.9 | 0.9 | 410.9 | 9.3 | 1.7 | 1.2 | 1.4 | 1.2 |
| Donor_9 3. Aliquot F | 0.9 | 0.9 | 29.0 | 0.3 | 1.5 | 1.5 | 1.3 | 0.8 |
| Donor_9 3. Aliquot G | 0.9 | 1.0 | 3.0 | 0.2 | 1.3 | 0.6 | 1.4 | 0.9 |
| Donor_9 3. Aliquot H | 1.0 | 0.9 | 3.3 | 0.2 | 1.8 | 0.9 | 2.5 | 0.8 |
| Donor_9 3. Aliquot I | 1.0 | 1.0 | 1.0 | 1.0 | 1.0 | 1.0 | 1.0 | 1.0 |

FIG. 13G.1

| | IL-17 pg/mL 2.7 | IL-17E pg/mL 31 | IL-18 pg/mL 54 | IL-1alpha ng/mL 0.16 | IL-1beta pg/mL 1.5 | IL-1ra pg/mL 15 | IL-2 pg/mL 60 | IL-23 ng/mL <0.67 |
|---|---|---|---|---|---|---|---|---|
| Least Detectable Dose | | | | | | | | |
| RBM Low Plasma Range | PENDING | PENDING | 72 | 0.35 | 8.7 | 17 | 61 | PENDING |
| RBM High Plasma Range | PENDING | PENDING | 1020 | | | 622 | | PENDING |
| Donor_1 3. Aliquot A | 6.7 | 643 | 1930 | 0.0025 | 75 | 3780 | 60 | 3.7 |
| Donor_1 3. Aliquot B | 2.7 | 559 | 1910 | 0.16 | 50 | 2300 | 60 | 1.2 |
| Donor_1 3. Aliquot C | 2.7 | 62 | 1980 | 0.16 | 4.4 | 987 | 60 | 0.67 |
| Donor_1 3. Aliquot D | 2.7 | 580 | 2080 | 0.0077 | 348 | 4230 | 60 | 0.67 |
| Donor_1 3. Aliquot E | 2.7 | 604 | 2140 | 0.16 | 69 | 2740 | 60 | 0.67 |
| Donor_1 3. Aliquot F | 2.7 | 486 | 1630 | 0.16 | 10 | 1040 | 60 | 1.2 |
| Donor_1 3. Aliquot G | 7.5 | 646 | 2130 | 0.16 | 6.8 | 2830 | 60 | 2.1 |
| Donor_1 3. Aliquot H | 2.7 | 56 | 1860 | 0.16 | 4.6 | 944 | 60 | 1.9 |
| Donor_1 3. Aliquot I | 2.7 | 502 | 1810 | 0.16 | 5.4 | 660 | 60 | 0.67 |
| Donor_2 3. Aliquot A | 2.7 | 29 | 631 | 0.012 | 132 | 16500 | 60 | 1.2 |
| Donor_2 3. Aliquot B | 2.7 | 40 | 709 | 0.0057 | 71 | 15500 | 60 | 0.67 |
| Donor_2 3. Aliquot C | 2.7 | 11 | 616 | 0.16 | 4.7 | 2000 | 60 | 0.67 |
| Donor_2 3. Aliquot D | 2.7 | 37 | 830 | 0.36 | 5020 | 54600 | 60 | 2.3 |
| Donor_2 3. Aliquot E | 2.7 | 29 | 754 | 0.11 | 1310 | 52400 | 60 | 2.5 |
| Donor_2 3. Aliquot F | 2.7 | 17 | 594 | 0.0034 | 32 | 3140 | 60 | 0.67 |
| Donor_2 3. Aliquot G | 2.7 | 31 | 681 | 0.045 | 387 | 6790 | 60 | 0.67 |
| Donor_2 3. Aliquot H | 2.7 | 23 | 595 | 0.16 | 9.7 | 4400 | 60 | 0.67 |
| Donor_2 3. Aliquot I | 2.7 | 34 | 538 | 0.16 | 6.6 | 2520 | 60 | 0.67 |
| Donor_3 3. Aliquot A | 2.7 | 17 | 766 | 0.0054 | 62 | 12900 | 60 | 0.67 |
| Donor_3 3. Aliquot B | 2.7 | 34 | 720 | 0.0056 | 32 | 11000 | 60 | 2.1 |
| Donor_3 3. Aliquot C | 2.7 | 29 | 715 | 0.0036 | 5.3 | 2970 | 60 | 2.1 |
| Donor_3 3. Aliquot D | 2.7 | 37 | 735 | 0.074 | 3890 | 41000 | 60 | 0.67 |
| Donor_3 3. Aliquot E | 2.7 | 29 | 798 | 0.039 | 1610 | 32900 | 60 | 3.4 |
| Donor_3 3. Aliquot F | 2.7 | 29 | 694 | 0.0050 | 18 | 3850 | 60 | 1.2 |
| Donor_3 3. Aliquot G | 2.7 | 29 | 766 | 0.0045 | 8.6 | 3260 | 60 | 0.67 |
| Donor_3 3. Aliquot H | 2.7 | 31 | 553 | 0.0029 | 2.2 | 1010 | 60 | 0.67 |
| Donor_3 3. Aliquot I | 2.7 | 45 | 627 | 0.0043 | 1.5 | 79 | 60 | 2.1 |

FIG. 13G.2

| | IL-17 pg/mL 2.7 | IL-17E pg/mL 31 | IL-18 pg/mL 54 | IL-1alpha ng/mL 0.16 | IL-1beta pg/mL 1.5 | IL-1ra pg/mL 15 | IL-2 pg/mL 60 | IL-23 ng/mL <0.67 |
|---|---|---|---|---|---|---|---|---|
| Least Detectable Dose | | | | | | | | |
| RBM Low Plasma Range | PENDING | PENDING | 72 | | 8.7 | 17 | | PENDING |
| RBM High Plasma Range | PENDING | PENDING | 1020 | 0.35 | 8.7 | 622 | 61 | PENDING |
| Donor_4_3. Aliquot A | 2.7 | 42 | 690 | 0.16 | 7.3 | 2670 | 60 | 0.67 |
| Donor_4_3. Aliquot B | 2.7 | 40 | 700 | 0.16 | 46 | 3450 | 60 | 2.1 |
| Donor_4_3. Aliquot C | 2.7 | 56 | 608 | 0.16 | 3.8 | 336 | 60 | 2.1 |
| Donor_4_3. Aliquot D | 2.7 | 29 | 724 | 0.29 | 2830 | 13700 | 60 | 0.67 |
| Donor_4_3. Aliquot E | 2.7 | 51 | 633 | 0.075 | 957 | 13100 | 60 | 0.67 |
| Donor_4_3. Aliquot F | 2.7 | 51 | 623 | 0.0036 | 47 | 12900 | 60 | 0.67 |
| Donor_4_3. Aliquot G | 2.7 | 56 | 612 | 0.0025 | 7.0 | 2530 | 60 | 2.5 |
| Donor_4_3. Aliquot H | 2.7 | 62 | 566 | 0.16 | 4.1 | 1670 | 60 | 1.6 |
| Donor_4_3. Aliquot I | 2.7 | 62 | 597 | 0.16 | 0.63 | 228 | 60 | 2.1 |
| Donor_5_3. Aliquot A | 2.7 | 74 | 340 | 0.0066 | 73 | 22900 | 60 | 0.67 |
| Donor_5_3. Aliquot B | 2.7 | 40 | 295 | 0.0094 | 75 | 22500 | 60 | 0.67 |
| Donor_5_3. Aliquot C | 2.7 | 20 | 271 | 0.16 | 3.0 | 2100 | 60 | 1.4 |
| Donor_5_3. Aliquot D | 2.7 | 17 | 428 | 0.35 | 3910 | 53300 | 60 | 0.67 |
| Donor_5_3. Aliquot E | 2.7 | 11 | 467 | 0.32 | 3280 | 51000 | 60 | 0.67 |
| Donor_5_3. Aliquot F | 2.7 | 31 | 216 | 0.0043 | 73 | 11100 | 60 | 0.67 |
| Donor_5_3. Aliquot G | 2.7 | 45 | 479 | 0.0048 | 36 | 16700 | 60 | 1.6 |
| Donor_5_3. Aliquot H | 2.7 | 31 | 367 | 0.16 | 15 | 9910 | 60 | 2.5 |
| Donor_5_3. Aliquot I | 2.7 | 34 | 255 | 0.16 | 2.8 | 3530 | 60 | 1.6 |
| Donor_6_3. Aliquot A | 2.7 | 29 | 102 | 0.0052 | 35 | 7350 | 60 | 0.67 |
| Donor_6_3. Aliquot B | 2.7 | 51 | 95 | 0.012 | 46 | 9190 | 60 | 0.67 |
| Donor_6_3. Aliquot C | 2.7 | 11 | 98 | 0.0050 | 1.5 | 1220 | 60 | 0.67 |
| Donor_6_3. Aliquot D | 2.7 | 17 | 138 | 0.21 | 1870 | 26100 | 60 | 0.67 |
| Donor_6_3. Aliquot E | 2.7 | 17 | 134 | 0.41 | 3760 | 31600 | 60 | 1.2 |
| Donor_6_3. Aliquot F | 2.7 | 31 | 113 | 0.0073 | 43 | 4970 | 60 | 0.67 |
| Donor_6_3. Aliquot G | 2.7 | 11 | 170 | 0.0043 | 27 | 9870 | 60 | 0.67 |
| Donor_6_3. Aliquot H | 5.0 | 54 | 107 | 0.16 | 2.8 | 1530 | 60 | 3.7 |
| Donor_6_3. Aliquot I | 2.7 | 62 | 87 | 0.16 | 1.3 | 202 | 60 | 0.67 |

FIG. 13G.3

| | IL-17 pg/mL | IL-17E pg/mL | IL-18 pg/mL | IL-1alpha ng/mL | IL-1beta pg/mL | IL-1ra pg/mL | IL-2 pg/mL | IL-23 ng/mL |
|---|---|---|---|---|---|---|---|---|
| Least Detectable Dose | 2.7 | 31 | 54 | 0.16 | 1.5 | 15 | 60 | <0.67 |
| RBM Low Plasma Range | PENDING | PENDING | 72 | | | 17 | | PENDING |
| RBM High Plasma Range | PENDING | PENDING | 1020 | 0.35 | 8.7 | 622 | 61 | PENDING |
| Donor_7_3. Aliquot A | 2.7 | 40 | 295 | 0.025 | 147 | 6320 | 60 | 0.67 |
| Donor_7_3. Aliquot B | 2.7 | 34 | 277 | 0.015 | 99 | 4590 | 60 | 0.67 |
| Donor_7_3. Aliquot C | 2.7 | 17 | 255 | 0.010 | 16 | 244 | 60 | 0.67 |
| Donor_7_3. Aliquot D | 2.7 | 23 | 275 | 0.31 | 2120 | 11000 | 60 | 0.67 |
| Donor_7_3. Aliquot E | 2.7 | 62 | 298 | 0.071 | 548 | 7580 | 60 | 0.67 |
| Donor_7_3. Aliquot F | 2.7 | 31 | 209 | 0.016 | 20 | 578 | 60 | 0.67 |
| Donor_7_3. Aliquot G | 2.7 | 85 | 300 | 0.0054 | 6.2 | 2730 | 60 | 0.67 |
| Donor_7_3. Aliquot H | 2.7 | 31 | 214 | 0.0057 | 3.4 | 361 | 60 | 0.67 |
| Donor_7_3. Aliquot I | 2.7 | 26 | 227 | 0.0066 | 1.5 | 61 | 60 | 1.2 |
| Donor_8_3. Aliquot A | 2.7 | 17 | 150 | 0.0073 | 73 | 3870 | 60 | 1.6 |
| Donor_8_3. Aliquot B | 2.7 | 31 | 173 | 0.0089 | 59 | 3010 | 60 | 0.67 |
| Donor_8_3. Aliquot C | 2.7 | 31 | 157 | 0.0071 | 76 | 10200 | 60 | 0.67 |
| Donor_8_3. Aliquot D | 5.0 | 17 | 408 | 0.28 | 24700 | 11400 | 60 | 3.0 |
| Donor_8_3. Aliquot E | 9.7 | 45 | 359 | 0.27 | 17500 | 12800 | 60 | 1.6 |
| Donor_8_3. Aliquot F | 4.2 | 31 | 175 | 0.013 | 204 | 16400 | 60 | 3.0 |
| Donor_8_3. Aliquot G | 5.4 | 23 | 152 | 0.16 | 32 | 4000 | 60 | 1.6 |
| Donor_8_3. Aliquot H | 2.7 | 17 | 220 | 0.0041 | 75 | 7720 | 60 | 0.67 |
| Donor_8_3. Aliquot I | 2.7 | 29 | 195 | 0.0061 | 7.9 | 839 | 60 | 1.2 |
| Donor_9_3. Aliquot A | 17 | 34 | 58 | 0.0080 | 29 | 3980 | 60 | 5.8 |
| Donor_9_3. Aliquot B | 7.2 | 66 | 48 | 0.013 | 42 | 4200 | 60 | 1.1 |
| Donor_9_3. Aliquot C | 2.7 | 83 | 52 | 0.018 | 67 | 9410 | 60 | 0.67 |
| Donor_9_3. Aliquot D | 8.1 | 44 | 340 | 2.6 | 26100 | 18300 | 60 | 2.4 |
| Donor_9_3. Aliquot E | 22 | 55 | 161 | 0.80 | 7830 | 15100 | 60 | 0.67 |
| Donor_9_3. Aliquot F | 13 | 28 | 38 | 0.011 | 60 | 12700 | 60 | 0.67 |
| Donor_9_3. Aliquot G | 22 | 44 | 92 | 0.0075 | 48 | 8240 | 60 | 0.67 |
| Donor_9_3. Aliquot H | 9.8 | 77 | 96 | 0.0086 | 39 | 4920 | 60 | 0.67 |
| Donor_9_3. Aliquot I | 8.1 | 83 | 69 | 0.0035 | 5.7 | 2110 | 60 | 1.7 |

FIG. 13G.4

| | IL-17 pg/mL | IL-17E pg/mL | IL-18 pg/mL | IL-1alpha ng/mL | IL-1beta pg/mL | IL-1ra pg/mL | IL-2 pg/mL | IL-23 ng/mL |
|---|---|---|---|---|---|---|---|---|
| Least Detectable Dose | 2.7 | 31 | 54 | 0.16 | 1.5 | 15 | 60 | <0.67 |
| RBM Low Plasma Range | PENDING | PENDING | 72 | | | 17 | | PENDING |
| RBM High Plasma Range | PENDING | PENDING | 1020 | 0.35 | 8.7 | 622 | 61 | PENDING |
| EDTA Plasma | | | | | | | | |
| donor #1 plasma | 11 | 228 | 1670 | 0.16 | 2.8 | 1800 | 60 | 3.4 |
| donor #2 plasma | 2.7 | 31 | 628 | 0.16 | 1.5 | 555 | 60 | 1.1 |
| donor #3 plasma | 2.7 | 34 | 644 | 0.0027 | 1.1 | 137 | 60 | 2.7 |
| donor #4 plasma | 2.7 | 31 | 805 | 0.16 | 1.5 | 410 | 60 | 2.4 |
| donor #5 plasma | 2.7 | 31 | 188 | 0.16 | 1.5 | 354 | 60 | 1.7 |
| donor #6 plasma | 11 | 44 | 112 | 0.16 | 1.5 | 84 | 60 | 1.9 |
| donor #7 plasma | 2.7 | 28 | 404 | 0.16 | 1.5 | 559 | 60 | 0.67 |
| donor #8 plasma | 2.7 | 31 | 196 | 0.0035 | 1.4 | 68 | 60 | 0.67 |
| donor #9 plasma | 2.7 | 44 | 104 | 0.0032 | 1.5 | 80 | 60 | 1.7 |
| | | | | | | | | |
| Stimulations indices | | | | | | | | |
| Donor_1 3. Aliquot A | 2.5 | 1.3 | 1.1 | 0.0 | 13.8 | 5.7 | 1.0 | 5.4 |
| Donor_1 3. Aliquot B | 1.0 | 1.1 | 1.1 | 1.0 | 9.2 | 3.5 | 1.0 | 1.8 |
| Donor_1 3. Aliquot C | 1.0 | 0.1 | 1.1 | 1.0 | 0.8 | 1.5 | 1.0 | 1.0 |
| Donor_1 3. Aliquot D | 1.0 | 1.2 | 1.1 | 0.0 | 64.1 | 6.4 | 1.0 | 1.0 |
| Donor_1 3. Aliquot E | 1.0 | 1.2 | 1.2 | 1.0 | 12.6 | 4.2 | 1.0 | 1.0 |
| Donor_1 3. Aliquot F | 1.0 | 1.0 | 0.9 | 1.0 | 1.8 | 1.6 | 1.0 | 1.8 |
| Donor_1 3. Aliquot G | 2.8 | 1.3 | 1.2 | 1.0 | 1.2 | 4.3 | 1.0 | 3.1 |
| Donor_1 3. Aliquot H | 1.0 | 0.1 | 1.0 | 1.0 | 0.8 | 1.4 | 1.0 | 2.8 |
| Donor_1 3. Aliquot I | 1.0 | 1.0 | 1.0 | 1.0 | 1.0 | 1.0 | 1.0 | 1.0 |
| | | | | | | | | |
| Donor_2 3. Aliquot A | 1.0 | 0.8 | 1.2 | 0.1 | 20.0 | 6.5 | 1.0 | 1.8 |
| Donor_2 3. Aliquot B | 1.0 | 1.2 | 1.3 | 0.0 | 10.7 | 6.2 | 1.0 | 1.0 |
| Donor_2 3. Aliquot C | 1.0 | 0.3 | 1.1 | 1.0 | 0.7 | 0.8 | 1.0 | 1.0 |
| Donor_2 3. Aliquot D | 1.0 | 1.1 | 1.5 | 2.3 | 760.6 | 21.7 | 1.0 | 3.4 |
| Donor_2 3. Aliquot E | 1.0 | 0.8 | 1.4 | 0.7 | 198.5 | 20.8 | 1.0 | 3.7 |
| Donor_2 3. Aliquot F | 1.0 | 0.5 | 1.1 | 0.0 | 4.8 | 1.2 | 1.0 | 1.0 |
| Donor_2 3. Aliquot G | 1.0 | 0.9 | 1.3 | 0.3 | 58.6 | 2.7 | 1.0 | 1.0 |

FIG. 13G.5

| | IL-17 pg/mL | IL-17E pg/mL | IL-18 pg/mL | IL-1alpha ng/mL | IL-1beta pg/mL | IL-1ra pg/mL | IL-2 pg/mL | IL-23 ng/mL |
|---|---|---|---|---|---|---|---|---|
| Least Detectable Dose | 2.7 | 31 | 54 | 0.16 | 1.5 | 15 | 60 | <0.67 |
| RBM Low Plasma Range | PENDING | PENDING | 72 | | | 17 | | PENDING |
| RBM High Plasma Range | PENDING | PENDING | 1020 | 0.35 | 8.7 | 622 | 61 | PENDING |
| Donor_2 3. Aliquot H | 1.0 | 0.7 | 1.1 | 1.0 | 1.5 | 1.7 | 1.0 | 1.0 |
| Donor_2 3. Aliquot I | 1.0 | 1.0 | 1.0 | 1.0 | 1.0 | 1.0 | 1.0 | 1.0 |
| | | | | | | | | |
| Donor_3 3. Aliquot A | 1.0 | 0.4 | 1.2 | 1.3 | 41.6 | 164.1 | 1.0 | 0.3 |
| Donor_3 3. Aliquot B | 1.0 | 0.8 | 1.1 | 1.3 | 21.0 | 139.9 | 1.0 | 1.0 |
| Donor_3 3. Aliquot C | 1.0 | 0.6 | 1.1 | 0.8 | 3.5 | 37.8 | 1.0 | 1.0 |
| Donor_3 3. Aliquot D | 1.0 | 0.8 | 1.2 | 17.1 | 2593.3 | 521.6 | 1.0 | 0.3 |
| Donor_3 3. Aliquot E | 1.0 | 0.6 | 1.3 | 8.9 | 1073.3 | 418.6 | 1.0 | 1.7 |
| Donor_3 3. Aliquot F | 1.0 | 0.6 | 1.1 | 1.2 | 12.1 | 49.0 | 1.0 | 0.6 |
| Donor_3 3. Aliquot G | 1.0 | 0.6 | 1.2 | 1.1 | 5.7 | 41.5 | 1.0 | 0.3 |
| Donor_3 3. Aliquot H | 1.0 | 0.7 | 0.9 | 0.7 | 1.5 | 12.8 | 1.0 | 0.3 |
| Donor_3 3. Aliquot I | 1.0 | 1.0 | 1.0 | 1.0 | 1.0 | 1.0 | 1.0 | 1.0 |
| | | | | | | | | |
| Donor_4 3. Aliquot A | 1.0 | 0.7 | 1.2 | 1.0 | 11.5 | 11.7 | 1.0 | 0.3 |
| Donor_4 3. Aliquot B | 1.0 | 0.6 | 1.2 | 1.0 | 72.2 | 15.1 | 1.0 | 1.0 |
| Donor_4 3. Aliquot C | 1.0 | 0.9 | 1.0 | 1.0 | 6.1 | 1.5 | 1.0 | 1.0 |
| Donor_4 3. Aliquot D | 1.0 | 0.5 | 1.2 | 1.8 | 4470.8 | 60.1 | 1.0 | 0.3 |
| Donor_4 3. Aliquot E | 1.0 | 0.8 | 1.1 | 0.5 | 1511.8 | 57.5 | 1.0 | 0.3 |
| Donor_4 3. Aliquot F | 1.0 | 0.8 | 1.0 | 0.0 | 74.9 | 56.6 | 1.0 | 0.3 |
| Donor_4 3. Aliquot G | 1.0 | 0.9 | 1.0 | 0.0 | 11.0 | 11.1 | 1.0 | 1.2 |
| Donor_4 3. Aliquot H | 1.0 | 1.0 | 0.9 | 1.0 | 6.4 | 7.3 | 1.0 | 0.8 |
| Donor_4 3. Aliquot I | 1.0 | 1.0 | 1.0 | 1.0 | 1.0 | 1.0 | 1.0 | 1.0 |
| | | | | | | | | |
| Donor_5 3. Aliquot A | 1.0 | 2.2 | 1.3 | 0.0 | 25.9 | 6.5 | 1.0 | 0.4 |
| Donor_5 3. Aliquot B | 1.0 | 1.2 | 1.2 | 0.1 | 26.9 | 6.4 | 1.0 | 0.4 |
| Donor_5 3. Aliquot C | 1.0 | 0.6 | 1.1 | 1.0 | 1.1 | 0.6 | 1.0 | 0.9 |
| Donor_5 3. Aliquot D | 1.0 | 0.5 | 1.7 | 2.2 | 1386.4 | 15.1 | 1.0 | 0.4 |
| Donor_5 3. Aliquot E | 1.0 | 0.3 | 1.8 | 2.0 | 1171.4 | 14.4 | 1.0 | 0.4 |
| Donor_5 3. Aliquot F | 1.0 | 0.9 | 0.8 | 0.0 | 26.0 | 3.1 | 1.0 | 0.4 |
| Donor_5 3. Aliquot G | 1.0 | 1.3 | 1.9 | 0.0 | 12.9 | 4.7 | 1.0 | 1.0 |

FIG. 13G.6

| | IL-17 pg/mL | IL-17E pg/mL | IL-18 pg/mL | IL-1alpha ng/mL | IL-1beta pg/mL | IL-1ra pg/mL | IL-2 pg/mL | IL-23 ng/mL |
|---|---|---|---|---|---|---|---|---|
| Least Detectable Dose | 2.7 | 31 | 54 | 0.16 | 1.5 | 15 | 60 | <0.67 |
| RBM Low Plasma Range | PENDING | PENDING | 72 | | | | | PENDING |
| RBM High Plasma Range | PENDING | PENDING | 1020 | 0.35 | 8.7 | 17 | 61 | PENDING |
| Donor_5_3. Aliquot H | 1.0 | 0.9 | 1.4 | 1.0 | 5.2 | 622 | 1.0 | 1.5 |
| Donor_5_3. Aliquot I | 1.0 | 1.0 | 1.0 | 1.0 | 1.0 | 2.8 | 1.0 | 1.0 |
| | | | | | | 1.0 | | |
| Donor_6_3. Aliquot A | 1.0 | 0.5 | 1.2 | 0.0 | 27.3 | 36.4 | 1.0 | 1.0 |
| Donor_6_3. Aliquot B | 1.0 | 0.8 | 1.1 | 0.1 | 35.3 | 45.5 | 1.0 | 1.0 |
| Donor_6_3. Aliquot C | 1.0 | 0.2 | 1.1 | 0.0 | 1.2 | 6.0 | 1.0 | 1.0 |
| Donor_6_3. Aliquot D | 1.0 | 0.3 | 1.6 | 1.3 | 1449.6 | 129.2 | 1.0 | 1.0 |
| Donor_6_3. Aliquot E | 1.0 | 0.3 | 1.5 | 2.5 | 2914.7 | 156.4 | 1.0 | 1.8 |
| Donor_6_3. Aliquot F | 1.0 | 0.5 | 1.3 | 0.0 | 33.0 | 24.6 | 1.0 | 1.0 |
| Donor_6_3. Aliquot G | 1.0 | 0.2 | 1.9 | 0.0 | 21.1 | 48.9 | 1.0 | 1.0 |
| Donor_6_3. Aliquot H | 1.9 | 0.9 | 1.2 | 1.0 | 2.2 | 7.6 | 1.0 | 5.4 |
| Donor_6_3. Aliquot I | 1.0 | 1.0 | 1.0 | 1.0 | 1.0 | 1.0 | 1.0 | 1.0 |
| | | | | | | | | |
| Donor_7_3. Aliquot A | 1.0 | 1.5 | 1.3 | 3.8 | 98.0 | 103.4 | 1.0 | 0.6 |
| Donor_7_3. Aliquot B | 1.0 | 1.3 | 1.2 | 2.2 | 65.9 | 75.1 | 1.0 | 0.6 |
| Donor_7_3. Aliquot C | 1.0 | 0.7 | 1.1 | 1.6 | 10.7 | 4.0 | 1.0 | 0.6 |
| Donor_7_3. Aliquot D | 1.0 | 0.9 | 1.2 | 47.5 | 1413.3 | 180.0 | 1.0 | 0.6 |
| Donor_7_3. Aliquot E | 1.0 | 2.4 | 1.3 | 10.8 | 365.3 | 124.1 | 1.0 | 0.6 |
| Donor_7_3. Aliquot F | 1.0 | 1.2 | 0.9 | 2.4 | 13.5 | 9.5 | 1.0 | 0.6 |
| Donor_7_3. Aliquot G | 1.0 | 3.3 | 1.3 | 0.8 | 4.1 | 44.7 | 1.0 | 0.6 |
| Donor_7_3. Aliquot H | 1.0 | 1.2 | 0.9 | 0.9 | 2.3 | 5.9 | 1.0 | 0.6 |
| Donor_7_3. Aliquot I | 1.0 | 1.0 | 1.0 | 1.0 | 1.0 | 1.0 | 1.0 | 1.0 |
| | | | | | | | | |
| Donor_8_3. Aliquot A | 1.0 | 0.6 | 0.8 | 1.2 | 9.2 | 4.6 | 1.0 | 1.4 |
| Donor_8_3. Aliquot B | 1.0 | 1.1 | 0.9 | 1.4 | 7.4 | 3.6 | 1.0 | 0.6 |
| Donor_8_3. Aliquot C | 1.0 | 1.1 | 0.8 | 1.2 | 9.5 | 12.2 | 1.0 | 0.6 |
| Donor_8_3. Aliquot D | 1.9 | 0.6 | 2.1 | 45.6 | 3110.8 | 13.6 | 1.0 | 2.5 |
| Donor_8_3. Aliquot E | 3.6 | 1.6 | 1.8 | 43.8 | 2204.0 | 15.3 | 1.0 | 1.4 |
| Donor_8_3. Aliquot F | 1.6 | 1.1 | 0.9 | 2.2 | 25.7 | 19.5 | 1.0 | 2.5 |
| Donor_8_3. Aliquot G | 2.0 | 0.8 | 0.8 | 26.1 | 4.1 | 4.8 | 1.0 | 1.4 |

FIG. 13G.7

| | IL-17 pg/mL | IL-17E pg/mL | IL-18 pg/mL | IL-1alpha ng/mL | IL-1beta pg/mL | IL-1ra pg/mL | IL-2 pg/mL | IL-23 ng/mL |
|---|---|---|---|---|---|---|---|---|
| Least Detectable Dose | 2.7 | 31 | 54 | 0.16 | 1.5 | 15 | 60 | <0.67 |
| RBM Low Plasma Range | PENDING | PENDING | 72 | | | 17 | | PENDING |
| RBM High Plasma Range | PENDING | PENDING | 1020 | 0.35 | 8.7 | 622 | 61 | PENDING |
| Donor_8_3. Aliquot H | 1.0 | 0.6 | 1.1 | 0.7 | 9.4 | 9.2 | 1.0 | 0.6 |
| Donor_8_3. Aliquot I | 1.0 | 1.0 | 1.0 | 1.0 | 1.0 | 1.0 | 1.0 | 1.0 |
| Donor_9_3. Aliquot A | 2.0 | 0.4 | 0.8 | 2.3 | 5.1 | 1.9 | 1.0 | 3.5 |
| Donor_9_3. Aliquot B | 0.9 | 0.8 | 0.7 | 3.7 | 7.4 | 2.0 | 1.0 | 0.7 |
| Donor_9_3. Aliquot C | 0.3 | 1.0 | 0.7 | 5.1 | 11.9 | 4.5 | 1.0 | 0.4 |
| Donor_9_3. Aliquot D | 1.0 | 0.5 | 4.9 | 727.3 | 4603.2 | 8.7 | 1.0 | 1.5 |
| Donor_9_3. Aliquot E | 2.7 | 0.7 | 2.3 | 227.3 | 1381.0 | 7.2 | 1.0 | 0.4 |
| Donor_9_3. Aliquot F | 1.6 | 0.3 | 0.5 | 3.2 | 10.6 | 6.0 | 1.0 | 0.4 |
| Donor_9_3. Aliquot G | 2.7 | 0.5 | 1.3 | 2.1 | 8.4 | 3.9 | 1.0 | 0.4 |
| Donor_9_3. Aliquot H | 1.2 | 0.9 | 1.4 | 2.4 | 6.8 | 2.3 | 1.0 | 0.4 |
| Donor_9_3. Aliquot I | 1.0 | 1.0 | 1.0 | 1.0 | 1.0 | 1.0 | 1.0 | 1.0 |

FIG. 13H.1

| | IL-3 ng/mL | IL-4 pg/mL | IL-5 pg/mL | IL-6 pg/mL | IL-7 pg/mL | IL-8 pg/mL | Insulin uIU/mL | Leptin ng/mL |
|---|---|---|---|---|---|---|---|---|
| Least Detectable Dose | 0.17 | 104 | 33 | 12 | 53 | 3.5 | 0.86 | 0.10 |
| RBM Low Plasma Range | | | | | 3.7 | | | 0.41 |
| RBM High Plasma Range | 1.2 | 103 | 62 | 25 | 125 | 59 | 34 | 41 |
| Donor_1 3. Aliquot A | 0.027 | 50 | 33 | 4690 | 169 | 23600 | 11 | 132 |
| Donor_1 3. Aliquot B | 0.17 | 53 | 33 | 1860 | 113 | 4450 | 9.8 | 115 |
| Donor_1 3. Aliquot C | 0.17 | 43 | 33 | 49 | 33 | 321 | 6.3 | 124 |
| Donor_1 3. Aliquot D | 0.17 | 49 | 33 | 7970 | 113 | 6730 | 11 | 121 |
| Donor_1 3. Aliquot E | 0.17 | 38 | 33 | 1700 | 131 | 6170 | 11 | 124 |
| Donor_1 3. Aliquot F | 0.17 | 42 | 33 | 77 | 57 | 1330 | 8.3 | 107 |
| Donor_1 3. Aliquot G | 0.17 | 38 | 33 | 57 | 100 | 5060 | 8.0 | 112 |
| Donor_1 3. Aliquot H | 0.17 | 51 | 33 | 54 | 33 | 672 | 9.4 | 119 |
| Donor_1 3. Aliquot I | 0.17 | 38 | 33 | 50 | 68 | 1480 | 9.9 | 119 |
| Donor_2 3. Aliquot A | 0.12 | 69 | 5.9 | 11100 | 215 | 100000 | 5.7 | 7.7 |
| Donor_2 3. Aliquot B | 0.095 | 78 | 8.2 | 6720 | 189 | 74900 | 6.1 | 8.4 |
| Donor_2 3. Aliquot C | 0.17 | 43 | 33 | 110 | 48 | 2290 | 2.3 | 9.0 |
| Donor_2 3. Aliquot D | 0.19 | 69 | 7.4 | 78400 | 201 | 146000 | 6.6 | 8.1 |
| Donor_2 3. Aliquot E | 0.21 | 77 | 8.2 | 63400 | 226 | 165000 | 6.4 | 8.3 |
| Donor_2 3. Aliquot F | 0.17 | 40 | 6.7 | 180 | 59 | 2230 | 4.7 | 7.7 |
| Donor_2 3. Aliquot G | 0.14 | 77 | 8.9 | 30900 | 223 | >344062 | 6.0 | 4.4 |
| Donor_2 3. Aliquot H | 0.17 | 45 | 5.1 | 187 | 74 | 3460 | 5.6 | 7.8 |
| Donor_2 3. Aliquot I | 0.17 | 56 | 33 | 153 | 48 | 3230 | 4.7 | 7.9 |
| Donor_3 3. Aliquot A | 0.12 | 9.4 | 4.3 | 6380 | 192 | 40600 | 19 | 8.1 |
| Donor_3 3. Aliquot B | 0.099 | 7.8 | 33 | 3880 | 201 | 32400 | 17 | 7.7 |
| Donor_3 3. Aliquot C | 0.17 | 104 | 33 | 90 | 66 | 1860 | 9.0 | 8.4 |
| Donor_3 3. Aliquot D | 0.15 | 20 | 33 | 105000 | 243 | 124000 | 15 | 7.8 |
| Donor_3 3. Aliquot E | 0.14 | 8.7 | 4.3 | 59800 | 234 | 146000 | 17 | 8.3 |
| Donor_3 3. Aliquot F | 0.050 | 7.8 | 5.9 | 169 | 82 | 2870 | 13 | 7.2 |
| Donor_3 3. Aliquot G | 0.17 | 104 | 2.5 | 63 | 78 | 24200 | 20 | 5.9 |
| Donor_3 3. Aliquot H | 0.17 | 104 | 33 | 26 | 38 | 924 | 15 | 6.9 |
| Donor_3 3. Aliquot I | 0.087 | 104 | 5.1 | 9.2 | 86 | 1080 | 15 | 7.8 |

FIG. 13H.2

| | IL-3 ng/mL | IL-4 pg/mL | IL-5 pg/mL | IL-6 pg/mL | IL-7 pg/mL | IL-8 pg/mL | Insulin uIU/mL | Leptin ng/mL |
|---|---|---|---|---|---|---|---|---|
| Least Detectable Dose | 0.17 | 104 | 33 | 12 | 53 | 3.5 | 0.86 | 0.10 |
| RBM Low Plasma Range | | | | | 3.7 | | | 0.41 |
| RBM High Plasma Range | 1.2 | 103 | 62 | 25 | 125 | 59 | 34 | 41 |
| Donor_4 3. Aliquot A | 0.17 | 33 | 33 | 177 | 82 | 3240 | 12 | 11 |
| Donor_4 3. Aliquot B | 0.17 | 35 | 33 | 405 | 106 | 4210 | 12 | 12 |
| Donor_4 3. Aliquot C | 0.17 | 37 | 33 | 70 | 38 | 751 | 3.8 | 10 |
| Donor_4 3. Aliquot D | 0.039 | 50 | 33 | 46300 | 215 | 76000 | 13 | 9.7 |
| Donor_4 3. Aliquot E | 0.087 | 54 | 33 | 24300 | 214 | 70800 | 12 | 8.0 |
| Donor_4 3. Aliquot F | 0.17 | 32 | 33 | 5050 | 98 | 4030 | 12 | 8.4 |
| Donor_4 3. Aliquot G | 0.17 | 49 | 33 | 59 | 74 | 23400 | 14 | 7.3 |
| Donor_4 3. Aliquot H | 0.17 | 31 | 33 | 62 | 66 | 731 | 15 | 11 |
| Donor_4 3. Aliquot I | 0.17 | 29 | 33 | 52 | 38 | 550 | 11 | 10 |
| Donor_5 3. Aliquot A | 0.099 | 49 | 4.7 | 2370 | 203 | 146000 | 5.2 | 2.0 |
| Donor_5 3. Aliquot B | 0.11 | 51 | 33 | 4460 | 217 | 198000 | 5.4 | 1.7 |
| Donor_5 3. Aliquot C | 0.17 | 39 | 33 | 46 | 52 | 1740 | 2.0 | 2.0 |
| Donor_5 3. Aliquot D | 0.19 | 76 | 3.5 | 60400 | 247 | 211000 | 6.5 | 1.8 |
| Donor_5 3. Aliquot E | 0.15 | 57 | 2.5 | 71300 | 200 | >344062 | 8.0 | 1.9 |
| Donor_5 3. Aliquot F | 0.17 | 42 | 33 | 316 | 115 | 20400 | 3.6 | 1.3 |
| Donor_5 3. Aliquot G | 0.17 | 46 | 33 | 70 | 145 | 85000 | 3.8 | 2.0 |
| Donor_5 3. Aliquot H | 0.17 | 41 | 33 | 55 | 84 | 20000 | 4.9 | 1.9 |
| Donor_5 3. Aliquot I | 0.17 | 35 | 33 | 43 | 94 | 2590 | 4.3 | 1.7 |
| Donor_6 3. Aliquot A | 0.11 | 51 | 5.9 | 1500 | 182 | 17400 | 1.3 | 0.12 |
| Donor_6 3. Aliquot B | 0.11 | 55 | 11 | 3190 | 189 | 33200 | 1.4 | 0.10 |
| Donor_6 3. Aliquot C | 0.081 | 43 | 4.3 | 85 | 90 | 271 | 0.98 | 0.11 |
| Donor_6 3. Aliquot D | 0.13 | 54 | 6.3 | 50700 | 215 | 67300 | 1.8 | 0.25 |
| Donor_6 3. Aliquot E | 0.10 | 60 | 21 | 71700 | 229 | 116000 | 1.2 | 0.26 |
| Donor_6 3. Aliquot F | 0.12 | 44 | 8.9 | 517 | 124 | 3980 | 1.5 | 0.1 |
| Donor_6 3. Aliquot G | 0.032 | 46 | 33 | 74 | 128 | 26500 | 1.2 | 0.27 |
| Donor_6 3. Aliquot H | 0.025 | 39 | 33 | 84 | 94 | 692 | 1.3 | 0.13 |
| Donor_6 3. Aliquot I | 0.17 | 29 | 3.5 | 65 | 68 | 243 | 1.1 | 0.10 |

FIG. 13H.3

| | IL-3 ng/mL | IL-4 pg/mL | IL-5 pg/mL | IL-6 pg/mL | IL-7 pg/mL | IL-8 pg/mL | Insulin uIU/mL | Leptin ng/mL |
|---|---|---|---|---|---|---|---|---|
| Least Detectable Dose | 0.17 | 104 | 33 | 12 | 53 | 3.5 | 0.86 | 0.10 |
| RBM Low Plasma Range | | | | | 3.7 | | | 0.41 |
| RBM High Plasma Range | 1.2 | 103 | 62 | 25 | 125 | 59 | 34 | 41 |
| Donor_7 3. Aliquot A | 0.27 | 33 | 11 | 19900 | 273 | 89600 | 8.4 | 11 |
| Donor_7 3. Aliquot B | 0.21 | 27 | 20 | 5190 | 243 | 33900 | 7.8 | 11 |
| Donor_7 3. Aliquot C | 0.037 | 9.4 | 8.9 | 26 | 80 | 500 | 4.1 | 12 |
| Donor_7 3. Aliquot D | 0.15 | 29 | 5.9 | 54800 | 211 | 80600 | 6.5 | 11 |
| Donor_7 3. Aliquot E | 0.16 | 37 | 12 | 21600 | 247 | 41300 | 7.5 | 11 |
| Donor_7 3. Aliquot F | 0.12 | 23 | 13 | 242 | 138 | 812 | 6.2 | 11 |
| Donor_7 3. Aliquot G | 0.17 | 18 | 33 | 48 | 109 | 7810 | 6.6 | 6.9 |
| Donor_7 3. Aliquot H | 0.17 | 104 | 33 | 34 | 45 | 373 | 6.4 | 12 |
| Donor_7 3. Aliquot I | 0.044 | 104 | 4.3 | 16 | 80 | 225 | 6.1 | 12 |
| Donor_8 3. Aliquot A | 0.083 | 43 | 8.2 | 1400 | 166 | 4320 | 1.9 | 0.50 |
| Donor_8 3. Aliquot B | 0.12 | 49 | 12 | 1140 | 184 | 4770 | 2.4 | 0.49 |
| Donor_8 3. Aliquot C | 0.12 | 45 | 2.5 | 840 | 120 | 846 | 0.73 | 0.38 |
| Donor_8 3. Aliquot D | 0.18 | 60 | 5.9 | 99400 | 205 | 66900 | 2.2 | 0.62 |
| Donor_8 3. Aliquot E | 0.11 | 48 | 14 | 83900 | 217 | 58300 | 2.4 | 0.64 |
| Donor_8 3. Aliquot F | 0.25 | 48 | 14 | 6720 | 185 | 952 | 3.3 | 0.49 |
| Donor_8 3. Aliquot G | 0.025 | 43 | 33 | 42 | 86 | 2470 | 0.91 | 0.36 |
| Donor_8 3. Aliquot H | 0.081 | 40 | 5.1 | 129 | 169 | 5280 | 1.7 | 0.53 |
| Donor_8 3. Aliquot I | 0.12 | 44 | 2.5 | 12 | 117 | 895 | 1.7 | 0.37 |
| Donor_9 3. Aliquot A | 0.14 | 59 | 2.6 | 642 | 143 | 3910 | 6.2 | 2.0 |
| Donor_9 3. Aliquot B | 0.21 | 54 | 7.8 | 1100 | 156 | 4840 | 5.9 | 2.0 |
| Donor_9 3. Aliquot C | 0.20 | 59 | 5.3 | 1680 | 167 | 3560 | 3.1 | 1.6 |
| Donor_9 3. Aliquot D | 0.21 | 70 | 8.6 | 93100 | 209 | 48600 | 6.5 | 2.0 |
| Donor_9 3. Aliquot E | 0.17 | 67 | 5.3 | 61700 | 192 | 62300 | 6.3 | 1.8 |
| Donor_9 3. Aliquot F | 0.18 | 51 | 8.6 | 1900 | 159 | 1200 | 6.6 | 1.9 |
| Donor_9 3. Aliquot G | 0.11 | 75 | 33 | 131 | 126 | 21300 | 5.7 | 1.3 |
| Donor_9 3. Aliquot H | 0.098 | 55 | 33 | 57 | 141 | 1590 | 7.1 | 1.9 |
| Donor_9 3. Aliquot I | 0.10 | 43 | 33 | 19 | 62 | 797 | 5.3 | 1.9 |

FIG. 13H.4

| | IL-3 ng/mL | IL-4 pg/mL | IL-5 pg/mL | IL-6 pg/mL | IL-7 pg/mL | IL-8 pg/mL | Insulin uIU/mL | Leptin ng/mL |
|---|---|---|---|---|---|---|---|---|
| Least Detectable Dose | 0.17 | 104 | 33 | 12 | 53 | 3.5 | 0.86 | 0.10 |
| RBM Low Plasma Range | | | | | 3.7 | | | 0.41 |
| RBM High Plasma Range | 1.2 | 103 | 62 | 25 | 125 | 59 | 34 | 41 |
| EDTA Plasma | | | | | | | | |
| donor #1 plasma | 0.17 | 104 | 33 | 30 | 87 | 239 | 6.9 | 89 |
| donor #2 plasma | 0.17 | 104 | 8.2 | 102 | 42 | 319 | 5.8 | 9.7 |
| donor #3 plasma | 0.17 | 104 | 12 | 8.5 | 130 | 18 | 21 | 9.4 |
| donor #4 plasma | 0.17 | 104 | 4.0 | 49 | 52 | 102 | 16 | 15 |
| donor #5 plasma | 0.17 | 104 | 7.0 | 27 | 101 | 32 | 5.5 | 1.9 |
| donor #6 plasma | 0.17 | 104 | 7.0 | 54 | 103 | 24 | 0.57 | 0.046 |
| donor #7 plasma | 0.17 | 104 | 7.4 | 15 | 106 | 43 | 11 | 21 |
| donor #8 plasma | 0.14 | 44 | 6.1 | 1.8 | 83 | 3.5 | 1.0 | 0.64 |
| donor #9 plasma | 0.042 | 42 | 7.0 | 12 | 77 | 3.5 | 9.9 | 2.4 |
| Stimulations indices | | | | | | | | |
| Donor_1 3. Aliquot A | 0.2 | 1.3 | 1.0 | 93.4 | 2.5 | 15.9 | 1.1 | 1.1 |
| Donor_1 3. Aliquot B | 1.0 | 1.4 | 1.0 | 37.1 | 1.7 | 3.0 | 1.0 | 1.0 |
| Donor_1 3. Aliquot C | 1.0 | 1.1 | 1.0 | 1.0 | 0.5 | 0.2 | 0.6 | 1.0 |
| Donor_1 3. Aliquot D | 1.0 | 1.3 | 1.0 | 158.8 | 1.7 | 4.5 | 1.1 | 1.0 |
| Donor_1 3. Aliquot E | 1.0 | 1.0 | 1.0 | 33.9 | 1.9 | 4.2 | 1.1 | 1.0 |
| Donor_1 3. Aliquot F | 1.0 | 1.1 | 1.0 | 1.5 | 0.8 | 0.9 | 0.8 | 0.9 |
| Donor_1 3. Aliquot G | 1.0 | 1.0 | 1.0 | 1.1 | 1.5 | 3.4 | 0.8 | 0.9 |
| Donor_1 3. Aliquot H | 1.0 | 1.3 | 1.0 | 1.1 | 0.5 | 0.5 | 0.9 | 1.0 |
| Donor_1 3. Aliquot I | 1.0 | 1.0 | 1.0 | | 1.0 | 1.0 | 1.0 | 1.0 |
| Donor_2 3. Aliquot A | 0.7 | 1.2 | 0.2 | 72.5 | 4.5 | 31.0 | 1.2 | 1.0 |
| Donor_2 3. Aliquot B | 0.6 | 1.4 | 0.2 | 43.9 | 4.0 | 23.2 | 1.3 | 1.1 |
| Donor_2 3. Aliquot C | 1.0 | 0.8 | 1.0 | 0.7 | 1.0 | 0.7 | 0.5 | 1.1 |
| Donor_2 3. Aliquot D | 1.1 | 1.2 | 0.2 | 512.4 | 4.2 | 45.2 | 1.4 | 1.0 |
| Donor_2 3. Aliquot E | 1.2 | 1.4 | 0.2 | 414.4 | 4.7 | 51.1 | 1.4 | 1.1 |
| Donor_2 3. Aliquot F | 1.0 | 0.7 | 0.2 | 1.2 | 1.2 | 0.7 | 1.0 | 1.0 |
| Donor_2 3. Aliquot G | 0.8 | 1.4 | 0.3 | 202.0 | 4.7 | #VALUE! | 1.3 | 0.6 |

FIG. 13H.5

| | IL-3 ng/mL 0.17 | IL-4 pg/mL 104 | IL-5 pg/mL 33 | IL-6 pg/mL 12 | IL-7 pg/mL 53 | IL-8 pg/mL 3.5 | Insulin uIU/mL 0.86 | Leptin ng/mL 0.10 |
|---|---|---|---|---|---|---|---|---|
| Least Detectable Dose | | | | | | | | |
| | | | | | | | | |
| RBM Low Plasma Range | 1.2 | 103 | 62 | 25 | 3.7 | 59 | 34 | 0.41 |
| RBM High Plasma Range | | | | | 125 | | | 41 |
| Donor_2_3. Aliquot H | 1.0 | 0.8 | 0.2 | 1.2 | 1.6 | 1.1 | 1.2 | 1.0 |
| Donor_2_3. Aliquot I | 1.0 | 1.0 | 1.0 | 1.0 | 1.0 | 1.0 | 1.0 | 1.0 |
| | | | | | | | | |
| Donor_3_3. Aliquot A | 1.4 | 0.1 | 0.8 | 690.5 | 2.2 | 37.6 | 1.2 | 1.0 |
| Donor_3_3. Aliquot B | 1.1 | 0.1 | 6.5 | 419.9 | 2.3 | 30.0 | 1.1 | 1.0 |
| Donor_3_3. Aliquot C | 2.0 | 1.0 | 6.5 | 9.7 | 0.8 | 1.7 | 0.6 | 1.1 |
| Donor_3_3. Aliquot D | 1.7 | 0.2 | 6.5 | 11363.6 | 2.8 | 114.8 | 1.0 | 1.0 |
| Donor_3_3. Aliquot E | 1.6 | 0.1 | 0.8 | 6471.9 | 2.7 | 135.2 | 1.1 | 1.1 |
| Donor_3_3. Aliquot F | 0.6 | 0.1 | 1.2 | 18.3 | 1.0 | 2.7 | 0.8 | 0.9 |
| Donor_3_3. Aliquot G | 2.0 | 1.0 | 0.5 | 6.8 | 0.9 | 22.4 | 1.3 | 0.8 |
| Donor_3_3. Aliquot H | 2.0 | 1.0 | 6.5 | 2.8 | 0.4 | 0.9 | 1.0 | 0.9 |
| Donor_3_3. Aliquot I | 1.0 | 1.0 | 1.0 | 1.0 | 1.0 | 1.0 | 1.0 | 1.0 |
| | | | | | | | | |
| Donor_4_3. Aliquot A | 1.0 | 1.1 | 1.0 | 3.4 | 2.2 | 5.9 | 1.0 | 1.0 |
| Donor_4_3. Aliquot B | 1.0 | 1.2 | 1.0 | 7.9 | 2.8 | 7.7 | 1.1 | 1.2 |
| Donor_4_3. Aliquot C | 1.0 | 1.3 | 1.0 | 1.3 | 1.0 | 1.4 | 0.3 | 1.0 |
| Donor_4_3. Aliquot D | 0.2 | 1.7 | 1.0 | 899.0 | 5.7 | 138.2 | 1.1 | 0.8 |
| Donor_4_3. Aliquot E | 0.5 | 1.8 | 1.0 | 471.8 | 5.6 | 128.7 | 1.0 | 0.8 |
| Donor_4_3. Aliquot F | 1.0 | 1.1 | 1.0 | 98.1 | 2.6 | 7.3 | 1.2 | 0.7 |
| Donor_4_3. Aliquot G | 1.0 | 1.7 | 1.0 | 1.1 | 1.9 | 42.5 | 1.3 | 1.1 |
| Donor_4_3. Aliquot H | 1.0 | 1.0 | 1.0 | 1.2 | 1.7 | 1.3 | 1.0 | 1.0 |
| Donor_4_3. Aliquot I | 1.0 | 1.0 | 1.0 | 1.0 | 1.0 | 1.0 | 1.0 | 1.0 |
| | | | | | | | | |
| Donor_5_3. Aliquot A | 0.6 | 1.4 | 0.1 | 55.5 | 2.2 | 56.4 | 1.2 | 1.2 |
| Donor_5_3. Aliquot B | 0.6 | 1.5 | 1.0 | 104.4 | 2.3 | 76.4 | 1.3 | 1.0 |
| Donor_5_3. Aliquot C | 1.0 | 1.1 | 1.0 | 1.1 | 0.6 | 0.7 | 0.5 | 1.2 |
| Donor_5_3. Aliquot D | 1.1 | 2.2 | 0.1 | 1414.5 | 2.6 | 81.5 | 1.5 | 1.1 |
| Donor_5_3. Aliquot E | 0.9 | 1.6 | 0.1 | 1669.8 | 2.1 | #VALUE! | 1.9 | 1.1 |
| Donor_5_3. Aliquot F | 1.0 | 1.2 | 1.0 | 7.4 | 1.2 | 7.9 | 0.8 | 0.8 |
| Donor_5_3. Aliquot G | 1.0 | 1.3 | 1.0 | 1.6 | 1.5 | 32.8 | 0.9 | 1.2 |

FIG. 13H.6

| | IL-3 ng/mL | IL-4 pg/mL | IL-5 pg/mL | IL-6 pg/mL | IL-7 pg/mL | IL-8 pg/mL | Insulin uIU/mL | Leptin ng/mL |
|---|---|---|---|---|---|---|---|---|
| Least Detectable Dose | 0.17 | 104 | 33 | 12 | 53 | 3.5 | 0.86 | 0.10 |
| RBM Low Plasma Range | 1.2 | 103 | 62 | 25 | 3.7 | | | 0.41 |
| RBM High Plasma Range | | | | | 125 | 59 | 34 | 41 |
| Donor_5_3, Aliquot H | 1.0 | 1.2 | 1.0 | 1.3 | 0.9 | 7.7 | 1.1 | 1.1 |
| Donor_5_3, Aliquot I | 1.0 | 1.0 | 1.0 | 1.0 | 1.0 | 1.0 | 1.0 | 1.0 |
| Donor_6_3, Aliquot A | 0.6 | 1.8 | 1.7 | 22.9 | 2.7 | 71.6 | 1.2 | 1.2 |
| Donor_6_3, Aliquot B | 0.6 | 1.9 | 3.0 | 48.8 | 2.8 | 136.6 | 1.3 | 1.0 |
| Donor_6_3, Aliquot C | 0.5 | 1.5 | 1.2 | 1.3 | 1.3 | 1.1 | 0.9 | 1.1 |
| Donor_6_3, Aliquot D | 0.8 | 1.9 | 1.8 | 775.2 | 3.2 | 277.0 | 1.6 | 2.5 |
| Donor_6_3, Aliquot E | 0.6 | 2.1 | 6.2 | 1096.3 | 3.4 | 477.4 | 1.0 | 2.5 |
| Donor_6_3, Aliquot F | 0.7 | 1.5 | 2.6 | 7.9 | 1.8 | 16.4 | 1.3 | 1.0 |
| Donor_6_3, Aliquot G | 0.2 | 1.6 | 9.5 | 1.1 | 1.9 | 109.1 | 1.1 | 2.7 |
| Donor_6_3, Aliquot H | 0.1 | 1.4 | 9.5 | 1.3 | 1.4 | 2.8 | 1.2 | 1.2 |
| Donor_6_3, Aliquot I | 1.0 | 1.0 | 1.0 | 1.0 | 1.0 | 1.0 | 1.0 | 1.0 |
| Donor_7_3, Aliquot A | 6.1 | 0.3 | 2.6 | 1251.6 | 3.4 | 398.2 | 1.4 | 1.0 |
| Donor_7_3, Aliquot B | 4.8 | 0.3 | 4.6 | 326.4 | 3.0 | 150.7 | 1.3 | 1.0 |
| Donor_7_3, Aliquot C | 0.8 | 0.1 | 2.1 | 1.6 | 1.0 | 2.2 | 0.7 | 1.1 |
| Donor_7_3, Aliquot D | 3.5 | 0.3 | 1.4 | 3446.5 | 2.6 | 358.2 | 1.1 | 0.9 |
| Donor_7_3, Aliquot E | 3.7 | 0.4 | 2.8 | 1358.5 | 3.1 | 183.6 | 1.2 | 1.0 |
| Donor_7_3, Aliquot F | 2.8 | 0.2 | 3.0 | 15.2 | 1.7 | 3.6 | 1.0 | 0.9 |
| Donor_7_3, Aliquot G | 3.9 | 0.2 | 7.7 | 3.0 | 1.4 | 34.7 | 1.1 | 0.6 |
| Donor_7_3, Aliquot H | 3.9 | 1.0 | 7.7 | 2.1 | 0.6 | 1.7 | 1.0 | 1.0 |
| Donor_7_3, Aliquot I | 1.0 | 1.0 | 1.0 | 1.0 | 1.0 | 1.0 | 1.0 | 1.0 |
| Donor_8_3, Aliquot A | 0.7 | 1.0 | 3.2 | 113.8 | 1.4 | 4.8 | 1.1 | 1.3 |
| Donor_8_3, Aliquot B | 1.0 | 1.1 | 4.7 | 92.7 | 1.6 | 5.3 | 1.4 | 1.3 |
| Donor_8_3, Aliquot C | 1.1 | 1.0 | 1.0 | 68.3 | 1.0 | 0.9 | 0.4 | 1.0 |
| Donor_8_3, Aliquot D | 1.5 | 1.4 | 2.3 | 8081.3 | 1.8 | 74.7 | 1.3 | 1.6 |
| Donor_8_3, Aliquot E | 1.0 | 1.1 | 5.5 | 6821.1 | 1.9 | 65.1 | 1.4 | 1.7 |
| Donor_8_3, Aliquot F | 2.2 | 1.1 | 5.7 | 546.3 | 1.6 | 1.1 | 2.0 | 1.3 |
| Donor_8_3, Aliquot G | 0.2 | 1.0 | 13.0 | 3.4 | 0.7 | 2.8 | 0.5 | 1.0 |

FIG. 13H.7

| | IL-3 ng/mL | IL-4 pg/mL | IL-5 pg/mL | IL-6 pg/mL | IL-7 pg/mL | IL-8 pg/mL | Insulin uIU/mL | Leptin ng/mL |
|---|---|---|---|---|---|---|---|---|
| Least Detectable Dose | 0.17 | 104 | 33 | 12 | 53 | 3.5 | 0.86 | 0.10 |
| RBM Low Plasma Range | | | | | 3.7 | | | 0.41 |
| RBM High Plasma Range | 1.2 | 103 | 62 | 25 | 125 | 59 | 34 | 41 |
| Donor_8_3. Aliquot H | 0.7 | 0.9 | 2.0 | 10.5 | 1.4 | 5.9 | 1.0 | 1.4 |
| Donor_8_3. Aliquot I | 1.0 | 1.0 | 1.0 | 1.0 | 1.0 | 1.0 | 1.0 | 1.0 |
| Donor_9_3. Aliquot A | 1.4 | 1.4 | 0.1 | 34.7 | 2.3 | 4.9 | 1.2 | 1.0 |
| Donor_9_3. Aliquot B | 2.0 | 1.3 | 0.2 | 59.5 | 2.5 | 6.1 | 1.1 | 1.0 |
| Donor_9_3. Aliquot C | 2.0 | 1.4 | 0.2 | 90.8 | 2.7 | 4.5 | 0.6 | 0.8 |
| Donor_9_3. Aliquot D | 2.1 | 1.6 | 0.3 | 5032.4 | 3.3 | 61.0 | 1.2 | 1.0 |
| Donor_9_3. Aliquot E | 1.6 | 1.6 | 0.2 | 3335.1 | 3.1 | 78.2 | 1.2 | 0.9 |
| Donor_9_3. Aliquot F | 1.8 | 1.2 | 0.3 | 102.7 | 2.5 | 1.5 | 1.3 | 1.0 |
| Donor_9_3. Aliquot G | 1.1 | 1.8 | 1.0 | 7.1 | 2.0 | 26.7 | 1.1 | 0.7 |
| Donor_9_3. Aliquot H | 1.0 | 1.3 | 1.0 | 3.1 | 2.3 | 2.0 | 1.3 | 1.0 |
| Donor_9_3. Aliquot I | 1.0 | 1.0 | 1.0 | 1.0 | 1.0 | 1.0 | 1.0 | 1.0 |

FIG. 131.1

| | Lipoprotein (a) | Lymphotactin | MCP-1 | MDC | MIP-1alpha | MIP-1beta | MMP-2 | MMP-3 |
|---|---|---|---|---|---|---|---|---|
| | ug/mL | ng/mL | pg/mL | pg/mL | pg/mL | pg/mL | ng/mL | ng/mL |
| Least Detectable Dose | 3.7 | 0.38 | 52 | 14 | 13 | 38 | 150 | 0.20 |
| RBM Low Plasma Range | 3.0 | | 35 | 162 | | 25 | 183 | |
| RBM High Plasma Range | 858 | 0.57 | 401 | 774 | 89 | 595 | 3070 | 1.8 |
| Donor_1 3. Aliquot A | 27 | 0.22 | 8710 | 197 | 3570 | 71300 | 474 | 12 |
| Donor_1 3. Aliquot B | 34 | 0.38 | 4230 | 187 | 1810 | 12800 | 440 | 11 |
| Donor_1 3. Aliquot C | 31 | 0.38 | 1210 | 180 | 94 | 610 | 71 | 12 |
| Donor_1 3. Aliquot D | 32 | 0.071 | 3940 | 203 | 3760 | 75700 | 443 | 13 |
| Donor_1 3. Aliquot E | 32 | 0.092 | 4040 | 185 | 1370 | 16800 | 456 | 12 |
| Donor_1 3. Aliquot F | 45 | 0.38 | 2120 | 146 | 197 | 2040 | 410 | 11 |
| Donor_1 3. Aliquot G | 37 | 0.38 | 8970 | 14 | 110 | 498 | 451 | 13 |
| Donor_1 3. Aliquot H | 32 | 0.38 | 1080 | 41 | 81 | 513 | 68 | 12 |
| Donor_1 3. Aliquot I | 30 | 0.38 | 1030 | 193 | 180 | 803 | 427 | 11 |
| Donor_2 3. Aliquot A | 38 | 0.26 | 9540 | 158 | 5430 | 94800 | 105 | 11 |
| Donor_2 3. Aliquot B | 46 | 0.22 | 3930 | 178 | 2250 | 52800 | 83 | 11 |
| Donor_2 3. Aliquot C | 47 | 0.15 | 499 | 160 | 91 | 1790 | 86 | 12 |
| Donor_2 3. Aliquot D | 48 | 0.28 | 3760 | 165 | 34700 | 460000 | 100 | 13 |
| Donor_2 3. Aliquot E | 58 | 0.25 | 4260 | 154 | 23000 | 331000 | 123 | 11 |
| Donor_2 3. Aliquot F | 128 | 0.38 | 810 | 141 | 191 | 4280 | 69 | 11 |
| Donor_2 3. Aliquot G | 46 | 0.28 | 42600 | 14 | 29600 | 95800 | 147 | 11 |
| Donor_2 3. Aliquot H | 47 | 0.38 | 917 | 33 | 360 | 7090 | 86 | 11 |
| Donor_2 3. Aliquot I | 48 | 0.38 | 555 | 156 | 179 | 5430 | 72 | 9.7 |
| Donor_3 3. Aliquot A | 61 | 0.33 | 11000 | 92 | 894 | 31700 | 30 | 5.4 |
| Donor_3 3. Aliquot B | 66 | 0.23 | 3820 | 86 | 387 | 17200 | 26 | 4.8 |
| Donor_3 3. Aliquot C | 68 | 0.15 | 228 | 87 | 46 | 1850 | 34 | 5.0 |
| Donor_3 3. Aliquot D | 58 | 0.32 | 2630 | 84 | 8550 | 254000 | 47 | 4.9 |
| Donor_3 3. Aliquot E | 70 | 0.39 | 2870 | 72 | 3710 | 126000 | 34 | 5.3 |
| Donor_3 3. Aliquot F | 83 | 0.39 | 246 | 70 | 66 | 2900 | 34 | 4.4 |
| Donor_3 3. Aliquot G | 57 | 0.21 | 521 | 14 | 60 | 1680 | 67 | 4.3 |
| Donor_3 3. Aliquot H | 61 | 0.38 | 126 | 12 | 42 | 633 | 23 | 3.9 |
| Donor_3 3. Aliquot I | 66 | 0.54 | 110 | 85 | 46 | 123 | 150 | 4.7 |

FIG. 131.2

| | Lipoprotein (a) | Lymphotactin | MCP-1 | MDC | MIP-1alpha | MIP-1beta | MMP-2 | MMP-3 |
|---|---|---|---|---|---|---|---|---|
| | ug/mL | ng/mL | pg/mL | pg/mL | pg/mL | pg/mL | ng/mL | ng/mL |
| Least Detectable Dose | 3.7 | 0.38 | 52 | 14 | 13 | 38 | 150 | 0.20 |
| | | | | | | | | |
| RBM Low Plasma Range | 3.0 | | 35 | 162 | | 25 | 183 | |
| RBM High Plasma Range | 858 | 0.57 | 401 | 774 | 89 | 595 | 3070 | 1.8 |
| Donor_4_3. Aliquot A | 23 | 0.38 | 2430 | 324 | 432 | 13100 | 150 | 7.5 |
| Donor_4_3. Aliquot B | 21 | 0.38 | 2960 | 346 | 288 | 9460 | 150 | 7.5 |
| Donor_4_3. Aliquot C | 21 | 0.38 | 578 | 280 | 137 | 994 | 150 | 6.8 |
| Donor_4_3. Aliquot D | 24 | 0.16 | 14900 | 335 | 31200 | 484000 | 43 | 7.4 |
| Donor_4_3. Aliquot E | 22 | 0.20 | 15800 | 259 | 17700 | 293000 | 50 | 6.6 |
| Donor_4_3. Aliquot F | 24 | 0.12 | 15400 | 251 | 1740 | 84100 | 150 | 6.6 |
| Donor_4_3. Aliquot G | 22 | 0.38 | 6110 | 14 | 547 | 3900 | 45 | 5.6 |
| Donor_4_3. Aliquot H | 21 | 0.38 | 641 | 66 | 106 | 3160 | 15 | 7.2 |
| Donor_4_3. Aliquot I | 25 | 0.38 | 269 | 298 | 63 | 287 | 150 | 6.8 |
| | | | | | | | | |
| Donor_5_3. Aliquot A | 22 | 0.31 | 11900 | 298 | 6820 | 150000 | 106 | 21 |
| Donor_5_3. Aliquot B | 20 | 0.33 | 7660 | 424 | 9780 | 174000 | 112 | 19 |
| Donor_5_3. Aliquot C | 21 | 0.15 | 226 | 221 | 111 | 1790 | 115 | 21 |
| Donor_5_3. Aliquot D | 19 | 0.36 | 3740 | 190 | 36200 | 543000 | 132 | 19 |
| Donor_5_3. Aliquot E | 21 | 0.33 | 5360 | 205 | 46800 | 600000 | 138 | 20 |
| Donor_5_3. Aliquot F | 39 | 0.071 | 2920 | 171 | 1790 | 24300 | 67 | 16 |
| Donor_5_3. Aliquot G | 18 | 0.22 | 14900 | 14 | 527 | 3130 | 120 | 20 |
| Donor_5_3. Aliquot H | 17 | 0.38 | 523 | 55 | 328 | 5000 | 90 | 20 |
| Donor_5_3. Aliquot I | 18 | 0.38 | 231 | 218 | 119 | 3870 | 83 | 20 |
| | | | | | | | | |
| Donor_6_3. Aliquot A | 36 | 0.72 | 3750 | 124 | 1810 | 27400 | 12 | 2.8 |
| Donor_6_3. Aliquot B | 40 | 0.72 | 2190 | 124 | 1690 | 22200 | 15 | 3.0 |
| Donor_6_3. Aliquot C | 39 | 0.62 | 218 | 110 | 55 | 376 | 150 | 2.5 |
| Donor_6_3. Aliquot D | 43 | 0.80 | 1360 | 136 | 29200 | 402000 | 20 | 2.9 |
| Donor_6_3. Aliquot E | 35 | 0.69 | 990 | 110 | 36100 | 441000 | 28 | 2.6 |
| Donor_6_3. Aliquot F | 79 | 0.79 | 2110 | 94 | 491 | 7470 | 150 | 2.6 |
| Donor_6_3. Aliquot G | 31 | 0.50 | 3670 | 14 | 800 | 3130 | 75 | 2.3 |
| Donor_6_3. Aliquot H | 32 | 0.50 | 240 | 29 | 143 | 3680 | 150 | 2.8 |
| Donor_6_3. Aliquot I | 25 | 0.52 | 146 | 113 | 49 | 317 | 150 | 2.7 |

FIG. 131.3

| | Lipoprotein (a) | Lymphotactin | MCP-1 | MDC | MIP-1alpha | MIP-1beta | MMP-2 | MMP-3 |
|---|---|---|---|---|---|---|---|---|
| | ug/mL | ng/mL | pg/mL | pg/mL | pg/mL | pg/mL | ng/mL | ng/mL |
| Least Detectable Dose | 3.7 | 0.38 | 52 | 14 | 13 | 38 | 150 | 0.20 |
| RBM Low Plasma Range | 3.0 | | 35 | 162 | | 25 | | |
| RBM High Plasma Range | 858 | 0.57 | 401 | 774 | 89 | 595 | 183 | 1.8 |
| Donor_7_3. Aliquot A | 203 | 0.96 | 14700 | 94 | 6080 | 188000 | 3070 | 16 |
| Donor_7_3. Aliquot B | 222 | 0.78 | 5090 | 99 | 2700 | 68500 | 16 | 16 |
| Donor_7_3. Aliquot C | 160 | 0.53 | 314 | 83 | 46 | 680 | 150 | 16 |
| Donor_7_3. Aliquot D | 192 | 0.75 | 5040 | 92 | 7530 | 349000 | 150 | 14 |
| Donor_7_3. Aliquot E | 215 | 0.83 | 8810 | 96 | 4790 | 179000 | 23 | 15 |
| Donor_7_3. Aliquot F | 548 | 0.88 | 1260 | 72 | 152 | 5030 | 23 | 15 |
| Donor_7_3. Aliquot G | 148 | 0.24 | 3610 | 14 | 469 | 2280 | 150 | 15 |
| Donor_7_3. Aliquot H | 155 | 0.33 | 309 | 17 | 43 | 762 | 47 | 14 |
| Donor_7_3. Aliquot I | 190 | 0.53 | 265 | 84 | 38 | 156 | 150 | 15 |
| Donor_8_3. Aliquot A | 16 | 0.93 | 4750 | 223 | 1840 | 22700 | 37 | 3.4 |
| Donor_8_3. Aliquot B | 16 | 0.96 | 3720 | 221 | 1450 | 21000 | 37 | 3.5 |
| Donor_8_3. Aliquot C | 16 | 0.91 | 5420 | 154 | 2130 | 58500 | 23 | 2.8 |
| Donor_8_3. Aliquot D | 13 | 1.1 | 2170 | 337 | 67800 | 572000 | 89 | 3.9 |
| Donor_8_3. Aliquot E | 18 | 1.2 | 4380 | 245 | 46800 | 387000 | 75 | 3.4 |
| Donor_8_3. Aliquot F | 18 | 1.2 | 12700 | 138 | 6380 | 129000 | 53 | 3.6 |
| Donor_8_3. Aliquot G | 12 | 0.47 | 1940 | 14 | 931 | 7690 | 58 | 3.2 |
| Donor_8_3. Aliquot H | 13 | 0.80 | 7890 | 90 | 3290 | 29900 | 43 | 3.6 |
| Donor_8_3. Aliquot I | 14 | 0.80 | 385 | 256 | 266 | 4590 | 26 | 3.2 |
| Donor_9_3. Aliquot A | 18 | 0.68 | 5430 | 169 | 1250 | 24500 | 38 | 4.3 |
| Donor_9_3. Aliquot B | 12 | 0.73 | 3060 | 175 | 1690 | 23200 | 43 | 4.8 |
| Donor_9_3. Aliquot C | 13 | 0.69 | 16600 | 180 | 2140 | 46900 | 72 | 4.2 |
| Donor_9_3. Aliquot D | 17 | 0.62 | 6120 | 196 | 42300 | 431000 | 132 | 4.7 |
| Donor_9_3. Aliquot E | 16 | 0.71 | 9540 | 194 | 29700 | 355000 | 82 | 4.9 |
| Donor_9_3. Aliquot F | 18 | 0.86 | 12800 | 142 | 2410 | 78800 | 46 | 4.3 |
| Donor_9_3. Aliquot G | 11 | 0.20 | 15500 | 14 | 1820 | 12300 | 95 | 3.9 |
| Donor_9_3. Aliquot H | 11 | 0.38 | 2420 | 70 | 467 | 14400 | 48 | 4.3 |
| Donor_9_3. Aliquot I | 14 | 0.53 | 346 | 181 | 240 | 3670 | 42 | 3.6 |

FIG. 131.4

| | Lipoprotein (a) ug/mL | Lymphotactin ng/mL | MCP-1 pg/mL | MDC pg/mL | MIP-1alpha pg/mL | MIP-1beta pg/mL | MMP-2 ng/mL | MMP-3 ng/mL |
|---|---|---|---|---|---|---|---|---|
| Least Detectable Dose | 3.7 | 0.38 | 52 | 14 | 13 | 38 | 150 | 0.20 |
| RBM Low Plasma Range | 3.0 | | 35 | 162 | | 25 | 183 | |
| RBM High Plasma Range | 858 | 0.57 | 401 | 774 | 89 | 595 | 3070 | 1.8 |
| EDTA Plasma | | | | | | | | |
| donor #1 plasma | 46 | 0.38 | 230 | 187 | 69 | 209 | 1750 | 0.12 |
| donor #2 plasma | 109 | 0.38 | 66 | 236 | 60 | 239 | 3910 | 0.047 |
| donor #3 plasma | 143 | 0.12 | 11 | 116 | 41 | 65 | 1540 | 0.2 |
| donor #4 plasma | 31 | 0.38 | 23 | 413 | 59 | 368 | 8190 | 0.2 |
| donor #5 plasma | 31 | 0.12 | 17 | 307 | 46 | 154 | 898 | 0.076 |
| donor #6 plasma | 91 | 0.28 | 32 | 155 | 34 | 68 | 972 | 0.2 |
| donor #7 plasma | 735 | 0.42 | 109 | 124 | 48 | 145 | 2270 | 0.090 |
| donor #8 plasma | 17 | 0.31 | 147 | 176 | 42 | 47 | 10 | 3.7 |
| donor #9 plasma | 23 | 0.33 | 89 | 159 | 44 | 38 | 46 | 4.2 |
| Stimulations indices | | | | | | | | |
| Donor_1 3. Aliquot A | 0.9 | 0.6 | 8.5 | 1.0 | 19.8 | 88.8 | 1.1 | 1.1 |
| Donor_1 3. Aliquot B | 1.1 | 1.0 | 4.1 | 1.0 | 10.1 | 15.9 | 1.0 | 1.0 |
| Donor_1 3. Aliquot C | 1.1 | 1.0 | 1.2 | 0.9 | 0.5 | 0.8 | 0.2 | 1.1 |
| Donor_1 3. Aliquot D | 1.1 | 0.2 | 3.8 | 1.1 | 20.9 | 94.3 | 1.0 | 1.2 |
| Donor_1 3. Aliquot E | 1.1 | 0.2 | 3.9 | 1.0 | 7.6 | 20.9 | 1.1 | 1.1 |
| Donor_1 3. Aliquot F | 1.5 | 1.0 | 2.1 | 0.8 | 1.1 | 2.5 | 1.0 | 1.0 |
| Donor_1 3. Aliquot G | 1.3 | 1.0 | 8.7 | 0.1 | 0.6 | 0.6 | 1.1 | 1.1 |
| Donor_1 3. Aliquot H | 1.1 | 1.0 | 1.0 | 0.2 | 0.4 | 0.6 | 0.2 | 1.1 |
| Donor_1 3. Aliquot I | 1.0 | 1.0 | 1.0 | 1.0 | 1.0 | 1.0 | 1.0 | 1.0 |
| Donor_2 3. Aliquot A | 0.8 | 0.7 | 17.2 | 1.0 | 30.3 | 17.5 | 1.5 | 1.1 |
| Donor_2 3. Aliquot B | 0.9 | 0.6 | 7.1 | 1.1 | 12.6 | 9.7 | 1.2 | 1.2 |
| Donor_2 3. Aliquot C | 1.0 | 1.0 | 0.9 | 1.0 | 0.5 | 0.3 | 1.2 | 1.1 |
| Donor_2 3. Aliquot D | 1.0 | 0.7 | 6.8 | 1.1 | 193.9 | 84.7 | 1.4 | 1.3 |
| Donor_2 3. Aliquot E | 1.2 | 0.7 | 7.7 | 1.0 | 128.5 | 61.0 | 1.7 | 1.2 |
| Donor_2 3. Aliquot F | 2.6 | 1.0 | 1.5 | 0.9 | 1.1 | 0.8 | 1.0 | 1.1 |
| Donor_2 3. Aliquot G | 0.9 | 0.7 | 76.8 | 0.1 | 165.4 | 17.6 | 2.0 | 1.2 |

FIG. 13I.5

| | Lipoprotein (a) | Lymphotactin | MCP-1 | MDC | MIP-1alpha | MIP-1beta | MMP-2 | MMP-3 |
|---|---|---|---|---|---|---|---|---|
| | ug/mL | ng/mL | pg/mL | pg/mL | pg/mL | pg/mL | ng/mL | ng/mL |
| Least Detectable Dose | 3.7 | 0.38 | 52 | 14 | 13 | 38 | 150 | 0.20 |
| RBM Low Plasma Range | 3.0 | | 35 | 162 | | 25 | 183 | |
| RBM High Plasma Range | 858 | 0.57 | 401 | 774 | 89 | 595 | 3070 | 1.8 |
| Donor_2_3. Aliquot H | 1.0 | 1.0 | 1.7 | 0.2 | 2.0 | 1.3 | 1.2 | 1.2 |
| Donor_2_3. Aliquot I | 1.0 | 1.0 | 1.0 | 1.0 | 1.0 | 1.0 | 1.0 | 1.0 |
| Donor_3_3. Aliquot A | 0.9 | 0.6 | 100.0 | 1.1 | 19.3 | 257.7 | 0.2 | 1.2 |
| Donor_3_3. Aliquot B | 1.0 | 0.4 | 34.7 | 1.0 | 8.3 | 139.8 | 0.2 | 1.0 |
| Donor_3_3. Aliquot C | 1.0 | 0.3 | 2.1 | 1.0 | 2.2 | 15.0 | 0.2 | 1.1 |
| Donor_3_3. Aliquot D | 0.9 | 0.6 | 23.9 | 1.0 | 184.3 | 2065.0 | 0.3 | 1.0 |
| Donor_3_3. Aliquot E | 1.1 | 0.7 | 26.1 | 0.8 | 80.0 | 1024.4 | 0.2 | 1.1 |
| Donor_3_3. Aliquot F | 1.3 | 0.7 | 2.2 | 0.8 | 1.4 | 23.6 | 0.2 | 0.9 |
| Donor_3_3. Aliquot G | 0.9 | 0.4 | 4.7 | 0.2 | 1.3 | 13.7 | 0.4 | 0.9 |
| Donor_3_3. Aliquot H | 0.9 | 0.7 | 1.1 | 0.1 | 0.9 | 5.1 | 0.2 | 0.8 |
| Donor_3_3. Aliquot I | 1.0 | 1.0 | 1.0 | 1.0 | 1.0 | 1.0 | 1.0 | 1.0 |
| Donor_4_3. Aliquot A | 0.9 | 1.0 | 9.0 | 1.1 | 6.9 | 45.6 | 1.0 | 1.1 |
| Donor_4_3. Aliquot B | 0.8 | 1.0 | 11.0 | 1.2 | 4.6 | 33.0 | 1.0 | 1.1 |
| Donor_4_3. Aliquot C | 0.8 | 1.0 | 2.1 | 0.9 | 2.2 | 3.5 | 1.0 | 1.0 |
| Donor_4_3. Aliquot D | 0.9 | 0.4 | 55.4 | 1.1 | 496.0 | 1896.4 | 0.3 | 1.1 |
| Donor_4_3. Aliquot E | 0.9 | 0.5 | 58.7 | 0.9 | 281.4 | 1020.9 | 0.3 | 1.0 |
| Donor_4_3. Aliquot F | 0.9 | 0.3 | 57.2 | 0.8 | 27.7 | 293.0 | 1.0 | 1.0 |
| Donor_4_3. Aliquot G | 0.9 | 1.0 | 22.7 | 0.0 | 8.7 | 13.6 | 0.3 | 0.8 |
| Donor_4_3. Aliquot H | 0.8 | 0.7 | 2.4 | 0.2 | 1.7 | 11.0 | 0.1 | 1.1 |
| Donor_4_3. Aliquot I | 1.0 | 1.0 | 1.0 | 1.0 | 1.0 | 1.0 | 1.0 | 1.0 |
| Donor_5_3. Aliquot A | 1.2 | 0.8 | 51.5 | 1.4 | 57.3 | 38.8 | 1.3 | 1.0 |
| Donor_5_3. Aliquot B | 1.1 | 0.9 | 33.2 | 1.9 | 82.2 | 45.0 | 1.3 | 1.0 |
| Donor_5_3. Aliquot C | 1.2 | 0.4 | 1.0 | 1.0 | 0.9 | 0.5 | 1.4 | 1.1 |
| Donor_5_3. Aliquot D | 1.0 | 0.9 | 16.2 | 0.9 | 304.2 | 140.3 | 1.6 | 1.0 |
| Donor_5_3. Aliquot E | 1.1 | 0.9 | 23.2 | 0.9 | 393.3 | 155.0 | 1.7 | 1.0 |
| Donor_5_3. Aliquot F | 2.1 | 0.2 | 12.6 | 0.8 | 15.0 | 6.3 | 0.8 | 0.8 |
| Donor_5_3. Aliquot G | 1.0 | 0.6 | 64.5 | 0.1 | 4.4 | 0.8 | 1.4 | 1.0 |

FIG. 13I.6

| | Lipoprotein (a) | Lymphotactin | MCP-1 | MDC | MIP-1alpha | MIP-1beta | MMP-2 | MMP-3 |
|---|---|---|---|---|---|---|---|---|
| | ug/mL | ng/mL | pg/mL | pg/mL | pg/mL | pg/mL | ng/mL | ng/mL |
| Least Detectable Dose | 3.7 | 0.38 | 52 | 14 | 13 | 38 | 150 | 0.20 |
| RBM Low Plasma Range | 3.0 | | 35 | 162 | 89 | 25 | 183 | |
| RBM High Plasma Range | 858 | 0.57 | 401 | 774 | | 595 | 3070 | 1.8 |
| Donor_5 3. Aliquot H | 0.9 | 1.0 | 2.3 | 0.3 | 2.8 | 1.3 | 1.1 | 1.0 |
| Donor_5 3. Aliquot I | 1.0 | 1.0 | 1.0 | 1.0 | 1.0 | 1.0 | 1.0 | 1.0 |
| Donor_6 3. Aliquot A | 1.5 | 1.4 | 25.7 | 1.1 | 36.7 | 86.4 | 0.1 | 1.0 |
| Donor_6 3. Aliquot B | 1.6 | 1.4 | 15.0 | 1.1 | 34.3 | 70.0 | 0.1 | 1.1 |
| Donor_6 3. Aliquot C | 1.6 | 1.2 | 1.5 | 1.0 | 1.1 | 1.2 | 1.0 | 0.9 |
| Donor_6 3. Aliquot D | 1.8 | 1.5 | 9.3 | 1.2 | 592.3 | 1268.1 | 0.1 | 1.1 |
| Donor_6 3. Aliquot E | 1.4 | 1.3 | 6.8 | 1.0 | 732.3 | 1391.2 | 0.2 | 0.9 |
| Donor_6 3. Aliquot F | 3.2 | 1.5 | 14.5 | 0.8 | 10.0 | 23.6 | 1.0 | 1.0 |
| Donor_6 3. Aliquot G | 1.3 | 1.0 | 25.1 | 0.1 | 16.2 | 9.9 | 0.5 | 0.9 |
| Donor_6 3. Aliquot H | 1.3 | 1.0 | 1.6 | 0.3 | 2.9 | 11.6 | 1.0 | 1.0 |
| Donor_6 3. Aliquot I | 1.0 | 1.0 | 1.0 | 1.0 | 1.0 | 1.0 | 1.0 | 1.0 |
| Donor_7 3. Aliquot A | 1.1 | 1.8 | 55.5 | 1.1 | 159.6 | 1205.1 | 0.1 | 1.1 |
| Donor_7 3. Aliquot B | 1.2 | 1.5 | 19.2 | 1.2 | 70.9 | 439.1 | 1.0 | 1.0 |
| Donor_7 3. Aliquot C | 0.8 | 1.0 | 1.2 | 1.0 | 1.2 | 4.4 | 1.0 | 1.1 |
| Donor_7 3. Aliquot D | 1.0 | 1.4 | 19.0 | 1.1 | 197.6 | 2237.2 | 0.2 | 0.9 |
| Donor_7 3. Aliquot E | 1.1 | 1.6 | 33.2 | 1.1 | 125.7 | 1147.4 | 0.2 | 1.0 |
| Donor_7 3. Aliquot F | 2.9 | 1.7 | 4.8 | 0.9 | 4.0 | 32.2 | 1.0 | 1.0 |
| Donor_7 3. Aliquot G | 0.8 | 0.5 | 13.6 | 0.2 | 12.3 | 14.6 | 0.3 | 1.0 |
| Donor_7 3. Aliquot H | 0.8 | 0.6 | 1.2 | 0.2 | 1.1 | 4.9 | 1.0 | 0.9 |
| Donor_7 3. Aliquot I | 1.0 | 1.0 | 1.0 | 1.0 | 1.0 | 1.0 | 1.0 | 1.0 |
| Donor_8 3. Aliquot A | 1.1 | 1.2 | 12.3 | 0.9 | 6.9 | 4.9 | 1.4 | 1.1 |
| Donor_8 3. Aliquot B | 1.1 | 1.2 | 9.7 | 0.9 | 5.5 | 4.6 | 1.4 | 1.1 |
| Donor_8 3. Aliquot C | 1.2 | 1.1 | 14.1 | 0.6 | 8.0 | 12.7 | 0.9 | 0.9 |
| Donor_8 3. Aliquot D | 1.0 | 1.4 | 5.6 | 1.3 | 254.9 | 124.6 | 3.5 | 1.2 |
| Donor_8 3. Aliquot E | 1.3 | 1.4 | 11.4 | 1.0 | 175.9 | 84.3 | 2.9 | 1.1 |
| Donor_8 3. Aliquot F | 1.3 | 1.5 | 33.0 | 0.5 | 24.0 | 28.1 | 2.1 | 1.1 |
| Donor_8 3. Aliquot G | 0.9 | 0.6 | 5.0 | 0.1 | 3.5 | 1.7 | 2.3 | 1.0 |

FIG. 13I.7

| | Lipoprotein (a) | Lymphotactin | MCP-1 | MDC | MIP-1alpha | MIP-1beta | MMP-2 | MMP-3 |
|---|---|---|---|---|---|---|---|---|
| | ug/mL | ng/mL | pg/mL | pg/mL | pg/mL | pg/mL | ng/mL | ng/mL |
| Least Detectable Dose | 3.7 | 0.38 | 52 | 14 | 13 | 38 | 150 | 0.20 |
| RBM Low Plasma Range | 3.0 | | 35 | 162 | 89 | 25 | 183 | |
| RBM High Plasma Range | 858 | 0.57 | 401 | 774 | | 595 | 3070 | 1.8 |
| Donor_8 3. Aliquot H | 0.9 | 1.0 | 20.5 | 0.4 | 12.4 | 6.5 | 1.7 | 1.1 |
| Donor_8 3. Aliquot I | 1.0 | 1.0 | 1.0 | 1.0 | 1.0 | 1.0 | 1.0 | 1.0 |
| Donor_9 3. Aliquot A | 1.3 | 1.3 | 15.7 | 0.9 | 5.2 | 6.7 | 0.9 | 1.2 |
| Donor_9 3. Aliquot B | 0.9 | 1.4 | 8.8 | 1.0 | 7.0 | 6.3 | 1.0 | 1.3 |
| Donor_9 3. Aliquot C | 0.9 | 1.3 | 48.0 | 1.0 | 8.9 | 12.8 | 1.7 | 1.1 |
| Donor_9 3. Aliquot D | 1.2 | 1.2 | 17.7 | 1.1 | 176.3 | 117.4 | 3.2 | 1.3 |
| Donor_9 3. Aliquot E | 1.1 | 1.3 | 27.6 | 1.1 | 123.8 | 96.7 | 2.0 | 1.3 |
| Donor_9 3. Aliquot F | 1.3 | 1.6 | 37.0 | 0.8 | 10.0 | 21.5 | 1.1 | 1.2 |
| Donor_9 3. Aliquot G | 0.8 | 0.4 | 44.8 | 0.1 | 7.6 | 3.4 | 2.3 | 1.1 |
| Donor_9 3. Aliquot H | 0.8 | 0.7 | 7.0 | 0.4 | 1.9 | 3.9 | 1.2 | 1.2 |
| Donor_9 3. Aliquot I | 1.0 | 1.0 | 1.0 | 1.0 | 1.0 | 1.0 | 1.0 | 1.0 |

FIG. 13J.1

| | MMP-9 | Myeloperoxidase | Myoglobin | OSM (Oncostatin M) | PAI-1 | Prostatic Acid Phosphatase | PAPP-A | Prostate Specific Antigen, Free |
|---|---|---|---|---|---|---|---|---|
| | ng/mL | ng/mL | ng/mL | pg/mL | ng/mL | ng/mL | mIU/mL | ng/mL |
| Least Detectable Dose | 37 | 68 | 1.1 | 28 | 0.90 | 0.034 | 0.037 | 0.023 |
| RBM Low Plasma Range | | | 3.6 | PENDING | 10 | 0.058 | | |
| RBM High Plasma Range | 1050 | 1110 | 37 | PENDING | 87 | 0.54 | 0.48 | 1.6 |
| Donor_1 3. Aliquot A | 74 | 2010 | 85 | 312 | 159 | 0.12 | 0.079 | 0.44 |
| Donor_1 3. Aliquot B | 53 | 1590 | 94 | 188 | 171 | 0.11 | 0.082 | 0.44 |
| Donor_1 3. Aliquot C | 30 | 1390 | 101 | 21 | 172 | 0.045 | 0.059 | 0.47 |
| Donor_1 3. Aliquot D | 56 | 2050 | 102 | 143 | 156 | 0.11 | 0.054 | 0.50 |
| Donor_1 3. Aliquot E | 57 | 2330 | 90 | 312 | 152 | 0.12 | 0.062 | 0.47 |
| Donor_1 3. Aliquot F | 33 | 1970 | 95 | 120 | 135 | 0.041 | 0.073 | 0.41 |
| Donor_1 3. Aliquot G | 49 | 1750 | 104 | 422 | 187 | 0.086 | 0.11 | 0.50 |
| Donor_1 3. Aliquot H | 46 | 1740 | 95 | 28 | 184 | 0.078 | 0.087 | 0.43 |
| Donor_1 3. Aliquot I | 38 | 1380 | 89 | 76 | 160 | 0.035 | 0.049 | 0.45 |
| Donor_2 3. Aliquot A | 59 | 3520 | 60 | 603 | 178 | 0.24 | 0.023 | 0.11 |
| Donor_2 3. Aliquot B | 59 | 2910 | 62 | 334 | 190 | 0.24 | 0.032 | 0.11 |
| Donor_2 3. Aliquot C | 42 | 1540 | 61 | 28 | 155 | 0.16 | 0.0049 | 0.072 |
| Donor_2 3. Aliquot D | 60 | 4180 | 58 | 222 | 165 | 0.46 | 0.024 | 0.20 |
| Donor_2 3. Aliquot E | 53 | 3380 | 60 | 188 | 161 | 0.38 | 0.022 | 0.16 |
| Donor_2 3. Aliquot F | 2.2 | 1610 | 63 | 65 | 156 | 0.12 | 0.018 | 0.087 |
| Donor_2 3. Aliquot G | 28 | 3280 | 64 | 765 | 205 | 0.33 | 0.043 | 0.13 |
| Donor_2 3. Aliquot H | 55 | 4200 | 59 | 82 | 177 | 0.14 | 0.023 | 0.083 |
| Donor_2 3. Aliquot I | 51 | 1730 | 57 | 44 | 164 | 0.13 | 0.018 | 0.082 |
| Donor_3 3. Aliquot A | 72 | 2890 | 165 | 301 | 246 | 0.24 | 0.0063 | 0.67 |
| Donor_3 3. Aliquot B | 59 | 2640 | 150 | 329 | 221 | 0.22 | 0.037 | 0.65 |
| Donor_3 3. Aliquot C | 55 | 2210 | 164 | 98 | 199 | 0.16 | 0.037 | 0.72 |
| Donor_3 3. Aliquot D | 91 | 3310 | 159 | 395 | 225 | 0.41 | 0.0049 | 0.71 |
| Donor_3 3. Aliquot E | 74 | 3500 | 172 | 466 | 208 | 0.47 | 0.0063 | 0.73 |
| Donor_3 3. Aliquot F | 54 | 2630 | 152 | 109 | 216 | 0.16 | 0.0063 | 0.65 |
| Donor_3 3. Aliquot G | 45 | 2240 | 162 | 705 | 246 | 0.17 | 0.037 | 0.74 |
| Donor_3 3. Aliquot H | 49 | 2830 | 143 | 165 | 207 | 0.14 | 0.0049 | 0.57 |
| Donor_3 3. Aliquot I | 42 | 2450 | 150 | 98 | 214 | 0.14 | 0.037 | 0.61 |

FIG. 13J.2

| | MMP-9 | Myeloperoxidase | Myoglobin | OSM (Oncostatin M) | PAI-1 | Prostatic Acid Phosphatase | PAPP-A | Prostate Specific Antigen, Free |
|---|---|---|---|---|---|---|---|---|
| | ng/mL | ng/mL | ng/mL | pg/mL | ng/mL | ng/mL | mIU/mL | ng/mL |
| Least Detectable Dose | 37 | 68 | 1.1 | 28 | 0.90 | 0.034 | 0.037 | 0.023 |
| RBM Low Plasma Range | | | 3.6 | PENDING | 10 | 0.058 | | |
| RBM High Plasma Range | 1050 | 1110 | 37 | PENDING | 87 | 0.54 | 0.48 | 1.6 |
| Donor_4_3. Aliquot A | 26 | 2710 | 55 | 28 | 253 | 0.27 | 0.13 | 0.023 |
| Donor_4_3. Aliquot B | 26 | 1940 | 52 | 54 | 236 | 0.38 | 0.14 | 0.023 |
| Donor_4_3. Aliquot C | 4.9 | 3400 | 54 | 28 | 229 | 0.28 | 0.029 | 0.023 |
| Donor_4_3. Aliquot D | 27 | 3920 | 52 | 120 | 216 | 0.42 | 0.13 | 0.045 |
| Donor_4_3. Aliquot E | 49 | 4430 | 53 | 165 | 222 | 0.46 | 0.15 | 0.023 |
| Donor_4_3. Aliquot F | 14 | 4210 | 56 | 28 | 237 | 0.26 | 0.14 | 0.023 |
| Donor_4_3. Aliquot G | 16 | 1950 | 56 | 455 | 203 | 0.56 | 0.16 | 0.023 |
| Donor_4_3. Aliquot H | 26 | 4140 | 55 | 76 | 219 | 0.23 | 0.13 | 0.023 |
| Donor_4_3. Aliquot I | 9.3 | 3360 | 55 | 21 | 235 | 0.26 | 0.12 | 0.023 |
| Donor_5_3. Aliquot A | 46 | 6630 | 92 | 844 | 158 | 0.46 | 0.021 | 0.49 |
| Donor_5_3. Aliquot B | 43 | 6720 | 93 | 834 | 183 | 0.73 | 0.021 | 0.48 |
| Donor_5_3. Aliquot C | 52 | 4350 | 97 | 171 | 144 | 0.28 | 0.0078 | 0.42 |
| Donor_5_3. Aliquot D | 78 | 7840 | 92 | 1850 | 145 | 1.5 | 0.040 | 0.61 |
| Donor_5_3. Aliquot E | 57 | 7880 | 91 | 2320 | 155 | 2.9 | 0.032 | 0.57 |
| Donor_5_3. Aliquot F | 55 | 5110 | 87 | 188 | 167 | 0.27 | 0.018 | 0.39 |
| Donor_5_3. Aliquot G | 28 | 3130 | 96 | 1040 | 181 | 0.52 | 0.029 | 0.45 |
| Donor_5_3. Aliquot H | 60 | 6880 | 87 | 834 | 156 | 0.50 | 0.014 | 0.46 |
| Donor_5_3. Aliquot I | 62 | 4080 | 82 | 211 | 147 | 0.27 | 0.014 | 0.49 |
| Donor_6_3. Aliquot A | 74 | 2300 | 52 | 82 | 192 | 0.13 | 0.0056 | 0.35 |
| Donor_6_3. Aliquot B | 76 | 2240 | 50 | 109 | 174 | 0.24 | 0.037 | 0.40 |
| Donor_6_3. Aliquot C | 33 | 2640 | 52 | 28 | 152 | 0.22 | 0.037 | 0.34 |
| Donor_6_3. Aliquot D | 80 | 1490 | 52 | 65 | 181 | 0.26 | 0.037 | 0.44 |
| Donor_6_3. Aliquot E | 99 | 1800 | 50 | 87 | 153 | 0.38 | 0.0063 | 0.40 |
| Donor_6_3. Aliquot F | 18 | 2660 | 54 | 28 | 173 | 0.15 | 0.037 | 0.31 |
| Donor_6_3. Aliquot G | 46 | 1430 | 54 | 715 | 250 | 0.54 | 0.037 | 0.33 |
| Donor_6_3. Aliquot H | 39 | 2490 | 50 | 65 | 181 | 0.12 | 0.037 | 0.33 |
| Donor_6_3. Aliquot I | 32 | 2270 | 51 | 28 | 176 | 0.17 | 0.037 | 0.35 |

FIG. 13J.3

| | MMP-9 | Myeloperoxidase | Myoglobin | OSM (Oncostatin M) | PAI-1 | Prostatic Acid Phosphatase | PAPP-A | Prostate Specific Antigen, Free |
|---|---|---|---|---|---|---|---|---|
| | ng/mL | ng/mL | ng/mL | pg/mL | ng/mL | ng/mL | mIU/mL | ng/mL |
| Least Detectable Dose | 37 | 68 | 1.1 | 28 | 0.90 | 0.034 | 0.037 | 0.023 |
| RBM Low Plasma Range | | | 3.6 | PENDING | 10 | 0.058 | | |
| RBM High Plasma Range | 1050 | 1110 | 37 | PENDING | 87 | 0.54 | 0.48 | 1.6 |
| Donor_7_3. Aliquot A | 55 | 2070 | 1790 | 194 | 210 | 0.10 | 0.012 | 0.65 |
| Donor_7_3. Aliquot B | 66 | 2710 | >1845 | 109 | 222 | 0.16 | 0.011 | 0.63 |
| Donor_7_3. Aliquot C | 37 | 1920 | >1845 | 28 | 215 | 0.068 | 0.037 | 0.65 |
| Donor_7_3. Aliquot D | 79 | 1780 | >1845 | 21 | 215 | 0.19 | 0.0085 | 0.61 |
| Donor_7_3. Aliquot E | 60 | 2160 | >1845 | 54 | 230 | 0.12 | 0.0049 | 0.66 |
| Donor_7_3. Aliquot F | 2.2 | 2150 | >1845 | 28 | 225 | 0.078 | 0.037 | 0.57 |
| Donor_7_3. Aliquot G | 44 | 1630 | >1845 | 143 | 229 | 0.063 | 0.037 | 0.68 |
| Donor_7_3. Aliquot H | 30 | 1880 | 1780 | 44 | 198 | 0.087 | 0.0092 | 0.64 |
| Donor_7_3. Aliquot I | 4.9 | 1800 | >1845 | 28 | 198 | 0.073 | 0.037 | 0.60 |
| Donor_8_3. Aliquot A | 8.2 | 1510 | 5.2 | 28 | 32 | 0.082 | 0.0070 | 0.023 |
| Donor_8_3. Aliquot B | 26 | 1450 | 3.7 | 28 | 35 | 0.13 | 0.0056 | 0.023 |
| Donor_8_3. Aliquot C | 23 | 3790 | 3.3 | 28 | 31 | 0.16 | 0.037 | 0.023 |
| Donor_8_3. Aliquot D | 94 | 8210 | 3.1 | 345 | 30 | 0.67 | 0.015 | 0.18 |
| Donor_8_3. Aliquot E | 81 | 6150 | 3.2 | 132 | 34 | 0.55 | 0.0092 | 0.13 |
| Donor_8_3. Aliquot F | 31 | 2590 | 3.2 | 28 | 30 | 0.15 | 0.0056 | 0.023 |
| Donor_8_3. Aliquot G | 9.3 | 1220 | 2.9 | 132 | 60 | 0.058 | 0.0092 | 0.023 |
| Donor_8_3. Aliquot H | 42 | 4710 | 3.3 | 54 | 41 | 0.14 | 0.014 | 0.023 |
| Donor_8_3. Aliquot I | 4.9 | 2000 | 3.5 | 28 | 40 | 0.079 | 0.0078 | 0.023 |
| Donor_9_3. Aliquot A | 27 | 1430 | 2.1 | 28 | 45 | 0.052 | 0.0053 | 0.023 |
| Donor_9_3. Aliquot B | 59 | 1150 | 1.9 | 28 | 63 | 0.088 | 0.037 | 0.023 |
| Donor_9_3. Aliquot C | 36 | 2030 | 1.7 | 28 | 71 | 0.074 | 0.037 | 0.023 |
| Donor_9_3. Aliquot D | 111 | 3500 | 1.3 | 96 | 72 | 0.50 | 0.013 | 0.18 |
| Donor_9_3. Aliquot E | 123 | 4800 | 1.9 | 42 | 65 | 0.34 | 0.037 | 0.10 |
| Donor_9_3. Aliquot F | 4.6 | 747 | 2.1 | 28 | 66 | 0.052 | 0.0077 | 0.023 |
| Donor_9_3. Aliquot G | 27 | 1560 | 1.7 | 247 | 97 | 0.040 | 0.010 | 0.023 |
| Donor_9_3. Aliquot H | 45 | 3250 | 2.1 | 42 | 71 | 0.037 | 0.037 | 0.023 |
| Donor_9_3. Aliquot I | 13 | 1070 | 2.1 | 28 | 70 | 0.034 | 0.037 | 0.023 |

FIG. 13.J.4

|  | MMP-9 | Myeloperoxidase | Myoglobin | OSM (Oncostatin M) | PAI-1 | Prostatic Acid Phosphatase | PAPP-A | Prostate Specific Antigen, Free |
|---|---|---|---|---|---|---|---|---|
|  | ng/mL | ng/mL | ng/mL | pg/mL | ng/mL | ng/mL | mIU/mL | ng/mL |
| Least Detectable Dose | 37 | 68 | 1.1 | 28 | 0.90 | 0.034 | 0.037 | 0.023 |
| RBM Low Plasma Range |  |  | 3.6 | PENDING | 10 | 0.058 |  |  |
| RBM High Plasma Range | 1050 | 1110 | 37 | PENDING | 87 | 0.54 | 0.48 | 1.6 |
| *EDTA Plasma* |  |  |  |  |  |  |  |  |
| donor #1 plasma | 211 | 111 | 77 | 1120 | 142 | 0.090 | 0.084 | 0.28 |
| donor #2 plasma | 1340 | 158 | 64 | 28 | 151 | 0.13 | 0.052 | 0.13 |
| donor #3 plasma | 653 | 85 | 182 | 28 | 208 | 0.050 | 0.029 | 0.74 |
| donor #4 plasma | 194 | 322 | 61 | 28 | 218 | 0.65 | 0.26 | 0.023 |
| donor #5 plasma | 236 | 372 | 86 | 28 | 154 | 0.41 | 0.040 | 0.47 |
| donor #6 plasma | 367 | 9.9 | 57 | 151 | 149 | 0.15 | 0.017 | 0.45 |
| donor #7 plasma | 115 | 135 | >1845 | 133 | 242 | 0.078 | 0.066 | 0.82 |
| donor #8 plasma | 30 | 183 | 3.8 | 28 | 39 | 0.13 | 0.010 | 0.024 |
| donor #9 plasma | 3.2 | 68 | 1.4 | 28 | 61 | 0.071 | 0.037 | 0.023 |
|  |  |  |  |  |  |  |  |  |
| *Stimulations indices* |  |  |  |  |  |  |  |  |
| Donor_1 3. Aliquot A | 2.0 | 1.5 | 1.0 | 4.1 | 1.0 | 3.3 | 1.6 | 1.0 |
| Donor_1 3. Aliquot B | 1.4 | 1.2 | 1.1 | 2.5 | 1.1 | 3.2 | 1.7 | 1.0 |
| Donor_1 3. Aliquot C | 0.8 | 1.0 | 1.1 | 0.3 | 1.1 | 1.3 | 1.2 | 1.0 |
| Donor_1 3. Aliquot D | 1.5 | 1.5 | 1.1 | 1.9 | 1.0 | 3.0 | 1.1 | 1.1 |
| Donor_1 3. Aliquot E | 1.5 | 1.7 | 1.0 | 4.1 | 1.0 | 3.5 | 1.3 | 1.1 |
| Donor_1 3. Aliquot F | 0.9 | 1.4 | 1.1 | 1.6 | 0.8 | 1.2 | 1.5 | 0.9 |
| Donor_1 3. Aliquot G | 1.3 | 1.3 | 1.2 | 5.5 | 1.2 | 2.4 | 2.2 | 1.1 |
| Donor_1 3. Aliquot H | 1.2 | 1.3 | 1.1 | 0.4 | 1.2 | 2.2 | 1.8 | 1.0 |
| Donor_1 3. Aliquot I | 1.0 | 1.0 | 1.0 | 1.0 | 1.0 | 1.0 | 1.0 | 1.0 |
|  |  |  |  |  |  |  |  |  |
| Donor_2 3. Aliquot A | 1.1 | 2.0 | 1.0 | 13.8 | 1.1 | 1.8 | 1.3 | 1.3 |
| Donor_2 3. Aliquot B | 1.1 | 1.7 | 1.1 | 7.7 | 1.2 | 1.8 | 1.8 | 1.4 |
| Donor_2 3. Aliquot C | 0.8 | 0.9 | 1.1 | 0.6 | 0.9 | 1.2 | 0.3 | 0.9 |
| Donor_2 3. Aliquot D | 1.2 | 2.4 | 1.0 | 5.1 | 1.0 | 3.4 | 1.3 | 2.5 |
| Donor_2 3. Aliquot E | 1.0 | 2.0 | 1.0 | 4.3 | 1.0 | 2.9 | 1.2 | 1.9 |
| Donor_2 3. Aliquot F | 0.0 | 0.9 | 1.1 | 1.5 | 1.0 | 0.9 | 1.0 | 1.1 |
| Donor_2 3. Aliquot G | 0.5 | 1.9 | 1.1 | 17.5 | 1.3 | 2.4 | 2.4 | 1.6 |

FIG. 13J.5

| | MMP-9 | Myeloperoxidase | Myoglobin | OSM (Oncostatin M) | PAI-1 | Prostatic Acid Phosphatase | PAPP-A | Prostate Specific Antigen, Free |
|---|---|---|---|---|---|---|---|---|
| | ng/mL | ng/mL | ng/mL | pg/mL | ng/mL | ng/mL | mIU/mL | ng/mL |
| Least Detectable Dose | 37 | 68 | 1.1 | 28 | 0.90 | 0.034 | 0.037 | 0.023 |
| RBM Low Plasma Range | | | 3.6 | PENDING | 10 | 0.058 | | |
| RBM High Plasma Range | 1050 | 1110 | 37 | PENDING | 87 | 0.54 | 0.48 | 1.6 |
| Donor_2_3. Aliquot H | 1.1 | 2.4 | 1.0 | 1.9 | 1.1 | 1.0 | 1.3 | 1.0 |
| Donor_2_3. Aliquot I | 1.0 | 1.0 | 1.0 | 1.0 | 1.0 | 1.0 | 1.0 | 1.0 |
| Donor_3_3. Aliquot A | 1.7 | 1.2 | 1.1 | 3.1 | 1.1 | 1.7 | 0.2 | 1.1 |
| Donor_3_3. Aliquot B | 1.4 | 1.1 | 1.0 | 3.4 | 1.0 | 1.6 | 1.0 | 1.1 |
| Donor_3_3. Aliquot C | 1.3 | 0.9 | 1.1 | 1.0 | 0.9 | 1.1 | 1.0 | 1.2 |
| Donor_3_3. Aliquot D | 2.2 | 1.4 | 1.1 | 4.0 | 1.1 | 2.9 | 0.1 | 1.2 |
| Donor_3_3. Aliquot E | 1.8 | 1.4 | 1.1 | 4.7 | 1.0 | 3.3 | 0.2 | 1.2 |
| Donor_3_3. Aliquot F | 1.3 | 1.1 | 1.0 | 1.1 | 1.0 | 1.1 | 0.2 | 1.1 |
| Donor_3_3. Aliquot G | 1.1 | 0.9 | 1.1 | 7.2 | 1.1 | 1.2 | 1.0 | 1.2 |
| Donor_3_3. Aliquot H | 1.2 | 1.2 | 1.0 | 1.7 | 1.0 | 1.0 | 0.1 | 0.9 |
| Donor_3_3. Aliquot I | 1.0 | 1.0 | 1.0 | 1.0 | 1.0 | 1.0 | 1.0 | 1.0 |
| Donor_4_3. Aliquot A | 2.8 | 0.8 | 1.0 | 1.3 | 1.1 | 1.0 | 1.1 | 1.0 |
| Donor_4_3. Aliquot B | 2.8 | 0.6 | 1.0 | 2.6 | 1.0 | 1.4 | 1.2 | 1.0 |
| Donor_4_3. Aliquot C | 0.5 | 1.0 | 1.0 | 1.3 | 1.0 | 1.0 | 0.2 | 1.0 |
| Donor_4_3. Aliquot D | 2.9 | 1.2 | 0.9 | 5.6 | 0.9 | 1.6 | 1.1 | 1.9 |
| Donor_4_3. Aliquot E | 5.3 | 1.3 | 1.0 | 7.7 | 0.9 | 1.7 | 1.3 | 1.0 |
| Donor_4_3. Aliquot F | 1.5 | 1.3 | 1.0 | 1.3 | 1.0 | 1.0 | 1.2 | 1.0 |
| Donor_4_3. Aliquot G | 1.7 | 0.6 | 1.0 | 21.4 | 0.9 | 2.1 | 1.4 | 1.0 |
| Donor_4_3. Aliquot H | 2.8 | 1.2 | 1.0 | 3.6 | 0.9 | 0.9 | 1.1 | 1.0 |
| Donor_4_3. Aliquot I | 1.0 | 1.0 | 1.0 | 1.0 | 1.0 | 1.0 | 1.0 | 1.0 |
| Donor_5_3. Aliquot A | 0.7 | 1.6 | 1.1 | 4.0 | 1.1 | 1.7 | 1.5 | 1.0 |
| Donor_5_3. Aliquot B | 0.7 | 1.6 | 1.1 | 4.0 | 1.2 | 2.7 | 1.5 | 1.0 |
| Donor_5_3. Aliquot C | 0.8 | 1.1 | 1.2 | 0.8 | 1.0 | 1.0 | 0.6 | 0.9 |
| Donor_5_3. Aliquot D | 1.2 | 1.9 | 1.1 | 8.8 | 1.0 | 5.6 | 2.9 | 1.3 |
| Donor_5_3. Aliquot E | 0.9 | 1.9 | 1.1 | 11.0 | 1.1 | 10.7 | 2.3 | 1.2 |
| Donor_5_3. Aliquot F | 0.9 | 1.3 | 1.1 | 0.9 | 1.1 | 1.0 | 1.3 | 0.8 |
| Donor_5_3. Aliquot G | 0.5 | 0.8 | 1.2 | 4.9 | 1.2 | 1.9 | 2.1 | 0.9 |

FIG. 13J.6

| | MMP-9 | Myeloperoxidase | Myoglobin | OSM (Oncostatin M) | PAI-1 | Prostatic Acid Phosphatase | PAPP-A | Prostate Specific Antigen, Free |
|---|---|---|---|---|---|---|---|---|
| | ng/mL | ng/mL | ng/mL | pg/mL | ng/mL | ng/mL | mIU/mL | ng/mL |
| Least Detectable Dose | 37 | 68 | 1.1 | 28 | 0.90 | 0.034 | 0.037 | 0.023 |
| RBM Low Plasma Range | | | 3.6 | PENDING | 10 | 0.058 | 0.48 | 1.6 |
| RBM High Plasma Range | 1050 | 1110 | 37 | PENDING | 87 | 0.54 | | |
| Donor_5_3. Aliquot H | 1.0 | 1.7 | 1.1 | 4.0 | 1.1 | 1.8 | 1.0 | 1.0 |
| Donor_5_3. Aliquot I | 1.0 | 1.0 | 1.0 | 1.0 | 1.0 | 1.0 | 1.0 | 1.0 |
| Donor_6_3. Aliquot A | 2.3 | 1.0 | 1.0 | 2.9 | 1.1 | 0.8 | 0.2 | 1.0 |
| Donor_6_3. Aliquot B | 2.4 | 1.0 | 1.0 | 3.9 | 1.0 | 1.4 | 1.0 | 1.2 |
| Donor_6_3. Aliquot C | 1.0 | 1.2 | 1.0 | 1.0 | 0.9 | 1.3 | 1.0 | 1.0 |
| Donor_6_3. Aliquot D | 2.5 | 0.7 | 1.0 | 2.3 | 1.0 | 1.5 | 0.2 | 1.2 |
| Donor_6_3. Aliquot E | 3.1 | 0.8 | 1.0 | 3.1 | 0.9 | 2.2 | 1.0 | 1.2 |
| Donor_6_3. Aliquot F | 0.6 | 1.2 | 1.1 | 1.0 | 1.0 | 0.9 | 1.0 | 0.9 |
| Donor_6_3. Aliquot G | 1.4 | 0.6 | 1.0 | 25.5 | 1.4 | 3.1 | 1.0 | 0.9 |
| Donor_6_3. Aliquot H | 1.2 | 1.1 | 1.0 | 2.3 | 1.0 | 0.7 | 1.0 | 1.0 |
| Donor_6_3. Aliquot I | 1.0 | 1.0 | 1.0 | 1.0 | 1.0 | 1.0 | 1.0 | 1.0 |
| Donor_7_3. Aliquot A | 11.3 | 1.2 | #VALUE! | 6.9 | 1.1 | 1.4 | 0.3 | 1.1 |
| Donor_7_3. Aliquot B | 13.5 | 1.5 | #VALUE! | 3.9 | 1.0 | 2.1 | 0.3 | 1.0 |
| Donor_7_3. Aliquot C | 7.6 | 1.1 | #VALUE! | 1.0 | 0.8 | 0.9 | 1.0 | 1.1 |
| Donor_7_3. Aliquot D | 16.2 | 1.0 | #VALUE! | 0.8 | 1.1 | 2.6 | 0.2 | 1.0 |
| Donor_7_3. Aliquot E | 12.5 | 1.2 | #VALUE! | 1.9 | 1.2 | 1.6 | 0.1 | 1.1 |
| Donor_7_3. Aliquot F | 0.5 | 1.2 | #VALUE! | 1.0 | 1.1 | 1.1 | 1.0 | 0.9 |
| Donor_7_3. Aliquot G | 9.0 | 0.9 | #VALUE! | 5.1 | 1.2 | 0.9 | 1.0 | 1.1 |
| Donor_7_3. Aliquot H | 6.2 | 1.0 | #VALUE! | 1.6 | 1.0 | 1.2 | 0.2 | 1.1 |
| Donor_7_3. Aliquot I | 1.0 | 1.0 | #VALUE! | 1.0 | 1.0 | 1.0 | 1.0 | 1.0 |
| Donor_8_3. Aliquot A | 1.7 | 0.8 | 1.5 | 1.0 | 0.8 | 1.0 | 0.9 | 1.0 |
| Donor_8_3. Aliquot B | 5.4 | 0.7 | 1.1 | 1.0 | 0.9 | 1.6 | 0.7 | 1.0 |
| Donor_8_3. Aliquot C | 4.7 | 1.9 | 1.0 | 1.0 | 0.8 | 2.0 | 4.8 | 1.0 |
| Donor_8_3. Aliquot D | 19.4 | 4.1 | 0.9 | 12.3 | 0.8 | 8.5 | 2.0 | 8.0 |
| Donor_8_3. Aliquot E | 16.7 | 3.1 | 0.9 | 4.7 | 0.8 | 6.9 | 1.2 | 5.8 |
| Donor_8_3. Aliquot F | 6.4 | 1.3 | 0.9 | 1.0 | 0.8 | 1.9 | 0.7 | 1.0 |
| Donor_8_3. Aliquot G | 1.9 | 0.6 | 0.9 | 4.7 | 1.5 | 0.7 | 1.2 | 1.0 |

FIG. 13J.7

| | MMP-9 | Myeloperoxidase | Myoglobin | OSM (Oncostatin M) | PAI-1 | Prostatic Acid Phosphatase | PAPP-A | Prostate Specific Antigen, Free |
|---|---|---|---|---|---|---|---|---|
| | ng/mL | ng/mL | ng/mL | pg/mL | ng/mL | ng/mL | mIU/mL | ng/mL |
| Least Detectable Dose | 37 | 68 | 1.1 | 28 | 0.90 | 0.034 | 0.037 | 0.023 |
| RBM Low Plasma Range | | | 3.6 | PENDING | 10 | 0.058 | | |
| RBM High Plasma Range | 1050 | 1110 | 37 | PENDING | 87 | 0.54 | 0.48 | 1.6 |
| Donor_8_3. Aliquot H | 8.6 | 2.4 | 1.0 | 1.9 | 1.0 | 1.7 | 1.8 | 1.0 |
| Donor_8_3. Aliquot I | 1.0 | 1.0 | 1.0 | 1.0 | 1.0 | 1.0 | 1.0 | 1.0 |
| Donor_9_3. Aliquot A | 2.1 | 1.3 | 1.0 | 1.0 | 0.6 | 1.5 | 0.1 | 1.0 |
| Donor_9_3. Aliquot B | 4.6 | 1.1 | 0.9 | 1.0 | 0.9 | 2.6 | 1.0 | 1.0 |
| Donor_9_3. Aliquot C | 2.8 | 1.9 | 0.8 | 1.0 | 1.0 | 2.2 | 1.0 | 1.0 |
| Donor_9_3. Aliquot D | 8.7 | 3.3 | 0.7 | 3.4 | 1.0 | 14.6 | 0.4 | 7.7 |
| Donor_9_3. Aliquot E | 9.6 | 4.5 | 0.9 | 1.5 | 0.9 | 9.8 | 1.0 | 4.5 |
| Donor_9_3. Aliquot F | 0.4 | 0.7 | 1.0 | 1.0 | 0.9 | 1.5 | 0.2 | 1.0 |
| Donor_9_3. Aliquot G | 2.1 | 1.5 | 0.8 | 8.8 | 1.4 | 1.2 | 0.3 | 1.0 |
| Donor_9_3. Aliquot H | 3.5 | 3.0 | 1.0 | 1.5 | 1.0 | 1.1 | 1.0 | 1.0 |
| Donor_9_3. Aliquot I | 1.0 | 1.0 | 1.0 | 1.0 | 1.0 | 1.0 | 1.0 | 1.0 |

FIG. 13K.1

| | RANTES | Serum Amyloid P | Stem Cell Factor | SGOT | SHBG | Thyroxine Binding Globulin | Tissue Factor | TGF-alpha |
|---|---|---|---|---|---|---|---|---|
| | ng/mL | ug/mL | pg/mL | ug/mL | nmol/L | ug/mL | ng/mL | pg/mL |
| Least Detectable Dose | 0.048 | 0.058 | 56 | 3.7 | 1.3 | 0.34 | 0.84 | 1.8 |
| RBM Low Plasma Range | 2.6 | 15 | | 3.9 | 12 | 40 | | Pending |
| RBM High Plasma Range | 83 | 50 | 281 | 28 | 106 | 104 | 2.4 | Pending |
| Donor_1_3. Aliquot A | 16 | 26 | 757 | 3.7 | 18 | 27 | 3.7 | 22 |
| Donor_1_3. Aliquot B | 25 | 28 | 587 | 3.7 | 19 | 31 | 2.7 | 15 |
| Donor_1_3. Aliquot C | 22 | 28 | 599 | 3.7 | 19 | 29 | 0.91 | 1.8 |
| Donor_1_3. Aliquot D | 18 | 33 | 657 | 3.7 | 19 | 31 | 3.3 | 9.7 |
| Donor_1_3. Aliquot E | 14 | 29 | 666 | 3.7 | 19 | 29 | 3.0 | 13 |
| Donor_1_3. Aliquot F | 14 | 29 | 430 | 3.7 | 18 | 29 | 2.0 | 3.8 |
| Donor_1_3. Aliquot G | 24 | 26 | 645 | 3.7 | 19 | 29 | 2.0 | 24 |
| Donor_1_3. Aliquot H | 26 | 29 | 508 | 3.7 | 19 | 26 | 1.8 | 1.5 |
| Donor_1_3. Aliquot I | 19 | 29 | 508 | 3.7 | 18 | 28 | 1.6 | 1.6 |
| Donor_2_3. Aliquot A | 20 | 22 | 1350 | 3.7 | 34 | 36 | 1.7 | 56 |
| Donor_2_3. Aliquot B | 24 | 26 | 1530 | 3.7 | 35 | 37 | 1.9 | 44 |
| Donor_2_3. Aliquot C | 15 | 23 | 607 | 3.7 | 36 | 36 | 0.84 | 7.5 |
| Donor_2_3. Aliquot D | 13 | 24 | 1640 | 3.7 | 35 | 38 | 7.1 | 46 |
| Donor_2_3. Aliquot E | 13 | 26 | 1670 | 3.7 | 34 | 37 | 3.5 | 43 |
| Donor_2_3. Aliquot F | 13 | 23 | 582 | 3.7 | 36 | 39 | 0.47 | 5.6 |
| Donor_2_3. Aliquot G | 21 | 22 | 1760 | 3.7 | 34 | 38 | 2.3 | 48 |
| Donor_2_3. Aliquot H | 13 | 27 | 595 | 3.7 | 36 | 34 | 0.84 | 20 |
| Donor_2_3. Aliquot I | 12 | 23 | 500 | 3.7 | 33 | 37 | 0.70 | 9.5 |
| Donor_3_3. Aliquot A | 16 | 14 | 666 | 3.7 | 42 | 56 | 1.9 | 20 |
| Donor_3_3. Aliquot B | 21 | 14 | 434 | 3.7 | 40 | 50 | 1.8 | 22 |
| Donor_3_3. Aliquot C | 17 | 17 | 213 | 3.7 | 43 | 57 | 0.15 | 5.6 |
| Donor_3_3. Aliquot D | 16 | 15 | 882 | 3.7 | 39 | 52 | 5.4 | 18 |
| Donor_3_3. Aliquot E | 21 | 15 | 1020 | 3.7 | 42 | 52 | 4.9 | 16 |
| Donor_3_3. Aliquot F | 13 | 16 | 202 | 3.7 | 40 | 53 | 1.5 | 4.4 |
| Donor_3_3. Aliquot G | 26 | 15 | 183 | 3.7 | 41 | 54 | 0.84 | 15 |
| Donor_3_3. Aliquot H | 13 | 16 | 113 | 3.7 | 38 | 49 | 0.56 | 2.1 |
| Donor_3_3. Aliquot I | 14 | 16 | 138 | 3.7 | 36 | 51 | 0.99 | 0.63 |

FIG. 13K.2

| | RANTES | Serum Amyloid P | Stem Cell Factor | SGOT | SHBG | Thyroxine Binding Globulin | Tissue Factor | TGF-alpha |
|---|---|---|---|---|---|---|---|---|
| | ng/mL | ug/mL | pg/mL | ug/mL | nmol/L | ug/mL | ng/mL | pg/mL |
| Least Detectable Dose | 0.048 | 0.058 | 56 | 3.7 | 1.3 | 0.34 | 0.84 | 1.8 |
| RBM Low Plasma Range | 2.6 | 15 | | 3.9 | 12 | 40 | | Pending |
| RBM High Plasma Range | 83 | 50 | 281 | 28 | 106 | 104 | 2.4 | Pending |
| Donor_4_3, Aliquot A | 4.4 | 8.7 | 426 | 3.7 | 54 | 38 | 1.5 | 15 |
| Donor_4_3, Aliquot B | 4.6 | 9.6 | 475 | 3.7 | 53 | 35 | 0.87 | 22 |
| Donor_4_3, Aliquot C | 2.7 | 9.9 | 377 | 3.7 | 54 | 35 | 0.84 | 6.4 |
| Donor_4_3, Aliquot D | 3.4 | 10 | 957 | 3.7 | 55 | 34 | 5.4 | 19 |
| Donor_4_3, Aliquot E | 2.6 | 10 | 1010 | 3.7 | 50 | 35 | 3.4 | 16 |
| Donor_4_3, Aliquot F | 2.5 | 12 | 459 | 3.7 | 58 | 36 | 1.5 | 4.6 |
| Donor_4_3, Aliquot G | 5.9 | 8.8 | 459 | 3.7 | 57 | 36 | 0.84 | 16 |
| Donor_4_3, Aliquot H | 2.5 | 11 | 405 | 3.7 | 53 | 32 | 0.99 | 3.5 |
| Donor_4_3, Aliquot I | 3.2 | 10 | 352 | 3.7 | 51 | 35 | 0.84 | 3.8 |
| Donor_5_3, Aliquot A | 17 | 43 | 936 | 3.7 | 33 | 47 | 0.87 | 22 |
| Donor_5_3, Aliquot B | 13 | 41 | 815 | 3.7 | 31 | 47 | 0.87 | 20 |
| Donor_5_3, Aliquot C | 11 | 38 | 320 | 3.7 | 35 | 42 | 0.84 | 7.3 |
| Donor_5_3, Aliquot D | 14 | 46 | 965 | 3.7 | 31 | 45 | 6.3 | 17 |
| Donor_5_3, Aliquot E | 14 | 45 | 1290 | 3.7 | 31 | 46 | 4.4 | 23 |
| Donor_5_3, Aliquot F | 9.5 | 38 | 288 | 0.62 | 31 | 43 | 0.15 | 7.1 |
| Donor_5_3, Aliquot G | 16 | 40 | 541 | 3.7 | 32 | 44 | 0.84 | 25 |
| Donor_5_3, Aliquot H | 12 | 43 | 292 | 3.7 | 29 | 40 | 0.56 | 7.0 |
| Donor_5_3, Aliquot I | 9.0 | 41 | 348 | 3.7 | 29 | 42 | 0.84 | 7.6 |
| Donor_6_3, Aliquot A | 35 | 25 | 217 | 3.7 | 18 | 29 | 0.84 | 13 |
| Donor_6_3, Aliquot B | 34 | 27 | 187 | 3.7 | 19 | 30 | 0.84 | 15 |
| Donor_6_3, Aliquot C | 23 | 24 | 99 | 3.7 | 19 | 27 | 0.84 | 1.2 |
| Donor_6_3, Aliquot D | 35 | 31 | 272 | 3.7 | 18 | 29 | 3.0 | 12 |
| Donor_6_3, Aliquot E | 23 | 26 | 316 | 3.7 | 17 | 28 | 5.1 | 16 |
| Donor_6_3, Aliquot F | 20 | 26 | 99 | 3.7 | 19 | 30 | 0.84 | 1.2 |
| Donor_6_3, Aliquot G | 47 | 22 | 164 | 3.7 | 18 | 30 | 0.84 | 11 |
| Donor_6_3, Aliquot H | 22 | 23 | 69 | 3.7 | 19 | 27 | 0.84 | 3.8 |
| Donor_6_3, Aliquot I | 23 | 25 | 92 | 3.7 | 18 | 28 | 0.84 | 1.5 |

FIG. 13K.3

| | RANTES | Serum Amyloid P | Stem Cell Factor | SGOT | SHBG | Thyroxine Binding Globulin | Tissue Factor | TGF-alpha |
|---|---|---|---|---|---|---|---|---|
| | ng/mL | ug/mL | pg/mL | ug/mL | nmol/L | ug/mL | ng/mL | pg/mL |
| Least Detectable Dose | 0.048 | 0.058 | 56 | 3.7 | 1.3 | 0.34 | 0.84 | 1.8 |
| RBM Low Plasma Range | 2.6 | 15 | | 3.9 | 12 | 40 | | Pending |
| RBM High Plasma Range | 83 | 50 | 281 | 28 | 106 | 104 | 2.4 | Pending |
| Donor_7 3. Aliquot A | 17 | 31 | 998 | 8.2 | 9.5 | 25 | 2.4 | 9.2 |
| Donor_7 3. Aliquot B | 17 | 35 | 607 | 12 | 11 | 27 | 1.9 | 4.8 |
| Donor_7 3. Aliquot C | 25 | 33 | 113 | 8.1 | 12 | 25 | 0.84 | 1.8 |
| Donor_7 3. Aliquot D | 19 | 30 | 790 | 11 | 10 | 25 | 4.1 | 4.6 |
| Donor_7 3. Aliquot E | 15 | 29 | 707 | 13 | 8.8 | 19 | 2.4 | 3.4 |
| Donor_7 3. Aliquot F | 9.7 | 35 | 127 | 11 | 10 | 26 | 0.15 | 1.8 |
| Donor_7 3. Aliquot G | 23 | 29 | 160 | 4.3 | 9.4 | 23 | 0.84 | 4.7 |
| Donor_7 3. Aliquot H | 12 | 31 | 72 | 16 | 9.7 | 22 | 0.84 | 1.8 |
| Donor_7 3. Aliquot I | 12 | 34 | 127 | 11 | 9.9 | 25 | 0.15 | 1.8 |
| Donor_8 3. Aliquot A | 12 | 5.7 | 92 | 3.7 | 65 | 31 | 1.2 | 2.7 |
| Donor_8 3. Aliquot B | 16 | 6.4 | 46 | 3.7 | 66 | 30 | 0.84 | 3.4 |
| Donor_8 3. Aliquot C | 17 | 5.4 | 69 | 3.7 | 61 | 29 | 0.84 | 2.7 |
| Donor_8 3. Aliquot D | 12 | 5.7 | 106 | 3.7 | 60 | 28 | 13 | 6.2 |
| Donor_8 3. Aliquot E | 14 | 5.9 | 72 | 3.7 | 62 | 29 | 12 | 5.5 |
| Donor_8 3. Aliquot F | 6.9 | 6.7 | 40 | 3.7 | 67 | 31 | 0.47 | 1.9 |
| Donor_8 3. Aliquot G | 19 | 5.2 | 99 | 3.7 | 57 | 27 | 0.84 | 4.2 |
| Donor_8 3. Aliquot H | 15 | 6.4 | 89 | 3.7 | 69 | 29 | 0.65 | 2.8 |
| Donor_8 3. Aliquot I | 17 | 6.5 | 56 | 3.7 | 64 | 31 | 0.65 | 1.8 |
| Donor_9 3. Aliquot A | 16 | Pending | 170 | 3.7 | Pending | Pending | 1.2 | 19 |
| Donor_9 3. Aliquot B | 21 | Pending | 229 | 3.7 | Pending | Pending | 2.0 | 16 |
| Donor_9 3. Aliquot C | 23 | Pending | 229 | 3.7 | Pending | Pending | 0.66 | 18 |
| Donor_9 3. Aliquot D | 21 | Pending | 307 | 3.7 | Pending | Pending | 15 | 18 |
| Donor_9 3. Aliquot E | 13 | Pending | 272 | 3.7 | Pending | Pending | 8.6 | 20 |
| Donor_9 3. Aliquot F | 9.1 | Pending | 137 | 3.7 | Pending | Pending | 2.1 | 12 |
| Donor_9 3. Aliquot G | 30 | Pending | 528 | 3.7 | Pending | Pending | 1.8 | 20 |
| Donor_9 3. Aliquot H | 21 | Pending | 97 | 3.7 | Pending | Pending | 1.5 | 12 |
| Donor_9 3. Aliquot I | 21 | Pending | 174 | 3.7 | Pending | Pending | 0.53 | 8.5 |

FIG. 13K.4

| | RANTES | Serum Amyloid P | Stem Cell Factor | SGOT | SHBG | Thyroxine Binding Globulin | Tissue Factor | TGF-alpha |
|---|---|---|---|---|---|---|---|---|
| | ng/mL | ug/mL | pg/mL | ug/mL | nmol/L | ug/mL | ng/mL | pg/mL |
| Least Detectable Dose | 0.048 | 0.058 | 56 | 3.7 | 1.3 | 0.34 | 0.84 | 1.8 |
| RBM Low Plasma Range | 2.6 | 15 | | 3.9 | 12 | 40 | | Pending |
| RBM High Plasma Range | 83 | 50 | 281 | 28 | 106 | 104 | 2.4 | Pending |
| EDTA Plasma | | | | | | | | |
| donor #1 plasma | 9.4 | Pending | 351 | 40 | Pending | Pending | 2.9 | 1.8 |
| donor #2 plasma | 3.4 | Pending | 492 | 45 | Pending | Pending | 1.1 | 1.2 |
| donor #3 plasma | 6.4 | Pending | 161 | 54 | Pending | Pending | 1.9 | 1.8 |
| donor #4 plasma | 1.3 | Pending | 368 | 32 | Pending | Pending | 2.0 | 1.8 |
| donor #5 plasma | 8.7 | Pending | 550 | 70 | Pending | Pending | 2.1 | 1.8 |
| donor #6 plasma | 14 | Pending | 62 | 35 | Pending | Pending | 0.95 | 1.8 |
| donor #7 plasma | 12 | Pending | 212 | 46 | Pending | Pending | 1.9 | 1.8 |
| donor #8 plasma | 5.3 | Pending | 161 | 3.7 | Pending | Pending | 1.0 | 1.8 |
| donor #9 plasma | 1.2 | Pending | 203 | 3.7 | Pending | Pending | 0.74 | 4.4 |
| | | | | | | | | |
| Stimulations Indices | | | | | | | | |
| Donor_1 3. Aliquot A | 0.9 | 0.9 | 1.5 | 1.0 | 1.0 | 1.0 | 2.3 | 14.2 |
| Donor_1 3. Aliquot B | 1.3 | 1.0 | 1.2 | 1.0 | 1.0 | 1.1 | 1.7 | 9.4 |
| Donor_1 3. Aliquot C | 1.2 | 1.0 | 1.2 | 1.0 | 1.0 | 1.1 | 0.6 | 1.2 |
| Donor_1 3. Aliquot D | 1.0 | 1.1 | 1.3 | 1.0 | 1.0 | 1.1 | 2.1 | 6.2 |
| Donor_1 3. Aliquot E | 0.8 | 1.0 | 1.3 | 1.0 | 1.0 | 1.0 | 1.9 | 8.0 |
| Donor_1 3. Aliquot F | 0.7 | 1.0 | 0.8 | 1.0 | 1.0 | 1.1 | 1.3 | 2.4 |
| Donor_1 3. Aliquot G | 1.3 | 0.9 | 1.3 | 1.0 | 1.0 | 1.1 | 1.2 | 15.6 |
| Donor_1 3. Aliquot H | 1.4 | 1.0 | 1.2 | 1.0 | 1.0 | 0.9 | 1.1 | 0.9 |
| Donor_1 3. Aliquot I | 1.0 | 1.0 | 1.0 | 1.0 | 1.0 | 1.0 | 1.0 | 1.0 |
| | | | | | | | | |
| Donor_2 3. Aliquot A | 1.8 | 1.0 | 2.7 | 1.0 | 1.0 | 1.0 | 2.4 | 5.9 |
| Donor_2 3. Aliquot B | 2.1 | 1.2 | 3.1 | 1.0 | 1.0 | 1.1 | 2.7 | 4.6 |
| Donor_2 3. Aliquot C | 1.3 | 1.0 | 1.2 | 1.0 | 1.0 | 1.1 | 1.2 | 0.8 |
| Donor_2 3. Aliquot D | 1.1 | 1.1 | 3.3 | 1.0 | 1.1 | 1.1 | 10.2 | 4.9 |
| Donor_2 3. Aliquot E | 1.1 | 1.1 | 3.3 | 1.0 | 1.1 | 1.0 | 5.0 | 4.5 |
| Donor_2 3. Aliquot F | 1.1 | 1.0 | 1.2 | 1.0 | 1.1 | 1.0 | 0.7 | 0.6 |
| Donor_2 3. Aliquot G | 1.8 | 1.0 | 3.5 | 1.0 | 1.0 | 1.0 | 3.3 | 5.0 |

FIG. 13K.5

| | RANTES | Serum Amyloid P | Stem Cell Factor | SGOT | SHBG | Thyroxine Binding Globulin | Tissue Factor | TGF-alpha |
|---|---|---|---|---|---|---|---|---|
| | ng/mL | ug/mL | pg/mL | ug/mL | nmol/L | ug/mL | ng/mL | pg/mL |
| Least Detectable Dose | 0.048 | 0.058 | 56 | 3.7 | 1.3 | 0.34 | 0.84 | 1.8 |
| RBM Low Plasma Range | 2.6 | 15 | | 3.9 | 12 | 40 | | Pending |
| RBM High Plasma Range | 83 | 50 | 281 | 28 | 106 | 104 | 2.4 | Pending |
| Donor_2 3. Aliquot H | 1.1 | 1.2 | 1.2 | 1.0 | 1.1 | 0.9 | 1.2 | 2.0 |
| Donor_2 3. Aliquot I | 1.0 | 1.0 | 1.0 | 1.0 | 1.0 | 1.0 | 1.0 | 1.0 |
| Donor_3 3. Aliquot A | 1.2 | 0.9 | 4.8 | 1.0 | 1.2 | 1.1 | 1.9 | 32.1 |
| Donor_3 3. Aliquot B | 1.5 | 0.9 | 3.1 | 1.0 | 1.1 | 1.0 | 1.8 | 34.0 |
| Donor_3 3. Aliquot C | 1.2 | 1.0 | 1.5 | 1.0 | 1.2 | 1.1 | 0.1 | 8.8 |
| Donor_3 3. Aliquot D | 1.1 | 1.0 | 6.4 | 1.0 | 1.1 | 1.0 | 5.4 | 28.9 |
| Donor_3 3. Aliquot E | 1.5 | 0.9 | 7.4 | 1.0 | 1.2 | 1.0 | 5.0 | 25.1 |
| Donor_3 3. Aliquot F | 0.9 | 1.0 | 1.5 | 1.0 | 1.1 | 1.0 | 1.5 | 6.9 |
| Donor_3 3. Aliquot G | 1.9 | 0.9 | 1.3 | 1.0 | 1.1 | 1.0 | 0.9 | 24.3 |
| Donor_3 3. Aliquot H | 1.0 | 1.0 | 0.8 | 1.0 | 1.0 | 1.0 | 0.6 | 3.3 |
| Donor_3 3. Aliquot I | 1.0 | 1.0 | 1.0 | 1.0 | 1.0 | 1.0 | 1.0 | 1.0 |
| Donor_4 3. Aliquot A | 1.4 | 0.8 | 1.2 | 1.0 | 1.1 | 1.1 | 1.7 | 3.9 |
| Donor_4 3. Aliquot B | 1.5 | 0.9 | 1.3 | 1.0 | 1.0 | 1.0 | 1.0 | 5.9 |
| Donor_4 3. Aliquot C | 0.9 | 1.0 | 1.1 | 1.0 | 1.0 | 1.0 | 1.0 | 1.7 |
| Donor_4 3. Aliquot D | 1.1 | 1.0 | 2.7 | 1.0 | 1.0 | 1.0 | 6.5 | 4.9 |
| Donor_4 3. Aliquot E | 0.8 | 1.0 | 2.9 | 1.0 | 1.0 | 1.0 | 4.1 | 4.2 |
| Donor_4 3. Aliquot F | 0.8 | 1.2 | 1.3 | 1.0 | 1.1 | 1.0 | 1.8 | 1.2 |
| Donor_4 3. Aliquot G | 1.9 | 0.9 | 1.3 | 1.0 | 1.1 | 1.0 | 1.0 | 4.2 |
| Donor_4 3. Aliquot H | 0.8 | 1.1 | 1.2 | 1.0 | 1.1 | 0.9 | 1.2 | 0.9 |
| Donor_4 3. Aliquot I | 1.0 | 1.0 | 1.0 | 1.0 | 1.0 | 1.0 | 1.0 | 1.0 |
| Donor_5 3. Aliquot A | 1.8 | 1.0 | 2.7 | 1.0 | 1.1 | 1.1 | 1.0 | 2.8 |
| Donor_5 3. Aliquot B | 1.5 | 1.0 | 2.3 | 1.0 | 1.1 | 1.1 | 1.0 | 2.7 |
| Donor_5 3. Aliquot C | 1.2 | 0.9 | 0.9 | 1.0 | 1.2 | 1.1 | 1.0 | 1.0 |
| Donor_5 3. Aliquot D | 1.6 | 1.1 | 2.8 | 1.0 | 1.0 | 1.1 | 7.5 | 2.2 |
| Donor_5 3. Aliquot E | 1.5 | 1.1 | 3.7 | 1.0 | 1.1 | 1.1 | 5.2 | 3.1 |
| Donor_5 3. Aliquot F | 1.1 | 0.9 | 0.8 | 0.2 | 1.1 | 1.0 | 0.2 | 0.9 |
| Donor_5 3. Aliquot G | 1.7 | 1.0 | 1.6 | 1.0 | 1.1 | 1.0 | 1.0 | 3.3 |

FIG. 13K.6

| | RANTES | Serum Amyloid P | Stem Cell Factor | SGOT | SHBG | Thyroxine Binding Globulin | Tissue Factor | TGF-alpha |
|---|---|---|---|---|---|---|---|---|
| | ng/mL | ug/mL | pg/mL | ug/mL | nmol/L | ug/mL | ng/mL | pg/mL |
| Least Detectable Dose | 0.048 | 0.058 | 56 | 3.7 | 1.3 | 0.34 | 0.84 | 1.8 |
| RBM Low Plasma Range | 2.6 | 15 | | 3.9 | 12 | 40 | | Pending |
| RBM High Plasma Range | 83 | 50 | 281 | 28 | 106 | 104 | 2.4 | Pending |
| Donor_5 3. Aliquot H | 1.4 | 1.1 | 0.8 | 1.0 | 1.0 | 1.0 | 0.7 | 0.9 |
| Donor_5 3. Aliquot I | 1.0 | 1.0 | 1.0 | 1.0 | 1.0 | 1.0 | 1.0 | 1.0 |
| Donor_6 3. Aliquot A | 1.5 | 1.0 | 2.4 | 1.0 | 1.0 | 1.1 | 1.0 | 8.9 |
| Donor_6 3. Aliquot B | 1.5 | 1.1 | 2.0 | 1.0 | 1.1 | 1.1 | 1.0 | 10.4 |
| Donor_6 3. Aliquot C | 1.0 | 0.9 | 1.1 | 1.0 | 1.0 | 1.0 | 1.0 | 0.8 |
| Donor_6 3. Aliquot D | 1.5 | 1.2 | 3.0 | 1.0 | 1.0 | 1.1 | 3.6 | 8.2 |
| Donor_6 3. Aliquot E | 1.0 | 1.0 | 3.4 | 1.0 | 1.0 | 1.1 | 6.0 | 10.7 |
| Donor_6 3. Aliquot F | 0.9 | 1.0 | 1.1 | 1.0 | 1.1 | 1.1 | 1.0 | 0.8 |
| Donor_6 3. Aliquot G | 2.1 | 0.9 | 1.8 | 1.0 | 1.0 | 1.1 | 1.0 | 7.4 |
| Donor_6 3. Aliquot H | 1.0 | 0.9 | 0.7 | 1.0 | 1.1 | 1.1 | 1.0 | 2.6 |
| Donor_6 3. Aliquot I | 1.0 | 1.0 | 1.0 | 1.0 | 1.0 | 1.0 | 1.0 | 1.0 |
| Donor_7 3. Aliquot A | 1.4 | 0.9 | 7.9 | 0.8 | 1.0 | 1.0 | 16.1 | 5.1 |
| Donor_7 3. Aliquot B | 1.4 | 1.0 | 4.8 | 1.1 | 1.1 | 1.1 | 13.0 | 2.7 |
| Donor_7 3. Aliquot C | 2.0 | 1.0 | 0.9 | 0.8 | 1.2 | 1.0 | 5.7 | 1.0 |
| Donor_7 3. Aliquot D | 1.6 | 0.9 | 6.2 | 1.0 | 1.0 | 1.0 | 28.0 | 2.6 |
| Donor_7 3. Aliquot E | 1.2 | 0.8 | 5.6 | 1.3 | 0.9 | 0.8 | 16.6 | 1.9 |
| Donor_7 3. Aliquot F | 0.8 | 1.0 | 1.0 | 1.0 | 1.0 | 1.0 | 1.0 | 1.0 |
| Donor_7 3. Aliquot G | 1.9 | 0.8 | 1.3 | 0.4 | 0.9 | 0.9 | 5.7 | 2.6 |
| Donor_7 3. Aliquot H | 1.0 | 0.9 | 0.6 | 1.6 | 1.0 | 0.9 | 5.7 | 1.0 |
| Donor_7 3. Aliquot I | 1.0 | 1.0 | 1.0 | 1.0 | 1.0 | 1.0 | 1.0 | 1.0 |
| Donor_8 3. Aliquot A | 0.7 | 0.9 | 1.7 | 1.0 | 1.0 | 1.0 | 1.9 | 1.5 |
| Donor_8 3. Aliquot B | 1.0 | 1.0 | 0.8 | 1.0 | 1.0 | 1.0 | 1.3 | 1.9 |
| Donor_8 3. Aliquot C | 1.0 | 0.8 | 1.2 | 1.0 | 0.9 | 1.0 | 1.3 | 1.5 |
| Donor_8 3. Aliquot D | 0.7 | 0.9 | 1.9 | 1.0 | 1.0 | 0.9 | 19.1 | 3.5 |
| Donor_8 3. Aliquot E | 0.8 | 0.9 | 1.3 | 1.0 | 1.0 | 0.9 | 17.7 | 3.1 |
| Donor_8 3. Aliquot F | 0.4 | 1.0 | 0.7 | 1.0 | 1.0 | 1.0 | 0.7 | 1.1 |
| Donor_8 3. Aliquot G | 1.2 | 0.8 | 1.8 | 1.0 | 0.9 | 0.9 | 1.3 | 2.3 |

FIG. 13K.7

| | RANTES | Serum Amyloid P | Stem Cell Factor | SGOT | SHBG | Thyroxine Binding Globulin | Tissue Factor | TGF-alpha |
|---|---|---|---|---|---|---|---|---|
| | ng/mL | ug/mL | pg/mL | ug/mL | nmol/L | ug/mL | ng/mL | pg/mL |
| Least Detectable Dose | 0.048 | 0.058 | 56 | 3.7 | 1.3 | 0.34 | 0.84 | 1.8 |
| | | | | | | | | |
| RBM Low Plasma Range | 2.6 | 15 | | 3.9 | 12 | 40 | | Pending |
| RBM High Plasma Range | 83 | 50 | 281 | 28 | 106 | 104 | 2.4 | Pending |
| Donor_8 3. Aliquot H | 0.9 | 1.0 | 1.6 | 1.0 | 1.1 | 1.0 | 1.0 | 1.5 |
| Donor_8 3. Aliquot I | 1.0 | 1.0 | 1.0 | 1.0 | 1.0 | 1.0 | 1.0 | 1.0 |
| | | | | | | | | |
| Donor_9 3. Aliquot A | 0.8 | #VALUE! | 1.0 | 1.0 | #VALUE! | #VALUE! | 2.3 | 2.2 |
| Donor_9 3. Aliquot B | 1.0 | #VALUE! | 1.3 | 1.0 | #VALUE! | #VALUE! | 3.7 | 1.8 |
| Donor_9 3. Aliquot C | 1.1 | #VALUE! | 1.3 | 1.0 | #VALUE! | #VALUE! | 1.2 | 2.1 |
| Donor_9 3. Aliquot D | 1.0 | #VALUE! | 1.8 | 1.0 | #VALUE! | #VALUE! | 27.6 | 2.1 |
| Donor_9 3. Aliquot E | 0.6 | #VALUE! | 1.6 | 1.0 | #VALUE! | #VALUE! | 16.2 | 2.4 |
| Donor_9 3. Aliquot F | 0.4 | #VALUE! | 0.8 | 1.0 | #VALUE! | #VALUE! | 4.0 | 1.4 |
| Donor_9 3. Aliquot G | 1.4 | #VALUE! | 3.0 | 1.0 | #VALUE! | #VALUE! | 3.4 | 2.4 |
| Donor_9 3. Aliquot H | 1.0 | #VALUE! | 0.6 | 1.0 | #VALUE! | #VALUE! | 2.9 | 1.5 |
| Donor_9 3. Aliquot I | 1.0 | #VALUE! | 1.0 | 1.0 | #VALUE! | #VALUE! | 1.0 | 1.0 |

FIG. 13L.1

| | TIMP-1 | TNF RII | TNF-alpha | TNF-beta | Thrombo poietin | Thyroid Stimulating Hormone | Thrombospondin-1 | VCAM-1 |
|---|---|---|---|---|---|---|---|---|
| | ng/mL | ng/mL | pg/mL | pg/mL | ng/mL | uIU/mL | ng/mL | ng/mL |
| Least Detectable Dose | 8.4 | 0.13 | 4.0 | 46 | 3.2 | 0.028 | <25 | 2.6 |
| RBM Low Plasma Range | 59 | 3.1 | | | | 0.18 | Pending | 284 |
| RBM High Plasma Range | 192 | 79 | 27 | 120 | 6.2 | 3.7 | Pending | 1310 |
| Donor_1 3. Aliquot A | 521 | 29 | 236 | 7.9 | 1.9 | 17 | 15200 | 1350 |
| Donor_1 3. Aliquot B | 615 | 31 | 75 | 46 | 1.5 | 16 | 21600 | 1440 |
| Donor_1 3. Aliquot C | 611 | 28 | 19 | 46 | 3.2 | 18 | 17000 | 1350 |
| Donor_1 3. Aliquot D | 620 | 30 | 300 | 46 | 1.9 | 17 | 15600 | 1420 |
| Donor_1 3. Aliquot E | 549 | 29 | 88 | 46 | 1.9 | 17 | 13100 | 1320 |
| Donor_1 3. Aliquot F | 553 | 27 | 35 | 46 | 3.2 | 17 | 12500 | 1310 |
| Donor_1 3. Aliquot G | 645 | 30 | 24 | 46 | 1.3 | 17 | 11800 | 1450 |
| Donor_1 3. Aliquot H | 580 | 27 | 19 | 46 | 0.86 | 17 | 24900 | 1320 |
| Donor_1 3. Aliquot I | 495 | 24 | 25 | 46 | 0.69 | 17 | 16200 | 1350 |
| Donor_2 3. Aliquot A | 354 | 47 | 212 | 4.6 | 2.7 | 10 | 19800 | 1090 |
| Donor_2 3. Aliquot B | 391 | 49 | 94 | 6.0 | 3.2 | 10 | 21600 | 1190 |
| Donor_2 3. Aliquot C | 303 | 41 | 12 | 46 | 3.2 | 9.9 | 12200 | 1160 |
| Donor_2 3. Aliquot D | 359 | 45 | 2700 | 6.0 | 2.4 | 12 | 13600 | 1070 |
| Donor_2 3. Aliquot E | 376 | 48 | 1690 | 3.2 | 2.7 | 11 | 12400 | 1150 |
| Donor_2 3. Aliquot F | 305 | 40 | 24 | 46 | 1.5 | 10 | 12800 | 1100 |
| Donor_2 3. Aliquot G | 499 | 47 | 544 | 18 | 3.0 | 9.9 | 12000 | 1180 |
| Donor_2 3. Aliquot H | 304 | 40 | 21 | 46 | 3.2 | 9.5 | 13300 | 1090 |
| Donor_2 3. Aliquot I | 278 | 36 | 19 | 46 | 0.49 | 9.1 | 12400 | 1080 |
| Donor_3 3. Aliquot A | 183 | 14 | 157 | 7.3 | 2.5 | 0.99 | 14000 | 749 |
| Donor_3 3. Aliquot B | 209 | 13 | 64 | 46 | 2.5 | 0.98 | 18300 | 722 |
| Donor_3 3. Aliquot C | 156 | 8.1 | 13 | 46 | 3.2 | 0.99 | 12000 | 740 |
| Donor_3 3. Aliquot D | 213 | 14 | 2600 | 14 | 2.2 | 1.1 | 13700 | 725 |
| Donor_3 3. Aliquot E | 221 | 14 | 1150 | 11 | 3.9 | 1.2 | 16800 | 775 |
| Donor_3 3. Aliquot F | 154 | 7.9 | 26 | 46 | 2.1 | 0.94 | 10500 | 695 |
| Donor_3 3. Aliquot G | 205 | 10.0 | 21 | 46 | 3.2 | 1.0 | 12200 | 758 |
| Donor_3 3. Aliquot H | 155 | 6.8 | 9.4 | 46 | 3.2 | 0.90 | 9670 | 694 |
| Donor_3 3. Aliquot I | 153 | 6.5 | 4.2 | 46 | 2.1 | 0.98 | 9250 | 690 |

FIG. 13L.2

| | TIMP-1 | TNF RII | TNF-alpha | TNF-beta | Thrombo poietin | Thyroid Stimulating Hormone | Thrombospondin-1 | VCAM-1 |
|---|---|---|---|---|---|---|---|---|
| | ng/mL | ng/mL | pg/mL | pg/mL | ng/mL | uIU/mL | ng/mL | ng/mL |
| Least Detectable Dose | 8.4 | 0.13 | 4.0 | 46 | 3.2 | 0.028 | <25 | 2.6 |
| RBM Low Plasma Range | 59 | 3.1 | | | | 0.18 | Pending | 284 |
| RBM High Plasma Range | 192 | 79 | 27 | 120 | 6.2 | 3.7 | Pending | 1310 |
| Donor_4_3. Aliquot A | 575 | 30 | 20 | 46 | 1.3 | 0.15 | 14100 | 2080 |
| Donor_4_3. Aliquot B | 590 | 30 | 17 | 46 | 1.4 | 0.15 | 16300 | 1940 |
| Donor_4_3. Aliquot C | 532 | 26 | 12 | 46 | 3.2 | 0.16 | 4160 | 1990 |
| Donor_4_3. Aliquot D | 622 | 33 | 1720 | 7.3 | 2.0 | 0.26 | 11500 | 1950 |
| Donor_4_3. Aliquot E | 632 | 36 | 618 | 15 | 2.3 | 0.19 | 10900 | 2070 |
| Donor_4_3. Aliquot F | 565 | 31 | 91 | 7.3 | 1.2 | 0.14 | 5780 | 2200 |
| Donor_4_3. Aliquot G | 499 | 30 | 12 | 46 | 3.2 | 0.13 | 4050 | 1970 |
| Donor_4_3. Aliquot H | 546 | 27 | 9.3 | 46 | 1.2 | 0.14 | 4460 | 1980 |
| Donor_4_3. Aliquot I | 557 | 28 | 4.8 | 46 | 3.2 | 0.13 | 6360 | 2020 |
| Donor_5_3. Aliquot A | 344 | 28 | 106 | 7.9 | 2.9 | 0.28 | 22300 | 521 |
| Donor_5_3. Aliquot B | 368 | 31 | 146 | 7.3 | 3.1 | 0.26 | 17800 | 510 |
| Donor_5_3. Aliquot C | 184 | 23 | 12 | 46 | 0.69 | 0.32 | 13300 | 489 |
| Donor_5_3. Aliquot D | 327 | 34 | 1900 | 9.8 | 2.8 | 0.41 | 18600 | 525 |
| Donor_5_3. Aliquot E | 360 | 35 | 1590 | 16 | 2.7 | 0.38 | 17800 | 539 |
| Donor_5_3. Aliquot F | 233 | 23 | 105 | 46 | 2.2 | 0.24 | 13200 | 495 |
| Donor_5_3. Aliquot G | 331 | 27 | 18 | 8.6 | 1.0 | 0.28 | 14000 | 545 |
| Donor_5_3. Aliquot H | 228 | 23 | 12 | 46 | 0.49 | 0.26 | 14800 | 510 |
| Donor_5_3. Aliquot I | 190 | 22 | 12 | 46 | 0.49 | 0.26 | 10900 | 489 |
| Donor_6_3. Aliquot A | 139 | 5.5 | 41 | 6.6 | 3.6 | 1.3 | 25000 | 258 |
| Donor_6_3. Aliquot B | 165 | 6.9 | 23 | 4.6 | 3.7 | 1.2 | 22900 | 252 |
| Donor_6_3. Aliquot C | 111 | 2.5 | 3.2 | 46 | 3.1 | 1.3 | 13800 | 261 |
| Donor_6_3. Aliquot D | 156 | 6.8 | 1910 | 46 | 3.4 | 1.4 | 21100 | 274 |
| Donor_6_3. Aliquot E | 164 | 7.8 | 3210 | 46 | 3.6 | 1.3 | 13800 | 253 |
| Donor_6_3. Aliquot F | 124 | 4.1 | 9.1 | 46 | 4.0 | 1.1 | 15700 | 254 |
| Donor_6_3. Aliquot G | 260 | 5.1 | 12 | 46 | 2.3 | 1.3 | 12400 | 284 |
| Donor_6_3. Aliquot H | 112 | 3.0 | 8.0 | 8.6 | 1.7 | 1.2 | 14500 | 258 |
| Donor_6_3. Aliquot I | 100 | 2.4 | 1.7 | 46 | 1.7 | 1.2 | 12500 | 256 |

FIG. 13L.3

| | TIMP-1 | TNF RII | TNF-alpha | TNF-beta | Thrombo poietin | Thyroid Stimulating Hormone | Thrombospondin-1 | VCAM-1 |
|---|---|---|---|---|---|---|---|---|
| | ng/mL | ng/mL | pg/mL | pg/mL | ng/mL | uIU/mL | ng/mL | ng/mL |
| Least Detectable Dose | 8.4 | 0.13 | 4.0 | 46 | 3.2 | 0.028 | <25 | 2.6 |
| RBM Low Plasma Range | 59 | 3.1 | | | | | Pending | 284 |
| RBM High Plasma Range | 192 | 79 | 27 | 120 | 6.2 | 0.18 | Pending | 1310 |
| Donor_7 3. Aliquot A | 210 | 14 | 240 | 24 | 4.2 | 3.7 | 12100 | 789 |
| Donor_7 3. Aliquot B | 237 | 14 | 67 | 14 | 4.3 | 0.52 | 14600 | 802 |
| Donor_7 3. Aliquot C | 198 | 7.8 | 4.3 | 7.9 | 1.4 | 0.51 | 15800 | 861 |
| Donor_7 3. Aliquot D | 241 | 13 | 1250 | 8.6 | 3.3 | 0.49 | 11600 | 740 |
| Donor_7 3. Aliquot E | 243 | 13 | 338 | 19 | 3.8 | 0.55 | 11200 | 816 |
| Donor_7 3. Aliquot F | 187 | 8.4 | 19 | 9.8 | 3.5 | 0.50 | 7230 | 781 |
| Donor_7 3. Aliquot G | 213 | 10.0 | 17 | 46 | 1.0 | 0.47 | 6360 | 803 |
| Donor_7 3. Aliquot H | 158 | 6.4 | 5.1 | 46 | 3.2 | 0.49 | 7470 | 721 |
| Donor_7 3. Aliquot I | 159 | 7.0 | 2.7 | 46 | 2.2 | 0.47 | 7470 | 738 |
| Donor_8 3. Aliquot A | 84 | 3.8 | 129 | 7.9 | 3.6 | 2.2 | 10800 | 352 |
| Donor_8 3. Aliquot B | 118 | 5.1 | 49 | 6.0 | 4.7 | 2.1 | 14000 | 350 |
| Donor_8 3. Aliquot C | 50 | 1.7 | 184 | 46 | 4.4 | 1.8 | 10800 | 320 |
| Donor_8 3. Aliquot D | 60 | 3.8 | 12200 | 11 | 4.4 | 2.4 | 8580 | 319 |
| Donor_8 3. Aliquot E | 88 | 4.7 | 7570 | 11 | 4.2 | 2.2 | 11900 | 322 |
| Donor_8 3. Aliquot F | 52 | 3.2 | 591 | 9.8 | 5.6 | 2.0 | 4870 | 341 |
| Donor_8 3. Aliquot G | 118 | 2.8 | 22 | 46 | 1.4 | 1.9 | 5370 | 337 |
| Donor_8 3. Aliquot H | 60 | 2.5 | 113 | 3.9 | 3.7 | 2.2 | 12600 | 331 |
| Donor_8 3. Aliquot I | 61 | 1.9 | 14 | 46 | 3.8 | 2.0 | 13200 | 347 |
| Donor_9 3. Aliquot A | 66 | 3.6 | 78 | 11 | 3.2 | 0.34 | 13600 | 298 |
| Donor_9 3. Aliquot B | 92 | 4.4 | 51 | 8.8 | 3.4 | 0.28 | 16400 | 303 |
| Donor_9 3. Aliquot C | 62 | 3.3 | 68 | 20 | 3.6 | 0.33 | 15500 | 324 |
| Donor_9 3. Aliquot D | 69 | 5.2 | 6000 | 15 | 2.9 | 0.65 | 13800 | 295 |
| Donor_9 3. Aliquot E | 93 | 5.6 | 4600 | 5.0 | 3.1 | 0.53 | 11300 | 312 |
| Donor_9 3. Aliquot F | 48 | 2.7 | 81 | 18 | 4.3 | 0.29 | 6910 | 314 |
| Donor_9 3. Aliquot G | 130 | 3.9 | 55 | 6.9 | 1.2 | 0.22 | 9900 | 297 |
| Donor_9 3. Aliquot H | 56 | 2.5 | 22 | 10 | 1.8 | 0.31 | 15900 | 297 |
| Donor_9 3. Aliquot I | 53 | 1.9 | 13 | 46 | 2.3 | 0.28 | 17000 | 290 |

FIG. 13L.4

| | TIMP-1 | TNF RII | TNF-alpha | TNF-beta | Thrombo poietin | Thyroid Stimulating Hormone | Thrombospondin-1 | VCAM-1 |
|---|---|---|---|---|---|---|---|---|
| | ng/mL | ng/mL | pg/mL | pg/mL | ng/mL | uIU/mL | ng/mL | ng/mL |
| Least Detectable Dose | 8.4 | 0.13 | 4.0 | 46 | 3.2 | 0.028 | <25 | 2.6 |
| RBM Low Plasma Range | 59 | 3.1 | | | | 0.18 | Pending | 284 |
| RBM High Plasma Range | 192 | 79 | 27 | 120 | 6.2 | 3.7 | Pending | 1310 |
| EDTA Plasma | | | | | | | | |
| donor #1 plasma | 379 | 27 | 14 | 10 | 3.2 | 12 | 14800 | 1230 |
| donor #2 plasma | 248 | 51 | 5.4 | 46 | 3.2 | 9.7 | 4670 | 1280 |
| donor #3 plasma | 144 | 8.2 | 5.4 | 8.8 | 0.81 | 1.0 | 7890 | 978 |
| donor #4 plasma | 478 | 34 | 1.1 | 46 | 1.4 | 0.11 | 2310 | 2580 |
| donor #5 plasma | 166 | 28 | 2.3 | 11 | 1.8 | 0.28 | 28600 | 577 |
| donor #6 plasma | 82 | 2.6 | 4 | 5.0 | 2.4 | 1.7 | 16800 | 301 |
| donor #7 plasma | 156 | 9.5 | 4 | 13 | 2.1 | 0.59 | 13800 | 980 |
| donor #8 plasma | 40 | 1.2 | 5.6 | 46 | 1.4 | 2.5 | 6520 | 340 |
| donor #9 plasma | 31 | 1.5 | 4 | 46 | 0.44 | 0.30 | 818 | 385 |
| | | | | | | | | |
| *Stimulations indices* | | | | | | | | |
| Donor_1 3. Aliquot A | 1.1 | 1.2 | 9.4 | 0.2 | 2.8 | 1.0 | 0.9 | 1.0 |
| Donor_1 3. Aliquot B | 1.2 | 1.3 | 3.0 | 1.0 | 2.2 | 0.9 | 1.3 | 1.1 |
| Donor_1 3. Aliquot C | 1.2 | 1.1 | 0.7 | 1.0 | 4.7 | 1.0 | 1.0 | 1.0 |
| Donor_1 3. Aliquot D | 1.3 | 1.2 | 12.0 | 1.0 | 2.8 | 1.0 | 1.1 | 1.1 |
| Donor_1 3. Aliquot E | 1.1 | 1.2 | 3.5 | 1.0 | 2.8 | 1.0 | 0.8 | 1.0 |
| Donor_1 3. Aliquot F | 1.1 | 1.1 | 1.4 | 1.0 | 4.7 | 1.0 | 0.8 | 1.0 |
| Donor_1 3. Aliquot G | 1.3 | 1.3 | 0.9 | 1.0 | 1.9 | 1.0 | 0.7 | 1.1 |
| Donor_1 3. Aliquot H | 1.2 | 1.1 | 0.7 | 1.0 | 1.2 | 1.0 | 1.5 | 1.0 |
| Donor_1 3. Aliquot I | 1.0 | 1.0 | 1.0 | 1.0 | 1.0 | 1.0 | 1.0 | 1.1 |
| Donor_2 3. Aliquot A | 1.3 | 1.3 | 11.2 | 0.1 | 5.6 | 1.1 | 1.6 | 1.0 |
| Donor_2 3. Aliquot B | 1.4 | 1.4 | 4.9 | 0.1 | 6.7 | 1.1 | 1.7 | 1.1 |
| Donor_2 3. Aliquot C | 1.1 | 1.1 | 0.6 | 1.0 | 6.6 | 1.0 | 1.0 | 1.1 |
| Donor_2 3. Aliquot D | 1.3 | 1.3 | 142.1 | 0.1 | 4.9 | 1.3 | 1.1 | 1.0 |
| Donor_2 3. Aliquot E | 1.4 | 1.3 | 88.9 | 0.1 | 5.6 | 1.2 | 1.0 | 1.1 |
| Donor_2 3. Aliquot F | 1.1 | 1.1 | 1.3 | 1.0 | 3.2 | 1.0 | 1.0 | 1.0 |
| Donor_2 3. Aliquot G | 1.8 | 1.3 | 28.6 | 0.4 | 6.1 | 1.1 | 1.0 | 1.1 |

FIG. 13L.5

|  | TIMP-1 | TNF RII | TNF-alpha | TNF-beta | Thrombo poietin | Thyroid Stimulating Hormone | Thrombospondin-1 | VCAM-1 |
|---|---|---|---|---|---|---|---|---|
|  | ng/mL | ng/mL | pg/mL | pg/mL | ng/mL | uIU/mL | ng/mL | ng/mL |
| Least Detectable Dose | 8.4 | 0.13 | 4.0 | 46 | 3.2 | 0.028 | <25 | 2.6 |
| RBM Low Plasma Range | 59 | 3.1 |  |  |  | 0.18 | Pending | 284 |
| RBM High Plasma Range | 192 | 79 | 27 | 120 | 6.2 | 3.7 | Pending | 1310 |
| Donor_2 3. Aliquot H | 1.1 | 1.1 | 1.1 | 1.0 | 6.6 | 1.1 | 1.1 | 1.0 |
| Donor_2 3. Aliquot I | 1.0 | 1.0 | 1.0 | 1.0 | 1.0 | 1.0 | 1.0 | 1.0 |
| Donor_3 3. Aliquot A | 1.2 | 2.1 | 37.7 | 0.2 | 1.2 | 1.0 | 1.5 | 1.1 |
| Donor_3 3. Aliquot B | 1.4 | 2.0 | 15.4 | 1.0 | 1.2 | 1.0 | 2.0 | 1.0 |
| Donor_3 3. Aliquot C | 1.0 | 1.2 | 3.2 | 1.0 | 1.5 | 1.0 | 1.3 | 1.1 |
| Donor_3 3. Aliquot D | 1.4 | 2.2 | 625.0 | 0.3 | 1.0 | 1.1 | 1.5 | 1.1 |
| Donor_3 3. Aliquot E | 1.4 | 2.2 | 276.4 | 0.2 | 1.9 | 1.2 | 1.8 | 1.1 |
| Donor_3 3. Aliquot F | 1.0 | 1.2 | 6.3 | 1.0 | 1.5 | 1.0 | 1.1 | 1.1 |
| Donor_3 3. Aliquot G | 1.3 | 1.5 | 5.0 | 1.0 | 1.5 | 1.1 | 1.3 | 1.1 |
| Donor_3 3. Aliquot H | 0.9 | 1.0 | 2.3 | 1.0 | 1.5 | 0.9 | 1.0 | 1.0 |
| Donor_3 3. Aliquot I | 1.0 | 1.0 | 1.0 | 1.0 | 1.0 | 1.0 | 1.0 | 1.0 |
| Donor_4 3. Aliquot A | 1.0 | 1.1 | 4.2 | 1.0 | 0.4 | 1.1 | 2.2 | 1.0 |
| Donor_4 3. Aliquot B | 1.1 | 1.1 | 3.6 | 1.0 | 0.4 | 1.1 | 2.6 | 1.0 |
| Donor_4 3. Aliquot C | 1.0 | 1.0 | 2.5 | 1.0 | 1.0 | 1.2 | 0.7 | 1.0 |
| Donor_4 3. Aliquot D | 1.1 | 1.2 | 357.6 | 0.2 | 0.6 | 2.0 | 1.8 | 1.0 |
| Donor_4 3. Aliquot E | 1.1 | 1.3 | 128.5 | 0.3 | 0.7 | 1.5 | 1.7 | 1.0 |
| Donor_4 3. Aliquot F | 1.0 | 1.1 | 18.8 | 0.2 | 0.4 | 1.1 | 0.9 | 1.1 |
| Donor_4 3. Aliquot G | 0.9 | 1.1 | 2.5 | 1.0 | 1.0 | 1.0 | 0.6 | 1.0 |
| Donor_4 3. Aliquot H | 1.0 | 1.0 | 1.9 | 1.0 | 0.4 | 1.1 | 0.7 | 1.0 |
| Donor_4 3. Aliquot I | 1.0 | 1.0 | 1.0 | 1.0 | 1.0 | 1.0 | 1.0 | 1.0 |
| Donor_5 3. Aliquot A | 1.8 | 1.3 | 8.7 | 0.2 | 5.9 | 1.1 | 2.0 | 1.1 |
| Donor_5 3. Aliquot B | 1.9 | 1.4 | 12.0 | 0.2 | 6.3 | 1.0 | 1.6 | 1.0 |
| Donor_5 3. Aliquot C | 1.0 | 1.1 | 1.0 | 1.0 | 1.4 | 1.2 | 1.2 | 1.0 |
| Donor_5 3. Aliquot D | 1.7 | 1.6 | 155.7 | 0.2 | 5.7 | 2.0 | 1.7 | 1.1 |
| Donor_5 3. Aliquot E | 1.9 | 1.6 | 130.3 | 0.4 | 5.6 | 1.5 | 1.6 | 1.1 |
| Donor_5 3. Aliquot F | 1.2 | 1.1 | 8.6 | 1.0 | 4.5 | 0.9 | 1.2 | 1.0 |
| Donor_5 3. Aliquot G | 1.7 | 1.2 | 1.4 | 0.2 | 2.1 | 1.1 | 1.3 | 1.1 |

FIG. 13L.6

| | TIMP-1 | TNF RII | TNF-alpha | TNF-beta | Thrombo poietin | Thyroid Stimulating Hormone | Thrombospondin-1 | VCAM-1 |
|---|---|---|---|---|---|---|---|---|
| | ng/mL | ng/mL | pg/mL | pg/mL | ng/mL | uIU/mL | ng/mL | ng/mL |
| Least Detectable Dose | 8.4 | 0.13 | 4.0 | 46 | 3.2 | 0.028 | <25 | 2.6 |
| RBM Low Plasma Range | 59 | 3.1 | 27 | | | 0.18 | Pending | 284 |
| RBM High Plasma Range | 192 | 79 | | 120 | 6.2 | 3.7 | Pending | 1310 |
| Donor_5 3. Aliquot H | 1.2 | 1.1 | 1.0 | 1.0 | 1.0 | 1.0 | 1.4 | 1.0 |
| Donor_5 3. Aliquot I | 1.0 | 1.0 | 1.0 | 1.0 | 1.0 | 1.0 | 1.0 | 1.0 |
| Donor_6 3. Aliquot A | 1.4 | 2.3 | 23.8 | 0.1 | 2.2 | 1.1 | 2.0 | 1.0 |
| Donor_6 3. Aliquot B | 1.7 | 2.9 | 13.4 | 0.1 | 2.2 | 1.0 | 1.8 | 1.0 |
| Donor_6 3. Aliquot C | 1.1 | 1.1 | 1.8 | 1.0 | 1.8 | 1.0 | 1.1 | 1.0 |
| Donor_6 3. Aliquot D | 1.6 | 2.9 | 1104.0 | 1.0 | 2.1 | 1.1 | 1.7 | 1.1 |
| Donor_6 3. Aliquot E | 1.6 | 3.3 | 1855.5 | 1.0 | 2.2 | 1.1 | 1.1 | 1.0 |
| Donor_6 3. Aliquot F | 1.2 | 1.7 | 5.3 | 1.0 | 2.4 | 0.9 | 1.3 | 1.1 |
| Donor_6 3. Aliquot G | 2.6 | 2.1 | 7.1 | 1.0 | 1.4 | 1.0 | 1.0 | 1.1 |
| Donor_6 3. Aliquot H | 1.1 | 1.3 | 4.6 | 0.2 | 1.0 | 1.0 | 1.2 | 1.0 |
| Donor_6 3. Aliquot I | 1.0 | 1.0 | 1.0 | 1.0 | 1.0 | 1.0 | 1.0 | 1.0 |
| Donor_7 3. Aliquot A | 1.3 | 2.0 | 90.6 | 0.5 | 1.9 | 1.1 | 1.6 | 1.1 |
| Donor_7 3. Aliquot B | 1.5 | 1.9 | 25.4 | 0.3 | 2.0 | 1.1 | 2.0 | 1.1 |
| Donor_7 3. Aliquot C | 1.2 | 1.1 | 1.6 | 0.2 | 0.6 | 1.0 | 2.1 | 1.2 |
| Donor_7 3. Aliquot D | 1.5 | 1.8 | 471.7 | 0.2 | 1.5 | 1.2 | 1.6 | 1.0 |
| Donor_7 3. Aliquot E | 1.5 | 1.8 | 127.5 | 0.4 | 1.8 | 1.1 | 1.5 | 1.1 |
| Donor_7 3. Aliquot F | 1.2 | 1.2 | 7.1 | 0.2 | 1.6 | 1.0 | 1.0 | 1.1 |
| Donor_7 3. Aliquot G | 1.3 | 1.4 | 6.6 | 1.0 | 0.5 | 1.0 | 0.9 | 1.1 |
| Donor_7 3. Aliquot H | 1.0 | 0.9 | 1.9 | 0.2 | 1.5 | 1.0 | 1.0 | 1.0 |
| Donor_7 3. Aliquot I | 1.0 | 1.0 | 1.0 | 1.0 | 1.0 | 1.0 | 1.0 | 1.0 |
| Donor_8 3. Aliquot A | 1.4 | 2.0 | 9.6 | 0.2 | 0.9 | 1.1 | 0.8 | 1.0 |
| Donor_8 3. Aliquot B | 1.9 | 2.6 | 3.7 | 0.1 | 1.2 | 1.1 | 1.1 | 1.0 |
| Donor_8 3. Aliquot C | 0.8 | 0.9 | 13.6 | 1.0 | 1.2 | 0.9 | 0.8 | 0.9 |
| Donor_8 3. Aliquot D | 1.0 | 2.0 | 903.7 | 0.2 | 1.2 | 1.2 | 0.7 | 0.9 |
| Donor_8 3. Aliquot E | 1.4 | 2.4 | 560.7 | 0.2 | 1.1 | 1.1 | 0.9 | 0.9 |
| Donor_8 3. Aliquot F | 0.8 | 1.7 | 43.8 | 0.2 | 1.5 | 1.0 | 0.4 | 1.0 |
| Donor_8 3. Aliquot G | 1.9 | 1.5 | 1.6 | 1.0 | 0.4 | 0.9 | 0.4 | 1.0 |

FIG. 13L.7

| | TIMP-1 | TNF RII | TNF-alpha | TNF-beta | Thrombo poietin | Thyroid Stimulating Hormone | Thrombospondin-1 | VCAM-1 |
|---|---|---|---|---|---|---|---|---|
| | ng/mL | ng/mL | pg/mL | pg/mL | ng/mL | uIU/mL | ng/mL | ng/mL |
| Least Detectable Dose | 8.4 | 0.13 | 4.0 | 46 | 3.2 | 0.028 | <25 | 2.6 |
| RBM Low Plasma Range | 59 | 3.1 | 27 | | | 0.18 | Pending | 284 |
| RBM High Plasma Range | 192 | 79 | | 120 | 6.2 | 3.7 | Pending | 1310 |
| Donor_8 3. Aliquot H | 1.0 | 1.3 | 8.4 | 0.1 | 1.0 | 1.1 | 1.0 | 1.0 |
| Donor_8 3. Aliquot I | 1.0 | 1.0 | 1.0 | 1.0 | 1.0 | 1.0 | 1.0 | 1.0 |
| | | | | | | | | |
| Donor_9 3. Aliquot A | 1.2 | 1.9 | 6.0 | 0.2 | 1.4 | 1.2 | 0.8 | 1.0 |
| Donor_9 3. Aliquot B | 1.7 | 2.3 | 3.9 | 0.2 | 1.5 | 1.0 | 1.0 | 1.0 |
| Donor_9 3. Aliquot C | 1.2 | 1.7 | 5.2 | 0.4 | 1.6 | 1.2 | 0.9 | 1.1 |
| Donor_9 3. Aliquot D | 1.3 | 2.7 | 461.5 | 0.3 | 1.3 | 2.3 | 0.8 | 1.0 |
| Donor_9 3. Aliquot E | 1.8 | 2.9 | 353.8 | 0.1 | 1.4 | 1.9 | 0.7 | 1.1 |
| Donor_9 3. Aliquot F | 0.9 | 1.4 | 6.2 | 0.4 | 1.9 | 1.0 | 0.4 | 1.1 |
| Donor_9 3. Aliquot G | 2.5 | 2.0 | 4.2 | 0.2 | 0.5 | 0.8 | 0.6 | 1.0 |
| Donor_9 3. Aliquot H | 1.1 | 1.3 | 1.7 | 0.2 | 0.8 | 1.1 | 0.9 | 1.0 |
| Donor_9 3. Aliquot I | 1.0 | 1.0 | 1.0 | 1.0 | 1.0 | 1.0 | 1.0 | 1.0 |

FIG. 13M.1

| | VEGF | von Willebrand Factor |
|---|---|---|
| | pg/mL | ug/mL |
| Least Detectable Dose | 7.5 | 0.40 |
| RBM Low Plasma Range | 91 | 5.3 |
| RBM High Plasma Range | 1790 | 74 |
| Donor_1_3. Aliquot A | 2090 | 211 |
| Donor_1_3. Aliquot B | 2090 | 203 |
| Donor_1_3. Aliquot C | 2070 | 213 |
| Donor_1_3. Aliquot D | 2120 | 198 |
| Donor_1_3. Aliquot E | 2030 | 184 |
| Donor_1_3. Aliquot F | 1860 | 196 |
| Donor_1_3. Aliquot G | 2570 | 180 |
| Donor_1_3. Aliquot H | 2210 | 207 |
| Donor_1_3. Aliquot I | 1940 | 203 |
| Donor_2_3. Aliquot A | 4570 | 188 |
| Donor_2_3. Aliquot B | 4900 | 200 |
| Donor_2_3. Aliquot C | 5240 | 191 |
| Donor_2_3. Aliquot D | 4400 | 190 |
| Donor_2_3. Aliquot E | 4630 | 189 |
| Donor_2_3. Aliquot F | 4870 | 178 |
| Donor_2_3. Aliquot G | 5490 | 215 |
| Donor_2_3. Aliquot H | 4920 | 213 |
| Donor_2_3. Aliquot I | 4680 | 187 |
| Donor_3_3. Aliquot A | 532 | 99 |
| Donor_3_3. Aliquot B | 618 | 110 |
| Donor_3_3. Aliquot C | 707 | 95 |
| Donor_3_3. Aliquot D | 505 | 123 |
| Donor_3_3. Aliquot E | 508 | 108 |
| Donor_3_3. Aliquot F | 714 | 104 |
| Donor_3_3. Aliquot G | 1590 | 109 |
| Donor_3_3. Aliquot H | 678 | 123 |
| Donor_3_3. Aliquot I | 734 | 119 |

FIG. 13M.2

| | VEGF | von Willebrand Factor |
|---|---|---|
| | pg/mL | ug/mL |
| Least Detectable Dose | 7.5 | 0.40 |
| RBM Low Plasma Range | 91 | 5.3 |
| RBM High Plasma Range | 1790 | 74 |
| Donor_4_3. Aliquot A | 1190 | 182 |
| Donor_4_3. Aliquot B | 1180 | 227 |
| Donor_4_3. Aliquot C | 1220 | 253 |
| Donor_4_3. Aliquot D | 1100 | 252 |
| Donor_4_3. Aliquot E | 1060 | 223 |
| Donor_4_3. Aliquot F | 1030 | 257 |
| Donor_4_3. Aliquot G | 2190 | 223 |
| Donor_4_3. Aliquot H | 1350 | 229 |
| Donor_4_3. Aliquot I | 1280 | 246 |
| Donor_5_3. Aliquot A | 3600 | 100 |
| Donor_5_3. Aliquot B | 3460 | 105 |
| Donor_5_3. Aliquot C | 4460 | 113 |
| Donor_5_3. Aliquot D | 3350 | 112 |
| Donor_5_3. Aliquot E | 3650 | 125 |
| Donor_5_3. Aliquot F | 3140 | 109 |
| Donor_5_3. Aliquot G | 5580 | 110 |
| Donor_5_3. Aliquot H | 3840 | 121 |
| Donor_5_3. Aliquot I | 3520 | 96 |
| Donor_6_3. Aliquot A | 874 | 79 |
| Donor_6_3. Aliquot B | 648 | 70 |
| Donor_6_3. Aliquot C | 840 | 74 |
| Donor_6_3. Aliquot D | 530 | 75 |
| Donor_6_3. Aliquot E | 471 | 72 |
| Donor_6_3. Aliquot F | 581 | 80 |
| Donor_6_3. Aliquot G | 2690 | 85 |
| Donor_6_3. Aliquot H | 878 | 76 |
| Donor_6_3. Aliquot I | 846 | 67 |

FIG. 13M.3

| | VEGF | von Willebrand Factor |
|---|---|---|
| | pg/mL | ug/mL |
| Least Detectable Dose | 7.5 | 0.40 |
| RBM Low Plasma Range | 91 | 5.3 |
| RBM High Plasma Range | 1790 | 74 |
| Donor_7 3. Aliquot A | 295 | 112 |
| Donor_7 3. Aliquot B | 237 | 129 |
| Donor_7 3. Aliquot C | 345 | 132 |
| Donor_7 3. Aliquot D | 210 | 124 |
| Donor_7 3. Aliquot E | 235 | 102 |
| Donor_7 3. Aliquot F | 203 | 135 |
| Donor_7 3. Aliquot G | 1260 | 114 |
| Donor_7 3. Aliquot H | 313 | 127 |
| Donor_7 3. Aliquot I | 257 | 123 |
| Donor_8 3. Aliquot A | 252 | 18 |
| Donor_8 3. Aliquot B | 203 | 23 |
| Donor_8 3. Aliquot C | 401 | 16 |
| Donor_8 3. Aliquot D | 416 | 19 |
| Donor_8 3. Aliquot E | 341 | 17 |
| Donor_8 3. Aliquot F | 321 | 20 |
| Donor_8 3. Aliquot G | 822 | 21 |
| Donor_8 3. Aliquot H | 322 | 22 |
| Donor_8 3. Aliquot I | 248 | 21 |
| Donor_9 3. Aliquot A | 326 | Pending |
| Donor_9 3. Aliquot B | 280 | Pending |
| Donor_9 3. Aliquot C | 367 | Pending |
| Donor_9 3. Aliquot D | 486 | Pending |
| Donor_9 3. Aliquot E | 398 | Pending |
| Donor_9 3. Aliquot F | 322 | Pending |
| Donor_9 3. Aliquot G | 1170 | Pending |
| Donor_9 3. Aliquot H | 380 | Pending |
| Donor_9 3. Aliquot I | 243 | Pending |

FIG. 13M.4

| | VEGF | von Willebrand Factor |
|---|---|---|
| | pg/mL | ug/mL |
| Least Detectable Dose | 7.5 | 0.40 |
| | | |
| RBM Low Plasma Range | 91 | 5.3 |
| RBM High Plasma Range | 1790 | 74 |
| EDTA Plasma | | |
| donor #1 plasma | 1500 | Pending |
| donor #2 plasma | 4500 | Pending |
| donor #3 plasma | 1290 | Pending |
| donor #4 plasma | 1400 | Pending |
| donor #5 plasma | 3840 | Pending |
| donor #6 plasma | 533 | Pending |
| donor #7 plasma | 521 | Pending |
| donor #8 plasma | 281 | Pending |
| donor #9 plasma | 295 | Pending |
| | | |
| *Stimulations Indices* | | |
| Donor_1 3. Aliquot A | 1.1 | 1.0 |
| Donor_1 3. Aliquot B | 1.1 | 1.0 |
| Donor_1 3. Aliquot C | 1.1 | 1.0 |
| Donor_1 3. Aliquot D | 1.1 | 1.0 |
| Donor_1 3. Aliquot E | 1.0 | 0.9 |
| Donor_1 3. Aliquot F | 1.0 | 1.0 |
| Donor_1 3. Aliquot G | 1.3 | 0.9 |
| Donor_1 3. Aliquot H | 1.1 | 1.0 |
| Donor_1 3. Aliquot I | 1.0 | 1.0 |
| | | |
| Donor_2 3. Aliquot A | 1.0 | 1.0 |
| Donor_2 3. Aliquot B | 1.0 | 1.1 |
| Donor_2 3. Aliquot C | 1.1 | 1.0 |
| Donor_2 3. Aliquot D | 0.9 | 1.0 |
| Donor_2 3. Aliquot E | 1.0 | 1.0 |
| Donor_2 3. Aliquot F | 1.0 | 1.0 |
| Donor_2 3. Aliquot G | 1.2 | 1.1 |

FIG. 13M.5

| | VEGF pg/mL | von Willebrand Factor ug/mL |
|---|---|---|
| Least Detectable Dose | 7.5 | 0.40 |
| RBM Low Plasma Range | 91 | 5.3 |
| RBM High Plasma Range | 1790 | 74 |
| Donor_2 3. Aliquot H | 1.1 | 1.1 |
| Donor_2 3. Aliquot I | 1.0 | 1.0 |
| Donor_3 3. Aliquot A | 0.7 | 0.8 |
| Donor_3 3. Aliquot B | 0.8 | 0.9 |
| Donor_3 3. Aliquot C | 1.0 | 0.8 |
| Donor_3 3. Aliquot D | 0.7 | 1.0 |
| Donor_3 3. Aliquot E | 0.7 | 0.9 |
| Donor_3 3. Aliquot F | 1.0 | 0.9 |
| Donor_3 3. Aliquot G | 2.2 | 0.9 |
| Donor_3 3. Aliquot H | 0.9 | 1.0 |
| Donor_3 3. Aliquot I | 1.0 | 1.0 |
| Donor_4 3. Aliquot A | 0.9 | 0.7 |
| Donor_4 3. Aliquot B | 0.9 | 0.9 |
| Donor_4 3. Aliquot C | 1.0 | 1.0 |
| Donor_4 3. Aliquot D | 0.9 | 0.9 |
| Donor_4 3. Aliquot E | 0.8 | 1.0 |
| Donor_4 3. Aliquot F | 1.7 | 1.0 |
| Donor_4 3. Aliquot H | 1.1 | 0.9 |
| Donor_4 3. Aliquot I | 1.0 | 1.0 |
| Donor_5 3. Aliquot A | 1.0 | 1.0 |
| Donor_5 3. Aliquot B | 1.0 | 1.1 |
| Donor_5 3. Aliquot C | 1.3 | 1.2 |
| Donor_5 3. Aliquot D | 1.0 | 1.2 |
| Donor_5 3. Aliquot E | 1.0 | 1.3 |
| Donor_5 3. Aliquot F | 0.9 | 1.1 |
| Donor_5 3. Aliquot G | 1.6 | 1.1 |

FIG. 13M.6

| | VEGF pg/mL | von Willebrand Factor ug/mL |
|---|---|---|
| Least Detectable Dose | 7.5 | 0.40 |
| RBM Low Plasma Range | 91 | 5.3 |
| RBM High Plasma Range | 1790 | 74 |
| Donor_5 3. Aliquot H | 1.1 | 1.3 |
| Donor_5 3. Aliquot I | 1.0 | 1.0 |
| Donor_6 3. Aliquot A | 1.0 | 1.2 |
| Donor_6 3. Aliquot B | 0.8 | 1.0 |
| Donor_6 3. Aliquot C | 1.0 | 1.1 |
| Donor_6 3. Aliquot D | 0.6 | 1.1 |
| Donor_6 3. Aliquot E | 0.6 | 1.1 |
| Donor_6 3. Aliquot F | 0.7 | 1.2 |
| Donor_6 3. Aliquot G | 3.2 | 1.3 |
| Donor_6 3. Aliquot H | 1.0 | 1.1 |
| Donor_6 3. Aliquot I | 1.0 | 1.0 |
| Donor_7 3. Aliquot A | 1.1 | 0.9 |
| Donor_7 3. Aliquot B | 0.9 | 1.0 |
| Donor_7 3. Aliquot C | 1.3 | 1.1 |
| Donor_7 3. Aliquot D | 0.8 | 1.0 |
| Donor_7 3. Aliquot E | 0.9 | 0.8 |
| Donor_7 3. Aliquot F | 0.8 | 1.1 |
| Donor_7 3. Aliquot G | 4.9 | 0.9 |
| Donor_7 3. Aliquot H | 1.2 | 1.0 |
| Donor_7 3. Aliquot I | 1.0 | 1.0 |
| Donor_8 3. Aliquot A | 1.0 | 0.9 |
| Donor_8 3. Aliquot B | 0.8 | 1.1 |
| Donor_8 3. Aliquot C | 1.6 | 0.8 |
| Donor_8 3. Aliquot D | 1.7 | 0.9 |
| Donor_8 3. Aliquot E | 1.4 | 0.8 |
| Donor_8 3. Aliquot F | 1.3 | 0.9 |
| Donor_8 3. Aliquot G | 3.3 | 1.0 |

FIG. 13M.7

| | VEGF | von Willebrand Factor |
|---|---|---|
| | pg/mL | ug/mL |
| Least Detectable Dose | 7.5 | 0.40 |
| RBM Low Plasma Range | 91 | 5.3 |
| RBM High Plasma Range | 1790 | 74 |
| Donor_8 3. Aliquot H | 1.3 | 1.1 |
| Donor_8 3. Aliquot I | 1.0 | 1.0 |
| Donor_9 3. Aliquot A | 1.3 | #VALUE! |
| Donor_9 3. Aliquot B | 1.2 | #VALUE! |
| Donor_9 3. Aliquot C | 1.5 | #VALUE! |
| Donor_9 3. Aliquot D | 2.0 | #VALUE! |
| Donor_9 3. Aliquot E | 1.6 | #VALUE! |
| Donor_9 3. Aliquot F | 1.3 | #VALUE! |
| Donor_9 3. Aliquot G | 4.8 | #VALUE! |
| Donor_9 3. Aliquot H | 1.6 | #VALUE! |
| Donor_9 3. Aliquot I | 1.0 | #VALUE! |

FIG. 14A.1

| | Alpha-1 Antitrypsin mg/mL | Adiponectin ug/mL | Alpha-2 Macroglobulin mg/mL | Alpha-Fetoprotein ng/mL | Amphiregulin pg/mL | Apolipoprotein A1 mg/mL | Apolipoprotein CIII ug/mL |
|---|---|---|---|---|---|---|---|
| Least Detectable Dose | 0.011 | 0.20 | 0.061 | 0.43 | 36 | 0.0066 | 2.7 |
| RBM Low Plasma Range | 1.2 | 1.6 | 0.13 | | Pending | 0.19 | 28 |
| RBM High Plasma Range | 3.1 | 14 | 1.0 | 6.7 | Pending | 0.89 | 224 |
| Samples | | | | | | | |
| Donor_1 3. Aliquot A | 2.6 | 2.0 | 0.29 | 2.8 | 469 | 0.10 | 52 |
| Donor_1 3. Aliquot B | 2.8 | 2.1 | 0.30 | 2.6 | 455 | 0.10 | 64 |
| Donor_1 3. Aliquot C | 2.9 | 2.1 | 0.30 | 2.3 | 104 | 0.11 | 60 |
| Donor_1 3. Aliquot D | 3.1 | 2.1 | 0.31 | 2.8 | 431 | 0.11 | 60 |
| Donor_1 3. Aliquot E | 2.8 | 2.1 | 0.27 | 2.5 | 443 | 0.11 | 53 |
| Donor_1 3. Aliquot F | 2.6 | 2.0 | 0.66 | 2.3 | 414 | 0.097 | 57 |
| Donor_1 3. Aliquot G | 2.9 | 2.1 | 0.30 | 2.5 | 401 | 0.098 | 61 |
| Donor_1 3. Aliquot H | 2.7 | 2.0 | 0.42 | 2.7 | 36 | 0.089 | 48 |
| Donor_1 3. Aliquot I | 2.7 | 2.0 | 0.26 | 2.5 | 419 | 0.11 | 60 |
| Donor_2 3. Aliquot A | 2.2 | 4.4 | 0.28 | 2.1 | 133 | 0.11 | 58 |
| Donor_2 3. Aliquot B | 2.3 | 4.5 | 0.30 | 2.3 | 50 | 0.12 | 64 |
| Donor_2 3. Aliquot C | 2.3 | 4.5 | 0.29 | 1.4 | 36 | 0.12 | 64 |
| Donor_2 3. Aliquot D | 2.2 | 4.3 | 0.29 | 3.4 | 104 | 0.098 | 48 |
| Donor_2 3. Aliquot E | 2.3 | 4.5 | 0.28 | 2.5 | 39 | 0.097 | 52 |
| Donor_2 3. Aliquot F | 2.3 | 4.2 | 0.64 | 2.0 | 36 | 0.090 | 66 |
| Donor_2 3. Aliquot G | 2.3 | 4.3 | 0.32 | 1.8 | 597 | 0.094 | 67 |
| Donor_2 3. Aliquot H | 2.2 | 4.4 | 0.33 | 1.8 | 36 | 0.095 | 61 |
| Donor_2 3. Aliquot I | 2.1 | 4.0 | 0.29 | 1.9 | 24 | 0.11 | 54 |
| Donor_3 3. Aliquot A | 2.9 | 3.0 | 0.35 | 2.7 | 36 | 0.13 | 38 |
| Donor_3 3. Aliquot B | 3.0 | 2.7 | 0.35 | 2.6 | 36 | 0.14 | 38 |
| Donor_3 3. Aliquot C | 3.0 | 2.8 | 0.34 | 1.9 | 36 | 0.13 | 41 |
| Donor_3 3. Aliquot D | 2.8 | 2.7 | 0.34 | 3.3 | 97 | 0.13 | 38 |
| Donor_3 3. Aliquot E | 3.1 | 2.8 | 0.36 | 3.5 | 116 | 0.14 | 36 |
| Donor_3 3. Aliquot F | 2.7 | 2.6 | 0.65 | 2.5 | 60 | 0.12 | 42 |
| Donor_3 3. Aliquot G | 3.1 | 2.8 | 0.35 | 1.4 | 97 | 0.15 | 44 |
| Donor_3 3. Aliquot H | 2.8 | 2.7 | 0.41 | 1.7 | 36 | 0.13 | 41 |
| Donor_3 3. Aliquot I | 2.8 | 2.6 | 0.33 | 1.3 | 39 | 0.14 | 42 |

FIG. 14A.2

| | Alpha-1 Antitrypsin | Adiponectin | Alpha-2 Macroglobulin | Alpha-Fetoprotein | Amphiregulin | Apolipoprotein A1 | Apolipoprotein CIII |
|---|---|---|---|---|---|---|---|
| | mg/mL | ug/mL | mg/mL | ng/mL | pg/mL | mg/mL | ug/mL |
| Least Detectable Dose | 0.011 | 0.20 | 0.061 | 0.43 | 36 | 0.0066 | 2.7 |
| RBM Low Plasma Range | 1.2 | 1.6 | 0.13 | | Pending | 0.19 | 28 |
| RBM High Plasma Range | 3.1 | 14 | 1.0 | 6.7 | Pending | 0.89 | 224 |
| Donor_4 3. Aliquot A | 1.7 | 5.3 | 0.40 | 2.4 | 36 | 0.056 | 13 |
| Donor_4 3. Aliquot B | 1.5 | 5.4 | 0.40 | 2.1 | 36 | 0.050 | 12 |
| Donor_4 3. Aliquot C | 1.6 | 5.2 | 0.41 | 2.0 | 39 | 0.049 | 11 |
| Donor_4 3. Aliquot D | 1.6 | 5.3 | 0.42 | 3.6 | 36 | 0.044 | 13 |
| Donor_4 3. Aliquot E | 1.5 | 5.3 | 0.38 | 2.8 | 36 | 0.048 | 9.1 |
| Donor_4 3. Aliquot F | 1.6 | 5.3 | 0.98 | 1.8 | 36 | 0.054 | 15 |
| Donor_4 3. Aliquot G | 1.6 | 5.5 | 0.48 | 2.1 | 76 | 0.047 | 11 |
| Donor_4 3. Aliquot H | 1.5 | 5.3 | 0.65 | 2.1 | 76 | 0.051 | 11 |
| Donor_4 3. Aliquot I | 1.5 | 5.4 | 0.41 | 1.9 | 36 | 0.052 | 12 |
| Donor_5 3. Aliquot A | 2.9 | 2.8 | 0.27 | 3.2 | 127 | 0.12 | 70 |
| Donor_5 3. Aliquot B | 2.9 | 2.6 | 0.29 | 3.2 | 178 | 0.13 | 77 |
| Donor_5 3. Aliquot C | 3.2 | 2.7 | 0.29 | 2.5 | 50 | 0.14 | 77 |
| Donor_5 3. Aliquot D | 3.2 | 2.6 | 0.28 | 4.1 | 159 | 0.14 | 78 |
| Donor_5 3. Aliquot E | 3.1 | 2.8 | 0.28 | 4.0 | 187 | 0.14 | 71 |
| Donor_5 3. Aliquot F | 2.9 | 2.6 | 0.46 | 2.3 | 36 | 0.12 | 83 |
| Donor_5 3. Aliquot G | 3.0 | 2.5 | 0.29 | 3.0 | 208 | 0.14 | 78 |
| Donor_5 3. Aliquot H | 3.0 | 2.5 | 0.33 | 3.0 | 138 | 0.14 | 81 |
| Donor_5 3. Aliquot I | 3.0 | 2.4 | 0.28 | 3.3 | 39 | 0.13 | 75 |
| Donor_6 3. Aliquot A | 2.8 | 1.2 | 0.26 | 1.5 | 36 | 0.100 | 43 |
| Donor_6 3. Aliquot B | 2.7 | 1.2 | 0.24 | 1.9 | 36 | 0.10 | 42 |
| Donor_6 3. Aliquot C | 2.8 | 1.2 | 0.24 | 1.8 | 36 | 0.12 | 36 |
| Donor_6 3. Aliquot D | 2.7 | 1.2 | 0.24 | 1.9 | 36 | 0.11 | 43 |
| Donor_6 3. Aliquot E | 2.6 | 1.2 | 0.25 | 2.4 | 39 | 0.12 | 42 |
| Donor_6 3. Aliquot F | 2.7 | 1.3 | 0.25 | 1.6 | 36 | 0.094 | 45 |
| Donor_6 3. Aliquot G | 2.9 | 1.2 | 0.27 | 1.8 | 599 | 0.12 | 52 |
| Donor_6 3. Aliquot H | 2.5 | 1.3 | 0.29 | 1.6 | 36 | 0.11 | 40 |
| Donor_6 3. Aliquot I | 2.5 | 1.1 | 0.26 | 1.5 | 24 | 0.12 | 40 |

FIG. 14A.3

| | Alpha-1 Antitrypsin mg/mL | Adiponectin ug/mL | Alpha-2 Macroglobulin mg/mL | Alpha-Fetoprotein ng/mL | Amphiregulin pg/mL | Apolipoprotein A1 mg/mL | Apolipoprotein CIII ug/mL |
|---|---|---|---|---|---|---|---|
| Least Detectable Dose | 0.011 | 0.20 | 0.061 | 0.43 | 36 | 0.0066 | 2.7 |
| RBM Low Plasma Range | 1.2 | 1.6 | 0.13 | | Pending | 0.19 | 28 |
| RBM High Plasma Range | 3.1 | 14 | 1.0 | 6.7 | Pending | 0.89 | 224 |
| Donor_7_3. Aliquot A | 1.8 | 0.90 | 0.39 | 1.9 | 104 | 0.14 | 50 |
| Donor_7_3. Aliquot B | 1.7 | 0.92 | 0.37 | 2.5 | 36 | 0.14 | 36 |
| Donor_7_3. Aliquot C | 1.9 | 0.83 | 0.38 | 1.3 | 36 | 0.16 | 44 |
| Donor_7_3. Aliquot D | 1.7 | 0.81 | 0.36 | 2.6 | 104 | 0.15 | 41 |
| Donor_7_3. Aliquot E | 1.2 | 0.90 | 0.40 | 2.5 | 36 | 0.12 | 33 |
| Donor_7_3. Aliquot F | 1.8 | 0.90 | 0.45 | 1.5 | 36 | 0.16 | 54 |
| Donor_7_3. Aliquot G | 1.6 | 0.87 | 0.43 | 2.2 | 370 | 0.14 | 43 |
| Donor_7_3. Aliquot H | 1.7 | 0.79 | 0.51 | 1.5 | 36 | 0.15 | 41 |
| Donor_7_3. Aliquot I | 1.8 | 0.82 | 0.38 | 1.9 | 36 | 0.13 | 42 |
| Donor_8_3. Aliquot A | 0.96 | 4.3 | 0.39 | 1.7 | 36 | 0.24 | 57 |
| Donor_8_3. Aliquot B | 0.97 | 4.3 | 0.39 | 1.3 | 36 | 0.28 | 72 |
| Donor_8_3. Aliquot C | 0.96 | 4.1 | 0.40 | 0.53 | 36 | 0.28 | 75 |
| Donor_8_3. Aliquot D | 0.88 | 4.0 | 0.39 | 4.4 | 36 | 0.26 | 55 |
| Donor_8_3. Aliquot E | 0.88 | 4.0 | 0.39 | 3.5 | 127 | 0.24 | 61 |
| Donor_8_3. Aliquot F | 0.99 | 4.5 | 0.46 | 1.6 | 50 | 0.29 | 69 |
| Donor_8_3. Aliquot G | 0.92 | 4.2 | 0.48 | 1.2 | 90 | 0.29 | 58 |
| Donor_8_3. Aliquot H | 1.0 | 4.4 | 0.58 | 1.6 | 36 | 0.25 | 59 |
| Donor_8_3. Aliquot I | 0.94 | 4.2 | 0.40 | 1.2 | 36 | 0.25 | 53 |
| Donor_9_3. Aliquot A | 1.2 | 3.5 | 0.34 | 1.1 | 51 | 0.21 | 39 |
| Donor_9_3. Aliquot B | 1.3 | 3.5 | 0.38 | 1.8 | 51 | 0.22 | 43 |
| Donor_9_3. Aliquot C | 1.3 | 3.6 | 0.41 | 2.0 | 51 | 0.21 | 33 |
| Donor_9_3. Aliquot D | 1.2 | 3.3 | 0.38 | 4.2 | 101 | 0.18 | 34 |
| Donor_9_3. Aliquot E | 1.3 | 3.7 | 0.45 | 3.2 | 42 | 0.20 | 36 |
| Donor_9_3. Aliquot F | 1.2 | 3.8 | 0.40 | 2.1 | 36 | 0.23 | 39 |
| Donor_9_3. Aliquot G | 1.4 | 3.5 | 0.49 | 2.1 | 169 | 0.22 | 42 |
| Donor_9_3. Aliquot H | 1.2 | 3.5 | 0.54 | 2.3 | 78 | 0.19 | 37 |
| Donor_9_3. Aliquot I | 1.3 | 3.6 | 0.36 | 1.3 | 36 | 0.21 | 33 |

FIG. 14A.4

| | Alpha-1 Antitrypsin mg/mL | Adiponectin ug/mL | Alpha-2 Macroglobulin mg/mL | Alpha-Fetoprotein ng/mL | Amphiregulin pg/mL | Apolipoprotein A1 mg/mL | Apolipoprotein CIII ug/mL |
|---|---|---|---|---|---|---|---|
| Least Detectable Dose | 0.011 | 0.20 | 0.061 | 0.43 | 36 | 0.0066 | 2.7 |
| RBM Low Plasma Range | 1.2 | 1.6 | 0.13 | | Pending | 0.19 | 28 |
| RBM High Plasma Range | 3.1 | 14 | 1.0 | 6.7 | Pending | 0.89 | 224 |
| EDTA Plasma | | | | | | | |
| donor #1 plasma | 2.9 | 2.1 | 0.25 | 2.3 | 441 | 0.069 | 34 |
| donor #2 plasma | 3.0 | 6.1 | 0.29 | 1.7 | 36 | 0.11 | 65 |
| donor #3 plasma | 4.7 | 4.2 | 0.36 | 2.9 | 36 | 0.14 | 47 |
| donor #4 plasma | 2.2 | 7.5 | 0.34 | 2.4 | 33 | 0.047 | 14 |
| donor #5 plasma | 4.4 | 3.6 | 0.25 | 3.6 | 36 | 0.12 | 91 |
| donor #6 plasma | 3.7 | 1.7 | 0.24 | 2.1 | 36 | 0.100 | 34 |
| donor #7 plasma | 2.3 | 1.3 | 0.35 | 2.8 | 78 | 0.17 | 52 |
| donor #8 plasma | 1.0 | 5.1 | 0.34 | 1.9 | 72 | 0.25 | 46 |
| donor #9 plasma | 1.9 | 4.8 | 0.37 | 2.1 | 36 | 0.30 | 39 |
| | | | | | | | |
| Stimulations indices | Alpha-1 Antitrypsin | Adiponectin | Alpha-2 Macroglobulin | Alpha-Fetoprotein | Amphiregulin | Apolipoprotein A1 | Apolipoprotein CIII |
| A  patient 1 | 1.0 | 1.0 | 1.1 | 1.1 | 1.1 | 0.9 | 0.9 |
| A  patient 7 | 1.1 | 1.1 | 1.0 | 1.1 | 5.5 | 1.0 | 1.1 |

FIG. 14A.5

| | | Alpha-1 Antitrypsin | Adiponectin | Alpha-2 Macroglobulin | Alpha-Fetoprotein | Amphiregulin | Apolipoprotein A1 | Apolipoprotein CIII |
|---|---|---|---|---|---|---|---|---|
| | | mg/mL | ug/mL | mg/mL | ng/mL | pg/mL | mg/mL | ug/mL |
| | Least Detectable Dose | 0.011 | 0.20 | 0.061 | 0.43 | 36 | 0.0066 | 2.7 |
| | RBM Low Plasma Range | 1.2 | 1.6 | 0.13 | | Pending | 0.19 | 28 |
| | RBM High Plasma Range | 3.1 | 14 | 1.0 | 6.7 | Pending | 0.89 | 224 |
| A | patient 2 | 1.1 | 1.2 | 1.1 | 2.1 | 0.9 | 1.0 | 0.9 |
| A | patient 3 | 1.1 | 1.0 | 1.0 | 1.2 | 1.0 | 1.1 | 1.1 |
| A | patient 5 | 1.0 | 1.1 | 1.0 | 0.9 | 3.2 | 1.0 | 0.9 |
| A | patient 4 | 1.1 | 1.1 | 1.0 | 1.0 | 1.5 | 0.8 | 1.1 |
| A | patient 6 | 1.0 | 1.1 | 1.0 | 1.0 | 2.9 | 1.0 | 1.2 |
| A | NHD 1 | 1.0 | 1.0 | 1.0 | 1.4 | 1.0 | 1.0 | 1.1 |
| A | NHD 2 | 0.9 | 1.0 | 0.9 | 0.8 | 1.4 | 1.0 | 1.2 |
| B | patient 1 | 1.0 | 1.1 | 1.2 | 1.0 | 1.1 | 0.9 | 1.1 |
| B | patient 7 | 1.1 | 1.1 | 1.0 | 1.2 | 2.1 | 1.2 | 1.2 |
| B | patient 2 | 1.1 | 1.0 | 1.0 | 2.0 | 0.9 | 1.0 | 0.9 |
| B | patient 3 | 1.0 | 1.0 | 1.0 | 1.1 | 1.0 | 1.0 | 1.0 |
| B | patient 5 | 1.0 | 1.1 | 1.0 | 1.0 | 4.5 | 1.0 | 1.0 |
| B | patient 4 | 1.0 | 1.1 | 0.9 | 1.3 | 1.5 | 0.9 | 1.0 |
| B | patient 6 | 1.0 | 1.1 | 1.0 | 1.3 | 1.0 | 1.0 | 0.9 |
| B | NHD 1 | 1.0 | 1.0 | 1.0 | 1.1 | 1.0 | 1.1 | 1.4 |
| B | NHD 2 | 1.0 | 1.0 | 1.1 | 1.4 | 1.4 | 1.0 | 1.3 |
| C | patient 1 | 1.0 | 1.0 | 1.1 | 0.9 | 0.2 | 1.0 | 1.0 |
| C | patient 7 | 1.1 | 1.1 | 1.0 | 0.7 | 1.5 | 1.1 | 1.2 |
| C | patient 2 | 1.1 | 1.0 | 1.0 | 1.5 | 0.9 | 1.0 | 1.0 |
| C | patient 3 | 1.0 | 1.0 | 1.1 | 1.0 | 1.1 | 1.0 | 0.9 |
| C | patient 5 | 1.1 | 1.1 | 1.1 | 0.8 | 1.3 | 1.1 | 1.0 |
| C | patient 4 | 1.1 | 1.1 | 0.9 | 1.2 | 1.5 | 1.0 | 0.9 |
| C | patient 6 | 1.0 | 1.0 | 1.0 | 0.7 | 1.0 | 1.2 | 1.0 |
| C | NHD 1 | 1.0 | 1.0 | 1.0 | 0.4 | 1.0 | 1.1 | 1.4 |
| C | NHD 2 | 1.0 | 1.0 | 1.1 | 1.5 | 1.4 | 1.0 | 1.0 |

FIG. 14A.6

| | | Alpha-1 Antitrypsin mg/mL | Adiponectin ug/mL | Alpha-2 Macroglobulin mg/mL | Alpha-Fetoprotein ng/mL | Amphiregulin pg/mL | Apolipoprotein A1 mg/mL | Apolipoprotein CIII ug/mL |
|---|---|---|---|---|---|---|---|---|
| | Least Detectable Dose | 0.011 | 0.20 | 0.061 | 0.43 | 36 | 0.0066 | 2.7 |
| | RBM Low Plasma Range | 1.2 | 1.6 | 0.13 | | Pending | 0.19 | 28 |
| | RBM High Plasma Range | 3.1 | 14 | 1.0 | 6.7 | Pending | 0.89 | 224 |
| D | patient 1 | 1.1 | 1.1 | 1.2 | 1.1 | 1.0 | 1.0 | 1.0 |
| D | patient 7 | 1.1 | 1.1 | 1.0 | 1.8 | 4.3 | 0.9 | 0.9 |
| D | patient 2 | 1.0 | 1.1 | 1.0 | 2.5 | 2.5 | 1.0 | 0.9 |
| D | patient 3 | 1.1 | 1.0 | 1.0 | 1.9 | 1.0 | 0.8 | 1.0 |
| D | patient 5 | 1.1 | 1.1 | 1.0 | 1.2 | 4.0 | 1.1 | 1.0 |
| D | patient 4 | 1.1 | 1.1 | 0.9 | 1.3 | 1.5 | 1.0 | 1.1 |
| D | patient 6 | 1.0 | 1.0 | 0.9 | 1.3 | 2.9 | 1.1 | 1.0 |
| D | NHD 1 | 0.9 | 0.9 | 1.0 | 3.6 | 1.0 | 1.0 | 1.0 |
| D | NHD 2 | 0.9 | 0.9 | 1.1 | 3.2 | 2.8 | 0.9 | 1.0 |
| E | patient 1 | 1.0 | 1.0 | 1.0 | 1.0 | 1.1 | 1.0 | 0.9 |
| E | patient 7 | 1.1 | 1.1 | 1.0 | 1.3 | 1.6 | 0.9 | 1.0 |
| E | patient 2 | 1.1 | 1.0 | 1.1 | 2.7 | 3.0 | 1.0 | 0.9 |
| E | patient 3 | 0.9 | 1.0 | 0.9 | 1.4 | 1.0 | 0.9 | 0.7 |
| E | patient 5 | 1.0 | 1.1 | 1.0 | 1.2 | 4.8 | 1.1 | 0.9 |
| E | patient 4 | 1.1 | 1.1 | 1.0 | 1.7 | 1.6 | 1.0 | 1.0 |
| E | patient 6 | 0.7 | 1.1 | 1.0 | 1.3 | 1.0 | 0.9 | 0.8 |
| E | NHD 1 | 0.9 | 0.9 | 1.0 | 2.9 | 3.5 | 1.0 | 1.1 |
| E | NHD 2 | 1.0 | 1.0 | 1.2 | 2.4 | 1.2 | 1.0 | 1.1 |
| F | patient 1 | 1.0 | 1.0 | 2.5 | 0.9 | 1.0 | 0.9 | 1.0 |
| F | patient 7 | 1.1 | 1.0 | 2.2 | 1.1 | 1.5 | 0.8 | 1.2 |
| F | patient 2 | 1.0 | 1.0 | 2.0 | 1.9 | 1.5 | 0.9 | 1.0 |
| F | patient 3 | 1.0 | 1.0 | 2.4 | 0.9 | 1.0 | 1.0 | 1.2 |
| F | patient 5 | 1.0 | 1.1 | 1.7 | 0.7 | 0.9 | 1.0 | 1.1 |
| F | patient 4 | 1.1 | 1.1 | 1.0 | 1.1 | 1.5 | 0.8 | 1.1 |
| F | patient 6 | 1.0 | 1.1 | 1.2 | 0.8 | 1.0 | 1.2 | 1.3 |

FIG. 14A.7

|  |  | Alpha-1 Antitrypsin mg/mL | Adiponectin ug/mL | Alpha-2 Macroglobulin mg/mL | Alpha-Fetoprotein ng/mL | Amphiregulin pg/mL | Apolipoprotein A1 mg/mL | Apolipoprotein CIII ug/mL |
|---|---|---|---|---|---|---|---|---|
|  | Least Detectable Dose | 0.011 | 0.20 | 0.061 | 0.43 | 36 | 0.0066 | 2.7 |
|  | RBM Low Plasma Range | 1.2 | 1.6 | 0.13 | | Pending | 0.19 | 28 |
|  | RBM High Plasma Range | 3.1 | 14 | 1.0 | 6.7 | Pending | 0.89 | 224 |
| F | NHD 1 | 1.1 | 1.1 | 1.1 | 1.3 | 1.4 | 1.2 | 1.3 |
| F | NHD 2 | 0.9 | 1.1 | 1.1 | 1.6 | 1.0 | 1.1 | 1.2 |
| G | patient 1 | 1.1 | 1.0 | 1.2 | 1.0 | 1.0 | 0.9 | 1.0 |
| G | patient 7 | 1.1 | 1.1 | 1.1 | 0.9 | 24.8 | 0.9 | 1.2 |
| G | patient 2 | 1.1 | 1.1 | 1.0 | 1.1 | 2.5 | 1.1 | 1.1 |
| G | patient 3 | 1.0 | 1.0 | 1.2 | 1.1 | 2.1 | 0.9 | 0.9 |
| G | patient 5 | 1.0 | 1.1 | 1.0 | 0.9 | 5.3 | 1.2 | 1.0 |
| G | patient 4 | 1.1 | 1.1 | 1.1 | 1.3 | 24.9 | 1.0 | 1.3 |
| G | patient 6 | 0.9 | 1.1 | 1.1 | 1.2 | 10.3 | 1.1 | 1.0 |
| G | NHD 1 | 1.0 | 1.0 | 1.2 | 1.0 | 2.5 | 1.2 | 1.1 |
| G | NHD 2 | 1.0 | 1.0 | 1.3 | 1.6 | 4.7 | 1.1 | 1.3 |
| H | patient 1 | 1.0 | 1.0 | 1.6 | 1.1 | 0.1 | 0.8 | 0.8 |
| H | patient 7 | 1.1 | 1.1 | 1.1 | 1.0 | 1.5 | 0.9 | 1.1 |
| H | patient 2 | 1.0 | 1.0 | 1.2 | 1.3 | 0.9 | 1.1 | 1.0 |
| H | patient 3 | 1.0 | 1.0 | 1.6 | 1.1 | 2.1 | 1.0 | 0.9 |
| H | patient 5 | 1.0 | 1.0 | 1.2 | 0.9 | 3.5 | 1.1 | 1.1 |
| H | patient 4 | 1.0 | 1.1 | 1.1 | 1.1 | 1.5 | 0.9 | 1.0 |
| H | patient 6 | 0.9 | 1.0 | 1.3 | 0.8 | 1.0 | 1.2 | 1.0 |
| H | NHD 1 | 1.1 | 1.0 | 1.4 | 1.3 | 1.0 | 1.0 | 1.1 |
| H | NHD 2 | 0.9 | 1.0 | 1.5 | 1.7 | 2.2 | 0.9 | 1.1 |
| I | patient 1 | 1.0 | 1.0 | 1.0 | 1.0 | 1.0 | 1.0 | 1.0 |
| I | patient 7 | 1.0 | 1.0 | 1.0 | 1.0 | 1.0 | 1.0 | 1.0 |
| I | patient 2 | 1.0 | 1.0 | 1.0 | 1.0 | 1.0 | 1.0 | 1.0 |
| I | patient 3 | 1.0 | 1.0 | 1.0 | 1.0 | 1.0 | 1.0 | 1.0 |

FIG. 14A.8

| | Alpha-1 Antitrypsin mg/mL | Adiponectin ug/mL | Alpha-2 Macroglobulin mg/mL | Alpha-Fetoprotein ng/mL | Amphiregulin pg/mL | Apolipoprotein A1 mg/mL | Apolipoprotein CIII ug/mL |
|---|---|---|---|---|---|---|---|
| Least Detectable Dose | 0.011 | 0.20 | 0.061 | 0.43 | 36 | 0.0066 | 2.7 |
| RBM Low Plasma Range | 1.2 | 1.6 | 0.13 | | Pending | 0.19 | 28 |
| RBM High Plasma Range | 3.1 | 14 | 1.0 | 6.7 | Pending | 0.89 | 224 |
| patient 5 | 1.0 | 1.0 | 1.0 | 1.0 | 1.0 | 1.0 | 1.0 |
| patient 4 | 1.0 | 1.0 | 1.0 | 1.0 | 1.0 | 1.0 | 1.0 |
| patient 6 | 1.0 | 1.0 | 1.0 | 1.0 | 1.0 | 1.0 | 1.0 |
| NHD 1 | 1.0 | 1.0 | 1.0 | 1.0 | 1.0 | 1.0 | 1.0 |
| NHD 2 | 1.0 | 1.0 | 1.0 | 1.0 | 1.0 | 1.0 | 1.0 |
| Messwert > ULD | | | | | | | |
| SI > 1,3 | | | | | | | |
| SI 0,7-1,3 | | | | | | | |
| SI 0-0,7 | | | | | | | |

FIG. 14B.1

| | Apolipoprotein H ug/mL | Beta-2 Microglobulin ug/mL | Brain-Derived Neurotrophic Factor ng/mL | Complement 3 mg/mL | Cancer Antigen 125 U/mL | Cancer Antigen 19-9 U/mL | Calcitonin pg/mL |
|---|---|---|---|---|---|---|---|
| Least Detectable Dose | 8.8 | 0.013 | 0.029 | 0.0053 | 4.2 | 0.25 | 6.0 |
| RBM Low Plasma Range | 131 | 1.2 | 0.32 | 0.76 | | | |
| RBM High Plasma Range | 430 | 6.2 | 16 | 2.1 | 12 | 9.2 | 12 |
| Samples | | | | | | | |
| Donor_1 3. Aliquot A | 138 | 17 | 2.4 | 0.73 | 132 | 28 | 36 |
| Donor_1 3. Aliquot B | 148 | 15 | 3.3 | 0.71 | 123 | 28 | 32 |
| Donor_1 3. Aliquot C | 143 | 16 | 1.6 | 0.71 | 141 | 13 | 34 |
| Donor_1 3. Aliquot D | 150 | 16 | 2.6 | 0.71 | 157 | 28 | 37 |
| Donor_1 3. Aliquot E | 141 | 16 | 2.3 | 0.69 | 135 | 28 | 36 |
| Donor_1 3. Aliquot F | 142 | 14 | 1.3 | 1.5 | 128 | 24 | 31 |
| Donor_1 3. Aliquot G | 151 | 16 | 0.048 | 0.77 | 140 | 32 | 32 |
| Donor_1 3. Aliquot H | 141 | 15 | 3.4 | 1.2 | 143 | 12 | 31 |
| Donor_1 3. Aliquot I | 150 | 16 | 2.8 | 0.71 | 125 | 28 | 33 |
| Donor_2 3. Aliquot A | 152 | 20 | 3.4 | 0.92 | 121 | 476 | 29 |
| Donor_2 3. Aliquot B | 143 | >24 | 4.6 | 0.93 | 125 | 510 | 31 |
| Donor_2 3. Aliquot C | 154 | 23 | 1.3 | 0.89 | 119 | 408 | 24 |
| Donor_2 3. Aliquot D | 142 | 19 | 2.5 | 0.92 | 197 | 468 | 33 |
| Donor_2 3. Aliquot E | 154 | 20 | 2.3 | 0.94 | 158 | 488 | 31 |
| Donor_2 3. Aliquot F | 152 | 19 | 1.6 | 2.3 | 123 | 413 | 30 |
| Donor_2 3. Aliquot G | 153 | 21 | 0.49 | 0.98 | 138 | 495 | 20 |
| Donor_2 3. Aliquot H | 148 | 21 | 2.3 | 1.3 | 106 | 459 | 29 |
| Donor_2 3. Aliquot I | 141 | 19 | 1.8 | 0.90 | 102 | 447 | 26 |
| Donor_3 3. Aliquot A | 150 | 2.6 | 3.0 | 0.68 | 35 | 3.3 | 6 |
| Donor_3 3. Aliquot B | 144 | 2.3 | 4.5 | 0.70 | 33 | 3.6 | 5.1 |
| Donor_3 3. Aliquot C | 153 | 2.4 | 2.9 | 0.73 | 35 | 3.6 | 6 |
| Donor_3 3. Aliquot D | 149 | 2.4 | 3.4 | 0.73 | 87 | 3.3 | 6 |
| Donor_3 3. Aliquot E | 157 | 2.5 | 3.8 | 0.77 | 74 | 3.6 | 7.3 |
| Donor_3 3. Aliquot F | 148 | 2.2 | 1.6 | 1.2 | 39 | 4.1 | 6 |
| Donor_3 3. Aliquot G | 149 | 2.3 | 0.047 | 0.72 | 29 | 4.6 | 6 |
| Donor_3 3. Aliquot H | 144 | 2.3 | 2.3 | 1.1 | 27 | 3.2 | 6 |
| Donor_3 3. Aliquot I | 150 | 2.2 | 2.2 | 0.74 | 31 | 2.8 | 6 |

FIG. 14B.2

| | Apolipoprotein H ug/mL | Beta-2 Microglobulin ug/mL | Brain-Derived Neurotrophic Factor ng/mL | Complement 3 mg/mL | Cancer Antigen 125 U/mL | Cancer Antigen 19-9 U/mL | Calcitonin pg/mL |
|---|---|---|---|---|---|---|---|
| Least Detectable Dose | 8.8 | 0.013 | 0.029 | 0.0053 | 4.2 | 0.25 | 6.0 |
| RBM Low Plasma Range | 131 | 1.2 | 0.32 | 0.76 | | | |
| RBM High Plasma Range | 430 | 6.2 | 16 | 2.1 | 12 | 9.2 | 12 |
| Donor_4_3. Aliquot A | 105 | 7.6 | 2.0 | 0.45 | 512 | 15 | 18 |
| Donor_4_3. Aliquot B | 96 | 7.2 | 2.8 | 0.41 | 495 | 16 | 20 |
| Donor_4_3. Aliquot C | 102 | 8.0 | 0.49 | 0.45 | 462 | 15 | 15 |
| Donor_4_3. Aliquot D | 102 | 7.7 | 1.6 | 0.43 | 542 | 16 | 19 |
| Donor_4_3. Aliquot E | 93 | 8.3 | 1.0 | 0.44 | 520 | 20 | 16 |
| Donor_4_3. Aliquot F | 93 | 8.5 | 0.88 | 0.80 | 465 | 16 | 15 |
| Donor_4_3. Aliquot G | 100 | 8.1 | 0.049 | 0.43 | 462 | 17 | 10 |
| Donor_4_3. Aliquot H | 91 | 8.2 | 0.53 | 0.69 | 509 | 15 | 17 |
| Donor_4_3. Aliquot I | 99 | 8.0 | 1.2 | 0.43 | 494 | 15 | 17 |
| Donor_5_3. Aliquot A | 253 | 12 | 5.8 | 0.72 | 21 | 8.8 | 105 |
| Donor_5_3. Aliquot B | 266 | 13 | 4.5 | 0.76 | 21 | 9.2 | 97 |
| Donor_5_3. Aliquot C | 265 | 13 | 2.3 | 0.77 | 21 | 9.9 | 74 |
| Donor_5_3. Aliquot D | 263 | 13 | 2.9 | 0.78 | 87 | 10 | 92 |
| Donor_5_3. Aliquot E | 257 | 15 | 4.5 | 0.73 | 74 | 10 | 90 |
| Donor_5_3. Aliquot F | 238 | 11 | 2.3 | 0.67 | 12 | 7.1 | 86 |
| Donor_5_3. Aliquot G | 246 | 12 | 0.16 | 1.2 | 20 | 8.6 | 67 |
| Donor_5_3. Aliquot H | 245 | 13 | 4.8 | 0.80 | 16 | 8.9 | 101 |
| Donor_5_3. Aliquot I | 250 | 11 | 3.1 | 1.1 | 17 | 8.0 | 94 |
| Donor_6_3. Aliquot A | 141 | 1.2 | 4.4 | 0.73 | 29 | 3.7 | 6 |
| Donor_6_3. Aliquot B | 148 | 1.1 | 3.4 | 0.77 | 42 | 2.6 | 6 |
| Donor_6_3. Aliquot C | 141 | 1.2 | 1.1 | 0.72 | 24 | 4.4 | 6 |
| Donor_6_3. Aliquot D | 143 | 1.2 | 3.9 | 0.75 | 82 | 3.9 | 6 |
| Donor_6_3. Aliquot E | 131 | 1.2 | 2.1 | 0.67 | 85 | 3.5 | 6 |
| Donor_6_3. Aliquot F | 143 | 1.2 | 1.9 | 0.71 | 27 | 2.9 | 6 |
| Donor_6_3. Aliquot G | 152 | 1.2 | 0.064 | 0.78 | 28 | 5.2 | 6 |
| Donor_6_3. Aliquot H | 131 | 1.1 | 3.1 | 1.1 | 23 | 3.7 | 6 |
| Donor_6_3. Aliquot I | 134 | 1.1 | 1.7 | 0.68 | 29 | 3.0 | 6 |

FIG. 14B.3

| | Apolipoprotein H ug/mL | Beta-2 Microglobulin ug/mL | Brain-Derived Neurotrophic Factor ng/mL | Complement 3 mg/mL | Cancer Antigen 125 U/mL | Cancer Antigen 19-9 U/mL | Calcitonin pg/mL |
|---|---|---|---|---|---|---|---|
| Least Detectable Dose | 8.8 | 0.013 | 0.029 | 0.0053 | 4.2 | 0.25 | 6.0 |
| RBM Low Plasma Range | 131 | 1.2 | 0.32 | 0.76 | | | |
| RBM High Plasma Range | 430 | 6.2 | 16 | 2.1 | 12 | 9.2 | 12 |
| Donor_7_3. Aliquot A | 180 | 2.0 | 2.8 | 0.67 | 53 | 5.3 | 1.5 |
| Donor_7_3. Aliquot B | 183 | 2.0 | 3.1 | 0.68 | 48 | 5.1 | 6 |
| Donor_7_3. Aliquot C | 183 | 2.1 | 2.2 | 0.73 | 39 | 5.1 | 6 |
| Donor_7_3. Aliquot D | 169 | 2.0 | 2.9 | 0.66 | 91 | 4.8 | 6 |
| Donor_7_3. Aliquot E | 138 | 2.1 | 2.3 | 0.51 | 53 | 5.2 | 6 |
| Donor_7_3. Aliquot F | 190 | 1.9 | 1.2 | 0.72 | 40 | 4.7 | 6 |
| Donor_7_3. Aliquot G | 161 | 1.9 | 0.043 | 0.74 | 38 | 7.8 | 6 |
| Donor_7_3. Aliquot H | 173 | 1.9 | 1.6 | 1.1 | 34 | 5.2 | 6 |
| Donor_7_3. Aliquot I | 173 | 1.9 | 1.6 | 0.67 | 39 | 3.7 | 3.3 |
| Donor_8_3. Aliquot A | 117 | 1.2 | 3.3 | 0.45 | 5.6 | 4.9 | 6 |
| Donor_8_3. Aliquot B | 117 | 1.2 | 5.3 | 0.49 | 9.0 | 3.9 | 6 |
| Donor_8_3. Aliquot C | 119 | 1.2 | 3.2 | 0.43 | 4.4 | 3.9 | 6 |
| Donor_8_3. Aliquot D | 111 | 1.2 | 4.5 | 0.44 | 164 | 5.5 | 4.6 |
| Donor_8_3. Aliquot E | 113 | 1.2 | 6.0 | 0.43 | 136 | 5.1 | 6.5 |
| Donor_8_3. Aliquot F | 121 | 1.3 | 2.3 | 0.51 | 16 | 4.5 | 6 |
| Donor_8_3. Aliquot G | 111 | 1.2 | 0.060 | 0.44 | 9.0 | 5.2 | 6 |
| Donor_8_3. Aliquot H | 127 | 1.2 | 6.3 | 0.72 | 13 | 4.0 | 6 |
| Donor_8_3. Aliquot I | 122 | 1.2 | 6.1 | 0.46 | 15 | 3.6 | 6 |
| Donor_9_3. Aliquot A | 101 | 0.83 | 2.5 | 0.39 | 14 | 3.0 | 6 |
| Donor_9_3. Aliquot B | 104 | 0.79 | 3.5 | 0.39 | 11 | 3.3 | 6 |
| Donor_9_3. Aliquot C | 96 | 0.93 | 1.2 | 0.39 | 21 | 3.3 | 6 |
| Donor_9_3. Aliquot D | 99 | 0.87 | 3.7 | 0.37 | 140 | 6.0 | 3.9 |
| Donor_9_3. Aliquot E | 105 | 0.88 | 2.6 | 0.40 | 104 | 3.7 | 3.2 |
| Donor_9_3. Aliquot F | 103 | 0.90 | 1.9 | 0.39 | 12 | 2.6 | 6 |
| Donor_9_3. Aliquot G | 113 | 0.86 | 0.21 | 0.41 | 14 | 3.1 | 0.91 |
| Donor_9_3. Aliquot H | 97 | 0.83 | 4.3 | 0.64 | 4.9 | 3.1 | 6 |
| Donor_9_3. Aliquot I | 97 | 0.82 | 3.5 | 0.39 | 8.3 | 2.6 | 6 |

FIG. 14B.4

| | Apolipoprotein H ug/mL | Beta-2 Microglobulin ug/mL | Brain-Derived Neurotrophic Factor ng/mL | Complement 3 mg/mL | Cancer Antigen 125 U/mL | Cancer Antigen 19-9 U/mL | Calcitonin pg/mL |
|---|---|---|---|---|---|---|---|
| Least Detectable Dose | 8.8 | 0.013 | 0.029 | 0.0053 | 4.2 | 0.25 | 6.0 |
| RBM Low Plasma Range | 131 | 1.2 | 0.32 | 0.76 | 12 | 9.2 | 12 |
| RBM High Plasma Range | 430 | 6.2 | 16 | 2.1 | | | |
| EDTA Plasma | | | | | | | |
| donor #1 plasma | 127 | 11 | 1.2 | 0.59 | 60 | 7.6 | 40 |
| donor #2 plasma | 166 | 19 | 0.40 | 0.98 | 63 | 241 | 51 |
| donor #3 plasma | 193 | 2.5 | 0.89 | 0.90 | 28 | 2.1 | 8.9 |
| donor #4 plasma | 106 | 9.1 | 0.35 | 0.47 | 431 | 10 | 36 |
| donor #5 plasma | 316 | 14 | 3.6 | 0.88 | 18 | 4.2 | 164 |
| donor #6 plasma | 163 | 1.1 | 1.5 | 0.87 | 18 | 1.6 | 3.7 |
| donor #7 plasma | 214 | 2.3 | 1.4 | 0.80 | 30 | 6.0 | 5.0 |
| donor #8 plasma | 113 | 1.1 | 3.1 | 0.42 | 16 | 7.5 | 6 |
| donor #9 plasma | 147 | 0.88 | 0.21 | 0.55 | 4.2 | 6.3 | 6 |
| Stimulations indices | Apolipoprotein H | Beta-2 Microglobulin | Brain-Derived Neurotrophic Factor | Complement 3 | Cancer Antigen 125 | Cancer Antigen 19-9 | Calcitonin |
| A patient 1 | 0.9 | 1.1 | 0.9 | 1.0 | 1.1 | 1.0 | 1.1 |
| A patient 7 | 1.1 | 1.0 | 1.9 | 1.0 | 1.2 | 1.1 | 1.1 |

FIG. 14B.5

| | | Apolipoprotein H ug/mL | Beta-2 Microglobulin ug/mL | Brain-Derived Neurotrophic Factor ng/mL | Complement 3 mg/mL | Cancer Antigen 125 U/mL | Cancer Antigen 19-9 U/mL | Calcitonin pg/mL |
|---|---|---|---|---|---|---|---|---|
| | Least Detectable Dose | 8.8 | 0.013 | 0.029 | 0.0053 | 4.2 | 0.25 | 6.0 |
| | RBM Low Plasma Range | 131 | 1.2 | 0.32 | 0.76 | | | |
| | RBM High Plasma Range | 430 | 6.2 | 16 | 2.1 | 12 | 9.2 | 12 |
| A | patient 2 | 1.0 | 1.1 | 1.4 | 0.9 | 1.1 | 1.2 | 1.0 |
| A | patient 3 | 1.1 | 0.9 | 1.6 | 1.0 | 1.0 | 1.0 | 1.1 |
| A | patient 5 | 1.0 | 1.1 | 1.9 | 1.0 | 1.2 | 1.1 | 1.1 |
| A | patient 4 | 1.1 | 1.1 | 2.6 | 1.1 | 1.0 | 1.2 | 1.0 |
| A | patient 6 | 1.0 | 1.1 | 1.7 | 1.0 | 1.4 | 1.4 | 0.4 |
| A | NHD 1 | 1.0 | 1.0 | 0.5 | 1.0 | 0.4 | 1.4 | 1.0 |
| A | NHD 2 | 1.0 | 1.0 | 0.7 | 1.0 | 1.7 | 1.1 | 1.0 |
| B | patient 1 | 1.0 | 1.0 | 1.2 | 1.0 | 1.0 | 1.0 | 1.0 |
| B | patient 7 | 1.0 | 1.2 | 2.6 | 1.0 | 1.2 | 1.1 | 1.2 |
| B | patient 2 | 1.0 | 1.0 | 2.1 | 0.9 | 1.1 | 1.3 | 0.9 |
| B | patient 3 | 1.0 | 0.9 | 2.2 | 0.9 | 1.0 | 1.1 | 1.2 |
| B | patient 5 | 1.1 | 1.1 | 1.5 | 1.1 | 1.3 | 1.2 | 1.0 |
| B | patient 4 | 1.1 | 1.1 | 2.0 | 1.1 | 1.4 | 0.9 | 1.0 |
| B | patient 6 | 1.1 | 1.1 | 1.9 | 1.0 | 1.2 | 1.4 | 1.8 |
| B | NHD 1 | 1.0 | 1.0 | 0.9 | 1.1 | 0.6 | 1.1 | 1.0 |
| B | NHD 2 | 1.1 | 1.0 | 1.0 | 1.1 | 1.3 | 1.3 | 1.0 |
| C | patient 1 | 1.0 | 1.0 | 0.6 | 1.0 | 1.1 | 0.5 | 1.0 |
| C | patient 7 | 1.1 | 1.2 | 0.7 | 1.0 | 1.2 | 0.9 | 0.9 |
| C | patient 2 | 1.0 | 1.1 | 1.3 | 1.0 | 1.1 | 1.3 | 1.0 |
| C | patient 3 | 1.0 | 1.0 | 0.4 | 1.0 | 0.9 | 1.0 | 0.9 |
| C | patient 5 | 1.1 | 1.1 | 0.7 | 1.1 | 1.2 | 1.2 | 0.8 |
| C | patient 4 | 1.1 | 1.1 | 0.6 | 1.1 | 0.8 | 1.4 | 1.0 |
| C | patient 6 | 1.1 | 1.1 | 1.3 | 1.1 | 1.0 | 1.4 | 1.8 |
| C | NHD 1 | 1.0 | 1.0 | 0.5 | 0.9 | 0.3 | 1.1 | 1.0 |
| C | NHD 2 | 1.0 | 1.1 | 0.3 | 1.0 | 2.5 | 1.3 | 1.0 |

Note: Beta-2 Microglobulin for RBM High Plasma Range shows #VALUE!

FIG. 14B.6

| | Apolipoprotein H ug/mL | Beta-2 Microglobulin ug/mL | Brain-Derived Neurotrophic Factor ng/mL | Complement 3 mg/mL | Cancer Antigen 125 U/mL | Cancer Antigen 19-9 U/mL | Calcitonin pg/mL |
|---|---|---|---|---|---|---|---|
| Least Detectable Dose | 8.8 | 0.013 | 0.029 | 0.0053 | 4.2 | 0.25 | 6.0 |
| RBM Low Plasma Range | 131 | 1.2 | 0.32 | 0.76 | 12 | | |
| RBM High Plasma Range | 430 | 6.2 | 16 | 2.1 | | 9.2 | 12 |
| D patient 1 | 1.0 | 1.0 | 0.9 | 1.0 | 1.3 | 1.0 | 1.1 |
| D patient 7 | 1.0 | 1.0 | 1.4 | 1.0 | 1.9 | 1.0 | 1.3 |
| D patient 2 | 1.0 | 1.1 | 1.6 | 1.0 | 2.8 | 1.2 | 1.0 |
| D patient 3 | 1.0 | 1.0 | 1.3 | 1.0 | 1.1 | 1.0 | 1.1 |
| D patient 5 | 1.1 | 1.2 | 0.9 | 1.1 | 5.1 | 1.3 | 1.0 |
| D patient 4 | 1.1 | 1.1 | 2.3 | 1.1 | 2.8 | 1.3 | 1.0 |
| D patient 6 | 1.0 | 1.1 | 1.7 | 1.0 | 2.4 | 1.3 | 1.8 |
| D NHD 1 | 0.9 | 1.0 | 0.7 | 1.0 | 11.2 | 1.5 | 0.8 |
| D NHD 2 | 1.0 | 1.1 | 1.1 | 1.0 | 16.9 | 2.3 | 0.6 |
| E patient 1 | 0.9 | 1.0 | 0.8 | 1.0 | 1.1 | 1.0 | 1.1 |
| E patient 7 | 1.1 | 1.1 | 1.3 | 1.1 | 1.5 | 1.1 | 1.2 |
| E patient 2 | 1.0 | 1.1 | 1.7 | 1.0 | 2.4 | 1.3 | 1.2 |
| E patient 3 | 0.9 | 1.0 | 0.8 | 1.0 | 1.1 | 1.3 | 0.9 |
| E patient 5 | 1.0 | 1.3 | 1.5 | 1.0 | 4.4 | 1.3 | 1.0 |
| E patient 4 | 1.0 | 1.1 | 1.3 | 1.0 | 2.9 | 1.2 | 1.0 |
| E patient 6 | 0.8 | 1.1 | 1.4 | 0.8 | 1.4 | 1.4 | 1.8 |
| E NHD 1 | 0.9 | 1.0 | 1.0 | 0.9 | 9.3 | 1.4 | 1.1 |
| E NHD 2 | 1.1 | 1.1 | 0.7 | 1.0 | 12.5 | 1.4 | 0.5 |
| F patient 1 | 0.9 | 0.9 | 0.4 | 2.0 | 1.0 | 0.9 | 0.9 |
| F patient 7 | 1.1 | 1.0 | 0.9 | 2.5 | 1.2 | 0.9 | 1.1 |
| F patient 2 | 1.0 | 1.0 | 0.7 | 1.6 | 1.3 | 1.5 | 1.0 |
| F patient 3 | 0.9 | 1.0 | 0.7 | 1.9 | 0.9 | 1.0 | 0.9 |
| F patient 5 | 1.0 | 1.0 | 0.8 | 1.7 | 0.7 | 0.9 | 0.9 |
| F patient 4 | 1.1 | 1.1 | 1.1 | 1.1 | 0.9 | 1.0 | 1.0 |
| F patient 6 | 1.1 | 1.0 | 0.7 | 1.1 | 1.0 | 1.3 | 1.8 |

FIG. 14B.7

| | Apolipoprotein H ug/mL | Beta-2 Microglobulin ug/mL | Brain-Derived Neurotrophic Factor ng/mL | Complement 3 mg/mL | Cancer Antigen 125 U/mL | Cancer Antigen 19-9 U/mL | Calcitonin pg/mL |
|---|---|---|---|---|---|---|---|
| Least Detectable Dose | 8.8 | 0.013 | 0.029 | 0.0053 | 4.2 | 0.25 | 6.0 |
| RBM Low Plasma Range | 131 | 1.2 | 0.32 | 0.76 | 12 | 9.2 | 12 |
| RBM High Plasma Range | 430 | 6.2 | 16 | 2.1 | | | |
| F NHD 1 | 1.0 | 1.1 | 0.4 | 1.1 | 1.1 | 1.2 | 1.0 |
| F NHD 2 | 1.1 | 1.1 | 0.5 | 1.0 | 1.4 | 1.0 | 1.0 |
| G patient 1 | 1.0 | 1.0 | 0.0 | 1.1 | 1.1 | 1.2 | 1.0 |
| G patient 7 | 1.1 | 1.1 | 0.3 | 1.1 | 1.4 | 1.1 | 0.8 |
| G patient 2 | 1.1 | 1.1 | 0.0 | 1.0 | 0.9 | 1.7 | 1.0 |
| G patient 3 | 1.0 | 1.0 | 0.0 | 1.0 | 0.9 | 1.1 | 0.6 |
| G patient 5 | 1.0 | 1.1 | 0.1 | 1.1 | 1.2 | 1.1 | 0.7 |
| G patient 4 | 1.1 | 1.1 | 0.0 | 1.1 | 1.0 | 1.7 | 1.0 |
| G patient 6 | 0.9 | 1.0 | 0.0 | 1.1 | 1.0 | 2.1 | 1.8 |
| G NHD 1 | 0.9 | 1.0 | 0.0 | 0.9 | 0.6 | 1.4 | 1.0 |
| G NHD 2 | 1.2 | 1.0 | 0.1 | 1.0 | 1.7 | 1.2 | 0.2 |
| H patient 1 | 0.9 | 0.9 | 1.2 | 1.6 | 1.1 | 0.4 | 0.9 |
| H patient 7 | 1.0 | 1.1 | 1.3 | 1.4 | 1.0 | 1.0 | 1.1 |
| H patient 2 | 1.0 | 1.0 | 1.1 | 1.5 | 0.9 | 1.1 | 1.0 |
| H patient 3 | 0.9 | 1.0 | 0.4 | 1.6 | 1.0 | 1.0 | 1.0 |
| H patient 5 | 1.0 | 1.1 | 1.6 | 1.5 | 1.0 | 1.1 | 1.1 |
| H patient 4 | 1.0 | 1.0 | 1.8 | 1.6 | 0.8 | 1.2 | 1.0 |
| H patient 6 | 1.0 | 1.0 | 1.0 | 1.7 | 0.9 | 1.4 | 1.8 |
| H NHD 1 | 1.0 | 1.0 | 1.0 | 1.6 | 0.9 | 1.1 | 1.0 |
| H NHD 2 | 1.0 | 1.0 | 1.2 | 1.6 | 0.6 | 1.2 | 1.0 |
| I patient 1 | 1.0 | 1.0 | 1.0 | 1.0 | 1.0 | 1.0 | 1.0 |
| I patient 7 | 1.0 | 1.0 | 1.0 | 1.0 | 1.0 | 1.0 | 1.0 |
| I patient 2 | 1.0 | 1.0 | 1.0 | 1.0 | 1.0 | 1.0 | 1.0 |
| I patient 3 | 1.0 | 1.0 | 1.0 | 1.0 | 1.0 | 1.0 | 1.0 |

FIG. 14B.8

| | Apolipoprotein H ug/mL | Beta-2 Microglobulin ug/mL | Brain-Derived Neurotrophic Factor ng/mL | Complement 3 mg/mL | Cancer Antigen 125 U/mL | Cancer Antigen 19-9 U/mL | Calcitonin pg/mL |
|---|---|---|---|---|---|---|---|
| Least Detectable Dose | 8.8 | 0.013 | 0.029 | 0.0053 | 4.2 | 0.25 | 6.0 |
| RBM Low Plasma Range | 131 | 1.2 | 0.32 | 0.76 | | | |
| RBM High Plasma Range | 430 | 6.2 | 16 | 2.1 | 12 | 9.2 | 12 |
| patient 5 | 1.0 | 1.0 | 1.0 | 1.0 | 1.0 | 1.0 | 1.0 |
| patient 4 | 1.0 | 1.0 | 1.0 | 1.0 | 1.0 | 1.0 | 1.0 |
| patient 6 | 1.0 | 1.0 | 1.0 | 1.0 | 1.0 | 1.0 | 1.0 |
| NHD 1 | 1.0 | 1.0 | 1.0 | 1.0 | 1.0 | 1.0 | 1.0 |
| NHD 2 | 1.0 | 1.0 | 1.0 | 1.0 | 1.0 | 1.0 | 1.0 |

Messwert > ULD

|  | CD40 ng/mL | CD40 Ligand ng/mL | Carcinoembryonic Antigen ng/mL | Creatine Kinase-MB ng/mL | C Reactive Protein ug/mL | EGF pg/mL | ENA-78 ng/mL |
|---|---|---|---|---|---|---|---|
| Least Detectable Dose | 0.021 | 0.020 | 0.84 | 0.42 | 0.0015 | 7.4 | 0.076 |
| RBM Low Plasma Range | 0.17 |  |  |  | 0.25 |  | 0.069 |
| RBM High Plasma Range | 1.5 | 1.1 | 4.8 | 1.1 | 50 | 505 | 5.3 |
| Samples |  |  |  |  |  |  |  |
| Donor_1 3. Aliquot A | 11 | 0.66 | 1.5 | 0.16 | >47 | 128 | 7.9 |
| Donor_1 3. Aliquot B | 9.2 | 0.82 | 1.4 | 0.11 | >47 | 131 | 8.2 |
| Donor_1 3. Aliquot C | 10 | 0.82 | 1.4 | 0.12 | >47 | 119 | 1.7 |
| Donor_1 3. Aliquot D | 9.0 | 0.60 | 1.7 | 0.18 | >47 | 109 | 10 |
| Donor_1 3. Aliquot E | 8.7 | 0.47 | 1.6 | 0.11 | >47 | 101 | 5.9 |
| Donor_1 3. Aliquot F | 9.3 | 0.39 | 1.2 | 0.15 | >47 | 101 | 1.2 |
| Donor_1 3. Aliquot G | 12 | 0.18 | 1.5 | 0.11 | >47 | 693 | 5.3 |
| Donor_1 3. Aliquot H | 11 | 0.55 | 1.9 | 0.11 | >47 | 197 | 1.6 |
| Donor_1 3. Aliquot I | 10 | 0.84 | 1.4 | 0.12 | >47 | 114 | 1.8 |
| Donor_2 3. Aliquot A | 16 | 0.70 | 4.6 | 0.40 | >47 | 92 | 45 |
| Donor_2 3. Aliquot B | 18 | 0.65 | 4.9 | 0.44 | >47 | 145 | 45 |
| Donor_2 3. Aliquot C | 16 | 0.61 | 4.7 | 0.32 | >47 | 83 | 0.66 |
| Donor_2 3. Aliquot D | 16 | 0.47 | 6.2 | 0.60 | >47 | 61 | 51 |
| Donor_2 3. Aliquot E | 19 | 0.50 | 5.0 | 0.43 | >47 | 62 | 55 |
| Donor_2 3. Aliquot F | 16 | 0.42 | 4.0 | 0.50 | >47 | 66 | 0.74 |
| Donor_2 3. Aliquot G | 21 | 0.28 | 5.4 | 0.49 | >47 | 792 | 214 |
| Donor_2 3. Aliquot H | 18 | 0.44 | 4.8 | 0.40 | >47 | 85 | 1.4 |
| Donor_2 3. Aliquot I | 17 | 0.47 | 4.5 | 0.21 | >47 | 59 | 1.2 |
| Donor_3 3. Aliquot A | 1.4 | 0.54 | 2.8 | 0.59 | 22 | 40 | 20 |
| Donor_3 3. Aliquot B | 1.7 | 0.43 | 3.3 | 0.67 | 24 | 64 | 13 |
| Donor_3 3. Aliquot C | 1.4 | 0.50 | 3.3 | 0.54 | 25 | 38 | 0.96 |
| Donor_3 3. Aliquot D | 1.5 | 0.52 | 3.6 | 0.53 | 25 | 47 | 35 |
| Donor_3 3. Aliquot E | 1.5 | 0.68 | 4.3 | 0.61 | 24 | 60 | 31 |
| Donor_3 3. Aliquot F | 1.4 | 0.36 | 3.2 | 0.24 | 26 | 39 | 0.65 |
| Donor_3 3. Aliquot G | 3.4 | 0.29 | 2.7 | 0.29 | 26 | 535 | 1.6 |
| Donor_3 3. Aliquot H | 1.4 | 0.50 | 2.4 | 0.37 | 23 | 39 | 0.47 |
| Donor_3 3. Aliquot I | 1.3 | 0.42 | 2.4 | 0.39 | 24 | 33 | 0.55 |

FIG. 14C.2

| | CD40 ng/mL | CD40 Ligand ng/mL | Carcinoembryonic Antigen ng/mL | Creatine Kinase-MB ng/mL | C Reactive Protein ug/mL | EGF pg/mL | ENA-78 ng/mL |
|---|---|---|---|---|---|---|---|
| Least Detectable Dose | 0.021 | 0.020 | 0.84 | 0.42 | 0.0015 | 7.4 | 0.076 |
| RBM Low Plasma Range | 0.17 | | | | 0.25 | | 0.069 |
| RBM High Plasma Range | 1.5 | 1.1 | 4.8 | 1.1 | 50 | 505 | 5.3 |
| Donor_4_3. Aliquot A | 4.3 | 0.20 | 3.4 | 0.078 | >47 | 25 | 0.77 |
| Donor_4_3. Aliquot B | 4.7 | 0.18 | 3.8 | 0.066 | >47 | 35 | 1.4 |
| Donor_4_3. Aliquot C | 4.3 | 0.088 | 3.6 | 0.064 | >47 | 12 | 0.18 |
| Donor_4_3. Aliquot D | 4.0 | 0.13 | 4.4 | 0.17 | >47 | 21 | 23 |
| Donor_4_3. Aliquot E | 4.3 | 0.13 | 3.7 | 0.066 | >47 | 15 | 21 |
| Donor_4_3. Aliquot F | 4.0 | 0.083 | 3.3 | 0.093 | >47 | 9.8 | 0.59 |
| Donor_4_3. Aliquot G | 4.9 | 0.063 | 3.3 | 0.057 | >47 | 256 | 1.2 |
| Donor_4_3. Aliquot H | 4.0 | 0.081 | 3.4 | 0.045 | >47 | 11 | 0.14 |
| Donor_4_3. Aliquot I | 3.9 | 0.092 | 3.2 | 0.076 | >47 | 19 | 0.20 |
| Donor_5_3. Aliquot A | 18 | 0.51 | 1.7 | 0.18 | >47 | 87 | 21 |
| Donor_5_3. Aliquot B | 18 | 0.34 | 2.4 | 0.18 | >47 | 90 | 23 |
| Donor_5_3. Aliquot C | 19 | 0.32 | 1.6 | 0.11 | >47 | 71 | 0.25 |
| Donor_5_3. Aliquot D | 20 | 0.40 | 3.1 | 0.24 | >47 | 60 | 31 |
| Donor_5_3. Aliquot E | 21 | 0.47 | 2.9 | 0.28 | >47 | 70 | 33 |
| Donor_5_3. Aliquot F | 18 | 0.29 | 1.4 | 0.086 | >47 | 59 | 0.71 |
| Donor_5_3. Aliquot G | 19 | 0.24 | 1.7 | 0.12 | >47 | 647 | 7.0 |
| Donor_5_3. Aliquot H | 18 | 0.32 | 4.2 | 0.17 | >47 | 83 | 0.41 |
| Donor_5_3. Aliquot I | 17 | 0.27 | 3.6 | 0.11 | >47 | 53 | 0.22 |
| Donor_6_3. Aliquot A | 0.98 | 0.88 | 0.82 | 0.25 | >47 | 195 | 4.4 |
| Donor_6_3. Aliquot B | 1.1 | 0.77 | 0.58 | 0.24 | >47 | 213 | 6.0 |
| Donor_6_3. Aliquot C | 1.0 | 0.61 | 1.1 | 0.26 | >47 | 160 | 0.54 |
| Donor_6_3. Aliquot D | 1.0 | 0.95 | 1.3 | 0.26 | >47 | 152 | 10 |
| Donor_6_3. Aliquot E | 0.96 | 0.60 | 1.6 | 0.30 | >47 | 110 | 12 |
| Donor_6_3. Aliquot F | 0.90 | 0.47 | 0.63 | 0.19 | >47 | 132 | 0.68 |
| Donor_6_3. Aliquot G | 3.8 | 0.30 | 0.44 | 0.30 | >47 | 2020 | 4.3 |
| Donor_6_3. Aliquot H | 0.81 | 0.45 | 0.91 | 0.21 | >47 | 139 | 0.43 |
| Donor_6_3. Aliquot I | 0.73 | 0.45 | 0.96 | 0.21 | >47 | 101 | 0.51 |

FIG. 14C.3

| | CD40 ng/mL | CD40 Ligand ng/mL | Carcinoembryonic Antigen ng/mL | Creatine Kinase-MB ng/mL | C Reactive Protein ug/mL | EGF pg/mL | ENA-78 ng/mL |
|---|---|---|---|---|---|---|---|
| Least Detectable Dose | 0.021 | 0.020 | 0.84 | 0.42 | 0.0015 | 7.4 | 0.076 |
| RBM Low Plasma Range | 0.17 | | | | 0.25 | | 0.069 |
| RBM High Plasma Range | 1.5 | 1.1 | 4.8 | 1.1 | 50 | 505 | 5.3 |
| Donor_7 3. Aliquot A | 0.93 | 0.25 | 3.6 | 1.2 | 29 | 30 | 33 |
| Donor_7 3. Aliquot B | 0.89 | 0.21 | 2.8 | 1.5 | 33 | 45 | 17 |
| Donor_7 3. Aliquot C | 0.77 | 0.40 | 3.0 | 0.99 | 30 | 37 | 0.56 |
| Donor_7 3. Aliquot D | 0.73 | 0.30 | 3.9 | 1.1 | 27 | 28 | 26 |
| Donor_7 3. Aliquot E | 0.62 | 0.20 | 3.2 | 1.1 | 24 | 22 | 20 |
| Donor_7 3. Aliquot F | 0.61 | 0.11 | 2.9 | 1.2 | 27 | 11 | 0.25 |
| Donor_7 3. Aliquot G | 1.8 | 0.071 | 3.0 | 1.1 | 27 | 403 | 3.6 |
| Donor_7 3. Aliquot H | 0.71 | 0.18 | 4.1 | 1.0 | 28 | 20 | 0.23 |
| Donor_7 3. Aliquot I | 0.50 | 0.15 | 2.7 | 0.93 | 29 | 15 | 0.19 |
| Donor_8 3. Aliquot A | 0.57 | 0.32 | 1.1 | 0.15 | 0.096 | 93 | 1.1 |
| Donor_8 3. Aliquot B | 0.60 | 0.42 | 0.82 | 0.19 | 0.14 | 110 | 1.3 |
| Donor_8 3. Aliquot C | 0.63 | 0.51 | 0.75 | 0.15 | 0.13 | 114 | 0.81 |
| Donor_8 3. Aliquot D | 0.72 | 0.33 | 3.5 | 0.36 | 0.14 | 105 | 1.4 |
| Donor_8 3. Aliquot E | 0.63 | 0.49 | 3.9 | 0.39 | 0.14 | 132 | 2.4 |
| Donor_8 3. Aliquot F | 0.49 | 0.15 | 1.4 | 0.24 | 0.12 | 63 | 0.37 |
| Donor_8 3. Aliquot G | 1.8 | 0.13 | 0.94 | 0.20 | 0.16 | 1050 | 4.5 |
| Donor_8 3. Aliquot H | 0.60 | 0.49 | 1.9 | 0.24 | 0.13 | 143 | 0.81 |
| Donor_8 3. Aliquot I | 0.65 | 0.45 | 1.6 | 0.14 | 0.13 | 125 | 0.87 |
| Donor_9 3. Aliquot A | 0.69 | 0.37 | 1.2 | 0.079 | Pending | 117 | 2.1 |
| Donor_9 3. Aliquot B | 0.69 | 0.43 | 1.5 | 0.19 | Pending | 156 | 2.2 |
| Donor_9 3. Aliquot C | 0.69 | 0.51 | 1.0 | 0.18 | Pending | 123 | 2.1 |
| Donor_9 3. Aliquot D | 0.81 | 0.46 | 5.3 | 0.40 | Pending | 131 | 2.4 |
| Donor_9 3. Aliquot E | 0.72 | 0.31 | 3.3 | 0.26 | Pending | 95 | 6.5 |
| Donor_9 3. Aliquot F | 0.61 | 0.19 | 1.7 | 0.16 | Pending | 78 | 0.65 |
| Donor_9 3. Aliquot G | 2.7 | 0.21 | 1.1 | 0.12 | Pending | 1300 | 16 |
| Donor_9 3. Aliquot H | 0.64 | 0.50 | 1.5 | 0.13 | Pending | 140 | 1.3 |
| Donor_9 3. Aliquot I | 0.66 | 0.45 | 0.89 | 0.083 | Pending | 134 | 1.5 |

FIG. 14C.4

| | CD40 ng/mL | CD40 Ligand ng/mL | Carcinoembryonic Antigen ng/mL | Creatine Kinase-MB ng/mL | C Reactive Protein ug/mL | EGF pg/mL | ENA-78 ng/mL |
|---|---|---|---|---|---|---|---|
| Least Detectable Dose | 0.021 | 0.020 | 0.84 | 0.42 | 0.0015 | 7.4 | 0.076 |
| RBM Low Plasma Range | 0.17 | | | | 0.25 | | 0.069 |
| RBM High Plasma Range | 1.5 | 1.1 | 4.8 | 1.1 | 50 | 505 | 5.3 |
| EDTA Plasma | | | | | | | |
| donor #1 plasma | 7.4 | 0.14 | 1.7 | 0.25 | Pending | 30 | 0.93 |
| donor #2 plasma | 18 | 0.21 | 3.9 | 0.99 | Pending | 7.4 | 0.076 |
| donor #3 plasma | 1.7 | 0.084 | 2.6 | 0.47 | Pending | 7.4 | 0.076 |
| donor #4 plasma | 5.2 | 0.10 | 4.9 | 0.24 | Pending | 7.4 | 0.076 |
| donor #5 plasma | 16 | 0.27 | 1.7 | 0.18 | Pending | 12 | 0.32 |
| donor #6 plasma | 0.46 | 0.021 | 1.1 | 0.39 | Pending | 7.4 | 0.26 |
| donor #7 plasma | 1.6 | 0.089 | 3.6 | 3.3 | Pending | 7.4 | 0.54 |
| donor #8 plasma | 0.58 | 0.16 | 1.4 | 0.56 | | 22 | 0.48 |
| donor #9 plasma | 0.47 | 0.053 | 0.71 | 0.27 | | 7.4 | 0.088 |
| | CD40 | CD40 Ligand | Carcinoembryonic Antigen | Creatine Kinase-MB | C Reactive Protein | EGF | ENA-78 |
| Stimulation indices | | | | | | | |
| patient 1 | A | 1.1 | 0.8 | 1.1 | 1.3 | #VALUE! | 1.1 | 4.3 |
| patient 7 | A | 1.0 | 1.5 | 1.0 | 1.9 | #VALUE! | 1.5 | 38.3 |

FIG. 14C.5

| | | CD40 ng/mL | CD40 Ligand ng/mL | Carcinoembryonic Antigen ng/mL | Creatine Kinase-MB ng/mL | C Reactive Protein ug/mL | EGF pg/mL | ENA-78 ng/mL |
|---|---|---|---|---|---|---|---|---|
| | Least Detectable Dose | 0.021 | 0.020 | 0.84 | 0.42 | 0.0015 | 7.4 | 0.076 |
| | RBM Low Plasma Range | 0.17 | | | | 0.25 | | 0.069 |
| | RBM High Plasma Range | 1.5 | 1.1 | 4.8 | 1.1 | 50 | 505 | 5.3 |
| A | patient 2 | 1.1 | 1.3 | 1.2 | 1.5 | 0.9 | 1.2 | 35.7 |
| A | patient 3 | 1.1 | 2.2 | 1.1 | 1.0 | #VALUE! | 1.3 | 3.9 |
| A | patient 5 | 1.0 | 1.9 | 0.5 | 1.6 | #VALUE! | 1.7 | 95.5 |
| A | patient 4 | 1.3 | 1.9 | 0.9 | 1.2 | #VALUE! | 1.9 | 8.6 |
| A | patient 6 | 1.9 | 1.8 | 1.3 | 1.3 | 1.0 | 2.0 | 169.3 |
| A | NHD 1 | 0.9 | 0.7 | 0.7 | 1.0 | 0.7 | 0.7 | 1.2 |
| A | NHD 2 | 1.1 | 0.8 | 1.3 | 1.0 | #VALUE! | 0.9 | 1.5 |
| B | patient 1 | 0.9 | 1.0 | 1.0 | 0.9 | #VALUE! | 1.1 | 4.5 |
| B | patient 7 | 1.0 | 1.4 | 1.1 | 2.1 | #VALUE! | 2.4 | 38.5 |
| B | patient 2 | 1.3 | 1.0 | 1.4 | 1.7 | 1.0 | 2.0 | 22.6 |
| B | patient 3 | 1.2 | 1.9 | 1.2 | 0.9 | #VALUE! | 1.9 | 7.2 |
| B | patient 5 | 1.1 | 1.3 | 0.7 | 1.6 | #VALUE! | 1.7 | 105.4 |
| B | patient 4 | 1.5 | 1.7 | 0.6 | 1.1 | #VALUE! | 2.1 | 11.7 |
| B | patient 6 | 1.8 | 1.5 | 1.0 | 1.6 | 1.1 | 2.9 | 89.1 |
| B | NHD 1 | 0.9 | 0.9 | 0.5 | 1.4 | 1.1 | 0.9 | 1.4 |
| B | NHD 2 | 1.1 | 1.0 | 1.7 | 2.3 | #VALUE! | 1.2 | 1.5 |
| C | patient 1 | 1.0 | 1.0 | 1.0 | 1.0 | #VALUE! | 1.0 | 0.9 |
| C | patient 7 | 1.0 | 1.3 | 1.1 | 1.5 | #VALUE! | 1.4 | 0.6 |
| C | patient 2 | 1.0 | 1.2 | 1.4 | 1.4 | 1.1 | 1.2 | 1.7 |
| C | patient 3 | 1.1 | 1.0 | 1.1 | 0.8 | #VALUE! | 0.7 | 0.9 |
| C | patient 5 | 1.1 | 1.2 | 0.5 | 1.0 | #VALUE! | 1.3 | 1.1 |
| C | patient 4 | 1.4 | 1.4 | 1.2 | 1.2 | #VALUE! | 1.6 | 1.1 |
| C | patient 6 | 1.6 | 2.8 | 1.1 | 1.1 | 1.1 | 2.4 | 2.9 |
| C | NHD 1 | 1.0 | 1.1 | 0.5 | 1.0 | 1.0 | 0.9 | 0.9 |
| C | NHD 2 | 1.1 | 1.1 | 1.2 | 2.1 | #VALUE! | 0.9 | 1.4 |

FIG. 14C.6

| | | CD40 ng/mL | CD40 Ligand ng/mL | Carcinoembryonic Antigen ng/mL | Creatine Kinase-MB ng/mL | C Reactive Protein ug/mL | EGF pg/mL | ENA-78 ng/mL |
|---|---|---|---|---|---|---|---|---|
| | Least Detectable Dose | 0.021 | 0.020 | 0.84 | 0.42 | 0.0015 | 7.4 | 0.076 |
| | RBM Low Plasma Range | 0.17 | | | | 0.25 | | 0.069 |
| | RBM High Plasma Range | 1.5 | 1.1 | 4.8 | 1.1 | 50 | 505 | 5.3 |
| D | patient 1 | 0.9 | 0.7 | 1.3 | 1.5 | #VALUE! | 1.0 | 5.5 |
| D | patient 7 | 0.9 | 1.0 | 1.4 | 2.8 | #VALUE! | 1.0 | 43.4 |
| D | patient 2 | 1.1 | 1.2 | 1.5 | 1.4 | 1.1 | 1.4 | 63.9 |
| D | patient 3 | 1.0 | 1.4 | 1.4 | 2.3 | #VALUE! | 1.1 | 117.9 |
| D | patient 5 | 1.1 | 1.5 | 0.9 | 2.1 | #VALUE! | 1.1 | 140.1 |
| D | patient 4 | 1.4 | 2.1 | 1.3 | 1.2 | #VALUE! | 1.5 | 20.3 |
| D | patient 6 | 1.5 | 2.1 | 1.4 | 1.2 | 1.0 | 1.9 | 133.3 |
| D | NHD 1 | 1.1 | 0.7 | 2.1 | 2.6 | 1.1 | 0.8 | 1.6 |
| D | NHD 2 | 1.2 | 1.0 | 6.0 | 4.9 | #VALUE! | 1.0 | 1.7 |
| E | patient 1 | 0.9 | 0.6 | 1.2 | 0.9 | #VALUE! | 0.9 | 3.2 |
| E | patient 7 | 1.1 | 1.1 | 1.1 | 2.0 | #VALUE! | 1.0 | 46.3 |
| E | patient 2 | 1.1 | 1.6 | 1.8 | 1.6 | 1.0 | 1.8 | 55.6 |
| E | patient 3 | 1.1 | 1.4 | 1.2 | 0.9 | #VALUE! | 0.8 | 105.6 |
| E | patient 5 | 1.2 | 1.8 | 0.8 | 2.5 | #VALUE! | 1.3 | 149.5 |
| E | patient 4 | 1.3 | 1.3 | 1.7 | 1.4 | #VALUE! | 1.1 | 22.7 |
| E | patient 6 | 1.2 | 1.4 | 1.2 | 1.2 | 0.8 | 1.4 | 105.7 |
| E | NHD 1 | 1.0 | 1.1 | 2.4 | 2.8 | 1.0 | 1.1 | 2.7 |
| E | NHD 2 | 1.1 | 0.7 | 3.6 | 3.1 | #VALUE! | 0.7 | 4.4 |
| F | patient 1 | 0.9 | 0.5 | 0.9 | 1.3 | #VALUE! | 0.9 | 0.7 |
| F | patient 7 | 0.9 | 0.9 | 0.9 | 2.4 | #VALUE! | 1.1 | 0.6 |
| F | patient 2 | 1.0 | 0.9 | 1.4 | 0.6 | 1.1 | 1.2 | 1.2 |
| F | patient 3 | 0.9 | 0.9 | 1.1 | 1.2 | #VALUE! | 0.5 | 3.0 |
| F | patient 5 | 1.0 | 1.1 | 0.4 | 0.8 | #VALUE! | 1.1 | 3.2 |
| F | patient 4 | 1.2 | 1.0 | 0.7 | 0.9 | #VALUE! | 1.3 | 1.3 |
| F | patient 6 | 1.2 | 0.8 | 1.1 | 1.3 | 0.9 | 0.7 | 1.3 |

FIG. 14C.7

| | CD40 ng/mL | CD40 Ligand ng/mL | Carcinoembryonic Antigen ng/mL | Creatine Kinase-MB ng/mL | C Reactive Protein ug/mL | EGF pg/mL | ENA-78 ng/mL |
|---|---|---|---|---|---|---|---|
| Least Detectable Dose | 0.021 | 0.020 | 0.84 | 0.42 | 0.0015 | 7.4 | 0.076 |
| RBM Low Plasma Range | 0.17 | | | | 0.25 | | 0.069 |
| RBM High Plasma Range | 1.5 | 1.1 | 4.8 | 1.1 | 50 | 505 | 5.3 |
| F  NHD 1 | 0.8 | 0.3 | 0.8 | 1.7 | 1.2 | 0.5 | 0.4 |
| F  NHD 2 | 0.9 | 0.4 | 2.0 | 1.9 | #VALUE! | 0.6 | 0.4 |
| G  patient 1 | 1.2 | 0.2 | 1.1 | 0.9 | #VALUE! | 6.1 | 2.9 |
| G  patient 7 | 1.3 | 0.6 | 1.2 | 2.3 | #VALUE! | 13.3 | 181.4 |
| G  patient 2 | 2.5 | 0.7 | 1.1 | 0.7 | 1.1 | 16.4 | 2.9 |
| G  patient 3 | 1.2 | 0.7 | 1.1 | 0.7 | #VALUE! | 13.5 | 6.0 |
| G  patient 5 | 1.1 | 0.9 | 0.5 | 1.0 | #VALUE! | 12.3 | 31.3 |
| G  patient 4 | 5.2 | 0.7 | 0.5 | 1.4 | #VALUE! | 20.0 | 8.3 |
| G  patient 6 | 3.6 | 0.5 | 1.1 | 1.2 | 0.9 | 26.5 | 18.9 |
| G  NHD 1 | 2.8 | 0.3 | 0.6 | 1.4 | 1.0 | 8.4 | 5.1 |
| G  NHD 2 | 4.1 | 0.5 | 1.3 | 1.4 | #VALUE! | 9.7 | 10.7 |
| H  patient 1 | 1.1 | 0.7 | 1.4 | 0.9 | #VALUE! | 1.7 | 0.9 |
| H  patient 7 | 1.1 | 0.9 | 1.1 | 1.9 | #VALUE! | 1.4 | 1.2 |
| H  patient 2 | 1.0 | 1.2 | 1.0 | 1.0 | 1.0 | 1.2 | 0.9 |
| H  patient 3 | 1.0 | 0.9 | 1.1 | 0.6 | #VALUE! | 0.6 | 0.7 |
| H  patient 5 | 1.0 | 1.2 | 1.2 | 1.5 | #VALUE! | 1.6 | 1.8 |
| H  patient 4 | 1.1 | 1.0 | 1.0 | 1.0 | #VALUE! | 1.4 | 0.8 |
| H  patient 6 | 1.4 | 1.2 | 1.5 | 1.1 | 1.0 | 1.3 | 1.2 |
| H  NHD 1 | 0.9 | 1.1 | 1.2 | 1.7 | 1.1 | 1.1 | 0.9 |
| H  NHD 2 | 1.0 | 1.1 | 1.6 | 1.6 | #VALUE! | 1.0 | 0.9 |
| I  patient 1 | 1.0 | 1.0 | 1.0 | 1.0 | #VALUE! | 1.0 | 1.0 |
| I  patient 7 | 1.0 | 1.0 | 1.0 | 1.0 | #VALUE! | 1.0 | 1.0 |
| I  patient 2 | 1.0 | 1.0 | 1.0 | 1.0 | 1.0 | 1.0 | 1.0 |
| I  patient 3 | 1.0 | 1.0 | 1.0 | 1.0 | #VALUE! | 1.0 | 1.0 |

FIG. 14C.8

| | CD40 ng/mL | CD40 Ligand ng/mL | Carcinoembryonic Antigen ng/mL | Creatine Kinase-MB ng/mL | C Reactive Protein ug/mL | EGF pg/mL | ENA-78 ng/mL |
|---|---|---|---|---|---|---|---|
| Least Detectable Dose | 0.021 | 0.020 | 0.84 | 0.42 | 0.0015 | 7.4 | 0.076 |
| RBM Low Plasma Range | 0.17 | | | | 0.25 | | 0.069 |
| RBM High Plasma Range | 1.5 | 1.1 | 4.8 | 1.1 | 50 | 505 | 5.3 |
| patient 5 | 1.0 | 1.0 | 1.0 | 1.0 | #VALUE! | 1.0 | 1.0 |
| patient 4 | 1.0 | 1.0 | 1.0 | 1.0 | #VALUE! | 1.0 | 1.0 |
| patient 6 | 1.0 | 1.0 | 1.0 | 1.0 | | 1.0 | 1.0 |
| NHD 1 | 1.0 | 1.0 | 1.0 | 1.0 | #VALUE! | 1.0 | 1.0 |
| NHD 2 | 1.0 | 1.0 | 1.0 | 1.0 | | 1.0 | 1.0 |

Messwert > ULD

| | Endothelin-1 pg/mL | EN-RAGE ng/mL | Eotaxin pg/mL | Epiregulin pg/mL | Erythropoietin pg/mL | Fatty Acid Binding Protein ng/mL | Factor VII ng/mL |
|---|---|---|---|---|---|---|---|
| Least Detectable Dose | 7.2 | 0.25 | 41 | 36 | 166 | 3.0 | 1.0 |
| RBM Low Plasma Range | | 4.6 | | Pending | | | 106 |
| RBM High Plasma Range | 26 | 592 | 177 | Pending | 284 | 10 | 443 |
| Samples | | | | | | | |
| Donor_1 3. Aliquot A | 8.1 | 82 | 179 | 161 | 166 | 32 | 157 |
| Donor_1 3. Aliquot B | 7.2 | 72 | 164 | 65 | 166 | 29 | 140 |
| Donor_1 3. Aliquot C | 7.2 | 74 | 130 | 33 | 37 | 34 | 89 |
| Donor_1 3. Aliquot D | 7.2 | 66 | 180 | 16 | 166 | 33 | 168 |
| Donor_1 3. Aliquot E | 7.2 | 75 | 170 | 40 | 166 | 33 | 171 |
| Donor_1 3. Aliquot F | 7.2 | 60 | 184 | 61 | 166 | 31 | 132 |
| Donor_1 3. Aliquot G | 22 | 54 | 10 | 149 | 166 | 41 | 174 |
| Donor_1 3. Aliquot H | 11 | 99 | 177 | 36 | 60 | 31 | 160 |
| Donor_1 3. Aliquot I | 7.2 | 76 | 172 | 31 | 166 | 29 | 139 |
| Donor_2 3. Aliquot A | 11 | 247 | 61 | 44 | 166 | 36 | 541 |
| Donor_2 3. Aliquot B | 7.2 | 230 | 48 | 26 | 166 | 40 | 577 |
| Donor_2 3. Aliquot C | 7.2 | 252 | 46 | 16 | 166 | 40 | 154 |
| Donor_2 3. Aliquot D | 15 | 212 | 48 | 52 | 166 | 45 | 694 |
| Donor_2 3. Aliquot E | 20 | 228 | 44 | 21 | 166 | 45 | 640 |
| Donor_2 3. Aliquot F | 7.2 | 258 | 27 | 36 | 166 | 40 | 580 |
| Donor_2 3. Aliquot G | 24 | 218 | 5.0 | 236 | 166 | 48 | 588 |
| Donor_2 3. Aliquot H | 7.2 | >269 | 36 | 26 | 166 | 39 | 567 |
| Donor_2 3. Aliquot I | 7.2 | 250 | 44 | 36 | 166 | 34 | 450 |
| Donor_3 3. Aliquot A | 7.2 | 142 | 66 | 40 | 166 | 14 | 147 |
| Donor_3 3. Aliquot B | 7.2 | 142 | 50 | 35 | 166 | 12 | 139 |
| Donor_3 3. Aliquot C | 7.2 | 135 | 44 | 24 | 166 | 12 | 31 |
| Donor_3 3. Aliquot D | 7.2 | 151 | 54 | 31 | 166 | 17 | 156 |
| Donor_3 3. Aliquot E | 11 | 159 | 52 | 36 | 166 | 16 | 160 |
| Donor_3 3. Aliquot F | 7.2 | 128 | 80 | 36 | 166 | 13 | 128 |
| Donor_3 3. Aliquot G | 7.2 | 122 | 5.0 | 36 | 166 | 15 | 116 |
| Donor_3 3. Aliquot H | 7.2 | 211 | 29 | 21 | 166 | 9.2 | 108 |
| Donor_3 3. Aliquot I | 7.2 | 169 | 36 | 13 | 166 | 11 | 123 |

FIG. 14D.2

| | Endothelin-1 pg/mL | EN-RAGE ng/mL | Eotaxin pg/mL | Epiregulin pg/mL | Erythropoietin pg/mL | Fatty Acid Binding Protein ng/mL | Factor VII ng/mL |
|---|---|---|---|---|---|---|---|
| Least Detectable Dose | 7.2 | 0.25 | 41 | 36 | 166 | 3.0 | 1.0 |
| RBM Low Plasma Range | | 4.6 | | Pending | | | 106 |
| RBM High Plasma Range | 26 | 592 | 177 | Pending | 284 | 10 | 443 |
| Donor_4_3. Aliquot A | 7.2 | >269 | 141 | 21 | 166 | 33 | 124 |
| Donor_4_3. Aliquot B | 7.2 | 239 | 133 | 35 | 166 | 33 | 129 |
| Donor_4_3. Aliquot C | 7.2 | 175 | 122 | 36 | 166 | 30 | 9.2 |
| Donor_4_3. Aliquot D | 11 | 84 | 133 | 36 | 166 | 33 | 142 |
| Donor_4_3. Aliquot E | 22 | 66 | 120 | 29 | 166 | 33 | 115 |
| Donor_4_3. Aliquot F | 7.2 | 94 | 130 | 36 | 166 | 32 | 105 |
| Donor_4_3. Aliquot G | 7.2 | 127 | 10 | 69 | 166 | 34 | 75 |
| Donor_4_3. Aliquot H | 7.2 | >269 | 124 | 36 | 166 | 37 | 111 |
| Donor_4_3. Aliquot I | 7.2 | 185 | 139 | 31 | 166 | 34 | 125 |
| Donor_5_3. Aliquot A | 20 | 95 | 27 | 129 | 166 | 9.2 | >1113 |
| Donor_5_3. Aliquot B | 11 | 88 | 34 | 101 | 41 | 7.8 | 1020 |
| Donor_5_3. Aliquot C | 7.2 | 108 | 32 | 149 | 166 | 9.2 | 243 |
| Donor_5_3. Aliquot D | 11 | 52 | 32 | 105 | 100 | 13 | 940 |
| Donor_5_3. Aliquot E | 15 | 41 | 30 | 111 | 64 | 14 | 1100 |
| Donor_5_3. Aliquot F | 7.2 | 73 | 27 | 87 | 166 | 6.5 | 808 |
| Donor_5_3. Aliquot G | 15 | 91 | 7.6 | 161 | 50 | 10 | 936 |
| Donor_5_3. Aliquot H | 7.2 | 236 | 25 | 117 | 50 | 8.8 | 1000 |
| Donor_5_3. Aliquot I | 7.2 | 100 | 22 | 95 | 166 | 8.8 | 1050 |
| Donor_6_3. Aliquot A | 7.2 | 236 | 22 | 26 | 166 | 2.3 | 320 |
| Donor_6_3. Aliquot B | 7.2 | 229 | 25 | 31 | 166 | 2.6 | 329 |
| Donor_6_3. Aliquot C | 7.2 | 265 | 36 | 36 | 166 | 2.6 | 62 |
| Donor_6_3. Aliquot D | 7.2 | 109 | 25 | 36 | 166 | 5.4 | 345 |
| Donor_6_3. Aliquot E | 11 | 106 | 20 | 36 | 166 | 5.6 | 285 |
| Donor_6_3. Aliquot F | 7.2 | 153 | 34 | 16 | 166 | 2.2 | 311 |
| Donor_6_3. Aliquot G | 7.2 | 147 | 15 | 177 | 166 | 2.6 | 252 |
| Donor_6_3. Aliquot H | 7.2 | >269 | 18 | 36 | 166 | 2.0 | 336 |
| Donor_6_3. Aliquot I | 7.2 | 237 | 22 | 36 | 166 | 1.7 | 309 |

FIG. 14D.3

| | Endothelin-1 pg/mL | EN-RAGE ng/mL | Eotaxin pg/mL | Epiregulin pg/mL | Erythropoietin pg/mL | Fatty Acid Binding Protein ng/mL | Factor VII ng/mL |
|---|---|---|---|---|---|---|---|
| Least Detectable Dose | 7.2 | 0.25 | 41 | 36 | 166 | 3.0 | 1.0 |
| RBM Low Plasma Range | | 4.6 | | Pending | | | 106 |
| RBM High Plasma Range | 26 | 592 | 177 | Pending | 284 | 10 | 443 |
| Donor_7_3. Aliquot A | 7.2 | 150 | 138 | 36 | 166 | 463 | 144 |
| Donor_7_3. Aliquot B | 7.2 | 161 | 119 | 36 | 166 | 459 | 149 |
| Donor_7_3. Aliquot C | 7.2 | >269 | 105 | 36 | 166 | 466 | 34 |
| Donor_7_3. Aliquot D | 7.2 | 128 | 106 | 36 | 166 | 422 | 128 |
| Donor_7_3. Aliquot E | 7.2 | 122 | 117 | 36 | 166 | 434 | 143 |
| Donor_7_3. Aliquot F | 7.2 | 227 | 121 | 36 | 166 | 426 | 143 |
| Donor_7_3. Aliquot G | 7.2 | 182 | 18 | 36 | 166 | 511 | 139 |
| Donor_7_3. Aliquot H | 7.2 | >269 | 125 | 36 | 166 | 440 | 136 |
| Donor_7_3. Aliquot I | 7.2 | >269 | 111 | 36 | 166 | 451 | 141 |
| Donor_8_3. Aliquot A | 8.1 | 48 | 162 | 36 | 166 | 3 | 376 |
| Donor_8_3. Aliquot B | 7.2 | 46 | 153 | 35 | 166 | 3 | 411 |
| Donor_8_3. Aliquot C | 7.2 | 41 | 117 | 44 | 166 | 3 | 18 |
| Donor_8_3. Aliquot D | 7.2 | 64 | 165 | 42 | 166 | 8.3 | 410 |
| Donor_8_3. Aliquot E | 7.2 | 45 | 157 | 35 | 166 | 7.8 | 351 |
| Donor_8_3. Aliquot F | 15 | 47 | 208 | 58 | 166 | 0.81 | 426 |
| Donor_8_3. Aliquot G | 7.2 | 57 | 5.0 | 56 | 166 | 3 | 253 |
| Donor_8_3. Aliquot H | 11 | 143 | 142 | 16 | 166 | 0.56 | 382 |
| Donor_8_3. Aliquot I | 7.2 | 122 | 157 | 36 | 166 | 0.14 | 381 |
| Donor_9_3. Aliquot A | 7.2 | 47 | 254 | 86 | 166 | 3 | 196 |
| Donor_9_3. Aliquot B | 13 | 33 | 223 | 75 | 166 | 1.6 | 196 |
| Donor_9_3. Aliquot C | 9.8 | 48 | 184 | 106 | 166 | 0.42 | 44 |
| Donor_9_3. Aliquot D | 18 | 46 | 239 | 101 | 166 | 10 | 243 |
| Donor_9_3. Aliquot E | 19 | 67 | 209 | 79 | 166 | 6.6 | 201 |
| Donor_9_3. Aliquot F | 13 | 22 | 231 | 77 | 166 | 0.68 | 196 |
| Donor_9_3. Aliquot G | 7.2 | 96 | 41 | 123 | 166 | 0.81 | 147 |
| Donor_9_3. Aliquot H | 5.1 | 115 | 201 | 97 | 166 | 3 | 229 |
| Donor_9_3. Aliquot I | 7.2 | 50 | 232 | 83 | 166 | 3 | 184 |

FIG. 14D.4

| | Endothelin-1 pg/mL | EN-RAGE ng/mL | Eotaxin pg/mL | Epiregulin pg/mL | Erythropoietin pg/mL | Fatty Acid Binding Protein ng/mL | Factor VII ng/mL |
|---|---|---|---|---|---|---|---|
| Least Detectable Dose | 7.2 | 0.25 | 41 | 36 | 166 | 3.0 | 1.0 |
| RBM Low Plasma Range | | 4.6 | | Pending | | | 106 |
| RBM High Plasma Range | 26 | 592 | 177 | Pending | 284 | 10 | 443 |
| EDTA Plasma | | | | | | | |
| donor #1 plasma | 7.7 | 65 | 97 | 83 | 84 | 32 | 141 |
| donor #2 plasma | 7.2 | >269 | 42 | 36 | 166 | 65 | 545 |
| donor #3 plasma | 17 | 49 | 36 | 32 | 166 | 25 | 135 |
| donor #4 plasma | 7.2 | 19 | 87 | 36 | 166 | 59 | 121 |
| donor #5 plasma | 22 | 145 | 64 | 35 | 118 | 13 | 891 |
| donor #6 plasma | 7.2 | 40 | 14 | 36 | 37 | 5.0 | 315 |
| donor #7 plasma | 7.2 | 71 | 86 | 36 | 166 | >617 | 187 |
| donor #8 plasma | 9.8 | 9.4 | 294 | 35 | 166 | 3 | 428 |
| donor #9 plasma | 7.2 | 4.3 | 330 | 65 | 166 | 0.55 | 299 |
| Stimulations indices | | | | | | | |
| patient 1 | 1.1 | 1.1 | 1.0 | 5.2 | 1.0 | 1.1 | 1.1 |
| patient 7 | 1.5 | 1.0 | 1.4 | 1.2 | 1.0 | 1.1 | 1.2 |
| | A | | | | | | |
| | A | | | | | | |

FIG. 14D.5

| | | Endothelin-1 pg/mL | EN-RAGE ng/mL | Eotaxin pg/mL | Epiregulin pg/mL | Erythropoietin pg/mL | Fatty Acid Binding Protein ng/mL | Factor VII ng/mL |
|---|---|---|---|---|---|---|---|---|
| | Least Detectable Dose | 7.2 | 0.25 | 41 | 36 | 166 | 3.0 | 1.0 |
| | RBM Low Plasma Range | | 4.6 | | Pending | | | 106 |
| | RBM High Plasma Range | 26 | 592 | 177 | Pending | 284 | 10 | 443 |
| A | patient 2 | 1.0 | 0.8 | 1.9 | 3.1 | 1.0 | 1.3 | 1.2 |
| A | patient 3 | 1.0 | #VALUE! | 1.0 | 0.7 | 1.0 | 1.0 | 1.0 |
| A | patient 5 | 2.8 | 0.9 | 1.2 | 1.4 | 1.0 | 1.0 | #VALUE! |
| A | patient 4 | 1.0 | 1.0 | 1.0 | 0.7 | 1.0 | 1.3 | 1.0 |
| A | patient 6 | 1.0 | #VALUE! | 1.2 | 1.0 | 1.0 | 1.0 | 1.0 |
| A | NHD 1 | 1.1 | 0.4 | 1.0 | 1.0 | 1.0 | 21.7 | 1.0 |
| A | NHD 2 | 1.0 | 0.9 | 1.1 | 1.0 | 1.0 | 1.0 | 1.1 |
| B | patient 1 | 1.0 | 0.9 | 1.0 | 2.1 | 1.0 | 1.0 | 1.0 |
| B | patient 7 | 1.0 | 0.9 | 1.1 | 0.7 | 1.0 | 1.2 | 1.3 |
| B | patient 2 | 1.0 | 0.8 | 1.4 | 2.7 | 1.0 | 1.1 | 1.1 |
| B | patient 3 | 1.0 | 1.3 | 1.0 | 1.1 | 1.0 | 1.0 | 1.0 |
| B | patient 5 | 1.5 | 0.9 | 1.5 | 1.1 | 0.2 | 0.9 | 1.0 |
| B | patient 4 | 1.0 | 1.0 | 1.1 | 0.9 | 1.0 | 1.5 | 1.1 |
| B | patient 6 | 1.0 | #VALUE! | 1.1 | 1.0 | 1.0 | 1.0 | 1.1 |
| B | NHD 1 | 1.0 | 0.4 | 1.0 | 1.0 | 1.0 | 21.7 | 1.1 |
| B | NHD 2 | 1.9 | 0.7 | 1.0 | 0.9 | 1.0 | 0.5 | 1.1 |
| C | patient 1 | 1.0 | 1.0 | 0.8 | 1.1 | 0.2 | 1.2 | 0.6 |
| C | patient 7 | 1.0 | 1.0 | 1.0 | 0.4 | 1.0 | 1.2 | 0.3 |
| C | patient 2 | 1.0 | 0.8 | 1.2 | 1.8 | 1.0 | 1.0 | 0.3 |
| C | patient 3 | 1.0 | 0.9 | 0.9 | 1.2 | 1.0 | 0.9 | 0.1 |
| C | patient 5 | 1.0 | 1.1 | 1.4 | 1.6 | 1.0 | 1.5 | 0.2 |
| C | patient 4 | 1.0 | 1.1 | 1.6 | 1.0 | 1.0 | 1.0 | 0.2 |
| C | patient 6 | 1.0 | #VALUE! | 0.9 | 1.0 | 1.0 | 1.0 | 0.2 |
| C | NHD 1 | 1.0 | 0.3 | 0.7 | 1.2 | 1.0 | 21.7 | 0.0 |
| C | NHD 2 | 1.4 | 1.0 | 0.8 | 1.3 | 1.0 | 0.1 | 0.2 |

FIG. 14D.6

| | | Endothelin-1 pg/mL | EN-RAGE ng/mL | Eotaxin pg/mL | Epiregulin pg/mL | Erythropoietin pg/mL | Fatty Acid Binding Protein ng/mL | Factor VII ng/mL |
|---|---|---|---|---|---|---|---|---|
| | Least Detectable Dose | 7.2 | 0.25 | 41 | 36 | 166 | 3.0 | 1.0 |
| | RBM Low Plasma Range | | 4.6 | | Pending | | | 106 |
| | RBM High Plasma Range | 26 | 592 | 177 | Pending | 284 | 10 | 443 |
| D | patient 1 | 1.0 | 0.9 | 1.0 | 0.5 | 1.0 | 1.1 | 1.2 |
| D | patient 7 | 2.0 | 0.8 | 1.1 | 1.5 | 1.0 | 1.3 | 1.5 |
| D | patient 2 | 1.0 | 0.9 | 1.5 | 2.4 | 1.0 | 1.5 | 1.3 |
| D | patient 3 | 1.5 | 0.5 | 1.0 | 1.2 | 1.0 | 1.0 | 1.1 |
| D | patient 5 | 1.5 | 0.5 | 1.4 | 1.1 | 0.6 | 1.5 | 0.9 |
| D | patient 4 | 1.0 | 0.5 | 1.1 | 1.0 | 1.0 | 3.1 | 1.1 |
| D | patient 6 | 1.0 | #VALUE! | 1.0 | 1.0 | 1.0 | 0.9 | 0.9 |
| D | NHD 1 | 1.0 | 0.5 | 1.1 | 1.2 | 1.0 | 60.3 | 1.1 |
| D | NHD 2 | 2.5 | 0.9 | 1.0 | 1.2 | 1.0 | 3.4 | 1.3 |
| E | patient 1 | 1.0 | 1.0 | 1.0 | 1.3 | 1.0 | 1.1 | 1.2 |
| E | patient 7 | 2.8 | 0.9 | 1.0 | 0.6 | 1.0 | 1.3 | 1.4 |
| E | patient 2 | 1.5 | 0.9 | 1.4 | 2.8 | 1.0 | 1.4 | 1.3 |
| E | patient 3 | 3.1 | 0.4 | 0.9 | 0.9 | 1.0 | 1.0 | 0.9 |
| E | patient 5 | 2.0 | 0.4 | 1.4 | 1.2 | 0.4 | 1.6 | 1.0 |
| E | patient 4 | 1.5 | 0.4 | 0.9 | 1.0 | 1.0 | 3.2 | 0.9 |
| E | patient 6 | 1.0 | #VALUE! | 1.1 | 1.0 | 1.0 | 1.0 | 1.0 |
| E | NHD 1 | 1.0 | 0.4 | 1.0 | 1.0 | 1.0 | 56.7 | 0.9 |
| E | NHD 2 | 2.7 | 1.3 | 0.9 | 1.0 | 1.0 | 2.2 | 1.1 |
| F | patient 1 | 1.0 | 0.8 | 1.1 | 2.0 | 1.0 | 1.1 | 0.9 |
| F | patient 7 | 1.0 | 1.0 | 0.6 | 1.0 | 1.0 | 1.2 | 1.3 |
| F | patient 2 | 1.0 | 0.8 | 2.2 | 2.8 | 1.0 | 1.2 | 1.0 |
| F | patient 3 | 1.0 | 0.5 | 0.9 | 1.2 | 1.0 | 1.0 | 0.8 |
| F | patient 5 | 1.0 | 0.7 | 1.2 | 0.9 | 1.0 | 0.7 | 0.8 |
| F | patient 4 | 1.0 | 0.6 | 1.5 | 0.4 | 1.0 | 1.2 | 1.0 |
| F | patient 6 | 1.0 | #VALUE! | 1.1 | 1.0 | 1.0 | 0.9 | 1.0 |

FIG. 14D.7

| | Endothelin-1 pg/mL | EN-RAGE ng/mL | Eotaxin pg/mL | Epiregulin pg/mL | Erythropoietin pg/mL | Fatty Acid Binding Protein ng/mL | Factor VII ng/mL |
|---|---|---|---|---|---|---|---|
| Least Detectable Dose | 7.2 | 0.25 | | | | | 1.0 |
| RBM Low Plasma Range | 26 | 4.6 | 41 | 36 | 166 | 3.0 | 106 |
| RBM High Plasma Range | | 592 | 177 | Pending | 284 | 10 | 443 |
| F NHD 1 | 2.0 | 0.4 | 1.3 | 1.6 | 1.0 | 5.8 | 1.1 |
| F NHD 2 | 1.9 | 0.4 | 1.0 | 0.9 | 1.0 | 0.2 | 1.1 |
| G patient 1 | 3.1 | 0.7 | 0.1 | 4.8 | 1.0 | 1.4 | 1.3 |
| G patient 7 | 3.4 | 0.9 | 0.1 | 6.6 | 1.0 | 1.4 | 1.3 |
| G patient 2 | 1.0 | 0.7 | 0.1 | 2.8 | 1.0 | 1.3 | 0.9 |
| G patient 3 | 1.0 | 0.7 | 0.1 | 2.2 | 1.0 | 1.0 | 0.6 |
| G patient 5 | 2.0 | 0.9 | 0.3 | 1.7 | 0.3 | 1.2 | 0.9 |
| G patient 4 | 1.0 | 0.6 | 0.7 | 4.9 | 1.0 | 1.5 | 0.8 |
| G patient 6 | 1.0 | #VALUE! | 0.2 | 1.0 | 1.0 | 1.1 | 1.0 |
| G NHD 1 | 1.0 | 0.5 | 0.0 | 1.6 | 1.0 | 21.7 | 0.7 |
| G NHD 2 | 1.0 | 1.9 | 0.2 | 1.5 | 1.0 | 0.3 | 0.8 |
| H patient 1 | 1.5 | 1.3 | 1.0 | 1.2 | 0.4 | 1.1 | 1.2 |
| H patient 7 | 1.0 | #VALUE! | 0.8 | 0.7 | 1.0 | 1.1 | 1.3 |
| H patient 2 | 1.0 | 1.2 | 0.8 | 1.7 | 1.0 | 0.8 | 0.9 |
| H patient 3 | 1.0 | #VALUE! | 0.9 | 1.2 | 1.0 | 1.1 | 0.9 |
| H patient 5 | 1.0 | 2.4 | 1.1 | 1.2 | 0.3 | 1.0 | 1.0 |
| H patient 4 | 1.0 | #VALUE! | 0.8 | 1.0 | 1.0 | 1.1 | 1.1 |
| H patient 6 | 1.0 | #VALUE! | 1.1 | 1.0 | 1.0 | 1.0 | 1.0 |
| H NHD 1 | 1.5 | 1.2 | 0.9 | 0.4 | 1.0 | 4.1 | 1.0 |
| H NHD 2 | 0.7 | 2.3 | 0.9 | 1.2 | 1.0 | 1.0 | 1.2 |
| I patient 1 | 1.0 | 1.0 | 1.0 | 1.0 | 1.0 | 1.0 | 1.0 |
| I patient 7 | 1.0 | 1.0 | 1.0 | 1.0 | 1.0 | 1.0 | 1.0 |
| I patient 2 | 1.0 | 1.0 | 1.0 | 1.0 | 1.0 | 1.0 | 1.0 |
| I patient 3 | 1.0 | 1.0 | 1.0 | 1.0 | 1.0 | 1.0 | 1.0 |

FIG. 14D.8

| | Endothelin-1 pg/mL | EN-RAGE ng/mL | Eotaxin pg/mL | Epiregulin pg/mL | Erythropoietin pg/mL | Fatty Acid Binding Protein ng/mL | Factor VII ng/mL |
|---|---|---|---|---|---|---|---|
| Least Detectable Dose | 7.2 | 0.25 | | | | 3.0 | 1.0 |
| RBM Low Plasma Range | | 4.6 | | Pending | 166 | | 106 |
| RBM High Plasma Range | 26 | 592 | 177 | Pending | 284 | 10 | 443 |
| patient 5 | 1.0 | 1.0 | 1.0 | 1.0 | 1.0 | 1.0 | 1.0 |
| patient 4 | 1.0 | 1.0 | 1.0 | 1.0 | 1.0 | 1.0 | 1.0 |
| patient 6 | 1.0 | #VALUE! | 1.0 | 1.0 | 1.0 | 1.0 | 1.0 |
| NHD 1 | 1.0 | 1.0 | 1.0 | 1.0 | 1.0 | 1.0 | 1.0 |
| NHD 2 | 1.0 | 1.0 | 1.0 | 1.0 | 1.0 | 1.0 | 1.0 |
| Messwert > ULD | | | | | | | |
| SI > 1,3 | | | | | | | |
| SI 0,7-1,3 | | | | | | | |
| SI 0-0,7 | | | | | | | |

FIG. 14E.1

| | Ferritin ng/mL | FGF basic pg/mL | Fibrinogen mg/mL | G-CSF pg/mL | Growth Hormone ng/mL | GM-CSF pg/mL | Glutathione S-Transferase ng/mL |
|---|---|---|---|---|---|---|---|
| Least Detectable Dose | 1.4 | 98 | 0.0098 | 5.0 | 0.13 | 57 | 0.40 |
| RBM Low Plasma Range | 5.0 | | 2.2 | | | | |
| RBM High Plasma Range | 552 | 2000 | 8.0 | 37 | 4.4 | 152 | 3.1 |
| Samples | | | | | | | |
| Donor_1 3. Aliquot A | 1290 | 1850 | 4.1 | 417 | 1.8 | 8.4 | 0.64 |
| Donor_1 3. Aliquot B | 1380 | 1710 | 4.4 | 279 | 1.7 | 2.5 | 0.84 |
| Donor_1 3. Aliquot C | 1300 | 414 | 4.2 | 221 | 1.9 | 5.0 | 0.55 |
| Donor_1 3. Aliquot D | 1400 | 2050 | 4.8 | 355 | 2.1 | 4.5 | 0.69 |
| Donor_1 3. Aliquot E | 1140 | 1840 | 4.1 | 270 | 2.0 | 10 | 0.59 |
| Donor_1 3. Aliquot F | 1280 | 1400 | 3.7 | 197 | 1.5 | 2.5 | 0.50 |
| Donor_1 3. Aliquot G | 1420 | 1760 | 4.6 | 236 | 1.8 | 57 | 0.52 |
| Donor_1 3. Aliquot H | 1280 | 159 | 4.0 | 211 | 1.8 | 4.5 | 0.52 |
| Donor_1 3. Aliquot I | 1160 | 1470 | 4.4 | 219 | 1.8 | 4.0 | 0.55 |
| Donor_2 3. Aliquot A | 1490 | 429 | 4.3 | 344 | 0.77 | 12 | 0.4 |
| Donor_2 3. Aliquot B | 1510 | 321 | 4.4 | 204 | 0.90 | 5.0 | 0.76 |
| Donor_2 3. Aliquot C | 1430 | 241 | 5.1 | 31 | 0.82 | 57 | 0.55 |
| Donor_2 3. Aliquot D | 1390 | 563 | 4.3 | 1470 | 1.2 | 24 | 1.7 |
| Donor_2 3. Aliquot E | 1390 | 563 | 4.0 | 1240 | 0.91 | 4.5 | 0.81 |
| Donor_2 3. Aliquot F | 1400 | 241 | 4.1 | 32 | 0.70 | 3.5 | 0.41 |
| Donor_2 3. Aliquot G | 1470 | 664 | 5.3 | 2160 | 0.87 | 180 | 0.69 |
| Donor_2 3. Aliquot H | 1330 | 176 | 3.9 | 36 | 0.78 | 3.5 | 0.4 |
| Donor_2 3. Aliquot I | 1320 | 225 | 5.2 | 32 | 0.71 | 57 | 0.4 |
| Donor_3 3. Aliquot A | 855 | 98 | 5.9 | 105 | 1.5 | 10 | 0.46 |
| Donor_3 3. Aliquot B | 757 | 29 | 5.5 | 41 | 1.4 | 7.8 | 1.4 |
| Donor_3 3. Aliquot C | 828 | 29 | 4.9 | 5 | 1.5 | 2.5 | 0.48 |
| Donor_3 3. Aliquot D | 799 | 209 | 5.2 | 1340 | 1.5 | 6.7 | 1.4 |
| Donor_3 3. Aliquot E | 797 | 159 | 6.0 | 1200 | 1.6 | 23 | 0.94 |
| Donor_3 3. Aliquot F | 824 | 29 | 5.2 | 5 | 1.3 | 18 | 0.4 |
| Donor_3 3. Aliquot G | 865 | 52 | 6.6 | 7.3 | 1.7 | 57 | 0.4 |
| Donor_3 3. Aliquot H | 758 | 98 | 5.3 | 5 | 1.3 | 57 | 0.4 |
| Donor_3 3. Aliquot I | 800 | 29 | 6.2 | 5 | 1.6 | 57 | 0.4 |

FIG. 14E.2

| | Ferritin ng/mL | FGF basic pg/mL | Fibrinogen mg/mL | G-CSF pg/mL | Growth Hormone ng/mL | GM-CSF pg/mL | Glutathione S-Transferase ng/mL |
|---|---|---|---|---|---|---|---|
| Least Detectable Dose | 1.4 | 98 | 0.0098 | 5.0 | 0.13 | 57 | 0.40 |
| RBM Low Plasma Range | 5.0 | | 2.2 | | | | |
| RBM High Plasma Range | 552 | 2000 | 8.0 | 37 | 4.4 | 152 | 3.1 |
| Donor_4_3. Aliquot A | 328 | 98 | 2.0 | 5.6 | 4.1 | 3.5 | 0.4 |
| Donor_4_3. Aliquot B | 311 | 52 | 2.0 | 9.6 | 4.2 | 57 | 0.99 |
| Donor_4_3. Aliquot C | 286 | 29 | 2.2 | 5 | 4.0 | 57 | 0.4 |
| Donor_4_3. Aliquot D | 308 | 459 | 2.0 | 976 | 4.2 | 18 | 1.2 |
| Donor_4_3. Aliquot E | 319 | 474 | 1.3 | 779 | 3.7 | 22 | 0.59 |
| Donor_4_3. Aliquot F | 347 | 99 | 1.8 | 18 | 3.3 | 5.0 | 0.4 |
| Donor_4_3. Aliquot G | 338 | 90 | 2.2 | 8.8 | 3.6 | 57 | 0.37 |
| Donor_4_3. Aliquot H | 315 | 98 | 1.7 | 5 | 4.1 | 57 | 0.39 |
| Donor_4_3. Aliquot I | 352 | 52 | 2.0 | 5 | 4.2 | 2.5 | 0.4 |
| Donor_5_3. Aliquot A | 1430 | 489 | 5.4 | 130 | 4.2 | 5.6 | 0.89 |
| Donor_5_3. Aliquot B | 1320 | 533 | 5.9 | 203 | 3.9 | 57 | 0.64 |
| Donor_5_3. Aliquot C | 1570 | 241 | 6.9 | 22 | 4.0 | 57 | 0.64 |
| Donor_5_3. Aliquot D | 1630 | 563 | 3.4 | 1480 | 3.7 | 23 | 1.3 |
| Donor_5_3. Aliquot E | 1510 | 533 | 5.2 | 3960 | 4.1 | 32 | 1.1 |
| Donor_5_3. Aliquot F | 1390 | 257 | 4.4 | 29 | 3.0 | 57 | 0.4 |
| Donor_5_3. Aliquot G | 1460 | 273 | 7.2 | 31 | 4.7 | 3.5 | 0.4 |
| Donor_5_3. Aliquot H | 1390 | 176 | 5.5 | 23 | 4.0 | 6.7 | 0.4 |
| Donor_5_3. Aliquot I | 1400 | 159 | 6.6 | 21 | 3.8 | 57 | 0.50 |
| Donor_6_3. Aliquot A | 382 | 72 | 4.1 | 12 | 3.0 | 7.8 | 0.4 |
| Donor_6_3. Aliquot B | 374 | 98 | 4.3 | 19 | 3.1 | 20 | 1.3 |
| Donor_6_3. Aliquot C | 370 | 98 | 4.9 | 5 | 2.8 | 3.0 | 0.4 |
| Donor_6_3. Aliquot D | 370 | 289 | 3.9 | 389 | 3.1 | 4.0 | 0.66 |
| Donor_6_3. Aliquot E | 364 | 289 | 3.2 | 975 | 2.9 | 7.8 | 1.4 |
| Donor_6_3. Aliquot F | 376 | 98 | 3.2 | 5 | 2.8 | 9.0 | 0.4 |
| Donor_6_3. Aliquot G | 391 | 192 | 5.5 | 20 | 3.2 | 6.7 | 0.4 |
| Donor_6_3. Aliquot H | 353 | 98 | 3.9 | 5 | 3.1 | 7.2 | 0.4 |
| Donor_6_3. Aliquot I | 375 | 98 | 3.4 | 5 | 3.0 | 57 | 0.37 |

FIG. 14E.3

| | Ferritin ng/mL | FGF basic pg/mL | Fibrinogen mg/mL | G-CSF pg/mL | Growth Hormone ng/mL | GM-CSF pg/mL | Glutathione S-Transferase ng/mL |
|---|---|---|---|---|---|---|---|
| Least Detectable Dose | 1.4 | 98 | 0.0098 | 5.0 | 0.13 | 57 | 0.40 |
| RBM Low Plasma Range | 5.0 | | 2.2 | | | | |
| RBM High Plasma Range | 552 | 2000 | 8.0 | 37 | 4.4 | 152 | 3.1 |
| Donor_7_3. Aliquot A | 468 | 391 | 3.0 | 334 | 0.32 | 20 | 0.39 |
| Donor_7_3. Aliquot B | 491 | 249 | 2.9 | 86 | 0.39 | 10 | 1.2 |
| Donor_7_3. Aliquot C | 535 | 98 | 3.2 | 5 | 0.22 | 5.6 | 0.48 |
| Donor_7_3. Aliquot D | 451 | 281 | 2.6 | 892 | 0.39 | 18 | 0.86 |
| Donor_7_3. Aliquot E | 490 | 265 | 2.1 | 270 | 0.31 | 18 | 0.50 |
| Donor_7_3. Aliquot F | 505 | 98 | 2.6 | 5 | 0.26 | 10 | 0.4 |
| Donor_7_3. Aliquot G | 471 | 233 | 2.9 | 5 | 0.23 | 3.0 | 0.4 |
| Donor_7_3. Aliquot H | 404 | 72 | 2.4 | 5 | 0.25 | 9.0 | 0.4 |
| Donor_7_3. Aliquot I | 409 | 98 | 3.0 | 5 | 0.29 | 9.0 | 0.4 |
| Donor_8_3. Aliquot A | 34 | 98 | 1.8 | 5.8 | 0.35 | 5.0 | 0.37 |
| Donor_8_3. Aliquot B | 32 | 98 | 1.7 | 4.7 | 0.35 | 6.7 | 1.8 |
| Donor_8_3. Aliquot C | 37 | 90 | 1.8 | 5 | 0.20 | 12 | 0.4 |
| Donor_8_3. Aliquot D | 48 | 414 | 1.7 | 1330 | 0.94 | 60 | 3.4 |
| Donor_8_3. Aliquot E | 39 | 336 | 1.7 | 1010 | 0.90 | 33 | 2.1 |
| Donor_8_3. Aliquot F | 32 | 273 | 1.7 | 4.7 | 0.36 | 18 | 0.4 |
| Donor_8_3. Aliquot G | 42 | 98 | 2.0 | 5 | 0.33 | 3.5 | 0.4 |
| Donor_8_3. Aliquot H | 38 | 142 | 1.7 | 5 | 0.30 | 17 | 0.4 |
| Donor_8_3. Aliquot I | 36 | 98 | 1.9 | 5 | 0.28 | 14 | 0.55 |
| Donor_9_3. Aliquot A | 4.8 | 98 | 1.5 | 17 | 7.2 | 11 | 0.73 |
| Donor_9_3. Aliquot B | 2.6 | 122 | 1.6 | 21 | 6.8 | 13 | 2.2 |
| Donor_9_3. Aliquot C | 5.7 | 94 | 1.4 | 19 | 6.6 | 21 | 0.40 |
| Donor_9_3. Aliquot D | 11 | 414 | 1.5 | 2320 | 6.8 | 29 | 2.6 |
| Donor_9_3. Aliquot E | 6.0 | 332 | 1.5 | 1490 | 6.8 | 13 | 2.4 |
| Donor_9_3. Aliquot F | 3.6 | 137 | 1.2 | 11 | 6.4 | 5.8 | 0.76 |
| Donor_9_3. Aliquot G | 12 | 179 | 1.9 | 39 | 6.2 | 17 | 0.56 |
| Donor_9_3. Aliquot H | 5.5 | 37 | 1.3 | 5.4 | 6.8 | 15 | 0.53 |
| Donor_9_3. Aliquot I | 3.3 | 37 | 1.6 | 5.4 | 6.4 | 8.7 | 0.37 |

FIG. 14E.4

| | Ferritin ng/mL | FGF basic pg/mL | Fibrinogen mg/mL | G-CSF pg/mL | Growth Hormone ng/mL | GM-CSF pg/mL | Glutathione S-Transferase ng/mL |
|---|---|---|---|---|---|---|---|
| Least Detectable Dose | 1.4 | 98 | 0.0098 | 5.0 | 0.13 | 57 | 0.40 |
| RBM Low Plasma Range | 5.0 | | 2.2 | | | | |
| RBM High Plasma Range | 552 | 2000 | 8.0 | 37 | 4.4 | 152 | 3.1 |
| EDTA Plasma | | | | | | | |
| donor #1 plasma | 1190 | 736 | 4.6 | 240 | 1.4 | 18 | 1.1 |
| donor #2 plasma | 1670 | 339 | 8.1 | 45 | 0.89 | 15 | 0.4 |
| donor #3 plasma | 934 | 94 | 8.7 | 5 | 1.5 | 27 | 1.0 |
| donor #4 plasma | 320 | 51 | 3.2 | 4.5 | 5.3 | 10.0 | 0.4 |
| donor #5 plasma | 1190 | 346 | 11 | 24 | 5.1 | 23 | 1.3 |
| donor #6 plasma | 382 | 21 | 6.7 | 6.2 | 4.1 | 20 | 0.69 |
| donor #7 plasma | 545 | 98 | 4.5 | 6.2 | 0.49 | 17 | 0.4 |
| donor #8 plasma | 22 | 87 | 2.0 | 5 | 0.38 | 15 | 0.46 |
| donor #9 plasma | 3.3 | 87 | 2.3 | 18 | 7.2 | 5.3 | 0.90 |
| Stimulations Indices | | | | | | | |
| patient 1 | 1.1 | 1.3 | 0.9 | 1.9 | 1.0 | 2.1 | 1.2 |
| patient 7 | 1.1 | 1.9 | 0.8 | 10.8 | 1.1 | 0.2 | 1.0 |

FIG. 14E.5

| | | Ferritin | FGF basic | Fibrinogen | G-CSF | Growth Hormone | GM-CSF | Glutathione S-Transferase |
|---|---|---|---|---|---|---|---|---|
| | | ng/mL | pg/mL | mg/mL | pg/mL | ng/mL | pg/mL | ng/mL |
| | Least Detectable Dose | 1.4 | 98 | 0.0098 | 5.0 | 0.13 | 57 | 0.40 |
| | RBM Low Plasma Range | 5.0 | 2000 | 2.2 | 37 | 4.4 | 152 | 3.1 |
| | RBM High Plasma Range | 552 | | 8.0 | 21.0 | 0.9 | 0.2 | 1.1 |
| A | patient 2 | 1.1 | 3.3 | 1.0 | 1.1 | 1.0 | 1.4 | 1.0 |
| A | patient 3 | 0.9 | 1.9 | 1.0 | 6.2 | 1.1 | 0.1 | 1.8 |
| A | patient 5 | 1.0 | 3.1 | 0.8 | 2.3 | 1.0 | 0.1 | 1.1 |
| A | patient 4 | 1.0 | 0.7 | 1.2 | 66.8 | 1.1 | 2.3 | 1.0 |
| A | patient 6 | 1.1 | 4.0 | 1.0 | | | | |
| A | NHD 1 | 1.0 | 1.0 | 1.0 | 1.2 | 1.3 | 0.4 | 0.7 |
| A | NHD 2 | 1.4 | 2.7 | 0.9 | 3.1 | 1.1 | 1.3 | 2.0 |
| B | patient 1 | 1.2 | 1.2 | 1.0 | 1.3 | 1.0 | 0.6 | 1.5 |
| B | patient 7 | 1.1 | 1.4 | 0.8 | 6.4 | 1.3 | 0.1 | 1.9 |
| B | patient 2 | 0.9 | 1.0 | 0.9 | 8.2 | 0.9 | 0.1 | 3.4 |
| B | patient 3 | 0.9 | 1.0 | 1.0 | 1.9 | 1.0 | 22.9 | 2.5 |
| B | patient 5 | 0.9 | 3.4 | 0.9 | 9.7 | 1.0 | 1.0 | 1.3 |
| B | patient 4 | 1.0 | 1.0 | 1.3 | 3.8 | 1.0 | 0.3 | 3.4 |
| B | patient 6 | 1.2 | 2.5 | 1.0 | 17.1 | 1.3 | 1.1 | 3.0 |
| B | NHD 1 | 0.9 | 1.0 | 0.9 | 0.9 | 1.3 | 0.5 | 3.3 |
| B | NHD 2 | 0.8 | 3.3 | 1.0 | 3.9 | 1.1 | 1.5 | 5.9 |
| C | patient 1 | 1.1 | 0.3 | 1.0 | 1.0 | 1.1 | 1.3 | 1.0 |
| C | patient 7 | 1.1 | 1.1 | 1.0 | 1.0 | 1.2 | 1.0 | 1.4 |
| C | patient 2 | 1.0 | 1.0 | 0.8 | 1.0 | 0.9 | 0.0 | 1.2 |
| C | patient 3 | 0.8 | 0.6 | 1.1 | 1.0 | 1.0 | 22.9 | 1.0 |
| C | patient 5 | 1.1 | 1.5 | 1.0 | 1.0 | 1.1 | 1.0 | 1.3 |
| C | patient 4 | 1.0 | 1.0 | 1.4 | 1.0 | 1.0 | 0.1 | 1.1 |
| C | patient 6 | 1.3 | 1.0 | 1.1 | 1.0 | 0.8 | 0.6 | 1.2 |
| C | NHD 1 | 1.0 | 0.9 | 0.9 | 1.0 | 0.7 | 0.8 | 0.7 |
| C | NHD 2 | 1.7 | 2.6 | 0.9 | 3.6 | 1.0 | 2.4 | 1.1 |

FIG. 14E.6

| | Ferritin ng/mL | FGF basic pg/mL | Fibrinogen mg/mL | G-CSF pg/mL | Growth Hormone ng/mL | GM-CSF pg/mL | Glutathione S-Transferase ng/mL |
|---|---|---|---|---|---|---|---|
| Least Detectable Dose | 1.4 | 98 | 0.0098 | 5.0 | 0.13 | 57 | 0.40 |
| RBM Low Plasma Range | 5.0 | 2000 | 2.2 | 37 | 4.4 | 152 | 3.1 |
| RBM High Plasma Range | 552 | | 8.0 | | | | |
| D patient 1 | 1.2 | 1.4 | 1.1 | 1.6 | 1.2 | 1.1 | 1.3 |
| D patient 7 | 1.1 | 2.5 | 0.8 | 45.9 | 1.6 | 0.4 | 4.1 |
| D patient 2 | 1.0 | 7.1 | 0.8 | 268.0 | 0.9 | 0.1 | 3.5 |
| D patient 3 | 0.9 | 8.8 | 1.0 | 195.2 | 1.0 | 7.3 | 2.9 |
| D patient 5 | 1.2 | 3.5 | 0.5 | 70.8 | 1.0 | 0.4 | 2.6 |
| D patient 4 | 1.0 | 2.9 | 1.1 | 77.8 | 1.1 | 0.1 | 1.8 |
| D patient 6 | 1.1 | 2.9 | 0.9 | 178.4 | 1.3 | 2.0 | 2.2 |
| D NHD 1 | 1.3 | 4.2 | 0.9 | 266.0 | 3.4 | 4.2 | 6.1 |
| D NHD 2 | 3.4 | 11.3 | 0.9 | 432.8 | 1.1 | 3.3 | 7.0 |
| E patient 1 | 1.0 | 1.3 | 0.9 | 1.2 | 1.1 | 2.6 | 1.1 |
| E patient 7 | 1.1 | 2.5 | 0.8 | 38.8 | 1.3 | 0.1 | 2.0 |
| E patient 2 | 1.0 | 5.4 | 1.0 | 240.0 | 1.0 | 0.4 | 2.3 |
| E patient 3 | 0.9 | 9.1 | 0.7 | 155.8 | 0.9 | 8.8 | 1.5 |
| E patient 5 | 1.1 | 3.4 | 0.8 | 189.5 | 1.1 | 0.6 | 2.2 |
| E patient 4 | 1.0 | 2.9 | 0.9 | 195.0 | 1.0 | 0.1 | 3.7 |
| E patient 6 | 1.2 | 2.7 | 0.7 | 54.0 | 1.1 | 2.0 | 1.3 |
| E NHD 1 | 1.1 | 3.4 | 0.9 | 262.0 | 3.3 | 2.3 | 3.8 |
| E NHD 2 | 1.8 | 9.0 | 0.9 | 278.0 | 1.1 | 1.4 | 6.6 |
| F patient 1 | 1.1 | 1.0 | 0.8 | 0.9 | 0.8 | 0.6 | 0.9 |
| F patient 7 | 1.1 | 1.1 | 0.8 | 1.0 | 1.0 | 0.1 | 1.0 |
| F patient 2 | 1.0 | 1.0 | 0.8 | 1.0 | 0.8 | 0.3 | 1.0 |
| F patient 3 | 1.0 | 1.9 | 0.9 | 3.6 | 0.8 | 2.0 | 1.0 |
| F patient 5 | 1.0 | 1.6 | 0.7 | 1.4 | 0.8 | 1.0 | 0.8 |
| F patient 4 | 1.0 | 1.0 | 0.9 | 1.0 | 0.9 | 0.2 | 1.1 |
| F patient 6 | 1.2 | 1.0 | 0.9 | 1.0 | 0.9 | 1.1 | 1.0 |

FIG. 14E.7

| | Ferritin ng/mL | FGF basic pg/mL | Fibrinogen mg/mL | G-CSF pg/mL | Growth Hormone ng/mL | GM-CSF pg/mL | Glutathione S-Transferase ng/mL |
|---|---|---|---|---|---|---|---|
| Least Detectable Dose | 1.4 | 98 | 0.0098 | 5.0 | 0.13 | 57 | 0.40 |
| RBM Low Plasma Range | 5.0 | 2000 | 2.2 | 37 | 4.4 | 152 | 3.1 |
| RBM High Plasma Range | 552 | | 8.0 | | | | |
| F NHD 1 | 0.9 | 2.8 | 0.9 | 0.9 | 1.3 | 1.3 | 0.7 |
| F NHD 2 | 1.1 | 3.7 | 0.8 | 2.1 | 1.0 | 0.7 | 2.1 |
| G patient 1 | 1.2 | 1.2 | 1.1 | 1.1 | 1.0 | 14.4 | 1.0 |
| G patient 7 | 1.1 | 3.0 | 1.0 | 67.5 | 1.2 | 3.2 | 1.7 |
| G patient 2 | 1.1 | 1.8 | 1.1 | 1.5 | 1.0 | 1.0 | 1.0 |
| G patient 3 | 1.0 | 1.7 | 1.1 | 1.8 | 0.9 | 22.9 | 0.9 |
| G patient 5 | 1.0 | 1.7 | 1.1 | 1.5 | 1.2 | 0.1 | 0.8 |
| G patient 4 | 1.0 | 2.0 | 1.6 | 4.1 | 1.1 | 0.1 | 1.1 |
| G patient 6 | 1.2 | 2.4 | 1.0 | 1.0 | 0.8 | 0.3 | 1.0 |
| G NHD 1 | 1.1 | 1.0 | 1.1 | 1.0 | 1.2 | 0.2 | 0.7 |
| G NHD 2 | 3.6 | 4.9 | 1.2 | 7.4 | 1.0 | 1.9 | 1.5 |
| H patient 1 | 1.1 | 0.1 | 0.9 | 1.0 | 1.0 | 1.1 | 1.0 |
| H patient 7 | 1.0 | 0.8 | 0.8 | 1.1 | 1.1 | 0.1 | 1.0 |
| H patient 2 | 0.9 | 3.3 | 0.9 | 1.0 | 0.8 | 1.0 | 1.0 |
| H patient 3 | 0.9 | 1.9 | 0.8 | 1.0 | 1.0 | 22.9 | 1.0 |
| H patient 5 | 1.0 | 1.1 | 0.8 | 1.1 | 1.1 | 0.1 | 0.8 |
| H patient 4 | 0.9 | 1.0 | 1.1 | 1.0 | 1.0 | 0.1 | 1.1 |
| H patient 6 | 1.0 | 0.7 | 0.8 | 1.0 | 0.9 | 1.0 | 1.0 |
| H NHD 1 | 1.1 | 1.4 | 0.9 | 1.0 | 1.1 | 1.2 | 0.7 |
| H NHD 2 | 1.7 | 1.0 | 0.8 | 1.0 | 1.1 | 1.7 | 1.4 |
| I patient 1 | 1.0 | 1.0 | 1.0 | 1.0 | 1.0 | 1.0 | 1.0 |
| I patient 7 | 1.0 | 1.0 | 1.0 | 1.0 | 1.0 | 1.0 | 1.0 |
| I patient 2 | 1.0 | 1.0 | 1.0 | 1.0 | 1.0 | 1.0 | 1.0 |
| I patient 3 | 1.0 | 1.0 | 1.0 | 1.0 | 1.0 | 1.0 | 1.0 |

FIG. 14E.8

| | Ferritin ng/mL | FGF basic pg/mL | Fibrinogen mg/mL | G-CSF pg/mL | Growth Hormone ng/mL | GM-CSF pg/mL | Glutathione S-Transferase ng/mL |
|---|---|---|---|---|---|---|---|
| Least Detectable Dose | 1.4 | 98 | 0.0098 | 5.0 | 0.13 | 57 | 0.40 |
| RBM Low Plasma Range | 5.0 | | 2.2 | | | | |
| RBM High Plasma Range | 552 | 2000 | 8.0 | 37 | 4.4 | 152 | 3.1 |
| patient 5 | 1.0 | 1.0 | 1.0 | 1.0 | 1.0 | 1.0 | 1.0 |
| patient 4 | 1.0 | 1.0 | 1.0 | 1.0 | 1.0 | 1.0 | 1.0 |
| patient 6 | 1.0 | 1.0 | 1.0 | 1.0 | 1.0 | 1.0 | 1.0 |
| NHD 1 | 1.0 | 1.0 | 1.0 | 1.0 | 1.0 | 1.0 | 1.0 |
| NHD 2 | 1.0 | 1.0 | 1.0 | 1.0 | 1.0 | 1.0 | 1.0 |

Messwert > ULD
SI > 1,3
SI 0,7-1,3
SI 0-0,7

FIG. 14F.1

| | Haptoglobin mg/mL | ICAM-1 ng/mL | IFN-gamma pg/mL | IgA mg/mL | IgE ng/mL | IGF-1 ng/mL | IgM mg/mL |
|---|---|---|---|---|---|---|---|
| Least Detectable Dose | 0.025 | 3.2 | 4.6 | 0.0084 | 14 | 4.0 | 0.015 |
| RBM Low Plasma Range | 0.047 | 42 | Pending | 0.58 | | | 0.24 |
| RBM High Plasma Range | 7.6 | 213 | Pending | 5.6 | 770 | 177 | 3.3 |
| Samples | | | | | | | |
| Donor_1 3. Aliquot A | 1.0 | 467 | 3.8 | 2.0 | 13 | 49 | 0.63 |
| Donor_1 3. Aliquot B | 1.2 | 432 | 4.5 | 2.3 | 11 | 49 | 0.66 |
| Donor_1 3. Aliquot C | 1.1 | 452 | 2.7 | 2.2 | 1.8 | 67 | 0.68 |
| Donor_1 3. Aliquot D | 1.2 | 465 | 4.6 | 2.4 | 12 | 46 | 0.71 |
| Donor_1 3. Aliquot E | 1.1 | 438 | 4.6 | 2.1 | 13 | 45 | 0.63 |
| Donor_1 3. Aliquot F | 1.2 | 441 | 4.6 | 2.1 | 4.4 | 55 | 0.60 |
| Donor_1 3. Aliquot G | 1.2 | 471 | 4.5 | 2.3 | 11 | 100 | 0.70 |
| Donor_1 3. Aliquot H | 1.1 | 491 | 4.6 | 2.1 | 9.6 | 46 | 0.60 |
| Donor_1 3. Aliquot I | 1.1 | 438 | 4.6 | 2.3 | 6.2 | 46 | 0.65 |
| Donor_2 3. Aliquot A | 1.3 | 491 | 7.2 | 2.5 | 210 | 94 | 0.15 |
| Donor_2 3. Aliquot B | 1.8 | 495 | 6.7 | 2.5 | 217 | 90 | 0.15 |
| Donor_2 3. Aliquot C | 1.9 | 499 | 4.6 | 2.5 | 98 | 87 | 0.21 |
| Donor_2 3. Aliquot D | 1.5 | 489 | 31 | 2.4 | 258 | 81 | 0.14 |
| Donor_2 3. Aliquot E | 2.2 | 479 | 9.5 | 2.5 | 221 | 86 | 0.18 |
| Donor_2 3. Aliquot F | 2.1 | 504 | 4.6 | 2.5 | 177 | 73 | 0.17 |
| Donor_2 3. Aliquot G | 2.3 | 514 | 14 | 2.5 | 151 | 221 | 0.18 |
| Donor_2 3. Aliquot H | 1.9 | 490 | 2.7 | 2.6 | 175 | 75 | 0.18 |
| Donor_2 3. Aliquot I | 1.7 | 479 | 3.8 | 2.5 | 195 | 73 | 0.19 |
| Donor_3 3. Aliquot A | 0.014 | 283 | 8.5 | 1.5 | 26 | 380 | 0.66 |
| Donor_3 3. Aliquot B | 0.018 | 239 | 4.6 | 1.6 | 27 | 368 | 0.67 |
| Donor_3 3. Aliquot C | 0.019 | 278 | 4.6 | 1.6 | 7.6 | 408 | 0.66 |
| Donor_3 3. Aliquot D | 0.013 | 231 | 8.2 | 1.6 | 45 | 387 | 0.67 |
| Donor_3 3. Aliquot E | 0.014 | 306 | 9.2 | 1.7 | 40 | 393 | 0.74 |
| Donor_3 3. Aliquot F | 0.021 | 249 | 4.6 | 1.5 | 26 | 338 | 0.69 |
| Donor_3 3. Aliquot G | 0.087 | 259 | 4.6 | 1.6 | 14 | 546 | 0.72 |
| Donor_3 3. Aliquot H | 0.022 | 208 | 4.6 | 1.5 | 21 | 386 | 0.67 |
| Donor_3 3. Aliquot I | 0.051 | 221 | 4.6 | 1.5 | 29 | 403 | 0.69 |

FIG. 14F.2

| | Haptoglobin mg/mL 0.025 | ICAM-1 ng/mL 3.2 | IFN-gamma pg/mL 4.6 | IgA mg/mL 0.0084 | IgE ng/mL 14 | IGF-1 ng/mL 4.0 | IgM mg/mL 0.015 |
|---|---|---|---|---|---|---|---|
| Least Detectable Dose | | | | | | | |
| RBM Low Plasma Range | 0.047 | 42 | Pending | 0.58 | 770 | 177 | 0.24 |
| RBM High Plasma Range | 7.6 | 213 | Pending | 5.6 | | | 3.3 |
| Donor_4_3. Aliquot A | 0.0075 | 456 | 4.6 | 2.5 | 12 | 4 | 0.39 |
| Donor_4_3. Aliquot B | 0.014 | 466 | 4.6 | 2.3 | 14 | 4 | 0.29 |
| Donor_4_3. Aliquot C | 0.0086 | 453 | 4.6 | 2.4 | 14 | 4 | 0.36 |
| Donor_4_3. Aliquot D | 0.014 | 471 | 6.2 | 2.2 | 32 | 4 | 0.31 |
| Donor_4_3. Aliquot E | 0.0086 | 477 | 7.0 | 2.3 | 24 | 4 | 0.29 |
| Donor_4_3. Aliquot F | 0.019 | 467 | 3.8 | 2.3 | 13 | 4 | 0.31 |
| Donor_4_3. Aliquot G | 0.019 | 462 | 4.6 | 2.4 | 8.0 | 22 | 0.29 |
| Donor_4_3. Aliquot H | 0.013 | 474 | 4.6 | 2.3 | 8.0 | 4 | 0.28 |
| Donor_4_3. Aliquot I | 0.011 | 447 | 4.6 | 2.3 | 9.6 | 4 | 0.30 |
| Donor_5_3. Aliquot A | 3.7 | 241 | 7.5 | 1.1 | 321 | 323 | 0.24 |
| Donor_5_3. Aliquot B | 3.6 | 213 | 8.2 | 1.1 | 270 | 337 | 0.25 |
| Donor_5_3. Aliquot C | 3.8 | 246 | 4.6 | 1.1 | 84 | 330 | 0.24 |
| Donor_5_3. Aliquot D | 3.4 | 263 | 20 | 1.1 | 271 | 373 | 0.22 |
| Donor_5_3. Aliquot E | 3.2 | 261 | 21 | 1.2 | 274 | 382 | 0.23 |
| Donor_5_3. Aliquot F | 3.1 | 164 | 7.2 | 1.0 | 204 | 350 | 0.23 |
| Donor_5_3. Aliquot G | 3.5 | 255 | 6.2 | 1.0 | 59 | 574 | 0.26 |
| Donor_5_3. Aliquot H | 3.2 | 223 | 3.8 | 1.0 | 296 | 355 | 0.26 |
| Donor_5_3. Aliquot I | 3.4 | 242 | 5.1 | 1.00 | 289 | 329 | 0.24 |
| Donor_6_3. Aliquot A | 4.2 | 130 | 4.6 | 0.79 | 317 | 47 | 0.38 |
| Donor_6_3. Aliquot B | 4.4 | 146 | 4.6 | 0.81 | 306 | 46 | 0.42 |
| Donor_6_3. Aliquot C | 4.2 | 157 | 4.6 | 0.78 | 139 | 54 | 0.37 |
| Donor_6_3. Aliquot D | 4.3 | 149 | 31 | 0.81 | 326 | 47 | 0.41 |
| Donor_6_3. Aliquot E | 3.9 | 120 | 74 | 0.94 | 269 | 50 | 0.34 |
| Donor_6_3. Aliquot F | 4.3 | 120 | 4.6 | 0.82 | 222 | 45 | 0.33 |
| Donor_6_3. Aliquot G | 4.2 | 156 | 4.6 | 0.81 | 91 | 189 | 0.35 |
| Donor_6_3. Aliquot H | 4.1 | 146 | 4.6 | 0.71 | 340 | 42 | 0.35 |
| Donor_6_3. Aliquot I | 3.7 | 127 | 4.6 | 0.76 | 272 | 45 | 0.34 |

FIG. 14F.3

| | Haptoglobin mg/mL | ICAM-1 ng/mL | IFN-gamma pg/mL | IgA mg/mL | IgE ng/mL | IGF-1 ng/mL | IgM mg/mL |
|---|---|---|---|---|---|---|---|
| Least Detectable Dose | 0.025 | 3.2 | 4.6 | 0.0084 | 14 | 4.0 | 0.015 |
| RBM Low Plasma Range | 0.047 | 42 | Pending | 0.58 | 770 | 177 | 0.24 |
| RBM High Plasma Range | 7.6 | 213 | Pending | 5.6 | | | 3.3 |
| Donor_7 3. Aliquot A | 2.6 | 85 | 4.6 | 1.5 | 56 | 14 | 0.63 |
| Donor_7 3. Aliquot B | 2.7 | 85 | 4.6 | 1.5 | 51 | 18 | 0.59 |
| Donor_7 3. Aliquot C | 2.7 | 89 | 4.6 | 1.6 | 14 | 26 | 0.63 |
| Donor_7 3. Aliquot D | 2.0 | 74 | 4.6 | 1.4 | 62 | 15 | 0.59 |
| Donor_7 3. Aliquot E | 1.9 | 84 | 4.6 | 1.1 | 56 | 17 | 0.48 |
| Donor_7 3. Aliquot F | 2.6 | 83 | 4.6 | 1.5 | 39 | 9.8 | 0.66 |
| Donor_7 3. Aliquot G | 2.3 | 93 | 4.6 | 1.4 | 25 | 98 | 0.60 |
| Donor_7 3. Aliquot H | 2.6 | 81 | 4.6 | 1.4 | 36 | 8.1 | 0.60 |
| Donor_7 3. Aliquot I | 2.7 | 79 | 4.6 | 1.5 | 46 | 12 | 0.60 |
| Donor_8 3. Aliquot A | 0.014 | 61 | 5.6 | 0.77 | 17 | 176 | 0.30 |
| Donor_8 3. Aliquot B | 0.016 | 66 | 4.6 | 0.85 | 8.0 | 168 | 0.34 |
| Donor_8 3. Aliquot C | 0.0065 | 50 | 550 | 0.83 | 14 | 163 | 0.31 |
| Donor_8 3. Aliquot D | 0.013 | 63 | 1880 | 0.73 | 77 | 179 | 0.36 |
| Donor_8 3. Aliquot E | 0.037 | 59 | 283 | 0.73 | 65 | 162 | 0.32 |
| Donor_8 3. Aliquot F | 0.018 | 63 | 118 | 0.85 | 15 | 166 | 0.32 |
| Donor_8 3. Aliquot G | 0.016 | 65 | 4.6 | 0.74 | 8.0 | 181 | 0.28 |
| Donor_8 3. Aliquot H | 0.016 | 64 | 41 | 0.84 | 10 | 177 | 0.37 |
| Donor_8 3. Aliquot I | 0.011 | 58 | 3.8 | 0.78 | 3.7 | 175 | 0.33 |
| Donor_9 3. Aliquot A | 0.018 | 79 | 17 | 1.0 | 9.3 | 745 | 1.0 |
| Donor_9 3. Aliquot B | 0.018 | 82 | 21 | 1.0 | 9.3 | 716 | 1.0 |
| Donor_9 3. Aliquot C | 0.012 | 69 | 519 | 1.0 | 4.1 | 784 | 0.97 |
| Donor_9 3. Aliquot D | 0.0062 | 75 | 2360 | 1.0 | 63 | 681 | 1.0 |
| Donor_9 3. Aliquot E | 0.013 | 71 | 490 | 1.00 | 39 | 651 | 1.0 |
| Donor_9 3. Aliquot F | 0.0076 | 78 | 26 | 1.0 | 5.8 | 688 | 0.95 |
| Donor_9 3. Aliquot G | 0.016 | 68 | 7.6 | 1.1 | 5.2 | 636 | 1.1 |
| Donor_9 3. Aliquot H | 0.017 | 75 | 9.0 | 1.0 | 6.0 | 703 | 1.0 |
| Donor_9 3. Aliquot I | 0.012 | 76 | 14 | 1.0 | 6.2 | 732 | 1.1 |

FIG. 14F.4

| | Haptoglobin mg/mL | ICAM-1 ng/mL | IFN-gamma pg/mL | IgA mg/mL | IgE ng/mL | IGF-1 ng/mL | IgM mg/mL |
|---|---|---|---|---|---|---|---|
| Least Detectable Dose | 0.025 | 3.2 | 4.6 | 0.0084 | 14 | 4.0 | 0.015 |
| RBM Low Plasma Range | 0.047 | 42 | Pending | 0.58 | 770 | 177 | 0.24 |
| RBM High Plasma Range | 7.6 | 213 | Pending | 5.6 | | | 3.3 |
| EDTA Plasma | | | | | | | |
| donor #1 plasma | 1.3 | 206 | 4.0 | 2.4 | 6.6 | 4 | 0.57 |
| donor #2 plasma | 3.6 | 371 | 10 | 4.0 | 172 | 4 | 0.22 |
| donor #3 plasma | 0.58 | 171 | 5.8 | 2.8 | 26 | 12 | 0.93 |
| donor #4 plasma | 0.0097 | 348 | 4.6 | 3.6 | 14 | 4 | 0.39 |
| donor #5 plasma | 5.9 | 136 | 13 | 1.8 | 318 | 18 | 0.32 |
| donor #6 plasma | 5.7 | 129 | 4.6 | 1.3 | 559 | 4 | 0.43 |
| donor #7 plasma | 4.6 | 109 | 5.8 | 2.4 | 81 | 4 | 0.79 |
| donor #8 plasma | 0.36 | 87 | 4.6 | 1.0 | 17 | 32 | 0.38 |
| donor #9 plasma | 0.32 | 100 | 4.0 | 1.4 | 3.5 | 325 | 1.5 |
| Stimulations indices | Haptoglobin | ICAM-1 | IFN-gamma | IgA | IgE | IGF-1 | IgM |
| patient 1 | 1.0 | 1.1 | 0.8 | 0.9 | 2.0 | 1.1 | 1.0 |
| patient 7 | 0.8 | 1.0 | 1.9 | 1.0 | 1.1 | 1.3 | 0.8 |
| | A | | | | | | |
| | A | | | | | | |

FIG. 14F.5

| | | | Haptoglobin mg/mL | ICAM-1 ng/mL | IFN-gamma pg/mL | IgA mg/mL | IgE ng/mL | IGF-1 ng/mL | IgM mg/mL |
|---|---|---|---|---|---|---|---|---|---|
| | | Least Detectable Dose | 0.025 | 3.2 | 4.6 | 0.0084 | 14 | 4.0 | 0.015 |
| | | RBM Low Plasma Range | 0.047 | 42 | Pending | 0.58 | 770 | 177 | 0.24 |
| | | RBM High Plasma Range | 7.6 | 213 | Pending | 5.6 | | | 3.3 |
| A | | patient 2 | 0.3 | 1.3 | 1.8 | 1.0 | 0.9 | 0.9 | 0.9 |
| A | | patient 3 | 0.7 | 1.0 | 1.0 | 1.1 | 1.2 | 1.0 | 1.3 |
| A | | patient 5 | 1.1 | 1.0 | 1.5 | 1.1 | 1.1 | 1.0 | 1.0 |
| A | | patient 4 | 1.1 | 1.0 | 1.0 | 1.0 | 1.2 | 1.0 | 1.1 |
| A | | patient 6 | 1.0 | 1.1 | 1.0 | 1.0 | 1.2 | 1.1 | 1.0 |
| A | | NHD 1 | 1.4 | 1.0 | 1.5 | 1.0 | 4.6 | 1.0 | 0.9 |
| A | | NHD 2 | 1.6 | 1.0 | 1.2 | 1.0 | 1.5 | 1.0 | 1.0 |
| B | | patient 1 | 1.1 | 1.0 | 1.0 | 1.0 | 1.8 | 1.1 | 1.0 |
| B | | patient 7 | 1.0 | 1.0 | 1.7 | 1.0 | 1.1 | 1.2 | 0.8 |
| B | | patient 2 | 0.4 | 1.1 | 1.0 | 1.1 | 0.9 | 0.9 | 1.0 |
| B | | patient 3 | 1.4 | 1.0 | 1.0 | 1.0 | 1.4 | 1.0 | 1.0 |
| B | | patient 5 | 1.1 | 0.9 | 1.6 | 1.1 | 0.9 | 1.0 | 1.1 |
| B | | patient 4 | 1.2 | 1.1 | 1.0 | 1.1 | 1.1 | 1.0 | 1.2 |
| B | | patient 6 | 1.0 | 1.1 | 1.0 | 1.0 | 1.1 | 1.4 | 1.0 |
| B | | NHD 1 | 1.6 | 1.1 | 1.2 | 1.1 | 2.2 | 1.0 | 1.0 |
| B | | NHD 2 | 1.6 | 1.1 | 1.5 | 1.0 | 1.5 | 1.0 | 0.9 |
| C | | patient 1 | 1.0 | 1.0 | 0.6 | 1.0 | 0.3 | 1.4 | 1.1 |
| C | | patient 7 | 1.1 | 1.0 | 1.2 | 1.0 | 0.5 | 1.2 | 1.1 |
| C | | patient 2 | 0.4 | 1.3 | 1.0 | 1.1 | 0.3 | 1.0 | 0.9 |
| C | | patient 3 | 0.8 | 1.0 | 1.0 | 1.0 | 1.5 | 1.0 | 1.2 |
| C | | patient 5 | 1.1 | 1.0 | 0.9 | 1.1 | 0.3 | 1.0 | 1.0 |
| C | | patient 4 | 1.1 | 1.2 | 1.0 | 1.0 | 0.5 | 1.2 | 1.1 |
| C | | patient 6 | 1.0 | 1.1 | 1.0 | 1.0 | 0.3 | 2.1 | 1.1 |
| C | | NHD 1 | 0.6 | 0.9 | 143.6 | 1.1 | 3.8 | 0.9 | 1.0 |
| C | | NHD 2 | 1.0 | 0.9 | 37.5 | 1.0 | 0.7 | 1.1 | 0.9 |

FIG. 14F.6

| | | Haptoglobin mg/mL | ICAM-1 ng/mL | IFN-gamma pg/mL | IgA mg/mL | IgE ng/mL | IGF-1 ng/mL | IgM mg/mL |
|---|---|---|---|---|---|---|---|---|
| | Least Detectable Dose | 0.025 | 3.2 | 4.6 | 0.0084 | 14 | 4.0 | 0.015 |
| | RBM Low Plasma Range | 0.047 | 42 | Pending | 0.58 | 770 | 177 | 0.24 |
| | RBM High Plasma Range | 7.6 | 213 | Pending | 5.6 | | | 3.3 |
| D | patient 1 | 1.1 | 1.1 | 1.0 | 1.1 | 1.9 | 1.0 | 1.1 |
| D | patient 7 | 0.9 | 1.0 | 8.1 | 1.0 | 1.3 | 1.1 | 0.7 |
| D | patient 2 | 0.2 | 1.0 | 1.8 | 1.0 | 1.5 | 1.0 | 1.0 |
| D | patient 3 | 1.3 | 1.1 | 1.3 | 1.0 | 3.3 | 1.0 | 1.1 |
| D | patient 5 | 1.0 | 1.1 | 4.0 | 1.1 | 0.9 | 1.1 | 0.9 |
| D | patient 4 | 1.1 | 1.2 | 6.8 | 1.2 | 1.2 | 1.0 | 1.2 |
| D | patient 6 | 0.7 | 0.9 | 1.0 | 0.9 | 1.3 | 1.2 | 1.0 |
| D | NHD 1 | 1.2 | 1.1 | 490.9 | 0.9 | 21.0 | 1.0 | 1.1 |
| D | NHD 2 | 0.5 | 1.0 | 171.0 | 1.0 | 10.2 | 0.9 | 1.0 |
| E | patient 1 | 1.0 | 1.0 | 1.0 | 0.9 | 2.1 | 1.0 | 1.0 |
| E | patient 7 | 1.3 | 1.0 | 2.5 | 1.0 | 1.1 | 1.2 | 0.9 |
| E | patient 2 | 0.3 | 1.4 | 2.0 | 1.1 | 1.4 | 1.0 | 1.1 |
| E | patient 3 | 0.8 | 1.1 | 1.5 | 1.0 | 2.4 | 1.0 | 1.0 |
| E | patient 5 | 0.9 | 1.1 | 4.2 | 1.2 | 0.9 | 1.2 | 1.0 |
| E | patient 4 | 1.1 | 0.9 | 16.1 | 1.2 | 1.0 | 1.1 | 1.0 |
| E | patient 6 | 0.7 | 1.1 | 1.0 | 0.7 | 1.2 | 1.4 | 0.8 |
| E | NHD 1 | 3.5 | 1.0 | 73.9 | 0.9 | 17.8 | 0.9 | 1.0 |
| E | NHD 2 | 1.1 | 0.9 | 35.5 | 1.0 | 6.2 | 0.9 | 0.9 |
| F | patient 1 | 1.1 | 1.0 | 1.0 | 0.9 | 0.7 | 1.2 | 0.9 |
| F | patient 7 | 1.2 | 1.1 | 1.2 | 1.0 | 0.9 | 1.0 | 0.9 |
| F | patient 2 | 0.4 | 1.1 | 1.0 | 1.0 | 0.9 | 0.8 | 1.0 |
| F | patient 3 | 1.8 | 1.0 | 0.8 | 1.0 | 1.4 | 1.0 | 1.0 |
| F | patient 5 | 0.9 | 0.7 | 1.4 | 1.0 | 0.7 | 1.1 | 1.0 |
| F | patient 4 | 1.2 | 0.9 | 1.0 | 1.1 | 0.8 | 1.0 | 1.0 |
| F | patient 6 | 1.0 | 1.1 | 1.0 | 1.0 | 0.8 | 0.8 | 1.1 |

FIG. 14F.7

| | Haptoglobin mg/mL | ICAM-1 ng/mL | IFN-gamma pg/mL | IgA mg/mL | IgE ng/mL | IGF-1 ng/mL | IgM mg/mL |
|---|---|---|---|---|---|---|---|
| Least Detectable Dose | 0.025 | 3.2 | 4.6 | 0.0084 | 14 | 4.0 | 0.015 |
| RBM Low Plasma Range | 0.047 | 42 | Pending | 0.58 | 770 | 177 | 0.24 |
| RBM High Plasma Range | 7.6 | 213 | Pending | 5.6 | | | 3.3 |
| F NHD 1 | 1.7 | 1.1 | 30.8 | 1.1 | 4.0 | 0.9 | 1.0 |
| F NHD 2 | 0.6 | 1.0 | 1.9 | 1.0 | 0.9 | 0.9 | 0.9 |
| G patient 1 | 1.1 | 1.1 | 1.0 | 1.0 | 1.8 | 2.2 | 1.1 |
| G patient 7 | 1.3 | 1.1 | 3.7 | 1.0 | 0.8 | 3.0 | 0.9 |
| G patient 2 | 1.7 | 1.2 | 1.0 | 1.0 | 0.5 | 1.4 | 1.0 |
| G patient 3 | 1.8 | 1.0 | 1.0 | 1.0 | 0.8 | 5.5 | 1.0 |
| G patient 5 | 1.0 | 1.1 | 1.2 | 1.1 | 0.2 | 1.7 | 1.1 |
| G patient 4 | 1.1 | 1.2 | 1.0 | 1.1 | 0.3 | 4.2 | 1.0 |
| G patient 6 | 0.9 | 1.2 | 1.0 | 0.9 | 0.5 | 7.9 | 1.0 |
| G NHD 1 | 1.6 | 1.1 | 1.2 | 1.0 | 2.2 | 1.0 | 0.9 |
| G NHD 2 | 1.3 | 0.9 | 0.6 | 1.1 | 0.8 | 0.9 | 1.0 |
| H patient 1 | 1.1 | 1.1 | 1.0 | 0.9 | 1.6 | 1.0 | 0.9 |
| H patient 7 | 1.1 | 1.0 | 0.7 | 1.1 | 0.9 | 1.0 | 0.9 |
| H patient 2 | 0.4 | 0.9 | 1.0 | 1.1 | 0.7 | 1.0 | 0.9 |
| H patient 3 | 1.2 | 1.1 | 1.0 | 1.0 | 0.8 | 1.0 | 1.0 |
| H patient 5 | 0.9 | 0.9 | 0.8 | 1.0 | 1.0 | 1.1 | 1.1 |
| H patient 4 | 1.1 | 1.0 | 1.0 | 0.9 | 1.3 | 0.9 | 1.0 |
| H patient 6 | 1.0 | 1.0 | 1.0 | 0.9 | 0.8 | 0.7 | 1.0 |
| H NHD 1 | 1.6 | 1.1 | 10.7 | 1.1 | 2.8 | 1.0 | 1.1 |
| H NHD 2 | 1.5 | 1.0 | 0.7 | 1.0 | 1.0 | 1.0 | 0.9 |
| I patient 1 | 1.0 | 1.0 | 1.0 | 1.0 | 1.0 | 1.0 | 1.0 |
| I patient 7 | 1.0 | 1.0 | 1.0 | 1.0 | 1.0 | 1.0 | 1.0 |
| I patient 2 | 1.0 | 1.0 | 1.0 | 1.0 | 1.0 | 1.0 | 1.0 |
| I patient 3 | 1.0 | 1.0 | 1.0 | 1.0 | 1.0 | 1.0 | 1.0 |

FIG. 14F.8

| | Haptoglobin mg/mL | ICAM-1 ng/mL | IFN-gamma pg/mL | IgA mg/mL | IgE ng/mL | IGF-1 ng/mL | IgM mg/mL |
|---|---|---|---|---|---|---|---|
| Least Detectable Dose | 0.025 | 3.2 | 4.6 | 0.0084 | 14 | 4.0 | 0.015 |
| RBM Low Plasma Range | 0.047 | 42 | Pending | 0.58 | 770 | 177 | 0.24 |
| RBM High Plasma Range | 7.6 | 213 | Pending | 5.6 | | | 3.3 |
| patient 5 | 1.0 | 1.0 | 1.0 | 1.0 | 1.0 | 1.0 | 1.0 |
| patient 4 | 1.0 | 1.0 | 1.0 | 1.0 | 1.0 | 1.0 | 1.0 |
| patient 6 | 1.0 | 1.0 | 1.0 | 1.0 | 1.0 | 1.0 | 1.0 |
| NHD 1 | 1.0 | 1.0 | 1.0 | 1.0 | 1.0 | 1.0 | 1.0 |
| NHD 2 | 1.0 | 1.0 | 1.0 | 1.0 | 1.0 | 1.0 | 1.0 |

Messwert > ULD

| | IL-10 pg/mL | IL-12p40 ng/mL | IL-12p70 pg/mL | IL-13 pg/mL | IL-15 ng/mL | IL-16 pg/mL | IL-17 pg/mL |
|---|---|---|---|---|---|---|---|
| Least Detectable Dose | 15 | 1.2 | 94 | 57 | 1.3 | 66 | 2.7 |
| RBM Low Plasma Range | 1.8 | | | | | 232 | PENDING |
| RBM High Plasma Range | 38 | 2.7 | 165 | 133 | 4.6 | 3380 | PENDING |
| Samples | | | | | | | |
| Donor_1 3. Aliquot A | 180 | 0.30 | 45 | 36 | 0.41 | 575 | 6.7 |
| Donor_1 3. Aliquot B | 135 | 0.16 | 35 | 37 | 0.40 | 535 | 2.7 |
| Donor_1 3. Aliquot C | 15 | 1.2 | 28 | 38 | 0.33 | 413 | 2.7 |
| Donor_1 3. Aliquot D | 134 | 0.43 | 42 | 21 | 0.45 | 619 | 2.7 |
| Donor_1 3. Aliquot E | 58 | 0.13 | 37 | 34 | 0.32 | 580 | 2.7 |
| Donor_1 3. Aliquot F | 18 | 1.2 | 28 | 36 | 0.30 | 502 | 2.7 |
| Donor_1 3. Aliquot G | 15 | 0.19 | 39 | 37 | 0.50 | 216 | 7.5 |
| Donor_1 3. Aliquot H | 14 | 1.2 | 52 | 35 | 0.28 | 299 | 2.7 |
| Donor_1 3. Aliquot I | 16 | 1.2 | 32 | 33 | 0.26 | 588 | 2.7 |
| | | | | | | | |
| Donor_2 3. Aliquot A | 500 | 0.51 | 61 | 37 | 0.41 | 654 | 2.7 |
| Donor_2 3. Aliquot B | 483 | 0.26 | 35 | 37 | 0.43 | 712 | 2.7 |
| Donor_2 3. Aliquot C | 19 | 1.2 | 18 | 29 | 0.32 | 609 | 2.7 |
| Donor_2 3. Aliquot D | 977 | 2.8 | 40 | 29 | 0.50 | 804 | 2.7 |
| Donor_2 3. Aliquot E | 963 | 2.4 | 37 | 36 | 0.37 | 782 | 2.7 |
| Donor_2 3. Aliquot F | 28 | 0.26 | 45 | 66 | 0.50 | 720 | 2.7 |
| Donor_2 3. Aliquot G | 131 | 0.88 | 45 | 40 | 0.66 | 432 | 2.7 |
| Donor_2 3. Aliquot H | 22 | 1.2 | 35 | 27 | 1.3 | 393 | 2.7 |
| Donor_2 3. Aliquot I | 21 | 1.2 | 35 | 36 | 0.21 | 642 | 2.7 |
| | | | | | | | |
| Donor_3 3. Aliquot A | 480 | 0.43 | 50 | 49 | 0.53 | 1310 | 2.7 |
| Donor_3 3. Aliquot B | 632 | 0.37 | 48 | 43 | 0.56 | 1230 | 2.7 |
| Donor_3 3. Aliquot C | 26 | 0.13 | 55 | 57 | 0.41 | 1190 | 2.7 |
| Donor_3 3. Aliquot D | 1640 | 3.3 | 45 | 40 | 0.47 | 1410 | 2.7 |
| Donor_3 3. Aliquot E | 1660 | 2.7 | 55 | 39 | 0.47 | 1490 | 2.7 |
| Donor_3 3. Aliquot F | 18 | 1.2 | 40 | 51 | 0.28 | 1340 | 2.7 |
| Donor_3 3. Aliquot G | 11 | 1.2 | 35 | 43 | 0.32 | 556 | 2.7 |
| Donor_3 3. Aliquot H | 4.9 | 1.2 | 22 | 55 | 0.28 | 706 | 2.7 |
| Donor_3 3. Aliquot I | 11 | 1.2 | 42 | 81 | 0.47 | 1280 | 2.7 |

FIG. 14G.2

| | IL-10 pg/mL | IL-12p40 ng/mL | IL-12p70 pg/mL | IL-13 pg/mL | IL-15 ng/mL | IL-16 pg/mL | IL-17 pg/mL |
|---|---|---|---|---|---|---|---|
| Least Detectable Dose | 15 | 1.2 | 94 | 57 | 1.3 | 66 | 2.7 |
| RBM Low Plasma Range | 1.8 | | | | | 232 | PENDING |
| RBM High Plasma Range | 38 | 2.7 | 165 | 133 | 4.6 | 3380 | PENDING |
| Donor_4 3. Aliquot A | 46 | 1.2 | 94 | 36 | 0.38 | 1240 | 2.7 |
| Donor_4 3. Aliquot B | 251 | 1.2 | 94 | 19 | 0.56 | 1130 | 2.7 |
| Donor_4 3. Aliquot C | 11 | 1.2 | 39 | 27 | 0.32 | 1050 | 2.7 |
| Donor_4 3. Aliquot D | 566 | 3.1 | 39 | 38 | 0.43 | 986 | 2.7 |
| Donor_4 3. Aliquot E | 543 | 1.5 | 30 | 23 | 0.56 | 812 | 2.7 |
| Donor_4 3. Aliquot F | 232 | 0.37 | 24 | 28 | 0.47 | 1030 | 2.7 |
| Donor_4 3. Aliquot G | 14 | 1.2 | 20 | 29 | 0.24 | 431 | 2.7 |
| Donor_4 3. Aliquot H | 10 | 1.2 | 15 | 9.7 | 0.19 | 564 | 2.7 |
| Donor_4 3. Aliquot I | 13 | 1.2 | 94 | 24 | 0.24 | 1150 | 2.7 |
| Donor_5 3. Aliquot A | 117 | 0.34 | 20 | 33 | 0.71 | 536 | 2.7 |
| Donor_5 3. Aliquot B | 417 | 0.26 | 32 | 32 | 0.50 | 584 | 2.7 |
| Donor_5 3. Aliquot C | 7.0 | 1.2 | 26 | 48 | 0.50 | 455 | 2.7 |
| Donor_5 3. Aliquot D | 763 | 2.7 | 59 | 32 | 0.73 | 592 | 2.7 |
| Donor_5 3. Aliquot E | 1520 | 1.8 | 94 | 36 | 0.68 | 561 | 2.7 |
| Donor_5 3. Aliquot F | 37 | 1.2 | 20 | 38 | 0.28 | 430 | 2.7 |
| Donor_5 3. Aliquot G | 15 | 0.28 | 24 | 29 | 0.26 | 323 | 2.7 |
| Donor_5 3. Aliquot H | 10 | 1.2 | 28 | 27 | 0.19 | 390 | 2.7 |
| Donor_5 3. Aliquot I | 9.2 | 1.2 | 44 | 47 | 0.13 | 492 | 2.7 |
| Donor_6 3. Aliquot A | 85 | 0.13 | 32 | 70 | 0.32 | 1030 | 2.7 |
| Donor_6 3. Aliquot B | 226 | 1.2 | 42 | 57 | 0.24 | 828 | 2.7 |
| Donor_6 3. Aliquot C | 7.0 | 1.2 | 50 | 59 | 0.24 | 1150 | 2.7 |
| Donor_6 3. Aliquot D | 637 | 4.7 | 94 | 68 | 0.56 | 682 | 2.7 |
| Donor_6 3. Aliquot E | 1870 | 4.3 | 30 | 68 | 0.16 | 648 | 2.7 |
| Donor_6 3. Aliquot F | 45 | 1.2 | 47 | 86 | 0.43 | 969 | 2.7 |
| Donor_6 3. Aliquot G | 7.0 | 1.2 | 20 | 65 | 1.3 | 439 | 2.7 |
| Donor_6 3. Aliquot H | 6.0 | 0.16 | 94 | 65 | 0.19 | 815 | 5.0 |
| Donor_6 3. Aliquot I | 7.0 | 1.2 | 94 | 59 | 0.28 | 1230 | 2.7 |

FIG. 14G.3

| | IL-10 pg/mL | IL-12p40 ng/mL | IL-12p70 pg/mL | IL-13 pg/mL | IL-15 ng/mL | IL-16 pg/mL | IL-17 pg/mL |
|---|---|---|---|---|---|---|---|
| Least Detectable Dose | 15 | 1.2 | 94 | 57 | 1.3 | 66 | 2.7 |
| RBM Low Plasma Range | 1.8 | | | | | 232 | PENDING |
| RBM High Plasma Range | 38 | 2.7 | 165 | 133 | 4.6 | 3380 | PENDING |
| Donor_7_3. Aliquot A | 379 | 0.64 | 39 | 91 | 0.79 | 664 | 2.7 |
| Donor_7_3. Aliquot B | 441 | 0.27 | 32 | 103 | 0.78 | 620 | 2.7 |
| Donor_7_3. Aliquot C | 13 | 1.2 | 39 | 70 | 0.53 | 817 | 2.7 |
| Donor_7_3. Aliquot D | 390 | 0.93 | 39 | 82 | 0.49 | 662 | 2.7 |
| Donor_7_3. Aliquot E | 297 | 0.93 | 42 | 104 | 0.58 | 651 | 2.7 |
| Donor_7_3. Aliquot F | 85 | 1.2 | 34 | 105 | 0.54 | 856 | 2.7 |
| Donor_7_3. Aliquot G | 13 | 1.2 | 22 | 56 | 0.19 | 428 | 2.7 |
| Donor_7_3. Aliquot H | 6.8 | 1.2 | 94 | 62 | 0.38 | 574 | 2.7 |
| Donor_7_3. Aliquot I | 11 | 1.2 | 94 | 88 | 0.41 | 918 | 2.7 |
| Donor_8_3. Aliquot A | 102 | 0.30 | 34 | 81 | 0.32 | 340 | 2.7 |
| Donor_8_3. Aliquot B | 218 | 0.19 | 22 | 97 | 0.24 | 341 | 2.7 |
| Donor_8_3. Aliquot C | 4.9 | 0.57 | 3920 | 80 | 0.32 | 309 | 2.7 |
| Donor_8_3. Aliquot D | 306 | 19 | 434 | 99 | 0.61 | 754 | 5.0 |
| Donor_8_3. Aliquot E | 1000 | 14 | 48 | 99 | 0.64 | 533 | 9.7 |
| Donor_8_3. Aliquot F | 219 | 0.71 | 42 | 111 | 0.45 | 410 | 4.2 |
| Donor_8_3. Aliquot G | 4.3 | 1.2 | 15 | 53 | 0.19 | 183 | 5.4 |
| Donor_8_3. Aliquot H | 4.1 | 0.23 | 30 | 75 | 0.28 | 231 | 2.7 |
| Donor_8_3. Aliquot I | 6.6 | 1.2 | 32 | 80 | 0.32 | 522 | 2.7 |
| Donor_9_3. Aliquot A | 220 | 0.26 | 52 | 68 | 0.31 | 463 | 17 |
| Donor_9_3. Aliquot B | 435 | 0.40 | 44 | 77 | 0.44 | 398 | 7.2 |
| Donor_9_3. Aliquot C | 43 | 0.80 | 1480 | 74 | 0.35 | 407 | 2.7 |
| Donor_9_3. Aliquot D | 1080 | 17 | 89 | 71 | 0.51 | 780 | 8.1 |
| Donor_9_3. Aliquot E | 1730 | 11 | 54 | 68 | 0.31 | 538 | 22 |
| Donor_9_3. Aliquot F | 122 | 0.34 | 46 | 83 | 0.30 | 369 | 13 |
| Donor_9_3. Aliquot G | 13 | 0.25 | 41 | 36 | 0.31 | 411 | 22 |
| Donor_9_3. Aliquot H | 14 | 0.24 | 56 | 51 | 0.56 | 369 | 9.8 |
| Donor_9_3. Aliquot I | 4.2 | 1.2 | 31 | 56 | 0.22 | 455 | 8.1 |

FIG. 14G.4

| | IL-10 pg/mL | IL-12p40 ng/mL | IL-12p70 pg/mL | IL-13 pg/mL | IL-15 ng/mL | IL-16 pg/mL | IL-17 pg/mL |
|---|---|---|---|---|---|---|---|
| Least Detectable Dose | 15 | 1.2 | 94 | 57 | 1.3 | 66 | 2.7 |
| RBM Low Plasma Range | 1.8 | | | | | 232 | PENDING |
| RBM High Plasma Range | 38 | 2.7 | 165 | 133 | 4.6 | 3380 | PENDING |
| EDTA Plasma | | | | | | | |
| donor #1 plasma | 16 | 0.26 | 34 | 39 | 0.30 | 329 | 11 |
| donor #2 plasma | 21 | 0.19 | 23 | 24 | 0.13 | 620 | 2.7 |
| donor #3 plasma | 9.9 | 1.2 | 49 | 37 | 0.39 | 892 | 2.7 |
| donor #4 plasma | 14 | 1.2 | 33 | 50 | 0.29 | 794 | 2.7 |
| donor #5 plasma | 12 | 0.15 | 56 | 37 | 0.64 | 314 | 2.7 |
| donor #6 plasma | 10 | 1.2 | 34 | 40 | 0.29 | 277 | 11 |
| donor #7 plasma | 16 | 1.2 | 23 | 39 | 0.29 | 514 | 2.7 |
| donor #8 plasma | 2.3 | 1.2 | 39 | 50 | 0.31 | 208 | 2.7 |
| donor #9 plasma | 5.1 | 0.14 | 35 | 41 | 0.18 | 327 | 2.7 |
| | IL-10 | IL-12p40 | IL-12p70 | IL-13 | IL-15 | IL-16 | IL-17 |
| Stimulations indices | | | | | | | |
| patient 1  A | 11.0 | 0.2 | 1.4 | 1.1 | 1.6 | 1.0 | 2.5 |
| patient 7  A | 24.0 | 0.4 | 1.7 | 1.0 | 1.9 | 1.0 | 1.0 |

FIG. 14G.5

| | | IL-10 pg/mL | IL-12p40 ng/mL | IL-12p70 pg/mL | IL-13 pg/mL | IL-15 ng/mL | IL-16 pg/mL | IL-17 pg/mL |
|---|---|---|---|---|---|---|---|---|
| | Least Detectable Dose | 15 | 1.2 | 94 | 57 | 1.3 | 66 | 2.7 |
| | RBM Low Plasma Range | 1.8 | | | | | 232 | PENDING |
| | RBM High Plasma Range | 38 | 2.7 | 165 | 133 | 4.6 | 3380 | PENDING |
| A | patient 2 | 44.4 | 0.4 | 1.2 | 0.6 | 1.1 | 1.0 | 1.0 |
| A | patient 3 | 3.5 | 1.0 | 1.0 | 1.5 | 1.6 | 1.1 | 1.0 |
| A | patient 5 | 12.7 | 0.3 | 0.5 | 0.7 | 5.6 | 1.1 | 1.0 |
| A | patient 4 | 12.0 | 0.1 | 0.3 | 1.2 | 1.1 | 0.8 | 1.0 |
| A | patient 6 | 33.2 | 0.5 | 0.4 | 1.0 | 1.9 | 0.7 | 1.0 |
| A | NHD 1 | 15.4 | 0.2 | 1.1 | 1.0 | 1.0 | 0.7 | 1.0 |
| A | NHD 2 | 52.3 | 0.2 | 1.7 | 1.2 | 1.4 | 1.0 | 2.0 |
| B | patient 1 | 8.3 | 0.1 | 1.1 | 1.1 | 1.5 | 0.9 | 1.0 |
| B | patient 7 | 23.2 | 0.2 | 1.0 | 1.0 | 2.0 | 1.1 | 1.0 |
| B | patient 2 | 58.5 | 0.3 | 1.2 | 0.5 | 1.2 | 1.0 | 1.0 |
| B | patient 3 | 19.0 | 1.0 | 1.0 | 0.8 | 2.4 | 1.0 | 1.0 |
| B | patient 5 | 45.2 | 0.2 | 0.7 | 0.7 | 4.0 | 1.2 | 1.0 |
| B | patient 4 | 32.1 | 1.0 | 0.4 | 1.0 | 0.9 | 0.7 | 1.0 |
| B | patient 6 | 38.7 | 0.2 | 0.3 | 1.2 | 1.9 | 0.7 | 1.0 |
| B | NHD 1 | 33.0 | 0.2 | 0.7 | 1.2 | 0.8 | 0.7 | 1.0 |
| B | NHD 2 | 103.3 | 0.3 | 1.4 | 1.4 | 2.0 | 0.9 | 0.9 |
| C | patient 1 | 0.9 | 1.0 | 0.9 | 1.2 | 1.3 | 0.7 | 1.0 |
| C | patient 7 | 0.9 | 1.0 | 0.5 | 0.8 | 1.5 | 0.9 | 1.0 |
| C | patient 2 | 2.4 | 0.1 | 1.3 | 0.7 | 0.9 | 0.9 | 1.0 |
| C | patient 3 | 0.8 | 1.0 | 0.4 | 1.1 | 1.3 | 0.9 | 1.0 |
| C | patient 5 | 0.8 | 1.0 | 0.6 | 1.0 | 4.0 | 0.9 | 1.0 |
| C | patient 4 | 1.0 | 1.0 | 0.5 | 1.0 | 0.9 | 0.9 | 1.0 |
| C | patient 6 | 1.2 | 1.0 | 0.4 | 0.8 | 1.3 | 0.9 | 1.0 |
| C | NHD 1 | 0.7 | 0.5 | 123.3 | 1.0 | 1.0 | 0.6 | 1.0 |
| C | NHD 2 | 10.2 | 0.7 | 48.2 | 1.3 | 1.6 | 0.9 | 0.3 |

FIG. 14G.6

| | | IL-10 pg/mL | IL-12p40 ng/mL | IL-12p70 pg/mL | IL-13 pg/mL | IL-15 ng/mL | IL-16 pg/mL | IL-17 pg/mL |
|---|---|---|---|---|---|---|---|---|
| | Least Detectable Dose | 15 | 1.2 | 94 | 57 | 1.3 | 66 | 2.7 |
| | RBM Low Plasma Range | 1.8 | 2.7 | | | | 232 | PENDING |
| | RBM High Plasma Range | 38 | 2.7 | 165 | 133 | 4.6 | 3380 | PENDING |
| D | patient 1 | 8.2 | 0.4 | 1.3 | 0.6 | 1.7 | 1.1 | 1.0 |
| D | patient 7 | 47.0 | 2.3 | 1.1 | 0.8 | 2.4 | 1.3 | 1.0 |
| D | patient 2 | 151.9 | 2.8 | 1.1 | 0.5 | 1.0 | 1.1 | 1.0 |
| D | patient 3 | 42.9 | 2.6 | 0.4 | 1.6 | 1.8 | 0.9 | 1.0 |
| D | patient 5 | 82.8 | 2.3 | 1.4 | 0.7 | 5.8 | 1.2 | 1.0 |
| D | patient 4 | 90.5 | 3.9 | 1.0 | 1.2 | 2.0 | 0.6 | 1.0 |
| D | patient 6 | 34.2 | 0.8 | 0.4 | 0.9 | 1.2 | 0.7 | 1.0 |
| D | NHD 1 | 46.3 | 16.2 | 13.5 | 1.2 | 1.9 | 1.4 | 1.9 |
| D | NHD 2 | 256.5 | 14.0 | 2.9 | 1.3 | 2.3 | 1.7 | 1.0 |
| E | patient 1 | 3.5 | 0.1 | 1.2 | 1.0 | 1.2 | 1.0 | 1.0 |
| E | patient 7 | 46.3 | 2.0 | 1.0 | 1.0 | 1.7 | 1.2 | 1.0 |
| E | patient 2 | 153.7 | 2.2 | 1.3 | 0.5 | 1.0 | 1.2 | 1.0 |
| E | patient 3 | 41.1 | 1.3 | 0.3 | 1.0 | 2.4 | 0.7 | 1.0 |
| E | patient 5 | 164.9 | 1.5 | 2.2 | 0.8 | 5.4 | 1.1 | 1.0 |
| E | patient 4 | 265.6 | 3.6 | 0.3 | 1.2 | 0.6 | 0.5 | 1.0 |
| E | patient 6 | 26.1 | 0.8 | 0.4 | 1.2 | 1.4 | 0.7 | 1.0 |
| E | NHD 1 | 151.3 | 11.4 | 1.5 | 1.2 | 2.0 | 1.0 | 3.6 |
| E | NHD 2 | 410.9 | 9.3 | 1.7 | 1.2 | 1.4 | 1.2 | 2.7 |
| F | patient 1 | 1.1 | 1.0 | 0.9 | 1.1 | 1.1 | 0.9 | 1.0 |
| F | patient 7 | 1.3 | 0.2 | 1.3 | 1.8 | 2.4 | 1.1 | 1.0 |
| F | patient 2 | 1.5 | 1.0 | 1.0 | 0.6 | 0.6 | 1.0 | 1.0 |
| F | patient 3 | 17.6 | 0.3 | 0.3 | 1.1 | 2.0 | 0.9 | 1.0 |
| F | patient 5 | 4.0 | 1.0 | 0.5 | 0.8 | 2.2 | 0.9 | 1.0 |
| F | patient 4 | 6.4 | 1.0 | 0.5 | 1.5 | 1.6 | 0.8 | 1.0 |
| F | patient 6 | 7.4 | 1.0 | 0.4 | 1.2 | 1.3 | 0.9 | 1.0 |

FIG. 14G.7

| | | IL-10 pg/mL | IL-12p40 ng/mL | IL-12p70 pg/mL | IL-13 pg/mL | IL-15 ng/mL | IL-16 pg/mL | IL-17 pg/mL |
|---|---|---|---|---|---|---|---|---|
| | Least Detectable Dose | 15 | 1.2 | 94 | 57 | 1.3 | 66 | 2.7 |
| | RBM Low Plasma Range | 1.8 | | | | | 232 | PENDING |
| | RBM High Plasma Range | 38 | 2.7 | 165 | 133 | 4.6 | 3380 | PENDING |
| F | NHD 1 | 33.1 | 0.6 | 1.3 | 1.4 | 1.4 | 0.8 | 1.6 |
| F | NHD 2 | 29.0 | 0.3 | 1.5 | 1.5 | 1.3 | 0.8 | 1.6 |
| G | patient 1 | 0.9 | 0.2 | 1.2 | 1.1 | 1.9 | 0.4 | 2.8 |
| G | patient 7 | 6.3 | 0.7 | 1.3 | 1.1 | 3.1 | 0.7 | 1.0 |
| G | patient 2 | 1.0 | 1.0 | 0.8 | 0.5 | 0.7 | 0.4 | 1.0 |
| G | patient 3 | 1.0 | 1.0 | 0.2 | 1.2 | 1.0 | 0.4 | 1.0 |
| G | patient 5 | 1.6 | 0.2 | 0.6 | 0.6 | 2.0 | 0.7 | 1.0 |
| G | patient 4 | 1.0 | 1.0 | 0.2 | 1.1 | 4.7 | 0.4 | 1.0 |
| G | patient 6 | 1.1 | 1.0 | 0.2 | 0.6 | 0.5 | 0.5 | 1.0 |
| G | NHD 1 | 0.6 | 1.0 | 0.5 | 0.7 | 0.6 | 0.4 | 2.0 |
| G | NHD 2 | 3.0 | 0.2 | 1.3 | 0.6 | 1.4 | 0.9 | 2.7 |
| H | patient 1 | 0.9 | 1.0 | 1.6 | 1.1 | 1.1 | 0.5 | 1.0 |
| H | patient 7 | 1.1 | 1.0 | 1.0 | 0.7 | 6.1 | 0.6 | 1.0 |
| H | patient 2 | 0.5 | 1.0 | 0.5 | 0.7 | 0.6 | 0.6 | 1.0 |
| H | patient 3 | 0.8 | 1.0 | 0.2 | 0.4 | 0.8 | 0.5 | 1.0 |
| H | patient 5 | 1.1 | 1.0 | 0.6 | 0.6 | 1.5 | 0.8 | 1.0 |
| H | patient 4 | 0.8 | 0.1 | 1.0 | 1.1 | 0.7 | 0.7 | 1.9 |
| H | patient 6 | 0.6 | 1.0 | 1.0 | 0.7 | 0.9 | 0.6 | 1.0 |
| H | NHD 1 | 0.6 | 0.2 | 0.9 | 0.9 | 0.9 | 0.4 | 1.0 |
| H | NHD 2 | 3.3 | 0.2 | 1.8 | 0.9 | 2.5 | 0.8 | 1.2 |
| I | patient 1 | 1.0 | 1.0 | 1.0 | 1.0 | 1.0 | 1.0 | 1.0 |
| I | patient 7 | 1.0 | 1.0 | 1.0 | 1.0 | 1.0 | 1.0 | 1.0 |
| I | patient 2 | 1.0 | 1.0 | 1.0 | 1.0 | 1.0 | 1.0 | 1.0 |
| I | patient 3 | 1.0 | 1.0 | 1.0 | 1.0 | 1.0 | 1.0 | 1.0 |

FIG. 14G.8

| | IL-10 pg/mL | IL-12p40 ng/mL | IL-12p70 pg/mL | IL-13 pg/mL | IL-15 ng/mL | IL-16 pg/mL | IL-17 pg/mL |
|---|---|---|---|---|---|---|---|
| Least Detectable Dose | 15 | 1.2 | 94 | 57 | 1.3 | 66 | 2.7 |
| RBM Low Plasma Range | 1.8 | | | | | 232 | PENDING |
| RBM High Plasma Range | 38 | 2.7 | 165 | 133 | 4.6 | 3380 | PENDING |
| patient 5 | 1.0 | 1.0 | 1.0 | 1.0 | 1.0 | 1.0 | 1.0 |
| patient 4 | 1.0 | 1.0 | 1.0 | 1.0 | 1.0 | 1.0 | 1.0 |
| patient 6 | 1.0 | 1.0 | 1.0 | 1.0 | 1.0 | 1.0 | 1.0 |
| NHD 1 | 1.0 | 1.0 | 1.0 | 1.0 | 1.0 | 1.0 | 1.0 |
| NHD 2 | 1.0 | 1.0 | 1.0 | 1.0 | 1.0 | 1.0 | 1.0 |

Messwert > ULD

| | IL-17E pg/mL | IL-18 pg/mL | IL-1alpha ng/mL | IL-1beta pg/mL | IL-1ra pg/mL | IL-2 pg/mL | IL-23 ng/mL |
|---|---|---|---|---|---|---|---|
| Least Detectable Dose | 31 | 54 | 0.16 | 1.5 | 15 | 60 | <0.67 |
| RBM Low Plasma Range | PENDING | 72 | | | 17 | | PENDING |
| RBM High Plasma Range | PENDING | 1020 | 0.35 | 8.7 | 622 | 61 | PENDING |
| Samples | | | | | | | |
| Donor_1 3. Aliquot A | 643 | 1930 | 0.0025 | 75 | 3780 | 60 | 3.7 |
| Donor_1 3. Aliquot B | 559 | 1910 | 0.16 | 50 | 2300 | 60 | 1.2 |
| Donor_1 3. Aliquot C | 62 | 1980 | 0.16 | 4.4 | 987 | 60 | 0.67 |
| Donor_1 3. Aliquot D | 580 | 2080 | 0.0077 | 348 | 4230 | 60 | 0.67 |
| Donor_1 3. Aliquot E | 604 | 2140 | 0.16 | 69 | 2740 | 60 | 0.67 |
| Donor_1 3. Aliquot F | 486 | 1630 | 0.16 | 10 | 1040 | 60 | 1.2 |
| Donor_1 3. Aliquot G | 646 | 2130 | 0.16 | 6.8 | 2830 | 60 | 2.1 |
| Donor_1 3. Aliquot H | 56 | 1860 | 0.16 | 4.6 | 944 | 60 | 1.9 |
| Donor_1 3. Aliquot I | 502 | 1810 | 0.16 | 5.4 | 660 | 60 | 0.67 |
| Donor_2 3. Aliquot A | 29 | 631 | 0.012 | 132 | 16500 | 60 | 1.2 |
| Donor_2 3. Aliquot B | 40 | 709 | 0.0057 | 71 | 15500 | 60 | 0.67 |
| Donor_2 3. Aliquot C | 11 | 616 | 0.16 | 4.7 | 2000 | 60 | 0.67 |
| Donor_2 3. Aliquot D | 37 | 830 | 0.36 | 5020 | 54600 | 60 | 2.3 |
| Donor_2 3. Aliquot E | 29 | 754 | 0.11 | 1310 | 52400 | 60 | 2.5 |
| Donor_2 3. Aliquot F | 17 | 594 | 0.0034 | 32 | 3140 | 60 | 0.67 |
| Donor_2 3. Aliquot G | 31 | 681 | 0.045 | 387 | 6790 | 60 | 0.67 |
| Donor_2 3. Aliquot H | 23 | 595 | 0.16 | 9.7 | 4400 | 60 | 0.67 |
| Donor_2 3. Aliquot I | 34 | 538 | 0.16 | 6.6 | 2520 | 60 | 0.67 |
| Donor_3 3. Aliquot A | 17 | 766 | 0.0054 | 62 | 12900 | 60 | 0.67 |
| Donor_3 3. Aliquot B | 34 | 720 | 0.0056 | 32 | 11000 | 60 | 2.1 |
| Donor_3 3. Aliquot C | 29 | 715 | 0.0036 | 5.3 | 2970 | 60 | 2.1 |
| Donor_3 3. Aliquot D | 37 | 735 | 0.074 | 3890 | 41000 | 60 | 0.67 |
| Donor_3 3. Aliquot E | 29 | 798 | 0.039 | 1610 | 32900 | 60 | 3.4 |
| Donor_3 3. Aliquot F | 29 | 694 | 0.0050 | 18 | 3850 | 60 | 1.2 |
| Donor_3 3. Aliquot G | 29 | 766 | 0.0045 | 8.6 | 3260 | 60 | 0.67 |
| Donor_3 3. Aliquot H | 31 | 553 | 0.0029 | 2.2 | 1010 | 60 | 0.67 |
| Donor_3 3. Aliquot I | 45 | 627 | 0.0043 | 1.5 | 79 | 60 | 2.1 |

FIG. 14H.2

| | IL-17E pg/mL | IL-18 pg/mL | IL-1alpha ng/mL | IL-1beta pg/mL | IL-1ra pg/mL | IL-2 pg/mL | IL-23 ng/mL |
|---|---|---|---|---|---|---|---|
| Least Detectable Dose | 31 | 54 | 0.16 | 1.5 | 15 | 60 | <0.67 |
| RBM Low Plasma Range | PENDING | 72 | | | 17 | | PENDING |
| RBM High Plasma Range | PENDING | 1020 | 0.35 | 8.7 | 622 | 61 | PENDING |
| Donor_4 3. Aliquot A | 42 | 690 | 0.16 | 7.3 | 2670 | 60 | 0.67 |
| Donor_4 3. Aliquot B | 40 | 700 | 0.16 | 46 | 3450 | 60 | 2.1 |
| Donor_4 3. Aliquot C | 56 | 608 | 0.16 | 3.8 | 336 | 60 | 2.1 |
| Donor_4 3. Aliquot D | 29 | 724 | 0.29 | 2830 | 13700 | 60 | 0.67 |
| Donor_4 3. Aliquot E | 51 | 633 | 0.075 | 957 | 13100 | 60 | 0.67 |
| Donor_4 3. Aliquot F | 51 | 623 | 0.0036 | 47 | 12900 | 60 | 0.67 |
| Donor_4 3. Aliquot G | 56 | 612 | 0.0025 | 7.0 | 2530 | 60 | 2.5 |
| Donor_4 3. Aliquot H | 62 | 566 | 0.16 | 4.1 | 1670 | 60 | 1.6 |
| Donor_4 3. Aliquot I | 62 | 597 | 0.16 | 0.63 | 228 | 60 | 2.1 |
| Donor_5 3. Aliquot A | 74 | 340 | 0.0066 | 73 | 22900 | 60 | 0.67 |
| Donor_5 3. Aliquot B | 40 | 295 | 0.0094 | 75 | 22500 | 60 | 0.67 |
| Donor_5 3. Aliquot C | 20 | 271 | 0.16 | 3.0 | 2100 | 60 | 1.4 |
| Donor_5 3. Aliquot D | 17 | 428 | 0.35 | 3910 | 53300 | 60 | 0.67 |
| Donor_5 3. Aliquot E | 11 | 467 | 0.32 | 3280 | 51000 | 60 | 0.67 |
| Donor_5 3. Aliquot F | 31 | 216 | 0.0043 | 73 | 11100 | 60 | 0.67 |
| Donor_5 3. Aliquot G | 45 | 479 | 0.0048 | 36 | 16700 | 60 | 1.6 |
| Donor_5 3. Aliquot H | 31 | 367 | 0.16 | 15 | 9910 | 60 | 2.5 |
| Donor_5 3. Aliquot I | 34 | 255 | 0.16 | 2.8 | 3530 | 60 | 1.6 |
| Donor_6 3. Aliquot A | 29 | 102 | 0.0052 | 35 | 7350 | 60 | 0.67 |
| Donor_6 3. Aliquot B | 51 | 95 | 0.012 | 46 | 9190 | 60 | 0.67 |
| Donor_6 3. Aliquot C | 11 | 98 | 0.0050 | 1.5 | 1220 | 60 | 0.67 |
| Donor_6 3. Aliquot D | 17 | 138 | 0.21 | 1870 | 26100 | 60 | 0.67 |
| Donor_6 3. Aliquot E | 17 | 134 | 0.41 | 3760 | 31600 | 60 | 1.2 |
| Donor_6 3. Aliquot F | 31 | 113 | 0.0073 | 43 | 4970 | 60 | 0.67 |
| Donor_6 3. Aliquot G | 11 | 170 | 0.0043 | 27 | 9870 | 60 | 0.67 |
| Donor_6 3. Aliquot H | 54 | 107 | 0.16 | 2.8 | 1530 | 60 | 3.7 |
| Donor_6 3. Aliquot I | 62 | 87 | 0.16 | 1.3 | 202 | 60 | 0.67 |

FIG. 14H.3

| | IL-17E pg/mL | IL-18 pg/mL | IL-1alpha ng/mL | IL-1beta pg/mL | IL-1ra pg/mL | IL-2 pg/mL | IL-23 ng/mL |
|---|---|---|---|---|---|---|---|
| Least Detectable Dose | 31 | 54 | 0.16 | 1.5 | 15 | 60 | <0.67 |
| RBM Low Plasma Range | PENDING | 72 | | | 17 | | PENDING |
| RBM High Plasma Range | PENDING | 1020 | 0.35 | 8.7 | 622 | 61 | PENDING |
| Donor_7 3. Aliquot A | 40 | 295 | 0.025 | 147 | 6320 | 60 | 0.67 |
| Donor_7 3. Aliquot B | 34 | 277 | 0.015 | 99 | 4590 | 60 | 0.67 |
| Donor_7 3. Aliquot C | 17 | 255 | 0.010 | 16 | 244 | 60 | 0.67 |
| Donor_7 3. Aliquot D | 23 | 275 | 0.31 | 2120 | 11000 | 60 | 0.67 |
| Donor_7 3. Aliquot E | 62 | 298 | 0.071 | 548 | 7580 | 60 | 0.67 |
| Donor_7 3. Aliquot F | 31 | 209 | 0.016 | 20 | 578 | 60 | 0.67 |
| Donor_7 3. Aliquot G | 85 | 300 | 0.0054 | 6.2 | 2730 | 60 | 0.67 |
| Donor_7 3. Aliquot H | 31 | 214 | 0.0057 | 3.4 | 361 | 60 | 0.67 |
| Donor_7 3. Aliquot I | 26 | 227 | 0.0066 | 1.5 | 61 | 60 | 1.2 |
| Donor_8 3. Aliquot A | 17 | 150 | 0.0073 | 73 | 3870 | 60 | 1.6 |
| Donor_8 3. Aliquot B | 31 | 173 | 0.0089 | 59 | 3010 | 60 | 0.67 |
| Donor_8 3. Aliquot C | 31 | 157 | 0.0071 | 76 | 10200 | 60 | 0.67 |
| Donor_8 3. Aliquot D | 17 | 408 | 0.28 | 24700 | 11400 | 60 | 3.0 |
| Donor_8 3. Aliquot E | 45 | 359 | 0.27 | 17500 | 12800 | 60 | 1.6 |
| Donor_8 3. Aliquot F | 31 | 175 | 0.013 | 204 | 16400 | 60 | 3.0 |
| Donor_8 3. Aliquot G | 23 | 152 | 0.16 | 32 | 4000 | 60 | 1.6 |
| Donor_8 3. Aliquot H | 17 | 220 | 0.0041 | 75 | 7720 | 60 | 0.67 |
| Donor_8 3. Aliquot I | 29 | 195 | 0.0061 | 7.9 | 839 | 60 | 1.2 |
| Donor_9 3. Aliquot A | 34 | 58 | 0.0080 | 29 | 3980 | 60 | 5.8 |
| Donor_9 3. Aliquot B | 66 | 48 | 0.013 | 42 | 4200 | 60 | 1.1 |
| Donor_9 3. Aliquot C | 83 | 52 | 0.018 | 67 | 9410 | 60 | 0.67 |
| Donor_9 3. Aliquot D | 44 | 340 | 2.6 | 26100 | 18300 | 60 | 2.4 |
| Donor_9 3. Aliquot E | 55 | 161 | 0.80 | 7830 | 15100 | 60 | 0.67 |
| Donor_9 3. Aliquot F | 28 | 38 | 0.011 | 60 | 12700 | 60 | 0.67 |
| Donor_9 3. Aliquot G | 44 | 92 | 0.0075 | 48 | 8240 | 60 | 0.67 |
| Donor_9 3. Aliquot H | 77 | 96 | 0.0086 | 39 | 4920 | 60 | 0.67 |
| Donor_9 3. Aliquot I | 83 | 69 | 0.0035 | 5.7 | 2110 | 60 | 1.7 |

FIG. 14H.4

| | IL-17E pg/mL | IL-18 pg/mL | IL-1alpha ng/mL | IL-1beta pg/mL | IL-1ra pg/mL | IL-2 pg/mL | IL-23 ng/mL |
|---|---|---|---|---|---|---|---|
| Least Detectable Dose | 31 | 54 | 0.16 | 1.5 | 15 | 60 | <0.67 |
| RBM Low Plasma Range | PENDING | 72 | | | 17 | | PENDING |
| RBM High Plasma Range | PENDING | 1020 | 0.35 | 8.7 | 622 | 61 | PENDING |
| EDTA Plasma | | | | | | | |
| donor #1 plasma | 228 | 1670 | 0.16 | 2.8 | 1800 | 60 | 3.4 |
| donor #2 plasma | 31 | 628 | 0.16 | 1.5 | 555 | 60 | 1.1 |
| donor #3 plasma | 34 | 644 | 0.0027 | 1.1 | 137 | 60 | 2.7 |
| donor #4 plasma | 31 | 805 | 0.16 | 1.5 | 410 | 60 | 2.4 |
| donor #5 plasma | 31 | 188 | 0.16 | 1.5 | 354 | 60 | 1.7 |
| donor #6 plasma | 44 | 112 | 0.16 | 1.5 | 84 | 60 | 1.9 |
| donor #7 plasma | 28 | 404 | 0.16 | 1.5 | 559 | 60 | 0.67 |
| donor #8 plasma | 31 | 196 | 0.0035 | 1.4 | 68 | 60 | 0.67 |
| donor #9 plasma | 44 | 104 | 0.0032 | 1.5 | 80 | 60 | 1.7 |

*Stimulations Indices*

| | IL-17E | IL-18 | IL-1alpha | IL-1beta | IL-1ra | IL-2 | IL-23 |
|---|---|---|---|---|---|---|---|
| patient 1 | 1.3 | 1.1 | 0.0 | 13.8 | 5.7 | 1.0 | 5.4 |
| patient 7 | 0.8 | 1.2 | 0.1 | 20.0 | 6.5 | 1.0 | 1.8 |

| | | |
|---|---|---|
| A | | |
| A | | |

FIG. 14H.5

| | | IL-17E pg/mL | IL-18 pg/mL | IL-1alpha ng/mL | IL-1beta pg/mL | IL-1ra pg/mL | IL-2 pg/mL | IL-23 ng/mL |
|---|---|---|---|---|---|---|---|---|
| | Least Detectable Dose | 31 | 54 | 0.16 | 1.5 | 15 | 60 | <0.67 |
| | RBM Low Plasma Range | PENDING | 72 | 0.35 | | 17 | | PENDING |
| | RBM High Plasma Range | PENDING | 1020 | 0.35 | 8.7 | 622 | 61 | PENDING |
| A | patient 2 | 0.4 | 1.2 | 1.3 | 41.6 | 164.1 | 1.0 | 0.3 |
| A | patient 3 | 0.7 | 1.2 | 1.0 | 11.5 | 11.7 | 1.0 | 0.3 |
| A | patient 5 | 2.2 | 1.3 | 0.0 | 25.9 | 6.5 | 1.0 | 0.4 |
| A | patient 4 | 0.5 | 1.2 | 0.0 | 27.3 | 36.4 | 1.0 | 1.0 |
| A | patient 6 | 1.5 | 1.3 | 3.8 | 98.0 | 103.4 | 1.0 | 0.6 |
| A | NHD 1 | 0.6 | 0.8 | 1.2 | 9.2 | 4.6 | 1.0 | 1.4 |
| A | NHD 2 | 0.4 | 0.8 | 2.3 | 5.1 | 1.9 | 1.0 | 3.5 |
| B | patient 1 | 1.1 | 1.1 | 1.0 | 9.2 | 3.5 | 1.0 | 1.8 |
| B | patient 7 | 1.2 | 1.3 | 0.0 | 10.7 | 6.2 | 1.0 | 1.0 |
| B | patient 2 | 0.8 | 1.1 | 1.3 | 21.0 | 139.9 | 1.0 | 1.0 |
| B | patient 3 | 0.6 | 1.2 | 1.0 | 72.2 | 15.1 | 1.0 | 1.0 |
| B | patient 5 | 1.2 | 1.2 | 0.1 | 26.9 | 6.4 | 1.0 | 0.4 |
| B | patient 4 | 0.8 | 1.1 | 0.1 | 35.3 | 45.5 | 1.0 | 1.0 |
| B | patient 6 | 1.3 | 1.2 | 2.2 | 65.9 | 75.1 | 1.0 | 0.6 |
| B | NHD 1 | 1.1 | 0.9 | 1.4 | 7.4 | 3.6 | 1.0 | 0.6 |
| B | NHD 2 | 0.8 | 0.7 | 3.7 | 7.4 | 2.0 | 1.0 | 0.7 |
| C | patient 1 | 0.1 | 1.1 | 1.0 | 0.8 | 1.5 | 1.0 | 1.0 |
| C | patient 7 | 0.3 | 1.1 | 1.0 | 0.7 | 0.8 | 1.0 | 1.0 |
| C | patient 2 | 0.6 | 1.1 | 0.8 | 3.5 | 37.8 | 1.0 | 1.0 |
| C | patient 3 | 0.9 | 1.0 | 1.0 | 6.1 | 1.5 | 1.0 | 1.0 |
| C | patient 5 | 0.6 | 1.1 | 1.0 | 1.1 | 0.6 | 1.0 | 0.9 |
| C | patient 4 | 0.2 | 1.1 | 0.0 | 1.2 | 6.0 | 1.0 | 1.0 |
| C | patient 6 | 0.7 | 1.1 | 1.6 | 10.7 | 4.0 | 1.0 | 0.6 |
| C | NHD 1 | 1.1 | 0.8 | 1.2 | 9.5 | 12.2 | 1.0 | 0.6 |
| C | NHD 2 | 1.0 | 0.7 | 5.1 | 11.9 | 4.5 | 1.0 | 0.4 |

FIG. 14H.6

| | | IL-17E pg/mL | IL-18 pg/mL | IL-1alpha ng/mL | IL-1beta pg/mL | IL-1ra pg/mL | IL-2 pg/mL | IL-23 ng/mL |
|---|---|---|---|---|---|---|---|---|
| | Least Detectable Dose | 31 | 54 | 0.16 | 1.5 | 15 | 60 | <0.67 |
| | RBM Low Plasma Range | PENDING | 72 | | | 17 | | PENDING |
| | RBM High Plasma Range | PENDING | 1020 | 0.35 | 8.7 | 622 | 61 | PENDING |
| D | patient 1 | 1.2 | 1.1 | 0.0 | 64.1 | 6.4 | 1.0 | 1.0 |
| D | patient 7 | 1.1 | 1.5 | 2.3 | 760.6 | 21.7 | 1.0 | 3.4 |
| D | patient 2 | 0.8 | 1.2 | 17.1 | 2593.3 | 521.6 | 1.0 | 0.3 |
| D | patient 3 | 0.5 | 1.2 | 1.8 | 4470.8 | 60.1 | 1.0 | 0.3 |
| D | patient 5 | 0.5 | 1.7 | 2.2 | 1396.4 | 15.1 | 1.0 | 0.4 |
| D | patient 4 | 0.3 | 1.6 | 1.3 | 1449.6 | 129.2 | 1.0 | 1.0 |
| D | patient 6 | 0.9 | 1.2 | 47.5 | 1413.3 | 180.0 | 1.0 | 0.6 |
| D | NHD 1 | 0.6 | 2.1 | 45.6 | 3110.8 | 13.6 | 1.0 | 2.5 |
| D | NHD 2 | 0.5 | 4.9 | 727.3 | 4603.2 | 8.7 | 1.0 | 1.5 |
| E | patient 1 | 1.2 | 1.2 | 1.0 | 126 | 4.2 | 1.0 | 1.0 |
| E | patient 7 | 0.8 | 1.4 | 0.7 | 198.5 | 20.8 | 1.0 | 3.7 |
| E | patient 2 | 0.6 | 1.3 | 8.9 | 1073.3 | 418.6 | 1.0 | 1.7 |
| E | patient 3 | 0.8 | 1.1 | 0.5 | 1511.8 | 57.5 | 1.0 | 0.3 |
| E | patient 5 | 0.3 | 1.8 | 2.0 | 1171.4 | 14.4 | 1.0 | 0.4 |
| E | patient 4 | 0.3 | 1.5 | 2.5 | 2914.7 | 156.4 | 1.0 | 1.8 |
| E | patient 6 | 2.4 | 1.3 | 10.8 | 365.3 | 124.1 | 1.0 | 0.6 |
| E | NHD 1 | 1.6 | 1.8 | 43.8 | 2204.0 | 15.3 | 1.0 | 1.4 |
| E | NHD 2 | 0.7 | 2.3 | 227.3 | 1381.0 | 7.2 | 1.0 | 0.4 |
| F | patient 1 | 1.0 | 0.9 | 1.0 | 1.8 | 1.6 | 1.0 | 1.8 |
| F | patient 7 | 0.5 | 1.1 | 0.0 | 4.8 | 1.2 | 1.0 | 1.0 |
| F | patient 2 | 0.6 | 1.1 | 1.2 | 12.1 | 49.0 | 1.0 | 0.6 |
| F | patient 3 | 0.8 | 1.0 | 0.0 | 74.9 | 56.5 | 1.0 | 0.3 |
| F | patient 5 | 0.9 | 0.8 | 0.0 | 26.0 | 3.1 | 1.0 | 0.4 |
| F | patient 4 | 0.5 | 1.3 | 0.0 | 33.0 | 24.5 | 1.0 | 1.0 |
| F | patient 6 | 1.2 | 0.9 | 2.4 | 13.5 | 9.5 | 1.0 | 0.6 |

FIG. 14H.7

| | | IL-17E pg/mL | IL-18 pg/mL | IL-1alpha ng/mL | IL-1beta pg/mL | IL-1ra pg/mL | IL-2 pg/mL | IL-23 ng/mL |
|---|---|---|---|---|---|---|---|---|
| | Least Detectable Dose | 31 | 54 | 0.16 | 1.5 | 15 | 60 | <0.67 |
| | RBM Low Plasma Range | PENDING | 72 | 0.35 | 8.7 | 17 | | PENDING |
| | RBM High Plasma Range | PENDING | 1020 | | | 622 | 61 | PENDING |
| F | NHD 1 | 1.1 | 0.9 | 2.2 | 25.7 | 19.5 | 1.0 | 2.5 |
| F | NHD 2 | 0.3 | 0.5 | 3.2 | 10.6 | 6.0 | 1.0 | 0.4 |
| G | patient 1 | 1.3 | 1.2 | 1.0 | 1.2 | 4.3 | 1.0 | 3.1 |
| G | patient 7 | 0.9 | 1.3 | 0.3 | 58.6 | 2.7 | 1.0 | 1.0 |
| G | patient 2 | 0.6 | 1.2 | 1.1 | 5.7 | 41.5 | 1.0 | 0.3 |
| G | patient 3 | 0.9 | 1.0 | 0.0 | 11.0 | 11.1 | 1.0 | 1.2 |
| G | patient 5 | 1.3 | 1.9 | 0.0 | 12.9 | 4.7 | 1.0 | 1.0 |
| G | patient 4 | 0.2 | 1.9 | 0.0 | 21.1 | 48.9 | 1.0 | 1.0 |
| G | patient 6 | 3.3 | 1.3 | 0.8 | 4.1 | 44.7 | 1.0 | 0.6 |
| G | NHD 1 | 0.8 | 0.8 | 26.1 | 4.1 | 4.8 | 1.0 | 1.4 |
| G | NHD 2 | 0.5 | 1.3 | 2.1 | 8.4 | 3.9 | 1.0 | 0.4 |
| H | patient 1 | 0.1 | 1.0 | 1.0 | 0.8 | 1.4 | 1.0 | 2.8 |
| H | patient 7 | 0.7 | 1.1 | 1.0 | 1.5 | 1.7 | 1.0 | 1.0 |
| H | patient 2 | 0.7 | 0.9 | 0.7 | 1.5 | 12.8 | 1.0 | 0.3 |
| H | patient 3 | 1.0 | 0.9 | 1.0 | 6.4 | 7.3 | 1.0 | 0.8 |
| H | patient 5 | 0.9 | 1.4 | 1.0 | 5.2 | 2.8 | 1.0 | 1.5 |
| H | patient 4 | 0.9 | 1.2 | 1.0 | 2.2 | 7.6 | 1.0 | 5.4 |
| H | patient 6 | 1.2 | 0.9 | 0.9 | 2.3 | 5.9 | 1.0 | 0.6 |
| H | NHD 1 | 0.6 | 1.1 | 0.7 | 9.4 | 9.2 | 1.0 | 0.6 |
| H | NHD 2 | 0.9 | 1.4 | 2.4 | 6.8 | 2.3 | 1.0 | 0.4 |
| I | patient 1 | 1.0 | 1.0 | 1.0 | 1.0 | 1.0 | 1.0 | 1.0 |
| I | patient 7 | 1.0 | 1.0 | 1.0 | 1.0 | 1.0 | 1.0 | 1.0 |
| I | patient 2 | 1.0 | 1.0 | 1.0 | 1.0 | 1.0 | 1.0 | 1.0 |
| I | patient 3 | 1.0 | 1.0 | 1.0 | 1.0 | 1.0 | 1.0 | 1.0 |

FIG. 14H.8

| | IL-17E pg/mL | IL-18 pg/mL | IL-1alpha ng/mL | IL-1beta pg/mL | IL-1ra pg/mL | IL-2 pg/mL | IL-23 ng/mL |
|---|---|---|---|---|---|---|---|
| Least Detectable Dose | 31 | 54 | 0.16 | 1.5 | 15 | 60 | <0.67 |
| RBM Low Plasma Range | PENDING | 72 | | | 17 | | PENDING |
| RBM High Plasma Range | PENDING | 1020 | 0.35 | 8.7 | 622 | 61 | PENDING |
| patient 5 | 1.0 | 1.0 | 1.0 | 1.0 | 1.0 | 1.0 | 1.0 |
| patient 4 | 1.0 | 1.0 | 1.0 | 1.0 | 1.0 | 1.0 | 1.0 |
| patient 6 | 1.0 | 1.0 | 1.0 | 1.0 | 1.0 | 1.0 | 1.0 |
| NHD 1 | 1.0 | 1.0 | 1.0 | 1.0 | 1.0 | 1.0 | 1.0 |
| NHD 2 | 1.0 | 1.0 | 1.0 | 1.0 | 1.0 | 1.0 | 1.0 |

| Messwert > ULD |
| SI > 1,3 |
| SI 0,7-1,3 |
| SI 0-0,7 |

FIG. 14I.1

| | IL-3 ng/mL | IL-4 pg/mL | IL-5 pg/mL | IL-6 pg/mL | IL-7 pg/mL | IL-8 pg/mL | Insulin uIU/mL |
|---|---|---|---|---|---|---|---|
| Least Detectable Dose | 0.17 | 104 | 33 | 12 | 53 | 3.5 | 0.86 |
| RBM Low Plasma Range | | | | | 3.7 | | |
| RBM High Plasma Range | 1.2 | 103 | 62 | 25 | 125 | 59 | 34 |
| Samples | | | | | | | |
| Donor_1 3. Aliquot A | 0.027 | 50 | 33 | 4690 | 169 | 23600 | 11 |
| Donor_1 3. Aliquot B | 0.17 | 53 | 33 | 1860 | 113 | 4450 | 9.8 |
| Donor_1 3. Aliquot C | 0.17 | 43 | 33 | 49 | 33 | 321 | 6.3 |
| Donor_1 3. Aliquot D | 0.17 | 49 | 33 | 7970 | 113 | 6730 | 11 |
| Donor_1 3. Aliquot E | 0.17 | 38 | 33 | 1700 | 131 | 6170 | 11 |
| Donor_1 3. Aliquot F | 0.17 | 42 | 33 | 77 | 57 | 1330 | 8.3 |
| Donor_1 3. Aliquot G | 0.17 | 38 | 33 | 57 | 100 | 5060 | 8.0 |
| Donor_1 3. Aliquot H | 0.17 | 51 | 33 | 54 | 33 | 672 | 9.4 |
| Donor_1 3. Aliquot I | 0.17 | 38 | 33 | 50 | 68 | 1480 | 9.9 |
| Donor_2 3. Aliquot A | 0.12 | 69 | 5.9 | 11100 | 215 | 100000 | 5.7 |
| Donor_2 3. Aliquot B | 0.095 | 78 | 8.2 | 6720 | 189 | 74900 | 6.1 |
| Donor_2 3. Aliquot C | 0.17 | 43 | 33 | 110 | 48 | 2290 | 2.3 |
| Donor_2 3. Aliquot D | 0.19 | 69 | 7.4 | 78400 | 201 | 146000 | 6.6 |
| Donor_2 3. Aliquot E | 0.21 | 77 | 8.2 | 63400 | 226 | 165000 | 6.4 |
| Donor_2 3. Aliquot F | 0.17 | 40 | 6.7 | 180 | 59 | 2230 | 4.7 |
| Donor_2 3. Aliquot G | 0.14 | 77 | 8.9 | 30900 | 223 | >344062 | 6.0 |
| Donor_2 3. Aliquot H | 0.17 | 45 | 5.1 | 187 | 74 | 3460 | 5.6 |
| Donor_2 3. Aliquot I | 0.17 | 56 | 33 | 153 | 48 | 3230 | 4.7 |
| Donor_3 3. Aliquot A | 0.12 | 9.4 | 4.3 | 6380 | 192 | 40600 | 19 |
| Donor_3 3. Aliquot B | 0.099 | 7.8 | 33 | 3880 | 201 | 32400 | 17 |
| Donor_3 3. Aliquot C | 0.17 | 104 | 33 | 90 | 66 | 1860 | 9.0 |
| Donor_3 3. Aliquot D | 0.15 | 20 | 33 | 105000 | 243 | 124000 | 15 |
| Donor_3 3. Aliquot E | 0.14 | 8.7 | 4.3 | 59800 | 234 | 146000 | 17 |
| Donor_3 3. Aliquot F | 0.050 | 7.8 | 5.9 | 169 | 82 | 2870 | 13 |
| Donor_3 3. Aliquot G | 0.17 | 104 | 2.5 | 63 | 78 | 24200 | 20 |
| Donor_3 3. Aliquot H | 0.17 | 104 | 33 | 26 | 38 | 924 | 15 |
| Donor_3 3. Aliquot I | 0.087 | 104 | 5.1 | 9.2 | 86 | 1080 | 15 |

FIG. 141.2

| | IL-3 ng/mL | IL-4 pg/mL | IL-5 pg/mL | IL-6 pg/mL | IL-7 pg/mL | IL-8 pg/mL | Insulin uIU/mL |
|---|---|---|---|---|---|---|---|
| Least Detectable Dose | 0.17 | 104 | 33 | 12 | 53 | 3.5 | 0.86 |
| RBM Low Plasma Range | | | | | 3.7 | | |
| RBM High Plasma Range | 1.2 | 103 | 62 | 25 | 125 | 59 | 34 |
| Donor_4 3. Aliquot A | 0.17 | 33 | 33 | 177 | 82 | 3240 | 12 |
| Donor_4 3. Aliquot B | 0.17 | 35 | 33 | 405 | 106 | 4210 | 12 |
| Donor_4 3. Aliquot C | 0.17 | 37 | 33 | 70 | 38 | 751 | 3.8 |
| Donor_4 3. Aliquot D | 0.039 | 50 | 33 | 46300 | 215 | 76000 | 13 |
| Donor_4 3. Aliquot E | 0.087 | 54 | 33 | 24300 | 214 | 70800 | 12 |
| Donor_4 3. Aliquot F | 0.17 | 32 | 33 | 5050 | 98 | 4030 | 12 |
| Donor_4 3. Aliquot G | 0.17 | 49 | 33 | 59 | 74 | 23400 | 14 |
| Donor_4 3. Aliquot H | 0.17 | 31 | 33 | 62 | 66 | 731 | 15 |
| Donor_4 3. Aliquot I | 0.17 | 29 | 33 | 52 | 38 | 550 | 11 |
| Donor_5 3. Aliquot A | 0.099 | 49 | 4.7 | 2370 | 203 | 146000 | 5.2 |
| Donor_5 3. Aliquot B | 0.11 | 51 | 33 | 4460 | 217 | 198000 | 5.4 |
| Donor_5 3. Aliquot C | 0.17 | 39 | 33 | 46 | 52 | 1740 | 2.0 |
| Donor_5 3. Aliquot D | 0.19 | 76 | 3.5 | 60400 | 247 | 211000 | 6.5 |
| Donor_5 3. Aliquot E | 0.15 | 57 | 2.5 | 71300 | 200 | >344062 | 8.0 |
| Donor_5 3. Aliquot F | 0.17 | 42 | 33 | 316 | 115 | 20400 | 3.6 |
| Donor_5 3. Aliquot G | 0.17 | 46 | 33 | 70 | 145 | 85000 | 3.8 |
| Donor_5 3. Aliquot H | 0.17 | 41 | 33 | 55 | 84 | 20000 | 4.9 |
| Donor_5 3. Aliquot I | 0.17 | 35 | 33 | 43 | 94 | 2590 | 4.3 |
| Donor_6 3. Aliquot A | 0.11 | 51 | 5.9 | 1500 | 182 | 17400 | 1.3 |
| Donor_6 3. Aliquot B | 0.11 | 55 | 11 | 3190 | 189 | 33200 | 1.4 |
| Donor_6 3. Aliquot C | 0.081 | 43 | 4.3 | 85 | 90 | 271 | 0.98 |
| Donor_6 3. Aliquot D | 0.13 | 54 | 6.3 | 50700 | 215 | 67300 | 1.8 |
| Donor_6 3. Aliquot E | 0.10 | 60 | 21 | 71700 | 229 | 116000 | 1.2 |
| Donor_6 3. Aliquot F | 0.12 | 44 | 8.9 | 517 | 124 | 3980 | 1.5 |
| Donor_6 3. Aliquot G | 0.032 | 46 | 33 | 74 | 128 | 26500 | 1.2 |
| Donor_6 3. Aliquot H | 0.025 | 39 | 33 | 84 | 94 | 692 | 1.3 |
| Donor_6 3. Aliquot I | 0.17 | 29 | 3.5 | 65 | 68 | 243 | 1.1 |

FIG. 14I.3

| | IL-3 ng/mL | IL-4 pg/mL | IL-5 pg/mL | IL-6 pg/mL | IL-7 pg/mL | IL-8 pg/mL | Insulin uIU/mL |
|---|---|---|---|---|---|---|---|
| Least Detectable Dose | 0.17 | 104 | 33 | 12 | 53 | 3.5 | 0.86 |
| RBM Low Plasma Range | | | | | 3.7 | | |
| RBM High Plasma Range | 1.2 | 103 | 62 | 25 | 125 | 59 | 34 |
| Donor_7_3. Aliquot A | 0.27 | 33 | 11 | 19900 | 273 | 89600 | 8.4 |
| Donor_7_3. Aliquot B | 0.21 | 27 | 20 | 5190 | 243 | 33900 | 7.8 |
| Donor_7_3. Aliquot C | 0.037 | 9.4 | 8.9 | 26 | 80 | 500 | 4.1 |
| Donor_7_3. Aliquot D | 0.15 | 29 | 5.9 | 54800 | 211 | 80600 | 6.5 |
| Donor_7_3. Aliquot E | 0.16 | 37 | 12 | 21600 | 247 | 41300 | 7.5 |
| Donor_7_3. Aliquot F | 0.12 | 23 | 13 | 242 | 138 | 812 | 6.2 |
| Donor_7_3. Aliquot G | 0.17 | 18 | 33 | 48 | 109 | 7810 | 6.6 |
| Donor_7_3. Aliquot H | 0.17 | 104 | 33 | 34 | 45 | 373 | 6.4 |
| Donor_7_3. Aliquot I | 0.044 | 104 | 4.3 | 16 | 80 | 225 | 6.1 |
| Donor_8_3. Aliquot A | 0.083 | 43 | 8.2 | 1400 | 166 | 4320 | 1.9 |
| Donor_8_3. Aliquot B | 0.12 | 49 | 12 | 1140 | 184 | 4770 | 2.4 |
| Donor_8_3. Aliquot C | 0.12 | 45 | 2.5 | 840 | 120 | 846 | 0.73 |
| Donor_8_3. Aliquot D | 0.18 | 60 | 5.9 | 99400 | 205 | 66900 | 2.2 |
| Donor_8_3. Aliquot E | 0.11 | 48 | 14 | 83900 | 217 | 58300 | 2.4 |
| Donor_8_3. Aliquot F | 0.25 | 48 | 14 | 6720 | 185 | 952 | 3.3 |
| Donor_8_3. Aliquot G | 0.025 | 43 | 33 | 42 | 86 | 2470 | 0.91 |
| Donor_8_3. Aliquot H | 0.081 | 40 | 5.1 | 129 | 169 | 5280 | 1.7 |
| Donor_8_3. Aliquot I | 0.12 | 44 | 2.5 | 12 | 117 | 895 | 1.7 |
| Donor_9_3. Aliquot A | 0.14 | 59 | 2.6 | 642 | 143 | 3910 | 6.2 |
| Donor_9_3. Aliquot B | 0.21 | 54 | 7.8 | 1100 | 156 | 4840 | 5.9 |
| Donor_9_3. Aliquot C | 0.20 | 59 | 5.3 | 1680 | 167 | 3560 | 3.1 |
| Donor_9_3. Aliquot D | 0.21 | 70 | 8.6 | 93100 | 209 | 48600 | 6.5 |
| Donor_9_3. Aliquot E | 0.17 | 67 | 5.3 | 61700 | 192 | 62300 | 6.3 |
| Donor_9_3. Aliquot F | 0.18 | 51 | 8.6 | 1900 | 159 | 1200 | 6.6 |
| Donor_9_3. Aliquot G | 0.11 | 75 | 33 | 131 | 126 | 21300 | 5.7 |
| Donor_9_3. Aliquot H | 0.098 | 55 | 33 | 57 | 141 | 1590 | 7.1 |
| Donor_9_3. Aliquot I | 0.10 | 43 | 33 | 19 | 62 | 797 | 5.3 |

FIG. 141.4

| | IL-3 ng/mL | IL-4 pg/mL | IL-5 pg/mL | IL-6 pg/mL | IL-7 pg/mL | IL-8 pg/mL | Insulin uIU/mL |
|---|---|---|---|---|---|---|---|
| Least Detectable Dose | 0.17 | 104 | 33 | 12 | 53 | 3.5 | 0.86 |
| RBM Low Plasma Range | | | | | 3.7 | | |
| RBM High Plasma Range | 1.2 | 103 | 62 | 25 | 125 | 59 | 34 |
| EDTA Plasma | | | | | | | |
| donor #1 plasma | 0.17 | 104 | 33 | 30 | 87 | 239 | 6.9 |
| donor #2 plasma | 0.17 | 104 | 8.2 | 102 | 42 | 319 | 5.8 |
| donor #3 plasma | 0.17 | 104 | 12 | 8.5 | 130 | 18 | 21 |
| donor #4 plasma | 0.17 | 104 | 4.0 | 49 | 52 | 102 | 16 |
| donor #5 plasma | 0.17 | 104 | 7.0 | 27 | 101 | 32 | 5.5 |
| donor #6 plasma | 0.17 | 104 | 7.0 | 54 | 103 | 24 | 0.57 |
| donor #7 plasma | 0.17 | 104 | 7.4 | 15 | 106 | 43 | 11 |
| donor #8 plasma | 0.14 | 44 | 6.1 | 1.8 | 83 | 3.5 | 1.0 |
| donor #9 plasma | 0.042 | 42 | 7.0 | 12 | 77 | 3.5 | 9.9 |

| Stimulations indices | IL-3 | IL-4 | IL-5 | IL-6 | IL-7 | IL-8 | Insulin |
|---|---|---|---|---|---|---|---|
| patient 1 | A | 0.2 | 1.3 | 1.0 | 93.4 | 2.5 | 15.9 | 1.1 |
| patient 7 | A | 0.7 | 1.2 | 0.2 | 72.5 | 4.5 | 31.0 | 1.2 |

FIG. 141.5

| | | IL-3 ng/mL | IL-4 pg/mL | IL-5 pg/mL | IL-6 pg/mL | IL-7 pg/mL | IL-8 pg/mL | Insulin uIU/mL |
|---|---|---|---|---|---|---|---|---|
| | Least Detectable Dose | 0.17 | 104 | 33 | 12 | 53 | 3.5 | 0.86 |
| | RBM Low Plasma Range | | | | | 3.7 | | |
| | RBM High Plasma Range | 1.2 | 103 | 62 | 25 | 125 | 59 | 34 |
| A | patient 2 | 1.4 | 0.1 | 0.8 | 690.5 | 2.2 | 37.6 | 1.2 |
| A | patient 3 | 1.0 | 1.1 | 1.0 | 3.4 | 2.2 | 5.9 | 1.0 |
| A | patient 5 | 0.6 | 1.4 | 0.1 | 55.5 | 2.2 | 56.4 | 1.2 |
| A | patient 4 | 0.6 | 1.8 | 1.7 | 22.9 | 2.7 | 71.6 | 1.2 |
| A | patient 6 | 6.1 | 0.3 | 2.6 | 1251.6 | 3.4 | 398.2 | 1.4 |
| A | NHD 1 | 0.7 | 1.0 | 3.2 | 113.8 | 1.4 | 4.8 | 1.1 |
| A | NHD 2 | 1.4 | 1.4 | 0.1 | 34.7 | 2.3 | 4.9 | 1.2 |
| B | patient 1 | 1.0 | 1.1 | 1.0 | 37.1 | 1.7 | 3.0 | 1.0 |
| B | patient 7 | 0.6 | 1.4 | 0.2 | 43.9 | 4.0 | 23.2 | 1.3 |
| B | patient 2 | 1.1 | 0.1 | 6.5 | 419.9 | 2.3 | 30.0 | 1.1 |
| B | patient 3 | 1.0 | 1.2 | 1.0 | 7.9 | 2.8 | 7.7 | 1.1 |
| B | patient 5 | 0.6 | 1.5 | 1.0 | 104.4 | 2.3 | 76.4 | 1.3 |
| B | patient 4 | 0.6 | 1.9 | 3.0 | 48.8 | 2.8 | 136.6 | 1.3 |
| B | patient 6 | 4.8 | 0.3 | 4.6 | 326.4 | 3.0 | 150.7 | 1.3 |
| B | NHD 1 | 1.0 | 1.1 | 4.7 | 92.7 | 1.6 | 5.3 | 1.4 |
| B | NHD 2 | 2.0 | 1.3 | 0.2 | 59.5 | 2.5 | 6.1 | 1.1 |
| C | patient 1 | 1.0 | 1.1 | 1.0 | 1.0 | 0.5 | 0.2 | 0.6 |
| C | patient 7 | 1.0 | 0.8 | 1.0 | 0.7 | 1.0 | 0.7 | 0.5 |
| C | patient 2 | 2.0 | 1.0 | 6.5 | 9.7 | 0.8 | 1.7 | 0.6 |
| C | patient 3 | 1.0 | 1.3 | 1.0 | 1.3 | 1.0 | 1.4 | 0.3 |
| C | patient 5 | 1.0 | 1.1 | 1.0 | 1.1 | 0.6 | 0.7 | 0.5 |
| C | patient 4 | 0.5 | 1.5 | 1.2 | 1.3 | 1.3 | 1.1 | 0.9 |
| C | patient 6 | 0.8 | 0.1 | 2.1 | 1.6 | 1.0 | 2.2 | 0.7 |
| C | NHD 1 | 1.1 | 1.0 | 1.0 | 68.3 | 1.0 | 0.9 | 0.4 |
| C | NHD 2 | 2.0 | 1.4 | 0.2 | 90.8 | 2.7 | 4.5 | 0.6 |

FIG. 14I.6

| | | IL-3 ng/mL | IL-4 pg/mL | IL-5 pg/mL | IL-6 pg/mL | IL-7 pg/mL | IL-8 pg/mL | Insulin uIU/mL |
|---|---|---|---|---|---|---|---|---|
| | Least Detectable Dose | 0.17 | 104 | 33 | 12 | 53 | 3.5 | 0.86 |
| | RBM Low Plasma Range | | | | | 3.7 | | |
| | RBM High Plasma Range | 1.2 | 103 | 62 | 25 | 125 | 59 | 34 |
| D | patient 1 | 1.0 | 1.3 | 1.0 | 158.8 | 1.7 | 4.5 | 1.1 |
| D | patient 7 | 1.1 | 1.2 | 0.2 | 512.4 | 4.2 | 45.2 | 1.4 |
| D | patient 2 | 1.7 | 0.2 | 6.5 | 11363.6 | 2.8 | 114.8 | 1.0 |
| D | patient 3 | 0.2 | 1.7 | 1.0 | 899.0 | 5.7 | 138.2 | 1.1 |
| D | patient 5 | 1.1 | 2.2 | 0.1 | 1414.5 | 2.6 | 81.5 | 1.5 |
| D | patient 4 | 0.8 | 1.9 | 1.8 | 775.2 | 3.2 | 277.0 | 1.6 |
| D | patient 6 | 3.5 | 0.3 | 1.4 | 3446.5 | 2.6 | 358.2 | 1.1 |
| D | NHD 1 | 1.5 | 1.4 | 2.3 | 8081.3 | 1.8 | 74.7 | 1.3 |
| D | NHD 2 | 2.1 | 1.6 | 0.3 | 5032.4 | 3.3 | 61.0 | 1.2 |
| E | patient 1 | 1.0 | 1.0 | 1.0 | 33.9 | 1.9 | 4.2 | 1.1 |
| E | patient 7 | 1.2 | 1.4 | 0.2 | 414.4 | 4.7 | 51.1 | 1.4 |
| E | patient 2 | 1.6 | 0.1 | 0.8 | 6471.9 | 2.7 | 135.2 | 1.1 |
| E | patient 3 | 0.5 | 1.8 | 1.0 | 471.8 | 5.6 | 128.7 | 1.0 |
| E | patient 5 | 0.9 | 1.6 | 0.1 | 1669.8 | 2.1 | #VALUE! | 1.9 |
| E | patient 4 | 0.6 | 2.1 | 6.2 | 1096.3 | 3.4 | 477.4 | 1.0 |
| E | patient 6 | 3.7 | 0.4 | 2.8 | 1358.5 | 3.1 | 183.6 | 1.2 |
| E | NHD 1 | 1.0 | 1.1 | 5.5 | 6821.1 | 1.9 | 65.1 | 1.4 |
| E | NHD 2 | 1.6 | 1.6 | 0.2 | 3335.1 | 3.1 | 78.2 | 1.2 |
| F | patient 1 | 1.0 | 1.1 | 1.0 | 1.5 | 0.8 | 0.9 | 0.8 |
| F | patient 7 | 1.0 | 0.7 | 0.2 | 1.2 | 1.2 | 0.7 | 1.0 |
| F | patient 2 | 0.6 | 0.1 | 1.2 | 18.3 | 1.0 | 2.7 | 0.8 |
| F | patient 3 | 1.0 | 1.1 | 1.0 | 98.1 | 2.6 | 7.3 | 1.0 |
| F | patient 5 | 1.0 | 1.2 | 1.0 | 7.4 | 1.2 | 7.9 | 0.8 |
| F | patient 4 | 0.7 | 1.5 | 2.6 | 7.9 | 1.8 | 16.4 | 1.3 |
| F | patient 6 | 2.8 | 0.2 | 3.0 | 15.2 | 1.7 | 3.6 | 1.0 |

FIG. 14I.7

| | | IL-3 ng/mL | IL-4 pg/mL | IL-5 pg/mL | IL-6 pg/mL | IL-7 pg/mL | IL-8 pg/mL | Insulin uIU/mL |
|---|---|---|---|---|---|---|---|---|
| | Least Detectable Dose | 0.17 | 104 | 33 | 12 | 53 | 3.5 | 0.86 |
| | RBM Low Plasma Range | | | | | 3.7 | | |
| | RBM High Plasma Range | 1.2 | 103 | 62 | 25 | 125 | 59 | 34 |
| F | NHD 1 | 2.2 | 1.1 | 5.7 | 546.3 | 1.6 | 1.1 | 2.0 |
| F | NHD 2 | 1.8 | 1.2 | 0.3 | 102.7 | 2.5 | 1.5 | 1.3 |
| G | patient 1 | 1.0 | 1.0 | 1.0 | 1.1 | 1.5 | 3.4 | 0.8 |
| G | patient 7 | 0.8 | 1.4 | 0.3 | 202.0 | 4.7 | #VALUE! | 1.3 |
| G | patient 2 | 2.0 | 1.0 | 0.5 | 6.8 | 0.9 | 22.4 | 1.3 |
| G | patient 3 | 1.0 | 1.7 | 1.0 | 1.1 | 1.9 | 42.5 | 1.2 |
| G | patient 5 | 1.0 | 1.3 | 1.0 | 1.6 | 1.5 | 32.8 | 0.9 |
| G | patient 4 | 0.2 | 1.6 | 9.5 | 1.1 | 1.9 | 109.1 | 1.1 |
| G | patient 6 | 3.9 | 0.2 | 7.7 | 3.0 | 1.4 | 34.7 | 1.0 |
| G | NHD 1 | 0.2 | 1.0 | 13.0 | 3.4 | 0.7 | 2.8 | 0.5 |
| G | NHD 2 | 1.1 | 1.8 | 1.0 | 7.1 | 2.0 | 26.7 | 1.1 |
| H | patient 1 | 1.0 | 1.3 | 1.0 | 1.1 | 0.5 | 0.5 | 0.9 |
| H | patient 7 | 1.0 | 0.8 | 0.2 | 1.2 | 1.6 | 1.1 | 1.2 |
| H | patient 2 | 2.0 | 1.0 | 6.5 | 2.8 | 0.4 | 0.9 | 1.0 |
| H | patient 3 | 1.0 | 1.0 | 1.0 | 1.2 | 1.7 | 1.3 | 1.3 |
| H | patient 5 | 1.0 | 1.2 | 1.0 | 1.3 | 0.9 | 7.7 | 1.1 |
| H | patient 4 | 0.1 | 1.4 | 9.5 | 1.3 | 1.4 | 2.8 | 1.2 |
| H | patient 6 | 3.9 | 1.0 | 7.7 | 2.1 | 0.6 | 1.7 | 1.0 |
| H | NHD 1 | 0.7 | 0.9 | 2.0 | 10.5 | 1.4 | 5.9 | 1.0 |
| H | NHD 2 | 1.0 | 1.3 | 1.0 | 3.1 | 2.3 | 2.0 | 1.3 |
| I | patient 1 | 1.0 | 1.0 | 1.0 | 1.0 | 1.0 | 1.0 | 1.0 |
| I | patient 7 | 1.0 | 1.0 | 1.0 | 1.0 | 1.0 | 1.0 | 1.0 |
| I | patient 2 | 1.0 | 1.0 | 1.0 | 1.0 | 1.0 | 1.0 | 1.0 |
| I | patient 3 | 1.0 | 1.0 | 1.0 | 1.0 | 1.0 | 1.0 | 1.0 |

FIG. 141.8

|  | IL-3 ng/mL | IL-4 pg/mL | IL-5 pg/mL | IL-6 pg/mL | IL-7 pg/mL | IL-8 pg/mL | Insulin uIU/mL |
|---|---|---|---|---|---|---|---|
| Least Detectable Dose | 0.17 | 104 | 33 | 12 | 53 | 3.5 | 0.86 |
| RBM Low Plasma Range |  |  |  |  | 3.7 |  |  |
| RBM High Plasma Range | 1.2 | 103 | 62 | 25 | 125 | 59 | 34 |
| patient 5 | 1.0 | 1.0 | 1.0 | 1.0 | 1.0 | 1.0 | 1.0 |
| patient 4 | 1.0 | 1.0 | 1.0 | 1.0 | 1.0 | 1.0 | 1.0 |
| patient 6 | 1.0 | 1.0 | 1.0 | 1.0 | 1.0 | 1.0 | 1.0 |
| NHD 1 | 1.0 | 1.0 | 1.0 | 1.0 | 1.0 | 1.0 | 1.0 |
| NHD 2 | 1.0 | 1.0 | 1.0 | 1.0 | 1.0 | 1.0 | 1.0 |
| Messwert > ULD |  |  |  |  |  |  |  |
| SI > 1,3 |  |  |  |  |  |  |  |
| SI 0,7-1,3 |  |  |  |  |  |  |  |
| SI 0-0,7 |  |  |  |  |  |  |  |

FIG. 14J.1

| | Leptin ng/mL | Lipoprotein (a) ug/mL | Lymphotactin ng/mL | MCP-1 pg/mL | MDC pg/mL | MIP-1alpha pg/mL | MIP-1beta pg/mL |
|---|---|---|---|---|---|---|---|
| Least Detectable Dose | 0.10 | 3.7 | 0.38 | 52 | 14 | 13 | 38 |
| RBM Low Plasma Range | 0.41 | 3.0 | | 35 | 162 | | 25 |
| RBM High Plasma Range | 41 | 858 | 0.57 | 401 | 774 | 89 | 595 |
| Samples | | | | | | | |
| Donor_1 3. Aliquot A | 132 | 27 | 0.22 | 8710 | 197 | 3570 | 71300 |
| Donor_1 3. Aliquot B | 115 | 34 | 0.38 | 4230 | 187 | 1810 | 12800 |
| Donor_1 3. Aliquot C | 124 | 31 | 0.38 | 1210 | 180 | 94 | 610 |
| Donor_1 3. Aliquot D | 121 | 32 | 0.071 | 3940 | 203 | 3760 | 75700 |
| Donor_1 3. Aliquot E | 124 | 32 | 0.092 | 4040 | 185 | 1370 | 16800 |
| Donor_1 3. Aliquot F | 107 | 45 | 0.38 | 2120 | 146 | 197 | 2040 |
| Donor_1 3. Aliquot G | 112 | 37 | 0.38 | 8970 | 14 | 110 | 498 |
| Donor_1 3. Aliquot H | 119 | 32 | 0.38 | 1080 | 41 | 81 | 513 |
| Donor_1 3. Aliquot I | 119 | 30 | 0.38 | 1030 | 193 | 180 | 803 |
| Donor_2 3. Aliquot A | 7.7 | 38 | 0.26 | 9540 | 158 | 5430 | 94800 |
| Donor_2 3. Aliquot B | 8.4 | 46 | 0.22 | 3930 | 178 | 2250 | 52800 |
| Donor_2 3. Aliquot C | 9.0 | 47 | 0.38 | 499 | 160 | 91 | 1790 |
| Donor_2 3. Aliquot D | 8.1 | 48 | 0.28 | 3760 | 165 | 34700 | 460000 |
| Donor_2 3. Aliquot E | 8.3 | 58 | 0.25 | 4260 | 154 | 23000 | 331000 |
| Donor_2 3. Aliquot F | 7.7 | 128 | 0.38 | 810 | 141 | 191 | 4280 |
| Donor_2 3. Aliquot G | 4.4 | 46 | 0.28 | 42600 | 14 | 29600 | 95800 |
| Donor_2 3. Aliquot H | 7.8 | 47 | 0.38 | 917 | 33 | 360 | 7090 |
| Donor_2 3. Aliquot I | 7.9 | 48 | 0.38 | 555 | 156 | 179 | 5430 |
| Donor_3 3. Aliquot A | 8.1 | 61 | 0.33 | 11000 | 92 | 894 | 31700 |
| Donor_3 3. Aliquot B | 7.7 | 66 | 0.23 | 3820 | 86 | 387 | 17200 |
| Donor_3 3. Aliquot C | 8.4 | 68 | 0.15 | 228 | 87 | 46 | 1850 |
| Donor_3 3. Aliquot D | 7.8 | 58 | 0.32 | 2630 | 84 | 8550 | 254000 |
| Donor_3 3. Aliquot E | 8.3 | 70 | 0.39 | 2870 | 72 | 3710 | 126000 |
| Donor_3 3. Aliquot F | 7.2 | 83 | 0.39 | 246 | 70 | 66 | 2900 |
| Donor_3 3. Aliquot G | 5.9 | 57 | 0.21 | 521 | 14 | 60 | 1680 |
| Donor_3 3. Aliquot H | 6.9 | 61 | 0.38 | 126 | 12 | 42 | 633 |
| Donor_3 3. Aliquot I | 7.8 | 66 | 0.54 | 110 | 85 | 46 | 123 |

FIG. 14J.2

| | Leptin ng/mL | Lipoprotein (a) ug/mL | Lymphotactin ng/mL | MCP-1 pg/mL | MDC pg/mL | MIP-1alpha pg/mL | MIP-1beta pg/mL |
|---|---|---|---|---|---|---|---|
| Least Detectable Dose | 0.10 | 3.7 | 0.38 | 52 | 14 | 13 | 38 |
| | | | | | | | |
| RBM Low Plasma Range | 0.41 | 3.0 | | 35 | 162 | | 25 |
| RBM High Plasma Range | 41 | 858 | 0.57 | 401 | 774 | 89 | 595 |
| | | | | | | | |
| Donor_4_3. Aliquot A | 11 | 23 | 0.38 | 2430 | 324 | 432 | 13100 |
| Donor_4_3. Aliquot B | 12 | 21 | 0.38 | 2960 | 346 | 288 | 9460 |
| Donor_4_3. Aliquot C | 10 | 21 | 0.38 | 578 | 280 | 137 | 994 |
| Donor_4_3. Aliquot D | 9.7 | 24 | 0.16 | 14900 | 335 | 31200 | 484000 |
| Donor_4_3. Aliquot E | 8.0 | 22 | 0.20 | 15800 | 259 | 17700 | 293000 |
| Donor_4_3. Aliquot F | 8.4 | 24 | 0.12 | 15400 | 251 | 1740 | 84100 |
| Donor_4_3. Aliquot G | 7.3 | 22 | 0.38 | 6110 | 14 | 547 | 3900 |
| Donor_4_3. Aliquot H | 11 | 21 | 0.38 | 641 | 66 | 106 | 3160 |
| Donor_4_3. Aliquot I | 10 | 25 | 0.38 | 269 | 298 | 63 | 287 |
| | | | | | | | |
| Donor_5_3. Aliquot A | 2.0 | 22 | 0.31 | 11900 | 298 | 6820 | 150000 |
| Donor_5_3. Aliquot B | 1.7 | 20 | 0.33 | 7660 | 424 | 9780 | 174000 |
| Donor_5_3. Aliquot C | 2.0 | 21 | 0.15 | 226 | 221 | 111 | 1790 |
| Donor_5_3. Aliquot D | 1.8 | 19 | 0.36 | 3740 | 190 | 36200 | 543000 |
| Donor_5_3. Aliquot E | 1.9 | 21 | 0.33 | 5360 | 205 | 46800 | 600000 |
| Donor_5_3. Aliquot F | 1.3 | 39 | 0.071 | 2920 | 171 | 1790 | 24300 |
| Donor_5_3. Aliquot G | 2.0 | 18 | 0.22 | 14900 | 14 | 527 | 3130 |
| Donor_5_3. Aliquot H | 1.9 | 17 | 0.38 | 523 | 55 | 328 | 5000 |
| Donor_5_3. Aliquot I | 1.7 | 18 | 0.38 | 231 | 218 | 119 | 3870 |
| | | | | | | | |
| Donor_6_3. Aliquot A | 0.12 | 36 | 0.72 | 3750 | 124 | 1810 | 27400 |
| Donor_6_3. Aliquot B | 0.10 | 40 | 0.72 | 2190 | 124 | 1690 | 22200 |
| Donor_6_3. Aliquot C | 0.11 | 39 | 0.62 | 218 | 110 | 55 | 376 |
| Donor_6_3. Aliquot D | 0.25 | 43 | 0.80 | 1360 | 136 | 29200 | 402000 |
| Donor_6_3. Aliquot E | 0.26 | 35 | 0.69 | 990 | 110 | 36100 | 441000 |
| Donor_6_3. Aliquot F | 0.1 | 79 | 0.79 | 2110 | 94 | 491 | 7470 |
| Donor_6_3. Aliquot G | 0.27 | 31 | 0.50 | 3670 | 14 | 800 | 3130 |
| Donor_6_3. Aliquot H | 0.13 | 32 | 0.50 | 240 | 29 | 143 | 3680 |
| Donor_6_3. Aliquot I | 0.10 | 25 | 0.52 | 146 | 113 | 49 | 317 |

FIG. 14J.3

| | Leptin ng/mL | Lipoprotein (a) ug/mL | Lymphotactin ng/mL | MCP-1 pg/mL | MDC pg/mL | MIP-1alpha pg/mL | MIP-1beta pg/mL |
|---|---|---|---|---|---|---|---|
| Least Detectable Dose | 0.10 | 3.7 | 0.38 | 52 | 14 | 13 | 38 |
| RBM Low Plasma Range | 0.41 | 3.0 | | 35 | 162 | | 25 |
| RBM High Plasma Range | 41 | 858 | 0.57 | 401 | 774 | 89 | 595 |
| Donor_7_3. Aliquot A | 11 | 203 | 0.96 | 14700 | 94 | 6080 | 188000 |
| Donor_7_3. Aliquot B | 11 | 222 | 0.78 | 5090 | 99 | 2700 | 68500 |
| Donor_7_3. Aliquot C | 12 | 160 | 0.53 | 314 | 83 | 46 | 680 |
| Donor_7_3. Aliquot D | 11 | 192 | 0.75 | 5040 | 92 | 7530 | 349000 |
| Donor_7_3. Aliquot E | 11 | 215 | 0.83 | 8810 | 96 | 4790 | 179000 |
| Donor_7_3. Aliquot F | 11 | 548 | 0.88 | 1260 | 72 | 152 | 5030 |
| Donor_7_3. Aliquot G | 6.9 | 148 | 0.24 | 3610 | 14 | 469 | 2280 |
| Donor_7_3. Aliquot H | 12 | 155 | 0.33 | 309 | 17 | 43 | 762 |
| Donor_7_3. Aliquot I | 12 | 190 | 0.53 | 265 | 84 | 38 | 156 |
| Donor_8_3. Aliquot A | 0.50 | 16 | 0.93 | 4750 | 223 | 1840 | 22700 |
| Donor_8_3. Aliquot B | 0.49 | 16 | 0.96 | 3720 | 221 | 1450 | 21000 |
| Donor_8_3. Aliquot C | 0.38 | 16 | 0.91 | 5420 | 154 | 2130 | 58500 |
| Donor_8_3. Aliquot D | 0.62 | 13 | 1.1 | 2170 | 337 | 67800 | 572000 |
| Donor_8_3. Aliquot E | 0.64 | 18 | 1.2 | 4380 | 245 | 46800 | 387000 |
| Donor_8_3. Aliquot F | 0.49 | 18 | 1.2 | 12700 | 138 | 6380 | 129000 |
| Donor_8_3. Aliquot G | 0.36 | 12 | 0.47 | 1940 | 14 | 931 | 7690 |
| Donor_8_3. Aliquot H | 0.53 | 13 | 0.80 | 7890 | 90 | 3290 | 29900 |
| Donor_8_3. Aliquot I | 0.37 | 14 | 0.80 | 385 | 256 | 266 | 4590 |
| Donor_9_3. Aliquot A | 2.0 | 18 | 0.68 | 5430 | 169 | 1250 | 24500 |
| Donor_9_3. Aliquot B | 2.0 | 12 | 0.73 | 3060 | 175 | 1690 | 23200 |
| Donor_9_3. Aliquot C | 1.6 | 13 | 0.69 | 16600 | 180 | 2140 | 46900 |
| Donor_9_3. Aliquot D | 2.0 | 17 | 0.62 | 6120 | 196 | 42300 | 431000 |
| Donor_9_3. Aliquot E | 1.8 | 16 | 0.71 | 9540 | 194 | 29700 | 355000 |
| Donor_9_3. Aliquot F | 1.9 | 18 | 0.86 | 12800 | 142 | 2410 | 78800 |
| Donor_9_3. Aliquot G | 1.3 | 11 | 0.20 | 15500 | 14 | 1820 | 12300 |
| Donor_9_3. Aliquot H | 1.9 | 11 | 0.38 | 2420 | 70 | 467 | 14400 |
| Donor_9_3. Aliquot I | 1.9 | 14 | 0.53 | 346 | 181 | 240 | 3670 |

FIG. 14J.4

| | Leptin ng/mL | Lipoprotein (a) ug/mL | Lymphotactin ng/mL | MCP-1 pg/mL | MDC pg/mL | MIP-1alpha pg/mL | MIP-1beta pg/mL |
|---|---|---|---|---|---|---|---|
| Least Detectable Dose | 0.10 | 3.7 | 0.38 | 52 | 14 | 13 | 38 |
| RBM Low Plasma Range | 0.41 | 3.0 | | 35 | 162 | | 25 |
| RBM High Plasma Range | 41 | 858 | 0.57 | 401 | 774 | 89 | 595 |
| EDTA Plasma | | | | | | | |
| donor #1 plasma | 89 | 46 | 0.38 | 230 | 187 | 69 | 209 |
| donor #2 plasma | 9.7 | 109 | 0.38 | 66 | 236 | 60 | 239 |
| donor #3 plasma | 9.4 | 143 | 0.12 | 11 | 116 | 41 | 65 |
| donor #4 plasma | 15 | 31 | 0.38 | 23 | 413 | 59 | 368 |
| donor #5 plasma | 1.9 | 31 | 0.12 | 17 | 307 | 46 | 154 |
| donor #6 plasma | 0.046 | 91 | 0.28 | 32 | 155 | 34 | 68 |
| donor #7 plasma | 21 | 735 | 0.42 | 109 | 124 | 48 | 145 |
| donor #8 plasma | 0.64 | 17 | 0.31 | 147 | 176 | 42 | 47 |
| donor #9 plasma | 2.4 | 23 | 0.33 | 89 | 159 | 44 | 38 |
| | | | | | | | |
| *Stimulations indices* | Leptin | Lipoprotein (a) | Lymphotactin | MCP-1 | MDC | MIP-1alpha | MIP-1beta |
| patient 1 | 1.1 | 0.9 | 0.6 | 8.5 | 1.0 | 19.8 | 88.8 |
| patient 7 | 1.0 | 0.8 | 0.7 | 17.2 | 1.0 | 30.3 | 17.5 |
| | A | | | | | | |
| | A | | | | | | |

FIG. 14J.5

| | | Leptin ng/mL | Lipoprotein (a) ug/mL | Lymphotactin ng/mL | MCP-1 pg/mL | MDC pg/mL | MIP-1alpha pg/mL | MIP-1beta pg/mL |
|---|---|---|---|---|---|---|---|---|
| | Least Detectable Dose | 0.10 | 3.7 | 0.38 | 52 | 14 | 13 | 38 |
| | RBM Low Plasma Range | 0.41 | 3.0 | | 35 | 162 | | 25 |
| | RBM High Plasma Range | 41 | 858 | 0.57 | 401 | 774 | 89 | 595 |
| A | patient 2 | 1.0 | 0.9 | 0.6 | 100.0 | 1.1 | 19.3 | 257.7 |
| A | patient 3 | 1.0 | 0.9 | 1.0 | 9.0 | 1.1 | 6.9 | 45.6 |
| A | patient 5 | 1.2 | 1.2 | 0.8 | 51.5 | 1.4 | 57.3 | 38.8 |
| A | patient 4 | 1.2 | 1.5 | 1.4 | 25.7 | 1.1 | 36.7 | 86.4 |
| A | patient 6 | 1.0 | 1.1 | 1.8 | 55.5 | 1.1 | 159.6 | 1205.1 |
| A | NHD 1 | 1.3 | 1.1 | 1.2 | 12.3 | 0.9 | 6.9 | 4.9 |
| A | NHD 2 | 1.0 | 1.3 | 1.3 | 15.7 | 0.9 | 5.2 | 6.7 |
| B | patient 1 | 1.0 | 1.1 | 1.0 | 4.1 | 1.0 | 10.1 | 15.9 |
| B | patient 7 | 1.1 | 0.9 | 0.6 | 7.1 | 1.1 | 12.6 | 9.7 |
| B | patient 2 | 1.0 | 1.0 | 0.4 | 34.7 | 1.0 | 8.3 | 139.8 |
| B | patient 3 | 1.2 | 0.8 | 1.0 | 11.0 | 1.2 | 4.6 | 33.0 |
| B | patient 5 | 1.0 | 1.1 | 0.9 | 33.2 | 1.9 | 82.2 | 45.0 |
| B | patient 4 | 1.0 | 1.6 | 1.4 | 15.0 | 1.1 | 34.3 | 70.0 |
| B | patient 6 | 1.0 | 1.2 | 1.5 | 19.2 | 1.2 | 70.9 | 439.1 |
| B | NHD 1 | 1.3 | 1.1 | 1.2 | 9.7 | 0.9 | 5.5 | 4.6 |
| B | NHD 2 | 1.0 | 0.9 | 1.4 | 8.8 | 1.0 | 7.0 | 6.3 |
| C | patient 1 | 1.0 | 1.1 | 1.0 | 1.2 | 0.9 | 0.5 | 0.8 |
| C | patient 7 | 1.1 | 1.0 | 1.0 | 0.9 | 1.0 | 0.5 | 0.3 |
| C | patient 2 | 1.1 | 1.0 | 0.3 | 2.1 | 1.0 | 1.0 | 15.0 |
| C | patient 3 | 1.0 | 0.8 | 1.0 | 2.1 | 0.9 | 2.2 | 3.5 |
| C | patient 5 | 1.2 | 1.2 | 0.4 | 1.0 | 1.0 | 0.9 | 0.5 |
| C | patient 4 | 1.1 | 1.6 | 1.2 | 1.5 | 1.0 | 1.1 | 1.2 |
| C | patient 6 | 1.1 | 0.8 | 1.0 | 1.2 | 1.0 | 1.2 | 4.4 |
| C | NHD 1 | 1.0 | 1.2 | 1.1 | 14.1 | 0.6 | 8.0 | 12.7 |
| C | NHD 2 | 0.8 | 0.9 | 1.3 | 48.0 | 1.0 | 8.9 | 12.8 |

FIG. 14J.6

| | | Leptin ng/mL | Lipoprotein (a) ug/mL | Lymphotactin ng/mL | MCP-1 pg/mL | MDC pg/mL | MIP-1alpha pg/mL | MIP-1beta pg/mL |
|---|---|---|---|---|---|---|---|---|
| | Least Detectable Dose | 0.10 | 3.7 | 0.38 | 52 | 14 | 13 | 38 |
| | RBM Low Plasma Range | 0.41 | 3.0 | | 35 | 162 | | 25 |
| | RBM High Plasma Range | 41 | 858 | 0.57 | 401 | 774 | 89 | 595 |
| D | patient 1 | 1.0 | 1.1 | 0.2 | 3.8 | 1.1 | 20.9 | 94.3 |
| D | patient 7 | 1.0 | 1.0 | 0.7 | 6.8 | 1.1 | 193.9 | 84.7 |
| D | patient 2 | 1.0 | 0.9 | 0.6 | 23.9 | 1.0 | 184.3 | 2065.0 |
| D | patient 3 | 1.0 | 0.9 | 0.4 | 55.4 | 1.1 | 496.0 | 1686.4 |
| D | patient 5 | 1.1 | 1.0 | 0.9 | 16.2 | 0.9 | 304.2 | 140.3 |
| D | patient 4 | 2.5 | 1.8 | 1.5 | 9.3 | 1.2 | 592.3 | 1268.1 |
| D | patient 6 | 0.9 | 1.0 | 1.4 | 19.0 | 1.1 | 197.6 | 2237.2 |
| D | NHD 1 | 1.6 | 1.0 | 1.4 | 5.6 | 1.3 | 254.9 | 124.6 |
| D | NHD 2 | 1.0 | 1.2 | 1.2 | 17.7 | 1.1 | 176.3 | 117.4 |
| E | patient 1 | 1.0 | 1.1 | 0.2 | 3.9 | 1.0 | 7.6 | 20.9 |
| E | patient 7 | 1.1 | 1.2 | 0.7 | 7.7 | 1.0 | 128.5 | 61.0 |
| E | patient 2 | 1.1 | 1.1 | 0.7 | 26.1 | 0.8 | 80.0 | 1024.4 |
| E | patient 3 | 0.8 | 0.9 | 0.5 | 58.7 | 0.9 | 281.4 | 1020.9 |
| E | patient 5 | 1.1 | 1.1 | 0.9 | 23.2 | 0.9 | 393.3 | 155.0 |
| E | patient 4 | 2.5 | 1.4 | 1.3 | 6.8 | 1.0 | 732.3 | 1391.2 |
| E | patient 6 | 1.0 | 1.1 | 1.6 | 33.2 | 1.1 | 125.7 | 1147.4 |
| E | NHD 1 | 1.7 | 1.3 | 1.4 | 11.4 | 1.0 | 175.9 | 84.3 |
| E | NHD 2 | 0.9 | 1.1 | 1.3 | 27.6 | 1.1 | 123.8 | 96.7 |
| F | patient 1 | 0.9 | 1.5 | 1.0 | 2.1 | 0.8 | 1.1 | 2.5 |
| F | patient 7 | 1.0 | 2.6 | 1.0 | 1.5 | 0.9 | 1.1 | 0.8 |
| F | patient 2 | 0.9 | 1.3 | 0.7 | 2.2 | 0.8 | 1.4 | 23.6 |
| F | patient 3 | 0.8 | 0.9 | 0.3 | 57.2 | 0.8 | 27.7 | 293.0 |
| F | patient 5 | 0.8 | 2.1 | 0.2 | 12.6 | 0.8 | 15.0 | 6.3 |
| F | patient 4 | 1.0 | 3.2 | 1.5 | 14.5 | 0.8 | 10.0 | 23.6 |
| F | patient 6 | 0.9 | 2.9 | 1.7 | 4.8 | 0.9 | 4.0 | 32.2 |

FIG. 14J.7

|  | | Leptin ng/mL | Lipoprotein (a) ug/mL | Lymphotactin ng/mL | MCP-1 pg/mL | MDC pg/mL | MIP-1alpha pg/mL | MIP-1beta pg/mL |
|---|---|---|---|---|---|---|---|---|
| | Least Detectable Dose | 0.10 | 3.7 | 0.38 | 52 | 14 | 13 | 38 |
| | RBM Low Plasma Range | 0.41 | 3.0 | | 35 | 162 | | 25 |
| | RBM High Plasma Range | 41 | 858 | 0.57 | 401 | 774 | 89 | 595 |
| F | NHD 1 | 1.3 | 1.3 | 1.5 | 33.0 | 0.5 | 24.0 | 28.1 |
| F | NHD 2 | 1.0 | 1.3 | 1.6 | 37.0 | 0.8 | 10.0 | 21.5 |
| G | patient 1 | 0.9 | 1.3 | 1.0 | 8.7 | 0.1 | 0.6 | 0.6 |
| G | patient 7 | 0.6 | 0.9 | 0.7 | 76.8 | 0.1 | 165.4 | 17.6 |
| G | patient 2 | 0.8 | 0.9 | 0.4 | 4.7 | 0.2 | 1.3 | 13.7 |
| G | patient 3 | 0.7 | 0.9 | 1.0 | 22.7 | 0.0 | 8.7 | 13.6 |
| G | patient 5 | 1.2 | 1.0 | 0.6 | 64.5 | 0.1 | 4.4 | 0.8 |
| G | patient 4 | 2.7 | 1.3 | 1.0 | 25.1 | 0.1 | 16.2 | 9.9 |
| G | patient 6 | 0.6 | 0.8 | 0.5 | 13.6 | 0.2 | 12.3 | 14.6 |
| G | NHD 1 | 1.0 | 0.9 | 0.6 | 5.0 | 0.1 | 3.5 | 1.7 |
| G | NHD 2 | 0.7 | 0.8 | 0.4 | 44.8 | 0.1 | 7.6 | 3.4 |
| H | patient 1 | 1.0 | 1.1 | 1.0 | 1.0 | 0.2 | 0.4 | 0.6 |
| H | patient 7 | 1.0 | 1.0 | 1.0 | 1.7 | 0.2 | 2.0 | 1.3 |
| H | patient 2 | 0.9 | 0.9 | 0.7 | 1.1 | 0.1 | 0.9 | 5.1 |
| H | patient 3 | 1.1 | 0.8 | 1.0 | 2.4 | 0.2 | 1.7 | 11.0 |
| H | patient 5 | 1.1 | 0.9 | 1.0 | 2.3 | 0.3 | 2.8 | 1.3 |
| H | patient 4 | 1.2 | 1.3 | 1.0 | 1.6 | 0.3 | 2.9 | 11.6 |
| H | patient 6 | 1.0 | 0.8 | 0.6 | 1.2 | 0.2 | 1.1 | 4.9 |
| H | NHD 1 | 1.4 | 0.9 | 1.0 | 20.5 | 0.4 | 12.4 | 6.5 |
| H | NHD 2 | 1.0 | 0.8 | 0.7 | 7.0 | 0.4 | 1.9 | 3.9 |
| – | patient 1 | 1.0 | 1.0 | 1.0 | 1.0 | 1.0 | 1.0 | 1.0 |
| – | patient 7 | 1.0 | 1.0 | 1.0 | 1.0 | 1.0 | 1.0 | 1.0 |
| – | patient 2 | 1.0 | 1.0 | 1.0 | 1.0 | 1.0 | 1.0 | 1.0 |
| – | patient 3 | 1.0 | 1.0 | 1.0 | 1.0 | 1.0 | 1.0 | 1.0 |

FIG. 14J.8

| | Leptin ng/mL | Lipoprotein (a) ug/mL | Lymphotactin ng/mL | MCP-1 pg/mL | MDC pg/mL | MIP-1alpha pg/mL | MIP-1beta pg/mL |
|---|---|---|---|---|---|---|---|
| Least Detectable Dose | 0.10 | 3.7 | 0.38 | 52 | 14 | 13 | 38 |
| RBM Low Plasma Range | 0.41 | 3.0 | | 35 | 162 | 89 | 25 |
| RBM High Plasma Range | 41 | 858 | 0.57 | 401 | 774 | | 595 |
| patient 5 | 1.0 | 1.0 | 1.0 | 1.0 | 1.0 | 1.0 | 1.0 |
| patient 4 | 1.0 | 1.0 | 1.0 | 1.0 | 1.0 | 1.0 | 1.0 |
| patient 6 | 1.0 | 1.0 | 1.0 | 1.0 | 1.0 | 1.0 | 1.0 |
| NHD 1 | 1.0 | 1.0 | 1.0 | 1.0 | 1.0 | 1.0 | 1.0 |
| NHD 2 | 1.0 | 1.0 | 1.0 | 1.0 | 1.0 | 1.0 | 1.0 |
| Messwert > ULD | | | | | | | |
| SI > 1,3 | | | | | | | |
| SI 0,7-1,3 | | | | | | | |
| SI 0-0,7 | | | | | | | |

FIG. 14K.1

| | MMP-2 ng/mL | MMP-3 ng/mL | MMP-9 ng/mL | Myeloperoxidase ng/mL | Myoglobin ng/mL | OSM (Oncostatin M) pg/mL | PAI-1 ng/mL |
|---|---|---|---|---|---|---|---|
| Least Detectable Dose | 150 | 0.20 | 37 | 68 | 1.1 | 28 | 0.90 |
| RBM Low Plasma Range | 183 | | | | 3.6 | PENDING | 10 |
| RBM High Plasma Range | 3070 | 1.8 | 1050 | 1110 | 37 | PENDING | 87 |
| Samples | | | | | | | |
| Donor_1 3. Aliquot A | 474 | 12 | 74 | 2010 | 85 | 312 | 159 |
| Donor_1 3. Aliquot B | 440 | 11 | 53 | 1590 | 94 | 188 | 171 |
| Donor_1 3. Aliquot C | 71 | 12 | 30 | 1390 | 101 | 21 | 172 |
| Donor_1 3. Aliquot D | 443 | 13 | 56 | 2050 | 102 | 143 | 156 |
| Donor_1 3. Aliquot E | 456 | 12 | 57 | 2330 | 90 | 312 | 152 |
| Donor_1 3. Aliquot F | 410 | 11 | 33 | 1970 | 95 | 120 | 135 |
| Donor_1 3. Aliquot G | 451 | 13 | 49 | 1750 | 104 | 422 | 187 |
| Donor_1 3. Aliquot H | 68 | 12 | 46 | 1740 | 95 | 28 | 184 |
| Donor_1 3. Aliquot I | 427 | 11 | 38 | 1380 | 89 | 76 | 160 |
| Donor_2 3. Aliquot A | 105 | 11 | 59 | 3520 | 60 | 603 | 178 |
| Donor_2 3. Aliquot B | 83 | 11 | 59 | 2910 | 62 | 334 | 190 |
| Donor_2 3. Aliquot C | 86 | 12 | 42 | 1540 | 61 | 28 | 155 |
| Donor_2 3. Aliquot D | 100 | 13 | 60 | 4180 | 58 | 222 | 165 |
| Donor_2 3. Aliquot E | 123 | 11 | 53 | 3380 | 60 | 188 | 161 |
| Donor_2 3. Aliquot F | 69 | 11 | 2.2 | 1610 | 63 | 65 | 156 |
| Donor_2 3. Aliquot G | 147 | 11 | 28 | 3280 | 64 | 765 | 205 |
| Donor_2 3. Aliquot H | 86 | 11 | 55 | 4200 | 59 | 82 | 177 |
| Donor_2 3. Aliquot I | 72 | 9.7 | 51 | 1730 | 57 | 44 | 164 |
| Donor_3 3. Aliquot A | 30 | 5.4 | 72 | 2890 | 165 | 301 | 246 |
| Donor_3 3. Aliquot B | 26 | 4.8 | 59 | 2640 | 150 | 329 | 221 |
| Donor_3 3. Aliquot C | 34 | 5.0 | 55 | 2210 | 164 | 98 | 199 |
| Donor_3 3. Aliquot D | 47 | 4.9 | 91 | 3310 | 159 | 395 | 225 |
| Donor_3 3. Aliquot E | 34 | 5.3 | 74 | 3500 | 172 | 466 | 208 |
| Donor_3 3. Aliquot F | 34 | 4.4 | 54 | 2630 | 152 | 109 | 216 |
| Donor_3 3. Aliquot G | 67 | 4.3 | 45 | 2240 | 162 | 705 | 246 |
| Donor_3 3. Aliquot H | 23 | 3.9 | 49 | 2830 | 143 | 165 | 207 |
| Donor_3 3. Aliquot I | 150 | 4.7 | 42 | 2450 | 150 | 98 | 214 |

FIG. 14K.2

| | MMP-2 ng/mL | MMP-3 ng/mL | MMP-9 ng/mL | Myeloperoxidase ng/mL | Myoglobin ng/mL | OSM (Oncostatin M) pg/mL | PAI-1 ng/mL |
|---|---|---|---|---|---|---|---|
| Least Detectable Dose | 150 | 0.20 | 37 | 68 | 1.1 | 28 | 0.90 |
| RBM Low Plasma Range | 183 | | | | 3.6 | PENDING | 10 |
| RBM High Plasma Range | 3070 | 1.8 | 1050 | 1110 | 37 | PENDING | 87 |
| Donor_4_3_Aliquot A | 150 | 7.5 | 26 | 2710 | 55 | 28 | 253 |
| Donor_4_3_Aliquot B | 150 | 7.5 | 26 | 1940 | 52 | 54 | 236 |
| Donor_4_3_Aliquot C | 150 | 6.8 | 4.9 | 3400 | 54 | 28 | 229 |
| Donor_4_3_Aliquot D | 43 | 7.4 | 27 | 3920 | 52 | 120 | 216 |
| Donor_4_3_Aliquot E | 50 | 6.6 | 49 | 4430 | 53 | 165 | 222 |
| Donor_4_3_Aliquot F | 150 | 6.6 | 14 | 4210 | 56 | 28 | 237 |
| Donor_4_3_Aliquot G | 45 | 5.6 | 16 | 1950 | 56 | 455 | 203 |
| Donor_4_3_Aliquot H | 15 | 7.2 | 26 | 4140 | 55 | 76 | 219 |
| Donor_4_3_Aliquot I | 150 | 6.8 | 9.3 | 3360 | 55 | 21 | 235 |
| Donor_5_3_Aliquot A | 106 | 21 | 46 | 6630 | 92 | 844 | 158 |
| Donor_5_3_Aliquot B | 112 | 19 | 43 | 6720 | 93 | 834 | 183 |
| Donor_5_3_Aliquot C | 115 | 21 | 52 | 4350 | 97 | 171 | 144 |
| Donor_5_3_Aliquot D | 132 | 19 | 78 | 7840 | 92 | 1850 | 145 |
| Donor_5_3_Aliquot E | 138 | 20 | 57 | 7880 | 91 | 2320 | 155 |
| Donor_5_3_Aliquot F | 67 | 16 | 55 | 5110 | 87 | 188 | 167 |
| Donor_5_3_Aliquot G | 120 | 20 | 28 | 3130 | 96 | 1040 | 181 |
| Donor_5_3_Aliquot H | 90 | 20 | 60 | 6880 | 87 | 834 | 156 |
| Donor_5_3_Aliquot I | 83 | 20 | 62 | 4080 | 82 | 211 | 147 |
| Donor_6_3_Aliquot A | 12 | 2.8 | 74 | 2300 | 52 | 82 | 192 |
| Donor_6_3_Aliquot B | 15 | 3.0 | 76 | 2240 | 50 | 109 | 174 |
| Donor_6_3_Aliquot C | 150 | 2.5 | 33 | 2640 | 52 | 28 | 152 |
| Donor_6_3_Aliquot D | 20 | 2.9 | 80 | 1490 | 52 | 65 | 181 |
| Donor_6_3_Aliquot E | 28 | 2.6 | 99 | 1800 | 50 | 87 | 153 |
| Donor_6_3_Aliquot F | 150 | 2.6 | 18 | 2660 | 54 | 28 | 173 |
| Donor_6_3_Aliquot G | 75 | 2.3 | 46 | 1430 | 54 | 715 | 250 |
| Donor_6_3_Aliquot H | 150 | 2.8 | 39 | 2490 | 50 | 65 | 181 |
| Donor_6_3_Aliquot I | 150 | 2.7 | 32 | 2270 | 51 | 28 | 176 |

FIG. 14K.3

| | MMP-2 ng/mL | MMP-3 ng/mL | MMP-9 ng/mL | Myeloperoxidase ng/mL | Myoglobin ng/mL | OSM (Oncostatin M) pg/mL | PAI-1 ng/mL |
|---|---|---|---|---|---|---|---|
| Least Detectable Dose | 150 | 0.20 | 37 | 68 | 1.1 | 28 | 0.90 |
| RBM Low Plasma Range | 183 | | | | 3.6 | PENDING | 10 |
| RBM High Plasma Range | 3070 | 1.8 | 1050 | 1110 | 37 | PENDING | 87 |
| Donor_7_3. Aliquot A | 16 | 16 | 55 | 2070 | 1790 | 194 | 210 |
| Donor_7_3. Aliquot B | 150 | 16 | 66 | 2710 | >1845 | 109 | 222 |
| Donor_7_3. Aliquot C | 150 | 16 | 37 | 1920 | >1845 | 28 | 215 |
| Donor_7_3. Aliquot D | 23 | 14 | 79 | 1780 | >1845 | 21 | 215 |
| Donor_7_3. Aliquot E | 23 | 15 | 60 | 2160 | >1845 | 54 | 230 |
| Donor_7_3. Aliquot F | 150 | 15 | 2.2 | 2150 | >1845 | 28 | 225 |
| Donor_7_3. Aliquot G | 47 | 15 | 44 | 1630 | >1845 | 143 | 229 |
| Donor_7_3. Aliquot H | 150 | 14 | 30 | 1880 | 1780 | 44 | 198 |
| Donor_7_3. Aliquot I | 150 | 15 | 4.9 | 1800 | >1845 | 28 | 198 |
| Donor_8_3. Aliquot A | 37 | 3.4 | 8.2 | 1510 | 5.2 | 28 | 32 |
| Donor_8_3. Aliquot B | 37 | 3.5 | 26 | 1450 | 3.7 | 28 | 35 |
| Donor_8_3. Aliquot C | 23 | 2.8 | 23 | 3790 | 3.3 | 28 | 31 |
| Donor_8_3. Aliquot D | 89 | 3.9 | 94 | 8210 | 3.1 | 345 | 30 |
| Donor_8_3. Aliquot E | 75 | 3.4 | 81 | 6150 | 3.2 | 132 | 34 |
| Donor_8_3. Aliquot F | 53 | 3.6 | 31 | 2590 | 3.2 | 28 | 30 |
| Donor_8_3. Aliquot G | 58 | 3.2 | 9.3 | 1220 | 2.9 | 132 | 60 |
| Donor_8_3. Aliquot H | 43 | 3.6 | 42 | 4710 | 3.3 | 54 | 41 |
| Donor_8_3. Aliquot I | 26 | 3.2 | 4.9 | 2000 | 3.5 | 28 | 40 |
| Donor_9_3. Aliquot A | 38 | 4.3 | 27 | 1430 | 2.1 | 28 | 45 |
| Donor_9_3. Aliquot B | 43 | 4.8 | 59 | 1150 | 1.9 | 28 | 63 |
| Donor_9_3. Aliquot C | 72 | 4.2 | 36 | 2030 | 1.7 | 28 | 71 |
| Donor_9_3. Aliquot D | 132 | 4.7 | 111 | 3500 | 1.3 | 96 | 72 |
| Donor_9_3. Aliquot E | 82 | 4.9 | 123 | 4800 | 1.9 | 42 | 65 |
| Donor_9_3. Aliquot F | 46 | 4.3 | 4.6 | 747 | 2.1 | 28 | 66 |
| Donor_9_3. Aliquot G | 95 | 3.9 | 27 | 1560 | 1.7 | 247 | 97 |
| Donor_9_3. Aliquot H | 48 | 4.3 | 45 | 3250 | 2.1 | 42 | 71 |
| Donor_9_3. Aliquot I | 42 | 3.6 | 13 | 1070 | 2.1 | 28 | 70 |

FIG. 14K.4

| | MMP-2 ng/mL | MMP-3 ng/mL | MMP-9 ng/mL | Myeloperoxidase ng/mL | Myoglobin ng/mL | OSM (Oncostatin M) pg/mL | PAI-1 ng/mL |
|---|---|---|---|---|---|---|---|
| Least Detectable Dose | 150 | 0.20 | 37 | 68 | 1.1 | 28 | 0.90 |
| RBM Low Plasma Range | 183 | | | | 3.6 | PENDING | 10 |
| RBM High Plasma Range | 3070 | 1.8 | 1050 | 1110 | 37 | PENDING | 87 |
| EDTA Plasma | | | | | | | |
| donor #1 plasma | 1750 | 0.12 | 211 | 111 | 77 | 1120 | 142 |
| donor #2 plasma | 3910 | 0.047 | 1340 | 158 | 64 | 28 | 151 |
| donor #3 plasma | 1540 | 0.2 | 653 | 85 | 182 | 28 | 208 |
| donor #4 plasma | 8190 | 0.2 | 194 | 322 | 61 | 28 | 218 |
| donor #5 plasma | 898 | 0.076 | 236 | 372 | 86 | 28 | 154 |
| donor #6 plasma | 972 | 0.2 | 367 | 9.9 | 57 | 151 | 149 |
| donor #7 plasma | 2270 | 0.090 | 115 | 135 | >1845 | 133 | 242 |
| donor #8 plasma | 10 | 3.7 | 30 | 183 | 3.8 | 28 | 39 |
| donor #9 plasma | 46 | 4.2 | 3.2 | 68 | 1.4 | 28 | 61 |
| Stimulations Indices | MMP-2 | MMP-3 | MMP-9 | Myeloperoxidase | Myoglobin | OSM (Oncostatin M) | PAI-1 |
| patient 1 | 1.1 | 1.1 | 2.0 | 1.5 | 1.0 | 4.1 | 1.0 | A |
| patient 7 | 1.5 | 1.1 | 1.1 | 2.0 | 1.0 | 13.8 | 1.1 | A |

FIG. 14K.5

|   |   | MMP-2 ng/mL | MMP-3 ng/mL | MMP-9 ng/mL | Myeloperoxidase ng/mL | Myoglobin ng/mL | OSM (Oncostatin M) pg/mL | PAI-1 ng/mL |
|---|---|---|---|---|---|---|---|---|
|   | Least Detectable Dose | 150 | 0.20 | 37 | 68 | 1.1 | 28 | 0.90 |
|   | RBM Low Plasma Range | 183 | | 1050 | 1110 | 3.6 | PENDING | 10 |
|   | RBM High Plasma Range | 3070 | 1.8 | | | 37 | PENDING | 87 |
| A | patient 2 | 0.2 | 1.2 | 1.7 | 1.2 | 1.1 | 3.1 | 1.1 |
| A | patient 3 | 1.0 | 1.1 | 2.8 | 0.8 | 1.0 | 1.3 | 1.1 |
| A | patient 5 | 1.3 | 1.0 | 0.7 | 1.6 | 1.1 | 4.0 | 1.1 |
| A | patient 4 | 0.1 | 1.0 | 2.3 | 1.0 | 1.0 | 2.9 | 1.1 |
| A | patient 6 | 0.1 | 1.1 | 11.3 | 1.2 | #VALUE! | 6.9 | 1.1 |
| A | NHD 1 | 1.4 | 1.1 | 1.7 | 0.8 | 1.5 | 1.0 | 0.8 |
| A | NHD 2 | 0.9 | 1.2 | 2.1 | 1.3 | 1.0 | 1.0 | 0.6 |
| B | patient 1 | 1.0 | 1.0 | 1.4 | 1.2 | 1.1 | 2.5 | 1.1 |
| B | patient 7 | 1.2 | 1.2 | 1.1 | 1.7 | 1.1 | 7.7 | 1.2 |
| B | patient 2 | 0.2 | 1.0 | 1.4 | 1.1 | 1.0 | 3.4 | 1.0 |
| B | patient 3 | 1.0 | 1.1 | 2.8 | 0.6 | 1.0 | 2.6 | 1.0 |
| B | patient 5 | 1.3 | 1.0 | 0.7 | 1.6 | 1.1 | 4.0 | 1.2 |
| B | patient 4 | 0.1 | 1.1 | 2.4 | 1.0 | 1.0 | 3.9 | 1.0 |
| B | patient 6 | 1.0 | 1.0 | 13.5 | 1.5 | #VALUE! | 3.9 | 1.1 |
| B | NHD 1 | 1.4 | 1.1 | 5.4 | 0.7 | 1.1 | 1.0 | 0.9 |
| B | NHD 2 | 1.0 | 1.3 | 4.6 | 1.1 | 0.9 | 1.0 | 0.9 |
| C | patient 1 | 0.2 | 1.1 | 0.8 | 1.0 | 1.1 | 0.3 | 1.1 |
| C | patient 7 | 1.2 | 1.2 | 0.8 | 0.9 | 1.1 | 0.6 | 0.9 |
| C | patient 2 | 0.2 | 1.1 | 1.3 | 0.9 | 1.1 | 1.0 | 0.9 |
| C | patient 3 | 1.0 | 1.0 | 0.5 | 1.0 | 1.0 | 1.3 | 1.0 |
| C | patient 5 | 1.4 | 1.1 | 0.8 | 1.1 | 1.2 | 0.8 | 1.0 |
| C | patient 4 | 1.0 | 0.9 | 1.0 | 1.2 | 1.0 | 1.0 | 0.9 |
| C | patient 6 | 1.0 | 1.1 | 7.6 | 1.1 | #VALUE! | 1.0 | 1.1 |
| C | NHD 1 | 0.9 | 0.9 | 4.7 | 1.9 | 1.0 | 1.0 | 0.8 |
| C | NHD 2 | 1.7 | 1.1 | 2.8 | 1.9 | 0.8 | 1.0 | 1.0 |

FIG. 14K.6

| | | MMP-2 ng/mL | MMP-3 ng/mL | MMP-9 ng/mL | Myeloperoxidase ng/mL | Myoglobin ng/mL | OSM (Oncostatin M) pg/mL | PAI-1 ng/mL |
|---|---|---|---|---|---|---|---|---|
| | Least Detectable Dose | 150 | 0.20 | 37 | 68 | 1.1 | 28 | 0.90 |
| | RBM Low Plasma Range | 183 | | | | 3.6 | PENDING | 10 |
| | RBM High Plasma Range | 3070 | 1.8 | 1050 | 1110 | 37 | PENDING | 87 |
| D | patient 1 | 1.0 | 1.2 | 1.5 | 1.5 | 1.1 | 1.9 | 1.0 |
| D | patient 7 | 1.4 | 1.3 | 1.2 | 2.4 | 1.0 | 5.1 | 1.0 |
| D | patient 2 | 0.3 | 1.0 | 2.2 | 1.4 | 1.1 | 4.0 | 1.1 |
| D | patient 3 | 0.3 | 1.1 | 2.9 | 1.2 | 0.9 | 5.6 | 0.9 |
| D | patient 5 | 1.6 | 1.0 | 1.2 | 1.9 | 1.1 | 8.8 | 1.0 |
| D | patient 4 | 0.1 | 1.1 | 2.5 | 0.7 | 1.0 | 2.3 | 1.0 |
| D | patient 6 | 0.2 | 0.9 | 16.2 | 1.0 | #VALUE! | 0.8 | 1.1 |
| D | NHD 1 | 3.5 | 1.2 | 19.4 | 4.1 | 0.9 | 12.3 | 0.8 |
| D | NHD 2 | 3.2 | 1.3 | 8.7 | 3.3 | 0.7 | 3.4 | 1.0 |
| E | patient 1 | 1.1 | 1.1 | 1.5 | 1.7 | 1.0 | 4.1 | 1.0 |
| E | patient 7 | 1.7 | 1.2 | 1.0 | 2.0 | 1.0 | 4.3 | 1.0 |
| E | patient 2 | 0.2 | 1.1 | 1.8 | 1.4 | 1.1 | 4.7 | 1.0 |
| E | patient 3 | 0.3 | 1.0 | 5.3 | 1.3 | 1.0 | 7.7 | 0.9 |
| E | patient 5 | 1.7 | 1.0 | 0.9 | 1.9 | 1.1 | 11.0 | 1.1 |
| E | patient 4 | 0.2 | 0.9 | 3.1 | 0.8 | 1.0 | 3.1 | 0.9 |
| E | patient 6 | 0.2 | 1.0 | 12.5 | 1.2 | #VALUE! | 1.9 | 1.2 |
| E | NHD 1 | 2.9 | 1.1 | 16.7 | 3.1 | 0.9 | 4.7 | 0.8 |
| E | NHD 2 | 2.0 | 1.3 | 9.6 | 4.5 | 0.9 | 1.5 | 0.9 |
| F | patient 1 | 1.0 | 1.0 | 0.9 | 1.4 | 1.1 | 1.6 | 0.8 |
| F | patient 7 | 1.0 | 1.1 | 0.0 | 0.9 | 1.1 | 1.5 | 1.0 |
| F | patient 2 | 0.2 | 0.9 | 1.3 | 1.1 | 1.0 | 1.1 | 1.0 |
| F | patient 3 | 1.0 | 1.0 | 1.5 | 1.3 | 1.0 | 1.3 | 1.0 |
| F | patient 5 | 0.8 | 0.8 | 0.9 | 1.3 | 1.1 | 0.9 | 1.0 |
| F | patient 4 | 1.0 | 1.0 | 0.6 | 1.2 | 1.1 | 1.0 | 1.0 |
| F | patient 6 | 1.0 | 1.0 | 0.5 | 1.2 | #VALUE! | 1.0 | 1.1 |

FIG. 14K.7

| | MMP-2 ng/mL | MMP-3 ng/mL | MMP-9 ng/mL | Myeloperoxidase ng/mL | Myoglobin ng/mL | OSM (Oncostatin M) pg/mL | PAI-1 ng/mL |
|---|---|---|---|---|---|---|---|
| Least Detectable Dose | 150 | 0.20 | 37 | 68 | 1.1 | 28 | 0.90 |
| | | | | | | | |
| RBM Low Plasma Range | 183 | 1.8 | 1050 | 1110 | 3.6 | PENDING | 10 |
| RBM High Plasma Range | 3070 | | | | 37 | PENDING | 87 |
| | | | | | | | |
| F NHD 1 | 2.1 | 1.1 | 6.4 | 1.3 | 0.9 | 1.0 | 0.8 |
| F NHD 2 | 1.1 | 1.2 | 0.4 | 0.7 | 1.0 | 1.0 | 0.9 |
| | | | | | | | |
| G patient 1 | 1.1 | 1.1 | 1.3 | 1.3 | 1.2 | 5.5 | 1.2 |
| G patient 7 | 2.0 | 1.2 | 0.5 | 1.9 | 1.1 | 17.5 | 1.3 |
| G patient 2 | 0.4 | 0.9 | 1.1 | 0.9 | 1.1 | 7.2 | 1.1 |
| G patient 3 | 0.3 | 0.8 | 1.7 | 0.6 | 1.0 | 21.4 | 0.9 |
| G patient 5 | 1.4 | 1.0 | 0.5 | 0.8 | 1.2 | 4.9 | 1.2 |
| G patient 4 | 0.5 | 0.9 | 1.4 | 0.6 | 1.1 | 25.5 | 1.4 |
| G patient 6 | 0.3 | 1.0 | 9.0 | 0.9 | #VALUE! | 5.1 | 1.2 |
| | | | | | | | |
| G NHD 1 | 2.3 | 1.0 | 1.9 | 0.6 | 0.9 | 4.7 | 1.5 |
| G NHD 2 | 2.3 | 1.1 | 2.1 | 1.5 | 0.8 | 8.8 | 1.4 |
| | | | | | | | |
| H patient 1 | 0.2 | 1.1 | 1.2 | 1.3 | 1.1 | 0.4 | 1.2 |
| H patient 7 | 1.2 | 1.2 | 1.1 | 2.4 | 1.0 | 1.9 | 1.1 |
| H patient 2 | 0.2 | 0.8 | 1.2 | 1.2 | 1.0 | 1.7 | 1.0 |
| H patient 3 | 0.1 | 1.1 | 2.8 | 1.2 | 1.0 | 3.6 | 0.9 |
| H patient 5 | 1.1 | 1.0 | 1.0 | 1.7 | 1.1 | 4.0 | 1.1 |
| H patient 4 | 1.0 | 1.0 | 1.2 | 1.1 | 1.0 | 2.3 | 1.1 |
| H patient 6 | 1.0 | 0.9 | 6.2 | 1.0 | #VALUE! | 1.6 | 1.0 |
| | | | | | | | |
| H NHD 1 | 1.7 | 1.1 | 8.6 | 2.4 | 1.0 | 1.9 | 1.0 |
| H NHD 2 | 1.2 | 1.2 | 3.5 | 3.0 | 1.0 | 1.5 | 1.0 |
| | | | | | | | |
| I patient 1 | 1.0 | 1.0 | 1.0 | 1.0 | 1.0 | 1.0 | 1.0 |
| I patient 7 | 1.0 | 1.0 | 1.0 | 1.0 | 1.0 | 1.0 | 1.0 |
| I patient 2 | 1.0 | 1.0 | 1.0 | 1.0 | 1.0 | 1.0 | 1.0 |
| I patient 3 | 1.0 | 1.0 | 1.0 | 1.0 | 1.0 | 1.0 | 1.0 |

FIG. 14K.8

|  | MMP-2 ng/mL | MMP-3 ng/mL | MMP-9 ng/mL | Myeloperoxidase ng/mL | Myoglobin ng/mL | OSM (Oncostatin M) pg/mL | PAI-1 ng/mL |
|---|---|---|---|---|---|---|---|
| Least Detectable Dose | 150 | 0.20 | 37 | 68 | 1.1 | 28 | 0.90 |
| RBM Low Plasma Range | 183 |  |  |  | 3.6 | PENDING | 10 |
| RBM High Plasma Range | 3070 | 1.8 | 1050 | 1110 | 37 | PENDING | 87 |
| patient 5 | 1.0 | 1.0 | 1.0 | 1.0 | 1.0 | 1.0 | 1.0 |
| patient 4 | 1.0 | 1.0 | 1.0 | 1.0 | 1.0 | 1.0 | 1.0 |
| patient 6 | 1.0 | 1.0 | 1.0 | 1.0 | #VALUE! | 1.0 | 1.0 |
| NHD 1 | 1.0 | 1.0 | 1.0 | 1.0 | 1.0 | 1.0 | 1.0 |
| NHD 2 | 1.0 | 1.0 | 1.0 | 1.0 | 1.0 | 1.0 | 1.0 |

Messwert > ULD
SI > 1,3
SI 0,7-1,3
SI 0-0,7

FIG. 14L.1

| | Prostatic Acid Phosphatase ng/mL | PAPP-A mIU/mL | Prostate Specific Antigen, Free ng/mL | RANTES ng/mL | Serum Amyloid P ug/mL | Stem Cell Factor pg/mL | SGOT ug/mL |
|---|---|---|---|---|---|---|---|
| Least Detectable Dose | 0.034 | 0.037 | 0.023 | 0.048 | 0.058 | 56 | 3.7 |
| RBM Low Plasma Range | 0.058 | | | 2.6 | 15 | | 3.9 |
| RBM High Plasma Range | 0.54 | 0.48 | 1.6 | 83 | 50 | 281 | 28 |
| Samples | | | | | | | |
| Donor_1 3. Aliquot A | 0.12 | 0.079 | 0.44 | 16 | 26 | 757 | 3.7 |
| Donor_1 3. Aliquot B | 0.11 | 0.082 | 0.44 | 25 | 28 | 587 | 3.7 |
| Donor_1 3. Aliquot C | 0.045 | 0.059 | 0.47 | 22 | 28 | 599 | 3.7 |
| Donor_1 3. Aliquot D | 0.11 | 0.054 | 0.50 | 18 | 33 | 657 | 3.7 |
| Donor_1 3. Aliquot E | 0.12 | 0.062 | 0.47 | 14 | 29 | 666 | 3.7 |
| Donor_1 3. Aliquot F | 0.041 | 0.073 | 0.41 | 14 | 29 | 430 | 3.7 |
| Donor_1 3. Aliquot G | 0.086 | 0.11 | 0.50 | 24 | 26 | 645 | 3.7 |
| Donor_1 3. Aliquot H | 0.078 | 0.087 | 0.43 | 26 | 29 | 508 | 3.7 |
| Donor_1 3. Aliquot I | 0.035 | 0.049 | 0.45 | 19 | 29 | 508 | 3.7 |
| Donor_2 3. Aliquot A | 0.24 | 0.023 | 0.11 | 20 | 22 | 1350 | 3.7 |
| Donor_2 3. Aliquot B | 0.24 | 0.032 | 0.11 | 24 | 26 | 1530 | 3.7 |
| Donor_2 3. Aliquot C | 0.16 | 0.0049 | 0.072 | 15 | 23 | 607 | 3.7 |
| Donor_2 3. Aliquot D | 0.46 | 0.024 | 0.20 | 13 | 24 | 1640 | 3.7 |
| Donor_2 3. Aliquot E | 0.38 | 0.022 | 0.16 | 13 | 26 | 1670 | 3.7 |
| Donor_2 3. Aliquot F | 0.12 | 0.018 | 0.087 | 13 | 23 | 582 | 3.7 |
| Donor_2 3. Aliquot G | 0.33 | 0.043 | 0.13 | 21 | 22 | 1760 | 3.7 |
| Donor_2 3. Aliquot H | 0.14 | 0.023 | 0.083 | 13 | 27 | 595 | 3.7 |
| Donor_2 3. Aliquot I | 0.13 | 0.018 | 0.082 | 12 | 23 | 500 | 3.7 |
| Donor_3 3. Aliquot A | 0.24 | 0.0063 | 0.67 | 16 | 14 | 666 | 3.7 |
| Donor_3 3. Aliquot B | 0.22 | 0.037 | 0.65 | 21 | 14 | 434 | 3.7 |
| Donor_3 3. Aliquot C | 0.16 | 0.037 | 0.72 | 17 | 17 | 213 | 3.7 |
| Donor_3 3. Aliquot D | 0.41 | 0.0049 | 0.71 | 16 | 15 | 882 | 3.7 |
| Donor_3 3. Aliquot E | 0.47 | 0.0063 | 0.73 | 21 | 15 | 1020 | 3.7 |
| Donor_3 3. Aliquot F | 0.16 | 0.0063 | 0.65 | 13 | 16 | 202 | 3.7 |
| Donor_3 3. Aliquot G | 0.17 | 0.037 | 0.74 | 26 | 15 | 183 | 3.7 |
| Donor_3 3. Aliquot H | 0.14 | 0.0049 | 0.57 | 13 | 16 | 113 | 3.7 |
| Donor_3 3. Aliquot I | 0.14 | 0.037 | 0.61 | 14 | 16 | 138 | 3.7 |

FIG. 14L.2

| | Prostatic Acid Phosphatase ng/mL | PAPP-A mIU/mL | Prostate Specific Antigen, Free ng/mL | RANTES ng/mL | Serum Amyloid P ug/mL | Stem Cell Factor pg/mL | SGOT ug/mL |
|---|---|---|---|---|---|---|---|
| Least Detectable Dose | 0.034 | 0.037 | 0.023 | 0.048 | 0.058 | 56 | 3.7 |
| RBM Low Plasma Range | 0.058 | | | 2.6 | 15 | | 3.9 |
| RBM High Plasma Range | 0.54 | 0.48 | 1.6 | 83 | 50 | 281 | 28 |
| Donor_4 3. Aliquot A | 0.27 | 0.13 | 0.023 | 4.4 | 8.7 | 426 | 3.7 |
| Donor_4 3. Aliquot B | 0.38 | 0.14 | 0.023 | 4.6 | 9.6 | 475 | 3.7 |
| Donor_4 3. Aliquot C | 0.28 | 0.029 | 0.023 | 2.7 | 9.9 | 377 | 3.7 |
| Donor_4 3. Aliquot D | 0.42 | 0.13 | 0.045 | 3.4 | 10 | 957 | 3.7 |
| Donor_4 3. Aliquot E | 0.46 | 0.15 | 0.023 | 2.6 | 10 | 1010 | 3.7 |
| Donor_4 3. Aliquot F | 0.26 | 0.14 | 0.023 | 2.5 | 12 | 459 | 3.7 |
| Donor_4 3. Aliquot G | 0.56 | 0.16 | 0.023 | 5.9 | 8.8 | 459 | 3.7 |
| Donor_4 3. Aliquot H | 0.23 | 0.13 | 0.023 | 2.5 | 11 | 405 | 3.7 |
| Donor_4 3. Aliquot I | 0.26 | 0.12 | 0.023 | 3.2 | 10 | 352 | 3.7 |
| Donor_5 3. Aliquot A | 0.46 | 0.021 | 0.49 | 17 | 43 | 936 | 3.7 |
| Donor_5 3. Aliquot B | 0.73 | 0.021 | 0.48 | 13 | 41 | 815 | 3.7 |
| Donor_5 3. Aliquot C | 0.28 | 0.0078 | 0.42 | 11 | 38 | 320 | 3.7 |
| Donor_5 3. Aliquot D | 1.5 | 0.040 | 0.61 | 14 | 46 | 965 | 3.7 |
| Donor_5 3. Aliquot E | 2.9 | 0.032 | 0.57 | 14 | 45 | 1290 | 3.7 |
| Donor_5 3. Aliquot F | 0.27 | 0.018 | 0.39 | 9.5 | 38 | 288 | 0.62 |
| Donor_5 3. Aliquot G | 0.52 | 0.029 | 0.45 | 16 | 40 | 541 | 3.7 |
| Donor_5 3. Aliquot H | 0.50 | 0.014 | 0.46 | 12 | 43 | 292 | 3.7 |
| Donor_5 3. Aliquot I | 0.27 | 0.014 | 0.49 | 9.0 | 41 | 348 | 3.7 |
| Donor_6 3. Aliquot A | 0.13 | 0.0056 | 0.35 | 35 | 25 | 217 | 3.7 |
| Donor_6 3. Aliquot B | 0.24 | 0.037 | 0.40 | 34 | 27 | 187 | 3.7 |
| Donor_6 3. Aliquot C | 0.22 | 0.037 | 0.34 | 23 | 24 | 99 | 3.7 |
| Donor_6 3. Aliquot D | 0.26 | 0.037 | 0.44 | 35 | 31 | 272 | 3.7 |
| Donor_6 3. Aliquot E | 0.38 | 0.0063 | 0.40 | 23 | 26 | 316 | 3.7 |
| Donor_6 3. Aliquot F | 0.15 | 0.037 | 0.31 | 20 | 26 | 99 | 3.7 |
| Donor_6 3. Aliquot G | 0.54 | 0.037 | 0.33 | 47 | 22 | 164 | 3.7 |
| Donor_6 3. Aliquot H | 0.12 | 0.037 | 0.33 | 22 | 23 | 69 | 3.7 |
| Donor_6 3. Aliquot I | 0.17 | 0.037 | 0.35 | 23 | 25 | 92 | 3.7 |

FIG. 14L.3

| | Prostatic Acid Phosphatase ng/mL | PAPP-A mIU/mL | Prostate Specific Antigen, Free ng/mL | RANTES ng/mL | Serum Amyloid P ug/mL | Stem Cell Factor pg/mL | SGOT ug/mL |
|---|---|---|---|---|---|---|---|
| Least Detectable Dose | 0.034 | 0.037 | 0.023 | 0.048 | 0.058 | 56 | 3.7 |
| RBM Low Plasma Range | 0.058 | 0.48 | 1.6 | 2.6 | 15 | 281 | 3.9 |
| RBM High Plasma Range | 0.54 | | | 83 | 50 | | 28 |
| Donor_7_3. Aliquot A | 0.10 | 0.012 | 0.65 | 17 | 31 | 998 | 8.2 |
| Donor_7_3. Aliquot B | 0.16 | 0.011 | 0.63 | 17 | 35 | 607 | 12 |
| Donor_7_3. Aliquot C | 0.068 | 0.037 | 0.65 | 25 | 33 | 113 | 8.1 |
| Donor_7_3. Aliquot D | 0.19 | 0.0085 | 0.61 | 19 | 30 | 790 | 11 |
| Donor_7_3. Aliquot E | 0.12 | 0.0049 | 0.66 | 15 | 29 | 707 | 13 |
| Donor_7_3. Aliquot F | 0.078 | 0.037 | 0.57 | 9.7 | 35 | 127 | 11 |
| Donor_7_3. Aliquot G | 0.063 | 0.037 | 0.68 | 23 | 29 | 160 | 4.3 |
| Donor_7_3. Aliquot H | 0.087 | 0.0092 | 0.64 | 12 | 31 | 72 | 16 |
| Donor_7_3. Aliquot I | 0.073 | 0.037 | 0.60 | 12 | 34 | 127 | 11 |
| Donor_8_3. Aliquot A | 0.082 | 0.0070 | 0.023 | 12 | 5.7 | 92 | 3.7 |
| Donor_8_3. Aliquot B | 0.13 | 0.0056 | 0.023 | 16 | 6.4 | 46 | 3.7 |
| Donor_8_3. Aliquot C | 0.16 | 0.037 | 0.023 | 17 | 5.4 | 69 | 3.7 |
| Donor_8_3. Aliquot D | 0.67 | 0.015 | 0.18 | 12 | 5.7 | 106 | 3.7 |
| Donor_8_3. Aliquot E | 0.55 | 0.0092 | 0.13 | 14 | 5.9 | 72 | 3.7 |
| Donor_8_3. Aliquot F | 0.15 | 0.0056 | 0.023 | 6.9 | 6.7 | 40 | 3.7 |
| Donor_8_3. Aliquot G | 0.058 | 0.0092 | 0.023 | 19 | 5.2 | 99 | 3.7 |
| Donor_8_3. Aliquot H | 0.14 | 0.014 | 0.023 | 15 | 6.4 | 89 | 3.7 |
| Donor_8_3. Aliquot I | 0.079 | 0.0078 | 0.023 | 17 | 6.5 | 56 | 3.7 |
| Donor_9_3. Aliquot A | 0.052 | 0.0053 | 0.023 | 16 | Pending | 170 | 3.7 |
| Donor_9_3. Aliquot B | 0.088 | 0.037 | 0.023 | 21 | Pending | 229 | 3.7 |
| Donor_9_3. Aliquot C | 0.074 | 0.037 | 0.023 | 23 | Pending | 229 | 3.7 |
| Donor_9_3. Aliquot D | 0.50 | 0.013 | 0.18 | 21 | Pending | 307 | 3.7 |
| Donor_9_3. Aliquot E | 0.34 | 0.037 | 0.10 | 13 | Pending | 272 | 3.7 |
| Donor_9_3. Aliquot F | 0.052 | 0.0077 | 0.023 | 9.1 | Pending | 137 | 3.7 |
| Donor_9_3. Aliquot G | 0.040 | 0.010 | 0.023 | 30 | Pending | 528 | 3.7 |
| Donor_9_3. Aliquot H | 0.037 | 0.037 | 0.023 | 21 | Pending | 97 | 3.7 |
| Donor_9_3. Aliquot I | 0.034 | 0.037 | 0.023 | 21 | Pending | 174 | 3.7 |

FIG. 14L.4

| | Prostatic Acid Phosphatase ng/mL | PAPP-A mIU/mL | Prostate Specific Antigen, Free ng/mL | RANTES ng/mL | Serum Amyloid P ug/mL | Stem Cell Factor pg/mL | SGOT ug/mL |
|---|---|---|---|---|---|---|---|
| Least Detectable Dose | 0.034 | 0.037 | 0.023 | 0.048 | 0.058 | 56 | 3.7 |
| RBM Low Plasma Range | 0.058 | | | 2.6 | 15 | | 3.9 |
| RBM High Plasma Range | 0.54 | 0.48 | 1.6 | 83 | 50 | 281 | 28 |
| EDTA Plasma | | | | | | | |
| donor #1 plasma | 0.090 | 0.084 | 0.28 | 9.4 | Pending | 351 | 40 |
| donor #2 plasma | 0.13 | 0.052 | 0.13 | 3.4 | Pending | 492 | 45 |
| donor #3 plasma | 0.050 | 0.029 | 0.74 | 6.4 | Pending | 161 | 54 |
| donor #4 plasma | 0.65 | 0.26 | 0.023 | 1.3 | Pending | 368 | 32 |
| donor #5 plasma | 0.41 | 0.040 | 0.47 | 8.7 | Pending | 550 | 70 |
| donor #6 plasma | 0.15 | 0.017 | 0.45 | 14 | Pending | 62 | 35 |
| donor #7 plasma | 0.078 | 0.066 | 0.82 | 12 | Pending | 212 | 46 |
| donor #8 plasma | 0.13 | 0.010 | 0.024 | 5.3 | Pending | 161 | 3.7 |
| donor #9 plasma | 0.071 | 0.037 | 0.023 | 1.2 | Pending | 203 | 3.7 |
| Stimulationsindices | | | | | | | |
| patient 1 | 3.3 | 1.6 | 1.0 | 0.9 | 0.9 | 1.5 | 1.0 |
| patient 7 | 1.8 | 1.3 | 1.3 | 1.8 | 1.0 | 2.7 | 1.0 |

FIG. 14L.5

| | | Prostatic Acid Phosphatase ng/mL | PAPP-A mIU/mL | Prostate Specific Antigen, Free ng/mL | RANTES ng/mL | Serum Amyloid P ug/mL | Stem Cell Factor pg/mL | SGOT ug/mL |
|---|---|---|---|---|---|---|---|---|
| | Least Detectable Dose | 0.034 | 0.037 | 0.023 | 0.048 | 0.058 | | |
| | RBM Low Plasma Range | 0.058 | | | 2.6 | 15 | 56 | 3.7 |
| | RBM High Plasma Range | 0.54 | 0.48 | 1.6 | 83 | 50 | 281 | 28 |
| A | patient 2 | 1.7 | 0.2 | 1.1 | 1.2 | 0.9 | 4.8 | 1.0 |
| A | patient 3 | 1.0 | 1.1 | 1.0 | 1.4 | 0.8 | 1.2 | 1.0 |
| A | patient 5 | 1.7 | 1.5 | 1.0 | 1.8 | 1.0 | 2.7 | 1.0 |
| A | patient 4 | 0.8 | 0.2 | 1.0 | 1.5 | 1.0 | 2.4 | 1.0 |
| A | patient 6 | 1.4 | 0.3 | 1.1 | 1.4 | 0.9 | 7.9 | 0.8 |
| A | NHD 1 | 1.0 | 0.9 | 1.0 | 0.7 | 0.9 | 1.7 | 1.0 |
| A | NHD 2 | 1.5 | 0.1 | 1.0 | 0.8 | #VALUE! | 1.0 | 1.0 |
| B | patient 1 | 3.2 | 1.7 | 1.0 | 1.3 | 1.0 | 1.2 | 1.0 |
| B | patient 7 | 1.8 | 1.8 | 1.4 | 2.1 | 1.2 | 3.1 | 1.0 |
| B | patient 2 | 1.6 | 1.0 | 1.1 | 1.5 | 0.9 | 3.1 | 1.0 |
| B | patient 3 | 1.4 | 1.2 | 1.0 | 1.5 | 0.9 | 1.3 | 1.0 |
| B | patient 5 | 2.7 | 1.5 | 1.0 | 1.5 | 1.0 | 2.3 | 1.0 |
| B | patient 4 | 1.4 | 1.0 | 1.2 | 1.2 | 1.1 | 2.0 | 1.0 |
| B | patient 6 | 2.1 | 0.3 | 1.0 | 1.4 | 1.0 | 4.8 | 1.1 |
| B | NHD 1 | 1.6 | 0.7 | 1.0 | 1.0 | 1.0 | 0.8 | 1.0 |
| B | NHD 2 | 2.6 | 1.0 | 1.0 | 1.0 | #VALUE! | 1.3 | 1.0 |
| C | patient 1 | 1.3 | 1.2 | 1.0 | 1.2 | 1.0 | 1.2 | 1.0 |
| C | patient 7 | 1.2 | 0.3 | 0.9 | 1.3 | 1.2 | 1.2 | 1.0 |
| C | patient 2 | 1.1 | 1.0 | 1.2 | 1.2 | 0.9 | 1.5 | 1.0 |
| C | patient 3 | 1.0 | 0.2 | 1.2 | 0.9 | 1.0 | 1.1 | 1.0 |
| C | patient 5 | 1.0 | 0.6 | 0.9 | 1.2 | 0.9 | 0.9 | 1.0 |
| C | patient 4 | 1.3 | 1.0 | 1.0 | 1.0 | 0.9 | 1.1 | 1.0 |
| C | patient 6 | 0.9 | 1.0 | 1.1 | 2.0 | 1.0 | 0.9 | 0.8 |
| C | NHD 1 | 2.0 | 4.8 | 1.0 | 1.0 | 0.8 | 1.2 | 1.0 |
| C | NHD 2 | 2.2 | 1.0 | 1.0 | 1.1 | #VALUE! | 1.3 | 1.0 |

FIG. 14L.6

| | | Prostatic Acid Phosphatase ng/mL | PAPP-A mIU/mL | Prostate Specific Antigen, Free ng/mL | RANTES ng/mL | Serum Amyloid P ug/mL | Stem Cell Factor pg/mL | SGOT ug/mL |
|---|---|---|---|---|---|---|---|---|
| | Least Detectable Dose | 0.034 | 0.037 | 0.023 | 0.048 | 0.058 | 56 | 3.7 |
| | RBM Low Plasma Range | 0.058 | 0.48 | 1.6 | 2.6 | 15 | | 3.9 |
| | RBM High Plasma Range | 0.54 | | | 83 | 50 | 281 | 28 |
| D | patient 1 | 3.0 | 1.1 | 1.1 | 1.0 | 1.1 | 1.3 | 1.0 |
| D | patient 7 | 3.4 | 1.3 | 2.5 | 1.1 | 1.1 | 3.3 | 1.0 |
| D | patient 2 | 2.9 | 0.1 | 1.2 | 1.1 | 1.0 | 6.4 | 1.0 |
| D | patient 3 | 1.6 | 1.1 | 1.9 | 1.1 | 1.0 | 2.7 | 1.0 |
| D | patient 5 | 5.6 | 2.9 | 1.3 | 1.6 | 1.1 | 2.8 | 1.0 |
| D | patient 4 | 1.5 | 1.0 | 1.2 | 1.5 | 1.2 | 3.0 | 1.0 |
| D | patient 6 | 2.6 | 0.2 | 1.0 | 1.6 | 0.9 | 6.2 | 1.0 |
| D | NHD 1 | 8.5 | 2.0 | 8.0 | 0.7 | 0.9 | 1.9 | 1.0 |
| D | NHD 2 | 14.6 | 0.4 | 7.7 | 1.0 | #VALUE! | 1.8 | 1.0 |
| E | patient 1 | 3.5 | 1.3 | 1.0 | 0.8 | 1.0 | 1.3 | 1.0 |
| E | patient 7 | 2.9 | 1.2 | 1.9 | 1.1 | 1.1 | 3.3 | 1.0 |
| E | patient 2 | 3.3 | 0.2 | 1.2 | 1.5 | 0.9 | 7.4 | 1.0 |
| E | patient 3 | 1.7 | 1.3 | 1.0 | 0.8 | 1.0 | 2.9 | 1.0 |
| E | patient 5 | 10.7 | 2.3 | 1.2 | 1.5 | 1.1 | 3.7 | 1.0 |
| E | patient 4 | 2.2 | 0.2 | 1.2 | 1.0 | 1.0 | 3.4 | 1.0 |
| E | patient 6 | 1.6 | 0.1 | 1.1 | 1.2 | 0.8 | 5.6 | 1.3 |
| E | NHD 1 | 6.9 | 1.2 | 5.8 | 0.8 | 0.9 | 1.3 | 1.0 |
| E | NHD 2 | 9.8 | 1.0 | 4.5 | 0.6 | #VALUE! | 1.6 | 1.0 |
| F | patient 1 | 1.2 | 1.5 | 0.9 | 0.7 | 1.0 | 0.8 | 1.0 |
| F | patient 7 | 0.9 | 1.0 | 1.1 | 1.1 | 1.0 | 1.2 | 1.0 |
| F | patient 2 | 1.1 | 0.2 | 1.1 | 0.9 | 1.0 | 1.5 | 1.0 |
| F | patient 3 | 1.0 | 1.2 | 1.0 | 0.8 | 1.2 | 1.3 | 1.0 |
| F | patient 5 | 1.0 | 1.3 | 0.8 | 1.1 | 0.9 | 0.8 | 0.2 |
| F | patient 4 | 0.9 | 1.0 | 0.9 | 0.9 | 1.0 | 1.1 | 1.0 |
| F | patient 6 | 1.1 | 1.0 | 0.9 | 0.8 | 1.0 | 1.0 | 1.0 |

FIG. 14L.7

| | Prostatic Acid Phosphatase ng/mL | PAPP-A mIU/mL | Prostate Specific Antigen, Free ng/mL | RANTES ng/mL | Serum Amyloid P ug/mL | Stem Cell Factor pg/mL | SGOT ug/mL |
|---|---|---|---|---|---|---|---|
| Least Detectable Dose | 0.034 | 0.037 | 0.023 | 0.048 | 0.058 | 56 | 3.7 |
| RBM Low Plasma Range | 0.058 | 0.48 | | 2.6 | 15 | | 3.9 |
| RBM High Plasma Range | 0.54 | | 1.6 | 83 | 50 | 281 | 28 |
| F NHD 1 | 1.9 | 0.7 | 1.0 | 0.4 | 1.0 | 0.7 | 1.0 |
| F NHD 2 | 1.5 | 0.2 | 1.0 | 0.4 | #VALUE! | 0.8 | 1.0 |
| G patient 1 | 2.4 | 2.2 | 1.1 | 1.3 | 0.9 | 1.3 | 1.0 |
| G patient 7 | 2.4 | 2.4 | 1.6 | 1.8 | 1.0 | 3.5 | 1.0 |
| G patient 2 | 1.2 | 1.0 | 1.2 | 1.9 | 0.9 | 1.3 | 1.0 |
| G patient 3 | 2.1 | 1.4 | 0.9 | 1.9 | 0.9 | 1.3 | 1.0 |
| G patient 5 | 1.9 | 2.1 | 0.9 | 1.7 | 1.0 | 1.6 | 1.0 |
| G patient 4 | 3.1 | 1.0 | 0.9 | 2.1 | 0.9 | 1.8 | 1.0 |
| G patient 6 | 0.9 | 1.0 | 1.1 | 1.9 | 0.8 | 1.3 | 0.4 |
| G NHD 1 | 0.7 | 1.2 | 1.0 | 1.2 | 0.8 | 1.8 | 1.0 |
| G NHD 2 | 1.2 | 0.3 | 1.0 | 1.4 | #VALUE! | 3.0 | 1.0 |
| H patient 1 | 2.2 | 1.8 | 1.0 | 1.4 | 1.0 | 1.0 | 1.0 |
| H patient 7 | 1.0 | 1.3 | 1.0 | 1.1 | 1.2 | 1.2 | 1.0 |
| H patient 2 | 1.0 | 0.1 | 0.9 | 1.0 | 1.0 | 0.8 | 1.0 |
| H patient 3 | 0.9 | 1.1 | 1.0 | 0.8 | 1.1 | 1.2 | 1.0 |
| H patient 5 | 1.8 | 1.0 | 1.0 | 1.4 | 1.1 | 0.8 | 1.0 |
| H patient 4 | 0.7 | 1.0 | 1.0 | 1.0 | 0.9 | 0.7 | 1.0 |
| H patient 6 | 1.2 | 0.2 | 1.1 | 1.0 | 0.9 | 0.6 | 1.6 |
| H NHD 1 | 1.7 | 1.8 | 1.0 | 0.9 | 1.0 | 1.6 | 1.0 |
| H NHD 2 | 1.1 | 1.0 | 1.0 | 1.0 | #VALUE! | 0.6 | 1.0 |
| I patient 1 | 1.0 | 1.0 | 1.0 | 1.0 | 1.0 | 1.0 | 1.0 |
| I patient 7 | 1.0 | 1.0 | 1.0 | 1.0 | 1.0 | 1.0 | 1.0 |
| I patient 2 | 1.0 | 1.0 | 1.0 | 1.0 | 1.0 | 1.0 | 1.0 |
| I patient 3 | 1.0 | 1.0 | 1.0 | 1.0 | 1.0 | 1.0 | 1.0 |

FIG. 14L.8

| | Prostatic Acid Phosphatase ng/mL | PAPP-A mIU/mL | Prostate Specific Antigen, Free ng/mL | RANTES ng/mL | Serum Amyloid P ug/mL | Stem Cell Factor pg/mL | SGOT ug/mL |
|---|---|---|---|---|---|---|---|
| Least Detectable Dose | 0.034 | 0.037 | 0.023 | 0.048 | 0.058 | | 3.7 |
| RBM Low Plasma Range | 0.058 | | | | | 56 | |
| RBM High Plasma Range | 0.54 | 0.48 | 1.6 | 2.6 | 15 | | 3.9 |
| patient 5 | 1.0 | 1.0 | 1.0 | 83 | 50 | 281 | 28 |
| patient 4 | 1.0 | 1.0 | 1.0 | 1.0 | 1.0 | 1.0 | 1.0 |
| patient 6 | 1.0 | 1.0 | 1.0 | 1.0 | 1.0 | 1.0 | 1.0 |
| NHD 1 | 1.0 | 1.0 | 1.0 | 1.0 | 1.0 | 1.0 | 1.0 |
| NHD 2 | 1.0 | 1.0 | 1.0 | 1.0 | #VALUE! | 1.0 | 1.0 |

| Messwert > ULD |
| SI > 1,3 |
| SI 0,7-1,3 |
| SI 0-0,7 |

FIG. 14M.1

| | SHBG<br>nmol/L | Thyroxine<br>Binding<br>Globulin<br>ug/mL | Tissue Factor<br>ng/mL | TGF-alpha<br>pg/mL | TIMP-1<br>ng/mL | TNF RII<br>ng/mL | TNF-alpha<br>pg/mL |
|---|---|---|---|---|---|---|---|
| Least Detectable Dose | 1.3 | 0.34 | 0.84 | 1.8 | 8.4 | 0.13 | 4.0 |
| RBM Low Plasma Range | 12 | 40 | | Pending | 59 | 3.1 | |
| RBM High Plasma Range | 106 | 104 | 2.4 | Pending | 192 | 79 | 27 |
| Samples | | | | | | | |
| Donor_1 3. Aliquot A | 18 | 27 | 3.7 | 22 | 521 | 29 | 236 |
| Donor_1 3. Aliquot B | 19 | 31 | 2.7 | 15 | 615 | 31 | 75 |
| Donor_1 3. Aliquot C | 19 | 29 | 0.91 | 1.8 | 611 | 28 | 19 |
| Donor_1 3. Aliquot D | 19 | 31 | 3.3 | 9.7 | 620 | 30 | 300 |
| Donor_1 3. Aliquot E | 19 | 29 | 3.0 | 13 | 549 | 29 | 88 |
| Donor_1 3. Aliquot F | 18 | 29 | 2.0 | 3.8 | 553 | 27 | 35 |
| Donor_1 3. Aliquot G | 19 | 29 | 2.0 | 24 | 645 | 30 | 24 |
| Donor_1 3. Aliquot H | 19 | 26 | 1.8 | 1.5 | 580 | 27 | 19 |
| Donor_1 3. Aliquot I | 18 | 28 | 1.6 | 1.6 | 495 | 24 | 25 |
| Donor_2 3. Aliquot A | 34 | 36 | 1.7 | 56 | 354 | 47 | 212 |
| Donor_2 3. Aliquot B | 35 | 37 | 1.9 | 44 | 391 | 49 | 94 |
| Donor_2 3. Aliquot C | 36 | 36 | 0.84 | 7.5 | 303 | 41 | 12 |
| Donor_2 3. Aliquot D | 35 | 38 | 7.1 | 46 | 359 | 45 | 2700 |
| Donor_2 3. Aliquot E | 34 | 37 | 3.5 | 43 | 376 | 48 | 1690 |
| Donor_2 3. Aliquot F | 36 | 39 | 0.47 | 5.6 | 305 | 40 | 24 |
| Donor_2 3. Aliquot G | 34 | 38 | 2.3 | 48 | 499 | 47 | 544 |
| Donor_2 3. Aliquot H | 36 | 34 | 0.84 | 20 | 304 | 40 | 21 |
| Donor_2 3. Aliquot I | 33 | 37 | 0.70 | 9.5 | 278 | 36 | 19 |
| Donor_3 3. Aliquot A | 42 | 56 | 1.9 | 20 | 183 | 14 | 157 |
| Donor_3 3. Aliquot B | 40 | 50 | 1.8 | 22 | 209 | 13 | 64 |
| Donor_3 3. Aliquot C | 43 | 57 | 0.15 | 5.6 | 156 | 8.1 | 13 |
| Donor_3 3. Aliquot D | 39 | 52 | 5.4 | 18 | 213 | 14 | 2600 |
| Donor_3 3. Aliquot E | 42 | 52 | 4.9 | 16 | 221 | 14 | 1150 |
| Donor_3 3. Aliquot F | 40 | 53 | 1.5 | 4.4 | 154 | 7.9 | 26 |
| Donor_3 3. Aliquot G | 41 | 54 | 0.84 | 15 | 205 | 10.0 | 21 |
| Donor_3 3. Aliquot H | 38 | 49 | 0.56 | 2.1 | 155 | 6.8 | 9.4 |
| Donor_3 3. Aliquot I | 36 | 51 | 0.99 | 0.63 | 153 | 6.5 | 4.2 |

FIG. 14M.2

| | SHBG nmol/L | Thyroxine Binding Globulin ug/mL | Tissue Factor ng/mL | TGF-alpha pg/mL | TIMP-1 ng/mL | TNF RII ng/mL | TNF-alpha pg/mL |
|---|---|---|---|---|---|---|---|
| Least Detectable Dose | 1.3 | 0.34 | 0.84 | 1.8 | 8.4 | 0.13 | 4.0 |
| RBM Low Plasma Range | 12 | 40 | | Pending | 59 | 3.1 | |
| RBM High Plasma Range | 106 | 104 | 2.4 | Pending | 192 | 79 | 27 |
| Donor_4_3. Aliquot A | 54 | 38 | 1.5 | 15 | 575 | 30 | 20 |
| Donor_4_3. Aliquot B | 53 | 35 | 0.87 | 22 | 590 | 30 | 17 |
| Donor_4_3. Aliquot C | 54 | 35 | 0.84 | 6.4 | 532 | 26 | 12 |
| Donor_4_3. Aliquot D | 55 | 34 | 5.4 | 19 | 622 | 33 | 1720 |
| Donor_4_3. Aliquot E | 50 | 35 | 3.4 | 16 | 632 | 36 | 618 |
| Donor_4_3. Aliquot F | 58 | 36 | 1.5 | 4.6 | 565 | 31 | 91 |
| Donor_4_3. Aliquot G | 57 | 36 | 0.84 | 16 | 499 | 30 | 12 |
| Donor_4_3. Aliquot H | 53 | 32 | 0.99 | 3.5 | 546 | 27 | 9.3 |
| Donor_4_3. Aliquot I | 51 | 35 | 0.84 | 3.8 | 557 | 28 | 4.8 |
| Donor_5_3. Aliquot A | 33 | 47 | 0.87 | 22 | 344 | 28 | 106 |
| Donor_5_3. Aliquot B | 31 | 47 | 0.87 | 20 | 368 | 31 | 146 |
| Donor_5_3. Aliquot C | 35 | 42 | 0.84 | 7.3 | 184 | 23 | 12 |
| Donor_5_3. Aliquot D | 31 | 45 | 6.3 | 17 | 327 | 34 | 1900 |
| Donor_5_3. Aliquot E | 31 | 46 | 4.4 | 23 | 360 | 35 | 1590 |
| Donor_5_3. Aliquot F | 31 | 43 | 0.15 | 7.1 | 233 | 23 | 105 |
| Donor_5_3. Aliquot G | 32 | 44 | 0.84 | 25 | 331 | 27 | 18 |
| Donor_5_3. Aliquot H | 29 | 40 | 0.56 | 7.0 | 228 | 23 | 12 |
| Donor_5_3. Aliquot I | 29 | 42 | 0.84 | 7.6 | 190 | 22 | 12 |
| Donor_6_3. Aliquot A | 18 | 29 | 0.84 | 13 | 139 | 5.5 | 41 |
| Donor_6_3. Aliquot B | 19 | 30 | 0.84 | 15 | 165 | 6.9 | 23 |
| Donor_6_3. Aliquot C | 19 | 27 | 0.84 | 1.2 | 111 | 2.5 | 3.2 |
| Donor_6_3. Aliquot D | 18 | 29 | 3.0 | 12 | 156 | 6.8 | 1910 |
| Donor_6_3. Aliquot E | 17 | 28 | 5.1 | 16 | 164 | 7.8 | 3210 |
| Donor_6_3. Aliquot F | 19 | 30 | 0.84 | 1.2 | 124 | 4.1 | 9.1 |
| Donor_6_3. Aliquot G | 18 | 30 | 0.84 | 11 | 260 | 5.1 | 12 |
| Donor_6_3. Aliquot H | 19 | 27 | 0.84 | 3.8 | 112 | 3.0 | 8.0 |
| Donor_6_3. Aliquot I | 18 | 28 | 0.84 | 1.5 | 100 | 2.4 | 1.7 |

FIG. 14M.3

| | SHBG nmol/L | Thyroxine Binding Globulin ug/mL | Tissue Factor ng/mL | TGF-alpha pg/mL | TIMP-1 ng/mL | TNF RII ng/mL | TNF-alpha pg/mL |
|---|---|---|---|---|---|---|---|
| Least Detectable Dose | 1.3 | 0.34 | 0.84 | 1.8 | 8.4 | 0.13 | 4.0 |
| RBM Low Plasma Range | 12 | 40 | | Pending | 59 | 3.1 | 27 |
| RBM High Plasma Range | 106 | 104 | 2.4 | Pending | 192 | 79 | |
| Donor_7_3. Aliquot A | 9.5 | 25 | 2.4 | 9.2 | 210 | 14 | 240 |
| Donor_7_3. Aliquot B | 11 | 27 | 1.9 | 4.8 | 237 | 14 | 67 |
| Donor_7_3. Aliquot C | 12 | 25 | 0.84 | 1.8 | 198 | 7.8 | 4.3 |
| Donor_7_3. Aliquot D | 10 | 25 | 4.1 | 4.6 | 241 | 13 | 1250 |
| Donor_7_3. Aliquot E | 8.8 | 19 | 2.4 | 3.4 | 243 | 13 | 338 |
| Donor_7_3. Aliquot F | 10 | 26 | 0.15 | 1.8 | 187 | 8.4 | 19 |
| Donor_7_3. Aliquot G | 9.4 | 23 | 0.84 | 4.7 | 213 | 10.0 | 17 |
| Donor_7_3. Aliquot H | 9.7 | 22 | 0.84 | 1.8 | 158 | 6.4 | 5.1 |
| Donor_7_3. Aliquot I | 9.9 | 25 | 0.15 | 1.8 | 159 | 7.0 | 2.7 |
| Donor_8_3. Aliquot A | 65 | 31 | 1.2 | 2.7 | 84 | 3.8 | 129 |
| Donor_8_3. Aliquot B | 66 | 30 | 0.84 | 3.4 | 118 | 5.1 | 49 |
| Donor_8_3. Aliquot C | 61 | 29 | 0.84 | 2.7 | 50 | 1.7 | 184 |
| Donor_8_3. Aliquot D | 60 | 28 | 13 | 6.2 | 60 | 3.8 | 12200 |
| Donor_8_3. Aliquot E | 62 | 29 | 12 | 5.5 | 88 | 4.7 | 7570 |
| Donor_8_3. Aliquot F | 67 | 31 | 0.47 | 1.9 | 52 | 3.2 | 591 |
| Donor_8_3. Aliquot G | 57 | 27 | 0.84 | 4.2 | 118 | 2.8 | 22 |
| Donor_8_3. Aliquot H | 69 | 29 | 0.65 | 2.8 | 60 | 2.5 | 113 |
| Donor_8_3. Aliquot I | 64 | 31 | 0.65 | 1.8 | 61 | 1.9 | 14 |
| Donor_9_3. Aliquot A | Pending | Pending | 1.2 | 19 | 66 | 3.6 | 78 |
| Donor_9_3. Aliquot B | Pending | Pending | 2.0 | 16 | 92 | 4.4 | 51 |
| Donor_9_3. Aliquot C | Pending | Pending | 0.66 | 18 | 62 | 3.3 | 68 |
| Donor_9_3. Aliquot D | Pending | Pending | 15 | 18 | 69 | 5.2 | 6000 |
| Donor_9_3. Aliquot E | Pending | Pending | 8.6 | 20 | 93 | 5.6 | 4600 |
| Donor_9_3. Aliquot F | Pending | Pending | 2.1 | 12 | 48 | 2.7 | 81 |
| Donor_9_3. Aliquot G | Pending | Pending | 1.8 | 20 | 130 | 3.9 | 55 |
| Donor_9_3. Aliquot H | Pending | Pending | 1.5 | 12 | 56 | 2.5 | 22 |
| Donor_9_3. Aliquot I | Pending | Pending | 0.53 | 8.5 | 53 | 1.9 | 13 |

FIG. 14M.4

| | SHBG nmol/L | Thyroxine Binding Globulin ug/mL | Tissue Factor ng/mL | TGF-alpha pg/mL | TIMP-1 ng/mL | TNF RII ng/mL | TNF-alpha pg/mL |
|---|---|---|---|---|---|---|---|
| Least Detectable Dose | 1.3 | 0.34 | 0.84 | 1.8 | 8.4 | 0.13 | 4.0 |
| RBM Low Plasma Range | 12 | 40 | | Pending | 59 | 3.1 | |
| RBM High Plasma Range | 106 | 104 | 2.4 | Pending | 192 | 79 | 27 |
| EDTA Plasma | | | | | | | |
| donor #1 plasma | Pending | Pending | 2.9 | 1.8 | 379 | 27 | 14 |
| donor #2 plasma | Pending | Pending | 1.1 | 1.2 | 248 | 51 | 5.4 |
| donor #3 plasma | Pending | Pending | 1.9 | 1.8 | 144 | 8.2 | 5.4 |
| donor #4 plasma | Pending | Pending | 2.0 | 1.8 | 478 | 34 | 1.1 |
| donor #5 plasma | Pending | Pending | 2.1 | 1.8 | 166 | 28 | 2.3 |
| donor #6 plasma | Pending | Pending | 0.95 | 1.8 | 82 | 2.6 | 4 |
| donor #7 plasma | Pending | Pending | 1.9 | 1.8 | 156 | 9.5 | 4 |
| donor #8 plasma | Pending | Pending | 1.0 | 1.8 | 40 | 1.2 | 5.6 |
| donor #9 plasma | Pending | Pending | 0.74 | 4.4 | 31 | 1.5 | 4 |
| | | | | | | | |
| Stimulations Indices | SHBG | Thyroxine Binding Globulin | Tissue Factor | TGF-alpha | TIMP-1 | TNF RII | TNF-alpha |
| patient 1 | 1.0 | 1.0 | 2.3 | 14.2 | 1.1 | 1.2 | 9.4 |
| patient 7 | 1.0 | 1.0 | 2.4 | 5.9 | 1.3 | 1.3 | 11.2 |

FIG. 14M.5

|   |   | SHBG | Thyroxine Binding Globulin | Tissue Factor | TGF-alpha | TIMP-1 | TNF RII | TNF-alpha |
|---|---|---|---|---|---|---|---|---|
|   |   | nmol/L | ug/mL | ng/mL | pg/mL | ng/mL | ng/mL | pg/mL |
|   | Least Detectable Dose | 1.3 | 0.34 | 0.84 | 1.8 | 8.4 | 0.13 | 4.0 |
|   |   |   |   |   |   |   |   |   |
|   | RBM Low Plasma Range | 12 | 40 |   | Pending | 59 | 3.1 | 27 |
|   | RBM High Plasma Range | 106 | 104 | 2.4 | Pending | 192 | 79 |   |
| A | patient 2 | 1.2 | 1.1 | 1.9 | 32.1 | 1.2 | 2.1 | 37.7 |
| A | patient 3 | 1.1 | 1.1 | 1.7 | 3.9 | 1.0 | 1.1 | 4.2 |
| A | patient 5 | 1.1 | 1.1 | 1.0 | 2.8 | 1.8 | 1.3 | 8.7 |
| A | patient 4 | 1.0 | 1.1 | 1.0 | 8.9 | 1.4 | 2.3 | 23.8 |
| A | patient 6 | 1.0 | 1.0 | 16.1 | 5.1 | 1.3 | 2.0 | 90.6 |
|   |   |   |   |   |   |   |   |   |
| A | NHD 1 | 1.0 | 1.0 | 1.9 | 1.5 | 1.4 | 2.0 | 9.6 |
| A | NHD 2 | #VALUE! | #VALUE! | 2.3 | 2.2 | 1.2 | 1.9 | 6.0 |
|   |   |   |   |   |   |   |   |   |
| B | patient 1 | 1.0 | 1.1 | 1.7 | 9.4 | 1.2 | 1.3 | 3.0 |
| B | patient 7 | 1.0 | 1.0 | 2.7 | 4.6 | 1.4 | 1.4 | 4.9 |
| B | patient 2 | 1.1 | 1.0 | 1.8 | 34.0 | 1.4 | 2.0 | 15.4 |
| B | patient 5 | 1.0 | 1.0 | 1.0 | 5.9 | 1.1 | 1.1 | 3.6 |
| B | patient 3 | 1.0 | 1.1 | 1.0 | 2.7 | 1.9 | 1.4 | 12.0 |
| B | patient 4 | 1.1 | 1.1 | 1.0 | 10.4 | 1.7 | 2.9 | 13.4 |
| B | patient 6 | 1.1 | 1.0 | 13.0 | 2.7 | 1.5 | 1.9 | 25.4 |
|   |   |   |   |   |   |   |   |   |
| B | NHD 1 | 1.0 | 1.0 | 1.3 | 1.9 | 1.9 | 2.6 | 3.7 |
| B | NHD 2 | #VALUE! | #VALUE! | 3.7 | 1.8 | 1.7 | 2.3 | 3.9 |
|   |   |   |   |   |   |   |   |   |
| C | patient 1 | 1.0 | 1.1 | 0.6 | 1.2 | 1.2 | 1.1 | 0.7 |
| C | patient 7 | 1.1 | 1.0 | 1.2 | 0.8 | 1.1 | 1.1 | 0.6 |
| C | patient 2 | 1.2 | 1.1 | 0.1 | 8.8 | 1.0 | 1.2 | 3.2 |
| C | patient 3 | 1.0 | 1.0 | 1.0 | 1.7 | 1.0 | 1.0 | 2.5 |
| C | patient 5 | 1.2 | 1.0 | 1.0 | 1.0 | 1.0 | 1.1 | 1.0 |
| C | patient 4 | 1.0 | 1.0 | 1.0 | 0.8 | 1.1 | 1.1 | 1.8 |
| C | patient 6 | 1.2 | 1.0 | 5.7 | 1.0 | 1.2 | 1.1 | 1.6 |
|   |   |   |   |   |   |   |   |   |
| C | NHD 1 | 0.9 | 1.0 | 1.3 | 1.5 | 0.8 | 0.9 | 13.6 |
| C | NHD 2 | #VALUE! | #VALUE! | 1.2 | 2.1 | 1.2 | 1.7 | 5.2 |

FIG. 14M.6

| | | SHBG nmol/L | Thyroxine Binding Globulin ug/mL | Tissue Factor ng/mL | TGF-alpha pg/mL | TIMP-1 ng/mL | TNF RII ng/mL | TNF-alpha pg/mL |
|---|---|---|---|---|---|---|---|---|
| | Least Detectable Dose | 1.3 | 0.34 | 0.84 | 1.8 | 8.4 | 0.13 | 4.0 |
| | RBM Low Plasma Range | 12 | 40 | | Pending | 59 | 3.1 | 27 |
| | RBM High Plasma Range | 106 | 104 | 2.4 | Pending | 192 | 79 | |
| D | patient 1 | 1.0 | 1.1 | 2.1 | 6.2 | 1.3 | 1.2 | 12.0 |
| D | patient 7 | 1.1 | 1.0 | 10.2 | 4.9 | 1.3 | 1.3 | 142.1 |
| D | patient 2 | 1.1 | 1.0 | 5.4 | 28.9 | 1.4 | 2.2 | 625.0 |
| D | patient 3 | 1.1 | 1.0 | 6.5 | 4.9 | 1.1 | 1.2 | 357.6 |
| D | patient 5 | 1.0 | 1.1 | 7.5 | 2.2 | 1.7 | 1.6 | 155.7 |
| D | patient 4 | 1.0 | 1.0 | 3.6 | 8.2 | 1.6 | 2.9 | 1104.0 |
| D | patient 6 | 1.0 | 1.0 | 28.0 | 2.6 | 1.5 | 1.8 | 471.7 |
| D | NHD 1 | 0.9 | 0.9 | 19.1 | 3.5 | 1.0 | 2.0 | 903.7 |
| D | NHD 2 | #VALUE! | #VALUE! | 27.6 | 2.1 | 1.3 | 2.7 | 461.5 |
| E | patient 1 | 1.0 | 1.0 | 1.9 | 8.0 | 1.1 | 1.2 | 3.5 |
| E | patient 7 | 1.1 | 1.0 | 5.0 | 4.5 | 1.1 | 1.3 | 88.9 |
| E | patient 2 | 1.2 | 1.0 | 5.0 | 25.1 | 1.4 | 2.2 | 276.4 |
| E | patient 3 | 1.0 | 1.0 | 4.1 | 4.2 | 1.4 | 1.3 | 128.5 |
| E | patient 5 | 1.1 | 1.1 | 5.2 | 3.1 | 1.9 | 1.6 | 130.3 |
| E | patient 4 | 1.0 | 1.0 | 6.0 | 10.7 | 1.6 | 3.3 | 1855.5 |
| E | patient 6 | 0.9 | 0.8 | 16.6 | 1.9 | 1.5 | 1.8 | 127.5 |
| E | NHD 1 | 1.0 | 0.9 | 17.7 | 3.1 | 1.4 | 2.4 | 560.7 |
| E | NHD 2 | #VALUE! | #VALUE! | 16.2 | 2.4 | 1.8 | 2.9 | 353.8 |
| F | patient 1 | 1.0 | 1.1 | 1.3 | 2.4 | 1.1 | 1.1 | 1.4 |
| F | patient 7 | 1.1 | 1.0 | 0.7 | 0.6 | 1.1 | 1.1 | 1.3 |
| F | patient 2 | 1.1 | 1.0 | 1.5 | 6.9 | 1.0 | 1.2 | 6.3 |
| F | patient 3 | 1.1 | 1.0 | 1.8 | 1.2 | 1.0 | 1.1 | 18.8 |
| F | patient 5 | 1.1 | 1.0 | 0.2 | 0.9 | 1.2 | 1.1 | 8.6 |
| F | patient 4 | 1.1 | 1.1 | 1.0 | 0.8 | 1.2 | 1.7 | 5.3 |
| F | patient 6 | 1.0 | 1.0 | 1.0 | 1.0 | 1.2 | 1.2 | 7.1 |

FIG. 14M.7

| | SHBG nmol/L | Thyroxine Binding Globulin ug/mL | Tissue Factor ng/mL | TGF-alpha pg/mL | TIMP-1 ng/mL | TNF RII ng/mL | TNF-alpha pg/mL |
|---|---|---|---|---|---|---|---|
| Least Detectable Dose | 1.3 | 0.34 | 0.84 | 1.8 | 8.4 | 0.13 | 4.0 |
| RBM Low Plasma Range | 12 | 40 | | Pending | 59 | 3.1 | |
| RBM High Plasma Range | 106 | 104 | 2.4 | Pending | 192 | 79 | 27 |
| F NHD 1 | 1.0 | | 0.7 | 1.1 | 0.8 | 1.7 | 43.8 |
| F NHD 2 | #VALUE! | #VALUE! | 4.0 | 1.4 | 0.9 | 1.4 | 6.2 |
| G patient 1 | 1.0 | 1.1 | 1.2 | 15.6 | 1.3 | 1.3 | 0.9 |
| G patient 7 | 1.0 | 1.0 | 3.3 | 5.0 | 1.8 | 1.3 | 28.6 |
| G patient 2 | 1.1 | 1.1 | 0.9 | 24.3 | 1.3 | 1.5 | 5.0 |
| G patient 3 | 1.1 | 1.0 | 1.0 | 4.2 | 0.9 | 1.1 | 2.5 |
| G patient 5 | 1.1 | 1.0 | 1.0 | 3.3 | 1.7 | 1.2 | 1.4 |
| G patient 4 | 1.0 | 1.1 | 1.0 | 7.4 | 2.6 | 2.1 | 7.1 |
| G patient 6 | 0.9 | 0.9 | 5.7 | 2.6 | 1.3 | 1.4 | 6.6 |
| G NHD 1 | 0.9 | 0.9 | 1.3 | 2.3 | 1.9 | 1.5 | 1.6 |
| G NHD 2 | #VALUE! | #VALUE! | 3.4 | 2.4 | 2.5 | 2.0 | 4.2 |
| H patient 1 | 1.0 | 0.9 | 1.1 | 0.9 | 1.2 | 1.1 | 0.7 |
| H patient 7 | 1.1 | 0.9 | 1.2 | 2.0 | 1.1 | 1.1 | 1.1 |
| H patient 2 | 1.0 | 1.0 | 0.6 | 3.3 | 1.0 | 1.0 | 2.3 |
| H patient 3 | 1.0 | 0.9 | 1.2 | 0.9 | 1.0 | 1.0 | 1.9 |
| H patient 5 | 1.0 | 1.0 | 0.7 | 0.9 | 1.2 | 1.1 | 1.0 |
| H patient 4 | 1.1 | 1.0 | 1.0 | 2.6 | 1.1 | 1.3 | 4.6 |
| H patient 6 | 1.0 | 0.9 | 5.7 | 1.0 | 1.0 | 0.9 | 1.9 |
| H NHD 1 | 1.1 | 1.0 | 1.0 | 1.5 | 1.0 | 1.3 | 8.4 |
| H NHD 2 | #VALUE! | #VALUE! | 2.9 | 1.5 | 1.1 | 1.3 | 1.7 |
| — patient 1 | 1.0 | 1.0 | 1.0 | 1.0 | 1.0 | 1.0 | 1.0 |
| — patient 7 | 1.0 | 1.0 | 1.0 | 1.0 | 1.0 | 1.0 | 1.0 |
| — patient 2 | 1.0 | 1.0 | 1.0 | 1.0 | 1.0 | 1.0 | 1.0 |
| — patient 3 | 1.0 | 1.0 | 1.0 | 1.0 | 1.0 | 1.0 | 1.0 |

FIG. 14M.8

| | SHBG nmol/L | Thyroxine Binding Globulin ug/mL | Tissue Factor ng/mL | TGF-alpha pg/mL | TIMP-1 ng/mL | TNF RII ng/mL | TNF-alpha pg/mL |
|---|---|---|---|---|---|---|---|
| Least Detectable Dose | 1.3 | 0.34 | 0.84 | 1.8 | 8.4 | 0.13 | 4.0 |
| RBM Low Plasma Range | 12 | 40 | | Pending | 59 | 3.1 | |
| RBM High Plasma Range | 106 | 104 | 2.4 | Pending | 192 | 79 | 27 |
| patient 5 | 1.0 | 1.0 | 1.0 | 1.0 | 1.0 | 1.0 | 1.0 |
| patient 4 | 1.0 | 1.0 | 1.0 | 1.0 | 1.0 | 1.0 | 1.0 |
| patient 6 | 1.0 | 1.0 | 1.0 | 1.0 | 1.0 | 1.0 | 1.0 |
| NHD 1 | 1.0 | 1.0 | 1.0 | 1.0 | 1.0 | 1.0 | 1.0 |
| NHD 2 | #VALUE! | #VALUE! | | | | | |

| Messwert > ULD |
| SI > 1,3 |
| SI 0,7-1,3 |
| SI 0-0,7 |

FIG. 14N.1

| Samples | TNF-beta pg/mL | Thrombopoietin ng/mL | Thyroid Stimulating Hormone uIU/mL | Thrombospondin-1 ng/mL | VCAM-1 ng/mL | VEGF pg/mL | von Willebrand Factor ug/mL |
|---|---|---|---|---|---|---|---|
| Least Detectable Dose | 46 | 3.2 | 0.028 | <25 | 2.6 | 7.5 | 0.40 |
| RBM Low Plasma Range | | | 0.18 | Pending | 284 | 91 | 5.3 |
| RBM High Plasma Range | 120 | 6.2 | 3.7 | Pending | 1310 | 1790 | 74 |
| Donor_1 3. Aliquot A | 7.9 | 1.9 | 17 | 15200 | 1350 | 2090 | 211 |
| Donor_1 3. Aliquot B | 46 | 1.5 | 16 | 21600 | 1440 | 2090 | 203 |
| Donor_1 3. Aliquot C | 46 | 3.2 | 18 | 17000 | 1350 | 2070 | 213 |
| Donor_1 3. Aliquot D | 46 | 1.9 | 17 | 15600 | 1420 | 2120 | 198 |
| Donor_1 3. Aliquot E | 46 | 1.9 | 17 | 13100 | 1320 | 2030 | 184 |
| Donor_1 3. Aliquot F | 46 | 3.2 | 17 | 12500 | 1310 | 1860 | 196 |
| Donor_1 3. Aliquot G | 46 | 1.3 | 17 | 11800 | 1450 | 2570 | 180 |
| Donor_1 3. Aliquot H | 46 | 0.86 | 17 | 24900 | 1320 | 2210 | 207 |
| Donor_1 3. Aliquot I | 46 | 0.69 | 17 | 16200 | 1350 | 1940 | 203 |
| Donor_2 3. Aliquot A | 4.6 | 2.7 | 10 | 19800 | 1090 | 4570 | 188 |
| Donor_2 3. Aliquot B | 6.0 | 3.2 | 10 | 21600 | 1190 | 4900 | 200 |
| Donor_2 3. Aliquot C | 46 | 3.2 | 9.9 | 12200 | 1160 | 5240 | 191 |
| Donor_2 3. Aliquot D | 6.0 | 2.4 | 12 | 13600 | 1070 | 4400 | 190 |
| Donor_2 3. Aliquot E | 3.2 | 2.7 | 11 | 12400 | 1150 | 4630 | 189 |
| Donor_2 3. Aliquot F | 46 | 1.5 | 10 | 12800 | 1100 | 4870 | 178 |
| Donor_2 3. Aliquot G | 18 | 3.0 | 9.9 | 12000 | 1180 | 5490 | 215 |
| Donor_2 3. Aliquot H | 46 | 3.2 | 9.5 | 13300 | 1090 | 4920 | 213 |
| Donor_2 3. Aliquot I | 46 | 0.49 | 9.1 | 12400 | 1080 | 4680 | 187 |
| Donor_3 3. Aliquot A | 7.3 | 2.5 | 0.99 | 14000 | 749 | 532 | 99 |
| Donor_3 3. Aliquot B | 46 | 2.5 | 0.98 | 18300 | 722 | 618 | 110 |
| Donor_3 3. Aliquot C | 46 | 3.2 | 0.99 | 12000 | 740 | 707 | 95 |
| Donor_3 3. Aliquot D | 14 | 2.2 | 1.1 | 13700 | 725 | 505 | 123 |
| Donor_3 3. Aliquot E | 11 | 3.9 | 1.2 | 16800 | 775 | 508 | 108 |
| Donor_3 3. Aliquot F | 46 | 2.1 | 0.94 | 10500 | 695 | 714 | 104 |
| Donor_3 3. Aliquot G | 46 | 3.2 | 1.0 | 12200 | 758 | 1590 | 109 |
| Donor_3 3. Aliquot H | 46 | 3.2 | 0.90 | 9670 | 694 | 678 | 123 |
| Donor_3 3. Aliquot I | 46 | 2.1 | 0.98 | 9250 | 690 | 734 | 119 |

FIG. 14N.2

| | TNF-beta pg/mL | Thrombopoietin ng/mL | Thyroid Stimulating Hormone uIU/mL | Thrombospondin-1 ng/mL | VCAM-1 ng/mL | VEGF pg/mL | von Willebrand Factor ug/mL |
|---|---|---|---|---|---|---|---|
| Least Detectable Dose | 46 | 3.2 | 0.028 | <25 | 2.6 | 7.5 | 0.40 |
| RBM Low Plasma Range | | | 0.18 | Pending | 284 | 91 | 5.3 |
| RBM High Plasma Range | 120 | 6.2 | 3.7 | Pending | 1310 | 1790 | 74 |
| Donor_4_3, Aliquot A | 46 | 1.3 | 0.15 | 14100 | 2080 | 1190 | 182 |
| Donor_4_3, Aliquot B | 46 | 1.4 | 0.15 | 16300 | 1940 | 1180 | 227 |
| Donor_4_3, Aliquot C | 46 | 3.2 | 0.16 | 4160 | 1990 | 1220 | 253 |
| Donor_4_3, Aliquot D | 7.3 | 2.0 | 0.26 | 11500 | 1950 | 1100 | 252 |
| Donor_4_3, Aliquot E | 15 | 2.3 | 0.19 | 10900 | 2070 | 1060 | 223 |
| Donor_4_3, Aliquot F | 7.3 | 1.2 | 0.14 | 5780 | 2200 | 1030 | 257 |
| Donor_4_3, Aliquot G | 46 | 3.2 | 0.13 | 4050 | 1970 | 2190 | 223 |
| Donor_4_3, Aliquot H | 46 | 1.2 | 0.14 | 4460 | 1980 | 1350 | 229 |
| Donor_4_3, Aliquot I | 46 | 3.2 | 0.13 | 6360 | 2020 | 1280 | 246 |
| Donor_5_3, Aliquot A | 7.9 | 2.9 | 0.28 | 22300 | 521 | 3600 | 100 |
| Donor_5_3, Aliquot B | 7.3 | 3.1 | 0.26 | 17800 | 510 | 3460 | 105 |
| Donor_5_3, Aliquot C | 46 | 0.69 | 0.32 | 13300 | 489 | 4460 | 113 |
| Donor_5_3, Aliquot D | 9.8 | 2.8 | 0.41 | 18600 | 525 | 3350 | 112 |
| Donor_5_3, Aliquot E | 16 | 2.7 | 0.38 | 17800 | 539 | 3650 | 125 |
| Donor_5_3, Aliquot F | 46 | 2.2 | 0.24 | 13200 | 495 | 3140 | 109 |
| Donor_5_3, Aliquot G | 8.6 | 1.0 | 0.28 | 14000 | 545 | 5580 | 110 |
| Donor_5_3, Aliquot H | 46 | 0.49 | 0.26 | 14800 | 510 | 3840 | 121 |
| Donor_5_3, Aliquot I | 46 | 0.49 | 0.26 | 10900 | 489 | 3520 | 96 |
| Donor_6_3, Aliquot A | 6.6 | 3.6 | 1.3 | 25000 | 258 | 874 | 79 |
| Donor_6_3, Aliquot B | 4.6 | 3.7 | 1.2 | 22900 | 252 | 648 | 70 |
| Donor_6_3, Aliquot C | 46 | 3.1 | 1.3 | 13800 | 261 | 840 | 74 |
| Donor_6_3, Aliquot D | 46 | 3.4 | 1.4 | 21100 | 274 | 530 | 75 |
| Donor_6_3, Aliquot E | 46 | 3.6 | 1.3 | 13800 | 253 | 471 | 72 |
| Donor_6_3, Aliquot F | 46 | 4.0 | 1.1 | 15700 | 254 | 581 | 80 |
| Donor_6_3, Aliquot G | 46 | 2.3 | 1.3 | 12400 | 284 | 2690 | 85 |
| Donor_6_3, Aliquot H | 8.6 | 1.7 | 1.2 | 14500 | 258 | 878 | 76 |
| Donor_6_3, Aliquot I | 46 | 1.7 | 1.2 | 12500 | 256 | 846 | 67 |

FIG. 14N.3

| | TNF-beta | Thrombopoietin | Thyroid Stimulating Hormone | Thrombospondin-1 | VCAM-1 | VEGF | von Willebrand Factor |
|---|---|---|---|---|---|---|---|
| | pg/mL | ng/mL | uIU/mL | ng/mL | ng/mL | pg/mL | ug/mL |
| Least Detectable Dose | 46 | 3.2 | 0.028 | <25 | 2.6 | 7.5 | 0.40 |
| RBM Low Plasma Range | | 6.2 | 0.18 | Pending | 284 | 91 | 5.3 |
| RBM High Plasma Range | 120 | 6.2 | 3.7 | Pending | 1310 | 1790 | 74 |
| Donor_7 3. Aliquot A | 24 | 4.2 | 0.52 | 12100 | 789 | 295 | 112 |
| Donor_7 3. Aliquot B | 14 | 4.3 | 0.51 | 14600 | 802 | 237 | 129 |
| Donor_7 3. Aliquot C | 7.9 | 1.4 | 0.49 | 15800 | 861 | 345 | 132 |
| Donor_7 3. Aliquot D | 8.6 | 3.3 | 0.55 | 11600 | 740 | 210 | 124 |
| Donor_7 3. Aliquot E | 19 | 3.8 | 0.50 | 11200 | 816 | 235 | 102 |
| Donor_7 3. Aliquot F | 9.8 | 3.5 | 0.47 | 7230 | 781 | 203 | 135 |
| Donor_7 3. Aliquot G | 46 | 1.0 | 0.49 | 6360 | 803 | 1260 | 114 |
| Donor_7 3. Aliquot H | 46 | 3.2 | 0.49 | 7470 | 721 | 313 | 127 |
| Donor_7 3. Aliquot I | 46 | 2.2 | 0.47 | 7470 | 738 | 257 | 123 |
| Donor_8 3. Aliquot A | 7.9 | 3.6 | 2.2 | 10800 | 352 | 252 | 18 |
| Donor_8 3. Aliquot B | 6.0 | 4.7 | 2.1 | 14000 | 350 | 203 | 23 |
| Donor_8 3. Aliquot C | 46 | 4.4 | 1.8 | 10800 | 320 | 401 | 16 |
| Donor_8 3. Aliquot D | 11 | 4.4 | 2.4 | 8580 | 319 | 416 | 19 |
| Donor_8 3. Aliquot E | 11 | 4.2 | 2.2 | 11900 | 322 | 341 | 17 |
| Donor_8 3. Aliquot F | 9.8 | 5.6 | 2.0 | 4870 | 341 | 321 | 20 |
| Donor_8 3. Aliquot G | 46 | 1.4 | 1.9 | 5370 | 337 | 822 | 21 |
| Donor_8 3. Aliquot H | 3.9 | 3.7 | 2.2 | 12600 | 331 | 322 | 22 |
| Donor_8 3. Aliquot I | 46 | 3.8 | 2.0 | 13200 | 347 | 248 | 21 |
| Donor_9 3. Aliquot A | 11 | 3.2 | 0.34 | 13600 | 298 | 326 | Pending |
| Donor_9 3. Aliquot B | 8.8 | 3.4 | 0.28 | 16400 | 303 | 280 | Pending |
| Donor_9 3. Aliquot C | 20 | 3.6 | 0.33 | 15500 | 324 | 367 | Pending |
| Donor_9 3. Aliquot D | 15 | 2.9 | 0.65 | 13800 | 295 | 486 | Pending |
| Donor_9 3. Aliquot E | 5.0 | 3.1 | 0.53 | 11300 | 312 | 398 | Pending |
| Donor_9 3. Aliquot F | 18 | 4.3 | 0.29 | 6910 | 314 | 322 | Pending |
| Donor_9 3. Aliquot G | 6.9 | 1.2 | 0.22 | 9900 | 297 | 1170 | Pending |
| Donor_9 3. Aliquot H | 10 | 1.8 | 0.31 | 15900 | 297 | 380 | Pending |
| Donor_9 3. Aliquot I | 46 | 2.3 | 0.28 | 17000 | 290 | 243 | Pending |

FIG. 14N.4

| | TNF-beta pg/mL | Thrombopoietin ng/mL | Thyroid Stimulating Hormone uIU/mL | Thrombospondin-1 ng/mL | VCAM-1 ng/mL | VEGF pg/mL | von Willebrand Factor ug/mL |
|---|---|---|---|---|---|---|---|
| Least Detectable Dose | 46 | 3.2 | 0.028 | <25 | 2.6 | 7.5 | 0.40 |
| RBM Low Plasma Range | | | 0.18 | Pending | 284 | 91 | 5.3 |
| RBM High Plasma Range | 120 | 6.2 | 3.7 | Pending | 1310 | 1790 | 74 |
| EDTA Plasma | | | | | | | |
| donor #1 plasma | 10 | 3.2 | 12 | 14800 | 1230 | 1500 | Pending |
| donor #2 plasma | 46 | 3.2 | 9.7 | 4670 | 1280 | 4500 | Pending |
| donor #3 plasma | 8.8 | 0.81 | 1.0 | 7890 | 978 | 1290 | Pending |
| donor #4 plasma | 46 | 1.4 | 0.11 | 2310 | 2580 | 1400 | Pending |
| donor #5 plasma | 11 | 1.8 | 0.28 | 28600 | 577 | 3840 | Pending |
| donor #6 plasma | 5.0 | 2.4 | 1.7 | 16800 | 301 | 533 | Pending |
| donor #7 plasma | 13 | 2.1 | 0.59 | 13800 | 980 | 521 | Pending |
| donor #8 plasma | 46 | 1.4 | 2.5 | 6520 | 340 | 281 | Pending |
| donor #9 plasma | 46 | 0.44 | 0.30 | 818 | 385 | 295 | Pending |
| Stimulations indices | | | | | | | |
| patient 1 | 0.2 | 2.8 | 1.0 | 0.9 | 1.0 | 1.1 | 1.0 |
| patient 7 | 0.1 | 5.6 | 1.1 | 1.6 | 1.0 | 1.0 | 1.0 |
| | A | | | | | | |
| | A | | | | | | |

FIG. 14N.5

| | | TNF-beta pg/mL | Thrombopoietin ng/mL | Thyroid Stimulating Hormone uIU/mL | Thrombospondin-1 ng/mL | VCAM-1 ng/mL | VEGF pg/mL | von Willebrand Factor ug/mL |
|---|---|---|---|---|---|---|---|---|
| | Least Detectable Dose | 46 | 3.2 | 0.028 | <25 | 2.6 | 7.5 | 0.40 |
| | RBM Low Plasma Range | 120 | 6.2 | 0.18 | Pending | 284 | 91 | 5.3 |
| | RBM High Plasma Range | 120 | 6.2 | 3.7 | Pending | 1310 | 1790 | 74 |
| A | patient 2 | 0.2 | 1.2 | 1.0 | 1.5 | 1.1 | 0.7 | 0.8 |
| A | patient 3 | 1.0 | 0.4 | 1.1 | 2.2 | 1.0 | 0.9 | 0.7 |
| A | patient 5 | 0.2 | 5.9 | 1.1 | 2.0 | 1.1 | 1.0 | 1.0 |
| A | patient 4 | 0.1 | 2.2 | 1.1 | 2.0 | 1.0 | 1.0 | 1.2 |
| A | patient 6 | 0.5 | 1.9 | 1.1 | 1.6 | 1.1 | 1.1 | 0.9 |
| A | NHD 1 | 0.2 | 0.9 | 1.1 | 0.8 | 1.0 | 1.0 | 0.9 |
| A | NHD 2 | 0.2 | 1.4 | 1.2 | 0.8 | 1.0 | 1.3 | #VALUE! |
| B | patient 1 | 1.0 | 2.2 | 0.9 | 1.3 | 1.1 | 1.1 | 1.0 |
| B | patient 7 | 0.1 | 6.7 | 1.1 | 1.7 | 1.1 | 1.0 | 1.1 |
| B | patient 2 | 1.0 | 1.2 | 1.0 | 2.0 | 1.0 | 0.8 | 0.9 |
| B | patient 3 | 1.0 | 0.4 | 1.1 | 2.6 | 1.0 | 0.9 | 0.9 |
| B | patient 5 | 0.2 | 6.3 | 1.0 | 1.6 | 1.0 | 1.0 | 1.1 |
| B | patient 4 | 0.1 | 2.2 | 1.0 | 1.8 | 1.0 | 0.8 | 1.0 |
| B | patient 6 | 0.3 | 2.0 | 1.1 | 2.0 | 1.1 | 0.9 | 1.0 |
| B | NHD 1 | 0.1 | 1.2 | 1.1 | 1.1 | 1.0 | 0.8 | 1.1 |
| B | NHD 2 | 0.2 | 1.5 | 1.0 | 1.0 | 1.0 | 1.2 | #VALUE! |
| C | patient 1 | 1.0 | 4.7 | 1.1 | 1.0 | 1.0 | 1.1 | 1.0 |
| C | patient 7 | 1.0 | 6.6 | 1.1 | 1.0 | 1.1 | 1.1 | 1.0 |
| C | patient 2 | 1.0 | 1.5 | 1.0 | 1.3 | 1.1 | 1.0 | 0.8 |
| C | patient 3 | 1.0 | 1.0 | 1.2 | 0.7 | 1.0 | 1.0 | 1.0 |
| C | patient 5 | 1.0 | 1.4 | 1.2 | 1.2 | 1.0 | 1.3 | 1.2 |
| C | patient 4 | 1.0 | 1.8 | 1.0 | 1.1 | 1.0 | 1.0 | 1.1 |
| C | patient 6 | 0.2 | 0.6 | 1.0 | 2.1 | 1.2 | 1.3 | 1.1 |
| C | NHD 1 | 1.0 | 1.2 | 0.9 | 0.8 | 0.9 | 1.6 | 0.8 |
| C | NHD 2 | 0.4 | 1.6 | 1.2 | 0.9 | 1.1 | 1.5 | #VALUE! |

FIG. 14N.6

| | | TNF-beta pg/mL | Thrombopoietin ng/mL | Thyroid Stimulating Hormone uIU/mL | Thrombospondin-1 ng/mL | VCAM-1 ng/mL | VEGF pg/mL | von Willebrand Factor ug/mL |
|---|---|---|---|---|---|---|---|---|
| | Least Detectable Dose | 46 | 3.2 | 0.028 | <25 | 2.6 | 7.5 | 0.40 |
| | RBM Low Plasma Range | 120 | 6.2 | 0.18 | Pending | 284 | 91 | 5.3 |
| | RBM High Plasma Range | | | 3.7 | Pending | 1310 | 1790 | 74 |
| D | patient 1 | 1.0 | 2.8 | 1.0 | 1.0 | 1.1 | 1.1 | 1.0 |
| D | patient 7 | 0.1 | 4.9 | 1.3 | 1.1 | 1.0 | 0.9 | 1.0 |
| D | patient 2 | 0.3 | 1.0 | 1.1 | 1.5 | 1.1 | 0.7 | 1.0 |
| D | patient 3 | 0.2 | 0.6 | 2.0 | 1.8 | 1.0 | 0.9 | 1.0 |
| D | patient 5 | 0.2 | 5.7 | 1.5 | 1.7 | 1.1 | 1.0 | 1.2 |
| D | patient 4 | 1.0 | 2.1 | 1.1 | 1.7 | 1.1 | 0.6 | 1.1 |
| D | patient 6 | 0.2 | 1.5 | 1.2 | 1.6 | 1.0 | 0.8 | 1.0 |
| D | NHD 1 | 0.2 | 1.2 | 1.2 | 0.7 | 0.9 | 1.7 | 0.9 |
| D | NHD 2 | 0.3 | 1.3 | 2.3 | 0.8 | 1.0 | 2.0 | #VALUE! |
| E | patient 1 | 1.0 | 2.8 | 1.0 | 0.8 | 1.0 | 1.0 | 0.9 |
| E | patient 7 | 0.1 | 5.6 | 1.2 | 1.0 | 1.1 | 1.0 | 1.0 |
| E | patient 2 | 0.2 | 1.9 | 1.2 | 1.8 | 1.1 | 0.7 | 0.9 |
| E | patient 3 | 0.3 | 0.7 | 1.5 | 1.7 | 1.1 | 0.8 | 0.9 |
| E | patient 5 | 0.4 | 5.6 | 1.5 | 1.6 | 1.0 | 1.0 | 1.3 |
| E | patient 4 | 1.0 | 2.2 | 1.1 | 1.1 | 1.0 | 0.6 | 1.1 |
| E | patient 6 | 0.4 | 1.8 | 1.1 | 1.5 | 1.1 | 0.9 | 0.8 |
| E | NHD 1 | 0.2 | 1.1 | 1.1 | 0.9 | 0.9 | 1.4 | 0.8 |
| E | NHD 2 | 0.1 | 1.4 | 1.9 | 0.7 | 1.1 | 1.6 | #VALUE! |
| F | patient 1 | 1.0 | 4.7 | 1.0 | 0.8 | 1.0 | 1.0 | 1.0 |
| F | patient 7 | 1.0 | 3.2 | 1.1 | 1.0 | 1.0 | 1.0 | 1.0 |
| F | patient 2 | 1.0 | 1.0 | 1.0 | 1.1 | 1.1 | 1.0 | 0.9 |
| F | patient 3 | 0.2 | 0.4 | 1.1 | 0.9 | 1.0 | 0.8 | 1.0 |
| F | patient 5 | 1.0 | 4.5 | 0.9 | 1.2 | 1.1 | 0.7 | 1.1 |
| F | patient 4 | 1.0 | 2.4 | 0.9 | 1.3 | 1.0 | 0.7 | 1.2 |
| F | patient 6 | 0.2 | 1.6 | 1.0 | 1.0 | 1.1 | 0.8 | 1.1 |

FIG. 14N.7

| | | TNF-beta pg/mL | Thrombopoietin ng/mL | Thyroid Stimulating Hormone uIU/mL | Thrombospondin-1 ng/mL | VCAM-1 ng/mL | VEGF pg/mL | von Willebrand Factor ug/mL |
|---|---|---|---|---|---|---|---|---|
| | Least Detectable Dose | 46 | 3.2 | 0.028 | <25 | 2.6 | 7.5 | 0.40 |
| | RBM Low Plasma Range | | | 0.18 | Pending | 284 | 91 | 5.3 |
| | RBM High Plasma Range | 120 | 6.2 | 3.7 | Pending | 1310 | 1790 | 74 |
| F | NHD 1 | 0.2 | 1.5 | 1.0 | 0.4 | 1.0 | 1.3 | 0.9 |
| F | NHD 2 | 0.4 | 1.9 | 1.0 | 0.4 | 1.1 | 1.3 | #VALUE! |
| G | patient 1 | 1.0 | 1.9 | 1.0 | 0.7 | 1.1 | 1.3 | 0.9 |
| G | patient 7 | 0.4 | 6.1 | 1.1 | 1.0 | 1.1 | 1.2 | 1.1 |
| G | patient 2 | 1.0 | 1.5 | 1.0 | 1.3 | 1.1 | 2.2 | 0.9 |
| G | patient 3 | 1.0 | 1.0 | 1.0 | 0.6 | 1.0 | 1.7 | 0.9 |
| G | patient 5 | 0.2 | 2.1 | 1.1 | 1.3 | 1.1 | 1.6 | 1.1 |
| G | patient 4 | 1.0 | 1.4 | 1.0 | 1.0 | 1.1 | 3.2 | 1.3 |
| G | patient 6 | 1.0 | 0.5 | 1.0 | 0.9 | 1.1 | 4.9 | 0.9 |
| G | NHD 1 | 1.0 | 0.4 | 0.9 | 0.4 | 1.0 | 3.3 | #VALUE! |
| G | NHD 2 | 0.2 | 0.5 | 0.8 | 0.6 | 1.0 | 4.8 | |
| H | patient 1 | 1.0 | 1.2 | 1.0 | 1.5 | 1.0 | 1.1 | 1.0 |
| H | patient 7 | 1.0 | 6.6 | 1.1 | 1.1 | 1.0 | 1.1 | 1.1 |
| H | patient 2 | 1.0 | 1.5 | 0.9 | 1.1 | 1.0 | 0.9 | 1.1 |
| H | patient 3 | 1.0 | 0.4 | 1.1 | 0.7 | 1.0 | 1.1 | 0.9 |
| H | patient 5 | 1.0 | 1.0 | 1.0 | 1.4 | 1.0 | 1.1 | 1.3 |
| H | patient 4 | 0.2 | 1.0 | 1.0 | 1.2 | 1.0 | 1.1 | 1.1 |
| H | patient 6 | 1.0 | 1.5 | 1.0 | 1.0 | 1.0 | 1.2 | 1.0 |
| H | NHD 1 | 0.1 | 1.0 | 1.1 | 1.0 | 1.0 | 1.3 | 1.1 |
| H | NHD 2 | 0.2 | 0.8 | 1.1 | 0.9 | 1.0 | 1.6 | #VALUE! |
| I | patient 1 | 1.0 | 1.0 | 1.0 | 1.0 | 1.0 | 1.0 | 1.0 |
| I | patient 7 | 1.0 | 1.0 | 1.0 | 1.0 | 1.0 | 1.0 | 1.0 |
| I | patient 2 | 1.0 | 1.0 | 1.0 | 1.0 | 1.0 | 1.0 | 1.0 |
| I | patient 3 | 1.0 | 1.0 | 1.0 | 1.0 | 1.0 | 1.0 | 1.0 |

FIG. 14N.8

| | TNF-beta pg/mL | Thrombopoietin ng/mL | Thyroid Stimulating Hormone uIU/mL | Thrombospondin-1 ng/mL | VCAM-1 ng/mL | VEGF pg/mL | von Willebrand Factor ug/mL |
|---|---|---|---|---|---|---|---|
| Least Detectable Dose | 46 | 3.2 | 0.028 | <25 | 2.6 | 7.5 | 0.40 |
| RBM Low Plasma Range | | | | | | | |
| RBM High Plasma Range | 120 | 6.2 | 0.18 | Pending | 284 | 91 | 5.3 |
| patient 5 | 1.0 | 1.0 | 3.7 | Pending | 1310 | 1790 | 74 |
| patient 4 | 1.0 | 1.0 | 1.0 | 1.0 | 1.0 | 1.0 | 1.0 |
| patient 6 | 1.0 | 1.0 | 1.0 | 1.0 | 1.0 | 1.0 | 1.0 |
| NHD 1 | 1.0 | 1.0 | 1.0 | 1.0 | 1.0 | 1.0 | 1.0 |
| NHD 2 | 1.0 | 1.0 | 1.0 | 1.0 | 1.0 | 1.0 | #VALUE! |

| Messwert > ULD |
| SI > 1,3 |
| SI 0,7-1,3 |
| SI 0-0,7 |

FIG. 15A.1

| | Alpha-1 Antitrypsin<br>mg/mL | Adiponectin<br>ug/mL | Alpha-2 Macroglobulin<br>mg/mL | Alpha-Fetoprotein<br>ng/mL | Amphiregulin<br>pg/mL |
|---|---|---|---|---|---|
| Least Detectable Dose | 0.011 | 0.20 | 0.061 | 0.43 | 36 |
| RBM Low Plasma Range | 1.2 | 1.6 | 0.13 | | Pending |
| RBM High Plasma Range | 3.1 | 14 | 1.0 | 6.7 | Pending |
| Samples | | | | | |
| Donor_1 3. Aliquot A | 2.6 | 2.0 | 0.29 | 2.8 | 469 |
| Donor_1 3. Aliquot B | 2.8 | 2.1 | 0.30 | 2.6 | 455 |
| Donor_1 3. Aliquot C | 2.9 | 2.1 | 0.30 | 2.3 | 104 |
| Donor_1 3. Aliquot D | 3.1 | 2.1 | 0.31 | 2.8 | 431 |
| Donor_1 3. Aliquot E | 2.8 | 2.1 | 0.27 | 2.5 | 443 |
| Donor_1 3. Aliquot F | 2.6 | 2.0 | 0.66 | 2.3 | 414 |
| Donor_1 3. Aliquot G | 2.9 | 2.1 | 0.30 | 2.5 | 401 |
| Donor_1 3. Aliquot H | 2.7 | 2.0 | 0.42 | 2.7 | 36 |
| Donor_1 3. Aliquot I | 2.7 | 2.0 | 0.26 | 2.5 | 419 |
| | | | | | |
| Donor_2 3. Aliquot A | 2.2 | 4.4 | 0.28 | 2.1 | 133 |
| Donor_2 3. Aliquot B | 2.3 | 4.5 | 0.30 | 2.3 | 50 |
| Donor_2 3. Aliquot C | 2.3 | 4.5 | 0.29 | 1.4 | 36 |
| Donor_2 3. Aliquot D | 2.2 | 4.3 | 0.29 | 3.4 | 104 |
| Donor_2 3. Aliquot E | 2.3 | 4.5 | 0.28 | 2.5 | 39 |
| Donor_2 3. Aliquot F | 2.3 | 4.2 | 0.64 | 2.0 | 36 |
| Donor_2 3. Aliquot G | 2.3 | 4.3 | 0.32 | 1.8 | 597 |
| Donor_2 3. Aliquot H | 2.2 | 4.4 | 0.33 | 1.8 | 36 |
| Donor_2 3. Aliquot I | 2.1 | 4.0 | 0.29 | 1.9 | 24 |
| | | | | | |
| Donor_3 3. Aliquot A | 2.9 | 3.0 | 0.35 | 2.7 | 36 |
| Donor_3 3. Aliquot B | 3.0 | 2.7 | 0.35 | 2.6 | 36 |
| Donor_3 3. Aliquot C | 3.0 | 2.8 | 0.34 | 1.9 | 36 |
| Donor_3 3. Aliquot D | 2.8 | 2.7 | 0.34 | 3.3 | 97 |
| Donor_3 3. Aliquot E | 3.1 | 2.8 | 0.36 | 3.5 | 116 |
| Donor_3 3. Aliquot F | 2.7 | 2.6 | 0.65 | 2.5 | 60 |
| Donor_3 3. Aliquot G | 3.1 | 2.8 | 0.35 | 1.4 | 97 |

FIG. 15A.2

| | Alpha-1 Antitrypsin mg/mL | Adiponectin ug/mL | Alpha-2 Macroglobulin mg/mL | Alpha-Fetoprotein ng/mL | Amphiregulin pg/mL |
|---|---|---|---|---|---|
| Least Detectable Dose | 0.011 | 0.20 | 0.061 | 0.43 | 36 |
| RBM Low Plasma Range | 1.2 | 1.6 | 0.13 | | Pending |
| RBM High Plasma Range | 3.1 | 14 | 1.0 | 6.7 | Pending |
| Donor_3_3. Aliquot H | 2.8 | 2.7 | 0.41 | 1.7 | 36 |
| Donor_3_3. Aliquot I | 2.8 | 2.6 | 0.33 | 1.3 | 39 |
| Donor_4_3. Aliquot A | 1.7 | 5.3 | 0.40 | 2.4 | 36 |
| Donor_4_3. Aliquot B | 1.5 | 5.4 | 0.40 | 2.1 | 36 |
| Donor_4_3. Aliquot C | 1.6 | 5.2 | 0.41 | 2.0 | 39 |
| Donor_4_3. Aliquot D | 1.6 | 5.3 | 0.42 | 3.6 | 36 |
| Donor_4_3. Aliquot E | 1.5 | 5.3 | 0.38 | 2.8 | 36 |
| Donor_4_3. Aliquot F | 1.6 | 5.3 | 0.98 | 1.8 | 36 |
| Donor_4_3. Aliquot G | 1.6 | 5.5 | 0.48 | 2.1 | 76 |
| Donor_4_3. Aliquot H | 1.5 | 5.3 | 0.65 | 2.1 | 76 |
| Donor_4_3. Aliquot I | 1.5 | 5.4 | 0.41 | 1.9 | 36 |
| Donor_5_3. Aliquot A | 2.9 | 2.8 | 0.27 | 3.2 | 127 |
| Donor_5_3. Aliquot B | 2.9 | 2.6 | 0.29 | 3.2 | 178 |
| Donor_5_3. Aliquot C | 3.2 | 2.7 | 0.29 | 2.5 | 50 |
| Donor_5_3. Aliquot D | 3.2 | 2.6 | 0.28 | 4.1 | 159 |
| Donor_5_3. Aliquot E | 3.1 | 2.8 | 0.28 | 4.0 | 187 |
| Donor_5_3. Aliquot F | 2.9 | 2.6 | 0.46 | 2.3 | 36 |
| Donor_5_3. Aliquot G | 3.0 | 2.6 | 0.29 | 3.0 | 208 |
| Donor_5_3. Aliquot H | 3.0 | 2.5 | 0.33 | 3.0 | 138 |
| Donor_5_3. Aliquot I | 3.0 | 2.4 | 0.28 | 3.3 | 39 |
| Donor_6_3. Aliquot A | 2.8 | 1.2 | 0.26 | 1.5 | 36 |
| Donor_6_3. Aliquot B | 2.7 | 1.2 | 0.24 | 1.9 | 36 |
| Donor_6_3. Aliquot C | 2.8 | 1.2 | 0.24 | 1.8 | 36 |
| Donor_6_3. Aliquot D | 2.7 | 1.2 | 0.24 | 1.9 | 36 |
| Donor_6_3. Aliquot E | 2.6 | 1.2 | 0.25 | 2.4 | 39 |

FIG. 15A.3

| | Alpha-1 Antitrypsin mg/mL | Adiponectin ug/mL | Alpha-2 Macroglobulin mg/mL | Alpha-Fetoprotein ng/mL | Amphiregulin pg/mL |
|---|---|---|---|---|---|
| Least Detectable Dose | 0.011 | 0.20 | 0.061 | 0.43 | 36 |
| RBM Low Plasma Range | 1.2 | 1.6 | 0.13 | | Pending |
| RBM High Plasma Range | 3.1 | 14 | 1.0 | 6.7 | Pending |
| Donor_6_3. Aliquot F | 2.7 | 1.3 | 0.25 | 1.6 | 36 |
| Donor_6_3. Aliquot G | 2.9 | 1.2 | 0.27 | 1.8 | 599 |
| Donor_6_3. Aliquot H | 2.5 | 1.3 | 0.29 | 1.6 | 36 |
| Donor_6_3. Aliquot I | 2.5 | 1.1 | 0.26 | 1.5 | 24 |
| Donor_7_3. Aliquot A | 1.8 | 0.90 | 0.39 | 1.9 | 104 |
| Donor_7_3. Aliquot B | 1.7 | 0.92 | 0.37 | 2.5 | 36 |
| Donor_7_3. Aliquot C | 1.9 | 0.83 | 0.38 | 1.3 | 36 |
| Donor_7_3. Aliquot D | 1.7 | 0.81 | 0.36 | 2.6 | 104 |
| Donor_7_3. Aliquot E | 1.2 | 0.90 | 0.40 | 2.5 | 36 |
| Donor_7_3. Aliquot F | 1.8 | 0.90 | 0.45 | 1.5 | 36 |
| Donor_7_3. Aliquot G | 1.6 | 0.87 | 0.43 | 2.2 | 370 |
| Donor_7_3. Aliquot H | 1.7 | 0.79 | 0.51 | 1.5 | 36 |
| Donor_7_3. Aliquot I | 1.8 | 0.82 | 0.38 | 1.9 | 36 |
| Donor_8_3. Aliquot A | 0.96 | 4.3 | 0.39 | 1.7 | 36 |
| Donor_8_3. Aliquot B | 0.97 | 4.3 | 0.39 | 1.3 | 36 |
| Donor_8_3. Aliquot C | 0.96 | 4.1 | 0.40 | 0.53 | 36 |
| Donor_8_3. Aliquot D | 0.88 | 4.0 | 0.39 | 4.4 | 36 |
| Donor_8_3. Aliquot E | 0.88 | 4.0 | 0.39 | 3.5 | 127 |
| Donor_8_3. Aliquot F | 0.99 | 4.5 | 0.46 | 1.6 | 50 |
| Donor_8_3. Aliquot G | 0.92 | 4.2 | 0.48 | 1.2 | 90 |
| Donor_8_3. Aliquot H | 1.0 | 4.4 | 0.58 | 1.6 | 36 |
| Donor_8_3. Aliquot I | 0.94 | 4.2 | 0.40 | 1.2 | 36 |
| Donor_9_3. Aliquot A | 1.2 | 3.5 | 0.34 | 1.1 | 51 |
| Donor_9_3. Aliquot B | 1.3 | 3.5 | 0.38 | 1.8 | 51 |
| Donor_9_3. Aliquot C | 1.3 | 3.6 | 0.41 | 2.0 | 51 |

FIG. 15A.4

| | Alpha-1 Antitrypsin mg/mL | Adiponectin ug/mL | Alpha-2 Macroglobulin mg/mL | Alpha-Fetoprotein ng/mL | Amphiregulin pg/mL |
|---|---|---|---|---|---|
| Least Detectable Dose | 0.011 | 0.20 | 0.061 | 0.43 | 36 |
| RBM Low Plasma Range | 1.2 | 1.6 | 0.13 | | Pending |
| RBM High Plasma Range | 3.1 | 14 | 1.0 | 6.7 | Pending |
| Donor_9 3. Aliquot D | 1.2 | 3.3 | 0.38 | 4.2 | 101 |
| Donor_9 3. Aliquot E | 1.3 | 3.7 | 0.45 | 3.2 | 42 |
| Donor_9 3. Aliquot F | 1.2 | 3.8 | 0.40 | 2.1 | 36 |
| Donor_9 3. Aliquot G | 1.4 | 3.5 | 0.49 | 2.1 | 169 |
| Donor_9 3. Aliquot H | 1.2 | 3.5 | 0.54 | 2.3 | 78 |
| Donor_9 3. Aliquot I | 1.3 | 3.6 | 0.36 | 1.3 | 36 |
| EDTA Plasma | | | | | |
| donor #1 plasma | 2.9 | 2.1 | 0.25 | 2.3 | 441 |
| donor #2 plasma | 3.0 | 6.1 | 0.29 | 1.7 | 36 |
| donor #3 plasma | 4.7 | 4.2 | 0.36 | 2.9 | 36 |
| donor #4 plasma | 2.2 | 7.5 | 0.34 | 2.4 | 33 |
| donor #5 plasma | 4.4 | 3.6 | 0.25 | 3.6 | 36 |
| donor #6 plasma | 3.7 | 1.7 | 0.24 | 2.1 | 36 |
| donor #7 plasma | 2.3 | 1.3 | 0.35 | 2.8 | 78 |
| donor #8 plasma | 1.0 | 5.1 | 0.34 | 1.9 | 72 |
| donor #9 plasma | 1.9 | 4.8 | 0.37 | 2.1 | 36 |
| Stimulations Indices | | | | | |

FIG. 15A.5

| | Alpha-1 Antitrypsin mg/mL | Adiponectin ug/mL | Alpha-2 Macroglobulin mg/mL | Alpha-Fetoprotein ng/mL | Amphiregulin pg/mL |
|---|---|---|---|---|---|
| Least Detectable Dose | 0.011 | 0.20 | 0.061 | 0.43 | 36 |
| RBM Low Plasma Range | 1.2 | 1.6 | 0.13 | | Pending |
| RBM High Plasma Range | 3.1 | 14 | 1.0 | 6.7 | Pending |
| | Alpha-1 Antitrypsin | Adiponectin | Alpha-2 Macroglobulin | Alpha-Fetoprotein | Amphiregulin |
| patient 1 | A | | | | |
| patient 7 | A | | | | |
| patient 2 | A | | | | |
| patient 3 | A | | | | |
| patient 5 | A | | | | |
| patient 4 | A | | | | |
| patient 6 | A | | | | |
| NHD 1 | A | | | | |
| NHD 2 | A | | | | |

FIG. 15A.6

| | Alpha-1 Antitrypsin mg/mL | Adiponectin ug/mL | Alpha-2 Macroglobulin mg/mL | Alpha-Fetoprotein ng/mL | Amphiregulin pg/mL |
|---|---|---|---|---|---|
| Least Detectable Dose | 0.011 | 0.20 | 0.061 | 0.43 | 36 |
| RBM Low Plasma Range | 1.2 | 1.6 | 0.13 | 6.7 | Pending |
| RBM High Plasma Range | 3.1 | 14 | 1.0 | | Pending |
| | Alpha-1 Antitrypsin | Adiponectin | Alpha-2 Macroglobulin | Alpha-Fetoprotein | Amphiregulin |
| patient 1 B | | | | | |
| patient 7 B | | | | | |
| patient 2 B | | | | | |
| patient 3 B | | | | | |
| patient 5 B | | | | | |
| patient 4 B | | | | | |
| patient 6 B | | | | | |
| NHD 1 B | | | | | |
| NHD 2 B | | | | | |

FIG. 15A.7

| | Alpha-1 Antitrypsin | Adiponectin | Alpha-2 Macroglobulin | Alpha-Fetoprotein | Amphiregulin |
|---|---|---|---|---|---|
| | mg/mL | ug/mL | mg/mL | ng/mL | pg/mL |
| Least Detectable Dose | 0.011 | 0.20 | 0.061 | 0.43 | 36 |
| RBM Low Plasma Range | 1.2 | 1.6 | 0.13 | | Pending |
| RBM High Plasma Range | 3.1 | 14 | 1.0 | 6.7 | Pending |
| | Alpha-1 Antitrypsin | Adiponectin | Alpha-2 Macroglobulin | Alpha-Fetoprotein | Amphiregulin |
| patient 1 | C | | | | |
| patient 7 | C | | | | |
| patient 2 | C | | | | |
| patient 3 | C | | | | |
| patient 5 | C | | | | |
| patient 4 | C | | | | |
| patient 6 | C | | | | |
| NHD 1 | C | | | | |
| NHD 2 | C | | | | |

FIG. 15A.8

| | Alpha-1 Antitrypsin mg/mL | Adiponectin ug/mL | Alpha-2 Macroglobulin mg/mL | Alpha-Fetoprotein ng/mL | Amphiregulin pg/mL |
|---|---|---|---|---|---|
| Least Detectable Dose | 0.011 | 0.20 | 0.061 | 0.43 | 36 |
| RBM Low Plasma Range | 1.2 | 1.6 | 0.13 | | Pending |
| RBM High Plasma Range | 3.1 | 14 | 1.0 | 6.7 | Pending |
| | Alpha-1 Antitrypsin | Adiponectin | Alpha-2 Macroglobulin | Alpha-Fetoprotein | Amphiregulin |
| patient 1 | D | | | | |
| patient 7 | D | | | | |
| patient 2 | D | | | | |
| patient 3 | D | | | | |
| patient 5 | D | | | | |
| patient 4 | D | | | | |
| patient 6 | D | | | | |
| NHD 1 | D | | | | |
| NHD 2 | D | | | | |

FIG. 15A.9

| | Alpha-1 Antitrypsin | Adiponectin | Alpha-2 Macroglobulin | Alpha-Fetoprotein | Amphiregulin |
|---|---|---|---|---|---|
| | mg/mL | ug/mL | mg/mL | ng/mL | pg/mL |
| Least Detectable Dose | 0.011 | 0.20 | 0.061 | 0.43 | 36 |
| RBM Low Plasma Range | 1.2 | 1.6 | 0.13 | | Pending |
| RBM High Plasma Range | 3.1 | 14 | 1.0 | 6.7 | Pending |
| patient 1 | | | | | |
| patient 7 | | | | | |
| patient 2 | | | | | |
| patient 3 | | | | | |
| patient 5 | | | | | |
| patient 4 | | | | | |
| patient 6 | | | | | |
| NHD 1 | | | | | |
| NHD 2 | | | | | |

FIG. 15A.10

| | Alpha-1 Antitrypsin mg/mL | Adiponectin ug/mL | Alpha-2 Macroglobulin mg/mL | Alpha-Fetoprotein ng/mL | Amphiregulin pg/mL |
|---|---|---|---|---|---|
| Least Detectable Dose | 0.011 | 0.20 | 0.061 | 0.43 | 36 |
| RBM Low Plasma Range | 1.2 | 1.6 | 0.13 | 6.7 | Pending |
| RBM High Plasma Range | 3.1 | 14 | 1.0 | | Pending |
| | Alpha-1 Antitrypsin | Adiponectin | Alpha-2 Macroglobulin | Alpha-Fetoprotein | Amphiregulin |
| patient 1 | F | | | | |
| patient 7 | F | | | | |
| patient 2 | F | | | | |
| patient 3 | F | | | | |
| patient 5 | F | | | | |
| patient 4 | F | | | | |
| patient 6 | F | | | | |
| NHD 1 | F | | | | |
| NHD 2 | F | | | | |

FIG. 15A.11

| | Alpha-1 Antitrypsin mg/mL | Adiponectin ug/mL | Alpha-2 Macroglobulin mg/mL | Alpha-Fetoprotein ng/mL | Amphiregulin pg/mL |
|---|---|---|---|---|---|
| Least Detectable Dose | 0.011 | 0.20 | 0.061 | 0.43 | 36 |
| RBM Low Plasma Range | 1.2 | 1.6 | 0.13 | 6.7 | Pending |
| RBM High Plasma Range | 3.1 | 14 | 1.0 | | Pending |
| | Alpha-1 Antitrypsin | Adiponectin | Alpha-2 Macroglobulin | Alpha-Fetoprotein | Amphiregulin |
| patient 1 | | | | | |
| patient 7 | | | | | |
| patient 2 | | | | | |
| patient 3 | | | | | |
| patient 5 | | | | | |
| patient 4 | | | | | |
| patient 6 | | | | | |
| NHD 1 | | | | | |
| NHD 2 | | | | | |
| G | | | | | |
| G | | | | | |
| G | | | | | |
| G | | | | | |
| G | | | | | |
| G | | | | | |
| G | | | | | |
| G | | | | | |
| G | | | | | |

FIG. 15A.12

| | Alpha-1 Antitrypsin mg/mL | Adiponectin ug/mL | Alpha-2 Macroglobulin mg/mL | Alpha-Fetoprotein ng/mL | Amphiregulin pg/mL |
|---|---|---|---|---|---|
| Least Detectable Dose | 0.011 | 0.20 | 0.061 | 0.43 | 36 |
| RBM Low Plasma Range | 1.2 | 1.6 | 0.13 | 6.7 | Pending |
| RBM High Plasma Range | 3.1 | 14 | 1.0 | | Pending |
| | Alpha-1 Antitrypsin | Adiponectin | Alpha-2 Macroglobulin | Alpha-Fetoprotein | Amphiregulin |
| patient 1 | H | | | | |
| patient 7 | H | | | | |
| patient 2 | H | | | | |
| patient 3 | H | | | | |
| patient 5 | H | | | | |
| patient 4 | H | | | | |
| patient 6 | H | | | | |
| NHD 1 | H | | | | |
| NHD 2 | H | | | | |

FIG. 15A.13

| | Alpha-1 Antitrypsin | Adiponectin | Alpha-2 Macroglobulin | Alpha-Fetoprotein | Amphiregulin |
|---|---|---|---|---|---|
| | mg/mL | ug/mL | mg/mL | ng/mL | pg/mL |
| Least Detectable Dose | 0.011 | 0.20 | 0.061 | 0.43 | 36 |
| RBM Low Plasma Range | 1.2 | 1.6 | 0.13 | | Pending |
| RBM High Plasma Range | 3.1 | 14 | 1.0 | 6.7 | Pending |
| patient 1 | | | | | |
| patient 7 | | | | | |
| patient 2 | | | | | |
| patient 3 | | | | | |
| patient 5 | | | | | |
| patient 4 | | | | | |
| patient 6 | | | | | |
| NHD 1 | | | | | |
| NHD 2 | | | | | |

FIG. 15A.14

| | Alpha-1 Antitrypsin mg/mL | Adiponectin ug/mL | Alpha-2 Macroglobulin mg/mL | Alpha-Fetoprotein ng/mL | Amphiregulin pg/mL |
|---|---|---|---|---|---|
| Least Detectable Dose | 0.011 | 0.20 | 0.061 | 0.43 | 36 |
| RBM Low Plasma Range | 1.2 | 1.6 | 0.13 | | Pending |
| RBM High Plasma Range | 3.1 | 14 | 1.0 | 6.7 | Pending |
| Messwert > ULD | | | | | |
| SI > 1,3 | | | | | |
| SI 0,7-1,3 | | | | | |
| SI 0-0,7 | | | | | |

FIG. 15B.1

| | Apolipoprotein A1 | Apolipoprotein CIII | Apolipoprotein H | Beta-2 Microglobulin | Brain-Derived Neurotrophic Factor |
|---|---|---|---|---|---|
| | mg/mL | ug/mL | ug/mL | ug/mL | ng/mL |
| Least Detectable Dose | 0.0066 | 2.7 | 8.8 | 0.013 | 0.029 |
| RBM Low Plasma Range | 0.19 | 28 | 131 | 1.2 | 0.32 |
| RBM High Plasma Range | 0.89 | 224 | 430 | 6.2 | 16 |
| Samples | | | | | |
| Donor_1 3. Aliquot A | 0.10 | 52 | 138 | 17 | 2.4 |
| Donor_1 3. Aliquot B | 0.10 | 64 | 148 | 15 | 3.3 |
| Donor_1 3. Aliquot C | 0.11 | 60 | 143 | 16 | 1.6 |
| Donor_1 3. Aliquot D | 0.11 | 60 | 150 | 16 | 2.6 |
| Donor_1 3. Aliquot E | 0.11 | 53 | 141 | 16 | 2.3 |
| Donor_1 3. Aliquot F | 0.097 | 57 | 142 | 14 | 1.3 |
| Donor_1 3. Aliquot G | 0.098 | 61 | 151 | 16 | 0.048 |
| Donor_1 3. Aliquot H | 0.089 | 48 | 141 | 15 | 3.4 |
| Donor_1 3. Aliquot I | 0.11 | 60 | 150 | 16 | 2.8 |
| Donor_2 3. Aliquot A | 0.11 | 58 | 152 | 20 | 3.4 |
| Donor_2 3. Aliquot B | 0.12 | 64 | 143 | >24 | 4.6 |
| Donor_2 3. Aliquot C | 0.12 | 64 | 154 | 23 | 1.3 |
| Donor_2 3. Aliquot D | 0.098 | 48 | 142 | 19 | 2.5 |
| Donor_2 3. Aliquot E | 0.097 | 52 | 154 | 20 | 2.3 |
| Donor_2 3. Aliquot F | 0.090 | 66 | 152 | 19 | 1.6 |
| Donor_2 3. Aliquot G | 0.094 | 67 | 153 | 19 | 0.49 |
| Donor_2 3. Aliquot H | 0.095 | 61 | 148 | 21 | 2.3 |
| Donor_2 3. Aliquot I | 0.11 | 54 | 141 | 19 | 1.8 |
| Donor_3 3. Aliquot A | 0.13 | 38 | 150 | 2.6 | 3.0 |
| Donor_3 3. Aliquot B | 0.14 | 38 | 144 | 2.3 | 4.5 |
| Donor_3 3. Aliquot C | 0.13 | 41 | 153 | 2.4 | 2.9 |
| Donor_3 3. Aliquot D | 0.13 | 38 | 149 | 2.4 | 3.4 |
| Donor_3 3. Aliquot E | 0.14 | 36 | 157 | 2.5 | 3.8 |
| Donor_3 3. Aliquot F | 0.12 | 42 | 148 | 2.2 | 1.6 |
| Donor_3 3. Aliquot G | 0.15 | 44 | 149 | 2.3 | 0.047 |

FIG. 15B.2

| | Apolipoprotein A1 | Apolipoprotein CIII | Apolipoprotein H | Beta-2 Microglobulin | Brain-Derived Neurotrophic Factor |
|---|---|---|---|---|---|
| | mg/mL | ug/mL | ug/mL | ug/mL | ng/mL |
| Least Detectable Dose | 0.0066 | 2.7 | 8.8 | 0.013 | 0.029 |
| | | | | | |
| RBM Low Plasma Range | 0.19 | 28 | 131 | 1.2 | 0.32 |
| RBM High Plasma Range | 0.89 | 224 | 430 | 6.2 | 16 |
| Donor_3 3. Aliquot H | 0.13 | 41 | 144 | 2.3 | 2.3 |
| Donor_3 3. Aliquot I | 0.14 | 42 | 150 | 2.2 | 2.2 |
| | | | | | |
| Donor_4 3. Aliquot A | 0.056 | 13 | 105 | 7.6 | 2.0 |
| Donor_4 3. Aliquot B | 0.050 | 12 | 96 | 7.2 | 2.8 |
| Donor_4 3. Aliquot C | 0.049 | 11 | 102 | 8.0 | 0.49 |
| Donor_4 3. Aliquot D | 0.044 | 13 | 102 | 7.7 | 1.6 |
| Donor_4 3. Aliquot E | 0.048 | 9.1 | 93 | 8.3 | 1.0 |
| Donor_4 3. Aliquot F | 0.054 | 15 | 93 | 8.5 | 0.88 |
| Donor_4 3. Aliquot G | 0.047 | 11 | 100 | 8.1 | 0.049 |
| Donor_4 3. Aliquot H | 0.051 | 11 | 91 | 8.2 | 0.53 |
| Donor_4 3. Aliquot I | 0.052 | 12 | 99 | 8.0 | 1.2 |
| | | | | | |
| Donor_5 3. Aliquot A | 0.12 | 70 | 253 | 12 | 5.8 |
| Donor_5 3. Aliquot B | 0.13 | 77 | 266 | 13 | 4.5 |
| Donor_5 3. Aliquot C | 0.14 | 77 | 265 | 13 | 2.3 |
| Donor_5 3. Aliquot D | 0.14 | 78 | 263 | 13 | 2.9 |
| Donor_5 3. Aliquot E | 0.14 | 71 | 257 | 15 | 4.5 |
| Donor_5 3. Aliquot F | 0.12 | 83 | 238 | 11 | 2.3 |
| Donor_5 3. Aliquot G | 0.14 | 78 | 246 | 12 | 0.16 |
| Donor_5 3. Aliquot H | 0.14 | 81 | 245 | 13 | 4.8 |
| Donor_5 3. Aliquot I | 0.13 | 75 | 250 | 11 | 3.1 |
| | | | | | |
| Donor_6 3. Aliquot A | 0.100 | 43 | 141 | 1.2 | 4.4 |
| Donor_6 3. Aliquot B | 0.10 | 42 | 148 | 1.1 | 3.4 |
| Donor_6 3. Aliquot C | 0.12 | 36 | 141 | 1.2 | 1.1 |
| Donor_6 3. Aliquot D | 0.11 | 43 | 143 | 1.2 | 3.9 |
| Donor_6 3. Aliquot E | 0.12 | 42 | 131 | 1.2 | 2.1 |

FIG. 15B.3

| | Apolipoprotein A1 mg/mL | Apolipoprotein CIII ug/mL | Apolipoprotein H ug/mL | Beta-2 Microglobulin ug/mL | Brain-Derived Neurotrophic Factor ng/mL |
|---|---|---|---|---|---|
| Least Detectable Dose | 0.0066 | 2.7 | 8.8 | 0.013 | 0.029 |
| | | | | | |
| RBM Low Plasma Range | 0.19 | 28 | 131 | 1.2 | 0.32 |
| RBM High Plasma Range | 0.89 | 224 | 430 | 6.2 | 16 |
| Donor_6_3. Aliquot F | 0.094 | 45 | 143 | 1.2 | 1.9 |
| Donor_6_3. Aliquot G | 0.12 | 52 | 152 | 1.2 | 0.064 |
| Donor_6_3. Aliquot H | 0.11 | 40 | 131 | 1.1 | 3.1 |
| Donor_6_3. Aliquot I | 0.12 | 40 | 134 | 1.1 | 1.7 |
| | | | | | |
| Donor_7_3. Aliquot A | 0.14 | 50 | 180 | 2.0 | 2.8 |
| Donor_7_3. Aliquot B | 0.14 | 36 | 183 | 2.0 | 3.1 |
| Donor_7_3. Aliquot C | 0.16 | 44 | 183 | 2.1 | 2.2 |
| Donor_7_3. Aliquot D | 0.15 | 41 | 169 | 2.0 | 2.9 |
| Donor_7_3. Aliquot E | 0.12 | 33 | 138 | 2.1 | 2.3 |
| Donor_7_3. Aliquot F | 0.16 | 54 | 190 | 1.9 | 1.2 |
| Donor_7_3. Aliquot G | 0.14 | 43 | 161 | 1.9 | 0.043 |
| Donor_7_3. Aliquot H | 0.15 | 41 | 173 | 1.9 | 1.6 |
| Donor_7_3. Aliquot I | 0.13 | 42 | 173 | 1.9 | 1.6 |
| | | | | | |
| Donor_8_3. Aliquot A | 0.24 | 57 | 117 | 1.2 | 3.3 |
| Donor_8_3. Aliquot B | 0.28 | 72 | 117 | 1.2 | 5.3 |
| Donor_8_3. Aliquot C | 0.28 | 75 | 119 | 1.2 | 3.2 |
| Donor_8_3. Aliquot D | 0.26 | 55 | 111 | 1.2 | 4.5 |
| Donor_8_3. Aliquot E | 0.24 | 61 | 113 | 1.2 | 6.0 |
| Donor_8_3. Aliquot F | 0.29 | 69 | 121 | 1.3 | 2.3 |
| Donor_8_3. Aliquot G | 0.29 | 58 | 111 | 1.2 | 0.060 |
| Donor_8_3. Aliquot H | 0.25 | 59 | 127 | 1.2 | 6.3 |
| Donor_8_3. Aliquot I | 0.25 | 53 | 122 | 1.2 | 6.1 |
| | | | | | |
| Donor_9_3. Aliquot A | 0.21 | 39 | 101 | 0.83 | 2.5 |
| Donor_9_3. Aliquot B | 0.22 | 43 | 104 | 0.79 | 3.5 |
| Donor_9_3. Aliquot C | 0.21 | 33 | 96 | 0.93 | 1.2 |

FIG. 15B.4

| | Apolipoprotein A1 | Apolipoprotein CIII | Apolipoprotein H | Beta-2 Microglobulin | Brain-Derived Neurotrophic Factor |
|---|---|---|---|---|---|
| | mg/mL | ug/mL | ug/mL | ug/mL | ng/mL |
| Least Detectable Dose | 0.0066 | 2.7 | 8.8 | 0.013 | 0.029 |
| | | | | | |
| RBM Low Plasma Range | 0.19 | 28 | 131 | 1.2 | 0.32 |
| RBM High Plasma Range | 0.89 | 224 | 430 | 6.2 | 16 |
| Donor_9_3. Aliquot D | 0.18 | 34 | 99 | 0.87 | 3.7 |
| Donor_9_3. Aliquot E | 0.20 | 36 | 105 | 0.88 | 2.6 |
| Donor_9_3. Aliquot F | 0.23 | 39 | 103 | 0.90 | 1.9 |
| Donor_9_3. Aliquot G | 0.22 | 42 | 113 | 0.86 | 0.21 |
| Donor_9_3. Aliquot H | 0.19 | 37 | 97 | 0.83 | 4.3 |
| Donor_9_3. Aliquot I | 0.21 | 33 | 97 | 0.82 | 3.5 |
| | | | | | |
| EDTA Plasma | | | | | |
| donor #1 plasma | 0.069 | 34 | 127 | 11 | 1.2 |
| donor #2 plasma | 0.11 | 65 | 166 | 19 | 0.40 |
| donor #3 plasma | 0.14 | 47 | 193 | 2.5 | 0.89 |
| donor #4 plasma | 0.047 | 14 | 106 | 9.1 | 0.35 |
| donor #5 plasma | 0.12 | 91 | 316 | 14 | 3.6 |
| donor #6 plasma | 0.100 | 34 | 163 | 1.1 | 1.5 |
| donor #7 plasma | 0.17 | 52 | 214 | 2.3 | 1.4 |
| donor #8 plasma | 0.25 | 46 | 113 | 1.1 | 3.1 |
| donor #9 plasma | 0.30 | 39 | 147 | 0.88 | 0.21 |
| | | | | | |
| *Stimulationsindices* | | | | | |

FIG. 15B.5

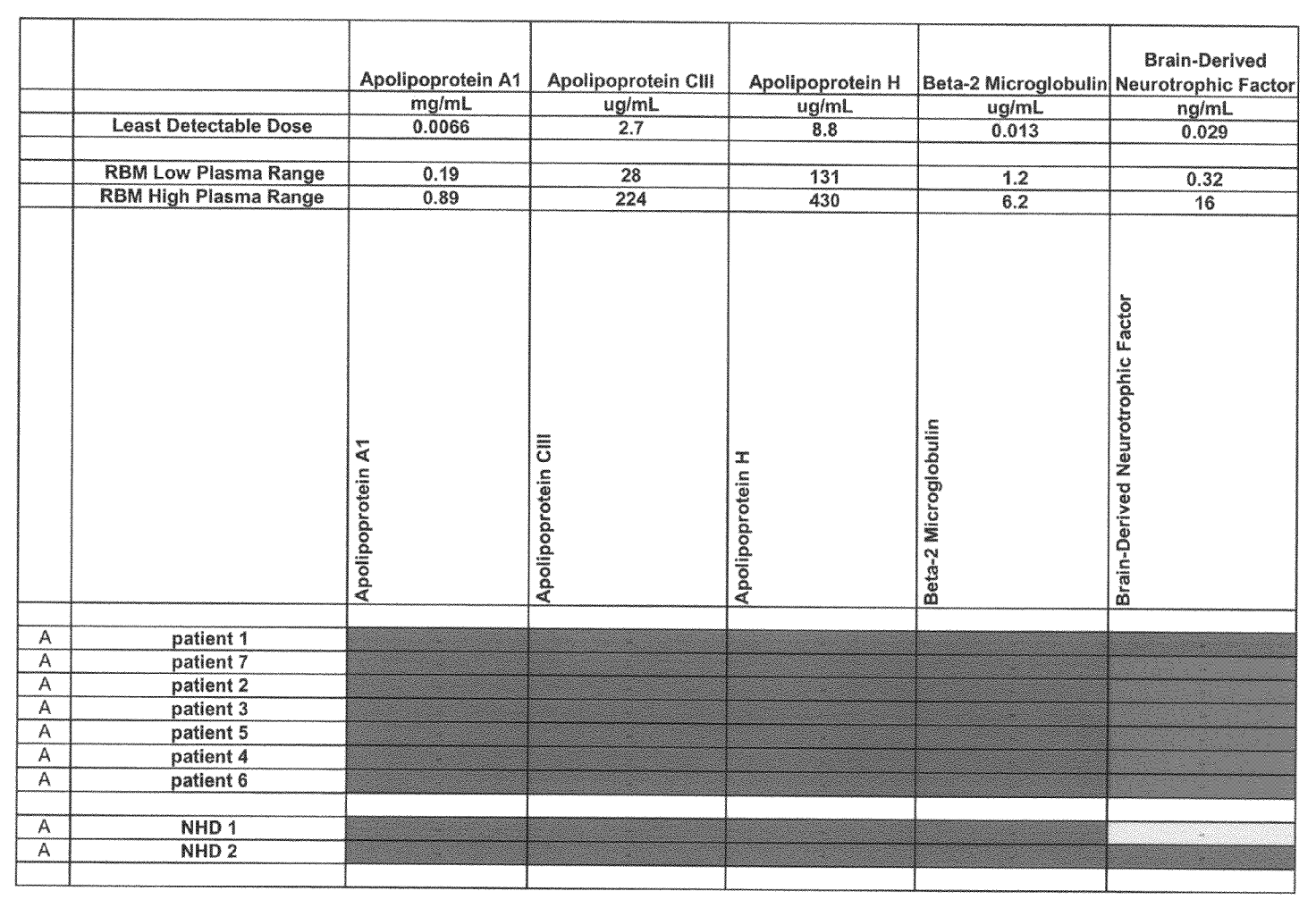

| | Apolipoprotein A1 | Apolipoprotein CIII | Apolipoprotein H | Beta-2 Microglobulin | Brain-Derived Neurotrophic Factor |
|---|---|---|---|---|---|
| | mg/mL | ug/mL | ug/mL | ug/mL | ng/mL |
| Least Detectable Dose | 0.0066 | | | 0.013 | 0.029 |
| RBM Low Plasma Range | 0.19 | 2.7 | 8.8 | 1.2 | 0.32 |
| RBM High Plasma Range | 0.89 | 28 | 131 | 6.2 | 16 |
| | | 224 | 430 | | |
| | Apolipoprotein A1 | Apolipoprotein CIII | Apolipoprotein H | Beta-2 Microglobulin | Brain-Derived Neurotrophic Factor |
| patient 1 | A | | | | |
| patient 7 | A | | | | |
| patient 2 | A | | | | |
| patient 3 | A | | | | |
| patient 5 | A | | | | |
| patient 4 | A | | | | |
| patient 6 | A | | | | |
| NHD 1 | A | | | | |
| NHD 2 | A | | | | |

FIG. 15B.6

| | Apolipoprotein A1 mg/mL | Apolipoprotein CIII ug/mL | Apolipoprotein H ug/mL | Beta-2 Microglobulin ug/mL | Brain-Derived Neurotrophic Factor ng/mL |
|---|---|---|---|---|---|
| Least Detectable Dose | 0.0066 | 2.7 | 8.8 | 0.013 | 0.029 |
| RBM Low Plasma Range | 0.19 | 28 | 131 | 1.2 | 0.32 |
| RBM High Plasma Range | 0.89 | 224 | 430 | 6.2 | 16 |

| | | | | | |
|---|---|---|---|---|---|
| patient 1 | B | | | | |
| patient 7 | B | | | | |
| patient 2 | B | | | | |
| patient 3 | B | | | | |
| patient 5 | B | | | | |
| patient 4 | B | | | | |
| patient 6 | B | | | | |
| NHD 1 | B | | | | |
| NHD 2 | B | | | | |

FIG. 15B.7

| | Apolipoprotein A1 mg/mL | Apolipoprotein CIII ug/mL | Apolipoprotein H ug/mL | Beta-2 Microglobulin ug/mL | Brain-Derived Neurotrophic Factor ng/mL |
|---|---|---|---|---|---|
| Least Detectable Dose | 0.0066 | 2.7 | 8.8 | 0.013 | 0.029 |
| RBM Low Plasma Range | 0.19 | 28 | 131 | 1.2 | 0.32 |
| RBM High Plasma Range | 0.89 | 224 | 430 | 6.2 | 16 |
| | Apolipoprotein A1 | Apolipoprotein CIII | Apolipoprotein H | Beta-2 Microglobulin | Brain-Derived Neurotrophic Factor |
| patient 1 | C | | | | |
| patient 7 | C | | | | |
| patient 2 | C | | | | |
| patient 3 | C | | | | |
| patient 5 | C | | | | |
| patient 4 | C | | | | |
| patient 6 | C | | | | |
| NHD 1 | C | | | | |
| NHD 2 | C | | | | |

FIG. 15B.8

| | Apolipoprotein A1 mg/mL | Apolipoprotein CIII ug/mL | Apolipoprotein H ug/mL | Beta-2 Microglobulin ug/mL | Brain-Derived Neurotrophic Factor ng/mL |
|---|---|---|---|---|---|
| Least Detectable Dose | 0.0066 | 2.7 | 8.8 | 0.013 | 0.029 |
| RBM Low Plasma Range | 0.19 | 28 | 131 | 1.2 | 0.32 |
| RBM High Plasma Range | 0.89 | 224 | 430 | 6.2 | 16 |

| | Apolipoprotein A1 | Apolipoprotein CIII | Apolipoprotein H | Beta-2 Microglobulin | Brain-Derived Neurotrophic Factor |
|---|---|---|---|---|---|
| patient 1 | D | | | | |
| patient 7 | D | | | | |
| patient 2 | D | | | | |
| patient 3 | D | | | | |
| patient 5 | D | | | | |
| patient 4 | D | | | | |
| patient 6 | D | | | | |
| NHD 1 | D | | | | |
| NHD 2 | D | | | | |

FIG. 15B.9

| | Apolipoprotein A1 mg/mL | Apolipoprotein CIII ug/mL | Apolipoprotein H ug/mL | Beta-2 Microglobulin ug/mL | Brain-Derived Neurotrophic Factor ng/mL |
|---|---|---|---|---|---|
| Least Detectable Dose | 0.0066 | 2.7 | 8.8 | 0.013 | 0.029 |
| RBM Low Plasma Range | 0.19 | 28 | 131 | 1.2 | 0.32 |
| RBM High Plasma Range | 0.89 | 224 | 430 | 6.2 | 16 |
| patient 1 | E | | | | |
| patient 7 | E | | | | |
| patient 2 | E | | | | |
| patient 3 | E | | | | |
| patient 5 | E | | | | |
| patient 4 | E | | | | |
| patient 6 | E | | | | |
| NHD 1 | E | | | | |
| NHD 2 | E | | | | |

FIG. 15B.10

| | Apolipoprotein A1 mg/mL | Apolipoprotein CIII ug/mL | Apolipoprotein H ug/mL | Beta-2 Microglobulin ug/mL | Brain-Derived Neurotrophic Factor ng/mL |
|---|---|---|---|---|---|
| Least Detectable Dose | 0.0066 | 2.7 | 8.8 | 0.013 | 0.029 |
| RBM Low Plasma Range | 0.19 | 28 | 131 | 1.2 | 0.32 |
| RBM High Plasma Range | 0.89 | 224 | 430 | 6.2 | 16 |
| patient 1 | | | | | |
| patient 7 | | | | | |
| patient 2 | | | | | |
| patient 3 | | | | | |
| patient 5 | | | | | |
| patient 4 | | | | | |
| patient 6 | | | | | |
| NHD 1 | | | | | |
| NHD 2 | | | | | |

FIG. 15B.11

| | Apolipoprotein A1 mg/mL | Apolipoprotein CIII ug/mL | Apolipoprotein H ug/mL | Beta-2 Microglobulin ug/mL | Brain-Derived Neurotrophic Factor ng/mL |
|---|---|---|---|---|---|
| Least Detectable Dose | 0.0066 | 2.7 | 8.8 | 0.013 | 0.029 |
| RBM Low Plasma Range | 0.19 | 28 | 131 | 1.2 | 0.32 |
| RBM High Plasma Range | 0.89 | 224 | 430 | 6.2 | 16 |
| | Apolipoprotein A1 | Apolipoprotein CIII | Apolipoprotein H | Beta-2 Microglobulin | Brain-Der. Neurotrophic Fact. |
| patient 1 | | | | | |
| patient 7 | | | | | |
| patient 2 | | | | | |
| patient 3 | | | | | |
| patient 5 | | | | | |
| patient 4 | | | | | |
| patient 6 | | | | | |
| NHD 1 | | | | | |
| NHD 2 | | | | | |
| G | | | | | |
| G | | | | | |
| G | | | | | |
| G | | | | | |
| G | | | | | |
| G | | | | | |
| G | | | | | |
| G | | | | | |
| G | | | | | |

FIG. 15B.12

| | Apolipoprotein A1 | Apolipoprotein CIII | Apolipoprotein H | Beta-2 Microglobulin | Brain-Derived Neurotrophic Factor |
|---|---|---|---|---|---|
| | mg/mL | ug/mL | ug/mL | ug/mL | ng/mL |
| Least Detectable Dose | 0.0066 | 2.7 | 8.8 | 0.013 | 0.029 |
| RBM Low Plasma Range | 0.19 | 28 | 131 | 1.2 | 0.32 |
| RBM High Plasma Range | 0.89 | 224 | 430 | 6.2 | 16 |
| | Apolipoprotein A1 | Apolipoprotein CIII | Apolipoprotein H | Beta-2 Microglobulin | Brain-Derived Neurotrophic Factor |
| patient 1 H | | | | | |
| patient 7 H | | | | | |
| patient 2 H | | | | | |
| patient 3 H | | | | | |
| patient 5 H | | | | | |
| patient 4 H | | | | | |
| patient 6 H | | | | | |
| NHD 1 H | | | | | |
| NHD 2 H | | | | | |

FIG. 15B.13

| | Apolipoprotein A1 | Apolipoprotein CIII | Apolipoprotein H | Beta-2 Microglobulin | Brain-Derived Neurotrophic Factor |
|---|---|---|---|---|---|
| | mg/mL | ug/mL | ug/mL | ug/mL | ng/mL |
| Least Detectable Dose | 0.0066 | 2.7 | 8.8 | 0.013 | 0.029 |
| RBM Low Plasma Range | 0.19 | 28 | 131 | 1.2 | 0.32 |
| RBM High Plasma Range | 0.89 | 224 | 430 | 6.2 | 16 |
| | Apolipoprotein A1 | Apolipoprotein CIII | Apolipoprotein H | Beta-2 Microglobulin | Brain-Derived Neurotrophic Factor |
| patient 1 | | | | | |
| patient 7 | | | | | |
| patient 2 | | | | | |
| patient 3 | | | | | |
| patient 5 | | | | | |
| patient 4 | | | | | |
| patient 6 | | | | | |
| NHD 1 | | | | | |
| NHD 2 | | | | | |

FIG. 15B.14

| | Apolipoprotein A1 | Apolipoprotein CIII | Apolipoprotein H | Beta-2 Microglobulin | Brain-Derived Neurotrophic Factor |
|---|---|---|---|---|---|
| | mg/mL | ug/mL | ug/mL | ug/mL | ng/mL |
| Least Detectable Dose | 0.0066 | 2.7 | 8.8 | 0.013 | 0.029 |
| RBM Low Plasma Range | 0.19 | 28 | 131 | 1.2 | 0.32 |
| RBM High Plasma Range | 0.89 | 224 | 430 | 6.2 | 16 |
| Messwert > ULD | | | | | |
| SI > 1,3 | | | | | |
| SI 0,7-1,3 | | | | | |
| SI 0-0,7 | | | | | |

FIG. 15C.1

| | Complement 3 mg/mL | Cancer Antigen 125 U/mL | Cancer Antigen 19-9 U/mL | Calcitonin pg/mL | CD40 ng/mL | CD40 Ligand ng/mL |
|---|---|---|---|---|---|---|
| Least Detectable Dose | 0.0053 | 4.2 | 0.25 | 6.0 | 0.021 | 0.020 |
| RBM Low Plasma Range | 0.76 | | | | 0.17 | |
| RBM High Plasma Range | 2.1 | 12 | 9.2 | 12 | 1.5 | 1.1 |
| Samples | | | | | | |
| Donor_1 3. Aliquot A | 0.73 | 132 | 28 | 36 | 11 | 0.66 |
| Donor_1 3. Aliquot B | 0.71 | 123 | 28 | 32 | 9.2 | 0.82 |
| Donor_1 3. Aliquot C | 0.71 | 141 | 13 | 34 | 10 | 0.82 |
| Donor_1 3. Aliquot D | 0.71 | 157 | 28 | 37 | 9.0 | 0.60 |
| Donor_1 3. Aliquot E | 0.69 | 135 | 28 | 36 | 8.7 | 0.47 |
| Donor_1 3. Aliquot F | 1.5 | 128 | 24 | 31 | 9.3 | 0.39 |
| Donor_1 3. Aliquot G | 0.77 | 140 | 32 | 32 | 12 | 0.18 |
| Donor_1 3. Aliquot H | 1.2 | 143 | 12 | 31 | 11 | 0.55 |
| Donor_1 3. Aliquot I | 0.71 | 125 | 28 | 33 | 10 | 0.84 |
| Donor_2 3. Aliquot A | 0.92 | 121 | 476 | 29 | 16 | 0.70 |
| Donor_2 3. Aliquot B | 0.93 | 125 | 510 | 31 | 18 | 0.65 |
| Donor_2 3. Aliquot C | 0.89 | 119 | 408 | 24 | 16 | 0.61 |
| Donor_2 3. Aliquot D | 0.92 | 197 | 468 | 33 | 16 | 0.47 |
| Donor_2 3. Aliquot E | 0.94 | 158 | 488 | 31 | 19 | 0.50 |
| Donor_2 3. Aliquot F | 2.3 | 123 | 413 | 30 | 16 | 0.42 |
| Donor_2 3. Aliquot G | 0.98 | 138 | 495 | 20 | 21 | 0.28 |
| Donor_2 3. Aliquot H | 1.3 | 106 | 459 | 29 | 18 | 0.44 |
| Donor_2 3. Aliquot I | 0.90 | 102 | 447 | 26 | 17 | 0.47 |
| Donor_3 3. Aliquot A | 0.68 | 35 | 3.3 | 6 | 1.4 | 0.54 |
| Donor_3 3. Aliquot B | 0.70 | 33 | 3.6 | 5.1 | 1.7 | 0.43 |
| Donor_3 3. Aliquot C | 0.73 | 35 | 3.6 | 6 | 1.4 | 0.50 |
| Donor_3 3. Aliquot D | 0.73 | 87 | 3.3 | 6 | 1.5 | 0.52 |
| Donor_3 3. Aliquot E | 0.77 | 74 | 3.6 | 7.3 | 1.5 | 0.68 |
| Donor_3 3. Aliquot F | 1.2 | 39 | 4.1 | 6 | 1.4 | 0.36 |
| Donor_3 3. Aliquot G | 0.72 | 29 | 4.6 | 6 | 3.4 | 0.29 |

FIG. 15C.2

| | Complement 3 mg/mL | Cancer Antigen 125 U/mL | Cancer Antigen 19-9 U/mL | Calcitonin pg/mL | CD40 ng/mL | CD40 Ligand ng/mL |
|---|---|---|---|---|---|---|
| Least Detectable Dose | 0.0053 | 4.2 | 0.25 | 6.0 | 0.021 | 0.020 |
| RBM Low Plasma Range | 0.76 | | | | 0.17 | |
| RBM High Plasma Range | 2.1 | 12 | 9.2 | 12 | 1.5 | 1.1 |
| Donor_3_3. Aliquot H | 1.1 | 27 | 3.2 | 6 | 1.4 | 0.50 |
| Donor_3_3. Aliquot I | 0.74 | 31 | 2.8 | 6 | 1.3 | 0.42 |
| Donor_4_3. Aliquot A | 0.45 | 512 | 15 | 18 | 4.3 | 0.20 |
| Donor_4_3. Aliquot B | 0.41 | 495 | 16 | 20 | 4.7 | 0.18 |
| Donor_4_3. Aliquot C | 0.45 | 462 | 15 | 15 | 4.3 | 0.088 |
| Donor_4_3. Aliquot D | 0.43 | 542 | 16 | 19 | 4.0 | 0.13 |
| Donor_4_3. Aliquot E | 0.44 | 520 | 20 | 16 | 4.3 | 0.13 |
| Donor_4_3. Aliquot F | 0.80 | 465 | 16 | 15 | 4.0 | 0.083 |
| Donor_4_3. Aliquot G | 0.43 | 462 | 17 | 10 | 4.9 | 0.063 |
| Donor_4_3. Aliquot H | 0.69 | 509 | 15 | 17 | 4.0 | 0.081 |
| Donor_4_3. Aliquot I | 0.43 | 494 | 15 | 17 | 3.9 | 0.092 |
| Donor_5_3. Aliquot A | 0.72 | 21 | 8.8 | 105 | 18 | 0.51 |
| Donor_5_3. Aliquot B | 0.76 | 21 | 9.2 | 97 | 18 | 0.34 |
| Donor_5_3. Aliquot C | 0.77 | 21 | 9.9 | 74 | 19 | 0.32 |
| Donor_5_3. Aliquot D | 0.78 | 87 | 10 | 92 | 20 | 0.40 |
| Donor_5_3. Aliquot E | 0.73 | 74 | 10 | 90 | 21 | 0.47 |
| Donor_5_3. Aliquot F | 1.2 | 12 | 7.1 | 86 | 18 | 0.29 |
| Donor_5_3. Aliquot G | 0.80 | 20 | 8.6 | 67 | 19 | 0.24 |
| Donor_5_3. Aliquot H | 1.1 | 16 | 8.9 | 101 | 18 | 0.32 |
| Donor_5_3. Aliquot I | 0.72 | 17 | 8.0 | 94 | 17 | 0.27 |
| Donor_6_3. Aliquot A | 0.73 | 29 | 3.7 | 6 | 0.98 | 0.88 |
| Donor_6_3. Aliquot B | 0.77 | 42 | 2.6 | 6 | 1.1 | 0.77 |
| Donor_6_3. Aliquot C | 0.72 | 24 | 4.4 | 6 | 1.0 | 0.61 |
| Donor_6_3. Aliquot D | 0.75 | 82 | 3.9 | 6 | 1.0 | 0.95 |
| Donor_6_3. Aliquot E | 0.67 | 85 | 3.5 | 6 | 0.96 | 0.60 |

FIG. 15C.3

| | Complement 3 mg/mL | Cancer Antigen 125 U/mL | Cancer Antigen 19-9 U/mL | Calcitonin pg/mL | CD40 ng/mL | CD40 Ligand ng/mL |
|---|---|---|---|---|---|---|
| Least Detectable Dose | 0.0053 | 4.2 | 0.25 | 6.0 | 0.021 | 0.020 |
| | | | | | | |
| RBM Low Plasma Range | 0.76 | | | | 0.17 | |
| RBM High Plasma Range | 2.1 | 12 | 9.2 | 12 | 1.5 | 1.1 |
| Donor_6 3. Aliquot F | 0.71 | 27 | 2.9 | 6 | 0.90 | 0.47 |
| Donor_6 3. Aliquot G | 0.78 | 28 | 5.2 | 6 | 3.8 | 0.30 |
| Donor_6 3. Aliquot H | 1.1 | 23 | 3.7 | 6 | 0.81 | 0.45 |
| Donor_6 3. Aliquot I | 0.68 | 29 | 3.0 | 6 | 0.73 | 0.45 |
| | | | | | | |
| Donor_7 3. Aliquot A | 0.67 | 53 | 5.3 | 1.5 | 0.93 | 0.25 |
| Donor_7 3. Aliquot B | 0.68 | 48 | 5.1 | 6 | 0.89 | 0.21 |
| Donor_7 3. Aliquot C | 0.73 | 39 | 5.1 | 6 | 0.77 | 0.40 |
| Donor_7 3. Aliquot D | 0.66 | 91 | 4.8 | 6 | 0.73 | 0.30 |
| Donor_7 3. Aliquot E | 0.51 | 53 | 5.2 | 6 | 0.62 | 0.20 |
| Donor_7 3. Aliquot F | 0.72 | 40 | 4.7 | 6 | 0.61 | 0.11 |
| Donor_7 3. Aliquot G | 0.74 | 38 | 7.8 | 6 | 1.8 | 0.071 |
| Donor_7 3. Aliquot H | 1.1 | 34 | 5.2 | 6 | 0.71 | 0.18 |
| Donor_7 3. Aliquot I | 0.67 | 39 | 3.7 | 3.3 | 0.50 | 0.15 |
| | | | | | | |
| Donor_8 3. Aliquot A | 0.45 | 5.6 | 4.9 | 6 | 0.57 | 0.32 |
| Donor_8 3. Aliquot B | 0.49 | 9.0 | 3.9 | 6 | 0.60 | 0.42 |
| Donor_8 3. Aliquot C | 0.43 | 4.4 | 3.9 | 6 | 0.63 | 0.51 |
| Donor_8 3. Aliquot D | 0.44 | 164 | 5.5 | 4.6 | 0.72 | 0.33 |
| Donor_8 3. Aliquot E | 0.43 | 136 | 5.1 | 6.5 | 0.63 | 0.49 |
| Donor_8 3. Aliquot F | 0.51 | 16 | 4.5 | 6 | 0.49 | 0.15 |
| Donor_8 3. Aliquot G | 0.44 | 9.0 | 5.2 | 6 | 1.8 | 0.13 |
| Donor_8 3. Aliquot H | 0.72 | 13 | 4.0 | 6 | 0.60 | 0.49 |
| Donor_8 3. Aliquot I | 0.46 | 15 | 3.6 | 6 | 0.65 | 0.45 |
| | | | | | | |
| Donor_9 3. Aliquot A | 0.39 | 14 | 3.0 | 6 | 0.69 | 0.37 |
| Donor_9 3. Aliquot B | 0.39 | 11 | 3.3 | 6 | 0.69 | 0.43 |
| Donor_9 3. Aliquot C | 0.39 | 21 | 3.3 | 6 | 0.69 | 0.51 |

FIG. 15C.4

| | Complement 3 mg/mL | Cancer Antigen 125 U/mL | Cancer Antigen 19-9 U/mL | Calcitonin pg/mL | CD40 ng/mL | CD40 Ligand ng/mL |
|---|---|---|---|---|---|---|
| Least Detectable Dose | 0.0053 | 4.2 | 0.25 | 6.0 | 0.021 | 0.020 |
| RBM Low Plasma Range | 0.76 | | | | 0.17 | |
| RBM High Plasma Range | 2.1 | 12 | 9.2 | 12 | 1.5 | 1.1 |
| Donor_9 3. Aliquot D | 0.37 | 140 | 6.0 | 3.9 | 0.81 | 0.46 |
| Donor_9 3. Aliquot E | 0.40 | 104 | 3.7 | 3.2 | 0.72 | 0.31 |
| Donor_9 3. Aliquot F | 0.39 | 12 | 2.6 | 6 | 0.61 | 0.19 |
| Donor_9 3. Aliquot G | 0.41 | 14 | 3.1 | 0.91 | 2.7 | 0.21 |
| Donor_9 3. Aliquot H | 0.64 | 4.9 | 3.1 | 6 | 0.64 | 0.50 |
| Donor_9 3. Aliquot I | 0.39 | 8.3 | 2.6 | 6 | 0.66 | 0.45 |
| EDTA Plasma | | | | | | |
| donor #1 plasma | 0.59 | 60 | 7.6 | 40 | 7.4 | 0.14 |
| donor #2 plasma | 0.98 | 63 | 241 | 51 | 18 | 0.21 |
| donor #3 plasma | 0.90 | 28 | 2.1 | 8.9 | 1.7 | 0.084 |
| donor #4 plasma | 0.47 | 431 | 10 | 36 | 5.2 | 0.10 |
| donor #5 plasma | 0.88 | 18 | 4.2 | 164 | 16 | 0.27 |
| donor #6 plasma | 0.87 | 18 | 1.6 | 3.7 | 0.46 | 0.021 |
| donor #7 plasma | 0.80 | 30 | 6.0 | 5.0 | 1.6 | 0.089 |
| donor #8 plasma | 0.42 | 16 | 7.5 | 6 | 0.58 | 0.16 |
| donor #9 plasma | 0.55 | 4.2 | 6.3 | 6 | 0.47 | 0.053 |
| *Stimulations indices* | | | | | | |

FIG. 15C.5

| | Least Detectable Dose | Complement 3 mg/mL 0.0053 | Cancer Antigen 125 U/mL 4.2 | Cancer Antigen 19-9 U/mL 0.25 | Calcitonin pg/mL | CD40 ng/mL 0.021 | CD40 Ligand ng/mL 0.020 |
|---|---|---|---|---|---|---|---|
| | RBM Low Plasma Range | 0.76 | | | 6.0 | 0.17 | |
| | RBM High Plasma Range | 2.1 | 12 | 9.2 | 12 | 1.5 | 1.1 |
| patient 1 | A | | | | | | |
| patient 7 | A | | | | | | |
| patient 2 | A | | | | | | |
| patient 3 | A | | | | | | |
| patient 5 | A | | | | | | |
| patient 4 | A | | | | | | |
| patient 6 | A | | | | | | |
| NHD 1 | A | | | | | | |
| NHD 2 | A | | | | | | |

FIG. 15C.6

| | Complement 3 mg/mL | Cancer Antigen 125 U/mL | Cancer Antigen 19-9 U/mL | Calcitonin pg/mL | CD40 ng/mL | CD40 Ligand ng/mL |
|---|---|---|---|---|---|---|
| Least Detectable Dose | 0.0053 | 4.2 | 0.25 | 6.0 | 0.021 | 0.020 |
| RBM Low Plasma Range | 0.76 | | | | 0.17 | |
| RBM High Plasma Range | 2.1 | 12 | 9.2 | 12 | 1.5 | 1.1 |

| | Complement 3 | Cancer Antigen 125 | Cancer Antigen 19-9 | Calcitonin | CD40 | CD40 Ligand |
|---|---|---|---|---|---|---|
| patient 1 | B | | | | | |
| patient 7 | B | | | | | |
| patient 2 | B | | | | | |
| patient 3 | B | | | | | |
| patient 5 | B | | | | | |
| patient 4 | B | | | | | |
| patient 6 | B | | | | | |
| NHD 1 | B | | | | | |
| NHD 2 | B | | | | | |

FIG. 15C.7

| | Complement 3 mg/mL | Cancer Antigen 125 U/mL | Cancer Antigen 19-9 U/mL | Calcitonin pg/mL | CD40 ng/mL | CD40 Ligand ng/mL |
|---|---|---|---|---|---|---|
| Least Detectable Dose | 0.0053 | 4.2 | 0.25 | 6.0 | 0.021 | 0.020 |
| RBM Low Plasma Range | 0.76 | | | | 0.17 | |
| RBM High Plasma Range | 2.1 | 12 | 9.2 | 12 | 1.5 | 1.1 |
| | Complement 3 | Cancer Antigen 125 | Cancer Antigen 19-9 | Calcitonin | CD40 | CD40 Ligand |
| patient 1 | | | | | | |
| patient 7 | | | | | | |
| patient 2 | | | | | | |
| patient 3 | | | | | | |
| patient 5 | | | | | | |
| patient 4 | | | | | | |
| patient 6 | | | | | | |
| NHD 1 | | | | | | |
| NHD 2 | | | | | | |

FIG. 15C.8

| | Least Detectable Dose | RBM Low Plasma Range | RBM High Plasma Range |
|---|---|---|---|
| Complement 3 mg/mL | 0.0053 | 0.76 | 2.1 |
| Cancer Antigen 125 U/mL | 4.2 | | 12 |
| Cancer Antigen 19-9 U/mL | 0.25 | | 9.2 |
| Calcitonin pg/mL | 6.0 | | 12 |
| CD40 ng/mL | 0.021 | 0.17 | 1.5 |
| CD40 Ligand ng/mL | 0.020 | | 1.1 |

| | Complement 3 | Cancer Antigen 125 | Cancer Antigen 19-9 | Calcitonin | CD40 | CD40 Ligand |
|---|---|---|---|---|---|---|
| patient 1 | D | D | D | D | D | D |
| patient 7 | D | D | D | D | D | D |
| patient 2 | D | D | D | D | D | D |
| patient 3 | D | D | D | D | D | D |
| patient 5 | D | D | D | D | D | D |
| patient 4 | D | D | D | D | D | D |
| patient 6 | D | D | D | D | D | D |
| NHD 1 | D | D | D | D | D | D |
| NHD 2 | D | D | D | D | D | D |

FIG. 15C.9

| | Complement 3 mg/mL | Cancer Antigen 125 U/mL | Cancer Antigen 19-9 U/mL | Calcitonin pg/mL | CD40 ng/mL | CD40 Ligand ng/mL |
|---|---|---|---|---|---|---|
| Least Detectable Dose | 0.0053 | 4.2 | 0.25 | 6.0 | 0.021 | 0.020 |
| RBM Low Plasma Range | 0.76 | | | | 0.17 | |
| RBM High Plasma Range | 2.1 | 12 | 9.2 | 12 | 1.5 | 1.1 |
| | Complement 3 | Cancer Antigen 125 | Cancer Antigen 19-9 | Calcitonin | CD40 | CD40 Ligand |
| patient 1 | | | | | | |
| patient 7 | | | | | | |
| patient 2 | | | | | | |
| patient 3 | | | | | | |
| patient 5 | | | | | | |
| patient 4 | | | | | | |
| patient 6 | | | | | | |
| NHD 1 | | | | | | |
| NHD 2 | | | | | | |

FIG. 15C.10

| | Complement 3 mg/mL | Cancer Antigen 125 U/mL | Cancer Antigen 19-9 U/mL | Calcitonin pg/mL | CD40 ng/mL | CD40 Ligand ng/mL |
|---|---|---|---|---|---|---|
| Least Detectable Dose | 0.0053 | 4.2 | 0.25 | 6.0 | 0.021 | 0.020 |
| RBM Low Plasma Range | 0.76 | | | | 0.17 | |
| RBM High Plasma Range | 2.1 | 12 | 9.2 | 12 | 1.5 | 1.1 |
| | Complement 3 | Cancer Antigen 125 | Cancer Antigen 19-9 | Calcitonin | CD40 | CD40 Ligand |
| patient 1 F | | | | | | |
| patient 7 F | | | | | | |
| patient 2 F | | | | | | |
| patient 3 F | | | | | | |
| patient 5 F | | | | | | |
| patient 4 F | | | | | | |
| patient 6 F | | | | | | |
| NHD 1 F | | | | | | |
| NHD 2 F | | | | | | |

FIG. 15C.11
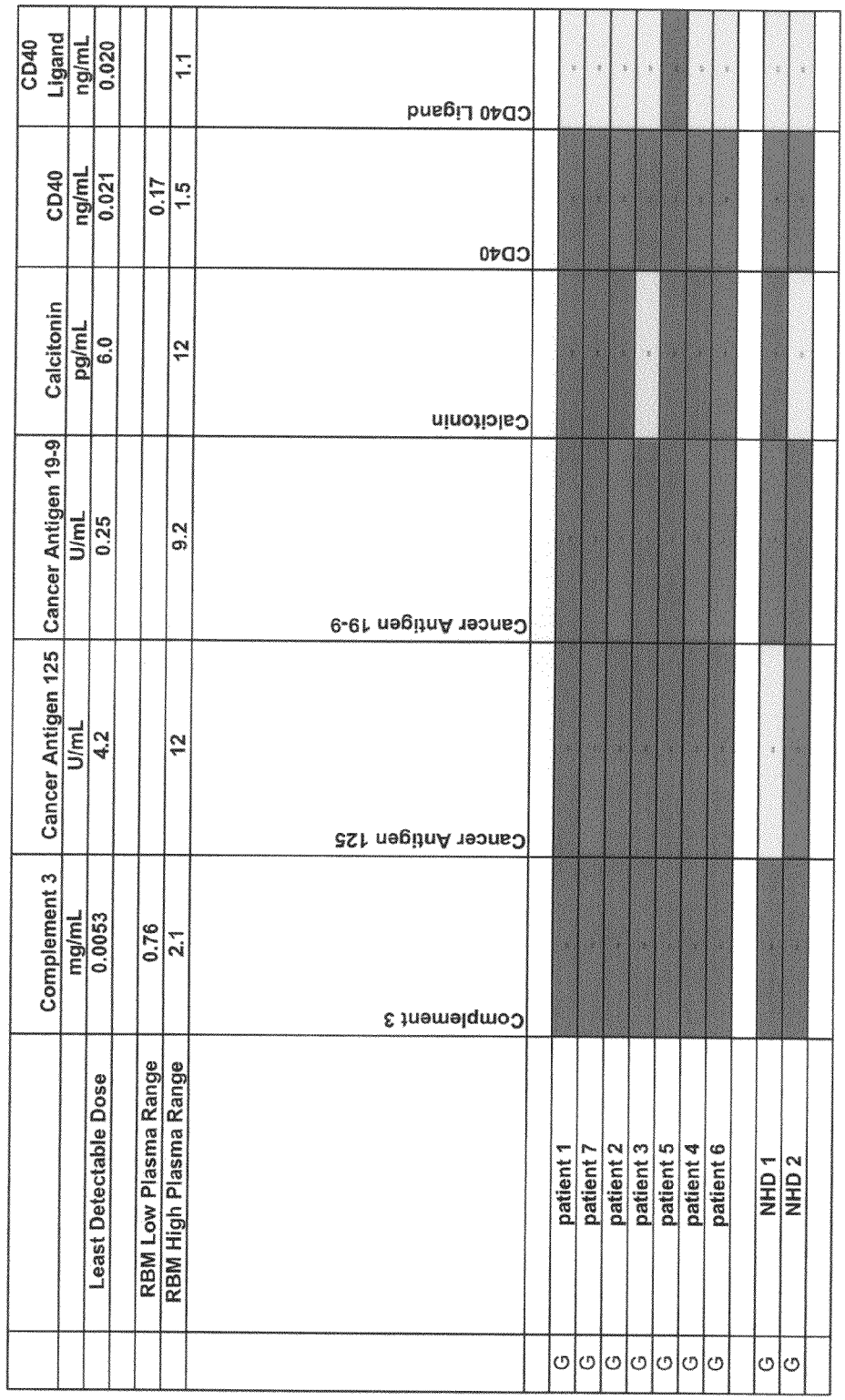

FIG. 15C.12

| | Complement 3 mg/mL | Cancer Antigen 125 U/mL | Cancer Antigen 19-9 U/mL | Calcitonin pg/mL | CD40 ng/mL | CD40 Ligand ng/mL |
|---|---|---|---|---|---|---|
| Least Detectable Dose | 0.0053 | 4.2 | 0.25 | 6.0 | 0.021 | 0.020 |
| RBM Low Plasma Range | 0.76 | | | | 0.17 | |
| RBM High Plasma Range | 2.1 | 12 | 9.2 | 12 | 1.5 | 1.1 |

| | Complement 3 | Cancer Antigen 125 | Cancer Antigen 19-9 | Calcitonin | CD40 | CD40 Ligand |
|---|---|---|---|---|---|---|
| patient 1 | H | | | | | |
| patient 7 | H | | | | | |
| patient 2 | H | | | | | |
| patient 3 | H | | | | | |
| patient 5 | H | | | | | |
| patient 4 | H | | | | | |
| patient 6 | H | | | | | |
| NHD 1 | H | | | | | |
| NHD 2 | H | | | | | |

FIG. 15C.13

| | Complement 3 mg/mL | Cancer Antigen 125 U/mL | Cancer Antigen 19-9 U/mL | Calcitonin pg/mL | CD40 ng/mL | CD40 Ligand ng/mL |
|---|---|---|---|---|---|---|
| Least Detectable Dose | 0.0053 | 4.2 | 0.25 | 6.0 | 0.021 | 0.020 |
| RBM Low Plasma Range | 0.76 | | | | 0.17 | |
| RBM High Plasma Range | 2.1 | 12 | 9.2 | 12 | 1.5 | 1.1 |
| patient 1 | | | | | | |
| patient 7 | | | | | | |
| patient 2 | | | | | | |
| patient 3 | | | | | | |
| patient 5 | | | | | | |
| patient 4 | | | | | | |
| patient 6 | | | | | | |
| NHD 1 | | | | | | |
| NHD 2 | | | | | | |

FIG. 15C.14

| | Complement 3 mg/mL | Cancer Antigen 125 U/mL | Cancer Antigen 19-9 U/mL | Calcitonin pg/mL | CD40 ng/mL | CD40 Ligand ng/mL |
|---|---|---|---|---|---|---|
| Least Detectable Dose | 0.0053 | 4.2 | 0.25 | 6.0 | 0.021 | 0.020 |
| RBM Low Plasma Range | 0.76 | | | | 0.17 | |
| RBM High Plasma Range | 2.1 | 12 | 9.2 | 12 | 1.5 | 1.1 |
| Messwert > ULD | | | | | | |
| SI > 1,3 | | | | | | |
| SI 0,7-1,3 | | | | | | |
| SI 0-0,7 | | | | | | |

FIG. 15D.1

| | Carcinoembryonic Antigen | Creatine Kinase-MB | C Reactive Protein | EGF | ENA-78 | Endothelin-1 |
|---|---|---|---|---|---|---|
| | ng/mL | ng/mL | ug/mL | pg/mL | ng/mL | pg/mL |
| Least Detectable Dose | 0.84 | 0.42 | 0.0015 | 7.4 | 0.076 | 7.2 |
| RBM Low Plasma Range | | | 0.25 | | 0.069 | |
| RBM High Plasma Range | 4.8 | 1.1 | 50 | 505 | 5.3 | 26 |
| Samples | | | | | | |
| Donor_1 3. Aliquot A | 1.5 | 0.16 | >47 | 128 | 7.9 | 8.1 |
| Donor_1 3. Aliquot B | 1.4 | 0.11 | >47 | 131 | 8.2 | 7.2 |
| Donor_1 3. Aliquot C | 1.4 | 0.12 | >47 | 119 | 1.7 | 7.2 |
| Donor_1 3. Aliquot D | 1.7 | 0.18 | >47 | 109 | 10 | 7.2 |
| Donor_1 3. Aliquot E | 1.6 | 0.11 | >47 | 101 | 5.9 | 7.2 |
| Donor_1 3. Aliquot F | 1.2 | 0.15 | >47 | 101 | 1.2 | 7.2 |
| Donor_1 3. Aliquot G | 1.5 | 0.11 | >47 | 693 | 5.3 | 22 |
| Donor_1 3. Aliquot H | 1.9 | 0.11 | >47 | 197 | 1.6 | 11 |
| Donor_1 3. Aliquot I | 1.4 | 0.12 | >47 | 114 | 1.8 | 7.2 |
| | | | | | | |
| Donor_2 3. Aliquot A | 4.6 | 0.40 | >47 | 92 | 45 | 11 |
| Donor_2 3. Aliquot B | 4.9 | 0.44 | >47 | 145 | 45 | 7.2 |
| Donor_2 3. Aliquot C | 4.7 | 0.32 | >47 | 83 | 0.66 | 7.2 |
| Donor_2 3. Aliquot D | 6.2 | 0.60 | >47 | 61 | 51 | 15 |
| Donor_2 3. Aliquot E | 5.0 | 0.43 | >47 | 62 | 55 | 20 |
| Donor_2 3. Aliquot F | 4.0 | 0.50 | >47 | 66 | 0.74 | 7.2 |
| Donor_2 3. Aliquot G | 5.4 | 0.49 | >47 | 792 | 214 | 24 |
| Donor_2 3. Aliquot H | 4.8 | 0.40 | >47 | 85 | 1.4 | 7.2 |
| Donor_2 3. Aliquot I | 4.5 | 0.21 | >47 | 59 | 1.2 | 7.2 |
| | | | | | | |
| Donor_3 3. Aliquot A | 2.8 | 0.59 | 22 | 40 | 20 | 7.2 |
| Donor_3 3. Aliquot B | 3.3 | 0.67 | 24 | 64 | 13 | 7.2 |
| Donor_3 3. Aliquot C | 3.3 | 0.54 | 25 | 38 | 0.96 | 7.2 |
| Donor_3 3. Aliquot D | 3.6 | 0.53 | 25 | 47 | 35 | 7.2 |
| Donor_3 3. Aliquot E | 4.3 | 0.61 | 24 | 60 | 31 | 11 |
| Donor_3 3. Aliquot F | 3.2 | 0.24 | 26 | 39 | 0.65 | 7.2 |
| Donor_3 3. Aliquot G | 2.7 | 0.29 | 26 | 535 | 1.6 | 7.2 |

FIG. 15D.2

| | Carcinoembryonic Antigen | Creatine Kinase-MB | C Reactive Protein | EGF | ENA-78 | Endothelin-1 |
|---|---|---|---|---|---|---|
| | ng/mL | ng/mL | ug/mL | pg/mL | ng/mL | pg/mL |
| Least Detectable Dose | 0.84 | 0.42 | 0.0015 | 7.4 | 0.076 | 7.2 |
| RBM Low Plasma Range | | | 0.25 | | 0.069 | |
| RBM High Plasma Range | 4.8 | 1.1 | 50 | 505 | 5.3 | 26 |
| Donor_3 3. Aliquot H | 2.4 | 0.37 | 23 | 39 | 0.47 | 7.2 |
| Donor_3 3. Aliquot I | 2.4 | 0.39 | 24 | 33 | 0.55 | 7.2 |
| Donor_4 3. Aliquot A | 3.4 | 0.078 | >47 | 25 | 0.77 | 7.2 |
| Donor_4 3. Aliquot B | 3.8 | 0.066 | >47 | 35 | 1.4 | 7.2 |
| Donor_4 3. Aliquot C | 3.6 | 0.064 | >47 | 12 | 0.18 | 7.2 |
| Donor_4 3. Aliquot D | 4.4 | 0.17 | >47 | 21 | 23 | 11 |
| Donor_4 3. Aliquot E | 3.7 | 0.066 | >47 | 15 | 21 | 22 |
| Donor_4 3. Aliquot F | 3.3 | 0.093 | >47 | 9.8 | 0.59 | 7.2 |
| Donor_4 3. Aliquot G | 3.3 | 0.057 | >47 | 256 | 1.2 | 7.2 |
| Donor_4 3. Aliquot H | 3.4 | 0.045 | >47 | 11 | 0.14 | 7.2 |
| Donor_4 3. Aliquot I | 3.2 | 0.076 | >47 | 19 | 0.20 | 7.2 |
| Donor_5 3. Aliquot A | 1.7 | 0.18 | >47 | 87 | 21 | 20 |
| Donor_5 3. Aliquot B | 2.4 | 0.18 | >47 | 90 | 23 | 11 |
| Donor_5 3. Aliquot C | 1.6 | 0.11 | >47 | 71 | 0.25 | 7.2 |
| Donor_5 3. Aliquot D | 3.1 | 0.24 | >47 | 60 | 31 | 11 |
| Donor_5 3. Aliquot E | 2.9 | 0.28 | >47 | 70 | 33 | 15 |
| Donor_5 3. Aliquot F | 1.4 | 0.086 | >47 | 59 | 0.71 | 7.2 |
| Donor_5 3. Aliquot G | 1.7 | 0.12 | >47 | 647 | 7.0 | 15 |
| Donor_5 3. Aliquot H | 4.2 | 0.17 | >47 | 83 | 0.41 | 7.2 |
| Donor_5 3. Aliquot I | 3.6 | 0.11 | >47 | 53 | 0.22 | 7.2 |
| Donor_6 3. Aliquot A | 0.82 | 0.25 | >47 | 195 | 4.4 | 7.2 |
| Donor_6 3. Aliquot B | 0.58 | 0.24 | >47 | 213 | 6.0 | 7.2 |
| Donor_6 3. Aliquot C | 1.1 | 0.26 | >47 | 160 | 0.54 | 7.2 |
| Donor_6 3. Aliquot D | 1.3 | 0.26 | >47 | 152 | 10 | 7.2 |
| Donor_6 3. Aliquot E | 1.6 | 0.30 | >47 | 110 | 12 | 11 |

FIG. 15D.3

| | Carcinoembryonic Antigen ng/mL | Creatine Kinase-MB ng/mL | C Reactive Protein ug/mL | EGF pg/mL | ENA-78 ng/mL | Endothelin-1 pg/mL |
|---|---|---|---|---|---|---|
| Least Detectable Dose | 0.84 | 0.42 | 0.0015 | 7.4 | 0.076 | 7.2 |
| RBM Low Plasma Range | | | | | | |
| RBM High Plasma Range | | | 0.25 | | 0.069 | |
| Donor_6 3. Aliquot F | 4.8 | 1.1 | 50 | 505 | 5.3 | 26 |
| Donor_6 3. Aliquot G | 0.63 | 0.19 | >47 | 132 | 0.68 | 7.2 |
| Donor_6 3. Aliquot H | 0.44 | 0.30 | >47 | 2020 | 4.3 | 7.2 |
| Donor_6 3. Aliquot I | 0.91 | 0.21 | >47 | 139 | 0.43 | 7.2 |
| | 0.96 | 0.21 | >47 | 101 | 0.51 | 7.2 |
| Donor_7 3. Aliquot A | 3.6 | 1.2 | 29 | 30 | 33 | 7.2 |
| Donor_7 3. Aliquot B | 2.8 | 1.5 | 33 | 45 | 17 | 7.2 |
| Donor_7 3. Aliquot C | 3.0 | 0.99 | 30 | 37 | 0.56 | 7.2 |
| Donor_7 3. Aliquot D | 3.9 | 1.1 | 27 | 28 | 26 | 7.2 |
| Donor_7 3. Aliquot E | 3.2 | 1.1 | 24 | 22 | 20 | 7.2 |
| Donor_7 3. Aliquot F | 2.9 | 1.2 | 27 | 11 | 0.25 | 7.2 |
| Donor_7 3. Aliquot G | 3.0 | 1.1 | 27 | 403 | 3.6 | 7.2 |
| Donor_7 3. Aliquot H | 4.1 | 1.0 | 28 | 20 | 0.23 | 7.2 |
| Donor_7 3. Aliquot I | 2.7 | 0.93 | 29 | 15 | 0.19 | 7.2 |
| Donor_8 3. Aliquot A | 1.1 | 0.15 | 0.096 | 93 | 1.1 | 8.1 |
| Donor_8 3. Aliquot B | 0.82 | 0.19 | 0.14 | 110 | 1.3 | 7.2 |
| Donor_8 3. Aliquot C | 0.75 | 0.15 | 0.13 | 114 | 0.81 | 7.2 |
| Donor_8 3. Aliquot D | 3.5 | 0.36 | 0.14 | 105 | 1.4 | 7.2 |
| Donor_8 3. Aliquot E | 3.9 | 0.39 | 0.12 | 132 | 2.4 | 7.2 |
| Donor_8 3. Aliquot F | 1.4 | 0.24 | 0.16 | 63 | 0.37 | 15 |
| Donor_8 3. Aliquot G | 0.94 | 0.20 | 0.13 | 1050 | 4.5 | 7.2 |
| Donor_8 3. Aliquot H | 1.9 | 0.24 | 0.15 | 143 | 0.81 | 11 |
| Donor_8 3. Aliquot I | 1.6 | 0.14 | 0.13 | 125 | 0.87 | 7.2 |
| Donor_9 3. Aliquot A | 1.2 | 0.079 | Pending | 117 | 2.1 | 7.2 |
| Donor_9 3. Aliquot B | 1.5 | 0.19 | Pending | 156 | 2.2 | 13 |
| Donor_9 3. Aliquot C | 1.0 | 0.18 | Pending | 123 | 2.1 | 9.8 |

FIG. 15D.4

| | Carcinoembryonic Antigen | Creatine Kinase-MB | C Reactive Protein | EGF | ENA-78 | Endothelin-1 |
|---|---|---|---|---|---|---|
| | ng/mL | ng/mL | ug/mL | pg/mL | ng/mL | pg/mL |
| Least Detectable Dose | 0.84 | 0.42 | 0.0015 | 7.4 | 0.076 | 7.2 |
| | | | | | | |
| RBM Low Plasma Range | | | 0.25 | | 0.069 | |
| RBM High Plasma Range | | | 50 | 505 | 5.3 | 26 |
| Donor_9 3. Aliquot D | 4.8 | 1.1 | Pending | 131 | 2.4 | 18 |
| Donor_9 3. Aliquot E | 5.3 | 0.40 | Pending | 95 | 6.5 | 19 |
| Donor_9 3. Aliquot F | 3.3 | 0.26 | Pending | 78 | 0.65 | 13 |
| Donor_9 3. Aliquot G | 1.7 | 0.16 | Pending | 1300 | 16 | 7.2 |
| Donor_9 3. Aliquot H | 1.1 | 0.12 | Pending | 140 | 1.3 | 5.1 |
| Donor_9 3. Aliquot I | 1.5 | 0.13 | Pending | 134 | 1.5 | 7.2 |
| | 0.89 | 0.083 | | | | |
| | | | | | | |
| EDTA Plasma | | | | | | |
| donor #1 plasma | 1.7 | 0.25 | Pending | 30 | 0.93 | 7.7 |
| donor #2 plasma | 3.9 | 0.99 | Pending | 7.4 | 0.076 | 7.2 |
| donor #3 plasma | 2.6 | 0.47 | Pending | 7.4 | 0.076 | 17 |
| donor #4 plasma | 4.9 | 0.24 | Pending | 7.4 | 0.076 | 7.2 |
| donor #5 plasma | 1.7 | 0.18 | Pending | 12 | 0.32 | 22 |
| donor #6 plasma | 1.1 | 0.39 | Pending | 7.4 | 0.26 | 7.2 |
| donor #7 plasma | 3.6 | 3.3 | Pending | 7.4 | 0.54 | 7.2 |
| donor #8 plasma | 1.4 | 0.56 | Pending | 22 | 0.48 | 9.8 |
| donor #9 plasma | 0.71 | 0.27 | | 7.4 | 0.088 | 7.2 |
| | | | | | | |
| Stimulations indices | | | | | | |

FIG. 15D.5

| | Carcinoembryonic Antigen | Creatine Kinase-MB | C Reactive Protein | EGF | ENA-78 | Endothelin-1 |
|---|---|---|---|---|---|---|
| | ng/mL | ng/mL | ug/mL | pg/mL | ng/mL | pg/mL |
| Least Detectable Dose | 0.84 | 0.42 | 0.0015 | 7.4 | 0.076 | 7.2 |
| RBM Low Plasma Range | | | | | | |
| RBM High Plasma Range | 4.8 | 1.1 | 50 | 505 | 0.069 | 26 |
| | | | | | 5.3 | |

| | | |
|---|---|---|
| patient 1 | | A |
| patient 7 | | A |
| patient 2 | | A |
| patient 3 | | A |
| patient 5 | | A |
| patient 4 | | A |
| patient 6 | | A |
| NHD 1 | | A |
| NHD 2 | | A |

FIG. 15D.6

| | Carcinoembryonic Antigen | Creatine Kinase-MB | C Reactive Protein | EGF | ENA-78 | Endothelin-1 |
|---|---|---|---|---|---|---|
| | ng/mL | ng/mL | ug/mL | pg/mL | ng/mL | pg/mL |
| Least Detectable Dose | 0.84 | 0.42 | 0.0015 | 7.4 | 0.076 | 7.2 |
| RBM Low Plasma Range | | | 0.25 | | 0.069 | |
| RBM High Plasma Range | 4.8 | 1.1 | 50 | 505 | 5.3 | 26 |

| | Carcinoembryonic Antigen | Creatine Kinase-MB | C Reactive Protein | EGF | ENA-78 | Endothelin-1 |
|---|---|---|---|---|---|---|
| patient 1 | | | | | | |
| patient 7 | | | | | | |
| patient 2 | | | | | | |
| patient 3 | | | | | | |
| patient 5 | | | | | | |
| patient 4 | | | | | | |
| patient 6 | | | | | | |
| NHD 1 | | | | | | |
| NHD 2 | | | | | | |

FIG. 15D.7

| | Carcinoembryonic Antigen | Creatine Kinase-MB | C Reactive Protein | EGF | ENA-78 | Endothelin-1 |
|---|---|---|---|---|---|---|
| | ng/mL | ng/mL | ug/mL | pg/mL | ng/mL | pg/mL |
| Least Detectable Dose | 0.84 | 0.42 | 0.0015 | 7.4 | 0.076 | 7.2 |
| RBM Low Plasma Range | | | 0.25 | | 0.069 | |
| RBM High Plasma Range | 4.8 | 1.1 | 50 | 505 | 5.3 | 26 |
| | Carcinoembryonic Antigen | Creatine Kinase-MB | C Reactive Protein | EGF | ENA-78 | Endothelin-1 |
| patient 1 | | | | | | |
| patient 7 | | | | | | |
| patient 2 | | | | | | |
| patient 3 | | | | | | |
| patient 5 | | | | | | |
| patient 4 | | | | | | |
| patient 6 | | | | | | |
| NHD 1 | | | | | | |
| NHD 2 | | | | | | |

FIG. 15D.8

| | Carcinoembryonic Antigen ng/mL | Creatine Kinase-MB ng/mL | C Reactive Protein ug/mL | EGF pg/mL | ENA-78 ng/mL | Endothelin-1 pg/mL |
|---|---|---|---|---|---|---|
| Least Detectable Dose | 0.84 | 0.42 | 0.0015 | 7.4 | 0.076 | 7.2 |
| RBM Low Plasma Range | | | | | 0.069 | |
| RBM High Plasma Range | 4.8 | 1.1 | 50 | 505 | 5.3 | 26 |
| | | | 0.25 | | | |

| | Carcinoembryonic Antigen | Creatine Kinase-MB | C Reactive Protein | EGF | ENA-78 | Endothelin-1 |
|---|---|---|---|---|---|---|
| patient 1 | D | | | | | |
| patient 7 | D | | | | | |
| patient 2 | D | | | | | |
| patient 3 | D | | | | | |
| patient 5 | D | | | | | |
| patient 4 | D | | | | | |
| patient 6 | D | | | | | |
| NHD 1 | D | | | | | |
| NHD 2 | D | | | | | |

FIG. 15D.9

| | Carcinoembryonic Antigen ng/mL | Creatine Kinase-MB ng/mL | C Reactive Protein ug/mL | EGF pg/mL | ENA-78 ng/mL | Endothelin-1 pg/mL |
|---|---|---|---|---|---|---|
| Least Detectable Dose | 0.84 | 0.42 | 0.0015 | 7.4 | 0.076 | 7.2 |
| RBM Low Plasma Range | | | 0.25 | | 0.069 | |
| RBM High Plasma Range | 4.8 | 1.1 | 50 | 505 | 5.3 | 26 |
| patient 1 | | | | | | |
| patient 7 | | | | | | |
| patient 2 | | | | | | |
| patient 3 | | | | | | |
| patient 5 | | | | | | |
| patient 4 | | | | | | |
| patient 6 | | | | | | |
| NHD 1 | | | | | | |
| NHD 2 | | | | | | |

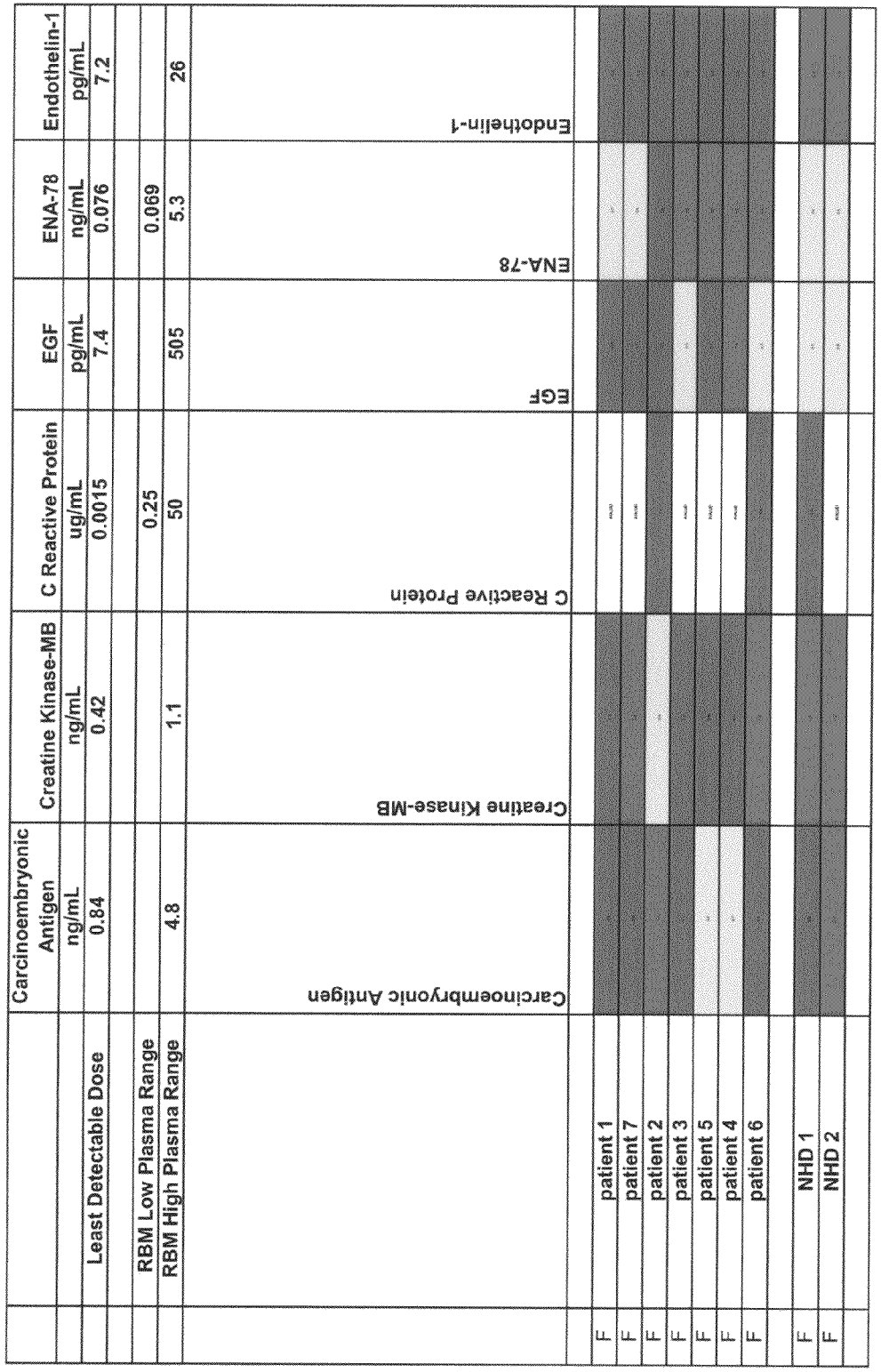
FIG. 15D.10

FIG. 15D.11

| | Carcinoembryonic Antigen ng/mL | Creatine Kinase-MB ng/mL | C Reactive Protein ug/mL | EGF pg/mL | ENA-78 ng/mL | Endothelin-1 pg/mL |
|---|---|---|---|---|---|---|
| Least Detectable Dose | 0.84 | 0.42 | 0.0015 | 7.4 | 0.076 | 7.2 |
| RBM Low Plasma Range | | | 0.25 | | 0.069 | |
| RBM High Plasma Range | 4.8 | 1.1 | 50 | 505 | 5.3 | 26 |
| | Carcinoembryonic Antigen | Creatine Kinase-MB | C Reactive Protein | EGF | ENA-78 | Endothelin-1 |
| patient 1 | G | | | | | |
| patient 7 | G | | | | | |
| patient 2 | G | | | | | |
| patient 3 | G | | | | | |
| patient 5 | G | | | | | |
| patient 4 | G | | | | | |
| patient 6 | G | | | | | |
| NHD 1 | G | | | | | |
| NHD 2 | G | | | | | |

FIG. 15D.12

| | Carcinoembryonic Antigen ng/mL | Creatine Kinase-MB ng/mL | C Reactive Protein ug/mL | EGF pg/mL | ENA-78 ng/mL | Endothelin-1 pg/mL |
|---|---|---|---|---|---|---|
| Least Detectable Dose | 0.84 | 0.42 | 0.0015 | 7.4 | 0.076 | 7.2 |
| RBM Low Plasma Range | | | 0.25 | | 0.069 | |
| RBM High Plasma Range | 4.8 | 1.1 | 50 | 505 | 5.3 | 26 |

FIG. 15D.13

| | Carcinoembryonic Antigen | Creatine Kinase-MB | C Reactive Protein | EGF | ENA-78 | Endothelin-1 |
|---|---|---|---|---|---|---|
| | ng/mL | ng/mL | ug/mL | pg/mL | ng/mL | pg/mL |
| Least Detectable Dose | 0.84 | 0.42 | 0.0015 | 7.4 | 0.076 | 7.2 |
| RBM Low Plasma Range | | | 0.25 | | 0.069 | |
| RBM High Plasma Range | 4.8 | 1.1 | 50 | 505 | 5.3 | 26 |
| | Carcinoembryonic Antigen | Creatine Kinase-MB | C Reactive Protein | EGF | ENA-78 | Endothelin-1 |
| patient 1 | | | | | | |
| patient 7 | | | | | | |
| patient 2 | | | | | | |
| patient 3 | | | | | | |
| patient 5 | | | | | | |
| patient 4 | | | | | | |
| patient 6 | | | | | | |
| NHD 1 | | | | | | |
| NHD 2 | | | | | | |

FIG. 15D.14

| | Carcinoembryonic Antigen ng/mL | Creatine Kinase-MB ng/mL | C Reactive Protein ug/mL | EGF pg/mL | ENA-78 ng/mL | Endothelin-1 pg/mL |
|---|---|---|---|---|---|---|
| Least Detectable Dose | 0.84 | 0.42 | 0.0015 | 7.4 | 0.076 | 7.2 |
| RBM Low Plasma Range | | | 0.25 | | 0.069 | |
| RBM High Plasma Range | 4.8 | 1.1 | 50 | 505 | 5.3 | 26 |
| | | | | | | |
| Messwert > ULD | | | | | | |
| SI > 1,3 | | | | | | |
| SI 0,7-1,3 | | | | | | |
| SI 0-0,7 | | | | | | |

FIG. 15E.1

| | EN-RAGE ng/mL | Eotaxin pg/mL | Epiregulin pg/mL | Erythropoietin pg/mL | Fatty Acid Binding Protein ng/mL | Factor VII ng/mL | Ferritin ng/mL |
|---|---|---|---|---|---|---|---|
| Least Detectable Dose | 0.25 | 41 | 36 | 166 | 3.0 | 1.0 | 1.4 |
| RBM Low Plasma Range | 4.6 | | Pending | | | 106 | 5.0 |
| RBM High Plasma Range | 592 | 177 | Pending | 284 | 10 | 443 | 552 |
| Samples | | | | | | | |
| Donor_1 3. Aliquot A | 82 | 179 | 161 | 166 | 32 | 157 | 1290 |
| Donor_1 3. Aliquot B | 72 | 164 | 65 | 166 | 29 | 140 | 1380 |
| Donor_1 3. Aliquot C | 74 | 130 | 33 | 37 | 34 | 89 | 1300 |
| Donor_1 3. Aliquot D | 66 | 180 | 16 | 166 | 33 | 168 | 1400 |
| Donor_1 3. Aliquot E | 75 | 170 | 40 | 166 | 33 | 171 | 1140 |
| Donor_1 3. Aliquot F | 60 | 184 | 61 | 166 | 31 | 132 | 1280 |
| Donor_1 3. Aliquot G | 54 | 10 | 149 | 166 | 41 | 174 | 1420 |
| Donor_1 3. Aliquot H | 99 | 177 | 36 | 60 | 31 | 160 | 1280 |
| Donor_1 3. Aliquot I | 76 | 172 | 31 | 166 | 29 | 139 | 1160 |
| Donor_2 3. Aliquot A | 247 | 61 | 44 | 166 | 36 | 541 | 1490 |
| Donor_2 3. Aliquot B | 230 | 48 | 26 | 166 | 40 | 577 | 1510 |
| Donor_2 3. Aliquot C | 252 | 46 | 16 | 166 | 40 | 154 | 1430 |
| Donor_2 3. Aliquot D | 212 | 48 | 52 | 166 | 45 | 694 | 1390 |
| Donor_2 3. Aliquot E | 228 | 44 | 21 | 166 | 45 | 640 | 1390 |
| Donor_2 3. Aliquot F | 258 | 27 | 36 | 166 | 40 | 580 | 1400 |
| Donor_2 3. Aliquot G | 218 | 5.0 | 236 | 166 | 48 | 588 | 1470 |
| Donor_2 3. Aliquot H | >269 | 36 | 26 | 166 | 39 | 567 | 1330 |
| Donor_2 3. Aliquot I | 250 | 44 | 36 | 166 | 34 | 450 | 1320 |
| Donor_3 3. Aliquot A | 142 | 66 | 40 | 166 | 14 | 147 | 855 |
| Donor_3 3. Aliquot B | 142 | 50 | 35 | 166 | 12 | 139 | 757 |
| Donor_3 3. Aliquot C | 135 | 44 | 24 | 166 | 12 | 31 | 828 |
| Donor_3 3. Aliquot D | 151 | 54 | 31 | 166 | 17 | 156 | 799 |
| Donor_3 3. Aliquot E | 159 | 52 | 36 | 166 | 16 | 160 | 797 |
| Donor_3 3. Aliquot F | 128 | 80 | 36 | 166 | 13 | 128 | 824 |
| Donor_3 3. Aliquot G | 122 | 5.0 | 36 | 166 | 15 | 116 | 865 |

FIG. 15E.2

| | EN-RAGE ng/mL | Eotaxin pg/mL | Epiregulin pg/mL | Erythropoietin pg/mL | Fatty Acid Binding Protein ng/mL | Factor VII ng/mL | Ferritin ng/mL |
|---|---|---|---|---|---|---|---|
| Least Detectable Dose | 0.25 | 41 | 36 | 166 | 3.0 | 1.0 | 1.4 |
| RBM Low Plasma Range | 4.6 | | | | | | |
| RBM High Plasma Range | 592 | 177 | Pending | 284 | 10 | 106 | 5.0 |
| Donor_3 3. Aliquot H | 211 | 29 | Pending | 166 | 9.2 | 443 | 552 |
| Donor_3 3. Aliquot I | 169 | 36 | 21 | 166 | 11 | 108 | 758 |
| | | | 13 | | | 123 | 800 |
| Donor_4 3. Aliquot A | >269 | 141 | 21 | 166 | 33 | 124 | 328 |
| Donor_4 3. Aliquot B | 239 | 133 | 35 | 166 | 33 | 129 | 311 |
| Donor_4 3. Aliquot C | 175 | 122 | 36 | 166 | 30 | 9.2 | 286 |
| Donor_4 3. Aliquot D | 84 | 133 | 36 | 166 | 33 | 142 | 308 |
| Donor_4 3. Aliquot E | 66 | 120 | 29 | 166 | 33 | 115 | 319 |
| Donor_4 3. Aliquot F | 94 | 130 | 36 | 166 | 32 | 105 | 347 |
| Donor_4 3. Aliquot G | 127 | 10 | 69 | 166 | 34 | 75 | 338 |
| Donor_4 3. Aliquot H | >269 | 124 | 36 | 166 | 37 | 111 | 315 |
| Donor_4 3. Aliquot I | 185 | 139 | 31 | 166 | 34 | 125 | 352 |
| Donor_5 3. Aliquot A | 95 | 27 | 129 | 166 | 9.2 | >1113 | 1430 |
| Donor_5 3. Aliquot B | 88 | 34 | 101 | 41 | 7.8 | 1020 | 1320 |
| Donor_5 3. Aliquot C | 108 | 32 | 149 | 166 | 9.2 | 243 | 1570 |
| Donor_5 3. Aliquot D | 52 | 32 | 105 | 100 | 13 | 940 | 1630 |
| Donor_5 3. Aliquot E | 41 | 30 | 111 | 64 | 14 | 1100 | 1510 |
| Donor_5 3. Aliquot F | 73 | 27 | 87 | 166 | 6.5 | 808 | 1390 |
| Donor_5 3. Aliquot G | 91 | 7.6 | 161 | 50 | 10 | 936 | 1460 |
| Donor_5 3. Aliquot H | 236 | 25 | 117 | 50 | 8.8 | 1000 | 1390 |
| Donor_5 3. Aliquot I | 100 | 22 | 95 | 166 | 8.8 | 1050 | 1400 |
| Donor_6 3. Aliquot A | 236 | 22 | 26 | 166 | 2.3 | 320 | 382 |
| Donor_6 3. Aliquot B | 229 | 25 | 31 | 166 | 2.6 | 329 | 374 |
| Donor_6 3. Aliquot C | 265 | 36 | 36 | 166 | 2.6 | 62 | 370 |
| Donor_6 3. Aliquot D | 109 | 25 | 36 | 166 | 5.4 | 345 | 370 |
| Donor_6 3. Aliquot E | 106 | 20 | 36 | 166 | 5.6 | 285 | 364 |

FIG. 15E.3

| | EN-RAGE ng/mL | Eotaxin pg/mL | Epiregulin pg/mL | Erythropoietin pg/mL | Fatty Acid Binding Protein ng/mL | Factor VII ng/mL | Ferritin ng/mL |
|---|---|---|---|---|---|---|---|
| Least Detectable Dose | 0.25 | 41 | 36 | 166 | 3.0 | 1.0 | 1.4 |
| RBM Low Plasma Range | 4.6 | 177 | Pending | 284 | 10 | 106 | 5.0 |
| RBM High Plasma Range | 592 | 177 | Pending | 284 | 10 | 443 | 552 |
| Donor_6_3. Aliquot F | 153 | 34 | 16 | 166 | 2.2 | 311 | 376 |
| Donor_6_3. Aliquot G | 147 | 15 | 177 | 166 | 2.6 | 252 | 391 |
| Donor_6_3. Aliquot H | >269 | 18 | 36 | 166 | 2.0 | 336 | 353 |
| Donor_6_3. Aliquot I | 237 | 22 | 36 | 166 | 1.7 | 309 | 375 |
| Donor_7_3. Aliquot A | 150 | 138 | 36 | 166 | 463 | 144 | 468 |
| Donor_7_3. Aliquot B | 161 | 119 | 36 | 166 | 459 | 149 | 491 |
| Donor_7_3. Aliquot C | >269 | 105 | 36 | 166 | 466 | 34 | 535 |
| Donor_7_3. Aliquot D | 128 | 106 | 36 | 166 | 422 | 128 | 451 |
| Donor_7_3. Aliquot E | 122 | 117 | 36 | 166 | 434 | 143 | 490 |
| Donor_7_3. Aliquot F | 227 | 121 | 36 | 166 | 426 | 143 | 505 |
| Donor_7_3. Aliquot G | 182 | 18 | 36 | 166 | 511 | 139 | 471 |
| Donor_7_3. Aliquot H | >269 | 125 | 36 | 166 | 440 | 136 | 404 |
| Donor_7_3. Aliquot I | >269 | 111 | 36 | 166 | 451 | 141 | 409 |
| Donor_8_3. Aliquot A | 48 | 162 | 36 | 166 | 3 | 376 | 34 |
| Donor_8_3. Aliquot B | 46 | 153 | 35 | 166 | 3 | 411 | 32 |
| Donor_8_3. Aliquot C | 41 | 117 | 44 | 166 | 3 | 18 | 37 |
| Donor_8_3. Aliquot D | 64 | 165 | 42 | 166 | 8.3 | 410 | 48 |
| Donor_8_3. Aliquot E | 45 | 157 | 35 | 166 | 7.8 | 351 | 39 |
| Donor_8_3. Aliquot F | 47 | 208 | 58 | 166 | 0.81 | 426 | 32 |
| Donor_8_3. Aliquot G | 57 | 5.0 | 56 | 166 | 3 | 253 | 42 |
| Donor_8_3. Aliquot H | 143 | 142 | 16 | 166 | 0.56 | 382 | 38 |
| Donor_8_3. Aliquot I | 122 | 157 | 36 | 166 | 0.14 | 381 | 36 |
| Donor_9_3. Aliquot A | 47 | 254 | 86 | 166 | 3 | 196 | 4.8 |
| Donor_9_3. Aliquot B | 33 | 223 | 75 | 166 | 1.6 | 196 | 2.6 |
| Donor_9_3. Aliquot C | 48 | 184 | 106 | 166 | 0.42 | 44 | 5.7 |

FIG. 15E.4

| | EN-RAGE ng/mL | Eotaxin pg/mL | Epiregulin pg/mL | Erythropoietin pg/mL | Fatty Acid Binding Protein ng/mL | Factor VII ng/mL | Ferritin ng/mL |
|---|---|---|---|---|---|---|---|
| Least Detectable Dose | 0.25 | 41 | 36 | 166 | 3.0 | 1.0 | 1.4 |
| RBM Low Plasma Range | 4.6 | | Pending | | | 106 | 5.0 |
| RBM High Plasma Range | 592 | 177 | Pending | 284 | 10 | 443 | 552 |
| Donor_9 3. Aliquot D | 46 | 239 | 101 | 166 | 10 | 243 | 11 |
| Donor_9 3. Aliquot E | 67 | 209 | 79 | 166 | 6.6 | 201 | 6.0 |
| Donor_9 3. Aliquot F | 22 | 231 | 77 | 166 | 0.68 | 196 | 3.6 |
| Donor_9 3. Aliquot G | 96 | 41 | 123 | 166 | 0.81 | 147 | 12 |
| Donor_9 3. Aliquot H | 115 | 201 | 97 | 166 | 3 | 229 | 5.5 |
| Donor_9 3. Aliquot I | 50 | 232 | 83 | 166 | 3 | 184 | 3.3 |
| EDTA Plasma | | | | | | | |
| donor #1 plasma | 65 | 97 | 83 | 84 | 32 | 141 | 1190 |
| donor #2 plasma | >269 | 42 | 36 | 166 | 65 | 545 | 1670 |
| donor #3 plasma | 49 | 36 | 32 | 166 | 25 | 135 | 934 |
| donor #4 plasma | 19 | 87 | 36 | 166 | 59 | 121 | 320 |
| donor #5 plasma | 145 | 64 | 35 | 118 | 13 | 891 | 1190 |
| donor #6 plasma | 40 | 14 | 36 | 37 | 5.0 | 315 | 382 |
| donor #7 plasma | 71 | 86 | 36 | 166 | >617 | 187 | 545 |
| donor #8 plasma | 9.4 | 294 | 35 | 166 | 3 | 428 | 22 |
| donor #9 plasma | 4.3 | 330 | 65 | 166 | 0.55 | 299 | 3.3 |
| Stimulationsindices | | | | | | | |

FIG. 15E.5

| | EN-RAGE ng/mL | Eotaxin pg/mL | Epiregulin pg/mL | Erythropoietin pg/mL | Fatty Acid Binding Protein ng/mL | Factor VII ng/mL | Ferritin ng/mL |
|---|---|---|---|---|---|---|---|
| Least Detectable Dose | 0.25 | | | | | | 1.4 |
| RBM Low Plasma Range | 4.6 | 41 | 36 | 166 | 3.0 | 1.0 | 5.0 |
| RBM High Plasma Range | 592 | 177 | Pending | 284 | 10 | 106 | 552 |
| | | | Pending | | | 443 | |
| patient 1 | | | | | | | |
| patient 7 | | | | | | | |
| patient 2 | | | | | | | |
| patient 3 | | | | | | | |
| patient 5 | | | | | | | |
| patient 4 | | | | | | | |
| patient 6 | | | | | | | |
| NHD 1 | | | | | | | |
| NHD 2 | | | | | | | |

FIG. 15E.6

| | EN-RAGE ng/mL | Eotaxin pg/mL | Epiregulin pg/mL | Erythropoietin pg/mL | Fatty Acid Binding Protein ng/mL | Factor VII ng/mL | Ferritin ng/mL |
|---|---|---|---|---|---|---|---|
| Least Detectable Dose | 0.25 | 41 | 36 | 166 | 3.0 | 1.0 | 1.4 |
| RBM Low Plasma Range | 4.6 | | Pending | | | 106 | 5.0 |
| RBM High Plasma Range | 592 | 177 | Pending | 284 | 10 | 443 | 552 |
| patient 1 | | | | | | | |
| patient 7 | | | | | | | |
| patient 2 | | | | | | | |
| patient 3 | | | | | | | |
| patient 5 | | | | | | | |
| patient 4 | | | | | | | |
| patient 6 | | | | | | | |
| NHD 1 | | | | | | | |
| NHD 2 | | | | | | | |

FIG. 15E.7
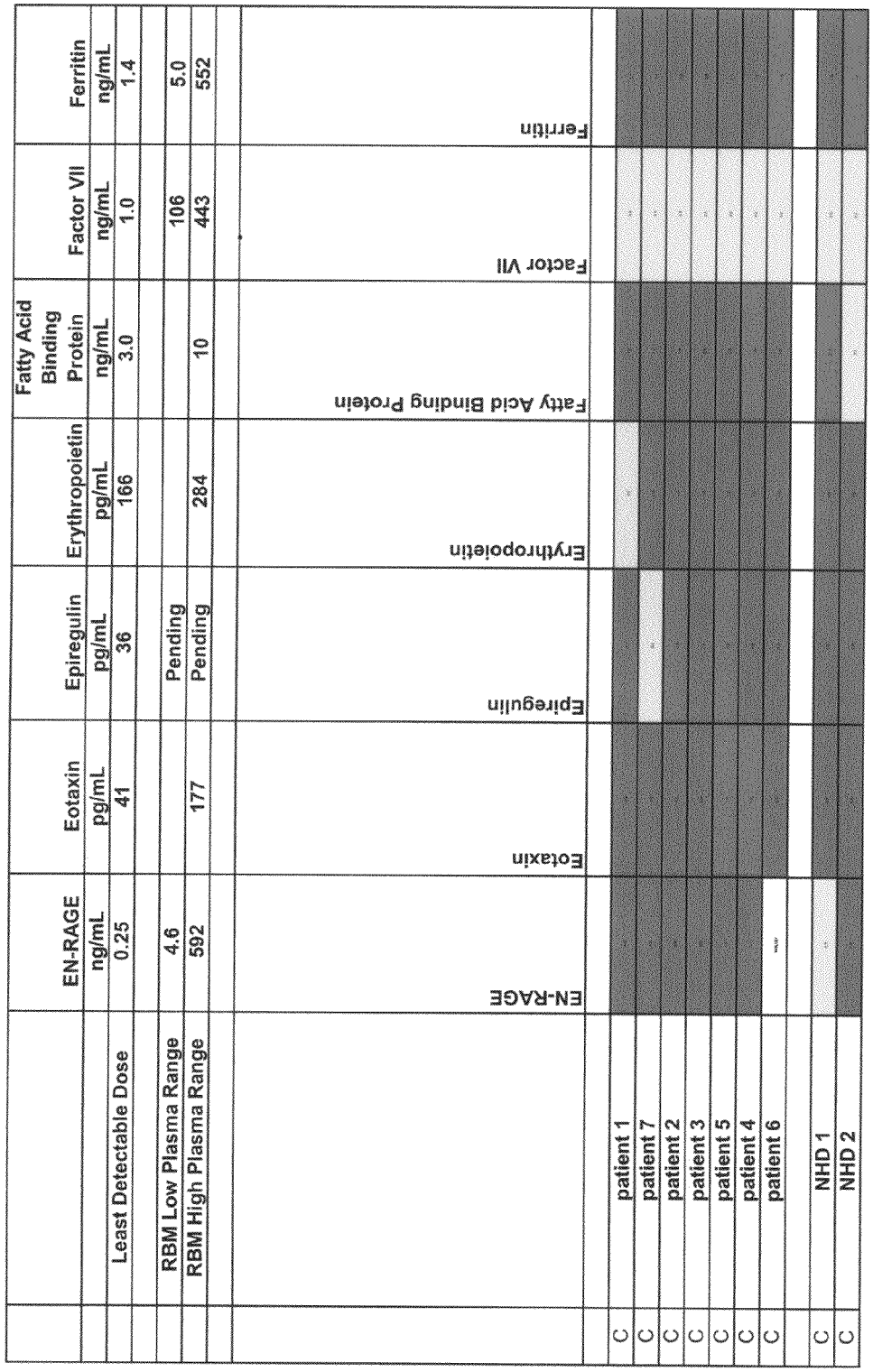

FIG. 15E.8

| | EN-RAGE ng/mL | Eotaxin pg/mL | Epiregulin pg/mL | Erythropoietin pg/mL | Fatty Acid Binding Protein ng/mL | Factor VII ng/mL | Ferritin ng/mL |
|---|---|---|---|---|---|---|---|
| Least Detectable Dose | 0.25 | 41 | 36 | 166 | 3.0 | 1.0 | 1.4 |
| RBM Low Plasma Range | 4.6 | 177 | Pending | 284 | 10 | 106 | 5.0 |
| RBM High Plasma Range | 592 | | Pending | | | 443 | 552 |
| patient 1 | D | | | | | | |
| patient 7 | D | | | | | | |
| patient 2 | D | | | | | | |
| patient 3 | D | | | | | | |
| patient 5 | D | | | | | | |
| patient 4 | D | | | | | | |
| patient 6 | D | | | | | | |
| NHD 1 | D | | | | | | |
| NHD 2 | D | | | | | | |

FIG. 15E.9

| | EN-RAGE ng/mL | Eotaxin pg/mL | Epiregulin pg/mL | Erythropoietin pg/mL | Fatty Acid Binding Protein ng/mL | Factor VII ng/mL | Ferritin ng/mL |
|---|---|---|---|---|---|---|---|
| Least Detectable Dose | 0.25 | | | | | 1.0 | 1.4 |
| RBM Low Plasma Range | 4.6 | 41 | 36 | 166 | 3.0 | 106 | 5.0 |
| RBM High Plasma Range | 592 | 177 | Pending | 284 | 10 | 443 | 552 |
| | EN-RAGE | Eotaxin | Epiregulin | Erythropoietin | Fatty Acid Binding Protein | Factor VII | Ferritin |
| patient 1 | | | | | | | |
| patient 7 | | | | | | | |
| patient 2 | | | | | | | |
| patient 3 | | | | | | | |
| patient 5 | | | | | | | |
| patient 4 | | | | | | | |
| patient 6 | | | | | | | |
| NHD 1 | | | | | | | |
| NHD 2 | | | | | | | |

FIG. 15E.10

| | EN-RAGE ng/mL | Eotaxin pg/mL | Epiregulin pg/mL | Erythropoietin pg/mL | Fatty Acid Binding Protein ng/mL | Factor VII ng/mL | Ferritin ng/mL |
|---|---|---|---|---|---|---|---|
| Least Detectable Dose | 0.25 | 41 | 36 | 166 | 3.0 | 1.0 | 1.4 |
| RBM Low Plasma Range | 4.6 | 177 | Pending | | | 106 | 5.0 |
| RBM High Plasma Range | 592 | | Pending | 284 | 10 | 443 | 552 |
| patient 1 | | | | | | | |
| patient 7 | | | | | | | |
| patient 2 | | | | | | | |
| patient 3 | | | | | | | |
| patient 5 | | | | | | | |
| patient 4 | | | | | | | |
| patient 6 | | | | | | | |
| NHD 1 | | | | | | | |
| NHD 2 | | | | | | | |

FIG. 15E.11
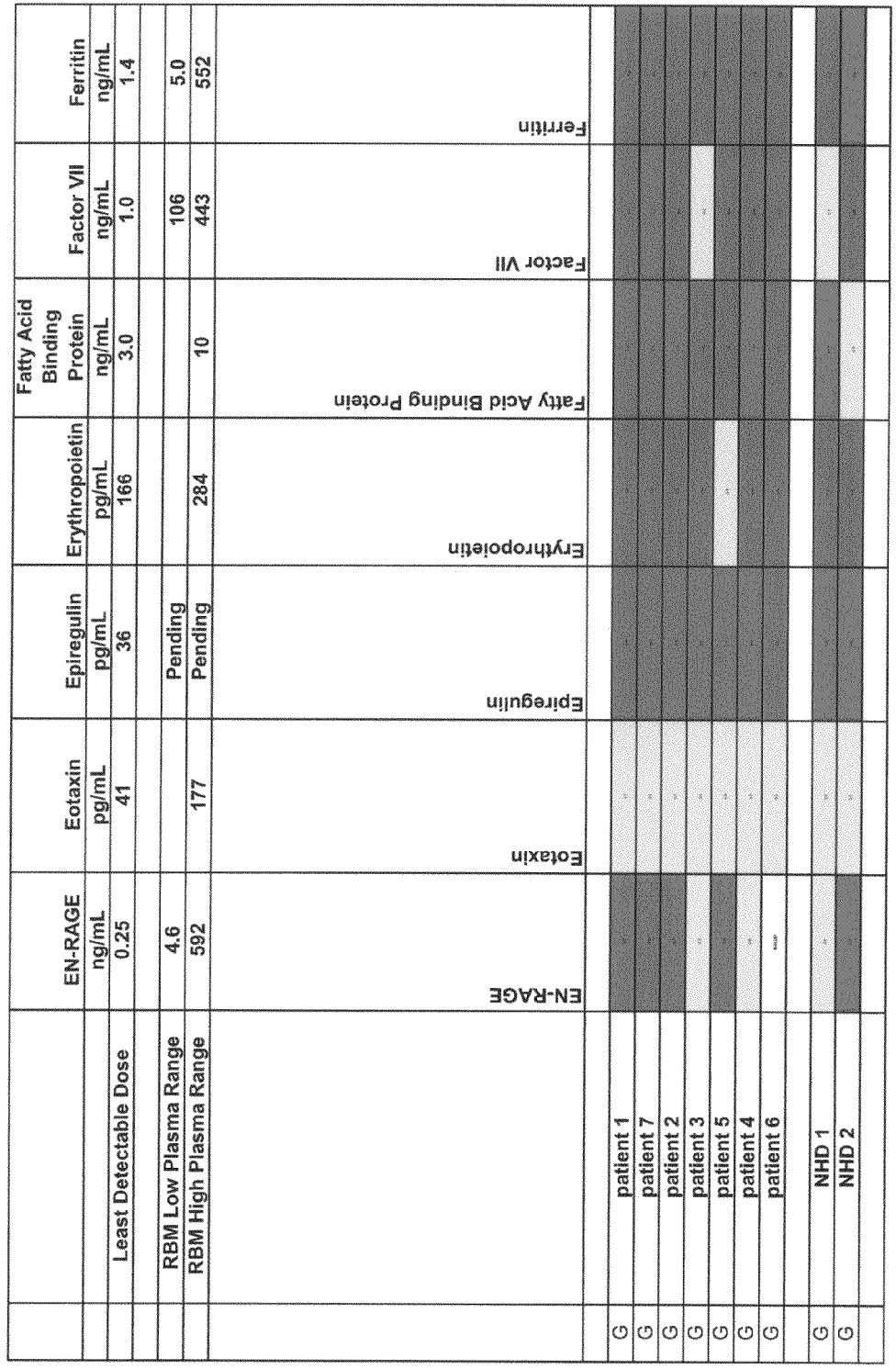

FIG. 15E.12

|  | EN-RAGE ng/mL | Eotaxin pg/mL | Epiregulin pg/mL | Erythropoietin pg/mL | Fatty Acid Binding Protein ng/mL | Factor VII ng/mL | Ferritin ng/mL |
|---|---|---|---|---|---|---|---|
| Least Detectable Dose | 0.25 | 41 | 36 | 166 | 3.0 | 1.0 | 1.4 |
| RBM Low Plasma Range | 4.6 |  | Pending |  |  | 106 | 5.0 |
| RBM High Plasma Range | 592 | 177 | Pending | 284 | 10 | 443 | 552 |

| | |
|---|---|
| patient 1 | H |
| patient 7 | H |
| patient 2 | H |
| patient 3 | H |
| patient 5 | H |
| patient 4 | H |
| patient 6 | H |
| NHD 1 | H |
| NHD 2 | H |

FIG. 15E.13

| | EN-RAGE ng/mL | Eotaxin pg/mL | Epiregulin pg/mL | Erythropoietin pg/mL | Fatty Acid Binding Protein ng/mL | Factor VII ng/mL | Ferritin ng/mL |
|---|---|---|---|---|---|---|---|
| Least Detectable Dose | 0.25 | | | | | 1.0 | 1.4 |
| RBM Low Plasma Range | 4.6 | 41 | 36 | 166 | 3.0 | 106 | 5.0 |
| RBM High Plasma Range | 592 | 177 | Pending | 284 | 10 | 443 | 552 |
| patient 1 | | | Pending | | | | |
| patient 7 | | | | | | | |
| patient 2 | | | | | | | |
| patient 3 | | | | | | | |
| patient 5 | | | | | | | |
| patient 4 | | | | | | | |
| patient 6 | | | | | | | |
| NHD 1 | | | | | | | |
| NHD 2 | | | | | | | |

FIG. 15E.14

| | EN-RAGE ng/mL | Eotaxin pg/mL | Epiregulin pg/mL | Erythropoietin pg/mL | Fatty Acid Binding Protein ng/mL | Factor VII ng/mL | Ferritin ng/mL |
|---|---|---|---|---|---|---|---|
| Least Detectable Dose | 0.25 | 41 | 36 | 166 | 3.0 | 1.0 | 1.4 |
| RBM Low Plasma Range | 4.6 | | Pending | | | 106 | 5.0 |
| RBM High Plasma Range | 592 | 177 | Pending | 284 | 10 | 443 | 552 |
| Messwert > ULD | | | | | | | |
| SI > 1,3 | | | | | | | |
| SI 0,7-1,3 | | | | | | | |
| SI 0-0,7 | | | | | | | |
| | | | | | | | |

FIG. 15F.1

| | FGF basic pg/mL | Fibrinogen mg/mL | G-CSF pg/mL | Growth Hormone ng/mL | GM-CSF pg/mL | Glutathione S-Transferase ng/mL | Haptoglobin mg/mL |
|---|---|---|---|---|---|---|---|
| Least Detectable Dose | 98 | 0.0098 | 5.0 | 0.13 | 57 | 0.40 | 0.025 |
| RBM Low Plasma Range | | 2.2 | | | | | 0.047 |
| RBM High Plasma Range | 2000 | 8.0 | 37 | 4.4 | 152 | 3.1 | 7.6 |
| Samples | | | | | | | |
| Donor_1 3. Aliquot A | 1850 | 4.1 | 417 | 1.8 | 8.4 | 0.64 | 1.0 |
| Donor_1 3. Aliquot B | 1710 | 4.4 | 279 | 1.7 | 2.5 | 0.84 | 1.2 |
| Donor_1 3. Aliquot C | 414 | 4.2 | 221 | 1.9 | 5.0 | 0.55 | 1.1 |
| Donor_1 3. Aliquot D | 2050 | 4.8 | 355 | 2.1 | 4.5 | 0.69 | 1.2 |
| Donor_1 3. Aliquot E | 1840 | 4.1 | 270 | 2.0 | 10 | 0.59 | 1.2 |
| Donor_1 3. Aliquot F | 1400 | 3.7 | 197 | 1.5 | 2.5 | 0.50 | 1.2 |
| Donor_1 3. Aliquot G | 1760 | 4.6 | 236 | 1.8 | 57 | 0.52 | 1.2 |
| Donor_1 3. Aliquot H | 159 | 4.0 | 211 | 1.8 | 4.5 | 0.52 | 1.1 |
| Donor_1 3. Aliquot I | 1470 | 4.4 | 219 | 1.8 | 4.0 | 0.55 | 1.1 |
| Donor_2 3. Aliquot A | 429 | 4.3 | 344 | 0.77 | 12 | 0.4 | 1.3 |
| Donor_2 3. Aliquot B | 321 | 4.4 | 204 | 0.90 | 5.0 | 0.76 | 1.8 |
| Donor_2 3. Aliquot C | 241 | 5.1 | 31 | 0.82 | 57 | 0.55 | 1.9 |
| Donor_2 3. Aliquot D | 563 | 4.3 | 1470 | 1.2 | 24 | 1.7 | 1.5 |
| Donor_2 3. Aliquot E | 563 | 4.0 | 1240 | 0.91 | 4.5 | 0.81 | 2.2 |
| Donor_2 3. Aliquot F | 241 | 4.1 | 32 | 0.70 | 3.5 | 0.41 | 2.1 |
| Donor_2 3. Aliquot G | 664 | 5.3 | 2160 | 0.87 | 180 | 0.69 | 2.3 |
| Donor_2 3. Aliquot H | 176 | 3.9 | 36 | 0.78 | 3.5 | 0.4 | 1.9 |
| Donor_2 3. Aliquot I | 225 | 5.2 | 32 | 0.71 | 57 | 0.4 | 1.7 |
| Donor_3 3. Aliquot A | 98 | 5.9 | 105 | 1.5 | 10 | 0.46 | 0.014 |
| Donor_3 3. Aliquot B | 29 | 5.5 | 41 | 1.4 | 7.8 | 1.4 | 0.018 |
| Donor_3 3. Aliquot C | 29 | 4.9 | 5 | 1.5 | 2.5 | 0.48 | 0.019 |
| Donor_3 3. Aliquot D | 209 | 5.2 | 1340 | 1.5 | 6.7 | 1.4 | 0.013 |
| Donor_3 3. Aliquot E | 159 | 6.0 | 1200 | 1.6 | 23 | 0.94 | 0.014 |
| Donor_3 3. Aliquot F | 29 | 5.2 | 5 | 1.3 | 18 | 0.4 | 0.021 |
| Donor_3 3. Aliquot G | 52 | 6.6 | 7.3 | 1.7 | 57 | 0.4 | 0.087 |

FIG. 15F.2

| | FGF basic pg/mL | Fibrinogen mg/mL | G-CSF pg/mL | Growth Hormone ng/mL | GM-CSF pg/mL | Glutathione S-Transferase ng/mL | Haptoglobin mg/mL |
|---|---|---|---|---|---|---|---|
| Least Detectable Dose | 98 | 0.0098 | 5.0 | 0.13 | 57 | 0.40 | 0.025 |
| RBM Low Plasma Range | | 2.2 | | | | | 0.047 |
| RBM High Plasma Range | 2000 | 8.0 | 37 | 4.4 | 152 | 3.1 | 7.6 |
| Donor_3_3. Aliquot H | 98 | 5.3 | 5 | 1.3 | 57 | 0.4 | 0.022 |
| Donor_3_3. Aliquot I | 29 | 6.2 | 5 | 1.6 | 57 | 0.4 | 0.051 |
| Donor_4_3. Aliquot A | 98 | 2.0 | 5.6 | 4.1 | 3.5 | 0.4 | 0.0075 |
| Donor_4_3. Aliquot B | 52 | 2.0 | 9.6 | 4.2 | 57 | 0.99 | 0.014 |
| Donor_4_3. Aliquot C | 29 | 2.2 | 5 | 4.0 | 57 | 0.4 | 0.0086 |
| Donor_4_3. Aliquot D | 459 | 2.0 | 976 | 4.2 | 18 | 1.2 | 0.014 |
| Donor_4_3. Aliquot E | 474 | 1.3 | 779 | 3.7 | 22 | 0.59 | 0.0086 |
| Donor_4_3. Aliquot F | 99 | 1.8 | 18 | 3.3 | 5.0 | 0.4 | 0.019 |
| Donor_4_3. Aliquot G | 90 | 2.2 | 8.8 | 3.6 | 57 | 0.37 | 0.019 |
| Donor_4_3. Aliquot H | 98 | 1.7 | 5 | 4.1 | 57 | 0.39 | 0.013 |
| Donor_4_3. Aliquot I | 52 | 2.0 | 5 | 4.2 | 2.5 | 0.4 | 0.011 |
| Donor_5_3. Aliquot A | 489 | 5.4 | 130 | 4.2 | 5.6 | 0.89 | 3.7 |
| Donor_5_3. Aliquot B | 533 | 5.9 | 203 | 3.9 | 57 | 0.64 | 3.6 |
| Donor_5_3. Aliquot C | 241 | 6.9 | 22 | 4.0 | 57 | 0.64 | 3.8 |
| Donor_5_3. Aliquot D | 563 | 3.4 | 1480 | 3.7 | 23 | 1.3 | 3.4 |
| Donor_5_3. Aliquot E | 53.3 | 5.2 | 3960 | 4.1 | 32 | 1.1 | 3.2 |
| Donor_5_3. Aliquot F | 257 | 4.4 | 29 | 3.0 | 57 | 0.4 | 3.1 |
| Donor_5_3. Aliquot G | 273 | 7.2 | 31 | 4.7 | 3.5 | 0.4 | 3.5 |
| Donor_5_3. Aliquot H | 176 | 5.5 | 23 | 4.0 | 6.7 | 0.4 | 3.2 |
| Donor_5_3. Aliquot I | 159 | 6.6 | 21 | 3.8 | 57 | 0.50 | 3.4 |
| Donor_6_3. Aliquot A | 72 | 4.1 | 12 | 3.0 | 7.8 | 0.4 | 4.2 |
| Donor_6_3. Aliquot B | 98 | 4.3 | 19 | 3.1 | 20 | 1.3 | 4.4 |
| Donor_6_3. Aliquot C | 98 | 4.9 | 5 | 2.8 | 3.0 | 0.4 | 4.2 |
| Donor_6_3. Aliquot D | 289 | 3.9 | 389 | 3.1 | 4.0 | 0.66 | 4.3 |
| Donor_6_3. Aliquot E | 289 | 3.2 | 975 | 2.9 | 7.8 | 1.4 | 3.9 |

FIG. 15F.3

| | FGF basic | Fibrinogen | G-CSF | Growth Hormone | GM-CSF | Glutathione S-Transferase | Haptoglobin |
|---|---|---|---|---|---|---|---|
| | pg/mL | mg/mL | pg/mL | ng/mL | pg/mL | ng/mL | mg/mL |
| Least Detectable Dose | 98 | 0.0098 | 5.0 | 0.13 | 57 | 0.40 | 0.025 |
| RBM Low Plasma Range | | 2.2 | | | | | 0.047 |
| RBM High Plasma Range | 2000 | 8.0 | 37 | 4.4 | 152 | 3.1 | 7.6 |
| Donor_6_3. Aliquot F | 98 | 3.2 | 5 | 2.8 | 9.0 | 0.4 | 4.3 |
| Donor_6_3. Aliquot G | 192 | 5.5 | 20 | 3.2 | 6.7 | 0.4 | 4.2 |
| Donor_6_3. Aliquot H | 98 | 3.9 | 5 | 3.1 | 7.2 | 0.4 | 4.1 |
| Donor_6_3. Aliquot I | 98 | 3.4 | 5 | 3.0 | 57 | 0.37 | 3.7 |
| Donor_7_3. Aliquot A | 391 | 3.0 | 334 | 0.32 | 20 | 0.39 | 2.6 |
| Donor_7_3. Aliquot B | 249 | 2.9 | 86 | 0.39 | 10 | 1.2 | 2.7 |
| Donor_7_3. Aliquot C | 98 | 3.2 | 5 | 0.22 | 5.6 | 0.48 | 2.7 |
| Donor_7_3. Aliquot D | 281 | 2.6 | 892 | 0.39 | 18 | 0.86 | 2.0 |
| Donor_7_3. Aliquot E | 265 | 2.1 | 270 | 0.31 | 18 | 0.50 | 1.9 |
| Donor_7_3. Aliquot F | 98 | 2.6 | 5 | 0.26 | 10 | 0.4 | 2.6 |
| Donor_7_3. Aliquot G | 233 | 2.9 | 5 | 0.23 | 3.0 | 0.4 | 2.3 |
| Donor_7_3. Aliquot H | 72 | 2.4 | 5 | 0.25 | 9.0 | 0.4 | 2.6 |
| Donor_7_3. Aliquot I | 98 | 3.0 | 5 | 0.29 | 9.0 | 0.4 | 2.7 |
| Donor_8_3. Aliquot A | 98 | 1.8 | 5.8 | 0.35 | 5.0 | 0.37 | 0.014 |
| Donor_8_3. Aliquot B | 98 | 1.7 | 4.7 | 0.35 | 6.7 | 1.8 | 0.016 |
| Donor_8_3. Aliquot C | 90 | 1.8 | 5 | 0.20 | 12 | 0.4 | 0.0065 |
| Donor_8_3. Aliquot D | 414 | 1.7 | 1330 | 0.94 | 60 | 3.4 | 0.013 |
| Donor_8_3. Aliquot E | 336 | 1.7 | 1010 | 0.90 | 33 | 2.1 | 0.037 |
| Donor_8_3. Aliquot F | 273 | 1.7 | 4.7 | 0.36 | 18 | 0.4 | 0.018 |
| Donor_8_3. Aliquot G | 98 | 2.0 | 5 | 0.33 | 3.5 | 0.4 | 0.016 |
| Donor_8_3. Aliquot H | 142 | 1.7 | 5 | 0.30 | 17 | 0.4 | 0.016 |
| Donor_8_3. Aliquot I | 98 | 1.9 | 5 | 0.28 | 14 | 0.55 | 0.011 |
| Donor_9_3. Aliquot A | 98 | 1.5 | 17 | 7.2 | 11 | 0.73 | 0.018 |
| Donor_9_3. Aliquot B | 122 | 1.6 | 21 | 6.8 | 13 | 2.2 | 0.018 |
| Donor_9_3. Aliquot C | 94 | 1.4 | 19 | 6.6 | 21 | 0.40 | 0.012 |

FIG. 15F.4

| | FGF basic pg/mL | Fibrinogen mg/mL | G-CSF pg/mL | Growth Hormone ng/mL | GM-CSF pg/mL | Glutathione S-Transferase ng/mL | Haptoglobin mg/mL |
|---|---|---|---|---|---|---|---|
| Least Detectable Dose | 98 | 0.0098 | 5.0 | 0.13 | 57 | 0.40 | 0.025 |
| RBM Low Plasma Range | | 2.2 | | | | | 0.047 |
| RBM High Plasma Range | 2000 | 8.0 | 37 | 4.4 | 152 | 3.1 | 7.6 |
| Donor_9_3. Aliquot D | 414 | 1.5 | 2320 | 6.8 | 29 | 2.6 | 0.0062 |
| Donor_9_3. Aliquot E | 332 | 1.5 | 1490 | 6.8 | 13 | 2.4 | 0.013 |
| Donor_9_3. Aliquot F | 137 | 1.2 | 11 | 6.4 | 5.8 | 0.76 | 0.0076 |
| Donor_9_3. Aliquot G | 179 | 1.9 | 39 | 6.2 | 17 | 0.56 | 0.016 |
| Donor_9_3. Aliquot H | 37 | 1.3 | 5.4 | 6.8 | 15 | 0.53 | 0.017 |
| Donor_9_3. Aliquot I | 37 | 1.6 | 5.4 | 6.4 | 8.7 | 0.37 | 0.012 |
| EDTA Plasma | | | | | | | |
| donor #1 plasma | 736 | 4.6 | 240 | 1.4 | 18 | 1.1 | 1.3 |
| donor #2 plasma | 339 | 8.1 | 45 | 0.89 | 15 | 0.4 | 3.6 |
| donor #3 plasma | 94 | 8.7 | 5 | 1.5 | 27 | 1.0 | 0.58 |
| donor #4 plasma | 51 | 3.2 | 4.5 | 5.3 | 10.0 | 0.4 | 0.0097 |
| donor #5 plasma | 346 | 11 | 24 | 5.1 | 23 | 1.3 | 5.9 |
| donor #6 plasma | 21 | 6.7 | 6.2 | 4.1 | 20 | 0.69 | 5.7 |
| donor #7 plasma | 98 | 4.5 | 6.2 | 0.49 | 17 | 0.4 | 4.6 |
| donor #8 plasma | 87 | 2.0 | 5 | 0.38 | 15 | 0.46 | 0.36 |
| donor #9 plasma | 87 | 2.3 | 18 | 7.2 | 5.3 | 0.90 | 0.32 |
| Stimulationsindices | | | | | | | |

FIG. 15F.5

| | FGF basic pg/mL | Fibrinogen mg/mL | G-CSF pg/mL | Growth Hormone ng/mL | GM-CSF pg/mL | Glutathione S-Transferase ng/mL | Haptoglobin mg/mL |
|---|---|---|---|---|---|---|---|
| Least Detectable Dose | 98 | 0.0098 | 5.0 | 0.13 | 57 | 0.40 | 0.025 |
| RBM Low Plasma Range | | 2.2 | | | | | 0.047 |
| RBM High Plasma Range | 2000 | 8.0 | 37 | 4.4 | 152 | 3.1 | 7.6 |
| | FGF basic | Fibrinogen | G-CSF | Growth Hormone | GM-CSF | Glutathione S-Transferase | Haptoglobin |
| patient 1 | A | | | | | | |
| patient 7 | A | | | | | | |
| patient 2 | A | | | | | | |
| patient 3 | A | | | | | | |
| patient 5 | A | | | | | | |
| patient 4 | A | | | | | | |
| patient 6 | A | | | | | | |
| NHD 1 | A | | | | | | |
| NHD 2 | A | | | | | | |

FIG. 15F.6

| | FGF basic pg/mL | Fibrinogen mg/mL | G-CSF pg/mL | Growth Hormone ng/mL | GM-CSF pg/mL | Glutathione S-Transferase ng/mL | Haptoglobin mg/mL |
|---|---|---|---|---|---|---|---|
| Least Detectable Dose | 98 | 0.0098 | 5.0 | 0.13 | 57 | 0.40 | 0.025 |
| RBM Low Plasma Range | | 2.2 | | | | | 0.047 |
| RBM High Plasma Range | 2000 | 8.0 | 37 | 4.4 | 152 | 3.1 | 7.6 |

| | |
|---|---|
| patient 1 | B |
| patient 7 | B |
| patient 2 | B |
| patient 3 | B |
| patient 5 | B |
| patient 4 | B |
| patient 6 | B |
| NHD 1 | B |
| NHD 2 | B |

FIG. 15F.7

| | FGF basic pg/mL | Fibrinogen mg/mL | G-CSF pg/mL | Growth Hormone ng/mL | GM-CSF pg/mL | Glutathione S-Transferase ng/mL | Haptoglobin mg/mL |
|---|---|---|---|---|---|---|---|
| Least Detectable Dose | 98 | 0.0098 | 5.0 | 0.13 | 57 | 0.40 | 0.025 |
| RBM Low Plasma Range | | 2.2 | | | | | 0.047 |
| RBM High Plasma Range | 2000 | 8.0 | 37 | 4.4 | 152 | 3.1 | 7.6 |

FIG. 15F.8

| | FGF basic | Fibrinogen | G-CSF | Growth Hormone | GM-CSF | Glutathione S-Transferase | Haptoglobin |
|---|---|---|---|---|---|---|---|
| | pg/mL | mg/mL | pg/mL | ng/mL | pg/mL | ng/mL | mg/mL |
| Least Detectable Dose | 98 | 0.0098 | 5.0 | 0.13 | 57 | 0.40 | 0.025 |
| RBM Low Plasma Range | | 2.2 | | | | | 0.047 |
| RBM High Plasma Range | 2000 | 8.0 | 37 | 4.4 | 152 | 3.1 | 7.6 |

| | FGF basic | Fibrinogen | G-CSF | Growth Hormone | GM-CSF | Glutathione S-Transferase | Haptoglobin |
|---|---|---|---|---|---|---|---|
| patient 1 | D | | | | | | |
| patient 7 | D | | | | | | |
| patient 2 | D | | | | | | |
| patient 3 | D | | | | | | |
| patient 5 | D | | | | | | |
| patient 4 | D | | | | | | |
| patient 6 | D | | | | | | |
| NHD 1 | D | | | | | | |
| NHD 2 | D | | | | | | |

FIG. 15F.9

| | FGF basic pg/mL | Fibrinogen mg/mL | G-CSF pg/mL | Growth Hormone ng/mL | GM-CSF pg/mL | Glutathione S-Transferase ng/mL | Haptoglobin mg/mL |
|---|---|---|---|---|---|---|---|
| Least Detectable Dose | 98 | 0.0098 | 5.0 | 0.13 | 57 | 0.40 | 0.025 |
| RBM Low Plasma Range | | 2.2 | | | | | 0.047 |
| RBM High Plasma Range | 2000 | 8.0 | 37 | 4.4 | 152 | 3.1 | 7.6 |
| patient 1 | | | | | | | |
| patient 7 | | | | | | | |
| patient 2 | | | | | | | |
| patient 3 | | | | | | | |
| patient 5 | | | | | | | |
| patient 4 | | | | | | | |
| patient 6 | | | | | | | |
| NHD 1 | | | | | | | |
| NHD 2 | | | | | | | |

FIG. 15F.10

| | FGF basic pg/mL | Fibrinogen mg/mL | G-CSF pg/mL | Growth Hormone ng/mL | GM-CSF pg/mL | Glutathione S-Transferase ng/mL | Haptoglobin mg/mL |
|---|---|---|---|---|---|---|---|
| Least Detectable Dose | 98 | 0.0098 | 5.0 | 0.13 | 57 | 0.40 | 0.025 |
| RBM Low Plasma Range | | 2.2 | | | | | 0.047 |
| RBM High Plasma Range | 2000 | 8.0 | 37 | 4.4 | 152 | 3.1 | 7.6 |

| | FGF basic | Fibrinogen | G-CSF | Growth Hormone | Glutathione S-Transferase | GM-CSF | Haptoglobin |
|---|---|---|---|---|---|---|---|
| patient 1 | F | | | | | | |
| patient 7 | F | | | | | | |
| patient 2 | F | | | | | | |
| patient 3 | F | | | | | | |
| patient 5 | F | | | | | | |
| patient 4 | F | | | | | | |
| patient 6 | F | | | | | | |
| NHD 1 | F | | | | | | |
| NHD 2 | F | | | | | | |

FIG. 15F.11

| | FGF basic pg/mL | Fibrinogen mg/mL | G-CSF pg/mL | Growth Hormone ng/mL | GM-CSF pg/mL | Glutathione S-Transferase ng/mL | Haptoglobin mg/mL |
|---|---|---|---|---|---|---|---|
| Least Detectable Dose | 98 | 0.0098 | 5.0 | 0.13 | 57 | 0.40 | 0.025 |
| RBM Low Plasma Range | | 2.2 | | | | | 0.047 |
| RBM High Plasma Range | 2000 | 8.0 | 37 | 4.4 | 152 | 3.1 | 7.6 |
| | FGF basic | Fibrinogen | G-CSF | Growth Hormone | GM-CSF | Glutathione S-Transferase | Haptoglobin |
| patient 1 | | | | | | | |
| patient 7 | | | | | | | |
| patient 2 | | | | | | | |
| patient 3 | | | | | | | |
| patient 5 | | | | | | | |
| patient 4 | | | | | | | |
| patient 6 | | | | | | | |
| NHD 1 | | | | | | | |
| NHD 2 | | | | | | | |

FIG. 15F.12

| | | FGF basic | Fibrinogen | G-CSF | Growth Hormone | GM-CSF | Glutathione S-Transferase | Haptoglobin |
|---|---|---|---|---|---|---|---|---|
| | | pg/mL | mg/mL | pg/mL | ng/mL | pg/mL | ng/mL | mg/mL |
| Least Detectable Dose | | 98 | 0.0098 | 5.0 | 0.13 | 57 | 0.40 | 0.025 |
| RBM Low Plasma Range | | | 2.2 | | | | | 0.047 |
| RBM High Plasma Range | | 2000 | 8.0 | 37 | 4.4 | 152 | 3.1 | 7.6 |
| patient 1 | H | | | | | | | |
| patient 7 | H | | | | | | | |
| patient 2 | H | | | | | | | |
| patient 3 | H | | | | | | | |
| patient 5 | H | | | | | | | |
| patient 4 | H | | | | | | | |
| patient 6 | H | | | | | | | |
| NHD 1 | H | | | | | | | |
| NHD 2 | H | | | | | | | |

FIG. 15F.13

| | FGF basic pg/mL | Fibrinogen mg/mL | G-CSF pg/mL | Growth Hormone ng/mL | GM-CSF pg/mL | Glutathione S-Transferase ng/mL | Haptoglobin mg/mL |
|---|---|---|---|---|---|---|---|
| Least Detectable Dose | 98 | 0.0098 | 5.0 | 0.13 | 57 | 0.40 | 0.025 |
| RBM Low Plasma Range | | 2.2 | | | | | 0.047 |
| RBM High Plasma Range | 2000 | 8.0 | 37 | 4.4 | 152 | 3.1 | 7.6 |
| | FGF basic | Fibrinogen | G-CSF | Growth Hormone | GM-CSF | Glutathione S-Transferase | Haptoglobin |
| patient 1 | | | | | | | |
| patient 7 | | | | | | | |
| patient 2 | | | | | | | |
| patient 3 | | | | | | | |
| patient 5 | | | | | | | |
| patient 4 | | | | | | | |
| patient 6 | | | | | | | |
| NHD 1 | | | | | | | |
| NHD 2 | | | | | | | |

FIG. 15F.14

| | FGF basic pg/mL | Fibrinogen mg/mL | G-CSF pg/mL | Growth Hormone ng/mL | GM-CSF pg/mL | Glutathione S-Transferase ng/mL | Haptoglobin mg/mL |
|---|---|---|---|---|---|---|---|
| Least Detectable Dose | 98 | 0.0098 | 5.0 | 0.13 | 57 | 0.40 | 0.025 |
| RBM Low Plasma Range | | 2.2 | | | | | 0.047 |
| RBM High Plasma Range | 2000 | 8.0 | 37 | 4.4 | 152 | 3.1 | 7.6 |
| Messwert > ULD | | | | | | | |
| SI > 1,3 | | | | | | | |
| SI 0,7-1,3 | | | | | | | |
| SI 0-0,7 | | | | | | | |

FIG. 15G.1

| | ICAM-1 ng/mL | IFN-gamma pg/mL | IgA mg/mL | IgE ng/mL | IGF-1 ng/mL | IgM mg/mL | IL-10 pg/mL | IL-12p40 ng/mL | IL-12p70 pg/mL |
|---|---|---|---|---|---|---|---|---|---|
| Least Detectable Dose | 3.2 | 4.6 | 0.0084 | 14 | 4.0 | 0.015 | 15 | 1.2 | 94 |
| RBM Low Plasma Range | 42 | Pending | 0.58 | 770 | 177 | 0.24 | 1.8 | | |
| RBM High Plasma Range | 213 | Pending | 5.6 | 770 | 177 | 3.3 | 38 | 2.7 | 165 |
| Samples | | | | | | | | | |
| Donor_1 3. Aliquot A | 467 | 3.8 | 2.0 | 13 | 49 | 0.63 | 180 | 0.30 | 45 |
| Donor_1 3. Aliquot B | 432 | 4.5 | 2.3 | 11 | 49 | 0.66 | 135 | 0.16 | 35 |
| Donor_1 3. Aliquot C | 452 | 2.7 | 2.2 | 1.8 | 67 | 0.68 | 15 | 1.2 | 28 |
| Donor_1 3. Aliquot D | 465 | 4.6 | 2.4 | 12 | 46 | 0.71 | 134 | 0.43 | 42 |
| Donor_1 3. Aliquot E | 438 | 4.6 | 2.1 | 13 | 45 | 0.63 | 58 | 0.13 | 37 |
| Donor_1 3. Aliquot F | 441 | 4.6 | 2.1 | 4.4 | 55 | 0.60 | 18 | 1.2 | 28 |
| Donor_1 3. Aliquot G | 471 | 4.5 | 2.3 | 11 | 100 | 0.70 | 15 | 0.19 | 39 |
| Donor_1 3. Aliquot H | 491 | 4.6 | 2.1 | 9.6 | 46 | 0.60 | 14 | 1.2 | 52 |
| Donor_1 3. Aliquot I | 438 | 4.6 | 2.3 | 6.2 | 46 | 0.65 | 16 | 1.2 | 32 |
| Donor_2 3. Aliquot A | 491 | 7.2 | 2.5 | 210 | 94 | 0.15 | 500 | 0.51 | 61 |
| Donor_2 3. Aliquot B | 495 | 6.7 | 2.5 | 217 | 90 | 0.15 | 483 | 0.26 | 35 |
| Donor_2 3. Aliquot C | 499 | 4.6 | 2.5 | 98 | 87 | 0.21 | 19 | 1.2 | 18 |
| Donor_2 3. Aliquot D | 489 | 31 | 2.4 | 258 | 81 | 0.14 | 977 | 2.8 | 40 |
| Donor_2 3. Aliquot E | 479 | 9.5 | 2.5 | 221 | 86 | 0.18 | 963 | 2.4 | 37 |
| Donor_2 3. Aliquot F | 504 | 4.6 | 2.5 | 177 | 73 | 0.17 | 28 | 0.26 | 45 |
| Donor_2 3. Aliquot G | 514 | 14 | 2.5 | 151 | 221 | 0.18 | 131 | 0.88 | 45 |
| Donor_2 3. Aliquot H | 490 | 2.7 | 2.6 | 175 | 75 | 0.18 | 22 | 1.2 | 35 |
| Donor_2 3. Aliquot I | 479 | 3.8 | 2.5 | 195 | 73 | 0.19 | 21 | 1.2 | 35 |
| Donor_3 3. Aliquot A | 283 | 8.5 | 1.5 | 26 | 380 | 0.66 | 480 | 0.43 | 50 |
| Donor_3 3. Aliquot B | 239 | 4.6 | 1.6 | 27 | 368 | 0.67 | 632 | 0.37 | 48 |
| Donor_3 3. Aliquot C | 278 | 4.6 | 1.6 | 7.6 | 408 | 0.66 | 26 | 0.13 | 55 |
| Donor_3 3. Aliquot D | 231 | 8.2 | 1.6 | 45 | 387 | 0.67 | 1640 | 3.3 | 45 |
| Donor_3 3. Aliquot E | 306 | 9.2 | 1.7 | 40 | 393 | 0.74 | 1660 | 2.7 | 55 |
| Donor_3 3. Aliquot F | 249 | 4.6 | 1.5 | 26 | 338 | 0.69 | 18 | 1.2 | 40 |
| Donor_3 3. Aliquot G | 259 | 4.6 | 1.6 | 14 | 546 | 0.72 | 11 | 1.2 | 35 |

FIG. 15G.2

| | ICAM-1 ng/mL | IFN-gamma pg/mL | IgA mg/mL | IgE ng/mL | IGF-1 ng/mL | IgM mg/mL | IL-10 pg/mL | IL-12p40 ng/mL | IL-12p70 pg/mL |
|---|---|---|---|---|---|---|---|---|---|
| Least Detectable Dose | 3.2 | 4.6 | 0.0084 | 14 | 4.0 | 0.015 | 15 | 1.2 | 94 |
| RBM Low Plasma Range | 42 | Pending | 0.58 | 770 | 177 | 0.24 | 1.8 | | 165 |
| RBM High Plasma Range | 213 | Pending | 5.6 | 770 | 177 | 3.3 | 38 | 2.7 | 165 |
| Donor_3 3. Aliquot H | 208 | 4.6 | 1.5 | 21 | 386 | 0.67 | 4.9 | 1.2 | 22 |
| Donor_3 3. Aliquot I | 221 | 4.6 | 1.5 | 29 | 403 | 0.69 | 11 | 1.2 | 42 |
| Donor_4 3. Aliquot A | 456 | 4.6 | 2.5 | 12 | 4 | 0.39 | 46 | 1.2 | 94 |
| Donor_4 3. Aliquot B | 466 | 4.6 | 2.3 | 14 | 4 | 0.29 | 251 | 1.2 | 94 |
| Donor_4 3. Aliquot C | 453 | 4.6 | 2.4 | 14 | 4 | 0.36 | 11 | 1.2 | 39 |
| Donor_4 3. Aliquot D | 471 | 6.2 | 2.2 | 32 | 4 | 0.31 | 566 | 3.1 | 39 |
| Donor_4 3. Aliquot E | 477 | 7.0 | 2.3 | 24 | 4 | 0.29 | 543 | 1.5 | 30 |
| Donor_4 3. Aliquot F | 467 | 3.8 | 2.3 | 13 | 4 | 0.31 | 232 | 0.37 | 24 |
| Donor_4 3. Aliquot G | 462 | 4.6 | 2.4 | 8.0 | 22 | 0.29 | 14 | 1.2 | 20 |
| Donor_4 3. Aliquot H | 474 | 4.6 | 2.3 | 8.0 | 4 | 0.28 | 10 | 1.2 | 15 |
| Donor_4 3. Aliquot I | 447 | 4.6 | 2.3 | 9.6 | 4 | 0.30 | 13 | 1.2 | 94 |
| Donor_5 3. Aliquot A | 241 | 7.5 | 1.1 | 321 | 323 | 0.24 | 117 | 0.34 | 20 |
| Donor_5 3. Aliquot B | 213 | 8.2 | 1.1 | 270 | 337 | 0.25 | 417 | 0.26 | 32 |
| Donor_5 3. Aliquot C | 246 | 4.6 | 1.1 | 84 | 330 | 0.24 | 7.0 | 1.2 | 26 |
| Donor_5 3. Aliquot D | 263 | 20 | 1.1 | 271 | 373 | 0.22 | 763 | 2.7 | 59 |
| Donor_5 3. Aliquot E | 261 | 21 | 1.2 | 274 | 382 | 0.23 | 1520 | 1.8 | 94 |
| Donor_5 3. Aliquot F | 164 | 7.2 | 1.0 | 204 | 350 | 0.23 | 37 | 1.2 | 20 |
| Donor_5 3. Aliquot G | 255 | 6.2 | 1.0 | 59 | 574 | 0.26 | 15 | 0.28 | 24 |
| Donor_5 3. Aliquot H | 223 | 3.8 | 1.0 | 296 | 355 | 0.26 | 10 | 1.2 | 28 |
| Donor_5 3. Aliquot I | 242 | 5.1 | 1.00 | 289 | 329 | 0.24 | 9.2 | 1.2 | 44 |
| Donor_6 3. Aliquot A | 130 | 4.6 | 0.79 | 317 | 47 | 0.38 | 85 | 0.13 | 32 |
| Donor_6 3. Aliquot B | 146 | 4.6 | 0.81 | 306 | 46 | 0.42 | 226 | 1.2 | 42 |
| Donor_6 3. Aliquot C | 157 | 4.6 | 0.78 | 139 | 54 | 0.37 | 7.0 | 1.2 | 50 |
| Donor_6 3. Aliquot D | 149 | 31 | 0.81 | 326 | 47 | 0.41 | 637 | 4.7 | 94 |
| Donor_6 3. Aliquot E | 120 | 74 | 0.94 | 269 | 50 | 0.34 | 1870 | 4.3 | 30 |

FIG. 15G.3

| | ICAM-1 ng/mL | IFN-gamma pg/mL | IgA mg/mL | IgE ng/mL | IGF-1 ng/mL | IgM mg/mL | IL-10 pg/mL | IL-12p40 ng/mL | IL-12p70 pg/mL |
|---|---|---|---|---|---|---|---|---|---|
| Least Detectable Dose | 3.2 | 4.6 | 0.0084 | 14 | 4.0 | 0.015 | 15 | 1.2 | 94 |
| RBM Low Plasma Range | 42 | Pending | 0.58 | 770 | 177 | 0.24 | 1.8 | | |
| RBM High Plasma Range | 213 | Pending | 5.6 | 222 | 45 | 3.3 | 38 | 2.7 | 165 |
| Donor_6_3. Aliquot F | 120 | 4.6 | 0.82 | 91 | 189 | 0.33 | 45 | 1.2 | 47 |
| Donor_6_3. Aliquot G | 156 | 4.6 | 0.81 | 340 | 42 | 0.35 | 7.0 | 1.2 | 20 |
| Donor_6_3. Aliquot H | 146 | 4.6 | 0.71 | 272 | 45 | 0.35 | 6.0 | 0.16 | 94 |
| Donor_6_3. Aliquot I | 127 | 4.6 | 0.76 | | | 0.34 | 7.0 | 1.2 | 94 |
| Donor_7_3. Aliquot A | 85 | 4.6 | 1.5 | 56 | 14 | 0.63 | 379 | 0.64 | 39 |
| Donor_7_3. Aliquot B | 85 | 4.6 | 1.5 | 51 | 18 | 0.59 | 441 | 0.27 | 32 |
| Donor_7_3. Aliquot C | 89 | 4.6 | 1.6 | 14 | 26 | 0.63 | 13 | 1.2 | 39 |
| Donor_7_3. Aliquot D | 74 | 4.6 | 1.4 | 62 | 15 | 0.59 | 390 | 0.93 | 39 |
| Donor_7_3. Aliquot E | 84 | 4.6 | 1.1 | 56 | 17 | 0.48 | 297 | 0.93 | 42 |
| Donor_7_3. Aliquot F | 83 | 4.6 | 1.5 | 39 | 9.8 | 0.66 | 85 | 1.2 | 34 |
| Donor_7_3. Aliquot G | 93 | 4.6 | 1.4 | 25 | 98 | 0.60 | 13 | 1.2 | 22 |
| Donor_7_3. Aliquot H | 81 | 4.6 | 1.4 | 36 | 8.1 | 0.60 | 6.8 | 1.2 | 94 |
| Donor_7_3. Aliquot I | 79 | 4.6 | 1.5 | 46 | 12 | 0.60 | 11 | 1.2 | 94 |
| Donor_8_3. Aliquot A | 61 | 5.6 | 0.77 | 17 | 176 | 0.30 | 102 | 0.30 | 34 |
| Donor_8_3. Aliquot B | 66 | 4.6 | 0.85 | 8.0 | 168 | 0.34 | 218 | 0.19 | 22 |
| Donor_8_3. Aliquot C | 50 | 550 | 0.83 | 14 | 163 | 0.31 | 4.9 | 0.57 | 3920 |
| Donor_8_3. Aliquot D | 63 | 1880 | 0.73 | 77 | 179 | 0.36 | 306 | 19 | 434 |
| Donor_8_3. Aliquot E | 59 | 283 | 0.73 | 65 | 162 | 0.32 | 1000 | 14 | 48 |
| Donor_8_3. Aliquot F | 63 | 118 | 0.85 | 15 | 166 | 0.32 | 219 | 0.71 | 42 |
| Donor_8_3. Aliquot G | 65 | 4.6 | 0.74 | 8.0 | 181 | 0.28 | 4.3 | 1.2 | 15 |
| Donor_8_3. Aliquot H | 64 | 41 | 0.84 | 10 | 177 | 0.37 | 4.1 | 0.23 | 30 |
| Donor_8_3. Aliquot I | 58 | 3.8 | 0.78 | 3.7 | 175 | 0.33 | 6.6 | 1.2 | 32 |
| Donor_9_3. Aliquot A | 79 | 17 | 1.0 | 9.3 | 745 | 1.0 | 220 | 0.26 | 52 |
| Donor_9_3. Aliquot B | 82 | 21 | 1.0 | 9.3 | 716 | 1.0 | 435 | 0.40 | 44 |
| Donor_9_3. Aliquot C | 69 | 519 | 1.0 | 4.1 | 784 | 0.97 | 43 | 0.80 | 1480 |

FIG. 15G.4

| | ICAM-1 ng/mL | IFN-gamma pg/mL | IgA mg/mL | IgE ng/mL | IGF-1 ng/mL | IgM mg/mL | IL-10 pg/mL | IL-12p40 ng/mL | IL-12p70 pg/mL |
|---|---|---|---|---|---|---|---|---|---|
| Least Detectable Dose | 3.2 | 4.6 | 0.0084 | 14 | 4.0 | 0.015 | 15 | 1.2 | 94 |
| RBM Low Plasma Range | 42 | Pending | 0.58 | | | 0.24 | 1.8 | | |
| RBM High Plasma Range | 213 | Pending | 5.6 | 770 | 177 | 3.3 | 38 | 2.7 | 165 |
| Donor_9 3. Aliquot D | 75 | 2360 | 1.0 | 63 | 681 | 1.0 | 1080 | 17 | 89 |
| Donor_9 3. Aliquot E | 71 | 490 | 1.00 | 39 | 651 | 1.0 | 1730 | 11 | 54 |
| Donor_9 3. Aliquot F | 78 | 26 | 1.0 | 5.8 | 688 | 0.95 | 122 | 0.34 | 46 |
| Donor_9 3. Aliquot G | 68 | 7.6 | 1.1 | 5.2 | 636 | 1.1 | 13 | 0.25 | 41 |
| Donor_9 3. Aliquot H | 75 | 9.0 | 1.0 | 6.0 | 703 | 1.0 | 14 | 0.24 | 56 |
| Donor_9 3. Aliquot I | 76 | 14 | 1.0 | 6.2 | 732 | 1.1 | 4.2 | 1.2 | 31 |
| EDTA Plasma | | | | | | | | | |
| donor #1 plasma | 206 | 4.0 | 2.4 | 6.6 | 4 | 0.57 | 16 | 0.26 | 34 |
| donor #2 plasma | 371 | 10 | 4.0 | 172 | 4 | 0.22 | 21 | 0.19 | 23 |
| donor #3 plasma | 171 | 5.8 | 2.8 | 26 | 12 | 0.93 | 9.9 | 1.2 | 49 |
| donor #4 plasma | 348 | 4.6 | 3.6 | 14 | 4 | 0.39 | 14 | 1.2 | 33 |
| donor #5 plasma | 136 | 13 | 1.8 | 318 | 18 | 0.32 | 12 | 0.15 | 56 |
| donor #6 plasma | 129 | 4.6 | 1.3 | 559 | 4 | 0.43 | 10 | 1.2 | 34 |
| donor #7 plasma | 109 | 5.8 | 2.4 | 81 | 4 | 0.79 | 16 | 1.2 | 23 |
| donor #8 plasma | 87 | 4.6 | 1.0 | 17 | 32 | 0.38 | 2.3 | 1.2 | 39 |
| donor #9 plasma | 100 | 4.0 | 1.4 | 3.5 | 325 | 1.5 | 5.1 | 0.14 | 35 |
| *Stimulations Indices* | | | | | | | | | |

FIG. 15G.5

| | ICAM-1 ng/mL | IFN-gamma pg/mL | IgA mg/mL | IgE ng/mL | IGF-1 ng/mL | IgM mg/mL | IL-10 pg/mL | IL-12p40 ng/mL | IL-12p70 pg/mL |
|---|---|---|---|---|---|---|---|---|---|
| Least Detectable Dose | 3.2 | 4.6 | 0.0084 | 14 | 4.0 | 0.015 | 15 | 1.2 | 94 |
| RBM Low Plasma Range | 42 | Pending | 0.58 | | | 0.24 | 1.8 | | |
| RBM High Plasma Range | 213 | Pending | 5.6 | 770 | 177 | 3.3 | 38 | 2.7 | 165 |

| | ICAM-1 | IFN-gamma | IgA | IgE | IGF-1 | IgM | IL-10 | IL-12p40 | IL-12p70 |
|---|---|---|---|---|---|---|---|---|---|
| patient 1 | A | | | | | | | | |
| patient 7 | A | | | | | | | | |
| patient 2 | A | | | | | | | | |
| patient 3 | A | | | | | | | | |
| patient 5 | A | | | | | | | | |
| patient 4 | A | | | | | | | | |
| patient 6 | A | | | | | | | | |
| NHD 1 | A | | | | | | | | |
| NHD 2 | A | | | | | | | | |

FIG. 15G.6

| | ICAM-1 ng/mL | IFN-gamma pg/mL | IgA mg/mL | IgE ng/mL | IGF-1 ng/mL | IgM mg/mL | IL-10 pg/mL | IL-12p40 ng/mL | IL-12p70 pg/mL |
|---|---|---|---|---|---|---|---|---|---|
| Least Detectable Dose | 3.2 | 4.6 | 0.0084 | 14 | 4.0 | 0.015 | 15 | 1.2 | 94 |
| RBM Low Plasma Range | 42 | Pending | 0.58 | | | 0.24 | 1.8 | | |
| RBM High Plasma Range | 213 | Pending | 5.6 | 770 | 177 | 3.3 | 38 | 2.7 | 165 |
| | ICAM-1 | IFN-gamma | IgA | IgE | IGF-1 | IgM | IL-10 | IL-12p40 | IL-12p70 |
| patient 1 | | | | | | | | | |
| patient 7 | | | | | | | | | |
| patient 2 | | | | | | | | | |
| patient 3 | | | | | | | | | |
| patient 5 | | | | | | | | | |
| patient 4 | | | | | | | | | |
| patient 6 | | | | | | | | | |
| NHD 1 | | | | | | | | | |
| NHD 2 | | | | | | | | | |

FIG. 15G.7

| | ICAM-1 ng/mL | IFN-gamma pg/mL | IgA mg/mL | IgE ng/mL | IGF-1 ng/mL | IgM mg/mL | IL-10 pg/mL | IL-12p40 ng/mL | IL-12p70 pg/mL |
|---|---|---|---|---|---|---|---|---|---|
| Least Detectable Dose | 3.2 | 4.6 | 0.0084 | 14 | 4.0 | 0.015 | 15 | 1.2 | 94 |
| RBM Low Plasma Range | 42 | Pending | 0.58 | | | 0.24 | 1.8 | | |
| RBM High Plasma Range | 213 | Pending | 5.6 | 770 | 177 | 3.3 | 38 | 2.7 | 165 |
| patient 1 | C | | | | | | | | |
| patient 7 | C | | | | | | | | |
| patient 2 | C | | | | | | | | |
| patient 3 | C | | | | | | | | |
| patient 5 | C | | | | | | | | |
| patient 4 | C | | | | | | | | |
| patient 6 | C | | | | | | | | |
| NHD 1 | C | | | | | | | | |
| NHD 2 | C | | | | | | | | |

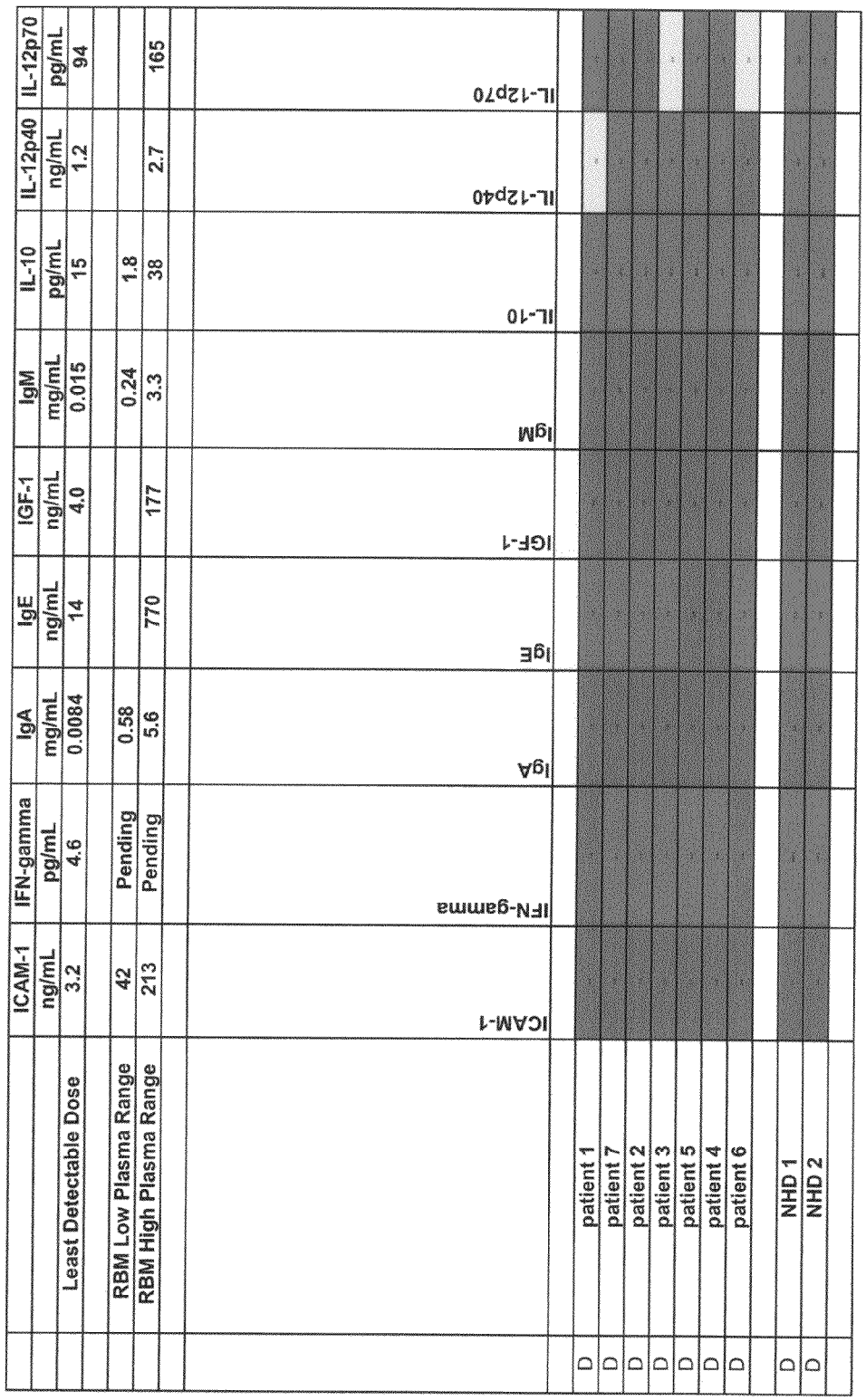
FIG. 15G.8

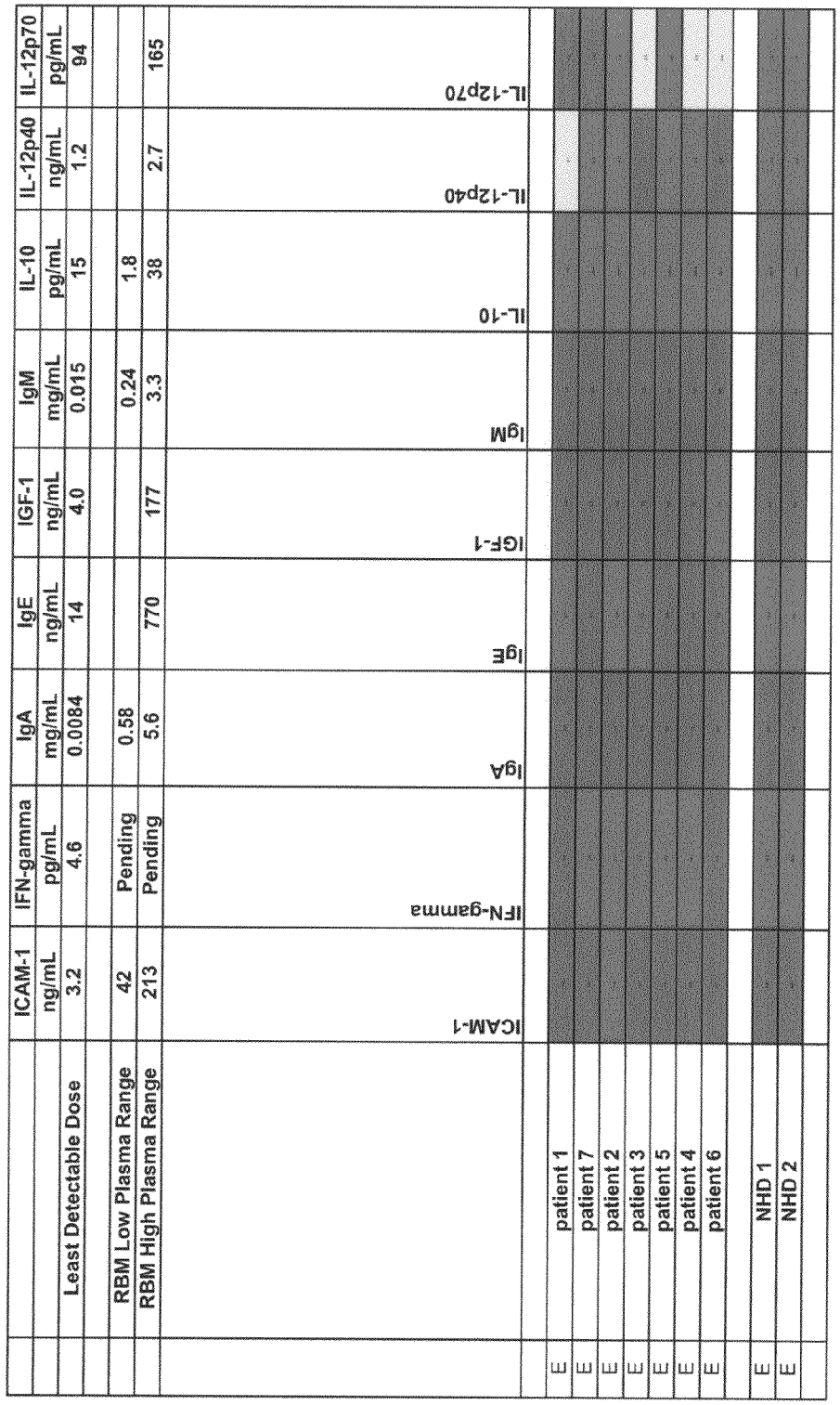
FIG. 15G.9

FIG. 15G.10

| | ICAM-1 ng/mL | IFN-gamma pg/mL | IgA mg/mL | IgE ng/mL | IGF-1 ng/mL | IgM mg/mL | IL-10 pg/mL | IL-12p40 ng/mL | IL-12p70 pg/mL |
|---|---|---|---|---|---|---|---|---|---|
| Least Detectable Dose | 3.2 | 4.6 | 0.0084 | 14 | 4.0 | 0.015 | 15 | 1.2 | 94 |
| RBM Low Plasma Range | 42 | Pending | 0.58 | | | 0.24 | 1.8 | | |
| RBM High Plasma Range | 213 | Pending | 5.6 | 770 | 177 | 3.3 | 38 | 2.7 | 165 |

| | | |
|---|---|---|
| patient 1 | | F |
| patient 7 | | F |
| patient 2 | | F |
| patient 3 | | F |
| patient 5 | | F |
| patient 4 | | F |
| patient 6 | | F |
| NHD 1 | | F |
| NHD 2 | | F |

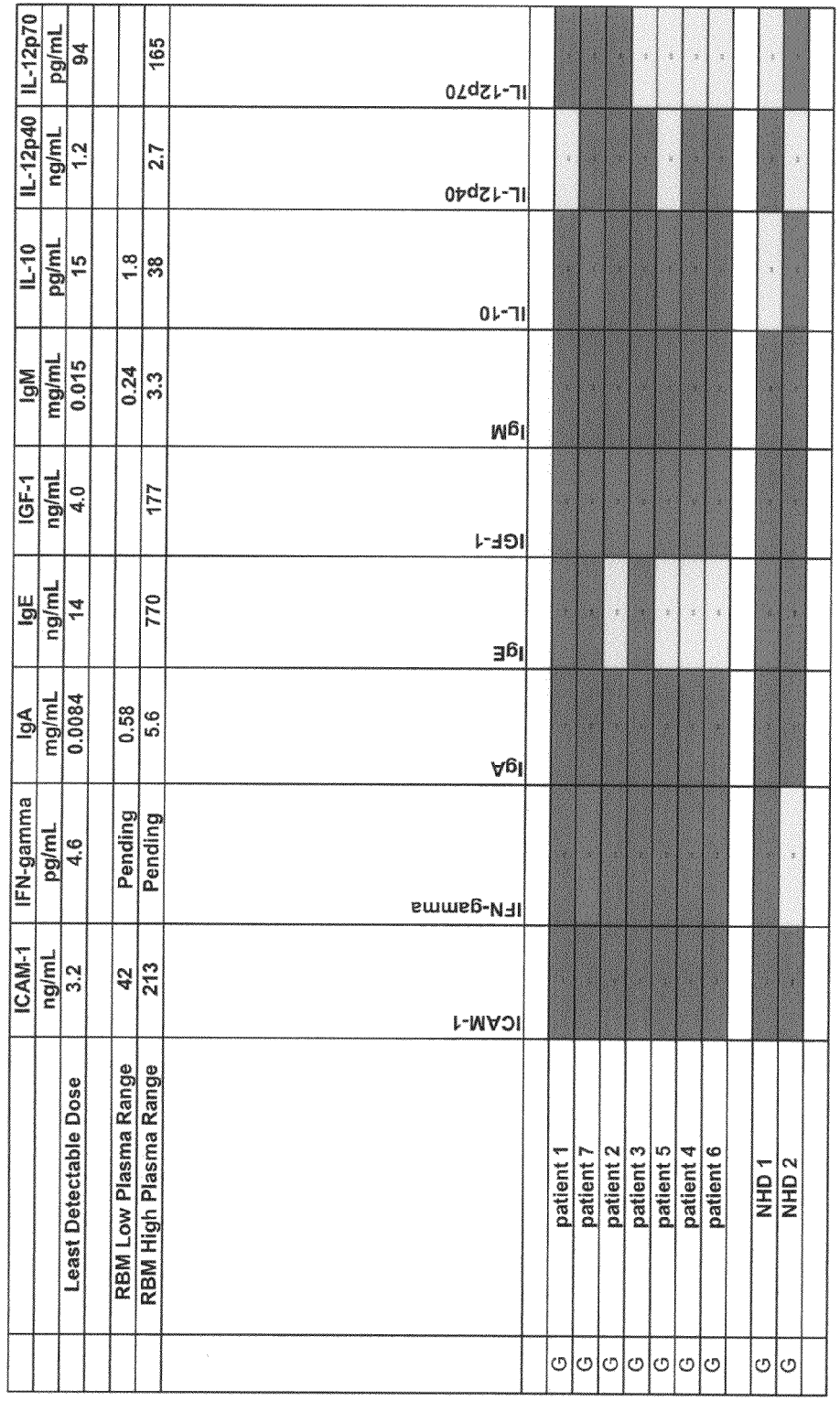
FIG. 15G.11

FIG. 15G.12

| | ICAM-1 ng/mL | IFN-gamma pg/mL | IgA mg/mL | IgE ng/mL | IGF-1 ng/mL | IgM mg/mL | IL-10 pg/mL | IL-12p40 ng/mL | IL-12p70 pg/mL |
|---|---|---|---|---|---|---|---|---|---|
| Least Detectable Dose | 3.2 | 4.6 | 0.0084 | 14 | 4.0 | 0.015 | 15 | 1.2 | 94 |
| RBM Low Plasma Range | 42 | Pending | 0.58 | | | 0.24 | 1.8 | | |
| RBM High Plasma Range | 213 | Pending | 5.6 | 770 | 177 | 3.3 | 38 | 2.7 | 165 |

| | ICAM-1 | IFN-gamma | IgA | IgE | IGF-1 | IgM | IL-10 | IL-12p40 | IL-12p70 |
|---|---|---|---|---|---|---|---|---|---|
| patient 1 | H | | | | | | | | |
| patient 7 | H | | | | | | | | |
| patient 2 | H | | | | | | | | |
| patient 3 | H | | | | | | | | |
| patient 5 | H | | | | | | | | |
| patient 4 | H | | | | | | | | |
| patient 6 | H | | | | | | | | |
| NHD 1 | H | | | | | | | | |
| NHD 2 | H | | | | | | | | |

FIG. 15G.13
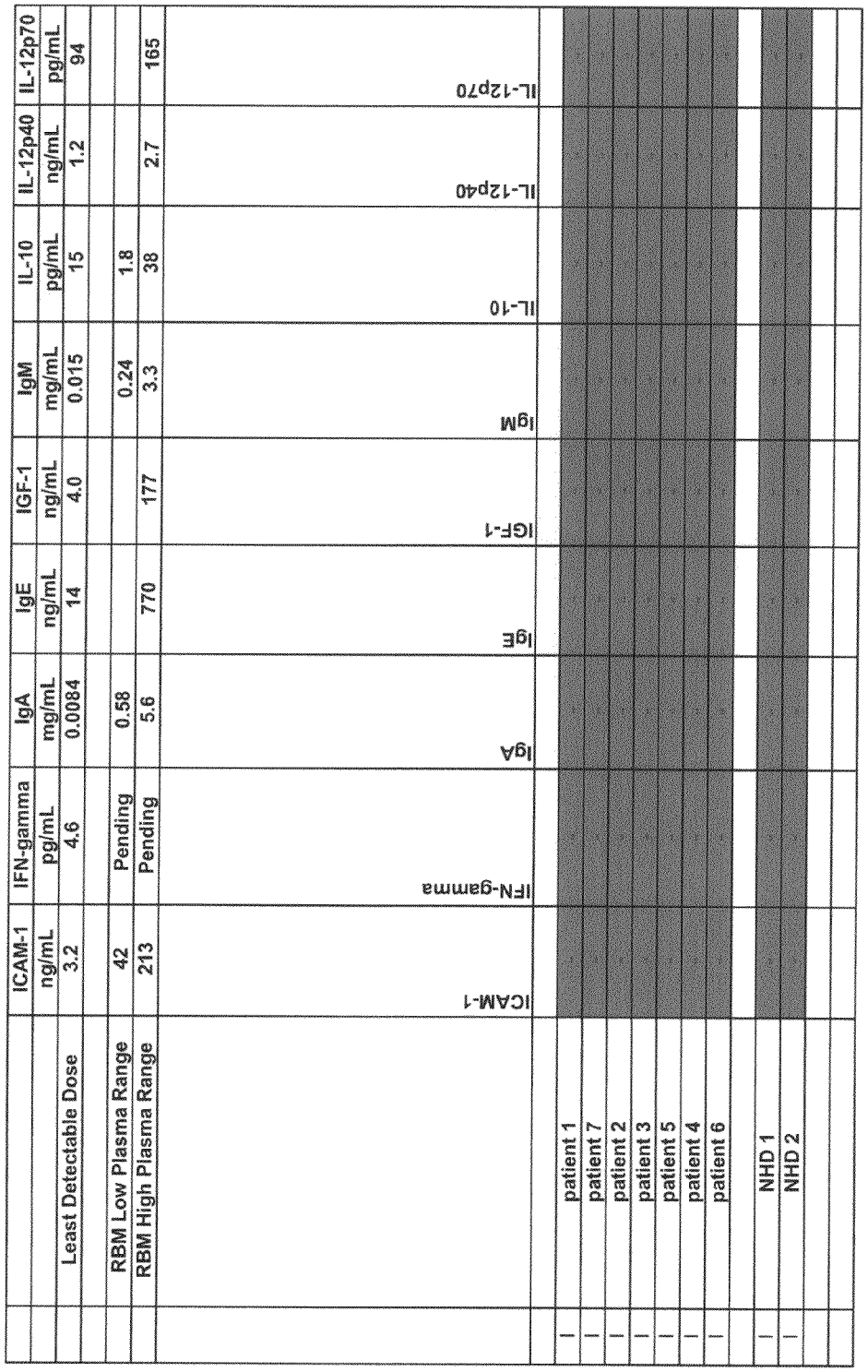

FIG. 15G.14

| | ICAM-1 ng/mL | IFN-gamma pg/mL | IgA mg/mL | IgE ng/mL | IGF-1 ng/mL | IgM mg/mL | IL-10 pg/mL | IL-12p40 ng/mL | IL-12p70 pg/mL |
|---|---|---|---|---|---|---|---|---|---|
| Least Detectable Dose | 3.2 | 4.6 | 0.0084 | 14 | 4.0 | 0.015 | 15 | 1.2 | 94 |
| RBM Low Plasma Range | 42 | Pending | 0.58 | | | 0.24 | 1.8 | | |
| RBM High Plasma Range | 213 | Pending | 5.6 | 770 | 177 | 3.3 | 38 | 2.7 | 165 |
| Messwert > ULD | | | | | | | | | |
| SI > 1,3 | | | | | | | | | |
| SI 0,7-1,3 | | | | | | | | | |
| SI 0-0,7 | | | | | | | | | |

FIG. 15H.1

| | IL-13 pg/mL | IL-15 ng/mL | IL-16 pg/mL | IL-17 pg/mL | IL-17E pg/mL | IL-18 pg/mL | IL-1alpha ng/mL | IL-1beta pg/mL | IL-1ra pg/mL |
|---|---|---|---|---|---|---|---|---|---|
| Least Detectable Dose | 57 | 1.3 | 66 | 2.7 | 31 | 54 | 0.16 | 1.5 | 15 |
| RBM Low Plasma Range | | | 232 | PENDING | PENDING | 72 | | | 17 |
| RBM High Plasma Range | 133 | 4.6 | 3380 | PENDING | PENDING | 1020 | 0.35 | 8.7 | 622 |
| Samples | | | | | | | | | |
| Donor_1 3. Aliquot A | 36 | 0.41 | 575 | 6.7 | 643 | 1930 | 0.0025 | 75 | 3780 |
| Donor_1 3. Aliquot B | 37 | 0.40 | 535 | 2.7 | 559 | 1910 | 0.16 | 50 | 2300 |
| Donor_1 3. Aliquot C | 38 | 0.33 | 413 | 2.7 | 62 | 1980 | 0.16 | 4.4 | 987 |
| Donor_1 3. Aliquot D | 21 | 0.45 | 619 | 2.7 | 580 | 2080 | 0.0077 | 348 | 4230 |
| Donor_1 3. Aliquot E | 34 | 0.32 | 580 | 2.7 | 604 | 2140 | 0.16 | 69 | 2740 |
| Donor_1 3. Aliquot F | 36 | 0.30 | 502 | 2.7 | 486 | 1630 | 0.16 | 10 | 1040 |
| Donor_1 3. Aliquot G | 37 | 0.50 | 216 | 7.5 | 646 | 2130 | 0.16 | 6.8 | 2830 |
| Donor_1 3. Aliquot H | 35 | 0.28 | 299 | 2.7 | 56 | 1860 | 0.16 | 4.6 | 944 |
| Donor_1 3. Aliquot I | 33 | 0.26 | 588 | 2.7 | 502 | 1810 | 0.16 | 5.4 | 660 |
| Donor_2 3. Aliquot A | 37 | 0.41 | 654 | 2.7 | 29 | 631 | 0.012 | 132 | 16500 |
| Donor_2 3. Aliquot B | 37 | 0.43 | 712 | 2.7 | 40 | 709 | 0.0057 | 71 | 15500 |
| Donor_2 3. Aliquot C | 29 | 0.32 | 609 | 2.7 | 11 | 616 | 0.16 | 4.7 | 2000 |
| Donor_2 3. Aliquot D | 29 | 0.50 | 804 | 2.7 | 37 | 830 | 0.36 | 5020 | 54600 |
| Donor_2 3. Aliquot E | 36 | 0.37 | 782 | 2.7 | 29 | 754 | 0.11 | 1310 | 52400 |
| Donor_2 3. Aliquot F | 66 | 0.50 | 720 | 2.7 | 17 | 594 | 0.0034 | 32 | 3140 |
| Donor_2 3. Aliquot G | 40 | 0.66 | 432 | 2.7 | 31 | 681 | 0.045 | 387 | 6790 |
| Donor_2 3. Aliquot H | 27 | 1.3 | 393 | 2.7 | 23 | 595 | 0.16 | 9.7 | 4400 |
| Donor_2 3. Aliquot I | 36 | 0.21 | 642 | 2.7 | 34 | 538 | 0.16 | 6.6 | 2520 |
| Donor_3 3. Aliquot A | 49 | 0.53 | 1310 | 2.7 | 17 | 766 | 0.0054 | 62 | 12900 |
| Donor_3 3. Aliquot B | 43 | 0.56 | 1230 | 2.7 | 34 | 720 | 0.0056 | 32 | 11000 |
| Donor_3 3. Aliquot C | 57 | 0.41 | 1190 | 2.7 | 29 | 715 | 0.0036 | 5.3 | 2970 |
| Donor_3 3. Aliquot D | 40 | 0.47 | 1410 | 2.7 | 37 | 735 | 0.074 | 3890 | 41000 |
| Donor_3 3. Aliquot E | 39 | 0.47 | 1490 | 2.7 | 29 | 798 | 0.039 | 1610 | 32900 |
| Donor_3 3. Aliquot F | 51 | 0.28 | 1340 | 2.7 | 29 | 694 | 0.0050 | 18 | 3850 |
| Donor_3 3. Aliquot G | 43 | 0.32 | 556 | 2.7 | 29 | 766 | 0.0045 | 8.6 | 3260 |

FIG. 15H.2

| | IL-13 pg/mL | IL-15 ng/mL | IL-16 pg/mL | IL-17 pg/mL | IL-17E pg/mL | IL-18 pg/mL | IL-1alpha ng/mL | IL-1beta pg/mL | IL-1ra pg/mL |
|---|---|---|---|---|---|---|---|---|---|
| Least Detectable Dose | 57 | 1.3 | 66 | 2.7 | 31 | 54 | 0.16 | 1.5 | 15 |
| RBM Low Plasma Range | | | 232 | PENDING | PENDING | 72 | | | 17 |
| RBM High Plasma Range | 133 | 4.6 | 3380 | PENDING | PENDING | 1020 | 0.35 | 8.7 | 622 |
| Donor_3 3. Aliquot H | 55 | 0.28 | 706 | 2.7 | 31 | 553 | 0.0029 | 2.2 | 1010 |
| Donor_3 3. Aliquot I | 81 | 0.47 | 1280 | 2.7 | 45 | 627 | 0.0043 | 1.5 | 79 |
| Donor_4 3. Aliquot A | 36 | 0.38 | 1240 | 2.7 | 42 | 690 | 0.16 | 7.3 | 2670 |
| Donor_4 3. Aliquot B | 19 | 0.56 | 1130 | 2.7 | 40 | 700 | 0.16 | 46 | 3450 |
| Donor_4 3. Aliquot C | 27 | 0.32 | 1050 | 2.7 | 56 | 608 | 0.16 | 3.8 | 336 |
| Donor_4 3. Aliquot D | 38 | 0.43 | 986 | 2.7 | 29 | 724 | 0.29 | 2830 | 13700 |
| Donor_4 3. Aliquot E | 23 | 0.56 | 812 | 2.7 | 51 | 633 | 0.075 | 957 | 13100 |
| Donor_4 3. Aliquot F | 28 | 0.47 | 1030 | 2.7 | 51 | 623 | 0.0036 | 47 | 12900 |
| Donor_4 3. Aliquot G | 29 | 0.24 | 431 | 2.7 | 56 | 612 | 0.0025 | 7.0 | 2530 |
| Donor_4 3. Aliquot H | 9.7 | 0.19 | 564 | 2.7 | 62 | 566 | 0.16 | 4.1 | 1670 |
| Donor_4 3. Aliquot I | 24 | 0.24 | 1150 | 2.7 | 62 | 597 | 0.16 | 0.63 | 228 |
| Donor_5 3. Aliquot A | 33 | 0.71 | 536 | 2.7 | 74 | 340 | 0.0066 | 73 | 22900 |
| Donor_5 3. Aliquot B | 32 | 0.50 | 584 | 2.7 | 40 | 295 | 0.0094 | 75 | 22500 |
| Donor_5 3. Aliquot C | 48 | 0.50 | 455 | 2.7 | 20 | 271 | 0.16 | 3.0 | 2100 |
| Donor_5 3. Aliquot D | 32 | 0.73 | 592 | 2.7 | 17 | 428 | 0.35 | 3910 | 53300 |
| Donor_5 3. Aliquot E | 36 | 0.68 | 561 | 2.7 | 11 | 467 | 0.32 | 3280 | 51000 |
| Donor_5 3. Aliquot F | 38 | 0.28 | 430 | 2.7 | 31 | 216 | 0.0043 | 73 | 11100 |
| Donor_5 3. Aliquot G | 29 | 0.26 | 323 | 2.7 | 45 | 479 | 0.0048 | 36 | 16700 |
| Donor_5 3. Aliquot H | 27 | 0.19 | 390 | 2.7 | 31 | 367 | 0.16 | 15 | 9910 |
| Donor_5 3. Aliquot I | 47 | 0.13 | 492 | 2.7 | 34 | 255 | 0.16 | 2.8 | 3530 |
| Donor_6 3. Aliquot A | 70 | 0.32 | 1030 | 2.7 | 29 | 102 | 0.0052 | 35 | 7350 |
| Donor_6 3. Aliquot B | 57 | 0.24 | 828 | 2.7 | 51 | 95 | 0.012 | 46 | 9190 |
| Donor_6 3. Aliquot C | 59 | 0.24 | 1150 | 2.7 | 11 | 98 | 0.0050 | 1.5 | 1220 |
| Donor_6 3. Aliquot D | 68 | 0.56 | 682 | 2.7 | 17 | 138 | 0.21 | 1870 | 26100 |
| Donor_6 3. Aliquot E | 68 | 0.16 | 648 | 2.7 | 17 | 134 | 0.41 | 3760 | 31600 |

FIG. 15H.3

|  | IL-13 pg/mL | IL-15 ng/mL | IL-16 pg/mL | IL-17 pg/mL | IL-17E pg/mL | IL-18 pg/mL | IL-1alpha ng/mL | IL-1beta pg/mL | IL-1ra pg/mL |
|---|---|---|---|---|---|---|---|---|---|
| Least Detectable Dose | 57 | 1.3 | 66 | 2.7 | 31 | 54 | 0.16 | 1.5 | 15 |
| RBM Low Plasma Range |  |  | 232 | PENDING | PENDING | 72 |  |  | 17 |
| RBM High Plasma Range | 133 | 4.6 | 3380 | PENDING | PENDING | 1020 | 0.35 | 8.7 | 622 |
| Donor_6 3. Aliquot F | 86 | 0.43 | 969 | 2.7 | 31 | 113 | 0.0073 | 43 | 4970 |
| Donor_6 3. Aliquot G | 65 | 1.3 | 439 | 2.7 | 11 | 170 | 0.0043 | 27 | 9870 |
| Donor_6 3. Aliquot H | 65 | 0.19 | 815 | 5.0 | 54 | 107 | 0.16 | 2.8 | 1530 |
| Donor_6 3. Aliquot I | 59 | 0.28 | 1230 | 2.7 | 62 | 87 | 0.16 | 1.3 | 202 |
| Donor_7 3. Aliquot A | 91 | 0.79 | 664 | 2.7 | 40 | 295 | 0.025 | 147 | 6320 |
| Donor_7 3. Aliquot B | 103 | 0.78 | 620 | 2.7 | 34 | 277 | 0.015 | 99 | 4590 |
| Donor_7 3. Aliquot C | 70 | 0.53 | 817 | 2.7 | 17 | 255 | 0.010 | 16 | 244 |
| Donor_7 3. Aliquot D | 82 | 0.49 | 662 | 2.7 | 23 | 275 | 0.31 | 2120 | 11000 |
| Donor_7 3. Aliquot E | 104 | 0.58 | 651 | 2.7 | 62 | 298 | 0.071 | 548 | 7580 |
| Donor_7 3. Aliquot F | 105 | 0.54 | 856 | 2.7 | 31 | 209 | 0.016 | 20 | 578 |
| Donor_7 3. Aliquot G | 56 | 0.19 | 428 | 2.7 | 85 | 300 | 0.0054 | 6.2 | 2730 |
| Donor_7 3. Aliquot H | 62 | 0.38 | 574 | 2.7 | 31 | 214 | 0.0057 | 3.4 | 361 |
| Donor_7 3. Aliquot I | 88 | 0.41 | 918 | 2.7 | 26 | 227 | 0.0066 | 1.5 | 61 |
| Donor_8 3. Aliquot A | 81 | 0.32 | 340 | 2.7 | 17 | 150 | 0.0073 | 73 | 3870 |
| Donor_8 3. Aliquot B | 97 | 0.24 | 341 | 2.7 | 31 | 173 | 0.0089 | 59 | 3010 |
| Donor_8 3. Aliquot C | 80 | 0.32 | 309 | 2.7 | 31 | 157 | 0.0071 | 76 | 10200 |
| Donor_8 3. Aliquot D | 99 | 0.61 | 754 | 5.0 | 17 | 408 | 0.28 | 24700 | 11400 |
| Donor_8 3. Aliquot E | 99 | 0.64 | 533 | 9.7 | 45 | 359 | 0.27 | 17500 | 12800 |
| Donor_8 3. Aliquot F | 111 | 0.45 | 410 | 4.2 | 31 | 175 | 0.013 | 204 | 16400 |
| Donor_8 3. Aliquot G | 53 | 0.19 | 183 | 5.4 | 23 | 152 | 0.16 | 32 | 4000 |
| Donor_8 3. Aliquot H | 75 | 0.28 | 231 | 2.7 | 17 | 220 | 0.0041 | 75 | 7720 |
| Donor_8 3. Aliquot I | 80 | 0.32 | 522 | 2.7 | 29 | 195 | 0.0061 | 7.9 | 839 |
| Donor_9 3. Aliquot A | 68 | 0.31 | 463 | 2.7 | 34 | 58 | 0.0080 | 29 | 3980 |
| Donor_9 3. Aliquot B | 77 | 0.44 | 398 | 7.2 | 66 | 48 | 0.013 | 42 | 4200 |
| Donor_9 3. Aliquot C | 74 | 0.35 | 407 | 2.7 | 83 | 52 | 0.018 | 67 | 9410 |

FIG. 15H.4

| | IL-13 pg/mL | IL-15 ng/mL | IL-16 pg/mL | IL-17 pg/mL | IL-17E pg/mL | IL-18 pg/mL | IL-1alpha ng/mL | IL-1beta pg/mL | IL-1ra pg/mL |
|---|---|---|---|---|---|---|---|---|---|
| Least Detectable Dose | 57 | 1.3 | 66 | 2.7 | 31 | 54 | 0.16 | 1.5 | 15 |
| RBM Low Plasma Range | | | 232 | PENDING | PENDING | 72 | | | 17 |
| RBM High Plasma Range | 133 | 4.6 | 3380 | PENDING | PENDING | 1020 | 0.35 | 8.7 | 622 |
| Donor_9_3. Aliquot D | 71 | 0.51 | 780 | 8.1 | 44 | 340 | 2.6 | 26100 | 18300 |
| Donor_9_3. Aliquot E | 68 | 0.31 | 538 | 22 | 55 | 161 | 0.80 | 7830 | 15100 |
| Donor_9_3. Aliquot F | 83 | 0.30 | 369 | 13 | 28 | 38 | 0.011 | 60 | 12700 |
| Donor_9_3. Aliquot G | 36 | 0.31 | 411 | 22 | 44 | 92 | 0.0075 | 48 | 8240 |
| Donor_9_3. Aliquot H | 51 | 0.56 | 369 | 9.8 | 77 | 96 | 0.0086 | 39 | 4920 |
| Donor_9_3. Aliquot I | 56 | 0.22 | 455 | 8.1 | 83 | 69 | 0.0035 | 5.7 | 2110 |
| EDTA Plasma | | | | | | | | | |
| donor #1 plasma | 39 | 0.30 | 329 | 11 | 228 | 1670 | 0.16 | 2.8 | 1800 |
| donor #2 plasma | 24 | 0.13 | 620 | 2.7 | 31 | 628 | 0.16 | 1.5 | 555 |
| donor #3 plasma | 37 | 0.39 | 892 | 2.7 | 34 | 644 | 0.0027 | 1.1 | 137 |
| donor #4 plasma | 50 | 0.29 | 794 | 2.7 | 31 | 805 | 0.16 | 1.5 | 410 |
| donor #5 plasma | 37 | 0.64 | 314 | 2.7 | 31 | 188 | 0.16 | 1.5 | 354 |
| donor #6 plasma | 40 | 0.29 | 277 | 11 | 44 | 112 | 0.16 | 1.5 | 84 |
| donor #7 plasma | 39 | 0.29 | 514 | 2.7 | 28 | 404 | 0.16 | 1.5 | 559 |
| donor #8 plasma | 50 | 0.31 | 208 | 2.7 | 31 | 196 | 0.0035 | 1.4 | 68 |
| donor #9 plasma | 41 | 0.18 | 327 | 2.7 | 44 | 104 | 0.0032 | 1.5 | 80 |
| *Stimulations Indices* | | | | | | | | | |

FIG. 15H.5

| | IL-13 pg/mL | IL-15 ng/mL | IL-16 pg/mL | IL-17 pg/mL | IL-17E pg/mL | IL-18 pg/mL | IL-1alpha ng/mL | IL-1beta pg/mL | IL-1ra pg/mL |
|---|---|---|---|---|---|---|---|---|---|
| Least Detectable Dose | 57 | 1.3 | 66 | 2.7 | 31 | 54 | 0.16 | 1.5 | 15 |
| RBM Low Plasma Range | | | 232 | PENDING | PENDING | 72 | | | 17 |
| RBM High Plasma Range | 133 | 4.6 | 3380 | PENDING | PENDING | 1020 | 0.35 | 8.7 | 622 |
| patient 1 | A | | | | | | | | |
| patient 7 | A | | | | | | | | |
| patient 2 | A | | | | | | | | |
| patient 3 | A | | | | | | | | |
| patient 5 | A | | | | | | | | |
| patient 4 | A | | | | | | | | |
| patient 6 | A | | | | | | | | |
| NHD 1 | A | | | | | | | | |
| NHD 2 | A | | | | | | | | |

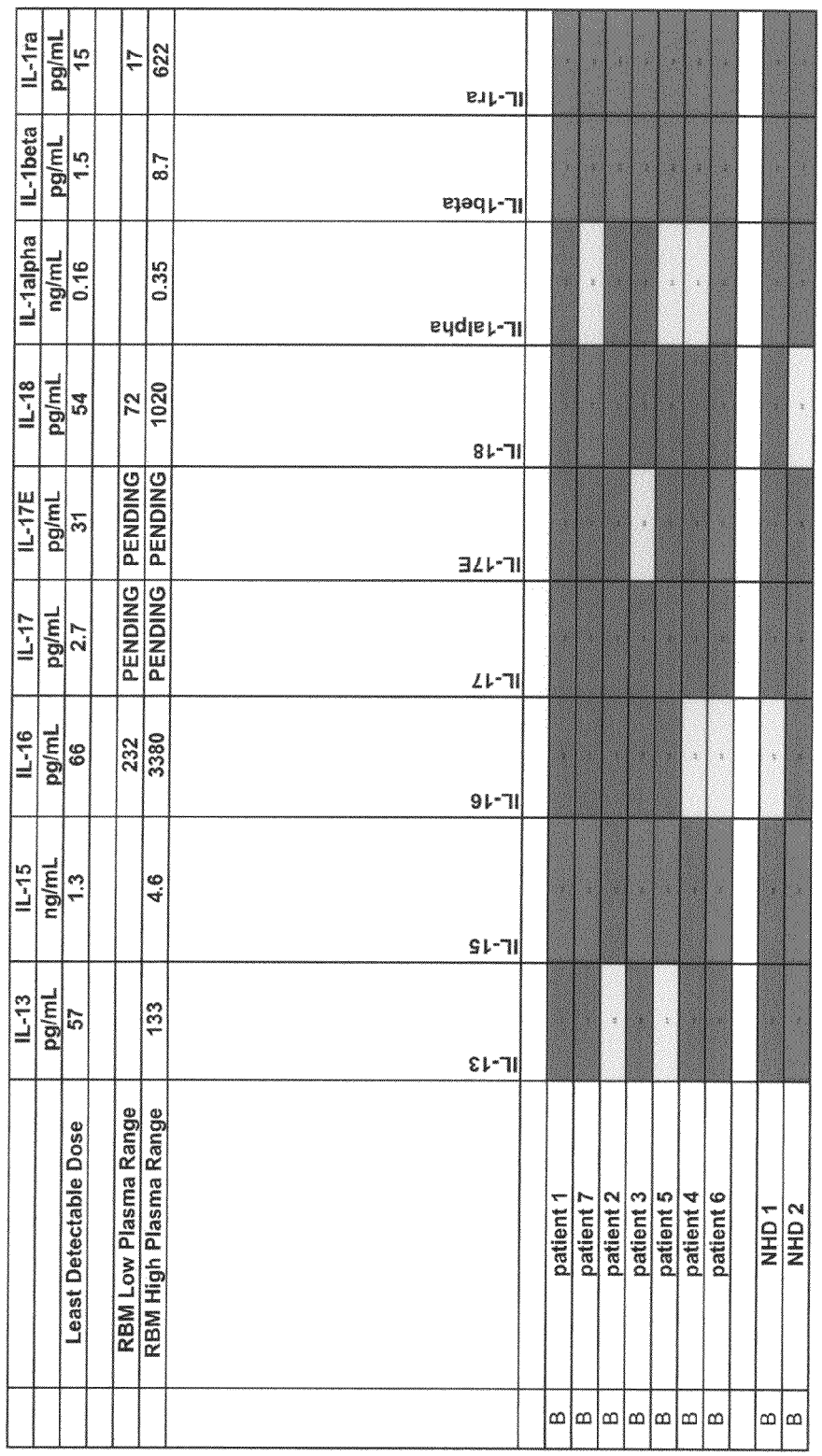
FIG. 15H.6

FIG. 15H.7
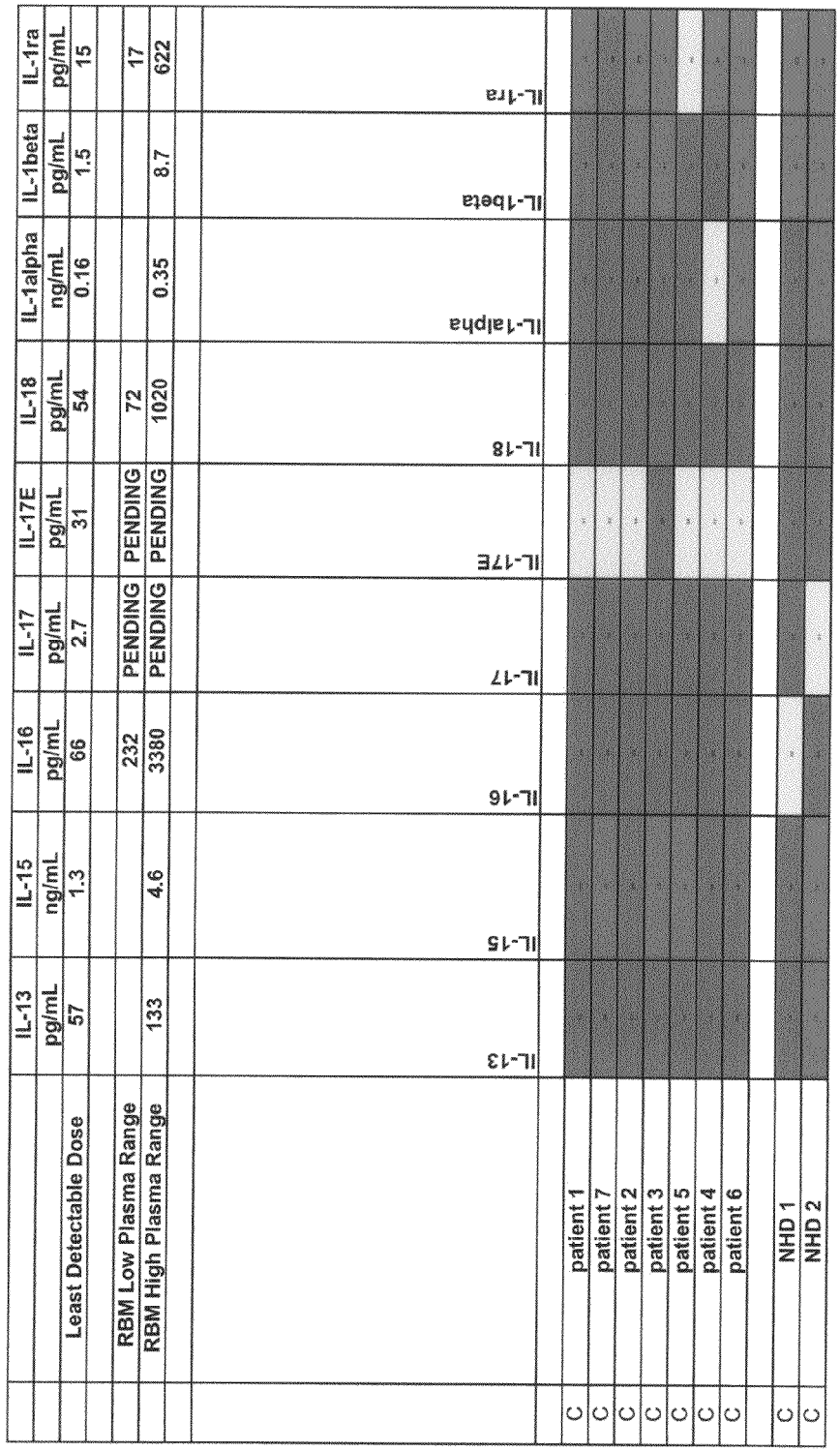

FIG. 15H.8

| | IL-13 pg/mL | IL-15 ng/mL | IL-16 pg/mL | IL-17 pg/mL | IL-17E pg/mL | IL-18 pg/mL | IL-1alpha ng/mL | IL-1beta pg/mL | IL-1ra pg/mL |
|---|---|---|---|---|---|---|---|---|---|
| Least Detectable Dose | 57 | 1.3 | 66 | 2.7 | 31 | 54 | 0.16 | 1.5 | 15 |
| RBM Low Plasma Range | | | 232 | PENDING | PENDING | 72 | | | 17 |
| RBM High Plasma Range | 133 | 4.6 | 3380 | PENDING | PENDING | 1020 | 0.35 | 8.7 | 622 |
| | IL-13 | IL-15 | IL-16 | IL-17 | IL-17E | IL-18 | IL-1alpha | IL-1beta | IL-1ra |
| patient 1 | | | | | | | | | |
| patient 7 | | | | | | | | | |
| patient 2 | | | | | | | | | |
| patient 3 | | | | | | | | | |
| patient 5 | | | | | | | | | |
| patient 4 | | | | | | | | | |
| patient 6 | | | | | | | | | |
| NHD 1 | | | | | | | | | |
| NHD 2 | | | | | | | | | |

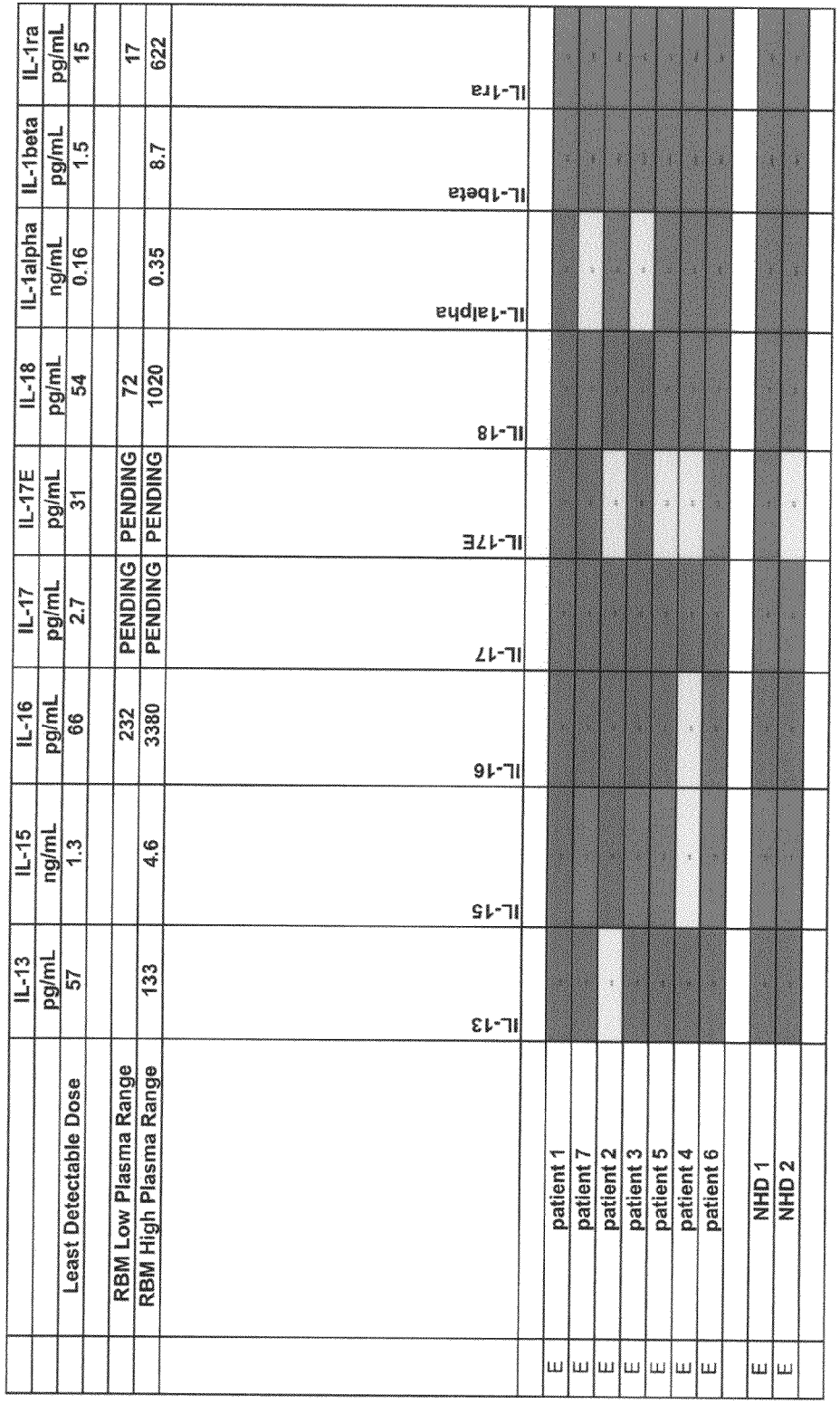
FIG. 15H.9

FIG. 15H.10
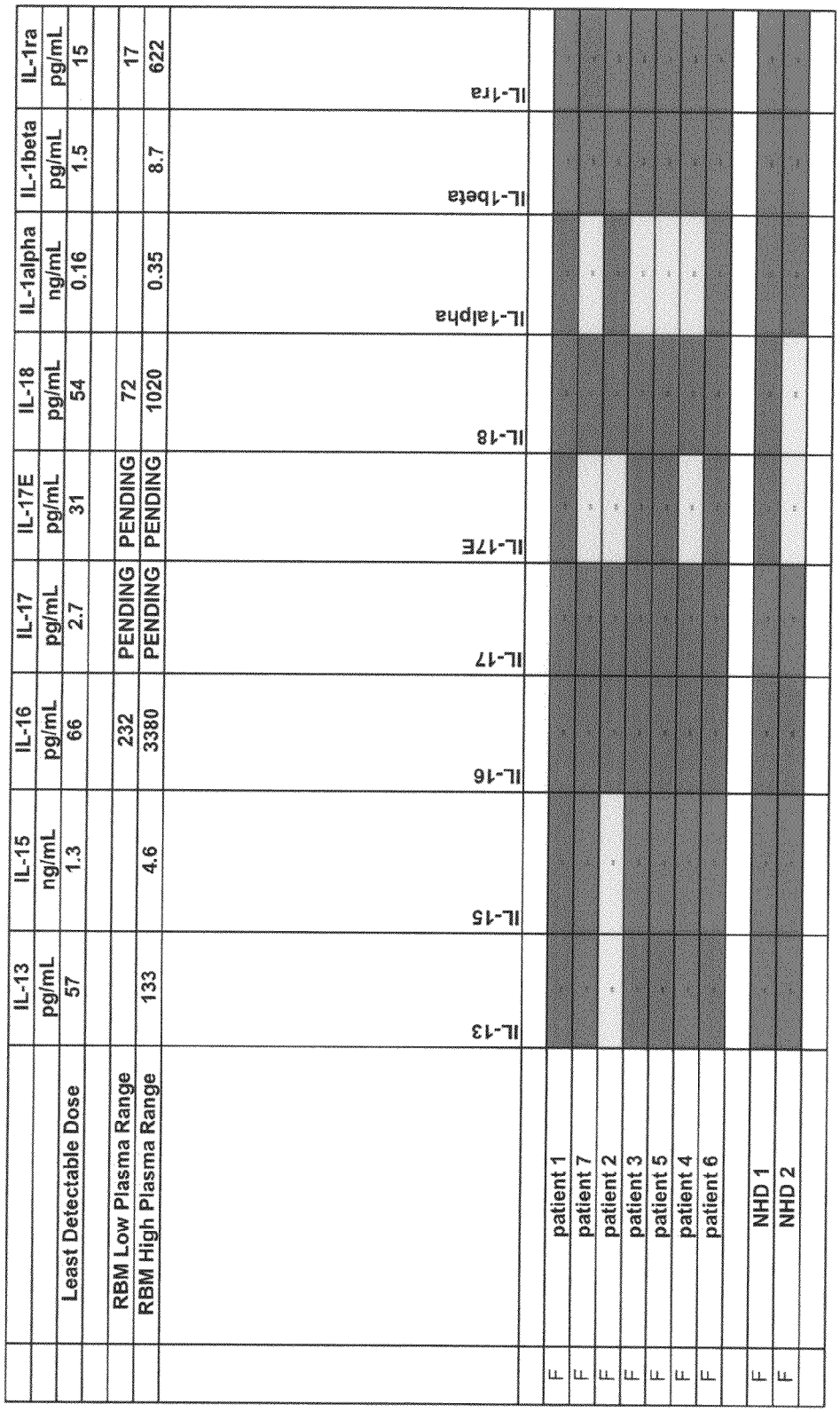

FIG. 15H.11
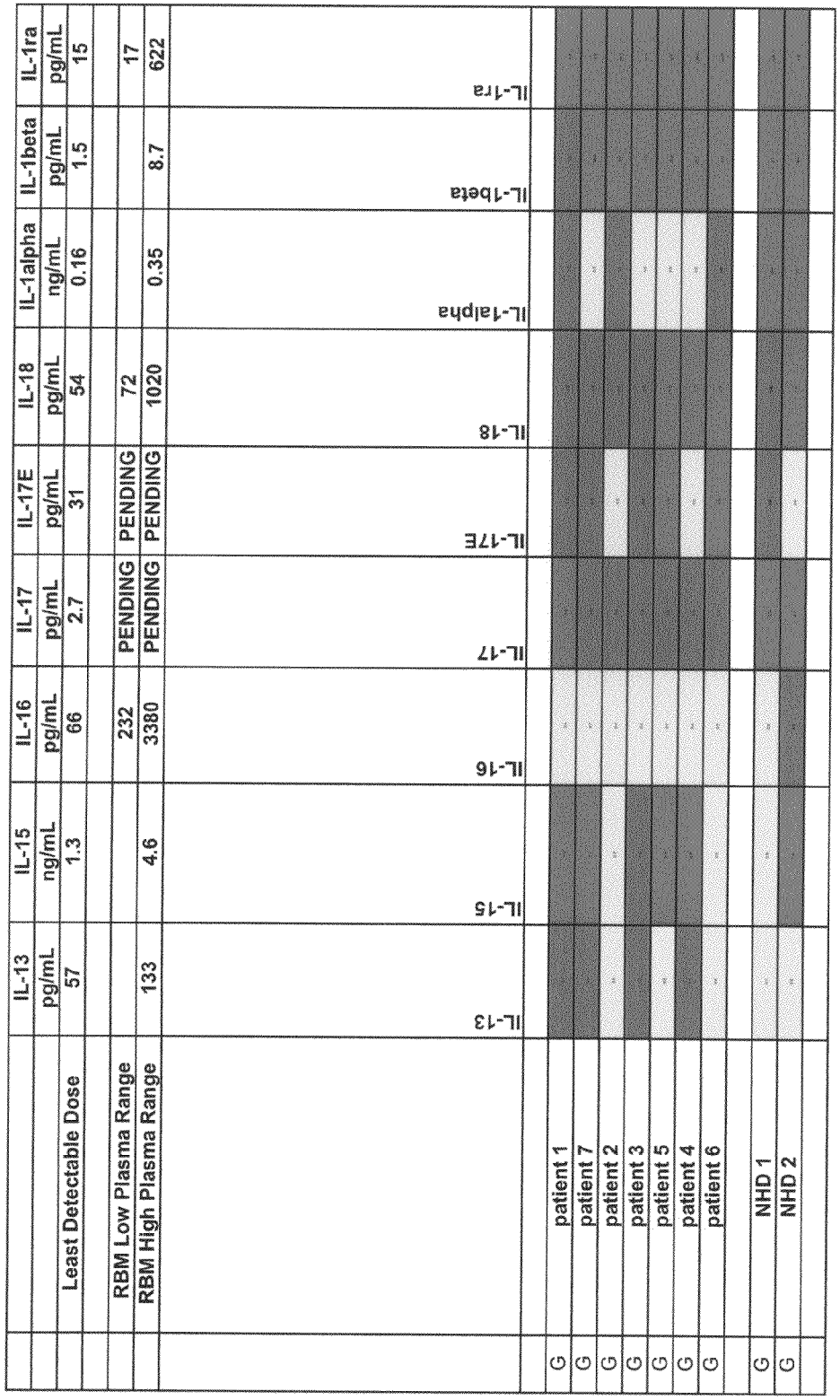

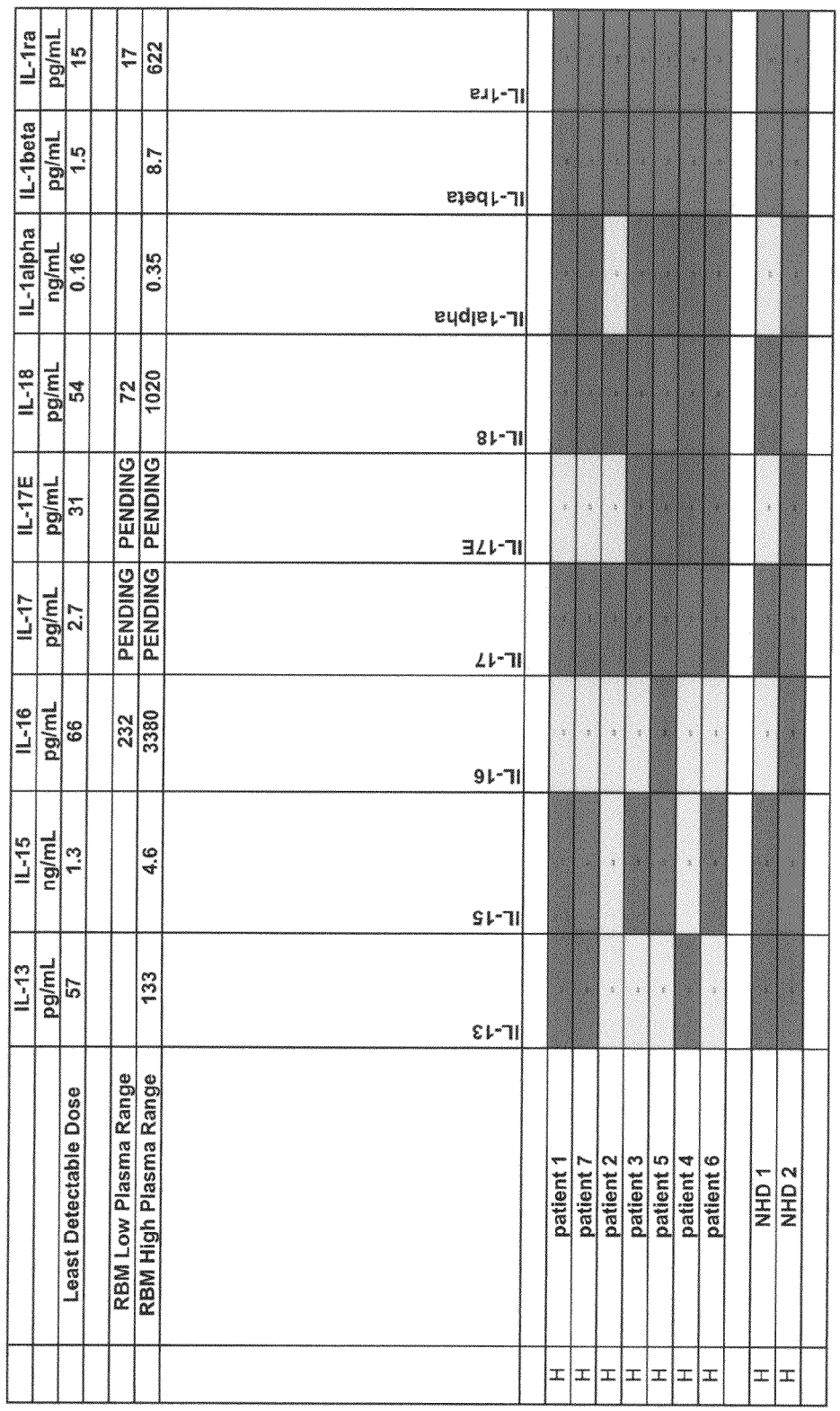
FIG. 15H.12

FIG. 15H.13

| | IL-13 pg/mL | IL-15 ng/mL | IL-16 pg/mL | IL-17 pg/mL | IL-17E pg/mL | IL-18 pg/mL | IL-1alpha ng/mL | IL-1beta pg/mL | IL-1ra pg/mL |
|---|---|---|---|---|---|---|---|---|---|
| Least Detectable Dose | 57 | 1.3 | 66 | 2.7 | 31 | 54 | 0.16 | 1.5 | 15 |
| RBM Low Plasma Range | | | 232 | PENDING | PENDING | 72 | | | 17 |
| RBM High Plasma Range | 133 | 4.6 | 3380 | PENDING | PENDING | 1020 | 0.35 | 8.7 | 622 |
| | IL-13 | IL-15 | IL-16 | IL-17 | IL-17E | IL-18 | IL-1alpha | IL-1beta | IL-1ra |
| patient 1 | | | | | | | | | |
| patient 7 | | | | | | | | | |
| patient 2 | | | | | | | | | |
| patient 3 | | | | | | | | | |
| patient 5 | | | | | | | | | |
| patient 4 | | | | | | | | | |
| patient 6 | | | | | | | | | |
| NHD 1 | | | | | | | | | |
| NHD 2 | | | | | | | | | |

FIG. 15H.14

| | IL-13 pg/mL | IL-15 ng/mL | IL-16 pg/mL | IL-17 pg/mL | IL-17E pg/mL | IL-18 pg/mL | IL-1alpha ng/mL | IL-1beta pg/mL | IL-1ra pg/mL |
|---|---|---|---|---|---|---|---|---|---|
| Least Detectable Dose | 57 | 1.3 | 66 | 2.7 | 31 | 54 | 0.16 | 1.5 | 15 |
| RBM Low Plasma Range | | | 232 | PENDING | PENDING | 72 | | | 17 |
| RBM High Plasma Range | 133 | 4.6 | 3380 | PENDING | PENDING | 1020 | 0.35 | 8.7 | 622 |
| Messwert > ULD | | | | | | | | | |
| SI > 1,3 | | | | | | | | | |
| SI 0,7-1,3 | | | | | | | | | |
| SI 0-0,7 | | | | | | | | | |

FIG. 15I.1

| Samples | IL-2 pg/mL | IL-23 ng/mL | IL-3 ng/mL | IL-4 pg/mL | IL-5 pg/mL | IL-6 pg/mL | IL-7 pg/mL | IL-8 pg/mL | Insulin uIU/mL | Leptin ng/mL |
|---|---|---|---|---|---|---|---|---|---|---|
| Least Detectable Dose | 60 | <0.67 | 0.17 | 104 | 33 | 12 | 53 | 3.5 | 0.86 | 0.10 |
| RBM Low Plasma Range | | PENDING | | | | | | | | 0.41 |
| RBM High Plasma Range | 61 | PENDING | 1.2 | 103 | 62 | 25 | 125 | 59 | 34 | 41 |
| Donor_1 3. Aliquot A | 60 | 3.7 | 0.027 | 50 | 33 | 4690 | 169 | 23600 | 11 | 132 |
| Donor_1 3. Aliquot B | 60 | 1.2 | 0.17 | 53 | 33 | 1860 | 113 | 4450 | 9.8 | 115 |
| Donor_1 3. Aliquot C | 60 | 0.67 | 0.17 | 43 | 33 | 49 | 33 | 321 | 6.3 | 124 |
| Donor_1 3. Aliquot D | 60 | 0.67 | 0.17 | 49 | 33 | 7970 | 113 | 6730 | 11 | 121 |
| Donor_1 3. Aliquot E | 60 | 0.67 | 0.17 | 38 | 33 | 1700 | 131 | 6170 | 11 | 124 |
| Donor_1 3. Aliquot F | 60 | 1.2 | 0.17 | 42 | 33 | 77 | 57 | 1330 | 8.3 | 107 |
| Donor_1 3. Aliquot G | 60 | 2.1 | 0.17 | 38 | 33 | 57 | 100 | 5060 | 8.0 | 112 |
| Donor_1 3. Aliquot H | 60 | 1.9 | 0.17 | 51 | 33 | 54 | 33 | 672 | 9.4 | 119 |
| Donor_1 3. Aliquot I | 60 | 0.67 | 0.17 | 38 | 33 | 50 | 68 | 1480 | 9.9 | 119 |
| Donor_2 3. Aliquot A | 60 | 1.2 | 0.12 | 69 | 5.9 | 11100 | 215 | 100000 | 5.7 | 7.7 |
| Donor_2 3. Aliquot B | 60 | 0.67 | 0.095 | 78 | 8.2 | 6720 | 189 | 74900 | 6.1 | 8.4 |
| Donor_2 3. Aliquot C | 60 | 0.67 | 0.17 | 43 | 33 | 110 | 48 | 2290 | 2.3 | 9.0 |
| Donor_2 3. Aliquot D | 60 | 2.3 | 0.19 | 69 | 7.4 | 78400 | 201 | 146000 | 6.6 | 8.1 |
| Donor_2 3. Aliquot E | 60 | 2.5 | 0.21 | 77 | 8.2 | 63400 | 226 | 165000 | 6.4 | 8.3 |
| Donor_2 3. Aliquot F | 60 | 0.67 | 0.17 | 40 | 6.7 | 180 | 59 | 2230 | 4.7 | 7.7 |
| Donor_2 3. Aliquot G | 60 | 0.67 | 0.14 | 77 | 8.9 | 30900 | 223 | >344062 | 6.0 | 4.4 |
| Donor_2 3. Aliquot H | 60 | 0.67 | 0.17 | 45 | 5.1 | 187 | 74 | 3460 | 5.6 | 7.8 |
| Donor_2 3. Aliquot I | 60 | 0.67 | 0.17 | 56 | 33 | 153 | 48 | 3230 | 4.7 | 7.9 |
| Donor_3 3. Aliquot A | 60 | 0.67 | 0.12 | 9.4 | 4.3 | 6380 | 192 | 40600 | 19 | 8.1 |
| Donor_3 3. Aliquot B | 60 | 2.1 | 0.099 | 7.8 | 33 | 3880 | 201 | 32400 | 17 | 7.7 |
| Donor_3 3. Aliquot C | 60 | 2.1 | 0.17 | 104 | 33 | 90 | 66 | 1860 | 9.0 | 8.4 |
| Donor_3 3. Aliquot D | 60 | 0.67 | 0.15 | 20 | 33 | 105000 | 243 | 124000 | 15 | 7.8 |
| Donor_3 3. Aliquot E | 60 | 3.4 | 0.14 | 8.7 | 4.3 | 59800 | 234 | 146000 | 17 | 8.3 |
| Donor_3 3. Aliquot F | 60 | 1.2 | 0.050 | 7.8 | 5.9 | 169 | 82 | 2870 | 13 | 7.2 |
| Donor_3 3. Aliquot G | 60 | 0.67 | 0.17 | 104 | 2.5 | 63 | 78 | 24200 | 20 | 5.9 |

FIG. 15I.2

| | IL-2 pg/mL | IL-23 ng/mL | IL-3 ng/mL | IL-4 pg/mL | IL-5 pg/mL | IL-6 pg/mL | IL-7 pg/mL | IL-8 pg/mL | Insulin uIU/mL | Leptin ng/mL |
|---|---|---|---|---|---|---|---|---|---|---|
| Least Detectable Dose | 60 | <0.67 | 0.17 | 104 | 33 | 12 | 53 | 3.5 | 0.86 | 0.10 |
| RBM Low Plasma Range | | PENDING | | | | | | | | 0.41 |
| RBM High Plasma Range | 61 | PENDING | | | 62 | 25 | 3.7 | 59 | 34 | 41 |
| Donor_3 3. Aliquot H | 60 | 0.67 | 0.17 | 103 | 33 | 26 | 125 | 924 | 15 | 6.9 |
| Donor_3 3. Aliquot I | 60 | 2.1 | 0.087 | 104 | 5.1 | 9.2 | 38 | 1080 | 15 | 7.8 |
| Donor_4 3. Aliquot A | 60 | 0.67 | 0.17 | 33 | 33 | 177 | 82 | 3240 | 12 | 11 |
| Donor_4 3. Aliquot B | 60 | 2.1 | 0.17 | 35 | 33 | 405 | 106 | 4210 | 12 | 12 |
| Donor_4 3. Aliquot C | 60 | 2.1 | 0.17 | 37 | 33 | 70 | 38 | 751 | 3.8 | 10 |
| Donor_4 3. Aliquot D | 60 | 0.67 | 0.039 | 50 | 33 | 46300 | 215 | 76000 | 13 | 9.7 |
| Donor_4 3. Aliquot E | 60 | 0.67 | 0.087 | 54 | 33 | 24300 | 214 | 70800 | 12 | 8.0 |
| Donor_4 3. Aliquot F | 60 | 0.67 | 0.17 | 32 | 33 | 5050 | 98 | 4030 | 12 | 8.4 |
| Donor_4 3. Aliquot G | 60 | 2.5 | 0.17 | 49 | 33 | 59 | 74 | 23400 | 14 | 7.3 |
| Donor_4 3. Aliquot H | 60 | 1.6 | 0.17 | 31 | 33 | 62 | 66 | 731 | 15 | 11 |
| Donor_4 3. Aliquot I | 60 | 2.1 | 0.17 | 29 | 33 | 52 | 38 | 550 | 11 | 10 |
| Donor_5 3. Aliquot A | 60 | 0.67 | 0.099 | 49 | 4.7 | 2370 | 203 | 146000 | 5.2 | 2.0 |
| Donor_5 3. Aliquot B | 60 | 0.67 | 0.11 | 51 | 33 | 4460 | 217 | 198000 | 5.4 | 1.7 |
| Donor_5 3. Aliquot C | 60 | 1.4 | 0.17 | 39 | 33 | 46 | 52 | 1740 | 2.0 | 2.0 |
| Donor_5 3. Aliquot D | 60 | 0.67 | 0.19 | 76 | 3.5 | 60400 | 247 | 211000 | 6.5 | 1.8 |
| Donor_5 3. Aliquot E | 60 | 0.67 | 0.15 | 57 | 2.5 | 71300 | 200 | >344062 | 8.0 | 1.9 |
| Donor_5 3. Aliquot F | 60 | 0.67 | 0.17 | 42 | 33 | 316 | 115 | 20400 | 3.6 | 1.3 |
| Donor_5 3. Aliquot G | 60 | 1.6 | 0.17 | 46 | 33 | 70 | 145 | 85000 | 3.8 | 2.0 |
| Donor_5 3. Aliquot H | 60 | 2.5 | 0.17 | 41 | 33 | 55 | 84 | 20000 | 4.9 | 1.9 |
| Donor_5 3. Aliquot I | 60 | 1.6 | 0.17 | 35 | 21 | 43 | 94 | 2590 | 4.3 | 1.7 |
| Donor_6 3. Aliquot A | 60 | 0.67 | 0.11 | 51 | 5.9 | 1500 | 182 | 17400 | 1.3 | 0.12 |
| Donor_6 3. Aliquot B | 60 | 0.67 | 0.11 | 55 | 11 | 3190 | 189 | 33200 | 1.4 | 0.10 |
| Donor_6 3. Aliquot C | 60 | 0.67 | 0.081 | 43 | 4.3 | 85 | 90 | 271 | 0.98 | 0.11 |
| Donor_6 3. Aliquot D | 60 | 0.67 | 0.13 | 54 | 6.3 | 50700 | 215 | 67300 | 1.8 | 0.25 |
| Donor_6 3. Aliquot E | 60 | 1.2 | 0.10 | 60 | 21 | 71700 | 229 | 116000 | 1.2 | 0.26 |

FIG. 15I.3

| | IL-2 pg/mL | IL-23 ng/mL | IL-3 ng/mL | IL-4 pg/mL | IL-5 pg/mL | IL-6 pg/mL | IL-7 pg/mL | IL-8 pg/mL | Insulin uIU/mL | Leptin ng/mL |
|---|---|---|---|---|---|---|---|---|---|---|
| Least Detectable Dose | 60 | <0.67 | 0.17 | 104 | 33 | 12 | 53 | 3.5 | 0.86 | 0.10 |
| | | | | | | | | | | |
| RBM Low Plasma Range | | PENDING | | | | | 3.7 | | | 0.41 |
| RBM High Plasma Range | 61 | PENDING | 1.2 | 103 | 62 | 25 | 125 | 59 | 34 | 41 |
| Donor_6_3. Aliquot F | 60 | 0.67 | 0.12 | 44 | 8.9 | 517 | 124 | 3980 | 1.5 | 0.1 |
| Donor_6_3. Aliquot G | 60 | 0.67 | 0.032 | 46 | 33 | 74 | 128 | 26500 | 1.2 | 0.27 |
| Donor_6_3. Aliquot H | 60 | 3.7 | 0.025 | 39 | 33 | 84 | 94 | 692 | 1.3 | 0.13 |
| Donor_6_3. Aliquot I | 60 | 0.67 | 0.17 | 29 | 3.5 | 65 | 68 | 243 | 1.1 | 0.10 |
| | | | | | | | | | | |
| Donor_7_3. Aliquot A | 60 | 0.67 | 0.27 | 33 | 11 | 19900 | 273 | 89600 | 8.4 | 11 |
| Donor_7_3. Aliquot B | 60 | 0.67 | 0.21 | 27 | 20 | 5190 | 243 | 33900 | 7.8 | 11 |
| Donor_7_3. Aliquot C | 60 | 0.67 | 0.037 | 9.4 | 8.9 | 26 | 80 | 500 | 4.1 | 12 |
| Donor_7_3. Aliquot D | 60 | 0.67 | 0.15 | 29 | 5.9 | 54800 | 211 | 80600 | 6.5 | 11 |
| Donor_7_3. Aliquot E | 60 | 0.67 | 0.16 | 37 | 12 | 21600 | 247 | 41300 | 7.5 | 11 |
| Donor_7_3. Aliquot F | 60 | 0.67 | 0.12 | 23 | 13 | 242 | 138 | 812 | 6.2 | 11 |
| Donor_7_3. Aliquot G | 60 | 0.67 | 0.25 | 18 | 33 | 48 | 109 | 7810 | 6.6 | 6.9 |
| Donor_7_3. Aliquot H | 60 | 0.67 | 0.17 | 104 | 33 | 34 | 45 | 373 | 6.4 | 12 |
| Donor_7_3. Aliquot I | 60 | 1.2 | 0.044 | 104 | 4.3 | 16 | 80 | 225 | 6.1 | 12 |
| | | | | | | | | | | |
| Donor_8_3. Aliquot A | 60 | 1.6 | 0.083 | 43 | 8.2 | 1400 | 166 | 4320 | 1.9 | 0.50 |
| Donor_8_3. Aliquot B | 60 | 0.67 | 0.12 | 49 | 12 | 1140 | 184 | 4770 | 2.4 | 0.49 |
| Donor_8_3. Aliquot C | 60 | 0.67 | 0.12 | 45 | 2.5 | 840 | 120 | 846 | 0.73 | 0.38 |
| Donor_8_3. Aliquot D | 60 | 3.0 | 0.18 | 60 | 5.9 | 99400 | 205 | 66900 | 2.2 | 0.62 |
| Donor_8_3. Aliquot E | 60 | 1.6 | 0.11 | 48 | 14 | 83900 | 217 | 58300 | 2.4 | 0.64 |
| Donor_8_3. Aliquot F | 60 | 3.0 | 0.25 | 48 | 14 | 6720 | 185 | 952 | 3.3 | 0.49 |
| Donor_8_3. Aliquot G | 60 | 1.6 | 0.025 | 43 | 33 | 42 | 86 | 2470 | 0.91 | 0.36 |
| Donor_8_3. Aliquot H | 60 | 0.67 | 0.081 | 40 | 5.1 | 129 | 169 | 5280 | 1.7 | 0.53 |
| Donor_8_3. Aliquot I | 60 | 1.2 | 0.12 | 44 | 2.5 | 12 | 117 | 895 | 1.7 | 0.37 |
| | | | | | | | | | | |
| Donor_9_3. Aliquot A | 60 | 5.8 | 0.14 | 59 | 2.6 | 642 | 143 | 3910 | 6.2 | 2.0 |
| Donor_9_3. Aliquot B | 60 | 1.1 | 0.21 | 54 | 7.8 | 1100 | 156 | 4840 | 5.9 | 2.0 |
| Donor_9_3. Aliquot C | 60 | 0.67 | 0.20 | 59 | 5.3 | 1680 | 167 | 3560 | 3.1 | 1.6 |

FIG. 151.4

| | IL-2 pg/mL | IL-23 ng/mL | IL-3 ng/mL | IL-4 pg/mL | IL-5 pg/mL | IL-6 pg/mL | IL-7 pg/mL | IL-8 pg/mL | Insulin uIU/mL | Leptin ng/mL |
|---|---|---|---|---|---|---|---|---|---|---|
| Least Detectable Dose | 60 | <0.67 | 0.17 | 104 | 33 | 12 | 53 | 3.5 | 0.86 | 0.10 |
| | | | | | | | | | | |
| RBM Low Plasma Range | | PENDING | | | | | | | | |
| RBM High Plasma Range | 61 | PENDING | 1.2 | 103 | 62 | 25 | 3.7 | 59 | 34 | 0.41 |
| Donor_9_3. Aliquot D | 60 | 2.4 | 0.21 | 70 | 8.6 | 93100 | 125 | 48600 | 6.5 | 41 |
| Donor_9_3. Aliquot E | 60 | 0.67 | 0.17 | 67 | 5.3 | 61700 | 209 | 62300 | 6.3 | 2.0 |
| Donor_9_3. Aliquot F | 60 | 0.67 | 0.18 | 51 | 8.6 | 1900 | 192 | 1200 | 6.6 | 1.8 |
| Donor_9_3. Aliquot G | 60 | 0.67 | 0.11 | 75 | 33 | 131 | 159 | 21300 | 5.7 | 1.9 |
| Donor_9_3. Aliquot H | 60 | 0.67 | 0.098 | 55 | 33 | 57 | 126 | 1590 | 7.1 | 1.3 |
| Donor_9_3. Aliquot I | 60 | 1.7 | 0.10 | 43 | 33 | 19 | 141 | 797 | 5.3 | 1.9 |
| | | | | | | | 62 | | | 1.9 |
| EDTA Plasma | | | | | | | | | | |
| donor #1 plasma | 60 | 3.4 | 0.17 | 104 | 33 | 30 | 87 | 239 | 6.9 | 89 |
| donor #2 plasma | 60 | 1.1 | 0.17 | 104 | 8.2 | 102 | 42 | 319 | 5.8 | 9.7 |
| donor #3 plasma | 60 | 2.7 | 0.17 | 104 | 12 | 8.5 | 130 | 18 | 21 | 9.4 |
| donor #4 plasma | 60 | 2.4 | 0.17 | 104 | 4.0 | 49 | 52 | 102 | 16 | 15 |
| donor #5 plasma | 60 | 1.7 | 0.17 | 104 | 7.0 | 27 | 101 | 32 | 5.5 | 1.9 |
| donor #6 plasma | 60 | 1.9 | 0.17 | 104 | 7.0 | 54 | 103 | 24 | 0.57 | 0.046 |
| donor #7 plasma | 60 | 0.67 | 0.17 | 104 | 7.4 | 15 | 106 | 43 | 11 | 21 |
| donor #8 plasma | 60 | 0.67 | 0.14 | 44 | 6.1 | 1.8 | 83 | 3.5 | 1.0 | 0.64 |
| donor #9 plasma | 60 | 1.7 | 0.042 | 42 | 7.0 | 12 | 77 | 3.5 | 9.9 | 2.4 |

*Stimulations indices*

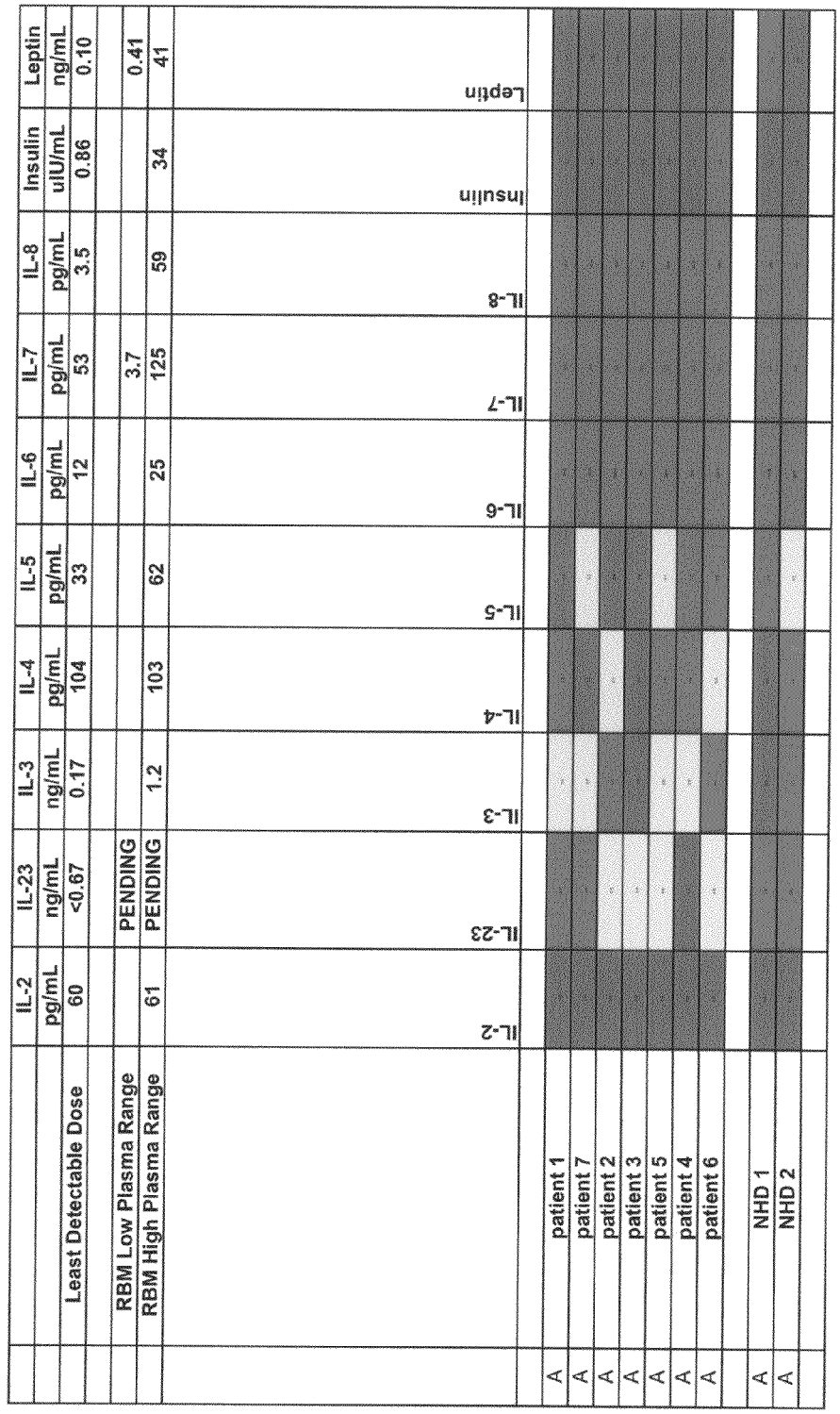
FIG. 151.5

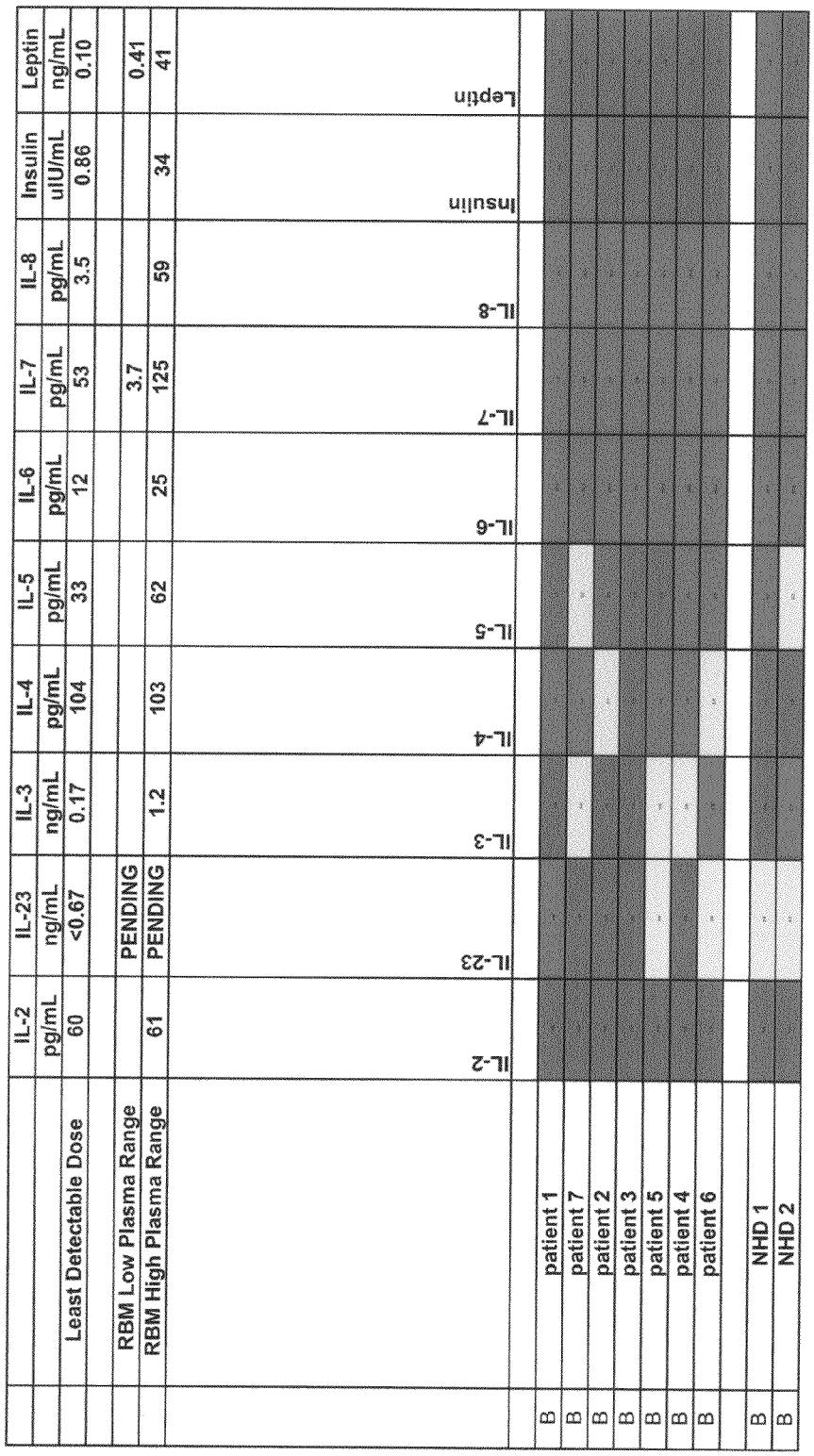
FIG. 151.6

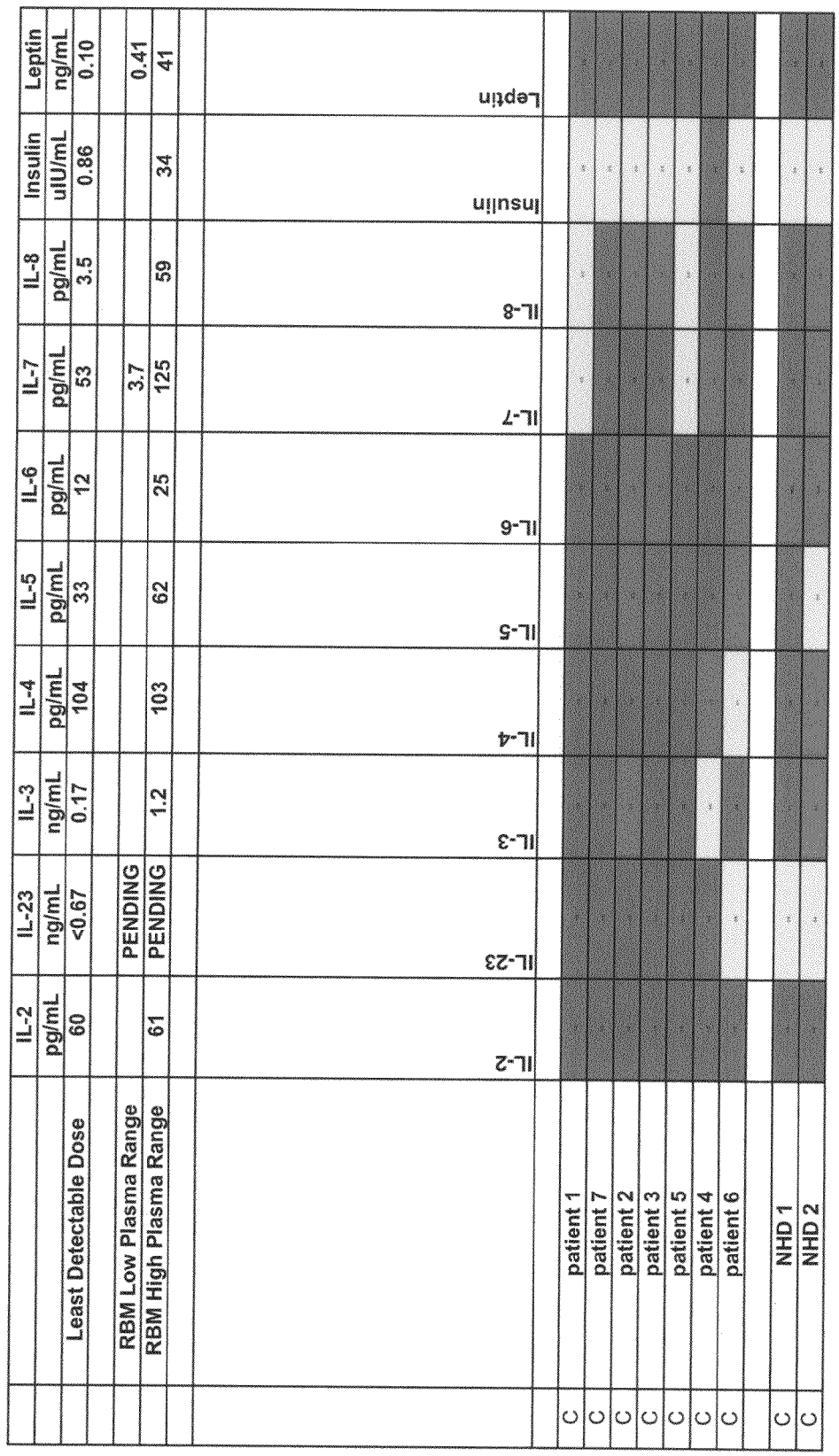
FIG. 151.7

FIG. 15I.8
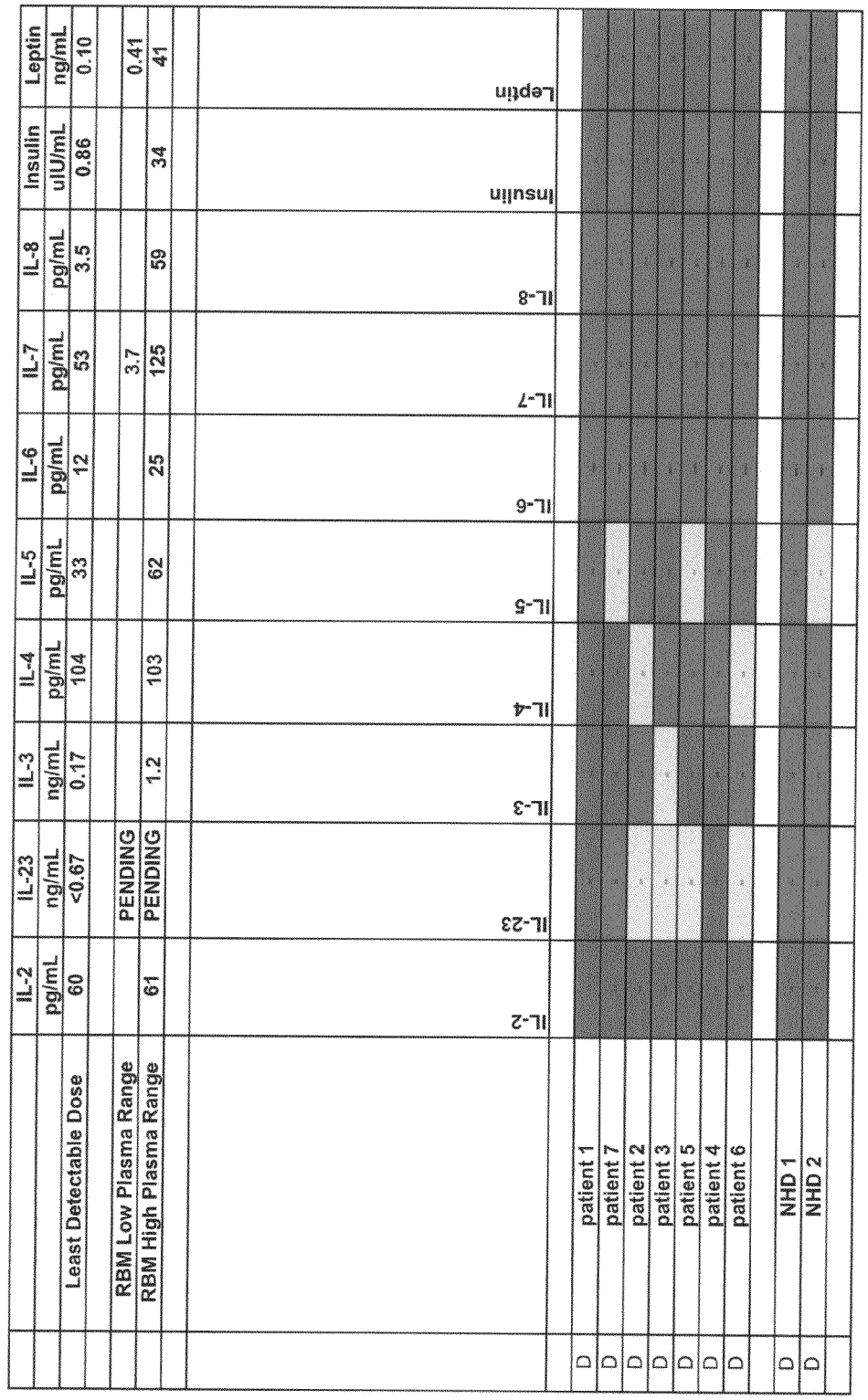

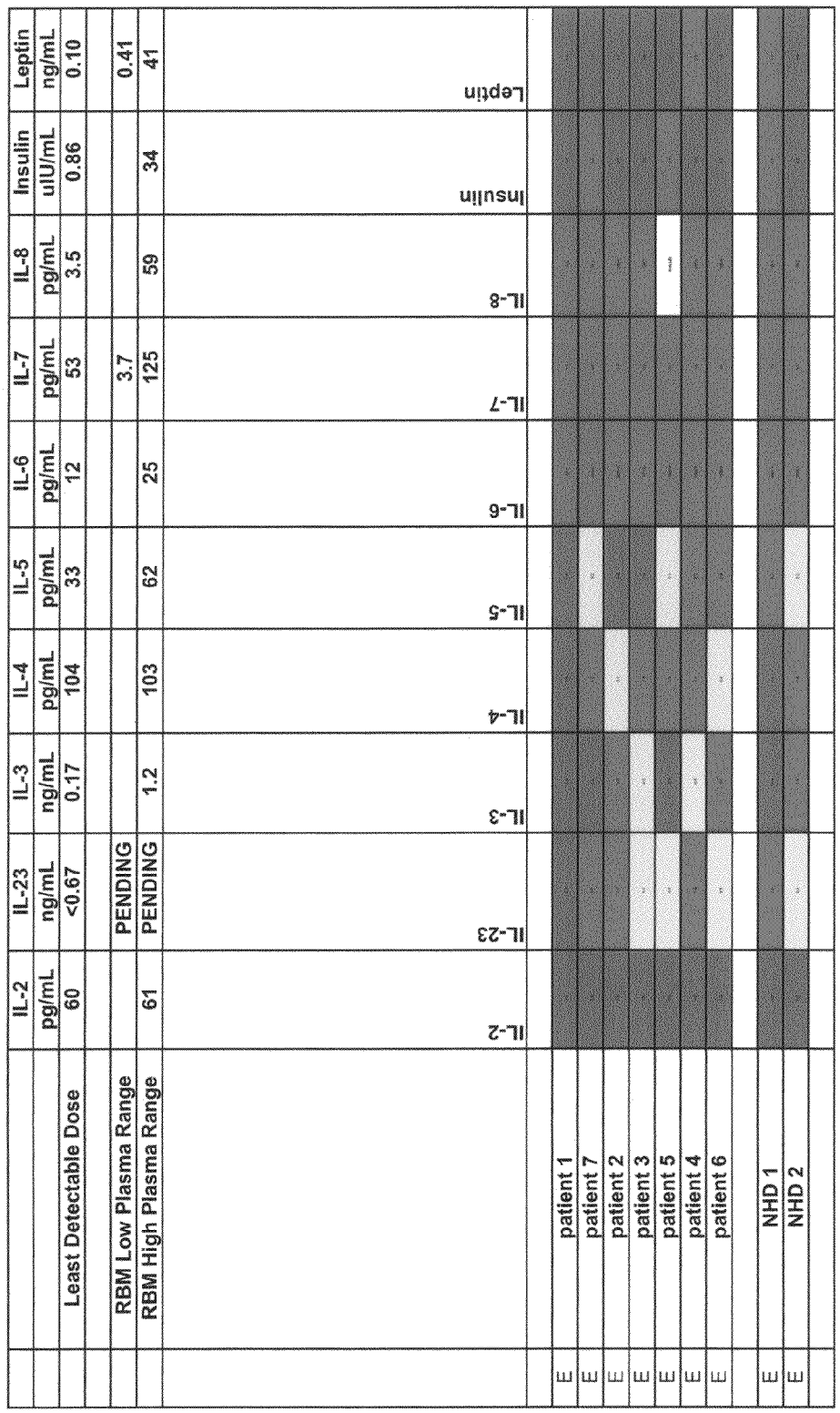
FIG. 15I.9

FIG. 15I.10
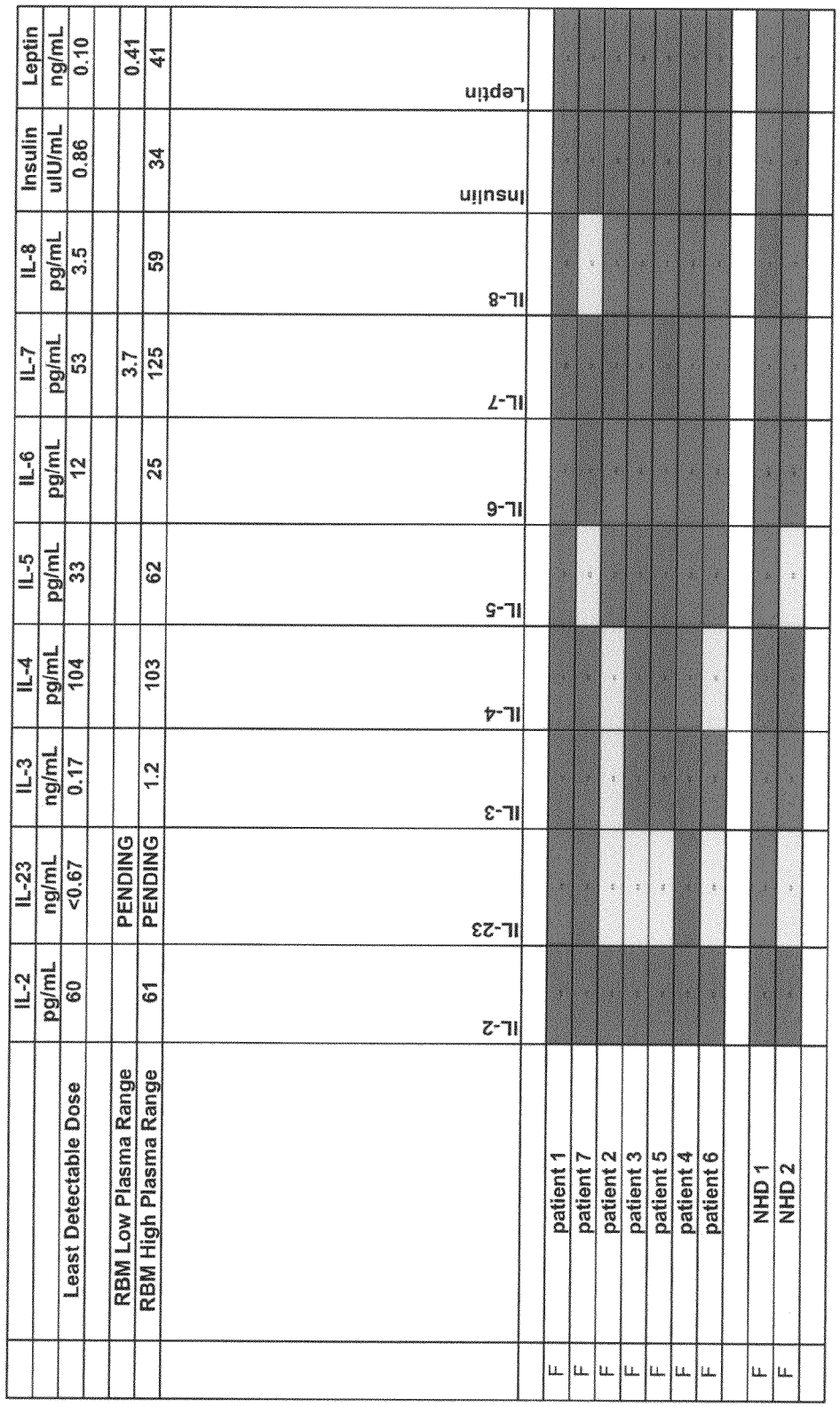

FIG. 15I.11
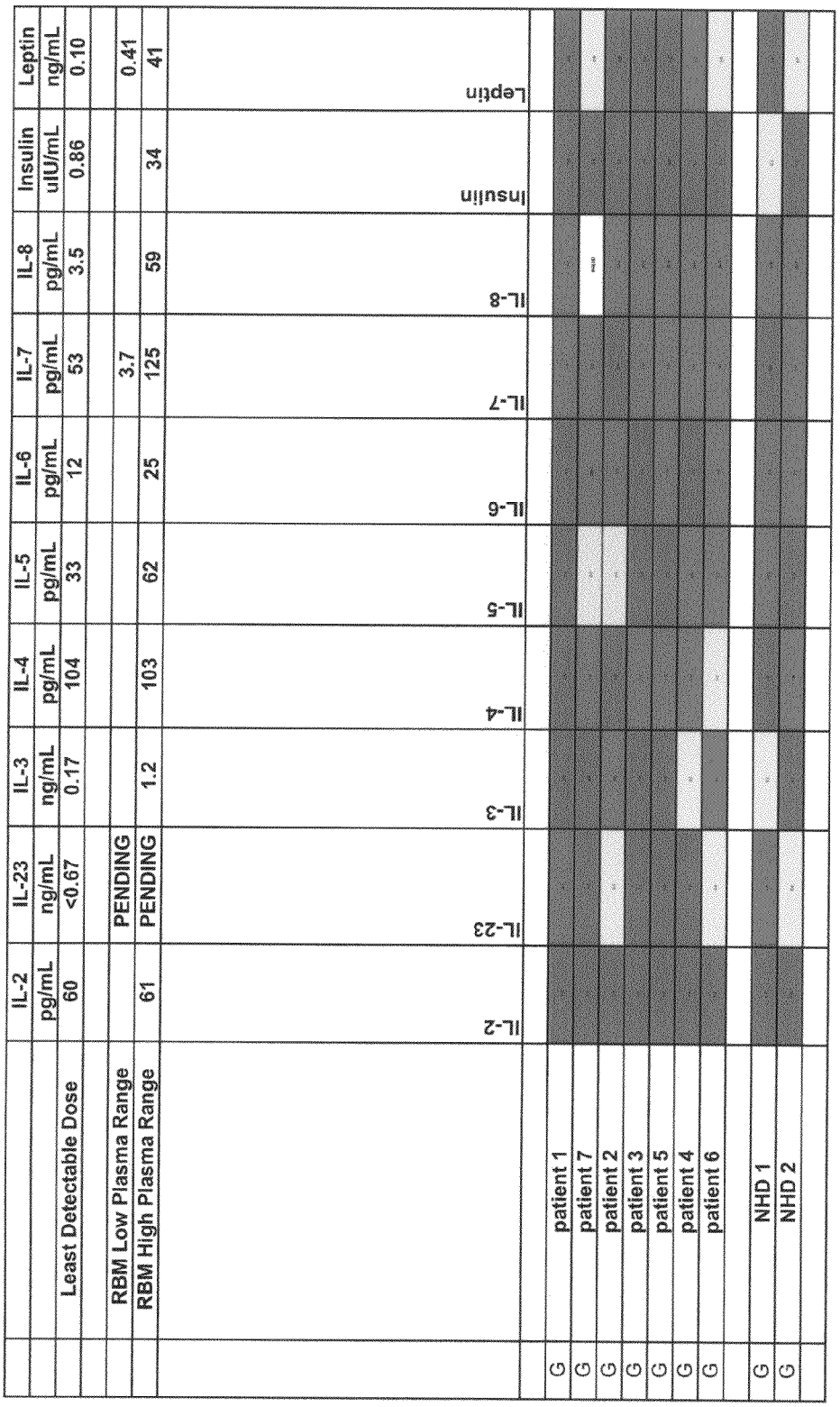

FIG. 15I.12
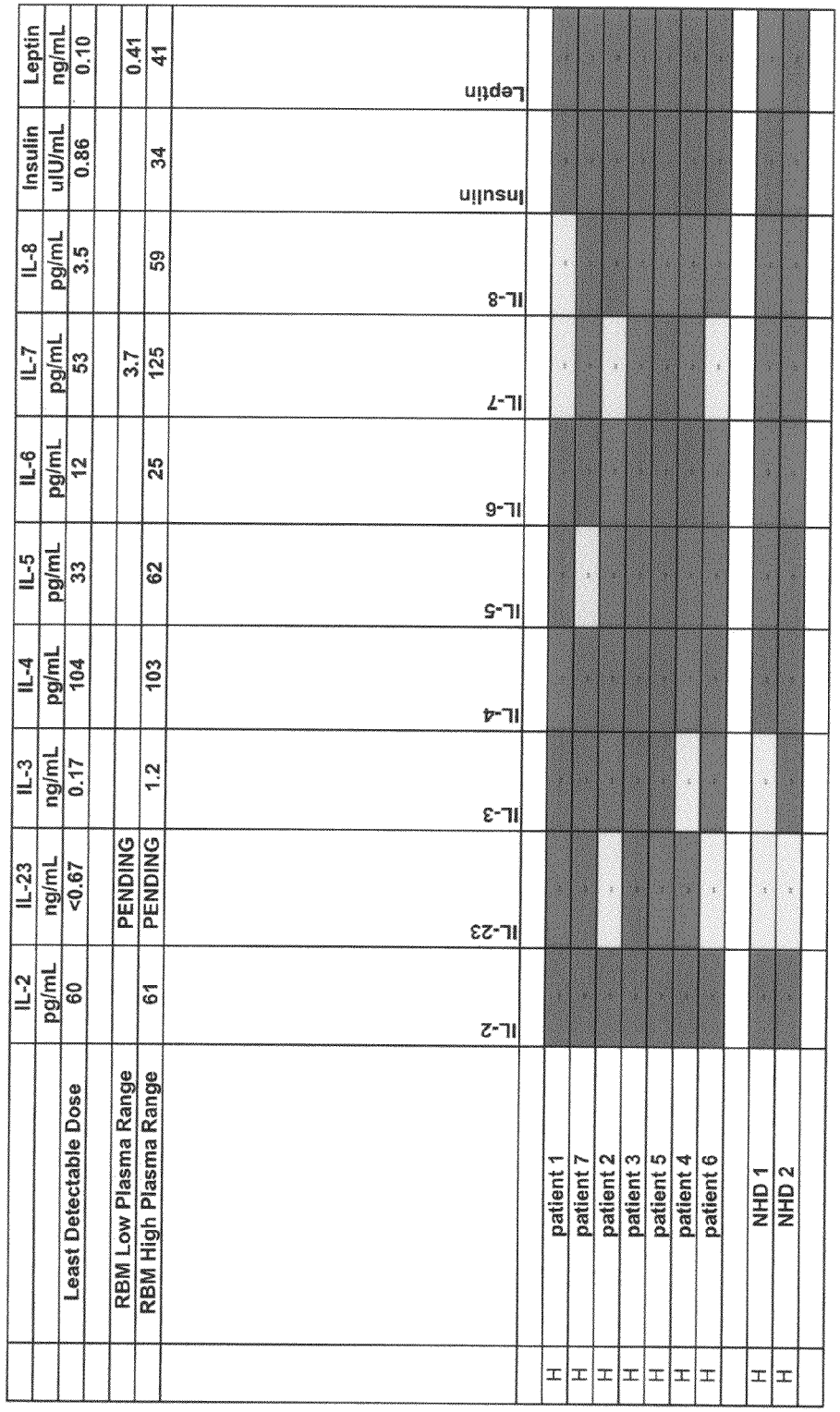

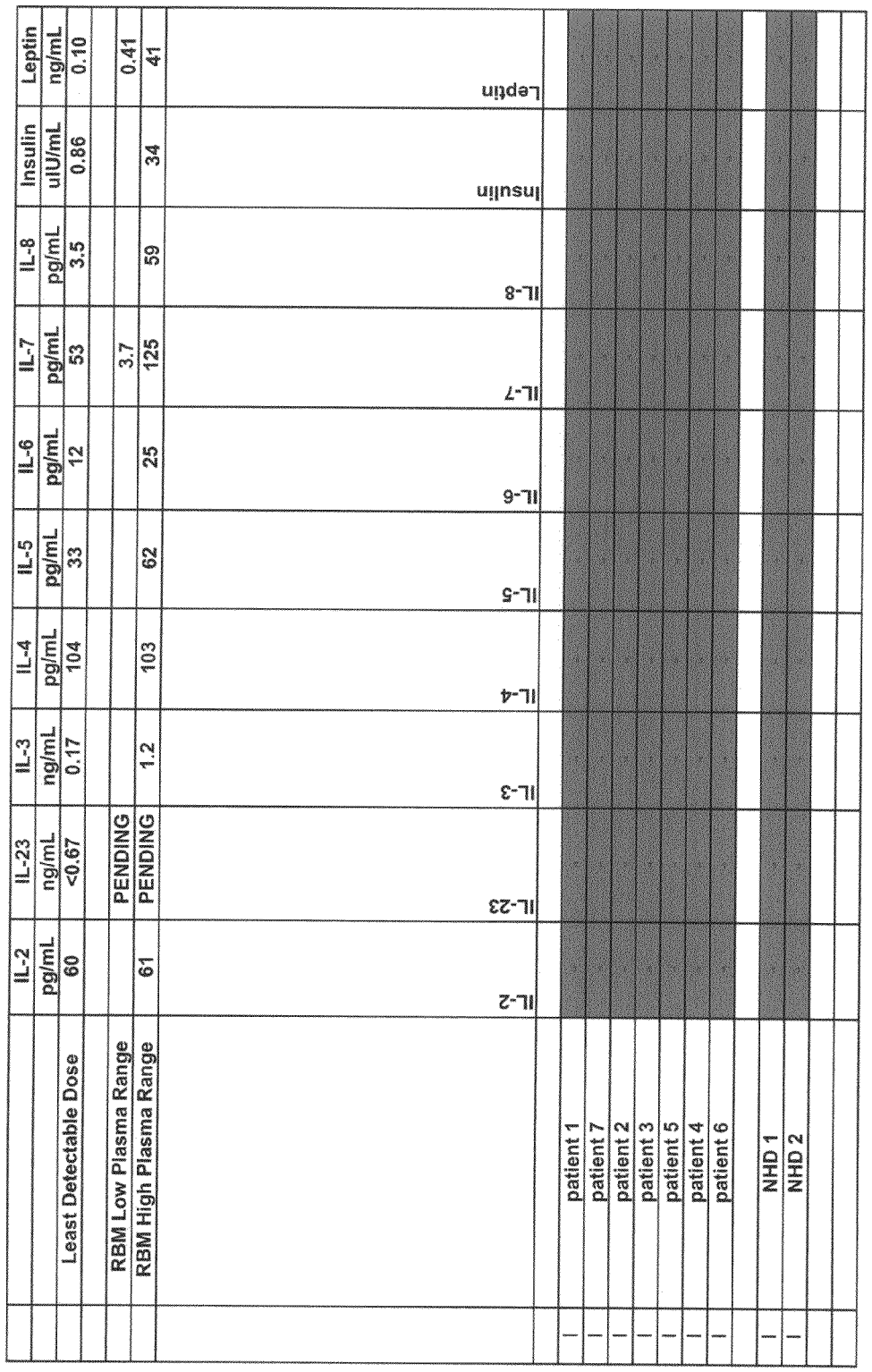
FIG. 15I.13

FIG. 15I.14

| | IL-2 pg/mL | IL-23 ng/mL | IL-3 ng/mL | IL-4 pg/mL | IL-5 pg/mL | IL-6 pg/mL | IL-7 pg/mL | IL-8 pg/mL | Insulin uIU/mL | Leptin ng/mL |
|---|---|---|---|---|---|---|---|---|---|---|
| Least Detectable Dose | 60 | <0.67 | 0.17 | 104 | 33 | 12 | 53 | 3.5 | 0.86 | 0.10 |
| RBM Low Plasma Range | | PENDING | | | | | 3.7 | | | 0.41 |
| RBM High Plasma Range | 61 | PENDING | 1.2 | 103 | 62 | 25 | 125 | 59 | 34 | 41 |
| Donor_6 3. Aliquot F | 60 | 0.67 | 0.12 | 44 | 8.9 | 517 | 124 | 3980 | 1.5 | 0.1 |
| Messwert > ULD | | | | | | | | | | |
| SI > 1,3 | | | | | | | | | | |
| SI 0,7-1,3 | | | | | | | | | | |
| SI 0-0,7 | | | | | | | | | | |

FIG. 15J.1

| | Lipoprotein (a) ug/mL | Lymphotactin ng/mL | MCP-1 pg/mL | MDC pg/mL | MIP-1alpha pg/mL | MIP-1beta pg/mL | MMP-2 ng/mL |
|---|---|---|---|---|---|---|---|
| Least Detectable Dose | 3.7 | 0.38 | 52 | 14 | 13 | 38 | 150 |
| RBM Low Plasma Range | 3.0 | | 35 | 162 | | 25 | 183 |
| RBM High Plasma Range | 858 | 0.57 | 401 | 774 | 89 | 595 | 3070 |
| Samples | | | | | | | |
| Donor_1 3. Aliquot A | 27 | 0.22 | 8710 | 197 | 3570 | 71300 | 474 |
| Donor_1 3. Aliquot B | 34 | 0.38 | 4230 | 187 | 1810 | 12800 | 440 |
| Donor_1 3. Aliquot C | 31 | 0.38 | 1210 | 180 | 94 | 610 | 71 |
| Donor_1 3. Aliquot D | 32 | 0.071 | 3940 | 203 | 3760 | 75700 | 443 |
| Donor_1 3. Aliquot E | 32 | 0.092 | 4040 | 185 | 1370 | 16800 | 456 |
| Donor_1 3. Aliquot F | 45 | 0.38 | 2120 | 146 | 197 | 2040 | 410 |
| Donor_1 3. Aliquot G | 37 | 0.38 | 8970 | 14 | 110 | 498 | 451 |
| Donor_1 3. Aliquot H | 32 | 0.38 | 1080 | 41 | 81 | 513 | 68 |
| Donor_1 3. Aliquot I | 30 | 0.38 | 1030 | 193 | 180 | 803 | 427 |
| Donor_2 3. Aliquot A | 38 | 0.26 | 9540 | 158 | 5430 | 94800 | 105 |
| Donor_2 3. Aliquot B | 46 | 0.22 | 3930 | 178 | 2250 | 52800 | 83 |
| Donor_2 3. Aliquot C | 47 | 0.15 | 499 | 160 | 91 | 1790 | 86 |
| Donor_2 3. Aliquot D | 48 | 0.28 | 3760 | 165 | 34700 | 460000 | 100 |
| Donor_2 3. Aliquot E | 58 | 0.25 | 4260 | 154 | 23000 | 331000 | 123 |
| Donor_2 3. Aliquot F | 128 | 0.38 | 810 | 141 | 191 | 4280 | 69 |
| Donor_2 3. Aliquot G | 46 | 0.28 | 42600 | 14 | 29600 | 95800 | 147 |
| Donor_2 3. Aliquot H | 47 | 0.38 | 917 | 33 | 360 | 7090 | 86 |
| Donor_2 3. Aliquot I | 48 | 0.38 | 555 | 156 | 179 | 5430 | 72 |
| Donor_3 3. Aliquot A | 61 | 0.33 | 11000 | 92 | 894 | 31700 | 30 |
| Donor_3 3. Aliquot B | 66 | 0.23 | 3820 | 86 | 387 | 17200 | 26 |
| Donor_3 3. Aliquot C | 68 | 0.15 | 228 | 87 | 46 | 1850 | 34 |
| Donor_3 3. Aliquot D | 58 | 0.32 | 2630 | 84 | 8550 | 254000 | 47 |
| Donor_3 3. Aliquot E | 70 | 0.39 | 2870 | 72 | 3710 | 126000 | 34 |
| Donor_3 3. Aliquot F | 83 | 0.39 | 246 | 70 | 66 | 2900 | 34 |
| Donor_3 3. Aliquot G | 57 | 0.21 | 521 | 14 | 60 | 1680 | 67 |

FIG. 15J.2

| | Lipoprotein (a) ug/mL | Lymphotactin ng/mL | MCP-1 pg/mL | MDC pg/mL | MIP-1alpha pg/mL | MIP-1beta pg/mL | MMP-2 ng/mL |
|---|---|---|---|---|---|---|---|
| Least Detectable Dose | 3.7 | 0.38 | 52 | 14 | 13 | 38 | 150 |
| RBM Low Plasma Range | 3.0 | | 35 | 162 | | 25 | 183 |
| RBM High Plasma Range | 858 | 0.57 | 401 | 774 | 89 | 595 | 3070 |
| Donor_3 3. Aliquot H | 61 | 0.38 | 126 | 12 | 42 | 633 | 23 |
| Donor_3 3. Aliquot I | 66 | 0.54 | 110 | 85 | 46 | 123 | 150 |
| Donor_4 3. Aliquot A | 23 | 0.38 | 2430 | 324 | 432 | 13100 | 150 |
| Donor_4 3. Aliquot B | 21 | 0.38 | 2960 | 346 | 288 | 9460 | 150 |
| Donor_4 3. Aliquot C | 21 | 0.38 | 578 | 280 | 137 | 994 | 150 |
| Donor_4 3. Aliquot D | 24 | 0.16 | 14900 | 335 | 31200 | 484000 | 43 |
| Donor_4 3. Aliquot E | 22 | 0.20 | 15800 | 259 | 17700 | 293000 | 50 |
| Donor_4 3. Aliquot F | 24 | 0.12 | 15400 | 251 | 1740 | 84100 | 150 |
| Donor_4 3. Aliquot G | 22 | 0.38 | 6110 | 14 | 547 | 3900 | 45 |
| Donor_4 3. Aliquot H | 21 | 0.38 | 641 | 66 | 106 | 3160 | 15 |
| Donor_4 3. Aliquot I | 25 | 0.38 | 269 | 298 | 63 | 287 | 150 |
| Donor_5 3. Aliquot A | 22 | 0.31 | 11900 | 298 | 6820 | 150000 | 106 |
| Donor_5 3. Aliquot B | 20 | 0.33 | 7660 | 424 | 9780 | 174000 | 112 |
| Donor_5 3. Aliquot C | 21 | 0.15 | 226 | 221 | 111 | 1790 | 115 |
| Donor_5 3. Aliquot D | 19 | 0.36 | 3740 | 190 | 36200 | 543000 | 132 |
| Donor_5 3. Aliquot E | 21 | 0.33 | 5360 | 205 | 46800 | 600000 | 138 |
| Donor_5 3. Aliquot F | 39 | 0.071 | 2920 | 171 | 1790 | 24300 | 67 |
| Donor_5 3. Aliquot G | 18 | 0.22 | 14900 | 14 | 527 | 3130 | 120 |
| Donor_5 3. Aliquot H | 17 | 0.38 | 523 | 55 | 328 | 5000 | 90 |
| Donor_5 3. Aliquot I | 18 | 0.38 | 231 | 218 | 119 | 3870 | 83 |
| Donor_6 3. Aliquot A | 36 | 0.72 | 3750 | 124 | 1810 | 27400 | 12 |
| Donor_6 3. Aliquot B | 40 | 0.72 | 2190 | 124 | 1690 | 22200 | 15 |
| Donor_6 3. Aliquot C | 39 | 0.62 | 218 | 110 | 55 | 376 | 150 |
| Donor_6 3. Aliquot D | 43 | 0.80 | 1360 | 136 | 29200 | 402000 | 20 |
| Donor_6 3. Aliquot E | 35 | 0.69 | 990 | 110 | 36100 | 441000 | 28 |

FIG. 15J.3

| | Lipoprotein (a) ug/mL | Lymphotactin ng/mL | MCP-1 pg/mL | MDC pg/mL | MIP-1alpha pg/mL | MIP-1beta pg/mL | MMP-2 ng/mL |
|---|---|---|---|---|---|---|---|
| Least Detectable Dose | 3.7 | 0.38 | 52 | 14 | 13 | 38 | 150 |
| RBM Low Plasma Range | 3.0 | | 35 | 162 | | 25 | 183 |
| RBM High Plasma Range | 858 | 0.57 | 401 | 774 | 89 | 595 | 3070 |
| Donor_6 3. Aliquot F | 79 | 0.79 | 2110 | 94 | 491 | 7470 | 150 |
| Donor_6 3. Aliquot G | 31 | 0.50 | 3670 | 14 | 800 | 3130 | 75 |
| Donor_6 3. Aliquot H | 32 | 0.50 | 240 | 29 | 143 | 3680 | 150 |
| Donor_6 3. Aliquot I | 25 | 0.52 | 146 | 113 | 49 | 317 | 150 |
| Donor_7 3. Aliquot A | 203 | 0.96 | 14700 | 94 | 6080 | 188000 | 16 |
| Donor_7 3. Aliquot B | 222 | 0.78 | 5090 | 99 | 2700 | 68500 | 150 |
| Donor_7 3. Aliquot C | 160 | 0.53 | 314 | 83 | 46 | 680 | 150 |
| Donor_7 3. Aliquot D | 192 | 0.75 | 5040 | 92 | 7530 | 349000 | 23 |
| Donor_7 3. Aliquot E | 215 | 0.83 | 8810 | 96 | 4790 | 179000 | 23 |
| Donor_7 3. Aliquot F | 548 | 0.88 | 1260 | 72 | 152 | 5030 | 150 |
| Donor_7 3. Aliquot G | 148 | 0.24 | 3610 | 14 | 469 | 2280 | 47 |
| Donor_7 3. Aliquot H | 155 | 0.33 | 309 | 17 | 43 | 762 | 150 |
| Donor_7 3. Aliquot I | 190 | 0.53 | 265 | 84 | 38 | 156 | 150 |
| Donor_8 3. Aliquot A | 16 | 0.93 | 4750 | 223 | 1840 | 22700 | 37 |
| Donor_8 3. Aliquot B | 16 | 0.96 | 3720 | 221 | 1450 | 21000 | 37 |
| Donor_8 3. Aliquot C | 16 | 0.91 | 5420 | 154 | 2130 | 58500 | 23 |
| Donor_8 3. Aliquot D | 13 | 1.1 | 2170 | 337 | 67800 | 572000 | 89 |
| Donor_8 3. Aliquot E | 18 | 1.2 | 4380 | 245 | 46800 | 387000 | 75 |
| Donor_8 3. Aliquot F | 18 | 1.2 | 12700 | 138 | 6380 | 129000 | 53 |
| Donor_8 3. Aliquot G | 12 | 0.47 | 1940 | 14 | 931 | 7690 | 58 |
| Donor_8 3. Aliquot H | 13 | 0.80 | 7890 | 90 | 3290 | 29900 | 43 |
| Donor_8 3. Aliquot I | 14 | 0.80 | 385 | 256 | 266 | 4590 | 26 |
| Donor_9 3. Aliquot A | 18 | 0.68 | 5430 | 169 | 1250 | 24500 | 38 |
| Donor_9 3. Aliquot B | 12 | 0.73 | 3060 | 175 | 1690 | 23200 | 43 |
| Donor_9 3. Aliquot C | 13 | 0.69 | 16600 | 180 | 2140 | 46900 | 72 |

FIG. 15J.4

| | Lipoprotein (a) ug/mL | Lymphotactin ng/mL | MCP-1 pg/mL | MDC pg/mL | MIP-1alpha pg/mL | MIP-1beta pg/mL | MMP-2 ng/mL |
|---|---|---|---|---|---|---|---|
| Least Detectable Dose | 3.7 | 0.38 | 52 | 14 | 13 | 38 | 150 |
| RBM Low Plasma Range | 3.0 | | 35 | 162 | | 25 | 183 |
| RBM High Plasma Range | 858 | 0.57 | 401 | 774 | 89 | 595 | 3070 |
| Donor_9 3. Aliquot D | 17 | 0.62 | 6120 | 196 | 42300 | 431000 | 132 |
| Donor_9 3. Aliquot E | 16 | 0.71 | 9540 | 194 | 29700 | 355000 | 82 |
| Donor_9 3. Aliquot F | 18 | 0.86 | 12800 | 142 | 2410 | 78800 | 46 |
| Donor_9 3. Aliquot G | 11 | 0.20 | 15500 | 14 | 1820 | 12300 | 95 |
| Donor_9 3. Aliquot H | 11 | 0.38 | 2420 | 70 | 467 | 14400 | 48 |
| Donor_9 3. Aliquot I | 14 | 0.53 | 346 | 181 | 240 | 3670 | 42 |
| EDTA Plasma | | | | | | | |
| donor #1 plasma | 46 | 0.38 | 230 | 187 | 69 | 209 | 1750 |
| donor #2 plasma | 109 | 0.38 | 66 | 236 | 60 | 239 | 3910 |
| donor #3 plasma | 143 | 0.12 | 11 | 116 | 41 | 65 | 1540 |
| donor #4 plasma | 31 | 0.38 | 23 | 413 | 59 | 368 | 8190 |
| donor #5 plasma | 31 | 0.12 | 17 | 307 | 46 | 154 | 898 |
| donor #6 plasma | 91 | 0.28 | 32 | 155 | 34 | 68 | 972 |
| donor #7 plasma | 735 | 0.42 | 109 | 124 | 48 | 145 | 2270 |
| donor #8 plasma | 17 | 0.31 | 147 | 176 | 42 | 47 | 10 |
| donor #9 plasma | 23 | 0.33 | 89 | 159 | 44 | 38 | 46 |
| *Stimulations indices* | | | | | | | |

FIG. 15J.5

| | Lipoprotein (a) ug/mL | Lymphotactin ng/mL | MCP-1 pg/mL | MDC pg/mL | MIP-1alpha pg/mL | MIP-1beta pg/mL | MMP-2 ng/mL |
|---|---|---|---|---|---|---|---|
| Least Detectable Dose | 3.7 | 0.38 | 52 | 14 | 13 | 38 | 150 |
| RBM Low Plasma Range | 3.0 | | 35 | 162 | | 25 | 183 |
| RBM High Plasma Range | 858 | 0.57 | 401 | 774 | 89 | 595 | 3070 |
| patient 1 | A | | | | | | |
| patient 7 | A | | | | | | |
| patient 2 | A | | | | | | |
| patient 3 | A | | | | | | |
| patient 5 | A | | | | | | |
| patient 4 | A | | | | | | |
| patient 6 | A | | | | | | |
| NHD 1 | A | | | | | | |
| NHD 2 | A | | | | | | |

FIG. 15J.6

| | Lipoprotein (a) ug/mL | Lymphotactin ng/mL | MCP-1 pg/mL | MDC pg/mL | MIP-1alpha pg/mL | MIP-1beta pg/mL | MMP-2 ng/mL |
|---|---|---|---|---|---|---|---|
| Least Detectable Dose | 3.7 | 0.38 | 52 | 14 | 13 | 38 | 150 |
| RBM Low Plasma Range | 3.0 | | 35 | 162 | | 25 | 183 |
| RBM High Plasma Range | 858 | 0.57 | 401 | 774 | 89 | 595 | 3070 |
| patient 1 | B | B | B | B | B | B | B |
| patient 7 | B | B | B | B | B | B | B |
| patient 2 | B | B | B | B | B | B | B |
| patient 3 | B | B | B | B | B | B | B |
| patient 5 | B | B | B | B | B | B | B |
| patient 4 | B | B | B | B | B | B | B |
| patient 6 | B | B | B | B | B | B | B |
| NHD 1 | B | | | | | | B |
| NHD 2 | B | | | | | | B |

FIG. 15J.7
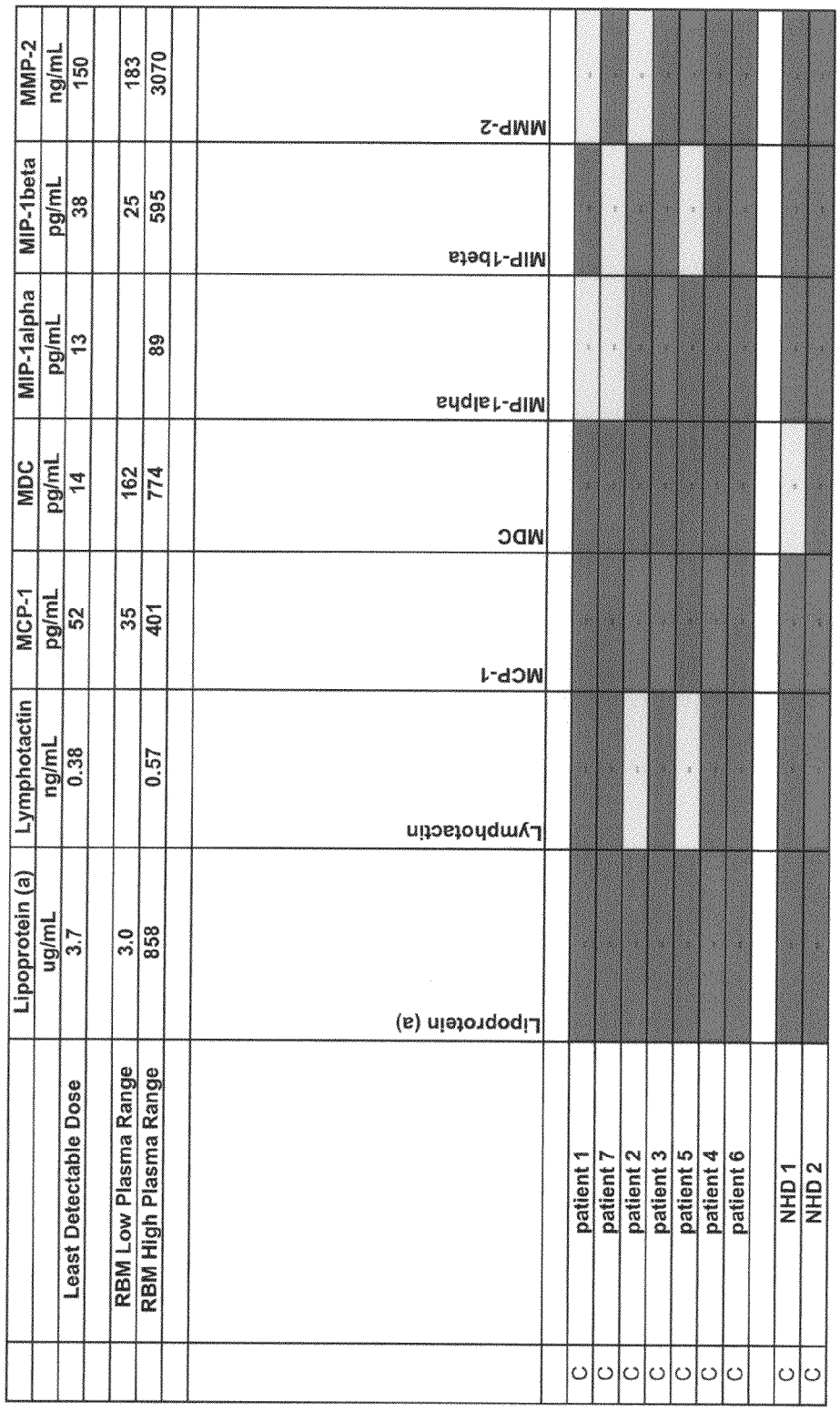

FIG. 15J.8
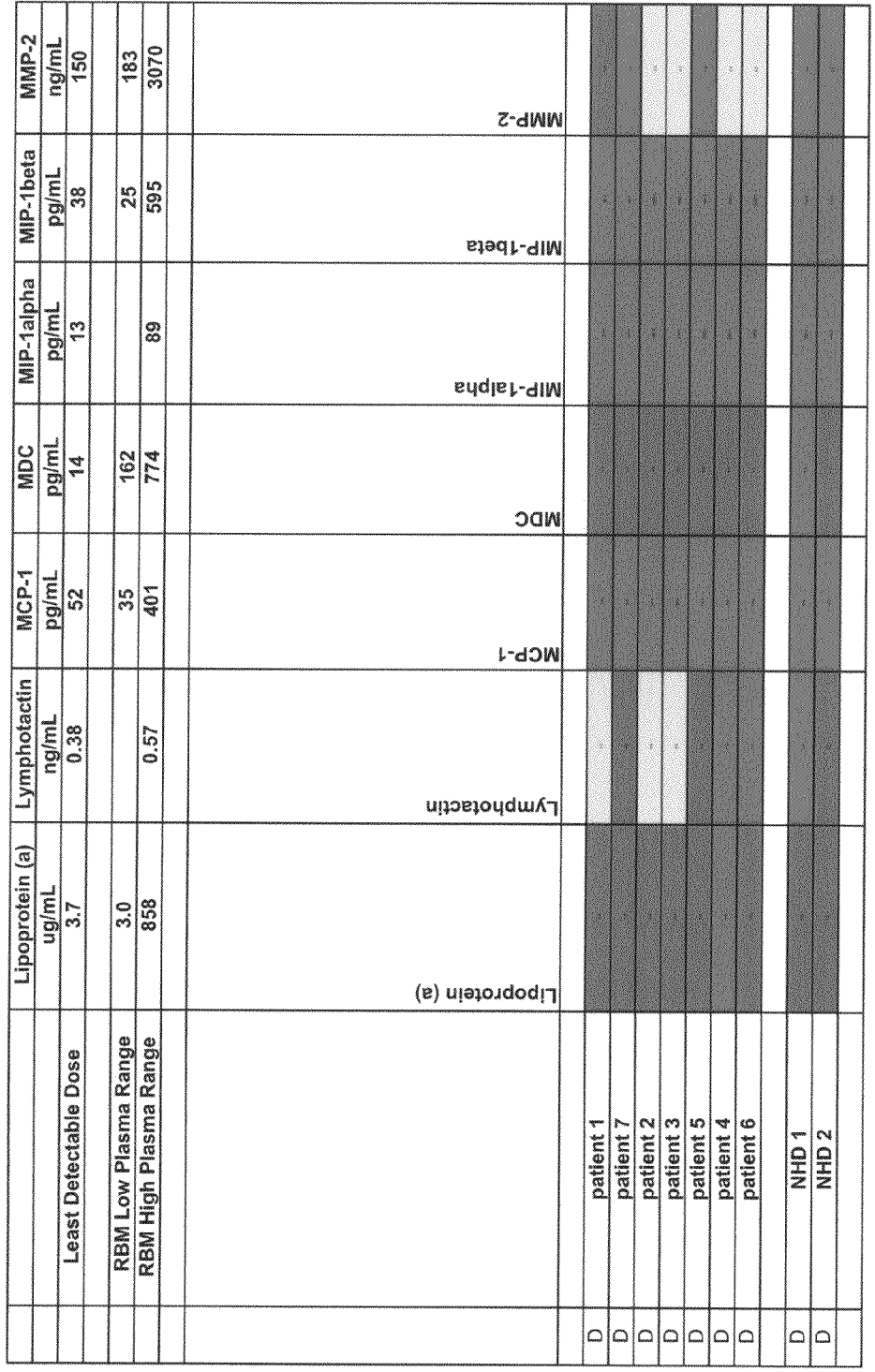

FIG. 15J.9

| | Lipoprotein (a) ug/mL | Lymphotactin ng/mL | MCP-1 pg/mL | MDC pg/mL | MIP-1alpha pg/mL | MIP-1beta pg/mL | MMP-2 ng/mL |
|---|---|---|---|---|---|---|---|
| Least Detectable Dose | 3.7 | 0.38 | 52 | 14 | 13 | 38 | 150 |
| RBM Low Plasma Range | 3.0 | | 35 | 162 | | 25 | 183 |
| RBM High Plasma Range | 858 | 0.57 | 401 | 774 | 89 | 595 | 3070 |
| patient 1 | | | | | | | |
| patient 7 | | | | | | | |
| patient 2 | | | | | | | |
| patient 3 | | | | | | | |
| patient 5 | | | | | | | |
| patient 4 | | | | | | | |
| patient 6 | | | | | | | |
| NHD 1 | | | | | | | |
| NHD 2 | | | | | | | |

FIG. 15J.10

| | Lipoprotein (a) ug/mL | Lymphotactin ng/mL | MCP-1 pg/mL | MDC pg/mL | MIP-1alpha pg/mL | MIP-1beta pg/mL | MMP-2 ng/mL |
|---|---|---|---|---|---|---|---|
| Least Detectable Dose | 3.7 | 0.38 | 52 | 14 | 13 | 38 | 150 |
| RBM Low Plasma Range | 3.0 | | 35 | 162 | | 25 | 183 |
| RBM High Plasma Range | 858 | 0.57 | 401 | 774 | 89 | 595 | 3070 |

| | Lipoprotein (a) | Lymphotactin | MCP-1 | MDC | MIP-1alpha | MIP-1beta | MMP-2 |
|---|---|---|---|---|---|---|---|
| patient 1 | F | | | | | | |
| patient 7 | F | | | | | | |
| patient 2 | F | | | | | | |
| patient 3 | F | | | | | | |
| patient 5 | F | | | | | | |
| patient 4 | F | | | | | | |
| patient 6 | F | | | | | | |
| NHD 1 | F | | | | | | |
| NHD 2 | F | | | | | | |

FIG. 15J.11

| | Lipoprotein (a) ug/mL | Lymphotactin ng/mL | MCP-1 pg/mL | MDC pg/mL | MIP-1alpha pg/mL | MIP-1beta pg/mL | MMP-2 ng/mL |
|---|---|---|---|---|---|---|---|
| Least Detectable Dose | 3.7 | 0.38 | 52 | 14 | 13 | 38 | 150 |
| RBM Low Plasma Range | 3.0 | 0.57 | 35 | 162 | 89 | 25 | 183 |
| RBM High Plasma Range | 858 | | 401 | 774 | | 595 | 3070 |

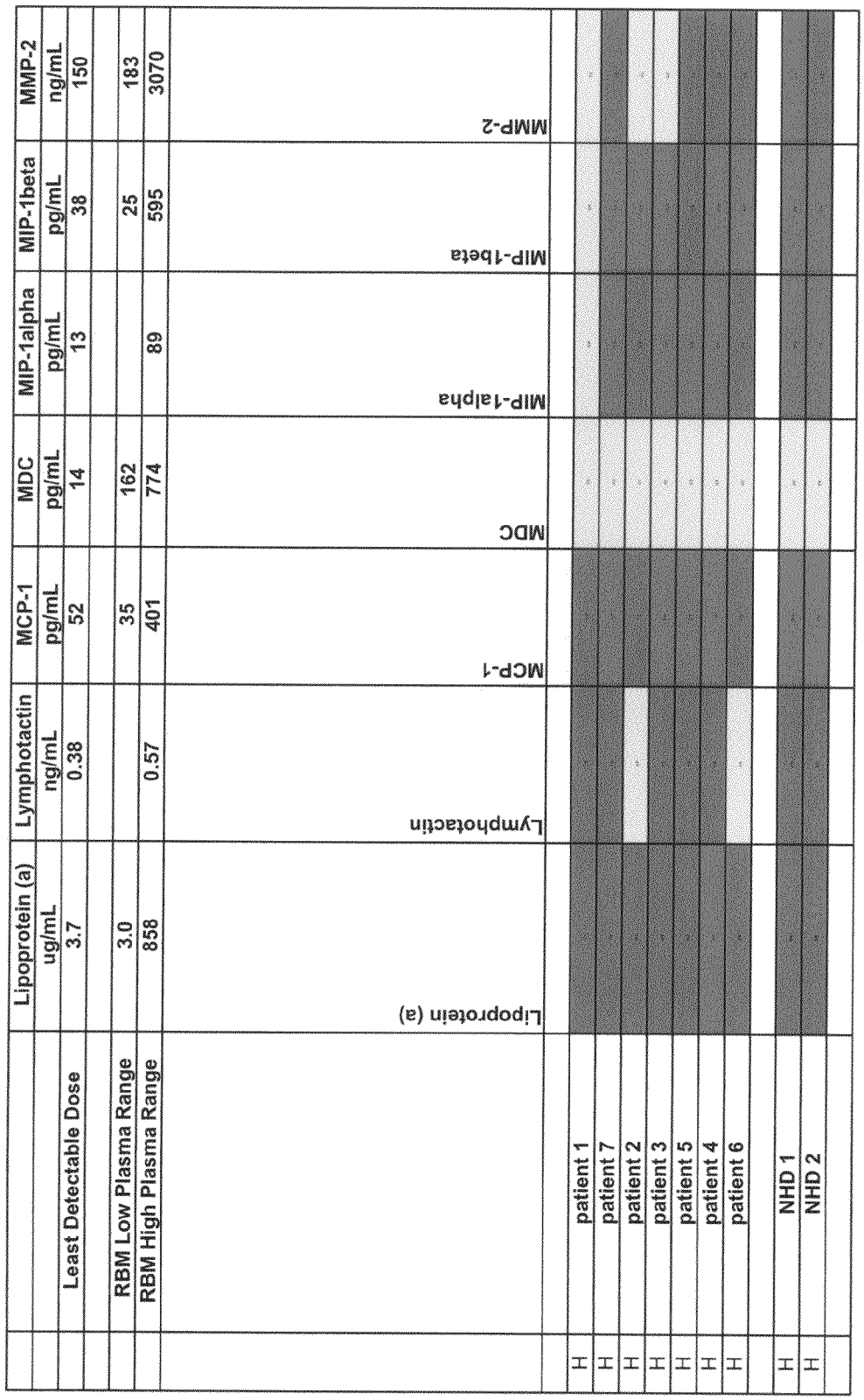
FIG. 15J.12

FIG. 15J.13

| | Lipoprotein (a) ug/mL | Lymphotactin ng/mL | MCP-1 pg/mL | MDC pg/mL | MIP-1alpha pg/mL | MIP-1beta pg/mL | MMP-2 ng/mL |
|---|---|---|---|---|---|---|---|
| Least Detectable Dose | 3.7 | 0.38 | 52 | 14 | 13 | 38 | 150 |
| RBM Low Plasma Range | 3.0 | | 35 | 162 | | 25 | 183 |
| RBM High Plasma Range | 858 | 0.57 | 401 | 774 | 89 | 595 | 3070 |
| patient 1 | | | | | | | |
| patient 7 | | | | | | | |
| patient 2 | | | | | | | |
| patient 3 | | | | | | | |
| patient 5 | | | | | | | |
| patient 4 | | | | | | | |
| patient 6 | | | | | | | |
| NHD 1 | | | | | | | |
| NHD 2 | | | | | | | |

FIG. 15J.14

|  | Lipoprotein (a) ug/mL | Lymphotactin ng/mL | MCP-1 pg/mL | MDC pg/mL | MIP-1alpha pg/mL | MIP-1beta pg/mL | MMP-2 ng/mL |
|---|---|---|---|---|---|---|---|
| Least Detectable Dose |  | 0.38 | 52 | 14 | 13 | 38 | 150 |
| RBM Low Plasma Range | 3.0 |  | 35 | 162 |  | 25 | 183 |
| RBM High Plasma Range | 858 | 0.57 | 401 | 774 | 89 | 595 | 3070 |
| Messwert > ULD |  |  |  |  |  |  |  |
| SI > 1,3 |  |  |  |  |  |  |  |
| SI 0,7-1,3 |  |  |  |  |  |  |  |
| SI 0-0,7 |  |  |  |  |  |  |  |

FIG. 15K.1

| | MMP-3 ng/mL | MMP-9 ng/mL | Myeloperoxidase ng/mL | Myoglobin ng/mL | OSM (Oncostatin M) pg/mL | PAI-1 ng/mL |
|---|---|---|---|---|---|---|
| Least Detectable Dose | 0.20 | 37 | 68 | 1.1 | 28 | 0.90 |
| RBM Low Plasma Range | | | | 3.6 | PENDING | 10 |
| RBM High Plasma Range | 1.8 | 1050 | 1110 | 37 | PENDING | 87 |
| Samples | | | | | | |
| Donor_1 3. Aliquot A | 12 | 74 | 2010 | 85 | 312 | 159 |
| Donor_1 3. Aliquot B | 11 | 53 | 1590 | 94 | 188 | 171 |
| Donor_1 3. Aliquot C | 12 | 30 | 1390 | 101 | 21 | 172 |
| Donor_1 3. Aliquot D | 13 | 56 | 2050 | 102 | 143 | 156 |
| Donor_1 3. Aliquot E | 12 | 57 | 2330 | 90 | 312 | 152 |
| Donor_1 3. Aliquot F | 11 | 33 | 1970 | 95 | 120 | 135 |
| Donor_1 3. Aliquot G | 13 | 49 | 1750 | 104 | 422 | 187 |
| Donor_1 3. Aliquot H | 12 | 46 | 1740 | 95 | 28 | 184 |
| Donor_1 3. Aliquot I | 11 | 38 | 1380 | 89 | 76 | 160 |
| Donor_2 3. Aliquot A | 11 | 59 | 3520 | 60 | 603 | 178 |
| Donor_2 3. Aliquot B | 11 | 59 | 2910 | 62 | 334 | 190 |
| Donor_2 3. Aliquot C | 12 | 42 | 1540 | 61 | 28 | 155 |
| Donor_2 3. Aliquot D | 13 | 60 | 4180 | 58 | 222 | 165 |
| Donor_2 3. Aliquot E | 11 | 53 | 3380 | 60 | 188 | 161 |
| Donor_2 3. Aliquot F | 11 | 2.2 | 1610 | 63 | 65 | 156 |
| Donor_2 3. Aliquot G | 11 | 28 | 3280 | 64 | 765 | 205 |
| Donor_2 3. Aliquot H | 11 | 55 | 4200 | 59 | 82 | 177 |
| Donor_2 3. Aliquot I | 9.7 | 51 | 1730 | 57 | 44 | 164 |
| Donor_3 3. Aliquot A | 5.4 | 72 | 2890 | 165 | 301 | 246 |
| Donor_3 3. Aliquot B | 4.8 | 59 | 2640 | 150 | 329 | 221 |
| Donor_3 3. Aliquot C | 5.0 | 55 | 2210 | 164 | 98 | 199 |
| Donor_3 3. Aliquot D | 4.9 | 91 | 3310 | 159 | 395 | 225 |
| Donor_3 3. Aliquot E | 5.3 | 74 | 3500 | 172 | 466 | 208 |
| Donor_3 3. Aliquot F | 4.4 | 54 | 2630 | 152 | 109 | 216 |
| Donor_3 3. Aliquot G | 4.3 | 45 | 2240 | 162 | 705 | 246 |

FIG. 15K.2

| | MMP-3 ng/mL | MMP-9 ng/mL | Myeloperoxidase ng/mL | Myoglobin ng/mL | OSM (Oncostatin M) pg/mL | PAI-1 ng/mL |
|---|---|---|---|---|---|---|
| Least Detectable Dose | 0.20 | 37 | 68 | 1.1 | 28 | 0.90 |
| RBM Low Plasma Range | | | | 3.6 | PENDING | 10 |
| RBM High Plasma Range | | | | 37 | PENDING | 87 |
| Donor_3 3. Aliquot H | 1.8 | 1050 | 1110 | 143 | 165 | 207 |
| Donor_3 3. Aliquot I | 3.9 | 49 | 2830 | 150 | 98 | 214 |
| | 4.7 | 42 | 2450 | | | |
| Donor_4 3. Aliquot A | 7.5 | 26 | 2710 | 55 | 28 | 253 |
| Donor_4 3. Aliquot B | 7.5 | 26 | 1940 | 52 | 54 | 236 |
| Donor_4 3. Aliquot C | 6.8 | 4.9 | 3400 | 54 | 28 | 229 |
| Donor_4 3. Aliquot D | 7.4 | 27 | 3920 | 52 | 120 | 216 |
| Donor_4 3. Aliquot E | 6.6 | 49 | 4430 | 53 | 165 | 222 |
| Donor_4 3. Aliquot F | 6.6 | 14 | 4210 | 56 | 28 | 237 |
| Donor_4 3. Aliquot G | 5.6 | 16 | 1950 | 56 | 455 | 203 |
| Donor_4 3. Aliquot H | 7.2 | 26 | 4140 | 55 | 76 | 219 |
| Donor_4 3. Aliquot I | 6.8 | 9.3 | 3360 | 55 | 21 | 235 |
| Donor_5 3. Aliquot A | 21 | 46 | 6630 | 92 | 844 | 158 |
| Donor_5 3. Aliquot B | 19 | 43 | 6720 | 93 | 834 | 183 |
| Donor_5 3. Aliquot C | 21 | 52 | 4350 | 97 | 171 | 144 |
| Donor_5 3. Aliquot D | 19 | 78 | 7840 | 92 | 1850 | 145 |
| Donor_5 3. Aliquot E | 20 | 57 | 7880 | 91 | 2320 | 155 |
| Donor_5 3. Aliquot F | 16 | 55 | 5110 | 87 | 188 | 167 |
| Donor_5 3. Aliquot G | 20 | 28 | 3130 | 96 | 1040 | 181 |
| Donor_5 3. Aliquot H | 20 | 60 | 6880 | 87 | 834 | 156 |
| Donor_5 3. Aliquot I | 20 | 62 | 4080 | 82 | 211 | 147 |
| Donor_6 3. Aliquot A | 2.8 | 74 | 2300 | 52 | 82 | 192 |
| Donor_6 3. Aliquot B | 3.0 | 76 | 2240 | 50 | 109 | 174 |
| Donor_6 3. Aliquot C | 2.5 | 33 | 2640 | 52 | 28 | 152 |
| Donor_6 3. Aliquot D | 2.9 | 80 | 1490 | 52 | 65 | 181 |
| Donor_6 3. Aliquot E | 2.6 | 99 | 1800 | 50 | 87 | 153 |

FIG. 15K.3

| | MMP-3 ng/mL | MMP-9 ng/mL | Myeloperoxidase ng/mL | Myoglobin ng/mL | OSM (Oncostatin M) pg/mL | PAI-1 ng/mL |
|---|---|---|---|---|---|---|
| Least Detectable Dose | 0.20 | 37 | 68 | 1.1 | 28 | 0.90 |
| RBM Low Plasma Range | | | | | | |
| RBM High Plasma Range | | | | | | |
| Donor_6_3. Aliquot F | 1.8 | 1050 | 1110 | 3.6 | PENDING | 10 |
| Donor_6_3. Aliquot G | 2.6 | 18 | 2660 | 37 | PENDING | 87 |
| Donor_6_3. Aliquot H | 2.3 | 46 | 1430 | 54 | 28 | 173 |
| Donor_6_3. Aliquot I | 2.8 | 39 | 2490 | 54 | 715 | 250 |
| Donor_6_3. Aliquot I | 2.7 | 32 | 2270 | 50 | 65 | 181 |
| | | | | 51 | 28 | 176 |
| Donor_7_3. Aliquot A | 16 | 55 | 2070 | 1790 | 194 | 210 |
| Donor_7_3. Aliquot B | 16 | 66 | 2710 | >1845 | 109 | 222 |
| Donor_7_3. Aliquot C | 16 | 37 | 1920 | >1845 | 28 | 215 |
| Donor_7_3. Aliquot D | 14 | 79 | 1780 | >1845 | 21 | 215 |
| Donor_7_3. Aliquot E | 15 | 60 | 2160 | >1845 | 54 | 230 |
| Donor_7_3. Aliquot F | 15 | 2.2 | 2150 | >1845 | 28 | 225 |
| Donor_7_3. Aliquot G | 15 | 44 | 1630 | >1845 | 143 | 229 |
| Donor_7_3. Aliquot H | 14 | 30 | 1880 | 1780 | 44 | 198 |
| Donor_7_3. Aliquot I | 15 | 4.9 | 1800 | >1845 | 28 | 198 |
| Donor_8_3. Aliquot A | 3.4 | 8.2 | 1510 | 5.2 | 28 | 32 |
| Donor_8_3. Aliquot B | 3.5 | 26 | 1450 | 3.7 | 28 | 35 |
| Donor_8_3. Aliquot C | 2.8 | 23 | 3790 | 3.3 | 28 | 31 |
| Donor_8_3. Aliquot D | 3.9 | 94 | 8210 | 3.1 | 345 | 30 |
| Donor_8_3. Aliquot E | 3.4 | 81 | 6150 | 3.2 | 132 | 34 |
| Donor_8_3. Aliquot F | 3.6 | 31 | 2590 | 3.2 | 28 | 30 |
| Donor_8_3. Aliquot G | 3.2 | 9.3 | 1220 | 2.9 | 132 | 60 |
| Donor_8_3. Aliquot H | 3.6 | 42 | 4710 | 3.3 | 54 | 41 |
| Donor_8_3. Aliquot I | 3.2 | 4.9 | 2000 | 3.5 | 28 | 40 |
| Donor_9_3. Aliquot A | 4.3 | 27 | 1430 | 2.1 | 28 | 45 |
| Donor_9_3. Aliquot B | 4.8 | 59 | 1150 | 1.9 | 28 | 63 |
| Donor_9_3. Aliquot C | 4.2 | 36 | 2030 | 1.7 | 28 | 71 |

FIG. 15K.4

| | MMP-3 ng/mL | MMP-9 ng/mL | Myeloperoxidase ng/mL | Myoglobin ng/mL | OSM (Oncostatin M) pg/mL | PAI-1 ng/mL |
|---|---|---|---|---|---|---|
| Least Detectable Dose | 0.20 | 37 | 68 | 1.1 | 28 | 0.90 |
| RBM Low Plasma Range | | | | | | |
| RBM High Plasma Range | | | | | | |
| Donor_9 3. Aliquot D | 1.8 | 1050 | 1110 | 3.6 | PENDING | 10 |
| Donor_9 3. Aliquot E | 4.7 | 111 | 3500 | 37 | PENDING | 87 |
| Donor_9 3. Aliquot F | 4.9 | 123 | 4800 | 1.3 | 96 | 72 |
| Donor_9 3. Aliquot G | 4.3 | 4.6 | 747 | 1.9 | 42 | 65 |
| Donor_9 3. Aliquot H | 3.9 | 27 | 1560 | 2.1 | 28 | 66 |
| Donor_9 3. Aliquot I | 4.3 | 45 | 3250 | 1.7 | 247 | 97 |
| | 3.6 | 13 | 1070 | 2.1 | 42 | 71 |
| | | | | 2.1 | 28 | 70 |
| EDTA Plasma | | | | | | |
| donor #1 plasma | 0.12 | 211 | 111 | 77 | 1120 | 142 |
| donor #2 plasma | 0.047 | 1340 | 158 | 64 | 28 | 151 |
| donor #3 plasma | 0.2 | 653 | 85 | 182 | 28 | 208 |
| donor #4 plasma | 0.2 | 194 | 322 | 61 | 28 | 218 |
| donor #5 plasma | 0.076 | 236 | 372 | 86 | 28 | 154 |
| donor #6 plasma | 0.2 | 367 | 9.9 | 57 | 151 | 149 |
| donor #7 plasma | 0.090 | 115 | 135 | >1845 | 133 | 242 |
| donor #8 plasma | 3.7 | 30 | 183 | 3.8 | 28 | 39 |
| donor #9 plasma | 4.2 | 3.2 | 68 | 1.4 | 28 | 61 |
| *Stimulations indices* | | | | | | |

FIG. 15K.5

| | MMP-3 ng/mL | MMP-9 ng/mL | Myeloperoxidase ng/mL | Myoglobin ng/mL | OSM (Oncostatin M) pg/mL | PAI-1 ng/mL |
|---|---|---|---|---|---|---|
| Least Detectable Dose | 0.20 | 37 | 68 | 1.1 | 28 | 0.90 |
| RBM Low Plasma Range | | | | 3.6 | PENDING | 10 |
| RBM High Plasma Range | 1.8 | 1050 | 1110 | 37 | PENDING | 87 |

| | | | | | | | |
|---|---|---|---|---|---|---|---|
| patient 1 | A | | | | | | |
| patient 7 | A | | | | | | |
| patient 2 | A | | | | | | |
| patient 3 | A | | | | | | |
| patient 5 | A | | | | | | |
| patient 4 | A | | | | | | |
| patient 6 | A | | | | | | |
| NHD 1 | A | | | | | | |
| NHD 2 | A | | | | | | |

FIG. 15K.6
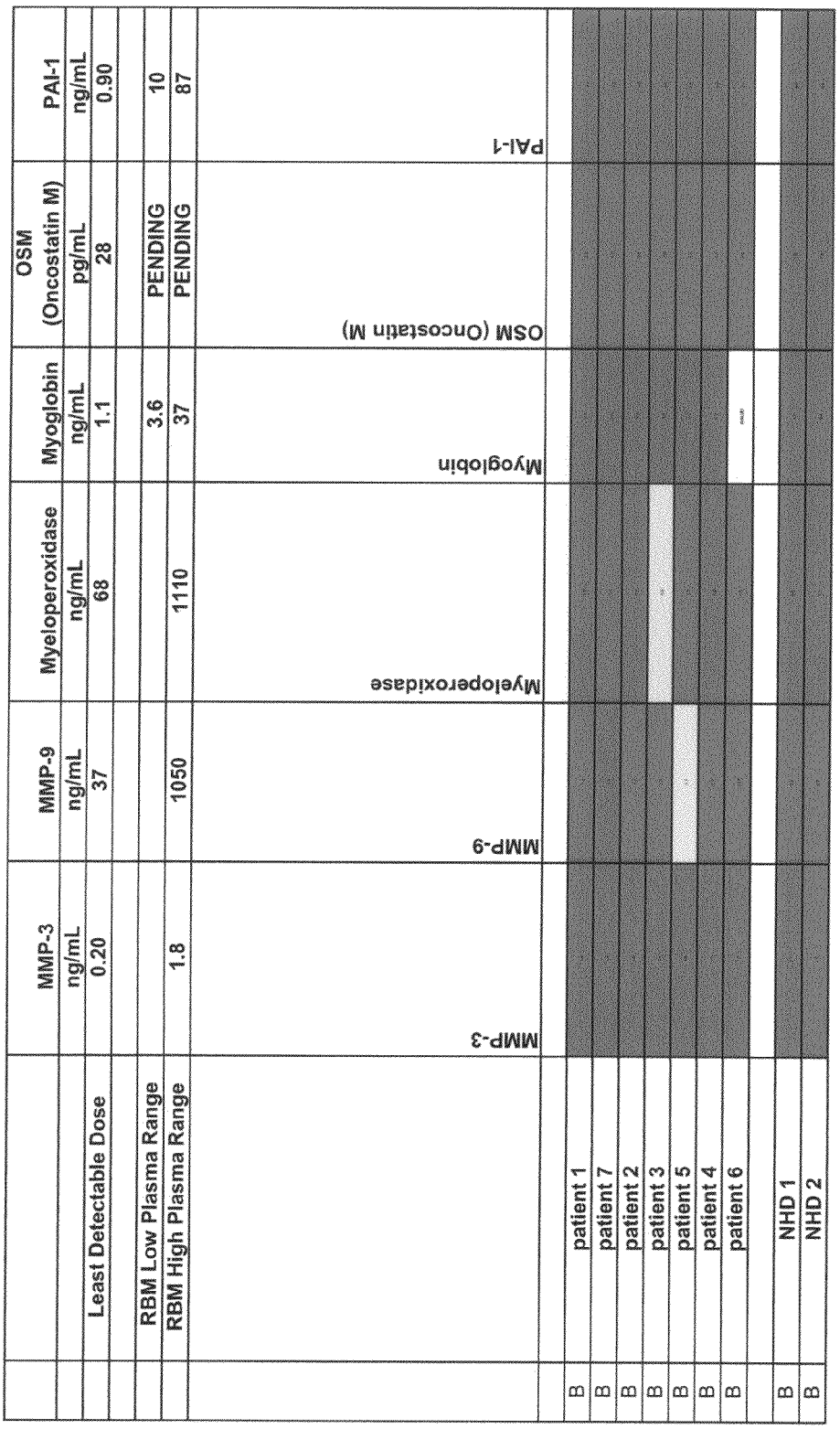

FIG. 15K.7

| | MMP-3 ng/mL | MMP-9 ng/mL | Myeloperoxidase ng/mL | Myoglobin ng/mL | OSM (Oncostatin M) pg/mL | PAI-1 ng/mL |
|---|---|---|---|---|---|---|
| Least Detectable Dose | 0.20 | 37 | 68 | 1.1 | 28 | 0.90 |
| RBM Low Plasma Range | | | | 3.6 | PENDING | 10 |
| RBM High Plasma Range | 1.8 | 1050 | 1110 | 37 | PENDING | 87 |

| | | |
|---|---|---|
| patient 1 | | C |
| patient 7 | | C |
| patient 2 | | C |
| patient 3 | | C |
| patient 5 | | C |
| patient 4 | | C |
| patient 6 | | C |
| NHD 1 | | C |
| NHD 2 | | C |

FIG. 15K.8
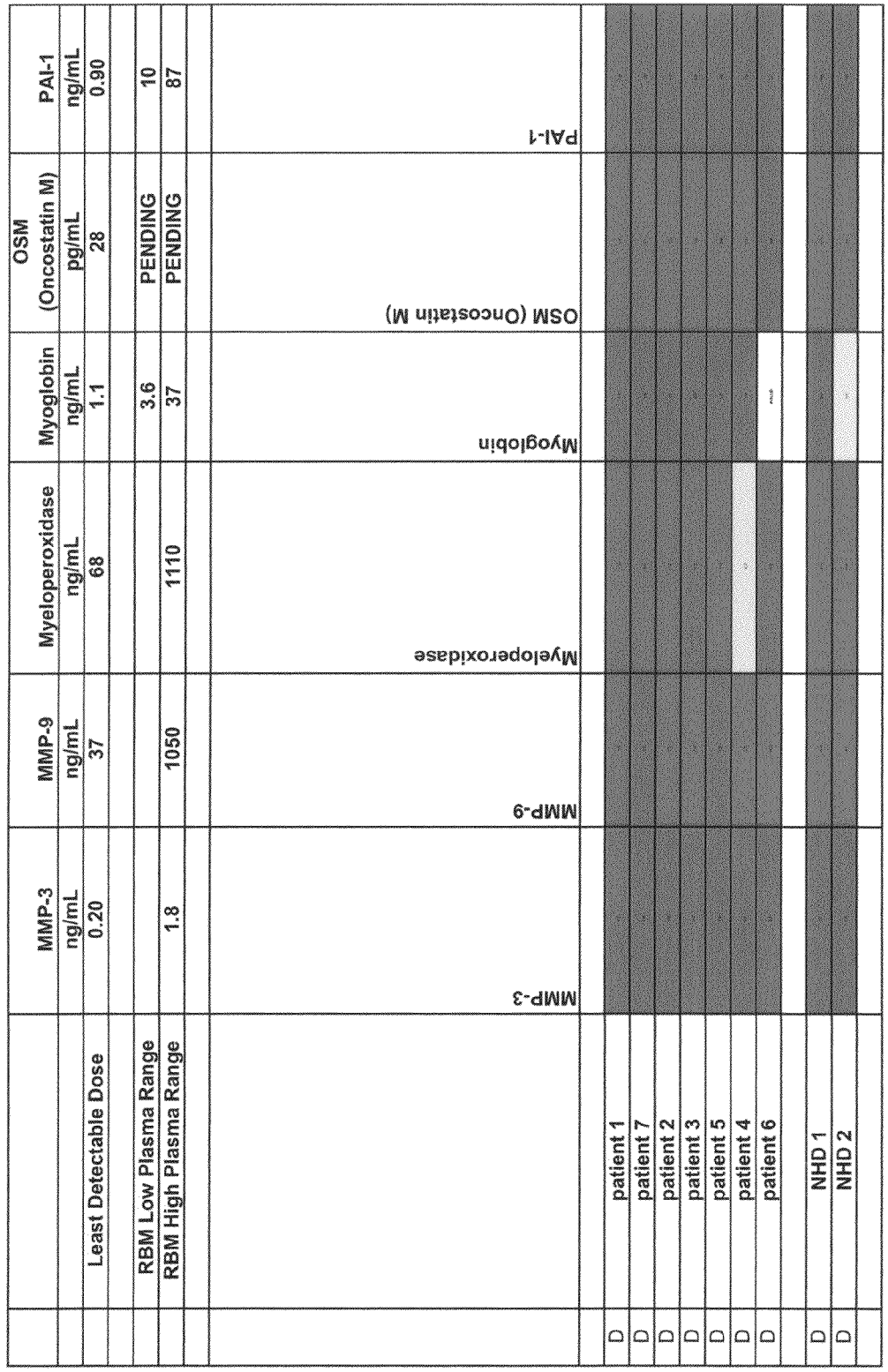

FIG. 15K.9

| | MMP-3 ng/mL | MMP-9 ng/mL | Myeloperoxidase ng/mL | Myoglobin ng/mL | OSM (Oncostatin M) pg/mL | PAI-1 ng/mL |
|---|---|---|---|---|---|---|
| Least Detectable Dose | 0.20 | 37 | 68 | 1.1 | 28 | 0.90 |
| RBM Low Plasma Range | | | | 3.6 | PENDING | 10 |
| RBM High Plasma Range | 1.8 | 1050 | 1110 | 37 | PENDING | 87 |
| patient 1 | | | | | | |
| patient 7 | | | | | | |
| patient 2 | | | | | | |
| patient 3 | | | | | | |
| patient 5 | | | | | | |
| patient 4 | | | | | | |
| patient 6 | | | | | | |
| NHD 1 | | | | | | |
| NHD 2 | | | | | | |

FIG. 15K.10
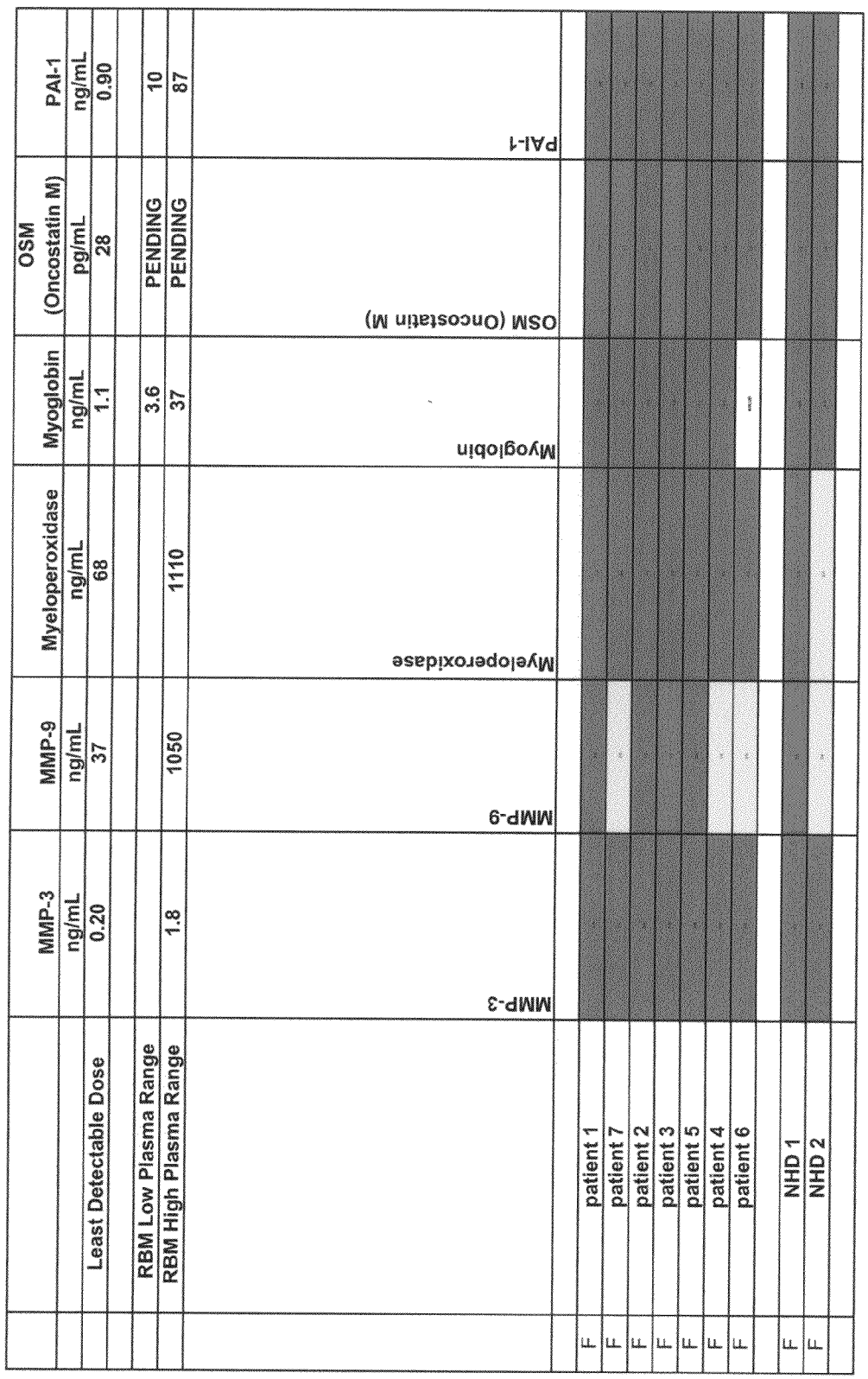

FIG. 15K.11

| | Least Detectable Dose | MMP-3 ng/mL | MMP-9 ng/mL | Myeloperoxidase ng/mL | Myoglobin ng/mL | OSM (Oncostatin M) pg/mL | PAI-1 ng/mL |
|---|---|---|---|---|---|---|---|
| RBM Low Plasma Range | | 0.20 | 37 | 68 | 1.1 | 28 | 0.90 |
| RBM High Plasma Range | | 1.8 | 1050 | 1110 | 3.6 | PENDING | 10 |
| | | | | | 37 | PENDING | 87 |

| | MMP-3 | MMP-9 | Myeloperoxidase | Myoglobin | OSM (Oncostatin M) | PAI-1 |
|---|---|---|---|---|---|---|
| patient 1 | G | | | | | | |
| patient 7 | G | | | | | | |
| patient 2 | G | | | | | | |
| patient 3 | G | | | | | | |
| patient 5 | G | | | | | | |
| patient 4 | G | | | | | | |
| patient 6 | G | | | | | | |
| NHD 1 | G | | | | | | |
| NHD 2 | G | | | | | | |

FIG. 15K.12

| | MMP-3 ng/mL | MMP-9 ng/mL | Myeloperoxidase ng/mL | Myoglobin ng/mL | OSM (Oncostatin M) pg/mL | PAI-1 ng/mL |
|---|---|---|---|---|---|---|
| Least Detectable Dose | 0.20 | 37 | 68 | 1.1 | 28 | 0.90 |
| RBM Low Plasma Range | | | | 3.6 | PENDING | 10 |
| RBM High Plasma Range | 1.8 | 1050 | 1110 | 37 | PENDING | 87 |
| patient 1 | | | | | | |
| patient 7 | | | | | | |
| patient 2 | | | | | | |
| patient 3 | | | | | | |
| patient 5 | | | | | | |
| patient 4 | | | | | | |
| patient 6 | | | | | | |
| NHD 1 | | | | | | |
| NHD 2 | | | | | | |

FIG. 15K.13

| | MMP-3 ng/mL | MMP-9 ng/mL | Myeloperoxidase ng/mL | Myoglobin ng/mL | OSM (Oncostatin M) pg/mL | PAI-1 ng/mL |
|---|---|---|---|---|---|---|
| Least Detectable Dose | 0.20 | 37 | 68 | 1.1 | 28 | 0.90 |
| RBM Low Plasma Range | | | | 3.6 | PENDING | 10 |
| RBM High Plasma Range | 1.8 | 1050 | 1110 | 37 | PENDING | 87 |
| patient 1 | | | | | | |
| patient 7 | | | | | | |
| patient 2 | | | | | | |
| patient 3 | | | | | | |
| patient 5 | | | | | | |
| patient 4 | | | | | | |
| patient 6 | | | | | | |
| NHD 1 | | | | | | |
| NHD 2 | | | | | | |

FIG. 15K.14

| | MMP-3 ng/mL | MMP-9 ng/mL | Myeloperoxidase ng/mL | Myoglobin ng/mL | OSM (Oncostatin M) pg/mL | PAI-1 ng/mL |
|---|---|---|---|---|---|---|
| Least Detectable Dose | 0.20 | 37 | 68 | 1.1 | 28 | 0.90 |
| RBM Low Plasma Range | | | | 3.6 | PENDING | 10 |
| RBM High Plasma Range | 1.8 | 1050 | 1110 | 37 | PENDING | 87 |
| Messwert > ULD | | | | | | |
| SI > 1,3 | | | | | | |
| SI 0,7-1,3 | | | | | | |
| SI 0-0,7 | | | | | | |
| | | | | | | |

FIG. 15L.1

| | Prostatic Acid Phosphatase ng/mL | PAPP-A mIU/mL | Prostate Specific Antigen, Free ng/mL | RANTES ng/mL | Serum Amyloid P ug/mL | Stem Cell Factor pg/mL | SGOT ug/mL |
|---|---|---|---|---|---|---|---|
| Least Detectable Dose | 0.034 | 0.037 | 0.023 | 0.048 | 0.058 | 56 | 3.7 |
| RBM Low Plasma Range | 0.058 | | | 2.6 | 15 | | 3.9 |
| RBM High Plasma Range | 0.54 | 0.48 | 1.6 | 83 | 50 | 281 | 28 |
| Samples | | | | | | | |
| Donor_1 3. Aliquot A | 0.12 | 0.079 | 0.44 | 16 | 26 | 757 | 3.7 |
| Donor_1 3. Aliquot B | 0.11 | 0.082 | 0.44 | 25 | 28 | 587 | 3.7 |
| Donor_1 3. Aliquot C | 0.045 | 0.059 | 0.47 | 22 | 28 | 599 | 3.7 |
| Donor_1 3. Aliquot D | 0.11 | 0.054 | 0.50 | 18 | 33 | 657 | 3.7 |
| Donor_1 3. Aliquot E | 0.12 | 0.062 | 0.47 | 14 | 29 | 666 | 3.7 |
| Donor_1 3. Aliquot F | 0.041 | 0.073 | 0.41 | 14 | 29 | 430 | 3.7 |
| Donor_1 3. Aliquot G | 0.086 | 0.11 | 0.50 | 24 | 26 | 645 | 3.7 |
| Donor_1 3. Aliquot H | 0.078 | 0.087 | 0.43 | 26 | 29 | 508 | 3.7 |
| Donor_1 3. Aliquot I | 0.035 | 0.049 | 0.45 | 19 | 29 | 508 | 3.7 |
| Donor_2 3. Aliquot A | 0.24 | 0.023 | 0.11 | 20 | 22 | 1350 | 3.7 |
| Donor_2 3. Aliquot B | 0.24 | 0.032 | 0.11 | 24 | 26 | 1530 | 3.7 |
| Donor_2 3. Aliquot C | 0.16 | 0.0049 | 0.072 | 15 | 23 | 607 | 3.7 |
| Donor_2 3. Aliquot D | 0.46 | 0.024 | 0.20 | 13 | 24 | 1640 | 3.7 |
| Donor_2 3. Aliquot E | 0.38 | 0.022 | 0.16 | 13 | 26 | 1670 | 3.7 |
| Donor_2 3. Aliquot F | 0.12 | 0.018 | 0.087 | 13 | 23 | 582 | 3.7 |
| Donor_2 3. Aliquot G | 0.33 | 0.043 | 0.13 | 21 | 22 | 1760 | 3.7 |
| Donor_2 3. Aliquot H | 0.14 | 0.023 | 0.083 | 13 | 27 | 595 | 3.7 |
| Donor_2 3. Aliquot I | 0.13 | 0.018 | 0.082 | 12 | 23 | 500 | 3.7 |
| Donor_3 3. Aliquot A | 0.24 | 0.0063 | 0.67 | 16 | 14 | 666 | 3.7 |
| Donor_3 3. Aliquot B | 0.22 | 0.037 | 0.65 | 21 | 14 | 434 | 3.7 |
| Donor_3 3. Aliquot C | 0.16 | 0.037 | 0.72 | 17 | 17 | 213 | 3.7 |
| Donor_3 3. Aliquot D | 0.41 | 0.0049 | 0.71 | 16 | 15 | 882 | 3.7 |
| Donor_3 3. Aliquot E | 0.47 | 0.0063 | 0.73 | 21 | 15 | 1020 | 3.7 |
| Donor_3 3. Aliquot F | 0.16 | 0.0063 | 0.65 | 13 | 16 | 202 | 3.7 |
| Donor_3 3. Aliquot G | 0.17 | 0.037 | 0.74 | 26 | 15 | 183 | 3.7 |

FIG. 15L.2

| | Prostatic Acid Phosphatase ng/mL | PAPP-A mIU/mL | Prostate Specific Antigen, Free ng/mL | RANTES ng/mL | Serum Amyloid P ug/mL | Stem Cell Factor pg/mL | SGOT ug/mL |
|---|---|---|---|---|---|---|---|
| Least Detectable Dose | 0.034 | 0.037 | 0.023 | 0.048 | 0.058 | 56 | 3.7 |
| RBM Low Plasma Range | 0.058 | | | | | | 3.9 |
| RBM High Plasma Range | 0.54 | 0.48 | 1.6 | 2.6 | 15 | 281 | 28 |
| Donor_3_3. Aliquot H | 0.14 | 0.0049 | 0.57 | 83 | 50 | 113 | 3.7 |
| Donor_3_3. Aliquot I | 0.14 | 0.037 | 0.61 | 13 | 16 | 138 | 3.7 |
| | | | | 14 | 16 | | |
| Donor_4_3. Aliquot A | 0.27 | 0.13 | 0.023 | 4.4 | 8.7 | 426 | 3.7 |
| Donor_4_3. Aliquot B | 0.38 | 0.14 | 0.023 | 4.6 | 9.6 | 475 | 3.7 |
| Donor_4_3. Aliquot C | 0.28 | 0.029 | 0.023 | 2.7 | 9.9 | 377 | 3.7 |
| Donor_4_3. Aliquot D | 0.42 | 0.13 | 0.045 | 3.4 | 10 | 957 | 3.7 |
| Donor_4_3. Aliquot E | 0.46 | 0.15 | 0.023 | 2.6 | 10 | 1010 | 3.7 |
| Donor_4_3. Aliquot F | 0.26 | 0.14 | 0.023 | 2.5 | 12 | 459 | 3.7 |
| Donor_4_3. Aliquot G | 0.56 | 0.16 | 0.023 | 5.9 | 8.8 | 459 | 3.7 |
| Donor_4_3. Aliquot H | 0.23 | 0.13 | 0.023 | 2.5 | 11 | 405 | 3.7 |
| Donor_4_3. Aliquot I | 0.26 | 0.12 | 0.023 | 3.2 | 10 | 352 | 3.7 |
| Donor_5_3. Aliquot A | 0.46 | 0.021 | 0.49 | 17 | 43 | 936 | 3.7 |
| Donor_5_3. Aliquot B | 0.73 | 0.021 | 0.48 | 13 | 41 | 815 | 3.7 |
| Donor_5_3. Aliquot C | 0.28 | 0.0078 | 0.42 | 11 | 38 | 320 | 3.7 |
| Donor_5_3. Aliquot D | 1.5 | 0.040 | 0.61 | 14 | 46 | 965 | 3.7 |
| Donor_5_3. Aliquot E | 2.9 | 0.032 | 0.57 | 14 | 45 | 1290 | 3.7 |
| Donor_5_3. Aliquot F | 0.27 | 0.018 | 0.39 | 9.5 | 38 | 288 | 0.62 |
| Donor_5_3. Aliquot G | 0.52 | 0.029 | 0.45 | 16 | 40 | 541 | 3.7 |
| Donor_5_3. Aliquot H | 0.50 | 0.014 | 0.46 | 12 | 43 | 292 | 3.7 |
| Donor_5_3. Aliquot I | 0.27 | 0.014 | 0.49 | 9.0 | 41 | 348 | 3.7 |
| Donor_6_3. Aliquot A | 0.13 | 0.0056 | 0.35 | 35 | 25 | 217 | 3.7 |
| Donor_6_3. Aliquot B | 0.24 | 0.037 | 0.40 | 34 | 27 | 187 | 3.7 |
| Donor_6_3. Aliquot C | 0.22 | 0.037 | 0.34 | 23 | 24 | 99 | 3.7 |
| Donor_6_3. Aliquot D | 0.26 | 0.037 | 0.44 | 35 | 31 | 272 | 3.7 |
| Donor_6_3. Aliquot E | 0.38 | 0.0063 | 0.40 | 23 | 26 | 316 | 3.7 |

FIG. 15L.3

| | Prostatic Acid Phosphatase ng/mL | PAPP-A mIU/mL | Prostate Specific Antigen, Free ng/mL | RANTES ng/mL | Serum Amyloid P ug/mL | Stem Cell Factor pg/mL | SGOT ug/mL |
|---|---|---|---|---|---|---|---|
| Least Detectable Dose | 0.034 | 0.037 | 0.023 | 0.048 | 0.058 | 56 | 3.7 |
| RBM Low Plasma Range | 0.058 | | | 2.6 | 15 | | 3.9 |
| RBM High Plasma Range | 0.54 | 0.48 | 1.6 | 83 | 50 | 281 | 28 |
| Donor_6 3. Aliquot F | 0.15 | 0.037 | 0.31 | 20 | 26 | 99 | 3.7 |
| Donor_6 3. Aliquot G | 0.54 | 0.037 | 0.33 | 47 | 22 | 164 | 3.7 |
| Donor_6 3. Aliquot H | 0.12 | 0.037 | 0.33 | 22 | 23 | 69 | 3.7 |
| Donor_6 3. Aliquot I | 0.17 | 0.037 | 0.35 | 23 | 25 | 92 | 3.7 |
| Donor_7 3. Aliquot A | 0.10 | 0.012 | 0.65 | 17 | 31 | 998 | 8.2 |
| Donor_7 3. Aliquot B | 0.16 | 0.011 | 0.63 | 17 | 35 | 607 | 12 |
| Donor_7 3. Aliquot C | 0.068 | 0.037 | 0.65 | 25 | 33 | 113 | 8.1 |
| Donor_7 3. Aliquot D | 0.19 | 0.0085 | 0.61 | 19 | 30 | 790 | 11 |
| Donor_7 3. Aliquot E | 0.12 | 0.0049 | 0.66 | 15 | 29 | 707 | 13 |
| Donor_7 3. Aliquot F | 0.078 | 0.037 | 0.57 | 9.7 | 35 | 127 | 11 |
| Donor_7 3. Aliquot G | 0.063 | 0.037 | 0.68 | 23 | 29 | 160 | 4.3 |
| Donor_7 3. Aliquot H | 0.087 | 0.0092 | 0.64 | 12 | 31 | 72 | 16 |
| Donor_7 3. Aliquot I | 0.073 | 0.037 | 0.60 | 12 | 34 | 127 | 11 |
| Donor_8 3. Aliquot A | 0.082 | 0.0070 | 0.023 | 12 | 5.7 | 92 | 3.7 |
| Donor_8 3. Aliquot B | 0.13 | 0.0056 | 0.023 | 16 | 6.4 | 46 | 3.7 |
| Donor_8 3. Aliquot C | 0.16 | 0.037 | 0.023 | 17 | 5.4 | 69 | 3.7 |
| Donor_8 3. Aliquot D | 0.67 | 0.015 | 0.18 | 12 | 5.7 | 106 | 3.7 |
| Donor_8 3. Aliquot E | 0.55 | 0.0092 | 0.13 | 14 | 5.9 | 72 | 3.7 |
| Donor_8 3. Aliquot F | 0.15 | 0.0056 | 0.023 | 6.9 | 6.7 | 40 | 3.7 |
| Donor_8 3. Aliquot G | 0.058 | 0.0092 | 0.023 | 19 | 5.2 | 99 | 3.7 |
| Donor_8 3. Aliquot H | 0.14 | 0.014 | 0.023 | 15 | 6.4 | 89 | 3.7 |
| Donor_8 3. Aliquot I | 0.079 | 0.0078 | 0.023 | 17 | 6.5 | 56 | 3.7 |
| Donor_9 3. Aliquot A | 0.052 | 0.0053 | 0.023 | 16 | Pending | 170 | 3.7 |
| Donor_9 3. Aliquot B | 0.088 | 0.037 | 0.023 | 21 | Pending | 229 | 3.7 |
| Donor_9 3. Aliquot C | 0.074 | 0.037 | 0.023 | 23 | Pending | 229 | 3.7 |

FIG. 15L.4

| | Prostatic Acid Phosphatase ng/mL | PAPP-A mIU/mL | Prostate Specific Antigen, Free ng/mL | RANTES ng/mL | Serum Amyloid P ug/mL | Stem Cell Factor pg/mL | SGOT ug/mL |
|---|---|---|---|---|---|---|---|
| Least Detectable Dose | 0.034 | 0.037 | 0.023 | 0.048 | 0.058 | 56 | 3.7 |
| RBM Low Plasma Range | 0.058 | | | 2.6 | 15 | | 3.9 |
| RBM High Plasma Range | 0.54 | 0.48 | 1.6 | 83 | 50 | 281 | 28 |
| Donor_9 3. Aliquot D | 0.50 | 0.013 | 0.18 | 21 | Pending | 307 | 3.7 |
| Donor_9 3. Aliquot E | 0.34 | 0.037 | 0.10 | 13 | Pending | 272 | 3.7 |
| Donor_9 3. Aliquot F | 0.052 | 0.0077 | 0.023 | 9.1 | Pending | 137 | 3.7 |
| Donor_9 3. Aliquot G | 0.040 | 0.010 | 0.023 | 30 | Pending | 528 | 3.7 |
| Donor_9 3. Aliquot H | 0.037 | 0.037 | 0.023 | 21 | Pending | 97 | 3.7 |
| Donor_9 3. Aliquot I | 0.034 | 0.037 | 0.023 | 21 | Pending | 174 | 3.7 |
| EDTA Plasma | | | | | | | |
| donor #1 plasma | 0.090 | 0.084 | 0.28 | 9.4 | Pending | 351 | 40 |
| donor #2 plasma | 0.13 | 0.052 | 0.13 | 3.4 | Pending | 492 | 45 |
| donor #3 plasma | 0.050 | 0.029 | 0.74 | 6.4 | Pending | 161 | 54 |
| donor #4 plasma | 0.65 | 0.26 | 0.023 | 1.3 | Pending | 368 | 32 |
| donor #5 plasma | 0.41 | 0.040 | 0.47 | 8.7 | Pending | 550 | 70 |
| donor #6 plasma | 0.15 | 0.017 | 0.45 | 14 | Pending | 62 | 35 |
| donor #7 plasma | 0.078 | 0.066 | 0.82 | 12 | Pending | 212 | 46 |
| donor #8 plasma | 0.13 | 0.010 | 0.024 | 5.3 | Pending | 161 | 3.7 |
| donor #9 plasma | 0.071 | 0.037 | 0.023 | 1.2 | Pending | 203 | 3.7 |
| *Stimulations indices* | | | | | | | |

FIG. 15L.5

| | Prostatic Acid Phosphatase ng/mL | PAPP-A mIU/mL | Prostate Specific Antigen, Free ng/mL | RANTES ng/mL | Serum Amyloid P ug/mL | Stem Cell Factor pg/mL | SGOT ug/mL |
|---|---|---|---|---|---|---|---|
| Least Detectable Dose | 0.034 | 0.037 | 0.023 | 0.048 | 0.058 | 56 | 3.7 |
| RBM Low Plasma Range | 0.058 | | | 2.6 | 15 | | 3.9 |
| RBM High Plasma Range | 0.54 | 0.48 | 1.6 | 83 | 50 | 281 | 28 |
| patient 1 | A | | | | | | |
| patient 7 | A | | | | | | |
| patient 2 | A | | | | | | |
| patient 3 | A | | | | | | |
| patient 5 | A | | | | | | |
| patient 4 | A | | | | | | |
| patient 6 | A | | | | | | |
| NHD 1 | A | | | | | | |
| NHD 2 | A | | | | | | |

FIG. 15L.6

| | Prostatic Acid Phosphatase ng/mL | PAPP-A mIU/mL | Prostate Specific Antigen, Free ng/mL | RANTES ng/mL | Serum Amyloid P ug/mL | Stem Cell Factor pg/mL | SGOT ug/mL |
|---|---|---|---|---|---|---|---|
| Least Detectable Dose | 0.034 | 0.037 | 0.023 | 0.048 | 0.058 | 56 | 3.7 |
| RBM Low Plasma Range | 0.058 | | | | | | 3.9 |
| RBM High Plasma Range | 0.54 | 0.48 | 1.6 | 2.6 | 15 | 281 | 28 |
| | | | | | 50 | | |

| | Prostatic Acid Phosphatase | PAPP-A | Prostate Specific Antigen, Free | RANTES | Serum Amyloid P | Stem Cell Factor | SGOT |
|---|---|---|---|---|---|---|---|
| patient 1 | B | | | | | | |
| patient 7 | B | | | | | | |
| patient 2 | B | | | | | | |
| patient 3 | B | | | | | | |
| patient 5 | B | | | | | | |
| patient 4 | B | | | | | | |
| patient 6 | B | | | | | | |
| NHD 1 | B | | | | | | |
| NHD 2 | B | | | | | | |

FIG. 15L.7

| | Prostatic Acid Phosphatase ng/mL | PAPP-A mIU/mL | Prostate Specific Antigen, Free ng/mL | RANTES ng/mL | Serum Amyloid P ug/mL | Stem Cell Factor pg/mL | SGOT ug/mL |
|---|---|---|---|---|---|---|---|
| Least Detectable Dose | 0.034 | 0.037 | 0.023 | 0.048 | 0.058 | 56 | 3.7 |
| RBM Low Plasma Range | 0.058 | 0.48 | 1.6 | 2.6 | 15 | | 3.9 |
| RBM High Plasma Range | 0.54 | | | 83 | 50 | 281 | 28 |

| | | | | | | | | |
|---|---|---|---|---|---|---|---|---|
| patient 1 | C | | | | | | | |
| patient 7 | C | | | | | | | |
| patient 2 | C | | | | | | | |
| patient 3 | C | | | | | | | |
| patient 5 | C | | | | | | | |
| patient 4 | C | | | | | | | |
| patient 6 | C | | | | | | | |
| NHD 1 | C | | | | | | | |
| NHD 2 | C | | | | | | | |

FIG. 15L.8

| | Prostatic Acid Phosphatase ng/mL | PAPP-A mIU/mL | Prostate Specific Antigen, Free ng/mL | RANTES ng/mL | Serum Amyloid P ug/mL | Stem Cell Factor pg/mL | SGOT ug/mL |
|---|---|---|---|---|---|---|---|
| Least Detectable Dose | 0.034 | 0.037 | 0.023 | 0.048 | 0.058 | 56 | 3.7 |
| RBM Low Plasma Range | 0.058 | 0.48 | 1.6 | 2.6 | 15 | | 3.9 |
| RBM High Plasma Range | 0.54 | | | 83 | 50 | 281 | 28 |

| | Prostatic Acid Phosphatase | PAPP-A | Prostate Specific Antigen, Free | RANTES | Serum Amyloid P | Stem Cell Factor | SGOT |
|---|---|---|---|---|---|---|---|
| patient 1 | D | | | | | | |
| patient 7 | D | | | | | | |
| patient 2 | D | | | | | | |
| patient 3 | D | | | | | | |
| patient 5 | D | | | | | | |
| patient 4 | D | | | | | | |
| patient 6 | D | | | | | | |
| NHD 1 | D | | | | | | |
| NHD 2 | D | | | | | | |

FIG. 15L.9

| | Least Detectable Dose | RBM Low Plasma Range | RBM High Plasma Range | Prostatic Acid Phosphatase ng/mL | PAPP-A mIU/mL | Prostate Specific Antigen, Free ng/mL | RANTES ng/mL | Serum Amyloid P ug/mL | Stem Cell Factor pg/mL | SGOT ug/mL |
|---|---|---|---|---|---|---|---|---|---|---|
| | | | | 0.034 | 0.037 | 0.023 | 0.048 | 0.058 | | 3.7 |
| | | | | 0.058 | | | 2.6 | 15 | 56 | 3.9 |
| | | | | 0.54 | 0.48 | 1.6 | 83 | 50 | 281 | 28 |
| patient 1 | E | | | | | | | | | |
| patient 7 | E | | | | | | | | | |
| patient 2 | E | | | | | | | | | |
| patient 3 | E | | | | | | | | | |
| patient 5 | E | | | | | | | | | |
| patient 4 | E | | | | | | | | | |
| patient 6 | E | | | | | | | | | |
| NHD 1 | E | | | | | | | | | |
| NHD 2 | E | | | | | | | | | |

FIG. 15L.10

| | | Prostatic Acid Phosphatase | PAPP-A | Prostate Specific Antigen, Free | RANTES | Serum Amyloid P | Stem Cell Factor | SGOT |
|---|---|---|---|---|---|---|---|---|
| | | ng/mL | mIU/mL | ng/mL | ng/mL | ug/mL | pg/mL | ug/mL |
| Least Detectable Dose | | 0.034 | 0.037 | 0.023 | 0.048 | 0.058 | 56 | 3.7 |
| RBM Low Plasma Range | | 0.058 | 0.48 | | 2.6 | 15 | | 3.9 |
| RBM High Plasma Range | | 0.54 | | 1.6 | 83 | 50 | 281 | 28 |
| patient 1 | F | | | | | | | |
| patient 7 | F | | | | | | | |
| patient 2 | F | | | | | | | |
| patient 3 | F | | | | | | | |
| patient 5 | F | | | | | | | |
| patient 4 | F | | | | | | | |
| patient 6 | F | | | | | | | |
| NHD 1 | F | | | | | | | |
| NHD 2 | F | | | | | | | |

FIG. 15L.11

| | Prostatic Acid Phosphatase | PAPP-A | Prostate Specific Antigen, Free | RANTES | Serum Amyloid P | Stem Cell Factor | SGOT |
|---|---|---|---|---|---|---|---|
| | ng/mL | mIU/mL | ng/mL | ng/mL | ug/mL | pg/mL | ug/mL |
| Least Detectable Dose | 0.034 | 0.037 | 0.023 | 0.048 | 0.058 | 56 | 3.7 |
| RBM Low Plasma Range | 0.058 | 0.48 | 1.6 | 2.6 | 15 | | 3.9 |
| RBM High Plasma Range | 0.54 | | | 83 | 50 | 281 | 28 |
| patient 1 | | | | | | | |
| patient 7 | | | | | | | |
| patient 2 | | | | | | | |
| patient 3 | | | | | | | |
| patient 5 | | | | | | | |
| patient 4 | | | | | | | |
| patient 6 | | | | | | | |
| NHD 1 | | | | | | | |
| NHD 2 | | | | | | | |

FIG. 15L.12

| | Prostatic Acid Phosphatase ng/mL | PAPP-A mIU/mL | Prostate Specific Antigen, Free ng/mL | RANTES ng/mL | Serum Amyloid P ug/mL | Stem Cell Factor pg/mL | SGOT ug/mL |
|---|---|---|---|---|---|---|---|
| Least Detectable Dose | 0.034 | 0.037 | 0.023 | 0.048 | 0.058 | | |
| RBM Low Plasma Range | 0.058 | | | 2.6 | 15 | 56 | 3.9 |
| RBM High Plasma Range | 0.54 | 0.48 | 1.6 | 83 | 50 | 281 | 28 |
| patient 1 | H | | | | | | |
| patient 7 | H | | | | | | |
| patient 2 | H | | | | | | |
| patient 3 | H | | | | | | |
| patient 5 | H | | | | | | |
| patient 4 | H | | | | | | |
| patient 6 | H | | | | | | |
| NHD 1 | H | | | | | | |
| NHD 2 | H | | | | | | |

FIG. 15L.13

| | Prostatic Acid Phosphatase | PAPP-A | Prostate Specific Antigen, Free | RANTES | Serum Amyloid P | Stem Cell Factor | SGOT |
|---|---|---|---|---|---|---|---|
| | ng/mL | mIU/mL | ng/mL | ng/mL | ug/mL | pg/mL | ug/mL |
| Least Detectable Dose | 0.034 | 0.037 | 0.023 | 0.048 | 0.058 | | 3.7 |
| RBM Low Plasma Range | 0.058 | 0.48 | | 2.6 | 15 | 56 | 3.9 |
| RBM High Plasma Range | 0.54 | | 1.6 | 83 | 50 | 281 | 28 |
| patient 1 | | | | | | | |
| patient 7 | | | | | | | |
| patient 2 | | | | | | | |
| patient 3 | | | | | | | |
| patient 5 | | | | | | | |
| patient 4 | | | | | | | |
| patient 6 | | | | | | | |
| NHD 1 | | | | | | | |
| NHD 2 | | | | | | | |

FIG. 15L.14

| | Prostatic Acid Phosphatase ng/mL | PAPP-A mIU/mL | Prostate Specific Antigen, Free ng/mL | RANTES ng/mL | Serum Amyloid P ug/mL | Stem Cell Factor pg/mL | SGOT ug/mL |
|---|---|---|---|---|---|---|---|
| Least Detectable Dose | 0.034 | 0.037 | 0.023 | 0.048 | 0.058 | 56 | 3.7 |
| RBM Low Plasma Range | 0.058 | | | 2.6 | 15 | | 3.9 |
| RBM High Plasma Range | 0.54 | 0.48 | 1.6 | 83 | 50 | 281 | 28 |
| Messwert > ULD | | | | | | | |
| SI > 1,3 | | | | | | | |
| SI 0,7-1,3 | | | | | | | |
| SI 0-0,7 | | | | | | | |

FIG. 15M.1

| | SHBG nmol/L | Thyroxine Binding Globulin ug/mL | Tissue Factor ng/mL | TGF-alpha pg/mL | TIMP-1 ng/mL | TNF RII ng/mL | TNF-alpha pg/mL |
|---|---|---|---|---|---|---|---|
| Least Detectable Dose | 1.3 | 0.34 | 0.84 | 1.8 | 8.4 | 0.13 | 4.0 |
| RBM Low Plasma Range | 12 | 40 | | Pending | 59 | 3.1 | |
| RBM High Plasma Range | 106 | 104 | 2.4 | Pending | 192 | 79 | 27 |
| Samples | | | | | | | |
| Donor_1_3. Aliquot A | 18 | 27 | 3.7 | 22 | 521 | 29 | 236 |
| Donor_1_3. Aliquot B | 19 | 31 | 2.7 | 15 | 615 | 31 | 75 |
| Donor_1_3. Aliquot C | 19 | 29 | 0.91 | 1.8 | 611 | 28 | 19 |
| Donor_1_3. Aliquot D | 19 | 31 | 3.3 | 9.7 | 620 | 30 | 300 |
| Donor_1_3. Aliquot E | 19 | 29 | 3.0 | 13 | 549 | 29 | 88 |
| Donor_1_3. Aliquot F | 18 | 29 | 2.0 | 3.8 | 553 | 27 | 35 |
| Donor_1_3. Aliquot G | 19 | 29 | 2.0 | 24 | 645 | 30 | 24 |
| Donor_1_3. Aliquot H | 19 | 26 | 1.8 | 1.5 | 580 | 27 | 19 |
| Donor_1_3. Aliquot I | 18 | 28 | 1.6 | 1.6 | 495 | 24 | 25 |
| Donor_2_3. Aliquot A | 34 | 36 | 1.7 | 56 | 354 | 47 | 212 |
| Donor_2_3. Aliquot B | 35 | 37 | 1.9 | 44 | 391 | 49 | 94 |
| Donor_2_3. Aliquot C | 36 | 36 | 0.84 | 7.5 | 303 | 41 | 12 |
| Donor_2_3. Aliquot D | 35 | 38 | 7.1 | 46 | 359 | 45 | 2700 |
| Donor_2_3. Aliquot E | 34 | 37 | 3.5 | 43 | 376 | 48 | 1690 |
| Donor_2_3. Aliquot F | 36 | 39 | 0.47 | 5.6 | 305 | 40 | 24 |
| Donor_2_3. Aliquot G | 34 | 38 | 2.3 | 48 | 499 | 47 | 544 |
| Donor_2_3. Aliquot H | 36 | 34 | 0.84 | 20 | 304 | 40 | 21 |
| Donor_2_3. Aliquot I | 33 | 37 | 0.70 | 9.5 | 278 | 36 | 19 |
| Donor_3_3. Aliquot A | 42 | 56 | 1.9 | 20 | 183 | 14 | 157 |
| Donor_3_3. Aliquot B | 40 | 50 | 1.8 | 22 | 209 | 13 | 64 |
| Donor_3_3. Aliquot C | 43 | 57 | 0.15 | 5.6 | 156 | 8.1 | 13 |
| Donor_3_3. Aliquot D | 39 | 52 | 5.4 | 18 | 213 | 14 | 2600 |
| Donor_3_3. Aliquot E | 42 | 52 | 4.9 | 16 | 221 | 14 | 1150 |
| Donor_3_3. Aliquot F | 40 | 53 | 1.5 | 4.4 | 154 | 7.9 | 26 |
| Donor_3_3. Aliquot G | 41 | 54 | 0.84 | 15 | 205 | 10.0 | 21 |

FIG. 15M.2

| | SHBG | Thyroxine Binding Globulin | Tissue Factor | TGF-alpha | TIMP-1 | TNF RII | TNF-alpha |
|---|---|---|---|---|---|---|---|
| | nmol/L | ug/mL | ng/mL | pg/mL | ng/mL | ng/mL | pg/mL |
| Least Detectable Dose | 1.3 | 0.34 | 0.84 | 1.8 | 8.4 | 0.13 | 4.0 |
| | | | | | | | |
| RBM Low Plasma Range | 12 | 40 | | Pending | 59 | 3.1 | 27 |
| RBM High Plasma Range | 106 | 104 | 2.4 | Pending | 192 | 79 | |
| Donor_3_3. Aliquot H | 38 | 49 | 0.56 | 2.1 | 155 | 6.8 | 9.4 |
| Donor_3_3. Aliquot I | 36 | 51 | 0.99 | 0.63 | 153 | 6.5 | 4.2 |
| | | | | | | | |
| Donor_4_3. Aliquot A | 54 | 38 | 1.5 | 15 | 575 | 30 | 20 |
| Donor_4_3. Aliquot B | 53 | 35 | 0.87 | 22 | 590 | 30 | 17 |
| Donor_4_3. Aliquot C | 54 | 35 | 0.84 | 6.4 | 532 | 26 | 12 |
| Donor_4_3. Aliquot D | 55 | 34 | 5.4 | 19 | 622 | 33 | 1720 |
| Donor_4_3. Aliquot E | 50 | 35 | 3.4 | 16 | 632 | 36 | 618 |
| Donor_4_3. Aliquot F | 58 | 36 | 1.5 | 4.6 | 565 | 31 | 91 |
| Donor_4_3. Aliquot G | 57 | 36 | 0.84 | 16 | 499 | 30 | 12 |
| Donor_4_3. Aliquot H | 53 | 32 | 0.99 | 3.5 | 546 | 27 | 9.3 |
| Donor_4_3. Aliquot I | 51 | 35 | 0.84 | 3.8 | 557 | 28 | 4.8 |
| | | | | | | | |
| Donor_5_3. Aliquot A | 33 | 47 | 0.87 | 22 | 344 | 28 | 106 |
| Donor_5_3. Aliquot B | 31 | 47 | 0.87 | 20 | 368 | 31 | 146 |
| Donor_5_3. Aliquot C | 35 | 42 | 0.84 | 7.3 | 184 | 23 | 12 |
| Donor_5_3. Aliquot D | 31 | 45 | 6.3 | 17 | 327 | 34 | 1900 |
| Donor_5_3. Aliquot E | 31 | 46 | 4.4 | 23 | 360 | 35 | 1590 |
| Donor_5_3. Aliquot F | 31 | 43 | 0.15 | 7.1 | 233 | 23 | 105 |
| Donor_5_3. Aliquot G | 32 | 44 | 0.84 | 25 | 331 | 27 | 18 |
| Donor_5_3. Aliquot H | 29 | 40 | 0.56 | 7.0 | 228 | 23 | 12 |
| Donor_5_3. Aliquot I | 29 | 42 | 0.84 | 7.6 | 190 | 22 | 12 |
| | | | | | | | |
| Donor_6_3. Aliquot A | 18 | 29 | 0.84 | 13 | 139 | 5.5 | 41 |
| Donor_6_3. Aliquot B | 19 | 30 | 0.84 | 15 | 165 | 6.9 | 23 |
| Donor_6_3. Aliquot C | 19 | 27 | 0.84 | 1.2 | 111 | 2.5 | 3.2 |
| Donor_6_3. Aliquot D | 18 | 29 | 3.0 | 12 | 156 | 6.8 | 1910 |
| Donor_6_3. Aliquot E | 17 | 28 | 5.1 | 16 | 164 | 7.8 | 3210 |

FIG. 15M.3

| | SHBG nmol/L | Thyroxine Binding Globulin ug/mL | Tissue Factor ng/mL | TGF-alpha pg/mL | TIMP-1 ng/mL | TNF RII ng/mL | TNF-alpha pg/mL |
|---|---|---|---|---|---|---|---|
| Least Detectable Dose | 1.3 | 0.34 | 0.84 | 1.8 | 8.4 | 0.13 | 4.0 |
| RBM Low Plasma Range | 12 | 40 | | Pending | 59 | 3.1 | 27 |
| RBM High Plasma Range | 106 | 104 | 2.4 | Pending | 192 | 79 | 9.1 |
| Donor_6_3. Aliquot F | 19 | 30 | 0.84 | 1.2 | 124 | 4.1 | 12 |
| Donor_6_3. Aliquot G | 18 | 30 | 0.84 | 11 | 260 | 5.1 | 8.0 |
| Donor_6_3. Aliquot H | 19 | 27 | 0.84 | 3.8 | 112 | 3.0 | 1.7 |
| Donor_6_3. Aliquot I | 18 | 28 | 0.84 | 1.5 | 100 | 2.4 | |
| Donor_7_3. Aliquot A | 9.5 | 25 | 2.4 | 9.2 | 210 | 14 | 240 |
| Donor_7_3. Aliquot B | 11 | 27 | 1.9 | 4.8 | 237 | 14 | 67 |
| Donor_7_3. Aliquot C | 12 | 25 | 0.84 | 1.8 | 198 | 7.8 | 4.3 |
| Donor_7_3. Aliquot D | 10 | 25 | 4.1 | 4.6 | 241 | 13 | 1250 |
| Donor_7_3. Aliquot E | 8.8 | 19 | 2.4 | 3.4 | 243 | 13 | 338 |
| Donor_7_3. Aliquot F | 10 | 26 | 0.15 | 1.8 | 187 | 8.4 | 19 |
| Donor_7_3. Aliquot G | 9.4 | 23 | 0.84 | 4.7 | 213 | 10.0 | 17 |
| Donor_7_3. Aliquot H | 9.7 | 22 | 0.84 | 1.8 | 158 | 6.4 | 5.1 |
| Donor_7_3. Aliquot I | 9.9 | 25 | 0.15 | 1.8 | 159 | 7.0 | 2.7 |
| Donor_8_3. Aliquot A | 65 | 31 | 1.2 | 2.7 | 84 | 3.8 | 129 |
| Donor_8_3. Aliquot B | 66 | 30 | 0.84 | 3.4 | 118 | 5.1 | 49 |
| Donor_8_3. Aliquot C | 61 | 29 | 0.84 | 2.7 | 50 | 1.7 | 184 |
| Donor_8_3. Aliquot D | 60 | 28 | 13 | 6.2 | 60 | 3.8 | 12200 |
| Donor_8_3. Aliquot E | 62 | 29 | 12 | 5.5 | 88 | 4.7 | 7570 |
| Donor_8_3. Aliquot F | 67 | 31 | 0.47 | 1.9 | 52 | 3.2 | 591 |
| Donor_8_3. Aliquot G | 57 | 27 | 0.84 | 4.2 | 118 | 2.8 | 22 |
| Donor_8_3. Aliquot H | 69 | 29 | 0.65 | 2.8 | 60 | 2.5 | 113 |
| Donor_8_3. Aliquot I | 64 | 31 | 0.65 | 1.8 | 61 | 1.9 | 14 |
| Donor_9_3. Aliquot A | Pending | Pending | 1.2 | 19 | 66 | 3.6 | 78 |
| Donor_9_3. Aliquot B | Pending | Pending | 2.0 | 16 | 92 | 4.4 | 51 |
| Donor_9_3. Aliquot C | Pending | Pending | 0.66 | 18 | 62 | 3.3 | 68 |

FIG. 15M.4

| | SHBG nmol/L | Thyroxine Binding Globulin ug/mL | Tissue Factor ng/mL | TGF-alpha pg/mL | TIMP-1 ng/mL | TNF RII ng/mL | TNF-alpha pg/mL |
|---|---|---|---|---|---|---|---|
| Least Detectable Dose | 1.3 | 0.34 | 0.84 | 1.8 | 8.4 | 0.13 | 4.0 |
| RBM Low Plasma Range | 12 | 40 | | Pending | 59 | 3.1 | 27 |
| RBM High Plasma Range | 106 | 104 | 2.4 | Pending | 192 | 79 | 6000 |
| Donor_9_3. Aliquot D | Pending | Pending | 15 | 18 | 69 | 5.2 | 4600 |
| Donor_9_3. Aliquot E | Pending | Pending | 8.6 | 20 | 93 | 5.6 | 81 |
| Donor_9_3. Aliquot F | Pending | Pending | 2.1 | 12 | 48 | 2.7 | 55 |
| Donor_9_3. Aliquot G | Pending | Pending | 1.8 | 20 | 130 | 3.9 | 22 |
| Donor_9_3. Aliquot H | Pending | Pending | 1.5 | 12 | 56 | 2.5 | 13 |
| Donor_9_3. Aliquot I | Pending | Pending | 0.53 | 8.5 | 53 | 1.9 | |
| EDTA Plasma | | | | | | | |
| donor #1 plasma | Pending | Pending | 2.9 | 1.8 | 379 | 27 | 14 |
| donor #2 plasma | Pending | Pending | 1.1 | 1.2 | 248 | 51 | 5.4 |
| donor #3 plasma | Pending | Pending | 1.9 | 1.8 | 144 | 8.2 | 5.4 |
| donor #4 plasma | Pending | Pending | 2.0 | 1.8 | 478 | 34 | 1.1 |
| donor #5 plasma | Pending | Pending | 2.1 | 1.8 | 166 | 28 | 2.3 |
| donor #6 plasma | Pending | Pending | 0.95 | 1.8 | 82 | 2.6 | 4 |
| donor #7 plasma | Pending | Pending | 1.9 | 1.8 | 156 | 9.5 | 4 |
| donor #8 plasma | Pending | Pending | 1.0 | 1.8 | 40 | 1.2 | 5.6 |
| donor #9 plasma | Pending | Pending | 0.74 | 4.4 | 31 | 1.5 | 4 |
| *Stimulations indices* | | | | | | | |

FIG. 15M.5

| | SHBG nmol/L | Thyroxine Binding Globulin ug/mL | Tissue Factor ng/mL | TGF-alpha pg/mL | TIMP-1 ng/mL | TNF RII ng/mL | TNF-alpha pg/mL |
|---|---|---|---|---|---|---|---|
| Least Detectable Dose | 1.3 | 0.34 | 0.84 | 1.8 | 8.4 | 0.13 | 4.0 |
| RBM Low Plasma Range | 12 | 40 | | Pending | 59 | 3.1 | 27 |
| RBM High Plasma Range | 106 | 104 | 2.4 | Pending | 192 | 79 | |
| patient 1 | A | | | | | | |
| patient 7 | A | | | | | | |
| patient 2 | A | | | | | | |
| patient 3 | A | | | | | | |
| patient 5 | A | | | | | | |
| patient 4 | A | | | | | | |
| patient 6 | A | | | | | | |
| NHD 1 | A | | | | | | |
| NHD 2 | A | | | | | | |

FIG. 15M.6

| | SHBG nmol/L | Thyroxine Binding Globulin ug/mL | Tissue Factor ng/mL | TGF-alpha pg/mL | TIMP-1 ng/mL | TNF RII ng/mL | TNF-alpha pg/mL |
|---|---|---|---|---|---|---|---|
| Least Detectable Dose | 1.3 | 0.34 | 0.84 | 1.8 | 8.4 | 0.13 | 4.0 |
| RBM Low Plasma Range | 12 | 40 | | Pending | 59 | 3.1 | 27 |
| RBM High Plasma Range | 106 | 104 | 2.4 | Pending | 192 | 79 | |
| patient 1 | B | | | | | | |
| patient 7 | B | | | | | | |
| patient 2 | B | | | | | | |
| patient 3 | B | | | | | | |
| patient 5 | B | | | | | | |
| patient 4 | B | | | | | | |
| patient 6 | B | | | | | | |
| NHD 1 | B | | | | | | |
| NHD 2 | B | | | | | | |

FIG. 15M.7

| | SHBG nmol/L | Thyroxine Binding Globulin ug/mL | Tissue Factor ng/mL | TGF-alpha pg/mL | TIMP-1 ng/mL | TNF RII ng/mL | TNF-alpha pg/mL |
|---|---|---|---|---|---|---|---|
| Least Detectable Dose | 1.3 | 0.34 | 0.84 | 1.8 | 8.4 | 0.13 | 4.0 |
| RBM Low Plasma Range | 12 | 40 | | Pending | 59 | 3.1 | |
| RBM High Plasma Range | 106 | 104 | 2.4 | Pending | 192 | 79 | 27 |
| | SHBG | Thyroxine Binding Globulin | Tissue Factor | TGF-alpha | TIMP-1 | TNF RII | TNF-alpha |
| patient 1 | | | | | | | |
| patient 7 | | | | | | | |
| patient 2 | | | | | | | |
| patient 3 | | | | | | | |
| patient 5 | | | | | | | |
| patient 4 | | | | | | | |
| patient 6 | | | | | | | |
| NHD 1 | | | | | | | |
| NHD 2 | | | | | | | |

FIG. 15M.8

| | | SHBG nmol/L | Thyroxine Binding Globulin ug/mL | Tissue Factor ng/mL | TGF-alpha pg/mL | TIMP-1 ng/mL | TNF RII ng/mL | TNF-alpha pg/mL |
|---|---|---|---|---|---|---|---|---|
| Least Detectable Dose | | 1.3 | 0.34 | 0.84 | 1.8 | 8.4 | 0.13 | 4.0 |
| RBM Low Plasma Range | | 12 | 40 | 2.4 | Pending | 59 | 3.1 | 27 |
| RBM High Plasma Range | | 106 | 104 | | Pending | 192 | 79 | |
| | | SHBG | Thyroxine Binding Globulin | Tissue Factor | TGF-alpha | TIMP-1 | TNF RII | TNF-alpha |
| patient 1 | D | | | | | | | |
| patient 7 | D | | | | | | | |
| patient 2 | D | | | | | | | |
| patient 3 | D | | | | | | | |
| patient 5 | D | | | | | | | |
| patient 4 | D | | | | | | | |
| patient 6 | D | | | | | | | |
| NHD 1 | D | | | | | | | |
| NHD 2 | D | | | | | | | |

FIG. 15M.9

| | SHBG nmol/L | Thyroxine Binding Globulin ug/mL | Tissue Factor ng/mL | TGF-alpha pg/mL | TIMP-1 ng/mL | TNF RII ng/mL | TNF-alpha pg/mL |
|---|---|---|---|---|---|---|---|
| Least Detectable Dose | 1.3 | 0.34 | 0.84 | 1.8 | 8.4 | 0.13 | 4.0 |
| RBM Low Plasma Range | 12 | 40 | | Pending | 59 | 3.1 | |
| RBM High Plasma Range | 106 | 104 | 2.4 | Pending | 192 | 79 | 27 |
| patient 1 | | | | | | | |
| patient 7 | | | | | | | |
| patient 2 | | | | | | | |
| patient 3 | | | | | | | |
| patient 5 | | | | | | | |
| patient 4 | | | | | | | |
| patient 6 | | | | | | | |
| NHD 1 | | | | | | | |
| NHD 2 | | | | | | | |

FIG. 15M.10

| | SHBG nmol/L | Thyroxine Binding Globulin ug/mL | Tissue Factor ng/mL | TGF-alpha pg/mL | TIMP-1 ng/mL | TNF RII ng/mL | TNF-alpha pg/mL |
|---|---|---|---|---|---|---|---|
| Least Detectable Dose | 1.3 | 0.34 | 0.84 | 1.8 | 8.4 | 0.13 | 4.0 |
| RBM Low Plasma Range | 12 | 40 | 2.4 | Pending | 59 | 3.1 | 27 |
| RBM High Plasma Range | 106 | 104 | | Pending | 192 | 79 | |

| | | | | | | | |
|---|---|---|---|---|---|---|---|
| patient 1 | F | | | | | | |
| patient 7 | F | | | | | | |
| patient 2 | F | | | | | | |
| patient 3 | F | | | | | | |
| patient 5 | F | | | | | | |
| patient 4 | F | | | | | | |
| patient 6 | F | | | | | | |
| NHD 1 | F | | | | | | |
| NHD 2 | F | | | | | | |

FIG. 15M.11

| | SHBG nmol/L | Thyroxine Binding Globulin ug/mL | Tissue Factor ng/mL | TGF-alpha pg/mL | TIMP-1 ng/mL | TNF RII ng/mL | TNF-alpha pg/mL |
|---|---|---|---|---|---|---|---|
| Least Detectable Dose | 1.3 | 0.34 | 0.84 | 1.8 | 8.4 | 0.13 | 4.0 |
| RBM Low Plasma Range | 12 | 40 | | Pending | 59 | 3.1 | |
| RBM High Plasma Range | 106 | 104 | 2.4 | Pending | 192 | 79 | 27 |
| | SHBG | Thyroxine Binding Globulin | Tissue Factor | TGF-alpha | TIMP-1 | TNF RII | TNF-alpha |
| patient 1 | | | | | | | |
| patient 7 | | | | | | | |
| patient 2 | | | | | | | |
| patient 3 | | | | | | | |
| patient 5 | | | | | | | |
| patient 4 | | | | | | | |
| patient 6 | | | | | | | |
| NHD 1 | | | | | | | |
| NHD 2 | | | | | | | |
| | G | G | G | G | G | G | G |
| | G | G | | | | | |

FIG. 15M.12

| | SHBG nmol/L | Thyroxine Binding Globulin ug/mL | Tissue Factor ng/mL | TGF-alpha pg/mL | TIMP-1 ng/mL | TNF RII ng/mL | TNF-alpha pg/mL |
|---|---|---|---|---|---|---|---|
| Least Detectable Dose | 1.3 | 0.34 | 0.84 | 1.8 | 8.4 | 0.13 | 4.0 |
| RBM Low Plasma Range | 12 | 40 | 2.4 | Pending | 59 | 3.1 | 27 |
| RBM High Plasma Range | 106 | 104 | | Pending | 192 | 79 | |
| | SHBG | Thyroxine Binding Globulin | Tissue Factor | TGF-alpha | TIMP-1 | TNF RII | TNF-alpha |
| patient 1 | H | | | | | | |
| patient 7 | H | | | | | | |
| patient 2 | H | | | | | | |
| patient 3 | H | | | | | | |
| patient 5 | H | | | | | | |
| patient 4 | H | | | | | | |
| patient 6 | H | | | | | | |
| NHD 1 | H | | | | | | |
| NHD 2 | H | | | | | | |

FIG. 15M.13

| | SHBG nmol/L | Thyroxine Binding Globulin ug/mL | Tissue Factor ng/mL | TGF-alpha pg/mL | TIMP-1 ng/mL | TNF RII ng/mL | TNF-alpha pg/mL |
|---|---|---|---|---|---|---|---|
| Least Detectable Dose | 1.3 | 0.34 | 0.84 | 1.8 | 8.4 | 0.13 | 4.0 |
| RBM Low Plasma Range | 12 | 40 | | Pending | 59 | 3.1 | |
| RBM High Plasma Range | 106 | 104 | 2.4 | Pending | 192 | 79 | 27 |
| patient 1 | | | | | | | |
| patient 7 | | | | | | | |
| patient 2 | | | | | | | |
| patient 3 | | | | | | | |
| patient 5 | | | | | | | |
| patient 4 | | | | | | | |
| patient 6 | | | | | | | |
| NHD 1 | | | | | | | |
| NHD 2 | | | | | | | |

FIG. 15M.14

| | SHBG nmol/L | Thyroxine Binding Globulin ug/mL | Tissue Factor ng/mL | TGF-alpha pg/mL | TIMP-1 ng/mL | TNF RII ng/mL | TNF-alpha pg/mL |
|---|---|---|---|---|---|---|---|
| Least Detectable Dose | 1.3 | 0.34 | 0.84 | 1.8 | 8.4 | 0.13 | 4.0 |
| RBM Low Plasma Range | 12 | 40 | | Pending | 59 | 3.1 | |
| RBM High Plasma Range | 106 | 104 | 2.4 | Pending | 192 | 79 | 27 |
| Messwert > ULD | | | | | | | |
| SI > 1,3 | | | | | | | |
| SI 0,7-1,3 | | | | | | | |
| SI 0-0,7 | | | | | | | |
| | | | | | | | |

FIG. 15N.1

| | TNF-beta pg/mL | Thrombopoietin ng/mL | Thyroid Stimulating Hormone uIU/mL | Thrombospondin-1 ng/mL | VCAM-1 ng/mL | VEGF pg/mL |
|---|---|---|---|---|---|---|
| Least Detectable Dose | 46 | 3.2 | 0.028 | <25 | 2.6 | 7.5 |
| RBM Low Plasma Range | | | 0.18 | Pending | 284 | 91 |
| RBM High Plasma Range | 120 | 6.2 | 3.7 | Pending | 1310 | 1790 |
| Samples | | | | | | |
| Donor_1 3. Aliquot A | 7.9 | 1.9 | 17 | 15200 | 1350 | 2090 |
| Donor_1 3. Aliquot B | 46 | 1.5 | 16 | 21600 | 1440 | 2090 |
| Donor_1 3. Aliquot C | 46 | 3.2 | 18 | 17000 | 1350 | 2070 |
| Donor_1 3. Aliquot D | 46 | 1.9 | 17 | 15600 | 1420 | 2120 |
| Donor_1 3. Aliquot E | 46 | 1.9 | 17 | 13100 | 1320 | 2030 |
| Donor_1 3. Aliquot F | 46 | 3.2 | 17 | 12500 | 1310 | 1860 |
| Donor_1 3. Aliquot G | 46 | 1.3 | 17 | 11800 | 1450 | 2570 |
| Donor_1 3. Aliquot H | 46 | 0.86 | 17 | 24900 | 1320 | 2210 |
| Donor_1 3. Aliquot I | 46 | 0.69 | 17 | 16200 | 1350 | 1940 |
| Donor_2 3. Aliquot A | 4.6 | 2.7 | 10 | 19800 | 1090 | 4570 |
| Donor_2 3. Aliquot B | 6.0 | 3.2 | 10 | 21600 | 1190 | 4900 |
| Donor_2 3. Aliquot C | 46 | 3.2 | 9.9 | 12200 | 1160 | 5240 |
| Donor_2 3. Aliquot D | 6.0 | 2.4 | 12 | 13600 | 1070 | 4400 |
| Donor_2 3. Aliquot E | 3.2 | 2.7 | 11 | 12400 | 1150 | 4630 |
| Donor_2 3. Aliquot F | 46 | 1.5 | 10 | 12800 | 1100 | 4870 |
| Donor_2 3. Aliquot G | 18 | 3.0 | 9.9 | 12000 | 1180 | 5490 |
| Donor_2 3. Aliquot H | 46 | 3.2 | 9.5 | 13300 | 1090 | 4920 |
| Donor_2 3. Aliquot I | 46 | 0.49 | 9.1 | 12400 | 1080 | 4680 |
| Donor_3 3. Aliquot A | 7.3 | 2.5 | 0.99 | 14000 | 749 | 532 |
| Donor_3 3. Aliquot B | 46 | 2.5 | 0.98 | 18300 | 722 | 618 |
| Donor_3 3. Aliquot C | 46 | 3.2 | 0.99 | 12000 | 740 | 707 |
| Donor_3 3. Aliquot D | 14 | 2.2 | 1.1 | 13700 | 725 | 505 |
| Donor_3 3. Aliquot E | 11 | 3.9 | 1.2 | 16800 | 775 | 508 |
| Donor_3 3. Aliquot F | 46 | 2.1 | 0.94 | 10500 | 695 | 714 |
| Donor_3 3. Aliquot G | 46 | 3.2 | 1.0 | 12200 | 758 | 1590 |

FIG. 15N.2

| | TNF-beta pg/mL | Thrombopoietin ng/mL | Thyroid Stimulating Hormone uIU/mL | Thrombospondin-1 ng/mL | VCAM-1 ng/mL | VEGF pg/mL |
|---|---|---|---|---|---|---|
| Least Detectable Dose | 46 | 3.2 | 0.028 | <25 | 2.6 | 7.5 |
| RBM Low Plasma Range | | | 0.18 | Pending | 284 | 91 |
| RBM High Plasma Range | 120 | 6.2 | 3.7 | Pending | 1310 | 1790 |
| Donor_3 3. Aliquot H | 46 | 3.2 | 0.90 | 9670 | 694 | 678 |
| Donor_3 3. Aliquot I | 46 | 2.1 | 0.98 | 9250 | 690 | 734 |
| Donor_4 3. Aliquot A | 46 | 1.3 | 0.15 | 14100 | 2080 | 1190 |
| Donor_4 3. Aliquot B | 46 | 1.4 | 0.15 | 16300 | 1940 | 1180 |
| Donor_4 3. Aliquot C | 46 | 3.2 | 0.16 | 4160 | 1990 | 1220 |
| Donor_4 3. Aliquot D | 7.3 | 2.0 | 0.26 | 11500 | 1950 | 1100 |
| Donor_4 3. Aliquot E | 15 | 2.3 | 0.19 | 10900 | 2070 | 1060 |
| Donor_4 3. Aliquot F | 7.3 | 1.2 | 0.14 | 5780 | 2200 | 1030 |
| Donor_4 3. Aliquot G | 46 | 3.2 | 0.13 | 4050 | 1970 | 2190 |
| Donor_4 3. Aliquot H | 46 | 1.2 | 0.14 | 4460 | 1980 | 1350 |
| Donor_4 3. Aliquot I | 46 | 3.2 | 0.13 | 6360 | 2020 | 1280 |
| Donor_5 3. Aliquot A | 7.9 | 2.9 | 0.28 | 22300 | 521 | 3600 |
| Donor_5 3. Aliquot B | 7.3 | 3.1 | 0.26 | 17800 | 510 | 3460 |
| Donor_5 3. Aliquot C | 46 | 0.69 | 0.32 | 13300 | 489 | 4460 |
| Donor_5 3. Aliquot D | 9.8 | 2.8 | 0.41 | 18600 | 525 | 3350 |
| Donor_5 3. Aliquot E | 16 | 2.7 | 0.38 | 17800 | 539 | 3650 |
| Donor_5 3. Aliquot F | 46 | 2.2 | 0.24 | 13200 | 495 | 3140 |
| Donor_5 3. Aliquot G | 8.6 | 1.0 | 0.28 | 14000 | 545 | 5580 |
| Donor_5 3. Aliquot H | 46 | 0.49 | 0.26 | 14800 | 510 | 3840 |
| Donor_5 3. Aliquot I | 46 | 0.49 | 0.26 | 10900 | 489 | 3520 |
| Donor_6 3. Aliquot A | 6.6 | 3.6 | 1.3 | 25000 | 258 | 874 |
| Donor_6 3. Aliquot B | 4.6 | 3.7 | 1.2 | 22900 | 252 | 648 |
| Donor_6 3. Aliquot C | 46 | 3.1 | 1.3 | 13800 | 261 | 840 |
| Donor_6 3. Aliquot D | 46 | 3.4 | 1.4 | 21100 | 274 | 530 |
| Donor_6 3. Aliquot E | 46 | 3.6 | 1.3 | 13800 | 253 | 471 |

FIG. 15N.3

| | TNF-beta | Thrombopoietin | Thyroid Stimulating Hormone | Thrombospondin-1 | VCAM-1 | VEGF |
|---|---|---|---|---|---|---|
| | pg/mL | ng/mL | uIU/mL | ng/mL | ng/mL | pg/mL |
| Least Detectable Dose | 46 | 3.2 | 0.028 | <25 | 2.6 | 7.5 |
| RBM Low Plasma Range | | | 0.18 | Pending | 284 | 91 |
| RBM High Plasma Range | 120 | 6.2 | 3.7 | Pending | 1310 | 1790 |
| Donor_6_3. Aliquot F | 46 | 4.0 | 1.1 | 15700 | 254 | 581 |
| Donor_6_3. Aliquot G | 46 | 2.3 | 1.3 | 12400 | 284 | 2690 |
| Donor_6_3. Aliquot H | 8.6 | 1.7 | 1.2 | 14500 | 258 | 878 |
| Donor_6_3. Aliquot I | 46 | 1.7 | 1.2 | 12500 | 256 | 846 |
| Donor_7_3. Aliquot A | 24 | 4.2 | 0.52 | 12100 | 789 | 295 |
| Donor_7_3. Aliquot B | 14 | 4.3 | 0.51 | 14600 | 802 | 237 |
| Donor_7_3. Aliquot C | 7.9 | 1.4 | 0.49 | 15800 | 861 | 345 |
| Donor_7_3. Aliquot D | 8.6 | 3.3 | 0.55 | 11600 | 740 | 210 |
| Donor_7_3. Aliquot E | 19 | 3.8 | 0.50 | 11200 | 816 | 235 |
| Donor_7_3. Aliquot F | 9.8 | 3.5 | 0.47 | 7230 | 781 | 203 |
| Donor_7_3. Aliquot G | 46 | 1.0 | 0.49 | 6360 | 803 | 1260 |
| Donor_7_3. Aliquot H | 46 | 3.2 | 0.49 | 7470 | 721 | 313 |
| Donor_7_3. Aliquot I | 46 | 2.2 | 0.47 | 7470 | 738 | 257 |
| Donor_8_3. Aliquot A | 7.9 | 3.6 | 2.2 | 10800 | 352 | 252 |
| Donor_8_3. Aliquot B | 6.0 | 4.7 | 2.1 | 14000 | 350 | 203 |
| Donor_8_3. Aliquot C | 46 | 4.4 | 1.8 | 10800 | 320 | 401 |
| Donor_8_3. Aliquot D | 11 | 4.4 | 2.4 | 8580 | 319 | 416 |
| Donor_8_3. Aliquot E | 11 | 4.2 | 2.2 | 11900 | 322 | 341 |
| Donor_8_3. Aliquot F | 9.8 | 5.6 | 2.0 | 4870 | 341 | 321 |
| Donor_8_3. Aliquot G | 46 | 1.4 | 1.9 | 5370 | 337 | 822 |
| Donor_8_3. Aliquot H | 3.9 | 3.7 | 2.2 | 12600 | 331 | 322 |
| Donor_8_3. Aliquot I | 46 | 3.8 | 2.0 | 13200 | 347 | 248 |
| Donor_9_3. Aliquot A | 11 | 3.2 | 0.34 | 13600 | 298 | 326 |
| Donor_9_3. Aliquot B | 8.8 | 3.4 | 0.28 | 16400 | 303 | 280 |
| Donor_9_3. Aliquot C | 20 | 3.6 | 0.33 | 15500 | 324 | 367 |

FIG. 15N.4

| | TNF-beta pg/mL | Thrombopoietin ng/mL | Thyroid Stimulating Hormone uIU/mL | Thrombospondin-1 ng/mL | VCAM-1 ng/mL | VEGF pg/mL |
|---|---|---|---|---|---|---|
| Least Detectable Dose | 46 | 3.2 | 0.028 | <25 | 2.6 | 7.5 |
| RBM Low Plasma Range | | | | | | |
| RBM High Plasma Range | 120 | 6.2 | 0.18 | Pending | 284 | 91 |
| Donor_9_3. Aliquot D | 15 | 2.9 | 3.7 | Pending | 1310 | 1790 |
| Donor_9_3. Aliquot E | 5.0 | 3.1 | 0.65 | 13800 | 295 | 486 |
| Donor_9_3. Aliquot F | 18 | 4.3 | 0.53 | 11300 | 312 | 398 |
| Donor_9_3. Aliquot G | 6.9 | 1.2 | 0.29 | 6910 | 314 | 322 |
| Donor_9_3. Aliquot H | 10 | 1.8 | 0.22 | 9900 | 297 | 1170 |
| Donor_9_3. Aliquot I | 46 | 2.3 | 0.31 | 15900 | 297 | 380 |
| | | | 0.28 | 17000 | 290 | 243 |
| EDTA Plasma | | | | | | |
| donor #1 plasma | 10 | 3.2 | 12 | 14800 | 1230 | 1500 |
| donor #2 plasma | 46 | 3.2 | 9.7 | 4670 | 1280 | 4500 |
| donor #3 plasma | 8.8 | 0.81 | 1.0 | 7890 | 978 | 1290 |
| donor #4 plasma | 46 | 1.4 | 0.11 | 2310 | 2580 | 1400 |
| donor #5 plasma | 11 | 1.8 | 0.28 | 28600 | 577 | 3840 |
| donor #6 plasma | 5.0 | 2.4 | 1.7 | 16800 | 301 | 533 |
| donor #7 plasma | 13 | 2.1 | 0.59 | 13800 | 980 | 521 |
| donor #8 plasma | 46 | 1.4 | 2.5 | 6520 | 340 | 281 |
| donor #9 plasma | 46 | 0.44 | 0.30 | 818 | 385 | 295 |
| Stimulations indices | | | | | | |

FIG. 15N.5

| | Least Detectable Dose | TNF-beta pg/mL 46 | Thrombopoietin ng/mL 3.2 | Thyroid Stimulating Hormone uIU/mL 0.028 | Thrombospondin-1 ng/mL <25 | VCAM-1 ng/mL 2.6 | VEGF pg/mL 7.5 |
|---|---|---|---|---|---|---|---|
| | RBM Low Plasma Range | | | 0.18 | Pending | 284 | 91 |
| | RBM High Plasma Range | 120 | 6.2 | 3.7 | Pending | 1310 | 1790 |
| patient 1 | A | | | | | | |
| patient 7 | A | | | | | | |
| patient 2 | A | | | | | | |
| patient 3 | A | | | | | | |
| patient 5 | A | | | | | | |
| patient 4 | A | | | | | | |
| patient 6 | A | | | | | | |
| NHD 1 | A | | | | | | |
| NHD 2 | A | | | | | | |

FIG. 15N.6

| | TNF-beta pg/mL | Thrombopoietin ng/mL | Thyroid Stimulating Hormone uIU/mL | Thrombospondin-1 ng/mL | VCAM-1 ng/mL | VEGF pg/mL |
|---|---|---|---|---|---|---|
| Least Detectable Dose | 46 | 3.2 | 0.028 | <25 | 2.6 | 7.5 |
| RBM Low Plasma Range | | | 0.18 | Pending | 284 | 91 |
| RBM High Plasma Range | 120 | 6.2 | 3.7 | Pending | 1310 | 1790 |

| | | | | | | | |
|---|---|---|---|---|---|---|---|
| patient 1 | B | | | | | | |
| patient 7 | B | | | | | | |
| patient 2 | B | | | | | | |
| patient 3 | B | | | | | | |
| patient 5 | B | | | | | | |
| patient 4 | B | | | | | | |
| patient 6 | B | | | | | | |
| NHD 1 | B | | | | | | |
| NHD 2 | B | | | | | | |

FIG. 15N.7

| | TNF-beta pg/mL | Thrombopoietin ng/mL | Thyroid Stimulating Hormone uIU/mL | Thrombospondin-1 ng/mL | VCAM-1 ng/mL | VEGF pg/mL |
|---|---|---|---|---|---|---|
| Least Detectable Dose | 46 | 3.2 | 0.028 | <25 | 2.6 | 7.5 |
| RBM Low Plasma Range | | | 0.18 | Pending | 284 | 91 |
| RBM High Plasma Range | 120 | 6.2 | 3.7 | Pending | 1310 | 1790 |
| | TNF-beta | Thrombopoietin | Thyroid Stimulating Hormone | Thrombospondin-1 | VCAM-1 | VEGF |
| patient 1 | | | | | | |
| patient 7 | | | | | | |
| patient 2 | | | | | | |
| patient 3 | | | | | | |
| patient 5 | | | | | | |
| patient 4 | | | | | | |
| patient 6 | | | | | | |
| NHD 1 | | | | | | |
| NHD 2 | | | | | | |

FIG. 15N.8
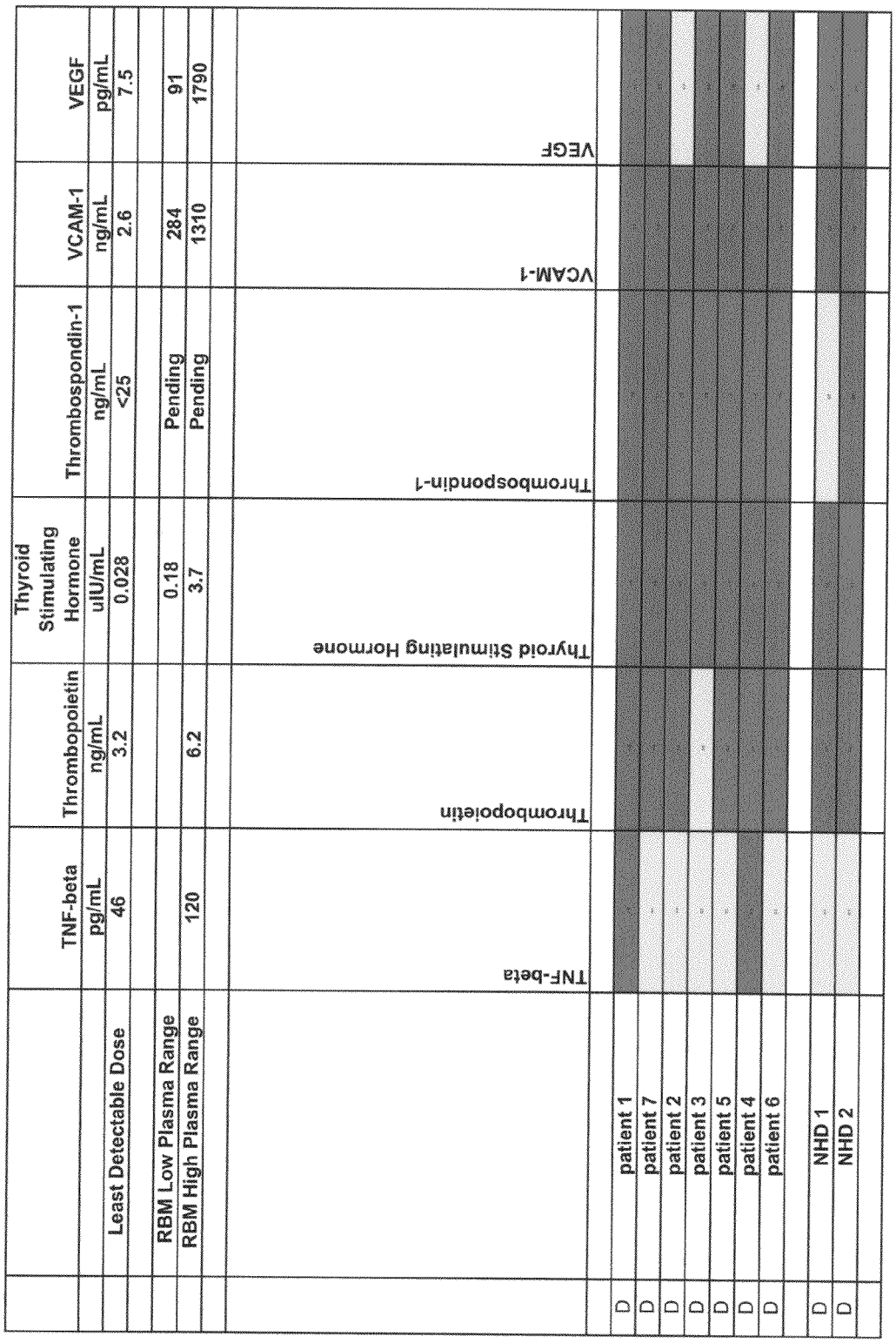

FIG. 15N.9

| | TNF-beta pg/mL | Thrombopoietin ng/mL | Thyroid Stimulating Hormone uIU/mL | Thrombospondin-1 ng/mL | VCAM-1 ng/mL | VEGF pg/mL |
|---|---|---|---|---|---|---|
| Least Detectable Dose | 46 | 3.2 | 0.028 | <25 | 2.6 | 7.5 |
| RBM Low Plasma Range | | | 0.18 | Pending | 284 | 91 |
| RBM High Plasma Range | 120 | 6.2 | 3.7 | Pending | 1310 | 1790 |
| patient 1 | | | | | | |
| patient 7 | | | | | | |
| patient 2 | | | | | | |
| patient 3 | | | | | | |
| patient 5 | | | | | | |
| patient 4 | | | | | | |
| patient 6 | | | | | | |
| NHD 1 | | | | | | |
| NHD 2 | | | | | | |

FIG. 15N.10

| | TNF-beta pg/mL | Thrombopoietin ng/mL | Thyroid Stimulating Hormone uIU/mL | Thrombospondin-1 ng/mL | VCAM-1 ng/mL | VEGF pg/mL |
|---|---|---|---|---|---|---|
| Least Detectable Dose | 46 | 3.2 | 0.028 | <25 | 2.6 | 7.5 |
| RBM Low Plasma Range | | | 0.18 | Pending | 284 | 91 |
| RBM High Plasma Range | 120 | 6.2 | 3.7 | Pending | 1310 | 1790 |
| patient 1 | F | | | | | |
| patient 7 | F | | | | | |
| patient 2 | F | | | | | |
| patient 3 | F | | | | | |
| patient 5 | F | | | | | |
| patient 4 | F | | | | | |
| patient 6 | F | | | | | |
| NHD 1 | F | | | | | |
| NHD 2 | F | | | | | |

FIG. 15N.11

| | Least Detectable Dose | RBM Low Plasma Range | RBM High Plasma Range | | TNF-beta pg/mL | Thrombopoietin ng/mL | Thyroid Stimulating Hormone uIU/mL | Thrombospondin-1 ng/mL | VCAM-1 ng/mL | VEGF pg/mL |
|---|---|---|---|---|---|---|---|---|---|---|
| | | | | | 46 | 3.2 | 0.028 | <25 | 2.6 | 7.5 |
| | | | | | 120 | 6.2 | 0.18 | Pending | 284 | 91 |
| | | | | | | | 3.7 | Pending | 1310 | 1790 |
| patient 1 | G | | | | | | | | | |
| patient 7 | G | | | | | | | | | |
| patient 2 | G | | | | | | | | | |
| patient 3 | G | | | | | | | | | |
| patient 5 | G | | | | | | | | | |
| patient 4 | G | | | | | | | | | |
| patient 6 | G | | | | | | | | | |
| NHD 1 | G | | | | | | | | | |
| NHD 2 | G | | | | | | | | | |

FIG. 15N.12

| | TNF-beta pg/mL | Thrombopoietin ng/mL | Thyroid Stimulating Hormone uIU/mL | Thrombospondin-1 ng/mL | VCAM-1 ng/mL | VEGF pg/mL |
|---|---|---|---|---|---|---|
| Least Detectable Dose | 46 | 3.2 | 0.028 | <25 | 2.6 | 7.5 |
| RBM Low Plasma Range | | | 0.18 | Pending | 284 | 91 |
| RBM High Plasma Range | 120 | 6.2 | 3.7 | Pending | 1310 | 1790 |

FIG. 15N.13

| | TNF-beta pg/mL | Thrombopoietin ng/mL | Thyroid Stimulating Hormone uIU/mL | Thrombospondin-1 ng/mL | VCAM-1 ng/mL | VEGF pg/mL |
|---|---|---|---|---|---|---|
| Least Detectable Dose | 46 | 3.2 | 0.028 | <25 | 2.6 | 7.5 |
| RBM Low Plasma Range | | | 0.18 | Pending | 284 | 91 |
| RBM High Plasma Range | 120 | 6.2 | 3.7 | Pending | 1310 | 1790 |
| patient 1 | | | | | | |
| patient 7 | | | | | | |
| patient 2 | | | | | | |
| patient 3 | | | | | | |
| patient 5 | | | | | | |
| patient 4 | | | | | | |
| patient 6 | | | | | | |
| NHD 1 | | | | | | |
| NHD 2 | | | | | | |

FIG. 15N.14

|  | TNF-beta pg/mL | Thrombopoietin ng/mL | Thyroid Stimulating Hormone uIU/mL | Thrombospondin-1 ng/mL | VCAM-1 ng/mL | VEGF pg/mL |
|---|---|---|---|---|---|---|
| Least Detectable Dose | 46 | 3.2 | 0.028 | <25 | 2.6 | 7.5 |
| RBM Low Plasma Range |  |  | 0.18 | Pending | 284 | 91 |
| RBM High Plasma Range | 120 | 6.2 | 3.7 | Pending | 1310 | 1790 |
| Messwert > ULD |  |  |  |  |  |  |
| SI > 1,3 |  |  |  |  |  |  |
| SI 0,7-1,3 |  |  |  |  |  |  |
| SI 0-0,7 |  |  |  |  |  |  |

FIG. 15O.1

| Samples | von Willebrand Factor ug/mL |
|---|---|
| Least Detectable Dose | 0.40 |
| RBM Low Plasma Range | 5.3 |
| RBM High Plasma Range | 74 |
| Donor_1 3. Aliquot A | 211 |
| Donor_1 3. Aliquot B | 203 |
| Donor_1 3. Aliquot C | 213 |
| Donor_1 3. Aliquot D | 198 |
| Donor_1 3. Aliquot E | 184 |
| Donor_1 3. Aliquot F | 196 |
| Donor_1 3. Aliquot G | 180 |
| Donor_1 3. Aliquot H | 207 |
| Donor_1 3. Aliquot I | 203 |
| Donor_2 3. Aliquot A | 188 |
| Donor_2 3. Aliquot B | 200 |
| Donor_2 3. Aliquot C | 191 |
| Donor_2 3. Aliquot D | 190 |
| Donor_2 3. Aliquot E | 189 |
| Donor_2 3. Aliquot F | 178 |
| Donor_2 3. Aliquot G | 215 |
| Donor_2 3. Aliquot H | 213 |
| Donor_2 3. Aliquot I | 187 |
| Donor_3 3. Aliquot A | 99 |
| Donor_3 3. Aliquot B | 110 |
| Donor_3 3. Aliquot C | 95 |
| Donor_3 3. Aliquot D | 123 |
| Donor_3 3. Aliquot E | 108 |
| Donor_3 3. Aliquot F | 104 |
| Donor_3 3. Aliquot G | 109 |

FIG. 150.2

| | von Willebrand Factor |
|---|---|
| | ug/mL |
| Least Detectable Dose | 0.40 |
| RBM Low Plasma Range | 5.3 |
| RBM High Plasma Range | 74 |
| Donor_3 3. Aliquot H | 123 |
| Donor_3 3. Aliquot I | 119 |
| Donor_4 3. Aliquot A | 182 |
| Donor_4 3. Aliquot B | 227 |
| Donor_4 3. Aliquot C | 253 |
| Donor_4 3. Aliquot D | 252 |
| Donor_4 3. Aliquot E | 223 |
| Donor_4 3. Aliquot F | 257 |
| Donor_4 3. Aliquot G | 223 |
| Donor_4 3. Aliquot H | 229 |
| Donor_4 3. Aliquot I | 246 |
| Donor_5 3. Aliquot A | 100 |
| Donor_5 3. Aliquot B | 105 |
| Donor_5 3. Aliquot C | 113 |
| Donor_5 3. Aliquot D | 112 |
| Donor_5 3. Aliquot E | 125 |
| Donor_5 3. Aliquot F | 109 |
| Donor_5 3. Aliquot G | 110 |
| Donor_5 3. Aliquot H | 121 |
| Donor_5 3. Aliquot I | 96 |
| Donor_6 3. Aliquot A | 79 |
| Donor_6 3. Aliquot B | 70 |
| Donor_6 3. Aliquot C | 74 |
| Donor_6 3. Aliquot D | 75 |
| Donor_6 3. Aliquot E | 72 |

FIG. 150.3

| | von Willebrand Factor |
|---|---|
| | ug/mL |
| Least Detectable Dose | 0.40 |
| RBM Low Plasma Range | 5.3 |
| RBM High Plasma Range | 74 |
| Donor_6 3. Aliquot F | 80 |
| Donor_6 3. Aliquot G | 85 |
| Donor_6 3. Aliquot H | 76 |
| Donor_6 3. Aliquot I | 67 |
| Donor_7 3. Aliquot A | 112 |
| Donor_7 3. Aliquot B | 129 |
| Donor_7 3. Aliquot C | 132 |
| Donor_7 3. Aliquot D | 124 |
| Donor_7 3. Aliquot E | 102 |
| Donor_7 3. Aliquot F | 135 |
| Donor_7 3. Aliquot G | 114 |
| Donor_7 3. Aliquot H | 127 |
| Donor_7 3. Aliquot I | 123 |
| Donor_8 3. Aliquot A | 18 |
| Donor_8 3. Aliquot B | 23 |
| Donor_8 3. Aliquot C | 16 |
| Donor_8 3. Aliquot D | 19 |
| Donor_8 3. Aliquot E | 17 |
| Donor_8 3. Aliquot F | 20 |
| Donor_8 3. Aliquot G | 21 |
| Donor_8 3. Aliquot H | 22 |
| Donor_8 3. Aliquot I | 21 |
| Donor_9 3. Aliquot A | Pending |
| Donor_9 3. Aliquot B | Pending |
| Donor_9 3. Aliquot C | Pending |

FIG. 15O.4

| | von Willebrand Factor |
|---|---|
| | ug/mL |
| Least Detectable Dose | 0.40 |
| RBM Low Plasma Range | 5.3 |
| RBM High Plasma Range | 74 |
| Donor_9_3. Aliquot D | Pending |
| Donor_9_3. Aliquot E | Pending |
| Donor_9_3. Aliquot F | Pending |
| Donor_9_3. Aliquot G | Pending |
| Donor_9_3. Aliquot H | Pending |
| Donor_9_3. Aliquot I | Pending |
| EDTA Plasma | |
| donor #1 plasma | Pending |
| donor #2 plasma | Pending |
| donor #3 plasma | Pending |
| donor #4 plasma | Pending |
| donor #5 plasma | Pending |
| donor #6 plasma | Pending |
| donor #7 plasma | Pending |
| donor #8 plasma | Pending |
| donor #9 plasma | Pending |
| *Stimulations Indices* | |

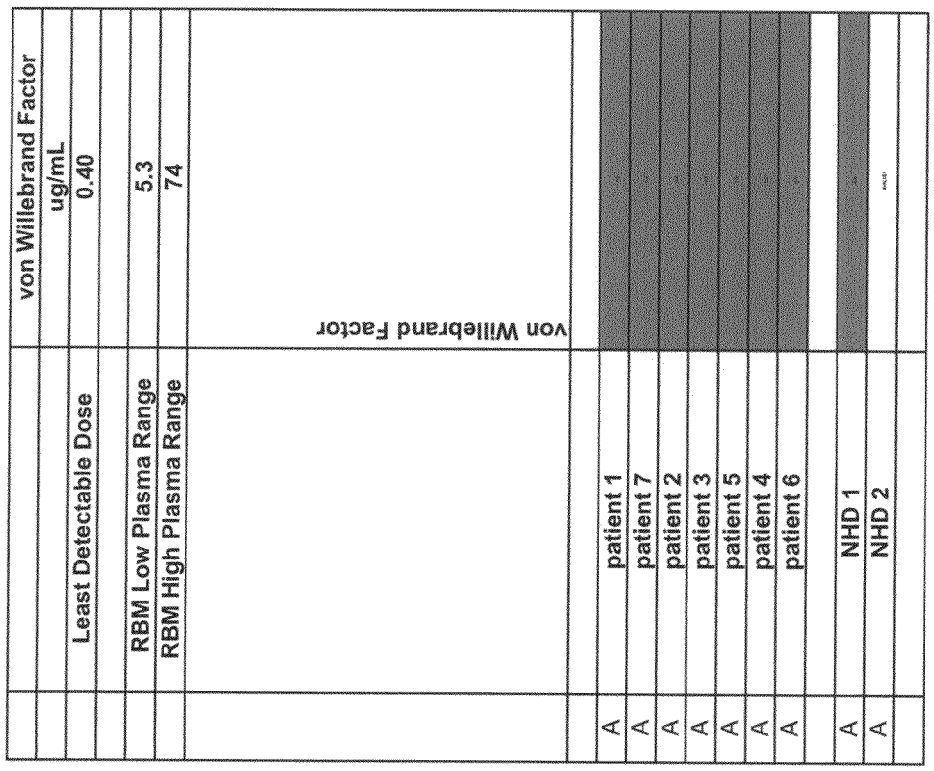
FIG. 150.5

FIG. 150.6

| | von Willebrand Factor ug/mL | |
|---|---|---|
| Least Detectable Dose | 0.40 | |
| RBM Low Plasma Range | 5.3 | |
| RBM High Plasma Range | 74 | |
| | von Willebrand Factor | |
| patient 1 | | B |
| patient 7 | | B |
| patient 2 | | B |
| patient 3 | | B |
| patient 5 | | B |
| patient 4 | | B |
| patient 6 | | B |
| NHD 1 | | B |
| NHD 2 | | B |

FIG. 150.7

| | von Willebrand Factor ug/mL |
|---|---|
| Least Detectable Dose | 0.40 |
| RBM Low Plasma Range | 5.3 |
| RBM High Plasma Range | 74 | von Willebrand Factor

| | |
|---|---|
| patient 1 | C |
| patient 7 | C |
| patient 2 | C |
| patient 3 | C |
| patient 5 | C |
| patient 4 | C |
| patient 6 | C |
| NHD 1 | C |
| NHD 2 | C |

FIG. 150.8

| | von Willebrand Factor |
|---|---|
| | ug/mL |
| Least Detectable Dose | 0.40 |
| RBM Low Plasma Range | 5.3 |
| RBM High Plasma Range | 74 |

| | von Willebrand Factor |
|---|---|
| patient 1 | D |
| patient 7 | D |
| patient 2 | D |
| patient 3 | D |
| patient 5 | D |
| patient 4 | D |
| patient 6 | D |
| NHD 1 | D |
| NHD 2 | D |

FIG. 15O.9

| | von Willebrand Factor ug/mL |
|---|---|
| Least Detectable Dose | 0.40 |
| RBM Low Plasma Range | 5.3 |
| RBM High Plasma Range | 74 | von Willebrand Factor

| | |
|---|---|
| patient 1 | E |
| patient 7 | E |
| patient 2 | E |
| patient 3 | E |
| patient 5 | E |
| patient 4 | E |
| patient 6 | E |
| NHD 1 | E |
| NHD 2 | E |

FIG. 15O.10

| | | von Willebrand Factor |
|---|---|---|
| | | ug/mL |
| Least Detectable Dose | | 0.40 |
| RBM Low Plasma Range | | 5.3 |
| RBM High Plasma Range | | 74 |
| | | von Willebrand Factor |
| patient 1 | F | |
| patient 7 | F | |
| patient 2 | F | |
| patient 3 | F | |
| patient 5 | F | |
| patient 4 | F | |
| patient 6 | F | |
| NHD 1 | F | |
| NHD 2 | F | |

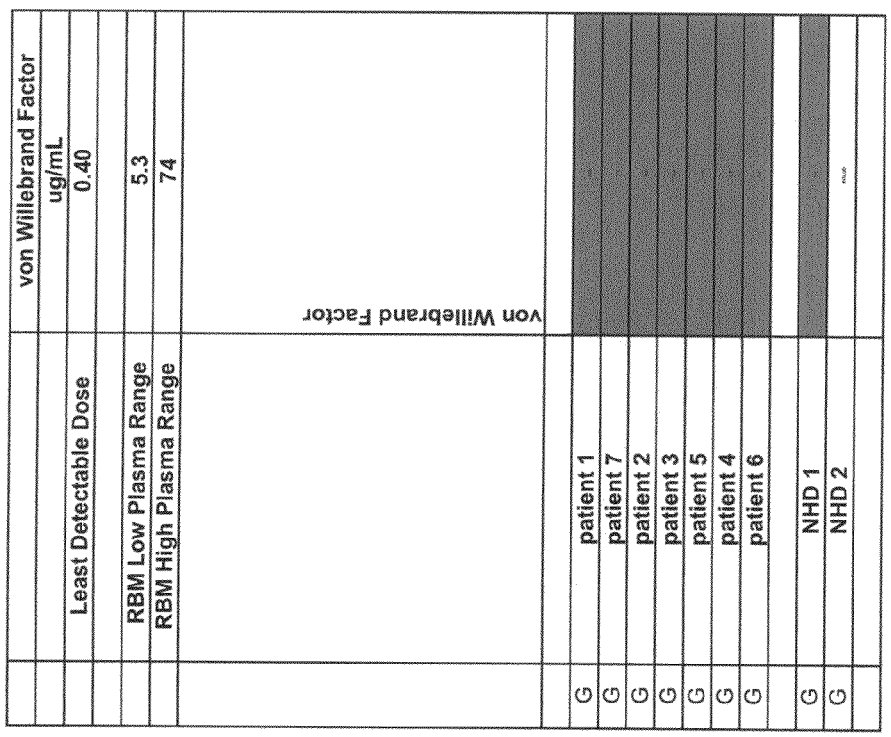
FIG. 15O.11

FIG. 15O.12

| | von Willebrand Factor ug/mL |
|---|---|
| Least Detectable Dose | 0.40 |
| RBM Low Plasma Range | 5.3 |
| RBM High Plasma Range | 74 |

| | von Willebrand Factor |
|---|---|
| patient 1 | H |
| patient 7 | H |
| patient 2 | H |
| patient 3 | H |
| patient 5 | H |
| patient 4 | H |
| patient 6 | H |
| NHD 1 | H |
| NHD 2 | H |

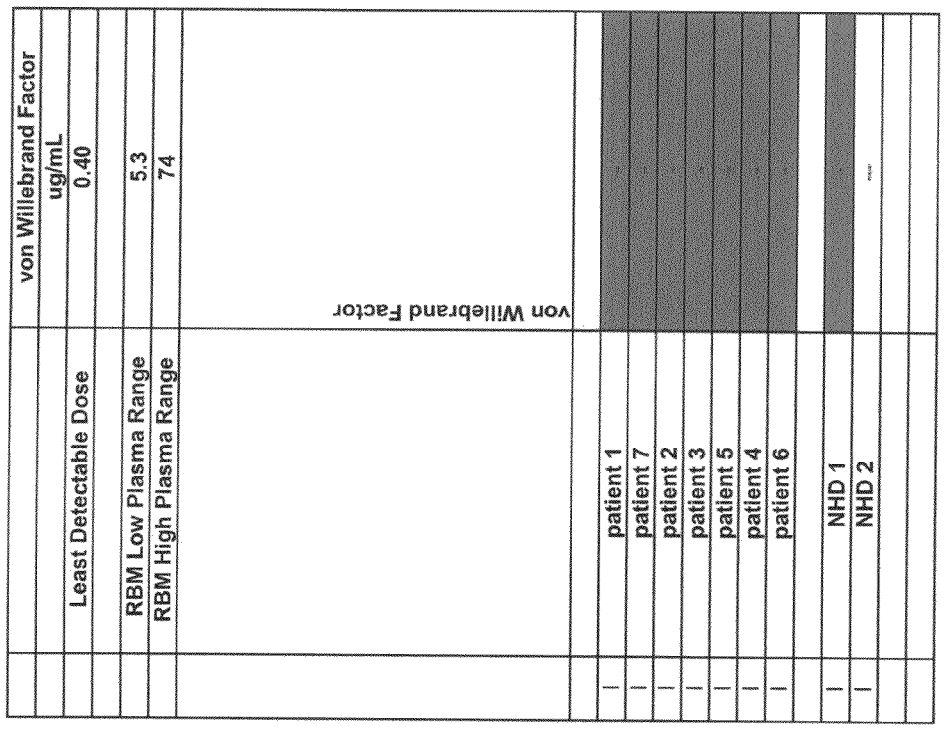
FIG. 150.13

FIG. 15O.14

| | von Willebrand Factor |
|---|---|
| | ug/mL |
| Least Detectable Dose | 0.40 |
| RBM Low Plasma Range | 5.3 |
| RBM High Plasma Range | 74 |
| Messwert > ULD | |
| SI > 1,3 | |
| SI 0,7-1,3 | |
| SI 0-0,7 | |

FIG. 16A.1

| | Alpha-1 Antitrypsin mg/mL | Adiponectin ug/mL | Alpha-2 Macroglobulin mg/mL | Alpha-Fetoprotein ng/mL | Amphiregulin pg/mL |
|---|---|---|---|---|---|
| Least Detectable Dose | 0.011 | 0.20 | 0.061 | 0.43 | 36 |
| RBM Low Plasma Range | 1.2 | 1.6 | 0.13 | | Pending |
| RBM High Plasma Range | 3.1 | 14 | 1.0 | 6.7 | Pending |
| Samples | | | | | |
| Donor_1 3. Aliquot A | 2.6 | 2.0 | 0.29 | 2.8 | 469 |
| Donor_1 3. Aliquot B | 2.8 | 2.1 | 0.30 | 2.6 | 455 |
| Donor_1 3. Aliquot C | 2.9 | 2.1 | 0.30 | 2.3 | 104 |
| Donor_1 3. Aliquot D | 3.1 | 2.1 | 0.31 | 2.8 | 431 |
| Donor_1 3. Aliquot E | 2.8 | 2.1 | 0.27 | 2.5 | 443 |
| Donor_1 3. Aliquot F | 2.6 | 2.0 | 0.66 | 2.3 | 414 |
| Donor_1 3. Aliquot G | 2.9 | 2.1 | 0.30 | 2.5 | 401 |
| Donor_1 3. Aliquot H | 2.7 | 2.0 | 0.42 | 2.7 | 36 |
| Donor_1 3. Aliquot I | 2.7 | 2.0 | 0.26 | 2.5 | 419 |
| | | | | | |
| Donor_2 3. Aliquot A | 2.2 | 4.4 | 0.28 | 2.1 | 133 |
| Donor_2 3. Aliquot B | 2.3 | 4.5 | 0.30 | 2.3 | 50 |
| Donor_2 3. Aliquot C | 2.3 | 4.5 | 0.29 | 1.4 | 36 |
| Donor_2 3. Aliquot D | 2.2 | 4.3 | 0.29 | 3.4 | 104 |
| Donor_2 3. Aliquot E | 2.3 | 4.5 | 0.28 | 2.5 | 39 |
| Donor_2 3. Aliquot F | 2.3 | 4.2 | 0.64 | 2.0 | 36 |
| Donor_2 3. Aliquot G | 2.3 | 4.3 | 0.32 | 1.8 | 597 |
| Donor_2 3. Aliquot H | 2.2 | 4.4 | 0.33 | 1.8 | 36 |
| Donor_2 3. Aliquot I | 2.1 | 4.0 | 0.29 | 1.9 | 24 |
| | | | | | |
| Donor_3 3. Aliquot A | 2.9 | 3.0 | 0.35 | 2.7 | 36 |
| Donor_3 3. Aliquot B | 3.0 | 2.7 | 0.35 | 2.6 | 36 |
| Donor_3 3. Aliquot C | 3.0 | 2.8 | 0.34 | 1.9 | 36 |
| Donor_3 3. Aliquot D | 2.8 | 2.7 | 0.34 | 3.3 | 97 |
| Donor_3 3. Aliquot E | 3.1 | 2.8 | 0.36 | 3.5 | 116 |

FIG. 16A.2

| | Alpha-1 Antitrypsin mg/mL | Adiponectin ug/mL | Alpha-2 Macroglobulin mg/mL | Alpha-Fetoprotein ng/mL | Amphiregulin pg/mL |
|---|---|---|---|---|---|
| Least Detectable Dose | 0.011 | 0.20 | 0.061 | 0.43 | 36 |
| RBM Low Plasma Range | | | | | Pending |
| RBM High Plasma Range | | | | | Pending |
| Donor_3 3. Aliquot F | 1.2 | 1.6 | 0.13 | 6.7 | 60 |
| Donor_3 3. Aliquot G | 3.1 | 14 | 1.0 | 2.5 | 97 |
| Donor_3 3. Aliquot H | 2.7 | 2.6 | 0.65 | 1.4 | 36 |
| Donor_3 3. Aliquot I | 3.1 | 2.8 | 0.35 | 1.7 | 39 |
| | 2.8 | 2.7 | 0.41 | 1.3 | |
| | 2.8 | 2.6 | 0.33 | | |
| Donor_4 3. Aliquot A | 1.7 | 5.3 | 0.40 | 2.4 | 36 |
| Donor_4 3. Aliquot B | 1.5 | 5.4 | 0.40 | 2.1 | 36 |
| Donor_4 3. Aliquot C | 1.6 | 5.2 | 0.41 | 2.0 | 39 |
| Donor_4 3. Aliquot D | 1.6 | 5.3 | 0.42 | 3.6 | 36 |
| Donor_4 3. Aliquot E | 1.5 | 5.3 | 0.38 | 2.8 | 36 |
| Donor_4 3. Aliquot F | 1.6 | 5.3 | 0.98 | 1.8 | 36 |
| Donor_4 3. Aliquot G | 1.6 | 5.5 | 0.48 | 2.1 | 76 |
| Donor_4 3. Aliquot H | 1.5 | 5.3 | 0.65 | 2.1 | 76 |
| Donor_4 3. Aliquot I | 1.5 | 5.4 | 0.41 | 1.9 | 36 |
| Donor_5 3. Aliquot A | 2.9 | 2.8 | 0.27 | 3.2 | 127 |
| Donor_5 3. Aliquot B | 2.9 | 2.6 | 0.29 | 3.2 | 178 |
| Donor_5 3. Aliquot C | 3.2 | 2.7 | 0.29 | 2.5 | 50 |
| Donor_5 3. Aliquot D | 3.2 | 2.6 | 0.28 | 4.1 | 159 |
| Donor_5 3. Aliquot E | 3.1 | 2.8 | 0.28 | 4.0 | 187 |
| Donor_5 3. Aliquot F | 2.9 | 2.6 | 0.46 | 2.3 | 36 |
| Donor_5 3. Aliquot G | 3.0 | 2.5 | 0.29 | 3.0 | 208 |
| Donor_5 3. Aliquot H | 3.0 | 2.5 | 0.33 | 3.0 | 138 |
| Donor_5 3. Aliquot I | 3.0 | 2.4 | 0.28 | 3.3 | 39 |
| Donor_6 3. Aliquot A | 2.8 | 1.2 | 0.26 | 1.5 | 36 |
| Donor_6 3. Aliquot B | 2.7 | 1.2 | 0.24 | 1.9 | 36 |

FIG. 16A.3

| | Alpha-1 Antitrypsin mg/mL | Adiponectin ug/mL | Alpha-2 Macroglobulin mg/mL | Alpha-Fetoprotein ng/mL | Amphiregulin pg/mL |
|---|---|---|---|---|---|
| Least Detectable Dose | 0.011 | 0.20 | 0.061 | 0.43 | 36 |
| RBM Low Plasma Range | 1.2 | 1.6 | 0.13 | 6.7 | Pending |
| RBM High Plasma Range | 3.1 | 14 | 1.0 | | Pending |
| Donor_6 3. Aliquot C | 2.8 | 1.2 | 0.24 | 1.8 | 36 |
| Donor_6 3. Aliquot D | 2.7 | 1.2 | 0.24 | 1.9 | 36 |
| Donor_6 3. Aliquot E | 2.6 | 1.2 | 0.25 | 2.4 | 39 |
| Donor_6 3. Aliquot F | 2.7 | 1.3 | 0.25 | 1.6 | 36 |
| Donor_6 3. Aliquot G | 2.9 | 1.2 | 0.27 | 1.8 | 599 |
| Donor_6 3. Aliquot H | 2.5 | 1.3 | 0.29 | 1.6 | 36 |
| Donor_6 3. Aliquot I | 2.5 | 1.1 | 0.26 | 1.5 | 24 |
| Donor_7 3. Aliquot A | 1.8 | 0.90 | 0.39 | 1.9 | 104 |
| Donor_7 3. Aliquot B | 1.7 | 0.92 | 0.37 | 2.5 | 36 |
| Donor_7 3. Aliquot C | 1.9 | 0.83 | 0.38 | 1.3 | 36 |
| Donor_7 3. Aliquot D | 1.7 | 0.81 | 0.36 | 2.6 | 104 |
| Donor_7 3. Aliquot E | 1.2 | 0.90 | 0.40 | 2.5 | 36 |
| Donor_7 3. Aliquot F | 1.8 | 0.90 | 0.45 | 1.5 | 36 |
| Donor_7 3. Aliquot G | 1.6 | 0.87 | 0.43 | 2.2 | 370 |
| Donor_7 3. Aliquot H | 1.7 | 0.79 | 0.51 | 1.5 | 36 |
| Donor_7 3. Aliquot I | 1.8 | 0.82 | 0.38 | 1.9 | 36 |
| Donor_8 3. Aliquot A | 0.96 | 4.3 | 0.39 | 1.7 | 36 |
| Donor_8 3. Aliquot B | 0.97 | 4.3 | 0.39 | 1.3 | 36 |
| Donor_8 3. Aliquot C | 0.96 | 4.1 | 0.40 | 0.53 | 36 |
| Donor_8 3. Aliquot D | 0.88 | 4.0 | 0.39 | 4.4 | 36 |
| Donor_8 3. Aliquot E | 0.88 | 4.0 | 0.39 | 3.5 | 127 |
| Donor_8 3. Aliquot F | 0.99 | 4.5 | 0.46 | 1.6 | 50 |
| Donor_8 3. Aliquot G | 0.92 | 4.2 | 0.48 | 1.2 | 90 |
| Donor_8 3. Aliquot H | 1.0 | 4.4 | 0.58 | 1.6 | 36 |
| Donor_8 3. Aliquot I | 0.94 | 4.2 | 0.40 | 1.2 | 36 |

FIG. 16A.4

| | Alpha-1 Antitrypsin mg/mL | Adiponectin ug/mL | Alpha-2 Macroglobulin mg/mL | Alpha-Fetoprotein ng/mL | Amphiregulin pg/mL |
|---|---|---|---|---|---|
| Least Detectable Dose | 0.011 | 0.20 | 0.061 | 0.43 | 36 |
| | | | | | |
| RBM Low Plasma Range | 1.2 | 1.6 | 0.13 | | Pending |
| RBM High Plasma Range | 3.1 | 14 | 1.0 | 6.7 | Pending |
| | | | | | |
| Donor_9 3. Aliquot A | 1.2 | 3.5 | 0.34 | 1.1 | 51 |
| Donor_9 3. Aliquot B | 1.3 | 3.5 | 0.38 | 1.8 | 51 |
| Donor_9 3. Aliquot C | 1.3 | 3.6 | 0.41 | 2.0 | 51 |
| Donor_9 3. Aliquot D | 1.2 | 3.3 | 0.38 | 4.2 | 101 |
| Donor_9 3. Aliquot E | 1.3 | 3.7 | 0.45 | 3.2 | 42 |
| Donor_9 3. Aliquot F | 1.2 | 3.8 | 0.40 | 2.1 | 36 |
| Donor_9 3. Aliquot G | 1.4 | 3.5 | 0.49 | 2.1 | 169 |
| Donor_9 3. Aliquot H | 1.2 | 3.5 | 0.54 | 2.3 | 78 |
| Donor_9 3. Aliquot I | 1.3 | 3.6 | 0.36 | 1.3 | 36 |
| | | | | | |
| EDTA Plasma | | | | | |
| donor #1 plasma | 2.9 | 2.1 | 0.25 | 2.3 | 441 |
| donor #2 plasma | 3.0 | 6.1 | 0.29 | 1.7 | 36 |
| donor #3 plasma | 4.7 | 4.2 | 0.36 | 2.9 | 36 |
| donor #4 plasma | 2.2 | 7.5 | 0.34 | 2.4 | 33 |
| donor #5 plasma | 4.4 | 3.6 | 0.25 | 3.6 | 36 |
| donor #6 plasma | 3.7 | 1.7 | 0.24 | 2.1 | 36 |
| donor #7 plasma | 2.3 | 1.3 | 0.35 | 2.8 | 78 |
| donor #8 plasma | 1.0 | 5.1 | 0.34 | 1.9 | 72 |
| donor #9 plasma | 1.9 | 4.8 | 0.37 | 2.1 | 36 |
| | | | | | |
| MW | | | | | |
| NHD plasma | 1.5 | 4.9 | 0.4 | 2.0 | 53.9 |
| Normal healthy donors | | | | | |
| | | | | | |
| MW | | | | | |
| NHD unstimuliert | 1.13 | 3.90 | 0.38 | 1.28 | 36.00 |

FIG. 16A.5

|  |  | Alpha-1 Antitrypsin mg/mL | Adiponectin ug/mL | Alpha-2 Macroglobulin mg/mL | Alpha-Fetoprotein ng/mL | Amphiregulin pg/mL |
|---|---|---|---|---|---|---|
|  | Least Detectable Dose | 0.011 | 0.20 | 0.061 | 0.43 | 36 |
|  | RBM Low Plasma Range | 1.2 | 1.6 | 0.13 |  | Pending |
|  | RBM High Plasma Range | 3.1 | 14 | 1.0 | 6.7 | Pending |
| Normal healthy donors |  |  |  |  |  |  |
|  | *Stimulations indices* | Alpha-1 Antitrypsin | Adiponectin | Alpha-2 Macroglobulin | Alpha-Fetoprotein | Amphiregulin |
| unstimuliert | Donor_1 3. Aliquot I | 2.4 | 0.5 | 0.7 | 2.0 | 11.6 |
| unstimuliert | Donor_2 3. Aliquot I | 1.8 | 1.0 | 0.8 | 1.5 | 0.7 |
| unstimuliert | Donor_3 3. Aliquot I | 2.5 | 0.7 | 0.9 | 1.0 | 1.1 |
| unstimuliert | Donor_4 3. Aliquot I | 1.4 | 1.4 | 1.1 | 1.5 | 1.0 |
| unstimuliert | Donor_5 3. Aliquot I | 2.6 | 0.6 | 0.7 | 2.6 | 1.1 |
| unstimuliert | Donor_6 3. Aliquot I | 2.2 | 0.3 | 0.7 | 1.2 | 0.7 |
| unstimuliert | Donor_7 3. Aliquot I | 1.6 | 0.2 | 1.0 | 1.5 | 1.0 |
| unstimuliert | Donor_8 3. Aliquot I | 0.8 | 1.1 | 1.0 | 1.0 | 1.0 |
| unstimuliert | Donor_9 3. Aliquot I | 1.2 | 0.9 | 1.0 | 1.0 | 1.0 |
|  | *Stimulations indices* |  |  |  |  |  |
|  | EDTA Plasma |  |  |  |  |  |
| PLASMA | donor #1 plasma | 2.0 | 0.4 | 0.7 | 1.1 | 8.2 |
| PLASMA | donor #2 plasma | 2.0 | 1.2 | 0.8 | 0.9 | 0.7 |
| PLASMA | donor #3 plasma | 3.2 | 0.9 | 1.0 | 1.5 | 0.7 |
| PLASMA | donor #4 plasma | 1.5 | 1.5 | 1.0 | 1.2 | 0.6 |
| PLASMA | donor #5 plasma | 3.0 | 0.7 | 0.7 | 1.8 | 0.7 |
| PLASMA | donor #6 plasma | 2.5 | 0.3 | 0.7 | 1.1 | 0.7 |
| PLASMA | donor #7 plasma | 1.6 | 0.3 | 1.0 | 1.4 | 1.5 |
| PLASMA | donor #8 plasma | 0.7 | 1.0 | 1.0 | 1.0 | 1.3 |

FIG. 16A.6

| | Alpha-1 Antitrypsin mg/mL | Adiponectin ug/mL | Alpha-2 Macroglobulin mg/mL | Alpha-Fetoprotein ng/mL | Amphiregulin pg/mL |
|---|---|---|---|---|---|
| Least Detectable Dose | 0.011 | 0.20 | 0.061 | 0.43 | 36 |
| RBM Low Plasma Range | 1.2 | 1.6 | 0.13 | | Pending |
| RBM High Plasma Range | 3.1 | 14 | 1.0 | 6.7 | Pending |
| PLASMA donor #9 plasma | 1.3 | 1.0 | 1.0 | 1.0 | 0.7 |

FIG. 16B.1

| | Apolipoprotein A1 | Apolipoprotein CIII | Apolipoprotein H | Beta-2 Microglobulin |
|---|---|---|---|---|
| | mg/mL | ug/mL | ug/mL | ug/mL |
| Least Detectable Dose | 0.0066 | 2.7 | 8.8 | 0.013 |
| | | | | |
| RBM Low Plasma Range | 0.19 | 28 | 131 | 1.2 |
| RBM High Plasma Range | 0.89 | 224 | 430 | 6.2 |
| Samples | | | | |
| Donor_1 3. Aliquot A | 0.10 | 52 | 138 | 17 |
| Donor_1 3. Aliquot B | 0.10 | 64 | 148 | 15 |
| Donor_1 3. Aliquot C | 0.11 | 60 | 143 | 16 |
| Donor_1 3. Aliquot D | 0.11 | 60 | 150 | 16 |
| Donor_1 3. Aliquot E | 0.11 | 53 | 141 | 16 |
| Donor_1 3. Aliquot F | 0.097 | 57 | 142 | 14 |
| Donor_1 3. Aliquot G | 0.098 | 61 | 151 | 16 |
| Donor_1 3. Aliquot H | 0.089 | 48 | 141 | 15 |
| Donor_1 3. Aliquot I | 0.11 | 60 | 150 | 16 |
| Donor_2 3. Aliquot A | 0.11 | 58 | 152 | 20 |
| Donor_2 3. Aliquot B | 0.12 | 64 | 143 | >24 |
| Donor_2 3. Aliquot C | 0.12 | 64 | 154 | 23 |
| Donor_2 3. Aliquot D | 0.098 | 48 | 142 | 19 |
| Donor_2 3. Aliquot E | 0.097 | 52 | 154 | 20 |
| Donor_2 3. Aliquot F | 0.090 | 66 | 152 | 19 |
| Donor_2 3. Aliquot G | 0.094 | 67 | 153 | 21 |
| Donor_2 3. Aliquot H | 0.095 | 61 | 148 | 21 |
| Donor_2 3. Aliquot I | 0.11 | 54 | 141 | 19 |
| Donor_3 3. Aliquot A | 0.13 | 38 | 150 | 2.6 |
| Donor_3 3. Aliquot B | 0.14 | 38 | 144 | 2.3 |
| Donor_3 3. Aliquot C | 0.13 | 41 | 153 | 2.4 |
| Donor_3 3. Aliquot D | 0.13 | 38 | 149 | 2.4 |
| Donor_3 3. Aliquot E | 0.14 | 36 | 157 | 2.5 |

FIG. 16B.2

| | Apolipoprotein A1 mg/mL | Apolipoprotein CIII ug/mL | Apolipoprotein H ug/mL | Beta-2 Microglobulin ug/mL |
|---|---|---|---|---|
| Least Detectable Dose | 0.0066 | 2.7 | 8.8 | 0.013 |
| RBM Low Plasma Range | | | | |
| RBM High Plasma Range | | | | |
| Donor_3 3. Aliquot F | 0.19 | 28 | 131 | 1.2 |
| Donor_3 3. Aliquot G | 0.89 | 224 | 430 | 6.2 |
| Donor_3 3. Aliquot H | 0.12 | 42 | 148 | 2.2 |
| Donor_3 3. Aliquot I | 0.15 | 44 | 149 | 2.3 |
| | 0.13 | 41 | 144 | 2.3 |
| | 0.14 | 42 | 150 | 2.2 |
| Donor_4 3. Aliquot A | 0.056 | 13 | 105 | 7.6 |
| Donor_4 3. Aliquot B | 0.050 | 12 | 96 | 7.2 |
| Donor_4 3. Aliquot C | 0.049 | 11 | 102 | 8.0 |
| Donor_4 3. Aliquot D | 0.044 | 13 | 102 | 7.7 |
| Donor_4 3. Aliquot E | 0.048 | 9.1 | 93 | 8.3 |
| Donor_4 3. Aliquot F | 0.054 | 15 | 93 | 8.5 |
| Donor_4 3. Aliquot G | 0.047 | 11 | 100 | 8.1 |
| Donor_4 3. Aliquot H | 0.051 | 11 | 91 | 8.2 |
| Donor_4 3. Aliquot I | 0.052 | 12 | 99 | 8.0 |
| Donor_5 3. Aliquot A | 0.12 | 70 | 253 | 12 |
| Donor_5 3. Aliquot B | 0.13 | 77 | 266 | 13 |
| Donor_5 3. Aliquot C | 0.14 | 77 | 265 | 13 |
| Donor_5 3. Aliquot D | 0.14 | 78 | 263 | 13 |
| Donor_5 3. Aliquot E | 0.14 | 71 | 257 | 15 |
| Donor_5 3. Aliquot F | 0.12 | 83 | 238 | 11 |
| Donor_5 3. Aliquot G | 0.14 | 78 | 246 | 12 |
| Donor_5 3. Aliquot H | 0.14 | 81 | 245 | 13 |
| Donor_5 3. Aliquot I | 0.13 | 75 | 250 | 11 |
| Donor_6 3. Aliquot A | 0.100 | 43 | 141 | 1.2 |
| Donor_6 3. Aliquot B | 0.10 | 42 | 148 | 1.1 |

FIG. 16B.3

| | Apolipoprotein A1 mg/mL | Apolipoprotein CIII ug/mL | Apolipoprotein H ug/mL | Beta-2 Microglobulin ug/mL |
|---|---|---|---|---|
| Least Detectable Dose | 0.0066 | 2.7 | 8.8 | 0.013 |
| RBM Low Plasma Range | 0.19 | 28 | 131 | 1.2 |
| RBM High Plasma Range | 0.89 | 224 | 430 | 6.2 |
| Donor_6_3. Aliquot C | 0.12 | 36 | 141 | 1.2 |
| Donor_6_3. Aliquot D | 0.11 | 43 | 143 | 1.2 |
| Donor_6_3. Aliquot E | 0.12 | 42 | 131 | 1.2 |
| Donor_6_3. Aliquot F | 0.094 | 45 | 143 | 1.2 |
| Donor_6_3. Aliquot G | 0.12 | 52 | 152 | 1.2 |
| Donor_6_3. Aliquot H | 0.11 | 40 | 131 | 1.1 |
| Donor_6_3. Aliquot I | 0.12 | 40 | 134 | 1.1 |
| Donor_7_3. Aliquot A | 0.14 | 50 | 180 | 2.0 |
| Donor_7_3. Aliquot B | 0.14 | 36 | 183 | 2.0 |
| Donor_7_3. Aliquot C | 0.16 | 44 | 183 | 2.1 |
| Donor_7_3. Aliquot D | 0.15 | 41 | 169 | 2.0 |
| Donor_7_3. Aliquot E | 0.12 | 33 | 138 | 2.1 |
| Donor_7_3. Aliquot F | 0.16 | 54 | 190 | 1.9 |
| Donor_7_3. Aliquot G | 0.14 | 43 | 161 | 1.9 |
| Donor_7_3. Aliquot H | 0.15 | 41 | 173 | 1.9 |
| Donor_7_3. Aliquot I | 0.13 | 42 | 173 | 1.9 |
| Donor_8_3. Aliquot A | 0.24 | 57 | 117 | 1.2 |
| Donor_8_3. Aliquot B | 0.28 | 72 | 117 | 1.2 |
| Donor_8_3. Aliquot C | 0.28 | 75 | 119 | 1.2 |
| Donor_8_3. Aliquot D | 0.26 | 55 | 111 | 1.2 |
| Donor_8_3. Aliquot E | 0.24 | 61 | 113 | 1.2 |
| Donor_8_3. Aliquot F | 0.29 | 69 | 121 | 1.3 |
| Donor_8_3. Aliquot G | 0.29 | 58 | 111 | 1.2 |
| Donor_8_3. Aliquot H | 0.25 | 59 | 127 | 1.2 |
| Donor_8_3. Aliquot I | 0.25 | 53 | 122 | 1.2 |

FIG. 16B.4

| | Apolipoprotein A1 mg/mL | Apolipoprotein CIII ug/mL | Apolipoprotein H ug/mL | Beta-2 Microglobulin ug/mL |
|---|---|---|---|---|
| Least Detectable Dose | 0.0066 | 2.7 | 8.8 | 0.013 |
| RBM Low Plasma Range | 0.19 | 28 | 131 | 1.2 |
| RBM High Plasma Range | 0.89 | 224 | 430 | 6.2 |
| Donor_9 3. Aliquot A | 0.21 | 39 | 101 | 0.83 |
| Donor_9 3. Aliquot B | 0.22 | 43 | 104 | 0.79 |
| Donor_9 3. Aliquot C | 0.21 | 33 | 96 | 0.93 |
| Donor_9 3. Aliquot D | 0.18 | 34 | 99 | 0.87 |
| Donor_9 3. Aliquot E | 0.20 | 36 | 105 | 0.88 |
| Donor_9 3. Aliquot F | 0.23 | 39 | 103 | 0.90 |
| Donor_9 3. Aliquot G | 0.22 | 42 | 113 | 0.86 |
| Donor_9 3. Aliquot H | 0.19 | 37 | 97 | 0.83 |
| Donor_9 3. Aliquot I | 0.21 | 33 | 97 | 0.82 |
| EDTA Plasma | | | | |
| donor #1 plasma | 0.069 | 34 | 127 | 11 |
| donor #2 plasma | 0.11 | 65 | 166 | 19 |
| donor #3 plasma | 0.14 | 47 | 193 | 2.5 |
| donor #4 plasma | 0.047 | 14 | 106 | 9.1 |
| donor #5 plasma | 0.12 | 91 | 316 | 14 |
| donor #6 plasma | 0.100 | 34 | 163 | 1.1 |
| donor #7 plasma | 0.17 | 52 | 214 | 2.3 |
| donor #8 plasma | 0.25 | 46 | 113 | 1.1 |
| donor #9 plasma | 0.30 | 39 | 147 | 0.88 |
| MW NHD plasma Normal healthy donors | 0.3 | 42.3 | 130.0 | 1.0 |
| MW NHD unstimuliert | 0.23 | 42.90 | 109.60 | 1.01 |

FIG. 16B.5

| | | Apolipoprotein A1 | Apolipoprotein CIII | Apolipoprotein H | Beta-2 Microglobulin |
|---|---|---|---|---|---|
| | | mg/mL | ug/mL | ug/mL | ug/mL |
| | Least Detectable Dose | 0.0066 | 2.7 | 8.8 | 0.013 |
| | | | | | |
| | RBM Low Plasma Range | 0.19 | 28 | 131 | 1.2 |
| | RBM High Plasma Range | 0.89 | 224 | 430 | 6.2 |
| Normal healthy donors | | | | | |
| | | | | | |
| | *Stimulations indices* | Apolipoprotein A1 | Apolipoprotein CIII | Apolipoprotein H | Beta-2 Microglobulin |
| unstimuliert | Donor_1 3. Aliquot I | 0.5 | 1.4 | 1.4 | 15.7 |
| unstimuliert | Donor_2 3. Aliquot I | 0.5 | 1.3 | 1.3 | 18.6 |
| unstimuliert | Donor_3 3. Aliquot I | 0.6 | 1.0 | 1.4 | 2.2 |
| unstimuliert | Donor_4 3. Aliquot I | 0.2 | 0.3 | 0.9 | 7.9 |
| unstimuliert | Donor_5 3. Aliquot I | 0.5 | 1.7 | 2.3 | 11.1 |
| unstimuliert | Donor_6 3. Aliquot I | 0.5 | 0.9 | 1.2 | 1.1 |
| unstimuliert | Donor_7 3. Aliquot I | 0.6 | 1.0 | 1.6 | 1.8 |
| unstimuliert | Donor_8 3. Aliquot I | 1.1 | 1.2 | 1.1 | 1.2 |
| unstimuliert | Donor_9 3. Aliquot I | 0.9 | 0.8 | 0.9 | 0.8 |
| | | | | | |
| | *Stimulations indices* | | | | |
| | EDTA Plasma | | | | |
| PLASMA | donor #1 plasma | 0.3 | 0.8 | 1.0 | 11.3 |
| PLASMA | donor #2 plasma | 0.4 | 1.5 | 1.3 | 19.1 |
| PLASMA | donor #3 plasma | 0.5 | 1.1 | 1.5 | 2.5 |
| PLASMA | donor #4 plasma | 0.2 | 0.3 | 0.8 | 9.2 |
| PLASMA | donor #5 plasma | 0.4 | 2.2 | 2.4 | 14.5 |
| PLASMA | donor #6 plasma | 0.4 | 0.8 | 1.3 | 1.1 |
| PLASMA | donor #7 plasma | 0.6 | 1.2 | 1.6 | 2.3 |
| PLASMA | donor #8 plasma | 0.9 | 1.1 | 0.9 | 1.1 |

FIG. 16B.6

| | Apolipoprotein A1 mg/mL | Apolipoprotein CIII ug/mL | Apolipoprotein H ug/mL | Beta-2 Microglobulin ug/mL |
|---|---|---|---|---|
| Least Detectable Dose | 0.0066 | 2.7 | 8.8 | 0.013 |
| RBM Low Plasma Range | 0.19 | 28 | 131 | 1.2 |
| RBM High Plasma Range | 0.89 | 224 | 430 | 6.2 |
| PLASMA donor #9 plasma | 1.1 | 0.9 | 1.1 | 0.9 |

FIG. 16C.1

| | Brain-Derived Neurotrophic Factor ng/mL | Complement 3 mg/mL | Cancer Antigen 125 U/mL | Cancer Antigen 19-9 U/mL | Calcitonin pg/mL |
|---|---|---|---|---|---|
| Least Detectable Dose | 0.029 | 0.0053 | 4.2 | 0.25 | 6.0 |
| | | | | | |
| RBM Low Plasma Range | 0.32 | 0.76 | | | |
| RBM High Plasma Range | 16 | 2.1 | 12 | 9.2 | 12 |
| | | | | | |
| Samples | | | | | |
| Donor_1 3. Aliquot A | 2.4 | 0.73 | 132 | 28 | 36 |
| Donor_1 3. Aliquot B | 3.3 | 0.71 | 123 | 28 | 32 |
| Donor_1 3. Aliquot C | 1.6 | 0.71 | 141 | 13 | 34 |
| Donor_1 3. Aliquot D | 2.6 | 0.71 | 157 | 28 | 37 |
| Donor_1 3. Aliquot E | 2.3 | 0.69 | 135 | 28 | 36 |
| Donor_1 3. Aliquot F | 1.3 | 1.5 | 128 | 24 | 31 |
| Donor_1 3. Aliquot G | 0.048 | 0.77 | 140 | 32 | 32 |
| Donor_1 3. Aliquot H | 3.4 | 1.2 | 143 | 12 | 31 |
| Donor_1 3. Aliquot I | 2.8 | 0.71 | 125 | 28 | 33 |
| | | | | | |
| Donor_2 3. Aliquot A | 3.4 | 0.92 | 121 | 476 | 29 |
| Donor_2 3. Aliquot B | 4.6 | 0.93 | 125 | 510 | 31 |
| Donor_2 3. Aliquot C | 1.3 | 0.89 | 119 | 408 | 24 |
| Donor_2 3. Aliquot D | 2.5 | 0.92 | 197 | 468 | 33 |
| Donor_2 3. Aliquot E | 2.3 | 0.94 | 158 | 488 | 31 |
| Donor_2 3. Aliquot F | 1.6 | 2.3 | 123 | 413 | 30 |
| Donor_2 3. Aliquot G | 0.49 | 0.98 | 138 | 495 | 20 |
| Donor_2 3. Aliquot H | 2.3 | 1.3 | 106 | 459 | 29 |
| Donor_2 3. Aliquot I | 1.8 | 0.90 | 102 | 447 | 26 |
| | | | | | |
| Donor_3 3. Aliquot A | 3.0 | 0.68 | 35 | 3.3 | 6 |
| Donor_3 3. Aliquot B | 4.5 | 0.70 | 33 | 3.6 | 5.1 |
| Donor_3 3. Aliquot C | 2.9 | 0.73 | 35 | 3.6 | 6 |
| Donor_3 3. Aliquot D | 3.4 | 0.73 | 87 | 3.3 | 6 |
| Donor_3 3. Aliquot E | 3.8 | 0.77 | 74 | 3.6 | 7.3 |

FIG. 16C.2

| | Brain-Derived Neurotrophic Factor ng/mL | Complement 3 mg/mL | Cancer Antigen 125 U/mL | Cancer Antigen 19-9 U/mL | Calcitonin pg/mL |
|---|---|---|---|---|---|
| Least Detectable Dose | 0.32 | 0.0053 | 4.2 | 0.25 | 6.0 |
| RBM Low Plasma Range | | | | | |
| RBM High Plasma Range | 16 | 0.76 | | | |
| Donor_3 3. Aliquot F | 1.6 | 2.1 | 12 | 9.2 | 12 |
| Donor_3 3. Aliquot G | 0.047 | 1.2 | 39 | 4.1 | 6 |
| Donor_3 3. Aliquot H | 2.3 | 0.72 | 29 | 4.6 | 6 |
| Donor_3 3. Aliquot I | 2.2 | 1.1 | 27 | 3.2 | 6 |
| | | 0.74 | 31 | 2.8 | 6 |
| Donor_4 3. Aliquot A | 2.0 | 0.45 | 512 | 15 | 18 |
| Donor_4 3. Aliquot B | 2.8 | 0.41 | 495 | 16 | 20 |
| Donor_4 3. Aliquot C | 0.49 | 0.45 | 462 | 15 | 15 |
| Donor_4 3. Aliquot D | 1.6 | 0.43 | 542 | 16 | 19 |
| Donor_4 3. Aliquot E | 1.0 | 0.44 | 520 | 20 | 16 |
| Donor_4 3. Aliquot F | 0.88 | 0.80 | 465 | 16 | 15 |
| Donor_4 3. Aliquot G | 0.049 | 0.43 | 462 | 17 | 10 |
| Donor_4 3. Aliquot H | 0.53 | 0.69 | 509 | 15 | 17 |
| Donor_4 3. Aliquot I | 1.2 | 0.43 | 494 | 15 | 17 |
| Donor_5 3. Aliquot A | 5.8 | 0.72 | 21 | 8.8 | 105 |
| Donor_5 3. Aliquot B | 4.5 | 0.76 | 21 | 9.2 | 97 |
| Donor_5 3. Aliquot C | 2.3 | 0.77 | 21 | 9.9 | 74 |
| Donor_5 3. Aliquot D | 2.9 | 0.78 | 87 | 10 | 92 |
| Donor_5 3. Aliquot E | 4.5 | 0.73 | 74 | 10 | 90 |
| Donor_5 3. Aliquot F | 2.3 | 1.2 | 12 | 7.1 | 86 |
| Donor_5 3. Aliquot G | 0.16 | 0.80 | 20 | 8.6 | 67 |
| Donor_5 3. Aliquot H | 4.8 | 1.1 | 16 | 8.9 | 101 |
| Donor_5 3. Aliquot I | 3.1 | 0.72 | 17 | 8.0 | 94 |
| Donor_6 3. Aliquot A | 4.4 | 0.73 | 29 | 3.7 | 6 |
| Donor_6 3. Aliquot B | 3.4 | 0.77 | 42 | 2.6 | 6 |

FIG. 16C.3

| | Brain-Derived Neurotrophic Factor ng/mL | Complement 3 mg/mL | Cancer Antigen 125 U/mL | Cancer Antigen 19-9 U/mL | Calcitonin pg/mL |
|---|---|---|---|---|---|
| Least Detectable Dose | 0.029 | 0.0053 | 4.2 | 0.25 | 6.0 |
| RBM Low Plasma Range | 0.32 | 0.76 | | | |
| RBM High Plasma Range | 16 | 2.1 | 12 | 9.2 | 12 |
| Donor_6_3. Aliquot C | 1.1 | 0.72 | 24 | 4.4 | 6 |
| Donor_6_3. Aliquot D | 3.9 | 0.75 | 82 | 3.9 | 6 |
| Donor_6_3. Aliquot E | 2.1 | 0.67 | 85 | 3.5 | 6 |
| Donor_6_3. Aliquot F | 1.9 | 0.71 | 27 | 2.9 | 6 |
| Donor_6_3. Aliquot G | 0.064 | 0.78 | 28 | 5.2 | 6 |
| Donor_6_3. Aliquot H | 3.1 | 1.1 | 23 | 3.7 | 6 |
| Donor_6_3. Aliquot I | 1.7 | 0.68 | 29 | 3.0 | 6 |
| Donor_7_3. Aliquot A | 2.8 | 0.67 | 53 | 5.3 | 1.5 |
| Donor_7_3. Aliquot B | 3.1 | 0.68 | 48 | 5.1 | 6 |
| Donor_7_3. Aliquot C | 2.2 | 0.73 | 39 | 5.1 | 6 |
| Donor_7_3. Aliquot D | 2.9 | 0.66 | 91 | 4.8 | 6 |
| Donor_7_3. Aliquot E | 2.3 | 0.51 | 53 | 5.2 | 6 |
| Donor_7_3. Aliquot F | 1.2 | 0.72 | 40 | 4.7 | 6 |
| Donor_7_3. Aliquot G | 0.043 | 0.74 | 38 | 7.8 | 6 |
| Donor_7_3. Aliquot H | 1.6 | 1.1 | 34 | 5.2 | 6 |
| Donor_7_3. Aliquot I | 1.6 | 0.67 | 39 | 3.7 | 3.3 |
| Donor_8_3. Aliquot A | 3.3 | 0.45 | 5.6 | 4.9 | 6 |
| Donor_8_3. Aliquot B | 5.3 | 0.49 | 9.0 | 3.9 | 6 |
| Donor_8_3. Aliquot C | 3.2 | 0.43 | 4.4 | 3.9 | 6 |
| Donor_8_3. Aliquot D | 4.5 | 0.44 | 164 | 5.5 | 4.6 |
| Donor_8_3. Aliquot E | 6.0 | 0.43 | 136 | 5.1 | 6.5 |
| Donor_8_3. Aliquot F | 2.3 | 0.51 | 16 | 4.5 | 6 |
| Donor_8_3. Aliquot G | 0.060 | 0.44 | 9.0 | 5.2 | 6 |
| Donor_8_3. Aliquot H | 6.3 | 0.72 | 13 | 4.0 | 6 |
| Donor_8_3. Aliquot I | 6.1 | 0.46 | 15 | 3.6 | 6 |

FIG. 16C.4

|  | Brain-Derived Neurotrophic Factor ng/mL | Complement 3 mg/mL | Cancer Antigen 125 U/mL | Cancer Antigen 19-9 U/mL | Calcitonin pg/mL |
|---|---|---|---|---|---|
| Least Detectable Dose | 0.029 | 0.0053 | 4.2 | 0.25 | 6.0 |
| RBM Low Plasma Range | 0.32 | 0.76 | | | |
| RBM High Plasma Range | 16 | 2.1 | 12 | 9.2 | 12 |
| Donor_9_3. Aliquot A | 2.5 | 0.39 | 14 | 3.0 | 6 |
| Donor_9_3. Aliquot B | 3.5 | 0.39 | 11 | 3.3 | 6 |
| Donor_9_3. Aliquot C | 1.2 | 0.39 | 21 | 3.3 | 6 |
| Donor_9_3. Aliquot D | 3.7 | 0.37 | 140 | 6.0 | 3.9 |
| Donor_9_3. Aliquot E | 2.6 | 0.40 | 104 | 3.7 | 3.2 |
| Donor_9_3. Aliquot F | 1.9 | 0.39 | 12 | 2.6 | 6 |
| Donor_9_3. Aliquot G | 0.21 | 0.41 | 14 | 3.1 | 0.91 |
| Donor_9_3. Aliquot H | 4.3 | 0.64 | 4.9 | 3.1 | 6 |
| Donor_9_3. Aliquot I | 3.5 | 0.39 | 8.3 | 2.6 | 6 |
| EDTA Plasma | | | | | |
| donor #1 plasma | 1.2 | 0.59 | 60 | 7.6 | 40 |
| donor #2 plasma | 0.40 | 0.98 | 63 | 241 | 51 |
| donor #3 plasma | 0.89 | 0.90 | 28 | 2.1 | 8.9 |
| donor #4 plasma | 0.35 | 0.47 | 431 | 10 | 36 |
| donor #5 plasma | 3.6 | 0.88 | 18 | 4.2 | 164 |
| donor #6 plasma | 1.5 | 0.87 | 18 | 1.6 | 3.7 |
| donor #7 plasma | 1.4 | 0.80 | 30 | 6.0 | 5.0 |
| donor #8 plasma | 3.1 | 0.42 | 16 | 7.5 | 6 |
| donor #9 plasma | 0.21 | 0.55 | 4.2 | 6.3 | 6 |
| MW | | | | | |
| NHD plasma Normal healthy donors | 1.7 | 0.5 | 10.3 | 6.9 | 6.0 |
| MW | | | | | |
| NHD unstimuliert | 4.80 | 0.43 | 11.50 | 3.10 | 6.00 |

FIG. 16C.5

| | | Brain-Derived Neurotrophic Factor | Complement 3 | Cancer Antigen 125 | Cancer Antigen 19-9 | Calcitonin |
|---|---|---|---|---|---|---|
| | Least Detectable Dose | ng/mL | mg/mL | U/mL | U/mL | pg/mL |
| | | 0.029 | 0.0053 | 4.2 | 0.25 | 6.0 |
| | RBM Low Plasma Range | 0.32 | 0.76 | | | |
| | RBM High Plasma Range | 16 | 2.1 | 12 | 9.2 | 12 |
| Normal healthy donors | | | | | | |
| | | Brain-Derived Neurotrophic Factor | Complement 3 | Cancer Antigen 125 | Cancer Antigen 19-9 | Calcitonin |
| *Stimulations indices* | | | | | | |
| unstimuliert | Donor_1 3. Aliquot I | 0.6 | 1.7 | 10.9 | 8.9 | 5.5 |
| unstimuliert | Donor_2 3. Aliquot I | 0.4 | 2.1 | 8.9 | 144.2 | 4.4 |
| unstimuliert | Donor_3 3. Aliquot I | 0.5 | 1.7 | 2.7 | 0.9 | 1.0 |
| unstimuliert | Donor_4 3. Aliquot I | 0.3 | 1.0 | 43.0 | 4.9 | 2.8 |
| unstimuliert | Donor_5 3. Aliquot I | 0.6 | 1.7 | 1.5 | 2.6 | 15.7 |
| unstimuliert | Donor_6 3. Aliquot I | 0.4 | 1.6 | 2.5 | 1.0 | 1.0 |
| unstimuliert | Donor_7 3. Aliquot I | 0.3 | 1.6 | 3.3 | 1.2 | 0.6 |
| unstimuliert | Donor_8 3. Aliquot I | 1.3 | 1.1 | 1.3 | 1.2 | 1.0 |
| unstimuliert | Donor_9 3. Aliquot I | 0.7 | 0.9 | 0.7 | 0.8 | 1.0 |
| *Stimulations indices* | EDTA Plasma | | | | | |
| PLASMA | donor #1 plasma | 0.7 | 1.2 | 5.9 | 1.1 | 6.7 |
| PLASMA | donor #2 plasma | 0.2 | 2.0 | 6.2 | 35.0 | 8.5 |
| PLASMA | donor #3 plasma | 0.5 | 1.9 | 2.7 | 0.3 | 1.5 |
| PLASMA | donor #4 plasma | 0.2 | 1.0 | 42.0 | 1.5 | 6.0 |
| PLASMA | donor #5 plasma | 2.1 | 1.8 | 1.7 | 0.6 | 27.3 |
| PLASMA | donor #6 plasma | 0.9 | 1.8 | 1.8 | 0.2 | 0.6 |
| PLASMA | donor #7 plasma | 0.8 | 1.6 | 2.9 | 0.9 | 0.8 |
| PLASMA | donor #8 plasma | 1.9 | 0.9 | 1.6 | 1.1 | 1.0 |

FIG. 16C.6

| | Brain-Derived Neurotrophic Factor ng/mL | Complement 3 mg/mL | Cancer Antigen 125 U/mL | Cancer Antigen 19-9 U/mL | Calcitonin pg/mL |
|---|---|---|---|---|---|
| Least Detectable Dose | 0.029 | 0.0053 | 4.2 | 0.25 | 6.0 |
| RBM Low Plasma Range | 0.32 | 0.76 | | | |
| RBM High Plasma Range | 16 | 2.1 | 12 | 9.2 | 12 |
| PLASMA donor #9 plasma | 0.1 | 1.1 | 0.4 | 0.9 | 1.0 |

FIG. 16D.1

| | CD40 ng/mL | CD40 Ligand ng/mL | Carcinoembryonic Antigen ng/mL | Creatine Kinase-MB ng/mL | C Reactive Protein ug/mL | EGF pg/mL | ENA-78 ng/mL |
|---|---|---|---|---|---|---|---|
| Least Detectable Dose | 0.021 | 0.020 | 0.84 | 0.42 | 0.0015 | 7.4 | 0.076 |
| | | | | | | | |
| RBM Low Plasma Range | 0.17 | | | | 0.25 | | 0.069 |
| RBM High Plasma Range | 1.5 | 1.1 | 4.8 | 1.1 | 50 | 505 | 5.3 |
| | | | | | | | |
| Samples | | | | | | | |
| Donor_1 3. Aliquot A | 11 | 0.66 | 1.5 | 0.16 | >47 | 128 | 7.9 |
| Donor_1 3. Aliquot B | 9.2 | 0.82 | 1.4 | 0.11 | >47 | 131 | 8.2 |
| Donor_1 3. Aliquot C | 10 | 0.82 | 1.4 | 0.12 | >47 | 119 | 1.7 |
| Donor_1 3. Aliquot D | 9.0 | 0.60 | 1.7 | 0.18 | >47 | 109 | 10 |
| Donor_1 3. Aliquot E | 8.7 | 0.47 | 1.6 | 0.11 | >47 | 101 | 5.9 |
| Donor_1 3. Aliquot F | 9.3 | 0.39 | 1.2 | 0.15 | >47 | 101 | 1.2 |
| Donor_1 3. Aliquot G | 12 | 0.18 | 1.5 | 0.11 | >47 | 693 | 5.3 |
| Donor_1 3. Aliquot H | 11 | 0.55 | 1.9 | 0.11 | >47 | 197 | 1.6 |
| Donor_1 3. Aliquot I | 10 | 0.84 | 1.4 | 0.12 | >47 | 114 | 1.8 |
| | | | | | | | |
| Donor_2 3. Aliquot A | 16 | 0.70 | 4.6 | 0.40 | >47 | 92 | 45 |
| Donor_2 3. Aliquot B | 18 | 0.65 | 4.9 | 0.44 | >47 | 145 | 45 |
| Donor_2 3. Aliquot C | 16 | 0.61 | 4.7 | 0.32 | >47 | 83 | 0.66 |
| Donor_2 3. Aliquot D | 16 | 0.47 | 6.2 | 0.60 | >47 | 61 | 51 |
| Donor_2 3. Aliquot E | 19 | 0.50 | 5.0 | 0.43 | >47 | 62 | 55 |
| Donor_2 3. Aliquot F | 16 | 0.42 | 4.0 | 0.50 | >47 | 66 | 0.74 |
| Donor_2 3. Aliquot G | 21 | 0.28 | 5.4 | 0.49 | >47 | 792 | 214 |
| Donor_2 3. Aliquot H | 18 | 0.44 | 4.8 | 0.40 | >47 | 85 | 1.4 |
| Donor_2 3. Aliquot I | 17 | 0.47 | 4.5 | 0.21 | >47 | 59 | 1.2 |
| | | | | | | | |
| Donor_3 3. Aliquot A | 1.4 | 0.54 | 2.8 | 0.59 | 22 | 40 | 20 |
| Donor_3 3. Aliquot B | 1.7 | 0.43 | 3.3 | 0.67 | 24 | 64 | 13 |
| Donor_3 3. Aliquot C | 1.4 | 0.50 | 3.3 | 0.54 | 25 | 38 | 0.96 |
| Donor_3 3. Aliquot D | 1.5 | 0.52 | 3.6 | 0.53 | 25 | 47 | 35 |
| Donor_3 3. Aliquot E | 1.5 | 0.68 | 4.3 | 0.61 | 24 | 60 | 31 |

FIG. 16D.2

| | CD40 ng/mL | CD40 Ligand ng/mL | Carcinoembryonic Antigen ng/mL | Creatine Kinase-MB ng/mL | C Reactive Protein ug/mL | EGF pg/mL | ENA-78 ng/mL |
|---|---|---|---|---|---|---|---|
| Least Detectable Dose | 0.021 | 0.020 | 0.84 | 0.42 | 0.0015 | 7.4 | 0.076 |
| RBM Low Plasma Range | 0.17 | | | | 0.25 | | 0.069 |
| RBM High Plasma Range | 1.5 | 1.1 | 4.8 | 1.1 | 50 | 505 | 5.3 |
| Donor_3_3. Aliquot F | 1.4 | 0.36 | 3.2 | 0.24 | 26 | 39 | 0.65 |
| Donor_3_3. Aliquot G | 3.4 | 0.29 | 2.7 | 0.29 | 26 | 535 | 1.6 |
| Donor_3_3. Aliquot H | 1.4 | 0.50 | 2.4 | 0.37 | 23 | 39 | 0.47 |
| Donor_3_3. Aliquot I | 1.3 | 0.42 | 2.4 | 0.39 | 24 | 33 | 0.55 |
| Donor_4_3. Aliquot A | 4.3 | 0.20 | 3.4 | 0.078 | >47 | 25 | 0.77 |
| Donor_4_3. Aliquot B | 4.7 | 0.18 | 3.8 | 0.066 | >47 | 35 | 1.4 |
| Donor_4_3. Aliquot C | 4.3 | 0.088 | 3.6 | 0.064 | >47 | 12 | 0.18 |
| Donor_4_3. Aliquot D | 4.0 | 0.13 | 4.4 | 0.17 | >47 | 21 | 23 |
| Donor_4_3. Aliquot E | 4.3 | 0.13 | 3.7 | 0.066 | >47 | 15 | 21 |
| Donor_4_3. Aliquot F | 4.0 | 0.083 | 3.3 | 0.093 | >47 | 9.8 | 0.59 |
| Donor_4_3. Aliquot G | 4.9 | 0.063 | 3.3 | 0.057 | >47 | 256 | 1.2 |
| Donor_4_3. Aliquot H | 4.0 | 0.081 | 3.4 | 0.045 | >47 | 11 | 0.14 |
| Donor_4_3. Aliquot I | 3.9 | 0.092 | 3.2 | 0.076 | >47 | 19 | 0.20 |
| Donor_5_3. Aliquot A | 18 | 0.51 | 1.7 | 0.18 | >47 | 87 | 21 |
| Donor_5_3. Aliquot B | 18 | 0.34 | 2.4 | 0.18 | >47 | 90 | 23 |
| Donor_5_3. Aliquot C | 19 | 0.32 | 1.6 | 0.11 | >47 | 71 | 0.25 |
| Donor_5_3. Aliquot D | 20 | 0.40 | 3.1 | 0.24 | >47 | 60 | 31 |
| Donor_5_3. Aliquot E | 21 | 0.47 | 2.9 | 0.28 | >47 | 70 | 33 |
| Donor_5_3. Aliquot F | 18 | 0.29 | 1.4 | 0.086 | >47 | 59 | 0.71 |
| Donor_5_3. Aliquot G | 19 | 0.24 | 1.7 | 0.12 | >47 | 647 | 7.0 |
| Donor_5_3. Aliquot H | 18 | 0.32 | 4.2 | 0.17 | >47 | 83 | 0.41 |
| Donor_5_3. Aliquot I | 17 | 0.27 | 3.6 | 0.11 | >47 | 53 | 0.22 |
| Donor_6_3. Aliquot A | 0.98 | 0.88 | 0.82 | 0.25 | >47 | 195 | 4.4 |
| Donor_6_3. Aliquot B | 1.1 | 0.77 | 0.58 | 0.24 | >47 | 213 | 6.0 |

FIG. 16D.3

|  | CD40 ng/mL | CD40 Ligand ng/mL | Carcinoembryonic Antigen ng/mL | Creatine Kinase-MB ng/mL | C Reactive Protein ug/mL | EGF pg/mL | ENA-78 ng/mL |
|---|---|---|---|---|---|---|---|
| Least Detectable Dose | 0.021 | 0.020 | 0.84 | 0.42 | 0.0015 | 7.4 | 0.076 |
| RBM Low Plasma Range |  |  |  |  | 0.25 |  | 0.069 |
| RBM High Plasma Range | 0.17 |  |  |  | 50 |  | 5.3 |
| Donor_6 3. Aliquot C | 1.5 | 1.1 | 4.8 | 1.1 | >47 | 505 | 0.54 |
| Donor_6 3. Aliquot D | 1.0 | 0.61 | 1.1 | 0.26 | >47 | 160 | 10 |
| Donor_6 3. Aliquot E | 1.0 | 0.95 | 1.3 | 0.26 | >47 | 152 | 12 |
| Donor_6 3. Aliquot F | 0.96 | 0.60 | 1.6 | 0.30 | >47 | 110 | 0.68 |
| Donor_6 3. Aliquot G | 0.90 | 0.47 | 0.63 | 0.19 | >47 | 132 | 4.3 |
| Donor_6 3. Aliquot H | 3.8 | 0.30 | 0.44 | 0.30 | >47 | 2020 | 0.43 |
| Donor_6 3. Aliquot I | 0.81 | 0.45 | 0.91 | 0.21 | >47 | 139 | 0.51 |
|  | 0.73 | 0.45 | 0.96 |  |  | 101 |  |
| Donor_7 3. Aliquot A | 0.93 | 0.25 | 3.6 | 1.2 | 29 | 30 | 33 |
| Donor_7 3. Aliquot B | 0.89 | 0.21 | 2.8 | 1.5 | 33 | 45 | 17 |
| Donor_7 3. Aliquot C | 0.77 | 0.40 | 3.0 | 0.99 | 30 | 37 | 0.56 |
| Donor_7 3. Aliquot D | 0.73 | 0.30 | 3.9 | 1.1 | 27 | 28 | 26 |
| Donor_7 3. Aliquot E | 0.62 | 0.20 | 3.2 | 1.2 | 24 | 22 | 20 |
| Donor_7 3. Aliquot F | 0.61 | 0.11 | 2.9 | 1.1 | 27 | 11 | 0.25 |
| Donor_7 3. Aliquot G | 1.8 | 0.071 | 3.0 | 1.2 | 27 | 403 | 3.6 |
| Donor_7 3. Aliquot H | 0.71 | 0.18 | 4.1 | 1.0 | 28 | 20 | 0.23 |
| Donor_7 3. Aliquot I | 0.50 | 0.15 | 2.7 | 0.93 | 29 | 15 | 0.19 |
| Donor_8 3. Aliquot A | 0.57 | 0.32 | 1.1 | 0.15 | 0.096 | 93 | 1.1 |
| Donor_8 3. Aliquot B | 0.60 | 0.42 | 0.82 | 0.19 | 0.14 | 110 | 1.3 |
| Donor_8 3. Aliquot C | 0.63 | 0.51 | 0.75 | 0.15 | 0.13 | 114 | 0.81 |
| Donor_8 3. Aliquot D | 0.72 | 0.33 | 3.5 | 0.36 | 0.14 | 105 | 1.4 |
| Donor_8 3. Aliquot E | 0.63 | 0.49 | 3.9 | 0.39 | 0.12 | 132 | 2.4 |
| Donor_8 3. Aliquot F | 0.49 | 0.15 | 1.4 | 0.24 | 0.16 | 63 | 0.37 |
| Donor_8 3. Aliquot G | 1.8 | 0.13 | 0.94 | 0.20 | 0.13 | 1050 | 4.5 |
| Donor_8 3. Aliquot H | 0.60 | 0.49 | 1.9 | 0.24 | 0.15 | 143 | 0.81 |
| Donor_8 3. Aliquot I | 0.65 | 0.45 | 1.6 | 0.14 | 0.13 | 125 | 0.87 |

FIG. 16D.4

| | CD40 ng/mL | CD40 Ligand ng/mL | Carcinoembryonic Antigen ng/mL | Creatine Kinase-MB ng/mL | C Reactive Protein ug/mL | EGF pg/mL | ENA-78 ng/mL |
|---|---|---|---|---|---|---|---|
| Least Detectable Dose | 0.021 | 0.020 | 0.84 | 0.42 | 0.0015 | 7.4 | 0.076 |
| RBM Low Plasma Range | 0.17 | | | | 0.25 | | 0.069 |
| RBM High Plasma Range | 1.5 | 1.1 | 4.8 | 1.1 | 50 | 505 | 5.3 |
| Donor_9_3. Aliquot A | 0.69 | 0.37 | 1.2 | 0.079 | Pending | 117 | 2.1 |
| Donor_9_3. Aliquot B | 0.69 | 0.43 | 1.5 | 0.19 | Pending | 156 | 2.2 |
| Donor_9_3. Aliquot C | 0.69 | 0.51 | 1.0 | 0.18 | Pending | 123 | 2.1 |
| Donor_9_3. Aliquot D | 0.81 | 0.46 | 5.3 | 0.40 | Pending | 131 | 2.4 |
| Donor_9_3. Aliquot E | 0.72 | 0.31 | 3.3 | 0.26 | Pending | 95 | 6.5 |
| Donor_9_3. Aliquot F | 0.61 | 0.19 | 1.7 | 0.16 | Pending | 78 | 0.65 |
| Donor_9_3. Aliquot G | 2.7 | 0.21 | 1.1 | 0.12 | Pending | 1300 | 16 |
| Donor_9_3. Aliquot H | 0.64 | 0.50 | 1.5 | 0.13 | Pending | 140 | 1.3 |
| Donor_9_3. Aliquot I | 0.66 | 0.45 | 0.89 | 0.083 | | 134 | 1.5 |
| EDTA Plasma | | | | | | | |
| donor #1 plasma | 7.4 | 0.14 | 1.7 | 0.25 | Pending | 30 | 0.93 |
| donor #2 plasma | 18 | 0.21 | 3.9 | 0.99 | Pending | 7.4 | 0.076 |
| donor #3 plasma | 1.7 | 0.084 | 2.6 | 0.47 | Pending | 7.4 | 0.076 |
| donor #4 plasma | 5.2 | 0.10 | 4.9 | 0.24 | Pending | 7.4 | 0.076 |
| donor #5 plasma | 16 | 0.27 | 1.7 | 0.18 | Pending | 12 | 0.32 |
| donor #6 plasma | 0.46 | 0.021 | 1.1 | 0.39 | Pending | 7.4 | 0.26 |
| donor #7 plasma | 1.6 | 0.089 | 3.6 | 3.3 | Pending | 7.4 | 0.54 |
| donor #8 plasma | 0.58 | 0.16 | 1.4 | 0.56 | Pending | 22 | 0.48 |
| donor #9 plasma | 0.47 | 0.053 | 0.71 | 0.27 | Pending | 7.4 | 0.088 |
| MW | | | | | | | |
| NHD plasma | 0.5 | 0.1 | 1.1 | 0.4 | #DIV/0! | 14.7 | 0.3 |
| Normal healthy donors | | | | | | | |
| MW | | | | | | | |
| NHD unstimuliert | 0.65 | 0.45 | 1.26 | 0.11 | 0.13 | 129.50 | 1.17 |

FIG. 16D.5

| | | CD40 | CD40 Ligand | Carcinoembryonic Antigen | Creatine Kinase-MB | C Reactive Protein | EGF | ENA-78 |
|---|---|---|---|---|---|---|---|---|
| | | ng/mL | ng/mL | ng/mL | ng/mL | ug/mL | pg/mL | ng/mL |
| | Least Detectable Dose | 0.021 | 0.020 | 0.84 | 0.42 | 0.0015 | 7.4 | 0.076 |
| | RBM Low Plasma Range | 0.17 | | | | 0.25 | | 0.069 |
| | RBM High Plasma Range | 1.5 | 1.1 | 4.8 | 1.1 | 50 | 505 | 5.3 |
| Normal healthy donors | | | | | | | | |
| | | CD40 | CD40 Ligand | Carcinoembryonic Antigen | Creatine Kinase-MB | C Reactive Protein | EGF | ENA-78 |
| Stimulationsindices | | | | | | | | |
| unstimuliert | Donor_1 3. Aliquot I | 15.3 | 1.9 | 1.1 | 1.1 | #VALUE! | 0.9 | 1.6 |
| unstimuliert | Donor_2 3. Aliquot I | 26.0 | 1.1 | 3.5 | 1.9 | #VALUE! | 0.5 | 1.0 |
| unstimuliert | Donor_3 3. Aliquot I | 2.1 | 0.9 | 1.9 | 3.5 | 185.3 | 0.3 | 0.5 |
| unstimuliert | Donor_4 3. Aliquot I | 6.0 | 0.2 | 2.5 | 0.7 | #VALUE! | 0.1 | 0.2 |
| unstimuliert | Donor_5 3. Aliquot I | 26.5 | 0.6 | 2.8 | 1.0 | #VALUE! | 0.4 | 0.2 |
| unstimuliert | Donor_6 3. Aliquot I | 1.1 | 1.0 | 0.8 | 1.9 | #VALUE! | 0.8 | 0.4 |
| unstimuliert | Donor_7 3. Aliquot I | 0.8 | 0.3 | 2.1 | 8.3 | 222.5 | 0.1 | 0.2 |
| unstimuliert | Donor_8 3. Aliquot I | 1.0 | 1.0 | 1.3 | 1.3 | 1.0 | 1.0 | 0.7 |
| unstimuliert | Donor_9 3. Aliquot I | 1.0 | 1.0 | 0.7 | 0.7 | #VALUE! | 1.0 | 1.3 |
| | | | | | | | | |
| Stimulationsindices | EDTA Plasma | | | | | | | |
| PLASMA | donor #1 plasma | 14.2 | 1.3 | 1.6 | 0.6 | #VALUE! | 2.0 | 3.3 |
| PLASMA | donor #2 plasma | 35.2 | 1.9 | 3.7 | 2.4 | #VALUE! | 0.5 | 0.3 |
| PLASMA | donor #3 plasma | 3.2 | 0.8 | 2.4 | 1.1 | #VALUE! | 0.5 | 0.3 |
| PLASMA | donor #4 plasma | 10.0 | 1.0 | 4.6 | 0.6 | #VALUE! | 0.5 | 0.3 |
| PLASMA | donor #5 plasma | 31.2 | 2.5 | 1.6 | 0.4 | #VALUE! | 0.8 | 1.1 |
| PLASMA | donor #6 plasma | 0.9 | 0.2 | 1.0 | 0.9 | #VALUE! | 0.5 | 0.9 |
| PLASMA | donor #7 plasma | 3.1 | 0.8 | 3.4 | 8.0 | #VALUE! | 0.5 | 1.9 |
| PLASMA | donor #8 plasma | 1.1 | 1.5 | 1.3 | 1.4 | #VALUE! | 1.5 | 1.7 |

FIG. 16D.6

| | CD40 ng/mL | CD40 Ligand ng/mL | Carcinoembryonic Antigen ng/mL | Creatine Kinase-MB ng/mL | C Reactive Protein ug/mL | EGF pg/mL | ENA-78 ng/mL |
|---|---|---|---|---|---|---|---|
| Least Detectable Dose | 0.021 | 0.020 | 0.84 | 0.42 | 0.0015 | 7.4 | 0.076 |
| RBM Low Plasma Range | 0.17 | | | | | | |
| RBM High Plasma Range | 1.5 | 1.1 | 4.8 | 1.1 | 0.25 | 505 | 0.069 |
| PLASMA donor #9 plasma | 0.9 | 0.5 | 0.7 | 0.6 | #VALUE! | 0.5 | 5.3 |
| | | | | | | | 0.3 |

FIG. 16E.1

| | Endothelin-1 pg/mL | EN-RAGE ng/mL | Eotaxin pg/mL | Epiregulin pg/mL | Erythropoietin pg/mL |
|---|---|---|---|---|---|
| Least Detectable Dose | 7.2 | 0.25 | 41 | 36 | 166 |
| RBM Low Plasma Range | | 4.6 | | Pending | |
| RBM High Plasma Range | 26 | 592 | 177 | Pending | 284 |
| Samples | | | | | |
| Donor_1 3. Aliquot A | 8.1 | 82 | 179 | 161 | 166 |
| Donor_1 3. Aliquot B | 7.2 | 72 | 164 | 65 | 166 |
| Donor_1 3. Aliquot C | 7.2 | 74 | 130 | 33 | 37 |
| Donor_1 3. Aliquot D | 7.2 | 66 | 180 | 16 | 166 |
| Donor_1 3. Aliquot E | 7.2 | 75 | 170 | 40 | 166 |
| Donor_1 3. Aliquot F | 7.2 | 60 | 184 | 61 | 166 |
| Donor_1 3. Aliquot G | 22 | 54 | 10 | 149 | 166 |
| Donor_1 3. Aliquot H | 11 | 99 | 177 | 36 | 60 |
| Donor_1 3. Aliquot I | 7.2 | 76 | 172 | 31 | 166 |
| Donor_2 3. Aliquot A | 11 | 247 | 61 | 44 | 166 |
| Donor_2 3. Aliquot B | 7.2 | 230 | 48 | 26 | 166 |
| Donor_2 3. Aliquot C | 7.2 | 252 | 46 | 16 | 166 |
| Donor_2 3. Aliquot D | 15 | 212 | 48 | 52 | 166 |
| Donor_2 3. Aliquot E | 20 | 228 | 44 | 21 | 166 |
| Donor_2 3. Aliquot F | 7.2 | 258 | 27 | 36 | 166 |
| Donor_2 3. Aliquot G | 24 | 218 | 5.0 | 236 | 166 |
| Donor_2 3. Aliquot H | 7.2 | >269 | 36 | 26 | 166 |
| Donor_2 3. Aliquot I | 7.2 | 250 | 44 | 36 | 166 |
| Donor_3 3. Aliquot A | 7.2 | 142 | 66 | 40 | 166 |
| Donor_3 3. Aliquot B | 7.2 | 142 | 50 | 35 | 166 |
| Donor_3 3. Aliquot C | 7.2 | 135 | 44 | 24 | 166 |
| Donor_3 3. Aliquot D | 7.2 | 151 | 54 | 31 | 166 |
| Donor_3 3. Aliquot E | 11 | 159 | 52 | 36 | 166 |

FIG. 16E.2

| | Endothelin-1 pg/mL | EN-RAGE ng/mL | Eotaxin pg/mL | Epiregulin pg/mL | Erythropoietin pg/mL |
|---|---|---|---|---|---|
| Least Detectable Dose | 7.2 | 0.25 | 41 | 36 | 166 |
| RBM Low Plasma Range | | | | | |
| RBM High Plasma Range | 26 | 4.6 | 177 | Pending | 284 |
| Donor_3 3. Aliquot F | 7.2 | 592 | 80 | Pending | 166 |
| Donor_3 3. Aliquot G | 7.2 | 128 | 5.0 | 36 | 166 |
| Donor_3 3. Aliquot H | 7.2 | 122 | 29 | 36 | 166 |
| Donor_3 3. Aliquot I | 7.2 | 211 | 36 | 21 | 166 |
| | | 169 | | 13 | |
| Donor_4 3. Aliquot A | 7.2 | >269 | 141 | 21 | 166 |
| Donor_4 3. Aliquot B | 7.2 | 239 | 133 | 35 | 166 |
| Donor_4 3. Aliquot C | 7.2 | 175 | 122 | 36 | 166 |
| Donor_4 3. Aliquot D | 11 | 84 | 133 | 36 | 166 |
| Donor_4 3. Aliquot E | 22 | 66 | 120 | 29 | 166 |
| Donor_4 3. Aliquot F | 7.2 | 94 | 130 | 36 | 166 |
| Donor_4 3. Aliquot G | 7.2 | 127 | 10 | 69 | 166 |
| Donor_4 3. Aliquot H | 7.2 | >269 | 124 | 36 | 166 |
| Donor_4 3. Aliquot I | 7.2 | 185 | 139 | 31 | 166 |
| Donor_5 3. Aliquot A | 20 | 95 | 27 | 129 | 166 |
| Donor_5 3. Aliquot B | 11 | 88 | 34 | 101 | 41 |
| Donor_5 3. Aliquot C | 7.2 | 108 | 32 | 149 | 166 |
| Donor_5 3. Aliquot D | 11 | 52 | 32 | 105 | 100 |
| Donor_5 3. Aliquot E | 15 | 41 | 30 | 111 | 64 |
| Donor_5 3. Aliquot F | 7.2 | 73 | 27 | 87 | 166 |
| Donor_5 3. Aliquot G | 15 | 91 | 7.6 | 161 | 50 |
| Donor_5 3. Aliquot H | 7.2 | 236 | 25 | 117 | 50 |
| Donor_5 3. Aliquot I | 7.2 | 100 | 22 | 95 | 166 |
| Donor_6 3. Aliquot A | 7.2 | 236 | 22 | 26 | 166 |
| Donor_6 3. Aliquot B | 7.2 | 229 | 25 | 31 | 166 |

FIG. 16E.3

| | Endothelin-1 pg/mL | EN-RAGE ng/mL | Eotaxin pg/mL | Epiregulin pg/mL | Erythropoietin pg/mL |
|---|---|---|---|---|---|
| Least Detectable Dose | 7.2 | 0.25 | 41 | 36 | 166 |
| RBM Low Plasma Range | | 4.6 | | Pending | |
| RBM High Plasma Range | 26 | 592 | 177 | Pending | 284 |
| Donor_6 3. Aliquot C | 7.2 | 265 | 36 | 36 | 166 |
| Donor_6 3. Aliquot D | 7.2 | 109 | 25 | 36 | 166 |
| Donor_6 3. Aliquot E | 11 | 106 | 20 | 36 | 166 |
| Donor_6 3. Aliquot F | 7.2 | 153 | 34 | 16 | 166 |
| Donor_6 3. Aliquot G | 7.2 | 147 | 15 | 177 | 166 |
| Donor_6 3. Aliquot H | 7.2 | >269 | 18 | 36 | 166 |
| Donor_6 3. Aliquot I | 7.2 | 237 | 22 | 36 | 166 |
| | | | | | |
| Donor_7 3. Aliquot A | 7.2 | 150 | 138 | 36 | 166 |
| Donor_7 3. Aliquot B | 7.2 | 161 | 119 | 36 | 166 |
| Donor_7 3. Aliquot C | 7.2 | >269 | 105 | 36 | 166 |
| Donor_7 3. Aliquot D | 7.2 | 128 | 106 | 36 | 166 |
| Donor_7 3. Aliquot E | 7.2 | 122 | 117 | 36 | 166 |
| Donor_7 3. Aliquot F | 7.2 | 227 | 121 | 36 | 166 |
| Donor_7 3. Aliquot G | 7.2 | 182 | 18 | 36 | 166 |
| Donor_7 3. Aliquot H | 7.2 | >269 | 125 | 36 | 166 |
| Donor_7 3. Aliquot I | 7.2 | >269 | 111 | 36 | 166 |
| | | | | | |
| Donor_8 3. Aliquot A | 8.1 | 48 | 162 | 36 | 166 |
| Donor_8 3. Aliquot B | 7.2 | 46 | 153 | 35 | 166 |
| Donor_8 3. Aliquot C | 7.2 | 41 | 117 | 44 | 166 |
| Donor_8 3. Aliquot D | 7.2 | 64 | 165 | 42 | 166 |
| Donor_8 3. Aliquot E | 7.2 | 45 | 157 | 35 | 166 |
| Donor_8 3. Aliquot F | 15 | 47 | 208 | 58 | 166 |
| Donor_8 3. Aliquot G | 7.2 | 57 | 5.0 | 56 | 166 |
| Donor_8 3. Aliquot H | 11 | 143 | 142 | 16 | 166 |
| Donor_8 3. Aliquot I | 7.2 | 122 | 157 | 36 | 166 |

FIG. 16E.4

| | Endothelin-1 pg/mL | EN-RAGE ng/mL | Eotaxin pg/mL | Epiregulin pg/mL | Erythropoietin pg/mL |
|---|---|---|---|---|---|
| Least Detectable Dose | 7.2 | 0.25 | 41 | 36 | 166 |
| RBM Low Plasma Range | | 4.6 | | Pending | |
| RBM High Plasma Range | 26 | 592 | 177 | Pending | 284 |
| Donor_9_3. Aliquot A | 7.2 | 47 | 254 | 86 | 166 |
| Donor_9_3. Aliquot B | 13 | 33 | 223 | 75 | 166 |
| Donor_9_3. Aliquot C | 9.8 | 48 | 184 | 106 | 166 |
| Donor_9_3. Aliquot D | 18 | 46 | 239 | 101 | 166 |
| Donor_9_3. Aliquot E | 19 | 67 | 209 | 79 | 166 |
| Donor_9_3. Aliquot F | 13 | 22 | 231 | 77 | 166 |
| Donor_9_3. Aliquot G | 7.2 | 96 | 41 | 123 | 166 |
| Donor_9_3. Aliquot H | 5.1 | 115 | 201 | 97 | 166 |
| Donor_9_3. Aliquot I | 7.2 | 50 | 232 | 83 | 166 |
| EDTA Plasma | | | | | |
| donor #1 plasma | 7.7 | 65 | 97 | 83 | 84 |
| donor #2 plasma | 7.2 | >269 | 42 | 36 | 166 |
| donor #3 plasma | 17 | 49 | 36 | 32 | 166 |
| donor #4 plasma | 7.2 | 19 | 87 | 36 | 166 |
| donor #5 plasma | 22 | 145 | 64 | 35 | 118 |
| donor #6 plasma | 7.2 | 40 | 14 | 36 | 37 |
| donor #7 plasma | 7.2 | 71 | 86 | 36 | 166 |
| donor #8 plasma | 9.8 | 9.4 | 294 | 35 | 166 |
| donor #9 plasma | 7.2 | 4.3 | 330 | 65 | 166 |
| MW NHD plasma | 8.5 | 6.8 | 312.0 | 49.9 | 166.0 |
| Normal healthy donors | | | | | |
| MW NHD unstimuliert | 7.20 | 86.10 | 194.50 | 59.35 | 166.00 |

FIG. 16E.5

| | | Endothelin-1 pg/mL | EN-RAGE ng/mL | Eotaxin pg/mL | Epiregulin pg/mL | Erythropoietin pg/mL |
|---|---|---|---|---|---|---|
| | Least Detectable Dose | 7.2 | 0.25 | 41 | 36 | 166 |
| | RBM Low Plasma Range | | 4.6 | | Pending | |
| | RBM High Plasma Range | 26 | 592 | 177 | Pending | 284 |
| Normal healthy donors | | | | | | |
| *Stimulationsindices* | | Endothelin-1 | EN-RAGE | Eotaxin | Epiregulin | Erythropoietin |
| unstimuliert | Donor_1 3. Aliquot I | 1.0 | 0.9 | 0.9 | 0.5 | 1.0 |
| unstimuliert | Donor_2 3. Aliquot I | 1.0 | 2.9 | 0.2 | 0.6 | 1.0 |
| unstimuliert | Donor_3 3. Aliquot I | 1.9 | 2.0 | 0.2 | 0.2 | 1.0 |
| unstimuliert | Donor_4 3. Aliquot I | 1.0 | 2.1 | 0.7 | 0.5 | 1.0 |
| unstimuliert | Donor_5 3. Aliquot I | 1.0 | 1.2 | 0.1 | 1.6 | 1.0 |
| unstimuliert | Donor_6 3. Aliquot I | 1.0 | 2.8 | 0.1 | 0.6 | 1.0 |
| unstimuliert | Donor_7 3. Aliquot I | 1.0 | #VALUE! | 0.6 | 0.6 | 1.0 |
| unstimuliert | Donor_8 3. Aliquot I | 1.0 | 1.4 | 0.8 | 0.6 | 1.0 |
| unstimuliert | Donor_9 3. Aliquot I | 1.0 | 0.6 | 1.2 | 1.4 | 1.0 |
| *Stimulationsindices* | EDTA Plasma | | | | | |
| PLASMA | donor #1 plasma | 0.9 | 9.5 | 0.3 | 1.7 | 0.5 |
| PLASMA | donor #2 plasma | 0.8 | #VALUE! | 0.1 | 0.7 | 1.0 |
| PLASMA | donor #3 plasma | 1.9 | 7.2 | 0.1 | 0.6 | 1.0 |
| PLASMA | donor #4 plasma | 0.8 | 2.7 | 0.3 | 0.7 | 1.0 |
| PLASMA | donor #5 plasma | 2.6 | 21.2 | 0.2 | 0.7 | 0.7 |
| PLASMA | donor #6 plasma | 0.8 | 5.9 | 0.0 | 0.7 | 0.2 |
| PLASMA | donor #7 plasma | 0.8 | 10.4 | 0.3 | 0.7 | 1.0 |
| PLASMA | donor #8 plasma | 1.2 | 1.4 | 0.9 | 0.7 | 1.0 |

FIG. 16E.6

| | Endothelin-1 pg/mL | EN-RAGE ng/mL | Eotaxin pg/mL | Epiregulin pg/mL | Erythropoietin pg/mL |
|---|---|---|---|---|---|
| Least Detectable Dose | 7.2 | 0.25 | | | |
| RBM Low Plasma Range | | | 41 | 36 | 166 |
| RBM High Plasma Range | 26 | 4.6 | 177 | Pending | |
| PLASMA donor #9 plasma | 0.8 | 592 | 1.1 | Pending | 284 |
| | | 0.6 | | 1.3 | 1.0 |

FIG. 16F.1

|  | Fatty Acid Binding Protein ng/mL | Factor VII ng/mL | Ferritin ng/mL | FGF basic pg/mL | Fibrinogen mg/mL | G-CSF pg/mL | Growth Hormone ng/mL |
|---|---|---|---|---|---|---|---|
| Least Detectable Dose | 3.0 | 1.0 | 1.4 | 98 | 0.0098 | 5.0 | 0.13 |
| RBM Low Plasma Range | | 106 | 5.0 | | 2.2 | | |
| RBM High Plasma Range | 10 | 443 | 552 | 2000 | 8.0 | 37 | 4.4 |
| Samples | | | | | | | |
| Donor_1 3. Aliquot A | 32 | 157 | 1290 | 1850 | 4.1 | 417 | 1.8 |
| Donor_1 3. Aliquot B | 29 | 140 | 1380 | 1710 | 4.4 | 279 | 1.7 |
| Donor_1 3. Aliquot C | 34 | 89 | 1300 | 414 | 4.2 | 221 | 1.9 |
| Donor_1 3. Aliquot D | 33 | 168 | 1400 | 2050 | 4.8 | 355 | 2.1 |
| Donor_1 3. Aliquot E | 33 | 171 | 1140 | 1840 | 4.1 | 270 | 2.0 |
| Donor_1 3. Aliquot F | 31 | 132 | 1280 | 1400 | 3.7 | 197 | 1.5 |
| Donor_1 3. Aliquot G | 41 | 174 | 1420 | 1760 | 4.6 | 236 | 1.8 |
| Donor_1 3. Aliquot H | 31 | 160 | 1280 | 159 | 4.0 | 211 | 1.8 |
| Donor_1 3. Aliquot I | 29 | 139 | 1160 | 1470 | 4.4 | 219 | 1.8 |
| Donor_2 3. Aliquot A | 36 | 541 | 1490 | 429 | 4.3 | 344 | 0.77 |
| Donor_2 3. Aliquot B | 40 | 577 | 1510 | 321 | 4.4 | 204 | 0.90 |
| Donor_2 3. Aliquot C | 40 | 154 | 1430 | 241 | 5.1 | 31 | 0.82 |
| Donor_2 3. Aliquot D | 45 | 694 | 1390 | 563 | 4.3 | 1470 | 1.2 |
| Donor_2 3. Aliquot E | 45 | 640 | 1390 | 563 | 4.0 | 1240 | 0.91 |
| Donor_2 3. Aliquot F | 40 | 580 | 1400 | 241 | 4.1 | 32 | 0.70 |
| Donor_2 3. Aliquot G | 48 | 588 | 1470 | 664 | 5.3 | 2160 | 0.87 |
| Donor_2 3. Aliquot H | 39 | 567 | 1330 | 176 | 3.9 | 36 | 0.78 |
| Donor_2 3. Aliquot I | 34 | 450 | 1320 | 225 | 5.2 | 32 | 0.71 |
| Donor_3 3. Aliquot A | 14 | 147 | 855 | 98 | 5.9 | 105 | 1.5 |
| Donor_3 3. Aliquot B | 12 | 139 | 757 | 29 | 5.5 | 41 | 1.4 |
| Donor_3 3. Aliquot C | 12 | 31 | 828 | 29 | 4.9 | 5 | 1.5 |
| Donor_3 3. Aliquot D | 17 | 156 | 799 | 209 | 5.2 | 1340 | 1.5 |
| Donor_3 3. Aliquot E | 16 | 160 | 797 | 159 | 6.0 | 1200 | 1.6 |

FIG. 16F.2

| | Fatty Acid Binding Protein ng/mL | Factor VII ng/mL | Ferritin ng/mL | FGF basic pg/mL | Fibrinogen mg/mL | G-CSF pg/mL | Growth Hormone ng/mL |
|---|---|---|---|---|---|---|---|
| Least Detectable Dose | 3.0 | 1.0 | 1.4 | 98 | 0.0098 | 5.0 | 0.13 |
| RBM Low Plasma Range | | 106 | 5.0 | | 2.2 | | |
| RBM High Plasma Range | 10 | 443 | 552 | 2000 | 8.0 | 37 | 4.4 |
| Donor_3_3. Aliquot F | 13 | 128 | 824 | 29 | 5.2 | 5 | 1.3 |
| Donor_3_3. Aliquot G | 15 | 116 | 865 | 52 | 6.6 | 7.3 | 1.7 |
| Donor_3_3. Aliquot H | 9.2 | 108 | 758 | 98 | 5.3 | 5 | 1.3 |
| Donor_3_3. Aliquot I | 11 | 123 | 800 | 29 | 6.2 | 5 | 1.6 |
| Donor_4_3. Aliquot A | 33 | 124 | 328 | 98 | 2.0 | 5.6 | 4.1 |
| Donor_4_3. Aliquot B | 33 | 129 | 311 | 52 | 2.0 | 9.6 | 4.2 |
| Donor_4_3. Aliquot C | 30 | 9.2 | 286 | 29 | 2.2 | 5 | 4.0 |
| Donor_4_3. Aliquot D | 33 | 142 | 308 | 459 | 2.0 | 976 | 4.2 |
| Donor_4_3. Aliquot E | 33 | 115 | 319 | 474 | 1.3 | 779 | 3.7 |
| Donor_4_3. Aliquot F | 32 | 105 | 347 | 99 | 1.8 | 18 | 3.3 |
| Donor_4_3. Aliquot G | 34 | 75 | 338 | 90 | 2.2 | 8.8 | 3.6 |
| Donor_4_3. Aliquot H | 37 | 111 | 315 | 98 | 1.7 | 5 | 4.1 |
| Donor_4_3. Aliquot I | 34 | 125 | 352 | 52 | 2.0 | 5 | 4.2 |
| Donor_5_3. Aliquot A | 9.2 | >1113 | 1430 | 489 | 5.4 | 130 | 4.2 |
| Donor_5_3. Aliquot B | 7.8 | 1020 | 1320 | 533 | 5.9 | 203 | 3.9 |
| Donor_5_3. Aliquot C | 9.2 | 243 | 1570 | 241 | 6.9 | 22 | 4.0 |
| Donor_5_3. Aliquot D | 13 | 940 | 1630 | 563 | 3.4 | 1480 | 3.7 |
| Donor_5_3. Aliquot E | 14 | 1100 | 1510 | 533 | 5.2 | 3960 | 4.1 |
| Donor_5_3. Aliquot F | 6.5 | 808 | 1390 | 257 | 4.4 | 29 | 3.0 |
| Donor_5_3. Aliquot G | 10 | 936 | 1460 | 273 | 7.2 | 31 | 4.7 |
| Donor_5_3. Aliquot H | 8.8 | 1000 | 1390 | 176 | 5.5 | 23 | 4.0 |
| Donor_5_3. Aliquot I | 8.8 | 1050 | 1400 | 159 | 6.6 | 21 | 3.8 |
| Donor_6_3. Aliquot A | 2.3 | 320 | 382 | 72 | 4.1 | 12 | 3.0 |
| Donor_6_3. Aliquot B | 2.6 | 329 | 374 | 98 | 4.3 | 19 | 3.1 |

FIG. 16F.3

| | Fatty Acid Binding Protein ng/mL | Factor VII ng/mL | Ferritin ng/mL | FGF basic pg/mL | Fibrinogen mg/mL | G-CSF pg/mL | Growth Hormone ng/mL |
|---|---|---|---|---|---|---|---|
| Least Detectable Dose | 3.0 | 1.0 | 1.4 | 98 | 0.0098 | 5.0 | 0.13 |
| RBM Low Plasma Range | | 106 | 5.0 | | 2.2 | | |
| RBM High Plasma Range | 10 | 443 | 552 | 2000 | 8.0 | 37 | 4.4 |
| Donor_6_3. Aliquot C | 2.6 | 62 | 370 | 98 | 4.9 | 5 | 2.8 |
| Donor_6_3. Aliquot D | 5.4 | 345 | 370 | 289 | 3.9 | 389 | 3.1 |
| Donor_6_3. Aliquot E | 5.6 | 285 | 364 | 289 | 3.2 | 975 | 2.9 |
| Donor_6_3. Aliquot F | 2.2 | 311 | 376 | 98 | 3.2 | 5 | 2.8 |
| Donor_6_3. Aliquot G | 2.6 | 252 | 391 | 192 | 5.5 | 20 | 3.2 |
| Donor_6_3. Aliquot H | 2.0 | 336 | 353 | 98 | 3.9 | 5 | 3.1 |
| Donor_6_3. Aliquot I | 1.7 | 309 | 375 | 98 | 3.4 | 5 | 3.0 |
| Donor_7_3. Aliquot A | 463 | 144 | 468 | 391 | 3.0 | 334 | 0.32 |
| Donor_7_3. Aliquot B | 459 | 149 | 491 | 249 | 2.9 | 86 | 0.39 |
| Donor_7_3. Aliquot C | 466 | 34 | 535 | 98 | 3.2 | 5 | 0.22 |
| Donor_7_3. Aliquot D | 422 | 128 | 451 | 281 | 2.6 | 892 | 0.39 |
| Donor_7_3. Aliquot E | 434 | 143 | 490 | 265 | 2.1 | 270 | 0.31 |
| Donor_7_3. Aliquot F | 426 | 143 | 505 | 98 | 2.6 | 5 | 0.26 |
| Donor_7_3. Aliquot G | 511 | 139 | 471 | 233 | 2.9 | 5 | 0.23 |
| Donor_7_3. Aliquot H | 440 | 136 | 404 | 72 | 2.4 | 5 | 0.25 |
| Donor_7_3. Aliquot I | 451 | 141 | 409 | 98 | 3.0 | 5 | 0.29 |
| Donor_8_3. Aliquot A | 3 | 376 | 34 | 98 | 1.8 | 5.8 | 0.35 |
| Donor_8_3. Aliquot B | 3 | 411 | 32 | 98 | 1.7 | 4.7 | 0.35 |
| Donor_8_3. Aliquot C | 3 | 18 | 37 | 90 | 1.8 | 5 | 0.20 |
| Donor_8_3. Aliquot D | 8.3 | 410 | 48 | 414 | 1.7 | 1330 | 0.94 |
| Donor_8_3. Aliquot E | 7.8 | 351 | 39 | 336 | 1.7 | 1010 | 0.90 |
| Donor_8_3. Aliquot F | 0.81 | 426 | 32 | 273 | 1.7 | 4.7 | 0.36 |
| Donor_8_3. Aliquot G | 3 | 253 | 42 | 98 | 2.0 | 5 | 0.33 |
| Donor_8_3. Aliquot H | 0.56 | 382 | 38 | 142 | 1.7 | 5 | 0.30 |
| Donor_8_3. Aliquot I | 0.14 | 381 | 36 | 98 | 1.9 | 5 | 0.28 |

FIG. 16F.4

| | Fatty Acid Binding Protein ng/mL | Factor VII ng/mL | Ferritin ng/mL | FGF basic pg/mL | Fibrinogen mg/mL | G-CSF pg/mL | Growth Hormone ng/mL |
|---|---|---|---|---|---|---|---|
| Least Detectable Dose | 3.0 | 1.0 | 1.4 | 98 | 0.0098 | 5.0 | 0.13 |
| RBM Low Plasma Range | | 106 | 5.0 | | 2.2 | | |
| RBM High Plasma Range | 10 | 443 | 552 | 2000 | 8.0 | 37 | 4.4 |
| Donor_9_3. Aliquot A | 3 | 196 | 4.8 | 98 | 1.5 | 17 | 7.2 |
| Donor_9_3. Aliquot B | 1.6 | 196 | 2.6 | 122 | 1.6 | 21 | 6.8 |
| Donor_9_3. Aliquot C | 0.42 | 44 | 5.7 | 94 | 1.4 | 19 | 6.6 |
| Donor_9_3. Aliquot D | 10 | 243 | 11 | 414 | 1.5 | 2320 | 6.8 |
| Donor_9_3. Aliquot E | 6.6 | 201 | 6.0 | 332 | 1.5 | 1490 | 6.8 |
| Donor_9_3. Aliquot F | 0.68 | 196 | 3.6 | 137 | 1.2 | 11 | 6.4 |
| Donor_9_3. Aliquot G | 0.81 | 147 | 12 | 179 | 1.9 | 39 | 6.2 |
| Donor_9_3. Aliquot H | 3 | 229 | 5.5 | 37 | 1.3 | 5.4 | 6.8 |
| Donor_9_3. Aliquot I | 3 | 184 | 3.3 | 37 | 1.6 | 5.4 | 6.4 |
| EDTA Plasma | | | | | | | |
| donor #1 plasma | 32 | 141 | 1190 | 736 | 4.6 | 240 | 1.4 |
| donor #2 plasma | 65 | 545 | 1670 | 339 | 8.1 | 45 | 0.89 |
| donor #3 plasma | 25 | 135 | 934 | 94 | 8.7 | 5 | 1.5 |
| donor #4 plasma | 59 | 121 | 320 | 51 | 3.2 | 4.5 | 5.3 |
| donor #5 plasma | 13 | 891 | 1190 | 346 | 11 | 24 | 5.1 |
| donor #6 plasma | 5.0 | 315 | 382 | 21 | 6.7 | 6.2 | 4.1 |
| donor #7 plasma | >617 | 187 | 545 | 98 | 4.5 | 6.2 | 0.49 |
| donor #8 plasma | 3 | 428 | 22 | 87 | 2.0 | 5 | 0.38 |
| donor #9 plasma | 0.55 | 299 | 3.3 | 87 | 2.3 | 18 | 7.2 |
| MW | | | | | | | |
| Normal healthy donors NHD plasma | 1.8 | 363.5 | 12.8 | 86.9 | 2.2 | 11.6 | 3.8 |
| MW | | | | | | | |
| NHD unstimuliert | 1.57 | 282.50 | 19.76 | 67.40 | 1.73 | 5.18 | 3.33 |

FIG. 16F.5

| | | Fatty Acid Binding Protein ng/mL | Factor VII ng/mL | Ferritin ng/mL | FGF basic pg/mL | Fibrinogen mg/mL | G-CSF pg/mL | Growth Hormone ng/mL |
|---|---|---|---|---|---|---|---|---|
| | Least Detectable Dose | 3.0 | 1.0 | 1.4 | 98 | 0.0098 | 5.0 | 0.13 |
| | RBM Low Plasma Range | | 106 | 5.0 | | 2.2 | | |
| | RBM High Plasma Range | 10 | 443 | 552 | 2000 | 8.0 | 37 | 4.4 |
| Normal healthy donors | | | | | | | | |
| | | Fatty Acid Binding Protein | Factor VII | Ferritin | FGF basic | Fibrinogen | G-CSF | Growth Hormone |
| Stimulations indices | | | | | | | | |
| unstimuliert | Donor_1 3. Aliquot I | 18.6 | 0.5 | 58.7 | 21.8 | 2.5 | 42.3 | 0.5 |
| unstimuliert | Donor_2 3. Aliquot I | 21.7 | 1.6 | 66.8 | 3.3 | 3.0 | 6.2 | 0.2 |
| unstimuliert | Donor_3 3. Aliquot I | 7.1 | 0.4 | 40.5 | 0.4 | 3.6 | 1.0 | 0.5 |
| unstimuliert | Donor_4 3. Aliquot I | 21.4 | 0.4 | 17.8 | 0.8 | 1.2 | 1.0 | 1.3 |
| unstimuliert | Donor_5 3. Aliquot I | 5.6 | 3.7 | 70.9 | 2.4 | 3.8 | 4.0 | 1.1 |
| unstimuliert | Donor_6 3. Aliquot I | 1.1 | 1.1 | 19.0 | 1.5 | 2.0 | 1.0 | 0.9 |
| unstimuliert | Donor_7 3. Aliquot I | 287.4 | 0.5 | 20.7 | 1.5 | 1.7 | 1.0 | 0.1 |
| unstimuliert | Donor_8 3. Aliquot I | 0.1 | 1.3 | 1.8 | 1.5 | 1.1 | 1.0 | 0.1 |
| unstimuliert | Donor_9 3. Aliquot I | 1.9 | 0.7 | 0.2 | 0.5 | 0.9 | 1.0 | 1.9 |
| | | | | | | | | |
| Stimulations indices | EDTA Plasma | | | | | | | |
| PLASMA | donor #1 plasma | 17.8 | 0.4 | 92.9 | 8.5 | 2.1 | 20.7 | 0.4 |
| PLASMA | donor #2 plasma | 36.5 | 1.5 | 130.4 | 3.9 | 3.8 | 3.9 | 0.2 |
| PLASMA | donor #3 plasma | 14.1 | 0.4 | 72.9 | 1.1 | 4.0 | 0.4 | 0.4 |
| PLASMA | donor #4 plasma | 33.1 | 0.3 | 25.0 | 0.6 | 1.5 | 0.4 | 1.4 |
| PLASMA | donor #5 plasma | 7.1 | 2.5 | 92.9 | 4.0 | 5.2 | 2.1 | 1.3 |
| PLASMA | donor #6 plasma | 2.8 | 0.9 | 29.8 | 0.2 | 3.1 | 0.5 | 1.1 |
| PLASMA | donor #7 plasma | #VALUE! | 0.5 | 42.6 | 1.1 | 2.1 | 0.5 | 0.1 |
| PLASMA | donor #8 plasma | 1.7 | 1.2 | 1.7 | 1.0 | 0.9 | 0.4 | 0.1 |

FIG. 16F.6

| | Fatty Acid Binding Protein ng/mL | Factor VII ng/mL | Ferritin ng/mL | FGF basic pg/mL | Fibrinogen mg/mL | G-CSF pg/mL | Growth Hormone ng/mL |
|---|---|---|---|---|---|---|---|
| Least Detectable Dose | 3.0 | 1.0 | 1.4 | 98 | 0.0098 | 5.0 | 0.13 |
| RBM Low Plasma Range | | 106 | 5.0 | | 2.2 | | |
| RBM High Plasma Range | 10 | 443 | 552 | 2000 | 8.0 | 37 | 4.4 |
| PLASMA donor #9 plasma | 0.3 | 0.8 | 0.3 | 1.0 | 1.1 | 1.6 | 1.9 |

FIG. 16G.1

| | GM-CSF pg/mL | Glutathione S-Transferase ng/mL | Haptoglobin mg/mL | ICAM-1 ng/mL | IFN-gamma pg/mL | IgA mg/mL | IgE ng/mL |
|---|---|---|---|---|---|---|---|
| Least Detectable Dose | 57 | 0.40 | 0.025 | 3.2 | 4.6 | 0.0084 | 14 |
| RBM Low Plasma Range | | | 0.047 | 42 | Pending | 0.58 | |
| RBM High Plasma Range | 152 | 3.1 | 7.6 | 213 | Pending | 5.6 | 770 |
| Samples | | | | | | | |
| Donor_1 3. Aliquot A | 8.4 | 0.64 | 1.0 | 467 | 3.8 | 2.0 | 13 |
| Donor_1 3. Aliquot B | 2.5 | 0.84 | 1.2 | 432 | 4.5 | 2.3 | 11 |
| Donor_1 3. Aliquot C | 5.0 | 0.55 | 1.1 | 452 | 2.7 | 2.2 | 1.8 |
| Donor_1 3. Aliquot D | 4.5 | 0.69 | 1.2 | 465 | 4.6 | 2.4 | 12 |
| Donor_1 3. Aliquot E | 10 | 0.59 | 1.1 | 438 | 4.6 | 2.1 | 13 |
| Donor_1 3. Aliquot F | 2.5 | 0.50 | 1.2 | 441 | 4.6 | 2.1 | 4.4 |
| Donor_1 3. Aliquot G | 57 | 0.52 | 1.2 | 471 | 4.5 | 2.3 | 11 |
| Donor_1 3. Aliquot H | 4.5 | 0.52 | 1.1 | 491 | 4.6 | 2.1 | 9.6 |
| Donor_1 3. Aliquot I | 4.0 | 0.55 | 1.1 | 438 | 4.6 | 2.3 | 6.2 |
| Donor_2 3. Aliquot A | 12 | 0.4 | 1.3 | 491 | 7.2 | 2.5 | 210 |
| Donor_2 3. Aliquot B | 5.0 | 0.76 | 1.8 | 495 | 6.7 | 2.5 | 217 |
| Donor_2 3. Aliquot C | 57 | 0.55 | 1.9 | 499 | 4.6 | 2.5 | 98 |
| Donor_2 3. Aliquot D | 24 | 1.7 | 1.5 | 489 | 31 | 2.4 | 258 |
| Donor_2 3. Aliquot E | 4.5 | 0.81 | 2.2 | 479 | 9.5 | 2.5 | 221 |
| Donor_2 3. Aliquot F | 3.5 | 0.41 | 2.1 | 504 | 4.6 | 2.5 | 177 |
| Donor_2 3. Aliquot G | 180 | 0.69 | 2.3 | 514 | 14 | 2.5 | 151 |
| Donor_2 3. Aliquot H | 3.5 | 0.4 | 1.9 | 490 | 2.7 | 2.6 | 175 |
| Donor_2 3. Aliquot I | 57 | 0.4 | 1.7 | 479 | 3.8 | 2.5 | 195 |
| Donor_3 3. Aliquot A | 10 | 0.46 | 0.014 | 283 | 8.5 | 1.5 | 26 |
| Donor_3 3. Aliquot B | 7.8 | 1.4 | 0.018 | 239 | 4.6 | 1.6 | 27 |
| Donor_3 3. Aliquot C | 2.5 | 0.48 | 0.019 | 278 | 4.6 | 1.6 | 7.6 |
| Donor_3 3. Aliquot D | 6.7 | 1.4 | 0.013 | 231 | 8.2 | 1.6 | 45 |
| Donor_3 3. Aliquot E | 23 | 0.94 | 0.014 | 306 | 9.2 | 1.7 | 40 |

FIG. 16G.2

| | GM-CSF pg/mL | Glutathione S-Transferase ng/mL | Haptoglobin mg/mL | ICAM-1 ng/mL | IFN-gamma pg/mL | IgA mg/mL | IgE ng/mL |
|---|---|---|---|---|---|---|---|
| Least Detectable Dose | 57 | 0.40 | 0.025 | 3.2 | 4.6 | 0.0084 | 14 |
| RBM Low Plasma Range | | | 0.047 | 42 | Pending | 0.58 | |
| RBM High Plasma Range | 152 | 3.1 | 7.6 | 213 | Pending | 5.6 | 770 |
| Donor_3_3. Aliquot F | 18 | 0.4 | 0.021 | 249 | 4.6 | 1.5 | 26 |
| Donor_3_3. Aliquot G | 57 | 0.4 | 0.087 | 259 | 4.6 | 1.6 | 14 |
| Donor_3_3. Aliquot H | 57 | 0.4 | 0.022 | 208 | 4.6 | 1.5 | 21 |
| Donor_3_3. Aliquot I | 57 | 0.4 | 0.051 | 221 | 4.6 | 1.5 | 29 |
| | | | | | | | |
| Donor_4_3. Aliquot A | 3.5 | 0.4 | 0.0075 | 456 | 4.6 | 2.5 | 12 |
| Donor_4_3. Aliquot B | 57 | 0.99 | 0.014 | 466 | 4.6 | 2.3 | 14 |
| Donor_4_3. Aliquot C | 57 | 0.4 | 0.0086 | 453 | 4.6 | 2.4 | 14 |
| Donor_4_3. Aliquot D | 18 | 1.2 | 0.014 | 471 | 6.2 | 2.2 | 32 |
| Donor_4_3. Aliquot E | 22 | 0.59 | 0.0086 | 477 | 7.0 | 2.3 | 24 |
| Donor_4_3. Aliquot F | 5.0 | 0.4 | 0.019 | 467 | 3.8 | 2.3 | 13 |
| Donor_4_3. Aliquot G | 57 | 0.37 | 0.019 | 462 | 4.6 | 2.4 | 8.0 |
| Donor_4_3. Aliquot H | 57 | 0.39 | 0.013 | 474 | 4.6 | 2.3 | 8.0 |
| Donor_4_3. Aliquot I | 2.5 | 0.4 | 0.011 | 447 | 4.6 | 2.3 | 9.6 |
| | | | | | | | |
| Donor_5_3. Aliquot A | 5.6 | 0.89 | 3.7 | 241 | 7.5 | 1.1 | 321 |
| Donor_5_3. Aliquot B | 57 | 0.64 | 3.6 | 213 | 8.2 | 1.1 | 270 |
| Donor_5_3. Aliquot C | 57 | 0.64 | 3.8 | 246 | 4.6 | 1.1 | 84 |
| Donor_5_3. Aliquot D | 23 | 1.3 | 3.4 | 263 | 20 | 1.1 | 271 |
| Donor_5_3. Aliquot E | 32 | 1.1 | 3.2 | 261 | 21 | 1.2 | 274 |
| Donor_5_3. Aliquot F | 57 | 0.4 | 3.1 | 164 | 7.2 | 1.0 | 204 |
| Donor_5_3. Aliquot G | 3.5 | 0.4 | 3.5 | 255 | 6.2 | 1.0 | 59 |
| Donor_5_3. Aliquot H | 6.7 | 0.4 | 3.2 | 223 | 3.8 | 1.0 | 296 |
| Donor_5_3. Aliquot I | 57 | 0.50 | 3.4 | 242 | 5.1 | 1.00 | 289 |
| | | | | | | | |
| Donor_6_3. Aliquot A | 7.8 | 0.4 | 4.2 | 130 | 4.6 | 0.79 | 317 |
| Donor_6_3. Aliquot B | 20 | 1.3 | 4.4 | 146 | 4.6 | 0.81 | 306 |

FIG. 16G.3

| | GM-CSF pg/mL | Glutathione S-Transferase ng/mL | Haptoglobin mg/mL | ICAM-1 ng/mL | IFN-gamma pg/mL | IgA mg/mL | IgE ng/mL |
|---|---|---|---|---|---|---|---|
| Least Detectable Dose | 57 | 0.40 | 0.025 | 3.2 | 4.6 | 0.0084 | 14 |
| RBM Low Plasma Range | | | | | | | |
| RBM High Plasma Range | | | 0.047 | 42 | Pending | 0.58 | |
| Donor_6_3. Aliquot C | 152 | 3.1 | 7.6 | 213 | Pending | 5.6 | 770 |
| Donor_6_3. Aliquot D | 3.0 | 0.4 | 4.2 | 157 | 4.6 | 0.78 | 139 |
| Donor_6_3. Aliquot E | 4.0 | 0.66 | 4.3 | 149 | 31 | 0.81 | 326 |
| Donor_6_3. Aliquot F | 7.8 | 1.4 | 3.9 | 120 | 74 | 0.94 | 269 |
| Donor_6_3. Aliquot G | 9.0 | 0.4 | 4.3 | 120 | 4.6 | 0.82 | 222 |
| Donor_6_3. Aliquot H | 6.7 | 0.4 | 4.2 | 156 | 4.6 | 0.81 | 91 |
| Donor_6_3. Aliquot I | 7.2 | 0.4 | 4.1 | 146 | 4.6 | 0.71 | 340 |
| Donor_6_3. Aliquot | 57 | 0.37 | 3.7 | 127 | 4.6 | 0.76 | 272 |
| | | | | | | | |
| Donor_7_3. Aliquot A | 20 | 0.39 | 2.6 | 85 | 4.6 | 1.5 | 56 |
| Donor_7_3. Aliquot B | 10 | 1.2 | 2.7 | 85 | 4.6 | 1.5 | 51 |
| Donor_7_3. Aliquot C | 5.6 | 0.48 | 2.7 | 89 | 4.6 | 1.6 | 14 |
| Donor_7_3. Aliquot D | 18 | 0.86 | 2.0 | 74 | 4.6 | 1.4 | 62 |
| Donor_7_3. Aliquot E | 18 | 0.50 | 1.9 | 84 | 4.6 | 1.1 | 56 |
| Donor_7_3. Aliquot F | 10 | 0.4 | 2.6 | 83 | 4.6 | 1.5 | 39 |
| Donor_7_3. Aliquot G | 3.0 | 0.4 | 2.3 | 93 | 4.6 | 1.4 | 25 |
| Donor_7_3. Aliquot H | 9.0 | 0.4 | 2.6 | 81 | 4.6 | 1.4 | 36 |
| Donor_7_3. Aliquot I | 9.0 | 0.4 | 2.7 | 79 | 4.6 | 1.5 | 46 |
| | | | | | | | |
| Donor_8_3. Aliquot A | 5.0 | 0.37 | 0.014 | 61 | 5.6 | 0.77 | 17 |
| Donor_8_3. Aliquot B | 6.7 | 1.8 | 0.016 | 66 | 4.6 | 0.85 | 8.0 |
| Donor_8_3. Aliquot C | 12 | 0.4 | 0.0065 | 50 | 550 | 0.83 | 14 |
| Donor_8_3. Aliquot D | 60 | 3.4 | 0.013 | 63 | 1880 | 0.73 | 77 |
| Donor_8_3. Aliquot E | 33 | 2.1 | 0.037 | 59 | 283 | 0.73 | 65 |
| Donor_8_3. Aliquot F | 18 | 0.4 | 0.018 | 63 | 118 | 0.85 | 15 |
| Donor_8_3. Aliquot G | 3.5 | 0.4 | 0.016 | 65 | 4.6 | 0.74 | 8.0 |
| Donor_8_3. Aliquot H | 17 | 0.4 | 0.016 | 64 | 41 | 0.84 | 10 |
| Donor_8_3. Aliquot I | 14 | 0.55 | 0.011 | 58 | 3.8 | 0.78 | 3.7 |

FIG. 16G.4

| | GM-CSF pg/mL | Glutathione S-Transferase ng/mL | Haptoglobin mg/mL | ICAM-1 ng/mL | IFN-gamma pg/mL | IgA mg/mL | IgE ng/mL |
|---|---|---|---|---|---|---|---|
| Least Detectable Dose | 57 | 0.40 | 0.025 | 3.2 | 4.6 | 0.0084 | 14 |
| RBM Low Plasma Range | | | 0.047 | 42 | Pending | 0.58 | |
| RBM High Plasma Range | 152 | 3.1 | 7.6 | 213 | Pending | 5.6 | 770 |
| Donor_9_3. Aliquot A | 11 | 0.73 | 0.018 | 79 | 17 | 1.0 | 9.3 |
| Donor_9_3. Aliquot B | 13 | 2.2 | 0.018 | 82 | 21 | 1.0 | 9.3 |
| Donor_9_3. Aliquot C | 21 | 0.40 | 0.012 | 69 | 519 | 1.0 | 4.1 |
| Donor_9_3. Aliquot D | 29 | 2.6 | 0.0062 | 75 | 2360 | 1.0 | 63 |
| Donor_9_3. Aliquot E | 13 | 2.4 | 0.013 | 71 | 490 | 1.00 | 39 |
| Donor_9_3. Aliquot F | 5.8 | 0.76 | 0.0076 | 78 | 26 | 1.0 | 5.8 |
| Donor_9_3. Aliquot G | 17 | 0.56 | 0.016 | 68 | 7.6 | 1.1 | 5.2 |
| Donor_9_3. Aliquot H | 15 | 0.53 | 0.017 | 75 | 9.0 | 1.0 | 6.0 |
| Donor_9_3. Aliquot I | 8.7 | 0.37 | 0.012 | 76 | 14 | 1.0 | 6.2 |
| EDTA Plasma | | | | | | | |
| donor #1 plasma | 18 | 1.1 | 1.3 | 206 | 4.0 | 2.4 | 6.6 |
| donor #2 plasma | 15 | 0.4 | 3.6 | 371 | 10 | 4.0 | 172 |
| donor #3 plasma | 27 | 1.0 | 0.58 | 171 | 5.8 | 2.8 | 26 |
| donor #4 plasma | 10.0 | 0.4 | 0.0097 | 348 | 4.6 | 3.6 | 14 |
| donor #5 plasma | 23 | 1.3 | 5.9 | 136 | 13 | 1.8 | 318 |
| donor #6 plasma | 20 | 0.69 | 5.7 | 129 | 4.6 | 1.3 | 559 |
| donor #7 plasma | 17 | 0.4 | 4.6 | 109 | 5.8 | 2.4 | 81 |
| donor #8 plasma | 15 | 0.46 | 0.36 | 87 | 4.6 | 1.0 | 17 |
| donor #9 plasma | 5.3 | 0.90 | 0.32 | 100 | 4.0 | 1.4 | 3.5 |
| MW NHD plasma Normal healthy donors | 10.3 | 0.7 | 0.3 | 93.5 | 4.3 | 1.2 | 10.3 |
| MW NHD unstimuliert | 11.41 | 0.46 | 0.01 | 67.00 | 8.82 | 0.89 | 4.93 |

FIG. 16G.5

|  | GM-CSF pg/mL | Glutathione S-Transferase ng/mL | Haptoglobin mg/mL | ICAM-1 ng/mL | IFN-gamma pg/mL | IgA mg/mL | IgE ng/mL |
|---|---|---|---|---|---|---|---|
| Least Detectable Dose | 57 | 0.40 | 0.025 | 3.2 | 4.6 | 0.0084 | 14 |
| RBM Low Plasma Range |  |  | 0.047 | 42 | Pending | 0.58 |  |
| RBM High Plasma Range | 152 | 3.1 | 7.6 | 213 | Pending | 5.6 | 770 |
| Normal healthy donors |  |  |  |  |  |  |  |

Stimulations indices

|  |  | GM-CSF | Glutathione S-Transferase | Haptoglobin | ICAM-1 | IFN-gamma | IgA | IgE |
|---|---|---|---|---|---|---|---|---|
| unstimuliert | Donor_1 3. Aliquot I | 0.3 | 1.2 | 95.5 | 6.5 | 0.5 | 2.6 | 1.2 |
| unstimuliert | Donor_2 3. Aliquot I | 5.0 | 0.9 | 155.0 | 7.1 | 0.4 | 2.8 | 39.6 |
| unstimuliert | Donor_3 3. Aliquot I | 5.0 | 0.9 | 4.6 | 3.3 | 0.5 | 1.7 | 5.9 |
| unstimuliert | Donor_4 3. Aliquot I | 0.2 | 0.9 | 0.9 | 6.7 | 0.5 | 2.6 | 1.9 |
| unstimuliert | Donor_5 3. Aliquot I | 5.0 | 1.1 | 307.2 | 3.6 | 0.6 | 1.1 | 58.6 |
| unstimuliert | Donor_6 3. Aliquot I | 5.0 | 0.8 | 335.1 | 1.9 | 0.5 | 0.9 | 55.2 |
| unstimuliert | Donor_7 3. Aliquot I | 0.8 | 0.9 | 238.7 | 1.2 | 0.5 | 1.7 | 9.4 |
| unstimuliert | Donor_8 3. Aliquot I | 1.2 | 1.2 | 0.9 | 0.9 | 0.4 | 0.9 | 0.7 |
| unstimuliert | Donor_9 3. Aliquot I | 0.8 | 0.8 | 1.1 | 1.1 | 1.6 | 1.1 | 1.3 |

Stimulations indices

|  | EDTA Plasma |  |  |  |  |  |  |  |
|---|---|---|---|---|---|---|---|---|
| PLASMA | donor #1 plasma | 1.8 | 1.6 | 3.9 | 2.2 | 0.9 | 2.0 | 0.6 |
| PLASMA | donor #2 plasma | 1.5 | 0.6 | 10.5 | 4.0 | 2.4 | 3.3 | 16.7 |
| PLASMA | donor #3 plasma | 2.6 | 1.5 | 1.7 | 1.8 | 1.4 | 2.3 | 2.5 |
| PLASMA | donor #4 plasma | 1.0 | 0.6 | 0.0 | 3.7 | 1.1 | 3.0 | 1.4 |
| PLASMA | donor #5 plasma | 2.2 | 1.8 | 17.3 | 1.5 | 2.9 | 1.5 | 31.0 |
| PLASMA | donor #6 plasma | 1.9 | 1.0 | 16.6 | 1.4 | 1.1 | 1.1 | 54.4 |
| PLASMA | donor #7 plasma | 1.6 | 0.6 | 13.5 | 1.2 | 1.4 | 2.0 | 7.9 |
| PLASMA | donor #8 plasma | 1.5 | 0.7 | 1.1 | 0.9 | 1.1 | 0.8 | 1.7 |

FIG. 16G.6

|  | GM-CSF pg/mL | Glutathione S-Transferase ng/mL | Haptoglobin mg/mL | ICAM-1 ng/mL | IFN-gamma pg/mL | IgA mg/mL | IgE ng/mL |
|---|---|---|---|---|---|---|---|
| Least Detectable Dose | 57 | 0.40 | 0.025 | 3.2 | 4.6 | 0.0084 | 14 |
| RBM Low Plasma Range |  |  | 0.047 | 42 | Pending | 0.58 |  |
| RBM High Plasma Range | 152 | 3.1 | 7.6 | 213 | Pending | 5.6 | 770 |
| PLASMA donor #9 plasma | 0.5 | 1.3 | 0.9 | 1.1 | 0.9 | 1.2 | 0.3 |

FIG. 16H.1

| Samples | IGF-1 ng/mL | IgM mg/mL | IL-10 pg/mL | IL-12p40 ng/mL | IL-12p70 pg/mL | IL-13 pg/mL | IL-15 ng/mL | IL-16 pg/mL | IL-17 pg/mL |
|---|---|---|---|---|---|---|---|---|---|
| Least Detectable Dose | 4.0 | 0.015 | 15 | 1.2 | 94 | 57 | 1.3 | 66 | 2.7 |
| RBM Low Plasma Range | 177 | 0.24 | 1.8 | | | | | 232 | PENDING |
| RBM High Plasma Range | | 3.3 | 38 | 2.7 | 165 | 133 | 4.6 | 3380 | PENDING |
| Donor_1 3. Aliquot A | 49 | 0.63 | 180 | 0.30 | 45 | 36 | 0.41 | 575 | 6.7 |
| Donor_1 3. Aliquot B | 49 | 0.66 | 135 | 0.16 | 35 | 37 | 0.40 | 535 | 2.7 |
| Donor_1 3. Aliquot C | 67 | 0.68 | 15 | 1.2 | 28 | 38 | 0.33 | 413 | 2.7 |
| Donor_1 3. Aliquot D | 46 | 0.71 | 134 | 0.43 | 42 | 21 | 0.45 | 619 | 2.7 |
| Donor_1 3. Aliquot E | 45 | 0.63 | 58 | 0.13 | 37 | 34 | 0.32 | 580 | 2.7 |
| Donor_1 3. Aliquot F | 55 | 0.60 | 18 | 1.2 | 28 | 36 | 0.30 | 502 | 2.7 |
| Donor_1 3. Aliquot G | 100 | 0.70 | 15 | 0.19 | 39 | 37 | 0.50 | 216 | 7.5 |
| Donor_1 3. Aliquot H | 46 | 0.60 | 14 | 1.2 | 52 | 35 | 0.28 | 299 | 2.7 |
| Donor_1 3. Aliquot I | 46 | 0.65 | 16 | 1.2 | 32 | 33 | 0.26 | 588 | 2.7 |
| Donor_2 3. Aliquot A | 94 | 0.15 | 500 | 0.51 | 61 | 37 | 0.41 | 654 | 2.7 |
| Donor_2 3. Aliquot B | 90 | 0.15 | 483 | 0.26 | 35 | 37 | 0.43 | 712 | 2.7 |
| Donor_2 3. Aliquot C | 87 | 0.21 | 19 | 1.2 | 18 | 29 | 0.32 | 609 | 2.7 |
| Donor_2 3. Aliquot D | 81 | 0.14 | 977 | 2.8 | 40 | 29 | 0.50 | 804 | 2.7 |
| Donor_2 3. Aliquot E | 86 | 0.18 | 963 | 2.4 | 37 | 36 | 0.37 | 782 | 2.7 |
| Donor_2 3. Aliquot F | 73 | 0.17 | 28 | 0.26 | 45 | 66 | 0.50 | 720 | 2.7 |
| Donor_2 3. Aliquot G | 221 | 0.18 | 131 | 0.88 | 45 | 40 | 0.66 | 432 | 2.7 |
| Donor_2 3. Aliquot H | 75 | 0.18 | 22 | 1.2 | 35 | 27 | 1.3 | 393 | 2.7 |
| Donor_2 3. Aliquot I | 73 | 0.19 | 21 | 1.2 | 35 | 36 | 0.21 | 642 | 2.7 |
| Donor_3 3. Aliquot A | 380 | 0.66 | 480 | 0.43 | 50 | 49 | 0.53 | 1310 | 2.7 |
| Donor_3 3. Aliquot B | 368 | 0.67 | 632 | 0.37 | 48 | 43 | 0.56 | 1230 | 2.7 |
| Donor_3 3. Aliquot C | 408 | 0.66 | 26 | 0.13 | 55 | 57 | 0.41 | 1190 | 2.7 |
| Donor_3 3. Aliquot D | 387 | 0.67 | 1640 | 3.3 | 45 | 40 | 0.47 | 1410 | 2.7 |
| Donor_3 3. Aliquot E | 393 | 0.74 | 1660 | 2.7 | 55 | 39 | 0.47 | 1490 | 2.7 |

FIG. 16H.2

| | IGF-1 ng/mL | IgM mg/mL | IL-10 pg/mL | IL-12p40 ng/mL | IL-12p70 pg/mL | IL-13 pg/mL | IL-15 ng/mL | IL-16 pg/mL | IL-17 pg/mL |
|---|---|---|---|---|---|---|---|---|---|
| Least Detectable Dose | 4.0 | 0.015 | 15 | 1.2 | 94 | 57 | 1.3 | 66 | 2.7 |
| RBM Low Plasma Range | 177 | 0.24 | 1.8 | | | | | 232 | PENDING |
| RBM High Plasma Range | | 3.3 | 38 | 2.7 | 165 | 133 | 4.6 | 3380 | PENDING |
| Donor_3 3. Aliquot F | 338 | 0.69 | 18 | 1.2 | 40 | 51 | 0.28 | 1340 | 2.7 |
| Donor_3 3. Aliquot G | 546 | 0.72 | 11 | 1.2 | 35 | 43 | 0.32 | 556 | 2.7 |
| Donor_3 3. Aliquot H | 386 | 0.67 | 4.9 | 1.2 | 22 | 55 | 0.28 | 706 | 2.7 |
| Donor_3 3. Aliquot I | 403 | 0.69 | 11 | 1.2 | 42 | 81 | 0.47 | 1280 | 2.7 |
| Donor_4 3. Aliquot A | 4 | 0.39 | 46 | 1.2 | 94 | 36 | 0.38 | 1240 | 2.7 |
| Donor_4 3. Aliquot B | 4 | 0.29 | 251 | 1.2 | 94 | 19 | 0.56 | 1130 | 2.7 |
| Donor_4 3. Aliquot C | 4 | 0.36 | 11 | 1.2 | 39 | 27 | 0.32 | 1050 | 2.7 |
| Donor_4 3. Aliquot D | 4 | 0.31 | 566 | 3.1 | 39 | 38 | 0.43 | 986 | 2.7 |
| Donor_4 3. Aliquot E | 4 | 0.29 | 543 | 1.5 | 30 | 23 | 0.56 | 812 | 2.7 |
| Donor_4 3. Aliquot F | 4 | 0.31 | 232 | 0.37 | 24 | 28 | 0.47 | 1030 | 2.7 |
| Donor_4 3. Aliquot G | 22 | 0.29 | 14 | 1.2 | 20 | 29 | 0.24 | 431 | 2.7 |
| Donor_4 3. Aliquot H | 4 | 0.28 | 10 | 1.2 | 15 | 9.7 | 0.19 | 564 | 2.7 |
| Donor_4 3. Aliquot I | 4 | 0.30 | 13 | 1.2 | 94 | 24 | 0.24 | 1150 | 2.7 |
| Donor_5 3. Aliquot A | 323 | 0.24 | 117 | 0.34 | 20 | 33 | 0.71 | 536 | 2.7 |
| Donor_5 3. Aliquot B | 337 | 0.25 | 417 | 0.26 | 32 | 32 | 0.50 | 584 | 2.7 |
| Donor_5 3. Aliquot C | 330 | 0.24 | 7.0 | 1.2 | 26 | 48 | 0.50 | 455 | 2.7 |
| Donor_5 3. Aliquot D | 373 | 0.22 | 763 | 2.7 | 59 | 32 | 0.73 | 592 | 2.7 |
| Donor_5 3. Aliquot E | 382 | 0.23 | 1520 | 1.8 | 94 | 36 | 0.68 | 561 | 2.7 |
| Donor_5 3. Aliquot F | 350 | 0.23 | 37 | 1.2 | 20 | 38 | 0.28 | 430 | 2.7 |
| Donor_5 3. Aliquot G | 574 | 0.26 | 15 | 0.28 | 24 | 29 | 0.26 | 323 | 2.7 |
| Donor_5 3. Aliquot H | 355 | 0.26 | 10 | 1.2 | 28 | 27 | 0.19 | 390 | 2.7 |
| Donor_5 3. Aliquot I | 329 | 0.24 | 9.2 | 1.2 | 44 | 47 | 0.13 | 492 | 2.7 |
| Donor_6 3. Aliquot A | 47 | 0.38 | 85 | 0.13 | 32 | 70 | 0.32 | 1030 | 2.7 |
| Donor_6 3. Aliquot B | 46 | 0.42 | 226 | 1.2 | 42 | 57 | 0.24 | 828 | 2.7 |

FIG. 16H.3

| | IGF-1 ng/mL | IgM mg/mL | IL-10 pg/mL | IL-12p40 ng/mL | IL-12p70 pg/mL | IL-13 pg/mL | IL-15 ng/mL | IL-16 pg/mL | IL-17 pg/mL |
|---|---|---|---|---|---|---|---|---|---|
| Least Detectable Dose | 4.0 | 0.015 | 15 | 1.2 | 94 | 57 | 1.3 | 66 | 2.7 |
| RBM Low Plasma Range | | 0.24 | 1.8 | | | | | 232 | PENDING |
| RBM High Plasma Range | 177 | 3.3 | 38 | 2.7 | 165 | 133 | 4.6 | 3380 | PENDING |
| Donor_6_3. Aliquot C | 54 | 0.37 | 7.0 | 1.2 | 50 | 59 | 0.24 | 1150 | 2.7 |
| Donor_6_3. Aliquot D | 47 | 0.41 | 637 | 4.7 | 94 | 68 | 0.56 | 682 | 2.7 |
| Donor_6_3. Aliquot E | 50 | 0.34 | 1870 | 4.3 | 30 | 68 | 0.16 | 648 | 2.7 |
| Donor_6_3. Aliquot F | 45 | 0.33 | 45 | 1.2 | 47 | 86 | 0.43 | 969 | 2.7 |
| Donor_6_3. Aliquot G | 189 | 0.35 | 7.0 | 1.2 | 20 | 65 | 1.3 | 439 | 2.7 |
| Donor_6_3. Aliquot H | 42 | 0.35 | 6.0 | 0.16 | 94 | 65 | 0.19 | 815 | 5.0 |
| Donor_6_3. Aliquot I | 45 | 0.34 | 7.0 | 1.2 | 94 | 59 | 0.28 | 1230 | 2.7 |
| Donor_7_3. Aliquot A | 14 | 0.63 | 379 | 0.64 | 39 | 91 | 0.79 | 664 | 2.7 |
| Donor_7_3. Aliquot B | 18 | 0.59 | 441 | 0.27 | 32 | 103 | 0.78 | 620 | 2.7 |
| Donor_7_3. Aliquot C | 26 | 0.63 | 13 | 1.2 | 39 | 70 | 0.53 | 817 | 2.7 |
| Donor_7_3. Aliquot D | 15 | 0.59 | 390 | 0.93 | 39 | 82 | 0.49 | 662 | 2.7 |
| Donor_7_3. Aliquot E | 17 | 0.48 | 297 | 0.93 | 42 | 104 | 0.58 | 651 | 2.7 |
| Donor_7_3. Aliquot F | 9.8 | 0.66 | 85 | 1.2 | 34 | 105 | 0.54 | 856 | 2.7 |
| Donor_7_3. Aliquot G | 98 | 0.60 | 13 | 1.2 | 22 | 56 | 0.19 | 428 | 2.7 |
| Donor_7_3. Aliquot H | 8.1 | 0.60 | 6.8 | 1.2 | 94 | 62 | 0.38 | 574 | 2.7 |
| Donor_7_3. Aliquot I | 12 | 0.60 | 11 | 1.2 | 94 | 88 | 0.41 | 918 | 2.7 |
| Donor_8_3. Aliquot A | 176 | 0.30 | 102 | 0.30 | 34 | 81 | 0.32 | 340 | 2.7 |
| Donor_8_3. Aliquot B | 168 | 0.34 | 218 | 0.19 | 22 | 97 | 0.24 | 341 | 2.7 |
| Donor_8_3. Aliquot C | 163 | 0.31 | 4.9 | 0.57 | 3920 | 80 | 0.32 | 309 | 2.7 |
| Donor_8_3. Aliquot D | 179 | 0.36 | 306 | 19 | 434 | 99 | 0.61 | 754 | 5.0 |
| Donor_8_3. Aliquot E | 162 | 0.32 | 1000 | 14 | 48 | 99 | 0.64 | 533 | 9.7 |
| Donor_8_3. Aliquot F | 166 | 0.32 | 219 | 0.71 | 42 | 111 | 0.45 | 410 | 4.2 |
| Donor_8_3. Aliquot G | 181 | 0.28 | 4.3 | 1.2 | 15 | 53 | 0.19 | 183 | 5.4 |
| Donor_8_3. Aliquot H | 177 | 0.37 | 4.1 | 0.23 | 30 | 75 | 0.28 | 231 | 2.7 |
| Donor_8_3. Aliquot I | 175 | 0.33 | 6.6 | 1.2 | 32 | 80 | 0.32 | 522 | 2.7 |

FIG. 16H.4

| | IGF-1 ng/mL | IgM mg/mL | IL-10 pg/mL | IL-12p40 ng/mL | IL-12p70 pg/mL | IL-13 pg/mL | IL-15 ng/mL | IL-16 pg/mL | IL-17 pg/mL |
|---|---|---|---|---|---|---|---|---|---|
| Least Detectable Dose | 4.0 | 0.015 | 15 | 1.2 | 94 | 57 | 1.3 | 66 | 2.7 |
| RBM Low Plasma Range | | 0.24 | 1.8 | | | | | 232 | PENDING |
| RBM High Plasma Range | 177 | 3.3 | 38 | 2.7 | 165 | 133 | 4.6 | 3380 | PENDING |
| Donor_9_3. Aliquot A | 745 | 1.0 | 220 | 0.26 | 52 | 68 | 0.31 | 463 | 17 |
| Donor_9_3. Aliquot B | 716 | 1.0 | 435 | 0.40 | 44 | 77 | 0.44 | 398 | 7.2 |
| Donor_9_3. Aliquot C | 784 | 0.97 | 43 | 0.80 | 1480 | 74 | 0.35 | 407 | 2.7 |
| Donor_9_3. Aliquot D | 681 | 1.0 | 1080 | 17 | 89 | 71 | 0.51 | 780 | 8.1 |
| Donor_9_3. Aliquot E | 651 | 1.0 | 1730 | 11 | 54 | 68 | 0.31 | 538 | 22 |
| Donor_9_3. Aliquot F | 688 | 0.95 | 122 | 0.34 | 46 | 83 | 0.30 | 369 | 13 |
| Donor_9_3. Aliquot G | 636 | 1.1 | 13 | 0.25 | 41 | 36 | 0.31 | 411 | 22 |
| Donor_9_3. Aliquot H | 703 | 1.0 | 14 | 0.24 | 56 | 51 | 0.56 | 369 | 9.8 |
| Donor_9_3. Aliquot I | 732 | 1.1 | 4.2 | 1.2 | 31 | 56 | 0.22 | 455 | 8.1 |
| EDTA Plasma | | | | | | | | | |
| donor #1 plasma | 4 | 0.57 | 16 | 0.26 | 34 | 39 | 0.30 | 329 | 11 |
| donor #2 plasma | 4 | 0.22 | 21 | 0.19 | 23 | 24 | 0.13 | 620 | 2.7 |
| donor #3 plasma | 12 | 0.93 | 9.9 | 1.2 | 49 | 37 | 0.39 | 892 | 2.7 |
| donor #4 plasma | 4 | 0.39 | 14 | 1.2 | 33 | 50 | 0.29 | 794 | 2.7 |
| donor #5 plasma | 18 | 0.32 | 12 | 0.15 | 56 | 37 | 0.64 | 314 | 2.7 |
| donor #6 plasma | 4 | 0.43 | 10 | 1.2 | 34 | 40 | 0.29 | 277 | 11 |
| donor #7 plasma | 4 | 0.79 | 16 | 1.2 | 23 | 39 | 0.29 | 514 | 2.7 |
| donor #8 plasma | 32 | 0.38 | 2.3 | 1.2 | 39 | 50 | 0.31 | 208 | 2.7 |
| donor #9 plasma | 325 | 1.5 | 5.1 | 0.14 | 35 | 41 | 0.18 | 327 | 2.7 |
| MW NHD plasma Normal healthy donors | 178.4 | 1.0 | 3.7 | 0.7 | 37.1 | 45.3 | 0.2 | 267.5 | 2.7 |
| MW NHD unstimuliert | 453.50 | 0.69 | 5.41 | 1.20 | 31.25 | 68.05 | 0.27 | 488.50 | 5.40 |

FIG. 16H.5

|  |  | IGF-1 ng/mL | IgM mg/mL | IL-10 pg/mL | IL-12p40 ng/mL | IL-12p70 pg/mL | IL-13 pg/mL | IL-15 ng/mL | IL-16 pg/mL | IL-17 pg/mL |
|---|---|---|---|---|---|---|---|---|---|---|
|  | Least Detectable Dose | 4.0 | 0.015 | 15 | 1.2 | 94 | 57 | 1.3 | 66 | 2.7 |
|  | RBM Low Plasma Range |  | 0.24 | 1.8 |  |  |  |  | 232 | PENDING |
|  | RBM High Plasma Range | 177 | 3.3 | 38 | 2.7 | 165 | 133 | 4.6 | 3380 | PENDING |
| Normal healthy donors |  |  |  |  |  |  |  |  |  |  |
|  | Stimulations indices | IGF-1 | IgM | IL-10 | IL-12p40 | IL-12p70 | IL-13 | IL-15 | IL-16 | IL-17 |
| unstimuliert | Donor_1 3. Aliquot I | 0.1 | 0.9 | 3.0 | 1.0 | 1.0 | 0.5 | 1.0 | 1.2 | 0.5 |
| unstimuliert | Donor_2 3. Aliquot I | 0.2 | 0.3 | 3.8 | 1.0 | 1.1 | 0.5 | 0.8 | 1.3 | 0.5 |
| unstimuliert | Donor_3 3. Aliquot I | 0.9 | 1.0 | 2.0 | 1.0 | 1.3 | 1.2 | 1.8 | 2.6 | 0.5 |
| unstimuliert | Donor_4 3. Aliquot I | 0.0 | 0.4 | 2.4 | 1.0 | 3.0 | 0.4 | 0.9 | 2.4 | 0.5 |
| unstimuliert | Donor_5 3. Aliquot I | 0.7 | 0.3 | 1.7 | 1.0 | 1.4 | 0.7 | 0.5 | 1.0 | 0.5 |
| unstimuliert | Donor_6 3. Aliquot I | 0.1 | 0.5 | 1.3 | 1.0 | 3.0 | 0.9 | 1.0 | 2.5 | 0.5 |
| unstimuliert | Donor_7 3. Aliquot I | 0.0 | 0.9 | 2.1 | 1.0 | 3.0 | 1.3 | 1.5 | 1.9 | 0.5 |
| unstimuliert | Donor_8 3. Aliquot I | 0.4 | 0.5 | 1.2 | 1.0 | 1.0 | 1.2 | 1.2 | 1.1 | 0.5 |
| unstimuliert | Donor_9 3. Aliquot I | 1.6 | 1.5 | 0.8 | 1.0 | 1.0 | 0.8 | 0.8 | 0.9 | 1.5 |
|  | Stimulations indices |  |  |  |  |  |  |  |  |  |
|  | EDTA Plasma |  |  |  |  |  |  |  |  |  |
| PLASMA | donor #1 plasma | 0.0 | 0.6 | 4.4 | 0.4 | 0.9 | 0.9 | 1.2 | 1.2 | 4.1 |
| PLASMA | donor #2 plasma | 0.0 | 0.2 | 5.7 | 0.3 | 0.6 | 0.5 | 0.5 | 2.3 | 1.0 |
| PLASMA | donor #3 plasma | 0.1 | 1.0 | 2.7 | 1.8 | 1.3 | 0.8 | 1.6 | 3.3 | 1.0 |
| PLASMA | donor #4 plasma | 0.0 | 0.4 | 3.8 | 1.8 | 0.9 | 1.1 | 1.2 | 3.0 | 1.0 |
| PLASMA | donor #5 plasma | 0.1 | 0.3 | 3.2 | 0.2 | 1.5 | 0.8 | 2.6 | 1.2 | 1.0 |
| PLASMA | donor #6 plasma | 0.0 | 0.4 | 2.7 | 1.8 | 0.9 | 0.9 | 1.2 | 1.0 | 4.1 |
| PLASMA | donor #7 plasma | 0.0 | 0.8 | 4.2 | 1.8 | 0.6 | 0.9 | 1.2 | 1.9 | 1.0 |
| PLASMA | donor #8 plasma | 0.2 | 0.4 | 0.6 | 1.8 | 1.0 | 1.1 | 1.3 | 0.8 | 1.0 |

FIG. 16H.6

| | | IGF-1 ng/mL | IgM mg/mL | IL-10 pg/mL | IL-12p40 ng/mL | IL-12p70 pg/mL | IL-13 pg/mL | IL-15 ng/mL | IL-16 pg/mL | IL-17 pg/mL |
|---|---|---|---|---|---|---|---|---|---|---|
| | Least Detectable Dose | 4.0 | 0.015 | 15 | 1.2 | 94 | 57 | 1.3 | 66 | 2.7 |
| | RBM Low Plasma Range | | 0.24 | 1.8 | | | | | 232 | PENDING |
| | RBM High Plasma Range | 177 | 3.3 | 38 | 2.7 | 165 | 133 | 4.6 | 3380 | PENDING |
| PLASMA | donor #9 plasma | 1.8 | 1.6 | 1.4 | 0.2 | 1.0 | 0.9 | 0.7 | 1.2 | 1.0 |

FIG. 16I.1

| | IL-17E pg/mL 31 | IL-18 pg/mL 54 | IL-1alpha ng/mL 0.16 | IL-1beta pg/mL 1.5 | IL-1ra pg/mL 15 | IL-2 pg/mL 60 | IL-23 ng/mL <0.67 | IL-3 ng/mL 0.17 |
|---|---|---|---|---|---|---|---|---|
| Least Detectable Dose | | | | | | | | |
| RBM Low Plasma Range | PENDING | 72 | | | 17 | | PENDING | |
| RBM High Plasma Range | PENDING | 1020 | 0.35 | 8.7 | 622 | 61 | PENDING | 1.2 |
| Samples | | | | | | | | |
| Donor_1_3. Aliquot A | 643 | 1930 | 0.0025 | 75 | 3780 | 60 | 3.7 | 0.027 |
| Donor_1_3. Aliquot B | 559 | 1910 | 0.16 | 50 | 2300 | 60 | 1.2 | 0.17 |
| Donor_1_3. Aliquot C | 62 | 1980 | 0.16 | 4.4 | 987 | 60 | 0.67 | 0.17 |
| Donor_1_3. Aliquot D | 580 | 2080 | 0.0077 | 348 | 4230 | 60 | 0.67 | 0.17 |
| Donor_1_3. Aliquot E | 604 | 2140 | 0.16 | 69 | 2740 | 60 | 0.67 | 0.17 |
| Donor_1_3. Aliquot F | 486 | 1630 | 0.16 | 10 | 1040 | 60 | 1.2 | 0.17 |
| Donor_1_3. Aliquot G | 646 | 2130 | 0.16 | 6.8 | 2830 | 60 | 2.1 | 0.17 |
| Donor_1_3. Aliquot H | 56 | 1860 | 0.16 | 4.6 | 944 | 60 | 1.9 | 0.17 |
| Donor_1_3. Aliquot I | 502 | 1810 | 0.16 | 5.4 | 660 | 60 | 0.67 | 0.17 |
| Donor_2_3. Aliquot A | 29 | 631 | 0.012 | 132 | 16500 | 60 | 1.2 | 0.12 |
| Donor_2_3. Aliquot B | 40 | 709 | 0.0057 | 71 | 15500 | 60 | 0.67 | 0.095 |
| Donor_2_3. Aliquot C | 11 | 616 | 0.16 | 4.7 | 2000 | 60 | 0.67 | 0.17 |
| Donor_2_3. Aliquot D | 37 | 830 | 0.36 | 5020 | 54600 | 60 | 2.3 | 0.19 |
| Donor_2_3. Aliquot E | 29 | 754 | 0.11 | 1310 | 52400 | 60 | 2.5 | 0.21 |
| Donor_2_3. Aliquot F | 17 | 594 | 0.0034 | 32 | 3140 | 60 | 0.67 | 0.17 |
| Donor_2_3. Aliquot G | 31 | 681 | 0.045 | 387 | 6790 | 60 | 0.67 | 0.14 |
| Donor_2_3. Aliquot H | 23 | 595 | 0.16 | 9.7 | 4400 | 60 | 0.67 | 0.17 |
| Donor_2_3. Aliquot I | 34 | 538 | 0.16 | 6.6 | 2520 | 60 | 0.67 | 0.17 |
| Donor_3_3. Aliquot A | 17 | 766 | 0.0054 | 62 | 12900 | 60 | 0.67 | 0.12 |
| Donor_3_3. Aliquot B | 34 | 720 | 0.0056 | 32 | 11000 | 60 | 2.1 | 0.099 |
| Donor_3_3. Aliquot C | 29 | 715 | 0.0036 | 5.3 | 2970 | 60 | 2.1 | 0.17 |
| Donor_3_3. Aliquot D | 37 | 735 | 0.074 | 3890 | 41000 | 60 | 0.67 | 0.15 |
| Donor_3_3. Aliquot E | 29 | 798 | 0.039 | 1610 | 32900 | 60 | 3.4 | 0.14 |

FIG. 16I.2

|  | IL-17E pg/mL | IL-18 pg/mL | IL-1alpha ng/mL | IL-1beta pg/mL | IL-1ra pg/mL | IL-2 pg/mL | IL-23 ng/mL | IL-3 ng/mL |
|---|---|---|---|---|---|---|---|---|
| Least Detectable Dose | 31 | 54 | 0.16 | 1.5 | 15 | 60 | <0.67 | 0.17 |
| RBM Low Plasma Range | PENDING |  |  |  |  |  | PENDING | |
| RBM High Plasma Range | PENDING | 72 | 0.35 | 8.7 | 17 | 61 | PENDING | 1.2 |
| Donor_3 3. Aliquot F | 29 | 1020 | 0.0050 | 18 | 622 | 60 | 1.2 | 0.050 |
| Donor_3 3. Aliquot G | 29 | 694 | 0.0045 | 8.6 | 3850 | 60 | 0.67 | 0.17 |
| Donor_3 3. Aliquot H | 31 | 766 | 0.0029 | 2.2 | 3260 | 60 | 0.67 | 0.17 |
| Donor_3 3. Aliquot I | 45 | 553 | 0.0043 | 1.5 | 1010 | 60 | 2.1 | 0.087 |
|  |  | 627 |  |  | 79 |  |  |  |
| Donor_4 3. Aliquot A | 42 | 690 | 0.16 | 7.3 | 2670 | 60 | 0.67 | 0.17 |
| Donor_4 3. Aliquot B | 40 | 700 | 0.16 | 46 | 3450 | 60 | 2.1 | 0.17 |
| Donor_4 3. Aliquot C | 56 | 608 | 0.16 | 3.8 | 336 | 60 | 2.1 | 0.17 |
| Donor_4 3. Aliquot D | 29 | 724 | 0.29 | 2830 | 13700 | 60 | 0.67 | 0.039 |
| Donor_4 3. Aliquot E | 51 | 633 | 0.075 | 957 | 13100 | 60 | 0.67 | 0.087 |
| Donor_4 3. Aliquot F | 51 | 623 | 0.0036 | 47 | 12900 | 60 | 0.67 | 0.17 |
| Donor_4 3. Aliquot G | 56 | 612 | 0.0025 | 7.0 | 2530 | 60 | 2.5 | 0.17 |
| Donor_4 3. Aliquot H | 62 | 566 | 0.16 | 4.1 | 1670 | 60 | 1.6 | 0.17 |
| Donor_4 3. Aliquot I | 62 | 597 | 0.16 | 0.63 | 228 | 60 | 2.1 | 0.17 |
| Donor_5 3. Aliquot A | 74 | 340 | 0.0066 | 73 | 22900 | 60 | 0.67 | 0.099 |
| Donor_5 3. Aliquot B | 40 | 295 | 0.0094 | 75 | 22500 | 60 | 0.67 | 0.11 |
| Donor_5 3. Aliquot C | 20 | 271 | 0.16 | 3.0 | 2100 | 60 | 1.4 | 0.17 |
| Donor_5 3. Aliquot D | 17 | 428 | 0.35 | 3910 | 53300 | 60 | 0.67 | 0.19 |
| Donor_5 3. Aliquot E | 11 | 467 | 0.32 | 3280 | 51000 | 60 | 0.67 | 0.15 |
| Donor_5 3. Aliquot F | 31 | 216 | 0.0043 | 73 | 11100 | 60 | 0.67 | 0.17 |
| Donor_5 3. Aliquot G | 45 | 479 | 0.0048 | 36 | 16700 | 60 | 1.6 | 0.17 |
| Donor_5 3. Aliquot H | 31 | 367 | 0.16 | 15 | 9910 | 60 | 2.5 | 0.17 |
| Donor_5 3. Aliquot I | 34 | 255 | 0.16 | 2.8 | 3530 | 60 | 1.6 | 0.17 |
| Donor_6 3. Aliquot A | 29 | 102 | 0.0052 | 35 | 7350 | 60 | 0.67 | 0.11 |
| Donor_6 3. Aliquot B | 51 | 95 | 0.012 | 46 | 9190 | 60 | 0.67 | 0.11 |

FIG. 16I.3

| | IL-17E pg/mL | IL-18 pg/mL | IL-1alpha ng/mL | IL-1beta pg/mL | IL-1ra pg/mL | IL-2 pg/mL | IL-23 ng/mL | IL-3 ng/mL |
|---|---|---|---|---|---|---|---|---|
| Least Detectable Dose | 31 | 54 | 0.16 | 1.5 | 15 | 60 | <0.67 | 0.17 |
| RBM Low Plasma Range | PENDING | 72 | | | 17 | | PENDING | |
| RBM High Plasma Range | PENDING | 1020 | 0.35 | 8.7 | 622 | 61 | PENDING | 1.2 |
| Donor_6 3. Aliquot C | 11 | 98 | 0.0050 | 1.5 | 1220 | 60 | 0.67 | 0.081 |
| Donor_6 3. Aliquot D | 17 | 138 | 0.21 | 1870 | 26100 | 60 | 0.67 | 0.13 |
| Donor_6 3. Aliquot E | 17 | 134 | 0.41 | 3760 | 31600 | 60 | 1.2 | 0.10 |
| Donor_6 3. Aliquot F | 31 | 113 | 0.0073 | 43 | 4970 | 60 | 0.67 | 0.12 |
| Donor_6 3. Aliquot G | 11 | 170 | 0.0043 | 27 | 9870 | 60 | 0.67 | 0.032 |
| Donor_6 3. Aliquot H | 54 | 107 | 0.16 | 2.8 | 1530 | 60 | 3.7 | 0.025 |
| Donor_6 3. Aliquot I | 62 | 87 | 0.16 | 1.3 | 202 | 60 | 0.67 | 0.17 |
| Donor_7 3. Aliquot A | 40 | 295 | 0.025 | 147 | 6320 | 60 | 0.67 | 0.27 |
| Donor_7 3. Aliquot B | 34 | 277 | 0.015 | 99 | 4590 | 60 | 0.67 | 0.21 |
| Donor_7 3. Aliquot C | 17 | 255 | 0.010 | 16 | 244 | 60 | 0.67 | 0.037 |
| Donor_7 3. Aliquot D | 23 | 275 | 0.31 | 2120 | 11000 | 60 | 0.67 | 0.15 |
| Donor_7 3. Aliquot E | 62 | 298 | 0.071 | 548 | 7580 | 60 | 0.67 | 0.16 |
| Donor_7 3. Aliquot F | 31 | 209 | 0.016 | 20 | 578 | 60 | 0.67 | 0.12 |
| Donor_7 3. Aliquot G | 85 | 300 | 0.0054 | 6.2 | 2730 | 60 | 0.67 | 0.17 |
| Donor_7 3. Aliquot H | 31 | 214 | 0.0057 | 3.4 | 361 | 60 | 0.67 | 0.17 |
| Donor_7 3. Aliquot I | 26 | 227 | 0.0066 | 1.5 | 61 | 60 | 1.2 | 0.044 |
| Donor_8 3. Aliquot A | 17 | 150 | 0.0073 | 73 | 3870 | 60 | 1.6 | 0.083 |
| Donor_8 3. Aliquot B | 31 | 173 | 0.0089 | 59 | 3010 | 60 | 0.67 | 0.12 |
| Donor_8 3. Aliquot C | 31 | 157 | 0.0071 | 76 | 10200 | 60 | 0.67 | 0.12 |
| Donor_8 3. Aliquot D | 17 | 408 | 0.28 | 24700 | 11400 | 60 | 3.0 | 0.18 |
| Donor_8 3. Aliquot E | 45 | 359 | 0.27 | 17500 | 12800 | 60 | 1.6 | 0.11 |
| Donor_8 3. Aliquot F | 31 | 175 | 0.013 | 204 | 16400 | 60 | 3.0 | 0.25 |
| Donor_8 3. Aliquot G | 23 | 152 | 0.16 | 32 | 4000 | 60 | 1.6 | 0.025 |
| Donor_8 3. Aliquot H | 17 | 220 | 0.0041 | 75 | 7720 | 60 | 0.67 | 0.081 |
| Donor_8 3. Aliquot I | 29 | 195 | 0.0061 | 7.9 | 839 | 60 | 1.2 | 0.12 |

FIG. 16I.4

| | IL-17E pg/mL | IL-18 pg/mL | IL-1alpha ng/mL | IL-1beta pg/mL | IL-1ra pg/mL | IL-2 pg/mL | IL-23 ng/mL | IL-3 ng/mL |
|---|---|---|---|---|---|---|---|---|
| Least Detectable Dose | 31 | 54 | 0.16 | 1.5 | 15 | 60 | <0.67 | 0.17 |
| RBM Low Plasma Range | PENDING | 72 | | | 17 | | PENDING | |
| RBM High Plasma Range | PENDING | 1020 | 0.35 | 8.7 | 622 | 61 | PENDING | 1.2 |
| | | | | | | | | |
| Donor_9_3. Aliquot A | 34 | 58 | 0.0080 | 29 | 3980 | 60 | 5.8 | 0.14 |
| Donor_9_3. Aliquot B | 66 | 48 | 0.013 | 42 | 4200 | 60 | 1.1 | 0.21 |
| Donor_9_3. Aliquot C | 83 | 52 | 0.018 | 67 | 9410 | 60 | 0.67 | 0.20 |
| Donor_9_3. Aliquot D | 44 | 340 | 2.6 | 26100 | 18300 | 60 | 2.4 | 0.21 |
| Donor_9_3. Aliquot E | 55 | 161 | 0.80 | 7830 | 15100 | 60 | 0.67 | 0.17 |
| Donor_9_3. Aliquot F | 28 | 38 | 0.011 | 60 | 12700 | 60 | 0.67 | 0.18 |
| Donor_9_3. Aliquot G | 44 | 92 | 0.0075 | 48 | 8240 | 60 | 0.67 | 0.11 |
| Donor_9_3. Aliquot H | 77 | 96 | 0.0086 | 39 | 4920 | 60 | 0.67 | 0.098 |
| Donor_9_3. Aliquot I | 83 | 69 | 0.0035 | 5.7 | 2110 | 60 | 1.7 | 0.10 |
| | | | | | | | | |
| EDTA Plasma | | | | | | | | |
| donor #1 plasma | 228 | 1670 | 0.16 | 2.8 | 1800 | 60 | 3.4 | 0.17 |
| donor #2 plasma | 31 | 628 | 0.16 | 1.5 | 555 | 60 | 1.1 | 0.17 |
| donor #3 plasma | 34 | 644 | 0.0027 | 1.1 | 137 | 60 | 2.7 | 0.17 |
| donor #4 plasma | 31 | 805 | 0.16 | 1.5 | 410 | 60 | 2.4 | 0.17 |
| donor #5 plasma | 31 | 188 | 0.16 | 1.5 | 354 | 60 | 1.7 | 0.17 |
| donor #6 plasma | 44 | 112 | 0.16 | 1.5 | 84 | 60 | 1.9 | 0.17 |
| donor #7 plasma | 28 | 404 | 0.16 | 1.5 | 559 | 60 | 0.67 | 0.17 |
| donor #8 plasma | 31 | 196 | 0.0035 | 1.4 | 68 | 60 | 0.67 | 0.14 |
| donor #9 plasma | 44 | 104 | 0.0032 | 1.5 | 80 | 60 | 1.7 | 0.042 |
| | | | | | | | | |
| MW NHD plasma Normal healthy donors | 37.7 | 150.0 | 0.0 | 1.5 | 73.7 | 60.0 | 1.2 | 0.1 |
| | | | | | | | | |
| MW NHD unstimuliert | 55.55 | 132.10 | 0.00 | 6.81 | 1474.50 | 60.00 | 1.42 | 0.11 |

FIG. 161.5

| | | IL-17E pg/mL | IL-18 pg/mL | IL-1alpha ng/mL | IL-1beta pg/mL | IL-1ra pg/mL | IL-2 pg/mL | IL-23 ng/mL | IL-3 ng/mL |
|---|---|---|---|---|---|---|---|---|---|
| | Least Detectable Dose | 31 | 54 | 0.16 | 1.5 | 15 | 60 | <0.67 | 0.17 |
| | RBM Low Plasma Range | PENDING | 72 | | | 17 | | PENDING | |
| | RBM High Plasma Range | PENDING | 1020 | 0.35 | 8.7 | 622 | 61 | PENDING | 1.2 |
| Normal healthy donors | | | | | | | | | |
| | Stimulations indices | IL-17E | IL-18 | IL-1alpha | IL-1beta | IL-1ra | IL-2 | IL-23 | IL-3 |
| unstimuliert | Donor_1 3. Aliquot I | 9.0 | 13.7 | 33.2 | 0.8 | 0.4 | 1.0 | 0.5 | 1.6 |
| unstimuliert | Donor_2 3. Aliquot I | 0.6 | 4.1 | 33.2 | 1.0 | 1.7 | 1.0 | 0.5 | 1.6 |
| unstimuliert | Donor_3 3. Aliquot I | 0.8 | 4.7 | 0.9 | 0.2 | 0.1 | 1.0 | 1.5 | 0.8 |
| unstimuliert | Donor_4 3. Aliquot I | 1.1 | 4.5 | 33.2 | 0.1 | 0.2 | 1.0 | 1.5 | 1.6 |
| unstimuliert | Donor_5 3. Aliquot I | 0.6 | 1.9 | 33.2 | 0.4 | 2.4 | 1.0 | 1.2 | 1.6 |
| unstimuliert | Donor_6 3. Aliquot I | 1.1 | 0.7 | 33.2 | 0.2 | 0.1 | 1.0 | 0.5 | 1.6 |
| unstimuliert | Donor_7 3. Aliquot I | 0.5 | 1.7 | 1.4 | 0.2 | 0.0 | 1.0 | 0.8 | 0.4 |
| unstimuliert | Donor_8 3. Aliquot I | 0.5 | 1.5 | 1.3 | 1.2 | 0.6 | 1.0 | 0.8 | 1.1 |
| unstimuliert | Donor_9 3. Aliquot I | 1.5 | 0.5 | 0.7 | 0.8 | 1.4 | 1.0 | 1.2 | 0.9 |
| | Stimulations indices | | | | | | | | |
| | EDTA Plasma | | | | | | | | |
| PLASMA | donor #1 plasma | 6.0 | 11.1 | 47.3 | 1.9 | 24.4 | 1.0 | 2.9 | 1.8 |
| PLASMA | donor #2 plasma | 0.8 | 4.2 | 47.3 | 1.0 | 7.5 | 1.0 | 1.0 | 1.8 |
| PLASMA | donor #3 plasma | 0.9 | 4.3 | 0.8 | 0.8 | 1.9 | 1.0 | 2.3 | 1.8 |
| PLASMA | donor #4 plasma | 0.8 | 5.4 | 47.3 | 1.0 | 5.6 | 1.0 | 2.1 | 1.8 |
| PLASMA | donor #5 plasma | 0.8 | 1.3 | 47.3 | 1.0 | 4.8 | 1.0 | 1.4 | 1.8 |
| PLASMA | donor #6 plasma | 1.2 | 0.7 | 47.3 | 1.0 | 1.1 | 1.0 | 1.6 | 1.8 |
| PLASMA | donor #7 plasma | 0.7 | 2.7 | 47.3 | 1.0 | 7.6 | 1.0 | 0.6 | 1.8 |
| PLASMA | donor #8 plasma | 0.8 | 1.3 | 1.0 | 1.0 | 0.9 | 1.0 | 0.6 | 1.5 |

FIG. 16I.6

| | IL-17E pg/mL | IL-18 pg/mL | IL-1alpha ng/mL | IL-1beta pg/mL | IL-1ra pg/mL | IL-2 pg/mL | IL-23 ng/mL | IL-3 ng/mL |
|---|---|---|---|---|---|---|---|---|
| Least Detectable Dose | 31 | 54 | 0.16 | 1.5 | 15 | 60 | <0.67 | 0.17 |
| RBM Low Plasma Range | PENDING | 72 | | | 17 | | PENDING | |
| RBM High Plasma Range | PENDING | 1020 | 0.35 | 8.7 | 622 | 61 | PENDING | 1.2 |
| PLASMA donor #9 plasma | 1.2 | 0.7 | 1.0 | 1.0 | 1.1 | 1.0 | 1.4 | 0.5 |

FIG. 16J.1

| Samples | IL-4 pg/mL | IL-5 pg/mL | IL-6 pg/mL | IL-7 pg/mL | IL-8 pg/mL | Insulin uIU/mL | Leptin ng/mL | Lipoprotein (a) ug/mL |
|---|---|---|---|---|---|---|---|---|
| Least Detectable Dose | 104 | 33 | 12 | 53 | 3.5 | 0.86 | 0.10 | 3.7 |
| RBM Low Plasma Range | 103 | 62 | 25 | 3.7 | 59 | 34 | 0.41 | 3.0 |
| RBM High Plasma Range |  |  |  | 125 |  |  | 41 | 858 |
| Samples |  |  |  |  |  |  |  |  |
| Donor_1 3. Aliquot A | 50 | 33 | 4690 | 169 | 23600 | 11 | 132 | 27 |
| Donor_1 3. Aliquot B | 53 | 33 | 1860 | 113 | 4450 | 9.8 | 115 | 34 |
| Donor_1 3. Aliquot C | 43 | 33 | 49 | 33 | 321 | 6.3 | 124 | 31 |
| Donor_1 3. Aliquot D | 49 | 33 | 7970 | 113 | 6730 | 11 | 121 | 32 |
| Donor_1 3. Aliquot E | 38 | 33 | 1700 | 131 | 6170 | 11 | 124 | 32 |
| Donor_1 3. Aliquot F | 42 | 33 | 77 | 57 | 1330 | 8.3 | 107 | 45 |
| Donor_1 3. Aliquot G | 38 | 33 | 57 | 100 | 5060 | 8.0 | 112 | 37 |
| Donor_1 3. Aliquot H | 51 | 33 | 54 | 33 | 672 | 9.4 | 119 | 32 |
| Donor_1 3. Aliquot I | 38 | 33 | 50 | 68 | 1480 | 9.9 | 119 | 30 |
| Donor_2 3. Aliquot A | 69 | 5.9 | 11100 | 215 | 100000 | 5.7 | 7.7 | 38 |
| Donor_2 3. Aliquot B | 78 | 8.2 | 6720 | 189 | 74900 | 6.1 | 8.4 | 46 |
| Donor_2 3. Aliquot C | 43 | 33 | 110 | 48 | 2290 | 2.3 | 9.0 | 47 |
| Donor_2 3. Aliquot D | 69 | 7.4 | 78400 | 201 | 146000 | 6.6 | 8.1 | 48 |
| Donor_2 3. Aliquot E | 77 | 8.2 | 63400 | 226 | 165000 | 6.4 | 8.3 | 58 |
| Donor_2 3. Aliquot F | 40 | 6.7 | 180 | 59 | 2230 | 4.7 | 7.7 | 128 |
| Donor_2 3. Aliquot G | 77 | 8.9 | 30900 | 223 | >344062 | 6.0 | 4.4 | 46 |
| Donor_2 3. Aliquot H | 45 | 5.1 | 187 | 74 | 3460 | 5.6 | 7.8 | 47 |
| Donor_2 3. Aliquot I | 56 | 33 | 153 | 48 | 3230 | 4.7 | 7.9 | 48 |
| Donor_3 3. Aliquot A | 9.4 | 4.3 | 6380 | 192 | 40600 | 19 | 8.1 | 61 |
| Donor_3 3. Aliquot B | 7.8 | 33 | 3880 | 201 | 32400 | 17 | 7.7 | 66 |
| Donor_3 3. Aliquot C | 104 | 33 | 90 | 66 | 1860 | 9.0 | 8.4 | 68 |
| Donor_3 3. Aliquot D | 20 | 33 | 105000 | 243 | 124000 | 15 | 7.8 | 58 |
| Donor_3 3. Aliquot E | 8.7 | 4.3 | 59800 | 234 | 146000 | 17 | 8.3 | 70 |

FIG. 16J.2

| | IL-4 pg/mL | IL-5 pg/mL | IL-6 pg/mL | IL-7 pg/mL | IL-8 pg/mL | Insulin uIU/mL | Leptin ng/mL | Lipoprotein (a) ug/mL |
|---|---|---|---|---|---|---|---|---|
| Least Detectable Dose | 104 | 33 | 12 | 53 | 3.5 | 0.86 | 0.10 | 3.7 |
| RBM Low Plasma Range | | | | 3.7 | | | | 3.0 |
| RBM High Plasma Range | 103 | 62 | 25 | 125 | 59 | 34 | 0.41 | 858 |
| Donor_3 3. Aliquot F | 7.8 | 5.9 | 169 | 82 | 2870 | 13 | 41 | 83 |
| Donor_3 3. Aliquot G | 104 | 2.5 | 63 | 78 | 24200 | 20 | 7.2 | 57 |
| Donor_3 3. Aliquot H | 104 | 33 | 26 | 38 | 924 | 15 | 5.9 | 61 |
| Donor_3 3. Aliquot I | 104 | 5.1 | 9.2 | 86 | 1080 | 15 | 6.9 | 66 |
| | | | | | | | 7.8 | |
| Donor_4 3. Aliquot A | 33 | 33 | 177 | 82 | 3240 | 12 | 11 | 23 |
| Donor_4 3. Aliquot B | 35 | 33 | 405 | 106 | 4210 | 12 | 12 | 21 |
| Donor_4 3. Aliquot C | 37 | 33 | 70 | 38 | 751 | 3.8 | 10 | 21 |
| Donor_4 3. Aliquot D | 50 | 33 | 46300 | 215 | 76000 | 13 | 9.7 | 24 |
| Donor_4 3. Aliquot E | 54 | 33 | 24300 | 214 | 70800 | 12 | 8.0 | 22 |
| Donor_4 3. Aliquot F | 32 | 33 | 5050 | 98 | 4030 | 12 | 8.4 | 24 |
| Donor_4 3. Aliquot G | 49 | 33 | 59 | 74 | 23400 | 14 | 7.3 | 22 |
| Donor_4 3. Aliquot H | 31 | 33 | 62 | 66 | 731 | 15 | 11 | 21 |
| Donor_4 3. Aliquot I | 29 | 33 | 52 | 38 | 550 | 11 | 10 | 25 |
| Donor_5 3. Aliquot A | 49 | 4.7 | 2370 | 203 | 146000 | 5.2 | 2.0 | 22 |
| Donor_5 3. Aliquot B | 51 | 33 | 4460 | 217 | 198000 | 5.4 | 1.7 | 20 |
| Donor_5 3. Aliquot C | 39 | 33 | 46 | 52 | 1740 | 2.0 | 2.0 | 21 |
| Donor_5 3. Aliquot D | 76 | 3.5 | 60400 | 247 | 211000 | 6.5 | 1.8 | 21 |
| Donor_5 3. Aliquot E | 57 | 2.5 | 71300 | 200 | >344062 | 8.0 | 1.9 | 19 |
| Donor_5 3. Aliquot F | 42 | 33 | 316 | 115 | 20400 | 3.6 | 1.3 | 21 |
| Donor_5 3. Aliquot G | 46 | 33 | 70 | 145 | 85000 | 3.8 | 2.0 | 39 |
| Donor_5 3. Aliquot H | 41 | 33 | 55 | 84 | 20000 | 4.9 | 1.9 | 18 |
| Donor_5 3. Aliquot I | 35 | 33 | 43 | 94 | 2590 | 4.3 | 1.7 | 17 |
| | | | | | | | | 18 |
| Donor_6 3. Aliquot A | 51 | 5.9 | 1500 | 182 | 17400 | 1.3 | 0.12 | 36 |
| Donor_6 3. Aliquot B | 55 | 11 | 3190 | 189 | 33200 | 1.4 | 0.10 | 40 |

FIG. 16J.3

| | IL-4 pg/mL | IL-5 pg/mL | IL-6 pg/mL | IL-7 pg/mL | IL-8 pg/mL | Insulin uIU/mL | Leptin ng/mL | Lipoprotein (a) ug/mL |
|---|---|---|---|---|---|---|---|---|
| Least Detectable Dose | 104 | 33 | 12 | 53 | 3.5 | 0.86 | 0.10 | 3.7 |
| RBM Low Plasma Range | | | | 3.7 | | | 0.41 | 3.0 |
| RBM High Plasma Range | 103 | 62 | 25 | 125 | 59 | 34 | 41 | 858 |
| Donor_6_3. Aliquot C | 43 | 4.3 | 85 | 90 | 271 | 0.98 | 0.11 | 39 |
| Donor_6_3. Aliquot D | 54 | 6.3 | 50700 | 215 | 67300 | 1.8 | 0.25 | 43 |
| Donor_6_3. Aliquot E | 60 | 21 | 71700 | 229 | 116000 | 1.2 | 0.26 | 35 |
| Donor_6_3. Aliquot F | 44 | 8.9 | 517 | 124 | 3980 | 1.5 | 0.1 | 79 |
| Donor_6_3. Aliquot G | 46 | 33 | 74 | 128 | 26500 | 1.2 | 0.27 | 31 |
| Donor_6_3. Aliquot H | 39 | 33 | 84 | 94 | 692 | 1.3 | 0.13 | 32 |
| Donor_6_3. Aliquot I | 29 | 3.5 | 65 | 68 | 243 | 1.1 | 0.10 | 25 |
| Donor_7_3. Aliquot A | 33 | 11 | 19900 | 273 | 89600 | 8.4 | 11 | 203 |
| Donor_7_3. Aliquot B | 27 | 20 | 5190 | 243 | 33900 | 7.8 | 11 | 222 |
| Donor_7_3. Aliquot C | 9.4 | 8.9 | 26 | 80 | 500 | 4.1 | 12 | 160 |
| Donor_7_3. Aliquot D | 29 | 5.9 | 54800 | 211 | 80600 | 6.5 | 11 | 192 |
| Donor_7_3. Aliquot E | 37 | 12 | 21600 | 247 | 41300 | 7.5 | 11 | 215 |
| Donor_7_3. Aliquot F | 23 | 13 | 242 | 138 | 812 | 6.2 | 11 | 548 |
| Donor_7_3. Aliquot G | 18 | 33 | 48 | 109 | 7810 | 6.6 | 6.9 | 148 |
| Donor_7_3. Aliquot H | 104 | 33 | 34 | 45 | 373 | 6.4 | 12 | 155 |
| Donor_7_3. Aliquot I | 104 | 4.3 | 16 | 80 | 225 | 6.1 | 12 | 190 |
| Donor_8_3. Aliquot A | 43 | 8.2 | 1400 | 166 | 4320 | 1.9 | 0.50 | 16 |
| Donor_8_3. Aliquot B | 49 | 12 | 1140 | 184 | 4770 | 2.4 | 0.49 | 16 |
| Donor_8_3. Aliquot C | 45 | 2.5 | 840 | 120 | 846 | 0.73 | 0.38 | 16 |
| Donor_8_3. Aliquot D | 60 | 5.9 | 99400 | 205 | 66900 | 2.2 | 0.62 | 13 |
| Donor_8_3. Aliquot E | 48 | 14 | 83900 | 217 | 58300 | 2.4 | 0.64 | 18 |
| Donor_8_3. Aliquot F | 48 | 14 | 6720 | 185 | 952 | 3.3 | 0.49 | 18 |
| Donor_8_3. Aliquot G | 43 | 33 | 42 | 86 | 2470 | 0.91 | 0.36 | 12 |
| Donor_8_3. Aliquot H | 40 | 5.1 | 129 | 169 | 5280 | 1.7 | 0.53 | 13 |
| Donor_8_3. Aliquot I | 44 | 2.5 | 12 | 117 | 895 | 1.7 | 0.37 | 14 |

FIG. 16J.4

| | IL-4 pg/mL | IL-5 pg/mL | IL-6 pg/mL | IL-7 pg/mL | IL-8 pg/mL | Insulin uIU/mL | Leptin ng/mL | Lipoprotein (a) ug/mL |
|---|---|---|---|---|---|---|---|---|
| Least Detectable Dose | 104 | 33 | 12 | 53 | 3.5 | 0.86 | 0.10 | 3.7 |
| RBM Low Plasma Range | 103 | 62 | 25 | 3.7 | 59 | 34 | 0.41 | 3.0 |
| RBM High Plasma Range | | | | 125 | | | 41 | 858 |
| Donor_9 3. Aliquot A | 59 | 2.6 | 642 | 143 | 3910 | 6.2 | 2.0 | 18 |
| Donor_9 3. Aliquot B | 54 | 7.8 | 1100 | 156 | 4840 | 5.9 | 2.0 | 12 |
| Donor_9 3. Aliquot C | 59 | 5.3 | 1680 | 167 | 3560 | 3.1 | 1.6 | 13 |
| Donor_9 3. Aliquot D | 70 | 8.6 | 93100 | 209 | 48600 | 6.5 | 2.0 | 17 |
| Donor_9 3. Aliquot E | 67 | 5.3 | 61700 | 192 | 62300 | 6.3 | 1.8 | 16 |
| Donor_9 3. Aliquot F | 51 | 8.6 | 1900 | 159 | 1200 | 6.6 | 1.9 | 18 |
| Donor_9 3. Aliquot G | 75 | 33 | 131 | 126 | 21300 | 5.7 | 1.3 | 11 |
| Donor_9 3. Aliquot H | 55 | 33 | 57 | 141 | 1590 | 7.1 | 1.9 | 11 |
| Donor_9 3. Aliquot I | 43 | 33 | 19 | 62 | 797 | 5.3 | 1.9 | 14 |
| EDTA Plasma | | | | | | | | |
| donor #1 plasma | 104 | 33 | 30 | 87 | 239 | 6.9 | 89 | 46 |
| donor #2 plasma | 104 | 8.2 | 102 | 42 | 319 | 5.8 | 9.7 | 109 |
| donor #3 plasma | 104 | 12 | 8.5 | 130 | 18 | 21 | 9.4 | 143 |
| donor #4 plasma | 104 | 4.0 | 49 | 52 | 102 | 16 | 15 | 31 |
| donor #5 plasma | 104 | 7.0 | 27 | 101 | 32 | 5.5 | 1.9 | 31 |
| donor #6 plasma | 104 | 7.0 | 54 | 103 | 24 | 0.57 | 0.046 | 91 |
| donor #7 plasma | 104 | 7.4 | 15 | 106 | 43 | 11 | 21 | 735 |
| donor #8 plasma | 44 | 6.1 | 1.8 | 83 | 3.5 | 1.0 | 0.64 | 17 |
| donor #9 plasma | 42 | 7.0 | 12 | 77 | 3.5 | 9.9 | 2.4 | 23 |
| MW NHD plasma | 43.0 | 6.5 | 6.9 | 79.7 | 3.5 | 5.4 | 1.5 | 20.0 |
| Normal healthy donors | | | | | | | | |
| MW NHD unstimuliert | 43.35 | 17.77 | 15.40 | 89.70 | 846.00 | 3.47 | 1.15 | 13.85 |

FIG. 16J.5

| | | IL-4 pg/mL | IL-5 pg/mL | IL-6 pg/mL | IL-7 pg/mL | IL-8 pg/mL | Insulin uIU/mL | Leptin ng/mL | Lipoprotein (a) ug/mL |
|---|---|---|---|---|---|---|---|---|---|
| | Least Detectable Dose | 104 | 33 | 12 | 53 | 3.5 | 0.86 | 0.10 | 3.7 |
| | RBM Low Plasma Range | | | | 3.7 | | | 0.41 | 3.0 |
| | RBM High Plasma Range | 103 | 62 | 25 | 125 | 59 | 34 | 41 | 858 |
| Normal healthy donors | | | | | | | | | |
| Stimulations indices | | | | | | | | | Lipoprotein (a) |
| unstimuliert | Donor_1 3. Aliquot I | 0.9 | 1.9 | 3.3 | 0.8 | 1.7 | 2.9 | 103.7 | 2.1 |
| unstimuliert | Donor_2 3. Aliquot I | 1.3 | 1.9 | 9.9 | 0.5 | 3.8 | 1.3 | 6.8 | 3.5 |
| unstimuliert | Donor_3 3. Aliquot I | 2.4 | 0.3 | 0.6 | 1.0 | 1.3 | 4.4 | 6.8 | 4.8 |
| unstimuliert | Donor_4 3. Aliquot I | 0.7 | 1.9 | 3.3 | 0.4 | 0.7 | 3.3 | 8.9 | 1.8 |
| unstimuliert | Donor_5 3. Aliquot I | 0.8 | 1.9 | 2.8 | 1.0 | 3.1 | 1.2 | 1.5 | 1.3 |
| unstimuliert | Donor_6 3. Aliquot I | 0.7 | 0.2 | 4.2 | 0.8 | 0.3 | 0.3 | 0.1 | 1.8 |
| unstimuliert | Donor_7 3. Aliquot I | 2.4 | 0.2 | 1.0 | 0.9 | 0.3 | 1.8 | 10.1 | 13.7 |
| unstimuliert | Donor_8 3. Aliquot I | 1.0 | 0.1 | 0.8 | 1.3 | 1.1 | 0.5 | 0.3 | 1.0 |
| unstimuliert | Donor_9 3. Aliquot I | 1.0 | 1.9 | 1.2 | 0.7 | 0.9 | 1.5 | 1.7 | 1.0 |
| Stimulations indices | | | | | | | | | |
| | EDTA Plasma | | | | | | | | |
| PLASMA | donor #1 plasma | 2.4 | 5.0 | 4.3 | 1.1 | 68.3 | 1.3 | 59.6 | 2.3 |
| PLASMA | donor #2 plasma | 2.4 | 1.3 | 14.8 | 0.5 | 91.1 | 1.1 | 6.5 | 5.5 |
| PLASMA | donor #3 plasma | 2.4 | 1.9 | 1.2 | 1.6 | 5.1 | 3.9 | 6.3 | 7.2 |
| PLASMA | donor #4 plasma | 2.4 | 0.6 | 7.1 | 0.7 | 29.1 | 3.0 | 9.8 | 1.6 |
| PLASMA | donor #5 plasma | 2.4 | 1.1 | 3.9 | 1.3 | 9.2 | 1.0 | 1.3 | 1.6 |
| PLASMA | donor #6 plasma | 2.4 | 1.1 | 7.8 | 1.3 | 7.0 | 0.1 | 0.0 | 4.6 |
| PLASMA | donor #7 plasma | 2.4 | 1.1 | 2.2 | 1.3 | 12.4 | 1.9 | 13.7 | 36.8 |
| PLASMA | donor #8 plasma | 1.0 | 0.9 | 0.3 | 1.0 | 1.0 | 0.2 | 0.4 | 0.9 |

FIG. 16J.6

| | IL-4 pg/mL | IL-5 pg/mL | IL-6 pg/mL | IL-7 pg/mL | IL-8 pg/mL | Insulin uIU/mL | Leptin ng/mL | Lipoprotein (a) ug/mL |
|---|---|---|---|---|---|---|---|---|
| Least Detectable Dose | 104 | 33 | 12 | 53 | 3.5 | 0.86 | 0.10 | 3.7 |
| RBM Low Plasma Range | | | | 3.7 | | | | 3.0 |
| RBM High Plasma Range | 103 | 62 | 25 | 125 | 59 | 34 | 41 | 858 |
| PLASMA donor #9 plasma | 1.0 | 1.1 | 1.7 | 1.0 | 1.0 | 1.8 | 1.6 | 1.1 |

FIG. 16K.1

| | Lymphotactin ng/mL | MCP-1 pg/mL | MDC pg/mL | MIP-1 alpha pg/mL | MIP-1 beta pg/mL | MMP-2 ng/mL | MMP-3 ng/mL | MMP-9 ng/mL |
|---|---|---|---|---|---|---|---|---|
| Least Detectable Dose | 0.38 | 52 | 14 | 13 | 38 | 150 | 0.20 | 37 |
| RBM Low Plasma Range | | 35 | 162 | | 25 | 183 | | |
| RBM High Plasma Range | 0.57 | 401 | 774 | 89 | 595 | 3070 | 1.8 | 1050 |
| Samples | | | | | | | | |
| Donor_1 3. Aliquot A | 0.22 | 8710 | 197 | 3570 | 71300 | 474 | 12 | 74 |
| Donor_1 3. Aliquot B | 0.38 | 4230 | 187 | 1810 | 12800 | 440 | 11 | 53 |
| Donor_1 3. Aliquot C | 0.38 | 1210 | 180 | 94 | 610 | 71 | 12 | 30 |
| Donor_1 3. Aliquot D | 0.071 | 3940 | 203 | 3760 | 75700 | 443 | 13 | 56 |
| Donor_1 3. Aliquot E | 0.092 | 4040 | 185 | 1370 | 16800 | 456 | 12 | 57 |
| Donor_1 3. Aliquot F | 0.38 | 2120 | 146 | 197 | 2040 | 410 | 11 | 33 |
| Donor_1 3. Aliquot G | 0.38 | 8970 | 14 | 110 | 498 | 451 | 13 | 49 |
| Donor_1 3. Aliquot H | 0.38 | 1080 | 41 | 81 | 513 | 68 | 12 | 46 |
| Donor_1 3. Aliquot I | 0.38 | 1030 | 193 | 180 | 803 | 427 | 11 | 38 |
| Donor_2 3. Aliquot A | 0.26 | 9540 | 158 | 5430 | 94800 | 105 | 11 | 59 |
| Donor_2 3. Aliquot B | 0.22 | 3930 | 178 | 2250 | 52800 | 83 | 11 | 59 |
| Donor_2 3. Aliquot C | 0.38 | 499 | 160 | 91 | 1790 | 86 | 12 | 42 |
| Donor_2 3. Aliquot D | 0.28 | 3760 | 165 | 34700 | 460000 | 100 | 13 | 60 |
| Donor_2 3. Aliquot E | 0.25 | 4260 | 154 | 23000 | 331000 | 123 | 11 | 53 |
| Donor_2 3. Aliquot F | 0.38 | 810 | 141 | 191 | 4280 | 69 | 11 | 2.2 |
| Donor_2 3. Aliquot G | 0.28 | 42600 | 14 | 29600 | 95800 | 147 | 11 | 28 |
| Donor_2 3. Aliquot H | 0.38 | 917 | 33 | 360 | 7090 | 86 | 11 | 55 |
| Donor_2 3. Aliquot I | 0.38 | 555 | 156 | 179 | 5430 | 72 | 9.7 | 51 |
| Donor_3 3. Aliquot A | 0.33 | 11000 | 92 | 894 | 31700 | 30 | 5.4 | 72 |
| Donor_3 3. Aliquot B | 0.23 | 3820 | 86 | 387 | 17200 | 26 | 4.8 | 59 |
| Donor_3 3. Aliquot C | 0.15 | 228 | 87 | 46 | 1850 | 34 | 5.0 | 55 |
| Donor_3 3. Aliquot D | 0.32 | 2630 | 84 | 8550 | 254000 | 47 | 4.9 | 91 |
| Donor_3 3. Aliquot E | 0.39 | 2870 | 72 | 3710 | 126000 | 34 | 5.3 | 74 |

FIG. 16K.2

| | Lymphotactin ng/mL | MCP-1 pg/mL | MDC pg/mL | MIP-1 alpha pg/mL | MIP-1 beta pg/mL | MMP-2 ng/mL | MMP-3 ng/mL | MMP-9 ng/mL |
|---|---|---|---|---|---|---|---|---|
| Least Detectable Dose | 0.38 | 52 | 14 | 13 | 38 | 150 | 0.20 | 37 |
| RBM Low Plasma Range | | 35 | 162 | | 25 | 183 | | |
| RBM High Plasma Range | 0.57 | 401 | 774 | 89 | 595 | 3070 | 1.8 | 1050 |
| Donor_3 3. Aliquot F | 0.39 | 246 | 70 | 66 | 2900 | 34 | 4.4 | 54 |
| Donor_3 3. Aliquot G | 0.21 | 521 | 14 | 60 | 1680 | 67 | 4.3 | 45 |
| Donor_3 3. Aliquot H | 0.38 | 126 | 12 | 42 | 633 | 23 | 3.9 | 49 |
| Donor_3 3. Aliquot I | 0.54 | 110 | 85 | 46 | 123 | 150 | 4.7 | 42 |
| Donor_4 3. Aliquot A | 0.38 | 2430 | 324 | 432 | 13100 | 150 | 7.5 | 26 |
| Donor_4 3. Aliquot B | 0.38 | 2960 | 346 | 288 | 9460 | 150 | 7.5 | 26 |
| Donor_4 3. Aliquot C | 0.38 | 578 | 280 | 137 | 994 | 150 | 6.8 | 4.9 |
| Donor_4 3. Aliquot D | 0.16 | 14900 | 335 | 31200 | 484000 | 43 | 7.4 | 27 |
| Donor_4 3. Aliquot E | 0.20 | 15800 | 259 | 17700 | 293000 | 50 | 6.6 | 49 |
| Donor_4 3. Aliquot F | 0.12 | 15400 | 251 | 1740 | 84100 | 150 | 6.6 | 14 |
| Donor_4 3. Aliquot G | 0.38 | 6110 | 14 | 547 | 3900 | 45 | 5.6 | 16 |
| Donor_4 3. Aliquot H | 0.38 | 641 | 66 | 106 | 3160 | 15 | 7.2 | 26 |
| Donor_4 3. Aliquot I | 0.38 | 269 | 298 | 63 | 287 | 150 | 6.8 | 9.3 |
| Donor_5 3. Aliquot A | 0.31 | 11900 | 298 | 6820 | 150000 | 106 | 21 | 46 |
| Donor_5 3. Aliquot B | 0.33 | 7660 | 424 | 9780 | 174000 | 112 | 19 | 43 |
| Donor_5 3. Aliquot C | 0.15 | 226 | 221 | 111 | 1790 | 115 | 21 | 52 |
| Donor_5 3. Aliquot D | 0.36 | 3740 | 190 | 36200 | 543000 | 132 | 19 | 78 |
| Donor_5 3. Aliquot E | 0.33 | 5360 | 205 | 46800 | 600000 | 138 | 20 | 57 |
| Donor_5 3. Aliquot F | 0.071 | 2920 | 171 | 1790 | 24300 | 67 | 16 | 55 |
| Donor_5 3. Aliquot G | 0.22 | 14900 | 14 | 527 | 3130 | 120 | 20 | 28 |
| Donor_5 3. Aliquot H | 0.38 | 523 | 55 | 328 | 5000 | 90 | 20 | 60 |
| Donor_5 3. Aliquot I | 0.38 | 231 | 218 | 119 | 3870 | 83 | 20 | 62 |
| Donor_6 3. Aliquot A | 0.72 | 3750 | 124 | 1810 | 27400 | 12 | 2.8 | 74 |
| Donor_6 3. Aliquot B | 0.72 | 2190 | 124 | 1690 | 22200 | 15 | 3.0 | 76 |

FIG. 16K.3

| | Lymphotactin ng/mL | MCP-1 pg/mL | MDC pg/mL | MIP-1 alpha pg/mL | MIP-1 beta pg/mL | MMP-2 ng/mL | MMP-3 ng/mL | MMP-9 ng/mL |
|---|---|---|---|---|---|---|---|---|
| Least Detectable Dose | 0.38 | 52 | 14 | 13 | 38 | 150 | 0.20 | 37 |
| RBM Low Plasma Range | | 35 | 162 | 89 | 25 | 183 | 1.8 | 1050 |
| RBM High Plasma Range | 0.57 | 401 | 774 | | 595 | 3070 | | |
| Donor_6_3. Aliquot C | 0.62 | 218 | 110 | 55 | 376 | 150 | 2.5 | 33 |
| Donor_6_3. Aliquot D | 0.80 | 1360 | 136 | 29200 | 402000 | 20 | 2.9 | 80 |
| Donor_6_3. Aliquot E | 0.69 | 990 | 110 | 36100 | 441000 | 28 | 2.6 | 99 |
| Donor_6_3. Aliquot F | 0.79 | 2110 | 94 | 491 | 7470 | 150 | 2.6 | 18 |
| Donor_6_3. Aliquot G | 0.50 | 3670 | 14 | 800 | 3130 | 75 | 2.3 | 46 |
| Donor_6_3. Aliquot H | 0.50 | 240 | 29 | 143 | 3680 | 150 | 2.8 | 39 |
| Donor_6_3. Aliquot I | 0.52 | 146 | 113 | 49 | 317 | 150 | 2.7 | 32 |
| Donor_7_3. Aliquot A | 0.96 | 14700 | 94 | 6080 | 188000 | 16 | 16 | 55 |
| Donor_7_3. Aliquot B | 0.78 | 5090 | 99 | 2700 | 68500 | 150 | 16 | 66 |
| Donor_7_3. Aliquot C | 0.53 | 314 | 83 | 46 | 680 | 150 | 16 | 37 |
| Donor_7_3. Aliquot D | 0.75 | 5040 | 92 | 7530 | 349000 | 23 | 14 | 79 |
| Donor_7_3. Aliquot E | 0.83 | 8810 | 96 | 4790 | 179000 | 23 | 15 | 60 |
| Donor_7_3. Aliquot F | 0.88 | 1260 | 72 | 152 | 5030 | 150 | 15 | 2.2 |
| Donor_7_3. Aliquot G | 0.24 | 3610 | 14 | 469 | 2280 | 47 | 15 | 44 |
| Donor_7_3. Aliquot H | 0.33 | 309 | 17 | 43 | 762 | 150 | 14 | 30 |
| Donor_7_3. Aliquot I | 0.53 | 265 | 84 | 38 | 156 | 150 | 15 | 4.9 |
| Donor_8_3. Aliquot A | 0.93 | 4750 | 223 | 1840 | 22700 | 37 | 3.4 | 8.2 |
| Donor_8_3. Aliquot B | 0.96 | 3720 | 221 | 1450 | 21000 | 37 | 3.5 | 26 |
| Donor_8_3. Aliquot C | 0.91 | 5420 | 154 | 2130 | 58500 | 23 | 2.8 | 23 |
| Donor_8_3. Aliquot D | 1.1 | 2170 | 337 | 67800 | 572000 | 89 | 3.9 | 94 |
| Donor_8_3. Aliquot E | 1.2 | 4380 | 245 | 46800 | 387000 | 75 | 3.4 | 81 |
| Donor_8_3. Aliquot F | 1.2 | 12700 | 138 | 6380 | 129000 | 53 | 3.6 | 31 |
| Donor_8_3. Aliquot G | 0.47 | 1940 | 14 | 931 | 7690 | 58 | 3.2 | 9.3 |
| Donor_8_3. Aliquot H | 0.80 | 7890 | 90 | 3290 | 29900 | 43 | 3.6 | 42 |
| Donor_8_3. Aliquot I | 0.80 | 385 | 256 | 266 | 4590 | 26 | 3.2 | 4.9 |

FIG. 16K.4

|  | Lymphotactin ng/mL | MCP-1 pg/mL | MDC pg/mL | MIP-1 alpha pg/mL | MIP-1 beta pg/mL | MMP-2 ng/mL | MMP-3 ng/mL | MMP-9 ng/mL |
|---|---|---|---|---|---|---|---|---|
| Least Detectable Dose | 0.38 | 52 | 14 | 13 | 38 | 150 | 0.20 | 37 |
| RBM Low Plasma Range |  | 35 | 162 |  | 25 | 183 |  |  |
| RBM High Plasma Range | 0.57 | 401 | 774 | 89 | 595 | 3070 | 1.8 | 1050 |
| Donor_9_3. Aliquot A | 0.68 | 5430 | 169 | 1250 | 24500 | 38 | 4.3 | 27 |
| Donor_9_3. Aliquot B | 0.73 | 3060 | 175 | 1690 | 23200 | 43 | 4.8 | 59 |
| Donor_9_3. Aliquot C | 0.69 | 16600 | 180 | 2140 | 46900 | 72 | 4.2 | 36 |
| Donor_9_3. Aliquot D | 0.62 | 6120 | 196 | 42300 | 431000 | 132 | 4.7 | 111 |
| Donor_9_3. Aliquot E | 0.71 | 9540 | 194 | 29700 | 355000 | 82 | 4.9 | 123 |
| Donor_9_3. Aliquot F | 0.86 | 12800 | 142 | 2410 | 78800 | 46 | 4.3 | 4.6 |
| Donor_9_3. Aliquot G | 0.20 | 15500 | 14 | 1820 | 12300 | 95 | 3.9 | 27 |
| Donor_9_3. Aliquot H | 0.38 | 2420 | 70 | 467 | 14400 | 48 | 4.3 | 45 |
| Donor_9_3. Aliquot I | 0.53 | 346 | 181 | 240 | 3670 | 42 | 3.6 | 13 |
| EDTA Plasma |  |  |  |  |  |  |  |  |
| donor #1 plasma | 0.38 | 230 | 187 | 69 | 209 | 1750 | 0.12 | 211 |
| donor #2 plasma | 0.38 | 66 | 236 | 60 | 239 | 3910 | 0.047 | 1340 |
| donor #3 plasma | 0.12 | 11 | 116 | 41 | 65 | 1540 | 0.2 | 653 |
| donor #4 plasma | 0.38 | 23 | 413 | 59 | 368 | 8190 | 0.2 | 194 |
| donor #5 plasma | 0.12 | 17 | 307 | 46 | 154 | 898 | 0.076 | 236 |
| donor #6 plasma | 0.28 | 32 | 155 | 34 | 68 | 972 | 0.2 | 367 |
| donor #7 plasma | 0.42 | 109 | 124 | 48 | 145 | 2270 | 0.090 | 115 |
| donor #8 plasma | 0.31 | 147 | 176 | 42 | 47 | 10 | 3.7 | 30 |
| donor #9 plasma | 0.33 | 89 | 159 | 44 | 38 | 46 | 4.2 | 3.2 |
| MW |  |  |  |  |  |  |  |  |
| Normal healthy donors NHD plasma | 0.3 | 118.2 | 167.5 | 43.3 | 42.5 | 28.0 | 3.9 | 16.6 |
| MW |  |  |  |  |  |  |  |  |
| NHD unstimuliert | 0.67 | 365.50 | 218.50 | 253.00 | 4130.00 | 33.80 | 3.42 | 8.83 |

FIG. 16K.5

| | Lymphotactin ng/mL | MCP-1 pg/mL | MDC pg/mL | MIP-1 alpha pg/mL | MIP-1 beta pg/mL | MMP-2 ng/mL | MMP-3 ng/mL | MMP-9 ng/mL |
|---|---|---|---|---|---|---|---|---|
| Least Detectable Dose | 0.38 | 52 | 14 | 13 | 38 | 150 | 0.20 | 37 |
| RBM Low Plasma Range | | 35 | 162 | | 25 | 183 | | |
| RBM High Plasma Range | 0.57 | 401 | 774 | 89 | 595 | 3070 | 1.8 | 1050 |
| Normal healthy donors | | | | | | | | |

| | | Lymphotactin | MCP-1 | MDC | MIP-1alpha | MIP-1beta | MMP-2 | MMP-3 | MMP-9 |
|---|---|---|---|---|---|---|---|---|---|
| *Stimulationsindices* | | | | | | | | | |
| unstimuliert | Donor 1 3. Aliquot I | 0.6 | 2.8 | 0.9 | 0.7 | 0.2 | 12.6 | 3.3 | 4.3 |
| unstimuliert | Donor 2 3. Aliquot I | 0.6 | 1.5 | 0.7 | 0.7 | 1.3 | 2.1 | 2.8 | 5.8 |
| unstimuliert | Donor 3 3. Aliquot I | 0.8 | 0.3 | 0.4 | 0.2 | 0.0 | 4.4 | 1.4 | 4.7 |
| unstimuliert | Donor 4 3. Aliquot I | 0.6 | 0.7 | 1.4 | 0.2 | 0.1 | 4.4 | 2.0 | 1.1 |
| unstimuliert | Donor 5 3. Aliquot I | 0.6 | 0.6 | 1.0 | 0.5 | 0.9 | 2.5 | 5.8 | 7.0 |
| unstimuliert | Donor 6 3. Aliquot I | 0.8 | 0.4 | 0.5 | 0.2 | 0.1 | 4.4 | 0.8 | 3.6 |
| unstimuliert | Donor 7 3. Aliquot I | 0.8 | 0.7 | 0.4 | 0.2 | 0.0 | 4.4 | 4.4 | 0.5 |
| unstimuliert | Donor 8 3. Aliquot I | 1.2 | 1.1 | 1.2 | 1.1 | 1.1 | 0.8 | 0.9 | 0.5 |
| unstimuliert | Donor 9 3. Aliquot I | 0.8 | 0.9 | 0.8 | 0.9 | 0.9 | 1.2 | 1.1 | 1.5 |
| *Stimulationsindices* | | | | | | | | | |
| | EDTA Plasma | | | | | | | | |
| PLASMA | donor #1 plasma | 1.2 | 1.9 | 1.1 | 1.6 | 4.9 | 62.5 | 0.0 | 12.7 |
| PLASMA | donor #2 plasma | 1.2 | 0.6 | 1.4 | 1.4 | 5.6 | 139.6 | 0.0 | 80.8 |
| PLASMA | donor #3 plasma | 0.4 | 0.1 | 0.7 | 0.9 | 1.5 | 55.0 | 0.1 | 39.4 |
| PLASMA | donor #4 plasma | 1.2 | 0.2 | 2.5 | 1.4 | 8.7 | 292.5 | 0.1 | 11.7 |
| PLASMA | donor #5 plasma | 0.4 | 0.1 | 1.8 | 1.1 | 3.6 | 32.1 | 0.0 | 14.2 |
| PLASMA | donor #6 plasma | 0.9 | 0.3 | 0.9 | 0.8 | 1.6 | 34.7 | 0.1 | 22.1 |
| PLASMA | donor #7 plasma | 1.3 | 0.9 | 0.7 | 1.1 | 3.4 | 81.1 | 0.0 | 6.9 |
| PLASMA | donor #8 plasma | 1.0 | 1.2 | 1.1 | 1.0 | 1.1 | 0.4 | 0.9 | 1.8 |

FIG. 16K.6

| | Lymphotactin ng/mL | MCP-1 pg/mL | MDC pg/mL | MIP-1 alpha pg/mL | MIP-1 beta pg/mL | MMP-2 ng/mL | MMP-3 ng/mL | MMP-9 ng/mL |
|---|---|---|---|---|---|---|---|---|
| Least Detectable Dose | 0.38 | 52 | 14 | 13 | 38 | 150 | 0.20 | 37 |
| RBM Low Plasma Range | | 35 | 162 | | 25 | 183 | | |
| RBM High Plasma Range | 0.57 | 401 | 774 | 89 | 595 | 3070 | 1.8 | 1050 |
| PLASMA donor #9 plasma | 1.0 | 0.8 | 0.9 | 1.0 | 0.9 | 1.6 | 1.1 | 0.2 |

FIG. 16L.1

| | Myelo-peroxidase | Myoglobin | OSM (Oncostatin M) | PAI-1 | Prostatic Acid Phosphatase | PAPP-A |
|---|---|---|---|---|---|---|
| | ng/mL | ng/mL | pg/mL | ng/mL | ng/mL | mIU/mL |
| Least Detectable Dose | 68 | 1.1 | | 0.90 | 0.034 | 0.037 |
| | | | | | | |
| RBM Low Plasma Range | | 3.6 | PENDING | 10 | 0.058 | |
| RBM High Plasma Range | 1110 | 37 | PENDING | 87 | 0.54 | 0.48 |
| | | | | | | |
| Samples | | | | | | |
| Donor_1 3. Aliquot A | 2010 | 85 | 312 | 159 | 0.12 | 0.079 |
| Donor_1 3. Aliquot B | 1590 | 94 | 188 | 171 | 0.11 | 0.082 |
| Donor_1 3. Aliquot C | 1390 | 101 | 21 | 172 | 0.045 | 0.059 |
| Donor_1 3. Aliquot D | 2050 | 102 | 143 | 156 | 0.11 | 0.054 |
| Donor_1 3. Aliquot E | 2330 | 90 | 312 | 152 | 0.12 | 0.062 |
| Donor_1 3. Aliquot F | 1970 | 95 | 120 | 135 | 0.041 | 0.073 |
| Donor_1 3. Aliquot G | 1750 | 104 | 422 | 187 | 0.086 | 0.11 |
| Donor_1 3. Aliquot H | 1740 | 95 | 28 | 184 | 0.078 | 0.087 |
| Donor_1 3. Aliquot I | 1380 | 89 | 76 | 160 | 0.035 | 0.049 |
| | | | | | | |
| Donor_2 3. Aliquot A | 3520 | 60 | 603 | 178 | 0.24 | 0.023 |
| Donor_2 3. Aliquot B | 2910 | 62 | 334 | 190 | 0.24 | 0.032 |
| Donor_2 3. Aliquot C | 1540 | 61 | 28 | 155 | 0.16 | 0.0049 |
| Donor_2 3. Aliquot D | 4180 | 58 | 222 | 165 | 0.46 | 0.024 |
| Donor_2 3. Aliquot E | 3380 | 60 | 188 | 161 | 0.38 | 0.022 |
| Donor_2 3. Aliquot F | 1610 | 63 | 65 | 156 | 0.12 | 0.018 |
| Donor_2 3. Aliquot G | 3280 | 64 | 765 | 205 | 0.33 | 0.043 |
| Donor_2 3. Aliquot H | 4200 | 59 | 82 | 177 | 0.14 | 0.023 |
| Donor_2 3. Aliquot I | 1730 | 57 | 44 | 164 | 0.13 | 0.018 |
| | | | | | | |
| Donor_3 3. Aliquot A | 2890 | 165 | 301 | 246 | 0.24 | 0.0063 |
| Donor_3 3. Aliquot B | 2640 | 150 | 329 | 221 | 0.22 | 0.037 |
| Donor_3 3. Aliquot C | 2210 | 164 | 98 | 199 | 0.16 | 0.037 |
| Donor_3 3. Aliquot D | 3310 | 159 | 395 | 225 | 0.41 | 0.0049 |
| Donor_3 3. Aliquot E | 3500 | 172 | 466 | 208 | 0.47 | 0.0063 |

FIG. 16L.2

|  | Myelo-peroxidase ng/mL | Myoglobin ng/mL | OSM (Oncostatin M) pg/mL | PAI-1 ng/mL | Prostatic Acid Phosphatase ng/mL | PAPP-A mIU/mL |
|---|---|---|---|---|---|---|
| Least Detectable Dose | 68 | 1.1 | 28 | 0.90 | 0.034 | 0.037 |
| RBM Low Plasma Range |  | 3.6 | PENDING | 10 | 0.058 |  |
| RBM High Plasma Range | 1110 | 37 | PENDING | 87 | 0.54 | 0.48 |
| Donor_3 3. Aliquot F | 2630 | 152 | 109 | 216 | 0.16 | 0.0063 |
| Donor_3 3. Aliquot G | 2240 | 162 | 705 | 246 | 0.17 | 0.037 |
| Donor_3 3. Aliquot H | 2830 | 143 | 165 | 207 | 0.14 | 0.0049 |
| Donor_3 3. Aliquot I | 2450 | 150 | 98 | 214 | 0.14 | 0.037 |
| Donor_4 3. Aliquot A | 2710 | 55 | 28 | 253 | 0.27 | 0.13 |
| Donor_4 3. Aliquot B | 1940 | 52 | 54 | 236 | 0.38 | 0.14 |
| Donor_4 3. Aliquot C | 3400 | 54 | 28 | 229 | 0.28 | 0.029 |
| Donor_4 3. Aliquot D | 3920 | 52 | 120 | 216 | 0.42 | 0.13 |
| Donor_4 3. Aliquot E | 4430 | 53 | 165 | 222 | 0.46 | 0.15 |
| Donor_4 3. Aliquot F | 4210 | 56 | 28 | 237 | 0.26 | 0.14 |
| Donor_4 3. Aliquot G | 1950 | 56 | 455 | 203 | 0.56 | 0.16 |
| Donor_4 3. Aliquot H | 4140 | 55 | 76 | 219 | 0.23 | 0.13 |
| Donor_4 3. Aliquot I | 3360 | 55 | 21 | 235 | 0.26 | 0.12 |
| Donor_5 3. Aliquot A | 6630 | 92 | 844 | 158 | 0.46 | 0.021 |
| Donor_5 3. Aliquot B | 6720 | 93 | 834 | 183 | 0.73 | 0.021 |
| Donor_5 3. Aliquot C | 4350 | 97 | 171 | 144 | 0.28 | 0.0078 |
| Donor_5 3. Aliquot D | 7840 | 92 | 1850 | 145 | 1.5 | 0.040 |
| Donor_5 3. Aliquot E | 7880 | 91 | 2320 | 155 | 2.9 | 0.032 |
| Donor_5 3. Aliquot F | 5110 | 87 | 188 | 167 | 0.27 | 0.018 |
| Donor_5 3. Aliquot G | 3130 | 96 | 1040 | 181 | 0.52 | 0.029 |
| Donor_5 3. Aliquot H | 6880 | 87 | 834 | 156 | 0.50 | 0.014 |
| Donor_5 3. Aliquot I | 4080 | 82 | 211 | 147 | 0.27 | 0.014 |
| Donor_6 3. Aliquot A | 2300 | 52 | 82 | 192 | 0.13 | 0.0056 |
| Donor_6 3. Aliquot B | 2240 | 50 | 109 | 174 | 0.24 | 0.037 |

FIG. 16L.3

| | Myelo-peroxidase ng/mL | Myoglobin ng/mL | OSM (Oncostatin M) pg/mL | PAI-1 ng/mL | Prostatic Acid Phosphatase ng/mL | PAPP-A mIU/mL |
|---|---|---|---|---|---|---|
| Least Detectable Dose | 68 | 1.1 | 28 | 0.90 | 0.034 | 0.037 |
| RBM Low Plasma Range | | 3.6 | PENDING | 10 | 0.058 | |
| RBM High Plasma Range | 1110 | 37 | PENDING | 87 | 0.54 | 0.48 |
| Donor_6_3. Aliquot C | 2640 | 52 | 28 | 152 | 0.22 | 0.037 |
| Donor_6_3. Aliquot D | 1490 | 52 | 65 | 181 | 0.26 | 0.037 |
| Donor_6_3. Aliquot E | 1800 | 50 | 87 | 153 | 0.38 | 0.0063 |
| Donor_6_3. Aliquot F | 2660 | 54 | 28 | 173 | 0.15 | 0.037 |
| Donor_6_3. Aliquot G | 1430 | 54 | 715 | 250 | 0.54 | 0.037 |
| Donor_6_3. Aliquot H | 2490 | 50 | 65 | 181 | 0.12 | 0.037 |
| Donor_6_3. Aliquot I | 2270 | 51 | 28 | 176 | 0.17 | 0.037 |
| Donor_7_3. Aliquot A | 2070 | 1790 | 194 | 210 | 0.10 | 0.012 |
| Donor_7_3. Aliquot B | 2710 | >1845 | 109 | 222 | 0.16 | 0.011 |
| Donor_7_3. Aliquot C | 1920 | >1845 | 28 | 215 | 0.068 | 0.037 |
| Donor_7_3. Aliquot D | 1780 | >1845 | 21 | 215 | 0.19 | 0.0085 |
| Donor_7_3. Aliquot E | 2160 | >1845 | 54 | 230 | 0.12 | 0.0049 |
| Donor_7_3. Aliquot F | 2150 | >1845 | 28 | 225 | 0.078 | 0.037 |
| Donor_7_3. Aliquot G | 1630 | >1845 | 143 | 229 | 0.063 | 0.037 |
| Donor_7_3. Aliquot H | 1880 | 1780 | 44 | 198 | 0.087 | 0.0092 |
| Donor_7_3. Aliquot I | 1800 | >1845 | 28 | 198 | 0.073 | 0.037 |
| Donor_8_3. Aliquot A | 1510 | 5.2 | 28 | 32 | 0.082 | 0.0070 |
| Donor_8_3. Aliquot B | 1450 | 3.7 | 28 | 35 | 0.13 | 0.0056 |
| Donor_8_3. Aliquot C | 3790 | 3.3 | 28 | 31 | 0.16 | 0.037 |
| Donor_8_3. Aliquot D | 8210 | 3.1 | 345 | 30 | 0.67 | 0.015 |
| Donor_8_3. Aliquot E | 6150 | 3.2 | 132 | 34 | 0.55 | 0.0092 |
| Donor_8_3. Aliquot F | 2590 | 3.2 | 28 | 30 | 0.15 | 0.0056 |
| Donor_8_3. Aliquot G | 1220 | 2.9 | 132 | 60 | 0.058 | 0.0092 |
| Donor_8_3. Aliquot H | 4710 | 3.3 | 54 | 41 | 0.14 | 0.014 |
| Donor_8_3. Aliquot I | 2000 | 3.5 | 28 | 40 | 0.079 | 0.0078 |

FIG. 16L.4

| | Myelo-peroxidase ng/mL | Myoglobin ng/mL | OSM (Oncostatin M) pg/mL | PAI-1 ng/mL | Prostatic Acid Phosphatase ng/mL | PAPP-A mIU/mL |
|---|---|---|---|---|---|---|
| Least Detectable Dose | 68 | 1.1 | 28 | 0.90 | 0.034 | 0.037 |
| RBM Low Plasma Range | | 3.6 | PENDING | 10 | 0.058 | |
| RBM High Plasma Range | 1110 | 37 | PENDING | 87 | 0.54 | 0.48 |
| Donor_9_3. Aliquot A | 1430 | 2.1 | 28 | 45 | 0.052 | 0.0053 |
| Donor_9_3. Aliquot B | 1150 | 1.9 | 28 | 63 | 0.088 | 0.037 |
| Donor_9_3. Aliquot C | 2030 | 1.7 | 28 | 71 | 0.074 | 0.037 |
| Donor_9_3. Aliquot D | 3500 | 1.3 | 96 | 72 | 0.50 | 0.013 |
| Donor_9_3. Aliquot E | 4800 | 1.9 | 42 | 65 | 0.34 | 0.037 |
| Donor_9_3. Aliquot F | 747 | 2.1 | 28 | 66 | 0.052 | 0.0077 |
| Donor_9_3. Aliquot G | 1560 | 1.7 | 247 | 97 | 0.040 | 0.010 |
| Donor_9_3. Aliquot H | 3250 | 2.1 | 42 | 71 | 0.037 | 0.037 |
| Donor_9_3. Aliquot I | 1070 | 2.1 | 28 | 70 | 0.034 | |
| EDTA Plasma | | | | | | |
| donor #1 plasma | 111 | 77 | 1120 | 142 | 0.090 | 0.084 |
| donor #2 plasma | 158 | 64 | 28 | 151 | 0.13 | 0.052 |
| donor #3 plasma | 85 | 182 | 28 | 208 | 0.050 | 0.029 |
| donor #4 plasma | 322 | 61 | 28 | 218 | 0.65 | 0.26 |
| donor #5 plasma | 372 | 86 | 28 | 154 | 0.41 | 0.040 |
| donor #6 plasma | 9.9 | 57 | 151 | 149 | 0.15 | 0.017 |
| donor #7 plasma | 135 | >1845 | 133 | 242 | 0.078 | 0.066 |
| donor #8 plasma | 183 | 3.8 | 28 | 39 | 0.13 | 0.010 |
| donor #9 plasma | 68 | 1.4 | 28 | 61 | 0.071 | 0.037 |
| MW NHD plasma | 125.5 | 2.6 | 28.0 | 50.0 | 0.1 | 0.0 |
| Normal healthy donors | | | | | | |
| MW NHD unstimuliert | 1535.00 | 2.75 | 28.00 | 54.95 | 0.06 | 0.02 |

FIG. 16L.5

| | | Myeloperoxidase ng/mL | Myoglobin ng/mL | OSM (Oncostatin M) pg/mL | PAI-1 ng/mL | Prostatic Acid Phosphatase ng/mL | PAPP-A mIU/mL |
|---|---|---|---|---|---|---|---|
| | Least Detectable Dose | 68 | 1.1 | 28 | 0.90 | 0.034 | 0.037 |
| | RBM Low Plasma Range | | 3.6 | PENDING | 10 | 0.058 | |
| | RBM High Plasma Range | 1110 | 37 | PENDING | 87 | 0.54 | 0.48 |
| Normal healthy donors | | | | | | | |
| Stimulations indices | | Myeloperoxidase | Myoglobin | OSM (Oncostatin M) | PAI-1 | Prostatic Acid Phosphatase | PAPP-A |
| unstimuliert | Donor_1 3. Aliquot I | 0.9 | 32.5 | 2.7 | 2.9 | 0.6 | 2.2 |
| unstimuliert | Donor_2 3. Aliquot I | 1.1 | 20.9 | 1.6 | 3.0 | 2.4 | 0.8 |
| unstimuliert | Donor_3 3. Aliquot I | 1.6 | 54.5 | 3.5 | 3.9 | 2.5 | 1.7 |
| unstimuliert | Donor_4 3. Aliquot I | 2.2 | 19.9 | 0.8 | 4.3 | 4.6 | 5.2 |
| unstimuliert | Donor_5 3. Aliquot I | 2.7 | 29.7 | 7.5 | 2.7 | 4.8 | 0.6 |
| unstimuliert | Donor_6 3. Aliquot I | 1.5 | 18.6 | 1.0 | 3.2 | 3.0 | 1.7 |
| unstimuliert | Donor_7 3. Aliquot I | 1.2 | #VALUE! | 1.0 | 3.6 | 1.3 | 1.7 |
| unstimuliert | Donor_8 3. Aliquot I | 1.3 | 1.3 | 1.0 | 0.7 | 1.4 | 0.3 |
| unstimuliert | Donor_9 3. Aliquot I | 0.7 | 0.7 | 1.0 | 1.3 | 0.6 | 1.7 |
| Stimulations indices | EDTA Plasma | | | | | | |
| PLASMA | donor #1 plasma | 0.9 | 29.1 | 40.0 | 2.8 | 0.9 | 3.6 |
| PLASMA | donor #2 plasma | 1.3 | 24.3 | 1.0 | 3.0 | 1.3 | 2.2 |
| PLASMA | donor #3 plasma | 0.7 | 69.1 | 1.0 | 4.2 | 0.5 | 1.2 |
| PLASMA | donor #4 plasma | 2.6 | 23.0 | 1.0 | 4.4 | 6.5 | 11.2 |
| PLASMA | donor #5 plasma | 3.0 | 32.7 | 1.0 | 3.1 | 4.1 | 1.7 |
| PLASMA | donor #6 plasma | 0.1 | 21.6 | 5.4 | 3.0 | 1.5 | 0.7 |
| PLASMA | donor #7 plasma | 1.1 | #VALUE! | 4.8 | 4.8 | 0.8 | 2.8 |
| PLASMA | donor #8 plasma | 1.5 | 1.5 | 1.0 | 0.8 | 1.3 | 0.4 |

FIG. 16L.6

| | Myelo-peroxidase ng/mL | Myoglobin ng/mL | OSM (Oncostatin M) pg/mL | PAI-1 ng/mL | Prostatic Acid Phosphatase ng/mL | PAPP-A mIU/mL |
|---|---|---|---|---|---|---|
| Least Detectable Dose | 68 | 1.1 | 28 | 0.90 | 0.034 | 0.037 |
| RBM Low Plasma Range | | 3.6 | PENDING | 10 | 0.058 | |
| RBM High Plasma Range | 1110 | 37 | PENDING | 87 | 0.54 | 0.48 |
| donor #9 plasma | 0.5 | 0.5 | 1.0 | 1.2 | 0.7 | 1.6 |
| PLASMA | | | | | | |

FIG. 16M.1

| | Prostate Specific Antigen, Free ng/mL | RANTES ng/mL | Serum Amyloid P ug/mL | Stem Cell Factor pg/mL | SGOT ug/mL | SHBG nmol/L | Thyroxine Binding Globulin ug/mL | Tissue Factor ng/mL |
|---|---|---|---|---|---|---|---|---|
| Least Detectable Dose | 0.023 | 0.048 | 0.058 | 56 | 3.7 | 1.3 | 0.34 | 0.84 |
| RBM Low Plasma Range | | 2.6 | 15 | | 3.9 | 12 | 40 | |
| RBM High Plasma Range | 1.6 | 83 | 50 | 281 | 28 | 106 | 104 | 2.4 |
| Samples | | | | | | | | |
| Donor_1 3. Aliquot A | 0.44 | 16 | 26 | 757 | 3.7 | 18 | 27 | 3.7 |
| Donor_1 3. Aliquot B | 0.44 | 25 | 28 | 587 | 3.7 | 19 | 31 | 2.7 |
| Donor_1 3. Aliquot C | 0.47 | 22 | 28 | 599 | 3.7 | 19 | 29 | 0.91 |
| Donor_1 3. Aliquot D | 0.50 | 18 | 33 | 657 | 3.7 | 19 | 31 | 3.3 |
| Donor_1 3. Aliquot E | 0.47 | 14 | 29 | 666 | 3.7 | 19 | 29 | 3.0 |
| Donor_1 3. Aliquot F | 0.41 | 14 | 29 | 430 | 3.7 | 18 | 29 | 2.0 |
| Donor_1 3. Aliquot G | 0.50 | 24 | 26 | 645 | 3.7 | 19 | 29 | 2.0 |
| Donor_1 3. Aliquot H | 0.43 | 26 | 29 | 508 | 3.7 | 19 | 26 | 1.8 |
| Donor_1 3. Aliquot I | 0.45 | 19 | 29 | 508 | 3.7 | 18 | 28 | 1.6 |
| Donor_2 3. Aliquot A | 0.11 | 20 | 22 | 1350 | 3.7 | 34 | 36 | 1.7 |
| Donor_2 3. Aliquot B | 0.11 | 24 | 26 | 1530 | 3.7 | 35 | 37 | 1.9 |
| Donor_2 3. Aliquot C | 0.072 | 15 | 23 | 607 | 3.7 | 36 | 36 | 0.84 |
| Donor_2 3. Aliquot D | 0.20 | 13 | 24 | 1640 | 3.7 | 35 | 38 | 7.1 |
| Donor_2 3. Aliquot E | 0.16 | 13 | 26 | 1670 | 3.7 | 34 | 37 | 3.5 |
| Donor_2 3. Aliquot F | 0.087 | 13 | 23 | 582 | 3.7 | 36 | 39 | 0.47 |
| Donor_2 3. Aliquot G | 0.13 | 21 | 22 | 1760 | 3.7 | 34 | 38 | 2.3 |
| Donor_2 3. Aliquot H | 0.083 | 13 | 27 | 595 | 3.7 | 36 | 34 | 0.84 |
| Donor_2 3. Aliquot I | 0.082 | 12 | 23 | 500 | 3.7 | 33 | 37 | 0.70 |
| Donor_3 3. Aliquot A | 0.67 | 16 | 14 | 666 | 3.7 | 42 | 56 | 1.9 |
| Donor_3 3. Aliquot B | 0.65 | 21 | 14 | 434 | 3.7 | 40 | 50 | 1.8 |
| Donor_3 3. Aliquot C | 0.72 | 17 | 17 | 213 | 3.7 | 43 | 57 | 0.15 |
| Donor_3 3. Aliquot D | 0.71 | 16 | 15 | 882 | 3.7 | 39 | 52 | 5.4 |
| Donor_3 3. Aliquot E | 0.73 | 21 | 15 | 1020 | 3.7 | 42 | 52 | 4.9 |

FIG. 16M.2

| | Prostate Specific Antigen, Free ng/mL | RANTES ng/mL | Serum Amyloid P ug/mL | Stem Cell Factor pg/mL | SGOT ug/mL | SHBG nmol/L | Thyroxine Binding Globulin ug/mL | Tissue Factor ng/mL |
|---|---|---|---|---|---|---|---|---|
| Least Detectable Dose | 0.023 | 0.048 | 0.058 | 56 | 3.7 | 1.3 | 0.34 | 0.84 |
| RBM Low Plasma Range | | | | | | | | |
| RBM High Plasma Range | 1.6 | 2.6 | 15 | | 3.9 | 12 | 40 | |
| Donor_3_3. Aliquot F | 0.65 | 83 | 50 | 281 | 28 | 106 | 104 | 2.4 |
| Donor_3_3. Aliquot G | 0.74 | 13 | 16 | 202 | 3.7 | 40 | 53 | 1.5 |
| Donor_3_3. Aliquot H | 0.57 | 26 | 15 | 183 | 3.7 | 41 | 54 | 0.84 |
| Donor_3_3. Aliquot I | 0.61 | 13 | 16 | 113 | 3.7 | 38 | 49 | 0.56 |
| | | 14 | 16 | 138 | 3.7 | 36 | 51 | 0.99 |
| Donor_4_3. Aliquot A | 0.023 | 4.4 | 8.7 | 426 | 3.7 | 54 | 38 | 1.5 |
| Donor_4_3. Aliquot B | 0.023 | 4.6 | 9.6 | 475 | 3.7 | 53 | 35 | 0.87 |
| Donor_4_3. Aliquot C | 0.023 | 2.7 | 9.9 | 377 | 3.7 | 54 | 35 | 0.84 |
| Donor_4_3. Aliquot D | 0.045 | 3.4 | 10 | 957 | 3.7 | 55 | 34 | 5.4 |
| Donor_4_3. Aliquot E | 0.023 | 2.6 | 10 | 1010 | 3.7 | 50 | 35 | 3.4 |
| Donor_4_3. Aliquot F | 0.023 | 2.5 | 12 | 459 | 3.7 | 58 | 36 | 1.5 |
| Donor_4_3. Aliquot G | 0.023 | 5.9 | 8.8 | 459 | 3.7 | 57 | 36 | 0.84 |
| Donor_4_3. Aliquot H | 0.023 | 2.5 | 11 | 405 | 3.7 | 53 | 32 | 0.99 |
| Donor_4_3. Aliquot I | 0.023 | 3.2 | 10 | 352 | 3.7 | 51 | 35 | 0.84 |
| Donor_5_3. Aliquot A | 0.49 | 17 | 43 | 936 | 3.7 | 33 | 47 | 0.87 |
| Donor_5_3. Aliquot B | 0.48 | 13 | 41 | 815 | 3.7 | 31 | 47 | 0.87 |
| Donor_5_3. Aliquot C | 0.42 | 11 | 38 | 320 | 3.7 | 35 | 42 | 0.84 |
| Donor_5_3. Aliquot D | 0.61 | 14 | 46 | 965 | 3.7 | 31 | 45 | 6.3 |
| Donor_5_3. Aliquot E | 0.57 | 14 | 45 | 1290 | 3.7 | 31 | 46 | 4.4 |
| Donor_5_3. Aliquot F | 0.39 | 9.5 | 38 | 288 | 0.62 | 31 | 43 | 0.15 |
| Donor_5_3. Aliquot G | 0.45 | 16 | 40 | 541 | 3.7 | 32 | 44 | 0.84 |
| Donor_5_3. Aliquot H | 0.46 | 12 | 43 | 292 | 3.7 | 29 | 40 | 0.56 |
| Donor_5_3. Aliquot I | 0.49 | 9.0 | 41 | 348 | 3.7 | 29 | 42 | 0.84 |
| Donor_6_3. Aliquot A | 0.35 | 35 | 25 | 217 | 3.7 | 18 | 29 | 0.84 |
| Donor_6_3. Aliquot B | 0.40 | 34 | 27 | 187 | 3.7 | 19 | 30 | 0.84 |

FIG. 16M.3

| | Prostate Specific Antigen, Free ng/mL | RANTES ng/mL | Serum Amyloid P ug/mL | Stem Cell Factor pg/mL | SGOT ug/mL | SHBG nmol/L | Thyroxine Binding Globulin ug/mL | Tissue Factor ng/mL |
|---|---|---|---|---|---|---|---|---|
| Least Detectable Dose | 0.023 | 0.048 | 0.058 | | 3.7 | 1.3 | 0.34 | 0.84 |
| RBM Low Plasma Range | | 2.6 | 15 | 56 | 3.9 | 12 | 40 | |
| RBM High Plasma Range | 1.6 | 83 | 50 | 281 | 28 | 106 | 104 | 2.4 |
| Donor_6_3. Aliquot C | 0.34 | 23 | 24 | 99 | 3.7 | 19 | 27 | 0.84 |
| Donor_6_3. Aliquot D | 0.44 | 35 | 31 | 272 | 3.7 | 18 | 29 | 3.0 |
| Donor_6_3. Aliquot E | 0.40 | 23 | 26 | 316 | 3.7 | 17 | 28 | 5.1 |
| Donor_6_3. Aliquot F | 0.31 | 20 | 26 | 99 | 3.7 | 19 | 30 | 0.84 |
| Donor_6_3. Aliquot G | 0.33 | 47 | 22 | 164 | 3.7 | 18 | 30 | 0.84 |
| Donor_6_3. Aliquot H | 0.33 | 22 | 23 | 69 | 3.7 | 19 | 27 | 0.84 |
| Donor_6_3. Aliquot I | 0.35 | 23 | 25 | 92 | 3.7 | 18 | 28 | 0.84 |
| Donor_7_3. Aliquot A | 0.65 | 17 | 31 | 998 | 8.2 | 9.5 | 25 | 2.4 |
| Donor_7_3. Aliquot B | 0.63 | 17 | 35 | 607 | 12 | 11 | 27 | 1.9 |
| Donor_7_3. Aliquot C | 0.65 | 25 | 33 | 113 | 8.1 | 12 | 25 | 0.84 |
| Donor_7_3. Aliquot D | 0.61 | 19 | 30 | 790 | 11 | 10 | 25 | 4.1 |
| Donor_7_3. Aliquot E | 0.66 | 15 | 29 | 707 | 13 | 8.8 | 19 | 2.4 |
| Donor_7_3. Aliquot F | 0.57 | 9.7 | 35 | 127 | 11 | 10 | 26 | 0.15 |
| Donor_7_3. Aliquot G | 0.68 | 23 | 29 | 160 | 4.3 | 9.4 | 23 | 0.84 |
| Donor_7_3. Aliquot H | 0.64 | 12 | 31 | 72 | 16 | 9.7 | 22 | 0.84 |
| Donor_7_3. Aliquot I | 0.60 | 12 | 34 | 127 | 11 | 9.9 | 25 | 0.15 |
| Donor_8_3. Aliquot A | 0.023 | 12 | 5.7 | 92 | 3.7 | 65 | 31 | 1.2 |
| Donor_8_3. Aliquot B | 0.023 | 16 | 6.4 | 46 | 3.7 | 66 | 30 | 0.84 |
| Donor_8_3. Aliquot C | 0.023 | 17 | 5.4 | 69 | 3.7 | 61 | 29 | 0.84 |
| Donor_8_3. Aliquot D | 0.18 | 12 | 5.7 | 106 | 3.7 | 60 | 28 | 13 |
| Donor_8_3. Aliquot E | 0.13 | 14 | 5.9 | 72 | 3.7 | 62 | 29 | 12 |
| Donor_8_3. Aliquot F | 0.023 | 6.9 | 6.7 | 40 | 3.7 | 67 | 31 | 0.47 |
| Donor_8_3. Aliquot G | 0.023 | 19 | 5.2 | 99 | 3.7 | 57 | 27 | 0.84 |
| Donor_8_3. Aliquot H | 0.023 | 15 | 6.4 | 89 | 3.7 | 69 | 29 | 0.65 |
| Donor_8_3. Aliquot I | 0.023 | 17 | 6.5 | 56 | 3.7 | 64 | 31 | 0.65 |

FIG. 16M.4

| | Prostate Specific Antigen, Free ng/mL | RANTES ng/mL | Serum Amyloid P ug/mL | Stem Cell Factor pg/mL | SGOT ug/mL | SHBG nmol/L | Thyroxine Binding Globulin ug/mL | Tissue Factor ng/mL |
|---|---|---|---|---|---|---|---|---|
| Least Detectable Dose | 0.023 | 0.048 | 0.058 | 56 | 3.7 | 1.3 | 0.34 | 0.84 |
| RBM Low Plasma Range | | 2.6 | 15 | | 3.9 | 12 | 40 | |
| RBM High Plasma Range | 1.6 | 83 | 50 | 281 | 28 | 106 | 104 | 2.4 |
| Donor_9_3. Aliquot A | 0.023 | 16 | Pending | 170 | 3.7 | Pending | Pending | 1.2 |
| Donor_9_3. Aliquot B | 0.023 | 21 | Pending | 229 | 3.7 | Pending | Pending | 2.0 |
| Donor_9_3. Aliquot C | 0.023 | 23 | Pending | 229 | 3.7 | Pending | Pending | 0.66 |
| Donor_9_3. Aliquot D | 0.18 | 21 | Pending | 307 | 3.7 | Pending | Pending | 15 |
| Donor_9_3. Aliquot E | 0.10 | 13 | Pending | 272 | 3.7 | Pending | Pending | 8.6 |
| Donor_9_3. Aliquot F | 0.023 | 9.1 | Pending | 137 | 3.7 | Pending | Pending | 2.1 |
| Donor_9_3. Aliquot G | 0.023 | 30 | Pending | 528 | 3.7 | Pending | Pending | 1.8 |
| Donor_9_3. Aliquot H | 0.023 | 21 | Pending | 97 | 3.7 | Pending | Pending | 1.5 |
| Donor_9_3. Aliquot I | 0.023 | 21 | Pending | 174 | 3.7 | Pending | Pending | 0.53 |
| EDTA Plasma | | | | | | | | |
| donor #1 plasma | 0.28 | 9.4 | Pending | 351 | 40 | Pending | Pending | 2.9 |
| donor #2 plasma | 0.13 | 3.4 | Pending | 492 | 45 | Pending | Pending | 1.1 |
| donor #3 plasma | 0.74 | 6.4 | Pending | 161 | 54 | Pending | Pending | 1.9 |
| donor #4 plasma | 0.023 | 1.3 | Pending | 368 | 32 | Pending | Pending | 2.0 |
| donor #5 plasma | 0.47 | 8.7 | Pending | 550 | 70 | Pending | Pending | 2.1 |
| donor #6 plasma | 0.45 | 14 | Pending | 62 | 35 | Pending | Pending | 0.95 |
| donor #7 plasma | 0.82 | 12 | Pending | 212 | 46 | Pending | Pending | 1.9 |
| donor #8 plasma | 0.024 | 5.3 | Pending | 161 | 3.7 | Pending | Pending | 1.0 |
| donor #9 plasma | 0.023 | 1.2 | Pending | 203 | 3.7 | Pending | Pending | 0.74 |
| MW NHD plasma | 0.0 | 3.2 | #DIV/0! | 182.0 | 3.7 | #DIV/0! | #DIV/0! | 0.9 |
| Normal healthy donors | | | | | | | | |
| | | 18.70 | 6.53 | 114.80 | 3.70 | 64.20 | 30.60 | |
| MW NHD unstimuliert | 0.02 | | | | | | | 0.59 |

FIG. 16M.5

| | | Prostate Specific Antigen, Free | RANTES | Serum Amyloid P | Stem Cell Factor | SGOT | SHBG | Thyroxine Binding Globulin | Tissue Factor |
|---|---|---|---|---|---|---|---|---|---|
| | | ng/mL | ng/mL | ug/mL | pg/mL | ug/mL | nmol/L | ug/mL | ng/mL |
| | Least Detectable Dose | 0.023 | 0.048 | 0.058 | 56 | 3.7 | 1.3 | 0.34 | 0.84 |
| | RBM Low Plasma Range | | 2.6 | 15 | | 3.9 | 12 | 40 | |
| | RBM High Plasma Range | 1.6 | 83 | 50 | 281 | 28 | 106 | 104 | 2.4 |
| Normal healthy donors | | | | | | | | | |
| Stimulations indices | | | | | | | | | |
| unstimuliert | Donor_1 3. Aliquot I | 19.5 | 1.0 | 4.4 | 4.4 | 1.0 | 0.3 | 0.9 | 2.7 |
| unstimuliert | Donor_2 3. Aliquot I | 3.6 | 0.6 | 3.5 | 4.4 | 1.0 | 0.5 | 1.2 | 1.2 |
| unstimuliert | Donor_3 3. Aliquot I | 26.4 | 0.7 | 2.4 | 1.2 | 1.0 | 0.6 | 1.7 | 1.7 |
| unstimuliert | Donor_4 3. Aliquot I | 1.0 | 0.2 | 1.6 | 3.1 | 1.0 | 0.8 | 1.1 | 1.4 |
| unstimuliert | Donor_5 3. Aliquot I | 21.1 | 0.5 | 6.2 | 3.0 | 1.0 | 0.5 | 1.4 | 1.4 |
| unstimuliert | Donor_6 3. Aliquot I | 15.2 | 1.2 | 3.9 | 0.8 | 1.0 | 0.3 | 0.9 | 1.4 |
| unstimuliert | Donor_7 3. Aliquot I | 26.3 | 0.6 | 5.3 | 1.1 | 2.8 | 0.2 | 0.8 | 0.2 |
| unstimuliert | Donor_8 3. Aliquot I | 1.0 | 0.9 | 1.0 | 0.5 | 1.0 | 1.0 | 1.0 | 1.1 |
| unstimuliert | Donor_9 3. Aliquot I | 1.0 | 1.1 | #VALUE! | 1.5 | 1.0 | #VALUE! | #VALUE! | 0.9 |
| Stimulations indices | | | | | | | | | |
| EDTA Plasma | | | | | | | | | |
| PLASMA | donor #1 plasma | 11.9 | 2.9 | #VALUE! | 1.9 | 10.9 | #VALUE! | #VALUE! | 3.2 |
| PLASMA | donor #2 plasma | 5.4 | 1.1 | #VALUE! | 2.7 | 12.0 | #VALUE! | #VALUE! | 1.2 |
| PLASMA | donor #3 plasma | 31.6 | 2.0 | #VALUE! | 0.9 | 14.6 | #VALUE! | #VALUE! | 2.1 |
| PLASMA | donor #4 plasma | 1.0 | 0.4 | #VALUE! | 2.0 | 8.7 | #VALUE! | #VALUE! | 2.2 |
| PLASMA | donor #5 plasma | 20.1 | 2.7 | #VALUE! | 3.0 | 19.0 | #VALUE! | #VALUE! | 2.3 |
| PLASMA | donor #6 plasma | 19.2 | 4.3 | #VALUE! | 0.3 | 9.5 | #VALUE! | #VALUE! | 1.1 |
| PLASMA | donor #7 plasma | 34.9 | 3.7 | #VALUE! | 1.2 | 12.5 | #VALUE! | #VALUE! | 2.2 |
| PLASMA | donor #8 plasma | 1.0 | 1.6 | #VALUE! | 0.9 | 1.0 | #VALUE! | #VALUE! | 1.0 |

FIG. 16M.6

| | Prostate Specific Antigen, Free ng/mL | RANTES ng/mL | Serum Amyloid P ug/mL | Stem Cell Factor pg/mL | SGOT ug/mL | SHBG nmol/L | Thyroxine Binding Globulin ug/mL | Tissue Factor ng/mL |
|---|---|---|---|---|---|---|---|---|
| Least Detectable Dose | 0.023 | 0.048 | 0.058 | 56 | 3.7 | 1.3 | 0.34 | 0.84 |
| RBM Low Plasma Range | 1.6 | 2.6 | 15 | | 3.9 | 12 | 40 | |
| RBM High Plasma Range | | 83 | 50 | 281 | 28 | 106 | 104 | 2.4 |
| PLASMA donor #9 plasma | 1.0 | 0.4 | #VALUE! | 1.1 | 1.0 | #VALUE! | #VALUE! | 0.8 |

FIG. 16N.1

| | TGF-alpha pg/mL | TIMP-1 ng/mL | TNF RII ng/mL | TNF-alpha pg/mL | TNF-beta pg/mL | Thrombopoietin ng/mL | Thyroid Stimulating Hormone uIU/mL | Thrombospondin-1 ng/mL |
|---|---|---|---|---|---|---|---|---|
| Least Detectable Dose | 1.8 | 8.4 | 0.13 | 4.0 | 46 | 3.2 | 0.028 | <25 |
| RBM Low Plasma Range | Pending | 59 | 3.1 | 27 | 120 | 6.2 | 0.18 | Pending |
| RBM High Plasma Range | Pending | 192 | 79 | | | | 3.7 | Pending |
| Samples | | | | | | | | |
| Donor_1 3. Aliquot A | 22 | 521 | 29 | 236 | 7.9 | 1.9 | 17 | 15200 |
| Donor_1 3. Aliquot B | 15 | 615 | 31 | 75 | 46 | 1.5 | 16 | 21600 |
| Donor_1 3. Aliquot C | 1.8 | 611 | 28 | 19 | 46 | 3.2 | 18 | 17000 |
| Donor_1 3. Aliquot D | 9.7 | 620 | 30 | 300 | 46 | 1.9 | 17 | 15600 |
| Donor_1 3. Aliquot E | 13 | 549 | 29 | 88 | 46 | 1.9 | 17 | 13100 |
| Donor_1 3. Aliquot F | 3.8 | 553 | 27 | 35 | 46 | 3.2 | 17 | 12500 |
| Donor_1 3. Aliquot G | 24 | 645 | 30 | 24 | 46 | 1.3 | 17 | 11800 |
| Donor_1 3. Aliquot H | 1.5 | 580 | 27 | 19 | 46 | 0.86 | 17 | 24900 |
| Donor_1 3. Aliquot I | 1.6 | 495 | 24 | 25 | 46 | 0.69 | 17 | 16200 |
| Donor_2 3. Aliquot A | 56 | 354 | 47 | 212 | 4.6 | 2.7 | 10 | 19800 |
| Donor_2 3. Aliquot B | 44 | 391 | 49 | 94 | 6.0 | 3.2 | 10 | 21600 |
| Donor_2 3. Aliquot C | 7.5 | 303 | 41 | 12 | 46 | 3.2 | 9.9 | 12200 |
| Donor_2 3. Aliquot D | 46 | 359 | 45 | 2700 | 6.0 | 2.4 | 12 | 13600 |
| Donor_2 3. Aliquot E | 43 | 376 | 48 | 1690 | 3.2 | 2.7 | 11 | 12400 |
| Donor_2 3. Aliquot F | 5.6 | 305 | 40 | 24 | 46 | 1.5 | 10 | 12800 |
| Donor_2 3. Aliquot G | 48 | 499 | 47 | 544 | 18 | 3.0 | 9.9 | 12000 |
| Donor_2 3. Aliquot H | 20 | 304 | 40 | 21 | 46 | 3.2 | 9.5 | 13300 |
| Donor_2 3. Aliquot I | 9.5 | 278 | 36 | 19 | 46 | 0.49 | 9.1 | 12400 |
| Donor_3 3. Aliquot A | 20 | 183 | 14 | 157 | 7.3 | 2.5 | 0.99 | 14000 |
| Donor_3 3. Aliquot B | 22 | 209 | 13 | 64 | 46 | 2.5 | 0.98 | 18300 |
| Donor_3 3. Aliquot C | 5.6 | 156 | 8.1 | 13 | 46 | 3.2 | 0.99 | 12000 |
| Donor_3 3. Aliquot D | 18 | 213 | 14 | 2600 | 14 | 2.2 | 1.1 | 13700 |
| Donor_3 3. Aliquot E | 16 | 221 | 14 | 1150 | 11 | 3.9 | 1.2 | 16800 |

FIG. 16N.2

| | TGF-alpha pg/mL | TIMP-1 ng/mL | TNF RII ng/mL | TNF-alpha pg/mL | TNF-beta pg/mL | Throm-bopoietin ng/mL | Thyroid Stimulating Hormone uIU/mL | Throm-bospondin-1 ng/mL |
|---|---|---|---|---|---|---|---|---|
| Least Detectable Dose | 1.8 | 8.4 | 0.13 | 4.0 | 46 | 3.2 | 0.028 | <25 |
| RBM Low Plasma Range | Pending | 59 | 3.1 | | | | 0.18 | Pending |
| RBM High Plasma Range | Pending | 192 | 79 | 27 | 120 | 6.2 | 3.7 | Pending |
| Donor_3 3. Aliquot F | 4.4 | 154 | 7.9 | 26 | 46 | 2.1 | 0.94 | 10500 |
| Donor_3 3. Aliquot G | 15 | 205 | 10.0 | 21 | 46 | 3.2 | 1.0 | 12200 |
| Donor_3 3. Aliquot H | 2.1 | 155 | 6.8 | 9.4 | 46 | 3.2 | 0.90 | 9670 |
| Donor_3 3. Aliquot I | 0.63 | 153 | 6.5 | 4.2 | 46 | 2.1 | 0.98 | 9250 |
| Donor_4 3. Aliquot A | 15 | 575 | 30 | 20 | 46 | 1.3 | 0.15 | 14100 |
| Donor_4 3. Aliquot B | 22 | 590 | 30 | 17 | 46 | 1.4 | 0.15 | 16300 |
| Donor_4 3. Aliquot C | 6.4 | 532 | 26 | 12 | 46 | 3.2 | 0.16 | 4160 |
| Donor_4 3. Aliquot D | 19 | 622 | 33 | 1720 | 7.3 | 2.0 | 0.26 | 11500 |
| Donor_4 3. Aliquot E | 16 | 632 | 36 | 618 | 15 | 2.3 | 0.19 | 10900 |
| Donor_4 3. Aliquot F | 4.6 | 565 | 31 | 91 | 7.3 | 1.2 | 0.14 | 5780 |
| Donor_4 3. Aliquot G | 16 | 499 | 30 | 12 | 46 | 3.2 | 0.13 | 4050 |
| Donor_4 3. Aliquot H | 3.5 | 546 | 27 | 9.3 | 46 | 1.2 | 0.14 | 4460 |
| Donor_4 3. Aliquot I | 3.8 | 557 | 28 | 4.8 | 46 | 3.2 | 0.13 | 6360 |
| Donor_5 3. Aliquot A | 22 | 344 | 28 | 106 | 7.9 | 2.9 | 0.28 | 22300 |
| Donor_5 3. Aliquot B | 20 | 368 | 31 | 146 | 7.3 | 3.1 | 0.26 | 17800 |
| Donor_5 3. Aliquot C | 7.3 | 184 | 23 | 12 | 46 | 0.69 | 0.32 | 13300 |
| Donor_5 3. Aliquot D | 17 | 327 | 34 | 1900 | 9.8 | 2.8 | 0.41 | 18600 |
| Donor_5 3. Aliquot E | 23 | 360 | 35 | 1590 | 16 | 2.7 | 0.38 | 17800 |
| Donor_5 3. Aliquot F | 7.1 | 233 | 23 | 105 | 46 | 2.2 | 0.24 | 13200 |
| Donor_5 3. Aliquot G | 25 | 331 | 27 | 18 | 8.6 | 1.0 | 0.28 | 14000 |
| Donor_5 3. Aliquot H | 7.0 | 228 | 23 | 12 | 46 | 0.49 | 0.26 | 14800 |
| Donor_5 3. Aliquot I | 7.6 | 190 | 22 | 12 | 46 | 0.49 | 0.26 | 10900 |
| Donor_6 3. Aliquot A | 13 | 139 | 5.5 | 41 | 6.6 | 3.6 | 1.3 | 25000 |
| Donor_6 3. Aliquot B | 15 | 165 | 6.9 | 23 | 4.6 | 3.7 | 1.2 | 22900 |

FIG. 16N.3

| | TGF-alpha pg/mL | TIMP-1 ng/mL | TNF RII ng/mL | TNF-alpha pg/mL | TNF-beta pg/mL | Throm-bopoietin ng/mL | Thyroid Stimulating Hormone uIU/mL | Throm-bospondin-1 ng/mL |
|---|---|---|---|---|---|---|---|---|
| Least Detectable Dose | 1.8 | 8.4 | 0.13 | 4.0 | 46 | 3.2 | 0.028 | <25 |
| RBM Low Plasma Range | Pending | 59 | 3.1 | | | | 0.18 | Pending |
| RBM High Plasma Range | Pending | 192 | 79 | 27 | 120 | 6.2 | 3.7 | Pending |
| Donor_6_3. Aliquot C | 1.2 | 111 | 2.5 | 3.2 | 46 | 3.1 | 1.3 | 13800 |
| Donor_6_3. Aliquot D | 12 | 156 | 6.8 | 1910 | 46 | 3.4 | 1.4 | 21100 |
| Donor_6_3. Aliquot E | 16 | 164 | 7.8 | 3210 | 46 | 3.6 | 1.3 | 13800 |
| Donor_6_3. Aliquot F | 1.2 | 124 | 4.1 | 9.1 | 46 | 4.0 | 1.1 | 15700 |
| Donor_6_3. Aliquot G | 11 | 260 | 5.1 | 12 | 46 | 2.3 | 1.3 | 12400 |
| Donor_6_3. Aliquot H | 3.8 | 112 | 3.0 | 8.0 | 8.6 | 1.7 | 1.2 | 14500 |
| Donor_6_3. Aliquot I | 1.5 | 100 | 2.4 | 1.7 | 46 | 1.7 | 1.2 | 12500 |
| Donor_7_3. Aliquot A | 9.2 | 210 | 14 | 240 | 24 | 4.2 | 0.52 | 12100 |
| Donor_7_3. Aliquot B | 4.8 | 237 | 14 | 67 | 14 | 4.3 | 0.51 | 14600 |
| Donor_7_3. Aliquot C | 1.8 | 198 | 7.8 | 4.3 | 7.9 | 1.4 | 0.49 | 15800 |
| Donor_7_3. Aliquot D | 4.6 | 241 | 13 | 1250 | 8.6 | 3.3 | 0.55 | 11600 |
| Donor_7_3. Aliquot E | 3.4 | 243 | 13 | 338 | 19 | 3.8 | 0.50 | 11200 |
| Donor_7_3. Aliquot F | 1.8 | 187 | 8.4 | 19 | 9.8 | 3.5 | 0.47 | 7230 |
| Donor_7_3. Aliquot G | 4.7 | 213 | 10.0 | 17 | 46 | 1.0 | 0.49 | 6360 |
| Donor_7_3. Aliquot H | 1.8 | 158 | 6.4 | 5.1 | 46 | 3.2 | 0.49 | 7470 |
| Donor_7_3. Aliquot I | 1.8 | 159 | 7.0 | 2.7 | 46 | 2.2 | 0.47 | 7470 |
| Donor_8_3. Aliquot A | 2.7 | 84 | 3.8 | 129 | 7.9 | 3.6 | 2.2 | 10800 |
| Donor_8_3. Aliquot B | 3.4 | 118 | 5.1 | 49 | 6.0 | 4.7 | 2.1 | 14000 |
| Donor_8_3. Aliquot C | 2.7 | 50 | 1.7 | 184 | 46 | 4.4 | 1.8 | 10800 |
| Donor_8_3. Aliquot D | 6.2 | 60 | 3.8 | 12200 | 11 | 4.4 | 2.4 | 8580 |
| Donor_8_3. Aliquot E | 5.5 | 88 | 4.7 | 7570 | 11 | 4.2 | 2.2 | 11900 |
| Donor_8_3. Aliquot F | 1.9 | 52 | 3.2 | 591 | 9.8 | 5.6 | 2.0 | 4870 |
| Donor_8_3. Aliquot G | 4.2 | 118 | 2.8 | 22 | 46 | 1.4 | 1.9 | 5370 |
| Donor_8_3. Aliquot H | 2.8 | 60 | 2.5 | 113 | 3.9 | 3.7 | 2.2 | 12600 |
| Donor_8_3. Aliquot I | 1.8 | 61 | 1.9 | 14 | 46 | 3.8 | 2.0 | 13200 |

FIG. 16N.4

|  | TGF-alpha pg/mL | TIMP-1 ng/mL | TNF RII ng/mL | TNF-alpha pg/mL | TNF-beta pg/mL | Thrombopoietin ng/mL | Thyroid Stimulating Hormone uIU/mL | Thrombospondin-1 ng/mL |
|---|---|---|---|---|---|---|---|---|
| Least Detectable Dose | 1.8 | 8.4 | 0.13 | 4.0 | 46 | 3.2 | 0.028 | <25 |
| RBM Low Plasma Range | Pending | 59 | 3.1 | | | | 0.18 | Pending |
| RBM High Plasma Range | Pending | 192 | 79 | 27 | 120 | 6.2 | 3.7 | Pending |
| Donor_9_3, Aliquot A | 19 | 66 | 3.6 | 78 | 11 | 3.2 | 0.34 | 13600 |
| Donor_9_3, Aliquot B | 16 | 92 | 4.4 | 51 | 8.8 | 3.4 | 0.28 | 16400 |
| Donor_9_3, Aliquot C | 18 | 62 | 3.3 | 68 | 20 | 3.6 | 0.33 | 15500 |
| Donor_9_3, Aliquot D | 18 | 69 | 5.2 | 6000 | 15 | 2.9 | 0.65 | 13800 |
| Donor_9_3, Aliquot E | 20 | 93 | 5.6 | 4600 | 5.0 | 3.1 | 0.53 | 11300 |
| Donor_9_3, Aliquot F | 12 | 48 | 2.7 | 81 | 18 | 4.3 | 0.29 | 6910 |
| Donor_9_3, Aliquot G | 20 | 130 | 3.9 | 55 | 6.9 | 1.2 | 0.22 | 9900 |
| Donor_9_3, Aliquot H | 12 | 56 | 2.5 | 22 | 10 | 1.8 | 0.31 | 15900 |
| Donor_9_3, Aliquot I | 8.5 | 53 | 1.9 | 13 | 46 | 2.3 | 0.28 | 17000 |
| EDTA Plasma | | | | | | | | |
| donor #1 plasma | 1.8 | 379 | 27 | 14 | 10 | 3.2 | 12 | 14800 |
| donor #2 plasma | 1.2 | 248 | 51 | 5.4 | 46 | 3.2 | 9.7 | 4670 |
| donor #3 plasma | 1.8 | 144 | 8.2 | 5.4 | 8.8 | 0.81 | 1.0 | 7890 |
| donor #4 plasma | 1.8 | 478 | 34 | 1.1 | 46 | 1.4 | 0.11 | 2310 |
| donor #5 plasma | 1.8 | 166 | 28 | 2.3 | 11 | 1.8 | 0.28 | 28600 |
| donor #6 plasma | 1.8 | 82 | 2.6 | 4 | 5.0 | 2.4 | 1.7 | 16800 |
| donor #7 plasma | 1.8 | 156 | 9.5 | 4 | 13 | 2.1 | 0.59 | 13800 |
| donor #8 plasma | 1.8 | 40 | 1.2 | 5.6 | 46 | 1.4 | 2.5 | 6520 |
| donor #9 plasma | 4.4 | 31 | 1.5 | 4 | 46 | 0.44 | 0.30 | 818 |
| MW NHD plasma Normal healthy donors | 3.1 | 35.7 | 1.3 | 4.8 | 46.0 | 0.9 | 1.4 | 3669.0 |
| MW NHD unstimuliert | 5.15 | 57.00 | 1.92 | 13.25 | 46.00 | 3.03 | 1.11 | 15100.00 |

FIG. 16N.5

|  | | TGF-alpha pg/mL | TIMP-1 ng/mL | TNF RII ng/mL | TNF-alpha pg/mL | TNF-beta pg/mL | Throm-bopoietin ng/mL | Thyroid Stimulating Hormone uIU/mL | Throm-bospondin-1 ng/mL |
|---|---|---|---|---|---|---|---|---|---|
|  | Least Detectable Dose | 1.8 | 8.4 | 0.13 | 4.0 | 46 | 3.2 | 0.028 | <25 |
|  | RBM Low Plasma Range | Pending | 59 | 3.1 | | | | 0.18 | Pending |
|  | RBM High Plasma Range | Pending | 192 | 79 | 27 | 120 | 6.2 | 3.7 | Pending |
|  | Normal healthy donors | | | | | | | | |
|  | *Stimulations indices* | TGF-alpha | TIMP-1 | TNF RII | TNF-alpha | TNF-beta | Throm-bopoietin | Thyroid Stimulating Hormone | Throm-bospondin-1 |
| unstimuliert | Donor_1 3. Aliquot I | 0.3 | 8.7 | 12.7 | 1.9 | 1.0 | 0.2 | 15.3 | 1.1 |
| unstimuliert | Donor_2 3. Aliquot I | 1.9 | 4.9 | 18.7 | 1.4 | 1.0 | 0.2 | 8.1 | 0.8 |
| unstimuliert | Donor_3 3. Aliquot I | 0.1 | 2.7 | 3.4 | 0.3 | 1.0 | 0.7 | 0.9 | 0.6 |
| unstimuliert | Donor_4 3. Aliquot I | 0.7 | 9.8 | 14.4 | 0.4 | 1.0 | 1.1 | 0.1 | 0.4 |
| unstimuliert | Donor_5 3. Aliquot I | 1.5 | 3.3 | 11.2 | 0.9 | 1.0 | 0.2 | 0.2 | 0.7 |
| unstimuliert | Donor_6 3. Aliquot I | 0.3 | 1.8 | 1.2 | 0.1 | 1.0 | 0.5 | 1.1 | 0.8 |
| unstimuliert | Donor_7 3. Aliquot I | 0.3 | 2.8 | 3.7 | 0.2 | 1.0 | 0.7 | 0.4 | 0.5 |
| unstimuliert | Donor_8 3. Aliquot I | 0.3 | 1.1 | 1.0 | 1.0 | 1.0 | 1.2 | 1.7 | 0.9 |
| unstimuliert | Donor_9 3. Aliquot I | 1.7 | 0.9 | 1.0 | 1.0 | 1.0 | 0.8 | 0.3 | 1.1 |
|  | *Stimulations indices* | | | | | | | | |
|  | EDTA Plasma | | | | | | | | |
| PLASMA | donor #1 plasma | 0.6 | 10.6 | 20.1 | 2.9 | 0.2 | 3.4 | 8.7 | 4.0 |
| PLASMA | donor #2 plasma | 0.4 | 6.9 | 37.5 | 1.1 | 1.0 | 3.4 | 7.0 | 1.3 |
| PLASMA | donor #3 plasma | 0.6 | 4.0 | 6.1 | 1.1 | 0.2 | 0.9 | 0.7 | 2.2 |
| PLASMA | donor #4 plasma | 0.6 | 13.4 | 25.1 | 0.2 | 1.0 | 1.5 | 0.1 | 0.6 |
| PLASMA | donor #5 plasma | 0.6 | 4.6 | 21.0 | 0.5 | 0.2 | 1.9 | 0.2 | 7.8 |
| PLASMA | donor #6 plasma | 0.6 | 2.3 | 1.9 | 0.8 | 0.1 | 2.6 | 1.2 | 4.6 |
| PLASMA | donor #7 plasma | 0.6 | 4.4 | 7.1 | 0.8 | 0.3 | 2.3 | 0.4 | 3.8 |
| PLASMA | donor #8 plasma | 0.6 | 1.1 | 0.9 | 1.2 | 1.0 | 1.5 | 1.8 | 1.8 |

FIG. 16N.6

| | TGF-alpha pg/mL | TIMP-1 ng/mL | TNF RII ng/mL | TNF-alpha pg/mL | TNF-beta pg/mL | Throm-bopoietin ng/mL | Thyroid Stimulating Hormone uIU/mL | Throm-bospondin-1 ng/mL |
|---|---|---|---|---|---|---|---|---|
| Least Detectable Dose | 1.8 | 8.4 | 0.13 | 4.0 | 46 | 3.2 | 0.028 | <25 |
| RBM Low Plasma Range | Pending | 59 | 3.1 | | | | 0.18 | Pending |
| RBM High Plasma Range | Pending | 192 | 79 | 27 | 120 | 6.2 | 3.7 | Pending |
| PLASMA donor #9 plasma | 1.4 | 0.9 | 1.1 | 0.8 | 1.0 | 0.5 | 0.2 | 0.2 |

FIG. 16O.1

| | VCAM-1 ng/mL | VEGF pg/mL | von Willebrand Factor ug/mL |
|---|---|---|---|
| Least Detectable Dose | 2.6 | 7.5 | 0.40 |
| RBM Low Plasma Range | 284 | 91 | 5.3 |
| RBM High Plasma Range | 1310 | 1790 | 74 |
| Samples | | | |
| Donor_1 3. Aliquot A | 1350 | 2090 | 211 |
| Donor_1 3. Aliquot B | 1440 | 2090 | 203 |
| Donor_1 3. Aliquot C | 1350 | 2070 | 213 |
| Donor_1 3. Aliquot D | 1420 | 2120 | 198 |
| Donor_1 3. Aliquot E | 1320 | 2030 | 184 |
| Donor_1 3. Aliquot F | 1310 | 1860 | 196 |
| Donor_1 3. Aliquot G | 1450 | 2570 | 180 |
| Donor_1 3. Aliquot H | 1320 | 2210 | 207 |
| Donor_1 3. Aliquot I | 1350 | 1940 | 203 |
| Donor_2 3. Aliquot A | 1090 | 4570 | 188 |
| Donor_2 3. Aliquot B | 1190 | 4900 | 200 |
| Donor_2 3. Aliquot C | 1160 | 5240 | 191 |
| Donor_2 3. Aliquot D | 1070 | 4400 | 190 |
| Donor_2 3. Aliquot E | 1150 | 4630 | 189 |
| Donor_2 3. Aliquot F | 1100 | 4870 | 178 |
| Donor_2 3. Aliquot G | 1180 | 5490 | 215 |
| Donor_2 3. Aliquot H | 1090 | 4920 | 213 |
| Donor_2 3. Aliquot I | 1080 | 4680 | 187 |
| Donor_3 3. Aliquot A | 749 | 532 | 99 |
| Donor_3 3. Aliquot B | 722 | 618 | 110 |
| Donor_3 3. Aliquot C | 740 | 707 | 95 |
| Donor_3 3. Aliquot D | 725 | 505 | 123 |
| Donor_3 3. Aliquot E | 775 | 508 | 108 |

FIG. 16O.2

| | VCAM-1 ng/mL | VEGF pg/mL | von Willebrand Factor ug/mL |
|---|---|---|---|
| Least Detectable Dose | 2.6 | 7.5 | 0.40 |
| RBM Low Plasma Range | 284 | 91 | 5.3 |
| RBM High Plasma Range | 1310 | 1790 | 74 |
| Donor_3 3. Aliquot F | 695 | 714 | 104 |
| Donor_3 3. Aliquot G | 758 | 1590 | 109 |
| Donor_3 3. Aliquot H | 694 | 678 | 123 |
| Donor_3 3. Aliquot I | 690 | 734 | 119 |
| Donor_4 3. Aliquot A | 2080 | 1190 | 182 |
| Donor_4 3. Aliquot B | 1940 | 1180 | 227 |
| Donor_4 3. Aliquot C | 1990 | 1220 | 253 |
| Donor_4 3. Aliquot D | 1950 | 1100 | 252 |
| Donor_4 3. Aliquot E | 2070 | 1060 | 223 |
| Donor_4 3. Aliquot F | 2200 | 1030 | 257 |
| Donor_4 3. Aliquot G | 1970 | 2190 | 223 |
| Donor_4 3. Aliquot H | 1980 | 1350 | 229 |
| Donor_4 3. Aliquot I | 2020 | 1280 | 246 |
| Donor_5 3. Aliquot A | 521 | 3600 | 100 |
| Donor_5 3. Aliquot B | 510 | 3460 | 105 |
| Donor_5 3. Aliquot C | 489 | 4460 | 113 |
| Donor_5 3. Aliquot D | 525 | 3350 | 112 |
| Donor_5 3. Aliquot E | 539 | 3650 | 125 |
| Donor_5 3. Aliquot F | 495 | 3140 | 109 |
| Donor_5 3. Aliquot G | 545 | 5580 | 110 |
| Donor_5 3. Aliquot H | 510 | 3840 | 121 |
| Donor_5 3. Aliquot I | 489 | 3520 | 96 |
| Donor_6 3. Aliquot A | 258 | 874 | 79 |
| Donor_6 3. Aliquot B | 252 | 648 | 70 |

FIG. 16O.3

| | VCAM-1 ng/mL | VEGF pg/mL | von Willebrand Factor ug/mL |
|---|---|---|---|
| Least Detectable Dose | 2.6 | 7.5 | 0.40 |
| RBM Low Plasma Range | 284 | 91 | 5.3 |
| RBM High Plasma Range | 1310 | 1790 | 74 |
| Donor_6_3. Aliquot C | 261 | 840 | 74 |
| Donor_6_3. Aliquot D | 274 | 530 | 75 |
| Donor_6_3. Aliquot E | 253 | 471 | 72 |
| Donor_6_3. Aliquot F | 254 | 581 | 80 |
| Donor_6_3. Aliquot G | 284 | 2690 | 85 |
| Donor_6_3. Aliquot H | 258 | 878 | 76 |
| Donor_6_3. Aliquot I | 256 | 846 | 67 |
| Donor_7_3. Aliquot A | 789 | 295 | 112 |
| Donor_7_3. Aliquot B | 802 | 237 | 129 |
| Donor_7_3. Aliquot C | 861 | 345 | 132 |
| Donor_7_3. Aliquot D | 740 | 210 | 124 |
| Donor_7_3. Aliquot E | 816 | 235 | 102 |
| Donor_7_3. Aliquot F | 781 | 203 | 135 |
| Donor_7_3. Aliquot G | 803 | 1260 | 114 |
| Donor_7_3. Aliquot H | 721 | 313 | 127 |
| Donor_7_3. Aliquot I | 738 | 257 | 123 |
| Donor_8_3. Aliquot A | 352 | 252 | 18 |
| Donor_8_3. Aliquot B | 350 | 203 | 23 |
| Donor_8_3. Aliquot C | 320 | 401 | 16 |
| Donor_8_3. Aliquot D | 319 | 416 | 19 |
| Donor_8_3. Aliquot E | 322 | 341 | 17 |
| Donor_8_3. Aliquot F | 341 | 321 | 20 |
| Donor_8_3. Aliquot G | 337 | 822 | 21 |
| Donor_8_3. Aliquot H | 331 | 322 | 22 |
| Donor_8_3. Aliquot I | 347 | 248 | 21 |

FIG. 160.4

| | VCAM-1 ng/mL | VEGF pg/mL | von Willebrand Factor ug/mL |
|---|---|---|---|
| Least Detectable Dose | 2.6 | 7.5 | 0.40 |
| | | | |
| RBM Low Plasma Range | 284 | 91 | 5.3 |
| RBM High Plasma Range | 1310 | 1790 | 74 |
| | | | |
| Donor_9 3. Aliquot A | 298 | 326 | Pending |
| Donor_9 3. Aliquot B | 303 | 280 | Pending |
| Donor_9 3. Aliquot C | 324 | 367 | Pending |
| Donor_9 3. Aliquot D | 295 | 486 | Pending |
| Donor_9 3. Aliquot E | 312 | 398 | Pending |
| Donor_9 3. Aliquot F | 314 | 322 | Pending |
| Donor_9 3. Aliquot G | 297 | 1170 | Pending |
| Donor_9 3. Aliquot H | 297 | 380 | Pending |
| Donor_9 3. Aliquot I | 290 | 243 | Pending |
| | | | |
| EDTA Plasma | | | |
| donor #1 plasma | 1230 | 1500 | Pending |
| donor #2 plasma | 1280 | 4500 | Pending |
| donor #3 plasma | 978 | 1290 | Pending |
| donor #4 plasma | 2580 | 1400 | Pending |
| donor #5 plasma | 577 | 3840 | Pending |
| donor #6 plasma | 301 | 533 | Pending |
| donor #7 plasma | 980 | 521 | Pending |
| donor #8 plasma | 340 | 281 | Pending |
| donor #9 plasma | 385 | 295 | Pending |
| | | | |
| MW | | | |
| Normal healthy donors | | | |
| NHD plasma | 362.5 | 288.0 | #DIV/0! |
| | | | |
| MW | | | |
| NHD unstimuliert | 318.50 | 245.50 | 21.20 |

FIG. 16O.5

| | | VCAM-1 ng/mL | VEGF pg/mL | von Willebrand Factor ug/mL |
|---|---|---|---|---|
| | Least Detectable Dose | 2.6 | 7.5 | 0.40 |
| | RBM Low Plasma Range | 284 | 91 | 5.3 |
| | RBM High Plasma Range | 1310 | 1790 | 74 |
| Normal healthy donors | | | | |
| | Stimulationsindices | VCAM-1 | VEGF | von Willebrand Factor |
| unstimuliert | Donor_1 3. Aliquot I | 4.2 | 7.9 | 9.6 |
| unstimuliert | Donor_2 3. Aliquot I | 3.4 | 19.1 | 8.8 |
| unstimuliert | Donor_3 3. Aliquot I | 2.2 | 3.0 | 5.6 |
| unstimuliert | Donor_4 3. Aliquot I | 6.3 | 5.2 | 11.6 |
| unstimuliert | Donor_5 3. Aliquot I | 1.5 | 14.3 | 4.5 |
| unstimuliert | Donor_6 3. Aliquot I | 0.8 | 3.4 | 3.2 |
| unstimuliert | Donor_7 3. Aliquot I | 2.3 | 1.0 | 5.8 |
| unstimuliert | Donor_8 3. Aliquot I | 1.1 | 1.0 | 1.0 |
| unstimuliert | Donor_9 3. Aliquot I | 0.9 | 1.0 | #VALUE! |
| | Stimulationsindices | | | |
| | EDTA Plasma | | | |
| PLASMA | donor #1 plasma | 3.4 | 5.2 | #VALUE! |
| PLASMA | donor #2 plasma | 3.5 | 15.6 | #VALUE! |
| PLASMA | donor #3 plasma | 2.7 | 4.5 | #VALUE! |
| PLASMA | donor #4 plasma | 7.1 | 4.9 | #VALUE! |
| PLASMA | donor #5 plasma | 1.6 | 13.3 | #VALUE! |
| PLASMA | donor #6 plasma | 0.8 | 1.9 | #VALUE! |
| PLASMA | donor #7 plasma | 2.7 | 1.8 | #VALUE! |
| PLASMA | donor #8 plasma | 0.9 | 1.0 | #VALUE! |

FIG. 16O.6

| | | VCAM-1 ng/mL | VEGF pg/mL | von Willebrand Factor ug/mL |
|---|---|---|---|---|
| | Least Detectable Dose | 2.6 | 7.5 | 0.40 |
| | RBM Low Plasma Range | 284 | 91 | 5.3 |
| | RBM High Plasma Range | 1310 | 1790 | 74 |
| PLASMA | donor #9 plasma | 1.1 | 1.0 | #VALUE! |

FIG. 17A.1

| | Alpha-1 Antitrypsin mg/mL | Adiponectin ug/mL | Alpha-2 Macroglobulin mg/mL |
|---|---|---|---|
| Least Detectable Dose | 0.011 | 0.20 | 0.061 |
| RBM Low Plasma Range | 1.2 | 1.6 | 0.13 |
| RBM High Plasma Range | 3.1 | 14 | 1.0 |
| Samples | | | |
| Donor_1 3. Aliquot A | 2.6 | 2.0 | 0.29 |
| Donor_1 3. Aliquot B | 2.8 | 2.1 | 0.30 |
| Donor_1 3. Aliquot C | 2.9 | 2.1 | 0.30 |
| Donor_1 3. Aliquot D | 3.1 | 2.1 | 0.31 |
| Donor_1 3. Aliquot E | 2.8 | 2.1 | 0.27 |
| Donor_1 3. Aliquot F | 2.6 | 2.0 | 0.66 |
| Donor_1 3. Aliquot G | 2.9 | 2.1 | 0.30 |
| Donor_1 3. Aliquot H | 2.7 | 2.0 | 0.42 |
| Donor_1 3. Aliquot I | 2.7 | 2.0 | 0.26 |
| Donor_2 3. Aliquot A | 2.2 | 4.4 | 0.28 |
| Donor_2 3. Aliquot B | 2.3 | 4.5 | 0.30 |
| Donor_2 3. Aliquot C | 2.3 | 4.5 | 0.29 |
| Donor_2 3. Aliquot D | 2.2 | 4.3 | 0.29 |
| Donor_2 3. Aliquot E | 2.3 | 4.5 | 0.28 |
| Donor_2 3. Aliquot F | 2.3 | 4.2 | 0.64 |
| Donor_2 3. Aliquot G | 2.3 | 4.3 | 0.32 |
| Donor_2 3. Aliquot H | 2.2 | 4.4 | 0.33 |
| Donor_2 3. Aliquot I | 2.1 | 4.0 | 0.29 |
| Donor_3 3. Aliquot A | 2.9 | 3.0 | 0.35 |
| Donor_3 3. Aliquot B | 3.0 | 2.7 | 0.35 |
| Donor_3 3. Aliquot C | 3.0 | 2.8 | 0.34 |
| Donor_3 3. Aliquot D | 2.8 | 2.7 | 0.34 |
| Donor_3 3. Aliquot E | 3.1 | 2.8 | 0.36 |
| Donor_3 3. Aliquot F | 2.7 | 2.6 | 0.65 |

FIG. 17A.2

|  | Alpha-1 Antitrypsin mg/mL | Adiponectin ug/mL | Alpha-2 Macroglobulin mg/mL |
|---|---|---|---|
| Least Detectable Dose | 0.011 | 0.20 | 0.061 |
|  |  |  |  |
| RBM Low Plasma Range | 1.2 | 1.6 | 0.13 |
| RBM High Plasma Range | 3.1 | 14 | 1.0 |
| Donor_3 3. Aliquot G | 3.1 | 2.8 | 0.35 |
| Donor_3 3. Aliquot H | 2.8 | 2.7 | 0.41 |
| Donor_3 3. Aliquot I | 2.8 | 2.6 | 0.33 |
|  |  |  |  |
| Donor_4 3. Aliquot A | 1.7 | 5.3 | 0.40 |
| Donor_4 3. Aliquot B | 1.5 | 5.4 | 0.40 |
| Donor_4 3. Aliquot C | 1.6 | 5.2 | 0.41 |
| Donor_4 3. Aliquot D | 1.6 | 5.3 | 0.42 |
| Donor_4 3. Aliquot E | 1.5 | 5.3 | 0.38 |
| Donor_4 3. Aliquot F | 1.6 | 5.3 | 0.98 |
| Donor_4 3. Aliquot G | 1.6 | 5.5 | 0.48 |
| Donor_4 3. Aliquot H | 1.5 | 5.3 | 0.65 |
| Donor_4 3. Aliquot I | 1.5 | 5.4 | 0.41 |
|  |  |  |  |
| Donor_5 3. Aliquot A | 2.9 | 2.8 | 0.27 |
| Donor_5 3. Aliquot B | 2.9 | 2.6 | 0.29 |
| Donor_5 3. Aliquot C | 3.2 | 2.7 | 0.29 |
| Donor_5 3. Aliquot D | 3.2 | 2.6 | 0.28 |
| Donor_5 3. Aliquot E | 3.1 | 2.8 | 0.28 |
| Donor_5 3. Aliquot F | 2.9 | 2.6 | 0.46 |
| Donor_5 3. Aliquot G | 3.0 | 2.5 | 0.29 |
| Donor_5 3. Aliquot H | 3.0 | 2.5 | 0.33 |
| Donor_5 3. Aliquot I | 3.0 | 2.4 | 0.28 |
|  |  |  |  |
| Donor_6 3. Aliquot A | 2.8 | 1.2 | 0.26 |
| Donor_6 3. Aliquot B | 2.7 | 1.2 | 0.24 |
| Donor_6 3. Aliquot C | 2.8 | 1.2 | 0.24 |
| Donor_6 3. Aliquot D | 2.7 | 1.2 | 0.24 |

FIG. 17A.3

| | Alpha-1 Antitrypsin mg/mL | Adiponectin ug/mL | Alpha-2 Macroglobulin mg/mL |
|---|---|---|---|
| Least Detectable Dose | 0.011 | 0.20 | 0.061 |
| | | | |
| RBM Low Plasma Range | 1.2 | 1.6 | 0.13 |
| RBM High Plasma Range | 3.1 | 14 | 1.0 |
| Donor_6 3. Aliquot E | 2.6 | 1.2 | 0.25 |
| Donor_6 3. Aliquot F | 2.7 | 1.3 | 0.25 |
| Donor_6 3. Aliquot G | 2.9 | 1.2 | 0.27 |
| Donor_6 3. Aliquot H | 2.5 | 1.3 | 0.29 |
| Donor_6 3. Aliquot I | 2.5 | 1.1 | 0.26 |
| | | | |
| Donor_7 3. Aliquot A | 1.8 | 0.90 | 0.39 |
| Donor_7 3. Aliquot B | 1.7 | 0.92 | 0.37 |
| Donor_7 3. Aliquot C | 1.9 | 0.83 | 0.38 |
| Donor_7 3. Aliquot D | 1.7 | 0.81 | 0.36 |
| Donor_7 3. Aliquot E | 1.2 | 0.90 | 0.40 |
| Donor_7 3. Aliquot F | 1.8 | 0.90 | 0.45 |
| Donor_7 3. Aliquot G | 1.6 | 0.87 | 0.43 |
| Donor_7 3. Aliquot H | 1.7 | 0.79 | 0.51 |
| Donor_7 3. Aliquot I | 1.8 | 0.82 | 0.38 |
| | | | |
| Donor_8 3. Aliquot A | 0.96 | 4.3 | 0.39 |
| Donor_8 3. Aliquot B | 0.97 | 4.3 | 0.39 |
| Donor_8 3. Aliquot C | 0.96 | 4.1 | 0.40 |
| Donor_8 3. Aliquot D | 0.88 | 4.0 | 0.39 |
| Donor_8 3. Aliquot E | 0.88 | 4.0 | 0.39 |
| Donor_8 3. Aliquot F | 0.99 | 4.5 | 0.46 |
| Donor_8 3. Aliquot G | 0.92 | 4.2 | 0.48 |
| Donor_8 3. Aliquot H | 1.0 | 4.4 | 0.58 |
| Donor_8 3. Aliquot I | 0.94 | 4.2 | 0.40 |
| | | | |
| Donor_9 3. Aliquot A | 1.2 | 3.5 | 0.34 |
| Donor_9 3. Aliquot B | 1.3 | 3.5 | 0.38 |

FIG. 17A.4

| | Alpha-1 Antitrypsin mg/mL | Adiponectin ug/mL | Alpha-2 Macroglobulin mg/mL |
|---|---|---|---|
| Least Detectable Dose | 0.011 | 0.20 | 0.061 |
| RBM Low Plasma Range | 1.2 | 1.6 | 0.13 |
| RBM High Plasma Range | 3.1 | 14 | 1.0 |
| Donor_9 3. Aliquot C | 1.3 | 3.6 | 0.41 |
| Donor_9 3. Aliquot D | 1.2 | 3.3 | 0.38 |
| Donor_9 3. Aliquot E | 1.3 | 3.7 | 0.45 |
| Donor_9 3. Aliquot F | 1.2 | 3.8 | 0.40 |
| Donor_9 3. Aliquot G | 1.4 | 3.5 | 0.49 |
| Donor_9 3. Aliquot H | 1.2 | 3.5 | 0.54 |
| Donor_9 3. Aliquot I | 1.3 | 3.6 | 0.36 |
| EDTA Plasma | | | |
| donor #1 plasma | 2.9 | 2.1 | 0.25 |
| donor #2 plasma | 3.0 | 6.1 | 0.29 |
| donor #3 plasma | 4.7 | 4.2 | 0.36 |
| donor #4 plasma | 2.2 | 7.5 | 0.34 |
| donor #5 plasma | 4.4 | 3.6 | 0.25 |
| donor #6 plasma | 3.7 | 1.7 | 0.24 |
| donor #7 plasma | 2.3 | 1.3 | 0.35 |
| donor #8 plasma | 1.0 | 5.1 | 0.34 |
| donor #9 plasma | 1.9 | 4.8 | 0.37 |
| MW | | | |
| NHD plasma | 1.5 | 4.9 | 0.4 |
| Normal healthy donors | | | |
| MW | | | |
| NHD unstimuliert | 1.13 | 3.90 | 0.38 |
| Normal healthy donors | | | |
| Stimulations Indices | | | |

FIG. 17A.5

| | | Alpha-1 Antitrypsin<br>mg/mL | Adiponectin<br>ug/mL | Alpha-2 Macroglobulin<br>mg/mL |
|---|---|---|---|---|
| | Least Detectable Dose | 0.011 | 0.20 | 0.061 |
| | RBM Low Plasma Range | 1.2 | 1.6 | 0.13 |
| | RBM High Plasma Range | 3.1 | 14 | 1.0 |
| | EDTA Plasma | | | |
| PLASMA | patient 1 | | | |
| PLASMA | patient 7 | | | |
| PLASMA | patient 2 | | | |
| PLASMA | patient 3 | | | |
| PLASMA | patient 5 | | | |
| PLASMA | patient 4 | | | |
| PLASMA | patient 6 | | | |
| PLASMA | NHD 1 | | | |
| PLASMA | NHD 2 | | | |

FIG. 17A.6

| | Alpha-1 Antitrypsin<br>mg/mL | Adiponectin<br>ug/mL | Alpha-2 Macroglobulin<br>mg/mL |
|---|---|---|---|
| Least Detectable Dose | 0.011 | 0.20 | 0.061 |
| RBM Low Plasma Range | 1.2 | 1.6 | 0.13 |
| RBM High Plasma Range | 3.1 | 14 | 1.0 |
| Messwert > ULD | | | |
| SI > 1,5 | | | |
| SI 0,7-1,5 | | | |
| SI 0-0,7 | | | |
| MW nur von 1 Kontrollperson | | | |
| Stimulationsindices | | | |

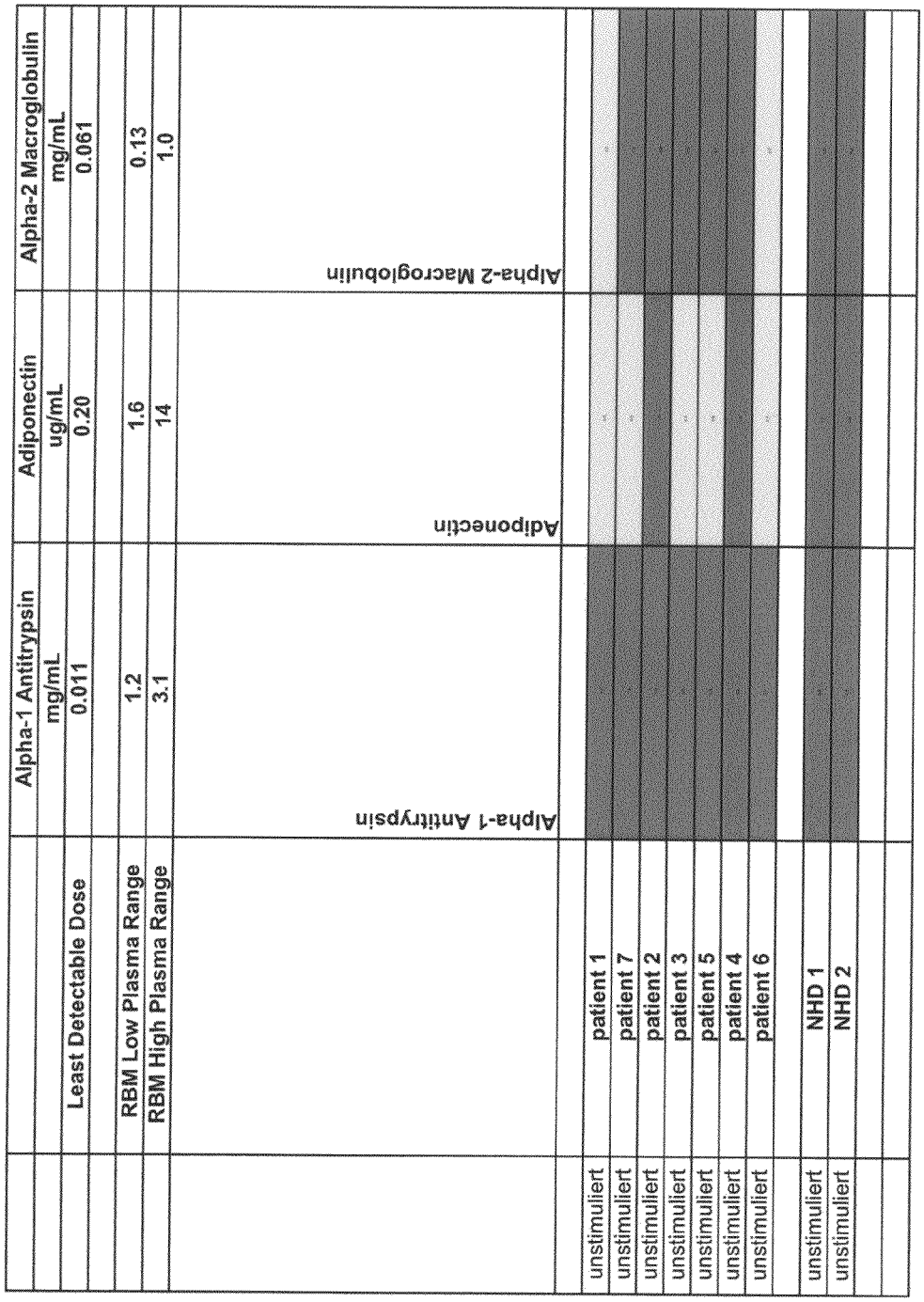
FIG. 17A.7

FIG. 17A.8

| | Alpha-1 Antitrypsin | Adiponectin | Alpha-2 Macroglobulin |
| --- | --- | --- | --- |
| | mg/mL | ug/mL | mg/mL |
| Least Detectable Dose | 0.011 | 0.20 | 0.061 |
| RBM Low Plasma Range | 1.2 | 1.6 | 0.13 |
| RBM High Plasma Range | 3.1 | 14 | 1.0 |
| NHD = normal healthy donor | | | |

FIG. 17B.1

| | Alpha-Fetoprotein ng/mL | Amphiregulin pg/mL | Apolipoprotein A1 mg/mL | Apolipoprotein CIII ug/mL |
|---|---|---|---|---|
| Least Detectable Dose | 0.43 | 36 | 0.0066 | 2.7 |
| RBM Low Plasma Range | | Pending | 0.19 | 28 |
| RBM High Plasma Range | 6.7 | Pending | 0.89 | 224 |
| Samples | | | | |
| Donor_1 3. Aliquot A | 2.8 | 469 | 0.10 | 52 |
| Donor_1 3. Aliquot B | 2.6 | 455 | 0.10 | 64 |
| Donor_1 3. Aliquot C | 2.3 | 104 | 0.11 | 60 |
| Donor_1 3. Aliquot D | 2.8 | 431 | 0.11 | 60 |
| Donor_1 3. Aliquot E | 2.5 | 443 | 0.11 | 53 |
| Donor_1 3. Aliquot F | 2.3 | 414 | 0.097 | 57 |
| Donor_1 3. Aliquot G | 2.5 | 401 | 0.098 | 61 |
| Donor_1 3. Aliquot H | 2.7 | 36 | 0.089 | 48 |
| Donor_1 3. Aliquot I | 2.5 | 419 | 0.11 | 60 |
| Donor_2 3. Aliquot A | 2.1 | 133 | 0.11 | 58 |
| Donor_2 3. Aliquot B | 2.3 | 50 | 0.12 | 64 |
| Donor_2 3. Aliquot C | 1.4 | 36 | 0.12 | 64 |
| Donor_2 3. Aliquot D | 3.4 | 104 | 0.098 | 48 |
| Donor_2 3. Aliquot E | 2.5 | 39 | 0.097 | 52 |
| Donor_2 3. Aliquot F | 2.0 | 36 | 0.090 | 66 |
| Donor_2 3. Aliquot G | 1.8 | 597 | 0.094 | 67 |
| Donor_2 3. Aliquot H | 1.8 | 36 | 0.095 | 61 |
| Donor_2 3. Aliquot I | 1.9 | 24 | 0.11 | 54 |
| Donor_3 3. Aliquot A | 2.7 | 36 | 0.13 | 38 |
| Donor_3 3. Aliquot B | 2.6 | 36 | 0.14 | 38 |
| Donor_3 3. Aliquot C | 1.9 | 36 | 0.13 | 41 |
| Donor_3 3. Aliquot D | 3.3 | 97 | 0.13 | 38 |
| Donor_3 3. Aliquot E | 3.5 | 116 | 0.14 | 36 |
| Donor_3 3. Aliquot F | 2.5 | 60 | 0.12 | 42 |

FIG. 17B.2

| | Alpha-Fetoprotein ng/mL | Amphiregulin pg/mL | Apolipoprotein A1 mg/mL | Apolipoprotein CIII ug/mL |
|---|---|---|---|---|
| Least Detectable Dose | 0.43 | 36 | 0.0066 | 2.7 |
| RBM Low Plasma Range | | Pending | 0.19 | 28 |
| RBM High Plasma Range | 6.7 | Pending | 0.89 | 224 |
| Donor_3 3. Aliquot G | 1.4 | 97 | 0.15 | 44 |
| Donor_3 3. Aliquot H | 1.7 | 36 | 0.13 | 41 |
| Donor_3 3. Aliquot I | 1.3 | 39 | 0.14 | 42 |
| Donor_4 3. Aliquot A | 2.4 | 36 | 0.056 | 13 |
| Donor_4 3. Aliquot B | 2.1 | 36 | 0.050 | 12 |
| Donor_4 3. Aliquot C | 2.0 | 39 | 0.049 | 11 |
| Donor_4 3. Aliquot D | 3.6 | 36 | 0.044 | 13 |
| Donor_4 3. Aliquot E | 2.8 | 36 | 0.048 | 9.1 |
| Donor_4 3. Aliquot F | 1.8 | 36 | 0.054 | 15 |
| Donor_4 3. Aliquot G | 2.1 | 76 | 0.047 | 11 |
| Donor_4 3. Aliquot H | 2.1 | 76 | 0.051 | 11 |
| Donor_4 3. Aliquot I | 1.9 | 36 | 0.052 | 12 |
| Donor_5 3. Aliquot A | 3.2 | 127 | 0.12 | 70 |
| Donor_5 3. Aliquot B | 3.2 | 178 | 0.13 | 77 |
| Donor_5 3. Aliquot C | 2.5 | 50 | 0.14 | 77 |
| Donor_5 3. Aliquot D | 4.1 | 159 | 0.14 | 78 |
| Donor_5 3. Aliquot E | 4.0 | 187 | 0.14 | 71 |
| Donor_5 3. Aliquot F | 2.3 | 36 | 0.12 | 83 |
| Donor_5 3. Aliquot G | 3.0 | 208 | 0.14 | 78 |
| Donor_5 3. Aliquot H | 3.0 | 138 | 0.14 | 81 |
| Donor_5 3. Aliquot I | 3.3 | 39 | 0.13 | 75 |
| Donor_6 3. Aliquot A | 1.5 | 36 | 0.100 | 43 |
| Donor_6 3. Aliquot B | 1.9 | 36 | 0.10 | 42 |
| Donor_6 3. Aliquot C | 1.8 | 36 | 0.12 | 36 |
| Donor_6 3. Aliquot D | 1.9 | 36 | 0.11 | 43 |

FIG. 17B.3

| | Alpha-Fetoprotein | Amphiregulin | Apolipoprotein A1 | Apolipoprotein CIII |
|---|---|---|---|---|
| | ng/mL | pg/mL | mg/mL | ug/mL |
| Least Detectable Dose | 0.43 | 36 | 0.0066 | 2.7 |
| | | | | |
| RBM Low Plasma Range | | Pending | 0.19 | 28 |
| RBM High Plasma Range | 6.7 | Pending | 0.89 | 224 |
| Donor_6 3. Aliquot E | 2.4 | 39 | 0.12 | 42 |
| Donor_6 3. Aliquot F | 1.6 | 36 | 0.094 | 45 |
| Donor_6 3. Aliquot G | 1.8 | 599 | 0.12 | 52 |
| Donor_6 3. Aliquot H | 1.6 | 36 | 0.11 | 40 |
| Donor_6 3. Aliquot I | 1.5 | 24 | 0.12 | 40 |
| | | | | |
| Donor_7 3. Aliquot A | 1.9 | 104 | 0.14 | 50 |
| Donor_7 3. Aliquot B | 2.5 | 36 | 0.14 | 36 |
| Donor_7 3. Aliquot C | 1.3 | 36 | 0.16 | 44 |
| Donor_7 3. Aliquot D | 2.6 | 104 | 0.15 | 41 |
| Donor_7 3. Aliquot E | 2.5 | 36 | 0.12 | 33 |
| Donor_7 3. Aliquot F | 1.5 | 36 | 0.16 | 54 |
| Donor_7 3. Aliquot G | 2.2 | 370 | 0.14 | 43 |
| Donor_7 3. Aliquot H | 1.5 | 36 | 0.15 | 41 |
| Donor_7 3. Aliquot I | 1.9 | 36 | 0.13 | 42 |
| | | | | |
| Donor_8 3. Aliquot A | 1.7 | 36 | 0.24 | 57 |
| Donor_8 3. Aliquot B | 1.3 | 36 | 0.28 | 72 |
| Donor_8 3. Aliquot C | 0.53 | 36 | 0.28 | 75 |
| Donor_8 3. Aliquot D | 4.4 | 36 | 0.26 | 55 |
| Donor_8 3. Aliquot E | 3.5 | 127 | 0.24 | 61 |
| Donor_8 3. Aliquot F | 1.6 | 50 | 0.29 | 69 |
| Donor_8 3. Aliquot G | 1.2 | 90 | 0.29 | 58 |
| Donor_8 3. Aliquot H | 1.6 | 36 | 0.25 | 59 |
| Donor_8 3. Aliquot I | 1.2 | 36 | 0.25 | 53 |
| | | | | |
| Donor_9 3. Aliquot A | 1.1 | 51 | 0.21 | 39 |
| Donor_9 3. Aliquot B | 1.8 | 51 | 0.22 | 43 |

FIG. 17B.4

|  | Alpha-Fetoprotein | Amphiregulin | Apolipoprotein A1 | Apolipoprotein CIII |
|---|---|---|---|---|
|  | ng/mL | pg/mL | mg/mL | ug/mL |
| Least Detectable Dose | 0.43 | 36 | 0.0066 | 2.7 |
| RBM Low Plasma Range |  | Pending | 0.19 | 28 |
| RBM High Plasma Range | 6.7 | Pending | 0.89 | 224 |
| Donor_9_3_Aliquot C | 2.0 | 51 | 0.21 | 33 |
| Donor_9_3_Aliquot D | 4.2 | 101 | 0.18 | 34 |
| Donor_9_3_Aliquot E | 3.2 | 42 | 0.20 | 36 |
| Donor_9_3_Aliquot F | 2.1 | 36 | 0.23 | 39 |
| Donor_9_3_Aliquot G | 2.1 | 169 | 0.22 | 42 |
| Donor_9_3_Aliquot H | 2.3 | 78 | 0.19 | 37 |
| Donor_9_3_Aliquot I | 1.3 | 36 | 0.21 | 33 |
| EDTA Plasma |  |  |  |  |
| donor #1 plasma | 2.3 | 441 | 0.069 | 34 |
| donor #2 plasma | 1.7 | 36 | 0.11 | 65 |
| donor #3 plasma | 2.9 | 36 | 0.14 | 47 |
| donor #4 plasma | 2.4 | 33 | 0.047 | 14 |
| donor #5 plasma | 3.6 | 36 | 0.12 | 91 |
| donor #6 plasma | 2.1 | 36 | 0.100 | 34 |
| donor #7 plasma | 2.8 | 78 | 0.17 | 52 |
| donor #8 plasma | 1.9 | 72 | 0.25 | 46 |
| donor #9 plasma | 2.1 | 36 | 0.30 | 39 |
| MW |  |  |  |  |
| Normal healthy donors | 2.0 | 53.9 | 0.3 | 42.3 |
| MW |  |  |  |  |
| NHD unstimuliert | 1.28 | 36.00 | 0.23 | 42.90 |
| Normal healthy donors |  |  |  |  |
| Stimulationsindices |  |  |  |  |

FIG. 17B.5

| | Alpha-Fetoprotein ng/mL | Amphiregulin pg/mL | Apolipoprotein A1 mg/mL | Apolipoprotein CIII ug/mL |
|---|---|---|---|---|
| Least Detectable Dose | 0.43 | 36 | 0.0066 | 2.7 |
| RBM Low Plasma Range | | Pending | 0.19 | 28 |
| RBM High Plasma Range | 6.7 | Pending | 0.89 | 224 |
| EDTA Plasma | | | | |
| patient 1 PLASMA | | | | |
| patient 7 PLASMA | | | | |
| patient 2 PLASMA | | | | |
| patient 3 PLASMA | | | | |
| patient 5 PLASMA | | | | |
| patient 4 PLASMA | | | | |
| patient 6 PLASMA | | | | |
| NHD 1 PLASMA | | | | |
| NHD 2 PLASMA | | | | |

FIG. 17B.6

| | Alpha-Fetoprotein | Amphiregulin | Apolipoprotein A1 | Apolipoprotein CIII |
|---|---|---|---|---|
| | ng/mL | pg/mL | mg/mL | ug/mL |
| Least Detectable Dose | 0.43 | 36 | 0.0066 | 2.7 |
| RBM Low Plasma Range | | Pending | 0.19 | 28 |
| RBM High Plasma Range | 6.7 | Pending | 0.89 | 224 |
| Messwert > ULD | | | | |
| SI > 1,5 | | | | |
| SI 0,7-1,5 | | | | |
| SI 0-0,7 | | | | |
| MW nur von 1 Kontrollperson | | | | |
| *Stimulationsindices* | | | | |

FIG. 17B.7

| | Alpha-Fetoprotein ng/mL | Amphiregulin pg/mL | Apolipoprotein A1 mg/mL | Apolipoprotein CIII ug/mL |
|---|---|---|---|---|
| Least Detectable Dose | 0.43 | 36 | 0.0066 | 2.7 |
| RBM Low Plasma Range | | Pending | 0.19 | 28 |
| RBM High Plasma Range | 6.7 | Pending | 0.89 | 224 |
| | Alpha-Fetoprotein | Amphiregulin | Apolipoprotein A1 | Apolipoprotein CIII |
| patient 1 | unstimuliert | | | |
| patient 7 | unstimuliert | | | |
| patient 2 | unstimuliert | | | |
| patient 3 | unstimuliert | | | |
| patient 5 | unstimuliert | | | |
| patient 4 | unstimuliert | | | |
| patient 6 | unstimuliert | | | |
| NHD 1 | unstimuliert | | | |
| NHD 2 | unstimuliert | | | |

FIG. 17B.8

| | Alpha-Fetoprotein | Amphiregulin | Apolipoprotein A1 | Apolipoprotein CIII |
|---|---|---|---|---|
| | ng/mL | pg/mL | mg/mL | ug/mL |
| Least Detectable Dose | 0.43 | 36 | 0.0066 | 2.7 |
| RBM Low Plasma Range | | Pending | 0.19 | 28 |
| RBM High Plasma Range | 6.7 | Pending | 0.89 | 224 |
| NHD = normal healthy donor | | | | |

FIG. 17C.1

| Samples | Apolipoprotein H ug/mL | Beta-2 Microglobulin ug/mL | Brain-Derived Neurotrophic Factor ng/mL |
|---|---|---|---|
| Least Detectable Dose | 8.8 | 0.013 | 0.029 |
| RBM Low Plasma Range | 131 | 1.2 | 0.32 |
| RBM High Plasma Range | 430 | 6.2 | 16 |
| Donor_1 3. Aliquot A | 138 | 17 | 2.4 |
| Donor_1 3. Aliquot B | 148 | 15 | 3.3 |
| Donor_1 3. Aliquot C | 143 | 16 | 1.6 |
| Donor_1 3. Aliquot D | 150 | 16 | 2.6 |
| Donor_1 3. Aliquot E | 141 | 16 | 2.3 |
| Donor_1 3. Aliquot F | 142 | 14 | 1.3 |
| Donor_1 3. Aliquot G | 151 | 16 | 0.048 |
| Donor_1 3. Aliquot H | 141 | 15 | 3.4 |
| Donor_1 3. Aliquot I | 150 | 16 | 2.8 |
| Donor_2 3. Aliquot A | 152 | 20 | 3.4 |
| Donor_2 3. Aliquot B | 143 | >24 | 4.6 |
| Donor_2 3. Aliquot C | 154 | 23 | 1.3 |
| Donor_2 3. Aliquot D | 142 | 19 | 2.5 |
| Donor_2 3. Aliquot E | 154 | 20 | 2.3 |
| Donor_2 3. Aliquot F | 152 | 19 | 1.6 |
| Donor_2 3. Aliquot G | 153 | 21 | 0.49 |
| Donor_2 3. Aliquot H | 148 | 21 | 2.3 |
| Donor_2 3. Aliquot I | 141 | 19 | 1.8 |
| Donor_3 3. Aliquot A | 150 | 2.6 | 3.0 |
| Donor_3 3. Aliquot B | 144 | 2.3 | 4.5 |
| Donor_3 3. Aliquot C | 153 | 2.4 | 2.9 |
| Donor_3 3. Aliquot D | 149 | 2.4 | 3.4 |
| Donor_3 3. Aliquot E | 157 | 2.5 | 3.8 |
| Donor_3 3. Aliquot F | 148 | 2.2 | 1.6 |

FIG. 17C.2

|  | Apolipoprotein H | Beta-2 Microglobulin | Brain-Derived Neurotrophic Factor |
|---|---|---|---|
|  | ug/mL | ug/mL | ng/mL |
| Least Detectable Dose | 8.8 | 0.013 | 0.029 |
| RBM Low Plasma Range | 131 | 1.2 | 0.32 |
| RBM High Plasma Range | 430 | 6.2 | 16 |
| Donor_3 3. Aliquot G | 149 | 2.3 | 0.047 |
| Donor_3 3. Aliquot H | 144 | 2.3 | 2.3 |
| Donor_3 3. Aliquot I | 150 | 2.2 | 2.2 |
| Donor_4 3. Aliquot A | 105 | 7.6 | 2.0 |
| Donor_4 3. Aliquot B | 96 | 7.2 | 2.8 |
| Donor_4 3. Aliquot C | 102 | 8.0 | 0.49 |
| Donor_4 3. Aliquot D | 102 | 7.7 | 1.6 |
| Donor_4 3. Aliquot E | 93 | 8.3 | 1.0 |
| Donor_4 3. Aliquot F | 93 | 8.5 | 0.88 |
| Donor_4 3. Aliquot G | 100 | 8.1 | 0.049 |
| Donor_4 3. Aliquot H | 91 | 8.2 | 0.53 |
| Donor_4 3. Aliquot I | 99 | 8.0 | 1.2 |
| Donor_5 3. Aliquot A | 253 | 12 | 5.8 |
| Donor_5 3. Aliquot B | 266 | 13 | 4.5 |
| Donor_5 3. Aliquot C | 265 | 13 | 2.3 |
| Donor_5 3. Aliquot D | 263 | 13 | 2.9 |
| Donor_5 3. Aliquot E | 257 | 15 | 4.5 |
| Donor_5 3. Aliquot F | 238 | 11 | 2.3 |
| Donor_5 3. Aliquot G | 246 | 12 | 0.16 |
| Donor_5 3. Aliquot H | 245 | 13 | 4.8 |
| Donor_5 3. Aliquot I | 250 | 11 | 3.1 |
| Donor_6 3. Aliquot A | 141 | 1.2 | 4.4 |
| Donor_6 3. Aliquot B | 148 | 1.1 | 3.4 |
| Donor_6 3. Aliquot C | 141 | 1.2 | 1.1 |
| Donor_6 3. Aliquot D | 143 | 1.2 | 3.9 |

FIG. 17C.3

| | Apolipoprotein H ug/mL | Beta-2 Microglobulin ug/mL | Brain-Derived Neurotrophic Factor ng/mL |
|---|---|---|---|
| Least Detectable Dose | 8.8 | 0.013 | 0.029 |
| RBM Low Plasma Range | | | |
| RBM High Plasma Range | | | |
| Donor_6 3. Aliquot E | 131 | 1.2 | 0.32 |
| Donor_6 3. Aliquot F | 430 | 6.2 | 16 |
| Donor_6 3. Aliquot G | 131 | 1.2 | 2.1 |
| Donor_6 3. Aliquot H | 143 | 1.2 | 1.9 |
| Donor_6 3. Aliquot I | 152 | 1.2 | 0.064 |
| Donor_6 3. Aliquot H | 131 | 1.1 | 3.1 |
| Donor_6 3. Aliquot I | 134 | 1.1 | 1.7 |
| Donor_7 3. Aliquot A | 180 | 2.0 | 2.8 |
| Donor_7 3. Aliquot B | 183 | 2.0 | 3.1 |
| Donor_7 3. Aliquot C | 183 | 2.1 | 2.2 |
| Donor_7 3. Aliquot D | 169 | 2.0 | 2.9 |
| Donor_7 3. Aliquot E | 138 | 2.1 | 2.3 |
| Donor_7 3. Aliquot F | 190 | 1.9 | 1.2 |
| Donor_7 3. Aliquot G | 161 | 1.9 | 0.043 |
| Donor_7 3. Aliquot H | 173 | 1.9 | 1.6 |
| Donor_7 3. Aliquot I | 173 | 1.9 | 1.6 |
| Donor_8 3. Aliquot A | 117 | 1.2 | 3.3 |
| Donor_8 3. Aliquot B | 117 | 1.2 | 5.3 |
| Donor_8 3. Aliquot C | 119 | 1.2 | 3.2 |
| Donor_8 3. Aliquot D | 111 | 1.2 | 4.5 |
| Donor_8 3. Aliquot E | 113 | 1.2 | 6.0 |
| Donor_8 3. Aliquot F | 121 | 1.3 | 2.3 |
| Donor_8 3. Aliquot G | 111 | 1.2 | 0.060 |
| Donor_8 3. Aliquot H | 127 | 1.2 | 6.3 |
| Donor_8 3. Aliquot I | 122 | 1.2 | 6.1 |
| Donor_9 3. Aliquot A | 101 | 0.83 | 2.5 |
| Donor_9 3. Aliquot B | 104 | 0.79 | 3.5 |

FIG. 17C.4

| | Apolipoprotein H | Beta-2 Microglobulin | Brain-Derived Neurotrophic Factor |
|---|---|---|---|
| | ug/mL | ug/mL | ng/mL |
| Least Detectable Dose | 8.8 | 0.013 | 0.029 |
| RBM Low Plasma Range | 131 | 1.2 | 0.32 |
| RBM High Plasma Range | 430 | 6.2 | 16 |
| Donor_9 3. Aliquot C | 96 | 0.93 | 1.2 |
| Donor_9 3. Aliquot D | 99 | 0.87 | 3.7 |
| Donor_9 3. Aliquot E | 105 | 0.88 | 2.6 |
| Donor_9 3. Aliquot F | 103 | 0.90 | 1.9 |
| Donor_9 3. Aliquot G | 113 | 0.86 | 0.21 |
| Donor_9 3. Aliquot H | 97 | 0.83 | 4.3 |
| Donor_9 3. Aliquot I | 97 | 0.82 | 3.5 |
| EDTA Plasma | | | |
| donor #1 plasma | 127 | 11 | 1.2 |
| donor #2 plasma | 166 | 19 | 0.40 |
| donor #3 plasma | 193 | 2.5 | 0.89 |
| donor #4 plasma | 106 | 9.1 | 0.35 |
| donor #5 plasma | 316 | 14 | 3.6 |
| donor #6 plasma | 163 | 1.1 | 1.5 |
| donor #7 plasma | 214 | 2.3 | 1.4 |
| donor #8 plasma | 113 | 1.1 | 3.1 |
| donor #9 plasma | 147 | 0.88 | 0.21 |
| MW | | | |
| NHD plasma | 130.0 | 1.0 | 1.7 |
| Normal healthy donors | | | |
| MW | | | |
| NHD unstimuliert | 109.60 | 1.01 | 4.80 |
| Normal healthy donors | | | |
| *Stimulationsindices* | | | |

FIG. 17C.5

| | | Apolipoprotein H ug/mL | Beta-2 Microglobulin ug/mL | Brain-Derived Neurotrophic Factor ng/mL |
|---|---|---|---|---|
| Least Detectable Dose | | 8.8 | 0.013 | 0.029 |
| RBM Low Plasma Range | | 131 | 1.2 | 0.32 |
| RBM High Plasma Range | | 430 | 6.2 | 16 |
| EDTA Plasma | | | | |
| patient 1 | PLASMA | | | |
| patient 7 | PLASMA | | | |
| patient 2 | PLASMA | | | |
| patient 3 | PLASMA | | | |
| patient 5 | PLASMA | | | |
| patient 4 | PLASMA | | | |
| patient 6 | PLASMA | | | |
| NHD 1 | PLASMA | | | |
| NHD 2 | PLASMA | | | |

FIG. 17C.6

| | Apolipoprotein H ug/mL | Beta-2 Microglobulin ug/mL | Brain-Derived Neurotrophic Factor ng/mL |
|---|---|---|---|
| Least Detectable Dose | 8.8 | 0.013 | 0.029 |
| RBM Low Plasma Range | 131 | 1.2 | 0.32 |
| RBM High Plasma Range | 430 | 6.2 | 16 |
| Messwert > ULD | | | |
| SI > 1,5 | | | |
| SI 0,7-1,5 | | | |
| SI 0-0,7 | | | |
| MW nur von 1 Kontrollperson | | | |
| *Stimulationsindices* | | | |

FIG. 17C.7

| | Apolipoprotein H ug/mL | Beta-2 Microglobulin ug/mL | Brain-Derived Neurotrophic Factor ng/mL |
|---|---|---|---|
| Least Detectable Dose | 8.8 | 0.013 | 0.029 |
| RBM Low Plasma Range | 131 | 1.2 | 0.32 |
| RBM High Plasma Range | 430 | 6.2 | 16 |

| | Apolipoprotein H | Beta-2 Microglobulin | Brain-Derived Neurotrophic Factor |
|---|---|---|---|
| patient 1 | unstimuliert | | |
| patient 7 | unstimuliert | | |
| patient 2 | unstimuliert | | |
| patient 3 | unstimuliert | | |
| patient 5 | unstimuliert | | |
| patient 4 | unstimuliert | | |
| patient 6 | unstimuliert | | |
| NHD 1 | unstimuliert | | |
| NHD 2 | unstimuliert | | |

FIG. 17C.8

| | Apolipoprotein H | Beta-2 Microglobulin | Brain-Derived Neurotrophic Factor |
|---|---|---|---|
| | ug/mL | ug/mL | ng/mL |
| Least Detectable Dose | 8.8 | 0.013 | 0.029 |
| RBM Low Plasma Range | 131 | 1.2 | 0.32 |
| RBM High Plasma Range | 430 | 6.2 | 16 |
| NHD = normal healthy donor | | | |

FIG. 17D.1

| | Complement 3 mg/mL | Cancer Antigen 125 U/mL | Cancer Antigen 19-9 U/mL | Calcitonin pg/mL | CD40 ng/mL |
|---|---|---|---|---|---|
| Least Detectable Dose | 0.0053 | 4.2 | 0.25 | 6.0 | 0.021 |
| RBM Low Plasma Range | 0.76 | | | | 0.17 |
| RBM High Plasma Range | 2.1 | 12 | 9.2 | 12 | 1.5 |
| Samples | | | | | |
| Donor_1 3. Aliquot A | 0.73 | 132 | 28 | 36 | 11 |
| Donor_1 3. Aliquot B | 0.71 | 123 | 28 | 32 | 9.2 |
| Donor_1 3. Aliquot C | 0.71 | 141 | 13 | 34 | 10 |
| Donor_1 3. Aliquot D | 0.71 | 157 | 28 | 37 | 9.0 |
| Donor_1 3. Aliquot E | 0.69 | 135 | 28 | 36 | 8.7 |
| Donor_1 3. Aliquot F | 1.5 | 128 | 24 | 31 | 9.3 |
| Donor_1 3. Aliquot G | 0.77 | 140 | 32 | 32 | 12 |
| Donor_1 3. Aliquot H | 1.2 | 143 | 12 | 31 | 11 |
| Donor_1 3. Aliquot I | 0.71 | 125 | 28 | 33 | 10 |
| Donor_2 3. Aliquot A | 0.92 | 121 | 476 | 29 | 16 |
| Donor_2 3. Aliquot B | 0.93 | 125 | 510 | 31 | 18 |
| Donor_2 3. Aliquot C | 0.89 | 119 | 408 | 24 | 16 |
| Donor_2 3. Aliquot D | 0.92 | 197 | 468 | 33 | 16 |
| Donor_2 3. Aliquot E | 0.94 | 158 | 488 | 31 | 19 |
| Donor_2 3. Aliquot F | 2.3 | 123 | 413 | 30 | 16 |
| Donor_2 3. Aliquot G | 0.98 | 138 | 495 | 20 | 21 |
| Donor_2 3. Aliquot H | 1.3 | 106 | 459 | 29 | 18 |
| Donor_2 3. Aliquot I | 0.90 | 102 | 447 | 26 | 17 |
| Donor_3 3. Aliquot A | 0.68 | 35 | 3.3 | 6 | 1.4 |
| Donor_3 3. Aliquot B | 0.70 | 33 | 3.6 | 5.1 | 1.7 |
| Donor_3 3. Aliquot C | 0.73 | 35 | 3.6 | 6 | 1.4 |
| Donor_3 3. Aliquot D | 0.73 | 87 | 3.3 | 6 | 1.5 |
| Donor_3 3. Aliquot E | 0.77 | 74 | 3.6 | 7.3 | 1.5 |
| Donor_3 3. Aliquot F | 1.2 | 39 | 4.1 | 6 | 1.4 |

FIG. 17D.2

| | Complement 3 mg/mL | Cancer Antigen 125 U/mL | Cancer Antigen 19-9 U/mL | Calcitonin pg/mL | CD40 ng/mL |
|---|---|---|---|---|---|
| Least Detectable Dose | 0.0053 | 4.2 | 0.25 | 6.0 | 0.021 |
| RBM Low Plasma Range | 0.76 | | | | 0.17 |
| RBM High Plasma Range | 2.1 | 12 | 9.2 | 12 | 1.5 |
| Donor_3 3. Aliquot G | 0.72 | 29 | 4.6 | 6 | 3.4 |
| Donor_3 3. Aliquot H | 1.1 | 27 | 3.2 | 6 | 1.4 |
| Donor_3 3. Aliquot I | 0.74 | 31 | 2.8 | 6 | 1.3 |
| Donor_4 3. Aliquot A | 0.45 | 512 | 15 | 18 | 4.3 |
| Donor_4 3. Aliquot B | 0.41 | 495 | 16 | 20 | 4.7 |
| Donor_4 3. Aliquot C | 0.45 | 462 | 15 | 15 | 4.3 |
| Donor_4 3. Aliquot D | 0.43 | 542 | 16 | 19 | 4.0 |
| Donor_4 3. Aliquot E | 0.44 | 520 | 20 | 16 | 4.3 |
| Donor_4 3. Aliquot F | 0.80 | 465 | 16 | 15 | 4.0 |
| Donor_4 3. Aliquot G | 0.43 | 462 | 17 | 10 | 4.9 |
| Donor_4 3. Aliquot H | 0.69 | 509 | 15 | 17 | 4.0 |
| Donor_4 3. Aliquot I | 0.43 | 494 | 15 | 17 | 3.9 |
| Donor_5 3. Aliquot A | 0.72 | 21 | 8.8 | 105 | 18 |
| Donor_5 3. Aliquot B | 0.76 | 21 | 9.2 | 97 | 18 |
| Donor_5 3. Aliquot C | 0.77 | 21 | 9.9 | 74 | 19 |
| Donor_5 3. Aliquot D | 0.78 | 87 | 10 | 92 | 20 |
| Donor_5 3. Aliquot E | 0.73 | 74 | 10 | 90 | 21 |
| Donor_5 3. Aliquot F | 1.2 | 12 | 7.1 | 86 | 18 |
| Donor_5 3. Aliquot G | 0.80 | 20 | 8.6 | 67 | 19 |
| Donor_5 3. Aliquot H | 1.1 | 16 | 8.9 | 101 | 18 |
| Donor_5 3. Aliquot I | 0.72 | 17 | 8.0 | 94 | 17 |
| Donor_6 3. Aliquot A | 0.73 | 29 | 3.7 | 6 | 0.98 |
| Donor_6 3. Aliquot B | 0.77 | 42 | 2.6 | 6 | 1.1 |
| Donor_6 3. Aliquot C | 0.72 | 24 | 4.4 | 6 | 1.0 |
| Donor_6 3. Aliquot D | 0.75 | 82 | 3.9 | 6 | 1.0 |

FIG. 17D.3

| | Complement 3 mg/mL | Cancer Antigen 125 U/mL | Cancer Antigen 19-9 U/mL | Calcitonin pg/mL | CD40 ng/mL |
|---|---|---|---|---|---|
| Least Detectable Dose | 0.0053 | 4.2 | 0.25 | 6.0 | 0.021 |
| RBM Low Plasma Range | 0.76 | | | | |
| RBM High Plasma Range | 2.1 | 12 | 9.2 | 12 | 0.17 |
| Donor_6_3. Aliquot E | 0.67 | 85 | 3.5 | 6 | 1.5 |
| Donor_6_3. Aliquot F | 0.71 | 27 | 2.9 | 6 | 0.96 |
| Donor_6_3. Aliquot G | 0.78 | 28 | 5.2 | 6 | 0.90 |
| Donor_6_3. Aliquot H | 1.1 | 23 | 3.7 | 6 | 3.8 |
| Donor_6_3. Aliquot I | 0.68 | 29 | 3.0 | 6 | 0.81 |
| | | | | | 0.73 |
| Donor_7_3. Aliquot A | 0.67 | 53 | 5.3 | 1.5 | 0.93 |
| Donor_7_3. Aliquot B | 0.68 | 48 | 5.1 | 6 | 0.89 |
| Donor_7_3. Aliquot C | 0.73 | 39 | 5.1 | 6 | 0.77 |
| Donor_7_3. Aliquot D | 0.66 | 91 | 4.8 | 6 | 0.73 |
| Donor_7_3. Aliquot E | 0.51 | 53 | 5.2 | 6 | 0.62 |
| Donor_7_3. Aliquot F | 0.72 | 40 | 4.7 | 6 | 0.61 |
| Donor_7_3. Aliquot G | 0.74 | 38 | 7.8 | 6 | 1.8 |
| Donor_7_3. Aliquot H | 1.1 | 34 | 5.2 | 6 | 0.71 |
| Donor_7_3. Aliquot I | 0.67 | 39 | 3.7 | 3.3 | 0.50 |
| Donor_8_3. Aliquot A | 0.45 | 5.6 | 4.9 | 6 | 0.57 |
| Donor_8_3. Aliquot B | 0.49 | 9.0 | 3.9 | 6 | 0.60 |
| Donor_8_3. Aliquot C | 0.43 | 4.4 | 3.9 | 6 | 0.63 |
| Donor_8_3. Aliquot D | 0.44 | 164 | 5.5 | 4.6 | 0.72 |
| Donor_8_3. Aliquot E | 0.43 | 136 | 5.1 | 6.5 | 0.63 |
| Donor_8_3. Aliquot F | 0.51 | 16 | 4.5 | 6 | 0.49 |
| Donor_8_3. Aliquot G | 0.44 | 9.0 | 5.2 | 6 | 1.8 |
| Donor_8_3. Aliquot H | 0.72 | 13 | 4.0 | 6 | 0.60 |
| Donor_8_3. Aliquot I | 0.46 | 15 | 3.6 | 6 | 0.65 |
| Donor_9_3. Aliquot A | 0.39 | 14 | 3.0 | 6 | 0.69 |
| Donor_9_3. Aliquot B | 0.39 | 11 | 3.3 | 6 | 0.69 |

FIG. 17D.4

| | Complement 3<br>mg/mL | Cancer Antigen 125<br>U/mL | Cancer Antigen 19-9<br>U/mL | Calcitonin<br>pg/mL | CD40<br>ng/mL |
|---|---|---|---|---|---|
| Least Detectable Dose | 0.0053 | 4.2 | 0.25 | 6.0 | 0.021 |
| RBM Low Plasma Range | 0.76 | | | | 0.17 |
| RBM High Plasma Range | 2.1 | 12 | 9.2 | 12 | 1.5 |
| Donor_9_3. Aliquot C | 0.39 | 21 | 3.3 | 6 | 0.69 |
| Donor_9_3. Aliquot D | 0.37 | 140 | 6.0 | 3.9 | 0.81 |
| Donor_9_3. Aliquot E | 0.40 | 104 | 3.7 | 3.2 | 0.72 |
| Donor_9_3. Aliquot F | 0.39 | 12 | 2.6 | 6 | 0.61 |
| Donor_9_3. Aliquot G | 0.41 | 14 | 3.1 | 0.91 | 2.7 |
| Donor_9_3. Aliquot H | 0.64 | 4.9 | 3.1 | 6 | 0.64 |
| Donor_9_3. Aliquot I | 0.39 | 8.3 | 2.6 | 6 | 0.66 |
| EDTA Plasma | | | | | |
| donor #1 plasma | 0.59 | 60 | 7.6 | 40 | 7.4 |
| donor #2 plasma | 0.98 | 63 | 241 | 51 | 18 |
| donor #3 plasma | 0.90 | 28 | 2.1 | 8.9 | 1.7 |
| donor #4 plasma | 0.47 | 431 | 10 | 36 | 5.2 |
| donor #5 plasma | 0.88 | 18 | 4.2 | 164 | 16 |
| donor #6 plasma | 0.87 | 18 | 1.6 | 3.7 | 0.46 |
| donor #7 plasma | 0.80 | 30 | 6.0 | 5.0 | 1.6 |
| donor #8 plasma | 0.42 | 16 | 7.5 | 6 | 0.58 |
| donor #9 plasma | 0.55 | 4.2 | 6.3 | 6 | 0.47 |
| MW | | | | | |
| NHD plasma | 0.5 | 10.3 | 6.9 | 6.0 | 0.5 |
| Normal healthy donors | | | | | |
| MW | | | | | |
| NHD unstimuliert | 0.43 | 11.50 | 3.10 | 6.00 | 0.65 |
| Normal healthy donors | | | | | |
| Stimulationsindices | | | | | |

FIG. 17D.5

| | Complement 3 mg/mL | Cancer Antigen 125 U/mL | Cancer Antigen 19-9 U/mL | Calcitonin pg/mL | CD40 ng/mL |
|---|---|---|---|---|---|
| Least Detectable Dose | 0.0053 | | 0.25 | | 0.021 |
| RBM Low Plasma Range | 0.76 | 4.2 | | 6.0 | 0.17 |
| RBM High Plasma Range | 2.1 | 12 | 9.2 | 12 | 1.5 |
| EDTA Plasma | | | | | |
| | Complement 3 | Cancer Antigen 125 | Cancer Antigen 19-9 | Calcitonin | CD40 |
| PLASMA patient 1 | | | | | |
| PLASMA patient 7 | | | | | |
| PLASMA patient 2 | | | | | |
| PLASMA patient 3 | | | | | |
| PLASMA patient 5 | | | | | |
| PLASMA patient 4 | | | | | |
| PLASMA patient 6 | | | | | |
| PLASMA NHD 1 | | | | | |
| PLASMA NHD 2 | | | | | |

FIG. 17D.6

| | Complement 3 mg/mL | Cancer Antigen 125 U/mL | Cancer Antigen 19-9 U/mL | Calcitonin pg/mL | CD40 ng/mL |
|---|---|---|---|---|---|
| Least Detectable Dose | 0.0053 | 4.2 | 0.25 | 6.0 | 0.021 |
| RBM Low Plasma Range | 0.76 | | | | 0.17 |
| RBM High Plasma Range | 2.1 | 12 | 9.2 | 12 | 1.5 |
| Messwert > ULD | | | | | |
| SI > 1,5 | | | | | |
| SI 0,7-1,5 | | | | | |
| SI 0-0,7 | | | | | |
| MW nur von 1 Kontrollperson | | | | | |
| *Stimulationsindices* | | | | | |

FIG. 17D.7

| | Complement 3 mg/mL | Cancer Antigen 125 U/mL | Cancer Antigen 19-9 U/mL | Calcitonin pg/mL | CD40 ng/mL |
|---|---|---|---|---|---|
| Least Detectable Dose | 0.0053 | | | | 0.021 |
| RBM Low Plasma Range | 0.76 | | | | 0.17 |
| RBM High Plasma Range | 2.1 | 12 | 9.2 | 12 | 1.5 |
| | Complement 3 | Cancer Antigen 125 | Cancer Antigen 19-9 | Calcitonin | CD40 |
| patient 1 | unstimuliert | | | | |
| patient 7 | unstimuliert | | | | |
| patient 2 | unstimuliert | | | | |
| patient 3 | unstimuliert | | | | |
| patient 5 | unstimuliert | | | | |
| patient 4 | unstimuliert | | | | |
| patient 6 | unstimuliert | | | | |
| NHD 1 | unstimuliert | | | | |
| NHD 2 | unstimuliert | | | | |

FIG. 17D.8

| | Complement 3 mg/mL | Cancer Antigen 125 U/mL | Cancer Antigen 19-9 U/mL | Calcitonin pg/mL | CD40 ng/mL |
|---|---|---|---|---|---|
| Least Detectable Dose | 0.0053 | 4.2 | 0.25 | 6.0 | 0.021 |
| RBM Low Plasma Range | 0.76 | | | | 0.17 |
| RBM High Plasma Range | 2.1 | 12 | 9.2 | 12 | 1.5 |
| NHD = normal healthy donor | | | | | |

FIG. 17E.1

| | CD40 Ligand ng/mL | Carcinoembryonic Antigen ng/mL | Creatine Kinase-MB ng/mL |
|---|---|---|---|
| Least Detectable Dose | 0.020 | 0.84 | 0.42 |
| RBM Low Plasma Range | | | |
| RBM High Plasma Range | 1.1 | 4.8 | 1.1 |
| Samples | | | |
| Donor_1 3. Aliquot A | 0.66 | 1.5 | 0.16 |
| Donor_1 3. Aliquot B | 0.82 | 1.4 | 0.11 |
| Donor_1 3. Aliquot C | 0.82 | 1.4 | 0.12 |
| Donor_1 3. Aliquot D | 0.60 | 1.7 | 0.18 |
| Donor_1 3. Aliquot E | 0.47 | 1.6 | 0.11 |
| Donor_1 3. Aliquot F | 0.39 | 1.2 | 0.15 |
| Donor_1 3. Aliquot G | 0.18 | 1.5 | 0.11 |
| Donor_1 3. Aliquot H | 0.55 | 1.9 | 0.11 |
| Donor_1 3. Aliquot I | 0.84 | 1.4 | 0.12 |
| Donor_2 3. Aliquot A | 0.70 | 4.6 | 0.40 |
| Donor_2 3. Aliquot B | 0.65 | 4.9 | 0.44 |
| Donor_2 3. Aliquot C | 0.61 | 4.7 | 0.32 |
| Donor_2 3. Aliquot D | 0.47 | 6.2 | 0.60 |
| Donor_2 3. Aliquot E | 0.50 | 5.0 | 0.43 |
| Donor_2 3. Aliquot F | 0.42 | 4.0 | 0.50 |
| Donor_2 3. Aliquot G | 0.28 | 5.4 | 0.49 |
| Donor_2 3. Aliquot H | 0.44 | 4.8 | 0.40 |
| Donor_2 3. Aliquot I | 0.47 | 4.5 | 0.21 |
| Donor_3 3. Aliquot A | 0.54 | 2.8 | 0.59 |
| Donor_3 3. Aliquot B | 0.43 | 3.3 | 0.67 |
| Donor_3 3. Aliquot C | 0.50 | 3.3 | 0.54 |
| Donor_3 3. Aliquot D | 0.52 | 3.6 | 0.53 |
| Donor_3 3. Aliquot E | 0.68 | 4.3 | 0.61 |
| Donor_3 3. Aliquot F | 0.36 | 3.2 | 0.24 |

FIG. 17E.2

| | CD40 Ligand<br>ng/mL | Carcinoembryonic Antigen<br>ng/mL | Creatine Kinase-MB<br>ng/mL |
|---|---|---|---|
| Least Detectable Dose | 0.020 | 0.84 | 0.42 |
| RBM Low Plasma Range | | | |
| RBM High Plasma Range | | | |
| Donor_3 3. Aliquot G | 1.1 | 4.8 | 1.1 |
| Donor_3 3. Aliquot H | 0.29 | 2.7 | 0.29 |
| Donor_3 3. Aliquot I | 0.50 | 2.4 | 0.37 |
| | 0.42 | 2.4 | 0.39 |
| Donor_4 3. Aliquot A | 0.20 | 3.4 | 0.078 |
| Donor_4 3. Aliquot B | 0.18 | 3.8 | 0.066 |
| Donor_4 3. Aliquot C | 0.088 | 3.6 | 0.064 |
| Donor_4 3. Aliquot D | 0.13 | 4.4 | 0.17 |
| Donor_4 3. Aliquot E | 0.13 | 3.7 | 0.066 |
| Donor_4 3. Aliquot F | 0.083 | 3.3 | 0.093 |
| Donor_4 3. Aliquot G | 0.063 | 3.3 | 0.057 |
| Donor_4 3. Aliquot H | 0.081 | 3.4 | 0.045 |
| Donor_4 3. Aliquot I | 0.092 | 3.2 | 0.076 |
| Donor_5 3. Aliquot A | 0.51 | 1.7 | 0.18 |
| Donor_5 3. Aliquot B | 0.34 | 2.4 | 0.18 |
| Donor_5 3. Aliquot C | 0.32 | 1.6 | 0.11 |
| Donor_5 3. Aliquot D | 0.40 | 3.1 | 0.24 |
| Donor_5 3. Aliquot E | 0.47 | 2.9 | 0.28 |
| Donor_5 3. Aliquot F | 0.29 | 1.4 | 0.086 |
| Donor_5 3. Aliquot G | 0.24 | 1.7 | 0.12 |
| Donor_5 3. Aliquot H | 0.32 | 4.2 | 0.17 |
| Donor_5 3. Aliquot I | 0.27 | 3.6 | 0.11 |
| Donor_6 3. Aliquot A | 0.88 | 0.82 | 0.25 |
| Donor_6 3. Aliquot B | 0.77 | 0.58 | 0.24 |
| Donor_6 3. Aliquot C | 0.61 | 1.1 | 0.26 |
| Donor_6 3. Aliquot D | 0.95 | 1.3 | 0.26 |

FIG. 17E.3

| | CD40 Ligand ng/mL | Carcinoembryonic Antigen ng/mL | Creatine Kinase-MB ng/mL |
|---|---|---|---|
| Least Detectable Dose | 0.020 | 0.84 | 0.42 |
| RBM Low Plasma Range | | | |
| RBM High Plasma Range | | | |
| Donor_6 3. Aliquot E | 1.1 | 4.8 | 1.1 |
| Donor_6 3. Aliquot F | 0.60 | 1.6 | 0.30 |
| Donor_6 3. Aliquot G | 0.47 | 0.63 | 0.19 |
| Donor_6 3. Aliquot H | 0.30 | 0.44 | 0.30 |
| Donor_6 3. Aliquot I | 0.45 | 0.91 | 0.21 |
| | 0.45 | 0.96 | 0.21 |
| Donor_7 3. Aliquot A | 0.25 | 3.6 | 1.2 |
| Donor_7 3. Aliquot B | 0.21 | 2.8 | 1.5 |
| Donor_7 3. Aliquot C | 0.40 | 3.0 | 0.99 |
| Donor_7 3. Aliquot D | 0.30 | 3.9 | 1.1 |
| Donor_7 3. Aliquot E | 0.20 | 3.2 | 1.1 |
| Donor_7 3. Aliquot F | 0.11 | 2.9 | 1.2 |
| Donor_7 3. Aliquot G | 0.071 | 3.0 | 1.1 |
| Donor_7 3. Aliquot H | 0.18 | 4.1 | 1.0 |
| Donor_7 3. Aliquot I | 0.15 | 2.7 | 0.93 |
| Donor_8 3. Aliquot A | 0.32 | 1.1 | 0.15 |
| Donor_8 3. Aliquot B | 0.42 | 0.82 | 0.19 |
| Donor_8 3. Aliquot C | 0.51 | 0.75 | 0.15 |
| Donor_8 3. Aliquot D | 0.33 | 3.5 | 0.36 |
| Donor_8 3. Aliquot E | 0.49 | 3.9 | 0.39 |
| Donor_8 3. Aliquot F | 0.15 | 1.4 | 0.24 |
| Donor_8 3. Aliquot G | 0.13 | 0.94 | 0.20 |
| Donor_8 3. Aliquot H | 0.49 | 1.9 | 0.24 |
| Donor_8 3. Aliquot I | 0.45 | 1.6 | 0.14 |
| Donor_9 3. Aliquot A | 0.37 | 1.2 | 0.079 |
| Donor_9 3. Aliquot B | 0.43 | 1.5 | 0.19 |

FIG. 17E.4

| | CD40 Ligand ng/mL | Carcinoembryonic Antigen ng/mL | Creatine Kinase-MB ng/mL |
|---|---|---|---|
| Least Detectable Dose | 0.020 | 0.84 | 0.42 |
| RBM Low Plasma Range | | | |
| RBM High Plasma Range | | | |
| Donor_9 3. Aliquot C | 1.1 | 4.8 | 1.1 |
| Donor_9 3. Aliquot D | 0.51 | 1.0 | 0.18 |
| Donor_9 3. Aliquot E | 0.46 | 5.3 | 0.40 |
| Donor_9 3. Aliquot F | 0.31 | 3.3 | 0.26 |
| Donor_9 3. Aliquot G | 0.19 | 1.7 | 0.16 |
| Donor_9 3. Aliquot H | 0.21 | 1.1 | 0.12 |
| Donor_9 3. Aliquot I | 0.50 | 1.5 | 0.13 |
| | 0.45 | 0.89 | 0.083 |
| EDTA Plasma | | | |
| donor #1 plasma | 0.14 | 1.7 | 0.25 |
| donor #2 plasma | 0.21 | 3.9 | 0.99 |
| donor #3 plasma | 0.084 | 2.6 | 0.47 |
| donor #4 plasma | 0.10 | 4.9 | 0.24 |
| donor #5 plasma | 0.27 | 1.7 | 0.18 |
| donor #6 plasma | 0.021 | 1.1 | 0.39 |
| donor #7 plasma | 0.089 | 3.6 | 3.3 |
| donor #8 plasma | 0.16 | 1.4 | 0.56 |
| donor #9 plasma | 0.053 | 0.71 | 0.27 |
| MW | | | |
| NHD plasma | 0.1 | 1.1 | 0.4 |
| Normal healthy donors | | | |
| MW | | | |
| NHD unstimuliert | 0.45 | 1.26 | 0.11 |
| Normal healthy donors | | | |
| Stimulationsindices | | | |

FIG. 17E.5

| | | CD40 Ligand<br>ng/mL | Carcinoembryonic Antigen<br>ng/mL | Creatine Kinase-MB<br>ng/mL |
|---|---|---|---|---|
| Least Detectable Dose | | 0.020 | 0.84 | 0.42 |
| RBM Low Plasma Range | | | | |
| RBM High Plasma Range | | 1.1 | 4.8 | 1.1 |
| EDTA Plasma | | | | |

| | | CD40 Ligand | Carcinoembryonic Antigen | Creatine Kinase-MB |
|---|---|---|---|---|
| patient 1 | PLASMA | | | |
| patient 7 | PLASMA | | | |
| patient 2 | PLASMA | | | |
| patient 3 | PLASMA | | | |
| patient 5 | PLASMA | | | |
| patient 4 | PLASMA | | | |
| patient 6 | PLASMA | | | |
| NHD 1 | PLASMA | | | |
| NHD 2 | PLASMA | | | |

FIG. 17E.6

| | CD40 Ligand ng/mL | Carcinoembryonic Antigen ng/mL | Creatine Kinase-MB ng/mL |
|---|---|---|---|
| Least Detectable Dose | 0.020 | 0.84 | 0.42 |
| RBM Low Plasma Range | | | |
| RBM High Plasma Range | 1.1 | 4.8 | 1.1 |
| Messwert > ULD | | | |
| SI > 1,5 | | | |
| SI 0,7-1,5 | | | |
| SI 0-0,7 | | | |
| MW nur von 1 Kontrollperson | | | |
| Stimulationsindices | | | |

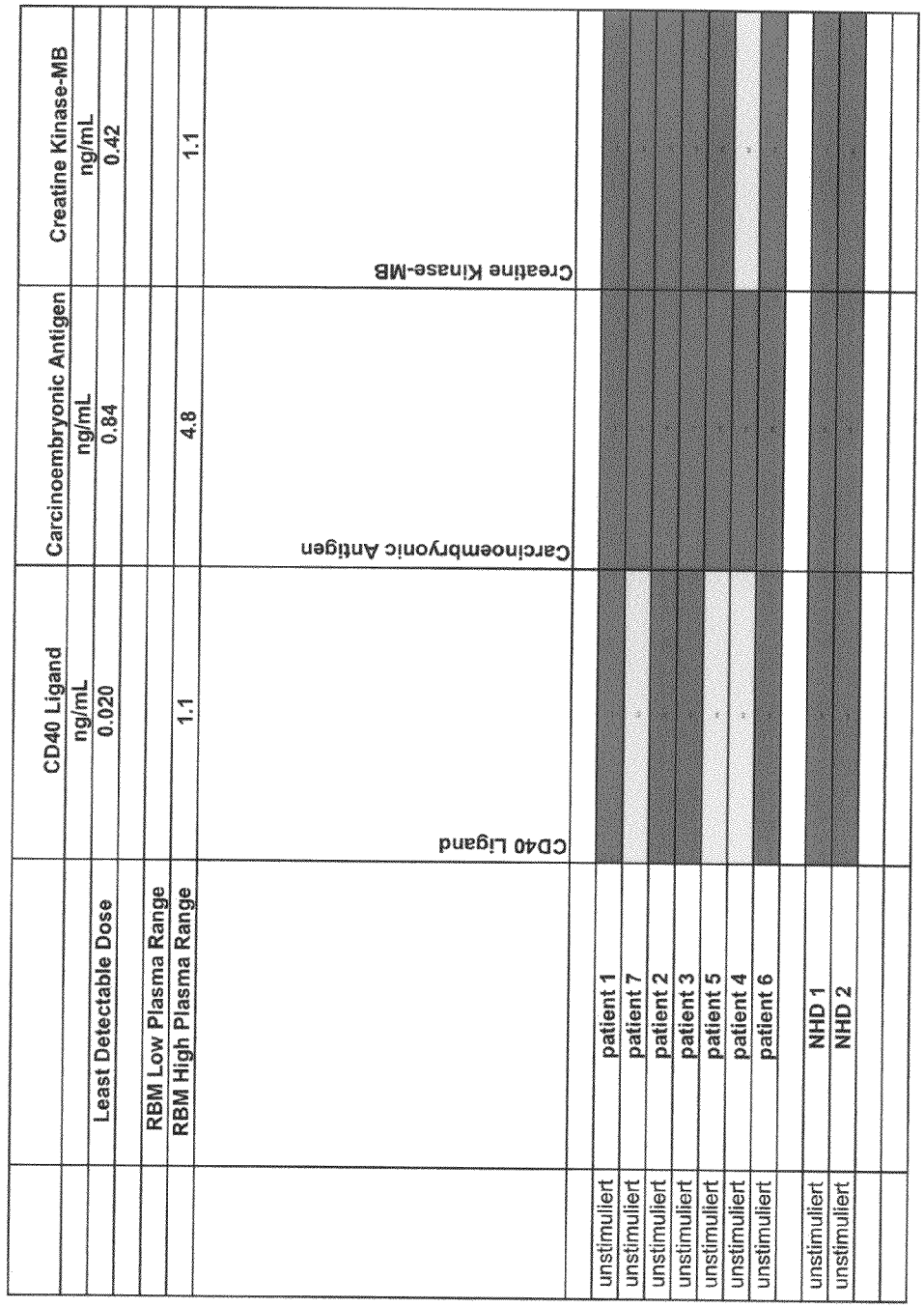
FIG. 17E.7

FIG. 17E.8

| | CD40 Ligand ng/mL | Carcinoembryonic Antigen ng/mL | Creatine Kinase-MB ng/mL |
|---|---|---|---|
| Least Detectable Dose | 0.020 | 0.84 | 0.42 |
| RBM Low Plasma Range | | | |
| RBM High Plasma Range | 1.1 | 4.8 | 1.1 |
| NHD = normal healthy donor | | | |

FIG. 17F.1

| | C Reactive Protein ug/mL | EGF pg/mL | ENA-78 ng/mL | Endothelin-1 pg/mL | EN-RAGE ng/mL | Eotaxin pg/mL |
|---|---|---|---|---|---|---|
| Least Detectable Dose | 0.0015 | 7.4 | 0.076 | 7.2 | 0.25 | 41 |
| RBM Low Plasma Range | 0.25 | | 0.069 | | 4.6 | |
| RBM High Plasma Range | 50 | 505 | 5.3 | 26 | 592 | 177 |
| Samples | | | | | | |
| Donor_1 3. Aliquot A | >47 | 128 | 7.9 | 8.1 | 82 | 179 |
| Donor_1 3. Aliquot B | >47 | 131 | 8.2 | 7.2 | 72 | 164 |
| Donor_1 3. Aliquot C | >47 | 119 | 1.7 | 7.2 | 74 | 130 |
| Donor_1 3. Aliquot D | >47 | 109 | 10 | 7.2 | 66 | 180 |
| Donor_1 3. Aliquot E | >47 | 101 | 5.9 | 7.2 | 75 | 170 |
| Donor_1 3. Aliquot F | >47 | 101 | 1.2 | 7.2 | 60 | 184 |
| Donor_1 3. Aliquot G | >47 | 693 | 5.3 | 22 | 54 | 10 |
| Donor_1 3. Aliquot H | >47 | 197 | 1.6 | 11 | 99 | 177 |
| Donor_1 3. Aliquot I | >47 | 114 | 1.8 | 7.2 | 76 | 172 |
| Donor_2 3. Aliquot A | >47 | 92 | 45 | 11 | 247 | 61 |
| Donor_2 3. Aliquot B | >47 | 145 | 45 | 7.2 | 230 | 48 |
| Donor_2 3. Aliquot C | >47 | 83 | 0.66 | 7.2 | 252 | 46 |
| Donor_2 3. Aliquot D | >47 | 61 | 51 | 15 | 212 | 48 |
| Donor_2 3. Aliquot E | >47 | 62 | 55 | 20 | 228 | 44 |
| Donor_2 3. Aliquot F | >47 | 66 | 0.74 | 7.2 | 258 | 27 |
| Donor_2 3. Aliquot G | >47 | 792 | 214 | 24 | 218 | 5.0 |
| Donor_2 3. Aliquot H | >47 | 85 | 1.4 | 7.2 | >269 | 36 |
| Donor_2 3. Aliquot I | >47 | 59 | 1.2 | 7.2 | 250 | 44 |
| Donor_3 3. Aliquot A | 22 | 40 | 20 | 7.2 | 142 | 66 |
| Donor_3 3. Aliquot B | 24 | 64 | 13 | 7.2 | 142 | 50 |
| Donor_3 3. Aliquot C | 25 | 38 | 0.96 | 7.2 | 135 | 44 |
| Donor_3 3. Aliquot D | 25 | 47 | 35 | 7.2 | 151 | 54 |
| Donor_3 3. Aliquot E | 24 | 60 | 31 | 11 | 159 | 52 |
| Donor_3 3. Aliquot F | 26 | 39 | 0.65 | 7.2 | 128 | 80 |

FIG. 17F.2

| | C Reactive Protein ug/mL | EGF pg/mL | ENA-78 ng/mL | Endothelin-1 pg/mL | EN-RAGE ng/mL | Eotaxin pg/mL |
|---|---|---|---|---|---|---|
| Least Detectable Dose | 0.0015 | 7.4 | 0.076 | 7.2 | 0.25 | 41 |
| RBM Low Plasma Range | 0.25 | | 0.069 | | 4.6 | |
| RBM High Plasma Range | 50 | 505 | 5.3 | 26 | 592 | 177 |
| Donor_3_3. Aliquot G | 26 | 535 | 1.6 | 7.2 | 122 | 5.0 |
| Donor_3_3. Aliquot H | 23 | 39 | 0.47 | 7.2 | 211 | 29 |
| Donor_3_3. Aliquot I | 24 | 33 | 0.55 | 7.2 | 169 | 36 |
| Donor_4_3. Aliquot A | >47 | 25 | 0.77 | 7.2 | >269 | 141 |
| Donor_4_3. Aliquot B | >47 | 35 | 1.4 | 7.2 | 239 | 133 |
| Donor_4_3. Aliquot C | >47 | 12 | 0.18 | 7.2 | 175 | 122 |
| Donor_4_3. Aliquot D | >47 | 21 | 23 | 11 | 84 | 133 |
| Donor_4_3. Aliquot E | >47 | 15 | 21 | 22 | 66 | 120 |
| Donor_4_3. Aliquot F | >47 | 9.8 | 0.59 | 7.2 | 94 | 130 |
| Donor_4_3. Aliquot G | >47 | 256 | 1.2 | 7.2 | 127 | 10 |
| Donor_4_3. Aliquot H | >47 | 11 | 0.14 | 7.2 | >269 | 124 |
| Donor_4_3. Aliquot I | >47 | 19 | 0.20 | 7.2 | 185 | 139 |
| Donor_5_3. Aliquot A | >47 | 87 | 21 | 20 | 95 | 27 |
| Donor_5_3. Aliquot B | >47 | 90 | 23 | 11 | 88 | 34 |
| Donor_5_3. Aliquot C | >47 | 71 | 0.25 | 7.2 | 108 | 32 |
| Donor_5_3. Aliquot D | >47 | 60 | 31 | 11 | 52 | 32 |
| Donor_5_3. Aliquot E | >47 | 70 | 33 | 15 | 41 | 30 |
| Donor_5_3. Aliquot F | >47 | 59 | 0.71 | 7.2 | 73 | 27 |
| Donor_5_3. Aliquot G | >47 | 647 | 7.0 | 15 | 91 | 7.6 |
| Donor_5_3. Aliquot H | >47 | 83 | 0.41 | 7.2 | 236 | 25 |
| Donor_5_3. Aliquot I | >47 | 53 | 0.22 | 7.2 | 100 | 22 |
| Donor_6_3. Aliquot A | >47 | 195 | 4.4 | 7.2 | 236 | 22 |
| Donor_6_3. Aliquot B | >47 | 213 | 6.0 | 7.2 | 229 | 25 |
| Donor_6_3. Aliquot C | >47 | 160 | 0.54 | 7.2 | 265 | 36 |
| Donor_6_3. Aliquot D | >47 | 152 | 10 | 7.2 | 109 | 25 |

FIG. 17F.3

| | C Reactive Protein ug/mL | EGF pg/mL | ENA-78 ng/mL | Endothelin-1 pg/mL | EN-RAGE ng/mL | Eotaxin pg/mL |
|---|---|---|---|---|---|---|
| Least Detectable Dose | 0.0015 | 7.4 | 0.076 | 7.2 | 0.25 | 41 |
| RBM Low Plasma Range | 0.25 | | 0.069 | | 4.6 | |
| RBM High Plasma Range | 50 | 505 | 5.3 | 26 | 592 | 177 |
| Donor_6 3. Aliquot E | >47 | 110 | 12 | 11 | 106 | 20 |
| Donor_6 3. Aliquot F | >47 | 132 | 0.68 | 7.2 | 153 | 34 |
| Donor_6 3. Aliquot G | >47 | 2020 | 4.3 | 7.2 | 147 | 15 |
| Donor_6 3. Aliquot H | >47 | 139 | 0.43 | 7.2 | >269 | 18 |
| Donor_6 3. Aliquot I | >47 | 101 | 0.51 | 7.2 | 237 | 22 |
| Donor_7 3. Aliquot A | 29 | 30 | 33 | 7.2 | 150 | 138 |
| Donor_7 3. Aliquot B | 33 | 45 | 17 | 7.2 | 161 | 119 |
| Donor_7 3. Aliquot C | 30 | 37 | 0.56 | 7.2 | >269 | 105 |
| Donor_7 3. Aliquot D | 27 | 28 | 26 | 7.2 | 128 | 106 |
| Donor_7 3. Aliquot E | 24 | 22 | 20 | 7.2 | 122 | 117 |
| Donor_7 3. Aliquot F | 27 | 11 | 0.25 | 7.2 | 227 | 121 |
| Donor_7 3. Aliquot G | 27 | 403 | 3.6 | 7.2 | 182 | 18 |
| Donor_7 3. Aliquot H | 28 | 20 | 0.23 | 7.2 | >269 | 125 |
| Donor_7 3. Aliquot I | 29 | 15 | 0.19 | 7.2 | >269 | 111 |
| Donor_8 3. Aliquot A | 0.096 | 93 | 1.1 | 8.1 | 48 | 162 |
| Donor_8 3. Aliquot B | 0.14 | 110 | 1.3 | 7.2 | 46 | 153 |
| Donor_8 3. Aliquot C | 0.13 | 114 | 0.81 | 7.2 | 41 | 117 |
| Donor_8 3. Aliquot D | 0.14 | 105 | 1.4 | 7.2 | 64 | 165 |
| Donor_8 3. Aliquot E | 0.12 | 132 | 2.4 | 7.2 | 45 | 157 |
| Donor_8 3. Aliquot F | 0.16 | 63 | 0.37 | 15 | 47 | 208 |
| Donor_8 3. Aliquot G | 0.13 | 1050 | 4.5 | 7.2 | 57 | 5.0 |
| Donor_8 3. Aliquot H | 0.15 | 143 | 0.81 | 11 | 143 | 142 |
| Donor_8 3. Aliquot I | 0.13 | 125 | 0.87 | 7.2 | 122 | 157 |
| Donor_9 3. Aliquot A | Pending | 117 | 2.1 | 7.2 | 47 | 254 |
| Donor_9 3. Aliquot B | Pending | 156 | 2.2 | 13 | 33 | 223 |

FIG. 17F.4

| | C Reactive Protein ug/mL | EGF pg/mL | ENA-78 ng/mL | Endothelin-1 pg/mL | EN-RAGE ng/mL | Eotaxin pg/mL |
|---|---|---|---|---|---|---|
| Least Detectable Dose | 0.0015 | 7.4 | 0.076 | 7.2 | 0.25 | 41 |
| RBM Low Plasma Range | 0.25 | | 0.069 | | 4.6 | 177 |
| RBM High Plasma Range | 50 | 505 | 5.3 | 26 | 592 | 184 |
| Donor_9_3. Aliquot C | Pending | 123 | 2.1 | 9.8 | 48 | 239 |
| Donor_9_3. Aliquot D | Pending | 131 | 2.4 | 18 | 46 | 209 |
| Donor_9_3. Aliquot E | Pending | 95 | 6.5 | 19 | 67 | 231 |
| Donor_9_3. Aliquot F | Pending | 78 | 0.65 | 13 | 22 | 41 |
| Donor_9_3. Aliquot G | Pending | 1300 | 16 | 7.2 | 96 | 201 |
| Donor_9_3. Aliquot H | Pending | 140 | 1.3 | 5.1 | 115 | 232 |
| Donor_9_3. Aliquot I | Pending | 134 | 1.5 | 7.2 | 50 | |
| EDTA Plasma | | | | | | |
| donor #1 plasma | Pending | 30 | 0.93 | 7.7 | 65 | 97 |
| donor #2 plasma | Pending | 7.4 | 0.076 | 7.2 | >269 | 42 |
| donor #3 plasma | Pending | 7.4 | 0.076 | 17 | 49 | 36 |
| donor #4 plasma | Pending | 7.4 | 0.076 | 7.2 | 19 | 87 |
| donor #5 plasma | Pending | 12 | 0.32 | 22 | 145 | 64 |
| donor #6 plasma | Pending | 7.4 | 0.26 | 7.2 | 40 | 14 |
| donor #7 plasma | Pending | 7.4 | 0.54 | 7.2 | 71 | 86 |
| donor #8 plasma | Pending | 22 | 0.48 | 9.8 | 9.4 | 294 |
| donor #9 plasma | Pending | 7.4 | 0.088 | 7.2 | 4.3 | 330 |
| MW | | | | | | |
| NHD plasma | #DIV/0! | 14.7 | 0.3 | 8.5 | 6.8 | 312.0 |
| Normal healthy donors | | | | | | |
| MW | | | | | | |
| NHD unstimuliert | 0.13 | 129.50 | 1.17 | 7.20 | 86.10 | 194.50 |
| Normal healthy donors | | | | | | |
| *Stimulationsindices* | | | | | | |

FIG. 17F.5

| | | C Reactive Protein ug/mL | EGF pg/mL | ENA-78 ng/mL | Endothelin-1 pg/mL | EN-RAGE ng/mL | Eotaxin pg/mL |
|---|---|---|---|---|---|---|---|
| | Least Detectable Dose | 0.0015 | 7.4 | 0.076 | 7.2 | 0.25 | 41 |
| | RBM Low Plasma Range | 0.25 | | 0.069 | | 4.6 | |
| | RBM High Plasma Range | 50 | 505 | 5.3 | 26 | 592 | 177 |
| | EDTA Plasma | | | | | | |
| PLASMA | patient 1 | | | | | | |
| PLASMA | patient 7 | | | | | | |
| PLASMA | patient 2 | | | | | | |
| PLASMA | patient 3 | | | | | | |
| PLASMA | patient 5 | | | | | | |
| PLASMA | patient 4 | | | | | | |
| PLASMA | patient 6 | | | | | | |
| PLASMA | NHD 1 | | | | | | |
| PLASMA | NHD 2 | | | | | | |

FIG. 17F.6

| | C Reactive Protein ug/mL | EGF pg/mL | ENA-78 ng/mL | Endothelin-1 pg/mL | EN-RAGE ng/mL | Eotaxin pg/mL |
|---|---|---|---|---|---|---|
| Least Detectable Dose | 0.0015 | 7.4 | 0.076 | 7.2 | 0.25 | 41 |
| RBM Low Plasma Range | 0.25 | | 0.069 | | 4.6 | |
| RBM High Plasma Range | 50 | 505 | 5.3 | 26 | 592 | 177 |
| Messwert > ULD | | | | | | |
| SI > 1,5 | | | | | | |
| SI 0,7-1,5 | | | | | | |
| SI 0-0,7 | | | | | | |
| MW nur von 1 Kontrollperson | | | | | | |
| *Stimulationsindices* | | | | | | |

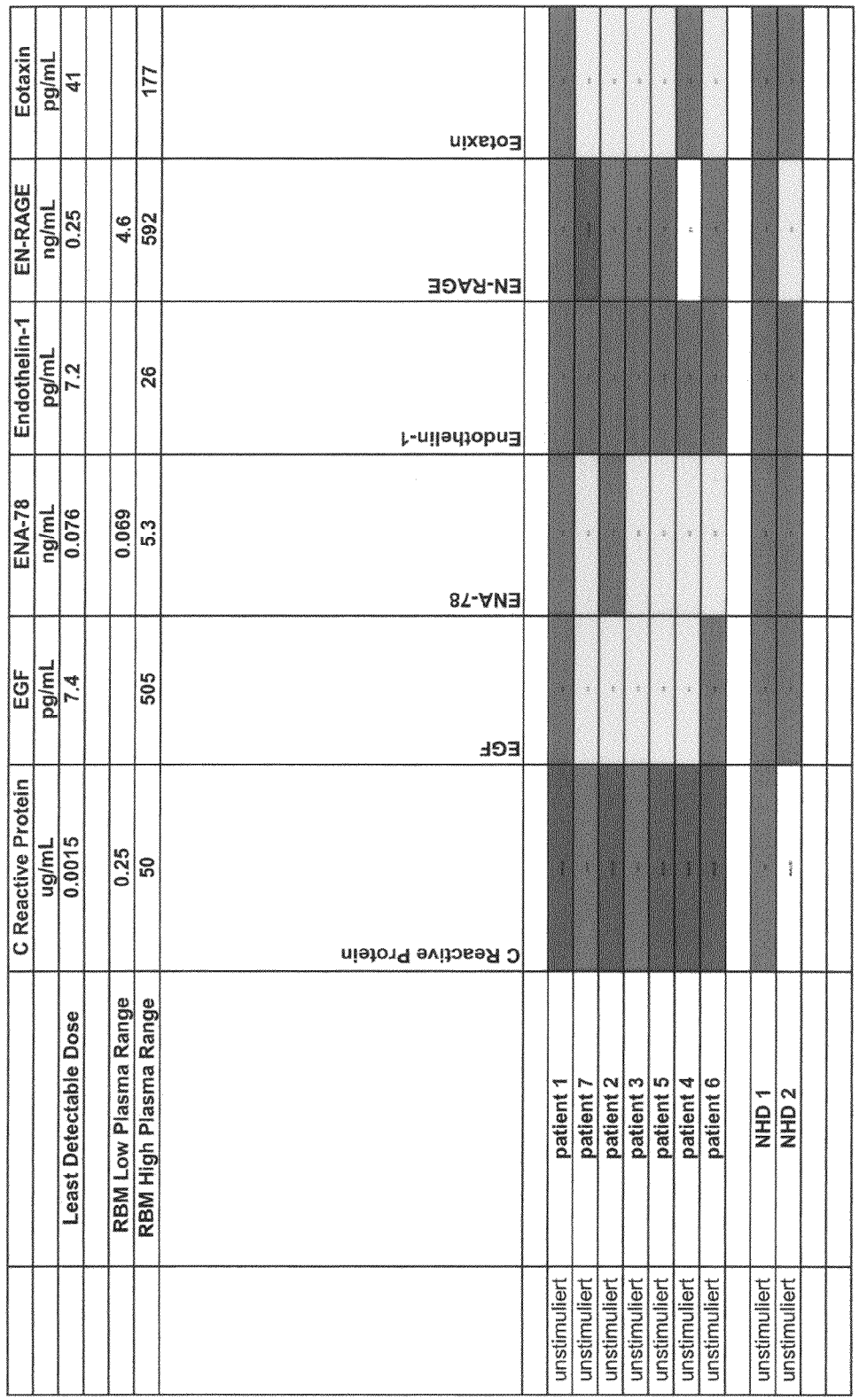
FIG. 17F.7

FIG. 17F.8

| | C Reactive Protein ug/mL | EGF pg/mL | ENA-78 ng/mL | Endothelin-1 pg/mL | EN-RAGE ng/mL | Eotaxin pg/mL |
|---|---|---|---|---|---|---|
| Least Detectable Dose | 0.0015 | 7.4 | 0.076 | 7.2 | 0.25 | 41 |
| RBM Low Plasma Range | 0.25 | | 0.069 | | 4.6 | |
| RBM High Plasma Range | 50 | 505 | 5.3 | 26 | 592 | 177 |
| NHD = normal healthy donor | | | | | | |

FIG. 17G.1

| | Epiregulin pg/mL | Erythropoietin pg/mL | Fatty Acid Binding Protein ng/mL | Factor VII ng/mL | Ferritin ng/mL |
|---|---|---|---|---|---|
| Least Detectable Dose | 36 | | 3.0 | 1.0 | 1.4 |
| RBM Low Plasma Range | Pending | | | 106 | 5.0 |
| RBM High Plasma Range | Pending | 284 | 10 | 443 | 552 |
| Samples | | | | | |
| Donor_1 3. Aliquot A | 161 | 166 | 32 | 157 | 1290 |
| Donor_1 3. Aliquot B | 65 | 166 | 29 | 140 | 1380 |
| Donor_1 3. Aliquot C | 33 | 37 | 34 | 89 | 1300 |
| Donor_1 3. Aliquot D | 16 | 166 | 33 | 168 | 1400 |
| Donor_1 3. Aliquot E | 40 | 166 | 33 | 171 | 1140 |
| Donor_1 3. Aliquot F | 61 | 166 | 31 | 132 | 1280 |
| Donor_1 3. Aliquot G | 149 | 166 | 41 | 174 | 1420 |
| Donor_1 3. Aliquot H | 36 | 60 | 31 | 160 | 1280 |
| Donor_1 3. Aliquot I | 31 | 166 | 29 | 139 | 1160 |
| Donor_2 3. Aliquot A | 44 | 166 | 36 | 541 | 1490 |
| Donor_2 3. Aliquot B | 26 | 166 | 40 | 577 | 1510 |
| Donor_2 3. Aliquot C | 16 | 166 | 40 | 154 | 1430 |
| Donor_2 3. Aliquot D | 52 | 166 | 45 | 694 | 1390 |
| Donor_2 3. Aliquot E | 21 | 166 | 45 | 640 | 1390 |
| Donor_2 3. Aliquot F | 36 | 166 | 40 | 580 | 1400 |
| Donor_2 3. Aliquot G | 236 | 166 | 48 | 588 | 1470 |
| Donor_2 3. Aliquot H | 26 | 166 | 39 | 567 | 1330 |
| Donor_2 3. Aliquot I | 36 | 166 | 34 | 450 | 1320 |
| Donor_3 3. Aliquot A | 40 | 166 | 14 | 147 | 855 |
| Donor_3 3. Aliquot B | 35 | 166 | 12 | 139 | 757 |
| Donor_3 3. Aliquot C | 24 | 166 | 12 | 31 | 828 |
| Donor_3 3. Aliquot D | 31 | 166 | 17 | 156 | 799 |
| Donor_3 3. Aliquot E | 36 | 166 | 16 | 160 | 797 |
| Donor_3 3. Aliquot F | 36 | 166 | 13 | 128 | 824 |

FIG. 17G.2

| | Epiregulin pg/mL | Erythropoietin pg/mL | Fatty Acid Binding Protein ng/mL | Factor VII ng/mL | Ferritin ng/mL |
|---|---|---|---|---|---|
| Least Detectable Dose | 36 | 166 | 3.0 | 1.0 | 1.4 |
| RBM Low Plasma Range | Pending | | | | 5.0 |
| RBM High Plasma Range | Pending | 284 | 10 | 106 | 552 |
| Donor_3 3. Aliquot G | 36 | 166 | 15 | 443 | 865 |
| Donor_3 3. Aliquot H | 21 | 166 | 9.2 | 116 | 758 |
| Donor_3 3. Aliquot I | 13 | 166 | 11 | 108 | 800 |
| | | | | 123 | |
| Donor_4 3. Aliquot A | 21 | 166 | 33 | 124 | 328 |
| Donor_4 3. Aliquot B | 35 | 166 | 33 | 129 | 311 |
| Donor_4 3. Aliquot C | 36 | 166 | 30 | 9.2 | 286 |
| Donor_4 3. Aliquot D | 36 | 166 | 33 | 142 | 308 |
| Donor_4 3. Aliquot E | 29 | 166 | 33 | 115 | 319 |
| Donor_4 3. Aliquot F | 36 | 166 | 32 | 105 | 347 |
| Donor_4 3. Aliquot G | 69 | 166 | 34 | 75 | 338 |
| Donor_4 3. Aliquot H | 36 | 166 | 37 | 111 | 315 |
| Donor_4 3. Aliquot I | 31 | 166 | 34 | 125 | 352 |
| | | | | | |
| Donor_5 3. Aliquot A | 129 | 166 | 9.2 | >1113 | 1430 |
| Donor_5 3. Aliquot B | 101 | 41 | 7.8 | 1020 | 1320 |
| Donor_5 3. Aliquot C | 149 | 166 | 9.2 | 243 | 1570 |
| Donor_5 3. Aliquot D | 105 | 100 | 13 | 940 | 1630 |
| Donor_5 3. Aliquot E | 111 | 64 | 14 | 1100 | 1510 |
| Donor_5 3. Aliquot F | 87 | 166 | 6.5 | 808 | 1390 |
| Donor_5 3. Aliquot G | 161 | 50 | 10 | 936 | 1460 |
| Donor_5 3. Aliquot H | 117 | 50 | 8.8 | 1000 | 1390 |
| Donor_5 3. Aliquot I | 95 | 166 | 8.8 | 1050 | 1400 |
| | | | | | |
| Donor_6 3. Aliquot A | 26 | 166 | 2.3 | 320 | 382 |
| Donor_6 3. Aliquot B | 31 | 166 | 2.6 | 329 | 374 |
| Donor_6 3. Aliquot C | 36 | 166 | 2.6 | 62 | 370 |
| Donor_6 3. Aliquot D | 36 | 166 | 5.4 | 345 | 370 |

FIG. 17G.3

| | Epiregulin pg/mL | Erythropoietin pg/mL | Fatty Acid Binding Protein ng/mL | Factor VII ng/mL | Ferritin ng/mL |
|---|---|---|---|---|---|
| Least Detectable Dose | 36 | 166 | 3.0 | 1.0 | 1.4 |
| RBM Low Plasma Range | Pending | | | | |
| RBM High Plasma Range | Pending | 284 | 10 | 106 | 5.0 |
| Donor_6_3. Aliquot E | 36 | 166 | 5.6 | 443 | 552 |
| Donor_6_3. Aliquot F | 16 | 166 | 2.2 | 285 | 364 |
| Donor_6_3. Aliquot G | 177 | 166 | 2.6 | 311 | 376 |
| Donor_6_3. Aliquot H | 36 | 166 | 2.0 | 252 | 391 |
| Donor_6_3. Aliquot I | 36 | 166 | 1.7 | 336 | 353 |
| | | | | 309 | 375 |
| Donor_7_3. Aliquot A | 36 | 166 | 463 | 144 | 468 |
| Donor_7_3. Aliquot B | 36 | 166 | 459 | 149 | 491 |
| Donor_7_3. Aliquot C | 36 | 166 | 466 | 34 | 535 |
| Donor_7_3. Aliquot D | 36 | 166 | 422 | 128 | 451 |
| Donor_7_3. Aliquot E | 36 | 166 | 434 | 143 | 490 |
| Donor_7_3. Aliquot F | 36 | 166 | 426 | 143 | 505 |
| Donor_7_3. Aliquot G | 36 | 166 | 511 | 139 | 471 |
| Donor_7_3. Aliquot H | 36 | 166 | 440 | 136 | 404 |
| Donor_7_3. Aliquot I | 36 | 166 | 451 | 141 | 409 |
| Donor_8_3. Aliquot A | 36 | 166 | 3 | 376 | 34 |
| Donor_8_3. Aliquot B | 35 | 166 | 3 | 411 | 32 |
| Donor_8_3. Aliquot C | 44 | 166 | 3 | 18 | 37 |
| Donor_8_3. Aliquot D | 42 | 166 | 8.3 | 410 | 48 |
| Donor_8_3. Aliquot E | 35 | 166 | 7.8 | 351 | 39 |
| Donor_8_3. Aliquot F | 58 | 166 | 0.81 | 426 | 32 |
| Donor_8_3. Aliquot G | 56 | 166 | 3 | 253 | 42 |
| Donor_8_3. Aliquot H | 16 | 166 | 0.56 | 382 | 38 |
| Donor_8_3. Aliquot I | 36 | 166 | 0.14 | 381 | 36 |
| Donor_9_3. Aliquot A | 86 | 166 | 3 | 196 | 4.8 |
| Donor_9_3. Aliquot B | 75 | 166 | 1.6 | 196 | 2.6 |

FIG. 17G.4

|  | Epiregulin pg/mL | Erythropoietin pg/mL | Fatty Acid Binding Protein ng/mL | Factor VII ng/mL | Ferritin ng/mL |
|---|---|---|---|---|---|
| Least Detectable Dose | 36 | 166 | 3.0 | 1.0 | 1.4 |
|  |  |  |  |  |  |
| RBM Low Plasma Range | Pending |  |  |  |  |
| RBM High Plasma Range | Pending |  |  |  |  |
| Donor_9_3, Aliquot C | 106 | 284 | 10 | 106 | 5.0 |
| Donor_9_3, Aliquot D | 101 | 166 | 0.42 | 443 | 552 |
| Donor_9_3, Aliquot E | 79 | 166 | 10 | 44 | 5.7 |
| Donor_9_3, Aliquot F | 77 | 166 | 6.6 | 243 | 11 |
| Donor_9_3, Aliquot G | 123 | 166 | 0.68 | 201 | 6.0 |
| Donor_9_3, Aliquot H | 97 | 166 | 0.81 | 196 | 3.6 |
| Donor_9_3, Aliquot I | 83 | 166 | 3 | 147 | 12 |
|  |  |  | 3 | 229 | 5.5 |
|  |  |  |  | 184 | 3.3 |
| EDTA Plasma |  |  |  |  |  |
| donor #1 plasma | 83 | 84 | 32 | 141 | 1190 |
| donor #2 plasma | 36 | 166 | 65 | 545 | 1670 |
| donor #3 plasma | 32 | 166 | 25 | 135 | 934 |
| donor #4 plasma | 36 | 166 | 59 | 121 | 320 |
| donor #5 plasma | 35 | 118 | 13 | 891 | 1190 |
| donor #6 plasma | 36 | 37 | 5.0 | 315 | 382 |
| donor #7 plasma | 36 | 166 | >617 | 187 | 545 |
| donor #8 plasma | 35 | 166 | 3 | 428 | 22 |
| donor #9 plasma | 65 | 166 | 0.55 | 299 | 3.3 |
|  |  |  |  |  |  |
| MW |  |  |  |  |  |
| Normal healthy donors NHD plasma | 49.9 | 166.0 | 1.8 | 363.5 | 12.8 |
|  |  |  |  |  |  |
| MW |  |  |  |  |  |
| Normal healthy donors NHD unstimuliert | 59.35 | 166.00 | 1.57 | 282.50 | 19.76 |
|  |  |  |  |  |  |
| *Stimulationsindices* |  |  |  |  |  |

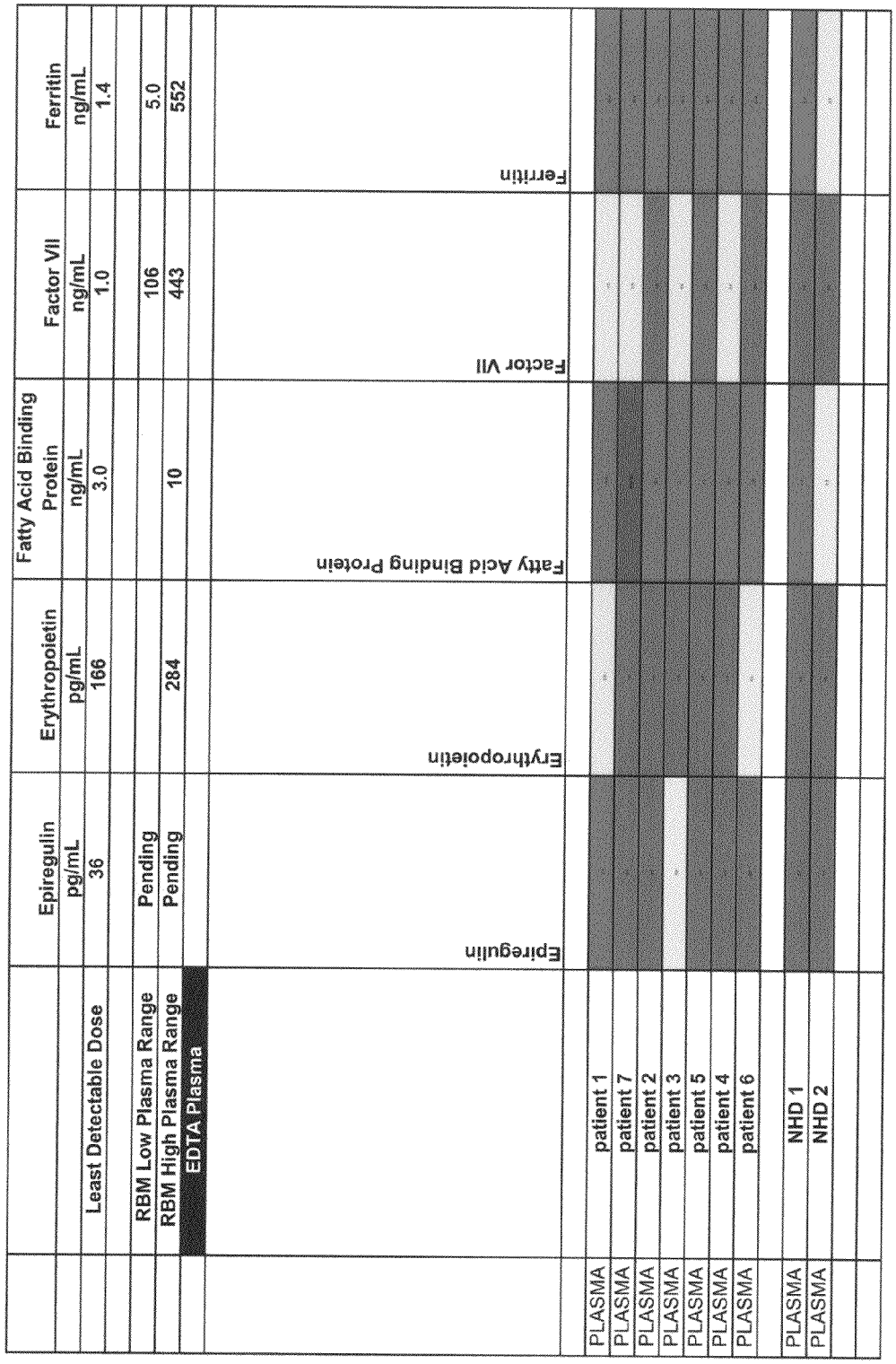
FIG. 17G.5

FIG. 17G.6

| | Epiregulin pg/mL | Erythropoietin pg/mL | Fatty Acid Binding Protein ng/mL | Factor VII ng/mL | Ferritin ng/mL |
|---|---|---|---|---|---|
| Least Detectable Dose | 36 | 166 | 3.0 | 1.0 | 1.4 |
| RBM Low Plasma Range | Pending | | | 106 | 5.0 |
| RBM High Plasma Range | Pending | 284 | 10 | 443 | 552 |
| Messwert > ULD | | | | | |
| SI > 1,5 | | | | | |
| SI 0,7-1,5 | | | | | |
| SI 0-0,7 | | | | | |
| MW nur von 1 Kontrollperson | | | | | |
| Stimulationsindices | | | | | |

FIG. 17G.7

| | Epiregulin pg/mL | Erythropoietin pg/mL | Fatty Acid Binding Protein ng/mL | Factor VII ng/mL | Ferritin ng/mL |
|---|---|---|---|---|---|
| Least Detectable Dose | 36 | 166 | 3.0 | 1.0 | 1.4 |
| RBM Low Plasma Range | Pending | | | 106 | 5.0 |
| RBM High Plasma Range | Pending | 284 | 10 | 443 | 552 |
| | Epiregulin | Erythropoietin | Fatty Acid Binding Protein | Factor VII | Ferritin |
| patient 1 unstimuliert | | | | | |
| patient 7 unstimuliert | | | | | |
| patient 2 unstimuliert | | | | | |
| patient 3 unstimuliert | | | | | |
| patient 5 unstimuliert | | | | | |
| patient 4 unstimuliert | | | | | |
| patient 6 unstimuliert | | | | | |
| NHD 1 unstimuliert | | | | | |
| NHD 2 unstimuliert | | | | | |

FIG. 17G.8

|  | Epiregulin pg/mL | Erythropoietin pg/mL | Fatty Acid Binding Protein ng/mL | Factor VII ng/mL | Ferritin ng/mL |
|---|---|---|---|---|---|
| Least Detectable Dose | 36 | 166 | 3.0 | 1.0 | 1.4 |
| RBM Low Plasma Range | Pending |  |  | 106 | 5.0 |
| RBM High Plasma Range | Pending | 284 | 10 | 443 | 552 |
| NHD = normal healthy donor |  |  |  |  |  |

FIG. 17H.1

| | FGF basic | Fibrinogen | G-CSF | Growth Hormone | GM-CSF | Glutathione S-Transferase |
|---|---|---|---|---|---|---|
| | pg/mL | mg/mL | pg/mL | ng/mL | pg/mL | ng/mL |
| Least Detectable Dose | 98 | 0.0098 | 5.0 | 0.13 | 57 | 0.40 |
| | | | | | | |
| RBM Low Plasma Range | | 2.2 | | | | |
| RBM High Plasma Range | 2000 | 8.0 | 37 | 4.4 | 152 | 3.1 |
| | | | | | | |
| Samples | | | | | | |
| Donor_1_3. Aliquot A | 1850 | 4.1 | 417 | 1.8 | 8.4 | 0.64 |
| Donor_1_3. Aliquot B | 1710 | 4.4 | 279 | 1.7 | 2.5 | 0.84 |
| Donor_1_3. Aliquot C | 414 | 4.2 | 221 | 1.9 | 5.0 | 0.55 |
| Donor_1_3. Aliquot D | 2050 | 4.8 | 355 | 2.1 | 4.5 | 0.69 |
| Donor_1_3. Aliquot E | 1840 | 4.1 | 270 | 2.0 | 10 | 0.59 |
| Donor_1_3. Aliquot F | 1400 | 3.7 | 197 | 1.5 | 2.5 | 0.50 |
| Donor_1_3. Aliquot G | 1760 | 4.6 | 236 | 1.8 | 57 | 0.52 |
| Donor_1_3. Aliquot H | 159 | 4.0 | 211 | 1.8 | 4.5 | 0.52 |
| Donor_1_3. Aliquot I | 1470 | 4.4 | 219 | 1.8 | 4.0 | 0.55 |
| | | | | | | |
| Donor_2_3. Aliquot A | 429 | 4.3 | 344 | 0.77 | 12 | 0.4 |
| Donor_2_3. Aliquot B | 321 | 4.4 | 204 | 0.90 | 5.0 | 0.76 |
| Donor_2_3. Aliquot C | 241 | 5.1 | 31 | 0.82 | 57 | 0.55 |
| Donor_2_3. Aliquot D | 563 | 4.3 | 1470 | 1.2 | 24 | 1.7 |
| Donor_2_3. Aliquot E | 563 | 4.0 | 1240 | 0.91 | 4.5 | 0.81 |
| Donor_2_3. Aliquot F | 241 | 4.1 | 32 | 0.70 | 3.5 | 0.41 |
| Donor_2_3. Aliquot G | 664 | 5.3 | 2160 | 0.87 | 180 | 0.69 |
| Donor_2_3. Aliquot H | 176 | 3.9 | 36 | 0.78 | 3.5 | 0.4 |
| Donor_2_3. Aliquot I | 225 | 5.2 | 32 | 0.71 | 57 | 0.4 |
| | | | | | | |
| Donor_3_3. Aliquot A | 98 | 5.9 | 105 | 1.5 | 10 | 0.46 |
| Donor_3_3. Aliquot B | 29 | 5.5 | 41 | 1.4 | 7.8 | 1.4 |
| Donor_3_3. Aliquot C | 29 | 4.9 | 5 | 1.5 | 2.5 | 0.48 |
| Donor_3_3. Aliquot D | 209 | 5.2 | 1340 | 1.5 | 6.7 | 1.4 |
| Donor_3_3. Aliquot E | 159 | 6.0 | 1200 | 1.6 | 23 | 0.94 |
| Donor_3_3. Aliquot F | 29 | 5.2 | 5 | 1.3 | 18 | 0.4 |

FIG. 17H.2

| | FGF basic pg/mL | Fibrinogen mg/mL | G-CSF pg/mL | Growth Hormone ng/mL | GM-CSF pg/mL | Glutathione S-Transferase ng/mL |
|---|---|---|---|---|---|---|
| Least Detectable Dose | 98 | 0.0098 | 5.0 | 0.13 | 57 | 0.40 |
| RBM Low Plasma Range | | 2.2 | | | | |
| RBM High Plasma Range | 2000 | 8.0 | 37 | 4.4 | 152 | 3.1 |
| Donor_3 3. Aliquot G | 52 | 6.6 | 7.3 | 1.7 | 57 | 0.4 |
| Donor_3 3. Aliquot H | 98 | 5.3 | 5 | 1.3 | 57 | 0.4 |
| Donor_3 3. Aliquot I | 29 | 6.2 | 5 | 1.6 | 57 | 0.4 |
| Donor_4 3. Aliquot A | 98 | 2.0 | 5.6 | 4.1 | 3.5 | 0.4 |
| Donor_4 3. Aliquot B | 52 | 2.0 | 9.6 | 4.2 | 57 | 0.99 |
| Donor_4 3. Aliquot C | 29 | 2.2 | 5 | 4.0 | 57 | 0.4 |
| Donor_4 3. Aliquot D | 459 | 2.0 | 976 | 4.2 | 18 | 1.2 |
| Donor_4 3. Aliquot E | 474 | 1.3 | 779 | 3.7 | 22 | 0.59 |
| Donor_4 3. Aliquot F | 99 | 1.8 | 18 | 3.3 | 5.0 | 0.4 |
| Donor_4 3. Aliquot G | 90 | 2.2 | 8.8 | 3.6 | 57 | 0.37 |
| Donor_4 3. Aliquot H | 98 | 1.7 | 5 | 4.1 | 57 | 0.39 |
| Donor_4 3. Aliquot I | 52 | 2.0 | 5 | 4.2 | 2.5 | 0.4 |
| Donor_5 3. Aliquot A | 489 | 5.4 | 130 | 4.2 | 5.6 | 0.89 |
| Donor_5 3. Aliquot B | 533 | 5.9 | 203 | 3.9 | 57 | 0.64 |
| Donor_5 3. Aliquot C | 241 | 6.9 | 22 | 4.0 | 57 | 0.64 |
| Donor_5 3. Aliquot D | 563 | 3.4 | 1480 | 3.7 | 23 | 1.3 |
| Donor_5 3. Aliquot E | 533 | 5.2 | 3960 | 4.1 | 32 | 1.1 |
| Donor_5 3. Aliquot F | 257 | 4.4 | 29 | 3.0 | 57 | 0.4 |
| Donor_5 3. Aliquot G | 273 | 7.2 | 31 | 4.7 | 3.5 | 0.4 |
| Donor_5 3. Aliquot H | 176 | 5.5 | 23 | 4.0 | 6.7 | 0.4 |
| Donor_5 3. Aliquot I | 159 | 6.6 | 21 | 3.8 | 57 | 0.50 |
| Donor_6 3. Aliquot A | 72 | 4.1 | 12 | 3.0 | 7.8 | 0.4 |
| Donor_6 3. Aliquot B | 98 | 4.3 | 19 | 3.1 | 20 | 1.3 |
| Donor_6 3. Aliquot C | 98 | 4.9 | 5 | 2.8 | 3.0 | 0.4 |
| Donor_6 3. Aliquot D | 289 | 3.9 | 389 | 3.1 | 4.0 | 0.66 |

FIG. 17H.3

| | FGF basic pg/mL | Fibrinogen mg/mL | G-CSF pg/mL | Growth Hormone ng/mL | GM-CSF pg/mL | Glutathione S-Transferase ng/mL |
|---|---|---|---|---|---|---|
| Least Detectable Dose | 98 | 0.0098 | 5.0 | 0.13 | 57 | 0.40 |
| RBM Low Plasma Range | | 2.2 | | | | |
| RBM High Plasma Range | 2000 | 8.0 | 37 | 4.4 | 152 | 3.1 |
| Donor_6 3. Aliquot E | 289 | 3.2 | 975 | 2.9 | 7.8 | 1.4 |
| Donor_6 3. Aliquot F | 98 | 3.2 | 5 | 2.8 | 9.0 | 0.4 |
| Donor_6 3. Aliquot G | 192 | 5.5 | 20 | 3.2 | 6.7 | 0.4 |
| Donor_6 3. Aliquot H | 98 | 3.9 | 5 | 3.1 | 7.2 | 0.4 |
| Donor_6 3. Aliquot I | 98 | 3.4 | 5 | 3.0 | 57 | 0.37 |
| Donor_7 3. Aliquot A | 391 | 3.0 | 334 | 0.32 | 20 | 0.39 |
| Donor_7 3. Aliquot B | 249 | 2.9 | 86 | 0.39 | 10 | 1.2 |
| Donor_7 3. Aliquot C | 98 | 3.2 | 5 | 0.22 | 5.6 | 0.48 |
| Donor_7 3. Aliquot D | 281 | 2.6 | 892 | 0.39 | 18 | 0.86 |
| Donor_7 3. Aliquot E | 265 | 2.1 | 270 | 0.31 | 18 | 0.50 |
| Donor_7 3. Aliquot F | 98 | 2.6 | 5 | 0.26 | 10 | 0.4 |
| Donor_7 3. Aliquot G | 233 | 2.9 | 5 | 0.23 | 3.0 | 0.4 |
| Donor_7 3. Aliquot H | 72 | 2.4 | 5 | 0.25 | 9.0 | 0.4 |
| Donor_7 3. Aliquot I | 98 | 3.0 | 5 | 0.29 | 9.0 | 0.4 |
| Donor_8 3. Aliquot A | 98 | 1.8 | 5.8 | 0.35 | 5.0 | 0.37 |
| Donor_8 3. Aliquot B | 98 | 1.7 | 4.7 | 0.35 | 6.7 | 1.8 |
| Donor_8 3. Aliquot C | 90 | 1.8 | 5 | 0.20 | 12 | 0.4 |
| Donor_8 3. Aliquot D | 414 | 1.7 | 1330 | 0.94 | 60 | 3.4 |
| Donor_8 3. Aliquot E | 336 | 1.7 | 1010 | 0.90 | 33 | 2.1 |
| Donor_8 3. Aliquot F | 273 | 1.7 | 4.7 | 0.36 | 18 | 0.4 |
| Donor_8 3. Aliquot G | 98 | 2.0 | 5 | 0.33 | 3.5 | 0.4 |
| Donor_8 3. Aliquot H | 142 | 1.7 | 5 | 0.30 | 17 | 0.4 |
| Donor_8 3. Aliquot I | 98 | 1.9 | 5 | 0.28 | 14 | 0.55 |
| Donor_9 3. Aliquot A | 98 | 1.5 | 17 | 7.2 | 11 | 0.73 |
| Donor_9 3. Aliquot B | 122 | 1.6 | 21 | 6.8 | 13 | 2.2 |

FIG. 17H.4

| | FGF basic pg/mL | Fibrinogen mg/mL | G-CSF pg/mL | Growth Hormone ng/mL | GM-CSF pg/mL | Glutathione S-Transferase ng/mL |
|---|---|---|---|---|---|---|
| Least Detectable Dose | 98 | 0.0098 | 5.0 | 0.13 | 57 | 0.40 |
| RBM Low Plasma Range | | 2.2 | | | | |
| RBM High Plasma Range | 2000 | 8.0 | 37 | 4.4 | 152 | 3.1 |
| Donor_9 3. Aliquot C | 94 | 1.4 | 19 | 6.6 | 21 | 0.40 |
| Donor_9 3. Aliquot D | 414 | 1.5 | 2320 | 6.8 | 29 | 2.6 |
| Donor_9 3. Aliquot E | 332 | 1.5 | 1490 | 6.8 | 13 | 2.4 |
| Donor_9 3. Aliquot F | 137 | 1.2 | 11 | 6.4 | 5.8 | 0.76 |
| Donor_9 3. Aliquot G | 179 | 1.9 | 39 | 6.2 | 17 | 0.56 |
| Donor_9 3. Aliquot H | 37 | 1.3 | 5.4 | 6.8 | 15 | 0.53 |
| Donor_9 3. Aliquot I | 37 | 1.6 | 5.4 | 6.4 | 8.7 | 0.37 |
| EDTA Plasma | | | | | | |
| donor #1 plasma | 736 | 4.6 | 240 | 1.4 | 18 | 1.1 |
| donor #2 plasma | 339 | 8.1 | 45 | 0.89 | 15 | 0.4 |
| donor #3 plasma | 94 | 8.7 | 5 | 1.5 | 27 | 1.0 |
| donor #4 plasma | 51 | 3.2 | 4.5 | 5.3 | 10.0 | 0.4 |
| donor #5 plasma | 346 | 11 | 24 | 5.1 | 23 | 1.3 |
| donor #6 plasma | 21 | 6.7 | 6.2 | 4.1 | 20 | 0.69 |
| donor #7 plasma | 98 | 4.5 | 6.2 | 0.49 | 17 | 0.4 |
| donor #8 plasma | 87 | 2.0 | 5 | 0.38 | 15 | 0.46 |
| donor #9 plasma | 87 | 2.3 | 18 | 7.2 | 5.3 | 0.90 |
| MW NHD plasma Normal healthy donors | 86.9 | 2.2 | 11.6 | 3.8 | 10.3 | 0.7 |
| MW NHD unstimuliert Normal healthy donors | 67.40 | 1.73 | 5.18 | 3.33 | 11.41 | 0.46 |
| Stimulationsindices | | | | | | |

FIG. 17H.5

| | FGF basic | Fibrinogen | G-CSF | Growth Hormone | GM-CSF | Glutathione S-Transferase |
|---|---|---|---|---|---|---|
| | pg/mL | mg/mL | pg/mL | ng/mL | pg/mL | ng/mL |
| Least Detectable Dose | 98 | 0.0098 | 5.0 | 0.13 | 57 | 0.40 |
| RBM Low Plasma Range | | 2.2 | | | | |
| RBM High Plasma Range | 2000 | 8.0 | 37 | 4.4 | 152 | 3.1 |
| EDTA Plasma | | | | | | |

| | | FGF basic | Fibrinogen | G-CSF | Growth Hormone | GM-CSF | Glutathione S-Transferase |
|---|---|---|---|---|---|---|---|
| PLASMA | patient 1 | | | | | | |
| PLASMA | patient 7 | | | | | | |
| PLASMA | patient 2 | | | | | | |
| PLASMA | patient 3 | | | | | | |
| PLASMA | patient 5 | | | | | | |
| PLASMA | patient 4 | | | | | | |
| PLASMA | patient 6 | | | | | | |
| PLASMA | NHD 1 | | | | | | |
| PLASMA | NHD 2 | | | | | | |

FIG. 17H.6

| | FGF basic pg/mL | Fibrinogen mg/mL | G-CSF pg/mL | Growth Hormone ng/mL | GM-CSF pg/mL | Glutathione S-Transferase ng/mL |
|---|---|---|---|---|---|---|
| Least Detectable Dose | 98 | 0.0098 | 5.0 | 0.13 | 57 | 0.40 |
| RBM Low Plasma Range | | 2.2 | | | | |
| RBM High Plasma Range | 2000 | 8.0 | 37 | 4.4 | 152 | 3.1 |
| Messwert > ULD | | | | | | |
| SI > 1,5 | | | | | | |
| SI 0,7-1,5 | | | | | | |
| SI 0-0,7 | | | | | | |
| MW nur von 1 Kontrollperson | | | | | | |
| StimulationsIndices | | | | | | |

FIG. 17H.7

| | FGF basic pg/mL | Fibrinogen mg/mL | G-CSF pg/mL | Growth Hormone ng/mL | GM-CSF pg/mL | Glutathione S-Transferase ng/mL |
|---|---|---|---|---|---|---|
| Least Detectable Dose | 98 | 0.0098 | 5.0 | 0.13 | 57 | 0.40 |
| RBM Low Plasma Range | | 2.2 | | | | |
| RBM High Plasma Range | 2000 | 8.0 | 37 | 4.4 | 152 | 3.1 |

| | FGF basic | Fibrinogen | G-CSF | Growth Hormone | GM-CSF | Glutathione S-Transferase |
|---|---|---|---|---|---|---|
| patient 1 | unstimuliert | | | | | |
| patient 7 | unstimuliert | | | | | |
| patient 2 | unstimuliert | | | | | |
| patient 3 | unstimuliert | | | | | |
| patient 5 | unstimuliert | | | | | |
| patient 4 | unstimuliert | | | | | |
| patient 6 | unstimuliert | | | | | |
| NHD 1 | unstimuliert | | | | | |
| NHD 2 | unstimuliert | | | | | |

FIG. 17H.8

| | FGF basic | Fibrinogen | G-CSF | Growth Hormone | GM-CSF | Glutathione S-Transferase |
|---|---|---|---|---|---|---|
| | pg/mL | mg/mL | pg/mL | ng/mL | pg/mL | ng/mL |
| Least Detectable Dose | 98 | 0.0098 | 5.0 | 0.13 | 57 | 0.40 |
| RBM Low Plasma Range | | 2.2 | | | | |
| RBM High Plasma Range | 2000 | 8.0 | 37 | 4.4 | 152 | 3.1 |
| NHD = normal healthy donor | | | | | | |

FIG. 17I.1

| | Haptoglobin mg/mL | ICAM-1 ng/mL | IFN-gamma pg/mL | IgA mg/mL | IgE ng/mL | IGF-1 ng/mL | IgM mg/mL | IL-10 pg/mL |
|---|---|---|---|---|---|---|---|---|
| Least Detectable Dose | 0.025 | 3.2 | 4.6 | 0.0084 | 14 | 4.0 | 0.015 | 15 |
| RBM Low Plasma Range | 0.047 | 42 | Pending | 0.58 | 770 | 177 | 0.24 | 1.8 |
| RBM High Plasma Range | 7.6 | 213 | Pending | 5.6 | | | 3.3 | 38 |
| Samples | | | | | | | | |
| Donor_1 3. Aliquot A | 1.0 | 467 | 3.8 | 2.0 | 13 | 49 | 0.63 | 180 |
| Donor_1 3. Aliquot B | 1.2 | 432 | 4.5 | 2.3 | 11 | 49 | 0.66 | 135 |
| Donor_1 3. Aliquot C | 1.1 | 452 | 2.7 | 2.2 | 1.8 | 67 | 0.68 | 15 |
| Donor_1 3. Aliquot D | 1.2 | 465 | 4.6 | 2.4 | 12 | 46 | 0.71 | 134 |
| Donor_1 3. Aliquot E | 1.1 | 438 | 4.6 | 2.1 | 13 | 45 | 0.63 | 58 |
| Donor_1 3. Aliquot F | 1.2 | 441 | 4.6 | 2.1 | 4.4 | 55 | 0.60 | 18 |
| Donor_1 3. Aliquot G | 1.2 | 471 | 4.5 | 2.3 | 11 | 100 | 0.70 | 15 |
| Donor_1 3. Aliquot H | 1.1 | 491 | 4.6 | 2.1 | 9.6 | 46 | 0.60 | 14 |
| Donor_1 3. Aliquot I | 1.1 | 438 | 4.6 | 2.3 | 6.2 | 46 | 0.65 | 16 |
| Donor_2 3. Aliquot A | 1.3 | 491 | 7.2 | 2.5 | 210 | 94 | 0.15 | 500 |
| Donor_2 3. Aliquot B | 1.8 | 495 | 6.7 | 2.5 | 217 | 90 | 0.15 | 483 |
| Donor_2 3. Aliquot C | 1.9 | 499 | 4.6 | 2.5 | 98 | 87 | 0.21 | 19 |
| Donor_2 3. Aliquot D | 1.5 | 489 | 31 | 2.4 | 258 | 81 | 0.14 | 977 |
| Donor_2 3. Aliquot E | 2.2 | 479 | 9.5 | 2.5 | 221 | 86 | 0.18 | 963 |
| Donor_2 3. Aliquot F | 2.1 | 504 | 4.6 | 2.5 | 177 | 73 | 0.17 | 28 |
| Donor_2 3. Aliquot G | 2.3 | 514 | 14 | 2.5 | 151 | 221 | 0.18 | 131 |
| Donor_2 3. Aliquot H | 1.9 | 490 | 2.7 | 2.6 | 175 | 75 | 0.18 | 22 |
| Donor_2 3. Aliquot I | 1.7 | 479 | 3.8 | 2.5 | 195 | 73 | 0.19 | 21 |
| Donor_3 3. Aliquot A | 0.014 | 283 | 8.5 | 1.5 | 26 | 380 | 0.66 | 480 |
| Donor_3 3. Aliquot B | 0.018 | 239 | 4.6 | 1.6 | 27 | 368 | 0.67 | 632 |
| Donor_3 3. Aliquot C | 0.019 | 278 | 4.6 | 1.6 | 7.6 | 408 | 0.66 | 26 |
| Donor_3 3. Aliquot D | 0.013 | 231 | 8.2 | 1.6 | 45 | 387 | 0.67 | 1640 |
| Donor_3 3. Aliquot E | 0.014 | 306 | 9.2 | 1.7 | 40 | 393 | 0.74 | 1660 |
| Donor_3 3. Aliquot F | 0.021 | 249 | 4.6 | 1.5 | 26 | 338 | 0.69 | 18 |

FIG. 171.2

| | Haptoglobin mg/mL | ICAM-1 ng/mL | IFN-gamma pg/mL | IgA mg/mL | IgE ng/mL | IGF-1 ng/mL | IgM mg/mL | IL-10 pg/mL |
|---|---|---|---|---|---|---|---|---|
| Least Detectable Dose | 0.025 | 3.2 | 4.6 | 0.0084 | 14 | 4.0 | 0.015 | 15 |
| RBM Low Plasma Range | 0.047 | 42 | Pending | 0.58 | 770 | 177 | 0.24 | 1.8 |
| RBM High Plasma Range | 7.6 | 213 | Pending | 5.6 | 14 | 546 | 3.3 | 38 |
| Donor_3_3. Aliquot G | 0.087 | 259 | 4.6 | 1.6 | 14 | 546 | 0.72 | 11 |
| Donor_3_3. Aliquot H | 0.022 | 208 | 4.6 | 1.5 | 21 | 386 | 0.67 | 4.9 |
| Donor_3_3. Aliquot I | 0.051 | 221 | 4.6 | 1.5 | 29 | 403 | 0.69 | 11 |
| Donor_4_3. Aliquot A | 0.0075 | 456 | 4.6 | 2.5 | 12 | 4 | 0.39 | 46 |
| Donor_4_3. Aliquot B | 0.014 | 466 | 4.6 | 2.3 | 14 | 4 | 0.29 | 251 |
| Donor_4_3. Aliquot C | 0.0086 | 453 | 4.6 | 2.4 | 14 | 4 | 0.36 | 11 |
| Donor_4_3. Aliquot D | 0.014 | 471 | 6.2 | 2.2 | 32 | 4 | 0.31 | 566 |
| Donor_4_3. Aliquot E | 0.0086 | 477 | 7.0 | 2.3 | 24 | 4 | 0.29 | 543 |
| Donor_4_3. Aliquot F | 0.019 | 467 | 3.8 | 2.3 | 13 | 4 | 0.31 | 232 |
| Donor_4_3. Aliquot G | 0.019 | 462 | 4.6 | 2.4 | 8.0 | 22 | 0.29 | 14 |
| Donor_4_3. Aliquot H | 0.013 | 474 | 4.6 | 2.3 | 8.0 | 4 | 0.28 | 10 |
| Donor_4_3. Aliquot I | 0.011 | 447 | 4.6 | 2.3 | 9.6 | 4 | 0.30 | 13 |
| Donor_5_3. Aliquot A | 3.7 | 241 | 7.5 | 1.1 | 321 | 323 | 0.24 | 117 |
| Donor_5_3. Aliquot B | 3.6 | 213 | 8.2 | 1.1 | 270 | 337 | 0.25 | 417 |
| Donor_5_3. Aliquot C | 3.8 | 246 | 4.6 | 1.1 | 84 | 330 | 0.24 | 7.0 |
| Donor_5_3. Aliquot D | 3.4 | 263 | 20 | 1.1 | 271 | 373 | 0.22 | 763 |
| Donor_5_3. Aliquot E | 3.2 | 261 | 21 | 1.2 | 274 | 382 | 0.23 | 1520 |
| Donor_5_3. Aliquot F | 3.1 | 164 | 7.2 | 1.0 | 204 | 350 | 0.23 | 37 |
| Donor_5_3. Aliquot G | 3.5 | 255 | 6.2 | 1.0 | 59 | 574 | 0.26 | 15 |
| Donor_5_3. Aliquot H | 3.2 | 223 | 3.8 | 1.0 | 296 | 355 | 0.26 | 10 |
| Donor_5_3. Aliquot I | 3.4 | 242 | 5.1 | 1.00 | 289 | 329 | 0.24 | 9.2 |
| Donor_6_3. Aliquot A | 4.2 | 130 | 4.6 | 0.79 | 317 | 47 | 0.38 | 85 |
| Donor_6_3. Aliquot B | 4.4 | 146 | 4.6 | 0.81 | 306 | 46 | 0.42 | 226 |
| Donor_6_3. Aliquot C | 4.2 | 157 | 4.6 | 0.78 | 139 | 54 | 0.37 | 7.0 |
| Donor_6_3. Aliquot D | 4.3 | 149 | 31 | 0.81 | 326 | 47 | 0.41 | 637 |

FIG. 171I.3

| | Haptoglobin mg/mL | ICAM-1 ng/mL | IFN-gamma pg/mL | IgA mg/mL | IgE ng/mL | IGF-1 ng/mL | IgM mg/mL | IL-10 pg/mL |
|---|---|---|---|---|---|---|---|---|
| Least Detectable Dose | 0.025 | 3.2 | 4.6 | 0.0084 | 14 | 4.0 | 0.015 | 15 |
| | | | | | | | | |
| RBM Low Plasma Range | 0.047 | 42 | Pending | 0.58 | | | 0.24 | 1.8 |
| RBM High Plasma Range | 7.6 | 213 | Pending | 5.6 | | 177 | 3.3 | 38 |
| Donor_6_3. Aliquot E | 3.9 | 120 | 74 | 0.94 | 770 | 50 | 0.34 | 1870 |
| Donor_6_3. Aliquot F | 4.3 | 120 | 4.6 | 0.82 | 269 | 45 | 0.33 | 45 |
| Donor_6_3. Aliquot G | 4.2 | 156 | 4.6 | 0.81 | 222 | 189 | 0.35 | 7.0 |
| Donor_6_3. Aliquot H | 4.1 | 146 | 4.6 | 0.71 | 91 | 42 | 0.35 | 6.0 |
| Donor_6_3. Aliquot I | 3.7 | 127 | 4.6 | 0.76 | 340 | 45 | 0.34 | 7.0 |
| | | | | | 272 | | | |
| Donor_7_3. Aliquot A | 2.6 | 85 | 4.6 | 1.5 | 56 | 14 | 0.63 | 379 |
| Donor_7_3. Aliquot B | 2.7 | 85 | 4.6 | 1.5 | 51 | 18 | 0.59 | 441 |
| Donor_7_3. Aliquot C | 2.7 | 89 | 4.6 | 1.6 | 14 | 26 | 0.63 | 13 |
| Donor_7_3. Aliquot D | 2.0 | 74 | 4.6 | 1.4 | 62 | 15 | 0.59 | 390 |
| Donor_7_3. Aliquot E | 1.9 | 84 | 4.6 | 1.1 | 56 | 17 | 0.48 | 297 |
| Donor_7_3. Aliquot F | 2.6 | 83 | 4.6 | 1.5 | 39 | 9.8 | 0.66 | 85 |
| Donor_7_3. Aliquot G | 2.3 | 93 | 4.6 | 1.4 | 25 | 98 | 0.60 | 13 |
| Donor_7_3. Aliquot H | 2.6 | 81 | 4.6 | 1.4 | 36 | 8.1 | 0.60 | 6.8 |
| Donor_7_3. Aliquot I | 2.7 | 79 | 4.6 | 1.5 | 46 | 12 | 0.60 | 11 |
| | | | | | | | | |
| Donor_8_3. Aliquot A | 0.014 | 61 | 5.6 | 0.77 | 17 | 176 | 0.30 | 102 |
| Donor_8_3. Aliquot B | 0.016 | 66 | 4.6 | 0.85 | 8.0 | 168 | 0.34 | 218 |
| Donor_8_3. Aliquot C | 0.0065 | 50 | 550 | 0.83 | 14 | 163 | 0.31 | 4.9 |
| Donor_8_3. Aliquot D | 0.013 | 63 | 1880 | 0.73 | 77 | 179 | 0.36 | 306 |
| Donor_8_3. Aliquot E | 0.037 | 59 | 283 | 0.73 | 65 | 162 | 0.32 | 1000 |
| Donor_8_3. Aliquot F | 0.018 | 63 | 118 | 0.85 | 15 | 166 | 0.32 | 219 |
| Donor_8_3. Aliquot G | 0.016 | 65 | 4.6 | 0.74 | 8.0 | 181 | 0.28 | 4.3 |
| Donor_8_3. Aliquot H | 0.016 | 64 | 41 | 0.84 | 10 | 177 | 0.37 | 4.1 |
| Donor_8_3. Aliquot I | 0.011 | 58 | 3.8 | 0.78 | 3.7 | 175 | 0.33 | 6.6 |
| | | | | | | | | |
| Donor_9_3. Aliquot A | 0.018 | 79 | 17 | 1.0 | 9.3 | 745 | 1.0 | 220 |
| Donor_9_3. Aliquot B | 0.018 | 82 | 21 | 1.0 | 9.3 | 716 | 1.0 | 435 |

FIG. 171.4

| | Haptoglobin mg/mL | ICAM-1 ng/mL | IFN-gamma pg/mL | IgA mg/mL | IgE ng/mL | IGF-1 ng/mL | IgM mg/mL | IL-10 pg/mL |
|---|---|---|---|---|---|---|---|---|
| Least Detectable Dose | 0.025 | 3.2 | 4.6 | 0.0084 | 14 | 4.0 | 0.015 | 15 |
| RBM Low Plasma Range | 0.047 | 42 | Pending | 0.58 | | | 0.24 | 1.8 |
| RBM High Plasma Range | 7.6 | 213 | Pending | 5.6 | 770 | 177 | 3.3 | 38 |
| Donor_9_3. Aliquot C | 0.012 | 69 | 519 | 1.0 | 4.1 | 784 | 0.97 | 43 |
| Donor_9_3. Aliquot D | 0.0062 | 75 | 2360 | 1.0 | 63 | 681 | 1.0 | 1080 |
| Donor_9_3. Aliquot E | 0.013 | 71 | 490 | 1.00 | 39 | 651 | 1.0 | 1730 |
| Donor_9_3. Aliquot F | 0.0076 | 78 | 26 | 1.0 | 5.8 | 688 | 0.95 | 122 |
| Donor_9_3. Aliquot G | 0.016 | 68 | 7.6 | 1.1 | 5.2 | 636 | 1.1 | 13 |
| Donor_9_3. Aliquot H | 0.017 | 75 | 9.0 | 1.0 | 6.0 | 703 | 1.0 | 14 |
| Donor_9_3. Aliquot I | 0.012 | 76 | 14 | 1.0 | 6.2 | 732 | 1.1 | 4.2 |
| EDTA Plasma | | | | | | | | |
| donor #1 plasma | 1.3 | 206 | 4.0 | 2.4 | 6.6 | 4 | 0.57 | 16 |
| donor #2 plasma | 3.6 | 371 | 10 | 4.0 | 172 | 4 | 0.22 | 21 |
| donor #3 plasma | 0.58 | 171 | 5.8 | 2.8 | 26 | 12 | 0.93 | 9.9 |
| donor #4 plasma | 0.0097 | 348 | 4.6 | 3.6 | 14 | 4 | 0.39 | 14 |
| donor #5 plasma | 5.9 | 136 | 13 | 1.8 | 318 | 18 | 0.32 | 12 |
| donor #6 plasma | 5.7 | 129 | 4.6 | 1.3 | 559 | 4 | 0.43 | 10 |
| donor #7 plasma | 4.6 | 109 | 5.8 | 2.4 | 81 | 4 | 0.79 | 16 |
| donor #8 plasma | 0.36 | 87 | 4.6 | 1.0 | 17 | 32 | 0.38 | 2.3 |
| donor #9 plasma | 0.32 | 100 | 4.0 | 1.4 | 3.5 | 325 | 1.5 | 5.1 |
| MW NHD plasma | 0.3 | 93.5 | 4.3 | 1.2 | 10.3 | 178.4 | 1.0 | 3.7 |
| Normal healthy donors | | | | | | | | |
| MW NHD unstimuliert | 0.01 | 67.00 | 8.82 | 0.89 | 4.93 | 453.50 | 0.69 | 5.41 |
| Normal healthy donors | | | | | | | | |
| Stimulations indices | | | | | | | | |

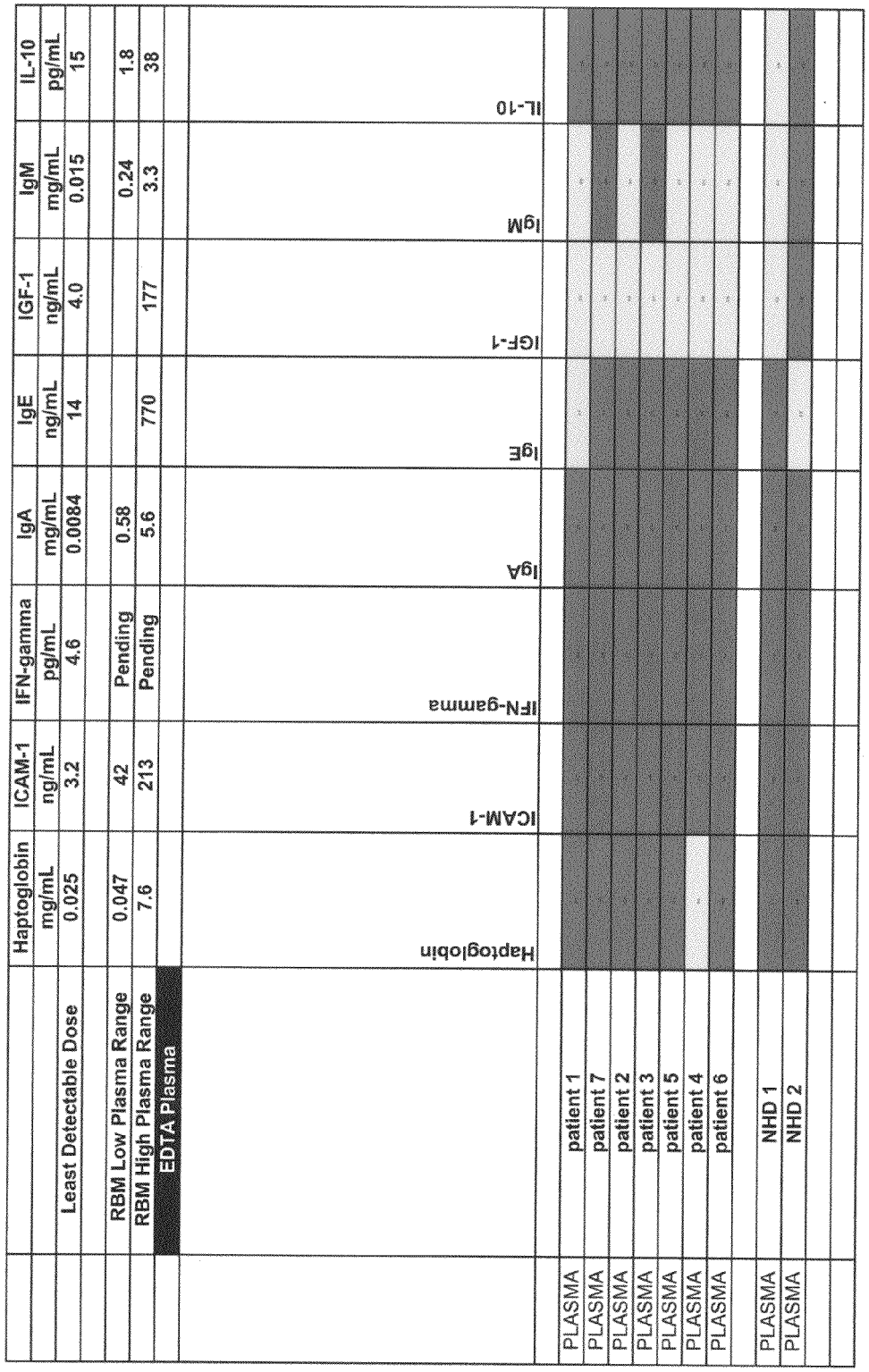
FIG. 171.5

FIG. 171.6

| | Haptoglobin mg/mL | ICAM-1 ng/mL | IFN-gamma pg/mL | IgA mg/mL | IgE ng/mL | IGF-1 ng/mL | IgM mg/mL | IL-10 pg/mL |
|---|---|---|---|---|---|---|---|---|
| Least Detectable Dose | 0.025 | 3.2 | 4.6 | 0.0084 | 14 | 4.0 | 0.015 | 15 |
| RBM Low Plasma Range | 0.047 | 42 | Pending | 0.58 | | | 0.24 | 1.8 |
| RBM High Plasma Range | 7.6 | 213 | Pending | 5.6 | 770 | 177 | 3.3 | 38 |
| Messwert > ULD | | | | | | | | |
| SI > 1,5 | | | | | | | | |
| SI 0,7-1,5 | | | | | | | | |
| SI 0-0,7 | | | | | | | | |
| MW nur von 1 Kontrollperson | | | | | | | | |
| Stimulationsindices | | | | | | | | |

FIG. 17I.7
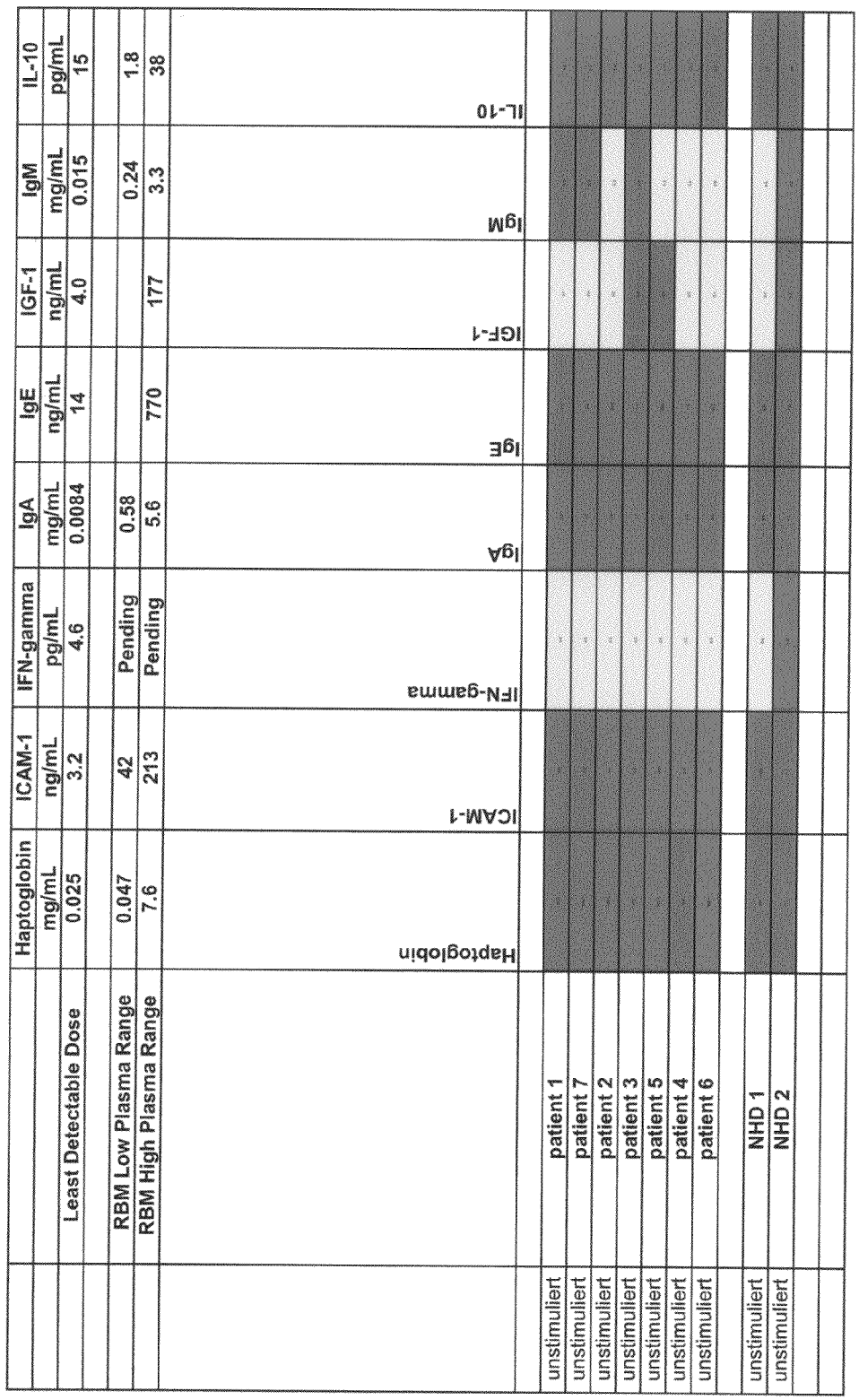

FIG. 171.8

| | Haptoglobin mg/mL | ICAM-1 ng/mL | IFN-gamma pg/mL | IgA mg/mL | IgE ng/mL | IGF-1 ng/mL | IgM mg/mL | IL-10 pg/mL |
|---|---|---|---|---|---|---|---|---|
| Least Detectable Dose | 0.025 | 3.2 | 4.6 | 0.0084 | 14 | 4.0 | 0.015 | 15 |
| RBM Low Plasma Range | 0.047 | 42 | Pending | 0.58 | | | 0.24 | 1.8 |
| RBM High Plasma Range | 7.6 | 213 | Pending | 5.6 | 770 | 177 | 3.3 | 38 |
| NHD = normal healthy donor | | | | | | | | |

FIG. 17J.1

| | IL-12p40 ng/mL | IL-12p70 pg/mL | IL-13 pg/mL | IL-15 ng/mL | IL-16 pg/mL | IL-17 pg/mL | IL-17E pg/mL | IL-18 pg/mL |
|---|---|---|---|---|---|---|---|---|
| Least Detectable Dose | 1.2 | 94 | 57 | 1.3 | 66 | 2.7 | 31 | 54 |
| RBM Low Plasma Range | 2.7 | 165 | 133 | 4.6 | 232 | PENDING | PENDING | 72 |
| RBM High Plasma Range | | | | | 3380 | PENDING | PENDING | 1020 |
| Samples | | | | | | | | |
| Donor_1 3. Aliquot A | 0.30 | 45 | 36 | 0.41 | 575 | 6.7 | 643 | 1930 |
| Donor_1 3. Aliquot B | 0.16 | 35 | 37 | 0.40 | 535 | 2.7 | 559 | 1910 |
| Donor_1 3. Aliquot C | 1.2 | 28 | 38 | 0.33 | 413 | 2.7 | 62 | 1980 |
| Donor_1 3. Aliquot D | 0.43 | 42 | 21 | 0.45 | 619 | 2.7 | 580 | 2080 |
| Donor_1 3. Aliquot E | 0.13 | 37 | 34 | 0.32 | 580 | 2.7 | 604 | 2140 |
| Donor_1 3. Aliquot F | 1.2 | 28 | 36 | 0.30 | 502 | 2.7 | 486 | 1630 |
| Donor_1 3. Aliquot G | 0.19 | 39 | 37 | 0.50 | 216 | 7.5 | 646 | 2130 |
| Donor_1 3. Aliquot H | 1.2 | 52 | 35 | 0.28 | 299 | 2.7 | 56 | 1860 |
| Donor_1 3. Aliquot I | 1.2 | 32 | 33 | 0.26 | 588 | 2.7 | 502 | 1810 |
| Donor_2 3. Aliquot A | 0.51 | 61 | 37 | 0.41 | 654 | 2.7 | 29 | 631 |
| Donor_2 3. Aliquot B | 0.26 | 35 | 37 | 0.43 | 712 | 2.7 | 40 | 709 |
| Donor_2 3. Aliquot C | 1.2 | 18 | 29 | 0.32 | 609 | 2.7 | 11 | 616 |
| Donor_2 3. Aliquot D | 2.8 | 40 | 29 | 0.50 | 804 | 2.7 | 37 | 830 |
| Donor_2 3. Aliquot E | 2.4 | 37 | 36 | 0.37 | 782 | 2.7 | 29 | 754 |
| Donor_2 3. Aliquot F | 0.26 | 45 | 66 | 0.50 | 720 | 2.7 | 17 | 594 |
| Donor_2 3. Aliquot G | 0.88 | 45 | 40 | 0.66 | 432 | 2.7 | 31 | 681 |
| Donor_2 3. Aliquot H | 1.2 | 35 | 27 | 1.3 | 393 | 2.7 | 23 | 595 |
| Donor_2 3. Aliquot I | 1.2 | 35 | 36 | 0.21 | 642 | 2.7 | 34 | 538 |
| Donor_3 3. Aliquot A | 0.43 | 50 | 49 | 0.53 | 1310 | 2.7 | 17 | 766 |
| Donor_3 3. Aliquot B | 0.37 | 48 | 43 | 0.56 | 1230 | 2.7 | 34 | 720 |
| Donor_3 3. Aliquot C | 0.13 | 55 | 57 | 0.41 | 1190 | 2.7 | 29 | 715 |
| Donor_3 3. Aliquot D | 3.3 | 45 | 40 | 0.47 | 1410 | 2.7 | 37 | 735 |
| Donor_3 3. Aliquot E | 2.7 | 55 | 39 | 0.47 | 1490 | 2.7 | 29 | 798 |
| Donor_3 3. Aliquot F | 1.2 | 40 | 51 | 0.28 | 1340 | 2.7 | 29 | 694 |

FIG. 17J.2

| | IL-12p40 ng/mL | IL-12p70 pg/mL | IL-13 pg/mL | IL-15 ng/mL | IL-16 pg/mL | IL-17 pg/mL | IL-17E pg/mL | IL-18 pg/mL |
|---|---|---|---|---|---|---|---|---|
| Least Detectable Dose | 1.2 | 94 | 57 | 1.3 | 66 | 2.7 | 31 | 54 |
| RBM Low Plasma Range | | | | | 232 | PENDING | PENDING | 72 |
| RBM High Plasma Range | 2.7 | 165 | 133 | 4.6 | 3380 | PENDING | PENDING | 1020 |
| Donor_3_3. Aliquot G | 1.2 | 35 | 43 | 0.32 | 556 | 2.7 | 29 | 766 |
| Donor_3_3. Aliquot H | 1.2 | 22 | 55 | 0.28 | 706 | 2.7 | 31 | 553 |
| Donor_3_3. Aliquot I | 1.2 | 42 | 81 | 0.47 | 1280 | 2.7 | 45 | 627 |
| Donor_4_3. Aliquot A | 1.2 | 94 | 36 | 0.38 | 1240 | 2.7 | 42 | 690 |
| Donor_4_3. Aliquot B | 1.2 | 94 | 19 | 0.56 | 1130 | 2.7 | 40 | 700 |
| Donor_4_3. Aliquot C | 1.2 | 39 | 27 | 0.32 | 1050 | 2.7 | 56 | 608 |
| Donor_4_3. Aliquot D | 3.1 | 39 | 38 | 0.43 | 986 | 2.7 | 29 | 724 |
| Donor_4_3. Aliquot E | 1.5 | 30 | 23 | 0.56 | 812 | 2.7 | 51 | 633 |
| Donor_4_3. Aliquot F | 0.37 | 24 | 28 | 0.47 | 1030 | 2.7 | 51 | 623 |
| Donor_4_3. Aliquot G | 1.2 | 20 | 29 | 0.24 | 431 | 2.7 | 56 | 612 |
| Donor_4_3. Aliquot H | 1.2 | 15 | 9.7 | 0.19 | 564 | 2.7 | 62 | 566 |
| Donor_4_3. Aliquot I | 1.2 | 94 | 24 | 0.24 | 1150 | 2.7 | 62 | 597 |
| Donor_5_3. Aliquot A | 0.34 | 20 | 33 | 0.71 | 536 | 2.7 | 74 | 340 |
| Donor_5_3. Aliquot B | 0.26 | 32 | 32 | 0.50 | 584 | 2.7 | 40 | 295 |
| Donor_5_3. Aliquot C | 1.2 | 26 | 48 | 0.50 | 455 | 2.7 | 20 | 271 |
| Donor_5_3. Aliquot D | 2.7 | 59 | 32 | 0.73 | 592 | 2.7 | 17 | 428 |
| Donor_5_3. Aliquot E | 1.8 | 94 | 36 | 0.68 | 561 | 2.7 | 11 | 467 |
| Donor_5_3. Aliquot F | 1.2 | 20 | 38 | 0.28 | 430 | 2.7 | 31 | 216 |
| Donor_5_3. Aliquot G | 0.28 | 24 | 29 | 0.26 | 323 | 2.7 | 45 | 479 |
| Donor_5_3. Aliquot H | 1.2 | 28 | 27 | 0.19 | 390 | 2.7 | 31 | 367 |
| Donor_5_3. Aliquot I | 1.2 | 44 | 47 | 0.13 | 492 | 2.7 | 34 | 255 |
| Donor_6_3. Aliquot A | 0.13 | 32 | 70 | 0.32 | 1030 | 2.7 | 29 | 102 |
| Donor_6_3. Aliquot B | 1.2 | 42 | 57 | 0.24 | 828 | 2.7 | 51 | 95 |
| Donor_6_3. Aliquot C | 1.2 | 50 | 59 | 0.24 | 1150 | 2.7 | 11 | 98 |
| Donor_6_3. Aliquot D | 4.7 | 94 | 68 | 0.56 | 682 | 2.7 | 17 | 138 |

FIG. 17J.3

| | IL-12p40 ng/mL 1.2 | IL-12p70 pg/mL 94 | IL-13 pg/mL 57 | IL-15 ng/mL 1.3 | IL-16 pg/mL 66 | IL-17 pg/mL 2.7 | IL-17E pg/mL 31 | IL-18 pg/mL 54 |
|---|---|---|---|---|---|---|---|---|
| Least Detectable Dose | 1.2 | 94 | 57 | 1.3 | 66 | 2.7 | 31 | 54 |
| RBM Low Plasma Range | | | | | | | | |
| RBM High Plasma Range | 2.7 | 165 | 133 | 4.6 | 232 | PENDING | PENDING | 72 |
| Donor_6_3. Aliquot E | 4.3 | 30 | 68 | 0.16 | 3380 | PENDING | PENDING | 1020 |
| Donor_6_3. Aliquot F | 1.2 | 47 | 86 | 0.43 | 648 | 2.7 | 17 | 134 |
| Donor_6_3. Aliquot G | 1.2 | 20 | 65 | 1.3 | 969 | 2.7 | 31 | 113 |
| Donor_6_3. Aliquot H | 0.16 | 94 | 65 | 0.19 | 439 | 2.7 | 11 | 170 |
| Donor_6_3. Aliquot I | 1.2 | 94 | 59 | 0.28 | 815 | 5.0 | 54 | 107 |
| | | | | | 1230 | 2.7 | 62 | 87 |
| Donor_7_3. Aliquot A | 0.64 | 39 | 91 | 0.79 | 664 | 2.7 | 40 | 295 |
| Donor_7_3. Aliquot B | 0.27 | 32 | 103 | 0.78 | 620 | 2.7 | 34 | 277 |
| Donor_7_3. Aliquot C | 1.2 | 39 | 70 | 0.53 | 817 | 2.7 | 17 | 255 |
| Donor_7_3. Aliquot D | 0.93 | 39 | 82 | 0.49 | 662 | 2.7 | 23 | 275 |
| Donor_7_3. Aliquot E | 0.93 | 42 | 104 | 0.58 | 651 | 2.7 | 62 | 298 |
| Donor_7_3. Aliquot F | 1.2 | 34 | 105 | 0.54 | 856 | 2.7 | 31 | 209 |
| Donor_7_3. Aliquot G | 1.2 | 22 | 56 | 0.19 | 428 | 2.7 | 85 | 300 |
| Donor_7_3. Aliquot H | 1.2 | 94 | 62 | 0.38 | 574 | 2.7 | 31 | 214 |
| Donor_7_3. Aliquot I | 1.2 | 94 | 88 | 0.41 | 918 | 2.7 | 26 | 227 |
| Donor_8_3. Aliquot A | 0.30 | 34 | 81 | 0.32 | 340 | 2.7 | 17 | 150 |
| Donor_8_3. Aliquot B | 0.19 | 22 | 97 | 0.24 | 341 | 2.7 | 31 | 173 |
| Donor_8_3. Aliquot C | 0.57 | 3920 | 80 | 0.32 | 309 | 2.7 | 31 | 157 |
| Donor_8_3. Aliquot D | 19 | 434 | 99 | 0.61 | 754 | 5.0 | 17 | 408 |
| Donor_8_3. Aliquot E | 14 | 48 | 99 | 0.64 | 533 | 9.7 | 45 | 359 |
| Donor_8_3. Aliquot F | 0.71 | 42 | 111 | 0.45 | 410 | 4.2 | 31 | 175 |
| Donor_8_3. Aliquot G | 1.2 | 15 | 53 | 0.19 | 183 | 5.4 | 23 | 152 |
| Donor_8_3. Aliquot H | 0.23 | 30 | 75 | 0.28 | 231 | 2.7 | 17 | 220 |
| Donor_8_3. Aliquot I | 1.2 | 32 | 80 | 0.32 | 522 | 2.7 | 29 | 195 |
| Donor_9_3. Aliquot A | 0.26 | 52 | 68 | 0.31 | 463 | 17 | 34 | 58 |
| Donor_9_3. Aliquot B | 0.40 | 44 | 77 | 0.44 | 398 | 7.2 | 66 | 48 |

FIG. 17J.4

| | IL-12p40 ng/mL | IL-12p70 pg/mL | IL-13 pg/mL | IL-15 ng/mL | IL-16 pg/mL | IL-17 pg/mL | IL-17E pg/mL | IL-18 pg/mL |
|---|---|---|---|---|---|---|---|---|
| Least Detectable Dose | 1.2 | 94 | 57 | 1.3 | 66 | 2.7 | 31 | 54 |
| RBM Low Plasma Range | | | | | | | | |
| RBM High Plasma Range | 2.7 | 165 | 133 | 4.6 | 232 | PENDING | PENDING | 72 |
| Donor_9.3. Aliquot C | 0.80 | 1480 | 74 | 0.35 | 3380 | PENDING | PENDING | 1020 |
| Donor_9.3. Aliquot D | 17 | 89 | 71 | 0.51 | 407 | 2.7 | 83 | 52 |
| Donor_9.3. Aliquot E | 11 | 54 | 68 | 0.31 | 780 | 8.1 | 44 | 340 |
| Donor_9.3. Aliquot F | 0.34 | 46 | 83 | 0.30 | 538 | 22 | 55 | 161 |
| Donor_9.3. Aliquot G | 0.25 | 41 | 36 | 0.31 | 369 | 13 | 28 | 38 |
| Donor_9.3. Aliquot H | 0.24 | 56 | 51 | 0.56 | 411 | 22 | 44 | 92 |
| Donor_9.3. Aliquot I | 1.2 | 31 | 56 | 0.22 | 369 | 9.8 | 77 | 96 |
| | | | | | 455 | 8.1 | 83 | 69 |
| EDTA Plasma | | | | | | | | |
| donor #1 plasma | 0.26 | 34 | 39 | 0.30 | 329 | 11 | 228 | 1670 |
| donor #2 plasma | 0.19 | 23 | 24 | 0.13 | 620 | 2.7 | 31 | 628 |
| donor #3 plasma | 1.2 | 49 | 37 | 0.39 | 892 | 2.7 | 34 | 644 |
| donor #4 plasma | 1.2 | 33 | 50 | 0.29 | 794 | 2.7 | 31 | 805 |
| donor #5 plasma | 0.15 | 56 | 37 | 0.64 | 314 | 2.7 | 31 | 188 |
| donor #6 plasma | 1.2 | 34 | 40 | 0.29 | 277 | 11 | 44 | 112 |
| donor #7 plasma | 1.2 | 23 | 39 | 0.29 | 514 | 2.7 | 28 | 404 |
| donor #8 plasma | 1.2 | 39 | 50 | 0.31 | 208 | 2.7 | 31 | 196 |
| donor #9 plasma | 0.14 | 35 | 41 | 0.18 | 327 | 2.7 | 44 | 104 |
| MW | | | | | | | | |
| NHD plasma Normal healthy donors | 0.7 | 37.1 | 45.3 | 0.2 | 267.5 | 2.7 | 37.7 | 150.0 |
| MW | | | | | | | | |
| NHD unstimuliert Normal healthy donors | 1.20 | 31.25 | 68.05 | 0.27 | 488.50 | 5.40 | 55.55 | 132.10 |
| Stimulationsindices | | | | | | | | |

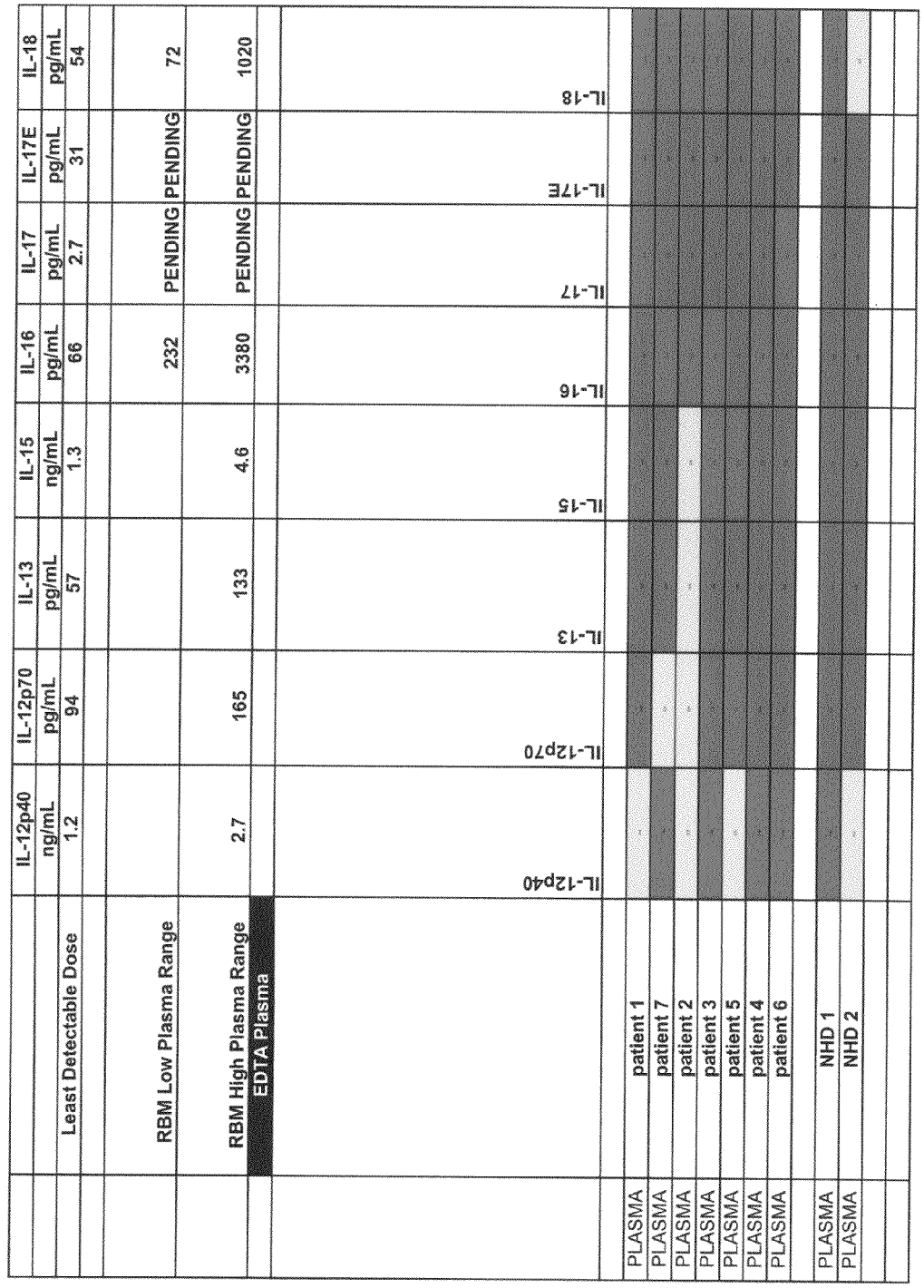
FIG. 17J.5

FIG. 17J.6

| | IL-12p40 ng/mL | IL-12p70 pg/mL | IL-13 pg/mL | IL-15 ng/mL | IL-16 pg/mL | IL-17 pg/mL | IL-17E pg/mL | IL-18 pg/mL |
|---|---|---|---|---|---|---|---|---|
| Least Detectable Dose | 1.2 | 94 | 57 | 1.3 | 66 | 2.7 | 31 | 54 |
| RBM Low Plasma Range | | | | | 232 | PENDING | PENDING | 72 |
| RBM High Plasma Range | 2.7 | 165 | 133 | 4.6 | 3380 | PENDING | PENDING | 1020 |
| Messwert > ULD | | | | | | | | |
| SI > 1,5 | | | | | | | | |
| SI 0,7-1,5 | | | | | | | | |
| SI 0-0,7 | | | | | | | | |
| MW nur von 1 Kontrollperson | | | | | | | | |
| *Stimulationsindices* | | | | | | | | |

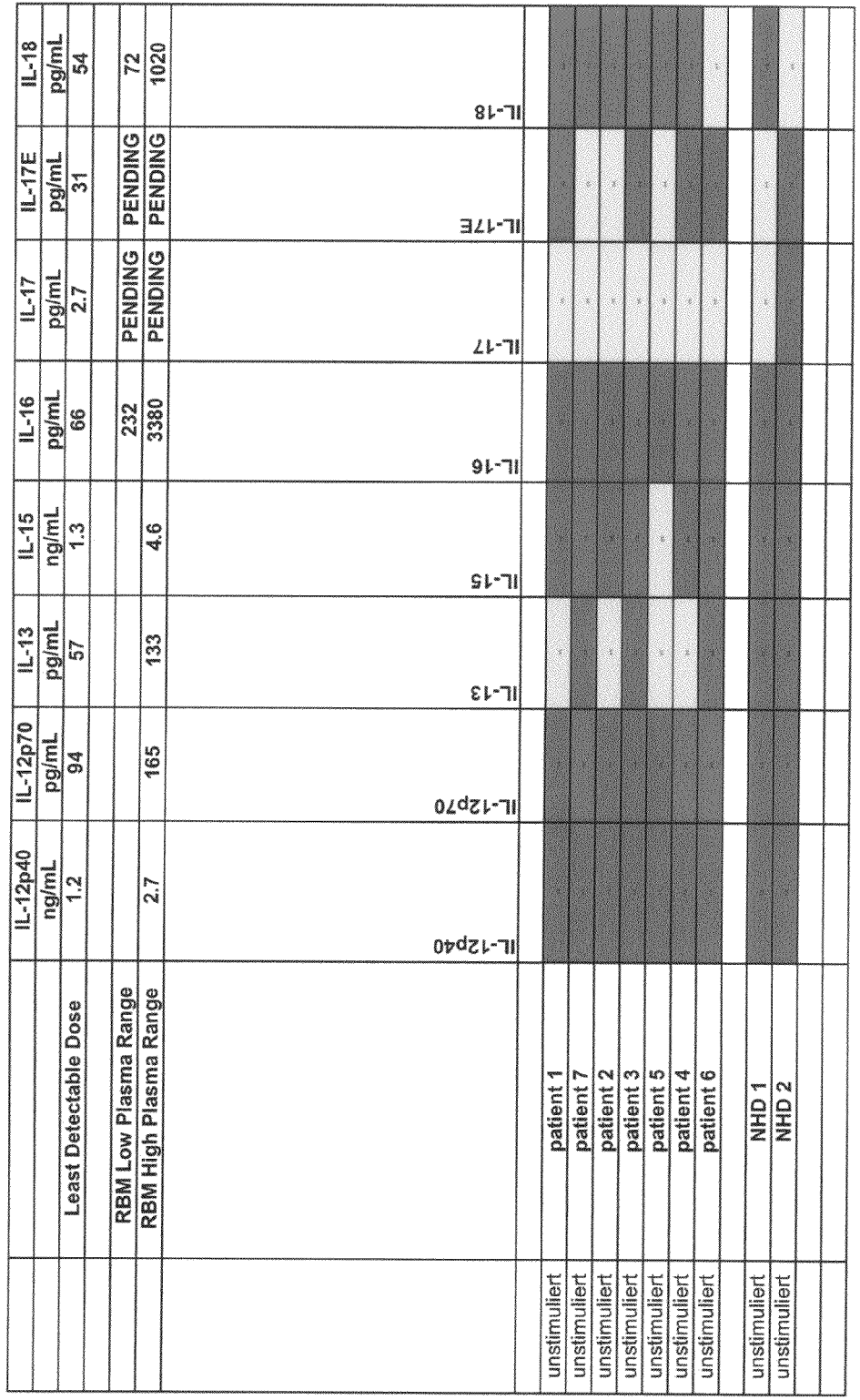
FIG. 17J.7

FIG. 17J.8

| | IL-12p40 ng/mL | IL-12p70 pg/mL | IL-13 pg/mL | IL-15 ng/mL | IL-16 pg/mL | IL-17 pg/mL | IL-17E pg/mL | IL-18 pg/mL |
|---|---|---|---|---|---|---|---|---|
| Least Detectable Dose | 1.2 | 94 | 57 | 1.3 | 66 | 2.7 | 31 | 54 |
| RBM Low Plasma Range | | | | | 232 | PENDING | PENDING | 72 |
| RBM High Plasma Range | 2.7 | 165 | 133 | 4.6 | 3380 | PENDING | PENDING | 1020 |
| NHD = normal healthy donor | | | | | | | | |

FIG. 17K.1

| | IL-1alpha ng/mL | IL-1beta pg/mL | IL-1ra pg/mL | IL-2 pg/mL | IL-23 ng/mL | IL-3 ng/mL | IL-4 pg/mL | IL-5 pg/mL |
|---|---|---|---|---|---|---|---|---|
| Least Detectable Dose | 0.16 | 1.5 | 15 | 60 | <0.67 | 0.17 | 104 | 33 |
| RBM Low Plasma Range | | | 17 | | PENDING | | | |
| RBM High Plasma Range | 0.35 | 8.7 | 622 | 61 | PENDING | 1.2 | 103 | 62 |
| Samples | | | | | | | | |
| Donor_1 3. Aliquot A | 0.0025 | 75 | 3780 | 60 | 3.7 | 0.027 | 50 | 33 |
| Donor_1 3. Aliquot B | 0.16 | 50 | 2300 | 60 | 1.2 | 0.17 | 53 | 33 |
| Donor_1 3. Aliquot C | 0.16 | 4.4 | 987 | 60 | 0.67 | 0.17 | 43 | 33 |
| Donor_1 3. Aliquot D | 0.0077 | 348 | 4230 | 60 | 0.67 | 0.17 | 49 | 33 |
| Donor_1 3. Aliquot E | 0.16 | 69 | 2740 | 60 | 0.67 | 0.17 | 38 | 33 |
| Donor_1 3. Aliquot F | 0.16 | 10 | 1040 | 60 | 1.2 | 0.17 | 42 | 33 |
| Donor_1 3. Aliquot G | 0.16 | 6.8 | 2830 | 60 | 2.1 | 0.17 | 38 | 33 |
| Donor_1 3. Aliquot H | 0.16 | 4.6 | 944 | 60 | 1.9 | 0.17 | 51 | 33 |
| Donor_1 3. Aliquot I | 0.16 | 5.4 | 660 | 60 | 0.67 | 0.17 | 38 | 33 |
| Donor_2 3. Aliquot A | 0.012 | 132 | 16500 | 60 | 1.2 | 0.12 | 69 | 5.9 |
| Donor_2 3. Aliquot B | 0.0057 | 71 | 15500 | 60 | 0.67 | 0.095 | 78 | 8.2 |
| Donor_2 3. Aliquot C | 0.16 | 4.7 | 2000 | 60 | 0.67 | 0.17 | 43 | 33 |
| Donor_2 3. Aliquot D | 0.36 | 5020 | 54600 | 60 | 2.3 | 0.19 | 69 | 7.4 |
| Donor_2 3. Aliquot E | 0.11 | 1310 | 52400 | 60 | 2.5 | 0.21 | 77 | 8.2 |
| Donor_2 3. Aliquot F | 0.0034 | 32 | 3140 | 60 | 0.67 | 0.17 | 40 | 6.7 |
| Donor_2 3. Aliquot G | 0.045 | 387 | 6790 | 60 | 0.67 | 0.14 | 77 | 8.9 |
| Donor_2 3. Aliquot H | 0.16 | 9.7 | 4400 | 60 | 0.67 | 0.17 | 45 | 5.1 |
| Donor_2 3. Aliquot I | 0.16 | 6.6 | 2520 | 60 | 0.67 | 0.17 | 56 | 33 |
| Donor_3 3. Aliquot A | 0.0054 | 62 | 12900 | 60 | 0.67 | 0.12 | 9.4 | 4.3 |
| Donor_3 3. Aliquot B | 0.0056 | 32 | 11000 | 60 | 2.1 | 0.099 | 7.8 | 33 |
| Donor_3 3. Aliquot C | 0.0036 | 5.3 | 2970 | 60 | 2.1 | 0.17 | 104 | 33 |
| Donor_3 3. Aliquot D | 0.074 | 3890 | 41000 | 60 | 0.67 | 0.15 | 20 | 33 |
| Donor_3 3. Aliquot E | 0.039 | 1610 | 32900 | 60 | 3.4 | 0.14 | 8.7 | 4.3 |
| Donor_3 3. Aliquot F | 0.0050 | 18 | 3850 | 60 | 1.2 | 0.050 | 7.8 | 5.9 |

FIG. 17K.2

| | IL-1alpha ng/mL | IL-1beta pg/mL | IL-1ra pg/mL | IL-2 pg/mL | IL-23 ng/mL | IL-3 ng/mL | IL-4 pg/mL | IL-5 pg/mL |
|---|---|---|---|---|---|---|---|---|
| Least Detectable Dose | 0.16 | 1.5 | 15 | 60 | <0.67 | 0.17 | 104 | 33 |
| RBM Low Plasma Range | | | 17 | | PENDING | | | |
| RBM High Plasma Range | 0.35 | 8.7 | 622 | 61 | PENDING | 1.2 | 103 | 62 |
| Donor_3_3. Aliquot G | 0.0045 | 8.6 | 3260 | 60 | 0.67 | 0.17 | 104 | 2.5 |
| Donor_3_3. Aliquot H | 0.0029 | 2.2 | 1010 | 60 | 0.67 | 0.17 | 104 | 33 |
| Donor_3_3. Aliquot I | 0.0043 | 1.5 | 79 | 60 | 2.1 | 0.087 | 104 | 5.1 |
| Donor_4_3. Aliquot A | 0.16 | 7.3 | 2670 | 60 | 0.67 | 0.17 | 33 | 33 |
| Donor_4_3. Aliquot B | 0.16 | 46 | 3450 | 60 | 2.1 | 0.17 | 35 | 33 |
| Donor_4_3. Aliquot C | 0.16 | 3.8 | 336 | 60 | 2.1 | 0.17 | 37 | 33 |
| Donor_4_3. Aliquot D | 0.29 | 2830 | 13700 | 60 | 0.67 | 0.039 | 50 | 33 |
| Donor_4_3. Aliquot E | 0.075 | 957 | 13100 | 60 | 0.67 | 0.087 | 54 | 33 |
| Donor_4_3. Aliquot F | 0.0036 | 47 | 12900 | 60 | 0.67 | 0.17 | 32 | 33 |
| Donor_4_3. Aliquot G | 0.0025 | 7.0 | 2530 | 60 | 2.5 | 0.17 | 49 | 33 |
| Donor_4_3. Aliquot H | 0.16 | 4.1 | 1670 | 60 | 1.6 | 0.17 | 31 | 33 |
| Donor_4_3. Aliquot I | 0.16 | 0.63 | 228 | 60 | 2.1 | 0.17 | 29 | 33 |
| Donor_5_3. Aliquot A | 0.0066 | 73 | 22900 | 60 | 0.67 | 0.099 | 49 | 4.7 |
| Donor_5_3. Aliquot B | 0.0094 | 75 | 22500 | 60 | 0.67 | 0.11 | 51 | 33 |
| Donor_5_3. Aliquot C | 0.16 | 3.0 | 2100 | 60 | 1.4 | 0.17 | 39 | 33 |
| Donor_5_3. Aliquot D | 0.35 | 3910 | 53300 | 60 | 0.67 | 0.19 | 76 | 3.5 |
| Donor_5_3. Aliquot E | 0.32 | 3280 | 51000 | 60 | 0.67 | 0.15 | 57 | 2.5 |
| Donor_5_3. Aliquot F | 0.0043 | 73 | 11100 | 60 | 0.67 | 0.17 | 42 | 33 |
| Donor_5_3. Aliquot G | 0.0048 | 36 | 16700 | 60 | 1.6 | 0.17 | 46 | 33 |
| Donor_5_3. Aliquot H | 0.16 | 15 | 9910 | 60 | 2.5 | 0.17 | 41 | 33 |
| Donor_5_3. Aliquot I | 0.16 | 2.8 | 3530 | 60 | 1.6 | 0.17 | 35 | 33 |
| Donor_6_3. Aliquot A | 0.0052 | 35 | 7350 | 60 | 0.67 | 0.11 | 51 | 5.9 |
| Donor_6_3. Aliquot B | 0.012 | 46 | 9190 | 60 | 0.67 | 0.11 | 55 | 11 |
| Donor_6_3. Aliquot C | 0.0050 | 1.5 | 1220 | 60 | 0.67 | 0.081 | 43 | 4.3 |
| Donor_6_3. Aliquot D | 0.21 | 1870 | 26100 | 60 | 0.67 | 0.13 | 54 | 6.3 |

FIG. 17K.3

| | IL-1alpha ng/mL | IL-1beta pg/mL | IL-1ra pg/mL | IL-2 pg/mL | IL-23 ng/mL | IL-3 ng/mL | IL-4 pg/mL | IL-5 pg/mL |
|---|---|---|---|---|---|---|---|---|
| Least Detectable Dose | 0.16 | 1.5 | 15 | 60 | <0.67 | 0.17 | 104 | 33 |
| RBM Low Plasma Range | | | 17 | | PENDING | | | |
| RBM High Plasma Range | 0.35 | 8.7 | 622 | 61 | PENDING | 1.2 | 103 | 62 |
| Donor_6_3. Aliquot E | 0.41 | 3760 | 31600 | 60 | 1.2 | 0.10 | 60 | 21 |
| Donor_6_3. Aliquot F | 0.0073 | 43 | 4970 | 60 | 0.67 | 0.12 | 44 | 8.9 |
| Donor_6_3. Aliquot G | 0.0043 | 27 | 9870 | 60 | 0.67 | 0.032 | 46 | 33 |
| Donor_6_3. Aliquot H | 0.16 | 2.8 | 1530 | 60 | 3.7 | 0.025 | 39 | 33 |
| Donor_6_3. Aliquot I | 0.16 | 1.3 | 202 | 60 | 0.67 | 0.17 | 29 | 3.5 |
| Donor_7_3. Aliquot A | 0.025 | 147 | 6320 | 60 | 0.67 | 0.27 | 33 | 11 |
| Donor_7_3. Aliquot B | 0.015 | 99 | 4590 | 60 | 0.67 | 0.21 | 27 | 20 |
| Donor_7_3. Aliquot C | 0.010 | 16 | 244 | 60 | 0.67 | 0.037 | 9.4 | 8.9 |
| Donor_7_3. Aliquot D | 0.31 | 2120 | 11000 | 60 | 0.67 | 0.15 | 29 | 5.9 |
| Donor_7_3. Aliquot E | 0.071 | 548 | 7580 | 60 | 0.67 | 0.16 | 37 | 12 |
| Donor_7_3. Aliquot F | 0.016 | 20 | 578 | 60 | 0.67 | 0.12 | 23 | 13 |
| Donor_7_3. Aliquot G | 0.0054 | 6.2 | 2730 | 60 | 0.67 | 0.17 | 18 | 33 |
| Donor_7_3. Aliquot H | 0.0057 | 3.4 | 361 | 60 | 0.67 | 0.17 | 104 | 33 |
| Donor_7_3. Aliquot I | 0.0066 | 1.5 | 61 | 60 | 1.2 | 0.044 | 104 | 4.3 |
| Donor_8_3. Aliquot A | 0.0073 | 73 | 3870 | 60 | 1.6 | 0.083 | 43 | 8.2 |
| Donor_8_3. Aliquot B | 0.0089 | 59 | 3010 | 60 | 0.67 | 0.12 | 49 | 12 |
| Donor_8_3. Aliquot C | 0.0071 | 76 | 10200 | 60 | 0.67 | 0.12 | 45 | 2.5 |
| Donor_8_3. Aliquot D | 0.28 | 24700 | 11400 | 60 | 3.0 | 0.18 | 60 | 5.9 |
| Donor_8_3. Aliquot E | 0.27 | 17500 | 12800 | 60 | 1.6 | 0.11 | 48 | 14 |
| Donor_8_3. Aliquot F | 0.013 | 204 | 16400 | 60 | 3.0 | 0.25 | 48 | 14 |
| Donor_8_3. Aliquot G | 0.16 | 32 | 4000 | 60 | 1.6 | 0.025 | 43 | 33 |
| Donor_8_3. Aliquot H | 0.0041 | 75 | 7720 | 60 | 0.67 | 0.081 | 40 | 5.1 |
| Donor_8_3. Aliquot I | 0.0061 | 7.9 | 839 | 60 | 1.2 | 0.12 | 44 | 2.5 |
| Donor_9_3. Aliquot A | 0.0080 | 29 | 3980 | 60 | 5.8 | 0.14 | 59 | 2.6 |
| Donor_9_3. Aliquot B | 0.013 | 42 | 4200 | 60 | 1.1 | 0.21 | 54 | 7.8 |

FIG. 17K.4

| | IL-1alpha ng/mL | IL-1beta pg/mL | IL-1ra pg/mL | IL-2 pg/mL | IL-23 ng/mL | IL-3 ng/mL | IL-4 pg/mL | IL-5 pg/mL |
|---|---|---|---|---|---|---|---|---|
| Least Detectable Dose | 0.16 | 1.5 | 15 | 60 | <0.67 | 0.17 | 104 | 33 |
| RBM Low Plasma Range | | | 17 | | PENDING | | | |
| RBM High Plasma Range | 0.35 | 8.7 | 622 | 61 | PENDING | 1.2 | 103 | 62 |
| Donor_9 3. Aliquot C | 0.018 | 67 | 9410 | 60 | 0.67 | 0.20 | 59 | 5.3 |
| Donor_9 3. Aliquot D | 2.6 | 26100 | 18300 | 60 | 2.4 | 0.21 | 70 | 8.6 |
| Donor_9 3. Aliquot E | 0.80 | 7830 | 15100 | 60 | 0.67 | 0.17 | 67 | 5.3 |
| Donor_9 3. Aliquot F | 0.011 | 60 | 12700 | 60 | 0.67 | 0.18 | 51 | 8.6 |
| Donor_9 3. Aliquot G | 0.0075 | 48 | 8240 | 60 | 0.67 | 0.11 | 75 | 33 |
| Donor_9 3. Aliquot H | 0.0086 | 39 | 4920 | 60 | 0.67 | 0.098 | 55 | 33 |
| Donor_9 3. Aliquot I | 0.0035 | 5.7 | 2110 | 60 | 1.7 | 0.10 | 43 | 33 |
| EDTA Plasma | | | | | | | | |
| donor #1 plasma | 0.16 | 2.8 | 1800 | 60 | 3.4 | 0.17 | 104 | 33 |
| donor #2 plasma | 0.16 | 1.5 | 555 | 60 | 1.1 | 0.17 | 104 | 8.2 |
| donor #3 plasma | 0.0027 | 1.1 | 137 | 60 | 2.7 | 0.17 | 104 | 12 |
| donor #4 plasma | 0.16 | 1.5 | 410 | 60 | 2.4 | 0.17 | 104 | 4.0 |
| donor #5 plasma | 0.16 | 1.5 | 354 | 60 | 1.7 | 0.17 | 104 | 7.0 |
| donor #6 plasma | 0.16 | 1.5 | 84 | 60 | 1.9 | 0.17 | 104 | 7.0 |
| donor #7 plasma | 0.16 | 1.5 | 559 | 60 | 0.67 | 0.17 | 104 | 7.4 |
| donor #8 plasma | 0.0035 | 1.4 | 68 | 60 | 0.67 | 0.14 | 44 | 6.1 |
| donor #9 plasma | 0.0032 | 1.5 | 80 | 60 | 1.7 | 0.042 | 42 | 7.0 |
| MW NHD plasma | 0.0 | 1.5 | 73.7 | 60.0 | 1.2 | 0.1 | 43.0 | 6.5 |
| Normal healthy donors | | | | | | | | |
| MW NHD unstimuliert | 0.00 | 6.81 | 1474.50 | 60.00 | 1.42 | 0.11 | 43.35 | 17.77 |
| Normal healthy donors | | | | | | | | |
| Stimulationsindices | | | | | | | | |

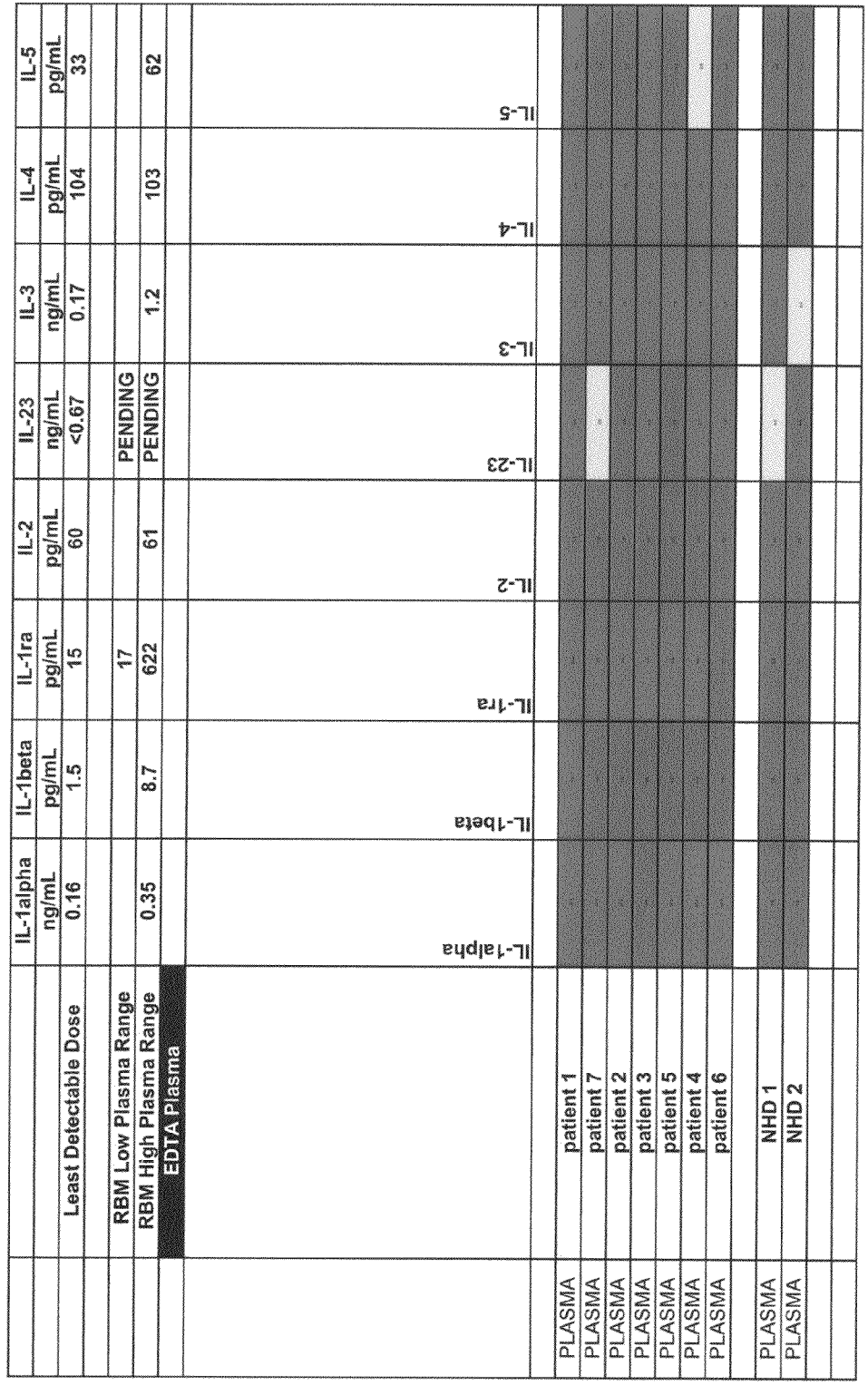
FIG. 17K.5

FIG. 17K.6

| | IL-1alpha ng/mL | IL-1beta pg/mL | IL-1ra pg/mL | IL-2 pg/mL | IL-23 ng/mL | IL-3 ng/mL | IL-4 pg/mL | IL-5 pg/mL |
|---|---|---|---|---|---|---|---|---|
| Least Detectable Dose | 0.16 | 1.5 | 15 | 60 | <0.67 | 0.17 | 104 | 33 |
| RBM Low Plasma Range | | | 17 | | PENDING | | | |
| RBM High Plasma Range | 0.35 | 8.7 | 622 | 61 | PENDING | 1.2 | 103 | 62 |
| Messwert > ULD | | | | | | | | |
| SI > 1,5 | | | | | | | | |
| SI 0,7-1,5 | | | | | | | | |
| SI 0-0,7 | | | | | | | | |
| MW nur von 1 Kontrollperson | | | | | | | | |
| Stimulationsindices | | | | | | | | |

FIG. 17K.7
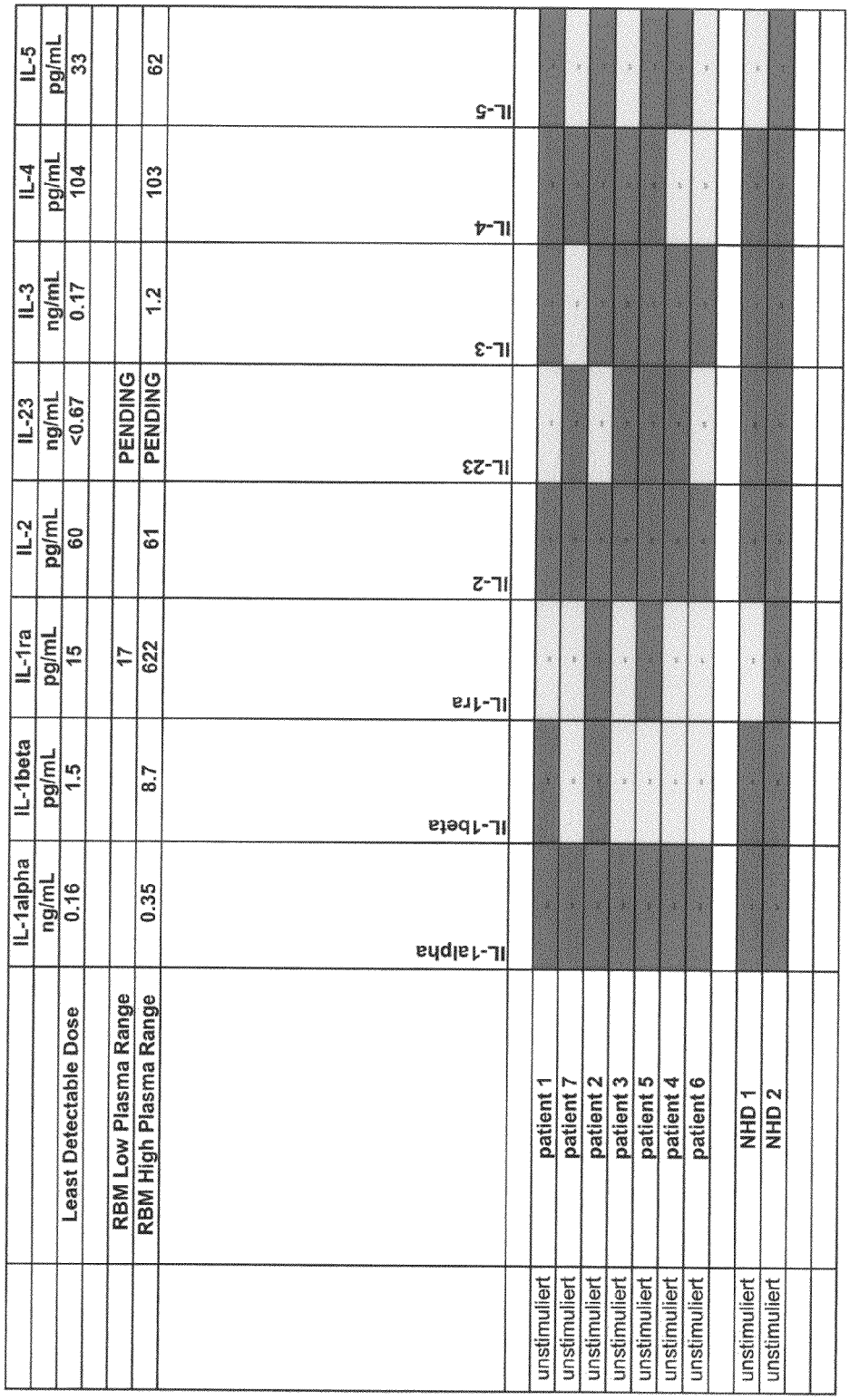

FIG. 17K.8

| | IL-1alpha ng/mL | IL-1beta pg/mL | IL-1ra pg/mL | IL-2 pg/mL | IL-23 ng/mL | IL-3 ng/mL | IL-4 pg/mL | IL-5 pg/mL |
|---|---|---|---|---|---|---|---|---|
| Least Detectable Dose | 0.16 | 1.5 | 15 | 60 | <0.67 | 0.17 | 104 | 33 |
| RBM Low Plasma Range | | | 17 | | PENDING | | | |
| RBM High Plasma Range | 0.35 | 8.7 | 622 | 61 | PENDING | 1.2 | 103 | 62 |
| NHD = normal healthy donor | | | | | | | | |

FIG. 17L.1

| | IL-6 pg/mL | IL-7 pg/mL | IL-8 pg/mL | Insulin uIU/mL | Leptin ng/mL | Lipo protein (a) ug/mL | Lymphotactin ng/mL | MCP-1 pg/mL |
|---|---|---|---|---|---|---|---|---|
| Least Detectable Dose | 12 | 53 | 3.5 | 0.86 | 0.10 | 3.7 | 0.38 | 52 |
| RBM Low Plasma Range | | 3.7 | | | 0.41 | 3.0 | | 35 |
| RBM High Plasma Range | 25 | 125 | 59 | 34 | 41 | 858 | 0.57 | 401 |
| Samples | | | | | | | | |
| Donor_1_3. Aliquot A | 4690 | 169 | 23600 | 11 | 132 | 27 | 0.22 | 8710 |
| Donor_1_3. Aliquot B | 1860 | 113 | 4450 | 9.8 | 115 | 34 | 0.38 | 4230 |
| Donor_1_3. Aliquot C | 49 | 33 | 321 | 6.3 | 124 | 31 | 0.38 | 1210 |
| Donor_1_3. Aliquot D | 7970 | 113 | 6730 | 11 | 121 | 32 | 0.071 | 3940 |
| Donor_1_3. Aliquot E | 1700 | 131 | 6170 | 11 | 124 | 32 | 0.092 | 4040 |
| Donor_1_3. Aliquot F | 77 | 57 | 1330 | 8.3 | 107 | 45 | 0.38 | 2120 |
| Donor_1_3. Aliquot G | 57 | 100 | 5060 | 8.0 | 112 | 37 | 0.38 | 8970 |
| Donor_1_3. Aliquot H | 54 | 33 | 672 | 9.4 | 119 | 32 | 0.38 | 1080 |
| Donor_1_3. Aliquot I | 50 | 68 | 1480 | 9.9 | 119 | 30 | 0.38 | 1030 |
| Donor_2_3. Aliquot A | 11100 | 215 | 100000 | 5.7 | 7.7 | 38 | 0.26 | 9540 |
| Donor_2_3. Aliquot B | 6720 | 189 | 74900 | 6.1 | 8.4 | 46 | 0.22 | 3930 |
| Donor_2_3. Aliquot C | 110 | 48 | 2290 | 2.3 | 9.0 | 47 | 0.38 | 499 |
| Donor_2_3. Aliquot D | 78400 | 201 | 146000 | 6.6 | 8.1 | 48 | 0.28 | 3760 |
| Donor_2_3. Aliquot E | 63400 | 226 | 165000 | 6.4 | 8.3 | 58 | 0.25 | 4260 |
| Donor_2_3. Aliquot F | 180 | 59 | 2230 | 4.7 | 7.7 | 128 | 0.38 | 810 |
| Donor_2_3. Aliquot G | 30900 | 223 | >344062 | 6.0 | 4.4 | 46 | 0.28 | 42600 |
| Donor_2_3. Aliquot H | 187 | 74 | 3460 | 5.6 | 7.8 | 47 | 0.38 | 917 |
| Donor_2_3. Aliquot I | 153 | 48 | 3230 | 4.7 | 7.9 | 48 | 0.38 | 555 |
| Donor_3_3. Aliquot A | 6380 | 192 | 40600 | 19 | 8.1 | 61 | 0.33 | 11000 |
| Donor_3_3. Aliquot B | 3880 | 201 | 32400 | 17 | 7.7 | 66 | 0.23 | 3820 |
| Donor_3_3. Aliquot C | 90 | 66 | 1860 | 9.0 | 8.4 | 68 | 0.15 | 228 |
| Donor_3_3. Aliquot D | 105000 | 243 | 124000 | 15 | 7.8 | 58 | 0.32 | 2630 |
| Donor_3_3. Aliquot E | 59800 | 234 | 146000 | 17 | 8.3 | 70 | 0.39 | 2870 |
| Donor_3_3. Aliquot F | 169 | 82 | 2870 | 13 | 7.2 | 83 | 0.39 | 246 |

FIG. 17L.2

| | IL-6 pg/mL | IL-7 pg/mL | IL-8 pg/mL | Insulin uIU/mL | Leptin ng/mL | Lipo protein (a) ug/mL | Lymphotactin ng/mL | MCP-1 pg/mL |
|---|---|---|---|---|---|---|---|---|
| Least Detectable Dose | 12 | 53 | 3.5 | 0.86 | 0.10 | 3.7 | 0.38 | 52 |
| RBM Low Plasma Range | | | | | | | | 35 |
| RBM High Plasma Range | 25 | 3.7 | 59 | 34 | 0.41 | 3.0 | 0.57 | 401 |
| Donor_3_3_Aliquot G | 63 | 125 | 24200 | 20 | 41 | 858 | 0.21 | 521 |
| Donor_3_3_Aliquot H | 26 | 78 | 924 | 15 | 5.9 | 57 | 0.38 | 126 |
| Donor_3_3_Aliquot I | 9.2 | 38 | 1080 | 15 | 6.9 | 61 | 0.54 | 110 |
| | | 86 | | | 7.8 | 66 | | |
| Donor_4_3_Aliquot A | 177 | 82 | 3240 | 12 | 11 | 23 | 0.38 | 2430 |
| Donor_4_3_Aliquot B | 405 | 106 | 4210 | 12 | 12 | 21 | 0.38 | 2960 |
| Donor_4_3_Aliquot C | 70 | 38 | 751 | 3.8 | 10 | 21 | 0.38 | 578 |
| Donor_4_3_Aliquot D | 46300 | 215 | 76000 | 13 | 9.7 | 24 | 0.16 | 14900 |
| Donor_4_3_Aliquot E | 24300 | 214 | 70800 | 12 | 8.0 | 22 | 0.20 | 15800 |
| Donor_4_3_Aliquot F | 5050 | 98 | 4030 | 12 | 8.4 | 24 | 0.12 | 15400 |
| Donor_4_3_Aliquot G | 59 | 74 | 23400 | 14 | 7.3 | 22 | 0.38 | 6110 |
| Donor_4_3_Aliquot H | 62 | 66 | 731 | 15 | 11 | 21 | 0.38 | 641 |
| Donor_4_3_Aliquot I | 52 | 38 | 550 | 11 | 10 | 25 | 0.38 | 269 |
| Donor_5_3_Aliquot A | 2370 | 203 | 146000 | 5.2 | 2.0 | 22 | 0.31 | 11900 |
| Donor_5_3_Aliquot B | 4460 | 217 | 198000 | 5.4 | 1.7 | 20 | 0.33 | 7660 |
| Donor_5_3_Aliquot C | 46 | 52 | 1740 | 2.0 | 2.0 | 21 | 0.15 | 226 |
| Donor_5_3_Aliquot D | 60400 | 247 | 211000 | 6.5 | 1.8 | 19 | 0.36 | 3740 |
| Donor_5_3_Aliquot E | 71300 | 200 | >344062 | 8.0 | 1.9 | 21 | 0.33 | 5360 |
| Donor_5_3_Aliquot F | 316 | 115 | 20400 | 3.6 | 1.3 | 39 | 0.071 | 2920 |
| Donor_5_3_Aliquot G | 70 | 145 | 85000 | 3.8 | 2.0 | 18 | 0.22 | 14900 |
| Donor_5_3_Aliquot H | 55 | 84 | 20000 | 4.9 | 1.9 | 17 | 0.38 | 523 |
| Donor_5_3_Aliquot I | 43 | 94 | 2590 | 4.3 | 1.7 | 18 | 0.38 | 231 |
| Donor_6_3_Aliquot A | 1500 | 182 | 17400 | 1.3 | 0.12 | 36 | 0.72 | 3750 |
| Donor_6_3_Aliquot B | 3190 | 189 | 33200 | 1.4 | 0.10 | 40 | 0.72 | 2190 |
| Donor_6_3_Aliquot C | 85 | 90 | 271 | 0.98 | 0.11 | 39 | 0.62 | 218 |
| Donor_6_3_Aliquot D | 50700 | 215 | 67300 | 1.8 | 0.25 | 43 | 0.80 | 1360 |

FIG. 17L.3

| | IL-6 pg/mL | IL-7 pg/mL | IL-8 pg/mL | Insulin uIU/mL | Leptin ng/mL | Lipo protein (a) ug/mL | Lymphotactiin ng/mL | MCP-1 pg/mL |
|---|---|---|---|---|---|---|---|---|
| Least Detectable Dose | 12 | 53 | 3.5 | 0.86 | 0.10 | 3.7 | 0.38 | 52 |
| RBM Low Plasma Range | | 3.7 | | | 0.41 | 3.0 | | 35 |
| RBM High Plasma Range | 25 | 125 | 59 | 34 | 41 | 858 | 0.57 | 401 |
| Donor_6_3. Aliquot E | 71700 | 229 | 116000 | 1.2 | 0.26 | 35 | 0.69 | 990 |
| Donor_6_3. Aliquot F | 517 | 124 | 3980 | 1.5 | 0.1 | 79 | 0.79 | 2110 |
| Donor_6_3. Aliquot G | 74 | 128 | 26500 | 1.2 | 0.27 | 31 | 0.50 | 3670 |
| Donor_6_3. Aliquot H | 84 | 94 | 692 | 1.3 | 0.13 | 32 | 0.50 | 240 |
| Donor_6_3. Aliquot I | 65 | 68 | 243 | 1.1 | 0.10 | 25 | 0.52 | 146 |
| Donor_7_3. Aliquot A | 19900 | 273 | 89600 | 8.4 | 11 | 203 | 0.96 | 14700 |
| Donor_7_3. Aliquot B | 5190 | 243 | 33900 | 7.8 | 11 | 222 | 0.78 | 5090 |
| Donor_7_3. Aliquot C | 26 | 80 | 500 | 4.1 | 12 | 160 | 0.53 | 314 |
| Donor_7_3. Aliquot D | 54800 | 211 | 80600 | 6.5 | 11 | 192 | 0.75 | 5040 |
| Donor_7_3. Aliquot E | 21600 | 247 | 41300 | 7.5 | 11 | 215 | 0.83 | 8810 |
| Donor_7_3. Aliquot F | 242 | 138 | 812 | 6.2 | 11 | 548 | 0.88 | 1260 |
| Donor_7_3. Aliquot G | 48 | 109 | 7810 | 6.6 | 6.9 | 148 | 0.24 | 3610 |
| Donor_7_3. Aliquot H | 34 | 45 | 373 | 6.4 | 12 | 155 | 0.33 | 309 |
| Donor_7_3. Aliquot I | 16 | 80 | 225 | 6.1 | 12 | 190 | 0.53 | 265 |
| Donor_8_3. Aliquot A | 1400 | 166 | 4320 | 1.9 | 0.50 | 16 | 0.93 | 4750 |
| Donor_8_3. Aliquot B | 1140 | 184 | 4770 | 2.4 | 0.49 | 16 | 0.96 | 3720 |
| Donor_8_3. Aliquot C | 840 | 120 | 846 | 0.73 | 0.38 | 16 | 0.91 | 5420 |
| Donor_8_3. Aliquot D | 99400 | 205 | 66900 | 2.2 | 0.62 | 13 | 1.1 | 2170 |
| Donor_8_3. Aliquot E | 83900 | 217 | 58300 | 2.4 | 0.64 | 18 | 1.2 | 4380 |
| Donor_8_3. Aliquot F | 6720 | 185 | 952 | 3.3 | 0.49 | 18 | 1.2 | 12700 |
| Donor_8_3. Aliquot G | 42 | 86 | 2470 | 0.91 | 0.36 | 12 | 0.47 | 1940 |
| Donor_8_3. Aliquot H | 129 | 169 | 5280 | 1.7 | 0.53 | 13 | 0.80 | 7890 |
| Donor_8_3. Aliquot I | 12 | 117 | 895 | 1.7 | 0.37 | 14 | 0.80 | 385 |
| Donor_9_3. Aliquot A | 642 | 143 | 3910 | 6.2 | 2.0 | 18 | 0.68 | 5430 |
| Donor_9_3. Aliquot B | 1100 | 156 | 4840 | 5.9 | 2.0 | 12 | 0.73 | 3060 |

FIG. 17L.4

| | IL-6 pg/mL | IL-7 pg/mL | IL-8 pg/mL | Insulin uIU/mL | Leptin ng/mL | Lipo protein (a) ug/mL | Lymphotactin ng/mL | MCP-1 pg/mL |
|---|---|---|---|---|---|---|---|---|
| Least Detectable Dose | 12 | 53 | 3.5 | 0.86 | 0.10 | 3.7 | 0.38 | 52 |
| RBM Low Plasma Range | | | | | 0.41 | 3.0 | | 35 |
| RBM High Plasma Range | 25 | 3.7 | 59 | 34 | 41 | 858 | 0.57 | 401 |
| Donor_9_3. Aliquot C | 1680 | 125 | 3560 | 3.1 | 1.6 | 13 | 0.69 | 16600 |
| Donor_9_3. Aliquot D | 93100 | 167 | 48600 | 6.5 | 2.0 | 17 | 0.62 | 6120 |
| Donor_9_3. Aliquot E | 61700 | 209 | 62300 | 6.3 | 1.8 | 16 | 0.71 | 9540 |
| Donor_9_3. Aliquot F | 1900 | 192 | 1200 | 6.6 | 1.9 | 18 | 0.86 | 12800 |
| Donor_9_3. Aliquot G | 131 | 159 | 21300 | 5.7 | 1.3 | 11 | 0.20 | 15500 |
| Donor_9_3. Aliquot H | 57 | 126 | 1590 | 7.1 | 1.9 | 11 | 0.38 | 2420 |
| Donor_9_3. Aliquot I | 19 | 141 | 797 | 5.3 | 1.9 | 14 | 0.53 | 346 |
| | | 62 | | | | | | |
| EDTA Plasma | | | | | | | | |
| donor #1 plasma | 30 | 87 | 239 | 6.9 | 89 | 46 | 0.38 | 230 |
| donor #2 plasma | 102 | 42 | 319 | 5.8 | 9.7 | 109 | 0.38 | 66 |
| donor #3 plasma | 8.5 | 130 | 18 | 21 | 9.4 | 143 | 0.12 | 11 |
| donor #4 plasma | 49 | 52 | 102 | 16 | 15 | 31 | 0.38 | 23 |
| donor #5 plasma | 27 | 101 | 32 | 5.5 | 1.9 | 31 | 0.12 | 17 |
| donor #6 plasma | 54 | 103 | 24 | 0.57 | 0.046 | 91 | 0.28 | 32 |
| donor #7 plasma | 15 | 106 | 43 | 11 | 21 | 735 | 0.42 | 109 |
| donor #8 plasma | 1.8 | 83 | 3.5 | 1.0 | 0.64 | 17 | 0.31 | 147 |
| donor #9 plasma | 12 | 77 | 3.5 | 9.9 | 2.4 | 23 | 0.33 | 89 |
| MW NHD plasma | 6.9 | 79.7 | 3.5 | 5.4 | 1.5 | 20.0 | 0.3 | 118.2 |
| Normal healthy donors | | | | | | | | |
| MW NHD unstimuliert | 15.40 | 89.70 | 846.00 | 3.47 | 1.15 | 13.85 | 0.67 | 365.50 |
| Normal healthy donors | | | | | | | | |
| *Stimulationsindices* | | | | | | | | |

FIG. 17L.5
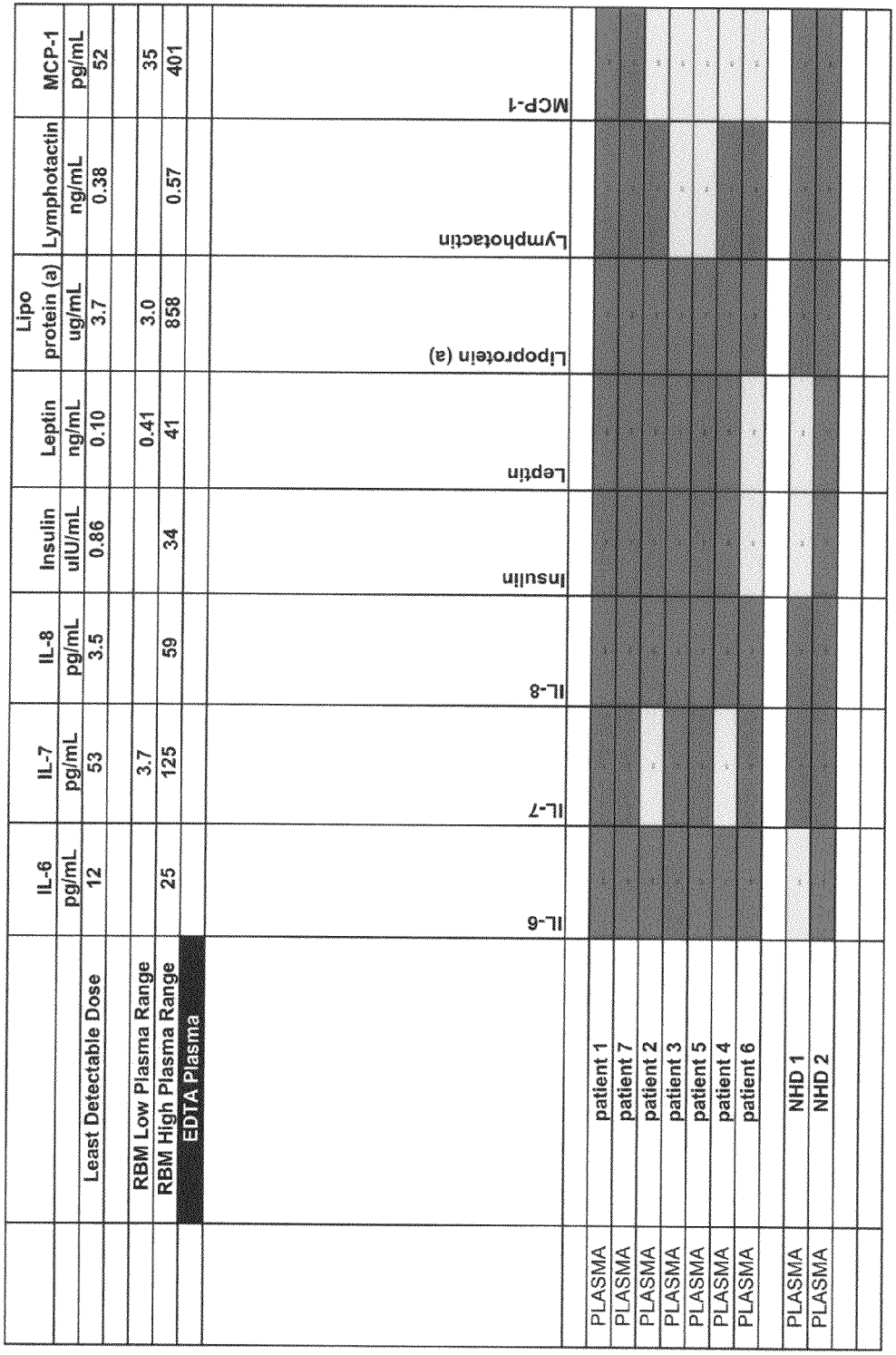

FIG. 17L.6

| | IL-6 pg/mL | IL-7 pg/mL | IL-8 pg/mL | Insulin uIU/mL | Leptin ng/mL | Lipo protein (a) ug/mL | Lymphotactin ng/mL | MCP-1 pg/mL |
|---|---|---|---|---|---|---|---|---|
| Least Detectable Dose | 12 | 53 | 3.5 | 0.86 | 0.10 | 3.7 | 0.38 | 52 |
| RBM Low Plasma Range | | 3.7 | | | 0.41 | 3.0 | | 35 |
| RBM High Plasma Range | 25 | 125 | 59 | 34 | 41 | 858 | 0.57 | 401 |
| Messwert > ULD | | | | | | | | |
| SI > 1,5 | | | | | | | | |
| SI 0,7-1,5 | | | | | | | | |
| SI 0-0,7 | | | | | | | | |
| MW nur von 1 Kontrollperson | | | | | | | | |
| *Stimulationsindices* | | | | | | | | |

FIG. 17L.7
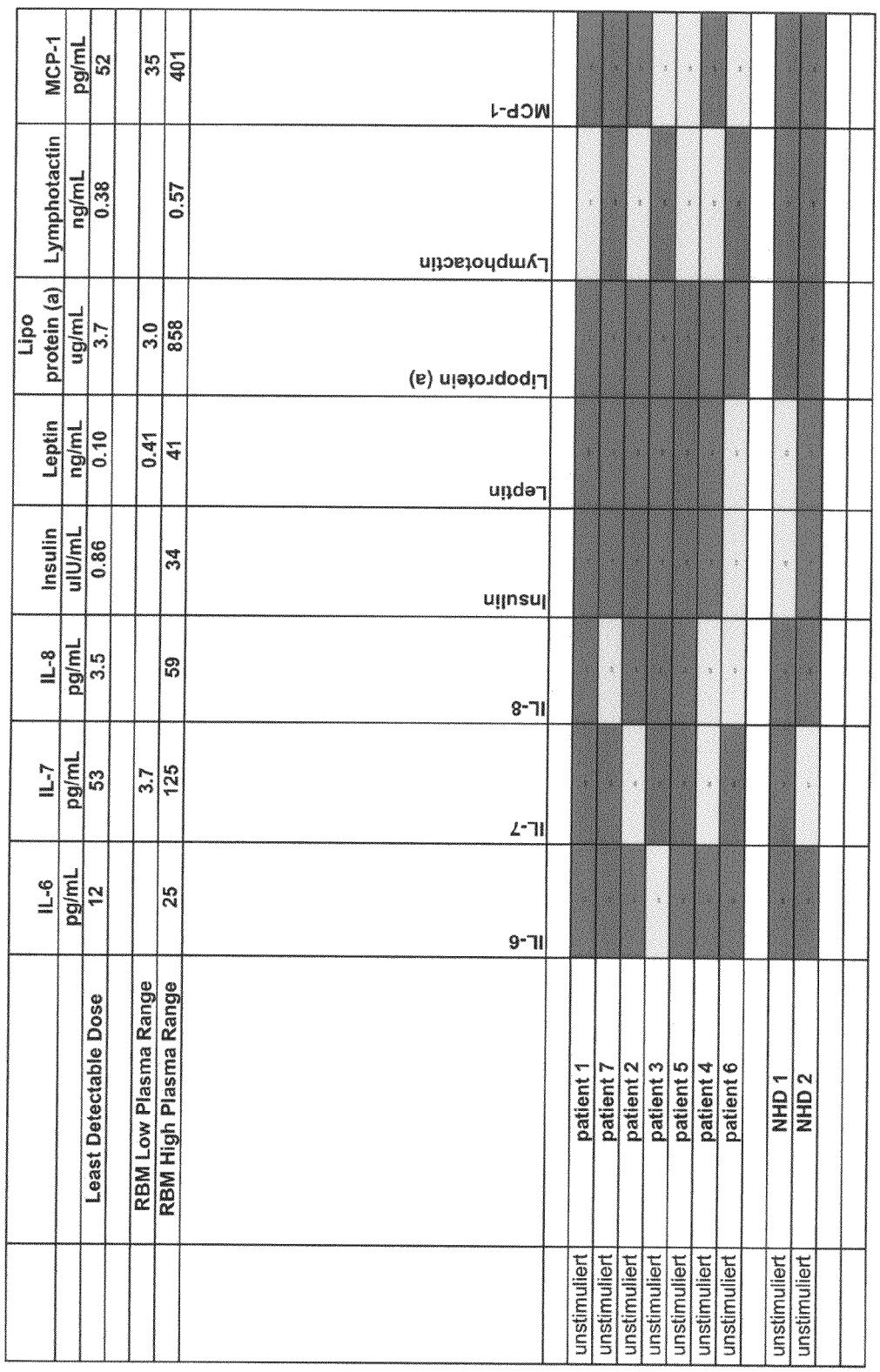

FIG. 17L.8

| | IL-6 pg/mL | IL-7 pg/mL | IL-8 pg/mL | Insulin uIU/mL | Leptin ng/mL | Lipo protein (a) ug/mL | Lymphotactin ng/mL | MCP-1 pg/mL |
|---|---|---|---|---|---|---|---|---|
| Least Detectable Dose | 12 | 53 | 3.5 | 0.86 | 0.10 | 3.7 | 0.38 | 52 |
| RBM Low Plasma Range | | 3.7 | | | 0.41 | 3.0 | | 35 |
| RBM High Plasma Range | 25 | 125 | 59 | 34 | 41 | 858 | 0.57 | 401 |
| NHD = normal healthy donor | | | | | | | | |

FIG. 17M.1

| | MDC pg/mL | MIP-1 alpha pg/mL | MIP-1beta pg/mL | MMP-2 ng/mL | MMP-3 ng/mL | MMP-9 ng/mL | Myelo-peroxidase ng/mL | Myoglobin ng/mL |
|---|---|---|---|---|---|---|---|---|
| Least Detectable Dose | 14 | 13 | 38 | 150 | 0.20 | 37 | 68 | 1.1 |
| RBM Low Plasma Range | 162 | | 25 | 183 | | | | 3.6 |
| RBM High Plasma Range | 774 | 89 | 595 | 3070 | 1.8 | 1050 | 1110 | 37 |
| Samples | | | | | | | | |
| Donor_1 3. Aliquot A | 197 | 3570 | 71300 | 474 | 12 | 74 | 2010 | 85 |
| Donor_1 3. Aliquot B | 187 | 1810 | 12800 | 440 | 11 | 53 | 1590 | 94 |
| Donor_1 3. Aliquot C | 180 | 94 | 610 | 71 | 12 | 30 | 1390 | 101 |
| Donor_1 3. Aliquot D | 203 | 3760 | 75700 | 443 | 13 | 56 | 2050 | 102 |
| Donor_1 3. Aliquot E | 185 | 1370 | 16800 | 456 | 12 | 57 | 2330 | 90 |
| Donor_1 3. Aliquot F | 146 | 197 | 2040 | 410 | 11 | 33 | 1970 | 95 |
| Donor_1 3. Aliquot G | 14 | 110 | 498 | 451 | 13 | 49 | 1750 | 104 |
| Donor_1 3. Aliquot H | 41 | 81 | 513 | 68 | 12 | 46 | 1740 | 95 |
| Donor_1 3. Aliquot I | 193 | 180 | 803 | 427 | 11 | 38 | 1380 | 89 |
| Donor_2 3. Aliquot A | 158 | 5430 | 94800 | 105 | 11 | 59 | 3520 | 60 |
| Donor_2 3. Aliquot B | 178 | 2250 | 52800 | 83 | 11 | 59 | 2910 | 62 |
| Donor_2 3. Aliquot C | 160 | 91 | 1790 | 86 | 12 | 42 | 1540 | 61 |
| Donor_2 3. Aliquot D | 165 | 34700 | 460000 | 100 | 13 | 60 | 4180 | 58 |
| Donor_2 3. Aliquot E | 154 | 23000 | 331000 | 123 | 11 | 53 | 3380 | 60 |
| Donor_2 3. Aliquot F | 141 | 191 | 4280 | 69 | 11 | 2.2 | 1610 | 63 |
| Donor_2 3. Aliquot G | 14 | 29600 | 95800 | 147 | 11 | 28 | 3280 | 64 |
| Donor_2 3. Aliquot H | 33 | 360 | 7090 | 86 | 11 | 55 | 4200 | 59 |
| Donor_2 3. Aliquot I | 156 | 179 | 5430 | 72 | 9.7 | 51 | 1730 | 57 |
| Donor_3 3. Aliquot A | 92 | 894 | 31700 | 30 | 5.4 | 72 | 2890 | 165 |
| Donor_3 3. Aliquot B | 86 | 387 | 17200 | 26 | 4.8 | 59 | 2640 | 150 |
| Donor_3 3. Aliquot C | 87 | 46 | 1850 | 34 | 5.0 | 55 | 2210 | 164 |
| Donor_3 3. Aliquot D | 84 | 8550 | 254000 | 47 | 4.9 | 91 | 3310 | 159 |
| Donor_3 3. Aliquot E | 72 | 3710 | 126000 | 34 | 5.3 | 74 | 3500 | 172 |
| Donor_3 3. Aliquot F | 70 | 66 | 2900 | 34 | 4.4 | 54 | 2630 | 152 |

FIG. 17M.2

| | MDC pg/mL | MIP-1 alpha pg/mL | MIP-1beta pg/mL | MMP-2 ng/mL | MMP-3 ng/mL | MMP-9 ng/mL | Myelo-peroxidase ng/mL | Myoglobin ng/mL |
|---|---|---|---|---|---|---|---|---|
| Least Detectable Dose | 14 | 13 | 38 | 150 | 0.20 | 37 | 68 | 1.1 |
| RBM Low Plasma Range | 162 | | | | | | | 3.6 |
| RBM High Plasma Range | 774 | 89 | 25 | 183 | 1.8 | 1050 | 1110 | 37 |
| Donor_3_3. Aliquot G | 14 | 60 | 595 | 3070 | 4.3 | 45 | 2240 | 162 |
| Donor_3_3. Aliquot H | 12 | 42 | 1680 | 67 | 3.9 | 49 | 2830 | 143 |
| Donor_3_3. Aliquot I | 85 | 46 | 633 | 23 | 4.7 | 42 | 2450 | 150 |
| | | | 123 | 150 | | | | |
| Donor_4_3. Aliquot A | 324 | 432 | 13100 | 150 | 7.5 | 26 | 2710 | 55 |
| Donor_4_3. Aliquot B | 346 | 288 | 9460 | 150 | 7.5 | 26 | 1940 | 52 |
| Donor_4_3. Aliquot C | 280 | 137 | 994 | 150 | 6.8 | 4.9 | 3400 | 54 |
| Donor_4_3. Aliquot D | 335 | 31200 | 484000 | 43 | 7.4 | 27 | 3920 | 52 |
| Donor_4_3. Aliquot E | 259 | 17700 | 293000 | 50 | 6.6 | 49 | 4430 | 53 |
| Donor_4_3. Aliquot F | 251 | 1740 | 84100 | 150 | 6.6 | 14 | 4210 | 56 |
| Donor_4_3. Aliquot G | 14 | 547 | 3900 | 45 | 5.6 | 16 | 1950 | 56 |
| Donor_4_3. Aliquot H | 66 | 106 | 3160 | 15 | 7.2 | 26 | 4140 | 55 |
| Donor_4_3. Aliquot I | 298 | 63 | 287 | 150 | 6.8 | 9.3 | 3360 | 55 |
| Donor_5_3. Aliquot A | 298 | 6820 | 150000 | 106 | 21 | 46 | 6630 | 92 |
| Donor_5_3. Aliquot B | 424 | 9780 | 174000 | 112 | 19 | 43 | 6720 | 93 |
| Donor_5_3. Aliquot C | 221 | 111 | 1790 | 115 | 21 | 52 | 4350 | 97 |
| Donor_5_3. Aliquot D | 190 | 36200 | 543000 | 132 | 19 | 78 | 7840 | 92 |
| Donor_5_3. Aliquot E | 205 | 46800 | 600000 | 138 | 20 | 57 | 7880 | 91 |
| Donor_5_3. Aliquot F | 171 | 1790 | 24300 | 67 | 16 | 55 | 5110 | 87 |
| Donor_5_3. Aliquot G | 14 | 527 | 3130 | 120 | 20 | 28 | 3130 | 96 |
| Donor_5_3. Aliquot H | 55 | 328 | 5000 | 90 | 20 | 60 | 6880 | 87 |
| Donor_5_3. Aliquot I | 218 | 119 | 3870 | 83 | 20 | 62 | 4080 | 82 |
| Donor_6_3. Aliquot A | 124 | 1810 | 27400 | 12 | 2.8 | 74 | 2300 | 52 |
| Donor_6_3. Aliquot B | 124 | 1690 | 22200 | 15 | 3.0 | 76 | 2240 | 50 |
| Donor_6_3. Aliquot C | 110 | 55 | 376 | 150 | 2.5 | 33 | 2640 | 52 |
| Donor_6_3. Aliquot D | 136 | 29200 | 402000 | 20 | 2.9 | 80 | 1490 | 52 |

FIG. 17M.3

| | MDC pg/mL | MIP-1 alpha pg/mL | MIP-1beta pg/mL | MMP-2 ng/mL | MMP-3 ng/mL | MMP-9 ng/mL | Myelo-peroxidase ng/mL | Myoglobin ng/mL |
|---|---|---|---|---|---|---|---|---|
| Least Detectable Dose | 14 | 13 | 38 | 150 | 0.20 | 37 | 68 | 1.1 |
| RBM Low Plasma Range | 162 | | 25 | 183 | | | | 3.6 |
| RBM High Plasma Range | 774 | 89 | 595 | 3070 | 1.8 | 1050 | 1110 | 37 |
| Donor_6_3. Aliquot E | 110 | 36100 | 441000 | 28 | 2.6 | 99 | 1800 | 50 |
| Donor_6_3. Aliquot F | 94 | 491 | 7470 | 150 | 2.6 | 18 | 2660 | 54 |
| Donor_6_3. Aliquot G | 14 | 800 | 3130 | 75 | 2.3 | 46 | 1430 | 54 |
| Donor_6_3. Aliquot H | 29 | 143 | 3680 | 150 | 2.8 | 39 | 2490 | 50 |
| Donor_6_3. Aliquot I | 113 | 49 | 317 | 150 | 2.7 | 32 | 2270 | 51 |
| Donor_7_3. Aliquot A | 94 | 6080 | 188000 | 16 | 16 | 55 | 2070 | 1790 |
| Donor_7_3. Aliquot B | 99 | 2700 | 68500 | 150 | 16 | 66 | 2710 | >1845 |
| Donor_7_3. Aliquot C | 83 | 46 | 680 | 150 | 16 | 37 | 1920 | >1845 |
| Donor_7_3. Aliquot D | 92 | 7530 | 349000 | 23 | 14 | 79 | 1780 | >1845 |
| Donor_7_3. Aliquot E | 96 | 4790 | 179000 | 23 | 15 | 60 | 2160 | >1845 |
| Donor_7_3. Aliquot F | 72 | 152 | 5030 | 150 | 15 | 2.2 | 2150 | >1845 |
| Donor_7_3. Aliquot G | 14 | 469 | 2280 | 47 | 15 | 44 | 1630 | >1845 |
| Donor_7_3. Aliquot H | 17 | 43 | 762 | 150 | 14 | 30 | 1880 | 1780 |
| Donor_7_3. Aliquot I | 84 | 38 | 156 | 150 | 15 | 4.9 | 1800 | >1845 |
| Donor_8_3. Aliquot A | 223 | 1840 | 22700 | 37 | 3.4 | 8.2 | 1510 | 5.2 |
| Donor_8_3. Aliquot B | 221 | 1450 | 21000 | 37 | 3.5 | 26 | 1450 | 3.7 |
| Donor_8_3. Aliquot C | 154 | 2130 | 58500 | 23 | 2.8 | 23 | 3790 | 3.3 |
| Donor_8_3. Aliquot D | 337 | 67800 | 572000 | 89 | 3.9 | 94 | 8210 | 3.1 |
| Donor_8_3. Aliquot E | 245 | 46800 | 387000 | 75 | 3.4 | 81 | 6150 | 3.2 |
| Donor_8_3. Aliquot F | 138 | 6380 | 129000 | 53 | 3.6 | 31 | 2590 | 3.2 |
| Donor_8_3. Aliquot G | 14 | 931 | 7690 | 58 | 3.2 | 9.3 | 1220 | 2.9 |
| Donor_8_3. Aliquot H | 90 | 3290 | 29900 | 43 | 3.6 | 42 | 4710 | 3.3 |
| Donor_8_3. Aliquot I | 256 | 266 | 4590 | 26 | 3.2 | 4.9 | 2000 | 3.5 |
| Donor_9_3. Aliquot A | 169 | 1250 | 24500 | 38 | 4.3 | 27 | 1430 | 2.1 |
| Donor_9_3. Aliquot B | 175 | 1690 | 23200 | 43 | 4.8 | 59 | 1150 | 1.9 |

FIG. 17M.4

| | MDC pg/mL | MIP-1 alpha pg/mL | MIP-1beta pg/mL | MMP-2 ng/mL | MMP-3 ng/mL | MMP-9 ng/mL | Myelo-peroxidase ng/mL | Myoglobin ng/mL |
|---|---|---|---|---|---|---|---|---|
| Least Detectable Dose | 14 | 13 | 38 | 150 | 0.20 | 37 | 68 | 1.1 |
| RBM Low Plasma Range | 162 | | | 183 | | | | 3.6 |
| RBM High Plasma Range | 774 | 89 | 25 | 3070 | 1.8 | 1050 | 1110 | 37 |
| Donor_9_3. Aliquot C | 180 | 2140 | 595 | 72 | 4.2 | 36 | 2030 | 1.7 |
| Donor_9_3. Aliquot D | 196 | 42300 | 46900 | 132 | 4.7 | 111 | 3500 | 1.3 |
| Donor_9_3. Aliquot E | 194 | 29700 | 431000 | 82 | 4.9 | 123 | 4800 | 1.9 |
| Donor_9_3. Aliquot F | 142 | 2410 | 355000 | 46 | 4.3 | 4.6 | 747 | 2.1 |
| Donor_9_3. Aliquot G | 14 | 1820 | 78800 | 95 | 3.9 | 27 | 1560 | 1.7 |
| Donor_9_3. Aliquot H | 70 | 467 | 12300 | 48 | 4.3 | 45 | 3250 | 2.1 |
| Donor_9_3. Aliquot I | 181 | 240 | 14400 | 42 | 3.6 | 13 | 1070 | 2.1 |
| EDTA Plasma | | | 3670 | | | | | |
| donor #1 plasma | 187 | 69 | 209 | 1750 | 0.12 | 211 | 111 | 77 |
| donor #2 plasma | 236 | 60 | 239 | 3910 | 0.047 | 1340 | 158 | 64 |
| donor #3 plasma | 116 | 41 | 65 | 1540 | 0.2 | 653 | 85 | 182 |
| donor #4 plasma | 413 | 59 | 368 | 8190 | 0.2 | 194 | 322 | 61 |
| donor #5 plasma | 307 | 46 | 154 | 898 | 0.076 | 236 | 372 | 86 |
| donor #6 plasma | 155 | 34 | 68 | 972 | 0.2 | 367 | 9.9 | 57 |
| donor #7 plasma | 124 | 48 | 145 | 2270 | 0.090 | 115 | 135 | >1845 |
| donor #8 plasma | 176 | 42 | 47 | 10 | 3.7 | 30 | 183 | 3.8 |
| donor #9 plasma | 159 | 44 | 38 | 46 | 4.2 | 3.2 | 68 | 1.4 |
| MW NHD plasma Normal healthy donors | 167.5 | 43.3 | 42.5 | 28.0 | 3.9 | 16.6 | 125.5 | 2.6 |
| MW NHD unstimuliert Normal healthy donors | 218.50 | 253.00 | 4130.00 | 33.80 | 3.42 | 8.83 | 1535.00 | 2.75 |
| Stimulationsindices | | | | | | | | |

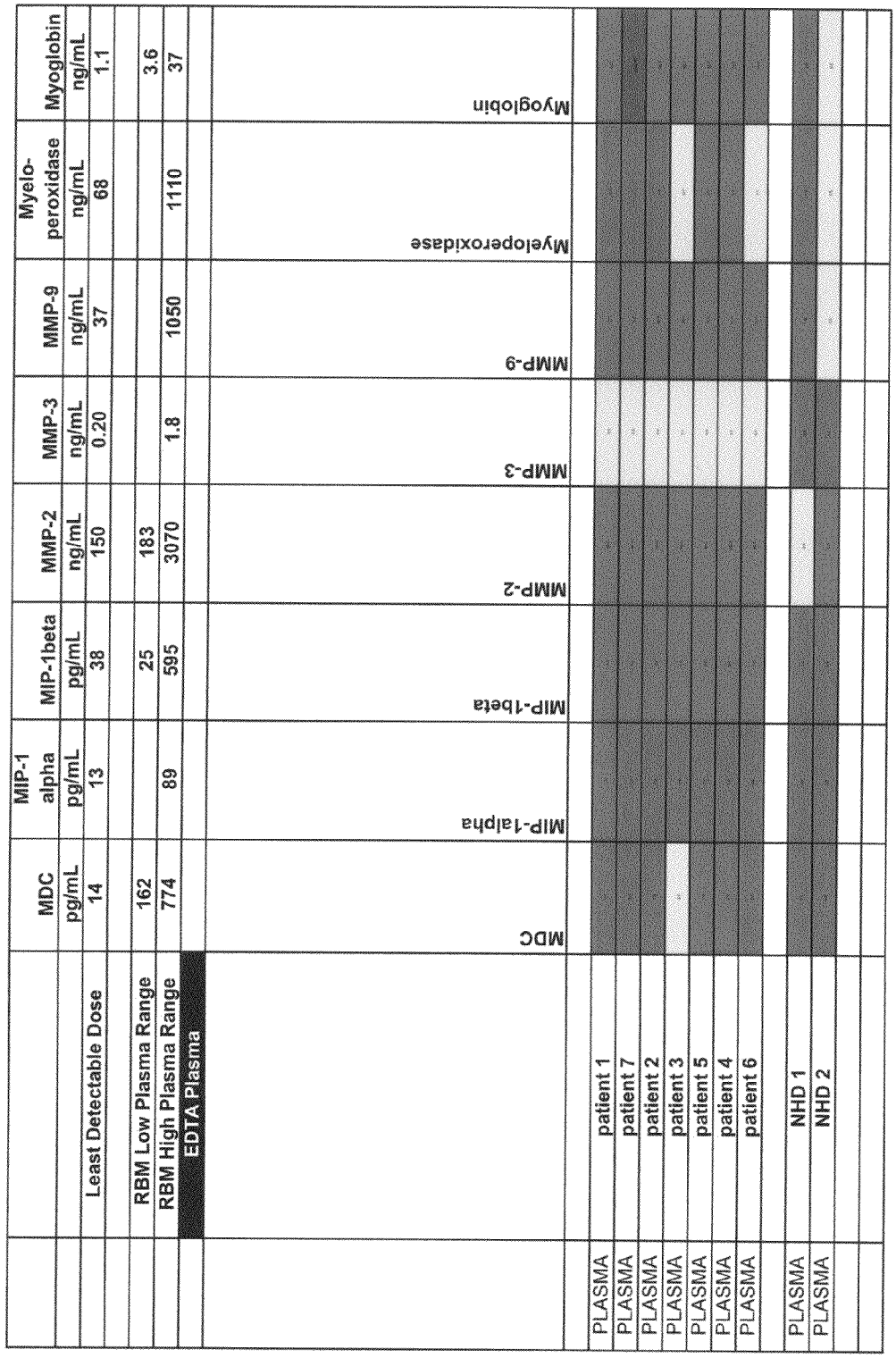
FIG. 17M.5

FIG. 17M.6

| | MDC pg/mL | MIP-1 alpha pg/mL | MIP-1beta pg/mL | MMP-2 ng/mL | MMP-3 ng/mL | MMP-9 ng/mL | Myelo-peroxidase ng/mL | Myoglobin ng/mL |
|---|---|---|---|---|---|---|---|---|
| Least Detectable Dose | 14 | 13 | 38 | 150 | 0.20 | 37 | 68 | 1.1 |
| RBM Low Plasma Range | 162 | 89 | 25 | 183 | | | | 3.6 |
| RBM High Plasma Range | 774 | | 595 | 3070 | 1.8 | 1050 | 1110 | 37 |
| Messwert > ULD | | | | | | | | |
| SI > 1,5 | | | | | | | | |
| SI 0,7-1,5 | | | | | | | | |
| SI 0-0,7 | | | | | | | | |
| MW nur von 1 Kontrollperson | | | | | | | | |
| *Stimulationsindices* | | | | | | | | |

FIG. 17M.7

| | MDC pg/mL | MIP-1 alpha pg/mL | MIP-1beta pg/mL | MMP-2 ng/mL | MMP-3 ng/mL | MMP-9 ng/mL | Myelo-peroxidase ng/mL | Myoglobin ng/mL |
|---|---|---|---|---|---|---|---|---|
| Least Detectable Dose | 14 | 13 | 38 | 150 | 0.20 | 37 | 68 | 1.1 |
| RBM Low Plasma Range | 162 | 89 | 25 | 183 | 1.8 | 1050 | 1110 | 3.6 |
| RBM High Plasma Range | 774 | | 595 | 3070 | | | | 37 |

| | | MDC | MIP-1alpha | MIP-1beta | MMP-2 | MMP-3 | MMP-9 | Myeloperoxidase | Myoglobin |
|---|---|---|---|---|---|---|---|---|---|
| unstimuliert | patient 1 | | | | | | | | |
| unstimuliert | patient 7 | | | | | | | | |
| unstimuliert | patient 2 | | | | | | | | |
| unstimuliert | patient 3 | | | | | | | | |
| unstimuliert | patient 5 | | | | | | | | |
| unstimuliert | patient 4 | | | | | | | | |
| unstimuliert | patient 6 | | | | | | | | |
| unstimuliert | NHD 1 | | | | | | | | |
| unstimuliert | NHD 2 | | | | | | | | |

FIG. 17M.8

| | MDC pg/mL | MIP-1 alpha pg/mL | MIP-1beta pg/mL | MMP-2 ng/mL | MMP-3 ng/mL | MMP-9 ng/mL | Myelo-peroxidase ng/mL | Myoglobin ng/mL |
|---|---|---|---|---|---|---|---|---|
| Least Detectable Dose | 14 | 13 | 38 | 150 | 0.20 | 37 | 68 | 1.1 |
| RBM Low Plasma Range | 162 | 89 | 25 | 183 | | | | 3.6 |
| RBM High Plasma Range | 774 | | 595 | 3070 | 1.8 | 1050 | 1110 | 37 |
| NHD = normal healthy donor | | | | | | | | |

FIG. 17N.1

| | OSM (Oncostatin M) pg/mL | PAI-1 ng/mL | Prostatic Acid Phosphatase ng/mL | PAPP-A mIU/mL | Prostate Specific Antigen, Free ng/mL | RANTES ng/mL |
|---|---|---|---|---|---|---|
| Least Detectable Dose | 28 | 0.90 | 0.034 | 0.037 | 0.023 | 0.048 |
| RBM Low Plasma Range | PENDING | 10 | 0.058 | | | 2.6 |
| RBM High Plasma Range | PENDING | 87 | 0.54 | 0.48 | 1.6 | 83 |
| Samples | | | | | | |
| Donor_1 3. Aliquot A | 312 | 159 | 0.12 | 0.079 | 0.44 | 16 |
| Donor_1 3. Aliquot B | 188 | 171 | 0.11 | 0.082 | 0.44 | 25 |
| Donor_1 3. Aliquot C | 21 | 172 | 0.045 | 0.059 | 0.47 | 22 |
| Donor_1 3. Aliquot D | 143 | 156 | 0.11 | 0.054 | 0.50 | 18 |
| Donor_1 3. Aliquot E | 312 | 152 | 0.12 | 0.062 | 0.47 | 14 |
| Donor_1 3. Aliquot F | 120 | 135 | 0.041 | 0.073 | 0.41 | 14 |
| Donor_1 3. Aliquot G | 422 | 187 | 0.086 | 0.11 | 0.50 | 24 |
| Donor_1 3. Aliquot H | 28 | 184 | 0.078 | 0.087 | 0.43 | 26 |
| Donor_1 3. Aliquot I | 76 | 160 | 0.035 | 0.049 | 0.45 | 19 |
| Donor_2 3. Aliquot A | 603 | 178 | 0.24 | 0.023 | 0.11 | 20 |
| Donor_2 3. Aliquot B | 334 | 190 | 0.24 | 0.032 | 0.11 | 24 |
| Donor_2 3. Aliquot C | 28 | 155 | 0.16 | 0.0049 | 0.072 | 15 |
| Donor_2 3. Aliquot D | 222 | 165 | 0.46 | 0.024 | 0.20 | 13 |
| Donor_2 3. Aliquot E | 188 | 161 | 0.38 | 0.022 | 0.16 | 13 |
| Donor_2 3. Aliquot F | 65 | 156 | 0.12 | 0.018 | 0.087 | 13 |
| Donor_2 3. Aliquot G | 765 | 205 | 0.33 | 0.043 | 0.13 | 21 |
| Donor_2 3. Aliquot H | 82 | 177 | 0.14 | 0.023 | 0.083 | 13 |
| Donor_2 3. Aliquot I | 44 | 164 | 0.13 | 0.018 | 0.082 | 12 |
| Donor_3 3. Aliquot A | 301 | 246 | 0.24 | 0.0063 | 0.67 | 16 |
| Donor_3 3. Aliquot B | 329 | 221 | 0.22 | 0.037 | 0.65 | 21 |
| Donor_3 3. Aliquot C | 98 | 199 | 0.16 | 0.037 | 0.72 | 17 |
| Donor_3 3. Aliquot D | 395 | 225 | 0.41 | 0.0049 | 0.71 | 16 |
| Donor_3 3. Aliquot E | 466 | 208 | 0.47 | 0.0063 | 0.73 | 21 |
| Donor_3 3. Aliquot F | 109 | 216 | 0.16 | 0.0063 | 0.65 | 13 |

FIG. 17N.2

| | OSM (Oncostatin M) pg/mL | PAI-1 ng/mL | Prostatic Acid Phosphatase ng/mL | PAPP-A mIU/mL | Prostate Specific Antigen, Free ng/mL | RANTES ng/mL |
|---|---|---|---|---|---|---|
| Least Detectable Dose | 28 | 0.90 | 0.034 | 0.037 | 0.023 | 0.048 |
| RBM Low Plasma Range | PENDING | 10 | 0.058 | | | 2.6 |
| RBM High Plasma Range | PENDING | 87 | 0.54 | 0.48 | 1.6 | 83 |
| Donor_3 3. Aliquot G | 705 | 246 | 0.17 | 0.037 | 0.74 | 26 |
| Donor_3 3. Aliquot H | 165 | 207 | 0.14 | 0.0049 | 0.57 | 13 |
| Donor_3 3. Aliquot I | 98 | 214 | 0.14 | 0.037 | 0.61 | 14 |
| Donor_4 3. Aliquot A | 28 | 253 | 0.27 | 0.13 | 0.023 | 4.4 |
| Donor_4 3. Aliquot B | 54 | 236 | 0.38 | 0.14 | 0.023 | 4.6 |
| Donor_4 3. Aliquot C | 28 | 229 | 0.28 | 0.029 | 0.023 | 2.7 |
| Donor_4 3. Aliquot D | 120 | 216 | 0.42 | 0.13 | 0.045 | 3.4 |
| Donor_4 3. Aliquot E | 165 | 222 | 0.46 | 0.15 | 0.023 | 2.6 |
| Donor_4 3. Aliquot F | 28 | 237 | 0.26 | 0.14 | 0.023 | 2.5 |
| Donor_4 3. Aliquot G | 455 | 203 | 0.56 | 0.16 | 0.023 | 5.9 |
| Donor_4 3. Aliquot H | 76 | 219 | 0.23 | 0.13 | 0.023 | 2.5 |
| Donor_4 3. Aliquot I | 21 | 235 | 0.26 | 0.12 | 0.023 | 3.2 |
| Donor_5 3. Aliquot A | 844 | 158 | 0.46 | 0.021 | 0.49 | 17 |
| Donor_5 3. Aliquot B | 834 | 183 | 0.73 | 0.021 | 0.48 | 13 |
| Donor_5 3. Aliquot C | 171 | 144 | 0.28 | 0.0078 | 0.42 | 11 |
| Donor_5 3. Aliquot D | 1850 | 145 | 1.5 | 0.040 | 0.61 | 14 |
| Donor_5 3. Aliquot E | 2320 | 155 | 2.9 | 0.032 | 0.57 | 14 |
| Donor_5 3. Aliquot F | 188 | 167 | 0.27 | 0.018 | 0.39 | 9.5 |
| Donor_5 3. Aliquot G | 1040 | 181 | 0.52 | 0.029 | 0.45 | 16 |
| Donor_5 3. Aliquot H | 834 | 156 | 0.50 | 0.014 | 0.46 | 12 |
| Donor_5 3. Aliquot I | 211 | 147 | 0.27 | 0.014 | 0.49 | 9.0 |
| Donor_6 3. Aliquot A | 82 | 192 | 0.13 | 0.0056 | 0.35 | 35 |
| Donor_6 3. Aliquot B | 109 | 174 | 0.24 | 0.037 | 0.40 | 34 |
| Donor_6 3. Aliquot C | 28 | 152 | 0.22 | 0.037 | 0.34 | 23 |
| Donor_6 3. Aliquot D | 65 | 181 | 0.26 | 0.037 | 0.44 | 35 |

FIG. 17N.3

| | OSM (Oncostatin M) pg/mL | PAI-1 ng/mL | Prostatic Acid Phosphatase ng/mL | PAPP-A mIU/mL | Prostate Specific Antigen, Free ng/mL | RANTES ng/mL |
|---|---|---|---|---|---|---|
| Least Detectable Dose | 28 | 0.90 | 0.034 | 0.037 | 0.023 | 0.048 |
| RBM Low Plasma Range | PENDING | 10 | 0.058 | 0.48 | 1.6 | 2.6 |
| RBM High Plasma Range | PENDING | 87 | 0.54 | | | 83 |
| Donor_6_3. Aliquot E | 87 | 153 | 0.38 | 0.0063 | 0.40 | 23 |
| Donor_6_3. Aliquot F | 28 | 173 | 0.15 | 0.037 | 0.31 | 20 |
| Donor_6_3. Aliquot G | 715 | 250 | 0.54 | 0.037 | 0.33 | 47 |
| Donor_6_3. Aliquot H | 65 | 181 | 0.12 | 0.037 | 0.33 | 22 |
| Donor_6_3. Aliquot I | 28 | 176 | 0.17 | 0.037 | 0.35 | 23 |
| Donor_7_3. Aliquot A | 194 | 210 | 0.10 | 0.012 | 0.65 | 17 |
| Donor_7_3. Aliquot B | 109 | 222 | 0.16 | 0.011 | 0.63 | 17 |
| Donor_7_3. Aliquot C | 28 | 215 | 0.068 | 0.037 | 0.65 | 25 |
| Donor_7_3. Aliquot D | 21 | 215 | 0.19 | 0.0085 | 0.61 | 19 |
| Donor_7_3. Aliquot E | 54 | 230 | 0.12 | 0.0049 | 0.66 | 15 |
| Donor_7_3. Aliquot F | 28 | 225 | 0.078 | 0.037 | 0.57 | 9.7 |
| Donor_7_3. Aliquot G | 143 | 229 | 0.063 | 0.037 | 0.68 | 23 |
| Donor_7_3. Aliquot H | 44 | 198 | 0.087 | 0.0092 | 0.64 | 12 |
| Donor_7_3. Aliquot I | 28 | 198 | 0.073 | 0.037 | 0.60 | 12 |
| Donor_8_3. Aliquot A | 28 | 32 | 0.082 | 0.0070 | 0.023 | 12 |
| Donor_8_3. Aliquot B | 28 | 35 | 0.13 | 0.0056 | 0.023 | 16 |
| Donor_8_3. Aliquot C | 28 | 31 | 0.16 | 0.037 | 0.023 | 17 |
| Donor_8_3. Aliquot D | 345 | 30 | 0.67 | 0.015 | 0.18 | 12 |
| Donor_8_3. Aliquot E | 132 | 34 | 0.55 | 0.0092 | 0.13 | 14 |
| Donor_8_3. Aliquot F | 28 | 30 | 0.15 | 0.0056 | 0.023 | 6.9 |
| Donor_8_3. Aliquot G | 132 | 60 | 0.058 | 0.0092 | 0.023 | 19 |
| Donor_8_3. Aliquot H | 54 | 41 | 0.14 | 0.014 | 0.023 | 15 |
| Donor_8_3. Aliquot I | 28 | 40 | 0.079 | 0.0078 | 0.023 | 17 |
| Donor_9_3. Aliquot A | 28 | 45 | 0.052 | 0.0053 | 0.023 | 16 |
| Donor_9_3. Aliquot B | 28 | 63 | 0.088 | 0.037 | 0.023 | 21 |

FIG. 17N.4

| | OSM (Oncostatin M) pg/mL | PAI-1 ng/mL | Prostatic Acid Phosphatase ng/mL | PAPP-A mIU/mL | Prostate Specific Antigen, Free ng/mL | RANTES ng/mL |
|---|---|---|---|---|---|---|
| Least Detectable Dose | 28 | 0.90 | 0.034 | 0.037 | 0.023 | 0.048 |
| | | | | | | |
| RBM Low Plasma Range | PENDING | | | | | 2.6 |
| RBM High Plasma Range | PENDING | | | | | 83 |
| Donor_9_3. Aliquot C | 28 | 10 | 0.058 | 0.48 | 1.6 | 23 |
| Donor_9_3. Aliquot D | 96 | 87 | 0.54 | 0.037 | 0.023 | 21 |
| Donor_9_3. Aliquot E | 42 | 71 | 0.074 | 0.013 | 0.18 | 13 |
| Donor_9_3. Aliquot F | 28 | 72 | 0.50 | 0.037 | 0.10 | 9.1 |
| Donor_9_3. Aliquot G | 247 | 65 | 0.34 | 0.0077 | 0.023 | 30 |
| Donor_9_3. Aliquot H | 42 | 66 | 0.052 | 0.010 | 0.023 | 21 |
| Donor_9_3. Aliquot I | 28 | 97 | 0.040 | 0.037 | 0.023 | 21 |
| | | 71 | 0.037 | 0.037 | 0.023 | |
| | | 70 | 0.034 | | | |
| EDTA Plasma | | | | | | |
| donor #1 plasma | 1120 | 142 | 0.090 | 0.084 | 0.28 | 9.4 |
| donor #2 plasma | 28 | 151 | 0.13 | 0.052 | 0.13 | 3.4 |
| donor #3 plasma | 28 | 208 | 0.050 | 0.029 | 0.74 | 6.4 |
| donor #4 plasma | 28 | 218 | 0.65 | 0.26 | 0.023 | 1.3 |
| donor #5 plasma | 28 | 154 | 0.41 | 0.040 | 0.47 | 8.7 |
| donor #6 plasma | 151 | 149 | 0.15 | 0.017 | 0.45 | 14 |
| donor #7 plasma | 133 | 242 | 0.078 | 0.066 | 0.82 | 12 |
| donor #8 plasma | 28 | 39 | 0.13 | 0.010 | 0.024 | 5.3 |
| donor #9 plasma | 28 | 61 | 0.071 | 0.037 | 0.023 | 1.2 |
| | | | | | | |
| MW NHD plasma Normal healthy donors | 28.0 | 50.0 | 0.1 | 0.0 | 0.0 | 3.2 |
| | | | | | | |
| MW NHD unstimuliert Normal healthy donors | 28.00 | 54.95 | 0.06 | 0.02 | 0.02 | 18.70 |
| | | | | | | |
| Stimulationsindices | | | | | | |

FIG. 17N.5

| | Least Detectable Dose | RBM Low Plasma Range | RBM High Plasma Range | EDTA Plasma | OSM (Oncostatin M) pg/mL | PAI-1 ng/mL | Prostatic Acid Phosphatase ng/mL | PAPP-A mIU/mL | Prostate Specific Antigen, Free ng/mL | RANTES ng/mL |
|---|---|---|---|---|---|---|---|---|---|---|
| | | | | | 28 | 0.90 | 0.034 | 0.037 | 0.023 | 0.048 |
| | | | | | PENDING | 10 | 0.058 | 0.48 | 1.6 | 2.6 |
| | | | | | PENDING | 87 | 0.54 | | | 83 |
| PLASMA | patient 1 | | | | | | | | | |
| PLASMA | patient 7 | | | | | | | | | |
| PLASMA | patient 2 | | | | | | | | | |
| PLASMA | patient 3 | | | | | | | | | |
| PLASMA | patient 5 | | | | | | | | | |
| PLASMA | patient 4 | | | | | | | | | |
| PLASMA | patient 6 | | | | | | | | | |
| PLASMA | NHD 1 | | | | | | | | | |
| PLASMA | NHD 2 | | | | | | | | | |

FIG. 17N.6

| | OSM (Oncostatin M) pg/mL | PAI-1 ng/mL | Prostatic Acid Phosphatase ng/mL | PAPP-A mIU/mL | Prostate Specific Antigen, Free ng/mL | RANTES ng/mL |
|---|---|---|---|---|---|---|
| Least Detectable Dose | 28 | 0.90 | 0.034 | 0.037 | 0.023 | 0.048 |
| RBM Low Plasma Range | PENDING | 10 | 0.058 | | | 2.6 |
| RBM High Plasma Range | PENDING | 87 | 0.54 | 0.48 | 1.6 | 83 |
| Messwert > ULD | | | | | | |
| SI > 1,5 | | | | | | |
| SI 0,7-1,5 | | | | | | |
| SI 0-0,7 | | | | | | |
| MW nur von 1 Kontrollperson | | | | | | |
| Stimulationsindices | | | | | | |

FIG. 17N.7

| | Least Detectable Dose | OSM (Oncostatin M) pg/mL 28 | PAI-1 ng/mL 0.90 | Prostatic Acid Phosphatase ng/mL 0.034 | PAPP-A mIU/mL 0.037 | Prostate Specific Antigen, Free ng/mL 0.023 | RANTES ng/mL 0.048 |
|---|---|---|---|---|---|---|---|
| | RBM Low Plasma Range | PENDING | 10 | 0.058 | | | 2.6 |
| | RBM High Plasma Range | PENDING | 87 | 0.54 | 0.48 | 1.6 | 83 |
| patient 1 | unstimuliert | | | | | | |
| patient 7 | unstimuliert | | | | | | |
| patient 2 | unstimuliert | | | | | | |
| patient 3 | unstimuliert | | | | | | |
| patient 5 | unstimuliert | | | | | | |
| patient 4 | unstimuliert | | | | | | |
| patient 6 | unstimuliert | | | | | | |
| NHD 1 | unstimuliert | | | | | | |
| NHD 2 | unstimuliert | | | | | | |

FIG. 17N.8

| | OSM (Oncostatin M) pg/mL | PAI-1 ng/mL | Prostatic Acid Phosphatase ng/mL | PAPP-A mIU/mL | Prostate Specific Antigen, Free ng/mL | RANTES ng/mL |
|---|---|---|---|---|---|---|
| Least Detectable Dose | 28 | 0.90 | 0.034 | 0.037 | 0.023 | 0.048 |
| RBM Low Plasma Range | PENDING | 10 | 0.058 | | | 2.6 |
| RBM High Plasma Range | PENDING | 87 | 0.54 | 0.48 | 1.6 | 83 |
| NHD = normal healthy donor | | | | | | |

FIG. 17O.1

| | Serum Amyloid P ug/mL | Stem Cell Factor pg/mL | SGOT ug/mL | SHBG nmol/L | Thyroxine Binding Globulin ug/mL | Tissue Factor ng/mL | TGF-alpha pg/mL | TIMP-1 ng/mL |
|---|---|---|---|---|---|---|---|---|
| Least Detectable Dose | 0.058 | 56 | | 1.3 | 0.34 | 0.84 | 1.8 | 8.4 |
| | | | | | | | | |
| RBM Low Plasma Range | 15 | | 3.9 | 12 | 40 | | Pending | 59 |
| RBM High Plasma Range | 50 | 281 | 28 | 106 | 104 | 2.4 | Pending | 192 |
| | | | | | | | | |
| Samples | | | | | | | | |
| Donor_1 3. Aliquot A | 26 | 757 | 3.7 | 18 | 27 | 3.7 | 22 | 521 |
| Donor_1 3. Aliquot B | 28 | 587 | 3.7 | 19 | 31 | 2.7 | 15 | 615 |
| Donor_1 3. Aliquot C | 28 | 599 | 3.7 | 19 | 29 | 0.91 | 1.8 | 611 |
| Donor_1 3. Aliquot D | 33 | 657 | 3.7 | 19 | 31 | 3.3 | 9.7 | 620 |
| Donor_1 3. Aliquot E | 29 | 666 | 3.7 | 19 | 29 | 3.0 | 13 | 549 |
| Donor_1 3. Aliquot F | 29 | 430 | 3.7 | 18 | 29 | 2.0 | 3.8 | 553 |
| Donor_1 3. Aliquot G | 26 | 645 | 3.7 | 19 | 29 | 2.0 | 24 | 645 |
| Donor_1 3. Aliquot H | 29 | 508 | 3.7 | 19 | 26 | 1.8 | 1.5 | 580 |
| Donor_1 3. Aliquot I | 29 | 508 | 3.7 | 18 | 28 | 1.6 | 1.6 | 495 |
| | | | | | | | | |
| Donor_2 3. Aliquot A | 22 | 1350 | 3.7 | 34 | 36 | 1.7 | 56 | 354 |
| Donor_2 3. Aliquot B | 26 | 1530 | 3.7 | 35 | 37 | 1.9 | 44 | 391 |
| Donor_2 3. Aliquot C | 23 | 607 | 3.7 | 36 | 36 | 0.84 | 7.5 | 303 |
| Donor_2 3. Aliquot D | 24 | 1640 | 3.7 | 35 | 38 | 7.1 | 46 | 359 |
| Donor_2 3. Aliquot E | 26 | 1670 | 3.7 | 34 | 37 | 3.5 | 43 | 376 |
| Donor_2 3. Aliquot F | 23 | 582 | 3.7 | 36 | 39 | 0.47 | 5.6 | 305 |
| Donor_2 3. Aliquot G | 22 | 1760 | 3.7 | 34 | 38 | 2.3 | 48 | 499 |
| Donor_2 3. Aliquot H | 27 | 595 | 3.7 | 36 | 34 | 0.84 | 20 | 304 |
| Donor_2 3. Aliquot I | 23 | 500 | 3.7 | 33 | 37 | 0.70 | 9.5 | 278 |
| | | | | | | | | |
| Donor_3 3. Aliquot A | 14 | 666 | 3.7 | 42 | 56 | 1.9 | 20 | 183 |
| Donor_3 3. Aliquot B | 14 | 434 | 3.7 | 40 | 50 | 1.8 | 22 | 209 |
| Donor_3 3. Aliquot C | 17 | 213 | 3.7 | 43 | 57 | 0.15 | 5.6 | 156 |
| Donor_3 3. Aliquot D | 15 | 882 | 3.7 | 39 | 52 | 5.4 | 18 | 213 |
| Donor_3 3. Aliquot E | 15 | 1020 | 3.7 | 42 | 52 | 4.9 | 16 | 221 |
| Donor_3 3. Aliquot F | 16 | 202 | 3.7 | 40 | 53 | 1.5 | 4.4 | 154 |

FIG. 17O.2

| | Serum Amyloid P ug/mL | Stem Cell Factor pg/mL | SGOT ug/mL | SHBG nmol/L | Thyroxine Binding Globulin ug/mL | Tissue Factor ng/mL | TGF-alpha pg/mL | TIMP-1 ng/mL |
|---|---|---|---|---|---|---|---|---|
| Least Detectable Dose | 0.058 | 56 | 3.7 | 1.3 | 0.34 | 0.84 | 1.8 | 8.4 |
| RBM Low Plasma Range | 15 | | 3.9 | 12 | 40 | | Pending | 59 |
| RBM High Plasma Range | 50 | 281 | 28 | 106 | 104 | 2.4 | Pending | 192 |
| Donor_3_3. Aliquot G | 15 | 183 | 3.7 | 41 | 54 | 0.84 | 15 | 205 |
| Donor_3_3. Aliquot H | 16 | 113 | 3.7 | 38 | 49 | 0.56 | 2.1 | 155 |
| Donor_3_3. Aliquot I | 16 | 138 | 3.7 | 36 | 51 | 0.99 | 0.63 | 153 |
| Donor_4_3. Aliquot A | 8.7 | 426 | 3.7 | 54 | 38 | 1.5 | 15 | 575 |
| Donor_4_3. Aliquot B | 9.6 | 475 | 3.7 | 53 | 35 | 0.87 | 22 | 590 |
| Donor_4_3. Aliquot C | 9.9 | 377 | 3.7 | 54 | 35 | 0.84 | 6.4 | 532 |
| Donor_4_3. Aliquot D | 10 | 957 | 3.7 | 55 | 34 | 5.4 | 19 | 622 |
| Donor_4_3. Aliquot E | 10 | 1010 | 3.7 | 50 | 35 | 3.4 | 16 | 632 |
| Donor_4_3. Aliquot F | 12 | 459 | 3.7 | 58 | 36 | 1.5 | 4.6 | 565 |
| Donor_4_3. Aliquot G | 8.8 | 459 | 3.7 | 57 | 36 | 0.84 | 16 | 499 |
| Donor_4_3. Aliquot H | 11 | 405 | 3.7 | 53 | 32 | 0.99 | 3.5 | 546 |
| Donor_4_3. Aliquot I | 10 | 352 | 3.7 | 51 | 35 | 0.84 | 3.8 | 557 |
| Donor_5_3. Aliquot A | 43 | 936 | 3.7 | 33 | 47 | 0.87 | 22 | 344 |
| Donor_5_3. Aliquot B | 41 | 815 | 3.7 | 31 | 47 | 0.87 | 20 | 368 |
| Donor_5_3. Aliquot C | 38 | 320 | 3.7 | 35 | 42 | 0.84 | 7.3 | 184 |
| Donor_5_3. Aliquot D | 46 | 965 | 3.7 | 31 | 45 | 6.3 | 17 | 327 |
| Donor_5_3. Aliquot E | 45 | 1290 | 3.7 | 31 | 46 | 4.4 | 23 | 360 |
| Donor_5_3. Aliquot F | 38 | 288 | 0.62 | 31 | 43 | 0.15 | 7.1 | 233 |
| Donor_5_3. Aliquot G | 40 | 541 | 3.7 | 32 | 44 | 0.84 | 25 | 331 |
| Donor_5_3. Aliquot H | 43 | 292 | 3.7 | 29 | 40 | 0.56 | 7.0 | 228 |
| Donor_5_3. Aliquot I | 41 | 348 | 3.7 | 29 | 42 | 0.84 | 7.6 | 190 |
| Donor_6_3. Aliquot A | 25 | 217 | 3.7 | 18 | 29 | 0.84 | 13 | 139 |
| Donor_6_3. Aliquot B | 27 | 187 | 3.7 | 19 | 30 | 0.84 | 15 | 165 |
| Donor_6_3. Aliquot C | 24 | 99 | 3.7 | 19 | 27 | 0.84 | 1.2 | 111 |
| Donor_6_3. Aliquot D | 31 | 272 | 3.7 | 18 | 29 | 3.0 | 12 | 156 |

FIG. 17O.3

| | Serum Amyloid P | Stem Cell Factor | SGOT | SHBG | Thyroxine Binding Globulin | Tissue Factor | TGF-alpha | TIMP-1 |
|---|---|---|---|---|---|---|---|---|
| | ug/mL | pg/mL | ug/mL | nmol/L | ug/mL | ng/mL | pg/mL | ng/mL |
| Least Detectable Dose | 0.058 | 56 | 3.7 | 1.3 | 0.34 | 0.84 | 1.8 | 8.4 |
| RBM Low Plasma Range | 15 | | 3.9 | 12 | 40 | | Pending | 59 |
| RBM High Plasma Range | 50 | 281 | 28 | 106 | 104 | 2.4 | Pending | 192 |
| Donor_6 3. Aliquot E | 26 | 316 | 3.7 | 17 | 28 | 5.1 | 16 | 164 |
| Donor_6 3. Aliquot F | 26 | 99 | 3.7 | 19 | 30 | 0.84 | 1.2 | 124 |
| Donor_6 3. Aliquot G | 22 | 164 | 3.7 | 18 | 30 | 0.84 | 11 | 260 |
| Donor_6 3. Aliquot H | 23 | 69 | 3.7 | 19 | 27 | 0.84 | 3.8 | 112 |
| Donor_6 3. Aliquot I | 25 | 92 | 3.7 | 18 | 28 | 0.84 | 1.5 | 100 |
| Donor_7 3. Aliquot A | 31 | 998 | 8.2 | 9.5 | 25 | 2.4 | 9.2 | 210 |
| Donor_7 3. Aliquot B | 35 | 607 | 12 | 11 | 27 | 1.9 | 4.8 | 237 |
| Donor_7 3. Aliquot C | 33 | 113 | 8.1 | 12 | 25 | 0.84 | 1.8 | 198 |
| Donor_7 3. Aliquot D | 30 | 790 | 11 | 10 | 25 | 4.1 | 4.6 | 241 |
| Donor_7 3. Aliquot E | 29 | 707 | 13 | 8.8 | 19 | 2.4 | 3.4 | 243 |
| Donor_7 3. Aliquot F | 35 | 127 | 11 | 10 | 26 | 0.15 | 1.8 | 187 |
| Donor_7 3. Aliquot G | 29 | 160 | 4.3 | 9.4 | 23 | 0.84 | 4.7 | 213 |
| Donor_7 3. Aliquot H | 31 | 72 | 16 | 9.7 | 22 | 0.84 | 1.8 | 158 |
| Donor_7 3. Aliquot I | 34 | 127 | 11 | 9.9 | 25 | 0.15 | 1.8 | 159 |
| Donor_8 3. Aliquot A | 5.7 | 92 | 3.7 | 65 | 31 | 1.2 | 2.7 | 84 |
| Donor_8 3. Aliquot B | 6.4 | 46 | 3.7 | 66 | 30 | 0.84 | 3.4 | 118 |
| Donor_8 3. Aliquot C | 5.4 | 69 | 3.7 | 61 | 29 | 0.84 | 2.7 | 50 |
| Donor_8 3. Aliquot D | 5.7 | 106 | 3.7 | 60 | 28 | 13 | 6.2 | 60 |
| Donor_8 3. Aliquot E | 5.9 | 72 | 3.7 | 62 | 29 | 12 | 5.5 | 88 |
| Donor_8 3. Aliquot F | 6.7 | 40 | 3.7 | 67 | 31 | 0.47 | 1.9 | 52 |
| Donor_8 3. Aliquot G | 5.2 | 99 | 3.7 | 57 | 27 | 0.84 | 4.2 | 118 |
| Donor_8 3. Aliquot H | 6.4 | 89 | 3.7 | 69 | 29 | 0.65 | 2.8 | 60 |
| Donor_8 3. Aliquot I | 6.5 | 56 | 3.7 | 64 | 31 | 0.65 | 1.8 | 61 |
| Donor_9 3. Aliquot A | Pending | 170 | 3.7 | Pending | Pending | 1.2 | 19 | 66 |
| Donor_9 3. Aliquot B | Pending | 229 | 3.7 | Pending | Pending | 2.0 | 16 | 92 |

FIG. 17O.4

| | Serum Amyloid P ug/mL | Stem Cell Factor pg/mL | SGOT ug/mL | SHBG nmol/L | Thyroxine Binding Globulin ug/mL | Tissue Factor ng/mL | TGF-alpha pg/mL | TIMP-1 ng/mL |
|---|---|---|---|---|---|---|---|---|
| Least Detectable Dose | 0.058 | 56 | 3.7 | 1.3 | 0.34 | 0.84 | 1.8 | 8.4 |
| RBM Low Plasma Range | 15 | | 3.9 | 12 | 40 | | Pending | 59 |
| RBM High Plasma Range | 50 | 281 | 28 | 106 | 104 | 2.4 | Pending | 192 |
| Donor_9 3. Aliquot C | Pending | 229 | 3.7 | Pending | Pending | 0.66 | 18 | 62 |
| Donor_9 3. Aliquot D | Pending | 307 | 3.7 | Pending | Pending | 15 | 18 | 69 |
| Donor_9 3. Aliquot E | Pending | 272 | 3.7 | Pending | Pending | 8.6 | 20 | 93 |
| Donor_9 3. Aliquot F | Pending | 137 | 3.7 | Pending | Pending | 2.1 | 12 | 48 |
| Donor_9 3. Aliquot G | Pending | 528 | 3.7 | Pending | Pending | 1.8 | 20 | 130 |
| Donor_9 3. Aliquot H | Pending | 97 | 3.7 | Pending | Pending | 1.5 | 12 | 56 |
| Donor_9 3. Aliquot I | Pending | 174 | 3.7 | Pending | Pending | 0.53 | 8.5 | 53 |
| EDTA Plasma | | | | | | | | |
| donor #1 plasma | Pending | 351 | 40 | Pending | Pending | 2.9 | 1.8 | 379 |
| donor #2 plasma | Pending | 492 | 45 | Pending | Pending | 1.1 | 1.2 | 248 |
| donor #3 plasma | Pending | 161 | 54 | Pending | Pending | 1.9 | 1.8 | 144 |
| donor #4 plasma | Pending | 368 | 32 | Pending | Pending | 2.0 | 1.8 | 478 |
| donor #5 plasma | Pending | 550 | 70 | Pending | Pending | 2.1 | 1.8 | 166 |
| donor #6 plasma | Pending | 62 | 35 | Pending | Pending | 0.95 | 1.8 | 82 |
| donor #7 plasma | Pending | 212 | 46 | Pending | Pending | 1.9 | 1.8 | 156 |
| donor #8 plasma | Pending | 161 | 3.7 | Pending | Pending | 1.0 | 1.8 | 40 |
| donor #9 plasma | Pending | 203 | 3.7 | Pending | Pending | 0.74 | 4.4 | 31 |
| MW | | | | | | | | |
| NHD plasma | #DIV/0! | 182.0 | 3.7 | #DIV/0! | #DIV/0! | 0.9 | 3.1 | 35.7 |
| Normal healthy donors | | | | | | | | |
| MW | | | | | | | | |
| NHD unstimuliert | 6.53 | 114.80 | 3.70 | 64.20 | 30.60 | 0.59 | 5.15 | 57.00 |
| Normal healthy donors | | | | | | | | |
| Stimulationsindices | | | | | | | | |

FIG. 170.5

| | Serum Amyloid P ug/mL | Stem Cell Factor pg/mL | SGOT ug/mL | SHBG nmol/L | Thyroxine Binding Globulin ug/mL | Tissue Factor ng/mL | TGF-alpha pg/mL | TIMP-1 ng/mL |
|---|---|---|---|---|---|---|---|---|
| Least Detectable Dose | 0.058 | 56 | 3.7 | 1.3 | 0.34 | 0.84 | 1.8 | 8.4 |
| RBM Low Plasma Range | 15 | | 3.9 | 12 | 40 | | Pending | 59 |
| RBM High Plasma Range | 50 | 281 | 28 | 106 | 104 | 2.4 | Pending | 192 |
| EDTA Plasma | | | | | | | | |
| | | Serum Amyloid P | Stem Cell Factor | SGOT | SHBG | Thyroxine Binding Globulin | Tissue Factor | TGF-alpha | TIMP-1 |
| PLASMA | patient 1 | | | | | | | | |
| PLASMA | patient 7 | | | | | | | | |
| PLASMA | patient 2 | | | | | | | | |
| PLASMA | patient 3 | | | | | | | | |
| PLASMA | patient 5 | | | | | | | | |
| PLASMA | patient 4 | | | | | | | | |
| PLASMA | patient 6 | | | | | | | | |
| PLASMA | NHD 1 | | | | | | | | |
| PLASMA | NHD 2 | | | | | | | | |

FIG. 17O.6

| | Serum Amyloid P ug/mL | Stem Cell Factor pg/mL | SGOT ug/mL | SHBG nmol/L | Thyroxine Binding Globulin ug/mL | Tissue Factor ng/mL | TGF-alpha pg/mL | TIMP-1 ng/mL |
|---|---|---|---|---|---|---|---|---|
| Least Detectable Dose | 0.058 | 56 | 3.7 | 1.3 | 0.34 | 0.84 | 1.8 | 8.4 |
| RBM Low Plasma Range | 15 | | 3.9 | 12 | 40 | | Pending | 59 |
| RBM High Plasma Range | 50 | 281 | 28 | 106 | 104 | 2.4 | Pending | 192 |
| Messwert > ULD | | | | | | | | |
| SI > 1,5 | | | | | | | | |
| SI 0,7-1,5 | | | | | | | | |
| SI 0-0,7 | | | | | | | | |
| MW nur von 1 Kontrollperson | | | | | | | | |
| *Stimulationsindices* | | | | | | | | |

FIG. 17O.7

| | Serum Amyloid P | Stem Cell Factor | SGOT | SHBG | Thyroxine Binding Globulin | Tissue Factor | TGF-alpha | TIMP-1 |
|---|---|---|---|---|---|---|---|---|
| | ug/mL | pg/mL | ug/mL | nmol/L | ug/mL | ng/mL | pg/mL | ng/mL |
| Least Detectable Dose | 0.058 | 56 | 3.7 | 1.3 | 0.34 | 0.84 | 1.8 | 8.4 |
| RBM Low Plasma Range | 15 | | 3.9 | 12 | 40 | | Pending | 59 |
| RBM High Plasma Range | 50 | 281 | 28 | 106 | 104 | 2.4 | Pending | 192 |
| | Serum Amyloid P | Stem Cell Factor | SGOT | SHBG | Thyroxine Binding Globulin | Tissue Factor | TGF-alpha | TIMP-1 |
| patient 1 unstimuliert | | | | | | | | |
| patient 7 unstimuliert | | | | | | | | |
| patient 2 unstimuliert | | | | | | | | |
| patient 3 unstimuliert | | | | | | | | |
| patient 5 unstimuliert | | | | | | | | |
| patient 4 unstimuliert | | | | | | | | |
| patient 6 unstimuliert | | | | | | | | |
| NHD 1 unstimuliert | | | | | | | | |
| NHD 2 unstimuliert | | | | | | | | |

FIG. 17O.8

| | Serum Amyloid P | Stem Cell Factor | SGOT | SHBG | Thyroxine Binding Globulin | Tissue Factor | TGF-alpha | TIMP-1 |
|---|---|---|---|---|---|---|---|---|
| | ug/mL | pg/mL | ug/mL | nmol/L | ug/mL | ng/mL | pg/mL | ng/mL |
| Least Detectable Dose | 0.058 | 56 | 3.7 | 1.3 | 0.34 | 0.84 | 1.8 | 8.4 |
| RBM Low Plasma Range | 15 | | 3.9 | 12 | 40 | | Pending | 59 |
| RBM High Plasma Range | 50 | 281 | 28 | 106 | 104 | 2.4 | Pending | 192 |
| NHD = normal healthy donor | | | | | | | | |

FIG. 17P.1

| | TNF RII ng/mL | TNF-alpha pg/mL | TNF-beta pg/mL | Thrombopoietin ng/mL | Thyroid Stimulating Hormone uIU/mL |
|---|---|---|---|---|---|
| Least Detectable Dose | 0.13 | 4.0 | 46 | 3.2 | 0.028 |
| RBM Low Plasma Range | 3.1 | | | | 0.18 |
| RBM High Plasma Range | 79 | 27 | 120 | 6.2 | 3.7 |
| Samples | | | | | |
| Donor_1 3. Aliquot A | 29 | 236 | 7.9 | 1.9 | 17 |
| Donor_1 3. Aliquot B | 31 | 75 | 46 | 1.5 | 16 |
| Donor_1 3. Aliquot C | 28 | 19 | 46 | 3.2 | 18 |
| Donor_1 3. Aliquot D | 30 | 300 | 46 | 1.9 | 17 |
| Donor_1 3. Aliquot E | 29 | 88 | 46 | 1.9 | 17 |
| Donor_1 3. Aliquot F | 27 | 35 | 46 | 3.2 | 17 |
| Donor_1 3. Aliquot G | 30 | 24 | 46 | 1.3 | 17 |
| Donor_1 3. Aliquot H | 27 | 19 | 46 | 0.86 | 17 |
| Donor_1 3. Aliquot I | 24 | 25 | 46 | 0.69 | 17 |
| Donor_2 3. Aliquot A | 47 | 212 | 4.6 | 2.7 | 10 |
| Donor_2 3. Aliquot B | 49 | 94 | 6.0 | 3.2 | 10 |
| Donor_2 3. Aliquot C | 41 | 12 | 46 | 3.2 | 9.9 |
| Donor_2 3. Aliquot D | 45 | 2700 | 6.0 | 2.4 | 12 |
| Donor_2 3. Aliquot E | 48 | 1690 | 3.2 | 2.7 | 11 |
| Donor_2 3. Aliquot F | 40 | 24 | 46 | 1.5 | 10 |
| Donor_2 3. Aliquot G | 47 | 544 | 18 | 3.0 | 9.9 |
| Donor_2 3. Aliquot H | 40 | 21 | 46 | 3.2 | 9.5 |
| Donor_2 3. Aliquot I | 36 | 19 | 46 | 0.49 | 9.1 |
| Donor_3 3. Aliquot A | 14 | 157 | 7.3 | 2.5 | 0.99 |
| Donor_3 3. Aliquot B | 13 | 64 | 46 | 2.5 | 0.98 |
| Donor_3 3. Aliquot C | 8.1 | 13 | 46 | 3.2 | 0.99 |
| Donor_3 3. Aliquot D | 14 | 2600 | 14 | 2.2 | 1.1 |
| Donor_3 3. Aliquot E | 14 | 1150 | 11 | 3.9 | 1.2 |
| Donor_3 3. Aliquot F | 7.9 | 26 | 46 | 2.1 | 0.94 |

FIG. 17P.2

| | TNF RII ng/mL | TNF-alpha pg/mL | TNF-beta pg/mL | Thrombopoietin ng/mL | Thyroid Stimulating Hormone uIU/mL |
|---|---|---|---|---|---|
| Least Detectable Dose | 0.13 | 4.0 | 46 | 3.2 | 0.028 |
| RBM Low Plasma Range | | | | | |
| RBM High Plasma Range | | | | | |
| Donor_3 3. Aliquot G | 3.1 | 27 | 120 | 6.2 | 0.18 |
| Donor_3 3. Aliquot H | 79 | 21 | 46 | 3.2 | 3.7 |
| Donor_3 3. Aliquot I | 10.0 | 9.4 | 46 | 3.2 | 1.0 |
| | 6.8 | 4.2 | 46 | 2.1 | 0.90 |
| | 6.5 | | | | 0.98 |
| Donor_4 3. Aliquot A | 30 | 20 | 46 | 1.3 | 0.15 |
| Donor_4 3. Aliquot B | 30 | 17 | 46 | 1.4 | 0.15 |
| Donor_4 3. Aliquot C | 26 | 12 | 46 | 3.2 | 0.16 |
| Donor_4 3. Aliquot D | 33 | 1720 | 7.3 | 2.0 | 0.26 |
| Donor_4 3. Aliquot E | 36 | 618 | 15 | 2.3 | 0.19 |
| Donor_4 3. Aliquot F | 31 | 91 | 7.3 | 1.2 | 0.14 |
| Donor_4 3. Aliquot G | 30 | 12 | 46 | 3.2 | 0.13 |
| Donor_4 3. Aliquot H | 27 | 9.3 | 46 | 1.2 | 0.14 |
| Donor_4 3. Aliquot I | 28 | 4.8 | 46 | 3.2 | 0.13 |
| Donor_5 3. Aliquot A | 28 | 106 | 7.9 | 2.9 | 0.28 |
| Donor_5 3. Aliquot B | 31 | 146 | 7.3 | 3.1 | 0.26 |
| Donor_5 3. Aliquot C | 23 | 12 | 46 | 0.69 | 0.32 |
| Donor_5 3. Aliquot D | 34 | 1900 | 9.8 | 2.8 | 0.41 |
| Donor_5 3. Aliquot E | 35 | 1590 | 16 | 2.7 | 0.38 |
| Donor_5 3. Aliquot F | 23 | 105 | 46 | 2.2 | 0.24 |
| Donor_5 3. Aliquot G | 27 | 18 | 8.6 | 1.0 | 0.28 |
| Donor_5 3. Aliquot H | 23 | 12 | 46 | 0.49 | 0.26 |
| Donor_5 3. Aliquot I | 22 | 12 | 46 | 0.49 | 0.26 |
| Donor_6 3. Aliquot A | 5.5 | 41 | 6.6 | 3.6 | 1.3 |
| Donor_6 3. Aliquot B | 6.9 | 23 | 4.6 | 3.7 | 1.2 |
| Donor_6 3. Aliquot C | 2.5 | 3.2 | 46 | 3.1 | 1.3 |
| Donor_6 3. Aliquot D | 6.8 | 1910 | 46 | 3.4 | 1.4 |

FIG. 17P.3

| | TNF RII ng/mL | TNF-alpha pg/mL | TNF-beta pg/mL | Thrombopoietin ng/mL | Thyroid Stimulating Hormone uIU/mL |
|---|---|---|---|---|---|
| Least Detectable Dose | 0.13 | 4.0 | 46 | 3.2 | 0.028 |
| RBM Low Plasma Range | 3.1 | | | | 0.18 |
| RBM High Plasma Range | 79 | 27 | 120 | 6.2 | 3.7 |
| Donor_6 3. Aliquot E | 7.8 | 3210 | 46 | 3.6 | 1.3 |
| Donor_6 3. Aliquot F | 4.1 | 9.1 | 46 | 4.0 | 1.1 |
| Donor_6 3. Aliquot G | 5.1 | 12 | 46 | 2.3 | 1.3 |
| Donor_6 3. Aliquot H | 3.0 | 8.0 | 8.6 | 1.7 | 1.2 |
| Donor_6 3. Aliquot I | 2.4 | 1.7 | 46 | 1.7 | 1.2 |
| Donor_7 3. Aliquot A | 14 | 240 | 24 | 4.2 | 0.52 |
| Donor_7 3. Aliquot B | 14 | 67 | 14 | 4.3 | 0.51 |
| Donor_7 3. Aliquot C | 7.8 | 4.3 | 7.9 | 1.4 | 0.49 |
| Donor_7 3. Aliquot D | 13 | 1250 | 8.6 | 3.3 | 0.55 |
| Donor_7 3. Aliquot E | 13 | 338 | 19 | 3.8 | 0.50 |
| Donor_7 3. Aliquot F | 8.4 | 19 | 9.8 | 3.5 | 0.47 |
| Donor_7 3. Aliquot G | 10.0 | 17 | 46 | 1.0 | 0.49 |
| Donor_7 3. Aliquot H | 6.4 | 5.1 | 46 | 3.2 | 0.49 |
| Donor_7 3. Aliquot I | 7.0 | 2.7 | 46 | 2.2 | 0.47 |
| Donor_8 3. Aliquot A | 3.8 | 129 | 7.9 | 3.6 | 2.2 |
| Donor_8 3. Aliquot B | 5.1 | 49 | 6.0 | 4.7 | 2.1 |
| Donor_8 3. Aliquot C | 1.7 | 184 | 46 | 4.4 | 1.8 |
| Donor_8 3. Aliquot D | 3.8 | 12200 | 11 | 4.4 | 2.4 |
| Donor_8 3. Aliquot E | 4.7 | 7570 | 11 | 4.2 | 2.2 |
| Donor_8 3. Aliquot F | 3.2 | 591 | 9.8 | 5.6 | 2.0 |
| Donor_8 3. Aliquot G | 2.8 | 22 | 46 | 1.4 | 1.9 |
| Donor_8 3. Aliquot H | 2.5 | 113 | 3.9 | 3.7 | 2.2 |
| Donor_8 3. Aliquot I | 1.9 | 14 | 46 | 3.8 | 2.0 |
| Donor_9 3. Aliquot A | 3.6 | 78 | 11 | 3.2 | 0.34 |
| Donor_9 3. Aliquot B | 4.4 | 51 | 8.8 | 3.4 | 0.28 |

FIG. 17P.4

| | | TNF RII<br>ng/mL | TNF-alpha<br>pg/mL | TNF-beta<br>pg/mL | Thrombopoietin<br>ng/mL | Thyroid Stimulating Hormone<br>uIU/mL |
|---|---|---|---|---|---|---|
| | Least Detectable Dose | 0.13 | 4.0 | 46 | 3.2 | 0.028 |
| | RBM Low Plasma Range | 3.1 | | | | 0.18 |
| | RBM High Plasma Range | 79 | 27 | 120 | 6.2 | 3.7 |
| | Donor_9 3. Aliquot C | 3.3 | 68 | 20 | 3.6 | 0.33 |
| | Donor_9 3. Aliquot D | 5.2 | 6000 | 15 | 2.9 | 0.65 |
| | Donor_9 3. Aliquot E | 5.6 | 4600 | 5.0 | 3.1 | 0.53 |
| | Donor_9 3. Aliquot F | 2.7 | 81 | 18 | 4.3 | 0.29 |
| | Donor_9 3. Aliquot G | 3.9 | 55 | 6.9 | 1.2 | 0.22 |
| | Donor_9 3. Aliquot H | 2.5 | 22 | 10 | 1.8 | 0.31 |
| | Donor_9 3. Aliquot I | 1.9 | 13 | 46 | 2.3 | 0.28 |
| | EDTA Plasma | | | | | |
| | donor #1 plasma | 27 | 14 | 10 | 3.2 | 12 |
| | donor #2 plasma | 51 | 5.4 | 46 | 3.2 | 9.7 |
| | donor #3 plasma | 8.2 | 5.4 | 8.8 | 0.81 | 1.0 |
| | donor #4 plasma | 34 | 1.1 | 46 | 1.4 | 0.11 |
| | donor #5 plasma | 28 | 2.3 | 11 | 1.8 | 0.28 |
| | donor #6 plasma | 2.6 | 4 | 5.0 | 2.4 | 1.7 |
| | donor #7 plasma | 9.5 | 4 | 13 | 2.1 | 0.59 |
| | donor #8 plasma | 1.2 | 5.6 | 46 | 1.4 | 2.5 |
| | donor #9 plasma | 1.5 | 4 | 46 | 0.44 | 0.30 |
| MW | NHD plasma | 1.3 | 4.8 | 46.0 | 0.9 | 1.4 |
| Normal healthy donors | | | | | | |
| MW | NHD unstimuliert | 1.92 | 13.25 | 46.00 | 3.03 | 1.11 |
| Normal healthy donors | | | | | | |
| | *Stimulations/indices* | | | | | |

FIG. 17P.5

| | | TNF RII ng/mL | TNF-alpha pg/mL | TNF-beta pg/mL | Thrombopoietin ng/mL | Thyroid Stimulating Hormone uIU/mL |
|---|---|---|---|---|---|---|
| Least Detectable Dose | | 0.13 | | | | 0.028 |
| RBM Low Plasma Range | | 3.1 | 4.0 | 46 | 3.2 | 0.18 |
| RBM High Plasma Range | | 79 | 27 | 120 | 6.2 | 3.7 |
| EDTA Plasma | | | | | | |
| patient 1 | PLASMA | | | | | |
| patient 7 | PLASMA | | | | | |
| patient 2 | PLASMA | | | | | |
| patient 3 | PLASMA | | | | | |
| patient 5 | PLASMA | | | | | |
| patient 4 | PLASMA | | | | | |
| patient 6 | PLASMA | | | | | |
| NHD 1 | PLASMA | | | | | |
| NHD 2 | PLASMA | | | | | |

FIG. 17P.6

|  | TNF RII ng/mL | TNF-alpha pg/mL | TNF-beta pg/mL | Thrombopoietin ng/mL | Thyroid Stimulating Hormone uIU/mL |
|---|---|---|---|---|---|
| Least Detectable Dose | 0.13 | 4.0 | 46 | 3.2 | 0.028 |
| RBM Low Plasma Range | 3.1 | | | | 0.18 |
| RBM High Plasma Range | 79 | 27 | 120 | 6.2 | 3.7 |
| Messwert > ULD | | | | | |
| SI > 1,5 | | | | | |
| SI 0,7-1,5 | | | | | |
| SI 0-0,7 | | | | | |
| MW nur von 1 Kontrollperson | | | | | |
| *Stimulationsindices* | | | | | |

FIG. 17P.7
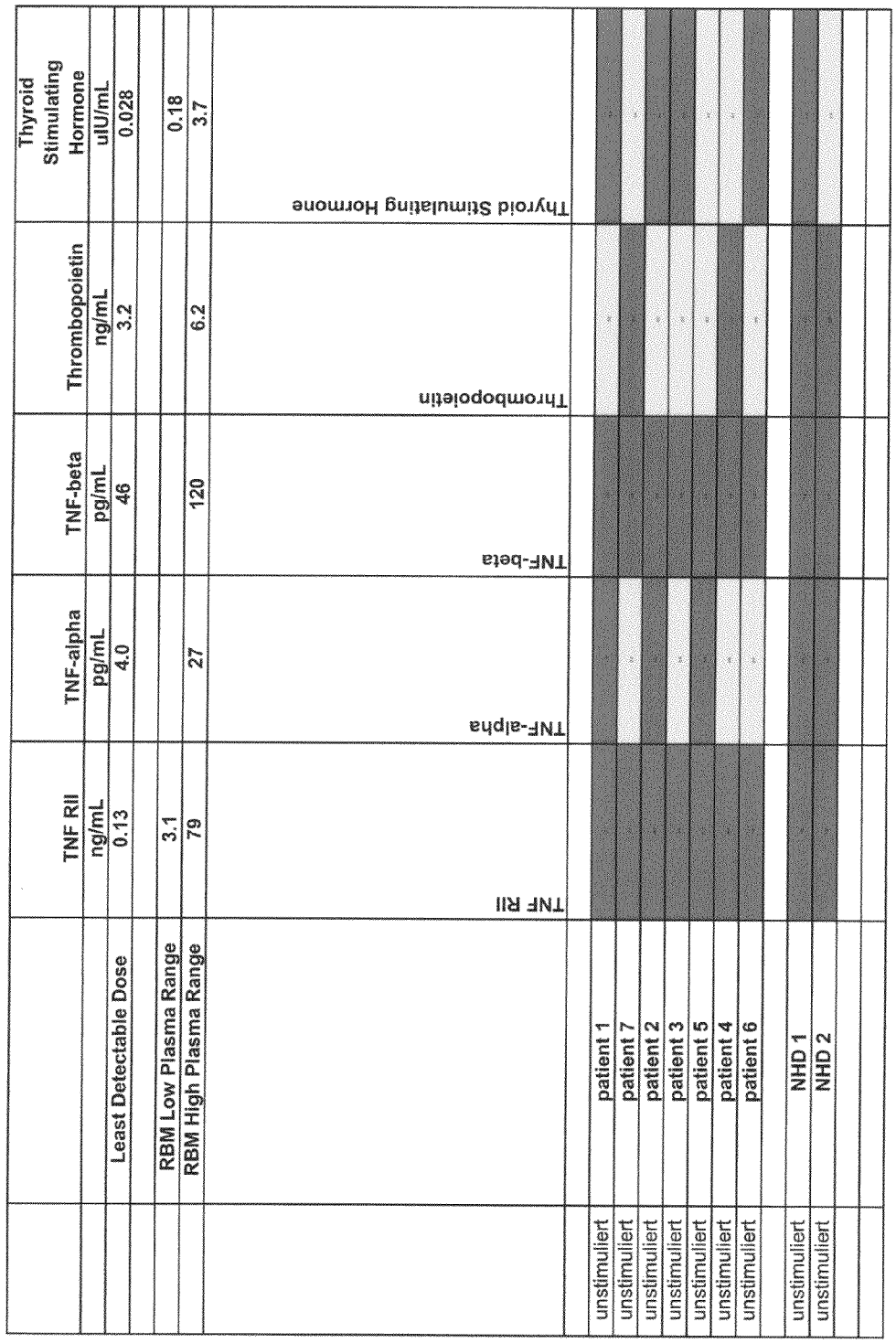

FIG. 17P.8

| | TNF RII | TNF-alpha | TNF-beta | Thrombopoietin | Thyroid Stimulating Hormone |
|---|---|---|---|---|---|
| | ng/mL | pg/mL | pg/mL | ng/mL | uIU/mL |
| Least Detectable Dose | 0.13 | 4.0 | 46 | 3.2 | 0.028 |
| RBM Low Plasma Range | 3.1 | 27 | | | 0.18 |
| RBM High Plasma Range | 79 | | 120 | 6.2 | 3.7 |
| NHD = normal healthy donor | | | | | |

FIG. 17Q.1

| | Thrombospondin-1 ng/mL | VCAM-1 ng/mL | VEGF pg/mL | von Willebrand Factor ug/mL |
|---|---|---|---|---|
| Least Detectable Dose | <25 | 2.6 | 7.5 | 0.40 |
| RBM Low Plasma Range | Pending | 284 | 91 | 5.3 |
| RBM High Plasma Range | Pending | 1310 | 1790 | 74 |
| Samples | | | | |
| Donor_1 3. Aliquot A | 15200 | 1350 | 2090 | 211 |
| Donor_1 3. Aliquot B | 21600 | 1440 | 2090 | 203 |
| Donor_1 3. Aliquot C | 17000 | 1350 | 2070 | 213 |
| Donor_1 3. Aliquot D | 15600 | 1420 | 2120 | 198 |
| Donor_1 3. Aliquot E | 13100 | 1320 | 2030 | 184 |
| Donor_1 3. Aliquot F | 12500 | 1310 | 1860 | 196 |
| Donor_1 3. Aliquot G | 11800 | 1450 | 2570 | 180 |
| Donor_1 3. Aliquot H | 24900 | 1320 | 2210 | 207 |
| Donor_1 3. Aliquot I | 16200 | 1350 | 1940 | 203 |
| Donor_2 3. Aliquot A | 19800 | 1090 | 4570 | 188 |
| Donor_2 3. Aliquot B | 21600 | 1190 | 4900 | 200 |
| Donor_2 3. Aliquot C | 12200 | 1160 | 5240 | 191 |
| Donor_2 3. Aliquot D | 13600 | 1070 | 4400 | 190 |
| Donor_2 3. Aliquot E | 12400 | 1150 | 4630 | 189 |
| Donor_2 3. Aliquot F | 12800 | 1100 | 4870 | 178 |
| Donor_2 3. Aliquot G | 12000 | 1180 | 5490 | 215 |
| Donor_2 3. Aliquot H | 13300 | 1090 | 4920 | 213 |
| Donor_2 3. Aliquot I | 12400 | 1080 | 4680 | 187 |
| Donor_3 3. Aliquot A | 14000 | 749 | 532 | 99 |
| Donor_3 3. Aliquot B | 18300 | 722 | 618 | 110 |
| Donor_3 3. Aliquot C | 12000 | 740 | 707 | 95 |
| Donor_3 3. Aliquot D | 13700 | 725 | 505 | 123 |
| Donor_3 3. Aliquot E | 16800 | 775 | 508 | 108 |
| Donor_3 3. Aliquot F | 10500 | 695 | 714 | 104 |

FIG. 17Q.2

| | Thrombospondin-1 ng/mL | VCAM-1 ng/mL | VEGF pg/mL | von Willebrand Factor ug/mL |
|---|---|---|---|---|
| Least Detectable Dose | <25 | 2.6 | 7.5 | 0.40 |
| RBM Low Plasma Range | Pending | 284 | 91 | 5.3 |
| RBM High Plasma Range | Pending | 1310 | 1790 | 74 |
| Donor_3_3. Aliquot G | 12200 | 758 | 1590 | 109 |
| Donor_3_3. Aliquot H | 9670 | 694 | 678 | 123 |
| Donor_3_3. Aliquot I | 9250 | 690 | 734 | 119 |
| Donor_4_3. Aliquot A | 14100 | 2080 | 1190 | 182 |
| Donor_4_3. Aliquot B | 16300 | 1940 | 1180 | 227 |
| Donor_4_3. Aliquot C | 4160 | 1990 | 1220 | 253 |
| Donor_4_3. Aliquot D | 11500 | 1950 | 1100 | 252 |
| Donor_4_3. Aliquot E | 10900 | 2070 | 1060 | 223 |
| Donor_4_3. Aliquot F | 5780 | 2200 | 1030 | 257 |
| Donor_4_3. Aliquot G | 4050 | 1970 | 2190 | 223 |
| Donor_4_3. Aliquot H | 4460 | 1980 | 1350 | 229 |
| Donor_4_3. Aliquot I | 6360 | 2020 | 1280 | 246 |
| Donor_5_3. Aliquot A | 22300 | 521 | 3600 | 100 |
| Donor_5_3. Aliquot B | 17800 | 510 | 3460 | 105 |
| Donor_5_3. Aliquot C | 13300 | 489 | 4460 | 113 |
| Donor_5_3. Aliquot D | 18600 | 525 | 3350 | 112 |
| Donor_5_3. Aliquot E | 17800 | 539 | 3650 | 125 |
| Donor_5_3. Aliquot F | 13200 | 495 | 3140 | 109 |
| Donor_5_3. Aliquot G | 14000 | 545 | 5580 | 110 |
| Donor_5_3. Aliquot H | 14800 | 510 | 3840 | 121 |
| Donor_5_3. Aliquot I | 10900 | 489 | 3520 | 96 |
| Donor_6_3. Aliquot A | 25000 | 258 | 874 | 79 |
| Donor_6_3. Aliquot B | 22900 | 252 | 648 | 70 |
| Donor_6_3. Aliquot C | 13800 | 261 | 840 | 74 |
| Donor_6_3. Aliquot D | 21100 | 274 | 530 | 75 |

FIG. 17Q.3

| | Thrombospondin-1 ng/mL | VCAM-1 ng/mL | VEGF pg/mL | von Willebrand Factor ug/mL |
|---|---|---|---|---|
| Least Detectable Dose | <25 | 2.6 | 7.5 | 0.40 |
| RBM Low Plasma Range | Pending | 284 | 91 | 5.3 |
| RBM High Plasma Range | Pending | 1310 | 1790 | 74 |
| Donor_6_3. Aliquot E | 13800 | 253 | 471 | 72 |
| Donor_6_3. Aliquot F | 15700 | 254 | 581 | 80 |
| Donor_6_3. Aliquot G | 12400 | 284 | 2690 | 85 |
| Donor_6_3. Aliquot H | 14500 | 258 | 878 | 76 |
| Donor_6_3. Aliquot I | 12500 | 256 | 846 | 67 |
| Donor_7_3. Aliquot A | 12100 | 789 | 295 | 112 |
| Donor_7_3. Aliquot B | 14600 | 802 | 237 | 129 |
| Donor_7_3. Aliquot C | 15800 | 861 | 345 | 132 |
| Donor_7_3. Aliquot D | 11600 | 740 | 210 | 124 |
| Donor_7_3. Aliquot E | 11200 | 816 | 235 | 102 |
| Donor_7_3. Aliquot F | 7230 | 781 | 203 | 135 |
| Donor_7_3. Aliquot G | 6360 | 803 | 1260 | 114 |
| Donor_7_3. Aliquot H | 7470 | 721 | 313 | 127 |
| Donor_7_3. Aliquot I | 7470 | 738 | 257 | 123 |
| Donor_8_3. Aliquot A | 10800 | 352 | 252 | 18 |
| Donor_8_3. Aliquot B | 14000 | 350 | 203 | 23 |
| Donor_8_3. Aliquot C | 10800 | 320 | 401 | 16 |
| Donor_8_3. Aliquot D | 8580 | 319 | 416 | 19 |
| Donor_8_3. Aliquot E | 11900 | 322 | 341 | 17 |
| Donor_8_3. Aliquot F | 4870 | 341 | 321 | 20 |
| Donor_8_3. Aliquot G | 5370 | 337 | 822 | 21 |
| Donor_8_3. Aliquot H | 12600 | 331 | 322 | 22 |
| Donor_8_3. Aliquot I | 13200 | 347 | 248 | 21 |
| Donor_9_3. Aliquot A | 13600 | 298 | 326 | Pending |
| Donor_9_3. Aliquot B | 16400 | 303 | 280 | Pending |

FIG. 17Q.4

| | | Thrombospondin-1 ng/mL | VCAM-1 ng/mL | VEGF pg/mL | von Willebrand Factor ug/mL |
|---|---|---|---|---|---|
| | Least Detectable Dose | <25 | 2.6 | 7.5 | 0.40 |
| | | | | | |
| | RBM Low Plasma Range | Pending | 284 | 91 | 5.3 |
| | RBM High Plasma Range | Pending | 1310 | 1790 | 74 |
| | Donor_9_3. Aliquot C | 15500 | 324 | 367 | Pending |
| | Donor_9_3. Aliquot D | 13800 | 295 | 486 | Pending |
| | Donor_9_3. Aliquot E | 11300 | 312 | 398 | Pending |
| | Donor_9_3. Aliquot F | 6910 | 314 | 322 | Pending |
| | Donor_9_3. Aliquot G | 9900 | 297 | 1170 | Pending |
| | Donor_9_3. Aliquot H | 15900 | 297 | 380 | Pending |
| | Donor_9_3. Aliquot I | 17000 | 290 | 243 | Pending |
| | | | | | |
| EDTA Plasma | | | | | |
| | donor #1 plasma | 14800 | 1230 | 1500 | Pending |
| | donor #2 plasma | 4670 | 1280 | 4500 | Pending |
| | donor #3 plasma | 7890 | 978 | 1290 | Pending |
| | donor #4 plasma | 2310 | 2580 | 1400 | Pending |
| | donor #5 plasma | 28600 | 577 | 3840 | Pending |
| | donor #6 plasma | 16800 | 301 | 533 | Pending |
| | donor #7 plasma | 13800 | 980 | 521 | Pending |
| | donor #8 plasma | 6520 | 340 | 281 | Pending |
| | donor #9 plasma | 818 | 385 | 295 | Pending |
| | | | | | |
| MW | NHD plasma | 3669.0 | 362.5 | 288.0 | #DIV/0! |
| Normal healthy donors | | | | | |
| | | | | | |
| MW | NHD unstimuliert | 15100.00 | 318.50 | 245.50 | 21.20 |
| Normal healthy donors | | | | | |
| | | | | | |
| *Stimulationsindices* | | | | | |

FIG. 17Q.5
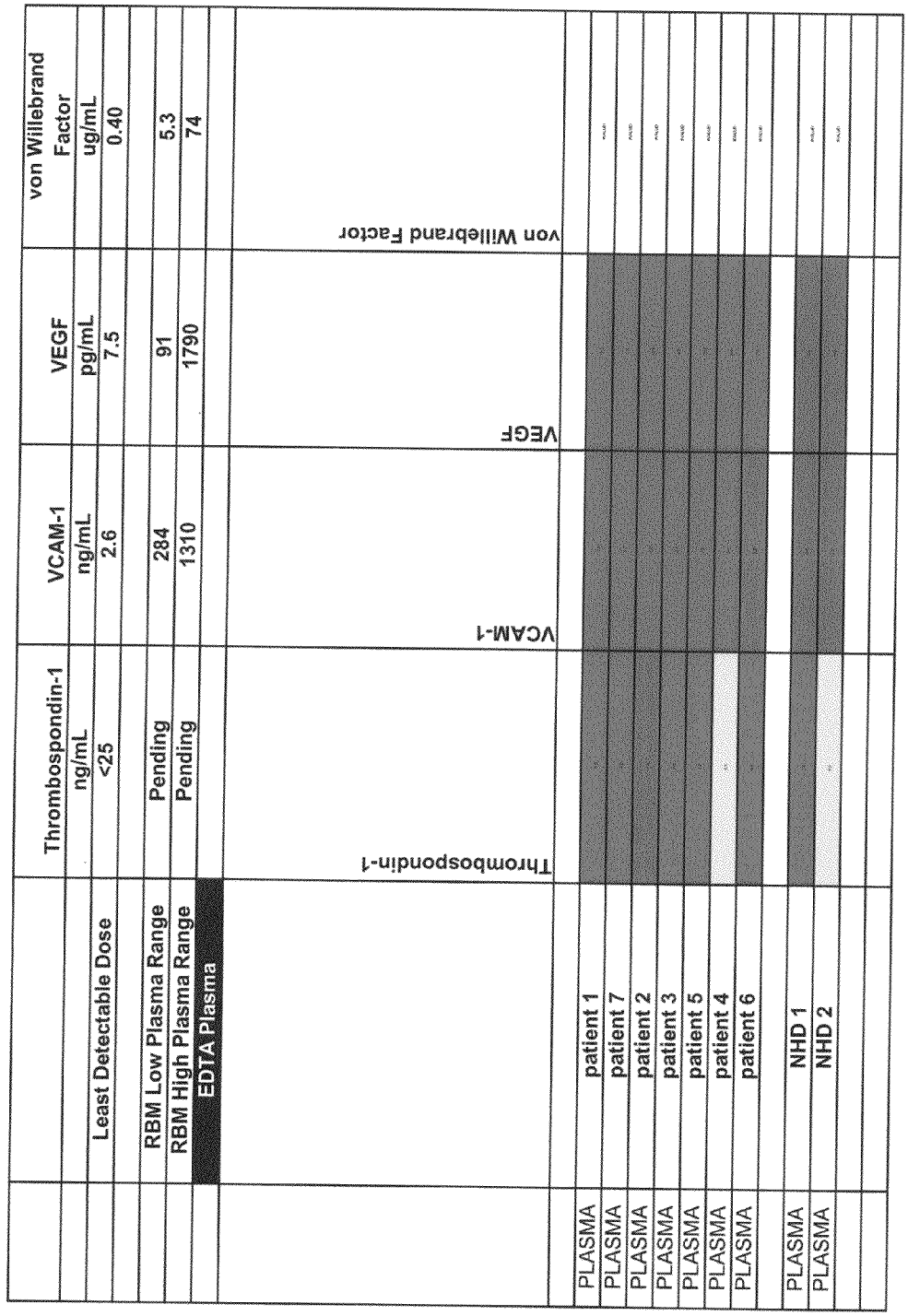

FIG. 17Q.6

| | Thrombospondin-1 ng/mL | VCAM-1 ng/mL | VEGF pg/mL | von Willebrand Factor ug/mL |
|---|---|---|---|---|
| Least Detectable Dose | <25 | 2.6 | 7.5 | 0.40 |
| RBM Low Plasma Range | Pending | 284 | 91 | 5.3 |
| RBM High Plasma Range | Pending | 1310 | 1790 | 74 |
| Messwert > ULD | | | | |
| SI > 1,5 | | | | |
| SI 0,7-1,5 | | | | |
| SI 0-0,7 | | | | |
| MW nur von 1 Kontrollperson | | | | |
| Stimulationsindices | | | | |

FIG. 17Q.7

| | Least Detectable Dose | RBM Low Plasma Range | RBM High Plasma Range | | Thrombospondin-1 ng/mL | VCAM-1 ng/mL | VEGF pg/mL | von Willebrand Factor ug/mL |
|---|---|---|---|---|---|---|---|---|
| | | | | | <25 | 2.6 | 7.5 | 0.40 |
| | | | | | Pending | 284 | 91 | 5.3 |
| | | | | | Pending | 1310 | 1790 | 74 |
| | | | | | Thrombospondin-1 | VCAM-1 | VEGF | von Willebrand Factor |
| unstimuliert | | | | patient 1 | | | | |
| unstimuliert | | | | patient 7 | | | | |
| unstimuliert | | | | patient 2 | | | | |
| unstimuliert | | | | patient 3 | | | | |
| unstimuliert | | | | patient 5 | | | | |
| unstimuliert | | | | patient 4 | | | | |
| unstimuliert | | | | patient 6 | | | | |
| unstimuliert | | | | NHD 1 | | | | |
| unstimuliert | | | | NHD 2 | | | | |

FIG. 17Q.8

| | Thrombospondin-1 ng/mL | VCAM-1 ng/mL | VEGF pg/mL | von Willebrand Factor ug/mL |
|---|---|---|---|---|
| Least Detectable Dose | <25 | 2.6 | 7.5 | 0.40 |
| RBM Low Plasma Range | Pending | 284 | 91 | 5.3 |
| RBM High Plasma Range | Pending | 1310 | 1790 | 74 |
| NHD = normal healthy donor | | | | |

FIG. 17R.1

| | Thrombospondin-1 | | VCAM-1 | | VEGF | | von Willebrand Factor | |
|---|---|---|---|---|---|---|---|---|
| | | ng/mL | | ng/mL | | pg/mL | | ug/mL |
| Least Detectable Dose | | <25 | | 2.6 | | 7.5 | | 0.40 |
| RBM Low Plasma Range | Pending | | 284 | | 91 | | 5.3 | |
| RBM High Plasma Range | Pending | | 1310 | | 1790 | | 74 | |
| Samples | | | | | | | | |
| Donor_1 3. Aliquot A | | 15200 | | 1350 | | 2090 | | 211 |
| Donor_1 3. Aliquot B | | 21600 | | 1440 | | 2090 | | 203 |
| Donor_1 3. Aliquot C | | 17000 | | 1350 | | 2070 | | 213 |
| Donor_1 3. Aliquot D | | 15600 | | 1420 | | 2120 | | 198 |
| Donor_1 3. Aliquot E | | 13100 | | 1320 | | 2030 | | 184 |
| Donor_1 3. Aliquot F | | 12500 | | 1310 | | 1860 | | 196 |
| Donor_1 3. Aliquot G | | 11800 | | 1450 | | 2570 | | 180 |
| Donor_1 3. Aliquot H | | 24900 | | 1320 | | 2210 | | 207 |
| Donor_1 3. Aliquot I | | 16200 | | 1350 | | 1940 | | 203 |
| Donor_2 3. Aliquot A | | 19800 | | 1090 | | 4570 | | 188 |
| Donor_2 3. Aliquot B | | 21600 | | 1190 | | 4900 | | 200 |
| Donor_2 3. Aliquot C | | 12200 | | 1160 | | 5240 | | 191 |
| Donor_2 3. Aliquot D | | 13600 | | 1070 | | 4400 | | 190 |
| Donor_2 3. Aliquot E | | 12400 | | 1150 | | 4630 | | 189 |
| Donor_2 3. Aliquot F | | 12800 | | 1100 | | 4870 | | 178 |
| Donor_2 3. Aliquot G | | 12000 | | 1180 | | 5490 | | 215 |
| Donor_2 3. Aliquot H | | 13300 | | 1090 | | 4920 | | 213 |
| Donor_2 3. Aliquot I | | 12400 | | 1080 | | 4680 | | 187 |
| Donor_3 3. Aliquot A | | 14000 | | 749 | | 532 | | 99 |
| Donor_3 3. Aliquot B | | 18300 | | 722 | | 618 | | 110 |
| Donor_3 3. Aliquot C | | 12000 | | 740 | | 707 | | 95 |
| Donor_3 3. Aliquot D | | 13700 | | 725 | | 505 | | 123 |
| Donor_3 3. Aliquot E | | 16800 | | 775 | | 508 | | 108 |
| Donor_3 3. Aliquot F | | 10500 | | 695 | | 714 | | 104 |

FIG. 17R.2

| | Thrombospondin-1 | VCAM-1 | VEGF | von Willebrand Factor |
|---|---|---|---|---|
| | ng/mL | ng/mL | pg/mL | ug/mL |
| Least Detectable Dose | <25 | 2.6 | 7.5 | 0.40 |
| RBM Low Plasma Range | Pending | 284 | 91 | 5.3 |
| RBM High Plasma Range | Pending | 1310 | 1790 | 74 |
| Donor_3 3. Aliquot G | 12200 | 758 | 1590 | 109 |
| Donor_3 3. Aliquot H | 9670 | 694 | 678 | 123 |
| Donor_3 3. Aliquot I | 9250 | 690 | 734 | 119 |
| Donor_4 3. Aliquot A | 14100 | 2080 | 1190 | 182 |
| Donor_4 3. Aliquot B | 16300 | 1940 | 1180 | 227 |
| Donor_4 3. Aliquot C | 4160 | 1990 | 1220 | 253 |
| Donor_4 3. Aliquot D | 11500 | 1950 | 1100 | 252 |
| Donor_4 3. Aliquot E | 10900 | 2070 | 1060 | 223 |
| Donor_4 3. Aliquot F | 5780 | 2200 | 1030 | 257 |
| Donor_4 3. Aliquot G | 4050 | 1970 | 2190 | 223 |
| Donor_4 3. Aliquot H | 4460 | 1980 | 1350 | 229 |
| Donor_4 3. Aliquot I | 6360 | 2020 | 1280 | 246 |
| Donor_5 3. Aliquot A | 22300 | 521 | 3600 | 100 |
| Donor_5 3. Aliquot B | 17800 | 510 | 3460 | 105 |
| Donor_5 3. Aliquot C | 13300 | 489 | 4460 | 113 |
| Donor_5 3. Aliquot D | 18600 | 525 | 3350 | 112 |
| Donor_5 3. Aliquot E | 17800 | 539 | 3650 | 125 |
| Donor_5 3. Aliquot F | 13200 | 495 | 3140 | 109 |
| Donor_5 3. Aliquot G | 14000 | 545 | 5580 | 110 |
| Donor_5 3. Aliquot H | 14800 | 510 | 3840 | 121 |
| Donor_5 3. Aliquot I | 10900 | 489 | 3520 | 96 |
| Donor_6 3. Aliquot A | 25000 | 258 | 874 | 79 |
| Donor_6 3. Aliquot B | 22900 | 252 | 648 | 70 |
| Donor_6 3. Aliquot C | 13800 | 261 | 840 | 74 |
| Donor_6 3. Aliquot D | 21100 | 274 | 530 | 75 |

FIG. 17R.3

| | Thrombospondin-1 | VCAM-1 | VEGF | von Willebrand Factor |
|---|---|---|---|---|
| | ng/mL | ng/mL | pg/mL | ug/mL |
| Least Detectable Dose | <25 | 2.6 | 7.5 | 0.40 |
| RBM Low Plasma Range | Pending | | | |
| RBM High Plasma Range | Pending | 284 | 91 | 5.3 |
| Donor_6 3. Aliquot E | 13800 | 1310 | 1790 | 74 |
| Donor_6 3. Aliquot F | 15700 | 253 | 471 | 72 |
| Donor_6 3. Aliquot G | 12400 | 254 | 581 | 80 |
| Donor_6 3. Aliquot H | 14500 | 284 | 2690 | 85 |
| Donor_6 3. Aliquot I | 12500 | 258 | 878 | 76 |
| | | 256 | 846 | 67 |
| Donor_7 3. Aliquot A | 12100 | 789 | 295 | 112 |
| Donor_7 3. Aliquot B | 14600 | 802 | 237 | 129 |
| Donor_7 3. Aliquot C | 15800 | 861 | 345 | 132 |
| Donor_7 3. Aliquot D | 11600 | 740 | 210 | 124 |
| Donor_7 3. Aliquot E | 11200 | 816 | 235 | 102 |
| Donor_7 3. Aliquot F | 7230 | 781 | 203 | 135 |
| Donor_7 3. Aliquot G | 6360 | 803 | 1260 | 114 |
| Donor_7 3. Aliquot H | 7470 | 721 | 313 | 127 |
| Donor_7 3. Aliquot I | 7470 | 738 | 257 | 123 |
| Donor_8 3. Aliquot A | 10800 | 352 | 252 | 18 |
| Donor_8 3. Aliquot B | 14000 | 350 | 203 | 23 |
| Donor_8 3. Aliquot C | 10800 | 320 | 401 | 16 |
| Donor_8 3. Aliquot D | 8580 | 319 | 416 | 19 |
| Donor_8 3. Aliquot E | 11900 | 322 | 341 | 17 |
| Donor_8 3. Aliquot F | 4870 | 341 | 321 | 20 |
| Donor_8 3. Aliquot G | 5370 | 337 | 822 | 21 |
| Donor_8 3. Aliquot H | 12600 | 331 | 322 | 22 |
| Donor_8 3. Aliquot I | 13200 | 347 | 248 | 21 |
| Donor_9 3. Aliquot A | 13600 | 298 | 326 | Pending |
| Donor_9 3. Aliquot B | 16400 | 303 | 280 | Pending |

FIG. 17R.4

| | Thrombospondin-1 | | VCAM-1 | | VEGF | | von Willebrand Factor | |
|---|---|---|---|---|---|---|---|---|
| | | ng/mL | | ng/mL | | pg/mL | | ug/mL |
| Least Detectable Dose | | <25 | | 2.6 | | 7.5 | | 0.40 |
| RBM Low Plasma Range | Pending | | 284 | | 91 | | 5.3 | |
| RBM High Plasma Range | Pending | | 1310 | | 1790 | | 74 | |
| Donor 9 3. Aliquot C | | 15500 | | 324 | | 367 | | Pending |
| Donor 9 3. Aliquot D | | 13800 | | 295 | | 486 | | Pending |
| Donor 9 3. Aliquot E | | 11300 | | 312 | | 398 | | Pending |
| Donor 9 3. Aliquot F | | 6910 | | 314 | | 322 | | Pending |
| Donor 9 3. Aliquot G | | 9900 | | 297 | | 1170 | | Pending |
| Donor 9 3. Aliquot H | | 15900 | | 297 | | 380 | | Pending |
| Donor 9 3. Aliquot I | | 17000 | | 290 | | 243 | | Pending |
| EDTA Plasma | | | | | | | | |
| donor #1 plasma | | 14800 | | 1230 | | 1500 | | Pending |
| donor #2 plasma | | 4670 | | 1280 | | 4500 | | Pending |
| donor #3 plasma | | 7890 | | 978 | | 1290 | | Pending |
| donor #4 plasma | | 2310 | | 2580 | | 1400 | | Pending |
| donor #5 plasma | | 28600 | | 577 | | 3840 | | Pending |
| donor #6 plasma | | 16800 | | 301 | | 533 | | Pending |
| donor #7 plasma | | 13800 | | 980 | | 521 | | Pending |
| donor #8 plasma | | 6520 | | 340 | | 281 | | Pending |
| donor #9 plasma | | 818 | | 385 | | 295 | | Pending |
| MW NHD plasma | | 3669.0 | | 362.5 | | 288.0 | | #DIV/0! |
| Normal healthy donors | | | | | | | | |
| MW NHD unstimuliert | | 15100.00 | | 318.50 | | 245.50 | | 21:20 |
| Normal healthy donors | | | | | | | | |

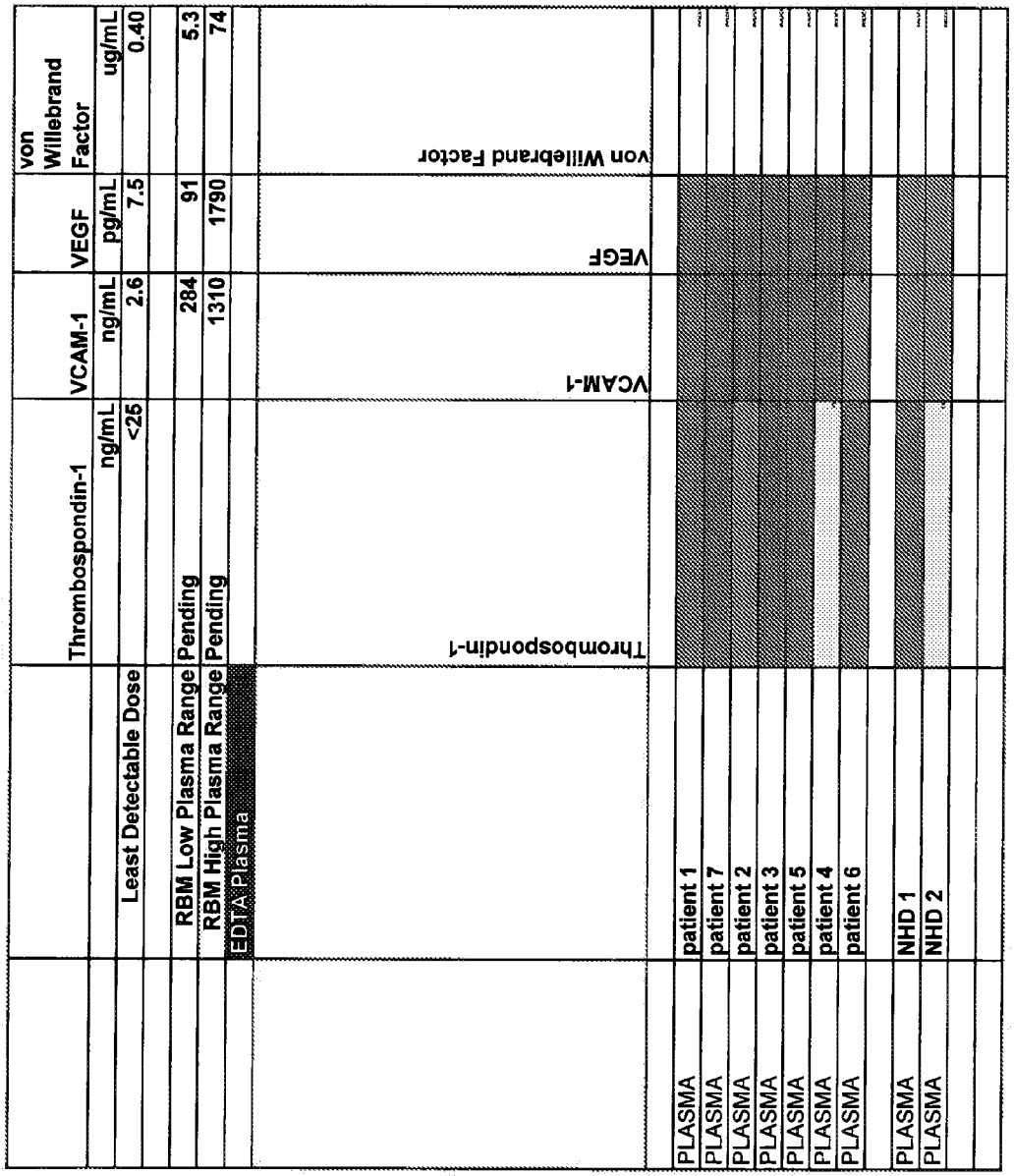
FIG. 17R.5

FIG. 17R.6

| | Thrombospondin-1 | VCAM-1 | | VEGF | | von Willebrand Factor | |
|---|---|---|---|---|---|---|---|
| | | ng/mL | | pg/mL | | ug/mL | |
| | | ng/mL | | | | | |
| Least Detectable Dose | <25 | 2.6 | | 7.5 | | 0.40 | |
| RBM Low Plasma Range | Pending | 284 | | 91 | | 5.3 | |
| RBM High Plasma Range | Pending | 1310 | | 1790 | | 74 | |
| Messwert > ULD | | | | | | | |
| SI > 1,5 | | | | | | | |
| SI 0,7-1,5 | | | | | | | |
| SI 0-0,7 | | | | | | | |
| MW nur von 1 Kontrollperson | | | | | | | |

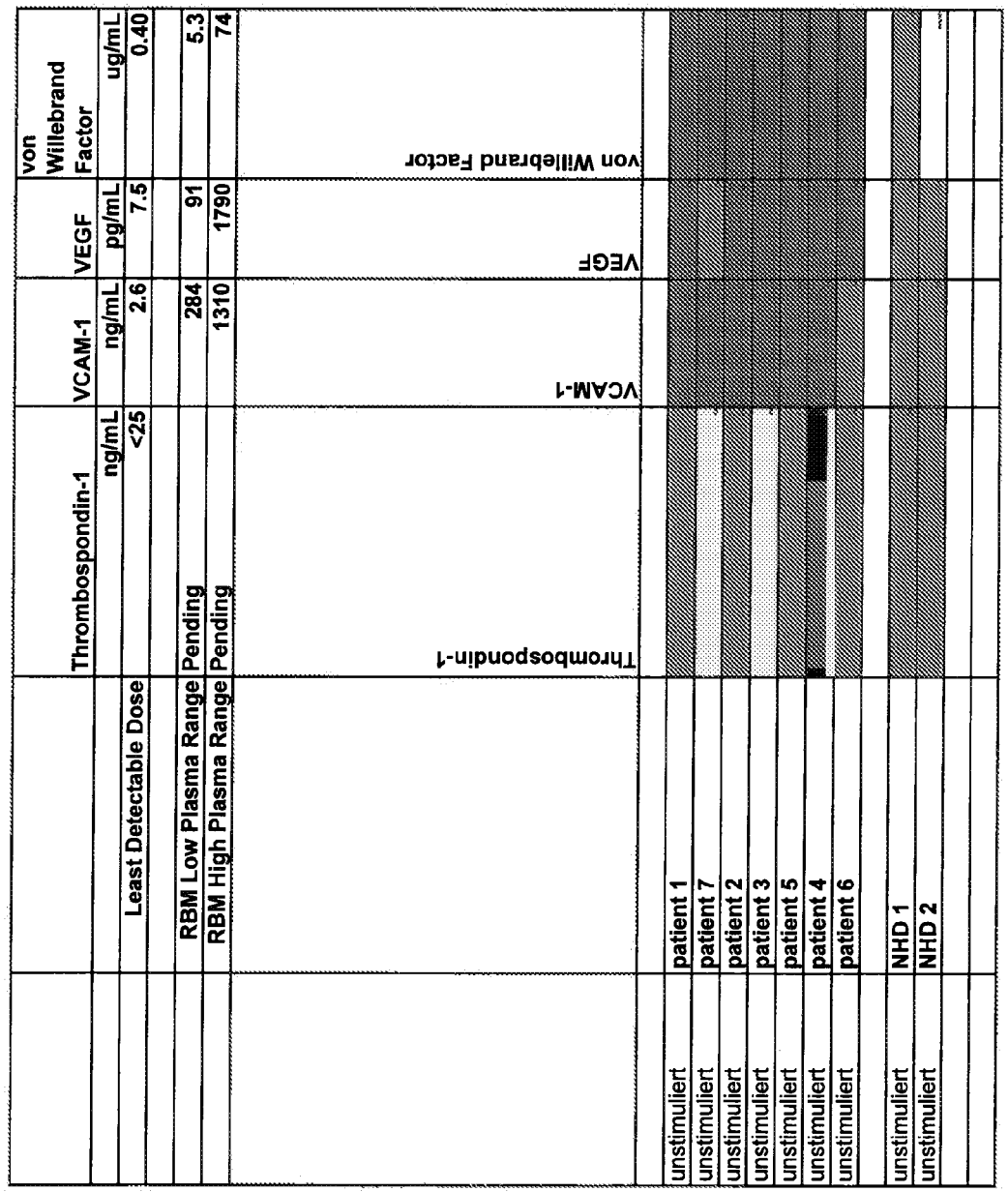
FIG. 17R.7

FIG. 17R.8

| | Thrombospondin-1 | VCAM-1 | | VEGF | | von Willebrand Factor | |
|---|---|---|---|---|---|---|---|
| | ng/mL | | ng/mL | | pg/mL | | ug/mL |
| Least Detectable Dose | <25 | | 2.6 | | 7.5 | | 0.40 |
| RBM Low Plasma Range | Pending | | 284 | | 91 | | 5.3 |
| RBM High Plasma Range | Pending | | 1310 | | 1790 | | 74 |

NHD = normal healthy donor

ILCS BASED PATTERN RECOGNITION OF SEPSIS

CROSS-REFERENCE TO RELATED PATENT APPLICATIONS

This application claims priority to GERM Priority Application DE102006062398.3, filed Dec. 20, 2006 including the specification, drawings, claims and abstract, which are incorporated herein by reference in their entireties.

BACKGROUND OF THE INVENTION

Early recognition of diseases and, in particular, the prognosis of the continued course of a disease is of fundamental importance in medicine. This point especially applies to inflammatory diseases. In the case of inflammatory diseases, however, diagnosis and monitoring is complicated by the fact that these diseases are frequently accompanied by an immune reaction that affects the whole body (systemic); this results in rapid and particularly serious developments. This applies to septic diseases, which are accompanied by an above-average mortality rate.

Blood analyses can be performed to diagnose diseases. When the blood is tested, as a rule ordinary blood counts, which are quick and cheap to produce, are performed. These provide a numerical analysis of the constituents of the blood, in particular the blood cells. It is therefore possible to establish shifts in the ratio of the individual blood constituents caused by disease. Morphological cell transformations can also be determined. It is, however, a disadvantage that these quick blood tests do not permit a dynamic examination, e.g., no examination of the immunological behavior of the blood cells towards the pathogen types. For inflammatory diseases, particularly in connection with an over-activation of the immune system, a dynamic examination is of special significance. If there is septic shock, in these forms of diseases the cells of the immune system suffer a state of exhaustion known as anergy. The occurrence of anergy correlates acutely to the further fate of the patient concerned.

In a case of sepsis, the immune system reacts to the intrusion of inflammatory pathogens by a systemic immune reaction. As a consequence of the systemic immune reaction, the blood vessels dilate, thereby limiting the blood supply to the organs and impairing their function, for example, the dilatation of the blood vessels causes an undersupply of nutrients and oxygen to the brain, which can result in a septic shock. Additionally, pathogens are exported through the dilated blood vessels into the tissue and, especially, the organs. Viable, inflammatory pathogens, therefore, are to be found not only in the blood, but basically in all regions of the body, irrespective of the primary focus of infection. Damage to organs and tissue can be caused both by bacterial toxins and by activated cells of the immune system. In many cases progressive septic diseases become manifest in multiple organ failure. In Germany, for example, 250,000 to 300,000 new cases of sepsis are registered each year.

Many aspects of the complex nature of the functioning of the immune system are unknown. Uncertainty in many regards can lead to severe consequences. Well-documented clinical trial problems highlight the fact that relatively little is still known about the complex functioning of the human immune system. It is possible to treat the septic vasodilation by administering catecholamines, which cause the blood vessels to contract. If the sepsis becomes more serious, however, it is frequently associated with a catecholamine resistance. Methods for diagnosing and monitoring different subtypes of sepsis and septic shock are, and further elucidation of immune system interactions, therefore, are necessary.

SUMMARY OF THE INVENTION

The present invention provides an in vitro method that permits the determination of the immunological performance of blood cells in response to certain pathogenic stimulants. In particular, the invention is directed to methods for recognizing and/or characterizing cellular activity patterns (pattern recognition) for the purpose of diagnosis and/or for monitoring the efficacy of therapy of diseases. Methods include the use of Multi-Analyte Profiling (MAP) to identify characteristic patterns. Blood cells are stimulated in a culture medium with toll-like receptor ligands (TLR ligands) and the stimulated blood cells and/or the culture medium are examined. The methods and kits for implementing the methods described herein are referred to as Instant Leukocyte Culture System (ILCS).

ILCS is used many ways. A container tube can be manufactured with a blood cell stimulant or without. Candidate effective agents can be added, for example, to determine if the agent impedes stimulation if a stimulant is present or if no stimulant is present then it can be determined whether the agent alone appropriately or inappropriately stimulates the immune system. It can also be used in allergy testing where the stimulant is a group of allergens whereby if the patient is allergic (primed) to one of the allergens they will react vigorously to that allergen. The true co-culture systems combine skin and blood or gastrointestinal epithelium and blood, as well as others into three dimensional systems.

In one embodiment, the present invention is directed to a method for determining cellular activity patterns of one or more molecules that are differentially expressed in blood cells in response to different or no stimuli, wherein the cellular activity pattern is indicative of an inflammatory disease. In a particular embodiment, the blood cells are stimulated with at least one toll-like receptor ligand. In one embodiment, the one or more molecules is detected in culture media in contact with the blood cell. In one embodiment, changes to the cellular activity pattern is measured by detecting changes in chemical, biochemical and/or biological parameters in the blood cells. In a particular embodiment, the one or more molecules is detected in the blood cells after recovery from the culture medium. In one embodiment, the one or more molecules comprise mRNA. In another embodiment, the one or more molecules comprise a polypeptide, e.g., a signal transducer or receptor. In one embodiment, the one or more molecules comprise blood cell nuclear constituents. In another embodiment, the stimulated blood cells are stimulated with one or more human toll-like receptors ligands, e.g., a human toll-like receptor ligand that is selected from the group consisting of: hTLR1, hTLR2, hTLR3, hTLR4, hTLR5, hTLR6, hTLR7, hTLR8, hTLR9, hTLR10 and hTLR11. In another embodiment, the stimulated blood cells are stimulated with one or more TLR ligands derived from a microbe, e.g., a bacterium, virus or fungus. In another embodiment, compounds that occur in bacterial cell walls and/or in cell membranes are used as TLR ligands to stimulate the blood cells. In one embodiment, the stimulated blood cells are stimulated with at least one TLR ligand selected from the group consisting of: lipopolysaccharides, lipoproteins, lipopeptides, lipoteichoic acids, glycans, muramyl peptides, mannans, DNA and RNA. In one embodiment, the stimulated blood cells are stimulated with Imiquimod (1-isobutyl-1H-imidazo[4,5-c]quinoline-4-amine) or Loxoribine (7-allyl-8-oxoguanosin). In one embodiment, the methods comprise a co-stimulation factor, e.g., a cell-receptor ligand, e.g., an integrin-receptor ligand or a NOD receptor ligand. In one embodiment, the blood cells are stimulated with exosomes or nucleosomes. In another embodiment, the blood cells are stimulated with a toll-like receptor ligand that binds more than one toll-like receptor. In one embodiment, the cellular activity patterns are determined in cells grown in parallel cultures, for example, wherein a primary culture is diluted about 1 to 100, about 1 to 50 or about 1 to 1 into parallel cultures. The culture media in each parallel culture can comprise a different TLR ligands or no TLR ligand. In one embodiment, the cellular activity pattern is determined in a biological sample from a subject. In one embodiment, the biological sample comprises immune cells of the peripheral blood or leukocytes. In one embodiment, the biological sample is a whole blood sample. In one embodiment, the blood cells are stimulated during a period of 0 to 48 hours, or during a period of 1 to 30 minutes, or during a period of 1 to 4 hours, or during a period of 6 to 24 hours. In one embodiment, the one or more molecules comprise at least one pre-formed mediator. In one embodiment, the one or more molecules comprise a newly synthesized low molecular weight substance. In one embodiment, the one or more molecules comprises at least one enzyme.

In another embodiment, the present invention is directed to a method for monitoring the severity of an inflammatory disease comprising comparing the cellular activity pattern of a biological sample from a subject to one or more control cellular activity patterns, wherein a statistical similarity of the sample to the control is indicative of a particular stage of the inflammatory disease. In one embodiment, the one or more control cellular activity patterns are determined in blood cells stimulated with at least one toll-like receptor ligand. In one embodiment, the inflammatory disease is associated with a systemic inflammatory response syndrome. The inflammatory disease can be, for example a septic disease or a macrophage activation syndrome.

In another embodiment, the present invention is directed to a method for determining the efficacy of a treatment for an inflammatory disease comprising comparing the cellular activity pattern of a biological sample from a patient being treated for an inflammatory disease with one or more control cellular activity patterns, wherein a statistical similarity to one or more control cellular activity patterns is indicative of the efficacy of the treatment for the inflammatory disease.

In another embodiment, the present invention is directed to a kit comprising a vessel for stimulating blood cells comprising at least one toll-like receptor ligand.

In another embodiment, the present invention is directed to a cell culture for pre-clinical testing of an agent, comprising a first and second cell culture separated by a permeable layer, wherein the first cell culture comprises a syntopic tissue cell and immune cell culture, and wherein the second cell culture comprises a blood cell culture. In one embodiment, the immune cells are phagocytosing immune cells, e.g., monocytes or macrophages. In another embodiment, the syntopic tissue cells are epithelial cells or epithelioid cells or epithelial cells lined around blood vessels. In one embodiment, the syntopic tissue cells are bronchial cells or intestinal epithelial cells. In one embodiment, the tissue cells are skin cells, synovial cells or chondrocytes. In one embodiment, any of the cells in culture are human cells. In one embodiment, the cells of the cell culture are derived from a tissue sample, body fluid sample or whole blood. In one embodiment, the tissue cells are modified during inflammation. In one embodiment, the a substance secreted by a cell in culture is secreted such that the secreted substance can pass through the permeable membrane, e.g., the secreted substance is a cellular activity indicator, e.g., a messenger or cytokine. In one embodiment, the permeable membrane comprises pores having a diameter of between about 0.1 to about 5 μm. In one embodiment, the permeable membrane comprises pores having a diameter of between about 0.2 to about 0.45 μm.

In another embodiment, the present invention is directed to a method for the pre-clinical testing of an agent for a desired activity or lack of activity, comprising: a) using a cell culture system comprising mutually communicating first and second compartments, and further comprising a separation layer that is permeable to at least one substance secreted from a cell, wherein the first compartment comprises a syntopic tissue cell and immune cell culture, and wherein the second compartment comprises a blood cell culture; b) contacting the cell culture system with a candidate agent; c) incubating the cell culture system in the presence of the candidate agent; and d) analyzing cellular activity indicators, wherein the cellular activity indicators are indicative of the presence or absence of a desired activity of the agent. In one embodiment, the cell culture system is primed with a mediator or activator prior to contact with the candidate agent. In one embodiment, the cells of the cell culture system are separated from the cell culture system prior to screening for cellular activity indicators.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 8 shows differential expression of select genes in TLR-3 (top) and TLR-5 (bottom) stimulated cells.

FIG. 11A: fungal sepsis. FIG. 11B: Gram negative bacterial sepsis. FIG. 11C: Gram negative+Gram positive sepsis. FIG. 11D: septic shock. FIG. 11E: Nocturnal haemodialysis (NHD).

FIGS. 12A.1 through 12N4 show expression values for the informative genes listed in Table 1 for 7 sepsis patients and two controls. Multiple aliquots from each donor to determine precision of the expression level measurements. Stimulation indices are as indicated.

FIGS. 12A.1 through 12A.4 show expression values for Alpha-1 Antitrypsin, Adiponectin, Alpha-2-macroglobulin, Alpha-fetoprotein, and Amphiregulin for 7 sepsis patients and two controls. Multiple aliquots from each donor to determine precision of the expression level measurements. Stimulation indices are as indicated.

FIGS. 12B.1 through 12B.4 shows expression values for apolipoprotein A1, Apoliporotein CIII, Apolipoprotein H, and Beta-2 Microglobulin for 7 sepsis patients and two controls. Multiple aliquots from each donor to determine precision of the expression level measurements. Stimulation indices are as indicated.

FIGS. 12C.1 through 12C.4 shows expression values for Brain-Derived neurotrophic Factor, Complement 3, Cancer Antigen 125, Cancer Antigen 19-9, and Calcitonin for 7 sepsis patients and two controls. Multiple aliquots from each donor to determine precision of the expression level measurements. Stimulation indices are as indicated.

FIGS. 12D.1 through 12D.4 shows expression values for CD40, CD40 Ligand, Carcinoembryonic Antigen, Creatine Kinase-MB, C Reactive Protein, EGF, ENA-78 for 7 sepsis patients and two controls. Multiple aliquots from each donor to determine precision of the expression level measurements. Stimulation indices are as indicated.

FIGS. 12E.1 through 12E.4 shows expression values for Endothelin-1, EN-RAGE, Eotaxin, Epiregulin, Erythropoietin, Fatty Acid Binding Protein, and Factor VII for 7 sepsis patients and two controls. Multiple aliquots from each donor to determine precision of the expression level measurements. Stimulation indices are as indicated.

FIGS. 12F.1 through 12F.4 shows expression values for Ferritin, FGF Basic, Fibrinogen, G-CSF, Growth Hormone, GM-CSF, Glutathione S-Transferase for 7 sepsis patients and two controls. Multiple aliquots from each donor to determine precision of the expression level measurements. Stimulation indices are as indicated.

FIGS. 12G.1 through 12G.4 shows expression values for Haptoglobin, ICAM-1, IFN-gamma, IgA, IgE, IGF-1, IGM, IL-10, IL-12p40, IL-12p70 for 7 sepsis patients and two controls. Multiple aliquots from each donor to determine precision of the expression level measurements. Stimulation indices are as indicated.

FIGS. 12H.1 through H.4 shows expression values for IL-13, IL-15, IL-16, IL-17, IL-17E, IL-18, IL-1alpha, IL-1beta, IL-1ra, IL-2 for 7 sepsis patients and two controls. Multiple aliquots from each donor to determine precision of the expression level measurements. Stimulation indices are as indicated.

FIGS. 12I.1 through 12I.4 shows expression values for IL-23, IL-3, IL-4, IL-5, IL-6, IL-7, IL-8, Insulin, Leptin, Lipoprotein (a) for 7 sepsis patients and two controls. Multiple aliquots from each donor to determine precision of the expression level measurements. Stimulation indices are as indicated.

FIGS. 12J.1 through 12J.4 shows expression values for Lymphotactin, MCP-1, MDC, MIP-1alpha, MIP-1beta, MMP-2, MMP-3, MMP-9 for 7 sepsis patients and two controls. Multiple aliquots from each donor to determine precision of the expression level measurements. Stimulation indices are as indicated.

FIGS. 12K.1 through 12K.4 shows expression values for Myeloperoxidase, Myoglobin, OSM (Oncostatin M), PAI-1, Prostatic Acid Phosphatase, PAPP-A for 7 sepsis patients and two controls. Multiple aliquots from each donor to determine precision of the expression level measurements. Stimulation indices are as indicated.

FIGS. 12L.1 through 12L.4 shows expression values for Prostate Specific Antigen Free, RANTES, Serum Amyloid P, Stem Cell Factor, SGOT, SHBG for 7 sepsis patients and two controls. Multiple aliquots from each donor to determine precision of the expression level measurements. Stimulation indices are as indicated.

FIGS. 12M.1 through 12M.4 shows expression values for Thyroxine Binding Globulin, Tissue Factor, TGF-alpha, TIMP-1, TNF RII, TNF-alpha, TNF-beta for 7 sepsis patients and two controls. Multiple aliquots from each donor to determine precision of the expression level measurements. Stimulation indices are as indicated.

FIGS. 12N.1 through 12N.4 shows expression values for Thrombopoietin, Thyroid Stimulating Hormone, Thrombospondin-1, VCAM-1, VEGF for 7 sepsis patients and two controls. Multiple aliquots from each donor to determine precision of the expression level measurements. Stimulation indices are as indicated.

FIGS. 13A1 through 13M.7 show expression values for the informative genes listed in Table 1 for 7 sepsis patients and two controls. Multiple aliquots from each donor to determine precision of the expression level measurements. Stimulation indices are as indicated.

FIGS. 13A.1 through 13A.7 shows expression values for Alpha-1 Antitrypsin, Adiponectin, Alpha-2-macroglobulin, Alpha-fetoprotein, and Amphiregulin, apolipoprotein A1, Apoliporotein CIII, Apolipoprotein H for 7 sepsis patients and two controls. Multiple aliquots from each donor to determine precision of the expression level measurements. Stimulation indices are as indicated.

FIGS. 13B.1 through 13B.7 shows expression values for Beta-2 Microglobulin, Brain-Derived neurotrophic Factor, Complement 3, Cancer Antigen 125, Cancer Antigen 19-9, Calcitonin, CD40, CD40 Ligand for 7 sepsis patients and two controls. Multiple aliquots from each donor to determine precision of the expression level measurements. Stimulation indices are as indicated.

FIGS. 13C.1 through 13C.7 shows expression values for Carcinoembryonic Antigen, Creatine Kinase-MB, C Reactive Protein, EGF, ENA-78, Endothelin-1, EN-RAGE, Eotaxin for 7 sepsis patients and two controls. Multiple aliquots from each donor to determine precision of the expression level measurements. Stimulation indices are as indicated.

FIGS. 13D.1 through 13D.7 shows expression values for Epiregulin, Erythropoietin, Fatty Acid Binding Protein, Factor VII, Ferritin, FGF Basic, Fibrinogen, G-CSF for 7 sepsis patients and two controls. Multiple aliquots from each donor to determine precision of the expression level measurements. Stimulation indices are as indicated.

FIGS. 13E.1 through 13E.7 shows expression values for Growth Hormone, GM-CSF, Glutathione S-Transferase, Haptoglobin, ICAM-1, IFN-gamma, IgA, IgE for 7 sepsis patients and two controls. Multiple aliquots from each donor to determine precision of the expression level measurements. Stimulation indices are as indicated.

FIGS. 13F.1 through 13F.7 shows expression values for IGF-1, IGM, IL-10, IL-12p40, IL-12p70, IL-13, IL-15, IL-16 for 7 sepsis patients and two controls. Multiple aliquots from each donor to determine precision of the expression level measurements. Stimulation indices are as indicated.

FIGS. 13G.1 through 13G.7 shows expression values for IL-17, IL-17E, IL-18, IL-1alpha, IL-1beta, IL-1ra, IL-2, IL-23 for 7 sepsis patients and two controls. Multiple aliquots from each donor to determine precision of the expression level measurements. Stimulation indices are as indicated.

FIGS. 13H.1 through 13H.7 shows expression values for IL-3, IL-4, IL-5, IL-6, IL-7, IL-8, Insulin, Leptin for 7 sepsis patients and two controls. Multiple aliquots from each donor to determine precision of the expression level measurements. Stimulation indices are as indicated.

FIGS. 13I.1 through 13I.7 shows expression values for Lipoprotein (a), Lymphotactin, MCP-1, MDC, MIP-1alpha, MIP-1beta, MMP-2, MMP-3 for 7 sepsis patients and two controls. Multiple aliquots from each donor to determine precision of the expression level measurements. Stimulation indices are as indicated.

FIGS. 13J.1 through 13J.7 shows expression values for MMP-9, Myeloperoxidase, Myoglobin, OSM (Oncostatin M), PAI-1, Prostatic Acid Phosphatase, PAPP-A, Prostate Specific Antigen Free for 7 sepsis patients and two controls. Multiple aliquots from each donor to determine precision of the expression level measurements. Stimulation indices are as indicated.

FIGS. 13K.1 through 13K.7 shows expression values for RANTES, Serum Amyloid P, Stem Cell Factor, SGOT, SHBG, Thyroxine Binding Globulin, Tissue Factor, TGF-alpha for 7 sepsis patients and two controls. Multiple aliquots from each donor to determine precision of the expression level measurements. Stimulation indices are as indicated.

FIGS. 13L.1 through 13L.7 shows expression values for TIMP-1, TNF RII, TNF-alpha, TNF-beta, Thrombopoietin, Thyroid Stimulating Hormone, Thrombospondin-1, VCAM-1 for 7 sepsis patients and two controls. Multiple aliquots from each donor to determine precision of the expression level measurements. Stimulation indices are as indicated.

FIGS. 13M.1 through 13M.7 shows expression values for VEGF, von Willebrand for 7 sepsis patients and two controls. Multiple aliquots from each donor to determine precision of the expression level measurements. Stimulation indices are as indicated.

FIGS. 14A.1 through 14N.8 show expression values for the informative genes listed in Table 1 for 7 sepsis patients and two controls. Multiple aliquots from each donor to determine precision of the expression level measurements. Stimulation indices are as indicated.

FIGS. 14A.1 through 14A.8 shows expression values for Alpha-1 Antitrypsin, Adiponectin, Alpha-2-macroglobulin, Alpha-fetoprotein, Amphiregulin, apolipoprotein A1, Apoliporotein CIII for 7 sepsis patients and two controls. Multiple aliquots from each donor to determine precision of the expression level measurements. Stimulation indices are as indicated.

FIGS. 14B.1 through 14B.8 shows expression values for Apolipoprotein H, Beta-2 Microglobulin, Brain-Derived neurotrophic Factor, Complement 3, Cancer Antigen 125, Cancer Antigen 19-9, Calcitonin for 7 sepsis patients and two controls. Multiple aliquots from each donor to determine precision of the expression level measurements. Stimulation indices are as indicated.

FIGS. 14C.1 through 14C.8 shows expression values for CD40, CD40 Ligand, Carcinoembryonic Antigen, Creatine Kinase-MB, C Reactive Protein, EGF, ENA-78 for 7 sepsis patients and two controls. Multiple aliquots from each donor to determine precision of the expression level measurements. Stimulation indices are as indicated.

FIGS. 14D.1 through 14D.8 shows expression values for Endothelin-1, EN-RAGE, Eotaxin, Epiregulin, Erythropoietin, Fatty Acid Binding Protein, Factor VII for 7 sepsis patients and two controls. Multiple aliquots from each donor to determine precision of the expression level measurements. Stimulation indices are as indicated.

FIGS. 14E.1 through 14E.8 shows expression values for Ferritin, FGF Basic, Fibrinogen, G-CSF, Growth Hormone, GM-CSF, Glutathione S-Transferase for 7 sepsis patients and two controls. Multiple aliquots from each donor to determine precision of the expression level measurements. Stimulation indices are as indicated.

FIGS. 14F.1 through 14F.8 shows expression values for Haptoglobin, ICAM-1, IFN-gamma, IgA, IgE, IGF-1, IGM for 7 sepsis patients and two controls. Multiple aliquots from each donor to determine precision of the expression level measurements. Stimulation indices are as indicated.

FIGS. 14G.1 through 14G.8 shows expression values for IL-10, IL-12p40, IL-12p70, IL-13, IL-15, IL-16, IL-17 for 7 sepsis patients and two controls. Multiple aliquots from each donor to determine precision of the expression level measurements. Stimulation indices are as indicated.

FIGS. 14H.1 through 14H.8 shows expression values for IL-17E, IL-18, IL-1alpha, IL-1beta, IL-1ra, IL-2, IL-23 for 7 sepsis patients and two controls. Multiple aliquots from each donor to determine precision of the expression level measurements. Stimulation indices are as indicated.

FIGS. 14I.1 through 14I.8 shows expression values for IL-3, IL-4, IL-5, IL-6, IL-7, IL-8, Insulin for 7 sepsis patients and two controls. Multiple aliquots from each donor to determine precision of the expression level measurements. Stimulation indices are as indicated.

FIGS. 14J.1 through 14J.8 shows expression values for Leptin, Lipoprotein (a), Lymphotactin, MCP-1, MDC, MIP-1alpha, MIP-1beta for 7 sepsis patients and two controls. Multiple aliquots from each donor to determine precision of the expression level measurements. Stimulation indices are as indicated.

FIGS. 14K.1 through 14K.8 shows expression values for MMP-2, MMP-3, MMP-9, Myeloperoxidase, Myoglobin, OSM (Oncostatin M), PAI-1 for 7 sepsis patients and two controls. Multiple aliquots from each donor to determine precision of the expression level measurements. Stimulation indices are as indicated.

FIGS. 14L.1 through 14L.8 shows expression values for Prostatic Acid Phosphatase, PAPP-A, Prostate Specific Antigen Free, RANTES, Serum Amyloid P, Stem Cell Factor, SGOT for 7 sepsis patients and two controls. Multiple aliquots from each donor to determine precision of the expression level measurements. Stimulation indices are as indicated.

FIGS. 14M.1 through 14M.8 shows expression values for SHBG, Thyroxine Binding Globulin, Tissue Factor, TGF-alpha, TIMP-1, TNF RII, TNF-alpha for 7 sepsis patients and two controls. Multiple aliquots from each donor to determine precision of the expression level measurements. Stimulation indices are as indicated.

FIGS. 14N.1 through 14N.8 shows expression values for TNF-beta, Thrombopoietin, Thyroid Stimulating Hormone, Thrombospondin-1, VCAM-1, VEGF, von Willebrand for 7 sepsis patients and two controls. Multiple aliquots from each donor to determine precision of the expression level measurements. Stimulation indices are as indicated.

FIGS. 15A.1 through 15O.14 show expression values for the informative genes listed in Table 1 for 7 sepsis patients and two controls. Multiple aliquots from each donor to determine precision of the expression level measurements. Stimulation indices are as indicated.

FIGS. 15A.1 through 15A.14 shows expression values for Alpha-1 Antitrypsin, Adiponectin, Alpha-2-macroglobulin, Alpha-fetoprotein, Amphiregulin for 7 sepsis patients and two controls. Multiple aliquots from each donor to determine precision of the expression level measurements. Stimulation indices are as indicated.

FIGS. 15B.1 through 15B.14 shows expression values for apolipoprotein A1, Apoliporotein CIII, Apolipoprotein H, Beta-2 Microglobulin, Brain-Derived neurotrophic Factor for 7 sepsis patients and two controls. Multiple aliquots from each donor to determine precision of the expression level measurements. Stimulation indices are as indicated.

FIGS. 15C.1 through 15C.14 shows expression values for Complement 3, Cancer Antigen 125, Cancer Antigen 19-9, Calcitonin, CD40, CD40 Ligand, for 7 sepsis patients and two controls. Multiple aliquots from each donor to determine precision of the expression level measurements. Stimulation indices are as indicated.

FIGS. 15D.1 through 15D.14 shows expression values for Carcinoembryonic Antigen, Creatine Kinase-MB, C Reactive Protein, EGF, ENA-78, Endothelin-1 for 7 sepsis patients and two controls. Multiple aliquots from each donor to determine precision of the expression level measurements. Stimulation indices are as indicated.

FIGS. 15E.1 through 15E.14 shows expression values for EN-RAGE, Eotaxin, Epiregulin, Erythropoietin, Fatty Acid Binding Protein, Factor VII, Ferritin for 7 sepsis patients and two controls. Multiple aliquots from each donor to determine precision of the expression level measurements. Stimulation indices are as indicated.

FIGS. 15F.1 through 15F.14 shows expression values for FGF Basic, Fibrinogen, G-CSF, Growth Hormone, GM-CSF, Glutathione S-Transferase, Haptoglobin for 7 sepsis patients and two controls. Multiple aliquots from each donor to determine precision of the expression level measurements. Stimulation indices are as indicated.

FIGS. 15G.1 through 15G.14 shows expression values for ICAM-1, IFN-gamma, IgA, IgE, IGF-1, IGM, IL-10, IL-12p40, IL-12p70 for 7 sepsis patients and two controls. Multiple aliquots from each donor to determine precision of the expression level measurements. Stimulation indices are as indicated.

FIGS. 15H.1 through 15H.14 shows expression values for IL-13, IL-15, IL-16, IL-17, IL-17E, IL-18, IL-1alpha, IL-1beta, IL-1ra for 7 sepsis patients and two controls. Multiple aliquots from each donor to determine precision of the expression level measurements. Stimulation indices are as indicated.

FIGS. 15I.1 through 15I.14 shows expression values for IL-2, IL-23, IL-3, IL-4, IL-5, IL-6, IL-7, IL-8, Insulin, Leptin for 7 sepsis patients and two controls. Multiple aliquots from each donor to determine precision of the expression level measurements. Stimulation indices are as indicated.

FIGS. 15J.1 through 15J.14 shows expression values for Lipoprotein (a), Lymphotactin, MCP-1, MDC, MIP-1alpha, MIP-1beta, MMP-2 for 7 sepsis patients and two controls. Multiple aliquots from each donor to determine precision of the expression level measurements. Stimulation indices are as indicated.

FIGS. 15K.1 through 15K.14 shows expression values for MMP-3, MMP-9, Myeloperoxidase, Myoglobin, OSM (Oncostatin M), PAI-1 for 7 sepsis patients and two controls. Multiple aliquots from each donor to determine precision of the expression level measurements. Stimulation indices are as indicated.

FIGS. 15L.1 through 15L.14 shows expression values for Prostatic Acid Phosphatase, PAPP-A, Prostate Specific Antigen Free, RANTES, Serum Amyloid P, Stem Cell Factor, SGOT for 7 sepsis patients and two controls. Multiple aliquots from each donor to determine precision of the expression level measurements. Stimulation indices are as indicated.

FIGS. 15M.1 through 15M.14 shows expression values for SHBG, Thyroxine Binding Globulin, Tissue Factor, TGF-alpha, TIMP-1, TNF RII, TNF-alpha for 7 sepsis patients and two controls. Multiple aliquots from each donor to determine precision of the expression level measurements. Stimulation indices are as indicated.

FIGS. 15N.1 through 15N.14 shows expression values for TNF-beta, Thrombopoietin, Thyroid Stimulating Hormone, Thrombospondin-1, VCAM-1, VEGF for 7 sepsis patients and two controls. Multiple aliquots from each donor to determine precision of the expression level measurements. Stimulation indices are as indicated.

FIGS. 15O.1 through 15O.14 shows expression values for von Willebrand for 7 sepsis patients and two controls. Multiple aliquots from each donor to determine precision of the expression level measurements. Stimulation indices are as indicated.

FIGS. 16A.1 through 16O.6 show expression values for the informative genes listed in Table 1 for 7 sepsis patients and two controls. Multiple aliquots from each donor to determine precision of the expression level measurements. Stimulation indices are as indicated.

FIGS. 16A.1 through 16A.6 shows expression values for Alpha-1 Antitrypsin, Adiponectin, Alpha-2-macroglobulin, Alpha-fetoprotein, Amphiregulin for 7 sepsis patients and two controls. Multiple aliquots from each donor to determine precision of the expression level measurements. Stimulation indices are as indicated.

FIGS. 16B.1 through 16B.6 shows expression values for apolipoprotein A1, Apoliporotein CIII, Apolipoprotein H, Beta-2 Microglobulin for 7 sepsis patients and two controls. Multiple aliquots from each donor to determine precision of the expression level measurements. Stimulation indices are as indicated.

FIGS. 16C.1 through 16C.6 shows expression values for Brain-Derived neurotrophic Factor, Complement 3, Cancer Antigen 125, Cancer Antigen 19-9, Calcitonin for 7 sepsis patients and two controls. Multiple aliquots from each donor to determine precision of the expression level measurements. Stimulation indices are as indicated.

FIGS. 16D.1 through 16D.6 shows expression values for CD40, CD40 Ligand, Carcinoembryonic Antigen, Creatine Kinase-MB, C Reactive Protein, EGF, ENA-78 for 7 sepsis patients and two controls. Multiple aliquots from each donor to determine precision of the expression level measurements. Stimulation indices are as indicated.

FIGS. 16E.1 through 16E.6 shows expression values for Endothelin-1, EN-RAGE, Eotaxin, Epiregulin, Erythropoietin for 7 sepsis patients and two controls. Multiple aliquots from each donor to determine precision of the expression level measurements. Stimulation indices are as indicated.

FIGS. 16F.1 through 16F.6 shows expression values for Fatty Acid Binding Protein, Factor VII, Ferritin, FGF Basic, Fibrinogen, G-CSF, Growth Hormone for 7 sepsis patients and two controls. Multiple aliquots from each donor to determine precision of the expression level measurements. Stimulation indices are as indicated.

FIGS. 16G.1 through 16G.6 shows expression values for GM-CSF, Glutathione S-Transferase, Haptoglobin, ICAM-1, IFN-gamma, IgA, IgE for 7 sepsis patients and two controls. Multiple aliquots from each donor to determine precision of the expression level measurements. Stimulation indices are as indicated.

FIGS. 16H.1 through 16H.6 shows expression values for IGF-1, IGM, IL-10, IL-12p40, IL-12p70, IL-13, IL-15, IL-16, IL-17 for 7 sepsis patients and two controls. Multiple aliquots from each donor to determine precision of the expression level measurements. Stimulation indices are as indicated.

FIGS. 16I.1 through 16I.6 shows expression values for IL-17E, IL-18, IL-1alpha, IL-1beta, IL-1ra, IL-2, IL-23, IL-3 for 7 sepsis patients and two controls. Multiple aliquots from each donor to determine precision of the expression level measurements. Stimulation indices are as indicated.

FIGS. 16J.1 through 16J.6 shows expression values for IL-4, IL-5, IL-6, IL-7, IL-8, Insulin, Leptin, Lipoprotein (a) for 7 sepsis patients and two controls. Multiple aliquots from each donor to determine precision of the expression level measurements. Stimulation indices are as indicated.

FIGS. 16K.1 through 16K.6 shows expression values for Lymphotactin, MCP-1, MDC, MIP-1alpha, MIP-1beta, MMP-2, MMP-3, MMP-9 for 7 sepsis patients and two controls. Multiple aliquots from each donor to determine precision of the expression level measurements. Stimulation indices are as indicated.

FIGS. 16L.1 through 16L.6 shows expression values for Myeloperoxidase, Myoglobin, OSM (Oncostatin M), PAI-1, Prostatic Acid Phosphatase, PAPP-A for 7 sepsis patients and two controls. Multiple aliquots from each donor to determine precision of the expression level measurements. Stimulation indices are as indicated.

FIGS. 16M.1 through 16M.6 shows expression values for Prostate Specific Antigen Free, RANTES, Serum Amyloid P, Stem Cell Factor, SGOT, SHBG, Thyroxine Binding Globulin, Tissue Factor for 7 sepsis patients and two controls. Multiple aliquots from each donor to determine precision of the expression level measurements. Stimulation indices are as indicated.

FIGS. 16N.1 through 16N.6 shows expression values for TGF-alpha, TIMP-1, TNF RII, TNF-alpha, TNF-beta, Thrombopoietin, Thyroid Stimulating Hormone, Thrombospondin-1 for 7 sepsis patients and two controls. Multiple aliquots from each donor to determine precision of the expression level measurements. Stimulation indices are as indicated.

FIGS. 16O.1 through 16O.6 shows expression values for VCAM-1, VEGF, von Willebrand for 7 sepsis patients and two controls. Multiple aliquots from each donor to determine precision of the expression level measurements. Stimulation indices are as indicated.

FIGS. 17A.1 through 17R.8 show expression values for the informative genes listed in Table 1 for 7 sepsis patients and two controls. Multiple aliquots from each donor to determine precision of the expression level measurements. Stimulation indices are as indicated.

FIGS. 17A.1 through 17A.8 shows expression values for Alpha-1 Antitrypsin, Adiponectin, Alpha-2-macroglobulin for 7 sepsis patients and two controls. Multiple aliquots from each donor to determine precision of the expression level measurements. Stimulation indices are as indicated.

FIGS. 17B.1 through 17B.8 shows expression values for Alpha-fetoprotein, Amphiregulin, apolipoprotein A1, Apoliporotein CIII for 7 sepsis patients and two controls. Multiple aliquots from each donor to determine precision of the expression level measurements. Stimulation indices are as indicated.

FIGS. 17C.1 through 17C.8 shows expression values for Apolipoprotein H, Beta-2 Microglobulin, Brain-Derived neurotrophic Factor for 7 sepsis patients and two controls. Multiple aliquots from each donor to determine precision of the expression level measurements. Stimulation indices are as indicated.

FIGS. 17D.1 through 17D.8 shows expression values for Complement 3, Cancer Antigen 125, Cancer Antigen 19-9, Calcitonin, CD40 for 7 sepsis patients and two controls. Multiple aliquots from each donor to determine precision of the expression level measurements. Stimulation indices are as indicated.

FIGS. 17E.1 through 17E.8 shows expression values for CD40 Ligand, Carcinoembryonic Antigen, Creatine Kinase-MB for 7 sepsis patients and two controls. Multiple aliquots from each donor to determine precision of the expression level measurements. Stimulation indices are as indicated.

FIGS. 17F.1 through 17F.8 shows expression values for C Reactive Protein, EGF, ENA-78, Endothelin-1, EN-RAGE, Eotaxin for 7 sepsis patients and two controls. Multiple aliquots from each donor to determine precision of the expression level measurements. Stimulation indices are as indicated.

FIGS. 17G.1 through 17G.8 shows expression values for Epiregulin, Erythropoietin, Fatty Acid Binding Protein, Factor VII, Ferritin for 7 sepsis patients and two controls. Multiple aliquots from each donor to determine precision of the expression level measurements. Stimulation indices are as indicated.

FIGS. 17H.1 through 17H.7 shows expression values for FGF Basic, Fibrinogen, G-CSF, Growth Hormone, GM-CSF, Glutathione S-Transferase for 7 sepsis patients and two controls. Multiple aliquots from each donor to determine precision of the expression level measurements. Stimulation indices are as indicated.

FIGS. 17I.1 through 17I.8 shows expression values for Haptoglobin, ICAM-1, IFN-gamma, IgA, IgE, IGF-1, IGM, IL-10 for 7 sepsis patients and two controls. Multiple aliquots from each donor to determine precision of the expression level measurements. Stimulation indices are as indicated.

FIGS. 17J.1 through 17J.8 shows expression values for IL-12p40, IL-12p70, IL-13, IL-15, IL-16, IL-17, IL-17E, IL-18 for 7 sepsis patients and two controls. Multiple aliquots from each donor to determine precision of the expression level measurements. Stimulation indices are as indicated.

FIGS. 17K.1 through 17K.8 shows expression values for IL-1alpha, IL-1beta, IL-1ra, IL-2, IL-23, IL-3, IL-4, IL-5 for 7 sepsis patients and two controls. Multiple aliquots from each donor to determine precision of the expression level measurements. Stimulation indices are as indicated.

FIGS. 17L.1 through 17L.8 shows expression values for IL-6, IL-7, IL-8, Insulin, Leptin, Lipoprotein (a), Lymphotactin, MCP-1 for 7 sepsis patients and two controls. Multiple aliquots from each donor to determine precision of the expression level measurements. Stimulation indices are as indicated.

FIGS. 17M.1 through 17M.8 shows expression values for MDC, MIP-1alpha, MIP-1beta, MMP-2, MMP-3, MMP-9, Myeloperoxidase, Myoglobin for 7 sepsis patients and two controls. Multiple aliquots from each donor to determine precision of the expression level measurements. Stimulation indices are as indicated.

FIGS. 17N.1 through 17N.8 shows expression values for OSM (Oncostatin M), PAI-1, Prostatic Acid Phosphatase, PAPP-A, Prostate Specific Antigen Free, RANTES for 7 sepsis patients and two controls. Multiple aliquots from each donor to determine precision of the expression level measurements. Stimulation indices are as indicated.

FIGS. 17O.1 through 17O.8 shows expression values for Serum Amyloid P, Stem Cell Factor, SGOT, SHBG, Thyroxine Binding Globulin, Tissue Factor, TGF-alpha, TIMP-1 for 7 sepsis patients and two controls. Multiple aliquots from each donor to determine precision of the expression level measurements. Stimulation indices are as indicated.

FIGS. 17P.1 through 17P.8 shows expression values for TNF RII, TNF-alpha, TNF-beta, Thrombopoietin, Thyroid Stimulating Hormone for 7 sepsis patients and two controls. Multiple aliquots from each donor to determine precision of the expression level measurements. Stimulation indices are as indicated.

FIGS. 17Q.1 through 17Q.8 shows expression values for Thrombospondin-1, VCAM-1, VEGF, von Willebrand for 7 sepsis patients and two controls. Multiple aliquots from each donor to determine precision of the expression level measurements. Stimulation indices are as indicated.

FIGS. 19A through 19F: IL-8. FIGS. 19K through 19N: MCP-1.

DETAILED DESCRIPTION OF THE INVENTION

Figure 1A:
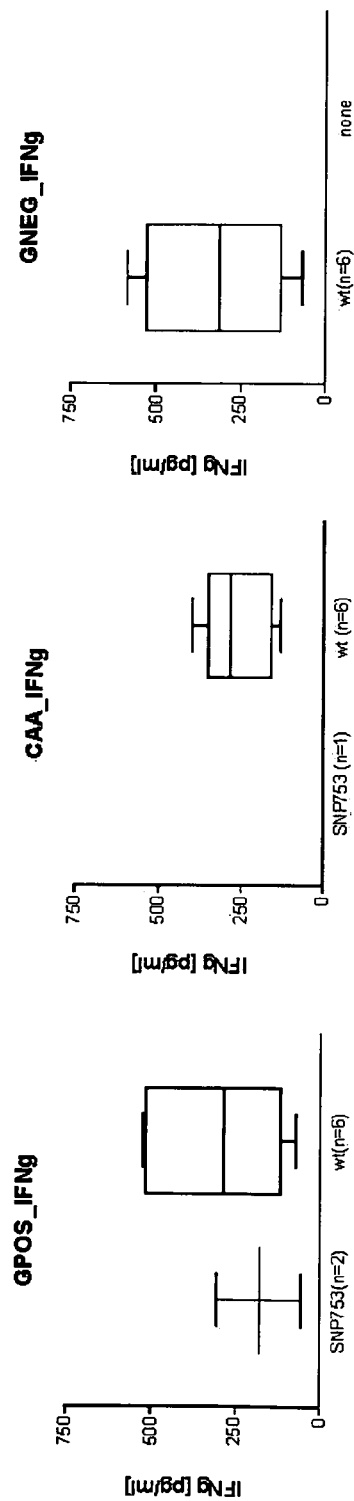
FIG. 1A-E is a series of plots showing the results of an examination of the activity patterns generated by leukocytes. The leukocytes stem from septic patients whose sepses were caused by three different pathogens: GPOS: gram-positive germs (far left), GNEG: gram-negative germs (far right) and CAA: *Candida albicans* (middle). The examination of the activity patterns was performed on the basis of a direct analysis of several mediators in serum samples of the patients (IFNg: Interferon γ (top), MCP1: monocyte chemoattractant protein-1 (second from top), IP10: INFγ-inducible protein 10 (middle), IL10: Interleukin 10 (second from bottom) and TNFα: tumor necrosis factor α (bottom)).
Figure 1B:
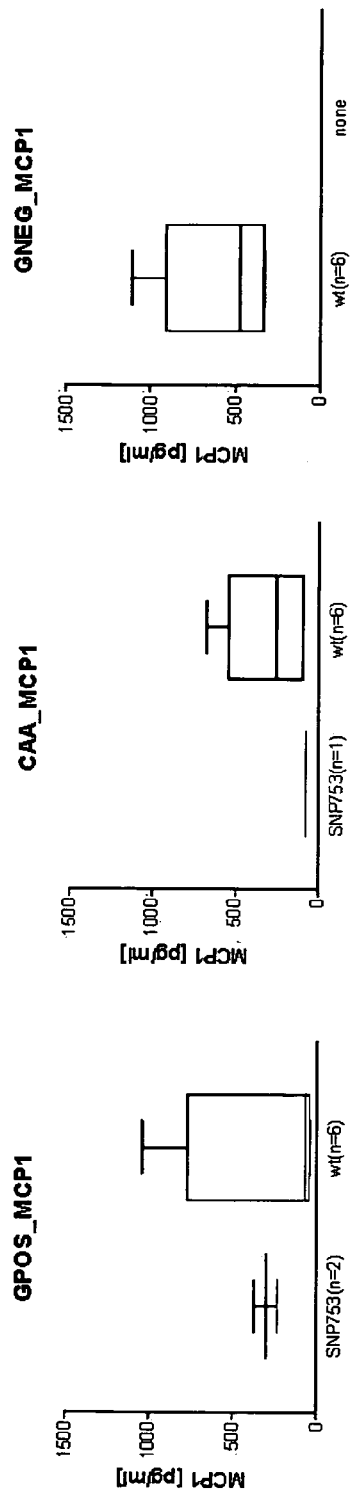
Figure 1C:
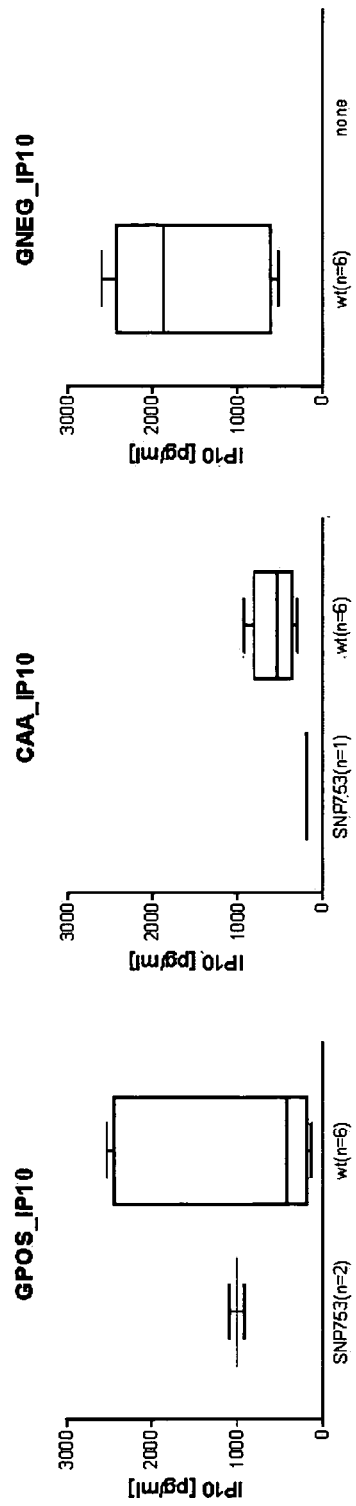
Figure 1D:
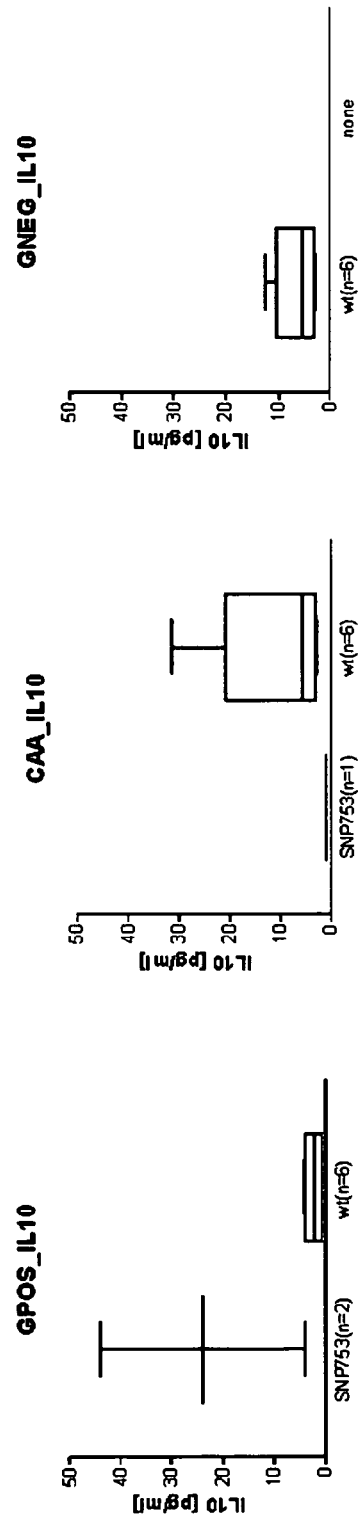
Figure 1E:
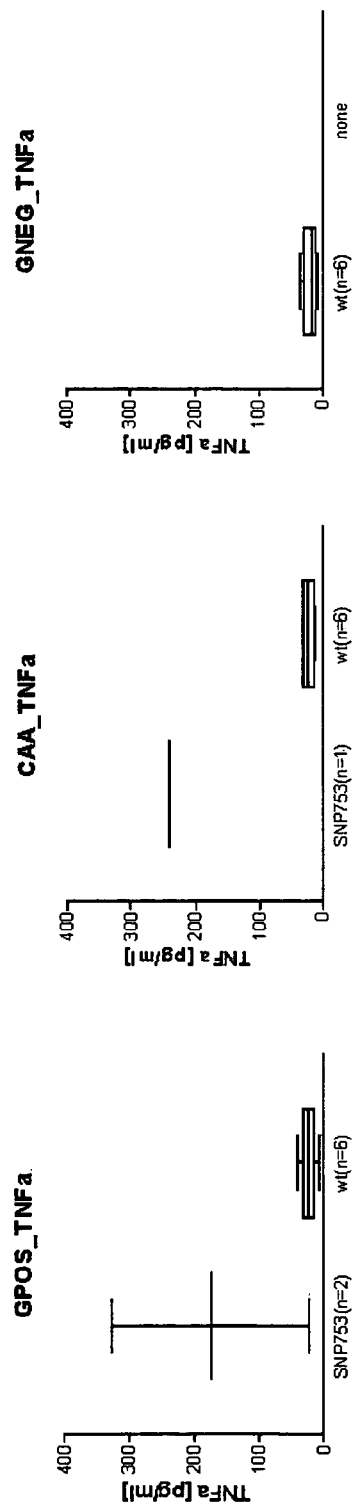
Figure 2:
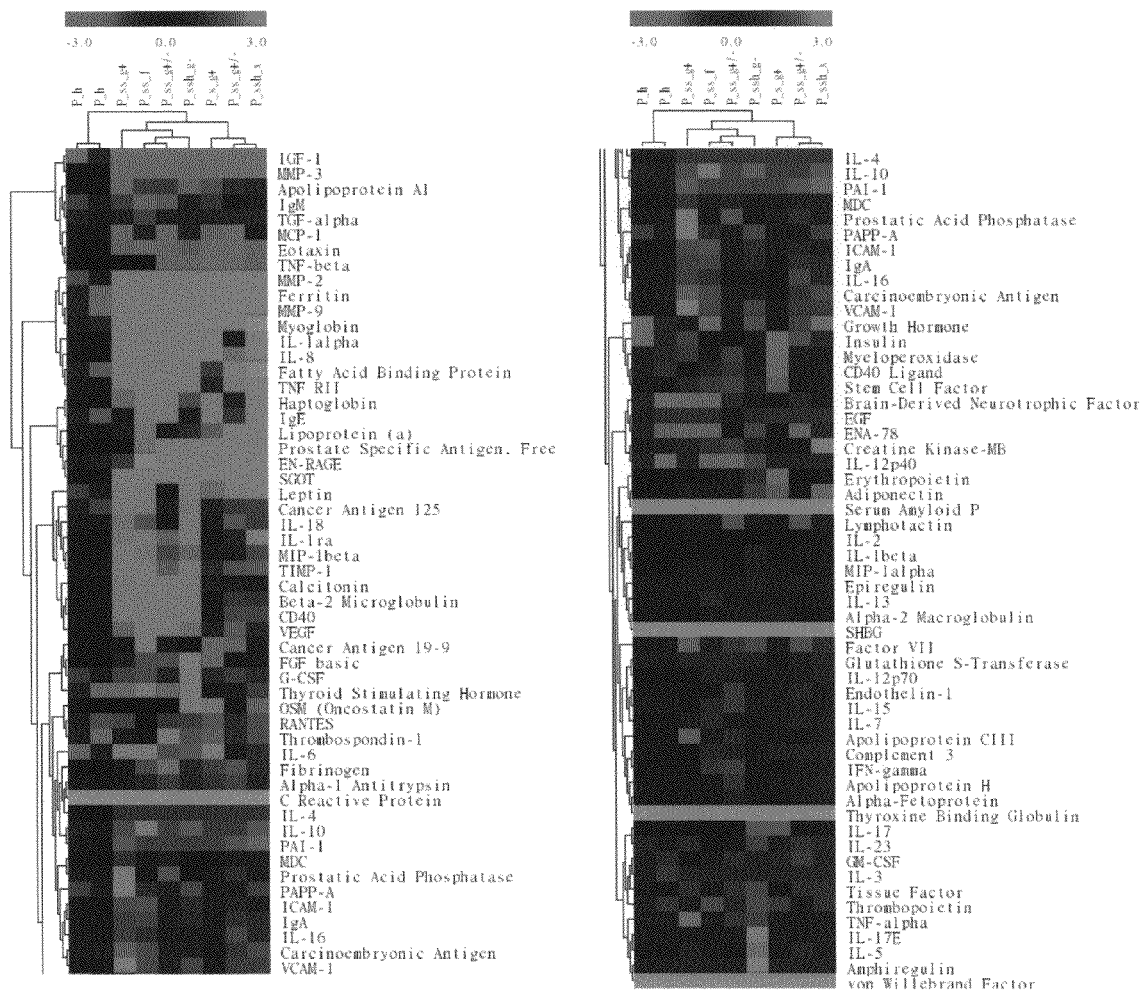
FIG. 2 is a representation of differential expression of the genes listed in Table 1. Table lists 98 mediators that are differentially expressed, as determined by a multiplexed assay. The assay included expression values for seven patients with sepsis, and the data was normalized against two healthy patients.
Figure 3:
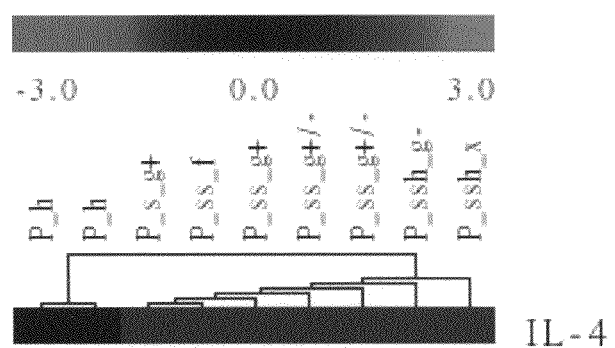
FIG. 3 shows the expression difference of IL-4 across the seven sepsis patients of FIG. 2, again normalized to two healthy patients.
Figure 4:
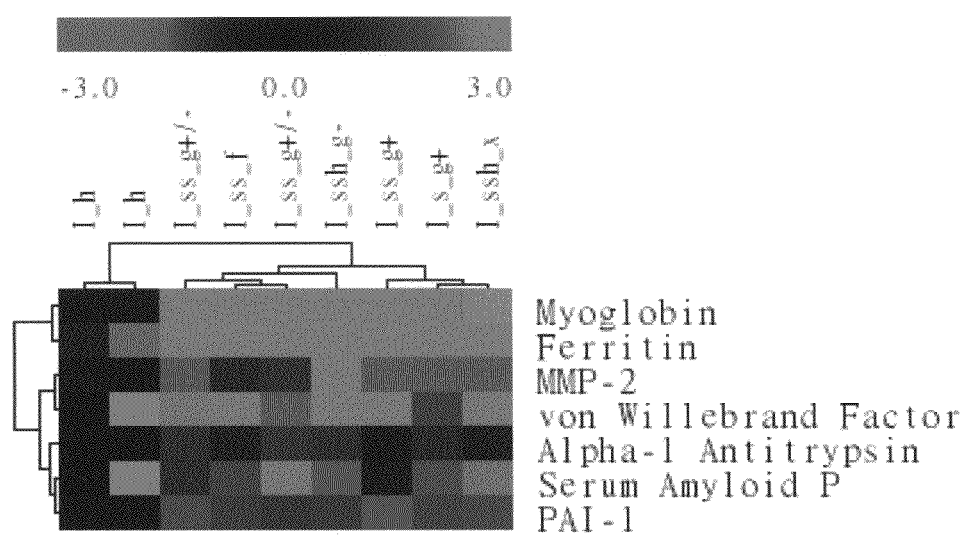
FIG. 4 shows differential expression of particular informative genes listed in Table 1 in seven patients with sepsis in ILCS cells stimulated with different TLR ligands.
Figure 5:
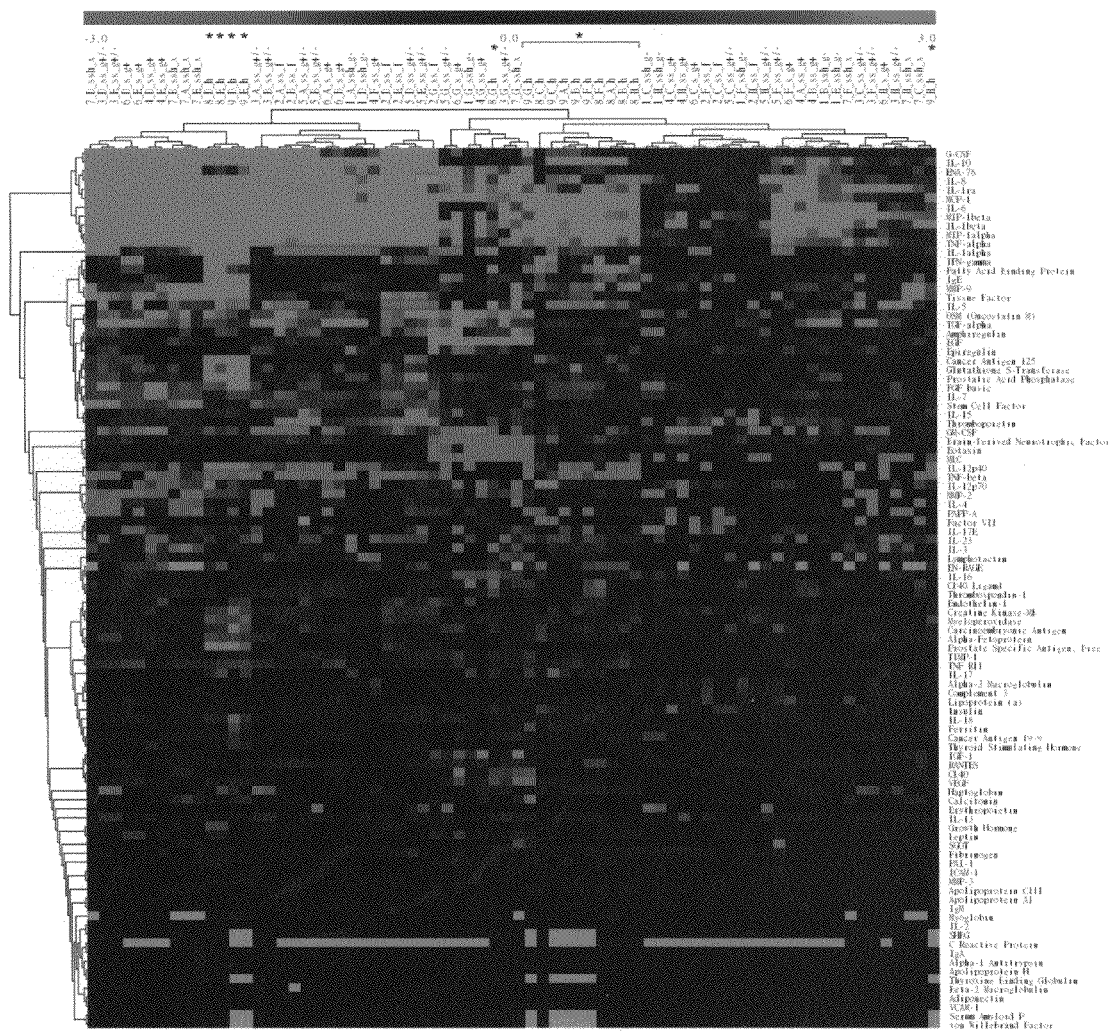
FIG. 5 is an overview of the differentially expressed mediators (informative genes) that can be included to create an expression profile specific to a particular cellular activity pattern. The data were derived from seven patients with sepsis stimulated in vitro with different TLR ligands. *=NHD; Ligands for TLR: A: 2/1, B: 6/2, C: 3, D: 4, E: 5, F: 7, G: 9, H: 9.
Figure 6:
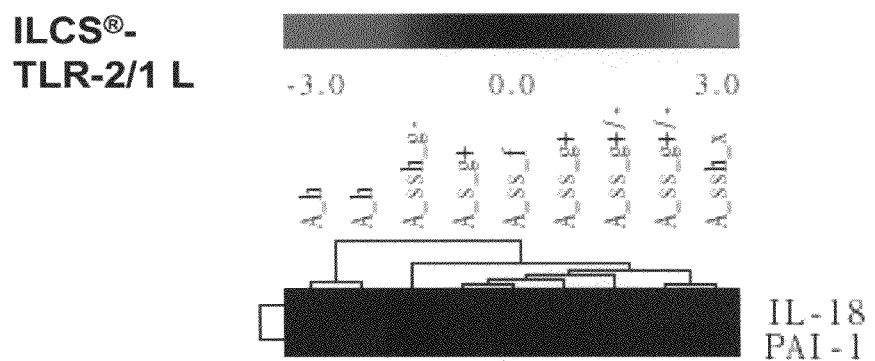
FIG. 6 shows differential expression of select genes in TLR-2/1 stimulated cells.
Figure 7:
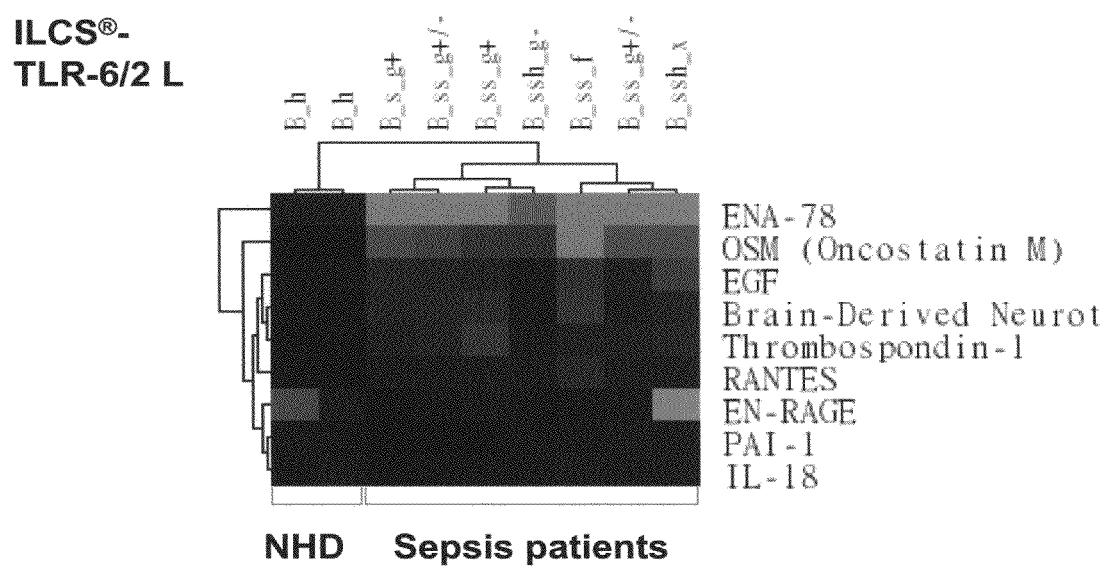
FIG. 7 shows differential expression of select genes in TLR-6/2 stimulated cells.
Figure 9:
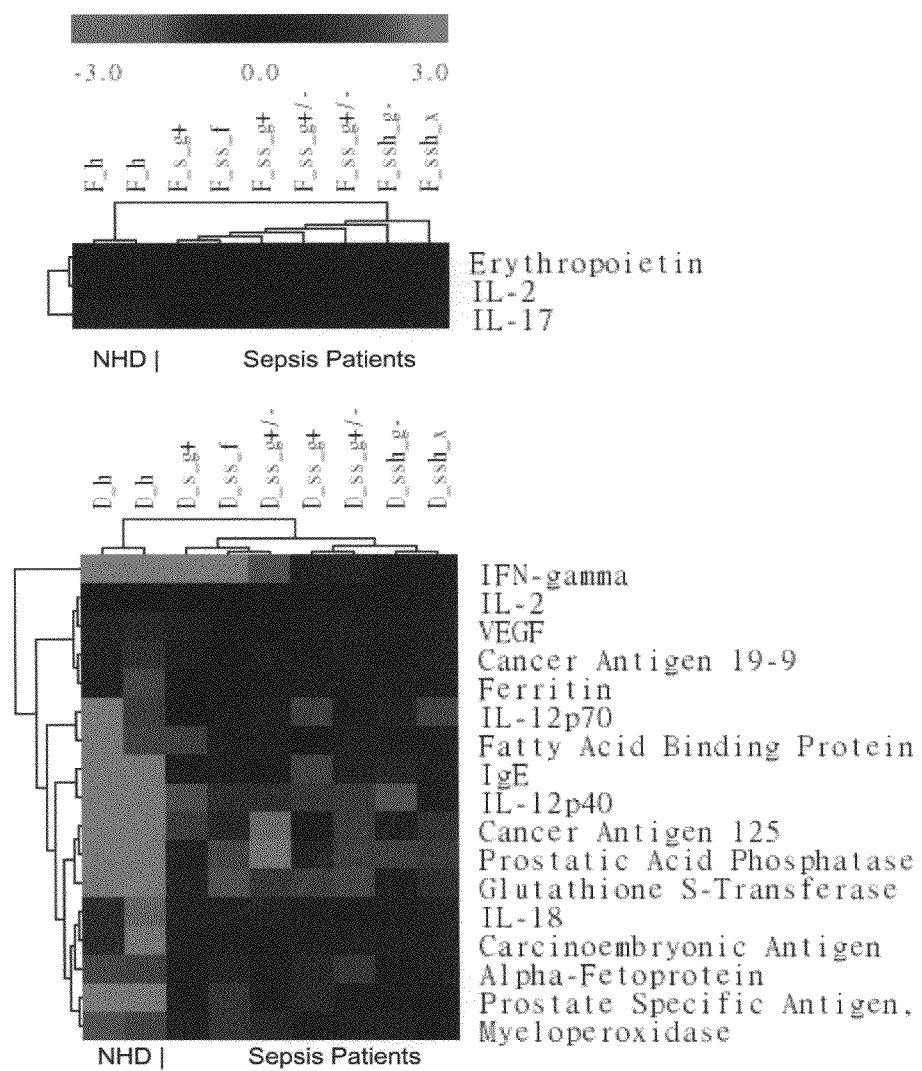
FIG. 9 shows differential expression of select genes in TLR-7 (top) and TLR-4 (bottom) stimulated cells.
Figure 10:
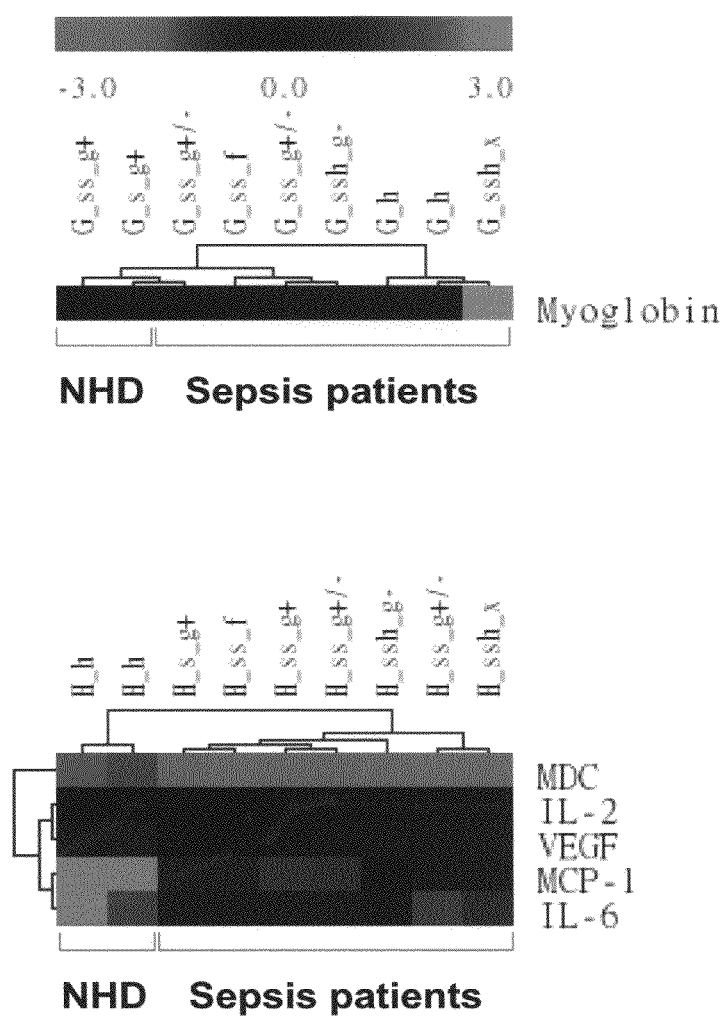
FIG. 10 shows differential expression of select genes in TLR-9 CpG-A (top) and TLR-9 CpG-B (bottom) stimulated cells.
Figure 11A:
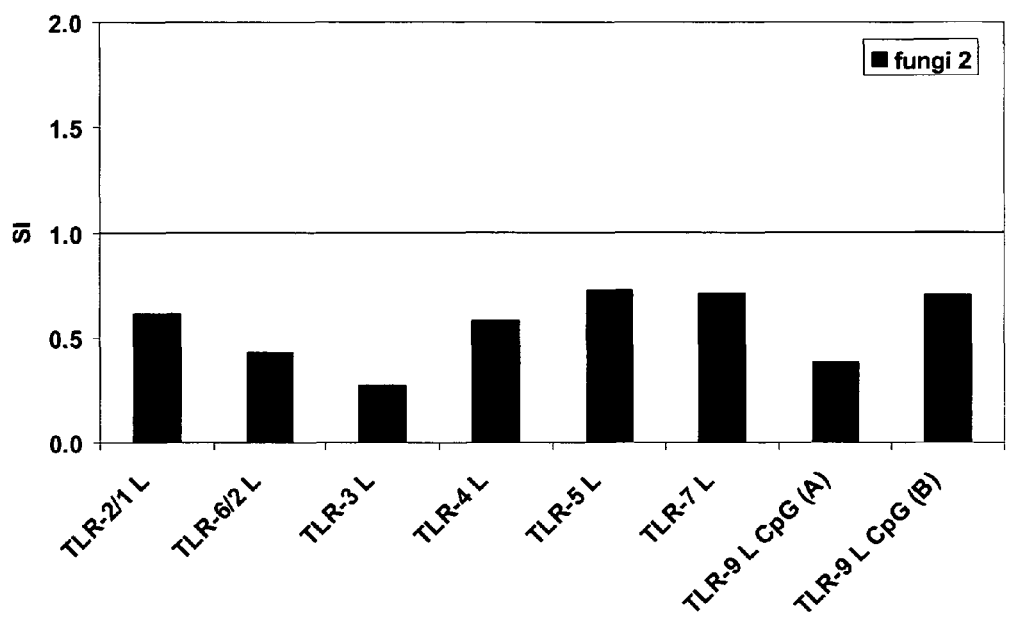
FIGS. 11A through 11E show a series of plots comparing cell activity in subgroups of patients after stimulation with various ligands.
Figure 11B:
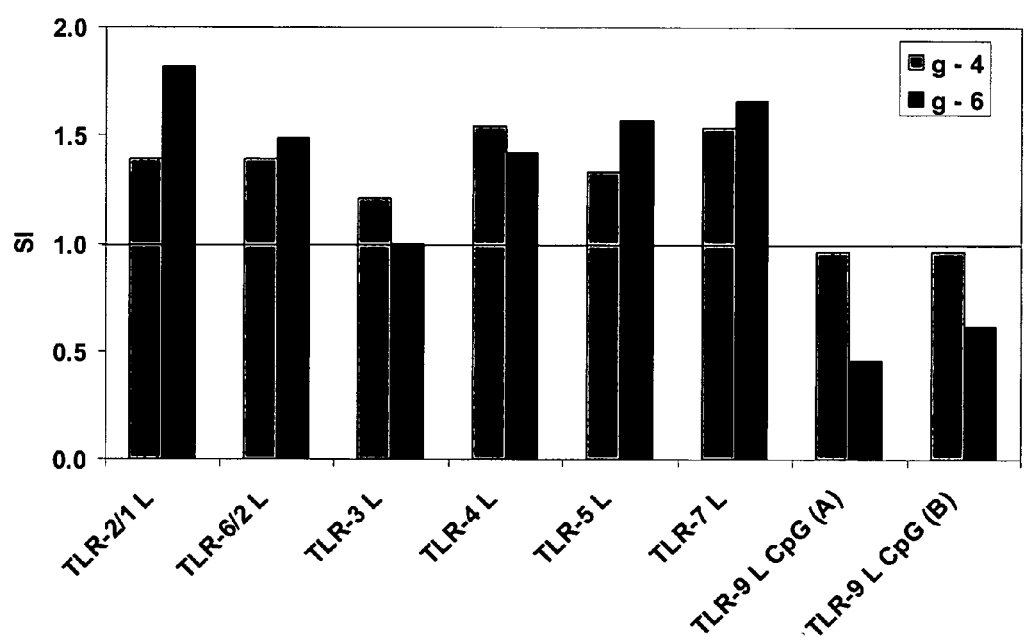
Figure 11C:
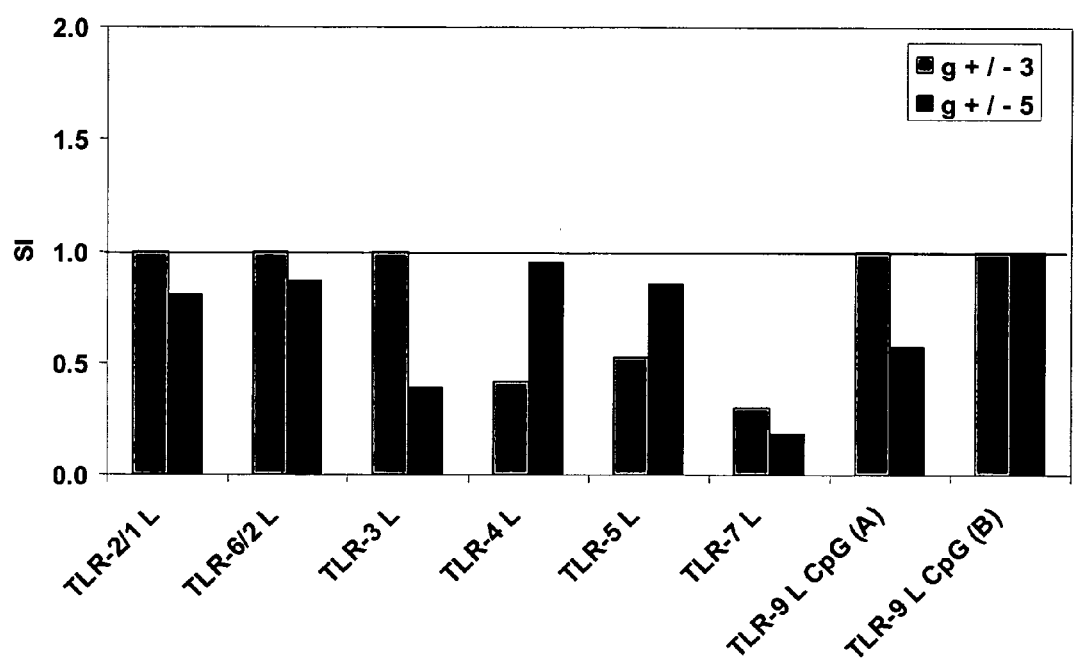
Figure 11D:
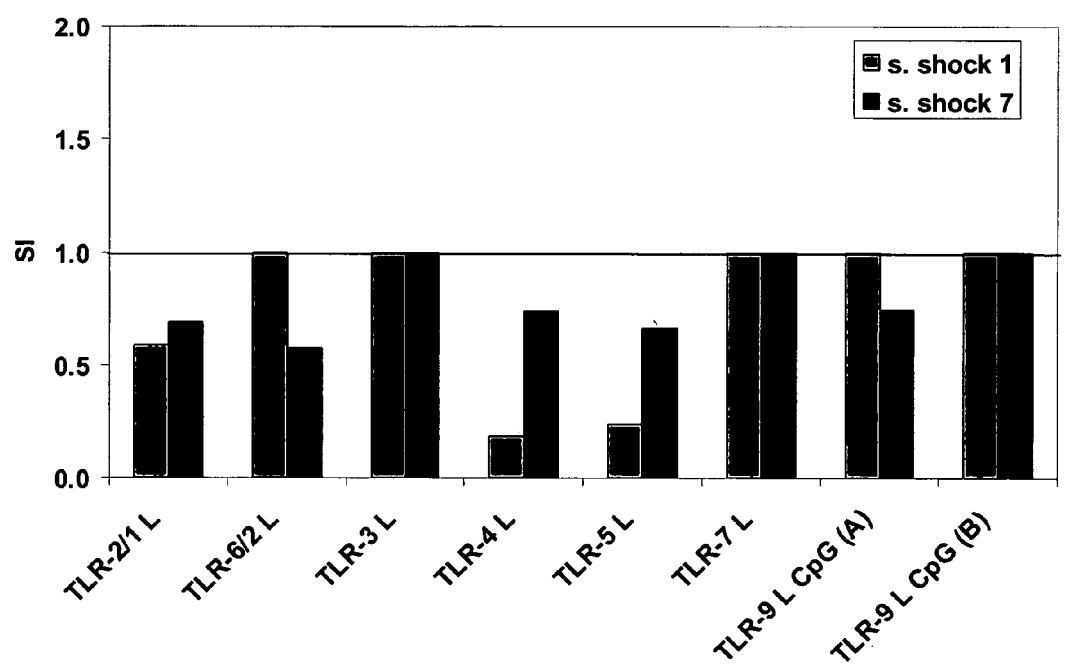
Figure 11E:
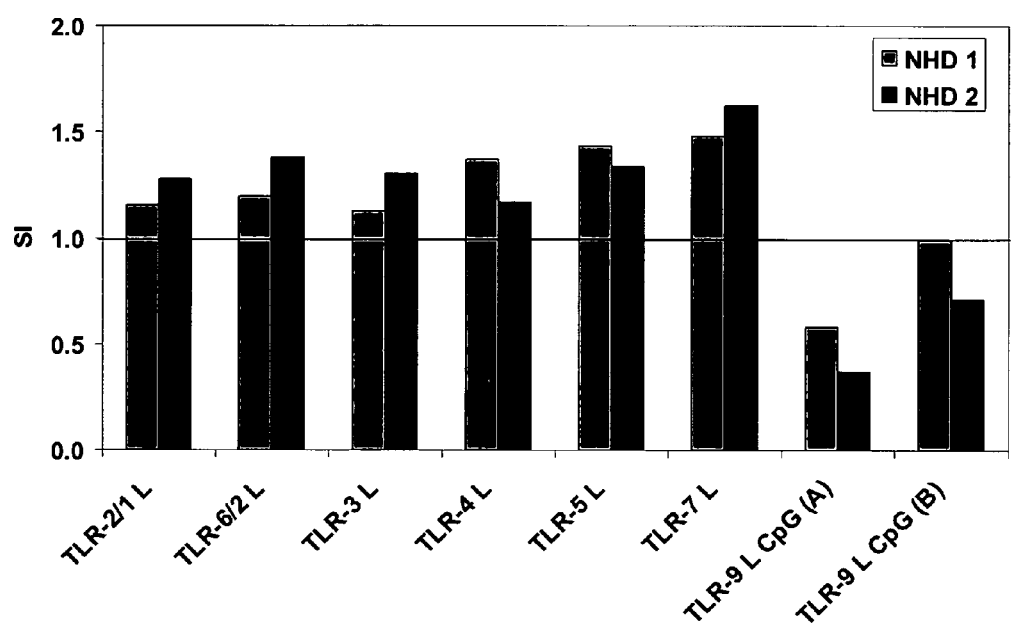
Figure 18A:
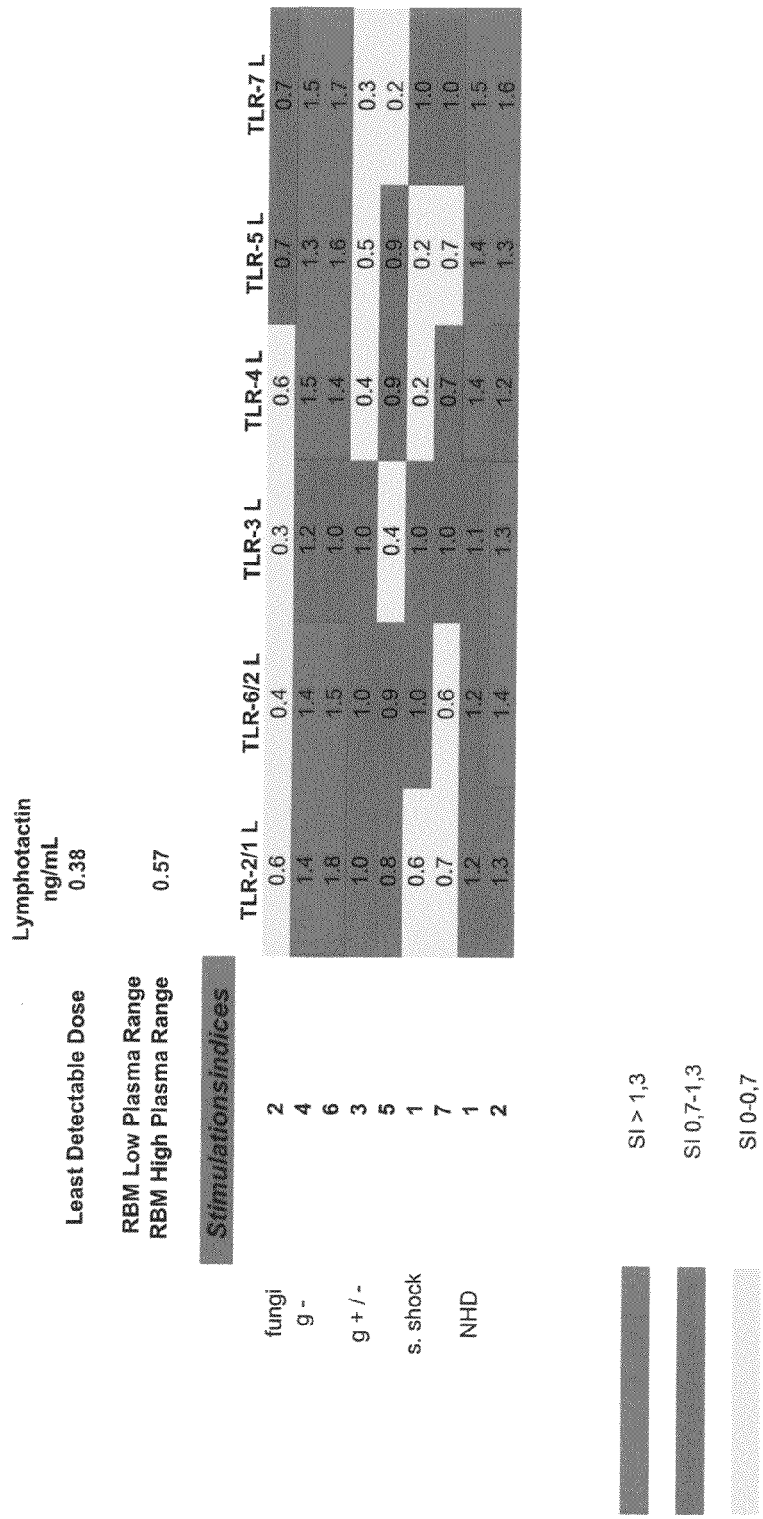
FIGS. 18A and 18B show stimulation indices and degree of stimulation for different TLR ligands for different forms of sepsis.
Figure 18B:
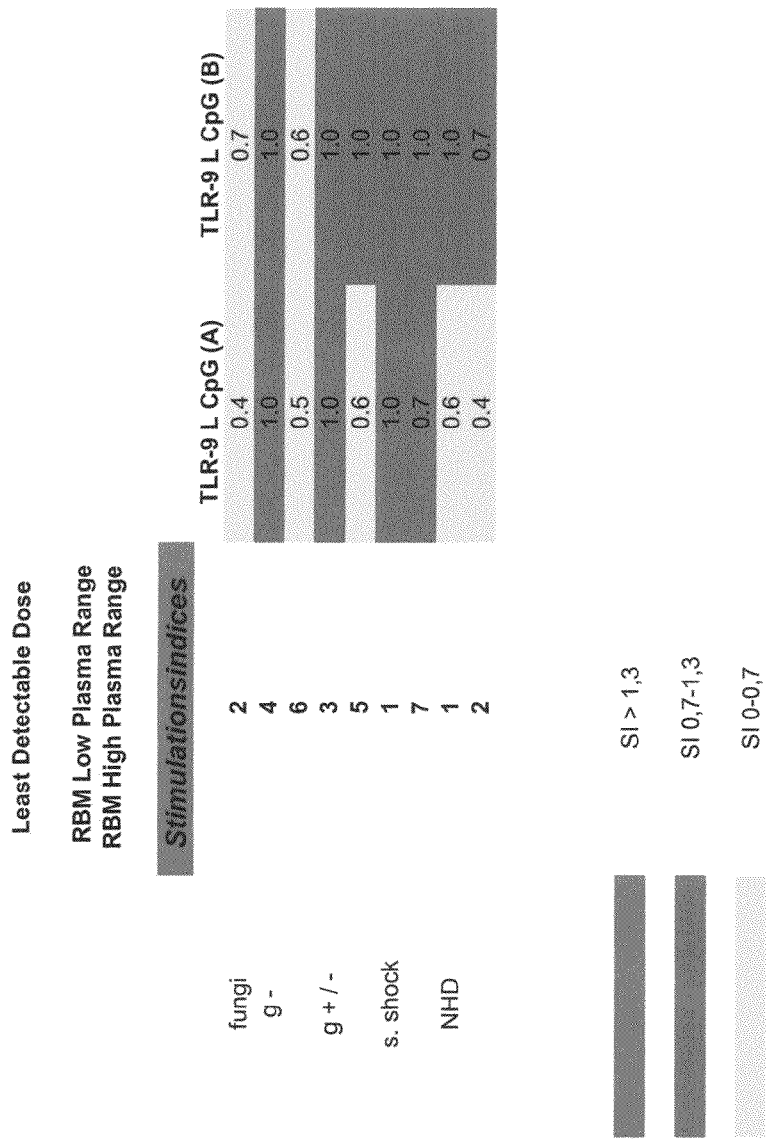
Figure 19A:
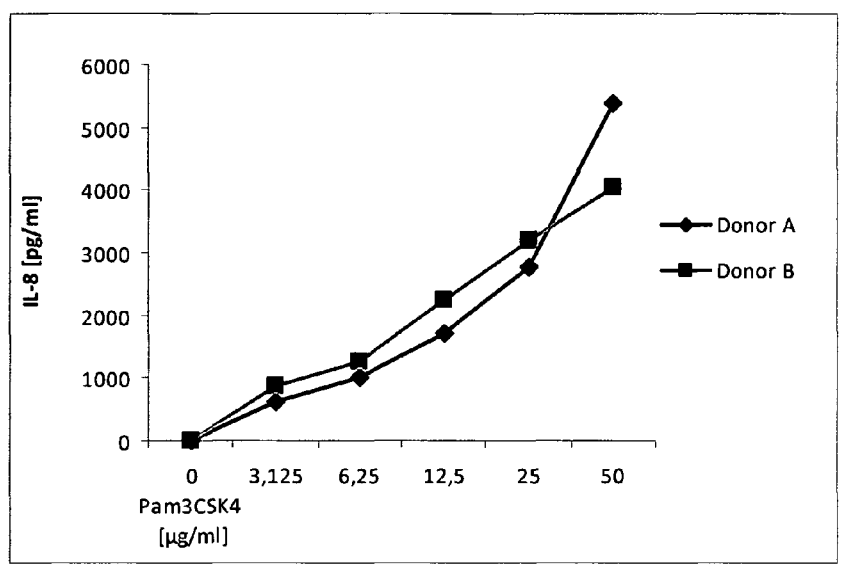
FIGS. 19A through 19N are titrations of various stimulants to determine the effect of the stimulant on specific informative genes, as indicated.
Figure 19B:
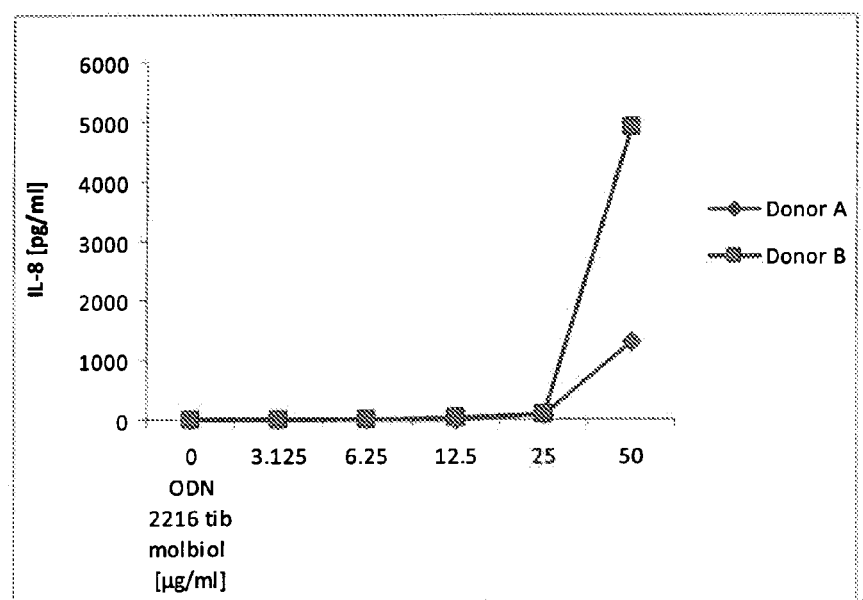
Figure 19C:
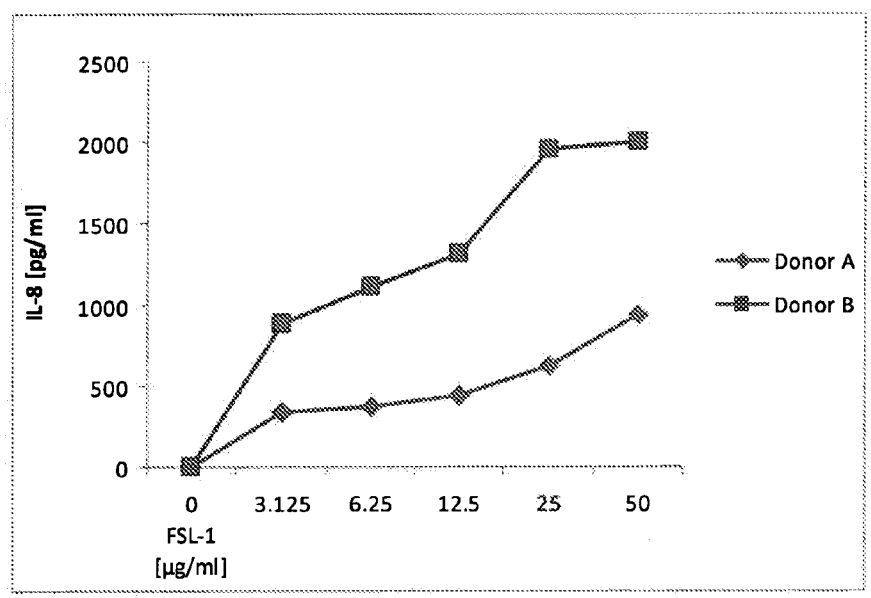
Figure 19D:
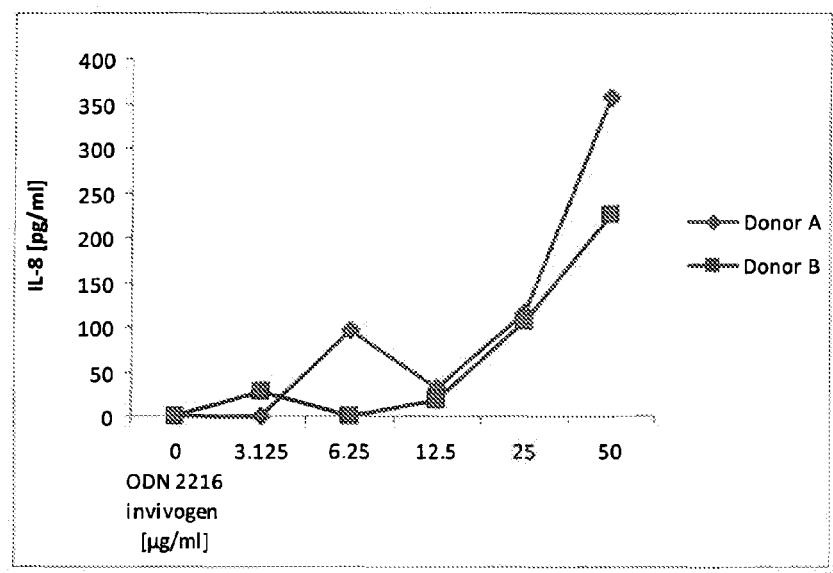
Figure 19E:
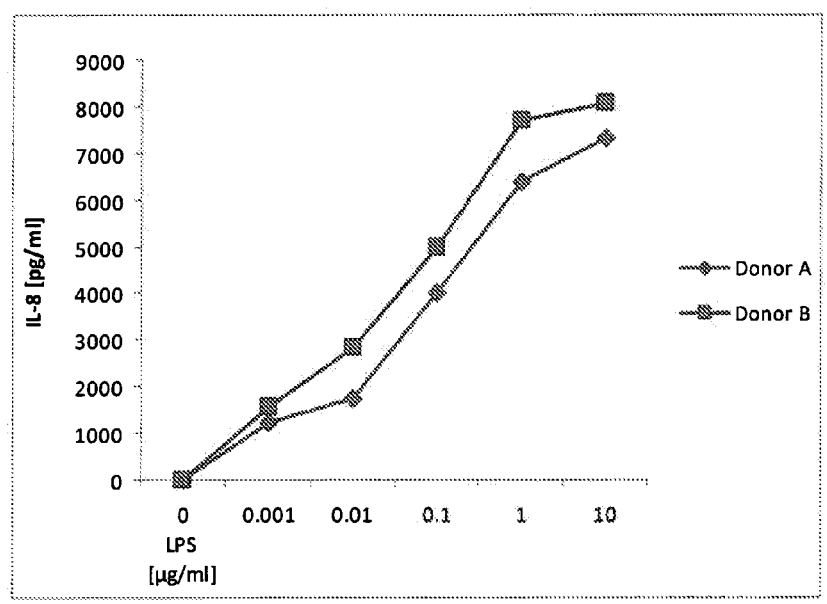
Figure 19F:
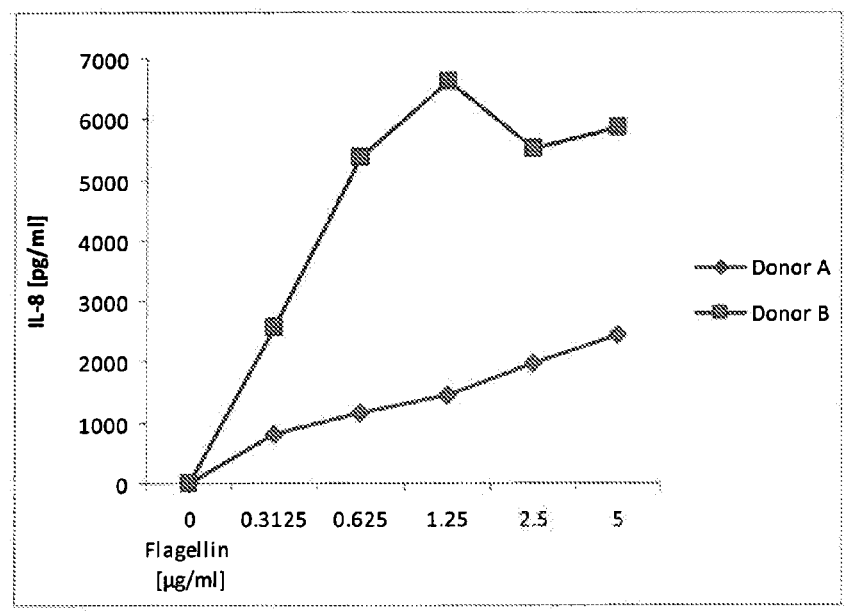
Figure 19G:
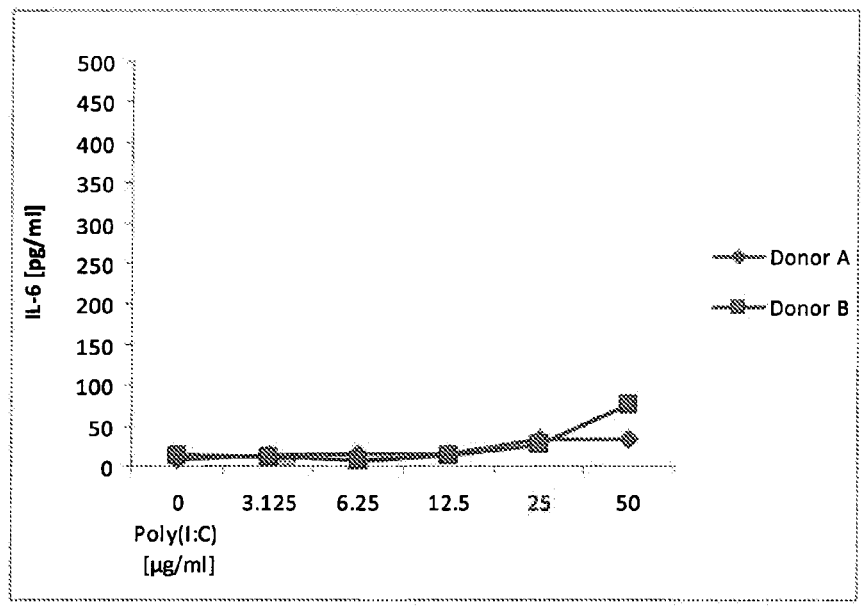
FIGS. 19G through 19J: IL-6.
Figure 19H:
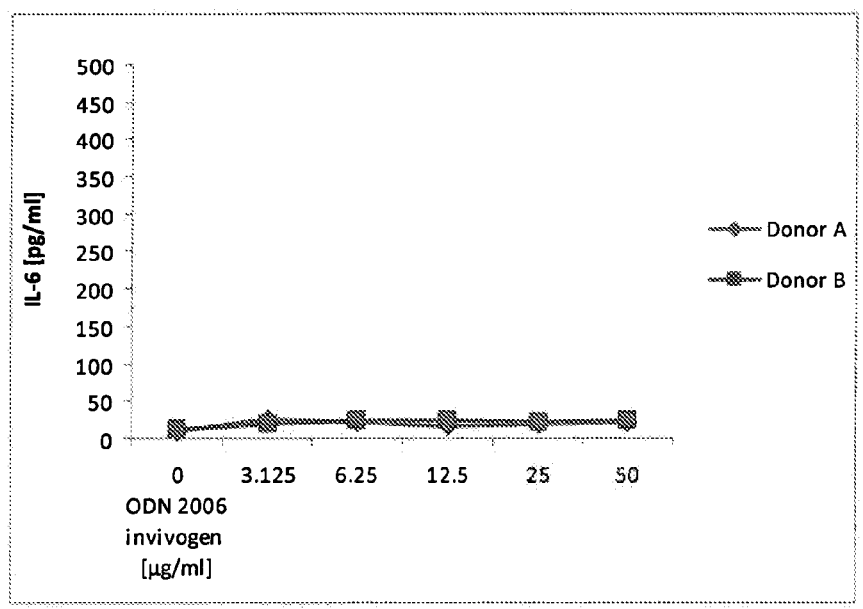
Figure 19I:
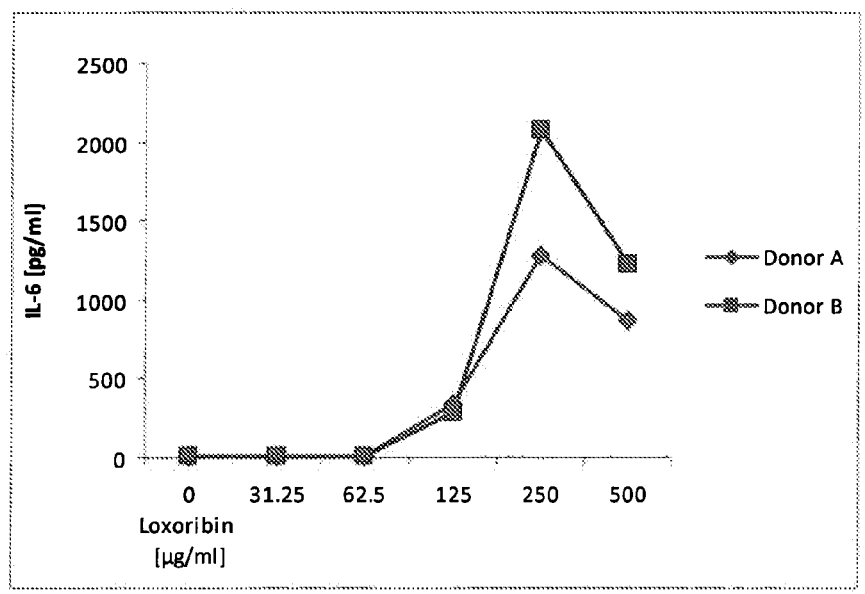
Figure 19J:
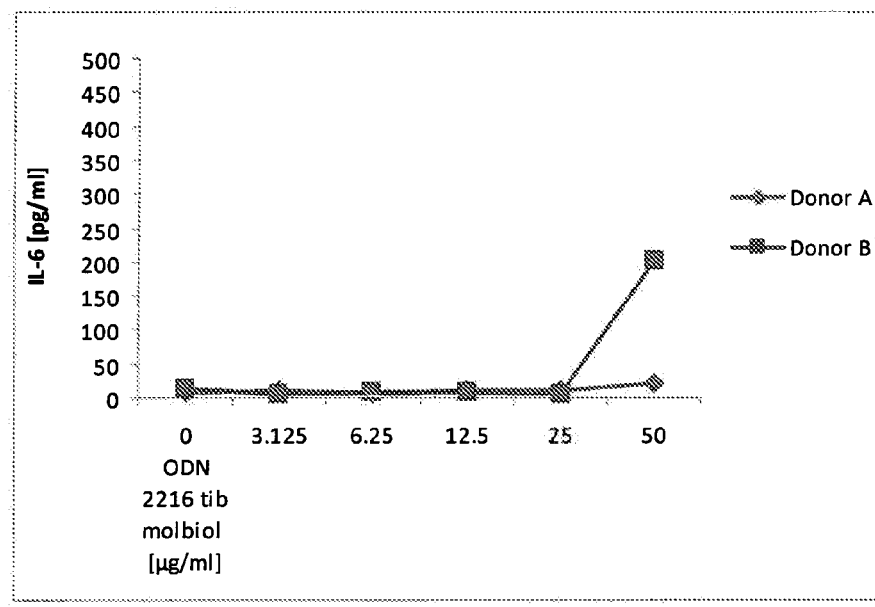
Figure 19K:
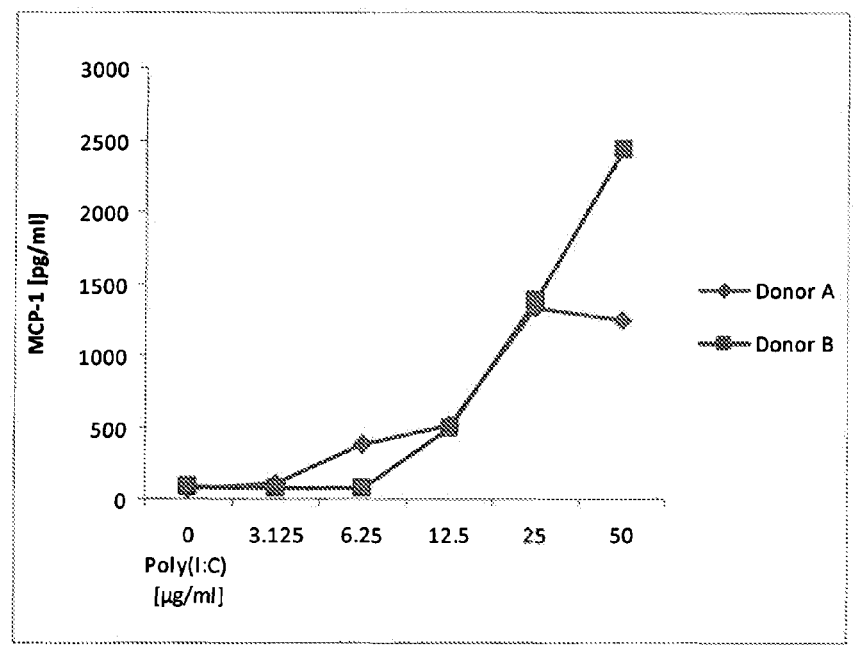
Figure 19L:
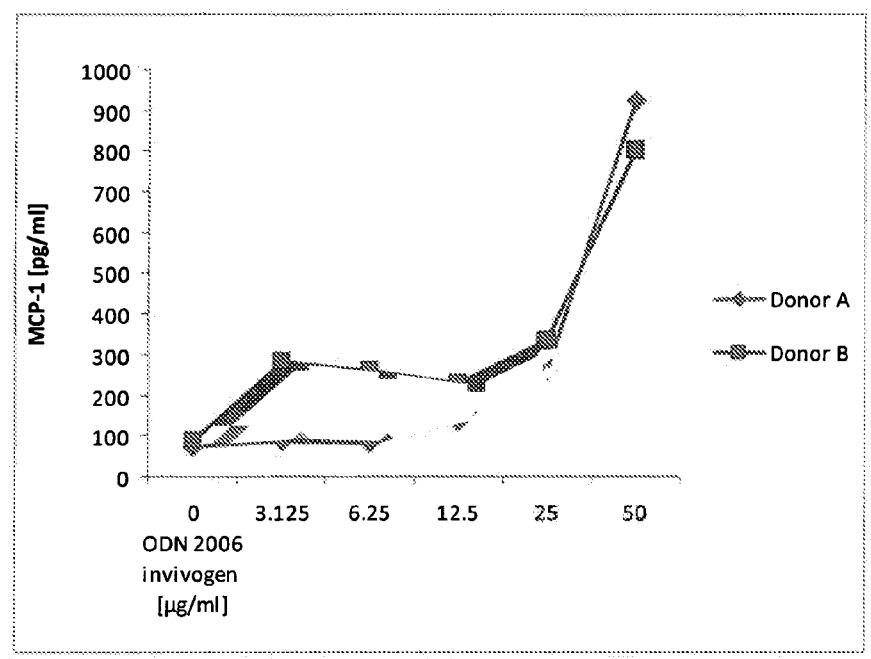
Figure 19M:
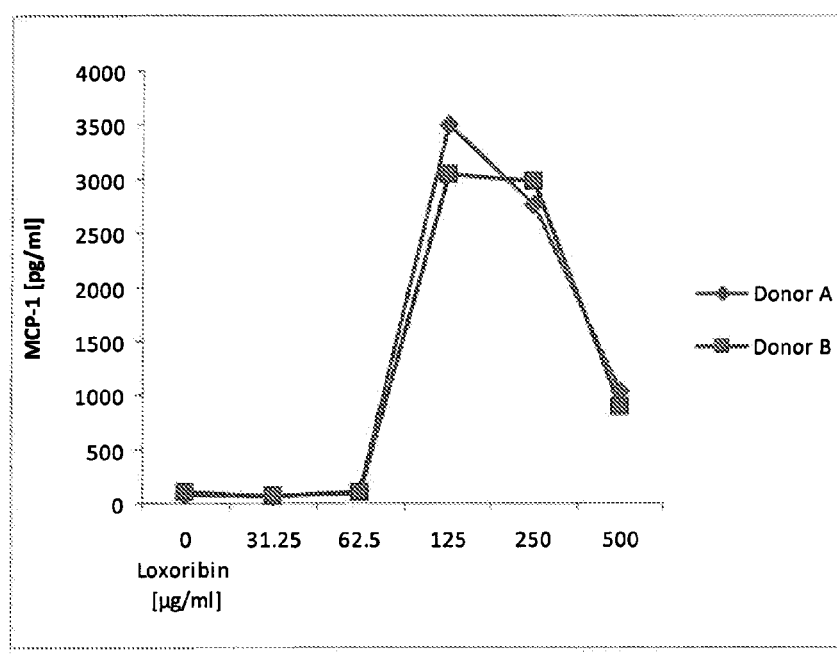
Figure 19N:
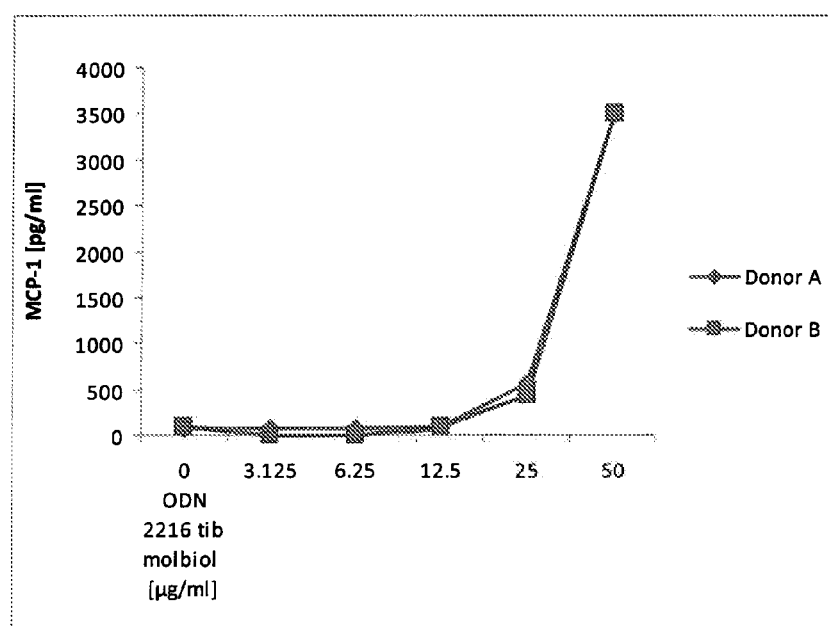

The present invention is directed to methods for the recognition and/or characterization of cellular activity patterns in a biological sample, the relevant use of toll-like receptor ligands (TLR ligands), and a kit. As used herein, "activity patterns" refers to changes in the state of cells and of cell cultures, particularly with respect to expression and activity of relevant genes, which occur in connection with stimulation by means of pathogenic stimulants. The changes in activity patterns can be biological and/or chemical—particularly biochemical—changes of state. The activity patterns can encompass one change of state or several changes of state.

As used herein, the term "biological sample" refers to a whole organism or a subset of its tissues, cells or component parts (e.g., body fluids, including but not limited to blood, mucus, lymphatic fluid, synovial fluid, cerebrospinal fluid, saliva, amniotic fluid, amniotic cord blood, urine, vaginal fluid and semen). A "biological sample" further refers to a homogenate, lysate or extract prepared from a whole organism or a subset of its tissues, cells or component parts, or a fraction or portion thereof, including but not limited to, for example, plasma, serum, spinal fluid, lymph fluid, the external sections of the skin, respiratory, intestinal, and genitourinary tracts, tears, saliva, milk, blood cells, tumors, organs. Most often, the sample has been removed from an animal, but the term "biological sample" can also refer to cells or tissue analyzed in vivo, e.g., without removal from animal. Typically, a "biological sample" will contain cells from the animal, but the term can also refer to non-cellular biological material, such as non-cellular fractions of blood, saliva, or urine, which can be used to measure the cancer-associated polynucleotide or polypeptides levels. A "biological sample" further refers to a medium, such as a nutrient broth or gel in which an organism has been propagated, which contains cellular components, such as, for example, proteins or nucleic acid molecules.

The immunological action of blood cells towards pathogens or pathogenic epitopes is in some cases associated with dynamic changes of state. The invention provides an extracorporeal, e.g., ex vivo, method that permits recognition and/or characterization of these transformations of cellular states. Surprisingly it has now become possible to show that as a consequence of stimulation with toll-like receptor ligands (TLR ligands), activity patterns generated by blood cells can be correlated with the general immunological performance of the blood cells. This can be utilized in a particularly advantageous manner for diagnosing particular versions of an inflammatory disease, e.g., sepsis, for monitoring the progression of the inflammatory disease, and for determining the efficacy or status of treating the inflammatory disease. As used herein, the term "efficacy" refers to the degree to which a desired effect is obtained, particularly in relation to treating an inflammatory disease, e.g., relief or reduction of symptoms. This applies, for example, to diseases that arise from the Systemic Inflammatory Response Syndrome (SIRS).

Patient-specific differences with regard to the immunological performance of the blood cells can also be determined such that, in principle, sub-typing of diseases is feasible, e.g., classification in patient subgroups. The sub-typing process can have important consequences for preventive and therapeutic measures. For example, the method according to the invention can be followed by an appropriate individual therapy. Furthermore, the method according to the invention is suitable to monitor manifested and treated diseases. Therefore the method according to the invention can be applied in combination with a defined therapeutic measure.

The methods described herein make it possible to determine the influence of a therapeutic measure on the cellular secretion of intracellular substances by extracorporeal means if the cells are activated by pathogen-typical stimulants. For example, it is possible to examine which medicinal products are capable of producing or altering a disease-associated activity pattern.

It is also possible to examine the immunological behavior of the blood cells over a longer period. For this purpose blood cells can be taken from a donor or patient at random intervals, which are then examined for their immunological behavior towards at least the toll-like receptor ligands (TLR ligands). This makes it possible to establish the dynamic fluctuations in the activity patterns of the blood cells.

Generally speaking, when examining stimulated blood cells and/or the culture medium, all cellular changes of state can be referred to, e.g., chemical, biochemical and/or biological changes of state of the stimulated blood cells and/or of the blood cells are measured. The chemical changes can be, for example, physico-chemical changes in state. Changes can include, for example, the calcium influx into the blood cells, pH value changes, membrane potentials and/or the cAMP/cGAMP level (cyclic adenosine-guanosine-monophosphate).

In one embodiment, the present invention is directed to methods of detecting altered states of cells wherein the culture medium of the cells is examined to determine the substances secreted into the culture medium by stimulated blood cells. Examination of the secreted substances can take place during the stimulation process or after the stimulation process at intervals that can be readily determined by one of skill in the art. The concentrations of the substances secreted by the stimulated blood cells are determined by methods described herein and known in the art. Whether secreted or not, changes in the expression levels of genes can be monitored to determine the activation state of cells. Biochemical molecules, e.g., expression products, mRNA, polypeptides, etc., are detectable and allow for the determination of the activation state of stimulated cells.

As used herein, the term "nucleic acid" refers to deoxyribonucleotides or ribonucleotides and polymers thereof in either single- or double-stranded form. The term encompasses a nucleic acid containing known nucleotide analogs or modified backbone residues or linkages, which are synthetic, naturally occurring, and non-naturally occurring, which have similar binding properties as the reference nucleic acids, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs). A nucleic acid sequence also encompasses naturally-occurring allelic variants of said nucleic acid.

As used herein, the term "oligonucleotide" refers to a nucleic acid molecule consisting of two or more deoxyribonucleotides or ribonucleotides joined by phosphodiester bonds, and preferably containing between about 6 and about 300 nucleotides in length. The size of the oligonucleotide will depend on many factors, including the ultimate function or use of the oligonucleotide. Preferably, an oligonucleotide that functions, for example, as an extension primer will be sufficiently long to prime the synthesis of extension products in the presence of a catalyst, e.g., DNA polymerase, and deoxynucleotide triphosphates. As used herein, the term "oligonucleotide" further refers to an oligonucleotide that has been modified structurally ("modified oligonucleotide") but functions similarly to the unmodified oligonucleotide. A modified oligonucleotide can contain non-naturally occurring portions, such as altered sugar moieties or inter-sugar linkages, such as a phosphorothioate.

As used herein, the term "polypeptide" refers to a polymer in which the monomers are amino acids and are joined together through peptide or disulfide bonds. It also refers to either a full-length naturally-occurring amino acid sequence or a fragment thereof between about 8 and about 500 amino acids in length. Additionally, unnatural amino acids, for example, beta-alanine, phenyl-glycine and homoarginine can be included. All of the amino acids used in the present invention can be either the D- or L-optical isomer. A polypeptide sequence also encompasses naturally-occurring allelic variants of said polypeptide.

As used herein, the term "a significant change in the expression level" refers to either an increase or a decrease of the expression level from the control level by an amount greater than the standard error of the assay employed to assess expression. The term also refers to a change by preferably at least about 10%, about 20%, about 25%, about 30%, preferably at least about 40%, about 50%, more preferably at least about 60%, about 70%, or about 90%, about 100%, about 150%, or about 200%, or greater. As used herein, the term "gene" refers to a nucleic acid sequence that encodes and regulates expression of a polypeptide. A gene includes, therefore, regulatory elements, e.g., promoters, splice sites, enhancers, repressor binding sites, etc. A gene can have many different "alleles," which are sequence variations that can affect the polypeptide sequence or expression level, or have no effect on the polypeptide. A gene can include one or more "open reading frames", which are nucleic acid sequences that encode a contiguous polypeptide. A gene can be present either endogenously or exogenously.

The present invention also relates to methods for determining genes that are differentially expressed, e.g., create cellular activity patterns, in response to different stimuli. The particular genes, herein referred to as "informative genes", are identified in cells, e.g., blood cells, that have been exposed to a particular stimulus or have been induced to mimic, for example, a sepsis-like state. Differential expression of informative genes can relate to, for example, differences in expression relative to an unstimulated state, or differences in expression observed over a range of two or more different stimulatory factors. A subset or all informative genes can be assayed for gene expression to generate an "expression profile" that includes genes that are characteristic of a particular cellular activity pattern. As used herein, an "expression profile" refers to the level or amount of gene expression of one or more informative genes in a given sample of cells at one or more time points. A "reference" expression profile is a profile of a particular set of informative genes under particular conditions such that the expression profile is characteristic of a particular condition. For example, a reference expression profile that quantitatively describes the expression of the informative genes listed in the Tables can be used as a reference expression profile. Thus by comparing gene expression from a cell or tissue samples with a reference expression profiles is indicative of a particular cellular activity pattern.

As used herein, the term "expression level" refers to the amount of mRNA transcribed from the corresponding gene, or other gene product, that is present in a biological sample. The expression level can be detected with or without comparison to a level from a control sample or a level expected of a control sample. A "control level" refers to a standard level of a biomarker by which a change is measured against. In one embodiment, the "control level" can be a normal level of a biomarker nucleic acid expression, or a biomarker polypeptide, or a biomarker biological activity from normal or healthy cells, tissues, or subjects, or from a population of normal or healthy cells, tissues, or subjects. The term "control expression level" can also refer to an established level of mRNA representative of the healthy population that has been previously established based on measurement from healthy subjects.

As used herein, "detecting" refers to the identification of the presence or absence of a molecule in a sample. Where the molecule to be detected is a polypeptide, the step of detecting can be performed, for example, by binding the polypeptide to an antibody that is detectably labeled. A detectable label is a molecule that is capable of generating, either independently, or in response to a stimulus, an observable signal. A detectable label can be, but is not limited to a fluorescent label, a chromogenic label, a luminescent label, or a radioactive label. Methods for "detecting" a label include, for example, quantitative and qualitative methods adapted for standard or confocal microscopy, flow-cytometry analysis, and those adapted for high throughput methods involving multiwell plates, arrays or microarrays. One of ordinary skill in the art can select appropriate filter sets and excitation energy sources for the detection of fluorescent emission from a given fluorescent polypeptide or dye. "Detecting" as used herein can also include the use of multiple antibodies to a polypeptide to be detected, wherein the multiple antibodies bind to different epitopes on the polypeptide to be detected. Antibodies used in this manner can employ two or more detectable labels, and can include, for example a FRET (fluorescence resonance energy transfer) pair. A polypeptide molecule is "detected" according to the present invention when the level of detectable signal is at all greater than the background level of the detectable label, or where the level of measured polypeptide is at all greater than the level measured in a control sample.

As used herein, "detecting" also refers to identification of the presence of a target nucleic acid molecule, for example, by a process wherein the signal generated by a directly or indirectly labeled probe nucleic acid molecule (capable of hybridizing to a target in a serum sample) is measured or observed. Detection of the probe nucleic acid is directly indicative of the presence, and thus the detection, of a target nucleic acid, such as a sequence encoding a marker gene. Methods and techniques for "detecting" fluorescent, radioactive, and other chemical labels may be found in Ausubel et al. (1995, Short Protocols in Molecular Biology, 3rd Ed. John Wiley and Sons, Inc.).

Alternatively, a nucleic acid can be "indirectly detected" wherein a moiety is attached to a probe nucleic acid that will hybridize with the target, wherein the moiety comprises, for example, an enzyme activity, allowing detection of the target in the presence of an appropriate substrate, or a specific antigen or other marker allowing detection by addition of an antibody or other specific indicator. Alternatively, a target nucleic acid molecule can be detected by amplifying a nucleic acid sample prepared from a patient clinical sample, using oligonucleotide primers that are specifically designed to hybridize with a portion of the target nucleic acid sequence. Quantitative amplification methods, such as, but not limited to TaqMan® (a commercially available quantitative PCR system). can also be used to "detect" a target nucleic acid according to the invention. A nucleic acid molecule is "detected" as used herein where the level of nucleic acid measured (such as by quantitative PCR), or the level of detectable signal provided by the detectable label is at all above the background level.

Nucleic acid molecules can be detected and/or isolated by specific hybridization under particular stringency conditions. "Stringency conditions" for hybridization is a term of art that refers to incubation and wash conditions, e.g., conditions of temperature and buffer concentration, which permit hybridization of a particular nucleic acid to a second nucleic acid. The first nucleic acid can be perfectly complementary to the second, or the first and second can share some degree of complementarity less than perfect (e.g., 70%, 75%, 85%, 95%). For example, certain high stringency conditions can be used that distinguish perfectly complementary nucleic acids from those of less complementarity. "High stringency conditions", "moderate stringency conditions" and "low stringency conditions" for nucleic acid hybridizations are explained on pages 2.10.1-2.10.16 and pages 6.3.1-6.3.6 in Current Protocols in Molecular Biology (Ausubel, F. M. et al., "Current Protocols in Molecular Biology", John Wiley & Sons, (1998), the entire teachings of which are incorporated by reference herein). The conditions that determine the stringency of hybridization depend on parameters such as, for example, ionic strength (e.g., 0.2×SSC, 0.1×SSC), temperature (e.g., room temperature, 42° C., 68° C.), the concentration of destabilizing agents such as formamide or denaturing agents such as SDS, and factors such as the length of the nucleic acid sequence, base composition, percent mismatch between hybridizing sequences and the frequency of occurrence of subsets of that sequence within other non-identical sequences. Thus, equivalent conditions can be determined by varying one or more of these parameters while maintaining a similar degree of identity or similarity between the two nucleic acid molecules.

The methods of the present invention are useful for diagnosing or characterizing inflammatory disease, e.g., sepsis. Diagnosis can be the early detection of inflammatory diseases, e.g., sepsis, preferably, prior to a time when a symptom is visible. The methods described herein are also useful for monitoring the progression of an inflammatory disease or the efficacy of treating an inflammatory disease. This monitoring and characterizing of an inflammatory disease refers to, for example, the measurement of a change in the degree of the inflammatory disease before and after treatment with a therapeutic compound. In this case, a change in degree of the inflammatory disease in response to a therapeutic compound refers to either an increase or a decrease by at least about 10% in the expression of one or more marker genes, or alternatively, in the amount of the marker gene polypeptides presented in a clinical sample, in response to the presence of a therapeutic compound relative to the expression level in the absence of the therapeutic compound.

As used herein, the term "antibody" refers to the conventional immunoglobulin molecule, as well as fragments thereof that are also specifically reactive with one of the subject polypeptides. Antibodies can be fragmented using conventional techniques and the fragments screened for utility in the same manner as described herein below for whole antibodies. For example, F(ab)$_2$ fragments can be generated by treating antibody with pepsin. The resulting F(ab)$_2$ fragments can be treated to reduce disulfide bridges to produce Fab fragments. The antibodies of the present invention are further intended to include bispecific, single-chain, and chimeric and humanized molecules having affinity for a polypeptide conferred by at least one CDR region of the antibody. In preferred embodiments, the antibodies further comprise a label attached thereto and able to be detected (e.g., the label can be a radioisotope, fluorescent compound, chemiluminescent compound, enzyme, or enzyme co-factor). A "monoclonal antibody" is an antibody that recognizes only one epitope of an antigen. This type of antibodies is produced, for example, by the daughter cells of a single antibody-producing hybridoma.

An antibody of the present invention can include, but is not limited to, polyclonal, monoclonal, multispecific, human, humanized, or chimeric antibodies, single chain antibodies, Fab fragments, Fv fragments, F(ab') fragments, fragments produced by a Fab expression library, anti-iodiotypic antibodies, or other epitope binding polypeptide. Preferably, an antibody, useful in the present invention for the detection of a polypeptide, is a human antibody or fragment thereof, including scFv, Fab, Fab', F(ab'), Fd, single chain antibody, of Fv. An antibody can include a complete heavy or light chain constant region, or a portion thereof, or an absence thereof. An antibody can be obtained from a host, such as rabbit, mouse, rat, donkey, sheep, goat, guinea pig, camel, horse, or chicken. In one embodiment, an antibody useful in the invention can be a humanized antibody, in which amino acids have been replaced in the non-antigen binding regions in order to more closely resemble a human antibody, while still retaining the original binding ability. Methods for making humanized antibodies are known in the art (Teng et al., *Proc. Natl. Acad. Sci. USA*, 80:7308-7312, 1983; Kozbor et al., *Immunology*

*Today*, 4:7279, 1983; Olsson et al., *Meth. Enzymol.*, 92:3-16, 1982; WO 92/06193; and EP 0239400).

A non-immunoglobulin binding scaffold can also be used to detect targets as provided by the present invention. Avimers (avidity multimers) or aptamers, for example, can be used to bind specific targets. Other non-immunoglobulin binding scaffolds can be used based on, for example, receptors, protein A, the lipocalins, a fibronectin domain, an ankyrin consensus repeat domain, and thioredoxin. These non-immunoglobulin binding scaffolds can be, for example, detectably labeled, thereby allowing for the detection of a specific binding target.

In addition to detecting secreted substances, activation markers of the cells can be examined at the transcriptional, translational and/or post-translational level, preferably accompanied by the determination of their concentrations. Methods for determining changes include, for example, an immunoassay or electrophoretic methods. The immunoassays are generally based on the recognition of a target molecule by specific antibodies. An appropriate immunoassay for example is the ELISA method (enzyme-linked immunosorbant assay). An appropriate electrophoretic method for determining the concentration is, for instance, gel electrophoresis, particularly the two-dimensional polyacrylamide gel electrophoresis (2D PAGE). Furthermore, array technologies and, in particular, multiplex bead arrays or planar arrays are also useful for determining changes in expression levels.

The substances secreted by the stimulated blood can be "messenger" substances, e.g., mediators. The secreted substances can be proteins and/or peptides. For example, the proteins can be receptors and/or proteins with enzymatic activity. The secreted substances can be glycosylated proteins and/or peptides, and the state of glycosylation can also be determined to indicate changes in the activation state of the cells. The substances secreted by the stimulated blood cells can be low-molecular messenger substances, in particular radical oxygen compounds, lipidic messenger substances, cytokines, chemokines, soluble receptors and/or adhesion molecules. The secreted substances can be membrane-enwrapped vesicles, particularly exosomes and/or nucleosomes.

In one embodiment of the invention, the stimulated blood cells are recovered from the culture medium for the purpose of examination. For example, the blood cells can be recovered by means of centrifugation techniques known to those of skill in the art, e.g., gradient centrifugation or other separation methods using antibodies or specific binding structures employed to positively or negatively select cell populations and subpopulations. The recovery of the blood cells can also be performed with magnetic or flow-cytometric sorting technology.

When the stimulated blood cells are examined, gene products formed by the blood cells can also be examined. For example, RNA that is formed by the blood cells, especially mRNA (messenger RNA), can be analyzed. RNA formed in cells can be isolated by methods known in the art and quantitated, for example, by hybridization assays, e.g., hybridization assays performed on chips containing microarrays. The RNA from the blood cells can be isolated, for example, by means of extraction. Isolated RNA can be subjected to amplification, in particular a polymerase chain reaction with reverse transcriptase (RT-PCR). Additional methods for detecting and quantitating mRNA expression include, for example, Northern blotting or FISH (fluorescence in situ hybridization).

In addition, when the blood cells are examined, expression levels of proteins and/or peptides can be determined. It is therefore possible to create expression patterns or profiles for examining proteins and/or peptides. Furthermore it is possible to draw on mass spectroscopic investigations in particular. It is also possible to apply array technologies.

Apoptotic signal pathways and processes in the stimulated blood cells can be determined. It is primarily the expression of signal transducers and/or receptors on and/or in the blood cells that are examined. Special priority is given to determining the density of the signal transducers and/or receptors on and/or in the blood cells. In addition, it is possible to examine the induction of enzymatic activities. For example, but not limited to, the enzymatic activities of phospholipases, cyclooxygenases, protein kinases, PARP (polyADP Ribose Polymerase), matrix-metalloproteinases, NADPH oxidases, phosphatases, kinases, ubiquitinylating enzymes and/or caspases can be examined. Methods for examining cellular signal transducers and/or receptors include, for example, analyses of surface markers and/or of phosphorylated signal transducer molecules, especially phosphorylated proteins. Appropriate analyses are based on, for example, histological staining techniques or flow cytometric methods known in the art.

In another embodiment, modified cell nucleus constituents of blood cells are examined to determine the activation state of stimulated blood cells. Modified cell nucleus constituents are, for example, DNA and formed microRNA. DNA modifications, e.g., methylation and/or acetylation, can also be determined to detect changes in the state of stimulated cells.

Blood cells of the present invention can be stimulated with TLR ligands. The toll-like receptors (TLR) that are known to date are transmembrane molecules that show an extracellular domain rich in leucine and an intracellular domain similar to the interleukin-1 receptor. Ligands of human toll-like receptors (hTLR ligands) are primarily used to stimulate the blood cells. For example, at least one ligand of human toll-like receptors (hTLR ligand) from the group encompassing hTLR1, hTLR2, hTLR3, hTLR4, hTLR5, hTLR6, hTLR7, hTLR8, hTLR9, hTLR10 and hTLR11 can be used to stimulate the blood cells. Moreover, ligands of TLR heterodimers, primarily ligands of the TLR heterodimer, hTLR1-hTLR2, and/or ligands of the TLR heterodimer, hTLR2-hTLR6, can be used.

The TLR ligands can be ligands that occur in nature or produced recombinantly or synthetically. Especially important for stimulating blood cells are TLR ligands of microbial origin. In particular, the TLR ligands can stem from bacteria, viruses and/or fungi, but primarily from bacteria. TLR ligands can also be proteolytic products of animal organisms, in particular of humans. Suitable proteolytic products are fibrin and/or fibrinogen.

Compounds that occur in bacterial cell walls and/or bacterial cell membranes are used as TLR ligands to stimulate the blood cells. Suitable compounds are compounds that occur in cell walls and/or cell membranes of gram-negative bacteria. In particular enterobacteria, *Pseudomonas aeruginasa, Neisseria meningitidis* and/or *bacteroides* come under consideration as gram-negative bacteria. The enterobacteria include, for example, are *Escherichia coli, Klebsiella, proteus* and/or *enterobacter*. Furthermore, compounds from cell walls and/or cell membranes of gram-positive bacteria can be used as TLR ligands, especially of staphylococci and/or streptococci, for example of *Staphylococcus aureus* and/or *Streptococcus pneumoniae*.

Stimulation of blood cells can be accomplished, in particular, by using at least one TLR ligand from the group that encompasses lipopolysaccharides (LPS), lipoproteins, lipopeptides, lipoteichic acids, glycans, muramyl-(lipo)-peptides, mannans, DNA and/or RNA. The glycans can be, for example, proteoglycans. RNA can be double-stranded RNA (dsRNA) and/or single-stranded RNA (ssRNA). The lipopeptides primarily used are those with two or three covalently bonded fatty acids. Other TLR ligands are proteins, especially bacterial proteins. For example, the proteins can be flagellin and/or heat shock proteins. According to the invention phosphodiester compounds of DNA bases can be used. For example, the phosphodiester compounds can be CpG (phosphodiester from cytosine and guanine).

In another form of implementation synthetic TLR ligands, in particular Imiquimod and/or Loxoribine (or related compounds) are used to stimulate the blood cells.

In another aspect of the invention, in addition to the TLR ligands, blood cells are stimulated with other substances that stimulate blood cells, e.g., co-stimulating cell receptor ligands. These ligands are primarily ligands for cell receptors that are activated by pathogen-associated molecular patterns (PAMPs), irrespective of their bonding specificity. In particular, integrin receptor ligands can be used as co-stimulating cell receptor ligands. The integrin receptors are adhesion receptors that are present in the cell membrane in the form of glycoproteins and they play an important role especially in cell-cell contacts and in the conveyance of signals from the extracellular space into the intracellular space (cytoplasm). The co-stimulating cell receptor ligands are ligands for intracellular and, in particular, receptors equivalent to the toll-like receptors in terms of function, especially ligands from the nucleotide-binding oligomerization domain family (NOD family, also referred to as CARD [N-terminal caspase recruitment domain] family). Particular ligands include, for example, the NOD 1 receptor and/or NOD 2 receptor as co-stimulating cell receptor ligands.

In another aspect of the inventions exosomes and/or nucleosomes are used to stimulate the blood cells.

TLR ligands of a variety of pathogens can be used to stimulate the blood cells. The activity patterns generated in this manner reflect particularly advantageously the current performance of the blood cells towards various TLR ligands. The resulting activity patterns can be used for diagnostic purposes and/or tracking therapy of diseases that are based on the simultaneous and/or sequential occurrence of multiple types of pathogens.

In another aspect of the invention, TLR ligands with binding specificities for different toll-like receptors can be used to stimulate the blood cells.

In one embodiment, the invention is directed to working with detecting molecules in culture media, particularly in parallel cultures. For example, blood cells can be diluted about 1 to 100, about 1 to 50 or about 1 to 11 into parallel cultures. Blood cells are transferred into the culture media before they are stimulated, and the culture media can be provided with different TLR ligands. In this way, irrespective of the TLR ligand, different activity patterns can be captured and in particular characterized. According to the invention each culture medium is intended to be provided with one TLR ligand. According to the invention it is also possible to provide the culture media with more than one TLR ligand. Hence it is possible to capture cellular activity patterns and, in particular, to characterize how they occur in an organism in the presence of several types of pathogens or how they arise owing to infection with more than one type of pathogen (polymicrobial sepsis).

In one embodiment, immune cells, particularly immune cells of the peripheral blood, primarily leukocytes, are used as blood cells. The blood cells are preferably whole blood. Leukocytes that contain lymphocytes, dendritic cells and/or macrophages can in particular be used as suitable blood cells. Primarily the stimulated blood cells are leukocytes. The leukocytes are in particular granulocytes, lymphocytes, NK-cells, dendritic cells, monocytes as well as precursors of these kinds of differentiation stages. The blood cells can be present especially as PBMC (peripheral blood mononuclear cells), which are primarily obtained by means of density gradient centrifugation. Leukocytes acquired in this way include, for example, T lymphocytes, B lymphocytes, NK cells (natural killer cells), monocytes, dendritic cells, eosinophils, plasma cells, as well as precursors thereof.

The blood cells useful in the present invention can already be present in an activated state before they are stimulated. This means that the blood cells can be pre-activated by stimulants, in particular by pathogenic stimulants. The stimulants can be TLR ligands. For example, the blood cells of a donor with an inflammatory disease can be used.

The blood cells can be enriched from blood prior to the stimulation process. A sample of the whole blood can be transferred to the culture medium with the whole blood cells being stimulated at least by the TLR ligands. Generally speaking "whole blood" is taken to be blood with all its blood constituents, including the blood cells, the blood plasma and the biologically active factors contained therein, for example the coagulation factors and complement proteins. Whole blood can be fresh blood, preferably fresh patient blood. In particular, blood cells can be obtained from a donor at specific intervals over an extended period. These samples obtained at different time points can be examined with regard to their activity patterns to, for example, monitor the progression of an inflammatory disease or to determine the efficacy of treating an inflammatory disease. This enables the current immunological performance of the blood cells to be observed over an extended period, if necessary.

In one embodiment, blood cells can be stimulated over a period between 0 and about 48 hours, in particular between about 2 and about 48 hours, between about 12 and about 36 hours, between about 10 and about 24 hours. In a preferred embodiment, cells can be stimulated over a period of about 24 hours. In other embodiment, blood cells are stimulated for about 1 to 30 min, in particular between about 1 and 10 min. This is especially advantageous for examining early signal transductions. In particular the method according to the invention can be implemented as an "ultra-quick test". In this way it is possible to capture and examine relatively unspecific indicators of cellular activity. For example the calcium influx into the blood cells, changes to the intracellular and extracellular pH value, the phosphorylation of proteins and/or the formation of cAMP/cGAMP can all be determined.

In another embodiment, blood cells are stimulated over a period of about 1 to about 4 hours (quick test). Such a test is useful to examine the secretion of substances, e.g., messenger substances. For example, it is possible to measure the release of interleukin 1 (IL-1), tumor necrosis factor α (TNFα), interleukin-8 (IL-8) granzyme B, tryptase, histamine and/or perforin, etc. The secreted substances are in particular substances that are already preformed in the blood cells. These are normally stored in the cells in secretory granules. In addition, within the stimulation time mentioned in this section, it is possible to examine the synthesis of low molecular substances, in particular of messenger substances, such as, for example, prostaglandins and leukotrienes, as well as, for example, to examine the redistribution of surface markers.

In another preferred form of implementation the blood cells are stimulated over a period of about 6 to about 24 hours. In this way it is possible to capture and examine specific indicators of cellular activity. Specific cellular activity indicators include, for example, cytokines, chemokines, surface receptors, enzymes and/or other proteins or peptides and exosomes and/or nucleosomes. The surface receptors can be, for example, adhesion molecules.

In accordance with the invention the blood cells can be stimulated in hollow cylindrical vessels, particularly of the blood vial or syringe cylinder type. Vessels of this type are particularly suitable for stimulating the blood cells if during the stimulation process a supernatant and a sediment form; the latter must essentially consist of the blood cells. In particular, a syringe can have a plunger that can be broken off and a sealing cap that opens up the entire cross section of the syringe cylinder. Syringe cylinders of this type can be handled like test tubes or centrifuge tubes after the plunger has been broken off. After the stimulation period, particularly after a period of stimulation lasting for over about 6 hours, after the blood cells sediment a valve plunger to fit the syringe cylinder can be inserted with the cap off and pushed into the supernatant. The supernatant then flows through the valve plunger. After the pressing-in of the valve and the withdrawal of the insertion aid has been completed, the valve plunger closes of its own accord so that it is no longer possible for the blood cells to mix with the supernatant. This is particularly advantageous if the examination of the activity of the blood cells is performed in a different location than where they were stimulated. Furthermore, in many cases preference is given to freezing the sample to be examined if it is to be kept for an extended period. This causes the blood cells contained in the sample to burst open, thus releasing their intracellular substances. The inserted valve plunger prevents the substances thus released from distorting the measuring results.

The present invention also applies at least to the use of TLR ligands for producing a means for diagnosing and/or tracking the therapy of diseases. The diseases are primarily inflammatory and especially chronic inflammatory diseases. According to the invention the intention is for the diseases to be associated with a systemic inflammatory response syndrome (SIRS), particularly of diverse origins. These include all endogenic inflammatory defense reactions of an organism as a whole. The causes of SIRS can be very diverse. Generally SIRS can arise from severe diseases, injuries, accidents, radiation, cardiac infarction and other pathomechanisms, such as enzyme defects or intoxication. Primarily the diseases are septic diseases, especially sepsis. A sepsis is referred to if SIRS is present and at the same time a systemic infection can be proved.

In another embodiment, the diseases concerned are the macrophage activation syndrome (MAS), which is accompanied by chronic inflammatory states.

In one embodiment, the TLR ligands used according to the invention are primarily present in a stable form that can be stored, particularly in frozen or freeze-dried form.

In another embodiment, the present invention is directed to a kit for diagnosis and/or tracking the therapy of diseases that includes a vessel for stimulating blood cells. TLR ligands can be included in the kit. The vessel contains at least one TLR ligand. The kit according to the invention can comprise, separately, a vessel and at least one TLR ligand. In particular the vessel can be a blood test tube or a syringe cylinder. Furthermore, the kit can further comprise a culture medium for the blood cells. Moreover, the kit according to the invention can also comprise a set of instruments for taking blood samples.

EXEMPLIFICATION

Example 1

Informative genes were identified that are useful in characterizing cellular activity patterns for various forms and causes of sepsis. FIG. 1 clearly shows that the activity patterns exhibit significant differences from one sepsis patient to another. These differences can be drawn on to characterize sepsis and especially for the subdivision into subtypes of sepsis. In this way it is in particular possible to recognize types of sepsis by diagnostic means on the basis of the measured activity patterns. This can be exploited in a targeted manner for tracking therapy.

Samples were obtained from sepsis patients and subjected to multi-analyte profiling (MAP). Expression values were obtained for 98 informative genes (see table 1; FIGS. 2-10 and 12-18). Parameters used for MAP analysis include lowest detectable dose, normal range, dynamic range, imprecision, spiked recovery, linearity, correlation, cross-reactives and matrix interferences. These parameters are combined or used in combination to evaluate analytes for their ability to characterize cellular activity patterns.

TABLE 1

| Informative genes. | | | |
|---|---|---|---|
| IGF-1 | IL-1 ra | ICAM-1 | SHBG |
| MMP-3 | MIP-1beta | IgA | Factor VII |
| Apolipoprotein A1 | TIMP-1 | IL-16 | Glutathione S-Transferase |
| IgM | Calcitonin | Carcinoembryonic Antigen | IL-12p70 |
| TGF-alpha | Beta-2 Microglobulin | VCAM-1 | Endothelin-1 |
| MCP-1 | CD40 | Growth Hormone | IL-15 |
| Eotaxin | VEGF | Insulin | IL-7 |
| TNF-beta | Cancer Antigen 19-9 | Myeloperoxidase | Apolipoprotein CIII |
| MMP-2 | FGF basic | CD40 Ligand | Complement 3 |
| Ferritin | G-CSF | Stem Cell Factor | IFN-gamma |
| MMP-9 | Thyroid Stimulating Hormone | Brain-Derived Neurotrophic Factor | Apolipoprotein H |
| Myoglobin | OSM (Oncostatin M) | EGF | Alpha-Fetoprotein |
| IL-1 alpha | RANTES | ENA-78 | Thyroxine Binding Globulin |
| IL-8 | Thrombospondin-1 | Creatine Kinase-MB | IL-17 |

TABLE 1-continued

Informative genes.

| IGF-1 | IL-1 ra | ICAM-1 | SHBG |
|---|---|---|---|
| Fatty Acid Binding Protein | IL-6 | IL-12p40 | IL-23 |
| TNF RII | Fibrinogen | Erythropoietin | GM-CSF |
| Haptoglobin | Alpha-1 Antitrypsin | Adiponectin | IL-3 |
| IgE | C Reactive Protein | Serum Amyloid P | Tissue Factor |
| Lipoprotein (a) | IL-4 | Lymphotactin | Thrombopoietin |
| Prostate Specific Antigen, Free | IL-10 | IL-2 | TNF-alpha |
| EN-RAGE | PAI-1 | IL-1beta | IL-17E |
| SGOT | MDC | MIP-1alpha | IL-5 |
| Leptin | Prostatic Acid Phosphatase | Epiregulin | Amphiregulin |
| Cancer Antigen 125 | PAPP-A | IL-13 | Von Willebrand Factor |
| IL-18 | | Alpha-2 Macroglobulin | |

The informative genes listed in Table 1 are classified in the following tables:

TABLE 2

Analysis of Immune Cell Function: Supernatants are collected and tested for various cell type specific parameters

| Cell Type | Cytokines | Chemokines | Others |
|---|---|---|---|
| Granulocytes | — | — | Elastase |
| Monocytes | IL-1β, IL-6, IL-12 TNFα, TGF β etc. | IL-8, MCP-1, etc. | MMPs |
| T-lymphocytes | IL-2, IL-4, IL-5, IFNγ etc. | IL-8, MCP-1, RANTES, etc. | — |
| B-Lymphocytes | IL-10 | — | — |

TABLE 3

Classification of genes for MAP analysis: cytokines

| Th1-related | TH2-related | Treg-related |
|---|---|---|
| Interferon-γ | Interleukin-4 | Interleukin-10 |
| Interleukin-12p40 | Interleukin-5 | |
| Interleukin-12p70 | Interleukin-13 | |

| Monocyte/MO-related | Others | |
|---|---|---|
| G-CSF | Epidermal Growth Factor | Interleukin-2 |
| Interleukin-1 ra | FGF-basic | Interleukin-3 |
| Interleukin-1 α | GM-CSF | Interleukin-7 |
| Interleukin-1 β | IGF-1 | Interleukin-15 |
| Interleukin-6 | Stem Cell Factor | Interleukin-16 |
| Tumor Necrosis Factor-α | Tumor Necrosis Factor-β | |

TABLE 4

Classification of genes for MAP analysis, cont.

| Enzymes | Hormones/BP | Receoptors/Ligands |
|---|---|---|
| GST | Adiponectin | CD40 |
| MMP-2 | Calcitonin | CD40Ligand |
| MMP-3 | Erythropoein | ICAM-1 |
| MMP-9 | Growth Hormone | Tissue Factor |
| Myeloperoxidase | Insulin | Tumor Necrosis Factor RII |
| SGOT | Leptin | |
| | Sex Hormone Binding Globullin | VCAM-1 |
| | Thrombopoietin | |
| | Thyroid Binding Globulin | |
| | Thyroid Stimulating Hormone | |

TABLE 5

Classification of genes for MAP analysis, cont.

| Chemokines | Cancer antigens |
|---|---|
| ENA-78 | Alpha-Fetoprotein |
| Eotaxin | Cancer Antigen 19-9 |
| Interleukin-8 | Cancer Antigen 125 |
| Lymphotactin | Carcinoembryonic Antigen |
| MCP-1 | Prostatic Acid Phosphatase |
| MDC | PSA, Free |
| MIP-1α | |
| MIP-1β | |
| RANTES | |

TABLE 6

Cardiovascular disease related

| Apolipoprotein A-1 | Fatty Acid BP |
|---|---|
| Apolipoprotein C-III | Lipoprotein (a) |
| CK-MB | Myoglobin |
| Endothelin-1 | PAPP-A |

TABLE 7

Other

| Alpha-1 Antitrypsin | Immunoglobulin A |
|---|---|
| Alpha-2 Macroglobulin | Immunoglobulin M |
| Apolipoprotein H | Immunoglobulin E |
| BDNF | |
| Beta-2 Microglobulin | VEGF |
| Complement 3 | |
| C-Reactive Protein | Factor VII |
| ENRAGE | Fibrinogen |
| Ferritin | von Willebrand Factor |

TABLE 7-continued

| Other | |
|---|---|
| Haptoglobin | PAI-1 |
| Serum Amyloid P | TIMP-1 |

Example 2

Figure 20:
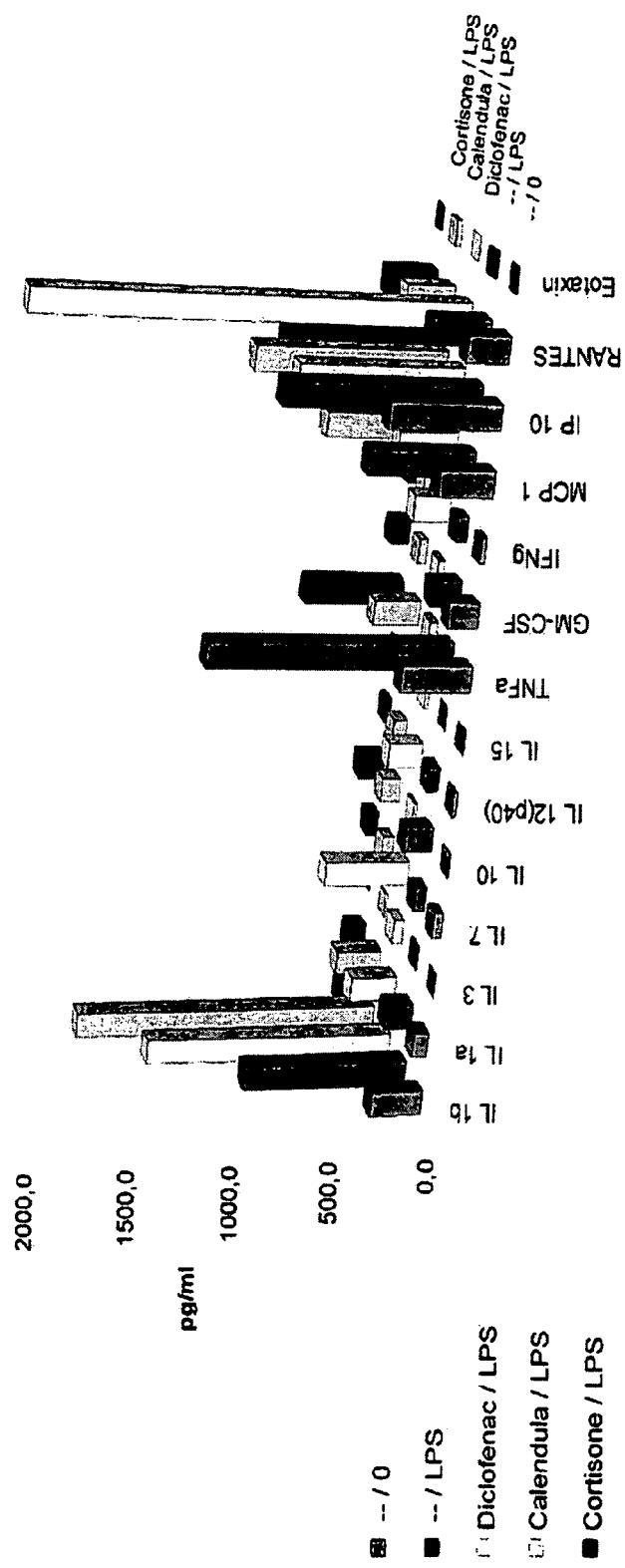
FIG. 20 shows the differential expression of various informative genes (IL-1β, IL-1α, IL-3, IL-7, IL-10, IL-12 (p40), IL-15, TNFα, GM-CSF, IFNγ, MCP1, IP10, RANTES and Eotaxin) in cells exposed to various stimulatory factors in combination with drugs (no drug/no stimulatory factor, no drug/LPS, Diclofenac/LPS, *Calendula*/LPS and Cortisone/LPS).

Informative genes were used to determine their utility in distinguishing different causes of sepsis. FIG. 20 shows cells stimulated with different factors and the effect of stimulation on specific informative genes.

Figure 21:
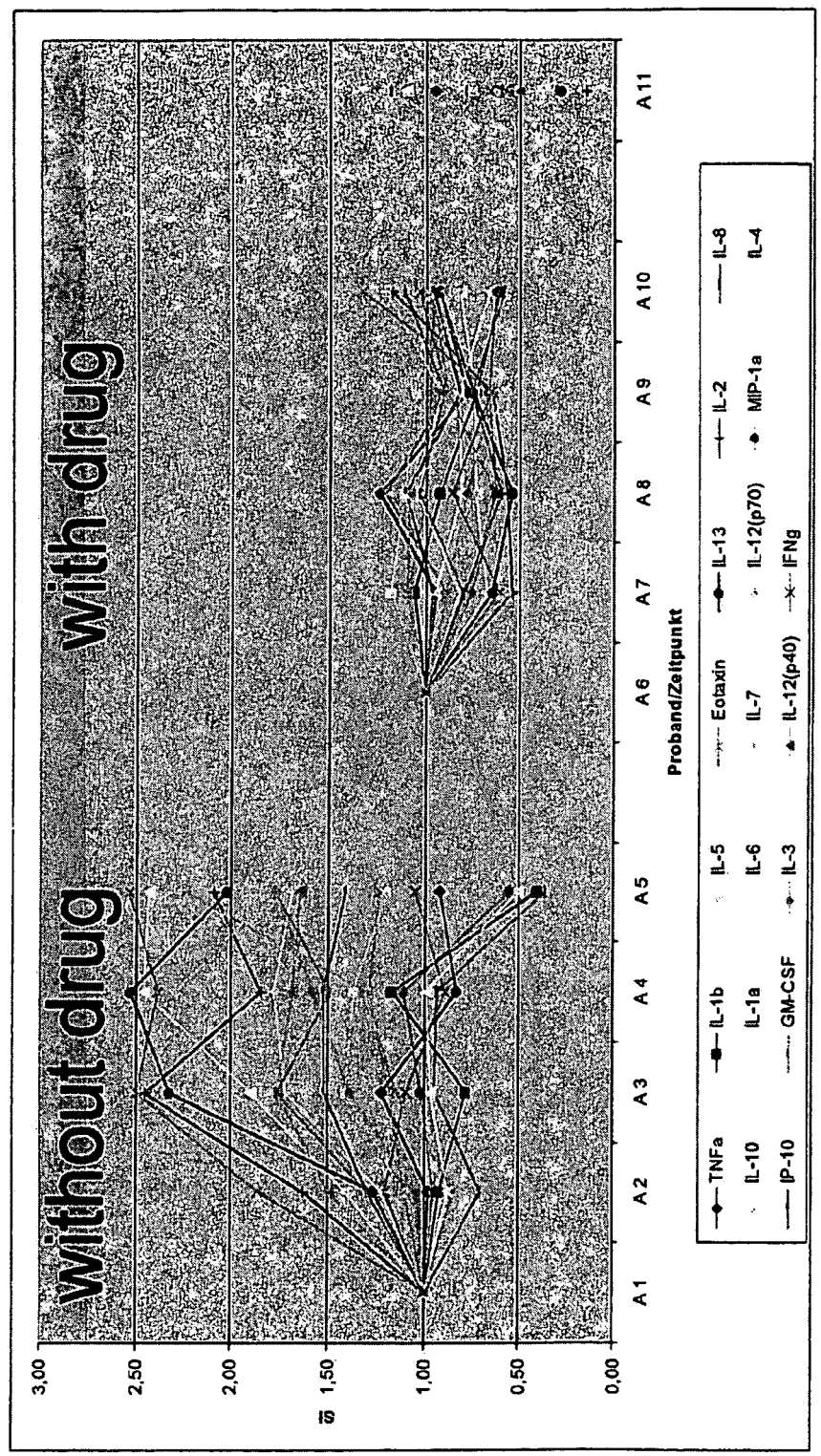
FIG. 21 shows the change in expression of particular informative genes in samples with and without drug exposure.

The effect on the cellular activity patterns of particular informative genes with respect to drug treatment are shown in FIG. 21.

What is claimed is:

1. A method for determining the severity of an inflammatory disease comprising:
   (a) contacting a fluid sample comprising blood cells from a subject with at least two toll-like receptor (TLR) ligands in vitro;
   (b) determining in the fluid sample concentrations of at least two proteins relevant to inflammatory disease; and
   (c) comparing the concentrations of the proteins relevant to inflammatory disease to control concentrations of the proteins relevant to inflammatory disease, wherein a statistically significant similarity of the sample to the control is indicative of a particular stage of the inflammatory disease,
   wherein the at least two proteins relevant to inflammatory disease are selected from the group consisting of IGF-1, IL-1 ra, ICAM-1, SHBG, MMP-3, Apolipoprotein A1, IgM, MIP-1beta, TIMP-1, Calcitonin, IgA, IL-16, Carcinoembryonic Antigen, Factor VII, Glutathione S-Transferase, IL-12p70, TGF-alpha, MCP-1, Eotaxin, TNF-beta, Beta-2 Microglobulin, CD40, VEGF, Cancer antigen 19-9, VCAM-1, Growth Hormone, Insulin, Myeloperoxidase, Endothelin-1, IL-15, IL-7, Apolipoprotein CIII, MMP-2, Ferritin, MMP-9, FGF Basic, G-CSF, Thyroid Stimulating Hormone, CD40 Ligand, Stem Cell Factor, Brain-Derived Neurotrophic Factor, Complement 3, IFN-gamma, Apolipoprotein H, Myoglobin, IL-1 alpha, OSM (Oncostatin M), RANTES, EGF, ENA-78, Alpha-Fetoprotein, Thyroxine Binding Globulin, IL-8, Thrombospondin-1, Creatine Kinase-MB, IL-17, Fatty Acid Binding Protein, IL-6, IL-12p40, IL-23, TNF RII, Haptoglobin, IgE, Lipoprotein (a), Free Prostate Specific Antigen, Fibrinogen, Alpha-1 Antitrypsin, C Reactive Protein, IL-4, IL-10, Erythropoietin, Adiponectin, Serum Amyloid P, Lymphotactin, IL-2, GM-CSF, IL-3, Tissue Factor, Thrombopoietin, EN-RAGE, SGOT, Leptin, PAI-1, MDC, Prostatic Acid Phosphatase, IL-1beta, MIP-1alpha, Epiregulin, IL-17E, IL-5, Amphiregulin, Cancer Antigen 125, PAPP-A, IL-13, Von Willebrand Factor, IL-18, or Alpha-2 Macroglobulin.

2. The method of claim 1, wherein one or more of the at least two proteins relevant to inflammatory disease is a signal transducer or receptor.

3. The method of claim 1, wherein one or more of the at least two proteins relevant to inflammatory disease is a blood cell nuclear constituent.

4. The method of claim 1, wherein one or more of the at least two TLR ligands is a human toll-like receptor ligand.

5. The method of claim 4, wherein one or more of the at least two TLR ligands is a ligand of a human TLR selected from the group consisting of: hTLR1, hTLR2, hTLR3, hTLR4, hTLR5, hTLR6, hTLR7, hTLR8, hTLR9, hTLR10 and hTLR11.

6. The method of claim 1, wherein one or more of the at least two TLR ligands is derived from a microbe.

7. The method of claim 6, wherein the microbe is a bacterium, virus or fungus.

8. The method of claim 1, wherein one or more of the at least two TLR ligands is a compound that occurs in bacterial cell walls or in cell membranes.

9. The method of claim 1, wherein one or more of the at least two TLR ligands is selected from the group consisting of: lipopolysaccharides, lipoproteins, lipopeptides, lipoteichoic acids, glycans, muramyl peptides, mannans, DNA and RNA.

10. The method of claim 1, wherein the blood cells are stimulated with Imiquimod or Loxoribine.

11. The method of claim 1, further comprising the step of contacting the fluid sample with a co-stimulation factor.

12. The method of claim 11, wherein the co-stimulation factor is a cell-receptor ligand.

13. The method of claim 12, wherein the cell receptor ligand is an integrin-receptor ligand or a NOD receptor ligand.

14. The method of claim 1, wherein one or more of the at least two TLR ligands is an exosome or a nucleosome.

15. The method of claim 1, wherein one or more of the at least two TLR ligands binds more than one toll-like receptor.

16. The method of claim 1, wherein the fluid sample is contacted with the at least two TLR ligands during a period of from 0 to 48 hours.

17. The method of claim 1, wherein the fluid sample is contacted with the at least two TLR ligands during a period of from 1 to 30 minutes.

18. The method of claim 1, wherein the fluid sample is contacted with the at least two TLR ligands during a period of from 1 to 4 hours.

19. The method of claim 1, wherein the fluid sample is contacted with the at least two TLR ligands during a period of from 6 to 24 hours.

20. The method of claim 1, wherein one or more control cellular activity patterns are determined in blood cells stimulated with at least one toll-like receptor ligand.

21. The method of claim 1, wherein the inflammatory disease is associated with a systemic inflammatory response syndrome.

22. The method of claim 1, wherein the inflammatory disease is a septic disease.

23. The method of claim 1, wherein the inflammatory disease is a macrophage activation syndrome.

24. A method for determining the efficacy of a treatment for an inflammatory disease comprising:
   (a) contacting a fluid sample from a subject with at least two toll-like receptor ligands in vitro;
   (b) determining in the fluid sample concentrations of at least two proteins relevant to inflammatory disease; and
   (c) repeating steps (a)-(b) after the subject is treated for an inflammatory disease; and
   (d) comparing said protein concentrations, before and after treatment, associated with inflammatory disease to one or more control proteins relevant to inflammatory disease, wherein a statistically significant similarity of the sample to the control is indicative of the efficacy of the treatment for the inflammatory disease, wherein the at least two proteins relevant to inflammatory disease are selected from the group consisting of IGF-1, IL-1 ra, ICAM-1, SHBG, MMP-3, Apolipoprotein A1, IgM, MIP-1beta, TIMP-1, Calcitonin, IgA, IL-16, Carcinoembryonic Antigen, Factor VII, Glutathione S-Transferase, IL-12p70, TGF-alpha, MCP-1, Eotaxin, TNF-beta, Beta-2 Microglobulin, CD40, VEGF, Cancer antigen 19-9, VCAM-1, Growth Hormone, Insulin, Myeloperoxidase, Endothelin-1, IL-15, IL-7, Apolipoprotein CIII, MMP-2, Ferritin, MMP-9, FGF Basic, G-CSF, Thyroid Stimulating Hormone, CD40 Ligand, Stem Cell Factor, Brain-Derived Neurotrophic Factor, Complement 3, IFN-gamma, Apolipoprotein H, Myoglobin, IL-1 alpha, OSM (Oncostatin M), RANTES, EGF, ENA-78, Alpha-Fetoprotein, Thyroxine Binding Globulin, IL-8, Thrombospondin-1, Creatine Kinase-MB, IL-17, Fatty Acid Binding Protein, IL-6, IL-12p40, IL-23, TNF RII, Haptoglobin, IgE, Lipoprotein (a), Free Prostate Specific Antigen, Fibrinogen, Alpha-1 Antitrypsin, C Reactive Protein, IL-4, IL-10, Erythropoietin, Adiponectin, Serum Amyloid P, Lymphotactin, IL-2, GM-CSF, IL-3, Tissue Factor, Thrombopoietin, EN-RAGE, SGOT, Leptin, PAI-1, MDC, Prostatic Acid Phosphatase, IL-1beta, MIP-1alpha, Epiregulin, IL-17E, IL-5, Amphiregulin, Cancer Antigen 125, PAPP-A, IL-13, Von Willebrand Factor, IL-18, or Alpha-2 Macroglobulin.

* * * * *